US011679120B2

(12) United States Patent
Horhota et al.

(10) Patent No.: US 11,679,120 B2
(45) **Date of Patent: *Jun. 20, 2023**

(54) CIRCULAR RNA COMPOSITIONS AND METHODS

(71) Applicant: Orna Therapeutics, Inc., Cambridge, MA (US)

(72) Inventors: Allen T. Horhota, Cambridge, MA (US); Brian Goodman, Cambridge, MA (US); Robert Alexander Wesselhoeft, Cambridge, MA (US); Junghoon Yang, Cambridge, MA (US)

(73) Assignee: Orna Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/202,223

(22) Filed: Mar. 15, 2021

(65) Prior Publication Data

US 2022/0323480 A1 Oct. 13, 2022

Related U.S. Application Data

(63) Continuation of application No. PCT/US2020/063494, filed on Dec. 4, 2020.

(60) Provisional application No. 63/087,582, filed on Oct. 5, 2020, provisional application No. 63/022,248, filed on May 8, 2020, provisional application No. 62/972,194, filed on Feb. 10, 2020, provisional application No. 62/943,779, filed on Dec. 4, 2019, provisional application No. 62/943,797, filed on Dec. 4, 2019.

(51) Int. Cl.
*A61K 31/7105* (2006.01)
*A61K 47/22* (2006.01)

(52) U.S. Cl.
CPC .......... *A61K 31/7105* (2013.01); *A61K 47/22* (2013.01)

(58) Field of Classification Search
CPC .............. A61K 48/005; A61K 48/0025; C12N 15/11; C12N 15/64; C12N 15/67; C12N 15/79; C12N 15/113; C12N 2830/42; C12N 2840/203; C12P 19/34
USPC ...... 424/9.1; 435/6.1, 91.1, 91.31, 455, 458; 536/23.1, 24.5
See application file for complete search history.

(56) References Cited

U.S. PATENT DOCUMENTS

| | | | |
|---|---|---|---|
| 4,323,689 | A | 4/1982 | Vogel et al. |
| 4,661,450 | A | 4/1987 | Kempe et al. |
| 5,434,261 | A | 7/1995 | Schoen et al. |
| 5,580,859 | A | 12/1996 | Felgner et al. |
| 5,591,737 | A | 1/1997 | Doherty et al. |
| 5,625,047 | A | 4/1997 | Been et al. |
| 5,629,304 | A | 5/1997 | Murakata et al. |
| 5,656,606 | A | 8/1997 | Nargund et al. |
| 5,672,596 | A | 9/1997 | Wyvratt et al. |
| 5,712,128 | A | 1/1998 | Been et al. |
| 5,747,485 | A | 5/1998 | Doherty et al. |
| 5,755,903 | A | 5/1998 | Garant et al. |
| 5,766,903 | A | 6/1998 | Sarnow et al. |
| 5,773,244 | A | 6/1998 | Ares, Jr. et al. |
| 5,972,964 | A | 10/1999 | Perregaard |
| 6,043,026 | A | 3/2000 | Patchett et al. |
| 6,210,931 | B1 | 4/2001 | Feldstein et al. |
| 6,211,174 | B1 | 4/2001 | Devita et al. |
| 6,368,802 | B1 | 4/2002 | Kool |
| 6,576,628 | B1 | 6/2003 | Grams et al. |
| 6,620,597 | B1 | 9/2003 | Chen et al. |
| 8,829,170 | B2 | 9/2014 | Dale et al. |
| 11,203,767 | B2 | 12/2021 | Anderson et al. |
| 11,352,640 | B2 | 6/2022 | Anderson et al. |
| 11,352,641 | B2 | 6/2022 | Anderson et al. |
| 2006/0199851 | A1 | 9/2006 | Kempf et al. |
| 2010/0137407 | A1 | 6/2010 | Abe et al. |
| 2011/0019782 | A1 | 1/2011 | Kobayashi et al. |
| 2015/0079630 | A1 | 3/2015 | Abe et al. |
| 2016/0194368 | A1 | 7/2016 | Hoge et al. |
| 2016/0331828 | A1 | 11/2016 | Ciaramella et al. |
| 2017/0204422 | A1 | 7/2017 | Nelson et al. |

(Continued)

FOREIGN PATENT DOCUMENTS

| | | | |
|---|---|---|---|
| CN | 101016264 | A | 8/2007 |
| CN | 105176981 | A | 12/2015 |

(Continued)

OTHER PUBLICATIONS

Badelt et al. "Computational Design of a Circular RNA with Prionlike Behavior," Artif Life., 2016, 22(2):172-84.
Barrett et al. "Circular RNAs: analysis, expression and potential functions," Development, 2016, 1143(11):1838-47.
Borchardt et al. "Inducing circular RNA formation using the CRISPR endoribonuclease Csy4," RNA, 2017, 23(5):619-627.
Branch et al. "Unusual properties of two branched RNA's with circular and linear components," Nucleic Acids Res., 1985, 13(13):4889-903.

(Continued)

*Primary Examiner* — Jane J Zara
(74) *Attorney, Agent, or Firm* — Goodwin Procter LLP

(57) ABSTRACT

Disclosed herein are circular RNAs and transfer vehicles, along with related compositions and methods of treatment. The circular RNAs can comprise group I intron fragments, spacers, an IRES, duplex forming regions, and/or an expression sequence, thereby having the features of improved expression, functional stability, low immunogenicity, ease of manufacturing, and/or extended half-life compared to linear RNA. Pharmaceutical compositions comprising such circular RNAs and transfer vehicles are particularly suitable for efficient protein expression in immune cells in vivo. Also disclosed are precursor RNAs and materials useful in producing the precursor or circular RNAs, which have improved circularization efficiency and/or are compatible with effective circular RNA purification methods.

19 Claims, 75 Drawing Sheets

Specification includes a Sequence Listing.

(56) References Cited

U.S. PATENT DOCUMENTS

| | | | | |
|---|---|---|---|---|
| 2018/0010175 | A1 | 1/2018 | Cheng | |
| 2018/0311343 | A1 | 11/2018 | Huang et al. | |
| 2018/0326045 | A1 | 11/2018 | Ciaramella et al. | |
| 2019/0290694 | A1 | 9/2019 | Gautron et al. | |
| 2019/0314291 | A1 | 10/2019 | Besin et al. | |
| 2019/0328769 | A1 | 10/2019 | Uchida et al. | |
| 2019/0345503 | A1 | 11/2019 | Chang et al. | |
| 2020/0040370 | A1 | 2/2020 | Eber et al. | |
| 2020/0080106 | A1 | 3/2020 | Anderson et al. | |
| 2021/0085719 | A1 | 3/2021 | Jensen | |
| 2021/0198688 | A1 * | 7/2021 | Anderson | C12N 15/85 |
| 2021/0363540 | A1 | 11/2021 | Anderson et al. | |
| 2021/0371494 | A1 | 12/2021 | Wesselhoeft et al. | |
| 2021/0403944 | A1 | 12/2021 | Anderson et al. | |
| 2022/0025395 | A1 | 1/2022 | Anderson et al. | |
| 2022/0106259 | A1 | 4/2022 | Benenato et al. | |
| 2022/0177540 | A1 | 6/2022 | Wesselhoeft et al. | |

FOREIGN PATENT DOCUMENTS

| | | | | |
|---|---|---|---|---|
| CN | 106801050 | A | 6/2017 | |
| EP | 2819377 | A1 | 12/2014 | |
| EP | 3630966 | A1 | 4/2020 | |
| EP | 3819377 | A1 | 5/2021 | |
| GB | 2308064 | A | 6/1997 | |
| JP | 2016/521133 | A | 7/2016 | |
| JP | 2017043556 | A | 3/2017 | |
| JP | 6284181 | B2 | 2/2018 | |
| KR | 2011/0095439 | A | 8/2011 | |
| WO | 1995/011029 | A1 | 4/1995 | |
| WO | 1995/024207 | A1 | 9/1995 | |
| WO | 2005/044201 | A2 | 5/2005 | |
| WO | 2005/079803 | A1 | 9/2005 | |
| WO | 2006/138380 | A2 | 12/2006 | |
| WO | 2007/044627 | A2 | 4/2007 | |
| WO | 2009/035541 | A1 | 3/2009 | |
| WO | 2010/084371 | A1 | 7/2010 | |
| WO | 2010/138652 | A1 | 12/2010 | |
| WO | 2010/138659 | A1 | 12/2010 | |
| WO | 2010/138685 | A1 | 12/2010 | |
| WO | 2010/138695 | A1 | 12/2010 | |
| WO | 2010/138706 | A1 | 12/2010 | |
| WO | 2010/138758 | A1 | 12/2010 | |
| WO | 2013/076509 | A1 | 5/2013 | |
| WO | 2013/118878 | A1 | 8/2013 | |
| WO | 2014/144871 | A1 | 9/2014 | |
| WO | 2014/186334 | A1 | 11/2014 | |
| WO | 2014/193857 | A1 | 12/2014 | |
| WO | 2015/034925 | A1 | 3/2015 | |
| WO | 2015/095340 | A1 | 6/2015 | |
| WO | 2016/020373 | A1 | 2/2016 | |
| WO | 2016/197121 | A1 | 12/2016 | |
| WO | 2017/046203 | A1 | 3/2017 | |
| WO | 2017/049245 | A2 | 3/2017 | |
| WO | 2017/055487 | A2 | 4/2017 | |
| WO | 2017/059357 | A1 | 4/2017 | |
| WO | 2017/118734 | A1 | 7/2017 | |
| WO | 2017/201332 | A1 | 11/2017 | |
| WO | 2017/201333 | A1 | 11/2017 | |
| WO | 2017/201340 | A2 | 11/2017 | |
| WO | 2017/201342 | A1 | 11/2017 | |
| WO | 2017/201346 | A1 | 11/2017 | |
| WO | 2017/201348 | A1 | 11/2017 | |
| WO | 2017/201349 | A1 | 11/2017 | |
| WO | 2017/201350 | A1 | 11/2017 | |
| WO | 2017/222911 | A1 | 12/2017 | |
| WO | 2018/144775 | A1 | 8/2018 | |
| WO | 2018/157009 | A1 | 8/2018 | |
| WO | 2018/170260 | A1 | 9/2018 | |
| WO | 2018/170306 | A1 | 9/2018 | |
| WO | WO-2018170306 | A1 * | 9/2018 | C07C 229/12 |
| WO | 2018/191722 | A1 | 10/2018 | |
| WO | 2018/237372 | A1 | 12/2018 | |
| WO | 2019/118919 | A1 | 6/2019 | |
| WO | 2019/213308 | A1 | 11/2019 | |
| WO | 2019/222275 | A2 | 11/2019 | |
| WO | 2019/236673 | A1 | 12/2019 | |
| WO | 2020/010242 | A1 | 1/2020 | |
| WO | 2020/023595 | A1 | 1/2020 | |
| WO | 2020/035070 | A1 | 2/2020 | |
| WO | 2020/061367 | A1 | 3/2020 | |
| WO | 2020/198403 | A2 | 10/2020 | |
| WO | 2020/237227 | A1 | 11/2020 | |
| WO | 2020/252436 | A1 | 12/2020 | |
| WO | 2021/041541 | A1 | 3/2021 | |
| WO | 2021/055849 | A1 | 3/2021 | |
| WO | 2021/113777 | A2 | 6/2021 | |

OTHER PUBLICATIONS

Chen et al. "Promising diagnostic and therapeutic circRNAs for skeletal and chondral disorders," Int J Biol Sci., 2021, 17(5):1428-1439.

Chen et al. "Sensing Self and Foreign Circular RNAs by Intron Identify," Molecular Cell, 2017, 67:228-238.

Costello et al. "Reinventing the Wheel: Synthetic Circular RNAs for Mammalian Cell Engineering." Trends Biotechnol., 2020, 38(2):217-230.

Foster et al. "Purification of mRNA Encoding Chimeric Antigen Receptor Is Critical for Generation of a Robust T-Cell Response," Hum Gene Ther, 2019, 30(2):168-178.

Holdt et al. "Circular RNAs as Therapeutic Agents and Targets," Front Physiol., 2018, 9:1262.

International Preliminary Report on Patentability and Written Opinion for International Application No. PCT/US2019/035531, dated Dec. 8, 2020, 8 pages.

International Search Report and Written Opinion for International Application No. PCT/US2020/034418, dated Sep. 28, 2020, 15 pages.

Invitation to Pay Additional Fees and, Where Applicable, Protest Fee for International Application No. PCT/US2020/063494, mailed Apr. 28, 2021, 12 pages.

Jeck et al. "Detecting and characterizing circular RNAs," Nat Biotechnol., 2014, 32(5):453-61.

Kaczmarek et al. "Advances in the Delivery of RNA Therapeutics: from Concept to Clinical Reality," Genome Medicine, 2017, 9(1):60.

Li et al. "The Biogenesis, Functions, and Challenges of Circular RNAs," Mol Cell., 2018, 71(3):428-442.

Litke et al. "Trans ligation of RNAs to generate hybrid circular RNAs using highly efficient autocatalytic transcripts," Methods, 2021, S1046-2023(21)00135-3.

Mao et al. "Biological roles and therapeutic potential of circular RNAs in osteoarthritis," Mol Ther Nucleic Acids, 2021, 24:856-867.

Meganck et al. "Engineering highly efficient backsplicing and translation of synthetic circRNAs," Mol Ther Nucleic Acids, 2021, 23:821-834.

Nakamoto et al. "Chemical Synthesis of Circular RNAs with Phosphoramidate Linkages for Rolling-Circle Translation," Curr Protoc., 2021, 1(3):e43.

Obi et al. "The design and synthesis of circular RNAs," Methods, 2021, S1046-2023(21)00065-7.

Petkovic et al. "RNA Circularization Strategies in vivo and in vitro," Nucleic Acids Research, 2015, 43(4):2454-2465.

Puttaraju et al. "Group I Permuted Intron-exon (PIE) Sequences Self-splice to Produce Circular Exons," Nucleic Acids Research, 1992, 20(20):5357-5364.

Rausch et al. "Characterizing and circumventing sequence restrictions for synthesis of circular RNA in vitro," Nucleic Acids Res., 2021, 49(6):e35.

Sullenger et al. "From the RNA world to the clinic," Science, 2016, 352(6292):1417-1420.

Umekage et al. "In vivo circular RNA production using a constitutive promoter for high-level expression," J Biosci Bioeng, 2009, 108(4):354-6.

Wesselhoeft et al. "Engineering Circular RNA for Potent and Stable Translation in Eukaryotic Cells," Nature Communications, 2018, 9(1):2629, 10 pages.

(56) References Cited

OTHER PUBLICATIONS

Wesselhoeft et al. "RNA Circulation Diminishes Immunogenicity and can Extend Translation Duration In Vivo," Molecular Cell, 2019, 74(3):508-520.
Wiesinger et al. "Clinical-Scale Production of CAR-T Cells for the Treatment of Melanoma Patients by mRNA Transfection of a CSPG4-Specific CAR under Full GMP Compliance," Cancers (Basel), 2019, 11(8):1198.
Xue et al. "Lipid-based nanocarriers for RNA delivery," Curr Pharm Des, 2015, 21(22):3140-7.
Yang et al. "Circular RNAs: Expression, localization, and therapeutic potentials," Mol Ther, 2021, 29(5):1683-1702.
Unpublished U.S. Appl. No. 17/374,497, entitled: "Circular RNA for Translation in Eukaryotic Cells," filed Jul. 13, 2021, Inventors: Daniel G. Anderson, Robert Alexander Wesselhoeft, and Piotr S. Kowalski.
Unpublished U.S. Appl. No. 17/384,460, entitled: "Circular RNA Compositions and Methods," filed Jul. 23, 2021; Inventors: Alexander Wesselhoeft, Daniel G. Anderson, Shinichiro Fuse, Brian Goodman, Allen Horhota, and Raffaella Squilloni.
Unpublished U.S. Appl. No. 17/468,100, entitled: "Circular RNA for Translation in Eukaryotic Cells," filed Sep. 7, 2021, Inventors: Daniel G. Anderson, Robert Alexander Wesselhoeft, and Piotr S. Kowalski.
Unpublished U.S. Appl. No. 17/492,512, entitled: "Circular RNA for Translation in Eukaryotic Cells," filed Oct. 1, 2021, Inventors: Daniel G. Anderson, Robert Alexander Wesselhoeft, and Piotr S. Kowalski.
Unpublished U.S. Appl. No. 17/503,208, entitled "Circular RNA Compositions and Methods," filed Oct. 15, 2021; Inventors: Brian Goodman, Alexander Wesselhoeft, Allen Horhota, and Junghoon Yang.
Unpublished U.S. Appl. No. 17/548,241, entitled "Circular RNA Compositions and Methods," filed Dec. 10, 2021; Inventors: Brian Goodman, Alexander Wesselhoeft, Allen Horhota, and Junghoon Yang.
Unpublished U.S. Appl. No. 17/548,247, entitled "Circular RNA Compositions and Methods," filed Dec. 10, 2021; Inventors: Alexander Wesselhoeft, Daniel G. Anderson, Shinichiro Fuse, Brian Goodman, Allen Horhota, and Raffaella Squilloni.
Valdmanis, P.N. and Kay, M.A., "The Expanding Repertoire of Circular RNAs," The American Society of Gene and Cell Therapy, vol. 21; No. 6; 1112-1114 (2013).
Wang, Y. and Wang, Z., "Efficient backsplicing produces translatable circular mRNAs," RNA, vol. 21; No. 2; 172-179 (2014).
Yang, E. et al., "Decay Rates of Human mRNAs: Correlation with Functional Characteristics and Sequence Attributes," Genome Research, vol. 13; 1863-1872 (2003).
Yeku et al. "Armored CAR T-cells: utilizing cytokines and pro-inflammatory ligands to enhance CAR T-cell anti-tumour efficacy," Biochem Soc Trans, 2016, 44(2):412-8.
Zeng et al., "A Circular RNA Binds to and Activates AKT Phosphorylation and Nuclear Localization Reducing Apoptosis and Enhancing Cardia Repair," Theranostics 7(16):3842-3855 (2017).
Benenato, Ciaramella, and Huang. "Structures of Lipids," 2022, 28 pages.
Final Office Action for U.S. Appl. No. 17/384,460, dated Jul. 22, 2022.
Final Office Action for U.S. Appl. No. 17/503,208, dated Aug. 30, 2022.
Final Office Action for U.S. Appl. No. 17/548,241, dated Sep. 28, 2022.
Koos et al. "Influence of structure on antimicrobial activity of some heterocycles. IV. 1-(3-alkylamino-2-hydroxypropyl)-2-methyl-5-nitroimidazoles," Chem Papers. 1994, 48(1):54-57.
Liang et al. "Short intronic repeat sequences facilitate circular RNA production," Genes & Development, 2014, 28:2233-2247.
Liang et al. "The Output of Protein-Coding Genes Shifts to Circular RNAs When the Pre-mRNA Processing Machinery Is Limiting," Molecular Cell, 2017, 68:940-954.
Non-Final Office Action for U.S. Appl. No. 17/503,208, dated May 5, 2022.
Non-Final Office Action for U.S. Appl. No. 17/548,241, dated May 24, 2022.
Notice of Allowance for U.S. Appl. No. 17/492,512, dated Apr. 26, 2022.
Notice of Allowance for U.S. Appl. No. 17/548,247, dated Jul. 22, 2022.
Starke et al. "Exon Circularization Requires Canonical Splice Signals," Cell Reports, 2015, 10:103-111.
STN Registry Database Entry for 1333432-38-4 entered STN Sep. 27, 2011.
STN Registry Database Entry for 1333626-46-2 entered STN Sep. 28, 2011.
STN Registry Database Entry for 156811-31-3 entered STN Aug. 5, 1994.
STN Registry Database Entry for 157493-54-4 entered STN Sep. 7, 1994.
STN Registry Database Entry for 1609534-48-6 entered STN Jun. 4, 2014.
STN Registry Database Entry for 2086785-24-0 entered STN Mar. 17, 2017.
STN Registry Database Entry for 2086785-25-1 entered STN Mar. 17, 2017.
STN Registry Database Entry for 2086785-26-2 entered STN Mar. 17, 2017.
STN Registry Database Entry for 2086785-27-3 entered STN Mar. 17, 2017.
STN Registry Database Entry for 2086785-32-0 entered STN Mar. 17, 2017.
STN Registry Database Entry for 2086785-33-1 entered STN Mar. 17, 2017.
STN Registry Database Entry for 2089251-16-9 entered STN Apr. 10, 2017.
STN Registry Database Entry for 79111-60-7 entered STN Nov. 16, 1984.
Unpublished U.S. Appl. No. 17/853,576, entitled "Circular RNA Vectors Encoding Chimeric Antigen Receptors Targeting BCMA," filed Jun. 29, 2022; Inventors: Robert Alexander Wesselhoeft, Kristen Ott, Thomas Barnes, Gregory Motz, Amy M. Becker, Allen T. Horhota, and Brian Goodman.
Unpublished U.S. Appl. No. 17/894,141, entitled "Circular RNA for Translation in Eukaryotic Cells," filed Aug. 23, 2022; Inventors: Daniel G. Anderson, Robert Alexander Wesselhoeft, and Piotr S. Kowalski.
Van Esch et al. "Aggregation behavior and copper-binding properties of surfactants containing imidazole and pyrazole ligands," Recl Trav Chim Pays-Bas. 1994, 113(4):186-193.
Wang et al. "Combinatorially designed lipid-like nanoparticles for intracellular delivery of cytotoxic protein for cancer therapy," Angew Chem Int Ed Engl. 2014, 53(11):2893-2898.
U.S. Appl. No. 17/492,512, filed Oct. 1, 2021, Daniel G. Anderson et al., Issued as U.S. Pat. No. 11,447,796 on Sep. 20, 2022.
U.S. Appl. No. 16/432,177, filed Jun. 5, 2019, Daniel G. Anderson et al., Pending.
Bail et al. "Tri- to be mono- for bacterial mRNA decay," Structure, 2009, 17(3):317-9.
Bohjanen, P. R. et al., "A small circular TAR RNA decoy specifically inhibits Tat-activated HIV-1 transcription," , Nucleic Acids Res., vol. 24; No. 19; 3733-3738 (1996).
Bohjanen, P. R., et al., "TAR RNA decoys inhibit Tat-activated HIV-1 transcription after preinitiation complex formation", Nucleic Acids Res., vol. 25; 4481-4486 (1997).
Cech, T.R., "Self-Splicing of Group 1 Introns," Ann. Rev. Biochem., vol. 59; 543-568 (1990).
Chen, C. and Sarnow, P., "Initiation of protein synthesis by the eukaryotic translational apparatus on circular RNAs," America Association for the Advancement of Science, Abstract 268.5209; p. 415 (1995).
Dahlman, J.E., et al., "Barcoded nanoparticles for high throughput in vivo discovery of targeted therapeutics," PNAS, vol. 114; No. 8; 2060-2065 (2017).

(56) References Cited

OTHER PUBLICATIONS

Devaux, Y. et al., "Circular RNAs in heart failure", European Journal of Heart Failure, vol. 19; 701-709 (2017).
Durymanov, M. and Reineke, J., "Non-viral Delivery of Nucleic Acids: Insight Into Mechanisms of Overcoming Intracellular Barriers," Frontiers in Pharmacology, vol. 9; Article 971; 15 pages (2018).
Examination Report issued in EP19739422.4 dated Mar. 17, 2022. 6 pages.
Fenton et al., "Customizable Lipid Nanoparticle Materials for the Delivery of siRNAs and mRNAs," Angew Chem Int Ed Engl. 57(41):13582-86 (2018).
Final Office Action for U.S. Appl. No. 17/191,697, dated Sep. 30, 2021.
Greene, J. et al., "Circular RNAs: Biogenesis, Function and Role in Human Diseases", Frontiers in Molecular Biosciences, vol. 4; Article 38; 11 pages (2017).
Han et al. "Multi-antigen-targeted chimeric antigen receptor T cells for cancer therapy," J Hematol Oncol., 2019, 12 (1):128.
Harrer et al. "RNA-transfection of gamma/delta T cells with a chimeric antigen receptor or an alpha/beta T-cell receptor: a safer alternative to genetically engineered alpha/beta T cells for the immunotherapy of melanoma," BMC Cancer, 2017, 17:551, 17 pages.
He, J. et al., "Cicular RNAs and cancer", Cancer Letters, vol. 396, 138-144 (2017).
International Preliminary Report on Patentability for International Application No. PCT/US2019/035531, entitled: "Circular RNA for Translation in Eukaryotic Cells," dated Dec. 17, 2020 (9 pages).
International Preliminary Report on Patentability for International Application No. PCT/US2020/034418 dated Nov. 16, 2021. 8 pages.
International Search Report and Written Opinion for International Application No. PCT/US2019/035531, entitled: "Circular RNA for Translation in Eukaryotic Cells," dated Sep. 27, 2019 (17 pages).
International Search Report and Written Opinion for International Application No. PCT/US2021/023540 dated Oct. 11, 2021.
International Search Report and Written Opinion for International Application No. PCT/US2021/031629 dated Feb. 4, 2022.
International Search Report and Written Opinion for International Appliction No. PCT/US2021/033276 dated Oct. 18, 2021.
Jemielity et al. "Synthetic mRNA cap analogs with a modified triphosphate bridge—synthesis, applications and prospects," New Journal of Chemistry, 2010, 34:829-844.
Kariko, K. et al., "Generating the optimal mRNA for therapy: HPLC purification eliminates immune activation and improves translation of nucleoside-modified, protein-encoding mRNA", Nucleic Acids Research, vol. 39; No. 21; e142, 10 pages (2011).
Kariko, K. et al., "Incorporation of Pseudouridine Into mRNA Yields Superior Nonimmunogenic Vector With Increased Translational Capacity and Biological Stability," Molecular Therapy, Vo. 16; No. 11; 1833-1840 (2008).
Kauffman, K.J. et al., "Efficacy and Immunogenicity of Unmodified and Pseudouridine-Modified mRNA Delivered Systemically with Lipid Nanoparticles in Vivo," Biomaterials, vol. 109; 78-87 (2016).
Kauffman, K.J. et al., "Rapid, Single-cell Analysis and Discovery of Vectored mRNA Transfection in Vivo wth a loxP-Flanked tdTomato Reporter Mouse," Molecular Therapy: Nucleic Acids, vol. 10; 55-63 (2018).
Kauffman, K.J., "Optimization and analysis of lipid nanoparticles for in vivo mRNA delivery," Ph.D. Thesis, Massachusetts Institute of Technology, Department of Chemical Engineering; 167 pages (2017).
Kotterman, M.A. and Schaffer, D.V., "Engineering adeno-associated viruses for clinical gene therapy," Nature Reviews, vol. 15; 445-451 (2014).
Legnini, I. et al., "Circ-ZNF609 Is a Circular RNA that Can Be Translated and Functions in Myogenesis," Molecular Cell, vol. 66; No. 1; 22-37 (2017).
Lenzi et al., "Gene Transfer Research: The Evolution of the Clinical Science," NCBI Bookshelf, A Service of the National Library of Medicine, National Institutes of Health, 16 pages (2014).
Memczak, S. et al., "Circular RNAs and a large class of animal RNAs with regulatory potency," Nature, vol. 495; 333-338 (2013).
Metzgar et al. "Abrupt emergence of diverse species B adenoviruses at US military recruit training centers," J Infect Dis. 2007, 196(10):1465-73.
Mu, X. et al., "An origin of the immunogenicity of in vitro transcribed RNA," Nucleic Acids Research, vol. 46; No. 10; 5239-5249 (2018).
Non-Final Office Action for U.S. Appl. No. 17/191,697, dated Jun. 18, 2021.
Non-Final Office Action for U.S. Appl. No. 17/374,497, dated Dec. 7, 2021.
Non-Final Office Action for U.S. Appl. No. 17/468,100, dated Dec. 8, 2021.
Non-Final Office Action for U.S. Appl. No. 17/492,512, dated Mar. 1, 2022.
Non-Final Office Action for U.S. Appl. No. 17/384,460, dated Mar. 24, 2022.
Non-Final Office Action for U.S. Appl. No. 17/548,247, dated Apr. 1, 2022.
Notice of Allowance for U.S. Appl. No. 17/191,697, dated Nov. 2, 2021.
Notice of Allowance for U.S. Appl. No. 17/374,497, dated Apr. 13, 2022.
Notice of Allowance for U.S. Appl. No. 17/468,100, dated Apr. 8, 2022.
Oberli et al. "Lipid Nanoparticle Assisted mRNA Delivery for Potent Cancer Immunotherapy," Nano Letters, 2017, 17:1326-1335.
Ochi, A., et al., Nucleic Acids Symp. Ser. vol. 53, pp. 275-276 (2009).
Pamudurti, N.R. et al., "Translation of CircRNAs," Molecular Cell, vol. 66; No. 1; 9-21 (2017).
Puttaraju, M. and Been, M. D., Circular Ribozymes Generated in *Escherichia coli* Using Group I Self-splicing Permuted Intron-Exon Sequences, J. Biol. Chem., vol. 271, pp. 26081-26087 (1996).
Rafiq et al. "Targeted delivery of a PD-1-blocking scFv by CAR-T cells enhances anti-tumor efficacy in vivo," Nat Biotechnol., 2018, 36(9):847-856.
Sahin, U. et al., "mRNA-based therapeutics—developing a new class of drugs," Nature Reviews, vol. 13; 759-780 (2014).
Shim, G. et al., "Nonviral Delivery Systems for Cancer Gene Therapy: Strategies and Challenges," Current Gene Therapy, vol. 17; 18 pages (2017).
Umekage, U. et al., In Vivo Circular RNA Expression by the Permuted Intron-Exon Method, Innovations in Biotechnology, Chapter 4, 17 pages (2012).

* cited by examiner

CIRCULAR RNA COMPOSITIONS AND METHODS

CROSS REFERENCE TO RELATED APPLICATIONS

This application is a continuation of International Application No. PCT/US2020/063494, filed Dec. 4, 2020, which claims the benefit of U.S. Provisional Application No. 62/943,779, filed on Dec. 4, 2019; U.S. Provisional Application No. 62/972,194, filed on Feb. 10, 2020; U.S. Provisional Application No. 63/022,248, filed on May 8, 2020; U.S. Provisional Application No. 63/087,582, filed on Oct. 5, 2020; and U.S. Provisional Application No. 62/943,797, filed on Dec. 4, 2019, the contents of each of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Apr. 8, 2021, is named OBS-011WOC1_Sequence_Listing.txt and is 588,501 bytes in size.

BACKGROUND

Conventional gene therapy involves the use of DNA for insertion of desired genetic information into host cells. The DNA introduced into the cell is usually integrated to a certain extent into the genome of one or more transfected cells, allowing for long-lasting action of the introduced genetic material in the host. While there may be substantial benefits to such sustained action, integration of exogenous DNA into a host genome may also have many deleterious effects. For example, it is possible that the introduced DNA will be inserted into an intact gene, resulting in a mutation which impedes or even totally eliminates the function of the endogenous gene. Thus, gene therapy with DNA may result in the impairment of a vital genetic function in the treated host, such as, e.g., elimination or deleteriously reduced production of an essential enzyme or interruption of a gene critical for the regulation of cell growth, resulting in unregulated or cancerous cell proliferation. In addition, with conventional DNA based gene therapy it is necessary for effective expression of the desired gene product to include a strong promoter sequence, which again may lead to undesirable changes in the regulation of normal gene expression in the cell. It is also possible that the DNA based genetic material will result in the induction of undesired anti-DNA antibodies, which in turn, may trigger a possibly fatal immune response. Gene therapy approaches using viral vectors can also result in an adverse immune response. In some circumstances, the viral vector may even integrate into the host genome. In addition, production of clinical grade viral vectors is also expensive and time consuming. Targeting delivery of the introduced genetic material using viral vectors can also be difficult to control. Thus, while DNA based gene therapy has been evaluated for delivery of secreted proteins using viral vectors (U.S. Pat. No. 6,066,626; US2004/0110709), these approaches may be limited for these various reasons.

In contrast to DNA, the use of RNA as a gene therapy agent is substantially safer because RNA does not involve the risk of being stably integrated into the genome of the transfected cell, thus eliminating the concern that the introduced genetic material will disrupt the normal functioning of an essential gene, or cause a mutation that results in deleterious or oncogenic effects, and extraneous promoter sequences are not required for effective translation of the encoded protein, again avoiding possible deleterious side effects. In addition, it is not necessary for mRNA to enter the nucleus to perform its function, while DNA must overcome this major barrier.

Circular RNA is useful in the design and production of stable forms of RNA. The circularization of an RNA molecule provides an advantage to the study of RNA structure and function, especially in the case of molecules that are prone to folding in an inactive conformation (Wang and Ruffner, 1998). Circular RNA can also be particularly interesting and useful for in vivo applications, especially in the research area of RNA-based control of gene expression and therapeutics, including protein replacement therapy and vaccination.

Prior to this invention, there were three main techniques for making circularized RNA in vitro: the splint-mediated method, the permuted intron-exon method, and the RNA ligase-mediated method. However, the existing methodologies are limited by the size of RNA that can be circularized, thus limiting their therapeutic application.

SUMMARY

The present application provides circular RNAs and transfer vehicles, along with related compositions and methods of treatment. The transfer vehicles can comprise, e.g., ionizable lipid, PEG-modified lipid, and/or structural lipid, thereby forming lipid nanoparticles encapsulating the circular RNAs. The circular RNAs can comprise group I intron fragments, spacers, an IRES, duplex forming regions, and/or an expression sequence, thereby having the features of improved expression, functional stability, low immunogenicity, ease of manufacturing, and/or extended half-life compared to linear RNA. Pharmaceutical compositions comprising such circular RNAs and transfer vehicles are particularly suitable for efficient protein expression in immune cells in vivo. The present application also provides precursor RNAs and materials useful in producing the precursor or circular RNAs, which have improved circularization efficiency and/or are compatible with effective circular RNA purification methods.

Accordingly, one aspect of the present application provides a pharmaceutical composition comprising a circular RNA polynucleotide and a transfer vehicle comprising an ionizable lipid represented by Formula (1):

Formula (1)

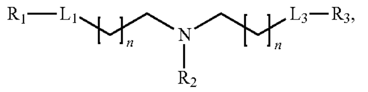

wherein:

each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl) amino carbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

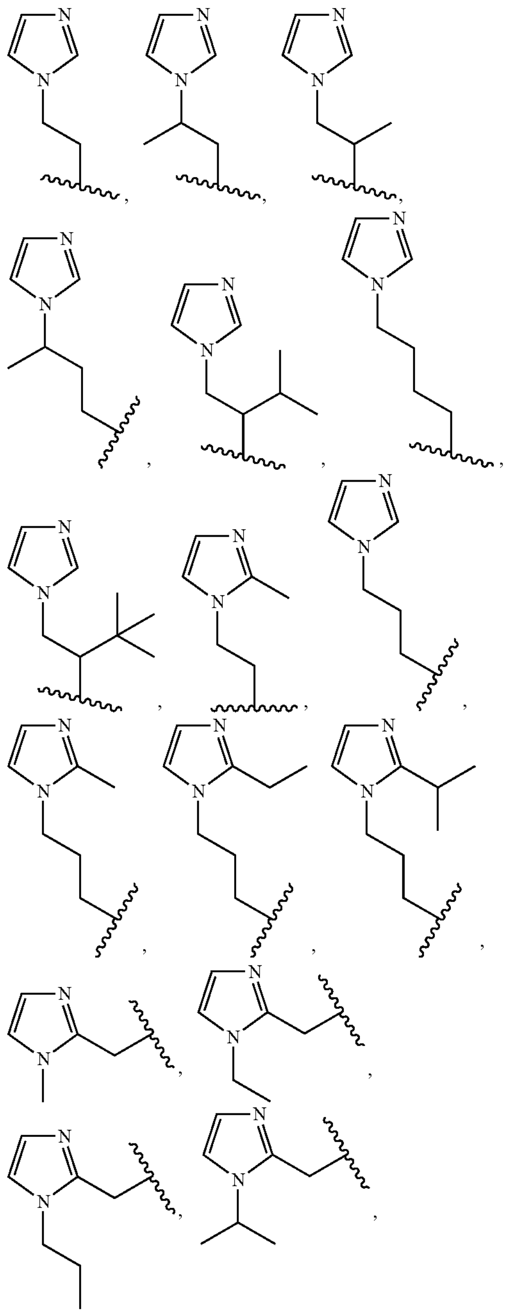

-continued

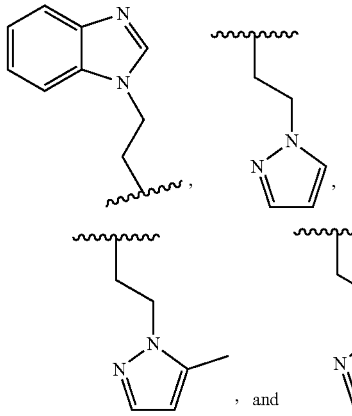

, and

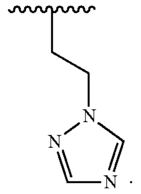

In some embodiments, $R_1$ and $R_3$ are each independently selected from a group consisting of:

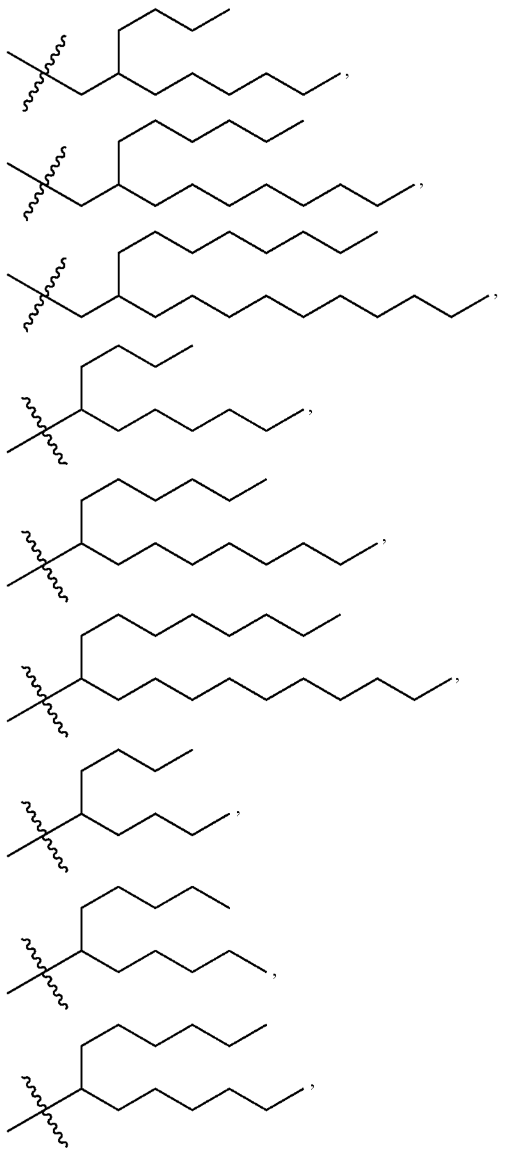

-continued
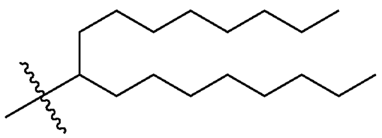
, and
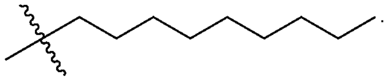
.
In some embodiments, $R_1$ and $R_3$ are the same. In some embodiments, $R_1$ and $R_3$ are different.
In some embodiments, the ionizable lipid of Formula (1) is represented by Formula (1-1) or Formula (1-2):
Formula (1-1)
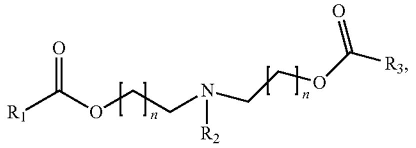
Formula (1-2)
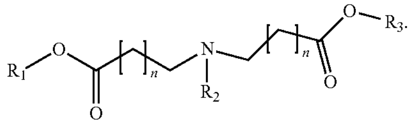
In some embodiments, the ionizable lipid is selected from the group consisting of:
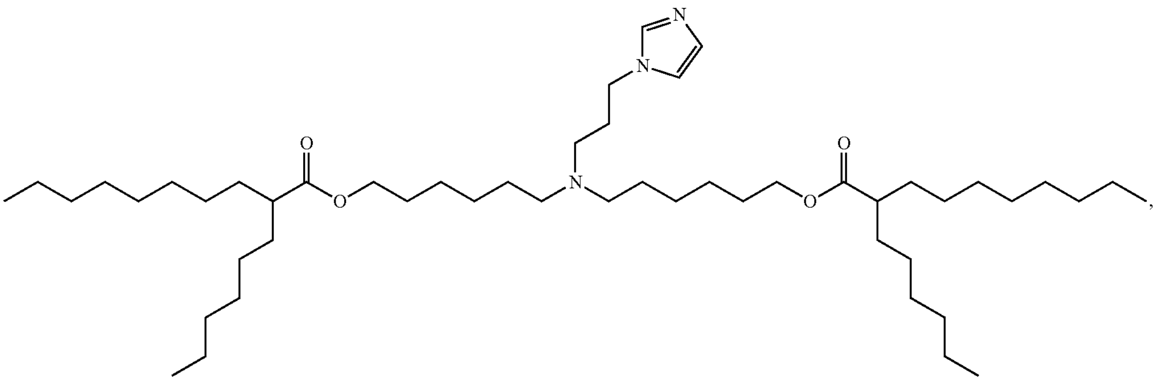
,
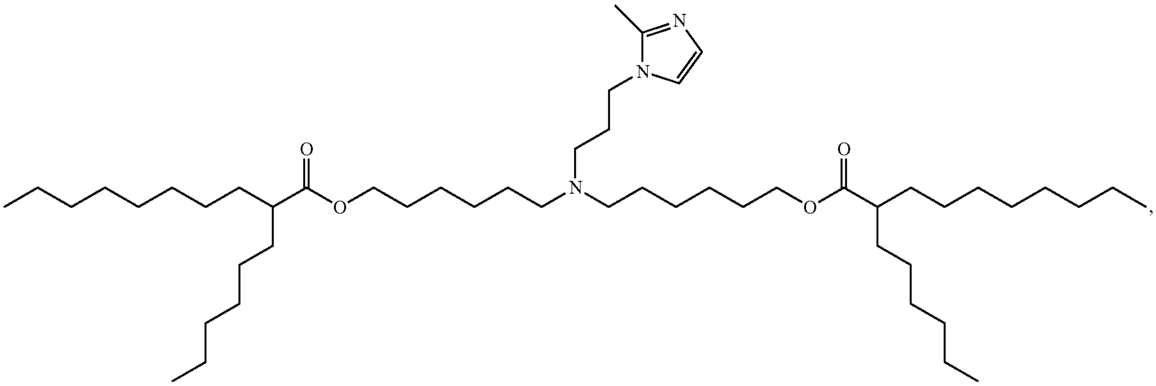
,
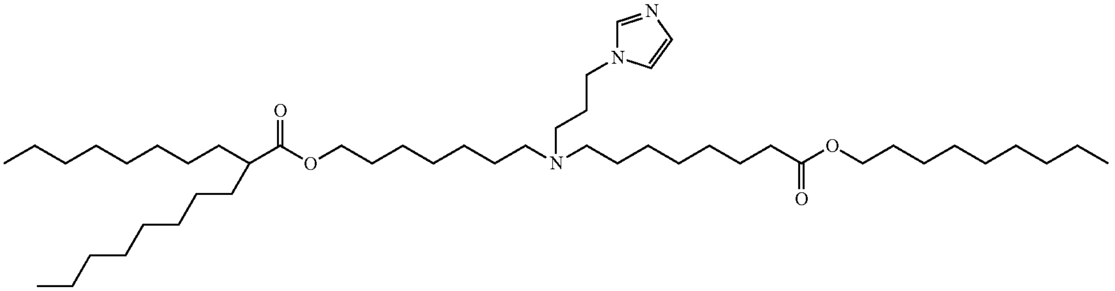
, and -continued
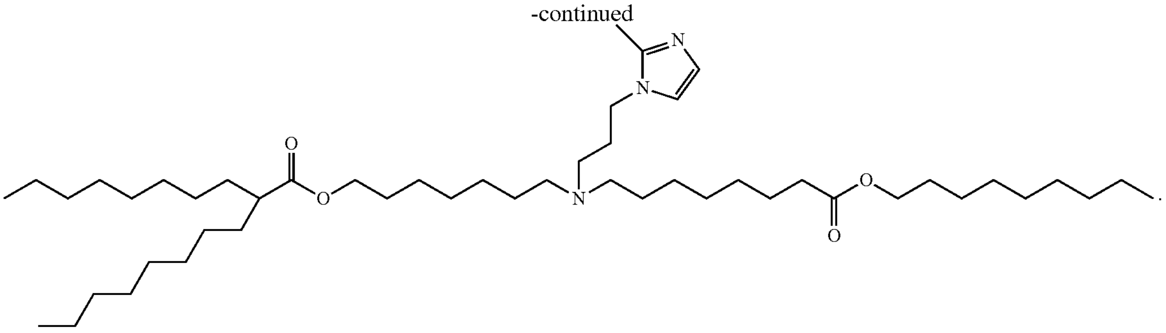
In another aspect, the present application provides a pharmaceutical composition comprising: a circular RNA polynucleotide and a transfer vehicle comprising an ionizable lipid represented by Formula (2):
Formula (2)
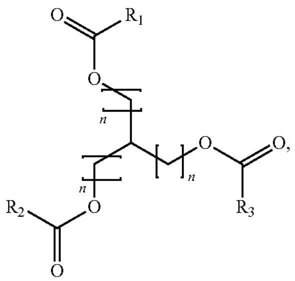
wherein:
each n is independently an integer from 1-15;
$R_1$ and $R_2$ are each independently selected from a group consisting of:
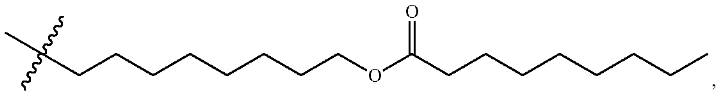
,
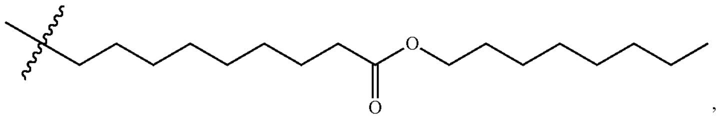
,
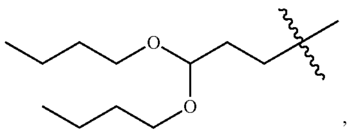
,
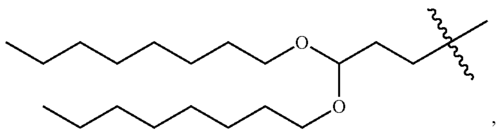
,
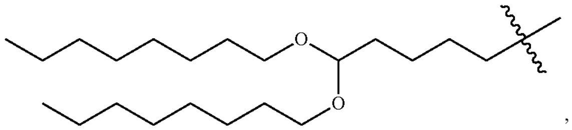
,
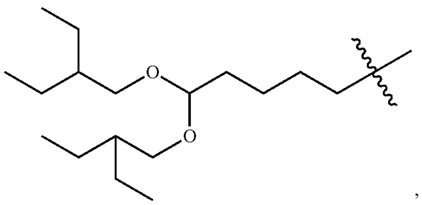
, -continued
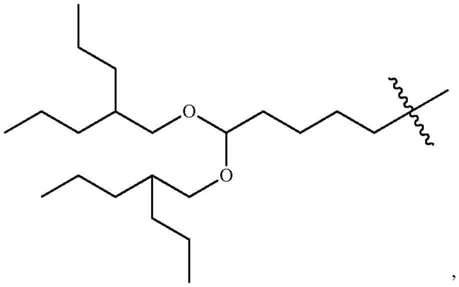
,
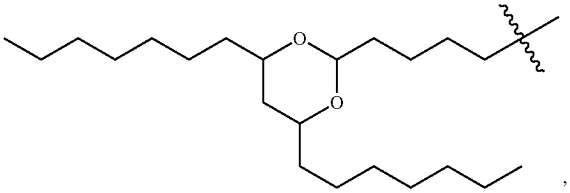
,
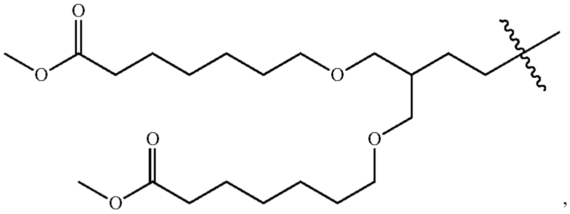
,
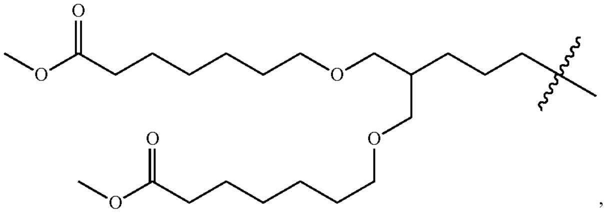
,
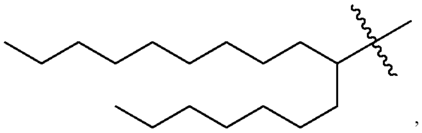
,
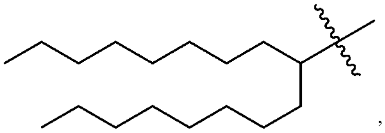
,
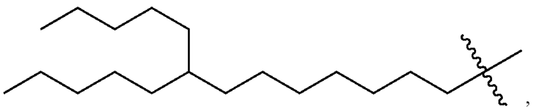
,
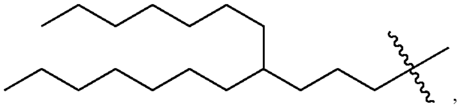
,
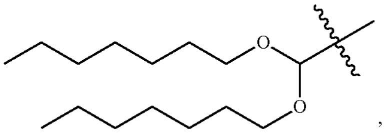
,
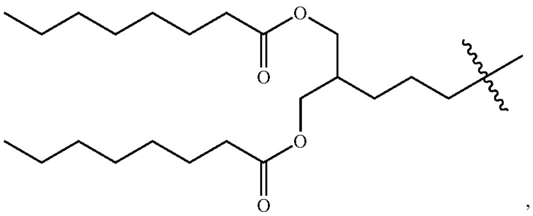
,
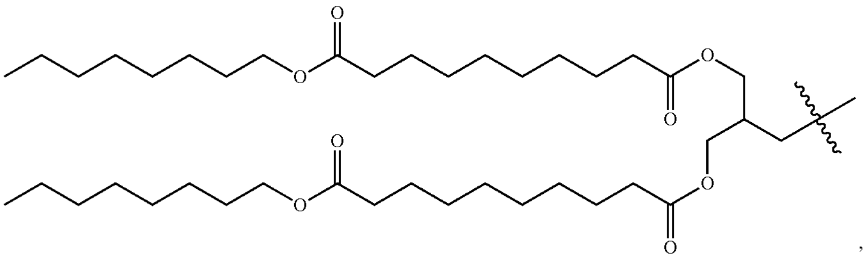
,
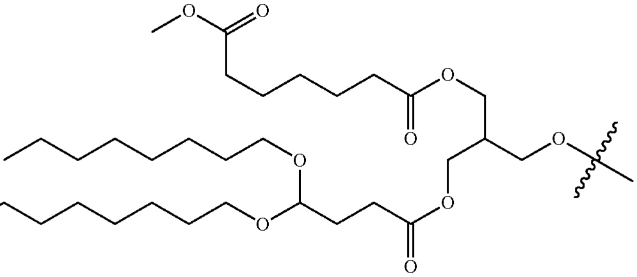
,
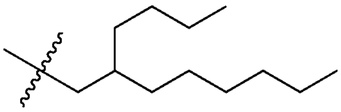
, -continued
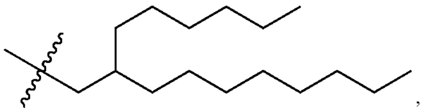,
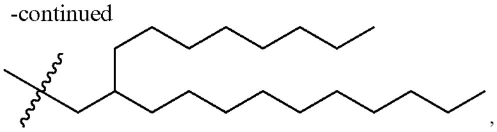,
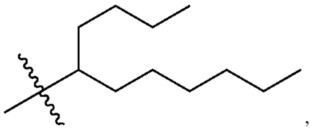,
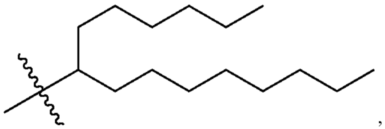,
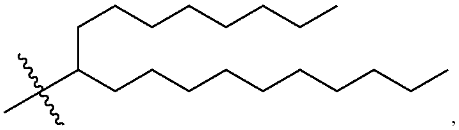,
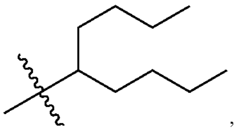,
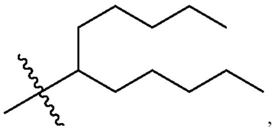,
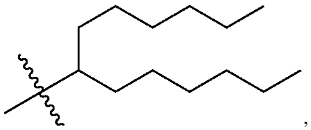,
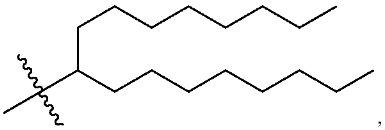,
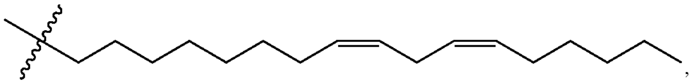,
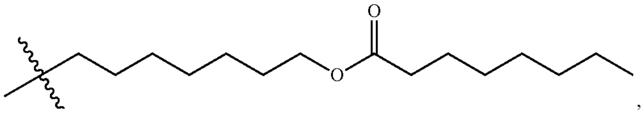, and
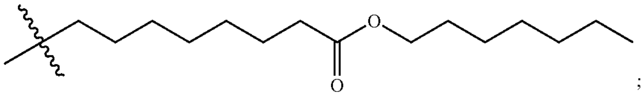;
and
$R_1$ is selected from a group consisting of:
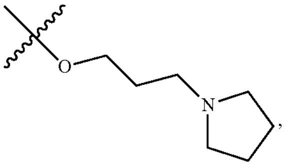
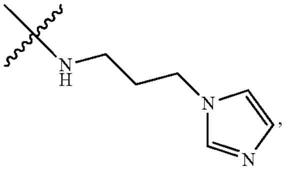
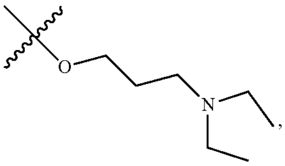
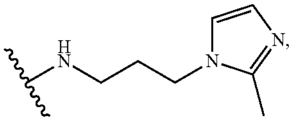
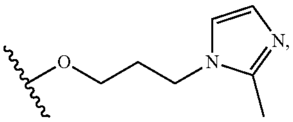
-continued
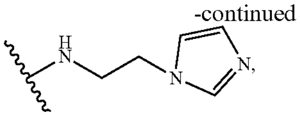
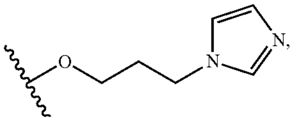
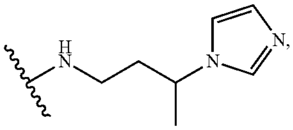
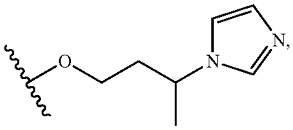
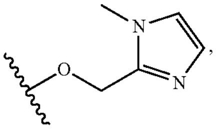
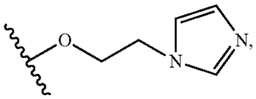 and
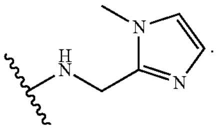
In another aspect, the present application provides a pharmaceutical composition comprising: a circular RNA polynucleotide, and a transfer vehicle comprising an ionizable lipid represented by Formula (3):

Formula (3)
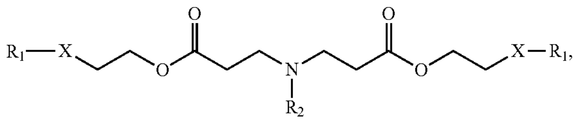
wherein:
X is selected from —O—, —S—, or —OC(O)—*, wherein * indicates the attachment point to $R_1$;
$R_1$ is selected from a group consisting of:
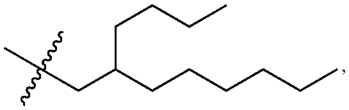,
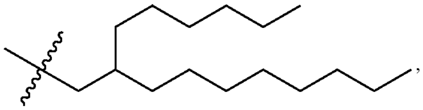,
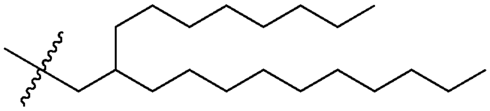,
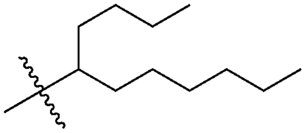,
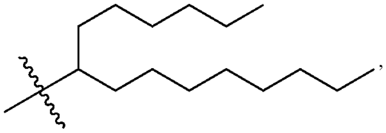,
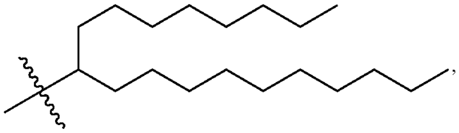,
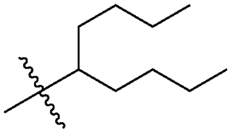,
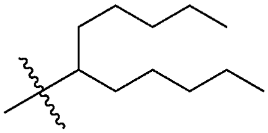,
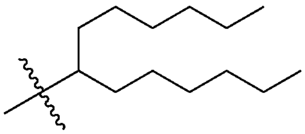, and
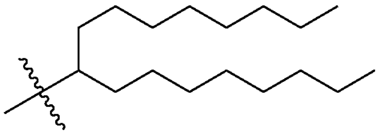;
and
$R_2$ is selected from a group consisting of:
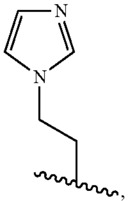, 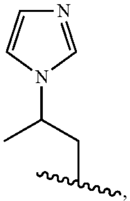, 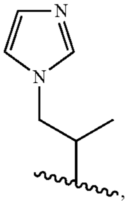,
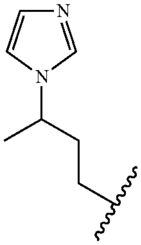, 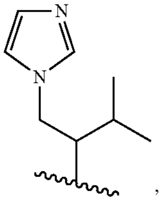, 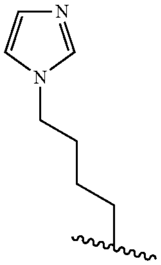,
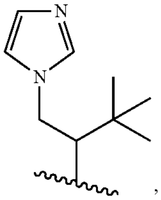, 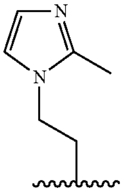,
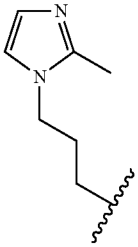, 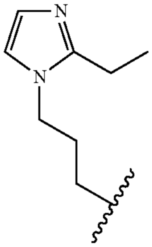, 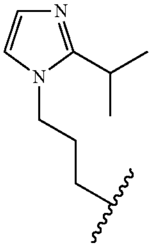,
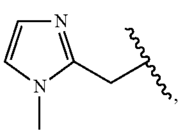, 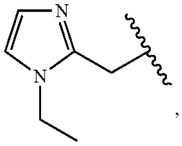,
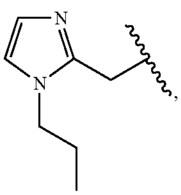, 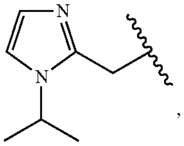,
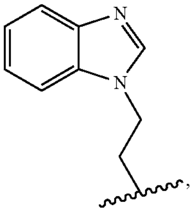, 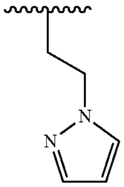,
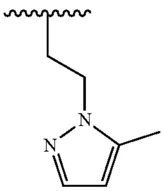, 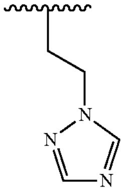, and -continued

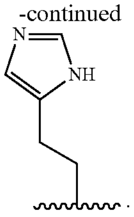

In some embodiments, the ionizable lipid of Formula (3) is represented by Formula (3-1), Formula (3-2), or Formula (3-3):

Formula (3-1)

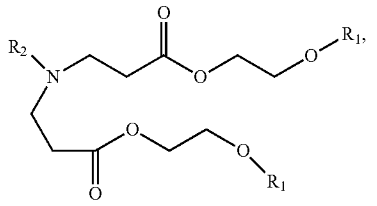

Formula (3-2)

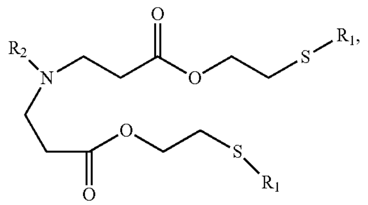

Formula (3-3)

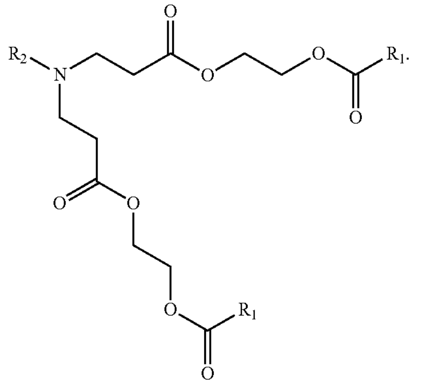

In another aspect, the present application provides a pharmaceutical composition comprising: a circular RNA polynucleotide, and a transfer vehicle comprising an ionizable lipid represented by Formula (4):

Formula (4)

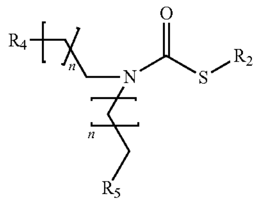

wherein: each n is independently an integer from 2-15; and $R_2$ is defined in Formula (1).

In another aspect, the present application provides a pharmaceutical composition comprising: a circular RNA polynucleotide, and a transfer vehicle comprising an ionizable lipid selected from Table 10a.

In some embodiments, the circular RNA comprises a first expression sequence. In some embodiments, the first expression sequence encodes a therapeutic protein. In some embodiments, the first expression sequence encodes a cytokine or a functional fragment thereof. In some embodiments, the first expression sequence encodes a transcription factor. In some embodiments, the first expression sequence encodes an immune checkpoint inhibitor. In some embodiments, the first expression sequence encodes a chimeric antigen receptor.

In some embodiments, the circular RNA polynucleotide further comprises a second expression sequence. In some embodiments, the circular RNA polynucleotide further comprises an internal ribosome entry site (IRES).

In some embodiments, the first and second expression sequences are separated by a ribosomal skipping element or a nucleotide sequence encoding a protease cleavage site. In some embodiments, the first expression sequence encodes a first T-cell receptor (TCR) chain and the second expression sequence encodes a second TCR chain.

In some embodiments, the circular RNA polynucleotide comprises one or more microRNA binding sites. the microRNA binding site is recognized by a microRNA expressed in the liver. In some embodiments, the microRNA binding site is recognized by miR-122.

In some embodiments, the circular RNA polynucleotide comprises a first IRES associated with greater protein expression in a human immune cell than in a reference human cell. In some embodiments, the human immune cell is a T cell, an NK cell, an NKT cell, a macrophage, or a neutrophil. In some embodiments, the reference human cell is a hepatic cell.

In some embodiments, the circular RNA polynucleotide comprises, in the following order: a) a post-splicing intron fragment of a 3' group I intron fragment, b) an IRES, c) an expression sequence, and d) a post-splicing intron fragment of a 5' group I intron fragment. In some embodiments, the circular RNA polynucleotide comprises. In some embodiments, the circular RNA polynucleotide comprises a first spacer before the post-splicing intron fragment of the 3' group I intron fragment, and a second spacer after the post-splicing intron fragment of the 5' group I intron fragment. In some embodiments, the first and second spacers each have a length of about 10 to about 60 nucleotides.

In some embodiments, the circular RNA polynucleotide is made via circularization of a RNA polynucleotide comprising, in the following order: a 3' group I intron fragment, an IRES, an expression sequence, and a 5' group I intron fragment.

In some embodiments, the circular RNA polynucleotide is made via circularization of a RNA polynucleotide comprising, in the following order: a 5' external duplex forming region, a 3' group I intron fragment, a 5' internal spacer optionally comprising a 5' internal duplex forming region, an IRES, an expression sequence, a 3' internal spacer optionally comprising a 3' internal duplex forming region, a 5' group I intron fragment, and a 3' external duplex forming region.

In some embodiments, the circular RNA polynucleotide is made via circularization of a RNA polynucleotide comprising, in the following order: a 5' external duplex forming region, a 5' external spacer, a 3' group I intron fragment, a 5' internal spacer optionally comprising a 5' internal duplex forming region, an IRES, an expression sequence, a 3' internal spacer optionally comprising a 3' internal duplex forming region, a 5' group I intron fragment, a 3' external spacer, and a 3' external duplex forming region.

In some embodiments, the circular RNA polynucleotide is made via circularization of a RNA polynucleotide comprising, in the following order: a 3' group I intron fragment, a 5' internal spacer comprising a 5' internal duplex forming region, an IRES, an expression sequence, a 3' internal spacer comprising a 3' internal duplex forming region, and a 5' group I intron fragment.

In some embodiments, the circular RNA polynucleotide is made via circularization of a RNA polynucleotide comprising, in the following order: a 5' external duplex forming region, a 5' external spacer, a 3' group I intron fragment, a 5' internal spacer comprising a 5' internal duplex forming region, an IRES, an expression sequence, a 3' internal spacer comprising a 3' internal duplex forming region, a 5' group I intron fragment, a 3' external spacer, and a 3' external duplex forming region.

In some embodiments, the circular RNA polynucleotide is made via circularization of a RNA polynucleotide comprising, in the following order: a first polyA sequence, a 5' external duplex forming region, a 5' external spacer, a 3' group I intron fragment, a 5' internal spacer comprising a 5' internal duplex forming region, an IRES, an expression sequence, a 3' internal spacer comprising a 3' internal duplex forming region, a 5' group I intron fragment, a 3' external spacer, a 3' external duplex forming region, and a second polyA sequence.

In some embodiments, the circular RNA polynucleotide is made via circularization of a RNA polynucleotide comprising, in the following order: a first polyA sequence, a 5' external spacer, a 3' group I intron fragment, a 5' internal spacer comprising a 5' internal duplex forming region, an IRES, an expression sequence, a 3' internal spacer comprising a 3' internal duplex forming region, a 5' group I intron fragment, a 3' external spacer, and a second polyA sequence.

In some embodiments, the circular RNA polynucleotide is made via circularization of a RNA polynucleotide comprising, in the following order: a first polyA sequence, a 5' external spacer, a 3' group I intron fragment, a 5' internal spacer comprising a 5' internal duplex forming region, an IRES, an expression sequence, a stop condon, a 3' internal spacer comprising a 3' internal duplex forming region, a 5' group I intron fragment, a 3' external spacer, and a second polyA sequence.

In some embodiments, at least one of the 3' or 5' internal or external spacers has a length of about 8 to about 60 nucleotides. In some embodiments, the 3' and 5' external duplex forming regions each has a length of about 10-50 nucleotides. In some embodiments, the 3' and 5' internal duplex forming regions each has a length of about 6-30 nucleotides.

In some embodiments, the IRES is selected from Table 17, or is a functional fragment or variant thereof. In some embodiments, the IRES has a sequence of an IRES from *Taura* syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia* stall intestine virus, Kashmir bee virus, Human rhinovirus 2, *Homalodisca coagulata* virus-1, Human Immunodeficiency Virus type 1, *Homalodisca coagulata* virus-1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, *Apodemus Agrarius* Picornavirus, Caprine Kobuvirus, Parabovirus, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24, or an aptamer to eIF4G.

In some embodiments, the first and second polyA sequences each have a length of about 15-50 nt. In some embodiments, the first and second polyA sequences each have a length of about 20-25 nt.

In some embodiments, the circular RNA polynucleotide contains at least about 80%, at least about 90%, at least about 95%, or at least about 99% naturally occurring nucleotides. In some embodiments, the circular RNA polynucleotide consists of naturally occurring nucleotides.

In some embodiments, the expression sequence is codon optimized. In some embodiments, the circular RNA polynucleotide is optimized to lack at least one microRNA binding site present in an equivalent pre-optimized polynucleotide. In some embodiments, the circular RNA polynucleotide is optimized to lack at least one microRNA binding site capable of binding to a microRNA present in a cell within which the circular RNA polynucleotide is expressed. In some embodiments, the circular RNA polynucleotide is optimized to lack at least one endonuclease susceptible site present in an equivalent pre-optimized polynucleotide. In some embodiments, the circular RNA polynucleotide is optimized to lack at least one endonuclease susceptible site capable of being cleaved by an endonuclease present in a cell within which the endonuclease is expressed. In some embodiments, the circular RNA polynucleotide is optimized to lack at least one RNA editing susceptible site present in an equivalent pre-optimized polynucleotide.

In some embodiments, the circular RNA polynucleotide is from about 100 nt to about 10,000 nt in length. In some embodiments, the circular RNA polynucleotide is from about 100 nt to about 15,000 nt in length. In some embodiments, the circular RNA is more compact than a reference linear RNA polynucleotide having the same expression sequence as the circular RNA polynucleotide.

In some embodiments, the pharmaceutical composition has a duration of therapeutic effect in a human cell greater than or equal to that of a composition comprising a reference linear RNA polynucleotide having the same expression sequence as the circular RNA polynucleotide. In some embodiments, the reference linear RNA polynucleotide is a linear, unmodified or nucleoside-modified, fully-processed mRNA comprising a cap1 structure and a polyA tail at least 80 nt in length.

In some embodiments, the pharmaceutical composition has a duration of therapeutic effect in vivo in humans greater than that of a composition comprising a reference linear RNA polynucleotide having the same expression sequence as the circular RNA polynucleotide. In some embodiments, the pharmaceutical composition has an duration of therapeutic effect in vivo in humans of at least about 10, at least about 20, at least about 30, at least about 40, at least about 50, at least about 60, at least about 70, at least about 80, at least about 90, or at least about 100 hours.

In some embodiments, the pharmaceutical composition has a functional half-life in a human cell greater than or equal to that of a pre-determined threshold value. In some embodiments, the pharmaceutical composition has a functional half-life in vivo in humans greater than that of a pre-determined threshold value. In some embodiments, the functional half-life is determined by a functional protein assay. In some embodiments, the functional protein assay is an in vitro luciferase assay. In some embodiments, the functional protein assay comprises measuring levels of protein encoded by the expression sequence of the circular RNA polynucleotide in a patient serum or tissue sample. In some embodiments, wherein the pre-determined threshold value is the functional half-life of a reference linear RNA polynucleotide comprising the same expression sequence as the circular RNA polynucleotide. In some embodiments, the pharmaceutical composition has a functional half-life of at least about 20 hours.

In some embodiments, the pharmaceutic composition comprises a structural lipid and a PEG-modified lipid. In some embodiments, the structural lipid binds to C1q and/or promotes the binding of the transfer vehicle comprising said lipid to C1q compared to a control transfer vehicle lacking the structural lipid and/or increases uptake of C1q-bound transfer vehicle into an immune cell compared to a control transfer vehicle lacking the structural lipid. In some embodiments, the immune cell is a T cell, an NK cell, an NKT cell, a macrophage, or a neutrophil.

In some embodiments, the structural lipid is cholesterol. In some embodiments, the structural lipid is beta-sitosterol. In some embodiments, the structural lipid is not beta-sitosterol.

In some embodiments, the PEG-modified lipid is DSPE-PEG, DMG-PEG, or PEG-1. In some embodiments, the PEG-modified lipid is DSPE-PEG(2000).

In some embodiments, the pharmaceutic composition further comprises a helper lipid. In some embodiments, the helper lipid is DSPC or DOPE.

In some embodiments, the pharmaceutic composition comprises DOPE, cholesterol, and DSPE-PEG.

In some embodiments, the transfer vehicle comprises about 0.5% to about 4% PEG-modified lipids by molar ratio. In some embodiments, the transfer vehicle comprises about 1% to about 2% PEG-modified lipids by molar ratio.

In some embodiments, the transfer vehicle comprises a. an ionizable lipid is represented by

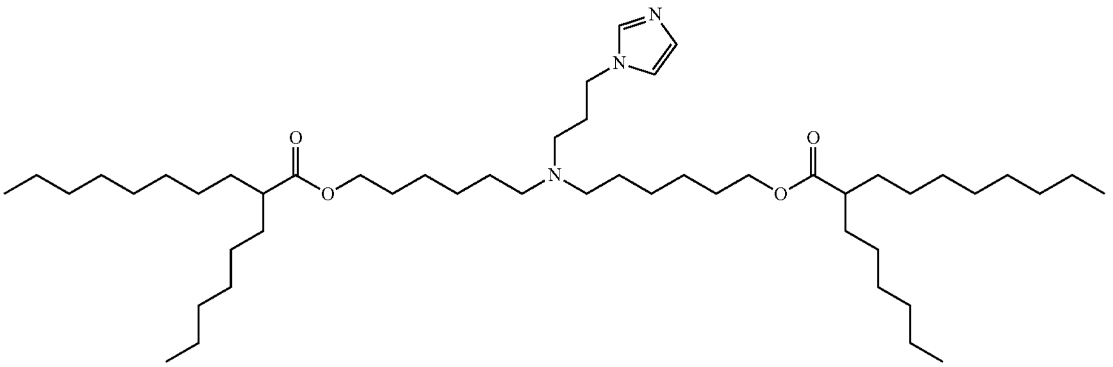

or

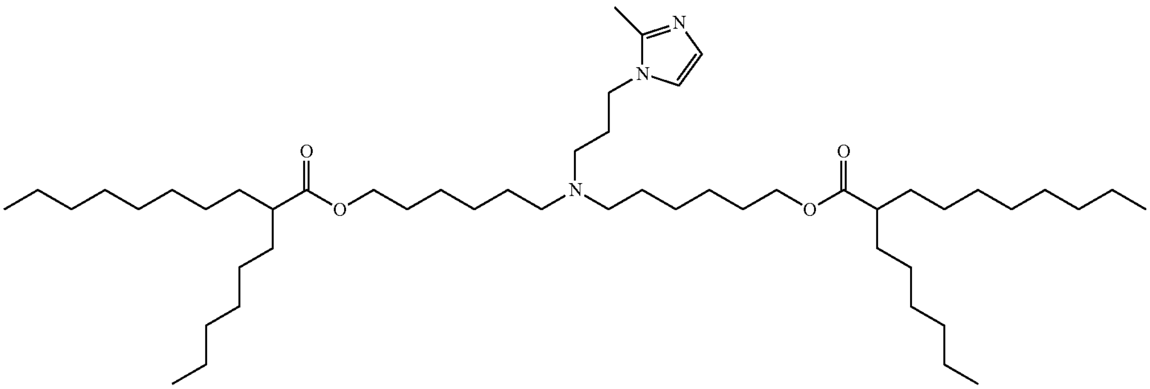

b. DOPE,
c. cholesterol, and
d. DSPE-PEG(2000).

In some embodiments, the molar ration of ionizable lipid:DSPC:cholesterol:DSPE-PEG(2000) is 62:4:33:1.

In some embodiments, the transfer vehicle comprises
a. an ionizable lipid is represented by

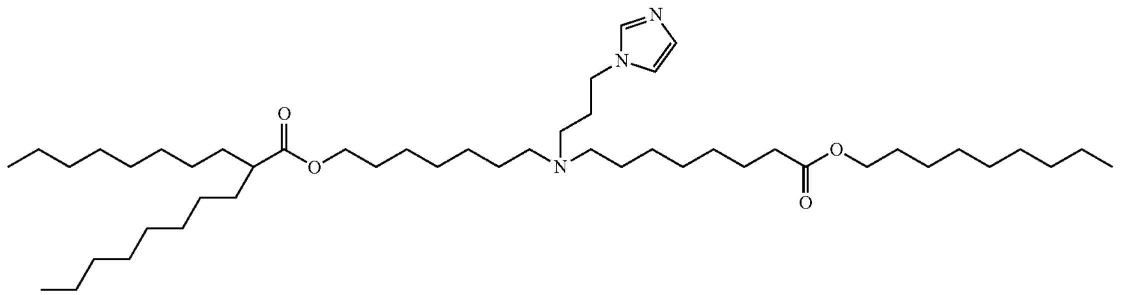

or

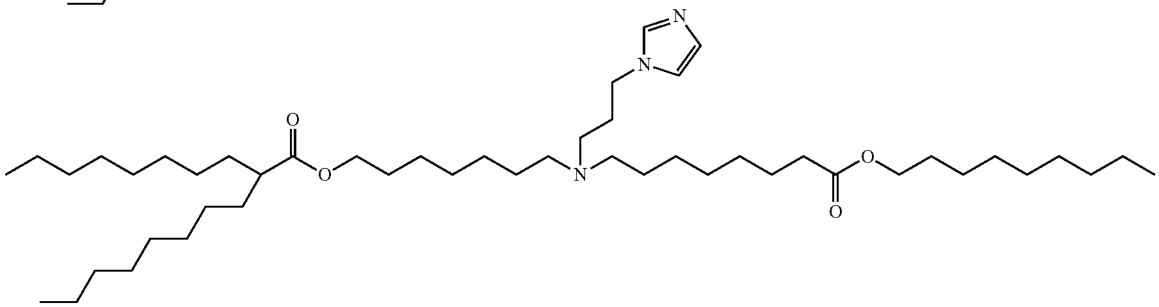

.

b. DOPE,
c. cholesterol, and
d. DSPE-PEG(2000).

In some embodiments, the molar ration of ionizable lipid:DSPC:cholesterol:DSPE-PEG(2000) is 50:10:38.5:1.5.

In some embodiments, the transfer vehicle has a nitrogen: phosphate (N:P) ratio of about 3 to about 6.

In some embodiments, the transfer vehicle is formulated for endosomal release of the circular RNA polynucleotide.

In some embodiments, the transfer vehicle is capable of binding to APOE. In some embodiments, the transfer vehicle interacts with apolipoprotein E (APOE) less than an equivalent transfer vehicle loaded with a reference linear RNA having the same expression sequence as the circular RNA polynucleotide. In some embodiments, the exterior surface of the transfer vehicle is substantially free of APOE binding sites.

In some embodiments, the transfer vehicle has a diameter of less than about 120 nm. In some embodiments, the transfer vehicle does not form aggregates with a diameter of more than 300 nm.

In some embodiments, the transfer vehicle has an in vivo half-life of less than about 30 hours.

In some embodiments, the transfer vehicle is capable of low density lipoprotein receptor (LDLR) dependent uptake into a cell. In some embodiments, the transfer vehicle is capable of LDLR independent uptake into a cell.

In some embodiments, the pharmaceutical composition is substantially free of linear RNA.

In some embodiments, the pharmaceutical composition further comprises a targeting moiety operably connected to the transfer vehicle. In some embodiments, the targeting moiety specifically binds an immune cell antigen or indirectly. In some embodiments, the immune cell antigen is a T cell antigen. In some embodiments, the T cell antigen is selected from the group consisting of CD2, CD3, CD5, CD7, CD8, CD4, beta7 integrin, beta2 integrin, and C1q.

In some embodiments, the pharmaceutical composition further comprises an adapter molecule comprising a transfer vehicle binding moiety and a cell binding moiety, wherein the targeting moiety specifically binds the transfer vehicle binding moiety and the cell binding moiety specifically binds a target cell antigen. In some embodiments, the target cell antigen is an immune cell antigen. In some embodiments, the immune cell antigen is a T cell antigen, an NK cell, an NKT cell, a macrophage, or a neutrophil. In some embodiments, the T cell antigen is selected from the group consisting of CD2, CD3, CD5, CD7, CD8, CD4, beta7 integrin, beta2 integrin, CD25, CD39, CD73, A2a Receptor, A2b Receptor, and C1q. In some embodiments, the immune cell antigen is a macrophage antigen. In some embodiments, the macrophage antigen is selected from the group consisting of mannose receptor, CD206, and C1q.

In some embodiments, the targeting moiety is a small molecule. In some embodiments, the small molecule binds to an ectoenzyme on an immune cell, wherein the ectoenzyme is selected from the group consisting of CD38, CD73, adenosine 2a receptor, and adenosine 2b receptor. In some embodiments, the small molecule is mannose, a lectin, acivicin, biotin, or digoxigenin.

In some embodiments, the targeting moiety is a single chain Fv (scFv) fragment, nanobody, peptide, peptide-based macrocycle, minibody, small molecule ligand such as folate, arginylglycylaspartic acid (RGD), or phenol-soluble modulin alpha 1 peptide (PSMA1), heavy chain variable region, light chain variable region or fragment thereof.

In some embodiments, the ionizable lipid has a half-life in a cell membrane less than about 2 weeks. In some embodiments, the ionizable lipid has a half-life in a cell membrane less than about 1 week. In some embodiments, the ionizable lipid has a half-life in a cell membrane less than about 30 hours. In some embodiments, the ionizable lipid has a half-life in a cell membrane less than the functional half-life of the circular RNA polynucleotide.

In another aspect, the present application provides a method of treating or preventing a disease, disorder, or condition, comprising administering an effective amount of a pharmaceutical composition disclosed herein. In some embodiments, the disease, disorder, or condition is associated with aberrant expression, activity, or localization of a polypeptide selected from Tables 27 or 28. In some embodiments, the circular RNA polynucleotide encodes a therapeutic protein. In some embodiments, therapeutic protein expression in the spleen is higher than therapeutic protein expression in the liver. In some embodiments, therapeutic protein expression in the spleen is at least about 2.9× therapeutic protein expression in the liver. In some embodiments, the therapeutic protein is not expressed at functional levels in the liver. In some embodiments, the therapeutic protein is not expressed at detectable levels in the liver. In some embodiments, therapeutic protein expression in the spleen is at least about 63% of total therapeutic protein expression.

In another aspect, the present application provides a linear RNA polynucleotide comprising, from 5' to 3', a 3' group I intron fragment, an Internal Ribosome Entry Site (IRES), an expression sequence, and a 5' group I intron fragment, further comprising a first spacer 5' to the 3' group I intron fragment and/or a second spacer 3' to the 5' group I intron fragment.

In some embodiments, the linear RNA polynucleotide comprises a first spacer 5' to the 3' group I intron fragment. In some embodiments, the first spacer has a length of 10-50 nucleotides, optionally 10-20 nucleotides, further optionally about 15 nucleotides. In some embodiments, the first spacer comprises a polyA sequence.

In some embodiments, the linear RNA polynucleotide comprises a second spacer 3' to the 5' group I intron fragment. In some embodiments, the second spacer has a length of 10-50 nucleotides, optionally 10-20 nucleotides, further optionally about 15 nucleotides. In some embodiments, the second spacer comprises a polyA sequence.

In some embodiments, the linear RNA polynucleotide further comprises a third spacer between the 3' group I intron fragment and IRES. In some embodiments, the third spacer has a length of about 10 to about 60 nucleotides. In some embodiments, the linear RNA polynucleotide further comprises a first and a second duplex forming regions capable of forming a duplex. In some embodiments, the first and second duplex forming regions each have a length of about 9 to 19 nucleotides. In some embodiments, the first and second duplex forming regions each have a length of about 30 nucleotides.

In some embodiments, the linear RNA polynucleotide has enhanced expression, circularization efficiency, functional stability, and/or stability as compared to a reference linear RNA polynucleotide, wherein the reference linear RNA polynucleotide comprises, from 5' to 3', a first polyA sequence, a 5' external spacer, a 3' group I intron fragment, a 5' internal spacer comprising a 5' internal duplex forming region, an IRES, an expression sequence, a stop condon, a 3' internal spacer comprising a 3' internal duplex forming region, a 5' group I intron fragment, a 3' external spacer, and a second polyA sequence.

In some embodiments, the linear RNA polynucleotide has enhanced expression, circularization efficiency, functional stability, and/or stability as compared to a reference linear RNA polynucleotide, wherein the reference linear RNA polynucleotide comprises, from 5' to 3', a reference 3' group I intron fragment, a reference IRES, a reference expression sequence, and a reference 5' group I intron fragment, and does not comprise a spacer 5' to the 3' group I intron fragment or a spacer 3' to the 5' group I intron fragment. In some embodiments, the expression sequence and the reference expression sequence have the same sequence. In some embodiments, the IRES and the reference IRES have the same sequence.

In some embodiments, the linear RNA polynucleotide comprises a 3′ *Anabaena* group I intron fragment and a 5′ *Anabaena* group I intron fragment. In some embodiments, the reference RNA polynucleotide comprises a reference 3′ *Anabaena* group I intron fragment and a reference 5′ *Anabaena* group I intron fragment. In some embodiments, the reference 3′ *Anabaena* group I intron fragment and reference 5′ *Anabaena* group I intron fragment were generated using the L6-5 permutation site. In some embodiments, the 3′ *Anabaena* group I intron fragment and 5′ *Anabaena* group I intron fragment were not generated using the L6-5 permutation site. In some embodiments, the 3′ *Anabaena* group I intron fragment comprises or consists of a sequence selected from SEQ ID NO: 112-123 and 125-150. In some embodiments, the 5′ *Anabaena* group I intron fragment comprises a corresponding sequence selected from SEQ ID NO: 73-84 and 86-111. In some embodiments, the 5′ *Anabaena* group I intron fragment comprises or consists of a sequence selected from SEQ ID NO: 73-84 and 86-111. In some embodiments, the 3′ *Anabaena* group I intron fragment comprises or consists of a corresponding sequence selected from SEQ ID NO: 112-124 and 125-150.

In some embodiments, the IRES comprises a nucleotide sequence selected from SEQ ID NOs: 348-351. In some embodiments, the reference IRES is CVB3. In some embodiments, the IRES is not CVB3. In some embodiments, the IRES comprises a sequence selected from SEQ ID NOs: 1-64 and 66-72.

In another aspect, the present application discloses a circular RNA polynucleotide produced from the linear RNA disclosed herein.

In another aspect, the present application discloses a circular RNA comprising, from 5' to 3', a 3' group I intron fragment, an IRES, an expression sequence, and a 5' group I intron fragment, wherein the IRES comprises a nucleotide sequence selected from SEQ ID NOs: 348-351.

In some embodiments, the circular RNA polynucleotide further comprises a spacer between the 3' group I intron fragment and the IRES.

In some embodiments, the circular RNA polynucleotide further comprises a first and a second duplex forming regions capable of forming a duplex. In some embodiments, the first and second duplex forming regions each have a length of about 9 to 19 nucleotides. In some embodiments, the first and second duplex forming regions each have a length of about 30 nucleotides.

In some embodiments, the expression sequence has a size of at least about 1,000 nt, at least about 2,000 nt, at least about 3,000 nt, at least about 4,000 nt, or at least about 5,000 nt.

In some embodiments, the RNA polynucleotide comprises natural nucleotides. In some embodiments, the expression sequence is codon optimized. In some embodiments, the RNA polynucleotide further comprises a translation termination cassette comprising at least one stop codon in each reading frame. In some embodiments, the translation termination cassette comprises at least two stop codons in the reading frame of the expression sequence. In some embodiments, the RNA polynucleotide is optimized to lack at least one microRNA binding site present in an equivalent pre-optimized polynucleotide. In some embodiments, the RNA polynucleotide is optimized to lack at least one endonuclease susceptible site present in an equivalent pre-optimized polynucleotide. In some embodiments, the RNA polynucleotide is optimized to lack at least one RNA editing susceptible site present in an equivalent pre-optimized polynucleotide.

In some embodiments, the RNA polynucleotide comprises at least 2 expression sequences. In some embodiments, each expression sequence encodes a different therapeutic protein.

In some embodiments, a circular RNA polynucleotide disclosed herein is from about 100 to 15,000 nucleotides, optionally about 100 to 12,000 nucleotides, further optionally about 100 to 10,000 nucleotides in length.

In some embodiments, a circular RNA polynucleotide disclosed herein has an in vivo duration of therapeutic effect in humans of at least about 20 hours. In some embodiments, a circular RNA polynucleotide disclosed herein has a functional half-life of at least about 20 hours. In some embodiments, the circular RNA polynucleotide has a duration of therapeutic effect in a human cell greater than or equal to that of an equivalent linear RNA polynucleotide comprising the same expression sequence. In some embodiments, the circular RNA polynucleotide has a functional half-life in a human cell greater than or equal to that of an equivalent linear RNA polynucleotide comprising the same expression sequence. In some embodiments, the circular RNA polynucleotide has an in vivo duration of therapeutic effect in humans greater than that of an equivalent linear RNA polynucleotide having the same expression sequence. In some embodiments, the circular RNA polynucleotide has an in vivo functional half-life in humans greater than that of an equivalent linear RNA polynucleotide having the same expression sequence.

In another aspect, the present disclosure provides a composition comprising a circular RNA polynucleotide disclosed herein, a nanoparticle, and optionally, a targeting moiety operably connected to the nanoparticle. In some embodiments, the nanoparticle is a lipid nanoparticle, a core-shell nanoparticle, a biodegradable nanoparticle, a biodegradable lipid nanoparticle, a polymer nanoparticle, or a biodegradable polymer nanoparticle. In some embodiments, the pharmaceutical composition comprises a targeting moiety, wherein the targeting moiety mediates receptor-mediated endocytosis or direct fusion selectively into cells of a selected cell population or tissue in the absence of cell isolation or purification. In some embodiments, the targeting moiety is a scfv, nanobody, peptide, minibody, polynucleotide aptamer, heavy chain variable region, light chain variable region or fragment thereof. In some embodiments, wherein less than 1%, by weight, of the polynucleotides in the composition are double stranded RNA, DNA splints, or triphosphorylated RNA. In some embodiments, less than 1%, by weight, of the polynucleotides and proteins in the pharmaceutical composition are double stranded RNA, DNA splints, triphosphorylated RNA, phosphatase proteins, protein ligases, and capping enzymes.

In another aspect, the present disclosure provides a method of treating a subject in need thereof comprising administering a therapeutically effective amount of a composition comprising the circular RNA polynucleotide disclosed herein, a nanoparticle, and optionally, a targeting moiety operably connected to the nanoparticle.

In another aspect, the present disclosure provides a method of treating a subject in need thereof comprising administering a therapeutically effective amount of the pharmaceutical composition disclosed herein. In some embodiments, the targeting moiety is an scfv, nanobody, peptide, minibody, heavy chain variable region, light chain variable region, an extracellular domain of a TCR, or a fragment thereof. In some embodiments, the nanoparticle is a lipid nanoparticle, a core-shell nanoparticle, or a biodegradable nanoparticle. In some embodiments, the nanoparticle comprises one or more cationic lipids, ionizable lipids, or poly β-amino esters. In some embodiments, the nanoparticle comprises one or more non-cationic lipids. In some embodiments, the nanoparticle comprises one or more PEG-modified lipids, polyglutamic acid lipids, or Hyaluronic acid lipids. In some embodiments, the nanoparticle comprises cholesterol. In some embodiments, the nanoparticle comprises arachidonic acid or oleic acid.

In some embodiments, a provided pharmaceutical composition comprises a targeting moiety, wherein the targeting moiety mediates receptor-mediated endocytosis selectively into cells of a selected cell population in the absence of cell selection or purification.

In some embodiments, a provided nanoparticle comprises more than one circular RNA polynucleotide.

In another aspect, the present application provides a DNA vector encoding the RNA polynucleotide disclosed herein. In some embodiments, the DNA vector further comprises a transcription regulatory sequence. In some embodiments, the transcription regulatory sequence comprises a promoter and/or an enhancer. In some embodiments, the promoter comprises a T7 promoter. In some embodiments, the DNA vector comprises a circular DNA. In some embodiments, the DNA vector comprises a linear DNA.

In another aspect, the present application provides a prokaryotic cell comprising the DNA vector disclosed herein.

In another aspect, the present application provides a eukaryotic cell comprising the circular RNA polynucleotide disclosed herein. In some embodiments, the eukaryotic cell is a human cell.

In another aspect, the present application provides a method of producing a circular RNA polynucleotide, the method comprising incubating the linear RNA polynucleotide disclosed herein under suitable conditions for circularization. In some embodiments, the method comprises incubating the DNA disclosed herein under suitable conditions for transcription. In some embodiments, the DNA is transcribed in vitro. In some embodiments, the suitable conditions comprises adenosine triphosphate (ATP), guanine triphosphate (GTP), cytosine triphosphate (CTP), uridine triphosphate (UTP), and an RNA polymerase. In some embodiments, the suitable conditions further comprises guanine monophosphate (GMP). In some embodiments, the ratio of GMP concentration to GTP concentration is within the range of about 3:1 to about 15:1, optionally about 4:1, 5:1, or 6:1.

In another aspect, the present application provides a method of producing a circular RNA polynucleotide, the method comprising culturing the prokaryotic cell disclosed herein under suitable conditions for transcribing the DNA in the cell. In some embodiments, the method further comprising purifying a circular RNA polynucleotide. In some embodiments, the circular RNA polynucleotide is purified by negative selection using an affinity oligonucleotide that hybridizes with the first or second spacer conjugated to a solid surface. In some embodiments, the first or second spacer comprises a polyA sequence, and wherein the affinity oligonucleotide is a deoxythymine oligonucleotide.

BRIEF DESCRIPTION OF THE DRAWINGS

FIG. 27 depicts molecular characterization of Lipids 26 and 27 from Table 10a.

FIG. 28 depicts molecular characterization of Lipid 22-S14 and its synthetic intermediates.

FIG. 30 depicts molecular characterization of heptadecan-9-yl 8-((3-(2-methyl-1H-imidazol-1-yl)propyl)(8-(nonyloxy)-8-oxooctyl)amino)octanoate (Lipid 54 from Table 10a).

FIG. 31 depicts molecular characterization of heptadecan-9-yl 8-((3-(1H-imidazol-1-yl)propyl)(8-(nonyloxy)-8-oxooctyl)amino)octanoate (Lipid 53 from Table 10a).

DETAILED DESCRIPTION

Figure 1A:
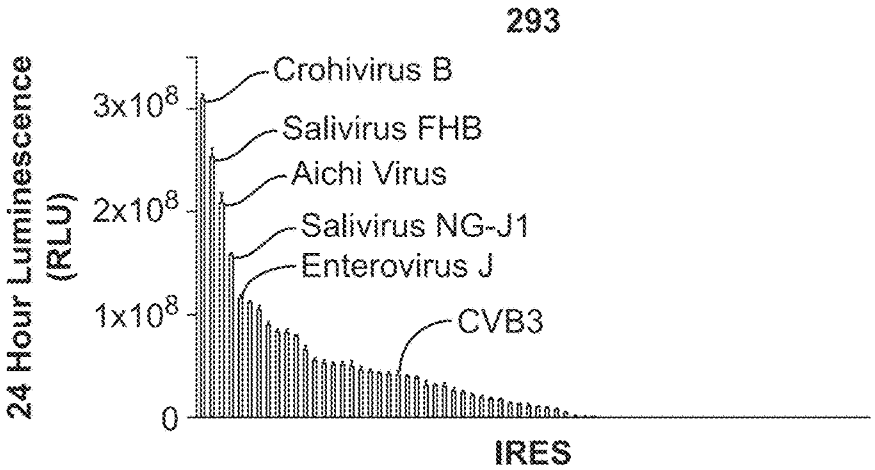
FIG. 1 depicts luminescence in supernatants of HEK293 (FIGS. 1A, 1D, and 1E), HepG2 (FIG. 1B), or 1C1C7 (FIG. 1C) cells 24 hours after transfection with circular RNA comprising a *Gaussia* luciferase expression sequence and various IRES sequences.

Provided herein are pharmaceutical compositions and transfer vehicles, e.g., lipid nanoparticles, comprising circular RNA. The circular RNA provided herein may be delivered and/or targeted to a cell in a transfer vehicle, e.g., a nanoparticle, or a composition comprising a transfer vehicle. In some embodiments, the circular RNA may also be delivered to a subject in a transfer vehicle or a composition comprising a transfer vehicle. In some embodiments, the transfer vehicle is a nanoparticle. In some embodiments, the nanoparticle is a lipid nanoparticle, a polymeric core-shell nanoparticle, or a biodegradable nanoparticle. In some embodiments, the nanoparticle is a lipid nanoparticle. In some embodiments, the transfer vehicle comprises one or more ionizable lipids, PEG modified lipids, helper lipids, and/or structural lipids.

In some embodiments, a transfer vehicle encapsulates circular RNA and comprises an ionizable lipid, a structural lipid, and a PEG-modified lipid. In some embodiments, a transfer vehicle encapsulates circular RNA and comprises an ionizable lipid, a structural lipid, a PEG-modified lipid, and a helper lipid.

In some embodiments, the transfer vehicle comprises an ionizable lipid described herein. In some embodiments, the transfer vehicle comprises an ionizable lipid shown in any one of Tables 1-10, 10a, 10b, 11-15, and 15b. In some embodiments, the transfer vehicle comprises an ionizable lipid shown in Table 10a.

In some embodiments, the RNA in a transfer vehicle is at least about 80%, 85%, 90%, 91%, 92%, 93%, 94%, 95%, 96%, 97%, 98%, 99%, 99.5%, 99.9%, or more circular RNA. In some embodiments, less than 5%, 10%, 15%, 20%, 25%, 30%, 35%, 40%, 45%, 50%, 55%, 60%, 65%, or 70% of loaded RNA is on or associated with a transfer vehicle exterior surface.

In some embodiments, the transfer vehicle is capable of binding to APOE. In some embodiments, the surface of the transfer vehicle comprises APOE binding sites. In some embodiments, the surface of the transfer vehicle is substantially free of APOE binding sites. In some embodiments, a transfer vehicle interacts with APOE less than an equivalent transfer vehicle loaded with linear RNA. In some embodiments, APOE interaction may be measured by comparing nanoparticle uptake in cells in APO depleted serum or APO complement serum.

Without wishing to be bound by theory, it is contemplated that transfer vehicles comprising APOE binding sites deliver circular RNAs more efficiently to the liver. Accordingly, in some embodiments, the transfer vehicle comprising the ionizable lipids described herein and loaded with circular RNA substantially comprises APOE binding sites on the transfer vehicle surface, thereby delivering the circular RNA to the liver at a higher efficiency compared to a transfer vehicle substantially lacking APOE binding sites on the surface. In some embodiments, the transfer vehicle comprising the ionizable lipids described herein and loaded with circular RNA substantially lacks APOE binding sites on the transfer vehicle surface, thereby delivering the circular RNA to the liver at a lower efficiency compared to a transfer vehicle comprising APOE binding sites on the surface.

In some embodiments, the transfer vehicle delivers, or is capable of delivering, circular RNA to the spleen. In some embodiments, a circular RNA encodes a therapeutic protein. In some embodiments, at least about 10%, 15%, 20%, 25%, 30%, 35%, 40%, 45%, 50%, 55%, 60%, 65%, 70%, 75%, 80%, 85%, 90%, 95%, or 99% of the total therapeutic protein expressed in the subject is expressed in the spleen. In some embodiments, more therapeutic protein is expressed in the spleen than in the liver (e.g., 2×, 3×, 4×, or 5× more). In some embodiments, the lipid nanoparticle has an ionizable lipid:phosphate ratio of 3-7. In some embodiments, the lipid nanoparticle has an ionizable lipid:phosphate ratio of 4-6. In some embodiments, the lipid nanoparticle has an ionizable lipid:phosphate ratio of 4.5. In some embodiments, the lipid nanoparticle has an nitrogen:phosphate (N:P) ratio of 3-6. In some embodiments, the lipid nanoparticle has an N:P ratio of 5-6. In some embodiments, the lipid nanoparticle has an N:P ratio of 5.7. In some embodiments, expression of a nonsecreted protein may be measured using an ELISA, normalizing to tissue weight.

Without wishing to be bound by theory, it is thought that transfer vehicles described herein shield encapsulated circular RNA from degradation and provide for effective delivery of circular RNA to target cells in vivo and in vitro.

Embodiments of the present disclosure provide lipid compositions described according to the respective molar ratios of the component lipids in the formulation. In one embodiment, the mol-% of the ionizable lipid may be from about 10 mol-% to about 80 mol-%. In one embodiment, the mol-% of the ionizable lipid may be from about 20 mol-% to about 70 mol-%. In one embodiment, the mol-% of the ionizable lipid may be from about 30 mol-% to about 60 mol-%. In one embodiment, the mol-% of the ionizable lipid may be from about 35 mol-% to about 55 mol-%. In one embodiment, the mol-% of the ionizable lipid may be from about 40 mol-% to about 50 mol-%. In some embodiments, the ionizable lipid mol-% of the transfer vehicle batch will be ±30%, ±25%, ±20%, ±15%, ±10%, ±5%, or ±2.5% of the target mol-%. In certain embodiments, transfer vehicle inter-lot variability will be less than 15%, less than 10% or less than 5%.

In one embodiment, the mol-% of the helper lipid may be from about 1 mol-% to about 50 mol-%. In one embodiment, the mol-% of the helper lipid may be from about 2 mol-% to about 45 mol-%. In one embodiment, the mol-% of the helper lipid may be from about 3 mol-% to about 40 mol-%. In one embodiment, the mol-% of the helper lipid may be from about 4 mol-% to about 35 mol-%. In one embodiment, the mol-% of the helper lipid may be from about 5 mol-% to about 30 mol-%. In one embodiment, the mol-% of the helper lipid may be from about 10 mol-% to about 20 mol-%. In some embodiments, the helper lipid mol-% of the transfer vehicle batch will be ±30%, ±25%, ±20%, ±15%, ±10%, ±5%, or ±2.5% of the target mol-%.

In one embodiment, the mol-% of the structural lipid may be from about 10 mol-% to about 80 mol-%. In one embodiment, the mol-% of the structural lipid may be from about 20 mol-% to about 70 mol-%. In one embodiment, the mol-% of the structural lipid may be from about 30 mol-% to about 60 mol-%. In one embodiment, the mol-% of the structural lipid may be from about 35 mol-% to about 55 mol-%. In one embodiment, the mol-% of the structural lipid may be from about 40 mol-% to about 50 mol-%. In some embodiments, the structural lipid mol-% of the transfer vehicle batch will be ±30%, ±25%, ±20%, ±15%, ±10%, ±5%, or ±2.5% of the target mol-%.

In one embodiment, the mol-% of the PEG modified lipid may be from about 0.1 mol-% to about 10 mol-%. In one embodiment, the mol-% of the PEG modified lipid may be from about 0.2 mol-% to about 5 mol-%. In one embodiment, the mol-% of the PEG modified lipid may be from about 0.5 mol-% to about 3 mol-%. In one embodiment, the mol-% of the PEG modified lipid may be from about 1 mol-% to about 2 mol-%. In one embodiment, the mol-% of the PEG modified lipid may be about 1.5 mol-%. In some embodiments, the PEG modified lipid mol-% of the transfer vehicle batch will be ±30%, ±25%, +20%, ±15%, ±10%, ±5%, or ±2.5% of the target mol-%.

Also contemplated are pharmaceutical compositions, and in particular transfer vehicles, that comprise one or more of the compounds disclosed herein. In certain embodiments, such transfer vehicles comprise one or more of PEG-modified lipids, an ionizable lipid, a helper lipid, and/or a structural lipid disclosed herein. Also contemplated are transfer vehicles that comprise one or more of the compounds disclosed herein and that further comprise one or more additional lipids. In certain embodiments, such transfer vehicles are loaded with or otherwise encapsulate circular RNA.

Transfer vehicles of the invention encapsulate circular RNA. In certain embodiments, the polynucleotides encapsulated by the compounds or pharmaceutical and liposomal compositions of the invention include RNA encoding a protein or enzyme (e.g., circRNA encoding, for example, phenylalanine hydroxylase (PAH)). The present invention contemplates the use of such polynucleotides as a therapeutic that is capable of being expressed by target cells to thereby facilitate the production (and in certain instances, the excretion) of a functional enzyme or protein as disclosed bu such target cells, for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells, the production of a functional enzyme or protein in which a subject is deficient (e.g., a urea cycle enzyme or an enzyme associated with a lysosomal storage disorder) may be observed. As another example, circular RNA encapsulated by a transfer vehicle may encode one or both polypeptide chains of a T cell receptor protein or encode a chimeric antigen receptor (CAR).

Also provided herein are methods of treating a disease in a subject by administering an effective amount of a composition comprising circular RNA encoding a functional protein and a transfer vehicle described herein to the subject. In some embodiments, the circular RNA is encapsulated within the transfer vehicle. In certain embodiments, such methods may enhance (e.g., increase) the expression of a polynucleotide and/or increase the production and secretion of a functional polypeptide product in one or more target cells and tissues (e.g., immune cells or hepatocytes). Generally, such methods comprise contacting the target cells with one or more compounds and/or transfer vehicles that comprise or otherwise encapsulate the circRNA.

In certain embodiments, the transfer vehicles (e.g., lipid nanoparticles) are formulated based in part upon their ability to facilitate the transfection (e.g., of a circular RNA) of a target cell. In another embodiment, the transfer vehicles (e.g., lipid nanoparticles) may be selected and/or prepared to optimize delivery of circular RNA to a target cell, tissue or organ. For example, if the target cell is a hepatocyte, or if the target organ is the spleen, the properties of the pharmaceutical and/or liposomal compositions (e.g., size, charge and/or pH) may be optimized to effectively deliver such composition (e.g., lipid nanoparticles) to the target cell or organ, reduce immune clearance and/or promote retention in the target cell or organ. Alternatively, if the target tissue is the central nervous system, the selection and preparation of the transfer vehicle must consider penetration of, and retention within. the blood brain barrier and/or the use of alternate means of directly delivering such compositions (e.g., lipid nanoparticles) to such target tissue (e.g., via intracerebrovascular administration). In certain embodiments, the transfer vehicles may be combined with agents that facilitate the transfer of encapsulated materials across the blood brain barrier (e.g., agents which disrupt or improve the permeability of the blood brain barrier and thereby enhance the transfer of circular RNA to the target cells). While the transfer vehicles described herein (e.g., lipid nanoparticles) can facilitate introduction of circRNA into target cells, the addition of polycations (e.g., poly L-lysine and protamine) to, for example, one or more of the lipid nanoparticles that comprise the pharmaceutical compositions as a copolymer can also facilitate, and in some instances markedly enhance, the transfection efficiency of several types of transfer vehicles by 2-28 fold in a number of cell lines both in vitro and in vivo (See, N. J. Caplen, et al., Gene Ther. 1995; 2: 603; S. Li, et al., Gene Ther. 1997; 4, 891.). In some embodiments, a target cell is an immune cell. In some embodiments, a target cell is a T cell.

In certain embodiments, the transfer vehicles described herein (e.g., lipid nanoparticles) are prepared by combining multiple lipid components (e.g., one or more of the compounds disclosed herein) with one or more polymer components. For example, a lipid nanoparticle may be prepared using HGT4003, DOPE, cholesterol and DMG-PEG2000. A lipid nanoparticle may be comprised of additional lipid combinations in various ratios, including for example, HGT4001, DOPE and DMG-PEG2000. The selection of ionizable lipids, helper lipids, structural lipids, and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

Transfer vehicles described herein can allow the encapsulated polynucleotide to reach the target cell or may preferentially allow the encapsulated polynucleotide to reach the target cells or organs on a discriminatory basis (e.g., the transfer vehicles may concentrate in the liver or spleen of a subject to which such transfer vehicles are administered). Alternatively, the transfer vehicles may limit the delivery of encapsulated polynucleotides to other non-targeted cells or organs where the presence of the encapsulated polynucleotides may be undesirable or of limited utility.

Loading or encapsulating a polynucleotide, e.g., circRNA, into a transfer vehicle may serve to protect the polynucleotide from an environment (e.g., serum) which may contain enzymes or chemicals that degrade such polynucleotides and/or systems or receptors that cause the rapid excretion of such polynucleotides. Accordingly, in some embodiments, the compositions described herein are capable of enhancing the stability of the encapsulated polynucleotide(s), particularly with respect to the environments into which such polynucleotides will be exposed.

In certain embodiments, provided herein is a vector for making circular RNA, the vector comprising a 5' duplex forming region, a 3' group I intron fragment, optionally a first spacer, an Internal Ribosome Entry Site (IRES), an expression sequence, optionally a second spacer, a 5' group I intron fragment, and a 3' duplex forming region. In some embodiments, these elements are positioned in the vector in the above order. In some embodiments, the vector further comprises an internal 5' duplex forming region between the 3' group I intron fragment and the IRES and an internal 3' duplex forming region between the expression sequence and the 5' group I intron fragment. In some embodiments, the internal duplex forming regions are capable of forming a duplex between each other but not with the external duplex forming regions. In some embodiments, the internal duplex forming regions are part of the first and second spacers. Additional embodiments include circular RNA polynucleotides, including circular RNA polynucleotides made using the vectors provided herein, compositions comprising such circular RNA, cells comprising such circular RNA, methods of using and making such vectors, circular RNA, compositions and cells.

In some embodiments, provided herein are methods comprising administration of circular RNA polynucleotides provided herein into cells for therapy or production of useful proteins, such as PAH. In some embodiments, the method is advantageous in providing the production of a desired polypeptide inside eukaryotic cells with a longer half-life than linear RNA, due to the resistance of the circular RNA to ribonucleases.

Circular RNA polynucleotides lack the free ends necessary for exonuclease-mediated degradation, causing them to be resistant to several mechanisms of RNA degradation and granting extended half-lives when compared to an equivalent linear RNA. Circularization may allow for the stabilization of RNA polynucleotides that generally suffer from short half-lives and may improve the overall efficacy of exogenous mRNA in a variety of applications. In an embodiment, the half-life of the circular RNA polynucleotides provided herein in eukaryotic cells (e.g., mammalian cells, such as human cells) is at least 20 hours (e.g., at least 80 hours).

1. Definitions

As used herein, the terms “circRNA” or “circular polyribonucleotide” or “circular RNA” or “oRNA” are used interchangeably and refers to a polyribonucleotide that forms a circular structure through covalent bonds.

As used herein, the term “3' group I intron fragment” refers to a sequence with 75% or higher similarity to the 3'-proximal end of a natural group I intron including the splice site dinucleotide and optionally a stretch of natural exon sequence.

As used herein, the term “5' group I intron fragment” refers to a sequence with 75% or higher similarity to the 5'-proximal end of a natural group I intron including the splice site dinucleotide and optionally a stretch of natural exon sequence.

As used herein, the term “permutation site” refers to the site in a group I intron where a cut is made prior to permutation of the intron. This cut generates 3' and 5' group I intron fragments that are permuted to be on either side of a stretch of precursor RNA to be circularized.

As used herein, the term “splice site” refers to a dinucleotide that is partially or fully included in a group I intron and between which a phosphodiester bond is cleaved during RNA circularization.

As used herein, the term “therapeutic protein” refers to any protein that, when administered to a subject directly or indirectly in the form of a translated nucleic acid, has a therapeutic, diagnostic, and/or prophylactic effect and/or elicits a desired biological and/or pharmacological effect.

As used herein, the term “immunogenic” refers to a potential to induce an immune response to a substance. An immune response may be induced when an immune system of an organism or a certain type of immune cells is exposed to an immunogenic substance. The term “non-immunogenic” refers to a lack of or absence of an immune response above a detectable threshold to a substance. No immune response is detected when an immune system of an organism or a certain type of immune cells is exposed to a non-immunogenic substance. In some embodiments, a non-immunogenic circular polyribonucleotide as provided herein, does not induce an immune response above a predetermined threshold when measured by an immunogenicity assay. In some embodiments, no innate immune response is detected when an immune system of an organism or a certain type of immune cells is exposed to a non-immunogenic circular polyribonucleotide as provided herein. In some embodiments, no adaptive immune response is detected when an immune system of an organism or a certain type of immune cell is exposed to a non-immunogenic circular polyribonucleotide as provided herein.

As used herein, the term “circularization efficiency” refers to a measurement of resultant circular polyribonucleotide as compared to its linear starting material.

As used herein, the term “translation efficiency” refers to a rate or amount of protein or peptide production from a ribonucleotide transcript. In some embodiments, translation efficiency can be expressed as amount of protein or peptide produced per given amount of transcript that codes for the protein or peptide.

The term “nucleotide” refers to a ribonucleotide, a deoxyribonucleotide, a modified form thereof, or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine; sugars such as 2'-methyl ribose; non-natural phosphodiester linkages such as methylphosphonate, phosphorothioate and peptide linkages. Nucleotide analogs include 5-methoxyuridine, 1-methylpseudouridine, and 6-methyladenosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, or up to about 10,000 or more bases, composed of nucleotides, e.g., deoxyribonucleotides or ribonucleotides, and may be produced enzymatically or synthetically (e.g., as described in U.S. Pat. No. 5,948,902 and the references cited therein), which can hybridize with naturally occurring nucleic acids in a sequence specific manner analogous to that of two naturally occurring nucleic acids, e.g., can participate in Watson-Crick base pairing interactions. Naturally occurring nucleic acids are comprised of nucleotides including guanine, cytosine, adenine, thymine, and uracil (G, C, A, T, and U respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (for example, in some embodiments, a compound, a polynucleotide, a protein, a polypeptide, a polynucleotide composition, or a polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90%-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is more than as it is found naturally.

The terms "duplexed," "double-stranded," or "hybridized" as used herein refer to nucleic acids formed by hybridization of two single strands of nucleic acids containing complementary sequences. In most cases, genomic DNA is double-stranded. Sequences can be fully complementary or partially complementary.

As used herein, "unstructured" with regard to RNA refers to an RNA sequence that is not predicted by the RNAFold software or similar predictive tools to form a structure (e.g., a hairpin loop) with itself or other sequences in the same RNA molecule. In some embodiments, unstructured RNA can be functionally characterized using nuclease protection assays.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, two "duplex forming regions," "homology arms," or "homology regions," may be any two regions that are thermodynamically favored to cross-pair in a sequence specific interaction. In some embodiments, two duplex forming regions, homology arms, or homology regions, share a sufficient level of sequence identity to one another's reverse complement to act as substrates for a hybridization reaction. As used herein polynucleotide sequences have "homology" when they are either identical or share sequence identity to a reverse complement or "complementary" sequence. The percent sequence identity between a homology region and a counterpart homology region's reverse complement can be any percent of sequence identity that allows for hybridization to occur. In some embodiments, an internal duplex forming region of an inventive polynucleotide is capable of forming a duplex with another internal duplex forming region and does not form a duplex with an external duplex forming region.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end nucleotide of a polynucleotide at which a new linkage would be to a 5' carbon is its 5' terminal nucleotide. The end nucleotide of a polynucleotide at which a new linkage would be to a 3' carbon is its 3' terminal nucleotide. A terminal nucleotide, as used herein, is the nucleotide at the end position of the 3'- or 5'-terminus "Transcription" means the formation or synthesis of an RNA molecule by an RNA polymerase using a DNA molecule as a template. The invention is not limited with respect to the RNA polymerase that is used for transcription. For example, in some embodiments, a T7-type RNA polymerase can be used.

"Translation" means the formation of a polypeptide molecule by a ribosome based upon an RNA template.

It is to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about," is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

As used herein, the term "encode" refers broadly to any process whereby the information in a polymeric macromolecule is used to direct the production of a second molecule that is different from the first. The second molecule may have a chemical structure that is different from the chemical nature of the first molecule.

By "co-administering" is meant administering a therapeutic agent provided herein in conjunction with one or more additional therapeutic agents sufficiently close in time such that the therapeutic agent provided herein can enhance the effect of the one or more additional therapeutic agents, or vice versa.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. The treatment or prevention provided by the method disclosed herein can include treatment or prevention of one or more conditions or symptoms of the disease. Also, for purposes herein, "prevention" can encompass delaying the onset of the disease, or a symptom or condition thereof.

As used herein, the term "expression sequence" refers to a nucleic acid sequence that encodes a product, e.g., a peptide or polypeptide, regulatory nucleic acid, or non-coding nucleic acid. An exemplary expression sequence that codes for a peptide or polypeptide can comprise a plurality of nucleotide triads, each of which can code for an amino acid and is termed as a "codon".

As used herein, a "spacer" refers to a region of a polynucleotide sequence ranging from 1 nucleotide to hundreds or thousands of nucleotides separating two other elements along a polynucleotide sequence. The sequences can be defined or can be random. A spacer is typically non-coding. In some embodiments, spacers include duplex forming regions.

As used herein, "splice site" refers to the dinucleotide or dinucleotides between which cleavage of the phosphodiester bond occurs during a splicing reaction. A "5' splice site" refers to the natural 5' dinucleotide of the intron e.g., group I intron, while a "3' splice site" refers to the natural 3' dinucleotide of the intron.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An IRES is typically about 500 nt to about 700 nt in length.

As used herein, a "miRNA site" refers to a stretch of nucleotides within a polynucleotide that is capable of forming a duplex with at least 8 nucleotides of a natural miRNA sequence.

As used herein, an "endonuclease site" refers to a stretch of nucleotides within a polynucleotide that is capable of being recognized and cleaved by an endonuclease protein.

As used herein, "bicistronic RNA" refers to a polynucleotide that includes two expression sequences coding for two distinct proteins. These expression sequences can be separated by a nucleotide sequence encoding a cleavable peptide such as a protease cleavage site. They can also be separated by a ribosomal skipping element.

As used herein, the term"ribosomal skipping element" refers to a nucleotide sequence encoding a short peptide sequence capable of causing generation of two peptide chains from translation of one RNA molecule. While not wishing to be bound by theory, it is hypothesized that ribosomal skipping elements function by (1) terminating translation of the first peptide chain and re-initiating translation of the second peptide chain; or (2) cleavage of a peptide bond in the peptide sequence encoded by the ribosomai skipping element by an intrinsic protease activity of the encoded peptide, or by another protease in the environment (e.g., cytosol).

As used herein, the term "co-formulate" refers to a nanoparticle formulation comprising two or more nucleic acids or a nucleic acid and other active drug substance. Typically, the ratios are equimolar or defined in the ratiometric amount of the two or more nucleic acids or the nucleic acid and other active drug substance.

As used herein, "transfer vehicle" includes any of the standard pharmaceutical carriers, diluents, excipients, and the like, which are generally intended for use in connection with the administration of biologically active agents, including nucleic acids.

As used herein, the phrase "lipid nanoparticle" refers to a transfer vehicle comprising one or more lipids (e.g., in some embodiments, cationic lipids, non-cationic lipids, and PEG-modified lipids).

As used herein, the phrase "ionizable lipid" refers to any of a number of lipid species that carry a net positive charge at a selected pH, such as physiological pH 4 and a neutral charge at other pHs such as physiological pH 7.

In some embodiments, a lipid, e.g., an ionizable lipid, disclosed herein comprises one or more cleavable groups. The terms "cleave" and "cleavable" are used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group. In some embodiments, a cleavable group is bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl).

As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl.

In certain embodiments, at least one of the functional groups of moieties that comprise the compounds disclosed herein is hydrophobic in nature (e.g., a hydrophobic tail-group comprising a naturally occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated C6-$C_{20}$ alkyl and/or an optionally substituted, variably saturated or unsaturated C6-C20 acyl.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

In certain embodiments, the compounds disclosed herein comprise, for example, at least one hydrophilic head-group and at least one hydrophobic tail-group, each bound to at least one cleavable group, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a $C_6$-$C_{20}$ alkyl) and at least one hydrophilic head-group (e.g., imidazole), each bound to a cleavable group (e.g., disulfide).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable functional group (e.g., a disulfide group), which in turn is bound to a hydrophobic tail-group (e.g., cholesterol).

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z, 12Z)-octadeca-9,12-dien. The use of designations such as, for example, "$C_6$-$C_{20}$" is intended to refer to an alkyl (e.g., straight or branched chain and inclusive of alkenes and alkyls) having the recited range carbon atoms. In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of C2-4 alkenyl groups include ethenyl ($C_2$), 1-propenyl ($C_3$), 2-propenyl ($C_3$), 1-butenyl ($C_4$), 2-butenyl (C4), butadienyl (C4), and the like. Examples of C2-6 alkenyl groups include the aforementioned C2-4 alkenyl groups as well as pentenyl ($C_5$), pentadienyl ($C_5$), hexenyl (C6), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("C220 alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl (C6), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl).

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

As used herein, "heterocyclyl" or "heterocyclic" refers to a radical of a 3-to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

As used herein, "cyano" refers to —CN.

The terms "halo" and "halogen" as used herein refer to an atom selected from fluorine (fluoro, —F), chlorine (chloro, —Cl), bromine (bromo, —Br), and iodine (iodo, —I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, Stereochemistry of Carbon Compounds (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

In certain embodiments the compounds and the transfer vehicles of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein such that the one or more target cells are transfected with the circular RNA encapsulated therein. As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) up-taken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the ionizable lipid compounds disclosed herein). Such liposomes may be unilamellar or multilamellar vesicles which have a membrane formed from a lipophilic material and an aqueous interior that contains the encapsulated circRNA to be delivered to one or more target cells, tissues and organs. In certain embodiments, the compositions described herein comprise one or more lipid nanoparticles. Examples of suitable lipids (e.g., ionizable lipids) that may be used to form the liposomes and lipid nanoparticles contemplated include one or more of the compounds disclosed herein (e.g., HGT4001, HGT4002, HGT4003, HGT4004 and/or HGT4005). Such liposomes and lipid nanoparticles may also comprise additional ionizable lipids such as C12-200, DLin-KC2-DMA, and/or HGT5001, helper lipids, structural lipids, PEG-modified lipids, MC3, DLinDMA, DLinkC2DMA, cKK-E12, ICE, HGT5000, DODAC, DDAB, DMRIE, DOSPA, DOGS, DODAP, DODMA, DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

As used herein, the phrases "non-cationic lipid", "non-cationic helper lipid", and "helper lipid" are used interchangeably and refer to any neutral, zwitterionic or anionic lipid.

As used herein, the phrase "anionic lipid" refers to any of a number of lipid species that carry a net negative charge at a selected pH, such as physiological pH.

As used herein, the phrase "biodegradable lipid" or "degradable lipid" refers to any of a number of lipid species that are broken down in a host environment on the order of minutes, hours, or days ideally making them less toxic and unlikely to accumulate in a host over time. Common modifications to lipids include ester bonds, and disulfide bonds among others to increase the biodegradability of a lipid.

As used herein, the phrase "biodegradable PEG lipid" or "degradable PEG lipid" refers to any of a number of lipid species where the PEG molecules are cleaved from the lipid in a host environment on the order of minutes, hours, or days ideally making them less immunogenic. Common modifications to PEG lipids include ester bonds, and disulfide bonds among others to increase the biodegradability of a lipid.

In certain embodiments of the present invention, the transfer vehicles (e.g., lipid nanoparticles) are prepared to encapsulate one or more materials or therapeutic agents (e.g., circRNA). The process of incorporating a desired therapeutic agent (e.g., circRNA) into a transfer vehicle is referred to herein as or "loading" or "encapsulating" (Lasic, et al., FEBS Lett., 312: 255-258, 1992). The transfer vehicle-loaded or -encapsulated materials (e.g., circRNA) may be completely or partially located in the interior space of the transfer vehicle, within a bilayer membrane of the transfer vehicle, or associated with the exterior surface of the transfer vehicle.

As used herein, the term "structural lipid" refers to sterols and also to lipids containing sterol moieties.

As defined herein, "sterols" are a subgroup of steroids consisting of steroid alcohols.

As used herein, the term "structural lipid" refers to sterols and also to lipids containing sterol moieties.

As used herein, the term "PEG" means any polyethylene glycol or other polyalkylene ether polymer.

As generally defined herein, a "PEG-OH lipid" (also referred to herein as "hydroxy-PEGylated lipid") is a PEGylated lipid having one or more hydroxyl (—OH) groups on the lipid.

As used herein, a "phospholipid" is a lipid that includes a phosphate moiety and one or more carbon chains, such as unsaturated fatty acid chains.

All nucleotide sequences disclosed herein can represent an RNA sequence or a corresponding DNA sequence. It is understood that deoxythymidine (dT or T) in a DNA is transcribed into a uridine (U) in an RNA. As such, "T" and "U" are used interchangeably herein in nucleotide sequences.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

2. Vectors, Precursor RNA, and Circular RNA

Also provided herein are circular RNAs, precursor RNAs that can circularize into the circular RNAs, and vectors (e.g., DNA vectors) that can be transcribed into the precursor RNAs or the circular RNAs.

Two types of spacers have been designed for improving precursor RNA circularization and/or gene expression from circular RNA. The first type of spacer is external spacer, i.e., present in a precursor RNA but removed upon circularization. While not wishing to be bound by theory, it is contemplated that an external spacer may improve ribozyme-mediated circularization by maintaining the structure of the ribozyme itself and preventing other neighboring sequence elements from interfering with its folding and function. The second type of spacer is internal spacer, i.e., present in a precursor RNA and retained in a resulting circular RNA. While not wishing to be bound by theory, it is contemplated that an internal spacer may improve ribozyme-mediated circularization by maintaining the structure of the ribozyme itself and preventing other neighboring sequence elements, particularly the neighboring IRES and coding region, from interfering with its folding and function. It is also contemplated that an internal spacer may improve protein expression from the IRES by preventing neighboring sequence elements, particularly the intron elements, from hybridizing with sequences within the IRES and inhibiting its ability to fold into its most preferred and active conformation.

For driving protein expression, the circular RNA comprises an IRES operably linked to a protein coding sequence. Exemplary IRES sequences are provided in Table 17 below. In some embodiments, the circular RNA disclosed herein comprises an IRES sequence at least 80%, 85%, 90%, 91%, 92%, 93%, 94%, 95%, 96%, 97%, 98%, or 99% identical to an IRES sequence in Table 17. In some embodiments, the circular RNA disclosed herein comprises an IRES sequence in Table 17. Modifications of IRES and accessory sequences are disclosed herein to increase or reduce IRES activities, for example, by truncating the 5' and/or 3' ends of the IRES, adding a spacer 5' to the IRES, modifying the 6 nucleotides 5' to the translation initiation site (Kozak sequence), modification of alternative translation initiation sites, and creating chimeric/hybrid IRES sequences. In some embodiments, the IRES sequence in the circular RNA disclosed herein comprises one or more of these modifications relative to a native IRES (e.g., a native IRES disclosed in Table 17).

In certain aspects, provided herein are circular RNA polynucleotides comprising a 3' post splicing group I intron fragment, optionally a first spacer, an Internal Ribosome Entry Site (IRES), an expression sequence, optionally a second spacer, and a 5' post splicing group I intron fragment. In some embodiments, these regions are in that order. In some embodiments, the circular RNA is made by a method provided herein or from a vector provided herein.

In certain embodiments, transcription of a vector provided herein (e.g., comprising a 5' homology region, a 3' group I intron fragment, optionally a first spacer, an Internal Ribosome Entry Site (IRES), an expression sequence, optionally a second spacer, a 5' group I intron fragment, and a 3' homology region) results in the formation of a precursor linear RNA polynucleotide capable of circularizing. In some embodiments, this precursor linear RNA polynucleotide circularizes when incubated in the presence of guanosine nucleotide or nucleoside (e.g., GTP) and divalent cation (e.g., $Mg^{2+}$).

In some embodiments, the vectors and precursor RNA polynucleotides provided herein comprise a first (5') duplex forming region and a second (3') duplex forming region. In certain embodiments, the first and second homology regions may form perfect or imperfect duplexes. Thus, in certain embodiments at least 75%, 80%, 85%, 90%, 91%, 92%, 93%, 94%, 95%, 96%, 97%, 98%, 99% or 100% of the first and second duplex forming regions may be base paired with one another. In some embodiments, the duplex forming regions are predicted to have less than 50% (e.g., less than 45%, less than 40%, less than 35%, less than 30%, less than 25%) base pairing with unintended sequences in the RNA (e.g., non-duplex forming region sequences). In some embodiments, including such duplex forming regions on the ends of the precursor RNA strand, and adjacent or very close to the group I intron fragment, bring the group I intron fragments in close proximity to each other, increasing splicing efficiency. In some embodiments, the duplex forming regions are 3 to 100 nucleotides in length (e.g., 3-75 nucleotides in length, 3-50 nucleotides in length, 20-50 nucleotides in length, 35-50 nucleotides in length, 5-25 nucleotides in length, 9-19 nucleotides in length). In some embodiments, the duplex forming regions are about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, the duplex forming regions have a length of about 9 to about 50 nucleotides. In one embodiment, the duplex forming regions have a length of about 9 to about 19 nucleotides. In some embodiments, the duplex forming regions have a length of about 20 to about 40 nucleotides. In certain embodiments, the duplex forming regions have a length of about 30 nucleotides.

In certain embodiments, the vectors, precursor RNA and circular RNA provided herein comprise a first (5') and/or a second (3') spacer. In some embodiments, including a spacer between the 3' group I intron fragment and the IRES may conserve secondary structures in those regions by preventing them from interacting, thus increasing splicing efficiency. In some embodiments, the first (between 3' group I intron fragment and IRES) and second (between the expression sequence and 5' group I intron fragment) spacers comprise additional base pairing regions that are predicted to base pair with each other and not to the first and second duplex forming regions. In some embodiments, such spacer base pairing brings the group I intron fragments in close proximity to each other, further increasing splicing efficiency. Additionally, in some embodiments, the combination of base pairing between the first and second duplex forming regions, and separately, base pairing between the first and second spacers, promotes the formation of a splicing bubble containing the group I intron fragments flanked by adjacent regions of base pairing. Typical spacers are contiguous sequences with one or more of the following qualities: 1) predicted to avoid interfering with proximal structures, for example, the IRES, expression sequence, or intron; 2) is at least 7 nt long and no longer than 100 nt; 3) is located after and adjacent to the 3' intron fragment and/or before and adjacent to the 5' intron fragment; and 4) contains one or more of the following: a) an unstructured region at least 5 nt long, b) a region of base pairing at least 5 nt long to a distal sequence, including another spacer, and c) a structured region at least 7 nt long limited in scope to the sequence of the spacer. Spacers may have several regions, including an unstructured region, a base pairing region, a hairpin/structured region, and combinations thereof. In an embodiment, the spacer has a structured region with high GC content. In an embodiment, a region within a spacer base pairs with another region within the same spacer. In an embodiment, a region within a spacer base pairs with a region within another spacer. In an embodiment, a spacer comprises one or more hairpin structures. In an embodiment, a spacer comprises one or more hairpin structures with a stem of 4 to 12 nucleotides and a loop of 2 to 10 nucleotides. In an embodiment, there is an additional spacer between the 3' group I intron fragment and the IRES. In an embodiment, this additional spacer prevents the structured regions of the IRES from interfering with the folding of the 3' group I intron fragment or reduces the extent to which this occurs. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 5 and 50, 10 and 50, 20 and 50, 20 and 40, and/or 25 and 35 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyAC sequence. In one embodiment, a spacer comprises about 10%, 20%, 30%, 40%, 50%, 60%, 70%, 80%, 90%, or 100% polyAC content. In one embodiment, a spacer comprises about 10%, 20%, 30%, 40%, 50%, 60%, 70%, 80%, 90%, or 100% polypyrimidine (C/T or C/U) content.

In certain embodiments, a 3' group I intron fragment is a contiguous sequence at least 75% identical (e.g., at least 80%, 85%, 90%, 91%, 92%, 93%, 94%, 95%, 96%, 97%, 98%, 99% or 100% identical) to a 3' proximal fragment of a natural group I intron including the 3' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. Typically, a 5' group I intron fragment is a contiguous sequence at least 75% identical (e.g., at least 80%, 85%, 90%, 91%, 92%, 93%, 94%, 95%, 96%, 97%, 98%, 99% or 100% identical) to a 5' proximal fragment of a natural group I intron including the 5' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. As described by Umekage et al. (2012), external portions of the 3' group I intron fragment and 5' group I intron fragment are removed in circularization, causing the circular RNA provided herein to comprise only the portion of the 3' group I intron fragment formed by the optional exon sequence of at least 1 nt in length and 5' group I intron fragment formed by the optional exon sequence of at least 1 nt in length, if such sequences were present on the non-circularized precursor RNA. The part of the 3' group I intron fragment that is retained by a circular RNA is referred to herein as the post splicing 3' group I intron fragment. The part of the 5' group I intron fragment that is retained by a circular RNA is referred to herein as the post splicing 5' group I intron fragment.

In certain embodiments, the vectors, precursor RNA and circular RNA provided herein comprise an internal ribosome entry site (IRES). Inclusion of an IRES permits the translation of one or more open reading frames from a circular RNA (e.g., open reading frames that form the expression sequence). The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20: 102-110; Kobayashi et al., BioTechniques (1996) 21:399-402; and Mosser et al., BioTechniques 1997 22 150-161).

A multitude of IRES sequences are available and include sequences derived from a wide variety of viruses, such as from leader sequences of picornaviruses such as the encephalomyocarditis virus (EMCV) UTR (fang et al. J. Virol. (1989) 63: 1651-1660), the polio leader sequence, the hepatitis A virus leader, the hepatitis C virus IRES, human rhinovirus type 2 IRES (Dobrikova et al., Proc. Natl. Acad. Sci. (2003) 100(25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like.

In some embodiments, the IRES is an IRES sequence of *Taura* syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24 or an aptamer to eIF4G.

In some embodiments, the polynucleotides herein comprise an expression sequence. In some embodiments, the expression sequence encodes a therapeutic protein.

In some embodiments, the circular RNA encodes two or more polypeptides. In some embodiments, the circular RNA is a bicistronic RNA. The sequences encoding the two or more polypeptides can be separated by a ribosomal skipping element or a nucleotide sequence encoding a protease cleavage site. In certain embodiments, the ribosomai skipping element encodes thosea-asigna virus 2A peptide (T2A), porcine teschovirus-1 2 A peptide (P2A), foot-and-mouth disease virus 2 A peptide (F2A), equine rhinitis A vims 2A peptide (E2A), cytoplasmic polyhedrosis vims 2A peptide (BmCPV 2A), or flacherie vims of *B. mori* 2A peptide (BmIFV 2A).

In certain embodiments, the vectors provided herein comprise a 3' UTR. In some embodiments, the 3' UTR is from human beta globin, human alpha globin *xenopus* beta globin, *xenopus* alpha globin, human prolactin, human GAP-43, human eEFlal, human Tau, human TNFα, dengue virus, hantavirus small mRNA, bunyavirus small mRNA, turnip yellow mosaic virus, hepatitis C virus, rubella virus, tobacco mosaic virus, human IL-8, human actin, human GAPDH, human tubulin, hibiscus chlorotic ringspot virus, woodchuck hepatitis virus post translationally regulated element, sindbis virus, turnip crinkle virus, tobacco etch virus, or Venezuelan equine encephalitis virus.

In some embodiments, the vectors provided herein comprise a 5' UTR. In some embodiments, the 5' UTR is from human beta globin, *Xenopus laevis* beta globin, human alpha globin, *Xenopus laevis* alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or the adenovirus tripartite leader.

In some embodiments, a vector provided herein comprises a polyA region external of the 3' and/or 5' group I intron fragments. In some embodiments the polyA region is at least 15, 30, or 60 nucleotides long. In some embodiments, one or both polyA regions is 15-50 nucleotides long. In some embodiments, one or both polyA regions is 20-25 nucleotides long. The polyA sequence is removed upon circularization. Thus, an oligonucleotide hybridizing with the polyA sequence, such as a deoxythymine oligonucleotide (oligo(dT)) conjugated to a solid surface (e.g., a resin), can be used to separate circular RNA from its precursor RNA. Other sequences can also be disposed 5' to the 3' group I intron fragment or 3' to the 5' group I intron fragment and a complementary sequence can similarly be used for circular RNA purification.

In some embodiments, the DNA (e.g., vector), linear RNA (e.g., precursor RNA), and/or circular RNA polynucleotide provided herein is between 300 and 10000, 400 and 9000, 500 and 8000, 600 and 7000, 700 and 6000, 800 and 5000, 900 and 5000, 1000 and 5000, 1100 and 5000, 1200 and 5000, 1300 and 5000, 1400 and 5000, and/or 1500 and 5000 nucleotides in length. In some embodiments, the polynucleotide is at least 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, or 5000 nt in length. In some embodiments, the polynucleotide is no more than 3000 nt, 3500 nt, 4000 nt, 4500 nt, 5000 nt, 6000 nt, 7000 nt, 8000 nt, 9000 nt, or 10000 nt in length. In some embodiments, the length of a DNA, linear RNA, and/or circular RNA polynucleotide provided herein is about 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, 5000 nt, 6000 nt, 7000 nt, 8000 nt, 9000 nt, or 10000 nt.

In some embodiments, provided herein is a vector. In certain embodiments, the vector comprises, in the following order, a) a 5' homology region, b) a 3' group I intron fragment, c) optionally, a first spacer sequence, d) an IRES, e) an expression sequence, f) optionally, a second spacer sequence, g) a 5' group I intron fragment, and h) a 3' homology region. In some embodiments, the vector comprises a transcriptional promoter upstream of the 5' homology region. In certain embodiments, the precursor RNA comprises, in the following order, a) a polyA sequence, b) an external spacer, c) a 3' group I intron fragment, d) a duplex forming region, e) an internal spacer, f) an IRES, g) an expression sequence, h) a stop codon cassette, i) optionally, an internal spacer, j) a duplex forming region capable of forming a duplex with the duplex forming region of d, k) a 5' group I intron fragment, 1) an external spacer, and m) a polyA sequence.

In some embodiments, provided herein is a precursor RNA. In certain embodiments, the precursor RNA is a linear RNA produced by in vitro transcription of a vector provided herein. In some embodiments, the precursor RNA comprises, in the following order, a) a 5' homology region, b) a 3' group I intron fragment, c) optionally, a first spacer sequence, d) an IRES, e) an expression sequence, f) optionally, a second spacer sequence, g) a 5' group I intron fragment, and h) a 3' homology region. The precursor RNA can be unmodified, partially modified or completely modified.

In certain embodiments, provided herein is a circular RNA. In certain embodiments, the circular RNA is a circular RNA produced by a vector provided herein. In some embodiments, the circular RNA is circular RNA produced by circularization of a precursor RNA provided herein. In some embodiments, the circular RNA comprises, in the following sequence, a) a first spacer sequence, b) an IRES, c) an expression sequence, and d) a second spacer sequence. In some embodiments, the circular RNA further comprises the portion of the 3' group I intron fragment that is 3' of the 3' splice site. In some embodiments, the circular RNA further comprises the portion of the 5' group I intron fragment that is 5' of the 5' splice site. In some embodiments, the circular RNA is at least 500, 600, 700, 800, 900, 1000, 1500, 2000, 2500, 3000, 3500, 4000 or 4500 nucleotides in size. The circular RNA can be unmodified, partially modified or completely modified.

In some embodiments, the circular RNA provided herein has higher functional stability than mRNA comprising the same expression sequence. In some embodiments, the circular RNA provided herein has higher functional stability than mRNA comprising the same expression sequence, 5moU modifications, an optimized UTR, a cap, and/or a polyA tail.

In some embodiments, the circular RNA polynucleotide provided herein has a functional half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a functional half-life of 5-80, 10-70, 15-60, and/or 20-50 hours. In some embodiments, the circular RNA polynucleotide provided herein has a functional half-life greater than (e.g., at least 1.5-fold greater than, at least 2-fold greater than) that of an equivalent linear RNA polynucleotide encoding the same protein. In some embodiments, functional half-life can be assessed through the detection of functional protein synthesis.

In some embodiments, the circular RNA polynucleotide provided herein has a half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a half-life of 5-80, 10-70, 15-60, and/or 20-50 hours. In some embodiments, the circular RNA polynucleotide provided herein has a half-life greater than (e.g., at least 1.5-fold greater than, at least 2-fold greater than) that of an equivalent linear RNA polynucleotide encoding the same protein. In some embodiments, the circular RNA polynucleotide, or pharmaceutical composition thereof, has a functional half-life in a human cell greater than or equal to that of a pre-determined threshold value. In some embodiments the functional half-life is determined by a functional protein assay. For example in some embodiments, the functional half-life is determined by an in vitro luciferase assay, wherein the activity of *Gaussia* luciferase (GLuc) is measured in the media of human cells (e.g. HepG2) expressing the circular RNA polynucleotide every 1, 2, 6, 12, or 24 hours over 1, 2, 3, 4, 5, 6, 7, or 14 days. In other embodiments, the functional half-life is determined by an in vivo assay, wherein levels of a protein encoded by the expression sequence of the circular RNA polynucleotide are measured in patient serum or tissue samples every 1, 2, 6, 12, or 24 hours over 1, 2, 3, 4, 5, 6, 7, or 14 days. In some embodiments, the pre-determined threshold value is the functional half-life of a reference linear RNA polynucleotide comprising the same expression sequence as the circular RNA polynucleotide.

In some embodiments, the circular RNA provided herein may have a higher magnitude of expression than equivalent linear mRNA, e.g., a higher magnitude of expression 24 hours after administration of RNA to cells. In some embodiments, the circular RNA provided herein has a higher magnitude of expression than mRNA comprising the same expression sequence, 5moU modifications, an optimized UTR, a cap, and/or a polyA tail.

In some embodiments, the circular RNA provided herein may be less immunogenic than an equivalent mRNA when exposed to an immune system of an organism or a certain type of immune cell. In some embodiments, the circular RNA provided herein is associated with modulated production of cytokines when exposed to an immune system of an organism or a certain type of immune cell. For example, in some embodiments, the circular RNA provided herein is associated with reduced production of IFN-β1, RIG-I, IL-2, IL-6, IFNγ, and/or TNFα when exposed to an immune system of an organism or a certain type of immune cell as compared to mRNA comprising the same expression sequence. In some embodiments, the circular RNA provided herein is associated with less IFN-β1, RIG-I, IL-2, IL-6, IFNγ, and/or TNFα transcript induction when exposed to an immune system of an organism or a certain type of immune cell as compared to mRNA comprising the same expression sequence. In some embodiments, the circular RNA provided herein is less immunogenic than mRNA comprising the same expression sequence. In some embodiments, the circular RNA provided herein is less immunogenic than mRNA comprising the same expression sequence, 5moU modifications, an optimized UTR, a cap, and/or a polyA tail.

In certain embodiments, the circular RNA provided herein can be transfected into a cell as is, or can be transfected in DNA vector form and transcribed in the cell. Transcription of circular RNA from a transfected DNA vector can be via added polymerases or poylmerases encoded by nucleic acids transfected into the cell, or preferably via endogenous polymerases.

In certain embodiments, a circular RNA polynucleotide provided herein comprises modified RNA nucleotides and/or modified nucleosides. In some embodiments, the modified nucleoside is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is Ψ (pseudouridine). In another embodiment, the modified nucleoside is Um (2'-O-methyluridine). In other embodiments, the modified nucleoside is $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2$i6A (2-methylthio-$N^6$ isopentenyladenosine); $io^6A$ ($N^6$-(cis-hydroxyisopentenyl)adenosine); $ms^2t^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine);

$m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2{}_2G$ ($N^2$,$N^2$-dimethylguanosine); $m^2Gm$ ($N^2$,2'-O-dimethylguanosine); $m^2{}_2Gm$ ($N^2$,$N^2$,2'-O-trimethylguanosine); Gr(p) (2'-O-ribosylguanosine(phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5S^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6{}_2A$ ($N^6$,$N^6$-dimethyladenosine); Im (2'-O-methylinosine); $m^4C$ ($N^4$-methylcytidine); $m^4Cm$ ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6{}_2Am$ ($N^6$,$N^6$,O-2'-trimethyladenosine); $m^{2,7}G$ ($N^2$,7-dimethylguanosine); $m^{2,2,7}G$ ($N^2$,$N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine).

In some embodiments, the modified nucleoside may include a compound selected from the group of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In another embodiment, the modifications are independently selected from the group consisting of 5-methylcytosine, pseudouridine and 1-methylpseudouridine.

In some embodiments, the modified ribonucleosides include 5-methylcytidine, 5-methoxyuridine, 1-methyl-pseudouridine, N6-methyladenosine, and/or pseudouridine. In some embodiments, such modified nucleosides provide additional stability and resistance to immune activation.

In particular embodiments, polynucleotides may be codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

In certain embodiments circular RNA provided herein is produced inside a cell. In some embodiments, precursor RNA is transcribed using a DNA template (e.g., in some embodiments, using a vector provided herein) in the cytoplasm by a bacteriophage RNA polymerase, or in the nucleus by host RNA polymerase II and then circularized.

In certain embodiments, the circular RNA provided herein is injected into an animal (e.g., a human), such that a polypeptide encoded by the circular RNA molecule is expressed inside the animal.

3. Payload

In some embodiments, the expression sequence encodes a therapeutic protein. In some embodiments, the therapeutic protein is selected from the proteins listed in the following table.

| Payload | Sequence | Target cell/ organ | Preferred delivery formulation |
|---|---|---|---|
| CD19 CAR | Any of sequences 309-314 | T cells | 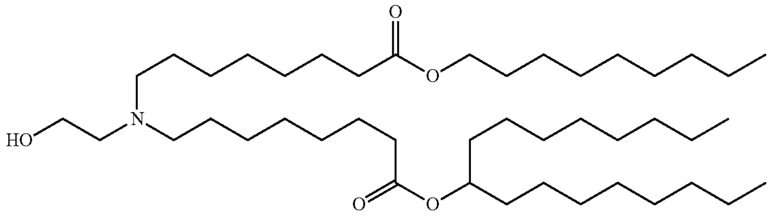<br>(50 mol %)<br>DSPC (10 mol %)<br>Beta-sitosterol (28.5% mol %)<br>Cholesterol (10 mol %)<br>PEG DMG (1.5 mol %) |
| BCMA CAR | MALPVTALLLPLALLL<br>HAARPDIVLTQSPASLA<br>VSLGERATINCRASESV<br>SVIGAHLIHWYQQKPG<br>QPPKLLIYLASNLETGV<br>PARFSGSGSGTDFTLTIS<br>SLQAEDAAIYYCLQSRI<br>FPRTFGQGTKLEIKGST<br>SGSGKPGSGEGSTKGQ<br>VQLVQSGSELKKPGAS<br>VKVSCKASGYTFTDYI<br>NWVRQAPGQGLEWMG<br>WINTETREPAYAYDFR<br>GRFVFSLDTSVSTAYLQ<br>ISSLKAEDTAVYYCAR<br>DYSYAMDYWGQGTLV<br>TVSSAAATTTPAPRPPT<br>PAPTIASQPLSLRPEACR<br>PAAGGAVHTRGLDFAC<br>DIYIWAPLAGTCGVLLL<br>SLVITLYCKRGRKKLLY<br>IFKQPFMRPVQTTQEED<br>GCSCRFPEEEEGGCELR<br>VKFSRSADAPAYQQGQ<br>NQLYNELNLGRREEYD<br>VLDKRRGRDPEMGGKP<br>RRKNPQEGLYNELQKD<br>KMAEAYSEIGMKGERR<br>RGKGHDGLYQGLSTAT<br>KDTYDALHMQALPPR | T cells | 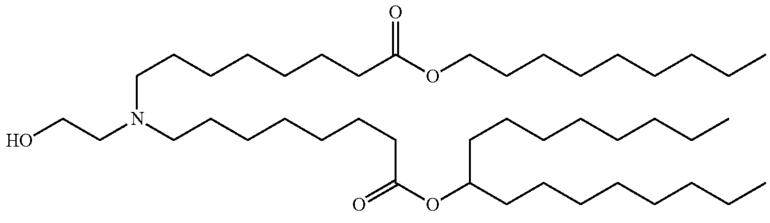<br>(50 mol %)<br>DSPC (10 mol %)<br>Beta-sitosterol (28.5% mol %)<br>Cholesterol (10 mol %)<br>PEG DMG (1.5 mol %) |
| MAGE-A4 TCR | TCR alpha chain:<br>KNQVEQSPQSLIILEGK<br>NCTLQCNYTVSPFSNLR<br>WYKQDTGRGPVSLTIM<br>TFSENTKSNGRYTATLD<br>ADTKQSSLHITASQLSD<br>SASYICVVNHSGGSYIP<br>TFGRGTSLIVHPYIQKP<br>DPAVYQLRDSKSSDKS<br>VCLFTDFDSQTNVSQSK<br>DSDVYITDKTVLDMRS<br>MDFKSNSAVAWSNKS<br>DFACANAFNNSIIPEDT<br>FFPSPESS<br>TCR beta chain:<br>DVKVTQSSRYLVKRTG<br>EKVFLECVQDMDHEN<br>MFWYRQDPGLGLRLIY<br>FSYDVKMKEKGDIPEG<br>YSVSREKKERFSLILES<br>ASTNQTSMYLCASSFL | T cells | 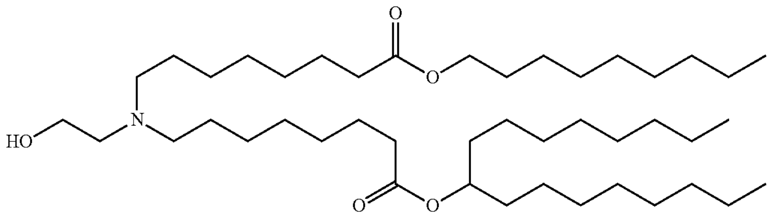<br>(50 mol %)<br>DSPC (10 mol %)<br>Beta-sitosterol (28.5% mol %)<br>Cholesterol (10 mol %)<br>PEG DMG (1.5 mol %) |

-continued

| Payload | Sequence | Target cell/ organ | Preferred delivery formulation |
|---|---|---|---|
| | MTSGDPYEQYFGPGTR<br>LTVTEDLKNVFPPEVA<br>VFEPSEAEISHTQKATL<br>VCLATGFYPDHVELSW<br>WVNGKEVHSGVSTDPQ<br>PLKEQPALNDSRYCLSS<br>RLRVSATFWQNPRNHF<br>RCQVQFYGLSENDEWT<br>QDRAKPVTQIVSAEAW<br>GRAD | | |
| NY-ESO TCR | TCRalpha extracellular sequence<br>MQEVTQIPAALSVPEGE<br>NLVLNCSFTDSAIYNLQ<br>WFRQDPGKGLTSLLLIQ<br>SSQREQTSGRLNASLDK<br>SSGRSTLYIAASQPGDS<br>ATYLCAVRPTSGGSYIP<br>TFGRGTSLIVHPY<br>TCRbeta cellular sequence<br>MGVTQTPKFQVLKTGQ<br>SMTLQCAQDMNHEYM<br>SWYRQDPGMGLRLIHY<br>SVGAGITDQGEVPNGY<br>NVSRSTTEDFPLRLLSA<br>APSQTSVYFCASSYVG<br>NTGELFFGEGSRLTVL | T cells | 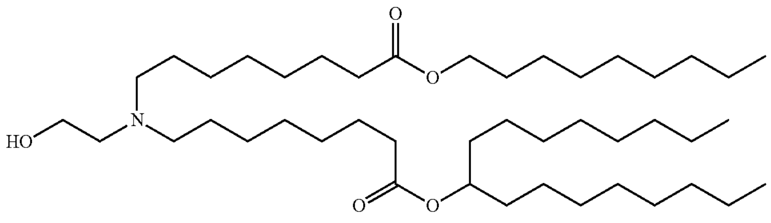<br>(50 mol %)<br>DSPC (10 mol %)<br>Beta-sitosterol (28.5% mol %)<br>Cholesterol (10 mol %)<br>PEG DMG (1.5 mol %) |
| EPO | APPRLICDSRVLERYLL<br>EAKEAENITTGCAEHCS<br>LNENITVPDTKVNFYA<br>WKRMEVGQQAVEVW<br>QGLALLSEAVLRGQAL<br>LVNSSQPWEPLQLHVD<br>KAVSGLRSLTTLLRALG<br>AQKEAISPPDAASAAPL<br>RTITADTFRKLFRVYSN<br>FLRGKLKLYTGEACRT<br>GDR | Kidney or bone marrow | |
| PAH | MSTAVLENPGLGRKLS<br>DFGQETSYIEDNCNQN<br>GAISLIFSLKEEVGALA<br>KVLRLFEENDVNLTHIE<br>SRPSRLKKDEYEFFTHL<br>DKRSLPALTNIIKILRHD<br>IGATVHELSRDKKKDT<br>VPWFPRTIQELDRFANQ<br>ILSYGAELDADHPGFKD<br>PVYRARRKQFADIAYN<br>YRHGQPIPRVEYMEEE<br>KKTWGTVFKTLKSLYK<br>THACYEYNHIFPLLEKY<br>CGFHEDNIPQLEDVSQF<br>LQTCTGFRLRPVAGLLS<br>SRDFLGGLAFRVFHCT<br>QYIRHGSKPMYTPEPDI<br>CHELLGHVPLFSDRSFA<br>QFSQEIGLASLGAPDEY<br>IEKLATIYWFTVEFGLC<br>KQGDSIKAYGAGLLSF<br>GELQYCLSEDPKLLPLE<br>LEKTAIQNYTVTEFQPL<br>YYVAESFNDAKEKVRN<br>FAATIPRPFSVRYDPYT<br>QRIEVLDNTQQLKILAD<br>SINSEIGILCSALQKIK | Hepatic cells | 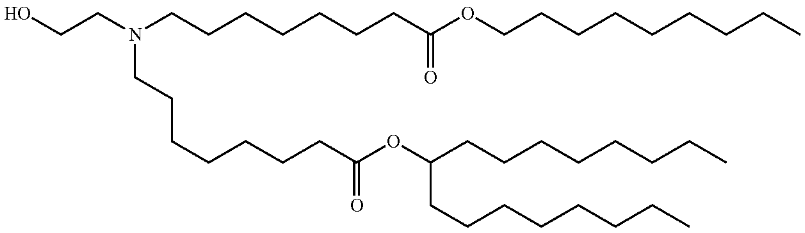<br>(50 mol %)<br>DSPC (10 mol %)<br>Cholesterol (38.5% mol %)<br>PEG-DMG (1.5 mol %)<br>OR<br>MC3 (50 mol %)<br>DSPC (10 mol %)<br>Cholesterol (38.5% mol %)<br>PEG-DMG (1.5%) |

-continued

| Payload | Sequence | Target cell/ organ | Preferred delivery formulation |
| --- | --- | --- | --- |
| CPS 1 | LSVKAQTAHIVLEDGT<br>KMKGYSFGHPSSVAGE<br>VVFNTGLGGYPEAITDP<br>AYKGQILTMANPIIGNG<br>GAPDTTALDELGLSKY<br>KDYNHWLATSLGQW<br>LQEEKVPAIYGVDTRM<br>LTKIIRDKGTMLGKEIF<br>EGQPVDFVDPNKQNLI<br>AEVSTKDVKVYGKGNP<br>TKVVAVDCGIKNNVIR<br>LLVKRGAEVHLVPWN<br>HDFTKMEYDGILIAGGP<br>GNPALAEPLIQNVRKIL<br>ESDRKEPLFGISTGNLIT<br>GLAAGAKTYKMSMAN<br>RGQNQPVLNITNKQAFI<br>TAQNHGYALDNTLPAG<br>WKPLFVNVNDQTNEGI<br>MHESKPFFAVQFHPEV<br>TPGPIDTEYLFDSFFSLI<br>KKGKATTITSVLPKPAL<br>VASRVEVSKVLILGSGG<br>LSIGQAGEFDYSGSQAV<br>KAMKEENVKTVLMNP<br>NIASVQTNEVGLKQAD<br>TVYFLPITPQFVTEVIKA<br>EQPDGLILGMGGQTAL<br>NCGVELFKRGVLKEYG<br>VKVLGTSVESIMATED<br>RQLFSDKLNEINEKIAPS<br>FAVESIEDALKAADTIG<br>YPVMIRSAYALGGLGS<br>GICPNRETLMDLSTKAF<br>AMTNQILVEKSVTGWK<br>EIEYEVVRDADDNCVT<br>VCNMENVDAMGVHTG<br>DSVVVAPAQTLSNAEF<br>QMLRRTSINVVRHLGIV<br>GECNIQFALHPTSMEYC<br>IIEVNARLSRSSALASK<br>ATGYPLAFIAAKIALGIP<br>LPEIKNVVSGKTSACFE<br>PSLDYMVTKIPRWDLD<br>RFHGTSSRIGSSMKSVG<br>EVMAIGRTFEESFQKAL<br>RMCHPSIEGFTPRLPMN<br>KEWPSNLDLRKELSEPS<br>STRIYAIAKAIDDNMSL<br>DEIEKLTYIDKWFLYK<br>MRDILNMEKTLKGLNS<br>ESMTEETLKRAKEIGFS<br>DKQISKCLGLTEAQTRE<br>LRLKKNIHPWVKQIDTL<br>AAEYPSVTNYLYVTYN<br>GQEHDVNFDDHGMMV<br>LGCGPYHIGSSVEFDW<br>CAVSSIRTLRQLGKKTV<br>VVNCNPETVSTDFDEC<br>DKLYFEELSLERILDIYH<br>QEACGGCIISVGGQIPN<br>NLAVPLYKNGVKIMGT<br>SPLQIDRAEDRSIFSAVL<br>DELKVAQAPWKAVNT<br>LNEALEFAKSVDYPCLL<br>RPSYVLSGSAMNVVFS<br>EDEMKKFLEEATRVSQ<br>EHPVVLTKFVEGAREV<br>EMDAVGDKGRVISHAI<br>SEHVEDAGVHSGDATL<br>MLPTQTISQGAIEKVKD<br>ATRKIAKAFAISGPFNV<br>QFLVKGNDVLVIECNL<br>RASRSFPFVSKTLGVDF<br>IDVATKVMIGENVDEK<br>HLPTLDHPIIPADYVAIK | Hepatic cells | 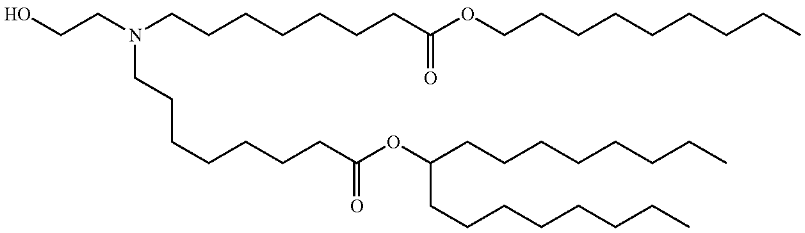<br>(50 mol %)<br>DSPC (10 mol %)<br>Cholesterol (38.5% mol %)<br>PEG-DMG (1.5 mol %)<br>OR<br>MC3 (50 mol %)<br>DSPC (10 mol %)<br>Cholesterol (38.5% mol %)<br>PEG-DMG (1.5%) |

-continued

| Payload | Sequence | Target cell/ organ | Preferred delivery formulation |
|---|---|---|---|
| | APMFSWPRLRDADPILR<br>CEMASTGEVACFGEGI<br>HTAFLKAMLSTGFKIPQ<br>KGILIGIQQSFRPRFLGV<br>AEQLHNEGFKLFATEA<br>TSDWLNANNVPATVA<br>WPSQEGQNPSLSSIRKLI<br>RDGSIDLVINLPNNNTK<br>FVHDNYVIRRTAVDSGI<br>PLLTNFQVTKLFAEAV<br>QKSRKVDSKSLFHYRQ<br>YSAGKAA | | |
| Cas9 | MKRNYILGLDIGITSVG<br>YGIIDYETRDVIDAGVR<br>LFKEANVENNEGRRSK<br>RGARRLKRRRRHRIQR<br>VKKLLFDYNLLTDHSE<br>LSGINPYEARVKGLSQK<br>LSEEEFSAALLHLAKRR<br>GVHNVNEVEEDTGNEL<br>STKEQISRNSKALEEKY<br>VAELQLERLKKDGEVR<br>GSINRFKTSDYVKEAK<br>QLLKVQKAYHQLDQSF<br>IDTYIDLLETRRTYYEG<br>PGEGSPFGWKDIKEWY<br>EMLMGHCTYFPEELRS<br>VKYAYNADLYNALND<br>LNNLVITRDENEKLEYY<br>EKFQIIENVFKQKKKPT<br>LKQIAKEILVNEEDIKG<br>YRVTSTGKPEFTNLKV<br>YHDIKDITARKEIINAE<br>LLDQIAKILTIYQSSEDI<br>QEELTNLNSELTQEEIE<br>QISNLKGYTGTHNLSLK<br>AINLILDELWHTNDNQI<br>AIFNRLKLVPKKVDLSQ<br>QKEIPTTLVDDFILSPVV<br>KRSFIQSIKVINAIIKKY<br>GLPNDIIIELAREKNSKD<br>AQKMINEMQKRNRQT<br>NERIEEIIRTTGKENAKY<br>LIEKIKLHDMQEGKCLY<br>SLEAIPLEDLLNNPFNY<br>EVDHIIPRSVSFDNSFNN<br>KVLVKQEENSKKGNRT<br>PFQYLSSSDSKISYETFK<br>KHILNLAKGKGRISKTK<br>KEYLLEERDINRFSVQK<br>DFINRNLVDTRYATRG<br>LMNLLRSYFRVNNLDV<br>KVKSINGGFTSFLRRK<br>WKFKKERNKGYKHHA<br>EDALIIANADFIFKEWK<br>KLDKAKKVMENQMFE<br>EKQAESMPEIETEQEYK<br>EIFITPHQIKHIKDFKDY<br>KYSHRVDKKPNRELIN<br>DTLYSTRKDDKGNTLI<br>VNNLNGLYDKDNDKL<br>KKLINKSPEKLLMYHH<br>DPQTYQKLKLIMEQYG<br>DEKNPLYKYYEETGNY<br>LTKYSKKDNGPVIKKIK<br>YYGNKLNAHLDITDDY<br>PNSRNKVVKLSLKPYR<br>FDVYLDNGVYKFVTVK<br>NLDVIKKENYYEVNSK<br>CYEEAKKLKKISNQAEF<br>IASFYNNDLIKINGELY<br>RVIGVNNDLLNRIEVN<br>MIDITYREYLENMNDK<br>RPPRIIKTIASKTQSIKK | Im-mune cells | 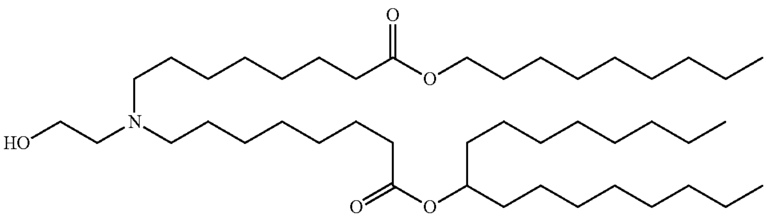<br>(50 mol %)<br>DSPC (10 mol %)<br>Beta-sitosterol (28.5% mol %)<br>Cholesterol (10 mol %)<br>PEG DMG (1.5 mol %) |

-continued

| Payload | Sequence | Target cell/ organ | Preferred delivery formulation |
|---|---|---|---|
| | YSTDILGNLYEVKSKK<br>HPQIIKKG | | |
| ADAM TS13 | AAGGILHLELLVAVGP<br>DVFQAHQEDTERYVLT<br>NLNIGAELLRDPSLGAQ<br>FRVHLVKMVILTEPEG<br>APNITANLTSSLLSVCG<br>WSQTINPEDDTDPGHA<br>DLVLYITRFDLELPDGN<br>RQVRGVTQLGGACSPT<br>WSCLITEDTGFDLGVTI<br>AHEIGHSFGLEHDGAPG<br>SGCGPSGHVMASDGAA<br>PRAGLAWSPCSRRQLL<br>SLLSAGRARCVWDPPR<br>PQPGSAGHPPDAQPGL<br>YYSANEQCRVAFGPKA<br>VACTFAREHLDMCQAL<br>SCHTDPLDQSSCSRLLV<br>PLLDGTECGVEKWCSK<br>GRCRSLVELTPIAAVHG<br>RWSSWGPRSPCSRSCG<br>GGVVTRRRQCNNPRPA<br>FGGRACVGADLQAEM<br>CNTQACEKTQLEFMSQ<br>QCARTDGQPLRSSPGG<br>ASFYHWGAAVPHSQG<br>DALCRHMCRAIGESFIM<br>KRGDSFLDGTRCMPSG<br>PREDGTLSLCVSGSCRT<br>FGCDGRMDSQQVWDR<br>CQVCGGDNSTCSPRKG<br>SFTAGRAREYVTFLTVT<br>PNLTSVYIANHRPLFTH<br>LAVRIGGRYVVAGKMS<br>ISPNTTYPSLLEDGRVE<br>YRVALTEDRLPRLEEIRI<br>WGPLQEDADIQVYRRY<br>GEEYGNLTRPDITFTYF<br>QPKPRQAWVWAAVRG<br>PCSVSCGAGLRWVNYS<br>CLDQARKELVETVQCQ<br>GSQQPPAWPEACVLEP<br>CPPYWAVGDFGPCSAS<br>CGGGLRERPVRCVEAQ<br>GSLLKTLPPARCRAGA<br>QQPAVALETCNPQPCP<br>ARWEVSEPSSCTSAGG<br>AGLALENETCVPGADG<br>LEAPVTEGPGSVDEKLP<br>APEPCVGMSCPPGWGH<br>LDATSAGEKAPSPWGSI<br>RTGAQAAHVWTPAAG<br>SCSVSCGRGLMELRFLC<br>MDSALRVPVQEELCGL<br>ASKPGSRREVCQAVPC<br>PARWQYKLAACSVSCG<br>RGVVRRILYCARAHGE<br>DDGEEILLDTQCQGLPR<br>PEPQEACSLEPCPPRWK<br>VMSLGPCSASCGLGTA<br>RRSVACVQLDQGQDVE<br>VDEAACAALVRPEASV<br>PCLIADCTYRWHVGTW<br>MECSVSCGDGIQRRRD<br>TCLGPQAQAPVPADFC<br>QHLPKPVTVRGCWAGP<br>CVGQGTPSLVPHEEAA<br>APGRTTATPAGASLEW<br>SQARGLLFSPAPQPRRL<br>LPGPQENSVQSSACGR<br>QHLEPTGTIDMRGPGQ<br>ADCAVAIGRPLGEVVT<br>LRVLESSLNCSAGDML<br>LLWGRLTWRKMCRKL | Hepatic cells | 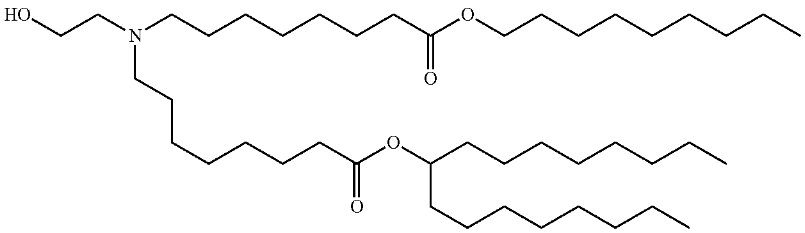<br>(50 mol %)<br>DSPC (10 mol %)<br>Cholesterol (38.5% mol %)<br>PEG-DMG (1.5 mol %)<br>OR<br>MC3 (50 mol %)<br>DSPC (10 mol %)<br>Cholesterol (38.5% mol %)<br>PEG-DMG (1.5%) |

-continued

| Payload | Sequence | Target cell/ organ | Preferred delivery formulation |
|---|---|---|---|
| | LDMTFSSKTNTLVVRQ<br>RCGRPGGGVLLRYGSQ<br>LAPETFYRECDMQLFG<br>PWGEIVSPSLSPATSNA<br>GGCRLFINVAPHARIAI<br>HALATNMGAGTEGAN<br>ASYILIRDTHSLRTTAFH<br>GQQVLYWESESSQAEM<br>EFSEGFLKAQASLRGQ<br>YWTLQSWVPEMQDPQ<br>SWKGKEGT | | |
| FOXP3 | MPNPRPGKPSAPSLALG<br>PSPGASPSWRAAPKAS<br>DLLGARGPGGTFQGRD<br>LRGGAHASSSSLNPMPP<br>SQLQLPTLPLVMVAPSG<br>ARLGPLPHLQALLDR<br>PHFMHQLSTVDAHART<br>PVLQVHPLESPAMISLT<br>PPTTATGVFSLKARPGL<br>PPGINVASLEWVSREPA<br>LLCTFPNPSAPRKDSTL<br>SAVPQSSYPLLANGVC<br>KWPGCEKVFEEPEDFL<br>KHCQADHLLDEKGRA<br>QCLLQREMVQSLEQQL<br>VLEKEKLSAMQAHLAG<br>KMALTKASSVASSDKG<br>SCCIVAAGSQGPVVPA<br>WSGPREAPDSLFAVRR<br>HLWGSHGNSTFPEFLH<br>NMDYFKFHNMRPPFTY<br>ATLIRWAILEAPEKQRT<br>LNEIYHWFTRMFAFFR<br>NHPATWKNAIRHNLSL<br>HKCFVRVESEKGAVWT<br>VDELEFRKKRSQRPSRC<br>SNPTPGP | Im-mune cells | 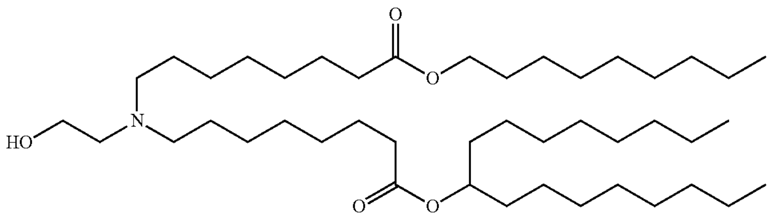<br>(50 mol %)<br>DSPC (10 mol %)<br>Beta-sitosterol (28.5% mol %)<br>Cholesterol (10 mol %)<br>PEG DMG (1.5 mol %) |
| IL-10 | SPGQGTQSENSCTHFPG<br>NLPNMLRDLRDAFSRV<br>KTFFQMKDQLDNLLLK<br>ESLLEDFKGYLGCQALS<br>EMIQFYLEEVMPQAEN<br>QDPDIKAHVNSLGENL<br>KTLRLRLRRCHRFLPCE<br>NKSKAVEQVKNAFNKL<br>QEKGIYKAMSEFDIFIN<br>YIEAYMTMKIRN | Im-mune cells | 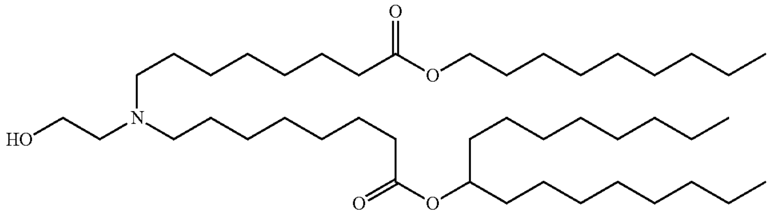<br>(50 mol %)<br>DSPC (10 mol %)<br>Beta-sitosterol (28.5% mol %)<br>Cholesterol (10 mol %)<br>PEG DMG (1.5 mol %) |
| IL-2 | APTSSSTKKTQLQLEHL<br>LLDLQMILNGINNYKNP<br>KLTRMLTFKFYMPKKA<br>TELKHLQCLEEELKPLE<br>EVLNLAQSKNFHLRPR<br>DLISNINVIVLELKGSET<br>TFMCEYADETATIVEFL<br>NRWITFCQSIISTLT | Im-mune cells | 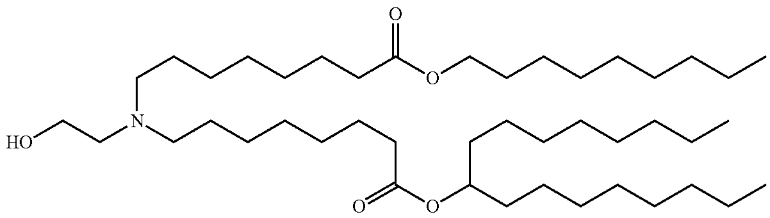<br>(50 mol %)<br>DSPC (10 mol %)<br>Beta-sitosterol (28.5% mol %)<br>Cholesterol (10 mol %)<br>PEG DMG (1.5 mol %) |

In some embodiments, the expression sequence encodes a therapeutic protein. In some embodiments, the expression sequence encodes a cytokine, e.g., IL-12p70, IL-15, IL-2, IL-18, IL-21, IFN-α, IFN-β, IL-10, TGF-beta, IL-4, or IL-35, or a functional fragment thereof. In some embodiments, the expression sequence encodes an immune checkpoint inhibitor. In some embodiments, the expression sequence encodes an agonist (e.g., a TNFR family member such as CD137L, OX40L, ICOSL, LIGHT, or CD70). In some embodiments, the expression sequence encodes a chimeric antigen receptor. In some embodiments, the expression sequence encodes an inhibitory receptor agonist (e.g., PDL1, PDL2, Galectin-9, VISTA, B7H4, or MHCII) or inhibitory receptor (e.g., PD1, CTLA4, TIGIT, LAGS, or TIM3). In some embodiments, the expression sequence encodes an inhibitory receptor antagonist. In some embodiments, the expression sequence encodes one or more TCR chains (alpha and beta chains or gamma and delta chains). In some embodiments, the expression sequence encodes a secreted T cell or immune cell engager (e.g., a bispecific antibody such as BiTE, targeting, e.g., CD3, CD137, or CD28 and a tumor-expressed protein e.g., CD19, CD20, or BCMA etc.). In some embodiments, the expression sequence encodes a transcription factor (e.g., FOXP3, HELIOS, TOX1, or TOX2). In some embodiments, the expression sequence encodes an immunosuppressive enzyme (e.g., IDO or CD39/CD73). In some embodiments, the expression sequence encodes a GvHD (e.g., anti-HLA-A2 CAR-Tregs).

In some embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit. In certain embodiments, separate circRNA molecules encoding the individual subunits may be administered in separate transfer vehicles.

3.1 Cytokines

Descriptions and/or amino acid sequences of IL-2, IL-7, IL-10, IL-12, IL-15, IL-18, IL-27beta, IFNgamma, and/or TGFbeta1 are provided herein and at the www.uniprot.org database at accession numbers: P60568 (IL-2), P29459 (IL-12A), P29460 (IL-12B), P13232 (IL-7), P22301 (IL-10), P40933 (IL-15), Q14116 (IL-18), Q14213 (IL-27beta), P01579 (IFNgamma), and/or P01137 (TGFbeta1).

3.2 PD-1 and PD-L1 Antagonists

In some embodiments, a PD-1 inhibitor is pembrolizumab, pidilizumab, or nivolumab. In some embodiments, Nivolumab is described in WO2006/121168. In some embodiments, Pembrolizumab is described in WO2009/114335. In some embodiments, Pidilizumab is described in WO2009/101611. Additional anti-PD1 antibodies are described in U.S. Pat. No. 8,609,089, US 2010028330, US 20120114649, WO2010/027827 and WO2011/066342.

In some embodiments, a PD-L1 inhibitor is atezolizumab, avelumab, durvalumab, BMS-936559, or CK-301.

Descriptions and/or amino acid sequences of heavy and light chains of PD-1, and/or PD-L1 antibodies are provided herein and at the www.drugbank.ca database at accession numbers: DB09037 (Pembrolizumab), DB09035 (Nivolumab), DB15383 (Pidilizumab), DB11595 (Atezolizumab), DB11945 (Avelumab), and DB11714 (Durvalumab).

3.3 T Cell Receptors

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain may comprise variable, joining and constant regions, and the beta chain also usually contains a short diversity region between the variable and joining regions, but this diversity region is often considered as part of the joining region. Each variable region may comprise three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR VP region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

Native TCRs exist in heterodimeric αβ or γδ forms. However, recombinant TCRs consisting of aa or ββ homodimers have previously been shown to bind to peptide MHC molecules. Therefore, the TCR of the invention may be a heterodimeric αβ TCR or may be an αα or ββ homodimeric TCR.

For use in adoptive therapy, an αβ heterodimeric TCR may, for example, be transfected as full length chains having both cytoplasmic and transmembrane domains. In certain embodiments TCRs of the invention may have an introduced disulfide bond between residues of the respective constant domains, as described, for example, in WO 2006/000830.

TCRs of the invention, particularly alpha-beta heterodimeric TCRs, may comprise an alpha chain TRAC constant domain sequence and/or a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulfide bond between the alpha and beta constant domains of the TCR.

Binding affinity (inversely proportional to the equilibrium constant $K_D$) and binding half-life (expressed as T½) can be determined by any appropriate method. It will be appreciated that doubling the affinity of a TCR results in halving the $K_D$. T½ is calculated as ln 2 divided by the off-rate (koff). So doubling of T½ results in a halving in koff. $K_D$ and koff values for TCRs are usually measured for soluble forms of the TCR, i.e. those forms which are truncated to remove cytoplasmic and transmembrane domain residues. Therefore, it is to be understood that a given TCR has an improved binding affinity for, and/or a binding half-life for the parental TCR if a soluble form of that TCR has the said characteristics. Preferably the binding affinity or binding half-life of a given TCR is measured several times, for example 3 or more times, using the same assay protocol, and an average of the results is taken.

Since the TCRs of the invention have utility in adoptive therapy, the invention includes a non-naturally occurring and/or purified and/or engineered cell, especially a T-cell, presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancers such as those of the pancreas and liver. As will be known to those skilled in the art, there are a number of suitable methods by which adoptive therapy can be carried out (see for example Rosenberg et al., (2008) Nat Rev Cancer 8(4): 299-308).

As is well-known in the art, TCRs of the invention may be subject to post-translational modifications when expressed by transfected cells. Glycosylation is one such modification, which may comprise the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Glycosylation of transfected TCRs may be controlled by mutations of the transfected gene (Kuball J et al. (2009), J Exp Med 206(2):463-475). Such mutations are also encompassed in this invention.

A TCR may be specific for an antigen in the group MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ES0-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAA0205, Mart2, Mum-2, and 3, neo-PAP, myosin class I, OS-9, pml-RARa fusion protein, PTPRK, K-ras, N-ras, Triosephosphate isomeras, GnTV, Herv-K-mel, Lage-1, Mage-C2, NA-88, Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, .beta.-Catenin, CDK4, Mum-1, p16, TAGE, PSMA, PSCA, CT7, telomerase, 43-9F, 5T4, 791Tgp72, α-fetoprotein (AFP), 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18,NB\170K, NY-CO-1, RCAS1, SDCCAG16, TA-90 (Mac-2 binding protein\cyclophilin C-associated protein), TAAL6, TAG72, TLP, and TPS.

3.4 Transcription Factors

Regulatory T cells (Treg) are important in maintaining homeostasis, controlling the magnitude and duration of the inflammatory response, and in preventing autoimmune and allergic responses.

In general, Tregs are thought to be mainly involved in suppressing immune responses, functioning in part as a "self-check" for the immune system to prevent excessive reactions. In particular, Tregs are involved in maintaining tolerance to self-antigens, harmless agents such as pollen or food, and abrogating autoimmune disease.

Tregs are found throughout the body including, without limitation, the gut, skin, lung, and liver. Additionally, Treg cells may also be found in certain compartments of the body that are not directly exposed to the external environment such as the spleen, lymph nodes, and even adipose tissue. Each of these Treg cell populations is known or suspected to have one or more unique features and additional information may be found in Lehtimaki and Lahesmaa, Regulatory T cells control immune responses through their non-redundant tissue specific features, 2013, FRONTIERS IN IMMUNOL., 4(294): 1-10, the disclosure of which is hereby incorporated in its entirety.

Typically, Tregs are known to require TGF-β and IL-2 for proper activation and development. Tregs, expressing abundant amounts of the IL-2 receptor (IL-2R), are reliant on IL-2 produced by activated T cells. Tregs are known to produce both IL-10 and TGF-β, both potent immunosuppressive cytokines. Additionally, Tregs are known to inhibit the ability of antigen presenting cells (APCs) to stimulate T cells. One proposed mechanism for APC inhibition is via CTLA-4, which is expressed by Foxp3+ Treg. It is thought that CTLA-4 may bind to B7 molecules on APCs and either block these molecules or remove them by causing internalization resulting in reduced availability of B7 and an inability to provide adequate co-stimulation for immune responses. Additional discussion regarding the origin, differentiation and function of Treg may be found in Dhamne et al., Peripheral and thymic Foxp3+ regulatory T cells in search of origin, distinction, and function, 2013, Frontiers in Immunol., 4 (253): 1-11, the disclosure of which is hereby incorporated in its entirety.

Descriptions and/or amino acid sequences of FOXP3, STAT5B, and/or HELIOS are provided herein and at the www.uniprot.org database at accession numbers: Q9BZS1 (FOXP3), P51692 (STAT5b), and/or Q9UKS7 (HELIOS).

Foxp3

In some embodiments, a transcription factor is the Forkhead box P3 transcription factor (Foxp3). Foxp3 has been shown to be a key regulator in the differentiation and activity of Treg. In fact, loss-of-function mutations in the Foxp3 gene have been shown to lead to the lethal IPEX syndrome (immune dysregulation, polyendocrinopathy, enteropathy, X-linked). Patients with IPEX suffer from severe autoimmune responses, persistent eczema, and colitis. Regulatory T (Treg) cells expressing Foxp3 play a key role in limiting inflammatory responses in the intestine (Josefowicz, S. Z. et al. Nature, 2012, 482, 395-U1510).

STAT

Members of the signal transducer and activator of transcription (STAT) protein family are intracellular transcription factors that mediate many aspects of cellular immunity, proliferation, apoptosis and differentiation. They are primarily activated by membrane receptor-associated Janus kinases (JAK). Dysregulation of this pathway is frequently observed in primary tumors and leads to increased angiogenesis, enhanced survival of tumors and immunosuppression. Gene knockout studies have provided evidence that STAT proteins are involved in the development and function of the immune system and play a role in maintaining immune tolerance and tumor surveillance.

There are seven mammalian STAT family members that have been identified: STAT1, STAT2, STAT5, STAT4, STAT5 (including STAT5A and STAT5B), and STATE.

Extracellular binding of cytokines or growth factors induce activation of receptor-associated Janus kinases, which phosphorylate a specific tyrosine residue within the STAT protein promoting dimerization via their SH2 domains. The phosphorylated dimer is then actively transported to the nucleus via an importin α/β ternary complex. Originally, STAT proteins were described as latent cytoplasmic transcription factors as phosphorylation was thought to be required for nuclear retention. However, unphosphorylated STAT proteins also shuttle between the cytosol and nucleus, and play a role in gene expression. Once STAT reaches the nucleus, it binds to a consensus DNA-recognition motif called gamma-activated sites (GAS) in the promoter region of cytokine-inducible genes and activates transcription. The STAT protein can be dephosphorylated by nuclear phosphatases, which leads to inactivation of STAT and subsequent transport out of the nucleus by a exportin-RanGTP complex.

In some embodiments, a STAT protein of the present disclosure may be a STAT protein that comprises a modification that modulates its expression level or activity. In some embodiments such modifications include, among other things, mutations that effect STAT dimerization, STAT protein binding to signaling partners, STAT protein localization or STAT protein degradation. In some embodiments, a STAT protein of the present disclosure is constitutively active. In some embodiments, a STAT protein of the present disclosure is constitutively active due to constitutive dimerization. In some embodiments, a STAT protein of the present disclosure is constitutively active due to constitutive phosphorylation as described in Onishi, M. et al., Mol. Cell. Biol. July 1998 vol. 18 no. 7 3871-3879 the entirety of which is herein incorporated by reference.

3.5 Chimeric Antigen Receptors

Chimeric antigen receptors (CARs or CAR-Ts) are genetically-engineered receptors. These engineered receptors may be inserted into and expressed by immune cells, including T cells via circular RNA as described herein. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. In some embodiments, the CAR encoded by the polynucleotide comprises (i) an antigen-binding molecule that specifically binds to a target antigen, (ii) a hinge domain, a transmembrane domain, and an intracellular domain, and (iii) an activating domain.

In some embodiments, an orientation of the CARs in accordance with the disclosure comprises an antigen binding domain (such as an scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem.

Antigen Binding Domain

CARs may be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment (scFv). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

In some embodiments, the antigen binding molecule comprises a nanobody. In some embodiments, the antigen binding molecule comprises a DARPin. In some embodiments, the antigen binding molecule comprises an anticalin or other synthetic protein capable of specific binding to target protein.

In some embodiments, the CAR comprises an antigen binding domain specific for an antigen selected from the group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HERS, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), thyroid stimulating hormone receptor (TSHR), G protein-coupled receptor class C group 5, member D (GPRCSD), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-1a), MAGE family members (including MAGE-A1, MAGE-A3 and MAGE-A4), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIR1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRLS), MUC16, 5T4, 8H9, αvβθ integrin, αvβδ integrin, alphafetoprotein (AFP), B7-H6, ca-125, CA9, CD44, CD44v7/8, CD52, E-cadherin, EMA (epithelial membrane antigen), epithelial glycoprotein-2 (EGP-2), epithelial glycoprotein-40 (EGP-40), ErbB4, epithelial tumor antigen (ETA), folate binding protein (FBP), kinase insert domain receptor (KDR), k-light chain, L1 cell adhesion molecule, MUC18,NKG2D, oncofetal antigen (h5T4), tumor/testis-antigen 1B, GAGE, GAGE-1, BAGE, SCP-1, CTZ9, SAGE, CAGE, CT10, MART-1, immunoglobulin lambda-like polypeptide 1 (IGLL1), Hepatitis B Surface Antigen Binding Protein (HBsAg), viral capsid antigen (VCA), early antigen (EA), EBV nuclear antigen (EBNA), HHV-6p41 early antigen, HHV-6B U94 latent antigen, HHV-6B p98 late antigen, cytomegalovirus (CMV) antigen, large T antigen, small T antigen, adenovirus antigen, respiratory syncytial virus (RSV) antigen, haemagglutinin (HA), neuraminidase (NA), parainfluenza type 1 antigen, parainfluenza type 2 antigen, parainfluenza type 3 antigen, parainfluenza type 4 antigen, Human Metapneumovirus (HMPV) antigen, hepatitis C virus (HCV) core antigen, HIV p24 antigen, human T-cell lympotrophic virus (HTLV-1) antigen, Merkel cell polyoma virus small T antigen, Merkel cell polyoma virus large T antigen, Kaposi sarcoma-associated herpesvirus (KSHV) lytic nuclear antigen and KSHV latent nuclear antigen. In some embodiments, an antigen binding domain comprises SEQ ID NO: 321 and/or 322.

Hinge/Spacer Domain

In some embodiments, a CAR of the instant disclosure comprises a hinge or spacer domain. In some embodiments, the hinge/spacer domain may comprise a truncated hinge/spacer domain (THD) the THD domain is a truncated version of a complete hinge/spacer domain ("CHD"). In some embodiments, an extracellular domain is from or derived from (e.g., comprises all or a fragment of) ErbB2, glycophorin A (GpA), CD2, CD3 delta, CD3 epsilon, CD3 gamma, CD4, CD7, CD8a, CD8[T CD11a (IT GAL), CD11b (IT GAM), CD11c (ITGAX), CD11d (IT GAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355

(CRT AM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. A hinge or spacer domain may be derived either from a natural or from a synthetic source.

In some embodiments, a hinge or spacer domain is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, a hinge or spacer domain is from or derived from an immunoglobulin. In some embodiments, a hinge or spacer domain is selected from the hinge/spacer regions of IgG1, IgG2, IgG3, IgG4, IgA, IgD, IgE, IgM, or a fragment thereof. In some embodiments, a hinge or spacer domain comprises, is from, or is derived from the hinge/spacer region of CD8 alpha. In some embodiments, a hinge or spacer domain comprises, is from, or is derived from the hinge/spacer region of CD28. In some embodiments, a hinge or spacer domain comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions may be derived from (i.e. comprise) a receptor tyrosine kinase (e.g., ErbB2), glycophorin A (GpA), 4-1BB/CD137, activating NK cell receptors, an immunoglobulin protein, B7-H3, BAFFR, BFAME (SEAMF8), BTEA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD1 Id, CDS, CEACAM1, CRT AM, cytokine receptor, DAP-10, DNAM1 (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, suitable intracellular signaling domain include, but are not limited to, activating Macrophage/Myeloid cell receptors CSFR1, MYD88, CD14, TIE2, TLR4, CR3, CD64, TREM2, DAP10, DAP12, CD169, DECTIN1, CD206, CD47, CD163, CD36, MARCO, TIM4, MERTK, F4/80, CD91, C1QR, LOX-1, CD68, SRA, BAI-1, ABCA7, CD36, CD31, Lactoferrin, or a fragment, truncation, or combination thereof.

In some embodiments, a receptor tyrosine kinase may be derived from (e.g., comprise) Insulin receptor (InsR), Insulin-like growth factor I receptor (IGF1R), Insulin receptor-related receptor (IRR), platelet derived growth factor receptor alpha (PDGFRa), platelet derived growth factor receptor beta (PDGFRfi). KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYRO3 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A 1 (EphA1), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphA10), EPH receptor B1 (EphB1), EPH receptor B2 (EphB2), EPH receptor B3 (EphB3), EPH receptor B4 (EphB4), EPH receptor B6 (EphB6), ret proto oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmr1), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

Costimulatory Domain

In certain embodiments, the CAR comprises a costimulatory domain. In some embodiments, the costimulatory domain comprises 4-1BB (CD137), CD28, or both, and/or an intracellular T cell signaling domain. In a preferred embodiment, the costimulatory domain is human CD28, human 4-1BB, or both, and the intracellular T cell signaling domain is human CD3 zeta (O. 4-1BB, CD28, CD3 zeta may comprise less than the whole 4-1BB, CD28 or CD3 zeta, respectively. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Amur. Rev. Pharmacol. Toxicol. 56:59-83 (2016).

In some embodiments, a costimulatory domain comprises the amino acid sequence of SEQ ID NO: 318 or 320.

Intracellular Signaling Domain

The intracellular (signaling) domain of the engineered T cells disclosed herein may provide signaling to an activating domain, which then activates at least one of the normal effector functions of the immune cell. Effector function of a T cell, for example, may be cytolytic activity or helper activity including the secretion of cytokines.

In some embodiments, suitable intracellular signaling domain include (e.g., comprise), but are not limited to 4-1BB/CD137, activating NK cell receptors, an Immunoglobulin protein, B7-H3, BAFFR, BLAME (SLAMF8), BTLA, CD 100 (SEMA4D), CD103, CD160 (BY55), CD18, CD19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD 11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, ligand that specifically binds with CD83, LIGHT, LTBR, Ly9 (CD229), Ly108, lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

CD3 is an element of the T cell receptor on native T cells, and has been shown to be an important intracellular activating element in CARs. In some embodiments, the CD3 is CD3 zeta. In some embodiments, the activating domain comprises an amino acid sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of SEQ ID NO: 319.

3.6 Trispecific Antigen-Binding Proteins and Bispecific Antigen-Binding Proteins Disclosed herein are circular RNA polypeptides encoding trispecific antigen-binding proteins (TRITEs), bispecific antigen-binding proteins (BITEs), functional fragments thereof, and pharmaceutical compositions thereof. Recombinant expression vectors useful for making circular RNA encoding trispecific antigen-binding proteins or bispecific antigen binding proteins, and cells comprising the inventive circular RNA are also provided herein. Also provided are methods of using the disclosed trispecific antigen-binding proteins or the bispecific antigen-binding proteins in the prevention and/or treatment of liver diseases, conditions and disorders. The trispecific antigen-binding proteins are capable of specifically binding to a target antigen, e.g., a cancer antigen, as well as CD3, TCR, CD16A, or NKp46, and a liver retention domain or a half-life extension domain, such as a domain binding human serum albumin (HSA). In some embodiments, the *TRITE* or BITE is created within a patient's liver post-administration of a composition comprising the inventive circular RNA polypeptides to a patient in need thereof.

In one aspect, trispecific antigen-binding proteins comprise a domain (A) which specifically binds to CD3, TCR, CD16A, or NKp46, a domain (B) which specifically binds to a half-life extension molecule or a liver retention molecule, and a domain (C) which specifically binds to a target antigen, e.g., a cancer cell antigen. The three domains in trispecific antigen-binding proteins may be arranged in any order. Thus, it is contemplated that the domain order of the trispecific antigen-binding proteins are in any of the following orders: (A)-(B)-(C), (A)-(C)-(B), (B)-(A)-(C), (B)-(C)-(A), (C)-(B)-(A), or (C)-(A)-(B).

In some embodiments, the trispecific antigen-binding proteins have a domain order of (A)-(B)-(C). In some embodiments, the trispecific antigen-binding proteins have a domain order of (A)-(C)-(B). In some embodiments, the trispecific antigen binding proteins have a domain order of (B)-(A)-(C). In some embodiments, the trispecific antigen-binding proteins have a domain order of (B)-(C)-(A). In some embodiments, the trispecific antigen-binding proteins have a domain order of (C)-(B)-(A). In some embodiments, the trispecific antigen-binding proteins have a domain order of (C)-(A)-(B).

In an embodiment, a bispecific antigen-binding protein comprises a domain (A) which specifically binds to CD3, TCR, CD16A, or NKp46, and a domain (B) which specifically binds to a target antigen. The two domains in a bispecific antigen-binding protein are arranged in any order. Thus, it is contemplated that the domain order of the bispecific antigen-binding proteins may be: (A)-(B), or (B)-(A).

The trispecific antigen-binding proteins or bispecific antigen-binding proteins described herein are designed to allow specific targeting of cells expressing a target antigen by recruiting cytotoxic T cells or NK cells. This improves efficacy compared to ADCC (antibody dependent cell-mediated cytotoxicity), which uses full length antibodies directed to a sole antigen and is not capable of directly recruiting cytotoxic T cells. In contrast, by engaging CD3 molecules expressed specifically on these cells, the trispecific antigen-binding proteins or bispecific antigen-binding proteins can cros slink cytotoxic T cells or NK cells with cells expressing a target antigen in a highly specific fashion, thereby directing the cytotoxic potential of the recruited T cell or NK cell towards the target cell. The trispecific antigen-binding proteins or bispecific antigen-binding proteins described herein engage cytotoxic T cells via binding to the surface-expressed CD3 proteins, which form part of the TCR, or CD16A or NKp46, which activates NK cells. Simultaneous binding of several trispecific antigen-binding protein or bispecific antigen-binding proteins to CD3 and to a target antigen expressed on the surface of particular cells causes T cell activation and mediates the subsequent lysis of the particular target antigen expressing cell. Thus, trispecific antigen-binding or bispecific antigen-binding proteins are contemplated to display strong, specific and efficient target cell killing. In some embodiments, the trispecific antigen-binding proteins or bispecific antigen-binding proteins described herein stimulate target cell killing by cytotoxic T cells to eliminate pathogenic cells (e.g., tumor cells, virally or bacterially infected cells, autoreactive T cells, etc). In some embodiments, cells are eliminated selectively, thereby reducing the potential for toxic side effects. In some embodiments anti-41bb or CD137 binding domains are used as the t cell engager.

Immune Cell Binding Domain

The specificity of the response of T cells is mediated by the recognition of antigen (displayed in context of a major histocompatibility complex, MHC) by the TCR. As part of the TCR, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the TCR as well as CD3 (zeta) altogether to comprise the complete TCR. Clustering of CD3 on T cells, such as by immobilized anti-CD3 antibodies leads to T cell activation similar to the engagement of the T cell receptor but independent of its clone-typical specificity.

In one aspect, the bispecific and trispecific proteins described herein comprise a domain which specifically binds to CD3. In one aspect, the trispecific proteins described herein comprise a domain which specifically binds to human CD3. In some embodiments, the trispecific proteins described herein comprise a domain which specifically binds to CD3γ. In some embodiments, the trispecific proteins described herein comprise a domain which specifically binds to CD36. In some embodiments, the trispecific proteins described herein comprise a domain which specifically binds to CD3c.

In further embodiments, the trispecific proteins described herein comprise a domain which specifically binds to the TCR. In certain instances, the trispecific proteins described herein comprise a domain which specifically binds the α chain of the TCR. In certain instances, the trispecific proteins described herein comprise a domain which specifically binds the β chain of the TCR.

In some embodiments, a trispecific antigen binding protein or bispecific antigen binding protein comprises a NKp46 specific binder. In some embodiments, a trispecific antigen binding protein or bispecific antigen binding protein comprises a CD16A specific binder.

In some embodiments, the CD3, TCR, NKp46, or CD16A binding domain of the antigen-binding protein can be any domain that binds to CD3, TCR, NKp46, or CD16A including but not limited to domains from a monoclonal antibody, a polyclonal antibody, a recombinant antibody, a human antibody, a humanized antibody. In some instances, it is beneficial for the CD3, TCR, NKp46, or CD16A binding domain to be derived from the same species in which the trispecific antigen-binding protein will ultimately be used in. For example, for use in humans, it may be beneficial for the CD3, TCR, NKp46, or CD16A binding domain of the trispecific antigen-binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3, TCR, NKp46, or CD16A binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3, TCR, NKp46, or CD16A binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3, TCR, NKp46, or CD16A binding domain described herein, e.g., a humanized or human anti-CD3, TCR, NKp46, or CD16A binding domain comprising one or more, e.g., all three, LC CDRs and one or more, e.g., all three, HC CDRs.

In some embodiments, the humanized or human anti-CD3, TCR, NKp46, or CD16A binding domain comprises a humanized or human heavy chain variable region specific to CD3, TCR, NKp46, or CD16A where the heavy chain variable region specific to CD3, TCR, NKp46, or CD16A comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In some embodiments, an anti-NKp46 binding domain comprises an antibody or fragment thereof described in U.S. patent application Ser. No. 16/451,051. In some embodiments, an anti-NKp46 binding domain comprises the antibodies BAB281, 9E2, 195314 or a fragment thereof.

In one embodiment, the anti-CD3, TCR, NKp46, or CD16A binding domain is a single chain variable fragment (scFv) comprising a light chain and a heavy chain of an amino acid sequence provided herein. In an embodiment, the anti-CD3, TCR, NKp46, or CD16A binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region.

In some embodiments, CD3, TCR, NKp46, or CD16A binding domain of trispecific antigen-binding protein has an affinity to CD3, TCR, NKp46, or CD16A on CD3, TCR, NKp46, or CD16A expressing cells with a KD of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of MSLN trispecific antigen-binding protein has an affinity to CD3ε, γ, or δ with a KD of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3, TCR, NKp46, or CD16A binding domain of trispecific antigen-binding protein has low affinity to CD3, TCR, NKp46, or CD16A, i.e., about 100 nM or greater.

The affinity to bind to CD3, TCR, NKp46, or CD16A can be determined, for example, by the ability of the trispecific antigen-binding protein itself or its CD3, TCR, NKp46, or CD16A binding domain to bind to CD3, TCR, NKp46, or CD16A coated on an assay plate; displayed on a microbial cell surface; in solution; etc. The binding activity of the trispecific antigen-binding protein itself or its CD3, TCR, NKp46, or CD16A binding domain of the present disclosure to CD3, TCR, NKp46, or CD16A can be assayed by immobilizing the ligand (e.g., CD3, TCR, NKp46, or CD16A) or the trispecific antigen-binding protein itself or its CD3, TCR, NKp46, or CD16A binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

In some embodiments, a bispecific antigen binding protein or bispecific antigen binding protein comprises a TCR binding domain. In some embodiments, a TCR binding domain is a viral antigen or a fragment thereof. In some embodiments, a viral antigen is from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., Ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses).

Linkers

In the trispecific proteins described herein, the domains are linked by internal linkers L1 and L2, where L1 links the first and second domain of the trispecific proteins and L2 links the second and third domains of the trispecific proteins. In some embodiments, linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the trispecific proteins, do not interfere with the binding domains as well as resist cleavage from proteases. For example, glycine and serine residues generally provide protease resistance. Examples of internal linkers suitable for linking the domains in the trispecific proteins include but are not limited to (GS)n, (GGS)n, (GGGS)n, (GGSG)n, (GGSGG)n, (GGGGS)n, (GGGGG)n, or (GGG)n, wherein n is 1, 2, 3, 4, 5, 6, 7, 8, 9, or 10. In one embodiment, internal linker L1 and/or L2 is (GGGGS)4 or $(GGGGS)_3$.

Half-Life Extension Domain

Contemplated herein are domains which extend the half-life of an antigen-binding domain. Such domains are contemplated to include but are not limited to Albumin binding domains, Fc domains, small molecules, and other half-life extension domains known in the art.

Human albumin (ALB) is the most abundant protein in plasma, present at about 50 mg/ml and has a half-life of around 20 days in humans. ALB serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins.

In one aspect, the trispecific proteins described herein comprise a half-life extension domain, for example a domain which specifically binds to ALB. In some embodiments, the ALB binding domain of a trispecific antigen-binding protein can be any domain that binds to ALB including but not limited to domains from a monoclonal antibody, a polyclonal antibody, a recombinant antibody, a human antibody, a humanized antibody. In some embodiments, the ALB binding domain is a single chain variable fragments (scFv), single-domain antibody such as a heavy chain variable domain (VH), a light chain variable domain (VL) and a variable domain (VHH) of camelid derived single domain antibody, peptide, ligand or small molecule entity specific for HSA. In certain embodiments, the ALB binding domain is a single-domain antibody. In other embodiments, the HSA binding domain is a peptide. In further embodiments, the HSA binding domain is a small molecule. It is contemplated that the HSA binding domain of MSLN trispecific antigen-binding protein is fairly small and no more than 25 kD, no more than 20 kD, no more than 15 kD, or no more than 10 kD in some embodiments. In certain instances, the ALB binding is 5 kD or less if it is a peptide or small molecule entity.

The half-life extension domain of a trispecific antigen-binding protein provides for altered pharmacodynamics and pharmacokinetics of the trispecific antigen-binding protein itself. As above, the half-life extension domain extends the elimination half-time. The half-life extension domain also alters pharmacodynamic properties including alteration of tissue distribution, penetration, and diffusion of the trispecific antigen-binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the trispecific antigen-binding protein, resulting in reduced side effects, such as reduced non-tumor cell cytotoxicity.

Further, the binding affinity of the half-life extension domain can be selected so as to target a specific elimination half-time in a particular trispecific antigen-binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include KD concentrations at 10 nM or less (high), between 10 nM and 100 nM (medium), and greater than 100 nM (low). As above, binding affinities to ALB are determined by known methods such as Surface Plasmon Resonance (SPR).

Liver Retention Domain

Contemplated herein are domains which allows for and promotes a higher retention of the trispecific antigen-binding protein within liver. The liver retention domain of the trispecific antigen-binding protein is directed to targeting a liver cell moiety. In an embodiment, a liver cell includes but is not limited to a hepatocyte, hepatic stellate cell, sinusoidal endothelial cell.

In an embodiment, a liver cell contains a receptor that binds to a liver targeting moiety. In an embodiment, the liver targeting moiety includes, but is not limited to lactose, cyanuric chloride, cellobiose, polylsine, polyarginine, Mannose-6-phosphate, PDGF, human serum albumin, galactoside, galactosamine, linoleic acid, Apoliopoprotein A-1, Acetyl CKNEKKNIERNNKLKQPP-amide, glycyrrhizin, lactobionic acid, Mannose-BSA, BSA, poly-ACO-HAS, KLGR peptide, hyaluronic acid, IFN-alpha, cRGD peptide, 6-phosphate-HSA, retinol, lactobiotin, galactoside, pullulan, soybean sterylglucoside, asialoorosomucoid, glycyrrhetinic acid/glycyrrhizin, linoleic acid, AMD3100, cleavable hyaluronic acid-glycyrrhetinic acid, Hepatitis B virus pre-S1 derived lipoprotein, Apo-A 1, or LDL. In an embodiment, the liver cell receptor includes but is not limited to galactose receptor, mannose receptor, scavenger receptor, low-density lipoprotein receptor, HARE, CD44, IFNα receptor, collagen type VI receptor, 6-phosphate/insulin-like growth factor 2 receptor, platelet-derived growth factor receptor β, RBP receptor, αVβ3 integrin receptor, ASGP receptor, glycyrrhetinic acid/glycyrrhizin receptor, PPAR, Heparan sulfate glycosaminoglycan receptor, CXC receptor type 4, glycyrrhetinic acid receptor, HBVP receptor, HDL receptor, scavenger receptor class B member 1 LDL receptor or combination thereof.

Target Antigen Binding Domain

The trispecific antigen-binding proteins and bispecific antigen-binding proteins described herein comprise a domain that binds to a target antigen. A target antigen is involved in and/or associated with a disease, disorder or condition, e.g., cancer. In some embodiments, a target antigen is a tumor antigen. In some embodiments, the target antigen is NY-ESO-1, SSX-2, Sp 17, AFP, Glypican-3, Gpa33, Annexin-A2, WT1, PSMA, Midkine, PRAME, Survivin, MUC-1. P53, CEA, RAS, Hsp70, Hsp27, squamous cell carcinoma antigen (SCCA), GP73, TAG-72, or a protein in the MAGE family.

In some embodiments, a target antigen is one found on a non-liver tumor cell that has metastasized into the liver. In some embodiments, a bispecific antigen-binding protein or trispecific antigen binding protein comprises a target antigen binding domain specific for group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HERS, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, or CD179a. In some embodiments, a target antigen is an antigen associated with a viral disease, e.g., a viral antigen. In some embodiments, a target antigen is a hepatitis A, hepatitis B, hepatitis C, hepatitis D or hepatitis E antigen.

The design of the trispecific antigen-binding proteins described herein allows the binding domain to a liver target antigen to be flexible in that the binding domain to a liver target antigen can be any type of binding domain, including but not limited to, domains from a monoclonal antibody, a polyclonal antibody, a recombinant antibody, a human antibody, a humanized antibody. In some embodiments, the binding domain to a liver target antigen is a single chain variable fragments (scFv), single-domain antibody such as a heavy chain variable domain (VH), a light chain variable domain (VL) and a variable domain (VHH) of camelid derived single domain antibody. In other embodiments, the binding domain to a liver target antigen is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to a liver target antigen is a ligand or peptide that binds to or associates with a target antigen.

3.7 PAH

In some embodiments, the present invention provides methods and compositions for delivering circRNA encoding PAH to a subject for the treatment of phenylketonuria (PKU). A suitable PAH circRNA encodes any full length, fragment or portion of a PAH protein which can be substituted for naturally-occurring PAH protein activity and/or reduce the intensity, severity, and/or frequency of one or more symptoms associated with PKU.

In some embodiments, a suitable RNA sequence for the present invention comprises a circRNA sequence encoding human PAH protein.

In some embodiments, a suitable RNA sequence may be an RNA sequence that encodes a homolog or an analog of human PAH. As used herein, a homolog or an analog of human PAH protein may be a modified human PAH protein containing one or more amino acid substitutions, deletions, and/or insertions as compared to a wild-type or naturally-occurring human PAH protein while retaining substantial PAH protein activity.

The present invention may be used to treat a subject who is suffering from or susceptible to Phenylketonuria (PKU). PKU is an autosomal recessive metabolic genetic disorder characterized by a mutation in the gene for the hepatic enzyme phenylalanine hydroxylase (PAH), rendering it non-functional. PAH is necessary to metabolize the amino acid phenylalanine (Phe) to the amino acid tyrosine (Tyr). When PAH activity is reduced, phenylalanine accumulates and is converted into phenylpyruvate (also known as phenylketone) which can be detected in the urine.

Phenylalanine is a large, neutral amino acid (LNAA). LNAAs compete for transport across the blood-brain barrier (BBB) via the large neutral amino acid transporter (LNAAT). Excess Phe in the blood saturates the transporter and tends to decrease the levels of other LNAAs in the brain. Because several of these other amino acids are necessary for protein and neurotransmitter synthesis, Phe buildup hinders the development of the brain, and can cause mental retardation.

In addition to hindered brain development, the disease can present clinically with a variety of symptoms including seizures, albinism hyperactivity, stunted growth, skin rashes (eczema), microcephaly, and/or a "musty" odor to the baby's sweat and urine, due to phenylacetate, one of the ketones produced). Untreated children are typically normal at birth, but have delayed mental and social skills, have a head size significantly below normal, and often demonstrate progressive impairment of cerebral function. As the child grows and develops, additional symptoms including hyperactivity, jerking movements of the arms or legs, EEG abnormalities, skin rashes, tremors, seizures, and severe learning disabilities tend to develop. However, PKU is commonly included in the routine newborn screening panel of most countries that is typically performed 2-7 days after birth.

If PKU is diagnosed early enough, an affected newborn can grow up with relatively normal brain development, but only by managing and controlling Phe levels through diet, or a combination of diet and medication. All PKU patients must adhere to a special diet low in Phe for optimal brain development. The diet requires severely restricting or eliminating foods high in Phe, such as meat, chicken, fish, eggs, nuts, cheese, legumes, milk and other dairy products. Starchy foods, such as potatoes, bread, pasta, and corn, must be monitored. Infants may still be breastfed to provide all of the benefits of breastmilk, but the quantity must also be monitored and supplementation for missing nutrients will be required. The sweetener aspartame, present in many diet foods and soft drinks, must also be avoided, as aspartame contains phenylalanine.

Throughout life, patients can use supplementary infant formulas, pills or specially formulated foods to acquire amino acids and other necessary nutrients that would otherwise be deficient in a low-phenylalanine diet. Some Phe is required for the synthesis of many proteins and is required for appropriate growth, but levels of it must be strictly controlled in PKU patients. Additionally, PKU patients must take supplements of tyrosine, which is normally derived from phenylalanine. Other supplements can include fish oil, to replace the long chain fatty acids missing from a standard Phe-free diet and improve neurological development and iron or carnitine. Another potential therapy for PKU is tetrahydrobiopterin (BH4), a cofactor for the oxidation of Phe that can reduce blood levels of Phe in certain patients. Patients who respond to BH4 therapy may also be able to increase the amount of natural protein that they can eat.

In some embodiments, the expression of PAH protein is detectable in liver, kidney, heart, spleen, serum, brain, skeletal muscle, lymph nodes, skin, and/or cerebrospinal fluid.

In some embodiments, administering the provided composition results in the expression of a PAH protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the PAH protein is detectable 1 to 96 hours after administration. For example, in some embodiments, expression of PAH protein is detectable 1 to 84 hours, 1 to 72 hours, 1 to 60 hours, 1 to 48 hours, 1 to 36 hours, 1 to 24 hours, 1 to 12 hours, 1 to 10 hours, 1 to 8 hours, 1 to 6 hours, 1 to 4 hours, 1 to 2 hours, 2 to 96 hours, 2 to 84 hours, 2 to 72 hours, 2 to 60 hours, 2 to 48 hours, 2 to 36 hours, 2 to 24 hours, 2 to 12 hours, 2 to 10 hours, 2 to 8 hours, 2 to 6 hours, 2 to 4 hours, 4 to 96 hours, 4 to 84 hours, 4 to 72 hours, 4 to 60 hours, 4 to 48 hours, 4 to 36 hours, 4 to 24 hours, 4 to 12 hours, 4 to 10 hours, 4 to 8 hours, 4 to 6 hours, 6 to 96 hours, 6 to 84 hours, 6 to 72 hours, 6 to 60 hours, 6 to 48 hours, 6 to 36 hours, 6 to 24 hours, 6 to 12 hours, 6 to 10 hours, 6 to 8 hours, 8 to 96 hours, 8 to 84 hours, 8 to 72 hours, 8 to 60 hours, 8 to 48 hours, 8 to 36 hours, 8 to 24 hours, 8 to 12 hours, 8 to 10 hours, 10 to 96 hours, 10 to 84 hours, 10 to 72 hours, 10 to 60 hours, 10 to 48 hours, 10 to 36 hours, 10 to 24 hours, 10 to 12 hours, 12 to 96 hours, 12 to 84 hours, 12 to 72 hours, 12 to 60 hours, 12 to 48 hours, 12 to 36 hours, 12 to 24 hours, 24 to 96 hours, 24 to 84 hours, 24 to 72 hours, 24 to 60 hours, 24 to 48 hours, 24 to 36 hours, 36 to 96 hours, 36 to 84 hours, 36 to 72 hours, 36 to 60 hours, 36 to 48 hours, 48 to 96 hours, 48 to 84 hours, 48 to 72 hours, 48 to 60 hours, 48 to 84 hours, 48 to 72 hours, 48 to 60 hours, 60 to 96 hours, 60 to 84 hours, 60 to 72 hours, 72 hours to 96 hours, 72 hours to 84 hours, or 84 hours to 96 hours after administration. For example, in certain embodiments, the expression of the PAH protein is detectable 6, 12, 18, 24, 30, 36, 42, 48, 54, 60, 66, and/or 72 hours after the administration. In some embodiments, the expression of the PAH protein is detectable 1 day to 7 days after the administration. For example, in some embodiments, PAH protein is detectable 1 day, 2 days, 3 days, 4 days, 5 days, 6 days, and/or 7 days after the administration. In some embodiments, the expression of the PAH protein is detectable 1 week to 8 weeks after the administration. For example, in some embodiments, the expression of the PAH protein is detectable 1 week, 2 weeks, 3 weeks, and/or 4 weeks after the administration. In some embodiments, the expression of the PAH protein is detectable after a month after the administration.

3.8 CPS1

In some embodiments, the present invention provides methods and compositions for delivering circRNA encoding CPS1 to a subject for the treatment of CPS1 deficiency. A suitable CPS1 circRNA encodes any full length, fragment or portion of a CPS1 protein which can be substituted for naturally-occurring CPS1 protein activity and/or reduce the intensity, severity, and/or frequency of one or more symptoms associated with CPS1 deficiency.

In some embodiments, a suitable RNA sequence for the present invention comprises a circRNA sequence encoding human CPS1 protein.

In some embodiments, a suitable RNA sequence may be an RNA sequence that encodes a homolog or an analog of human CPS1. As used herein, a homolog or an analog of human CPS1 protein may be a modified human CPS1 protein containing one or more amino acid substitutions, deletions, and/or insertions as compared to a wild-type or naturally-occurring human CPS1 protein while retaining substantial CPS1 protein activity.

Carbamoyl phosphate synthetase I (CPS1) catalyzes the conversion of ammonia, bicarbonate and 2 ATP with formation of carbamoyl phosphate in the first step of the urea cycle. It also plays a role in the biosynthesis of arginine, which in turn is a substrate for the biosynthesis of NO, e.g. in the case of an endotoxin shock (c.f. Shoko Tabuchi et al., Regulation of Genes for Inducible Nitric Oxide Synthase and Urea Cycle Enzymes in Rat Liver in Endotoxin Shock, Biochemical and Biophysical Research Communications 268, 221-224 (2000)). CPS 1 should be distinguished from the cytosolic enzyme CPS 2, which likewise plays a role in the urea cycle but processes the substrate glutamine. It is known that CPS 1 is localized in mitochondria and occurs in this form in large amounts in liver tissue (it accounts for 2-6% of total liver protein). Its amino acid sequence and genetic localization have long been known (c.f. Haraguchi Y. et al., Cloning and sequence of a cDNA encoding human carbamyl phosphate synthetase I: molecular analysis of hyperammonemia, Gene 1991, Nov. 1; 107 (2); 335-340; cf. also the publication WO 03/089933 A1 of the Applicant). Regarding its physiological role, reference may be made to review articles such as, for example, H. M. Holder et al., Carbamoyl phosphate synthetase: an amazing biochemical odyssey from substrate to product, CMLS, Cell. Mol. Life Sci. 56 (1999) 507-522, and the literature referred to therein, and the introduction to the publication by Mikiko Ozaki et al., Enzyme-Linked Immunosorbent Assay of Carbamoylphosphate Synthetase I: Plasma Enzyme in Rat Experimental Hepatitis and Its Clearance, Enzyme Protein 1994, 95:48:213-221.

Carbamoyl phosphate synthetase I (CPS1) deficiency is a genetic disorder characterized by a mutation in the gene for the enzyme Carbamoyl phosphate synthetase I, affecting its ability to catalyze synthesis of carbamoyl phosphate from ammonia and bicarbonate. This reaction is the first step of the urea cycle, which is important in the removal of excess urea from cells. Defects in the CPS1 protein disrupt the urea cycle and prevent the liver from properly processing excess nitrogen into urea.

In some embodiments, administering the provided composition results in the expression of a CPS1 protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the CPS1 protein is detectable 1 to 96 hours after administration. For example, in some embodiments, expression of CPS1 protein is detectable 1 to 84 hours, 1 to 72 hours, 1 to 60 hours, 1 to 48 hours, 1 to 36 hours, 1 to 24 hours, 1 to 12 hours, 1 to 10 hours, 1 to 8 hours, 1 to 6 hours, 1 to 4 hours, 1 to 2 hours, 2 to 96 hours, 2 to 84 hours, 2 to 72 hours, 2 to 60 hours, 2 to 48 hours, 2 to 36 hours, 2 to 24 hours, 2 to 12 hours, 2 to 10 hours, 2 to 8 hours, 2 to 6 hours, 2 to 4 hours, 4 to 96 hours, 4 to 84 hours, 4 to 72 hours, 4 to 60 hours, 4 to 48 hours, 4 to 36 hours, 4 to 24 hours, 4 to 12 hours, 4 to 10 hours, 4 to 8 hours, 4 to 6 hours, 6 to 96 hours, 6 to 84 hours, 6 to 72 hours, 6 to 60 hours, 6 to 48 hours, 6 to 36 hours, 6 to 24 hours, 6 to 12 hours, 6 to 10 hours, 6 to 8 hours, 8 to 96 hours, 8 to 84 hours, 8 to 72 hours, 8 to 60 hours, 8 to 48 hours, 8 to 36 hours, 8 to 24 hours, 8 to 12 hours, 8 to 10 hours, 10 to 96 hours, 10 to 84 hours, 10 to 72 hours, 10 to 60 hours, 10 to 48 hours, 10 to 36 hours, 10 to 24 hours, 10 to 12 hours, 12 to 96 hours, 12 to 84 hours, 12 to 72 hours, 12 to 60 hours, 12 to 48 hours, 12 to 36 hours, 12 to 24 hours, 24 to 96 hours, 24 to 84 hours, 24 to 72 hours, 24 to 60 hours, 24 to 48 hours, 24 to 36 hours, 36 to 96 hours, 36 to 84 hours, 36 to 72 hours, 36 to 60 hours, 36 to 48 hours, 48 to 96 hours, 48 to 84 hours, 48 to 72 hours, 48 to 60 hours, 48 to 84 hours, 48 to 72 hours, 48 to 60 hours, 60 to 96 hours, 60 to 84 hours, 60 to 72 hours, 72 hours to 96 hours, 72 hours to 84 hours, or 84 hours to 96 hours after administration. For example, in certain embodiments, the expression of the CPS1 protein is detectable 6, 12, 18, 24, 30, 36, 42, 48, 54, 60, 66, and/or 72 hours after the administration. In some embodiments, the expression of the CPS1 protein is detectable 1 day to 7 days after the administration. For example, in some embodiments, CPS1 protein is detectable 1 day, 2 days, 3 days, 4 days, 5 days, 6 days, and/or 7 days after the administration. In some embodiments, the expression of the CPS1 protein is detectable 1 week to 8 weeks after the administration. For example, in some embodiments, CPS1 protein is detectable 1 week, 2 weeks, 3 weeks, and/or 4 weeks after the administration. In some embodiments, the expression of the CPS1 protein is detectable after a month after the administration.

In some embodiments, administering of the composition results in reduced ammonia levels in a subject as compared to baseline levels before treatment. Typically, baseline levels are measured in the subject immediately before treatment. Typically, ammonia levels are measured in a biological sample. Suitable biological samples include, for example, whole blood, plasma, serum, urine or cerebral spinal fluid.

In some embodiments, administering the composition results in reduced ammonia levels in a biological sample (e.g., a serum, plasma, or urine sample) by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline levels in a subject immediately before treatment.

In some embodiments, administering the composition provided herein results in reduced ammonia levels in plasma or serum as compared to baseline ammonia levels in a subject immediately before treatment. In some embodiments, administering the provided composition results in reduced ammonia levels in plasma or serum as compared to the ammonia levels in subjects who are not treated. In some embodiments, administering the composition results in reduction of ammonia levels to about 3000 μmol/L or less, about 2750 μmol/L or less, about 2500 μmol/L or less, about 2250 μmol/L or less, about 2000 μmol/L or less, about 1750 μmol/L or less, about 1500 μmol/L or less, about 1250 μmol/L or less, about 1000 μmol/L or less, about 750 μmol/L or less, about 500 μmol/L or less, about 250 μmol/L or less, about 100 μmol/L or less or about 50 μmol/L or less in the plasma or serum of the subject. In a particular embodiment, administering the composition results in reduction of ammonia levels to about 50 μmol/L or less in the plasma or serum.

3.9 ADAMTS13

In some embodiments, the present invention provides methods and compositions for delivering circRNA encoding ADAMTS13 to a subject for the treatment of thrombotic thrombocytopenic purpura (TTP). A suitable ADAMTS13 circRNA encodes any full length ADAMTS13 protein, or functional fragment or portion thereof, which can be substituted for naturally-occurring ADAMTS13 protein and/or reduce the intensity, severity, and/or frequency of one or more symptoms associated with TTP.

In some embodiments, the RNA sequence of the present invention comprises a circRNA sequence encoding human ADAMTS13 protein.

In some embodiments, the RNA sequence may be an RNA sequence that encodes a homolog or an analog of human ADAMTS13. As used herein, a homolog or an analog of human ADAMTS13 protein may be a modified human ADAMTS13 protein containing one or more amino acid substitutions, deletions, and/or insertions as compared to a wild-type or naturally-occurring human ADAMTS13 protein while retaining substantial ADAMTS13 protein activity.

The ADAMTS13 enzyme cleaves von Willebrand factor, which, in its un-cleaved form, interacts with platelets and causes them to stick together and adhere to the walls of blood vessels, forming clots. Defects in ADAMTS13 are associated with TTP.

In some embodiments, administering the provided composition results in the expression of a ADAMTS13 protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the ADAMTS13 protein is detectable 1 to 96 hours after administration. For example, in some embodiments, expression of ADAMTS13 protein is detectable 1 to 84 hours, 1 to 72 hours, 1 to 60 hours, 1 to 48 hours, 1 to 36 hours, 1 to 24 hours, 1 to 12 hours, 1 to 10 hours, 1 to 8 hours, 1 to 6 hours, 1 to 4 hours, 1 to 2 hours, 2 to 96 hours, 2 to 84 hours, 2 to 72 hours, 2 to 60 hours, 2 to 48 hours, 2 to 36 hours, 2 to 24 hours, 2 to 12 hours, 2 to 10 hours, 2 to 8 hours, 2 to 6 hours, 2 to 4 hours, 4 to 96 hours, 4 to 84 hours, 4 to 72 hours, 4 to 60 hours, 4 to 48 hours, 4 to 36 hours, 4 to 24 hours, 4 to 12 hours, 4 to 10 hours, 4 to 8 hours, 4 to 6 hours, 6 to 96 hours, 6 to 84 hours, 6 to 72 hours, 6 to 60 hours, 6 to 48 hours, 6 to 36 hours, 6 to 24 hours, 6 to 12 hours, 6 to 10 hours, 6 to 8 hours, 8 to 96 hours, 8 to 84 hours, 8 to 72 hours, 8 to 60 hours, 8 to 48 hours, 8 to 36 hours, 8 to 24 hours, 8 to 12 hours, 8 to 10 hours, 10 to 96 hours, 10 to 84 hours, 10 to 72 hours, 10 to 60 hours, 10 to 48 hours, 10 to 36 hours, 10 to 24 hours, 10 to 12 hours, 12 to 96 hours, 12 to 84 hours, 12 to 72 hours, 12 to 60 hours, 12 to 48 hours, 12 to 36 hours, 12 to 24 hours, 24 to 96 hours, 24 to 84 hours, 24 to 72 hours, 24 to 60 hours, 24 to 48 hours, 24 to 36 hours, 36 to 96 hours, 36 to 84 hours, 36 to 72 hours, 36 to 60 hours, 36 to 48 hours, 48 to 96 hours, 48 to 84 hours, 48 to 72 hours, 48 to 60 hours, 48 to 84 hours, 48 to 72 hours, 48 to 60 hours, 60 to 96 hours, 60 to 84 hours, 60 to 72 hours, 72 hours to 96 hours, 72 hours to 84 hours, or 84 hours to 96 hours after administration. For example, in certain embodiments, the expression of the ADAMTS13 protein is detectable 6, 12, 18, 24, 30, 36, 42, 48, 54, 60, 66, and/or 72 hours after the administration. In some embodiments, the expression of the ADAMTS13 protein is detectable 1 day to 7 days after the administration. For example, in some embodiments, ADAMTS13 protein is detectable 1 day, 2 days, 3 days, 4 days, 5 days, 6 days, and/or 7 days after the administration. In some embodiments, the expression of the ADAMTS13 protein is detectable 1 week to 8 weeks after the administration. For example, in some embodiments, ADAMTS13 protein is detectable 1 week, 2 weeks, 3 weeks, and/or 4 weeks after the administration. In some embodiments, the expression of the ADAMTS13 protein is detectable after a month after the administration.

In some embodiments, administering the composition results in reduced von Willebrand factor (vWF) levels in a subject as compared to baseline vWR levels before treatment. Typically, the baseline levels are measured in the subject immediately before treatment. Typically, vWF levels are measured in a biological sample. Suitable biological samples include, for example, whole blood, plasma or serum.

In some embodiments, administering the composition results in reduced vWF levels in a biological sample taken from the subject by at least about 10%, 20%, 30%, 40%, 50%, 60%, 70%, 80%, 90%, or 95% as compared to baseline vWF levels immediately before treatment. In some embodiments, administering the composition results in reduced plasma vWF levels in the subject to less than about 2000 μM, 1500 μM, 1000 μM, 750 μM, 500 μM, 250 μM, 100 μM, 90 μM, 80 μM, 70 μM, 60 μM, 50 μM, 40 μM, or 30

In some embodiments, administering the provided composition results in reduced vWF levels in plasma or serum samples taken from the subject as compared to baseline vWF levels immediately before treatment. In some embodiments, administering the provided composition results in reduced vWF levels in plasma or serum as compared to vWF levels in subjects who are not treated. In some embodiments, administering the composition results in reduction of vWF levels to about 3000 μmol/L or less, about 2750 μmol/L or less, about 2500 μmol/L or less, about 2250 μmol/L or less, about 2000 μmol/L or less, about 1750 μmol/L or less, about 1500 μmol/L or less, about 1250 μmol/L or less, about 1000 μmol/L or less, about 750 μmol/L or less, about 500 μmol/L or less, about 250 μmol/L or less, about 100 μmol/L or less or about 50 μmol/L or less in the plasma or serum. In a particular embodiment, administering the composition results in reduction of vWF levels to about 50 μmol/L or less in the plasma or serum

4. Production of Polynucleotides

The vectors provided herein can be made using standard techniques of molecular biology. For example, the various elements of the vectors provided herein can be obtained using recombinant methods, such as by screening cDNA and genomic libraries from cells, or by deriving the polynucleotides from a vector known to include the same.

The various elements of the vectors provided herein can also be produced synthetically, rather than cloned, based on the known sequences. The complete sequence can be assembled from overlapping oligonucleotides prepared by standard methods and assembled into the complete sequence. See, e.g., Edge, Nature (1981) 292:756; Nambair et al., Science (1984) 223: 1299; and Jay et al., J. Biol. Chem. (1984) 259:631 1.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. One method of obtaining nucleotide sequences encoding the desired vector elements is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239: 1534-1536), and enzymatic filling-in of gapped oligonucleotides using T4 DNA polymerase (Queen et al., Proc. Natl. Acad. Sci. USA (1989) 86: 10029-10033) can be used.

The precursor RNA provided herein can be generated by incubating a vector provided herein under conditions permissive of transcription of the precursor RNA encoded by the vector. For example, in some embodiments a precursor RNA is synthesized by incubating a vector provided herein that comprises an RNA polymerase promoter upstream of its 5' duplex forming region and/or expression sequence with a compatible RNA polymerase enzyme under conditions permissive of in vitro transcription. In some embodiments, the vector is incubated inside of a cell by a bacteriophage RNA polymerase or in the nucleus of a cell by host RNA polymerase II.

In certain embodiments, provided herein is a method of generating precursor RNA by performing in vitro transcription using a vector provided herein as a template (e.g., a vector provided herein with a RNA polymerase promoter positioned upstream of the 5' homology region).

In certain embodiments, the resulting precursor RNA can be used to generate circular RNA (e.g., a circular RNA polynucleotide provided herein) by incubating it in the presence of magnesium ions and guanosine nucleotide or nucleoside at a temperature at which RNA circularization occurs (e.g., between 20° C. and 60° C.).

Thus, in certain embodiments provided herein is a method of making circular RNA. In certain embodiments, the method comprises synthesizing precursor RNA by transcription (e.g., run-off transcription) using a vector provided herein (e.g., a vector comprising, in the following order, a 5' homology region, a 3' group I intron fragment, a first spacer, an Internal Ribosome Entry Site (IRES), an expression sequence, a second spacer, a 5' group I intron fragment, and a 3' homology region) as a template, and incubating the resulting precursor RNA in the presence of divalent cations (e.g., magnesium ions) and GTP such that it circularizes to form circular RNA. In some embodiments, the precursor RNA disclosed herein is capable of circularizing in the absence of magnesium ions and GTP and/or without the step of incubation with magnesium ions and GTP. It has been discovered that circular RNA has reduced immunogenicity relative to a corresponding mRNA, at least partially because the mRNA contains an immunogenic 5' cap. When transcribing a DNA vector from certain promoters (e.g., a T7 promoter) to produce a precursor RNA, it is understood that the 5' end of the precursor RNA is G. To reduce the immunogenicity of a circular RNA composition that contains a low level of contaminant linear mRNA, an excess of GMP relative to GTP can be provided during transcription such that most transcripts contain a 5' GMP, which cannot be capped. Therefore, in some embodiments, transcription is carried out in the presence of an excess of GMP. In some embodiments, transcription is carried out where the ratio of GMP concentration to GTP concentration is within the range of about 3:1 to about 15:1, for example, about 3:1 to about 10:1, about 3:1 to about 5:1, about 3:1, about 4:1, or about 5:1.

In some embodiments, a composition comprising circular RNA has been purified. Circular RNA may be purified by any known method commonly used in the art, such as column chromatography, gel filtration chromatography, and size exclusion chromatography. In some embodiments, purification comprises one or more of the following steps: phosphatase treatment, HPLC size exclusion purification, and RNase R digestion. In some embodiments, purification comprises the following steps in order: RNase R digestion, phosphatase treatment, and HPLC size exclusion purification. In some embodiments, purification comprises reverse phase HPLC. In some embodiments, a purified composition contains less double stranded RNA, DNA splints, triphosphorylated RNA, phosphatase proteins, protein ligases, capping enzymes and/or nicked RNA than unpurified RNA. In some embodiments, a purified composition is less immunogenic than an unpurified composition. In some embodiments, immune cells exposed to a purified composition produce less IFN-β1, RIG-I, IL-2, IL-6, IFNγ, and/or TNFα than immune cells exposed to an unpurified composition.

5. Ionizable Lipids

In certain embodiments disclosed herein are ionizable lipids that may be used as a component of a transfer vehicle to facilitate or enhance the delivery and release of circular RNA to one or more target cells (e.g., by permeating or fusing with the lipid membranes of such target cells). In certain embodiments, an ionizable lipid comprises one or more cleavable functional groups (e.g., a disulfide) that allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells.

In some embodiments, an ionizable lipid is a lipid as described in international patent application PCT/US2018/058555.

In some of embodiments, a cationic lipid has the following formula:

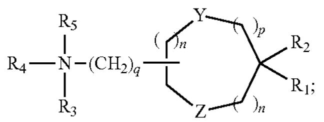

wherein:

$R_1$ and $R_2$ are either the same or different and independently optionally substituted C10-C24 alkyl, optionally substituted $C_{10}$-$C_{24}$ alkenyl, optionally substituted $C_{10}$-$C_{24}$ alkynyl, or optionally substituted C10-C24 acyl;

$R_3$ and $R_4$ are either the same or different and independently optionally substituted $C_1$-$C_6$alkyl, optionally substituted C2-C6 alkenyl, or optionally substituted C2-C6 alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl; m, n, and p are either the same or different and independently either 0 or 1 with the proviso that m, n, and p are not simultaneously 0; q is 0, 1, 2, 3, or 4; and Y and Z are either the same or different and independently O, S, or NH.

In one embodiment, $R_1$ and $R_2$ are each linoleyl, and the amino lipid is a dilinoleyl amino lipid.

In one embodiment, the amino lipid is a dilinoleyl amino lipid.

In various other embodiments, a cationic lipid has the following structure:

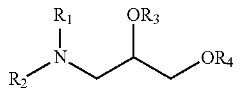

or a pharmaceutically acceptable salt, tautomer, prodrug or stereoisomer thereof, wherein:

$R_1$ and $R_2$ are each independently selected from the group consisting of H and $C_1$-$C_3$ alkyls; and $R_3$ and $R_4$ are each independently an alkyl group having from about 10 to about 20 carbon atoms, wherein at least one of $R_3$ and $R_4$ comprises at least two sites of unsaturation.

In some embodiments, $R_3$ and $R_4$ are each independently selected from dodecadienyl, tetradecadienyl, hexadecadienyl, linoleyl, and icosadienyl. In an embodiment, $R_3$ and $R_4$ and are both linoleyl. In some embodiments, $R_3$ and/or $R_4$ may comprise at least three sites of unsaturation (e.g., $R_3$ and/or $R_4$ may be, for example, dodecatrienyl, tetradectrienyl, hexadecatrienyl, linolenyl, and icosatrienyl).

In some embodiments, a cationic lipid has the following structure:

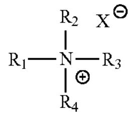

or a pharmaceutically acceptable salt, tautomer, prodrug or stereoisomer thereof, wherein:

$R_1$ and $R_2$ are each independently selected from H and $C_1$-$C_3$ alkyls;

$R_3$ and $R_4$ are each independently an alkyl group having from about 10 to about 20 carbon atoms, wherein at least one of $R_3$ and $R_4$ comprises at least two sites of unsaturation.

In one embodiment, $R_3$ and $R_4$ are the same, for example, in some embodiments $R_3$ and $R_4$ are both linoleyl ($C_{18}$-alkyl). In another embodiment, $R_3$ and $R_4$ are different, for example, in some embodiments, $R_3$ is tetradectrienyl ($C_{14}$-alkyl) and $R_4$ is linoleyl ($C_{is}$-alkyl). In a preferred embodiment, the cationic lipid(s) of the present invention are symmetrical, i.e., $R_3$ and $R_4$ are the same. In another preferred embodiment, both $R_3$ and $R_4$ comprise at least two sites of unsaturation. In some embodiments, $R_3$ and $R_4$ are each independently selected from dodecadienyl, tetradecadienyl, hexadecadienyl, linoleyl, and icosadienyl. In an embodiment, $R_3$ and $R_4$ are both linoleyl. In some embodiments, $R_3$ and/or $R_4$ comprise at least three sites of unsaturation and are each independently selected from dodecatrienyl, tetradectrienyl, hexadecatrienyl, linolenyl, and icosatrienyl.

In various embodiments, a cationic lipid has the formula:

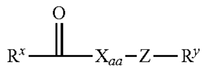

or a pharmaceutically acceptable salt, tautomer, prodrug or stereoisomer thereof, wherein:

$X_{aa}$ is a D- or L-amino acid residue having the formula —$NR^N$—$CR^1R^2$—C(C═O)—, or a peptide or a peptide of amino acid residues having the formula —{$NR^N$—$CR^1R^2$—C(C═O)}$_n$—, wherein n is an integer from 2 to 20;

$R^1$ is independently, for each occurrence, a non-hydrogen or a substituted or unsubstituted side chain of an amino acid;

$R^2$ and $R^N$ are independently, for each occurrence, hydrogen, an organic group consisting of carbon, oxygen, nitrogen, sulfur, and hydrogen atoms, or any combination of the foregoing, and having from 1 to 20 carbon atoms, $C_{(1-5)}$ alkyl, cycloalkyl, cycloalkylalkyl, $C_{(1-5)}$alkenyl, $C_{(1-5)}$alkynyl, $C_{(1-5)}$alkanoyl, $C_{(1-5)}$alkanoyloxy, $C_{(1-5)}$alkoxy, $C_{(1-5)}$alkoxy-$C_{(1-5)}$alkyl, $C_{(1-5)}$alkoxy-$C_{(1-5)}$alkoxy, $C_{(1-5)}$alkyl-amino-$C_{(1-5)}$alkyl-, $C_{(1-5)}$dialkyl-amino-$C_{(1-5)}$alkyl-, nitro-$C_{(1-5)}$alkyl, cyano-$C_{(1-5)}$alkyl, aryl-$C_{(1-5)}$alkyl, 4-biphenyl-$C_{(1-5)}$alkyl, carboxyl, or hydroxyl;

Z is —NH—, —O—, —S—, —$CH_2$S—, —$CH_2$S(O)—, or an organic linker consisting of 1-40 atoms selected from hydrogen, carbon, oxygen, nitrogen, and sulfur atoms (preferably, Z is —NH— or —O—);

$R^x$ and $R^y$ are, independently, (i) a lipophilic tail derived from a lipid (which can be naturally occurring or synthetic), e.g., a phospholipid, a glycolipid, a triacylglycerol, a glycerophospholipid, a sphingolipid, a ceramide, a sphingomyelin, a cerebroside, or a ganglioside, wherein the tail optionally includes a steroid; (ii) an amino acid terminal group selected from hydrogen, hydroxyl, amino, and an organic protecting group; or (iii) a substituted or unsubstituted $C_{(3-22)}$alkyl, $C_{(6-12)}$cycloalkyl, $C_{(6-12)}$cycloalkyl-$C_{(3-22)}$alkyl, $C_{(3-22)}$alkenyl, $C_{(3-22)}$alkynyl, $C_{(3-22)}$alkoxy, or $C_{(6-12)}$-alkoxy $C_{(3-22)}$alkyl;

In some embodiments, one of $R^x$ and $R^y$ is a lipophilic tail as defined above and the other is an amino acid terminal group. In some embodiments, both R and $R^y$ are lipophilic tails.

In some embodiments, at least one of $R^x$ and $R^y$ is interrupted by one or more biodegradable groups (e.g., —OC(O)—, —C(O)O—, —SC(O)—, —C(O)S—, —OC(S)—, —C(S)O—, —S—S—, —C(O)($NR^5$)—, —N($R^5$)C(O)—, —C(S)($NR^5$)—, —N($R^5$)C(O)—, —N($R^5$)C(O)N($R^5$)—, —OC(O)O—, —OSi($R^5$)$_2$O—, —C(O)($CR^3R^4$)C(O)O—, —OC(O)($CR^3R^4$)C(O)—, or

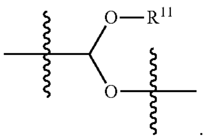

.

In some embodiments, $R^{11}$ is a $C_2$-$C_8$alkyl or alkenyl.

In some embodiments, each occurrence of $R^5$ is, independently, H or alkyl.

In some embodiments, each occurrence of $R^3$ and $R^4$ are, independently H, halogen, OH, alkyl, alkoxy, —$NH_2$, alkylamino, or dialkylamino; or $R_3$ and $R_4$, together with the carbon atom to which they are directly attached, form a cycloalkyl group. In some particular embodiments, each occurrence of $R^3$ and $R^4$ are, independently H or $C_1$-$C_4$alkyl.

In some embodiments, $R^x$ and $R^y$ each, independently, have one or more carbon-carbon double bonds.

In some embodiments, the cationic lipid is one of the following:

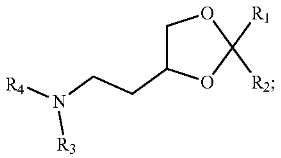

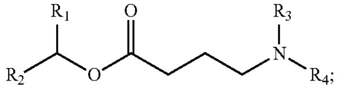

or

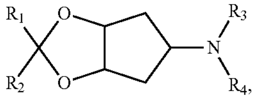

or a pharmaceutically acceptable salt, tautomer, prodrug or stereoisomer thereof, wherein:

$R_1$ and $R_2$ are each independently alkyl, alkenyl, or alkynyl, each of which can optionally substituted;

$R_3$ and $R_4$ are each independently a $C_1$-$C_6$ alkyl, or $R_3$ and $R_4$ are taken together to form an optionally substituted heterocyclic ring.

A representative useful dilinoleyl amino lipid has the formula:

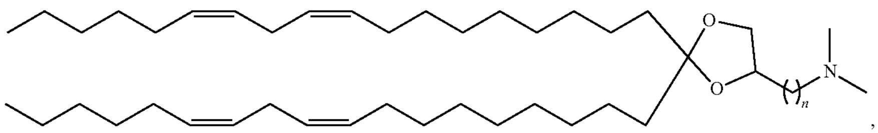

, wherein n is 0, 1, 2, 3, or 4.

In one embodiment, a cationic lipid is DLin-K-DMA. In one embodiment, a cationic lipid is DLin-KC2-DMA (DLin-K-DMA above, wherein n is 2).

In one embodiment, a cationic lipid has the following structure:

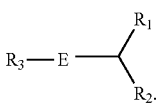

or a pharmaceutically acceptable salt, tautomer, prodrug or stereoisomer thereof, wherein:

$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl or optionally substituted $C_{10}$-$C_{30}$ acyl;

$R_3$ is H, optionally substituted $C_2$-$C_{10}$ alkyl, optionally substituted $C_2$-$C_{10}$ alkenyl, optionally substituted $C_2$-$C_{10}$ alkylyl, alkylhetrocycle, alkylpbosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K), heteroaryl, or heterocycle, or a linker ligand, for example, in some embodiments, $R_3$ is $(CH_3)_2N(CH_2)_n$—, wherein n is 1, 2, 3 or 4;

E is O, S, N(Q), C(O, OC(O), C(O)O, N(Q)C(O), C(O)N(Q), (Q)N(CO)O, O(CO)N(Q), S(O), $NS(O)_2N(Q)$, $S(O)_2$, $N(Q)S(O)_2$, SS, O═N, aryl, heteroaryl, cyclic or heterocycle, for example —C(O)O, wherein—is a point of connection to $R_3$; and Q is H, alkyl, ω-aminoalkyl ω-(substituted)aminoalkyl, ω-phosphoalkyl or ω-thiophosphoalkyl.

In one specific embodiment, the cationic lipid of Embodiments 1, 2, 3, 4 or 5 has the following structure:

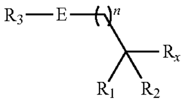

or a pharmaceutically acceptable salt, tautomer, prodrug or stereoisomer thereof, wherein:

E is O, S, N(Q), C(O), N(Q)C(O), C(O)N(Q), (Q)N(CO)O, O(CO)N(Q), S(O), $NS(O)_2N(Q)$, $S(O)_2$, $N(Q)S(O)_2$, SS, O═N, aryl, heteroaryl, cyclic or heterocycle;

Q is H, alkyl, ω-amninoalkyl, ω-(substituted)amninoalky, ω-phosphoalkyl or ω-thiophosphoalkyl;

$R_1$ and $R_2$ and $R_x$ are each independently for each occurrence H, optionally substituted $C_1$-$C_{10}$ alkyl, optionally substituted $C_{10}$-$C_{30}$ alkyl, optionally substituted $C_{10}$-$C_{30}$ alkenyl, optionally substituted $C_1$-$C_{30}$ alkynyl, optionally substituted $C_{10}$-$C_{30}$ acyl, or linker-ligand, provided that at least one of $R_1$, $R_2$ and $R_x$ is not H;

$R_3$ is H, optionally substituted $C_1$-$C_{10}$ alkyl, optionally substituted $C_2$-$C_{10}$ alkenyl, optionally substituted $C_2$-$C_{10}$alkynyl, alkylhetrocycle, alkylphosphate, alkylphosphorothioate, alkylphosphorodithioate, alkylphosphonate, alkylamine, hydroxyalkyl, ω-aminoalkyl, ω-(substituted) aminoalkyl, ω-phosphoalkyl, ω-thiophosphoalkyl, optionally substituted polyethylene glycol (PEG, mw 100-40K), optionally substituted mPEG (mw 120-40K), heteroaryl, or heterocycle, or linker-ligand; and n is 0, 1, 2, or 3

In one embodiment, the cationic lipid of Embodiments 1, 2, 3, 4 or 5 has the structure of Formula I:

I

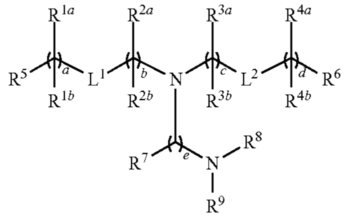

or a pharmaceutically acceptable salt, tautomer, prodrug or stereoisomer thereof, wherein:

one of $L^1$ or $L^2$ is —O(C═O)—, —(C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O—, and the other of $L^1$ or $L^2$ is —O(C═O)—, —(C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond;

$R^a$ is H or $C_1$-$C_{12}$ alkyl;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24;

e is 1 or 2; and x is 0, 1 or 2.

In some embodiments of Formula I, $L^1$ and $L^2$ are independently —O(C═O)— or —(C═O)O—.

In certain embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—. In other embodiments, $R^{1a}$ and $R^{1b}$ are not isopropyl when a is 6 or n-butyl when a is 8.

In still further embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—; and $R^{1a}$ and $R^{1b}$ are not isopropyl when a is 6 or n-butyl when a is 8.

In other embodiments of Formula I, $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula I, any one of $L^1$ or $L^2$ may be —O(C═O)— or a carbon-carbon double bond. $L^1$ and $L^2$ may each be —O(C═O)— or may each be a carbon-carbon double bond.

In some embodiments of Formula I, one of $L^1$ or $L^2$ is —O(C═O)—. In other embodiments, both $L^1$ and $L^2$ are —O(C═O)—.

In some embodiments of Formula I, one of $L^1$ or $L^2$ is —(C═O)O—. In other embodiments, both $L^1$ and $L^2$ are —(C═O)O—.

In some other embodiments of Formula I, one of $L^1$ or $L^2$ is a carbon-carbon double bond. In other embodiments, both $L^1$ and $L^2$ are a carbon-carbon double bond.

In still other embodiments of Formula I, one of $L^1$ or $L^2$ is —O(C═O)— and the other of $L^1$ or $L^2$ is —(C═O)O—. In more embodiments, one of $L^1$ or $L^2$ is —O(C═O)— and the other of $L^1$ or $L^2$ is a carbon-carbon double bond. In yet more embodiments, one of $L^1$ or $L^2$ is —(C═O)O— and the other of $L^1$ or $L^2$ is a carbon-carbon double bond.

It is understood that "carbon-carbon" double bond, as used throughout the specification, refers to one of the following structures:

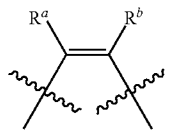

or

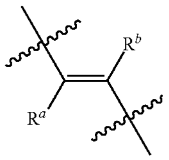

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula I have the following Formula (Ia):

(Ia)

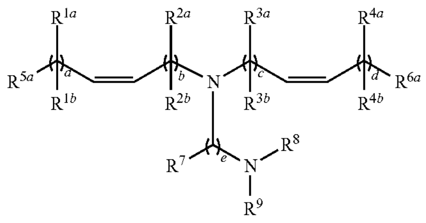

In other embodiments, the lipid compounds of Formula I have the following Formula (Ib):

(Ib)

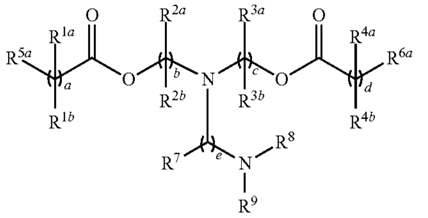

In yet other embodiments, the lipid compounds of Formula I have the following Formula (Ic):

(Ic)

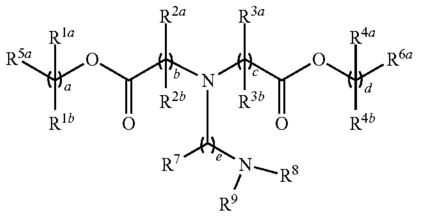

In certain embodiments of the lipid compound of Formula I, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula I, b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula I, c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain other embodiments of Formula I, d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula I, a and d are the same. In some other embodiments, b and c are the same. In some other specific embodiments, a and d are the same and b and c are the same.

The sum of a and b and the sum of c and d in Formula I are factors which may be varied to obtain a lipid of formula I having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such the sum of a and b and the sum of c and d is 12 or greater.

In some embodiments of Formula I, e is 1. In other embodiments, e is 2.

The substituents at $R^{1a}$, $R^{2a}$, $R^{3a}$ and $R^{4a}$ of Formula I are not particularly limited. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula I, $R^{1a}$, $R^{1b}$, $R^{4a}$ and $R^{4b}$ are $C_1$-$C_{12}$ alkyl at each occurrence.

In further embodiments of Formula I, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula I, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula I are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments the cycloalkyl may be substituted or not substituted. In certain other embodiments the cycloalkyl is substituted with $C_1$-$C_{12}$ alkyl, for example tert-butyl.

The substituents at $R^7$ are not particularly limited in the foregoing embodiments of Formula I. In certain embodiments at least one $R^7$ is H. In some other embodiments, $R^7$ is H at each occurrence. In certain other embodiments $R^7$ is $C_1$-$C_{12}$ alkyl.

In certain other of the foregoing embodiments of Formula I, one of $R^8$ or $R^9$ is methyl. In other embodiments, both $R^8$ and $R^9$ are methyl.

In some different embodiments of Formula I, $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In some embodiments of Embodiment 3, the first and second cationic lipids are each, independently selected from a lipid of Formula I.
In various different embodiments, the lipid of Formula I has one of the structures set forth in Table 1 below.
TABLE 1
Representative Lipids of Formula I
| No. | Structure | pKa |
|---|---|---|
| I-1 | 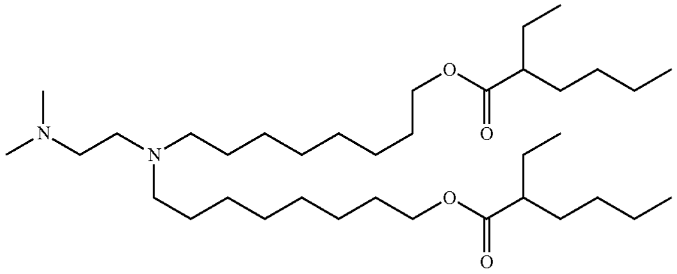 [SMILES: CCCCC(CC)C(=O)OCCCCCCCCN(CCCCCCCCOC(=O)C(CC)CCCC)CCN(C)C] | — |
| I-2 | 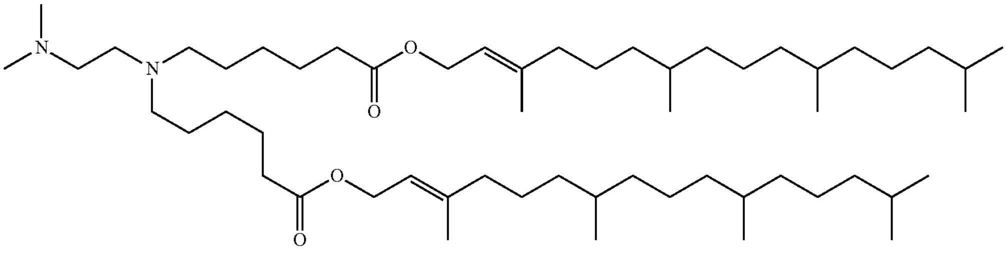 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | 5.64 |
| I-3 | 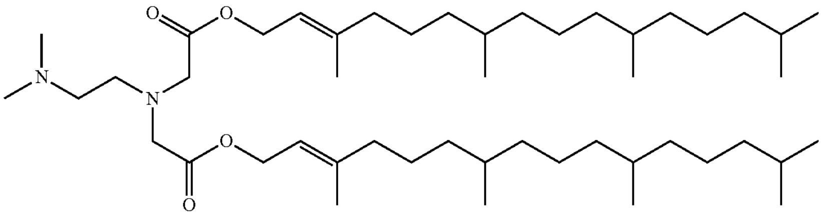 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | 7.15 |
| I-4 | 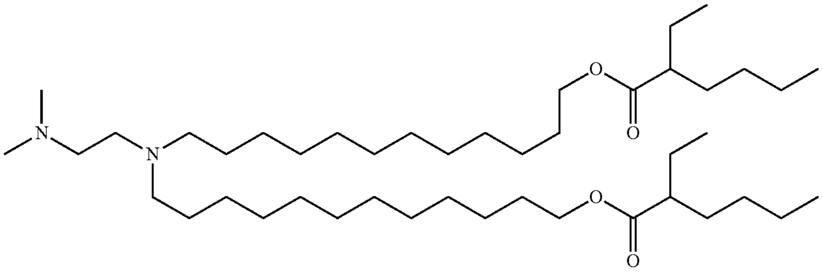 [SMILES: CCCCC(CC)C(=O)OCCCCCCCCCCCCN(CCCCCCCCCCCCOC(=O)C(CC)CCCC)CCN(C)C] | 6.43 |
| I-5 | 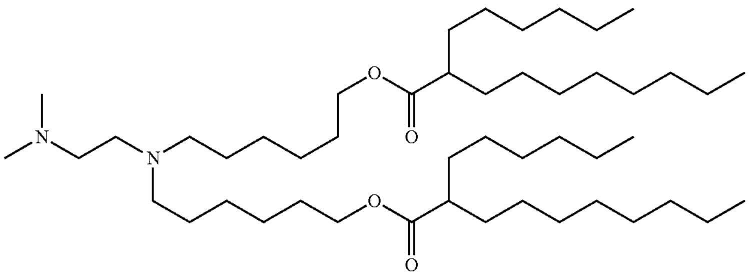 [SMILES: CCCCCCCCC(CCCCCC)C(=O)OCCCCCCN(CCCCCCOC(=O)C(CCCCCC)CCCCCCCC)CCN(C)C] | 6.28 |

TABLE 1-continued
| Representative Lipids of Formula I | | |
|---|---|---|
| No. | Structure | pKa |
| I-6 | 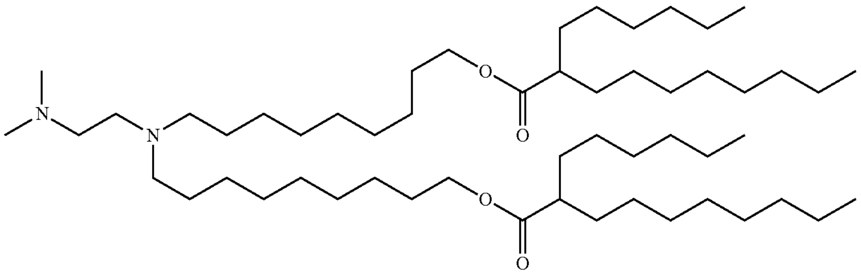 [SMILES: CCCCCCCCC(CCCCCC)C(=O)OCCCCCCCCCN(CCCCCCCCCOC(=O)C(CCCCCC)CCCCCCCC)CCN(C)C] | 6.12 |
| I-7 | 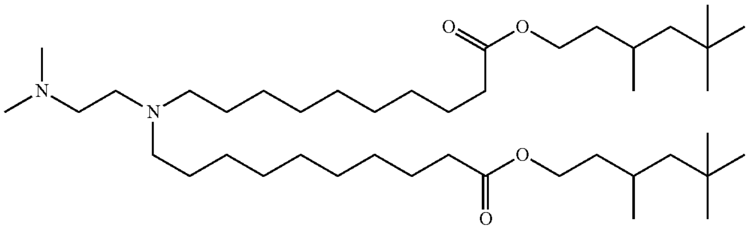 [SMILES: CC(CCOC(=O)CCCCCCCCCN(CCCCCCCCCC(=O)OCCC(C)CC(C)(C)C)CCN(C)C)CC(C)(C)C] | — |
| I-8 | 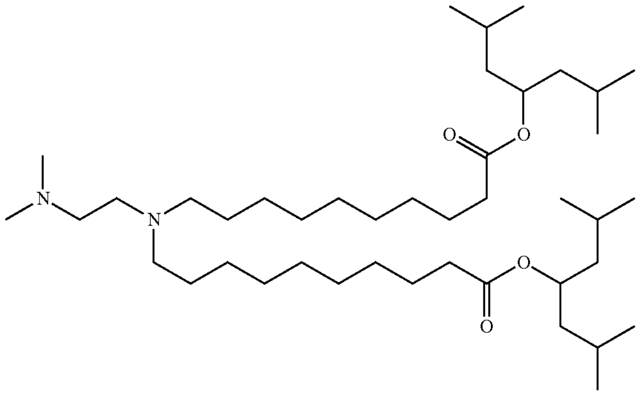 [SMILES: CC(C)CC(CC(C)C)OC(=O)CCCCCCCCCN(CCCCCCCCCC(=O)OC(CC(C)C)CC(C)C)CCN(C)C] | — |
| I-9 | 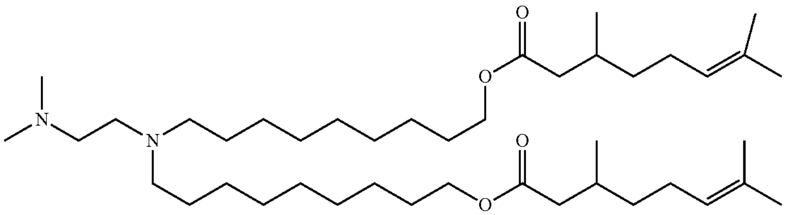 [SMILES: CC(C)=CCCC(C)CC(=O)OCCCCCCCCCN(CCCCCCCCCOC(=O)CC(C)CCC=C(C)C)CCN(C)C] | — |
| I-10 | 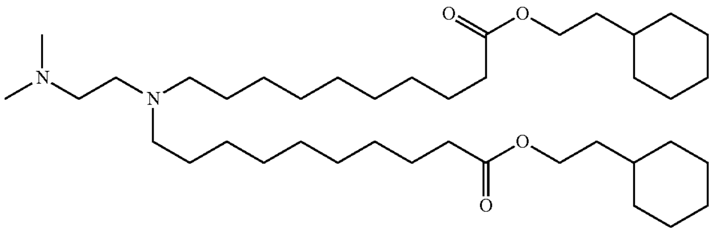 [SMILES: CN(C)CCN(CCCCCCCCCC(=O)OCCC1CCCCC1)CCCCCCCCCC(=O)OCCC1CCCCC1] | — |

TABLE 1-continued
| Representative Lipids of Formula I | | |
|---|---|---|
| No. | Structure | pKa |
| I-11 | 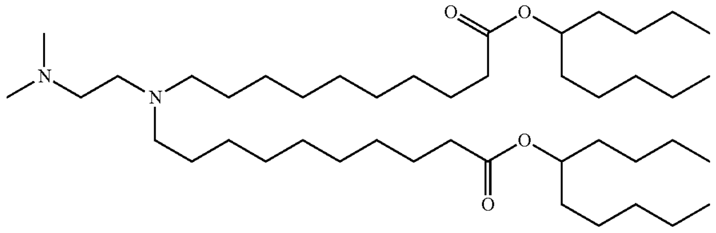 [SMILES: CCCCCC(CCCC)OC(=O)CCCCCCCCCN(CCCCCCCCCC(=O)OC(CCCC)CCCCC)CCN(C)C] | 6.36 |
| I-12 | 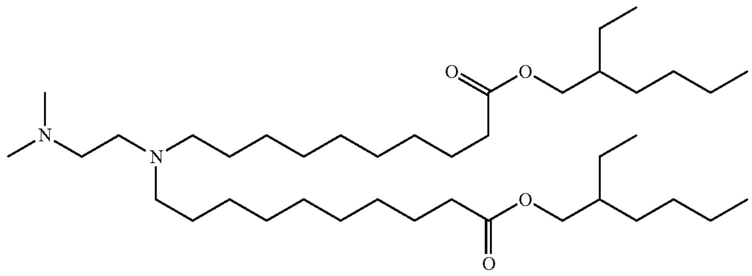 [SMILES: CCCCC(CC)COC(=O)CCCCCCCCCN(CCCCCCCCCC(=O)OCC(CC)CCCC)CCN(C)C] | — |
| I-13 | 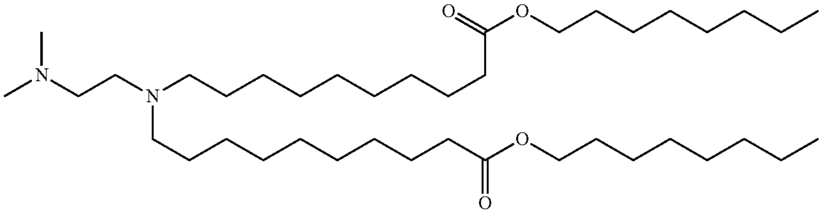 [SMILES: CCCCCCCCOC(=O)CCCCCCCCCN(CCCCCCCCCC(=O)OCCCCCCCC)CCN(C)C] | 6.51 |
| I-14 | 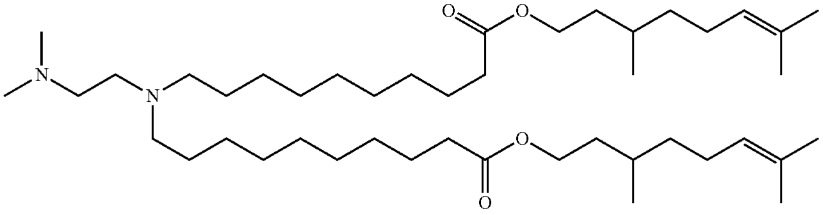 [SMILES: CC(C)=CCCC(C)CCOC(=O)CCCCCCCCCN(CCCCCCCCCC(=O)OCCC(C)CCC=C(C)C)CCN(C)C] | — |
| I-15 | 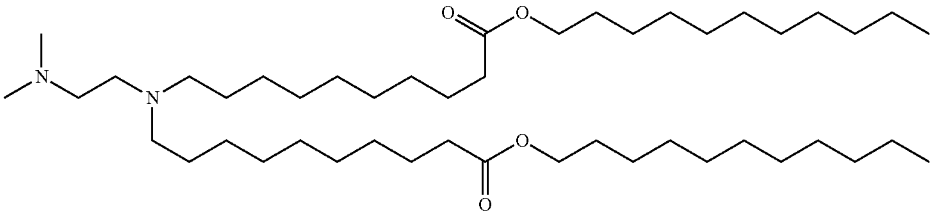 [SMILES: CCCCCCCCCCCOC(=O)CCCCCCCCCN(CCCCCCCCCC(=O)OCCCCCCCCCCC)CCN(C)C] | 6.30 |
| I-16 | 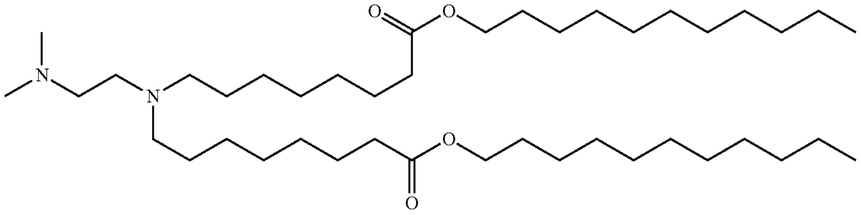 [SMILES: CCCCCCCCCCCOC(=O)CCCCCCCN(CCCCCCCC(=O)OCCCCCCCCCCC)CCN(C)C] | 6.63 |

TABLE 1-continued
| Representative Lipids of Formula I | | |
|---|---|---|
| No. | Structure | pKa |
| I-17 | 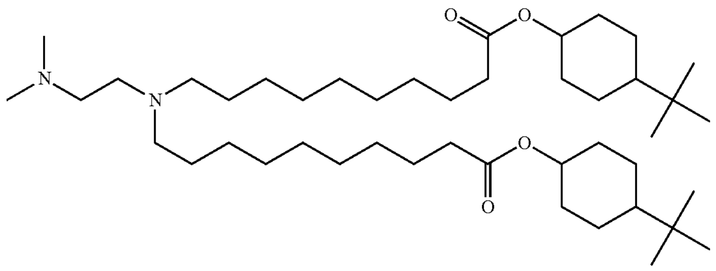 [SMILES: CN(C)CCN(CCCCCCCCCC(=O)OC1CCC(C(C)(C)C)CC1)CCCCCCCCCC(=O)OC1CCC(C(C)(C)C)CC1] | — |
| I-18 | 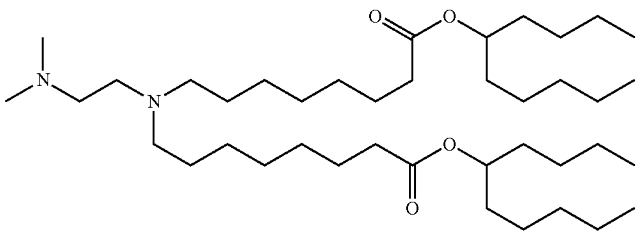 [SMILES: CCCCCC(CCCC)OC(=O)CCCCCCCN(CCCCCCCC(=O)OC(CCCC)CCCCC)CCN(C)C] | — |
| I-19 | 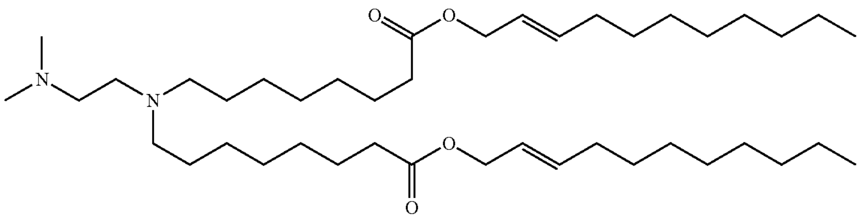 [SMILES: CCCCCCCC/C=C/COC(=O)CCCCCCCN(CCCCCCCC(=O)OC/C=C/CCCCCCCC)CCN(C)C] | 6.72 |
| I-20 | 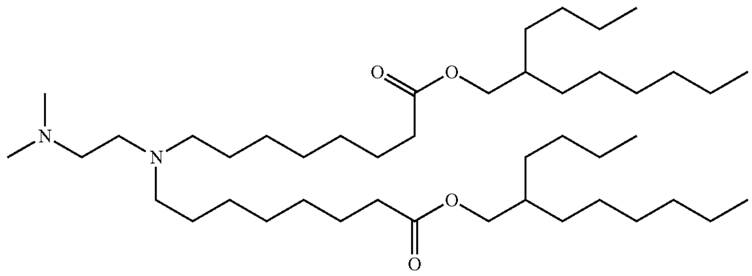 [SMILES: CCCCCCC(CCCC)COC(=O)CCCCCCCN(CCCCCCCC(=O)OCC(CCCC)CCCCCC)CCN(C)C] | 6.44 |
| I-21 | 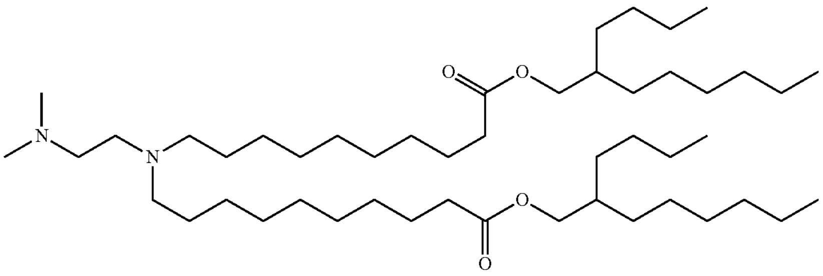 [SMILES: CCCCCCC(CCCC)COC(=O)CCCCCCCCCN(CCCCCCCCCC(=O)OCC(CCCC)CCCCCC)CCN(C)C] | 6.28 |

TABLE 1-continued
| Representative Lipids of Formula I | | |
|---|---|---|
| No. | Structure | pKa |
| I-22 | 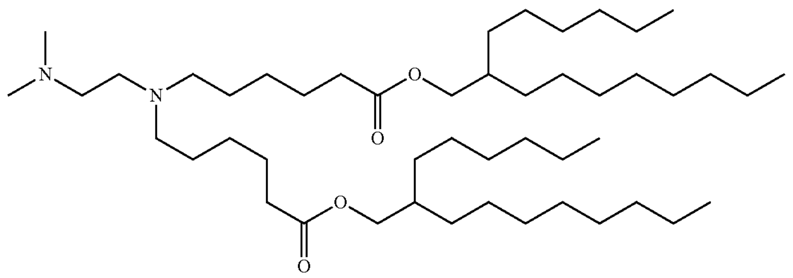 [SMILES: CCCCCCCCC(CCCCCC)COC(=O)CCCCCN(CCCCCC(=O)OCC(CCCCCC)CCCCCCCC)CCN(C)C] | 6.53 |
| I-23 | 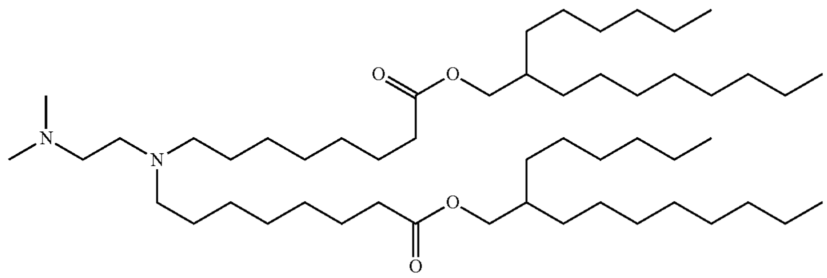 [SMILES: CCCCCCCCC(CCCCCC)COC(=O)CCCCCCCN(CCCCCCCC(=O)OCC(CCCCCC)CCCCCCCC)CCN(C)C] | 6.24 |
| I-24 | 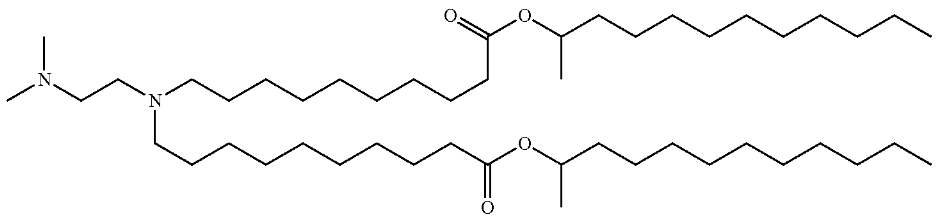 [SMILES: CCCCCCCCCCC(C)OC(=O)CCCCCCCCCN(CCCCCCCCCC(=O)OC(C)CCCCCCCCCC)CCN(C)C] | 6.28 |
| I-25 | 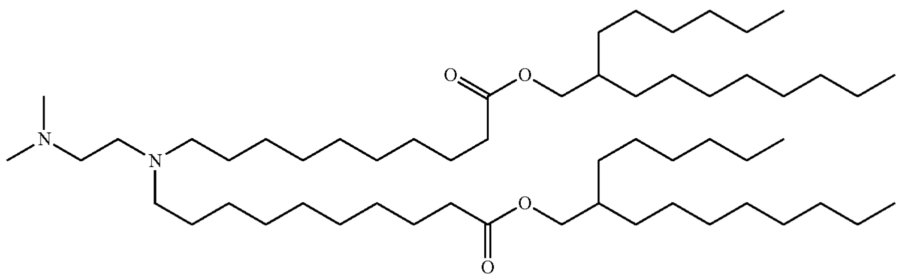 [SMILES: CCCCCCCCC(CCCCCC)COC(=O)CCCCCCCCCN(CCCCCCCCCC(=O)OCC(CCCCCC)CCCCCCCC)CCN(C)C] | 6.20 |
| I-33 | 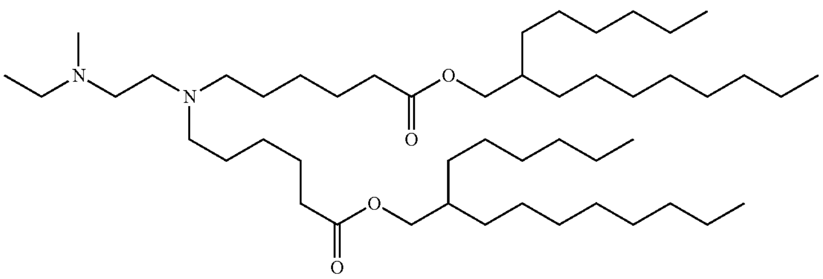 [SMILES: CCCCCCCCC(CCCCCC)COC(=O)CCCCCN(CCCCCC(=O)OCC(CCCCCC)CCCCCCCC)CCN(C)CC] | 6.27 |

TABLE 1-continued
| Representative Lipids of Formula I | | |
| --- | --- | --- |
| No. | Structure | pKa |
| I-34 | 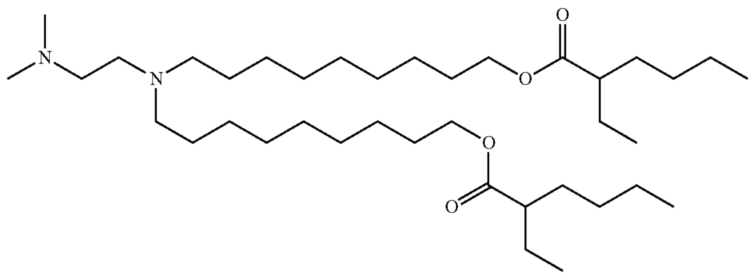 [SMILES: CCCCC(CC)C(=O)OCCCCCCCCCN(CCCCCCCCCOC(=O)C(CC)CCCC)CCN(C)C] | — |
| I-35 | 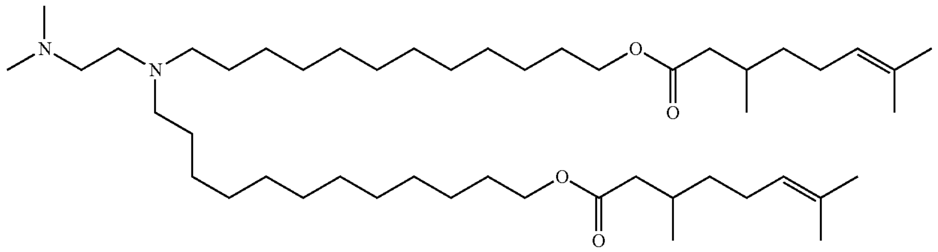 [SMILES: CC(C)=CCCC(C)CC(=O)OCCCCCCCCCCCCN(CCCCCCCCCCCCOC(=O)CC(C)CCC=C(C)C)CCN(C)C] | 6.21 |
| I-36 | 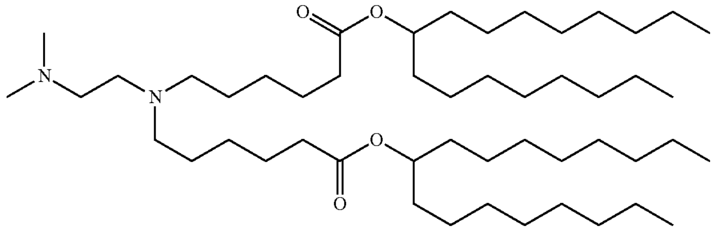 [SMILES: CCCCCCCCC(CCCCCCCC)OC(=O)CCCCCN(CCCCCC(=O)OC(CCCCCCCC)CCCCCCCC)CCN(C)C] | — |
| I-37 | 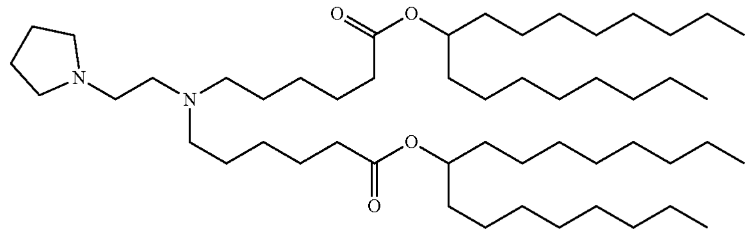 [SMILES: CCCCCCCCC(CCCCCCCC)OC(=O)CCCCCN(CCCCCC(=O)OC(CCCCCCCC)CCCCCCCC)CCN1CCCC1] | — |
| I-38 | 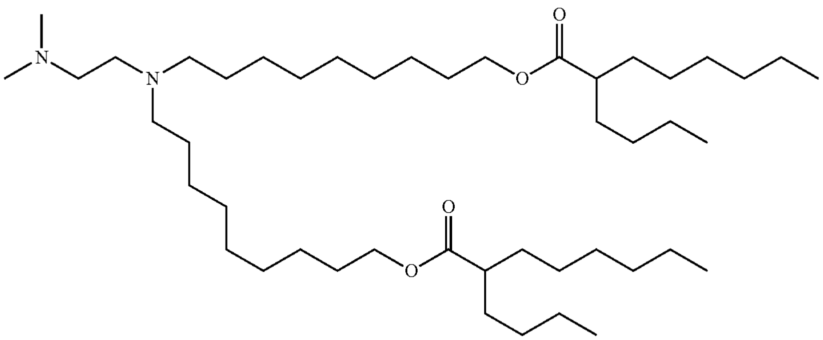 [SMILES: CCCCCCC(CCCC)C(=O)OCCCCCCCCCN(CCCCCCCCCOC(=O)C(CCCC)CCCCCC)CCN(C)C] | 6.24 |

TABLE 1-continued

Representative Lipids of Formula I

| No. | Structure | pKa |
| --- | --- | --- |
| I-39 | 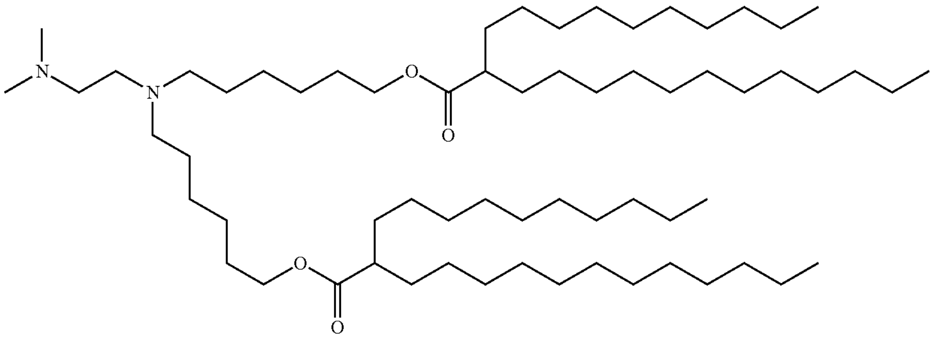 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] | 5.82 |
| I-40 | 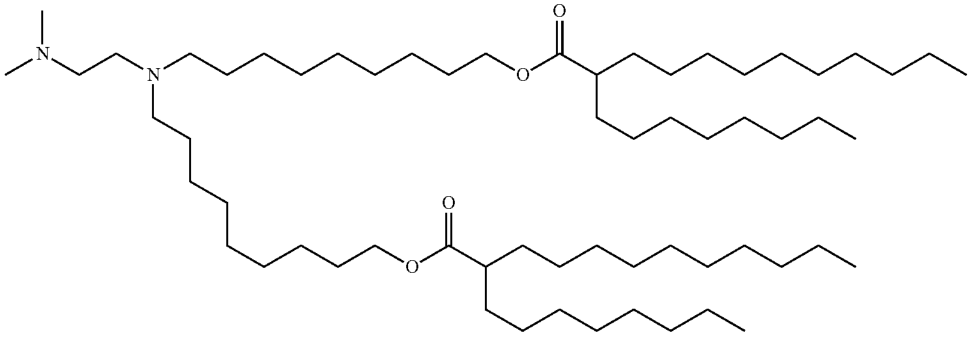 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | 6.38 |
| I-41 | 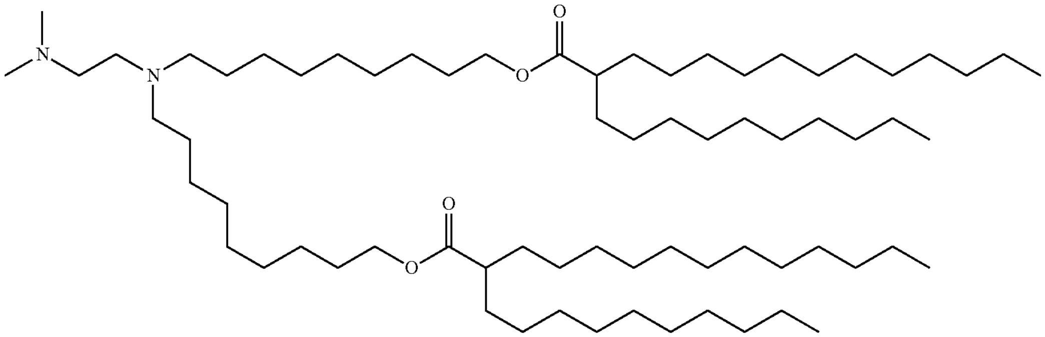 [SMILES: CCCCCCCCCCCCC(CCCCCCCCCC)C(=O)OCCCCCCCCCN(CCCCCCCCCOC(=O)C(CCCCCCCCCC)CCCCCCCCCCCC)CCN(C)C] | 5.91 |

In some embodiments, the cationic lipid of Embodiments 1, 2, 3, 4 or 5 has a structure of Formula II:

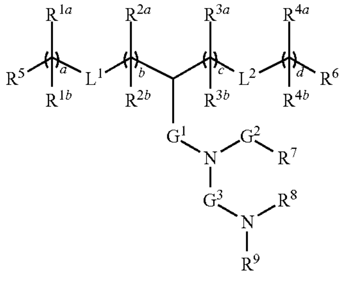

II or a pharmaceutically acceptable salt, tautomer, prodrug or stereoisomer thereof, wherein:

one of $L^1$ or $L^2$ is —O(C═O)—, —(C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O—, and the other of $L^1$ or $L^2$ is —O(C═O)—, —(C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$—
or
—NR$^a$C(═O)O— or a direct bond;

$G^1$ is $C_1$-$C_2$ alkylene, —(C═O)—, —O(C═O)—, —SC(═O)—, —NR$^a$C(═O)— or a direct bond;

$G^2$ is —C(═O)—, —(C═O)O—, —C(═O)S—, —C(═O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_2$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, forma 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C═O)—, —(C═O)O— or a direct bond. In other embodiments, $G^1$ and $G^2$ are each independently —(C═O)— or a direct bond. In some different embodiments, $L^1$ and $L^2$ are each independently —O(C═O)—, —(C═O)O— or a direct bond; and $G^1$ and $G^2$ are each independently —(C═O)— or a direct bond.

In some different embodiments of Formula (II), $L^1$ and $L^2$ are each independently —C(═O)—, —O—, —$S(O)_x$—, —S—S—, —C(═O)S—, —SC(═O)—, —$NR^a$—, —$NR^a$C(═O)—, —C(═O)$NR^a$—, —$NR^a$C(═O)$NR^a$, —OC(═O)$NR^a$—, —$NR^a$C(═O)O—, —$NR^aS(O)_x$ $NR^a$—, —$NR^aS(O)_x$ or —$S(O)_xNR^a$—.

In other of the foregoing embodiments of Formula (II), the lipid compound has one of the following Formulae (IIA) or (IIB):

(IIA)

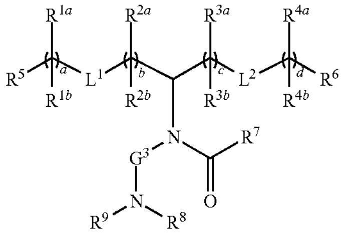

or (IIB)

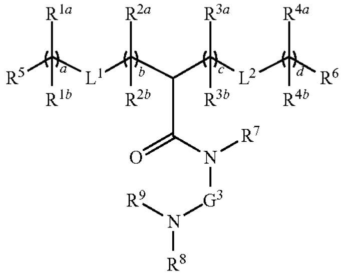

In some embodiments of Formula (II), the lipid compound has Formula (IIA). In other embodiments, the lipid compound has Formula (IIB).

In any of the foregoing embodiments of Formula (II), one of $L^1$ or $L^2$ is —O(C═O)—. For example, in some embodiments each of $L^1$ and $L^2$ are —O(C═O)—.

In some different embodiments of Formula (II), one of $L^1$ or $L^2$ is —(C═O)O—. For example, in some embodiments each of $L^1$ and $L^2$ is —(C═O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$, is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following Formulae (IIC) or (HD).

(IIC)

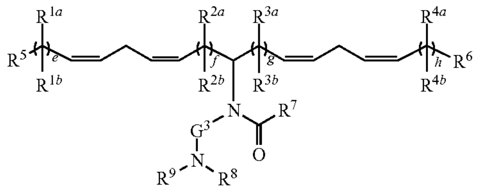

or (IID)

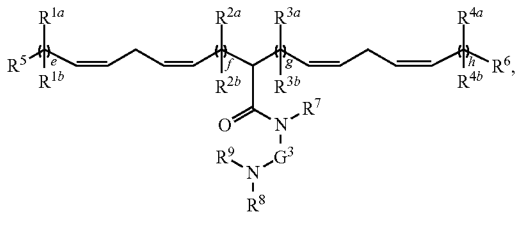

wherein e, f, g and h are each independently an integer from 1 to 12.

In some embodiments of Formula (II), the lipid compound has Formula (IIC). In other embodiments, the lipid compound has Formula (IID).

In various embodiments of Formulae (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7.

In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), his 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, his 11. In yet other embodiments, his 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_1$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with $-(C{=}O)OR^b$, $-O(C{=}O)R^b$, $-C({=}O)R^b$, $-OR^b$, $-S(O)_xR^b$, $-S-SR^b$, $-C({=}O)SR^b$, $-SC({=}O)R^b$, $-NR^aR^b$, $-NR^aC({=}O)R^b$, $-C({=}O)NR^aR^b$, $-NR^aC({=}O)NR^aR^b$, $-OC({=}O)NR^aR^b$, $-NR^aC({=}O)OR^b$, $-NR^aS(O)_xNR^aR^b$, $-NR^aS(O)_xR^b$ or $-S(O)_xNR^aR^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with $-(C{=}O)OR^b$ or $-O(C{=}O)R^b$.

In some of the foregoing embodiments of Formula (II), $R^b$ is branched $C_1$-$C_{16}$ alkyl. For example, in some embodiments $R^b$ has one of the following structures:

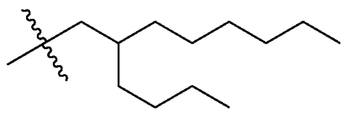

;

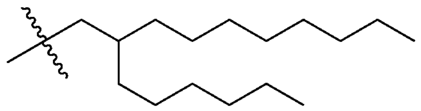

;

-continued

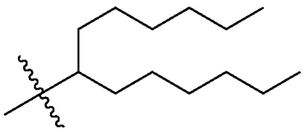

;

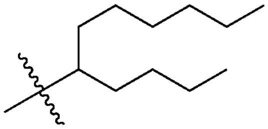

;

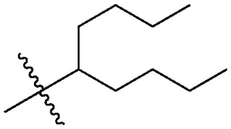

or

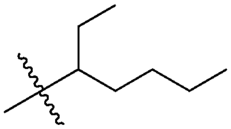

.

In certain other of the foregoing embodiments of Formula (II), one of $R^8$ or $R^9$ is methyl. In other embodiments, both $R^1$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In certain embodiments of Embodiment 3, the first and second cationic lipids are each, independently selected from a lipid of Formula II.

In still other embodiments of the foregoing lipids of Formula (II), $G^3$ is $C_2$-$C_4$ alkylene, for example $C_3$ alkylene. In various different embodiments, the lipid compound has one of the structures set forth in Table 2 below

TABLE 2

Representative Lipids of Formula (II)

| No. | Structure | pKa |
|---|---|---|
| II-1 | 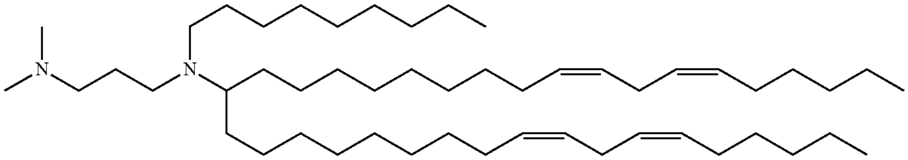 [SMILES: CCCCC/C=C\C/C=C\CCCCCCCCC(CCCCCCCC/C=C\C/C=C\CCCCC)N(CCCCCCCCC)CCCN(C)C] | 5.64 |
| II-2 | 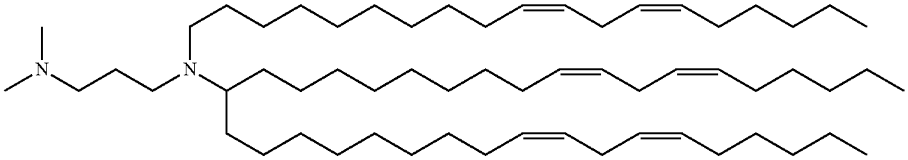 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | — |
| II-3 | 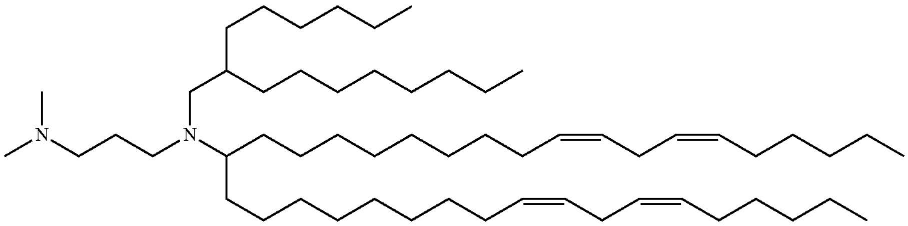 [SMILES: CCCCC/C=C\C/C=C\CCCCCCCCC(CCCCCCCC/C=C\C/C=C\CCCCC)N(CCCN(C)C)CC(CCCCCC)CCCCCCCC] | — |
| II-4 | 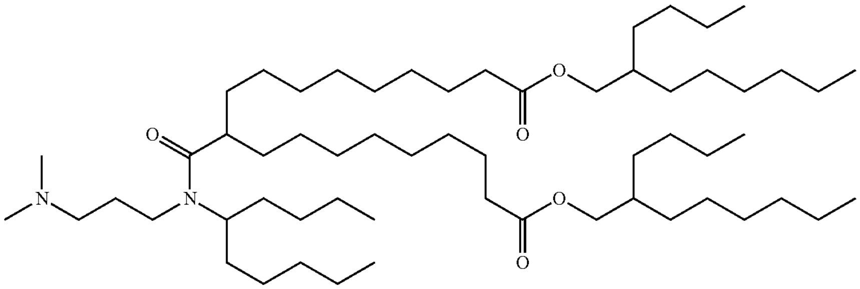 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | — |
| II-5 | 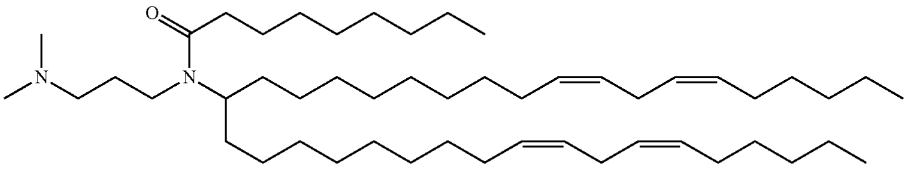 [SMILES: CCCCC/C=C\C/C=C\CCCCCCCCC(CCCCCCCC/C=C\C/C=C\CCCCC)N(CCCN(C)C)C(=O)CCCCCCCC] | 6.27 |

TABLE 2-continued
Representative Lipids of Formula (II)
| No. | Structure | pKa |
| --- | --- | --- |
| II-6 | 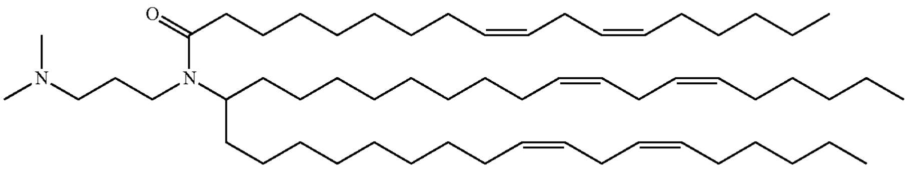 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | 6.14 |
| II-7 | 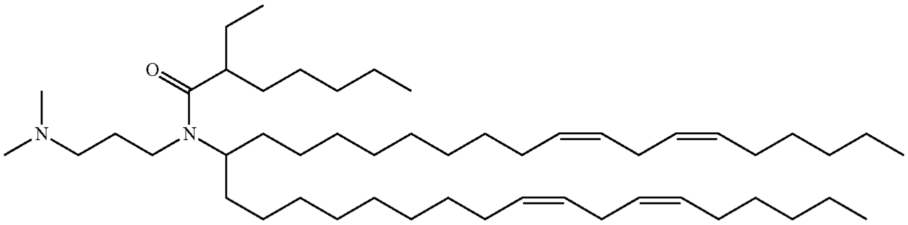 [SMILES: CCCCC/C=C\C/C=C\CCCCCCCCC(CCCCCCCC/C=C\C/C=C\CCCCC)N(CCCN(C)C)C(=O)C(CC)CCCCC] | 5.93 |
| II-8 | 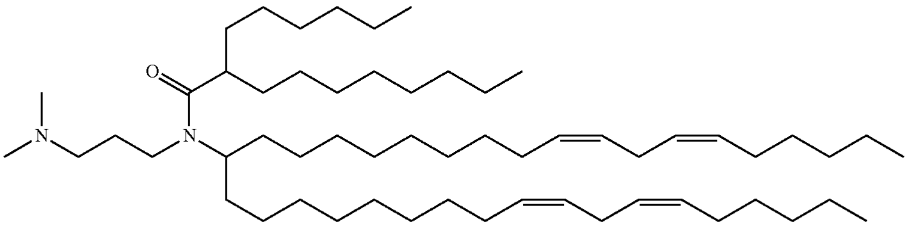 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | 5.35 |
| II-9 | 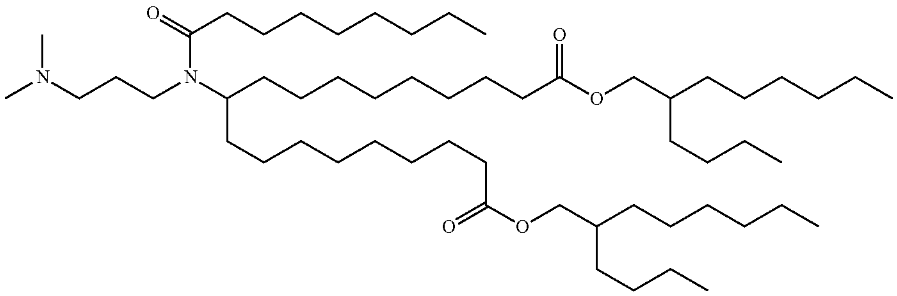 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | 6.27 |
| II-10 | 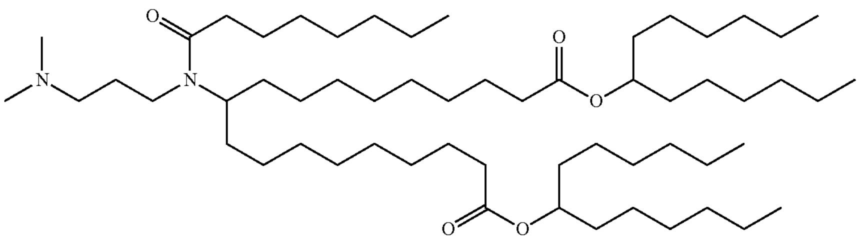 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | 6.16 |
| II-11 | 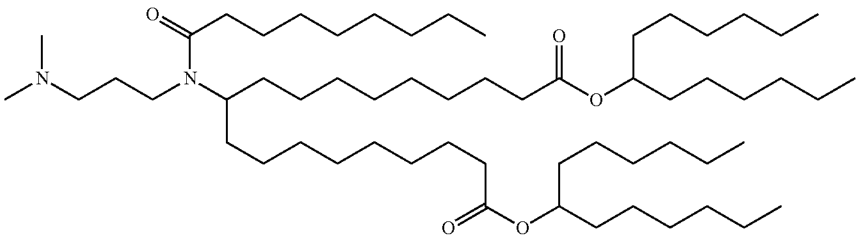 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | 6.13 |

TABLE 2-continued
| Representative Lipids of Formula (II) | | |
|---|---|---|
| No. | Structure | pKa |
| II-12 | 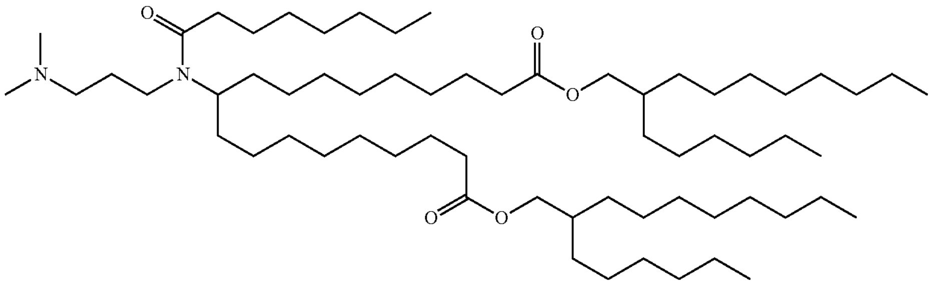 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | 6.21 |
| II-13 | 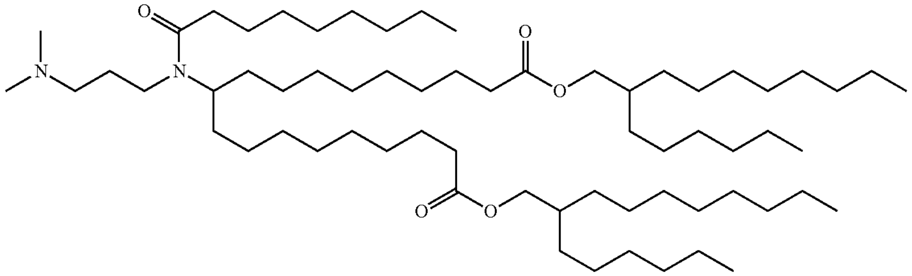 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] | 6.22 |
| II-14 | 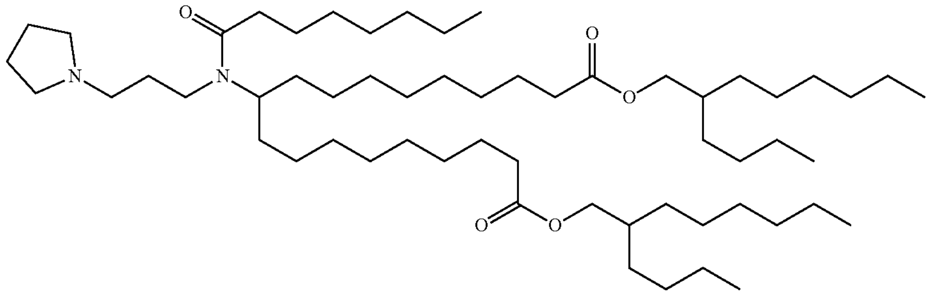 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] | 6.33 |
| II-15 | 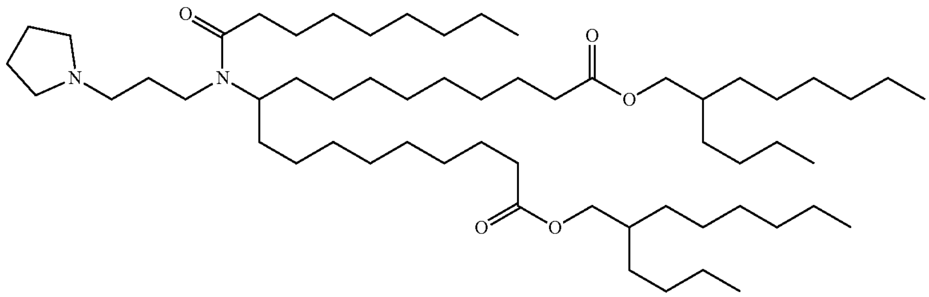 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] | 6.32 |
| II-16 | 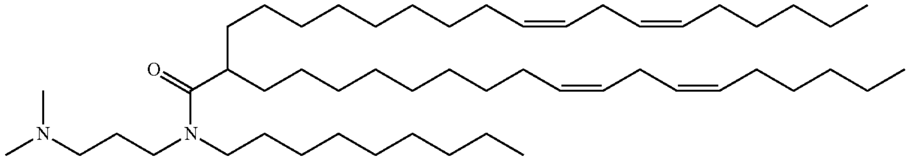 [SMILES: CCCCC/C=C\C/C=C\CCCCCCCCC(CCCCCCCC/C=C\C/C=C\CCCCC)C(=O)N(CCCCCCCCC)CCCN(C)C] | 6.37 |

TABLE 2-continued
| Representative Lipids of Formula (II) | | |
|---|---|---|
| No. | Structure | pKa |
| II-17 | 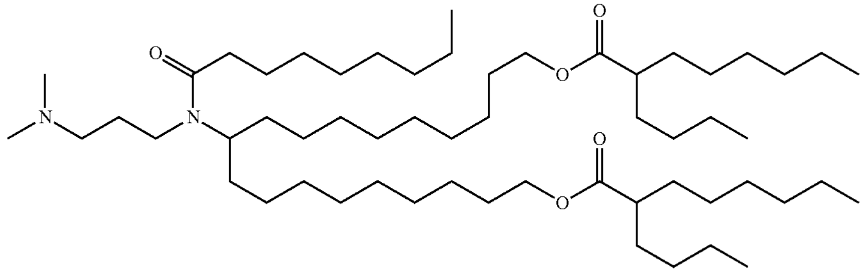 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] | 6.27 |
| II-18 | 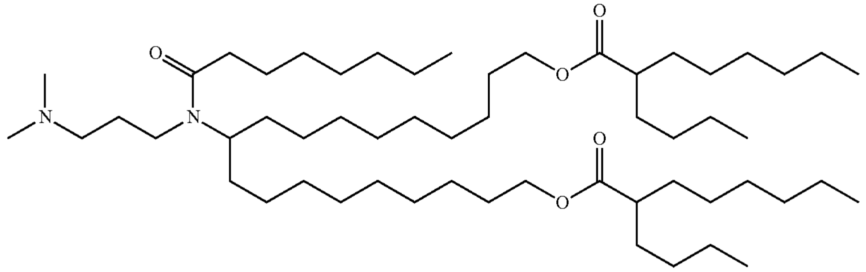 [SMILES: CCCCCCCC(=O)N(CCCN(C)C)C(CCCCCCCCCOC(=O)C(CCCC)CCCCCC)CCCCCCCCCOC(=O)C(CCCC)CCCCCC] | — |
| II-19 | 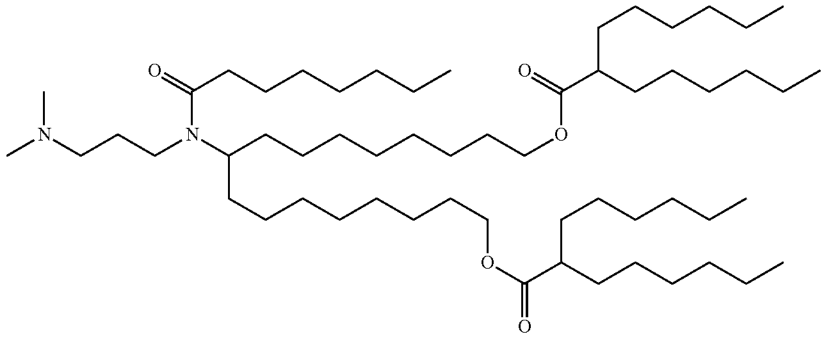 [SMILES: CCCCCCCC(=O)N(CCCN(C)C)C(CCCCCCCCOC(=O)C(CCCCCC)CCCCCC)CCCCCCCCOC(=O)C(CCCCCC)CCCCCC] | — |
| II-20 | 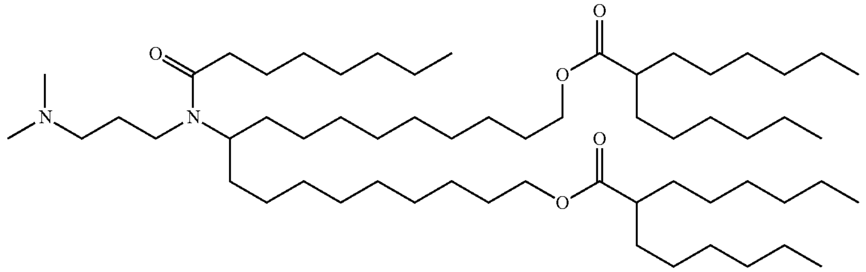 [SMILES: CCCCCCCC(=O)N(CCCN(C)C)C(CCCCCCCCCOC(=O)C(CCCCCC)CCCCCC)CCCCCCCCCOC(=O)C(CCCCCC)CCCCCC] | — |
| II-21 | 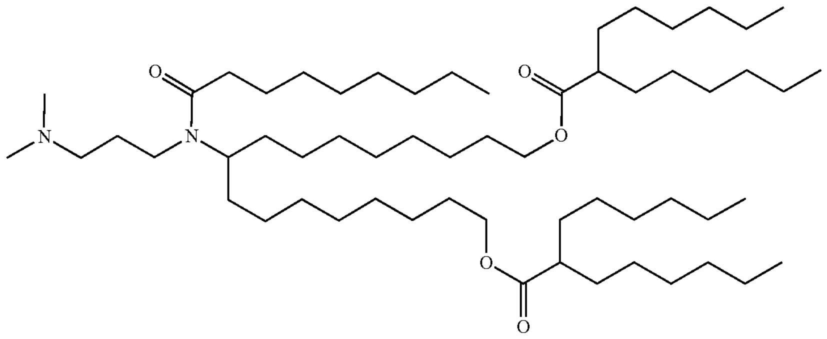 [SMILES: CCCCCCCCC(=O)N(CCCN(C)C)C(CCCCCCCCOC(=O)C(CCCCCC)CCCCCC)CCCCCCCCOC(=O)C(CCCCCC)CCCCCC] | — |

TABLE 2-continued
| Representative Lipids of Formula (II) | | |
|---|---|---|
| No. | Structure | pKa |
| II-22 | 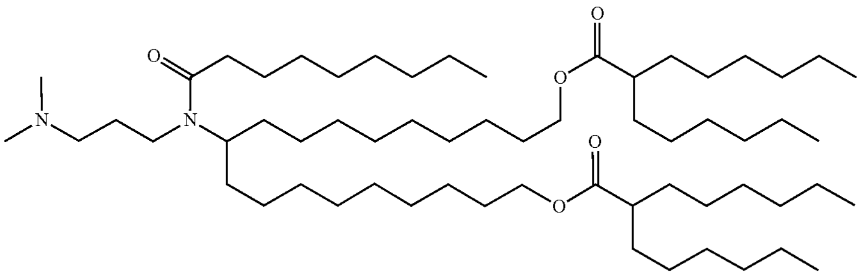 [SMILES: CCCCCCCCC(=O)N(CCCN(C)C)C(CCCCCCCCCOC(=O)C(CCCCCC)CCCCCC)CCCCCCCCCOC(=O)C(CCCCCC)CCCCCC] | — |
| II-23 | 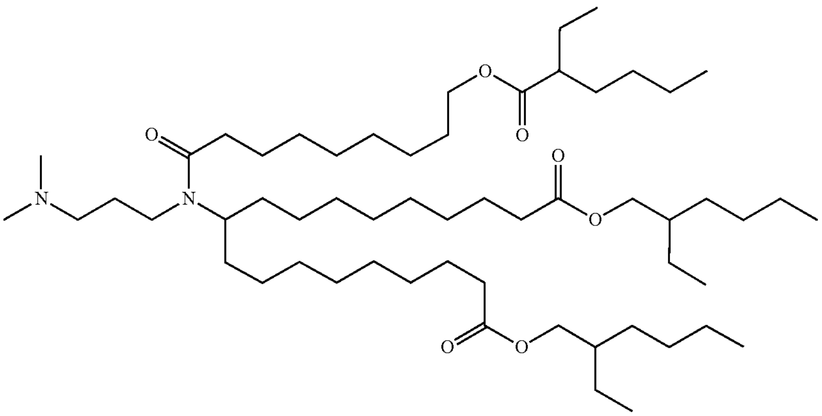 [SMILES: CCCCC(CC)COC(=O)CCCCCCCCC(CCCCCCCCC(=O)OCC(CC)CCCC)N(CCCN(C)C)C(=O)CCCCCCCCOC(=O)C(CC)CCCC] | — |
| II-24 | 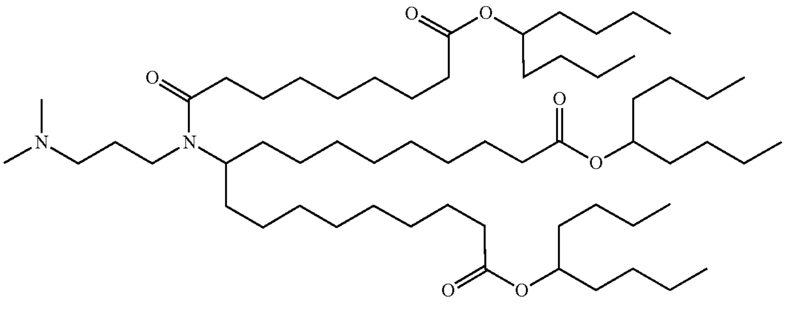 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] | 6.14 |
| II-25 | 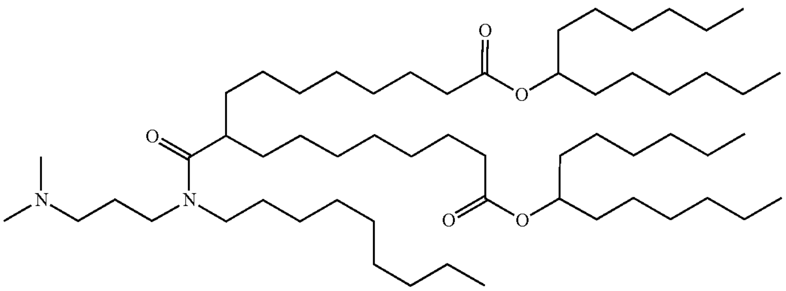 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | — |

TABLE 2-continued
| Representative Lipids of Formula (II) | | |
|---|---|---|
| No. | Structure | pKa |
| II-26 | 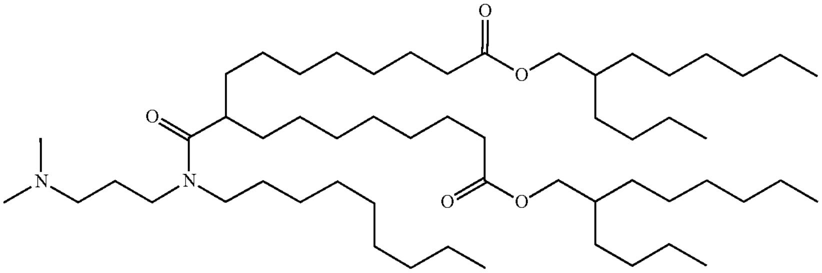 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | — |
| II-27 | 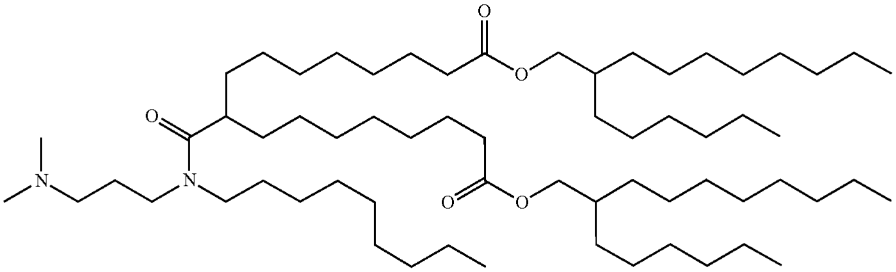 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | — |
| II-28 | 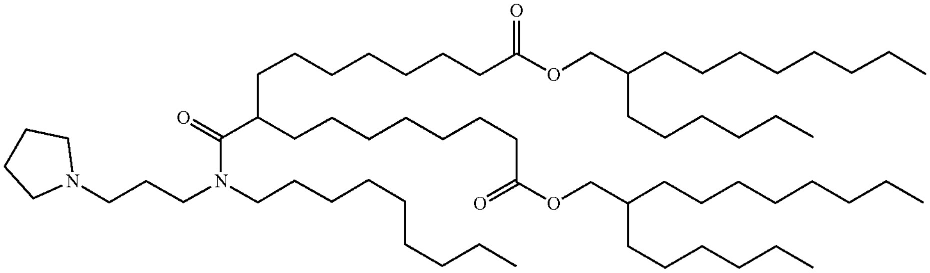 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | — |
| II-29 | 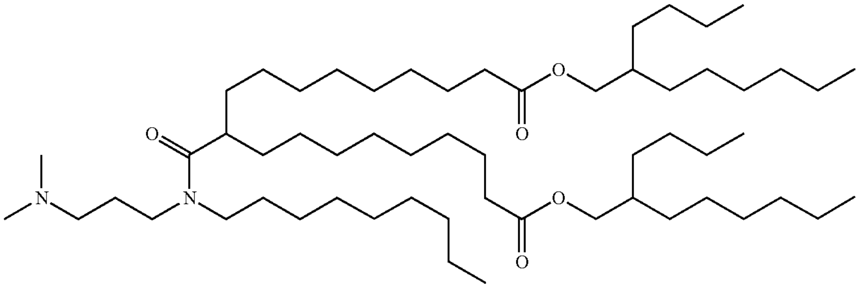 [SMILES: CCCCCCCCCN(CCCN(C)C)C(=O)C(CCCCCCCCC(=O)OCC(CCCC)CCCCCC)CCCCCCCCC(=O)OCC(CCCC)CCCCCC] | — |
| II-30 | 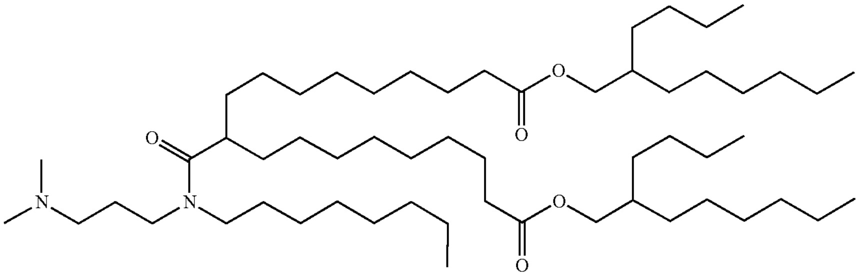 [SMILES: CCCCCCCCN(CCCN(C)C)C(=O)C(CCCCCCCCC(=O)OCC(CCCC)CCCCCC)CCCCCCCCC(=O)OCC(CCCC)CCCCCC] | — |

TABLE 2-continued
| Representative Lipids of Formula (II) | | |
|---|---|---|
| No. | Structure | pKa |
| II-31 | 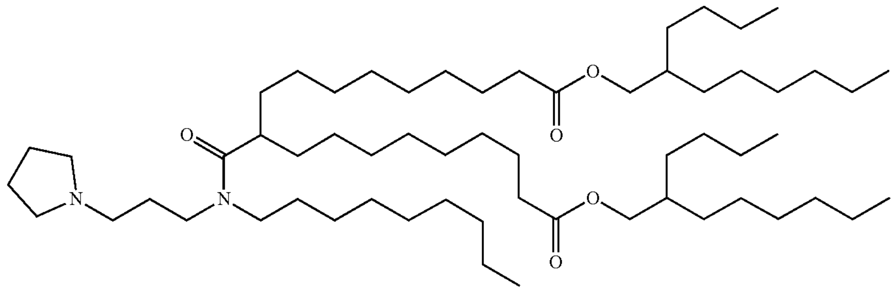 [SMILES: CCCCCCCCCN(CCCN1CCCC1)C(=O)C(CCCCCCCCC(=O)OCC(CCCC)CCCCCC)CCCCCCCCC(=O)OCC(CCCC)CCCCCC] | — |
| II-32 | 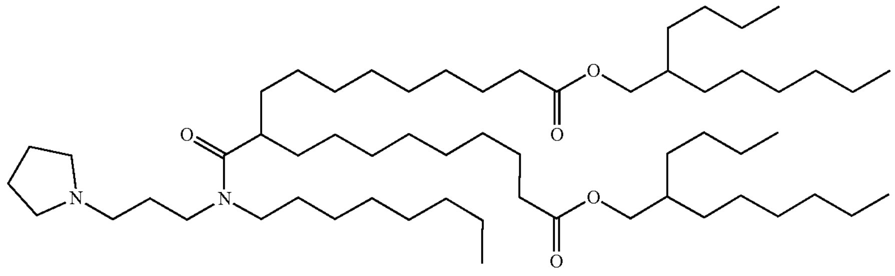 [SMILES: CCCCCCCCN(CCCN1CCCC1)C(=O)C(CCCCCCCCC(=O)OCC(CCCC)CCCCCC)CCCCCCCCC(=O)OCC(CCCC)CCCCCC] | — |
| II-33 | 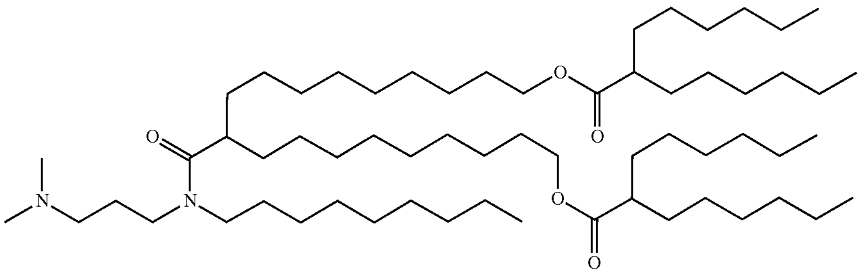 [SMILES: CCCCCCCCCN(CCCN(C)C)C(=O)C(CCCCCCCCCOC(=O)C(CCCCCC)CCCCCC)CCCCCCCCCOC(=O)C(CCCCCC)CCCCCC] | — |
| II-34 | 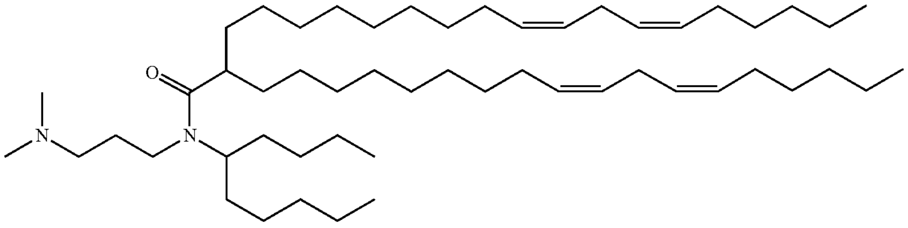 [SMILES: CCCCC/C=C\C/C=C\CCCCCCCCC(CCCCCCCC/C=C\C/C=C\CCCCC)C(=O)N(CCCN(C)C)C(CCCC)CCCCC] | — |
| II-35 | 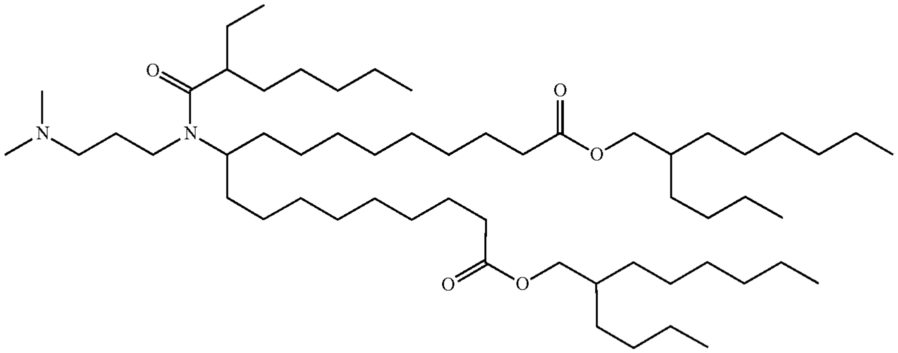 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC] | 5.97 |

TABLE 2-continued
| Representative Lipids of Formula (II) | | |
|---|---|---|
| No. | Structure | pKa |
| II-36 | 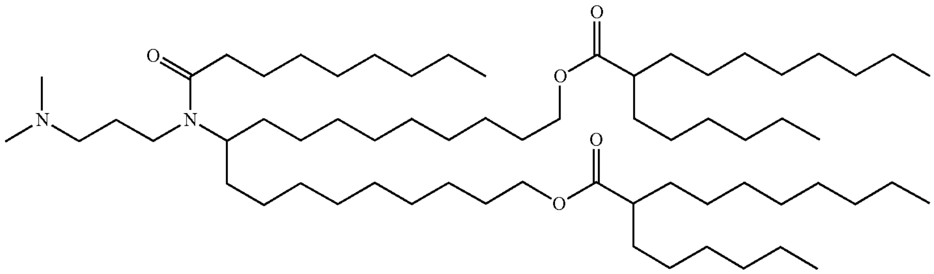 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC] | 6.13 |
| II-37 | 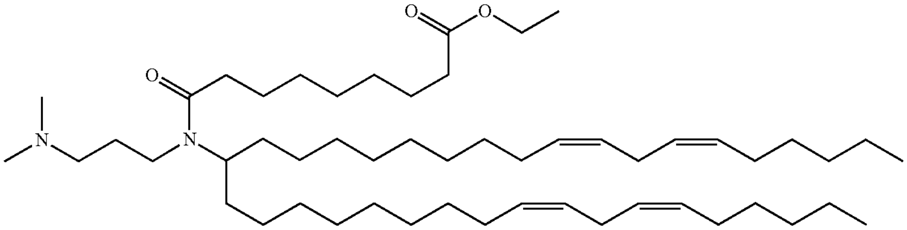 [SMILES: CCCCC/C=C\C/C=C\CCCCCCCCC(CCCCCCCC/C=C\C/C=C\CCCCC)N(CCCN(C)C)C(=O)CCCCCCCC(=O)OCC] | 5.61 |
| II-38 | 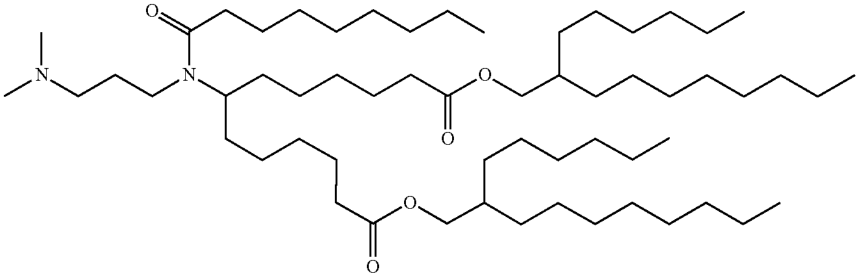 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC] | 6.45 |
| II-39 | 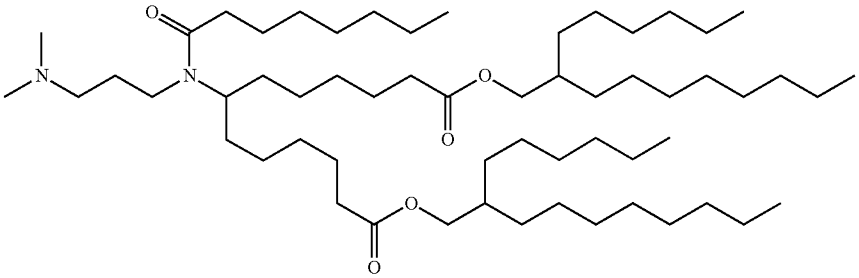 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC] | 6.45 |
| II-40 | 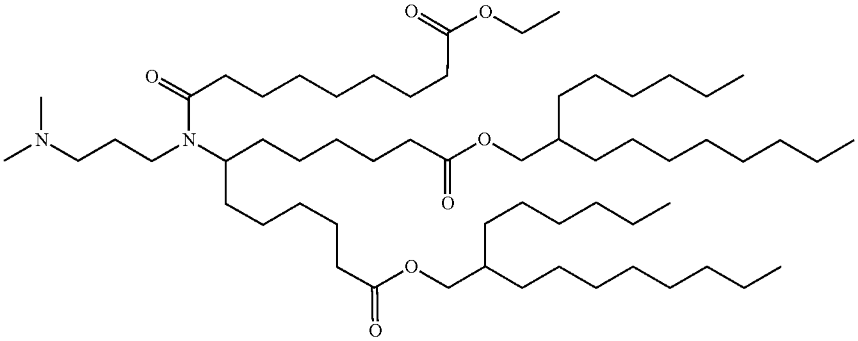 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] | 6.57 |

TABLE 2-continued
Representative Lipids of Formula (II)
| No. | Structure | pKa |
| --- | --- | --- |
| II-41 | 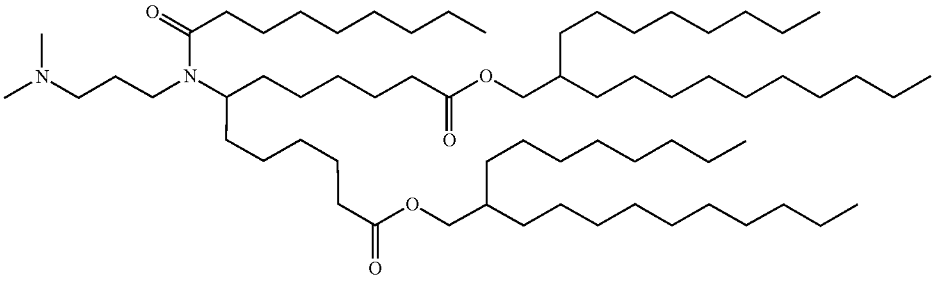 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] | — |
| II-42 | 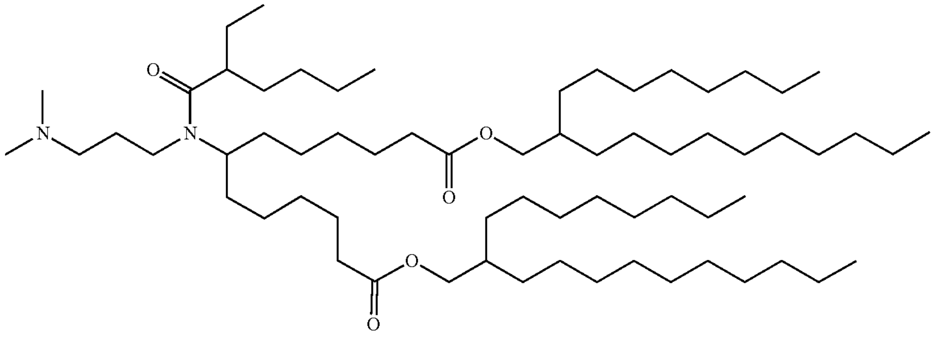 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)C(CC)CCCC] | — |
| II-43 | 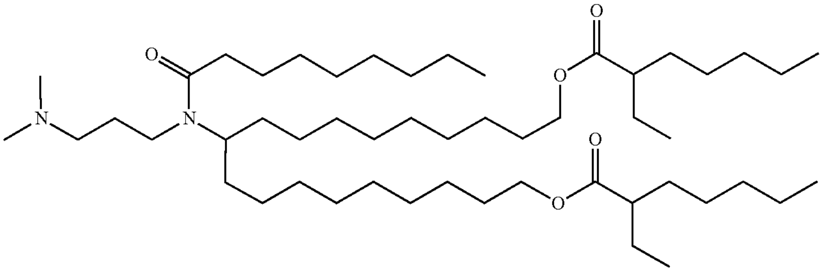 [SMILES: CCCCCCCCC(=O)N(CCCN(C)C)C(CCCCCCCCCOC(=O)C(CC)CCCCC)CCCCCCCCCOC(=O)C(CC)CCCCC] | — |
| II-44 | 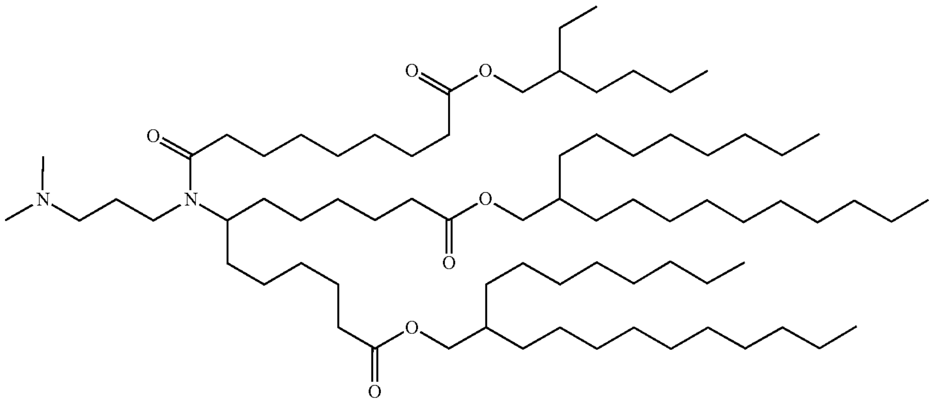 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC(=O)OCC(CC)CCCC] | — |

TABLE 2-continued

| Representative Lipids of Formula (II) | | |
| --- | --- | --- |
| No. | Structure | pKa |
| II-45 | 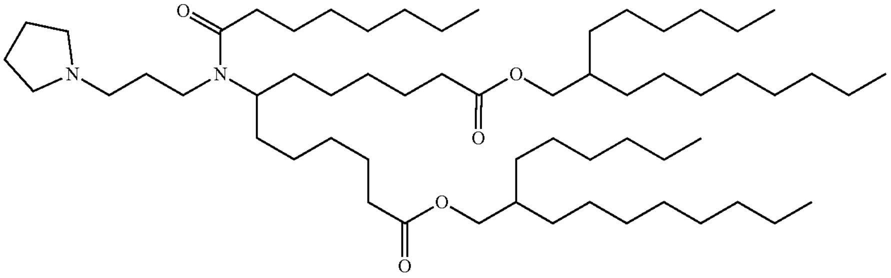 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | — |
| II-46 | 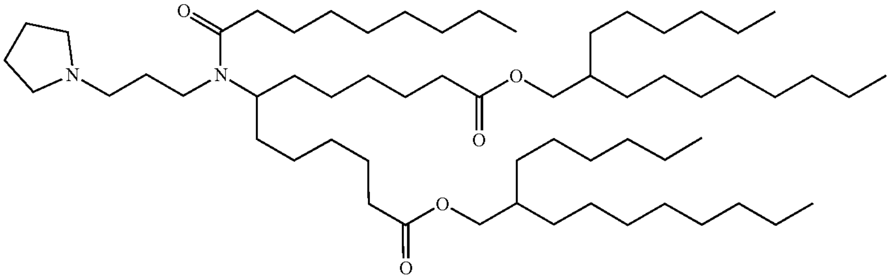 [SMILES: CCCCCCCCC(=O)N(CCCN1CCCC1)C(CCCCCC(=O)OCC(CCCCCC)CCCCCCCC)CCCCCC(=O)OCC(CCCCCC)CCCCCCCC] | — |

In some other embodiments, the cationic lipid of Embodiments 1, 2, 3, 4 or 5 has a structure of Formula III:

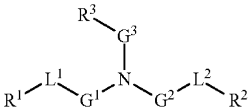

III or a pharmaceutically acceptable salt, prodrug or stereoisomer thereof, wherein:

one of $L^1$ or $L^2$ is —O(C=O)—, —(C=O)O—, —C(=O)—, —O—, —$S(O)_x$—, —S—S—, —C(=O)S—, SC(=O)—, —$NR^aC$(=O)—, —C(=O)$NR^a$—, $NR^aC$(=O)$NR^a$—, —OC(=O)$NR^a$— or —$NR^aC$(=O)O—, and the other of $L^1$ or $L^2$ is —O(C=O)—, —(C=O)O—, —C(=O)—, —O—, —$S(O)_x$—, —S—S—, —C(=O)S—, SC(=O)—, —$NR^aC$(=O)—, —C(=O)$NR^a$—, $NR^aC$(=O)$NR^a$—, —OC(=O)$NR^a$— or

—$NR^aC$(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_{12}$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(=O)$OR^4$, —OC(=O)$R^4$ or —$NR^5C$(=O)$R^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following Formulae (IIIA) or (IIIB):

(IIIA)

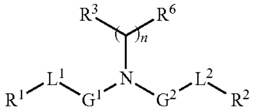

or (IIIB)

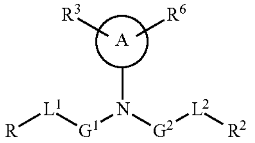

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has Formula (IIIA), and in other embodiments, the lipid has Formula (IIIB).

In other embodiments of Formula (III), the lipid has one of the following Formulae (IIC) or (IIID):

(IIIC)

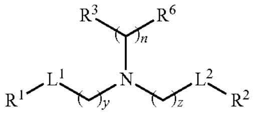

or

-continued (IIID)

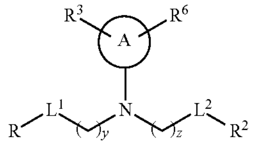

wherein y and z are each independently integers ranging from 1 to 12.

In any of the foregoing embodiments of Formula (III), one of $L^1$ or $L^2$ is —O(C═O)—. For example, in some embodiments each of $L^1$ and $L^2$ are —O(C═O)—. In some different embodiments of any of the foregoing, $L^1$ and $L^2$ are each independently —(C═)O— or —O(C═O)—. For example, in some embodiments each of L and $L^2$ is —(C═O)O—.

In some different embodiments of Formula (III), the lipid has one of the following Formulae (IIIE) or (IIIF):

(IIIE)

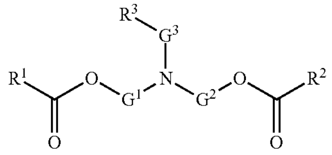

or (IIIF)

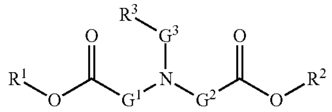

In some of the foregoing embodiments of Formula (III), the lipid has one of the following Formulae (IIIG), (IIIH), (IIII), or (IIIJ):

(IIIG)

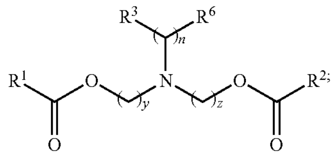

(IIIH)

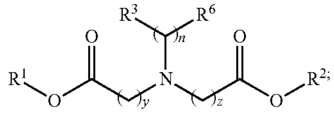

(IIII)

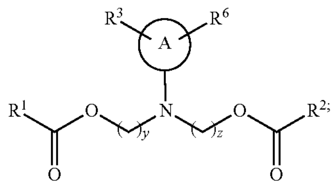

(IIIJ)

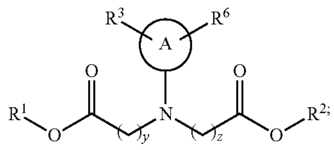

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

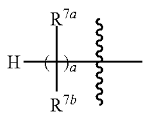, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

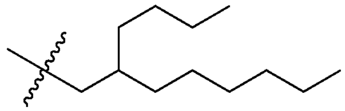,

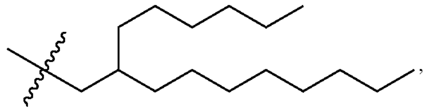,

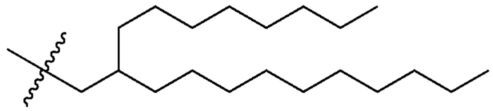,

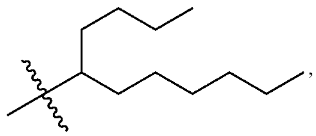,

-continued

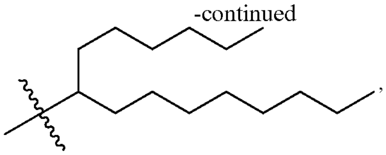,

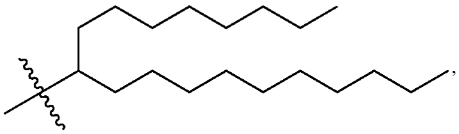,

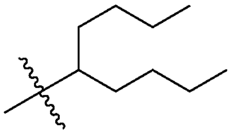,

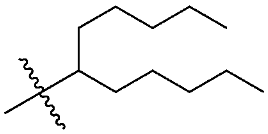,

-continued

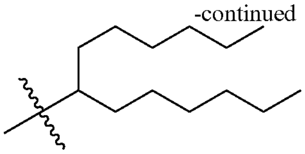,

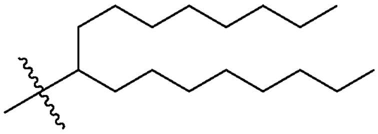.

In some of the foregoing embodiments of Formula (III), $R^3$ is OH, CN, —C(═O)OR$^4$, —OC(═O)R$^4$ or —NHC(═O)R$^4$. In some embodiments, $R^4$ is methyl or ethyl.

In some specific embodiments of Embodiment 3, the first and second cationic lipids are each, independently selected from a lipid of Formula III.

In various different embodiments, a cationic lipid of any one of the disclosed embodiments (e.g., the cationic lipid, the first cationic lipid, the second cationic lipid) of Formula (III) has one of the structures set forth in Table 3 below.

TABLE 3

Representative Compounds of Formula (III)

| No. | Structure | pKa |
| --- | --- | --- |
| III-1 | 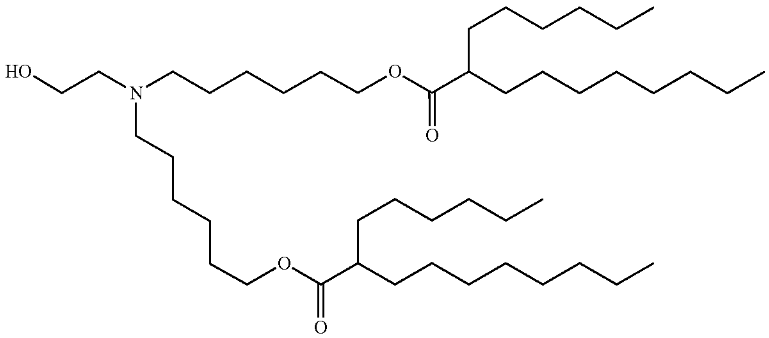 [SMILES: CCCCCCCCC(CCCCCC)C(=O)OCCCCCCN(CCO)CCCCCCOC(=O)C(CCCCCC)CCCCCCCC] | 5.89 |
| III-2 | 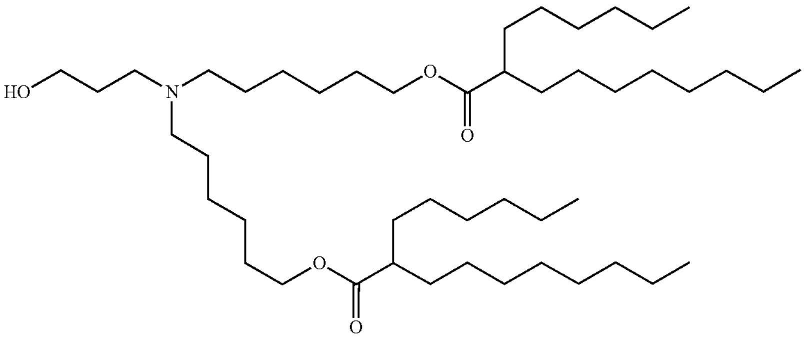 [SMILES: CCCCCCCCC(CCCCCC)C(=O)OCCCCCCN(CCCO)CCCCCCOC(=O)C(CCCCCC)CCCCCCCC] | 6.05 |

TABLE 3-continued
| Representative Compounds of Formula (III) | | |
|---|---|---|
| No. | Structure | pKa |
| III-3 | 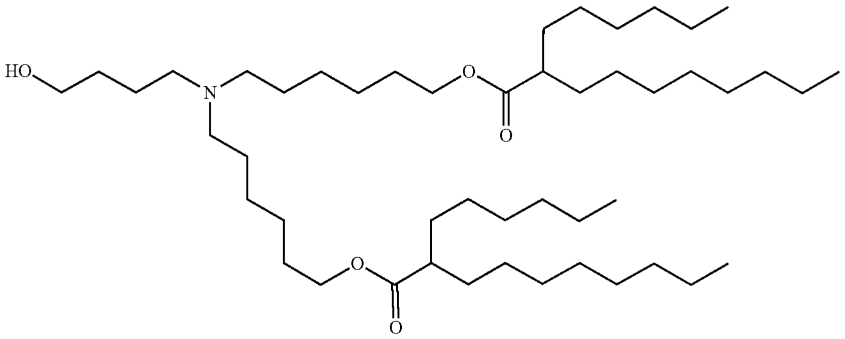 [SMILES: CCCCCCCCC(CCCCCC)C(=O)OCCCCCCN(CCCCO)CCCCCCOC(=O)C(CCCCCC)CCCCCCCC] | 6.09 |
| III-4 | 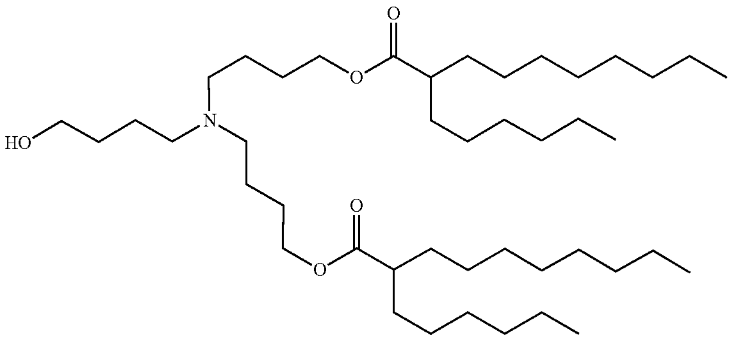 [SMILES: CCCCCCCCC(CCCCCC)C(=O)OCCCCN(CCCCO)CCCCOC(=O)C(CCCCCC)CCCCCCCC] | 5.60 |
| III-5 | 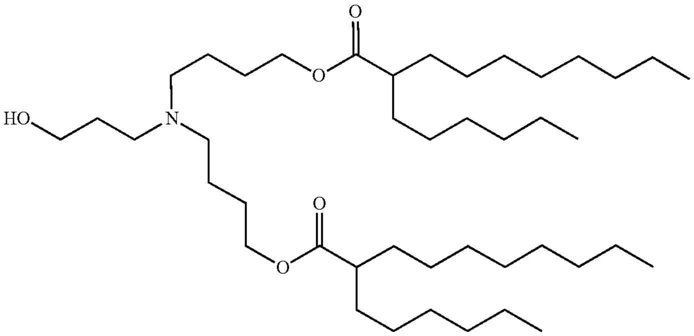 [SMILES: CCCCCCCCC(CCCCCC)C(=O)OCCCCN(CCCO)CCCCOC(=O)C(CCCCCC)CCCCCCCC] | 5.59 |
| III-6 | 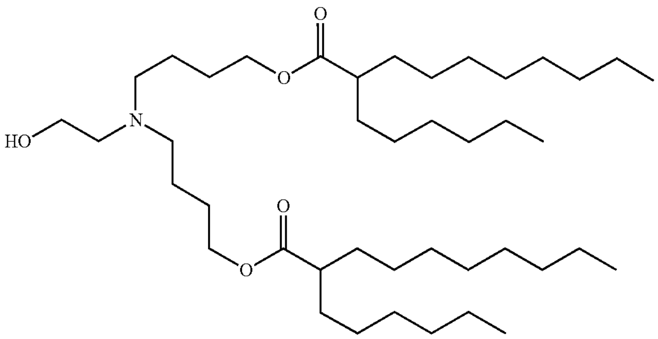 [SMILES: CCCCCCCCC(CCCCCC)C(=O)OCCCCN(CCO)CCCCOC(=O)C(CCCCCC)CCCCCCCC] | 5.42 |

TABLE 3-continued
| Representative Compounds of Formula (III) | | |
| --- | --- | --- |
| No. | Structure | pKa |
| III-7 | 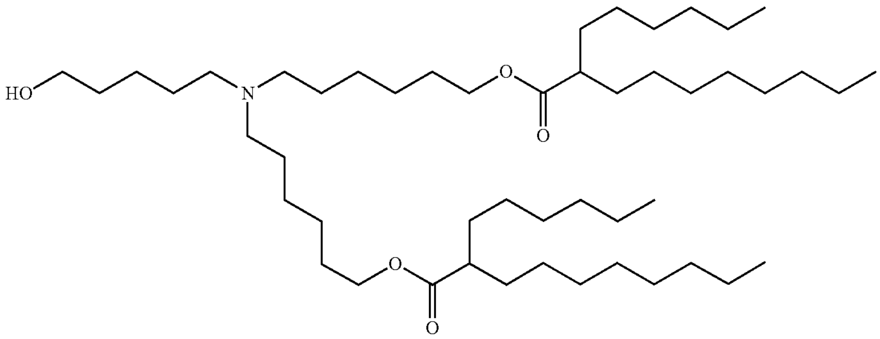 [SMILES: CCCCCCCCC(CCCCCC)C(=O)OCCCCCCN(CCCCCO)CCCCCCOC(=O)C(CCCCCC)CCCCCCCC] | 6.11 |
| III-8 | 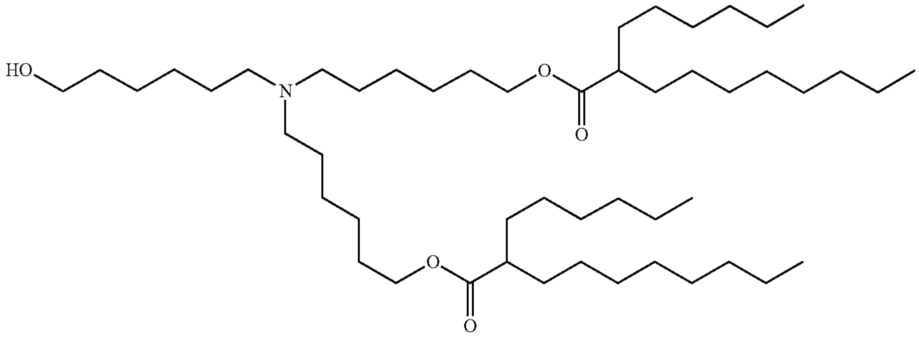 [SMILES: CCCCCCCCC(CCCCCC)C(=O)OCCCCCCN(CCCCCCO)CCCCCCOC(=O)C(CCCCCC)CCCCCCCC] | 5.84 |
| III-9 | 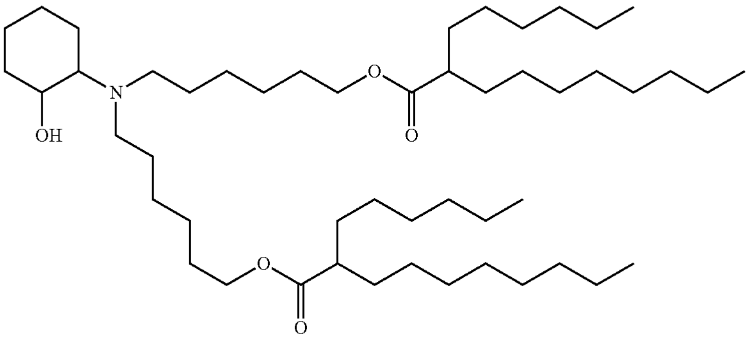 [SMILES: CCCCCCCCC(CCCCCC)C(=O)OCCCCCCN(CCCCCCOC(=O)C(CCCCCC)CCCCCCCC)C1CCCCC1O] | — |
| III-10 | 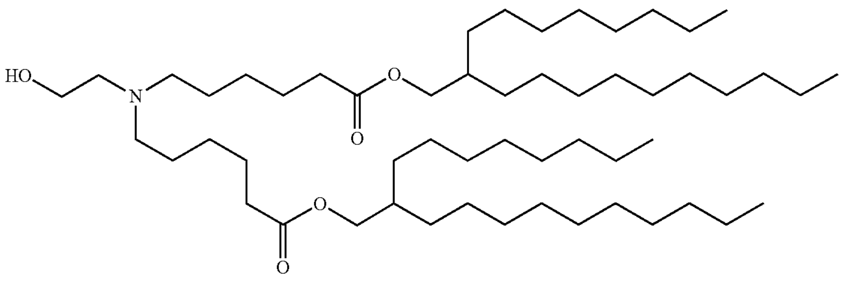 [SMILES: CCCCCCCCCCC(CCCCCCCC)COC(=O)CCCCCN(CCO)CCCCCC(=O)OCC(CCCCCCCC)CCCCCCCCCC] | — |

TABLE 3-continued
| Representative Compounds of Formula (III) | | |
|---|---|---|
| No. | Structure | pKa |
| III-11 | 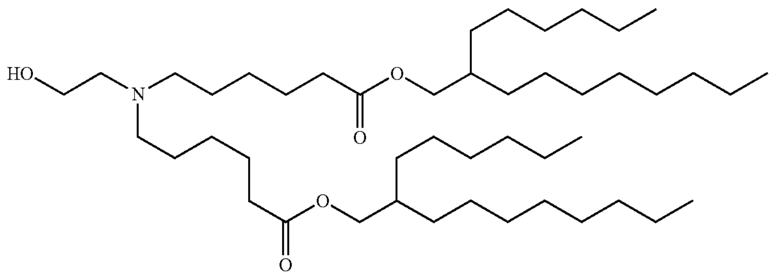 [SMILES: CCCCCCCCC(CCCCCC)COC(=O)CCCCCN(CCO)CCCCCC(=O)OCC(CCCCCC)CCCCCCCC] | — |
| III-12 | 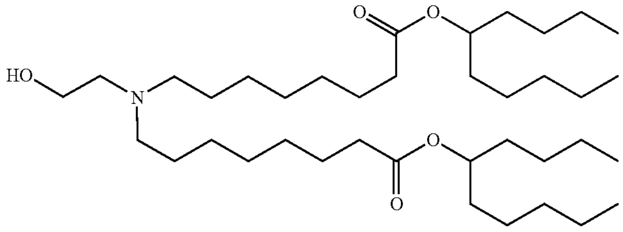 [SMILES: CCCCCC(CCCC)OC(=O)CCCCCCCN(CCO)CCCCCCCC(=O)OC(CCCC)CCCCC] | — |
| III-13 | 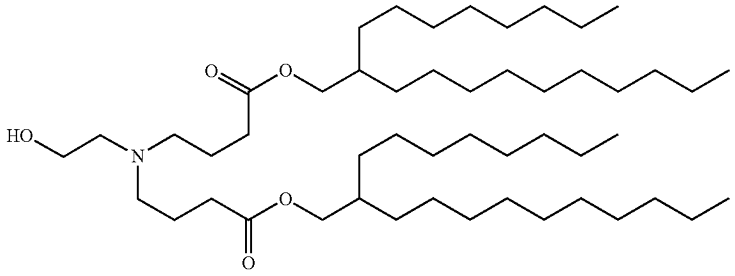 [SMILES: CCCCCCCCCCC(CCCCCCCC)COC(=O)CCCN(CCO)CCCC(=O)OCC(CCCCCCCC)CCCCCCCCCC] | — |
| III-14 | 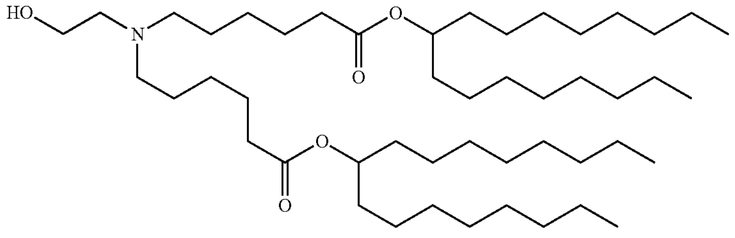 [SMILES: CCCCCCCCC(CCCCCCCC)OC(=O)CCCCCN(CCO)CCCCCC(=O)OC(CCCCCCCC)CCCCCCCC] | — |
| III-15 | 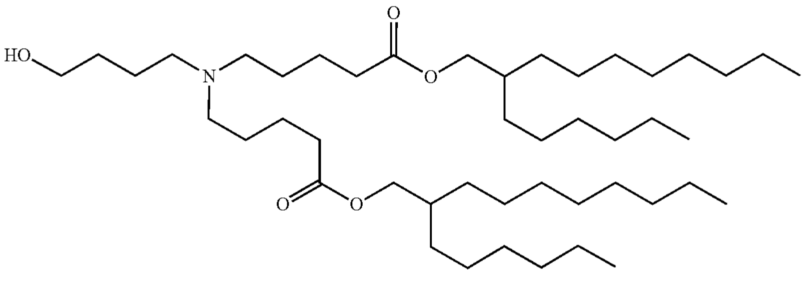 [SMILES: CCCCCCCCC(CCCCCC)COC(=O)CCCCN(CCCCO)CCCCC(=O)OCC(CCCCCC)CCCCCCCC] | 6.14 |

TABLE 3-continued
| Representative Compounds of Formula (III) | | |
|---|---|---|
| No. | Structure | pKa |
| III-16 | 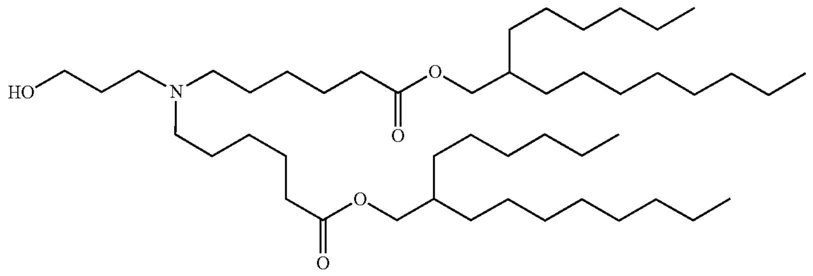 [SMILES: CCCCCCCCC(CCCCCC)COC(=O)CCCCCN(CCCO)CCCCCC(=O)OCC(CCCCCC)CCCCCCCC] | 6.31 |
| III-17 | 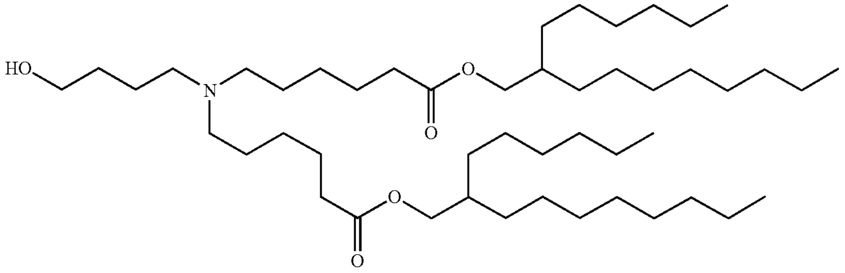 [SMILES: CCCCCCCCC(CCCCCC)COC(=O)CCCCCN(CCCCO)CCCCCC(=O)OCC(CCCCCC)CCCCCCCC] | 6.28 |
| III-18 | 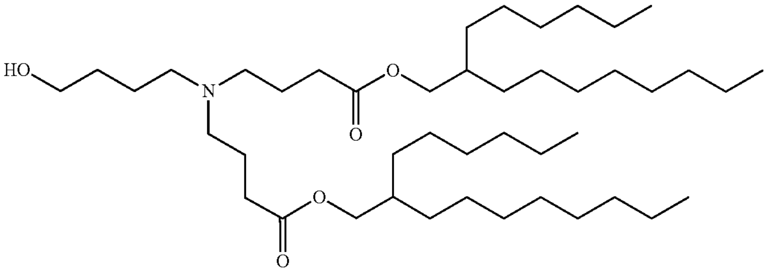 [SMILES: CCCCCCCCC(CCCCCC)COC(=O)CCCN(CCCCO)CCCC(=O)OCC(CCCCCC)CCCCCCCC] | — |
| III-19 | 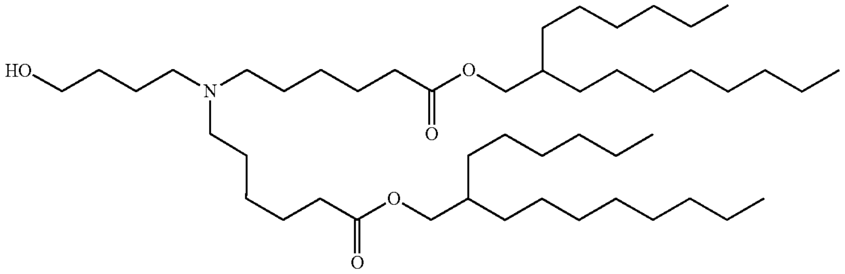 [SMILES: CCCCCCCCC(CCCCCC)COC(=O)CCCCCN(CCCCO)CCCCCC(=O)OCC(CCCCCC)CCCCCCCC] | — |
| III-20 | 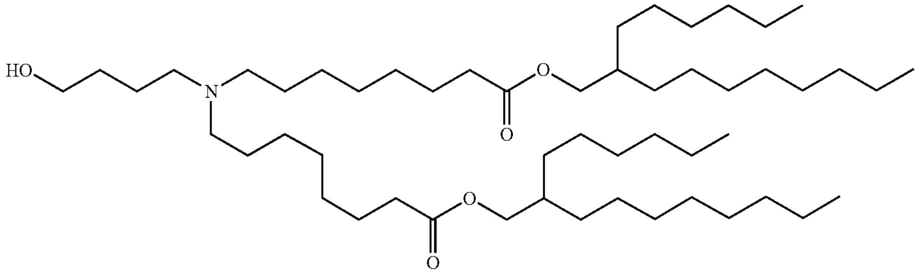 [SMILES: CCCCCCCCC(CCCCCC)COC(=O)CCCCCCCN(CCCCO)CCCCCCCC(=O)OCC(CCCCCC)CCCCCCCC] | 6.36 |

TABLE 3-continued
| Representative Compounds of Formula (III) | | |
|---|---|---|
| No. | Structure | pKa |
| III-21 | 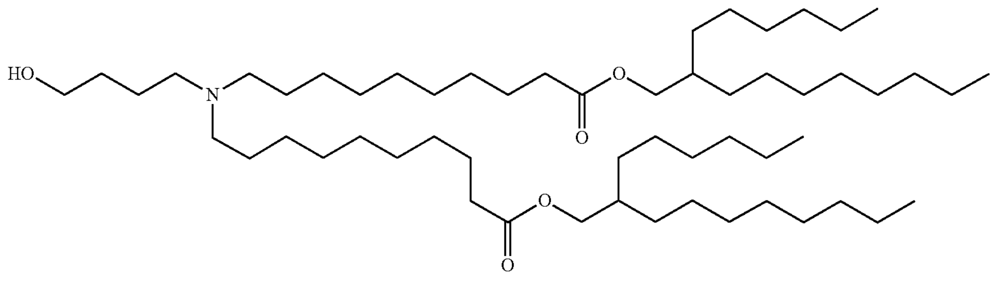 [SMILES: CCCCCCCCC(CCCCCC)COC(=O)CCCCCCCCCN(CCCCO)CCCCCCCCCC(=O)OCC(CCCCCC)CCCCCCCC] | — |
| III-22 | 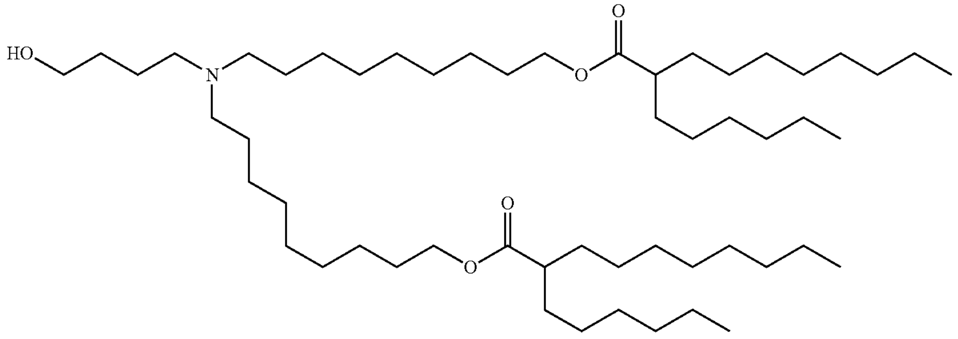 [SMILES: CCCCCCCCC(CCCCCC)C(=O)OCCCCCCCCCN(CCCCO)CCCCCCCCCOC(=O)C(CCCCCC)CCCCCCCC] | 6.10 |
| III-23 | 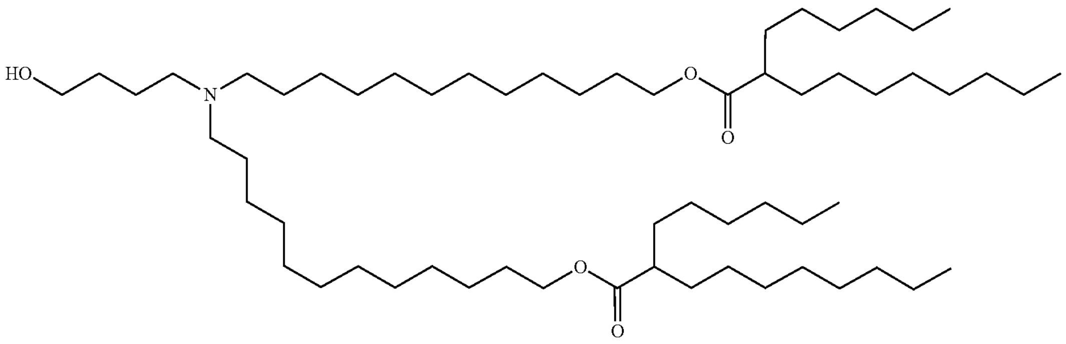 [SMILES: CCCCCCCCC(CCCCCC)C(=O)OCCCCCCCCCCCCN(CCCCO)CCCCCCCCCCCCOC(=O)C(CCCCCC)CCCCCCCC] | 5.98 |
| III-24 | 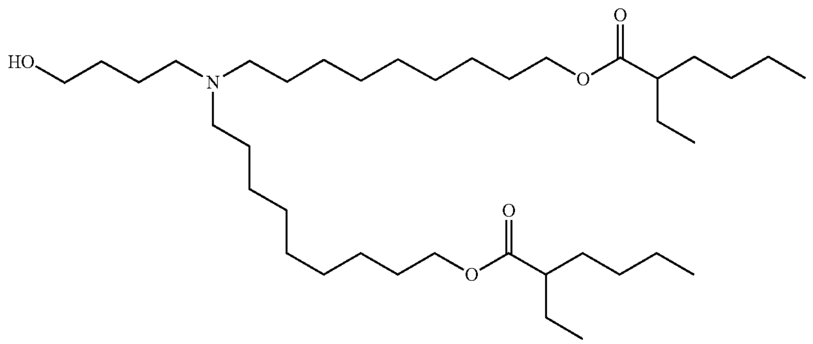 [SMILES: CCCCC(CC)C(=O)OCCCCCCCCCN(CCCCO)CCCCCCCCCOC(=O)C(CC)CCCC] | — |

TABLE 3-continued
| Representative Compounds of Formula (III) | | |
|---|---|---|
| No. | Structure | pKa |
| III-25 | 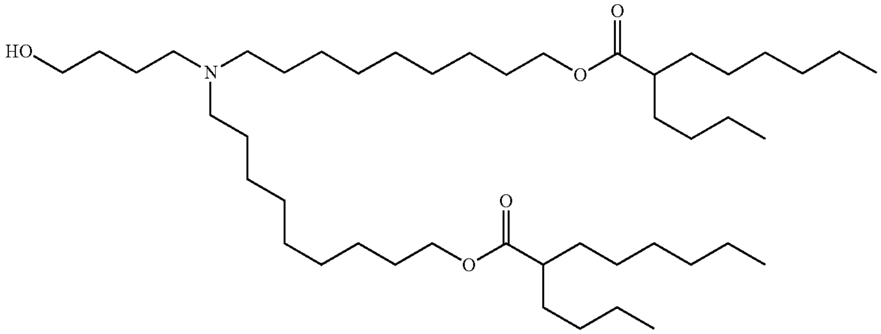 [SMILES: CCCCCCC(CCCC)C(=O)OCCCCCCCCCN(CCCCO)CCCCCCCCCOC(=O)C(CCCC)CCCCCC] | 6.22 |
| III-26 | 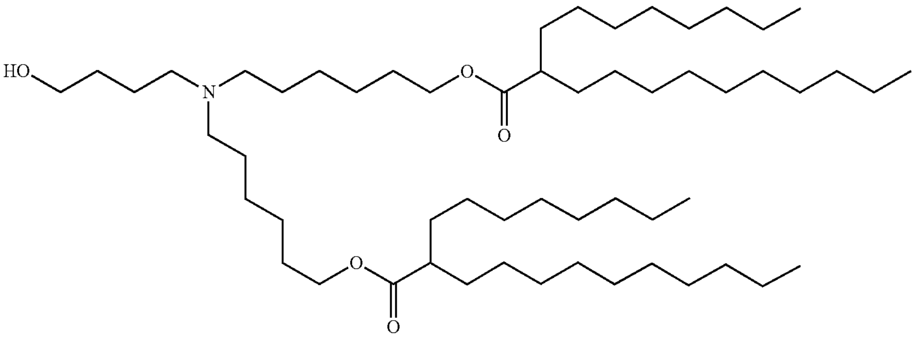 [SMILES: CCCCCCCCCCC(CCCCCCCC)C(=O)OCCCCCCN(CCCCO)CCCCCCOC(=O)C(CCCCCCCC)CCCCCCCCCC] | 5.84 |
| III-27 | 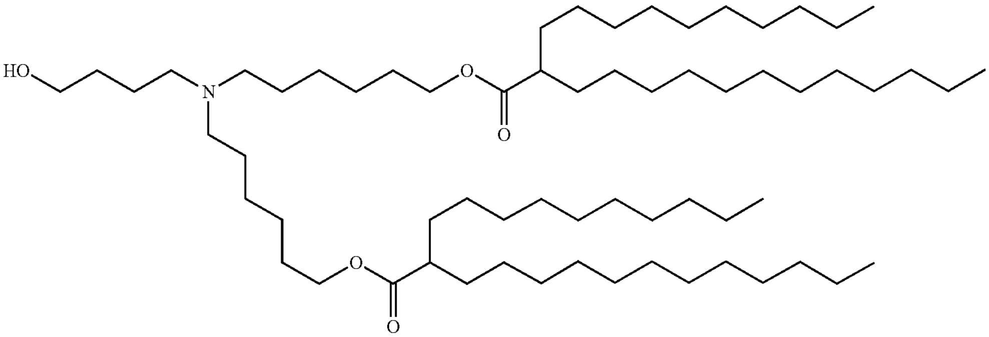 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] | 5.77 |
| III-28 | 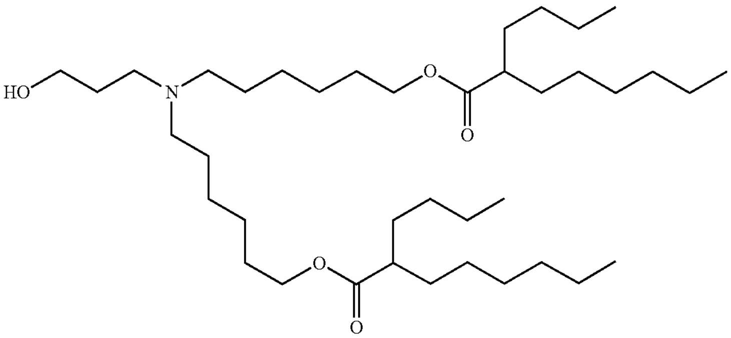 [SMILES: CCCCCCC(CCCC)C(=O)OCCCCCCN(CCCO)CCCCCCOC(=O)C(CCCC)CCCCCC] | — |

TABLE 3-continued
| Representative Compounds of Formula (III) | | |
|---|---|---|
| No. | Structure | pKa |
| III-29 | 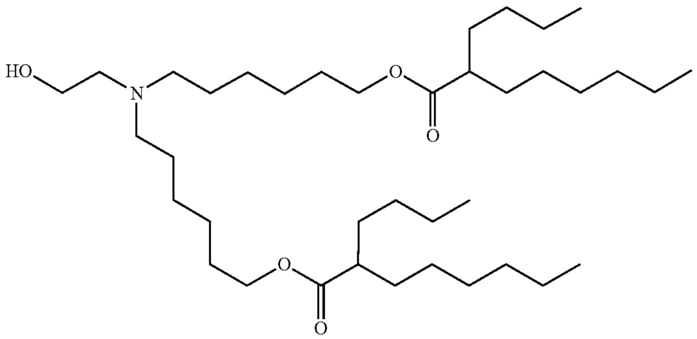 [SMILES: CCCCCCC(CCCC)C(=O)OCCCCCCN(CCO)CCCCCCOC(=O)C(CCCC)CCCCCC] | — |
| III-30 | 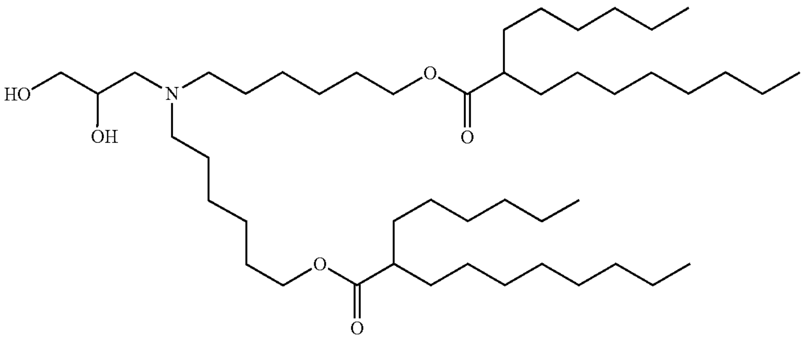 [SMILES: CCCCCCCCC(CCCCCC)C(=O)OCCCCCCN(CCCCCCOC(=O)C(CCCCCC)CCCCCCCC)CC(O)CO] | 6.09 |
| III-31 | 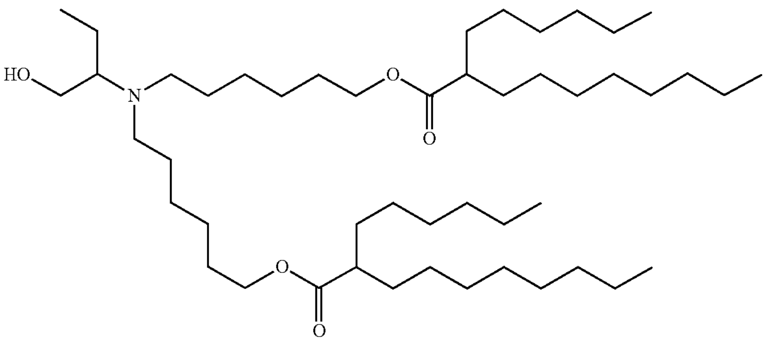 [SMILES: CCCCCCCCC(CCCCCC)C(=O)OCCCCCCN(CCCCCCOC(=O)C(CCCCCC)CCCCCCCC)C(CC)CO] | — |
| III-32 | 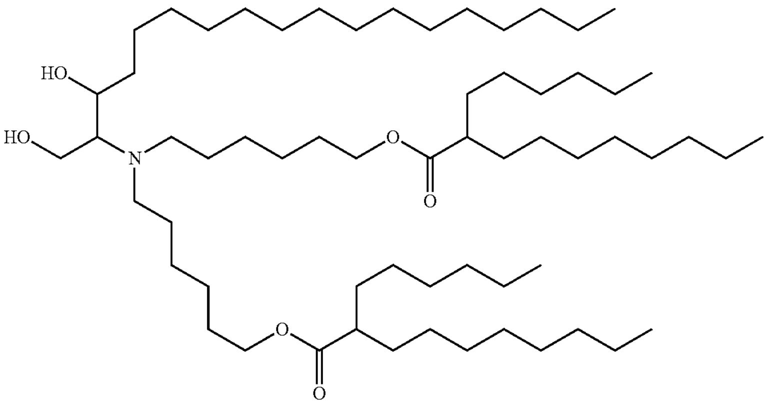 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | — |

TABLE 3-continued
| Representative Compounds of Formula (III) | | |
|---|---|---|
| No. | Structure | pKa |
| III-33 | 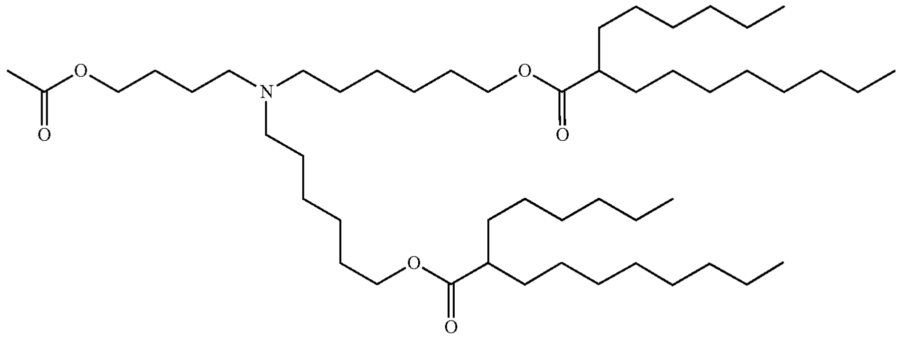 [SMILES: CCCCCCCCC(CCCCCC)C(=O)OCCCCCCN(CCCCCCOC(=O)C(CCCCCC)CCCCCCCC)CCCCOC(C)=O] | — |
| III-34 | 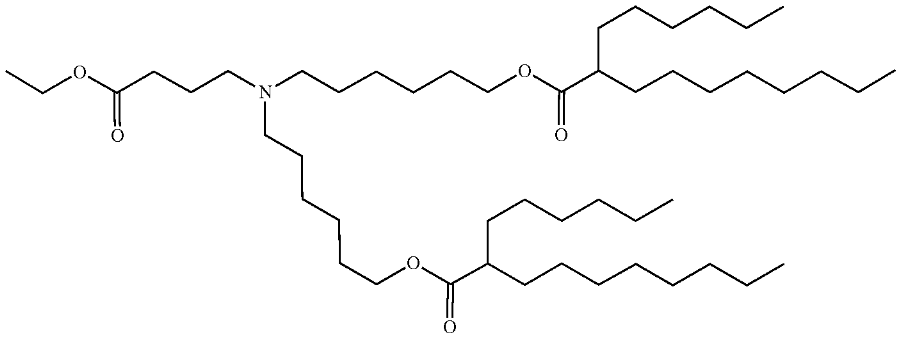 [SMILES: CCCCCCCCC(CCCCCC)C(=O)OCCCCCCN(CCCCCCOC(=O)C(CCCCCC)CCCCCCCC)CCCC(=O)OCC] | — |
| III-35 | 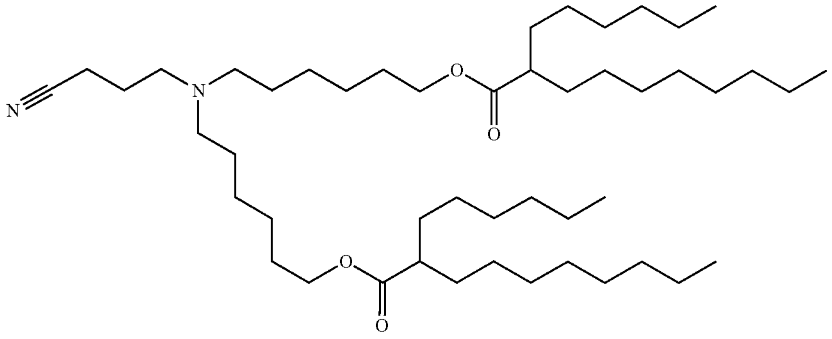 [SMILES: CCCCCCCCC(CCCCCC)C(=O)OCCCCCCN(CCCC#N)CCCCCCOC(=O)C(CCCCCC)CCCCCCCC] | — |
| III-36 | 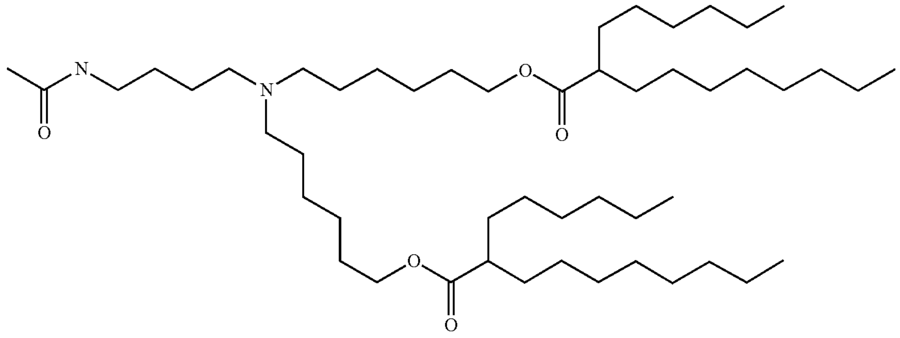 | — |

TABLE 3-continued
| Representative Compounds of Formula (III) | | |
|---|---|---|
| No. | Structure | pKa |
| III-37 | 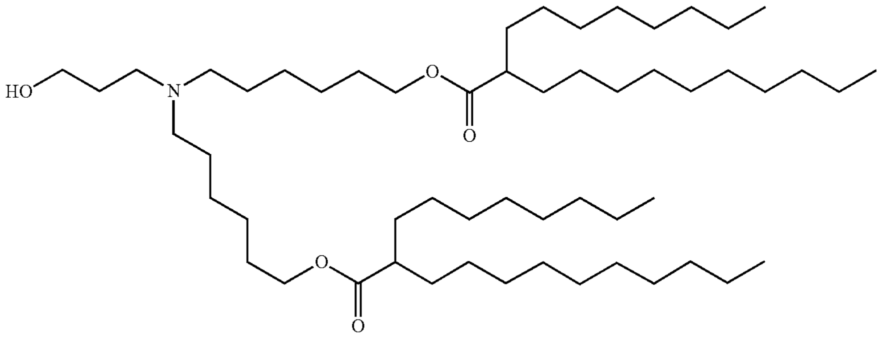 [SMILES: CCCCCCCCCCC(CCCCCCCC)C(=O)OCCCCCCN(CCCO)CCCCCCOC(=O)C(CCCCCCCC)CCCCCCCCCC] | — |
| III-38 | 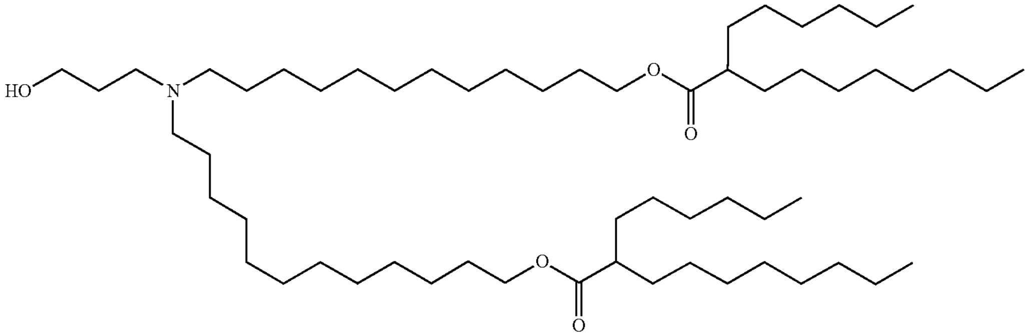 [SMILES: CCCCCCCCC(CCCCCC)C(=O)OCCCCCCCCCCCCN(CCCO)CCCCCCCCCCCCOC(=O)C(CCCCCC)CCCCCCCC] | — |
| III-39 | 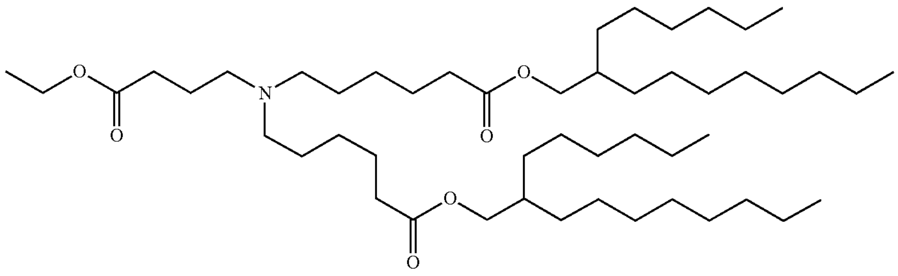 [SMILES: CCCCCCCCC(CCCCCC)COC(=O)CCCCCN(CCCCCC(=O)OCC(CCCCCC)CCCCCCCC)CCCC(=O)OCC] | — |
| III-40 | 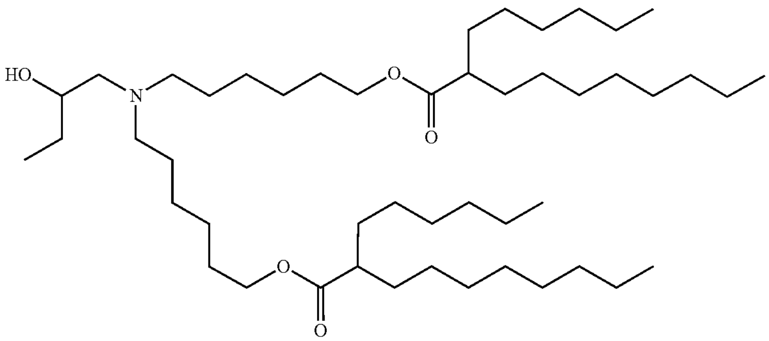 [SMILES: CCCCCCCCC(CCCCCC)C(=O)OCCCCCCN(CCCCCCOC(=O)C(CCCCCC)CCCCCCCC)CC(O)CC] | — |

TABLE 3-continued
| Representative Compounds of Formula (III) | | |
|---|---|---|
| No. | Structure | pKa |
| III-41 | 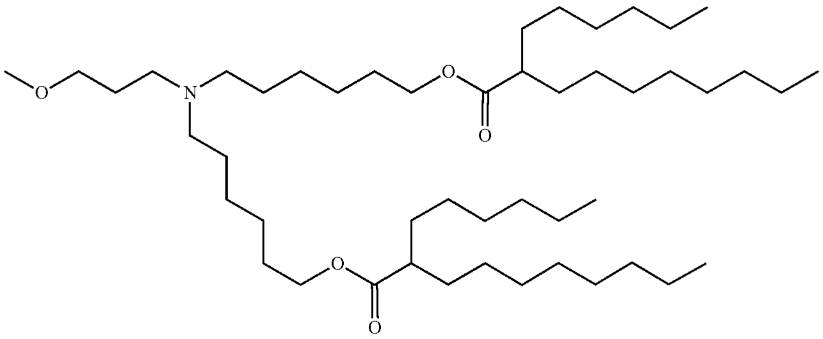 [SMILES: CCCCCCCCC(CCCCCC)C(=O)OCCCCCCN(CCCCCCOC(=O)C(CCCCCC)CCCCCCCC)CCCOC] | — |
| III-42 | 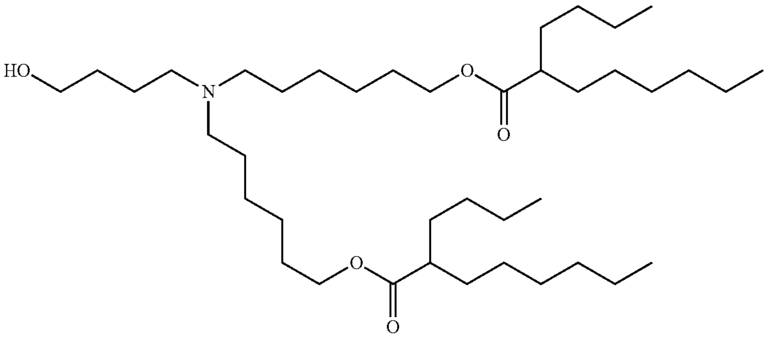 [SMILES: CCCCCCC(CCCC)C(=O)OCCCCCCN(CCCCO)CCCCCCOC(=O)C(CCCC)CCCCCC] | — |
| III-43 | 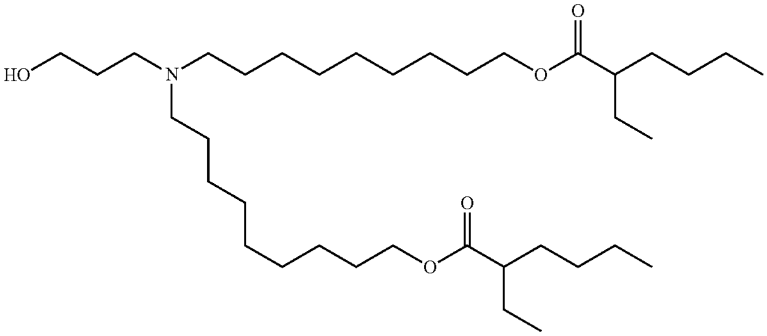 [SMILES: CCCCC(CC)C(=O)OCCCCCCCCCN(CCCO)CCCCCCCCCOC(=O)C(CC)CCCC] | — |
| III-44 | 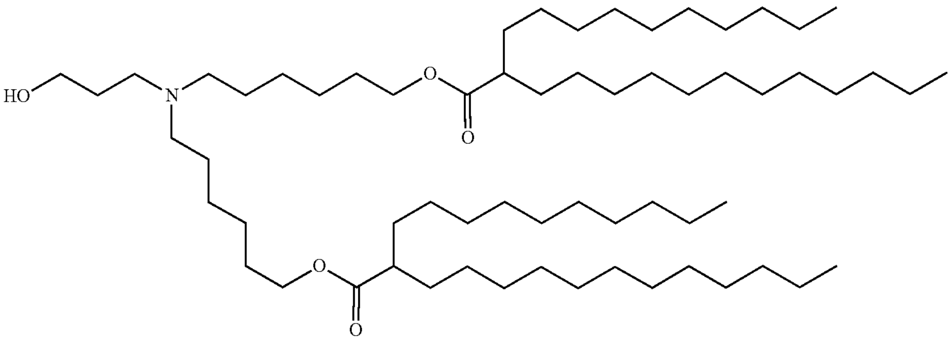 [SMILES: CCCCCCCCCCCCC(CCCCCCCCCC)C(=O)OCCCCCCN(CCCO)CCCCCCOC(=O)C(CCCCCCCCCC)CCCCCCCCCCCC] | — |

TABLE 3-continued
| No. | Structure | pKa |
|---|---|---|
| | Representative Compounds of Formula (III) | |
| III-45 | 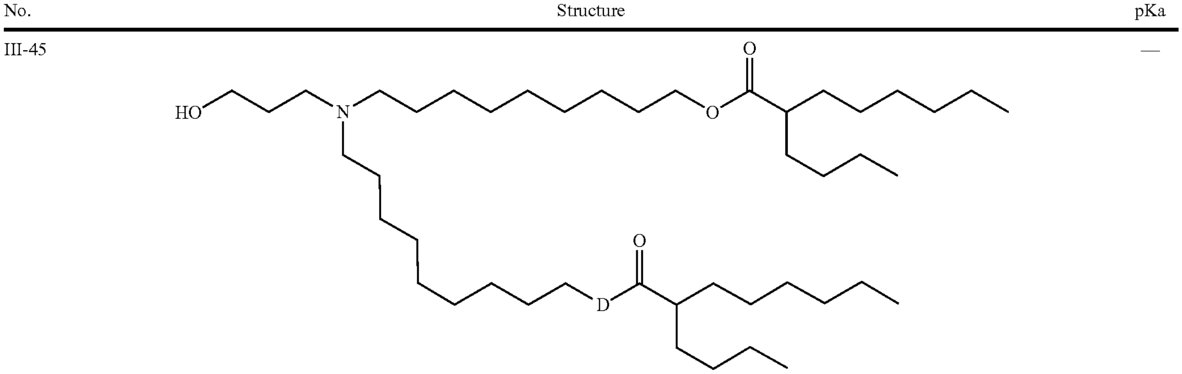 | — |
| III-46 | 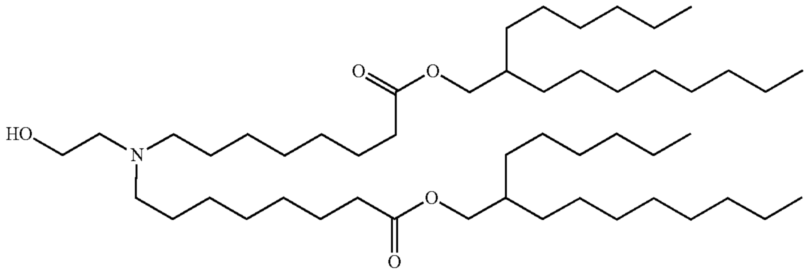 [SMILES: CCCCCCCCC(CCCCCC)COC(=O)CCCCCCCN(CCO)CCCCCCCC(=O)OCC(CCCCCC)CCCCCCCC] | — |
| III-47 | 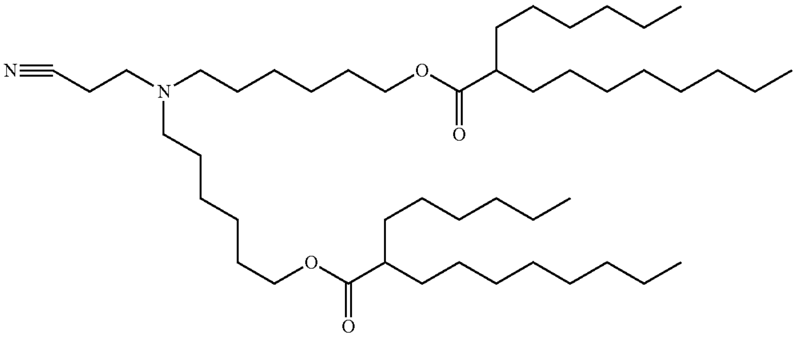 [SMILES: CCCCCCCCC(CCCCCC)C(=O)OCCCCCCN(CCC#N)CCCCCCOC(=O)C(CCCCCC)CCCCCCCC] | — |
| III-48 | 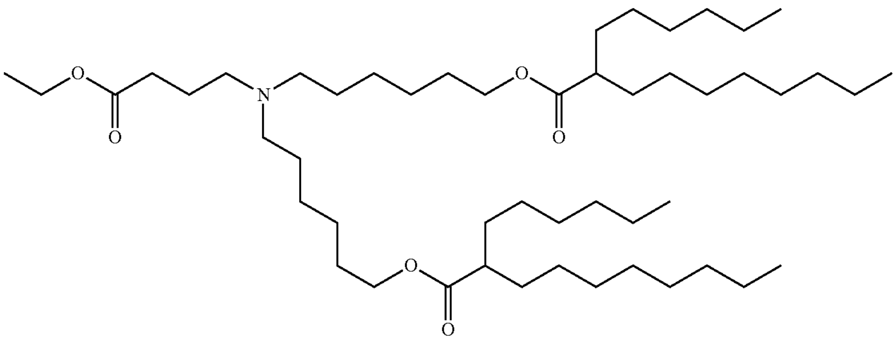 [SMILES: CCCCCCCCC(CCCCCC)C(=O)OCCCCCCN(CCCCCCOC(=O)C(CCCCCC)CCCCCCCC)CCCC(=O)OCC] | — |

TABLE 3-continued

| Representative Compounds of Formula (III) | | |
|---|---|---|
| No. | Structure | pKa |
| III-49 | 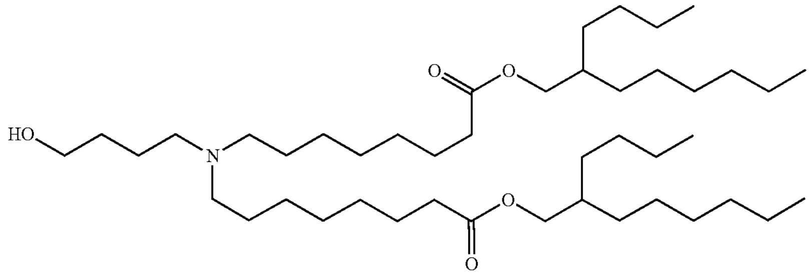 [SMILES: CCCCCCC(CCCC)COC(=O)CCCCCCCN(CCCCO)CCCCCCCC(=O)OCC(CCCC)CCCCCC] | — |

In one embodiment, the cationic lipid of any one of Embodiments 1, 2, 3, 4 or 5 has a structure of Formula (IV):

(IV)

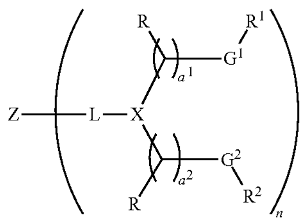

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —$S(O)_y$—, —S—S—, —C(═O)S—, SC(═O)—, —$N(R^a)C$(═O)—, —C(═O)$N(R^a)$—, —$N(R^a)C$(═O)$N(R^a)$—, —OC(═O)N($R^a$)— or —$N(R^a)C$(═O)O—, and the other of $G^1$ or $G^2$ is, at each occurrence, —O(C═O)—, —(C═O)O—, —C(═O)—, —O—, —$S(O)_y$—, —S—S—, —C(═O)S—, —SC(═O)—, —$N(R^a)C$(═O)—, —C(═O)$N(R^a)$—, —$N(R^a)C$(═O)$N(R^a)$—, —OC(═O)$N(R^a)$— or —$N(R^a)$C(═O)O— or a direct bond;

L is, at each occurrence, ~O(C═O)—, wherein represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_2$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

$R^1$

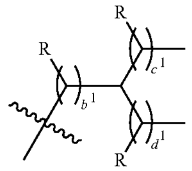

and $R^2$

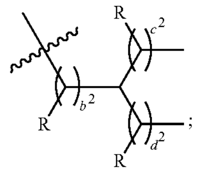

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 5 to 10;

$d^1$ and $d^2$ are, at each occurrence, independently an integer from 5 to 10;

y is, at each occurrence, independently an integer from 0 to 2; and n is an integer from 1 to 6, wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In some embodiments of Formula (IV), $G^1$ and $G^2$ are each independently

—O(C═O)— or —(C═O)O—.

In other embodiments of Formula (IV), X is CH.

In different embodiments of Formula (IV), the sum of $a^1+b^1+c^1$ or the sum of $a^2+b^2+c^2$ is an integer from 12 to 26.

In still other embodiments of Formula (IV), $a^1$ and $a^2$ are independently an integer from 3 to 10. For example, in some embodiments $a^1$ and $a^2$ are independently an integer from 4 to 9.

In various embodiments of Formula (IV), $b^1$ and $b^2$ are 0. Indifferent embodiments, $b^1$ and $b^2$ are 1.

In more embodiments of Formula (IV), $c^1$, $c^2$, $d^1$ and $d^2$ are independently an integer from 6 to 8.

In other embodiments of Formula (IV), $c^1$ and $c^2$ are, at each occurrence, independently an integer from 6 to 10, and $d^1$ and $d^2$ are, at each occurrence, independently an integer from 6 to 10.

In other embodiments of Formula (IV), $c^1$ and $c^2$ are, at each occurrence, independently an integer from 5 to 9, and $d^1$ and $d^2$ are, at each occurrence, independently an integer from 5 to 9.

In more embodiments of Formula (IV), Z is alkyl, cycloalkyl or a monovalent moiety comprising at least one polar functional group when n is 1. In other embodiments, Z is alkyl.

In various embodiments of the foregoing Formula (IV), R is, at each occurrence, independently either: (a) H or methyl; or (b) R together with the carbon atom to which it is bound is taken together with an adjacent R and the carbon atom to which it is bound to form a carbon-carbon double bond. In certain embodiments, each R is H. In other embodiments at least one R together with the carbon atom to which it is bound is taken together with an adjacent R and the carbon atom to which it is bound to form a carbon-carbon double bond.

In other embodiments of the compound of Formula (IV), $R^1$ and $R^2$ independently have one of the following structures:

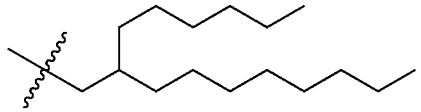
;

-continued

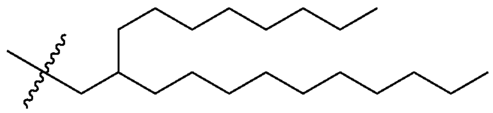
;

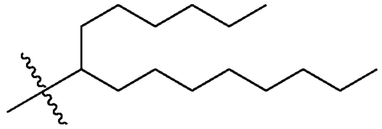
;

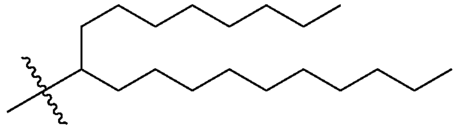
;

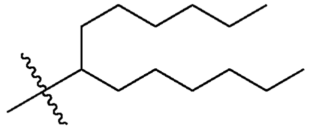
or

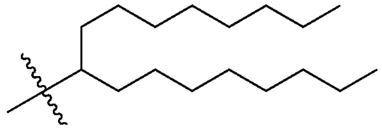
.

In certain embodiments of Formula (IV), the compound has one of the following structures:

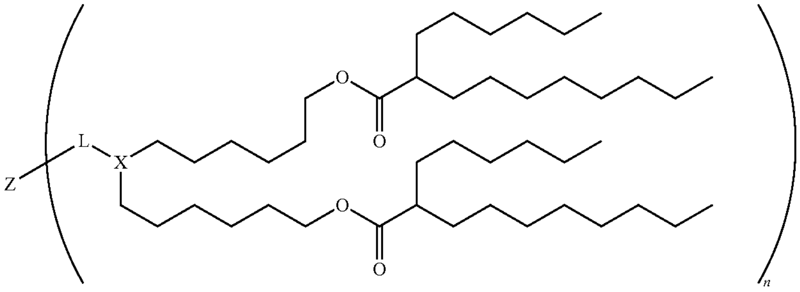
;

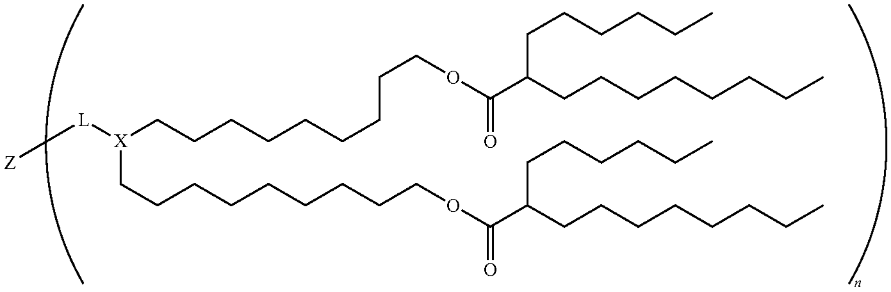
;

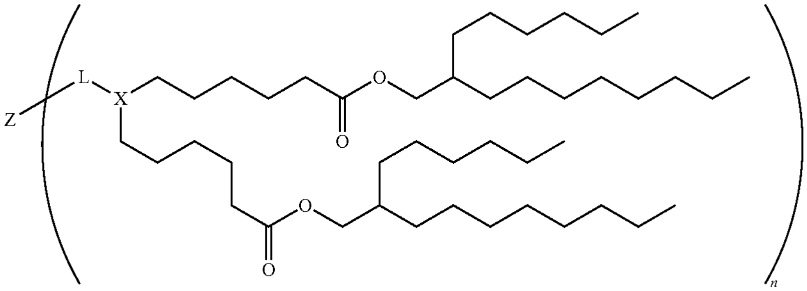
;

-continued
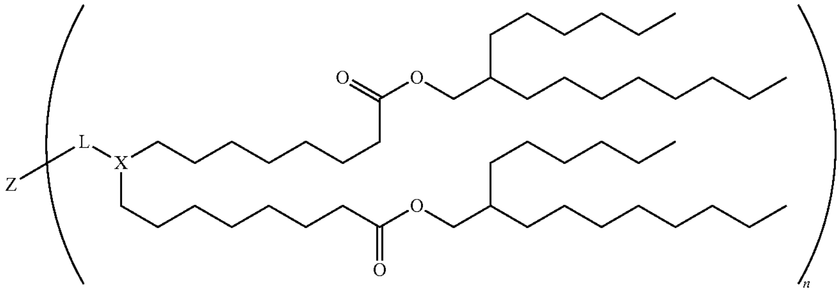
;
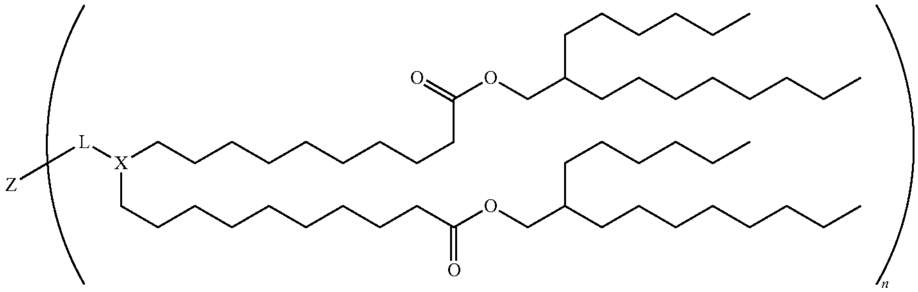
;
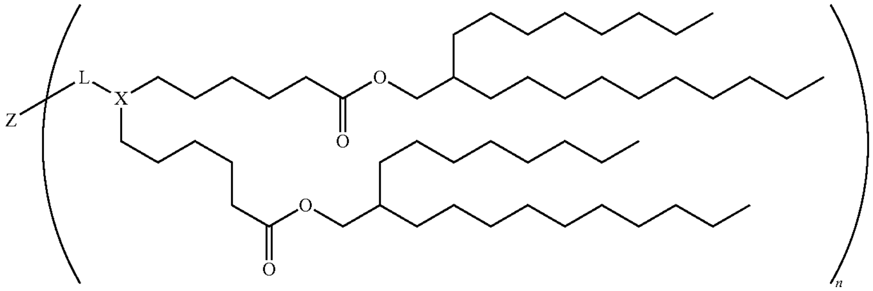
;
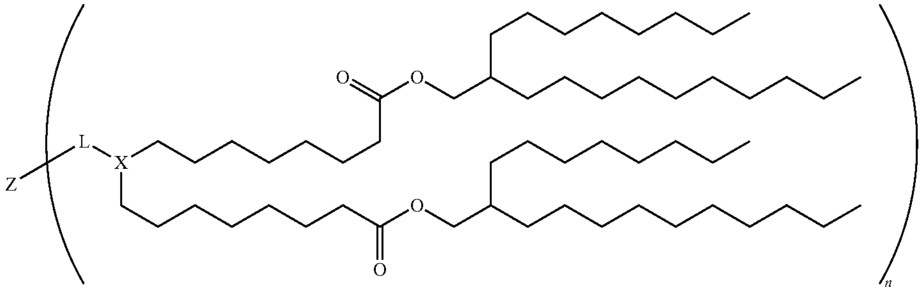
;
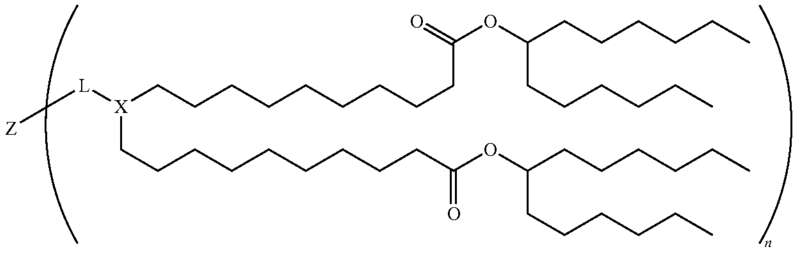
;
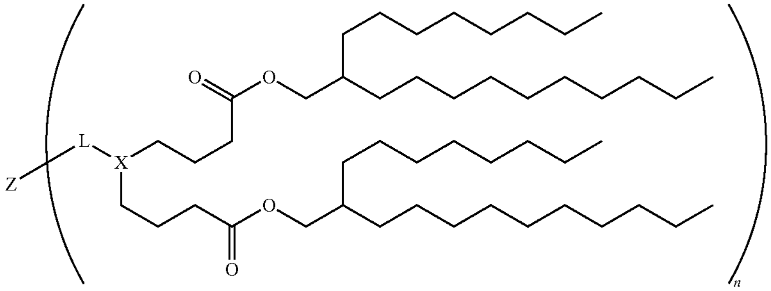
;

-continued
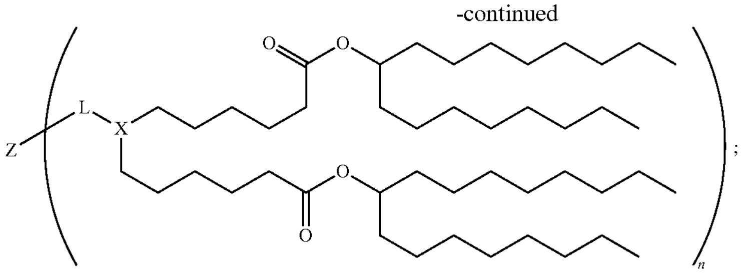
;
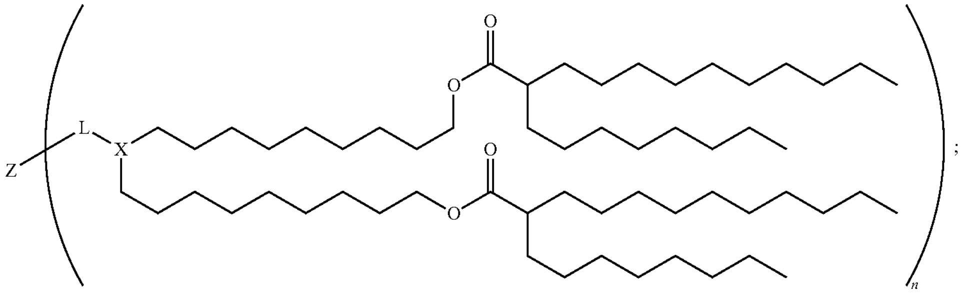
;
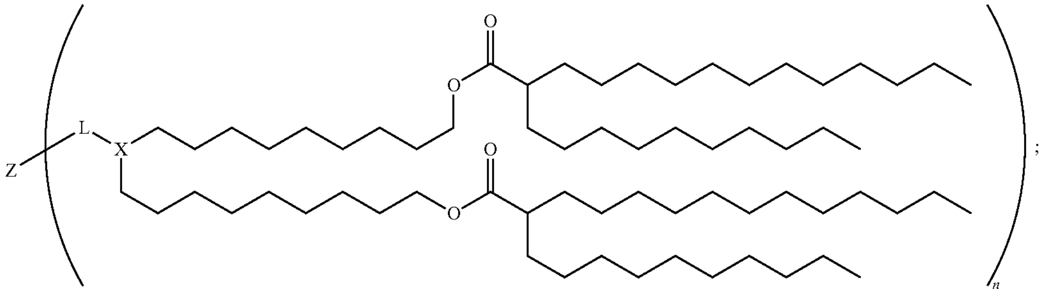
;
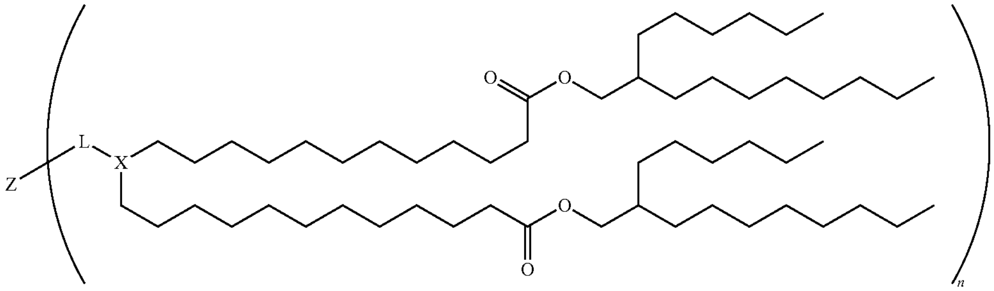
or
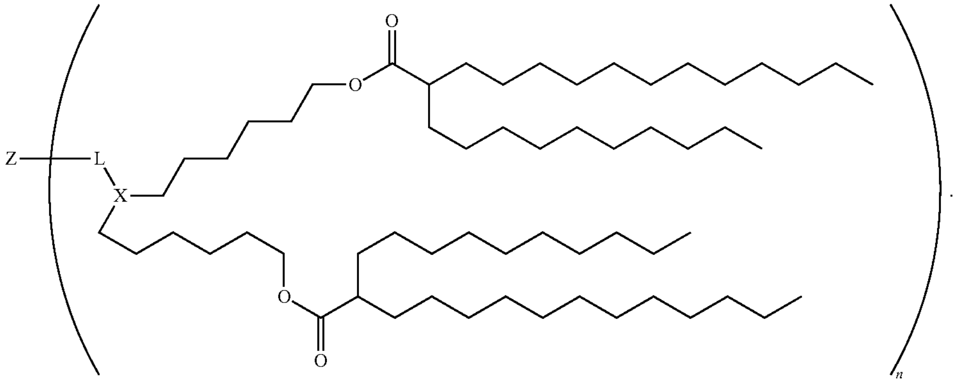
.

In still different embodiments the cationic lipid of Embodiments 1, 2, 3, 4 or 5 has the structure of Formula (V):

(V)

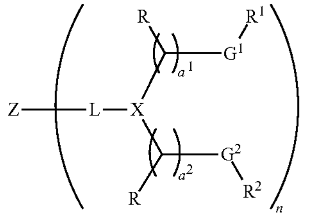

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —$S(O)_y$—, —S—S—, —C(═O)S—, SC(═O)—, —$N(R^a)C(=O)$—, —$C(=O)N(R^a)$—, —$N(R^a)C(=O)N(R^a)$—, —$OC(=O)N(R^a)$— or —$N(R^a)C(=O)O$—, and the other of $G^1$ or $G^2$ is, at each occurrence, —O(C═O)—, —(C═O)O—, —C(═O)—, —O—, —$S(O)_y$—, —S—S—, —C(═O)S—, —SC(═O)—, —$N(R^a)C(=O)$—, —$C(=O)N(R^a)$—, —$N(R^a)C(=O)N(R^a)$—, —$OC(=O)N(R^a)$— or —$N(R^a)C(=O)O$— or a direct bond;

L is, at each occurrence, ~O(C═O)—, wherein represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

$R^1$

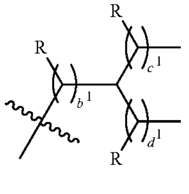

and $R^2$

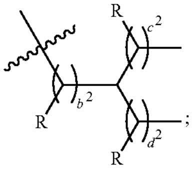

;

R' is, at each occurrence, independently H or $C_1$-$C_{12}$ alkyl;

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 2 to 12;

$d^1$ and $d^2$ are, at each occurrence, independently an integer from 2 to 12;

y is, at each occurrence, independently an integer from 0 to 2; and n is an integer from 1 to 6, wherein $a^1$, $a^2$, c, $c^2$, $d^1$ and $d^2$ are selected such that the sum of $a^1+c^1+d^1$ is an integer from 18 to 30, and the sum of $a^2+c^2+d^2$ is an integer from 18 to 30, and wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In certain embodiments of Formula (V), $G^1$ and $G^2$ are each independently

—O(C═O)— or —(C═O)O—.

In other embodiments of Formula (V), X is CH.

In some embodiments of Formula (V), the sum of $a^1+c^1+d^1$ is an integer from 20 to 30, and the sum of $a^2+c^2+d^2$ is an integer from 18 to 30. In other embodiments, the sum of $a^1+c^1+d^1$ is an integer from 20 to 30, and the sum of $a^2+c^2+d^2$ is an integer from 20 to 30. In more embodiments of Formula (V), the sum of $a^1+b^1+c^1$ or the sum of $a^2+b^2+c^2$ is an integer from 12 to 26. In other embodiments, $a^1$, $a^2$, $c^1$, $c^2$, $d^1$ and $d^2$ are selected such that the sum of $a^1+c^1+d^1$ is an integer from 18 to 28, and the sum of $a^2+c^2+d^2$ is an integer from 18 to 28, In still other embodiments of Formula (V), $a^1$ and $a^2$ are independently an integer from 3 to 10, for example an integer from 4 to 9.

In yet other embodiments of Formula (V), $b^1$ and $b^2$ are 0. Indifferent embodiments $b^1$ and $b^2$ are 1.

In certain other embodiments of Formula (V), $c^1$, $c^2$, $d^1$ and $d^2$ are independently an integer from 6 to 8.

In different other embodiments of Formula (V), Z is alkyl or a monovalent moiety comprising at least one polar functional group when n is 1; or Z is alkylene or a polyvalent moiety comprising at least one polar functional group when n is greater than 1.

In more embodiments of Formula (V), Z is alkyl, cycloalkyl or a monovalent moiety comprising at least one polar functional group when n is 1. In other embodiments, Z is alkyl.

In other different embodiments of Formula (V), R is, at each occurrence, independently either: (a) H or methyl; or (b) R together with the carbon atom to which it is bound is taken together with an adjacent R and the carbon atom to which it is bound to form a carbon-carbon double bond. For example in some embodiments each R is H. In other embodiments at least one R together with the carbon atom to which it is bound is taken together with an adjacent R and the carbon atom to which it is bound to form a carbon-carbon double bond.

In more embodiments, each R' is H.

In certain embodiments of Formula (V), the sum of $a^1+c^1+d^1$ is an integer from 20 to 25, and the sum of $a^2+c^2+d^2$ is an integer from 20 to 25.

In other embodiments of Formula (V), $R^1$ and $R^2$ independently have one of the following structures:

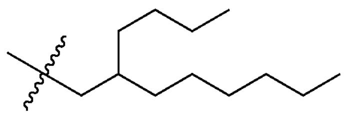

;

-continued
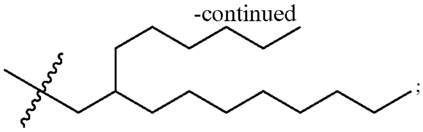
;
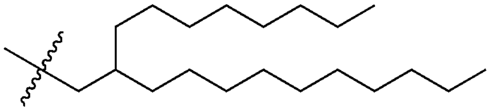
;
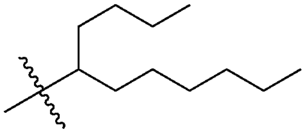
;
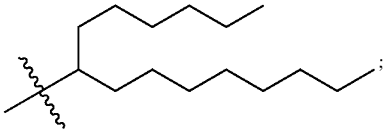
;
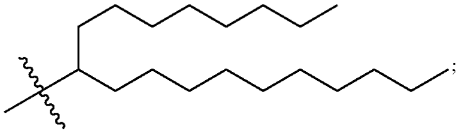
;
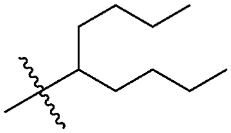
;
-continued
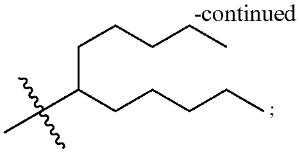
;
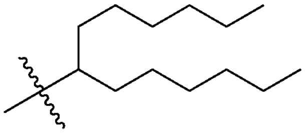
;
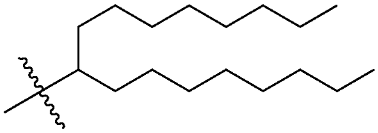
;
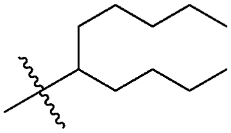
or
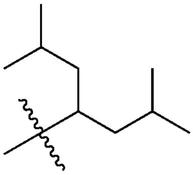
.
In more embodiments of Formula (V), the compound has one of the following structures:
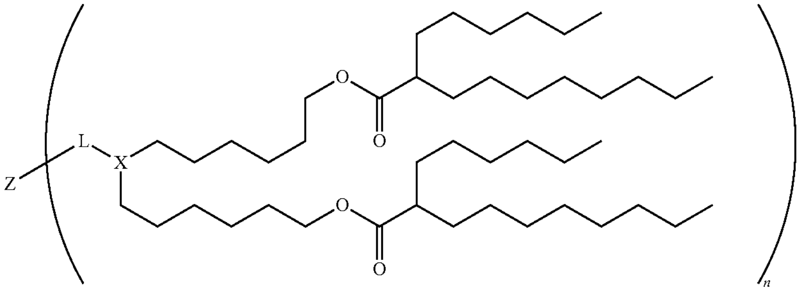
;
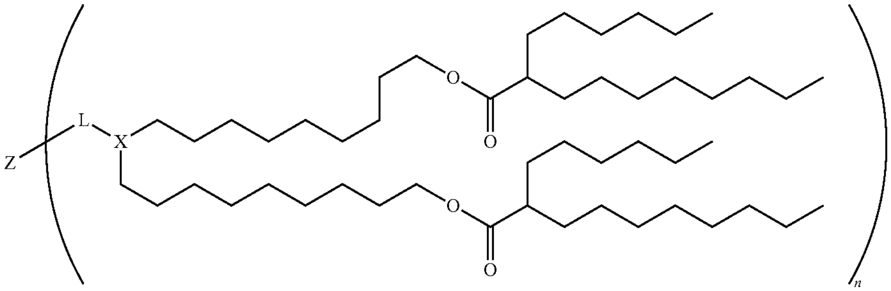
;
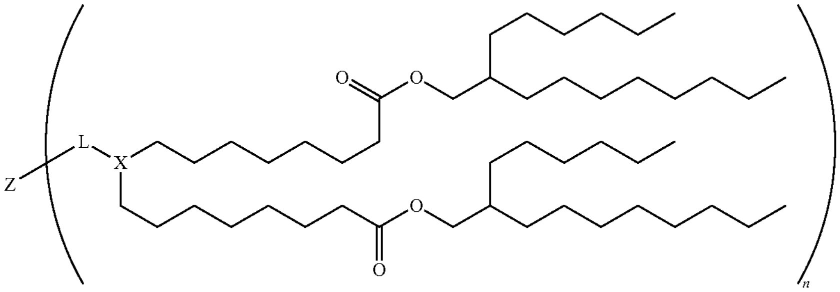
;

-continued
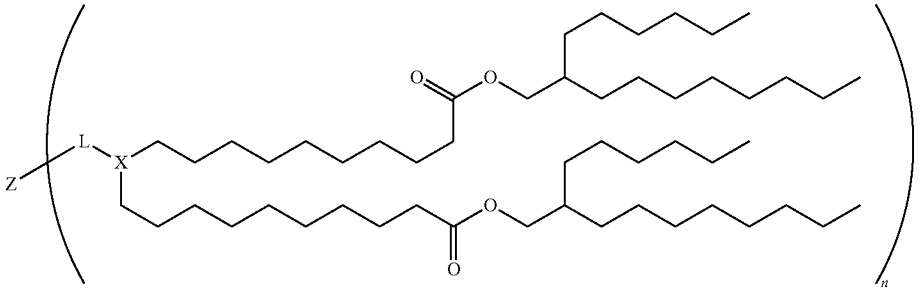
;
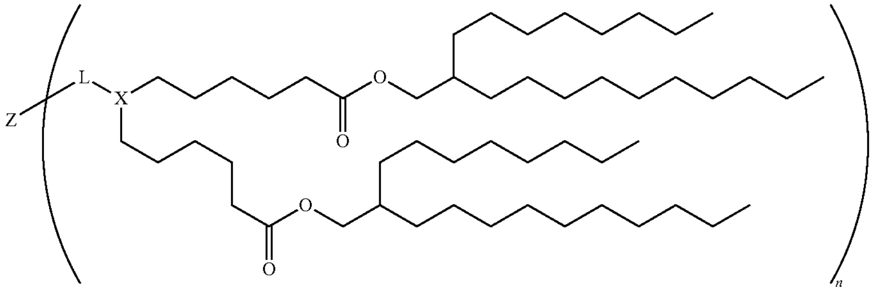
;
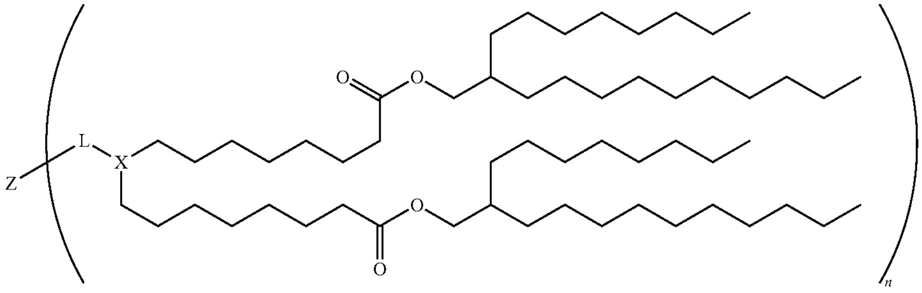
;
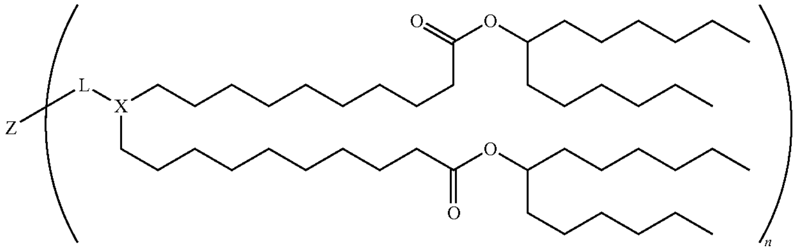
;
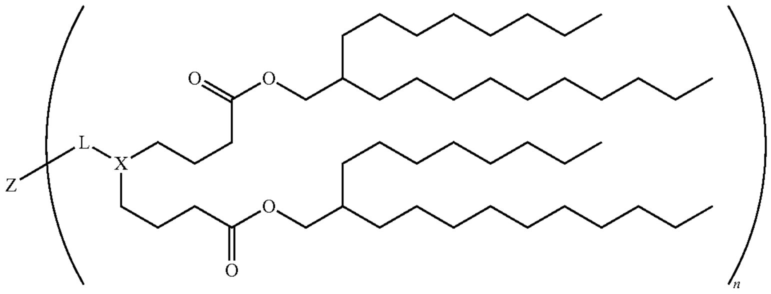
;
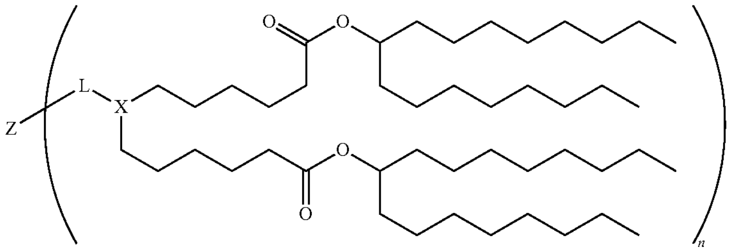
;

-continued

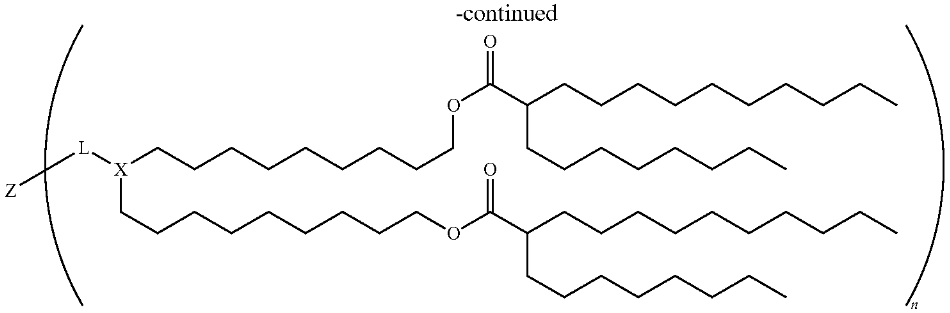

;

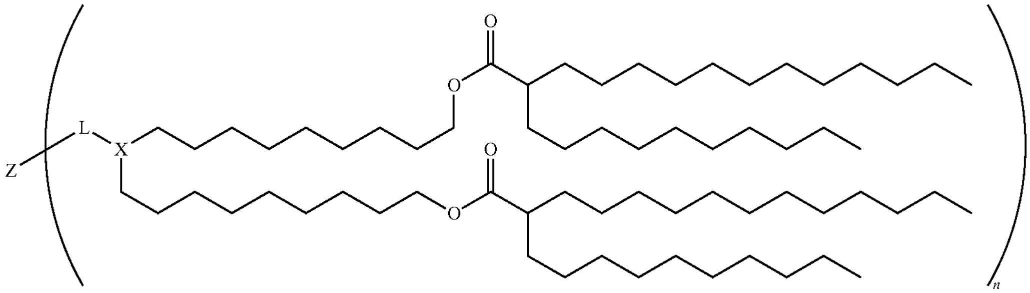

;

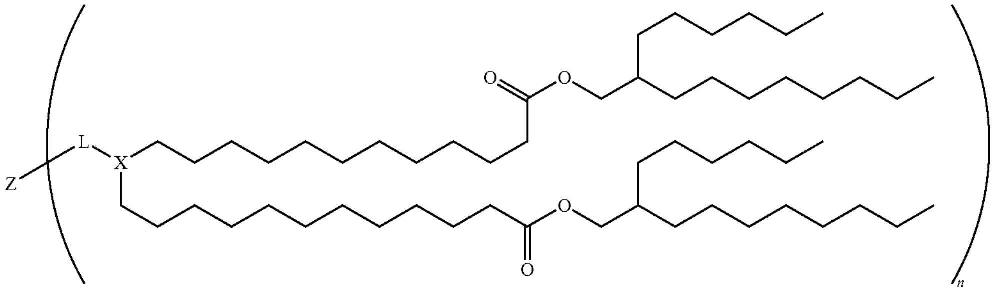

or

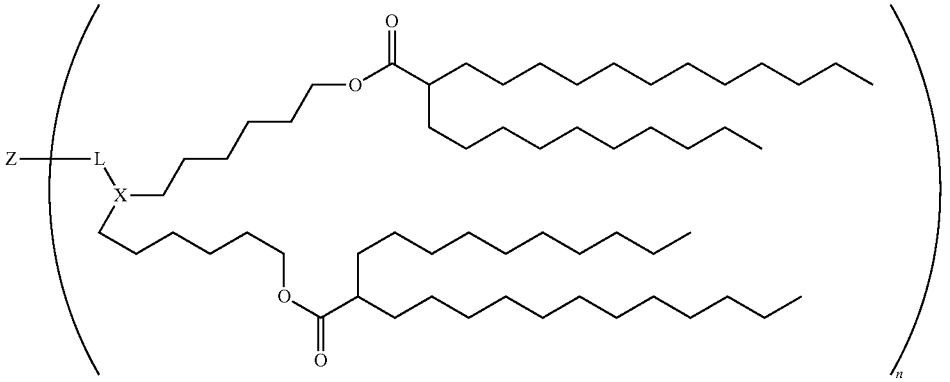

.

In any of the foregoing embodiments of Formula (IV) or (V), n is 1. In other of the foregoing embodiments of Formula (IV) or (V), n is greater than 1.

In more of any of the foregoing embodiments of Formula (IV) or (V), Z is a mono- or polyvalent moiety comprising at least one polar functional group. In some embodiments, Z is a monovalent moiety comprising at least one polar functional group. In other embodiments, Z is a polyvalent moiety comprising at least one polar functional group.

In more of any of the foregoing embodiments of Formula (IV) or (V), the polar functional group is a hydroxyl, alkoxy, ester, cyano, amide, amino, alkylaminyl, heterocyclyl or heteroaryl functional group.

In any of the foregoing embodiments of Formula (IV) or (V), Z is hydroxyl, hydroxylalkyl, alkoxyalkyl, amino, aminoalkyl, alkylaminyl, alkylaminylalkyl, heterocyclyl or heterocyclylalkyl.

In some other embodiments of Formula (IV) or (V), Z has the following structure:

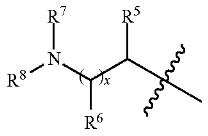

wherein:

$R^5$ and $R^6$ are independently H or $C_1$-$C_6$ alkyl;

$R^7$ and $R^8$ are independently H or $C_1$-$C_6$ alkyl or $R^7$ and $R^8$, together with the nitrogen atom to which they are attached, join to form a 3-7 membered heterocyclic ring; and x is an integer from 0 to 6.

In still different embodiments of Formula (IV) or (V), Z has the following structure:

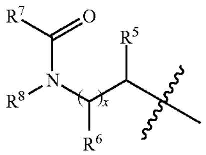

wherein:

$R^5$ and $R^6$ are independently H or $C_1$-$C_6$ alkyl;

$R^7$ and $R^8$ are independently H or $C_1$-$C_6$ alkyl or $R^7$ and $R^8$, together with the nitrogen atom to which they are attached, join to form a 3-7 membered heterocyclic ring; and x is an integer from 0 to 6.

In still different embodiments of formula (IV) or (V), Z has the following structure:

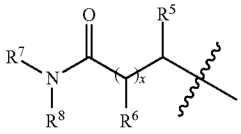

wherein:

$R^5$ and $R^6$ are independently H or $C_1$-$C_6$ alkyl;

$R^7$ and $R^8$ are independently H or $C_1$-$C_6$ alkyl or $R^7$ and $R^8$, together with the nitrogen atom to which they are attached, join to form a 3-7 membered heterocyclic ring; and x is an integer from 0 to 6.

In some other embodiments of Formula (IV) or (V), Z is hydroxylalkyl, cyanoalkyl or an alkyl substituted with one or more ester or amide groups.

For example, in any of the foregoing embodiments of Formula (IV) or (V), Z has one of the following structures:

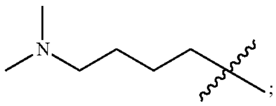 ;

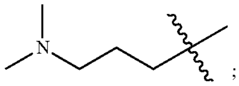 ; 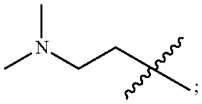 ;

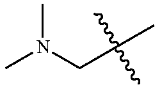 ; 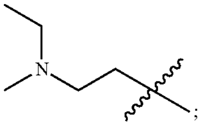 ;

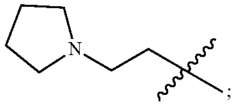 ; 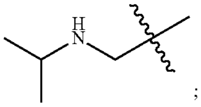 ;

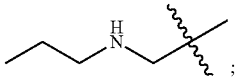 ; 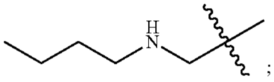 ;

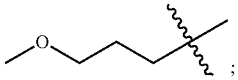 ; 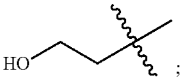 ;

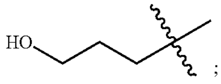 ; 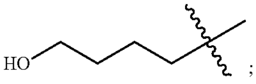 ;

-continued

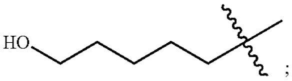 ;

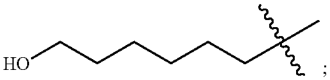 ;

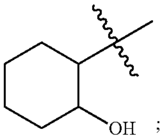 ; 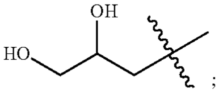 ;

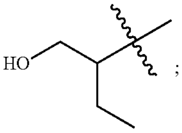 ;

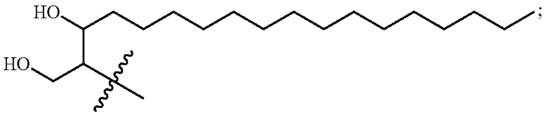 ;

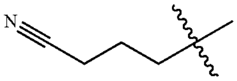 or

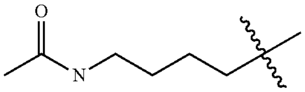 .

In other embodiments of Formula (IV) or (V), Z-L has one of the following structures:

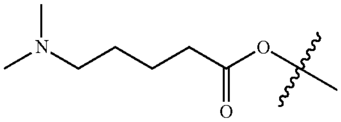 ;

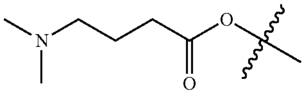 ;

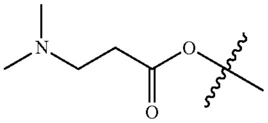 ;

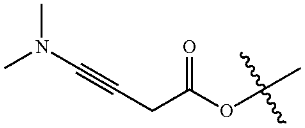 ;

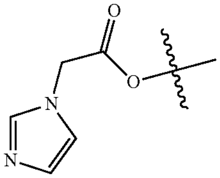 ;

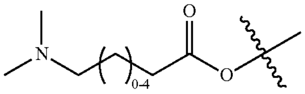 ;

-continued
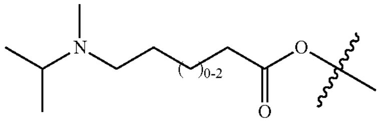
;
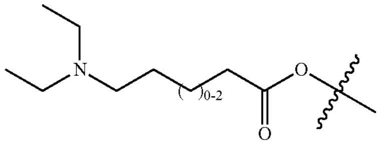
;
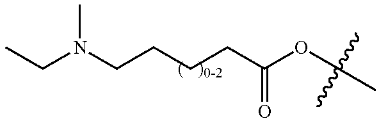
;
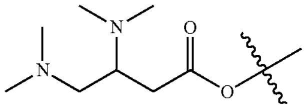
;
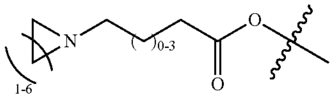
;
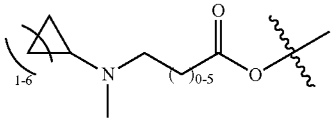
;
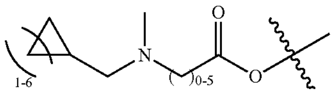
;
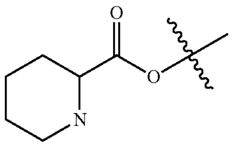
;
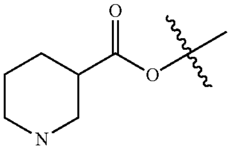
;
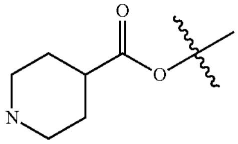
;
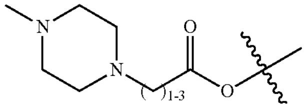
;
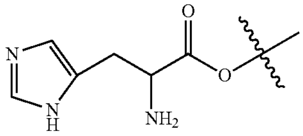
;
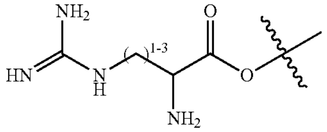
;
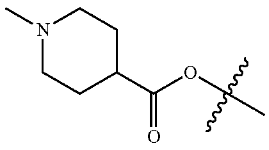
;
-continued
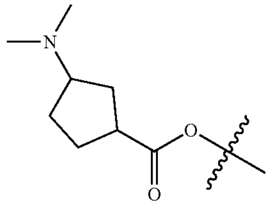
;
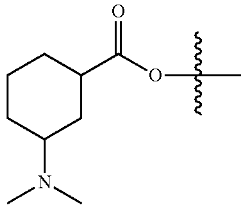
;
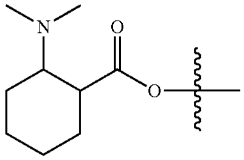
;
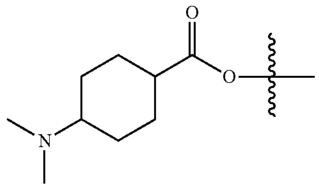
;
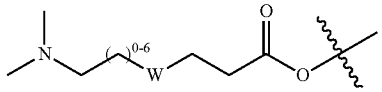
;
W = O, S, NH, NMe
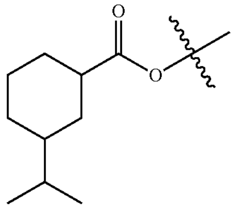
;
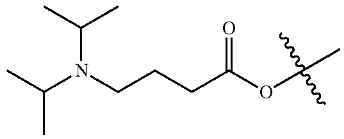
;
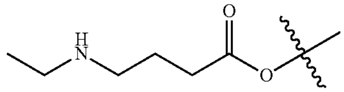
;
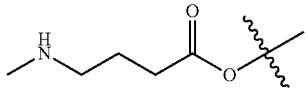
;
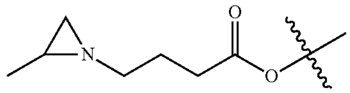
;
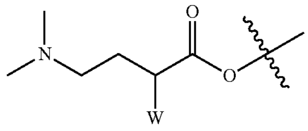
;
W = Me, OH, Cl
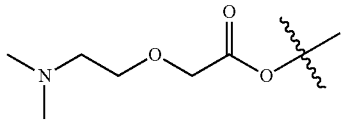
;

-continued
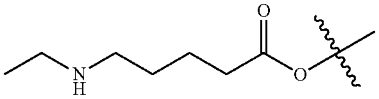
;
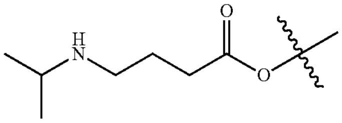
;
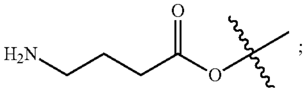
;
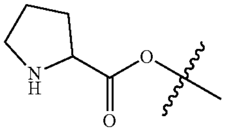
;
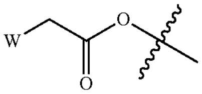
;
W = H, Me, Et, iPr
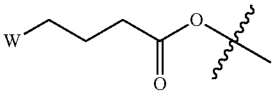
;
W = H, Me, Et, iPr
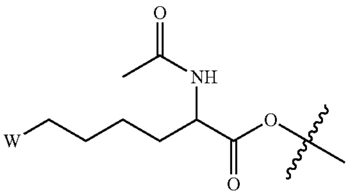
;
W = H, Me, Et, iPr
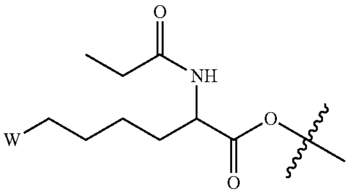
;
W = H, Me, Et, iPr
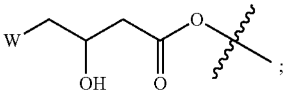
;
W = H, Me, Et, iPr
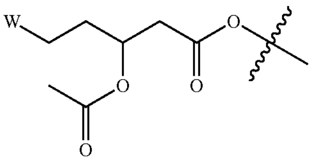
;
W = H, Me, Et, iPr
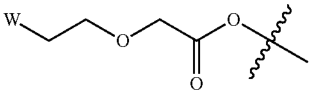
;
W = H, Me, Et, iPr
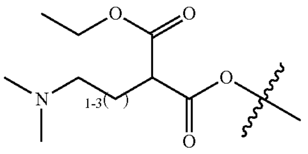
;
-continued
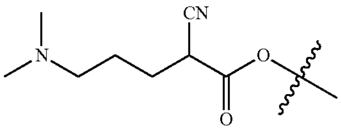
;
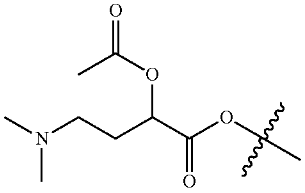
;
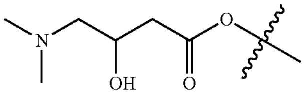
;
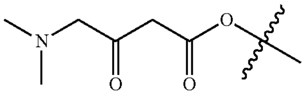
;
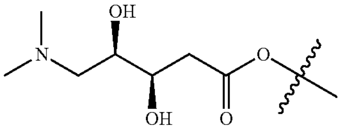
;
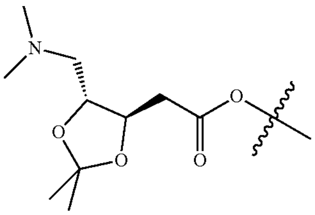
;
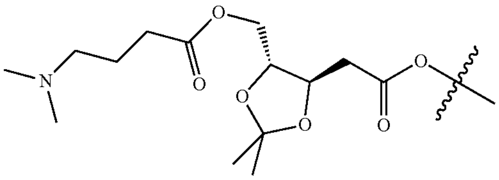
;
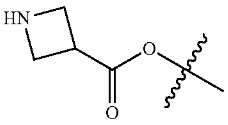
or
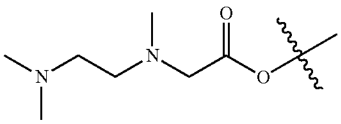
.
In other embodiments, Z-L has one of the following structures:
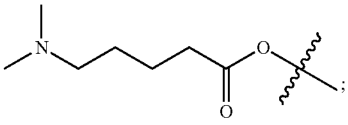
;
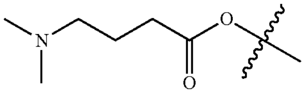
or -continued
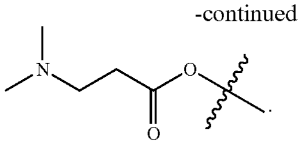
.
In still other embodiments, X is CH and Z-L has one of the following structures:
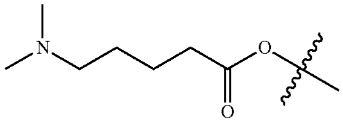
;
-continued
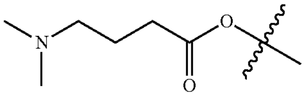
;
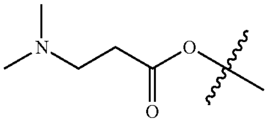
.
In various different embodiments, a cationic lipid of any one Embodiments 1, 2, 3, 4 or 5 has one of the structures set forth in Table 4 below.
TABLE 4
| Representative Compounds of Formula (IV) or (V) | |
|---|---|
| No. | Structure |
| IV-1 | 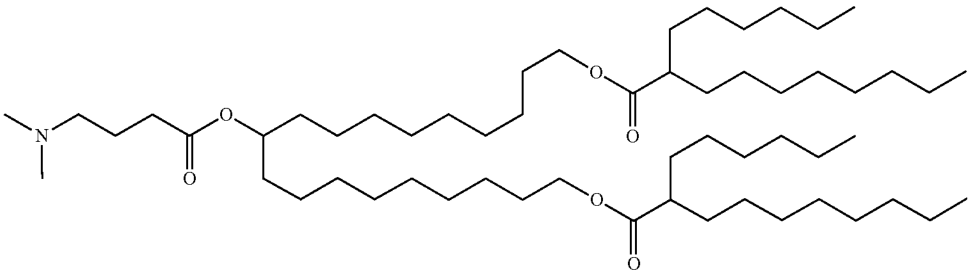 [SMILES: CCCCCCCCC(CCCCCC)C(=O)OCCCCCCCCCC(CCCCCCCCCOC(=O)C(CCCCCC)CCCCCCCC)OC(=O)CCCN(C)C] |
| IV-2 | 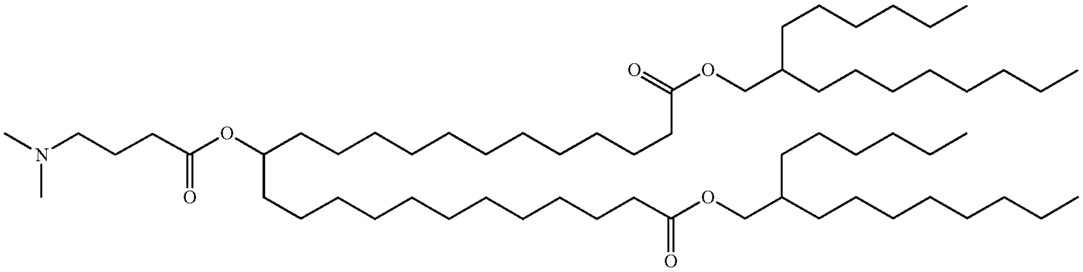 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C] |
| IV-3 | 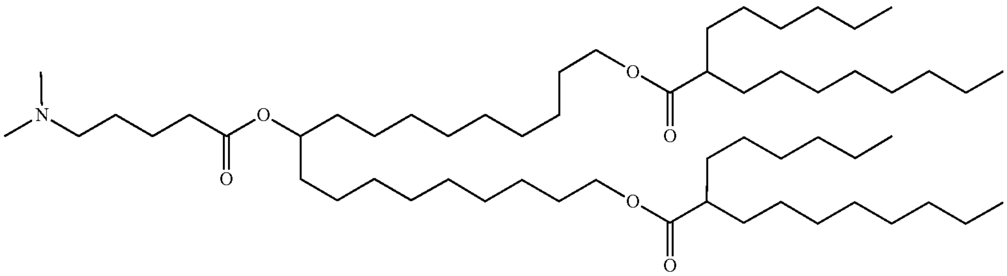 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] |

In one embodiment, the cationic lipid is a compound having the following structure (VI):

(VI)

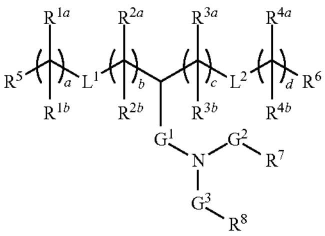

or a pharmaceutically acceptable salt, tautomer, prodrug or stereoisomer thereof, wherein:

$L^1$ and $L^2$ are each independently —O(C═)-, —(C═O)O—, —C(═O)—, —O—, —S(O)$_x$—, —S—S—, —C(═O)S—, —SC(═O)—, —NR$^a$C(═O)—, —C(═O)NR$^a$—, —NR$^a$C(═O)NR$^a$—, —OC(═O)NR$^a$—, —NR$^a$C(═O)O— or a direct bond;

$G^1$ is $C_1$-$C_2$ alkylene, —(C═O)—, —O(C═O)—, —SC(═O)—, —NR$^a$C(═O)— or a direct bond;

$G^2$ is —C(═O)—, —(C═O)O—, —C(═O)S—, —C(═O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$, is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is H or $C_1$-$C_{20}$ alkyl;

$R^8$ is OH, —N($R^9$)(C═O)$R^{10}$, —(C═O)N$R^9R^{10}$, —N$R^9R^{10}$, —(C═O)O$R^{11}$ or —O(C═O)$R^{11}$, provided that $G^3$ is $C_4$-$C_6$ alkylene when $R^8$ is —N$R^9R^{10}$ $R^9$ and $R^{10}$ are each independently H or $C_1$-$C_{12}$ alkyl;

$R^{11}$ is aralkyl;

a, b, c and d are each independently an integer from 1 to 24; and x is 0, 1 or 2, wherein each alkyl, alkylene and aralkyl is optionally substituted.

In some embodiments of structure (VI), $L^1$ and $L^2$ are each independently —O(C═O)—, —(C═O)O— or a direct bond. In other embodiments, $G^1$ and $G^2$ are each independently —(C═O)— or a direct bond. In some different embodiments, $L^1$ and $L^2$ are each independently —O(C═O)—, —(C═O)O— or a direct bond; and $G^1$ and $G^2$ are each independently —(C═O)— or a direct bond.

In some different embodiments of structure (VI), $L^1$ and $L^2$ are each independently —C(═O)—, —O—, —S(O)$_x$—, —S—S—, —C(═O)S—, —SC(═O)—, —NR$^a$—, —NR$^a$C(═O)—, —C(═O)NR$^a$—, —NR$^a$C(═O)NR$^a$, —OC(═O)NR$^a$—, —NR$^a$C(═O)O—, —NR$^a$S(O)$_x$NR$^a$, —NR$^a$S(O)$_x$— or —S(O)$_x$NR$^a$—.

In other of the foregoing embodiments of structure (VI), the compound has one of the following structures (VIA) or (VIB).

(VIA)

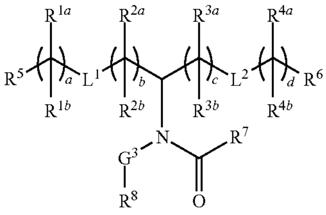

or (VIB)

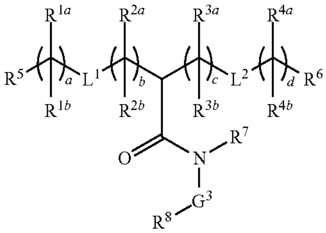

In some embodiments, the compound has structure (VIA). In other embodiments, the compound has structure (VIB).

In any of the foregoing embodiments of structure (VI), one of $L^1$ or $L^2$ is —O(C═O)—. For example, in some embodiments each of $L^1$ and $L^2$ are —O(C═O)—.

In some different embodiments of any of the foregoing, one of $L^1$ or $L^2$ is —(C═O)O—. For example, in some embodiments each of $L^1$ and $L^2$ is —(C═O)O—.

In different embodiments of structure (VI), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of the foregoing, for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of structure (VI), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of structure (VI), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of any of the foregoing, for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

It is understood that "carbon-carbon" double bond refers to one of the following structures:

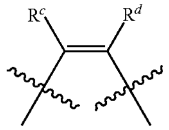

or

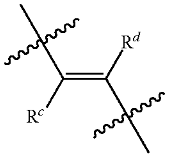

wherein $R^c$ and $R^d$ are, at each occurrence, independently H or a substituent. For example, in some embodiments $R^c$ and $R^d$ are, at each occurrence, independently H, $C_1$-$C_{12}$ alkyl or cycloalkyl, for example H or $C_1$-$C_{12}$ alkyl.

In various other embodiments, the compound has one of the following structures (VIC) or (VID):

(VIC)

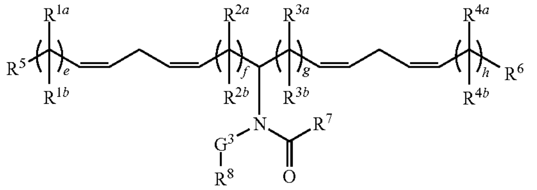

or (VID)

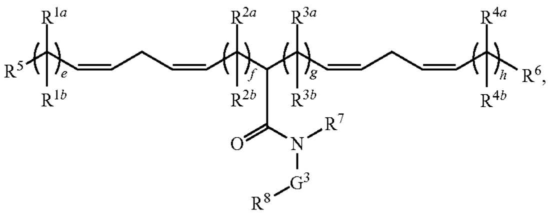

wherein e, f, g and h are each independently an integer from 1 to 12.

In some embodiments, the compound has structure (VIC). In other embodiments, the compound has structure (VID).

In various embodiments of the compounds of structures (VIC) or (VID), e, f, g and h are each independently an integer from 4 to 10.

In other different embodiments,

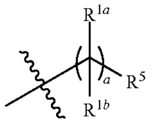

or

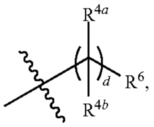

or both, independently has one of the following structures:

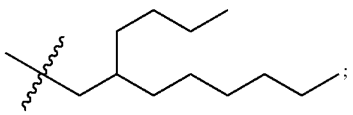

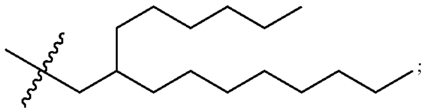

-continued

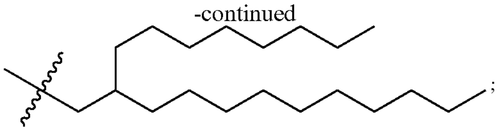

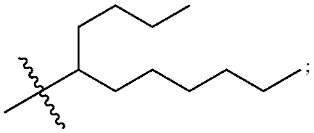

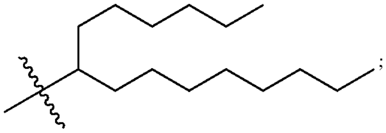

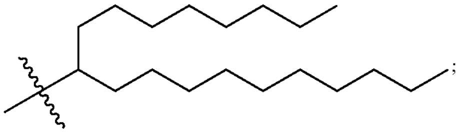

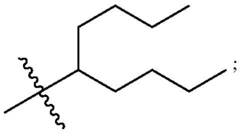

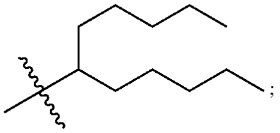

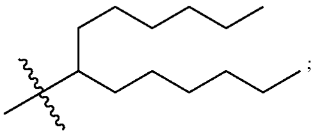

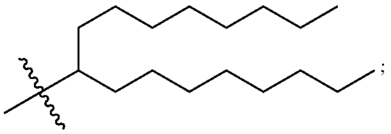

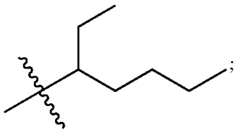

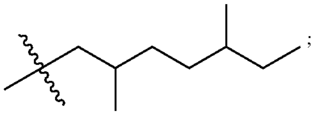

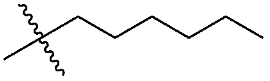

or

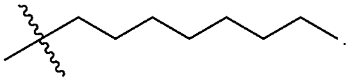

In certain embodiments of the foregoing, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of structure (VI), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of structure (VI), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of structure (VI), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of structure (VI), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of structure (VI), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of structure (VI), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of structure (VI), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, his 11. In yet other embodiments, his 12.

In some other various embodiments of structure (VI), a and d are the same. In some other embodiments, b and c are the same. In some other specific embodiments a and d are the same and b and c are the same.

The sum of a and b and the sum of c and d are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of the foregoing, $R^{1a}$, $R^{1b}$, $R^{4a}$ and $R^{4b}$ are $C_1$-$C_{12}$ alkyl at each occurrence.

In further embodiments of the foregoing, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of the foregoing, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ are not particularly limited in the foregoing embodiments. In certain embodiments one of $R^5$ or $R^6$ is methyl. In other embodiments each of $R^5$ or $R^6$ is methyl.

The substituents at $R^7$ are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with $-(C{=}O)OR^b$, $-O(C{=}O)R^b$, $-C({=}O)R^b$, $-OR^b$, $-S(O)R^b$, $-S-SR^b$, $-C({=}O)SR^b$, $-SC({=}O)R^b$, $-NR^aR^b$, $-NR^aC({=}O)R^b$, $-C({=}O)NR^aR^b$, $-NR^aC({=}O)NR^aR^b$, $-OC({=}O)NR^aR^b$, $-NR^aC({=}O)OR^b$, $-NR^aS(O)_xNR^aR^b$, $-NR^aS(O)_xR^b$ or $-S(O)_xNR^aR^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with $-(C{=}O)OR^b$ or $-O(C{=}O)R^b$.

In various of the foregoing embodiments of structure (VI), $R^b$ is branched $C_3$-$C_{15}$ alkyl. For example, in some embodiments $R^b$ has one of the following structures:

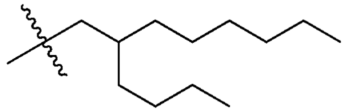
;

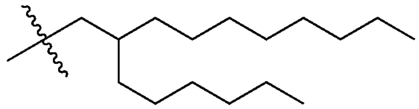
;

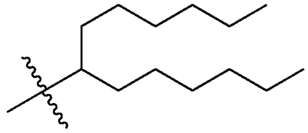
;

-continued

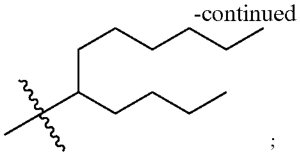

;

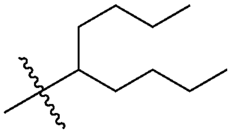

or

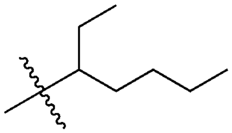

.

In certain embodiments, $R^8$ is OH.

In other embodiments of structure (VI), $R^8$ is —N($R^9$)(C═O)$R^{10}$. In some other embodiments, $R^8$ is —(C═O)N$R^9R^{10}$. In still more embodiments, $R^8$ is —N$R^9R^{10}$. In some of the foregoing embodiments, $R^9$ and $R^{10}$ are each independently H or $C_1$-$C_8$ alkyl, for example H or $C_1$-$C_3$ alkyl. In more specific of these embodiments, the $C_1$-$C_8$ alkyl or $C_1$-$C_3$ alkyl is unsubstituted or substituted with hydroxyl. In other of these embodiments, $R^9$ and $R^{10}$ are each methyl.

In yet more embodiments of structure (VI), $R^8$ is —(C═O)O$R^{11}$. In some of these embodiments $R^{11}$ is benzyl.

In yet more specific embodiments of structure (VI), $R^8$ has one of the following structures:

—OH;

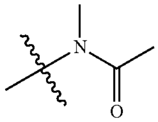

;

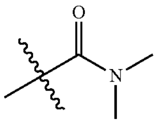

;

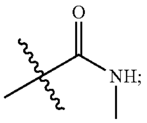

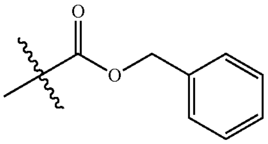

;

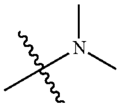

;

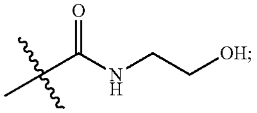

-continued

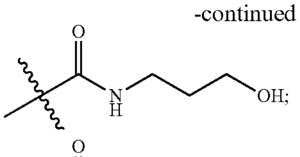

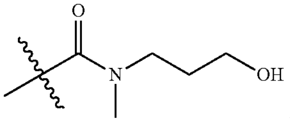

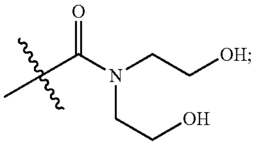

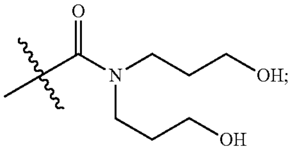

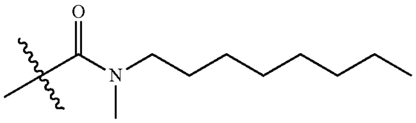

;

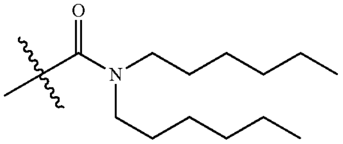

or

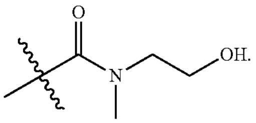

In still other embodiments of the foregoing compounds, $G^3$ is $C_2$-$C_5$ alkylene, for example $C_2$-$C_4$ alkylene, $C_3$ alkylene or $C_4$ alkylene. In some of these embodiments, $R^8$ is OH. In other embodiments, $G^2$ is absent and $R^7$ is $C_1$-$C_2$ alkylene, such as methyl.

In various different embodiments, the compound has one of the structures set forth in Table 5 below.

TABLE 5

| Representative cationic lipids of structure (VI) | |
|---|---|
| No. | Structure |
| VI-1 | 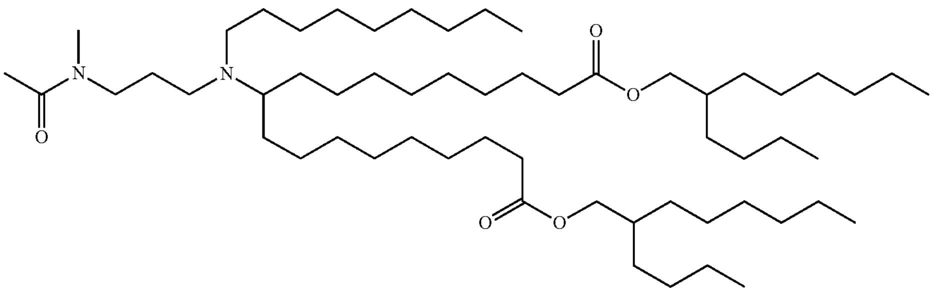 [SMILES: CCCCCCCCCN(CCCN(C)C(C)=O)C(CCCCCCCCC(=O)OCC(CCCC)CCCCCC)CCCCCCCCC(=O)OCC(CCCC)CCCCCC] |

TABLE 5-continued
| Representative cationic lipids of structure (VI) | |
|---|---|
| No. | Structure |
| VI-2 | 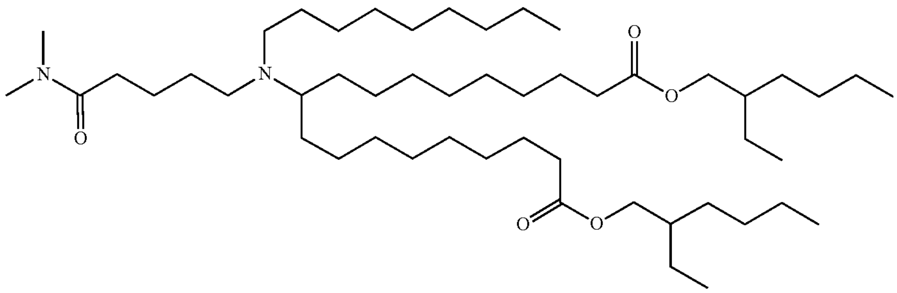 [SMILES: CCCCCCCCCN(CCCCC(=O)N(C)C)C(CCCCCCCCC(=O)OCC(CC)CCCC)CCCCCCCCC(=O)OCC(CC)CCCC] |
| VI-3 | 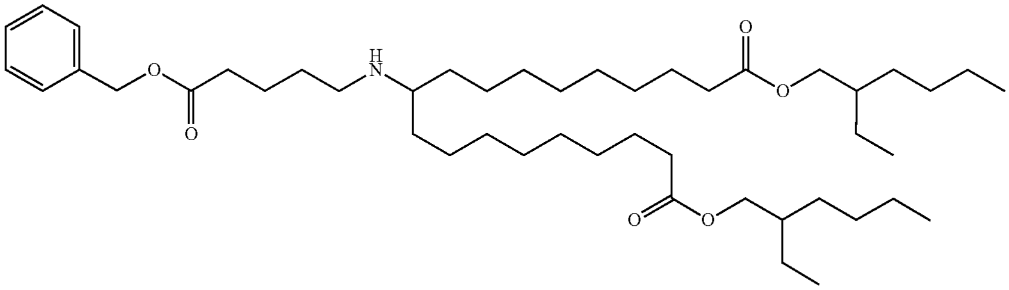 [SMILES: CCCCC(CC)COC(=O)CCCCCCCCC(CCCCCCCCC(=O)OCC(CC)CCCC)NCCCCC(=O)OCc1ccccc1] |
| VI-4 | 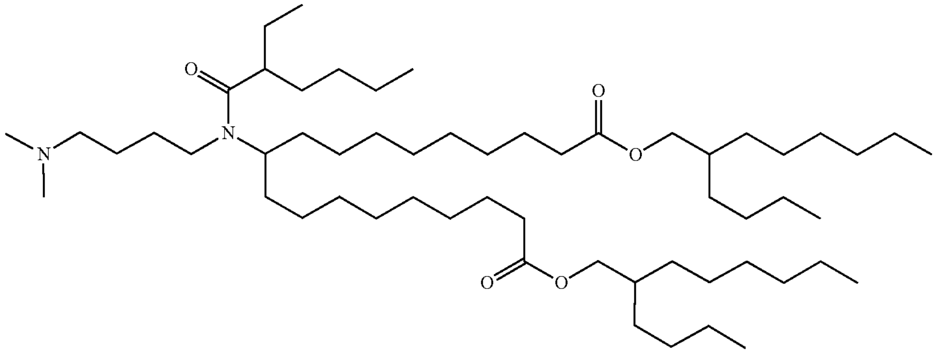 [SMILES: CCCCCCC(CCCC)COC(=O)CCCCCCCCC(CCCCCCCCC(=O)OCC(CCCC)CCCCCC)N(CCCCN(C)C)C(=O)C(CC)CCCC] |
| VI-5 | 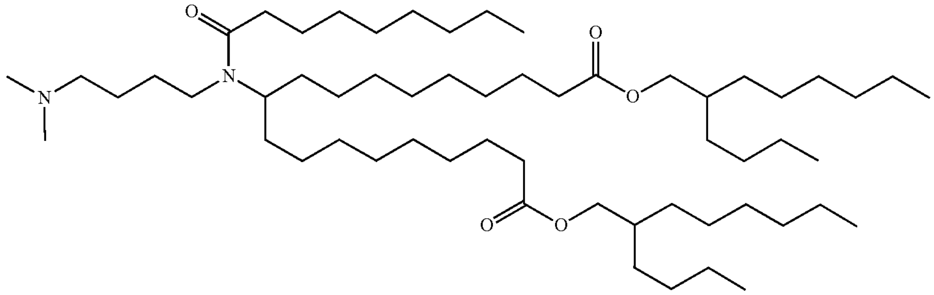 [SMILES: CCCCCCCCC(=O)N(CCCCN(C)C)C(CCCCCCCCC(=O)OCC(CCCC)CCCCCC)CCCCCCCCC(=O)OCC(CCCC)CCCCCC] |
| VI-6 | 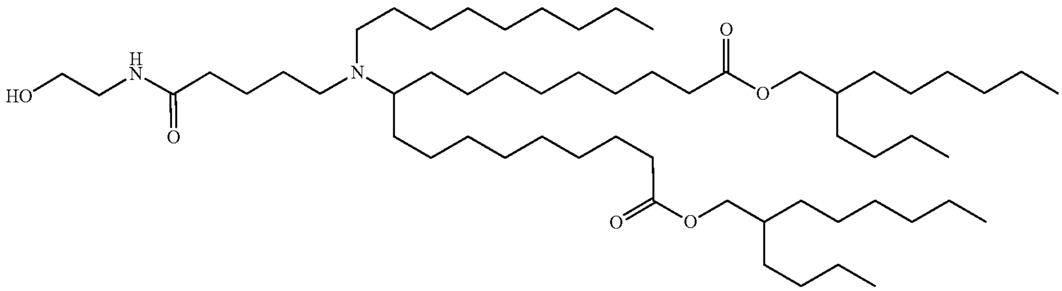 [SMILES: CCCCCCCCCN(CCCCC(=O)NCCO)C(CCCCCCCCC(=O)OCC(CCCC)CCCCCC)CCCCCCCCC(=O)OCC(CCCC)CCCCCC] |

TABLE 5-continued
| Representative cationic lipids of structure (VI) | |
|---|---|
| No. | Structure |
| VI-7 | 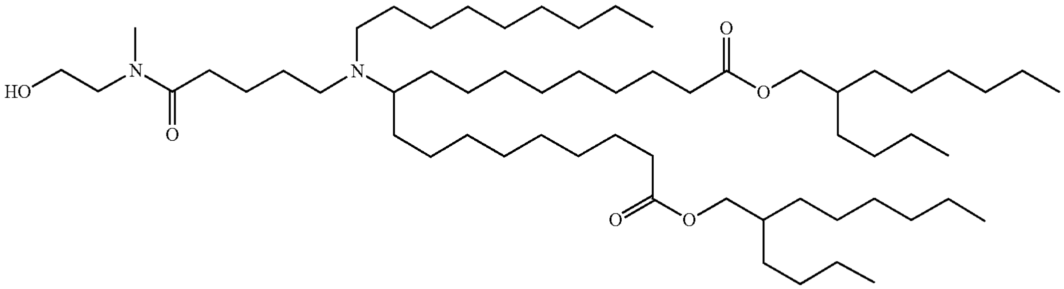 [SMILES: CCCCCCCCCN(CCCCC(=O)N(C)CCO)C(CCCCCCCCC(=O)OCC(CCCC)CCCCCC)CCCCCCCCC(=O)OCC(CCCC)CCCCCC] |
| VI-8 | 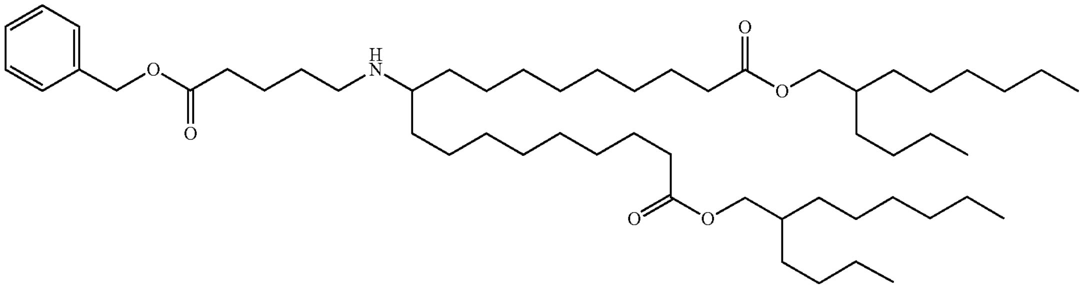 [SMILES: CCCCCCC(CCCC)COC(=O)CCCCCCCCC(CCCCCCCCC(=O)OCC(CCCC)CCCCCC)NCCCCC(=O)OCc1ccccc1] |
| VI-9 | 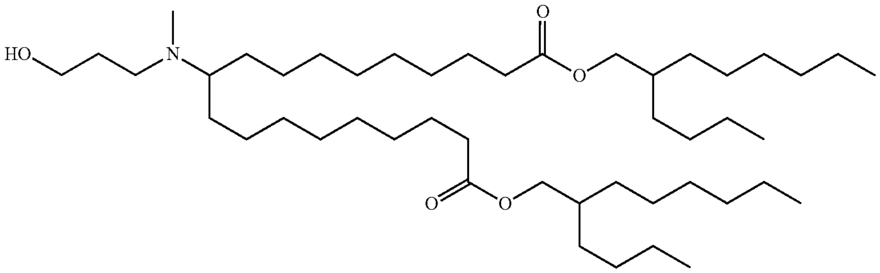 [SMILES: CCCCCCC(CCCC)COC(=O)CCCCCCCCC(CCCCCCCCC(=O)OCC(CCCC)CCCCCC)N(C)CCCO] |
| VI-10 | 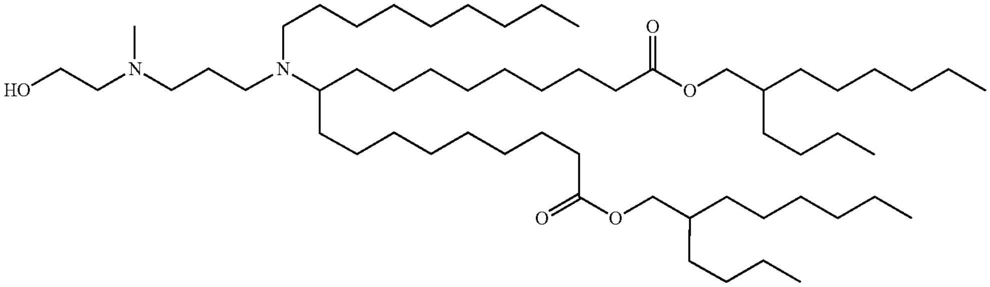 [SMILES: CCCCCCCCCN(CCCN(C)CCO)C(CCCCCCCCC(=O)OCC(CCCC)CCCCCC)CCCCCCCCC(=O)OCC(CCCC)CCCCCC] |
| VI-11 | 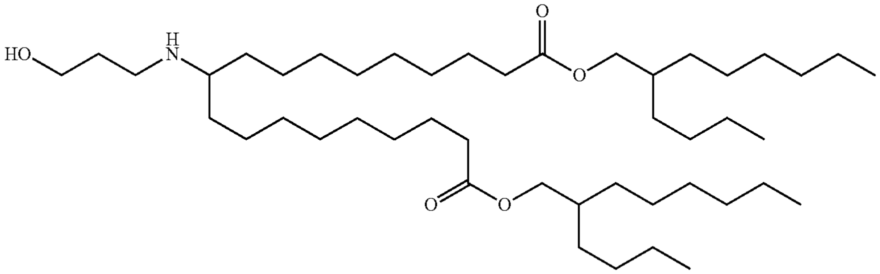 [SMILES: CCCCCCC(CCCC)COC(=O)CCCCCCCCC(CCCCCCCCC(=O)OCC(CCCC)CCCCCC)NCCCO] |

TABLE 5-continued
| Representative cationic lipids of structure (VI) | |
|---|---|
| No. | Structure |
| VI-12 | 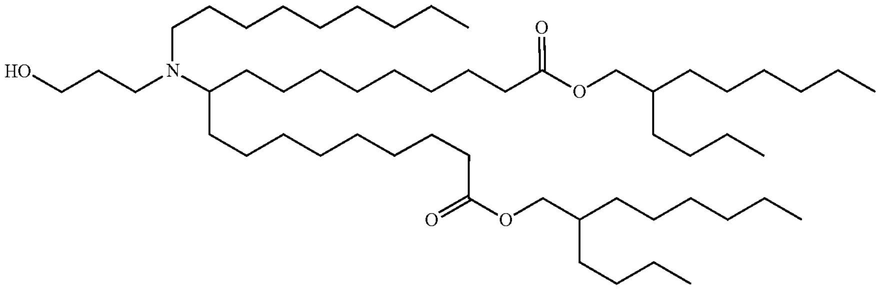 [SMILES: CCCCCCCCCN(CCCO)C(CCCCCCCCC(=O)OCC(CCCC)CCCCCC)CCCCCCCCC(=O)OCC(CCCC)CCCCCC] |
| VI-13 | 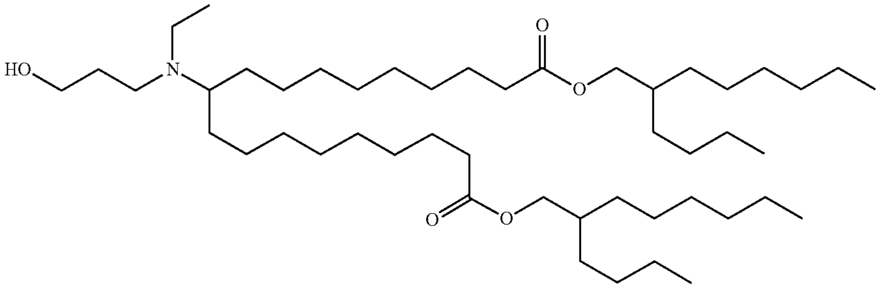 [SMILES: CCCCCCC(CCCC)COC(=O)CCCCCCCCC(CCCCCCCCC(=O)OCC(CCCC)CCCCCC)N(CC)CCCO] |
| VI-14 | 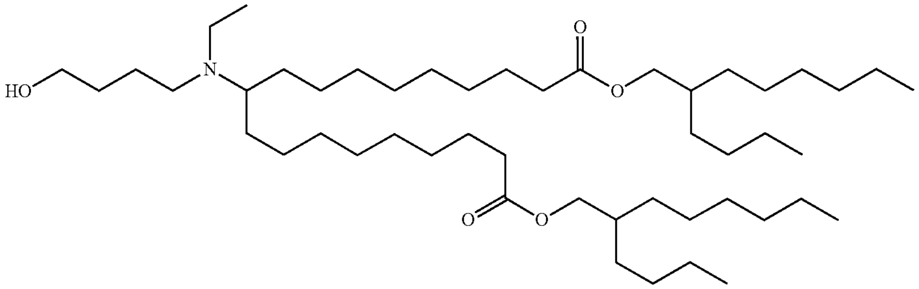 [SMILES: CCCCCCC(CCCC)COC(=O)CCCCCCCCC(CCCCCCCCC(=O)OCC(CCCC)CCCCCC)N(CC)CCCCO] |
| VI-15 | 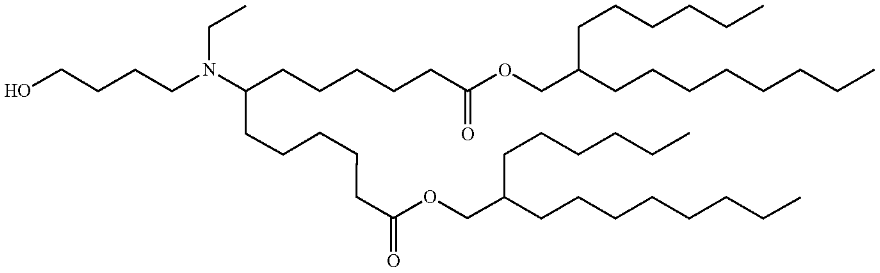 [SMILES: CCCCCCCCC(CCCCCC)COC(=O)CCCCCC(CCCCCC(=O)OCC(CCCCCC)CCCCCCCC)N(CC)CCCCO] |
| VI-16 | 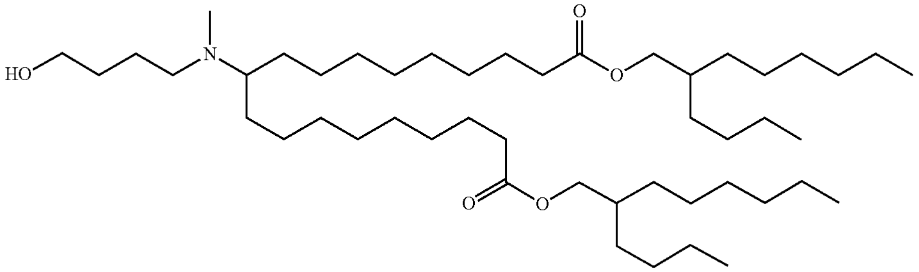 [SMILES: CCCCCCC(CCCC)COC(=O)CCCCCCCCC(CCCCCCCCC(=O)OCC(CCCC)CCCCCC)N(C)CCCCO] |

TABLE 5-continued
| Representative cationic lipids of structure (VI) | |
|---|---|
| No. | Structure |
| VI-17 | 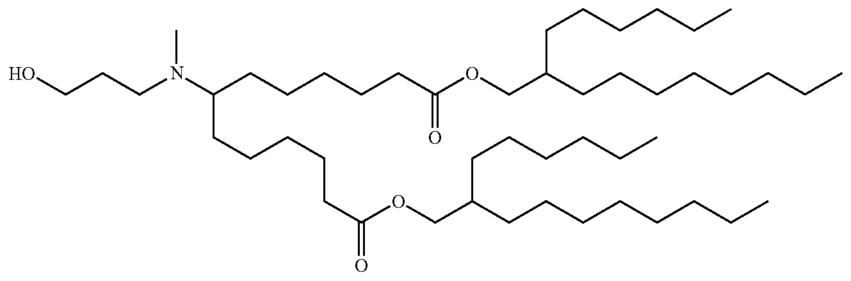 [SMILES: CCCCCCCCC(CCCCCC)COC(=O)CCCCCC(CCCCCC(=O)OCC(CCCCCC)CCCCCCCC)N(C)CCCO] |
| VI-18 | 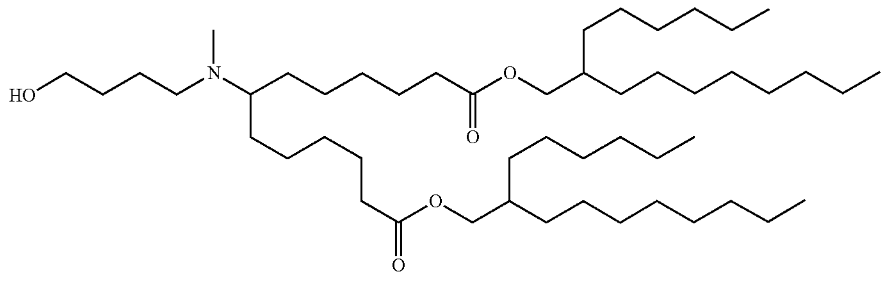 [SMILES: CCCCCCCCC(CCCCCC)COC(=O)CCCCCC(CCCCCC(=O)OCC(CCCCCC)CCCCCCCC)N(C)CCCCO] |
| VI-19 | 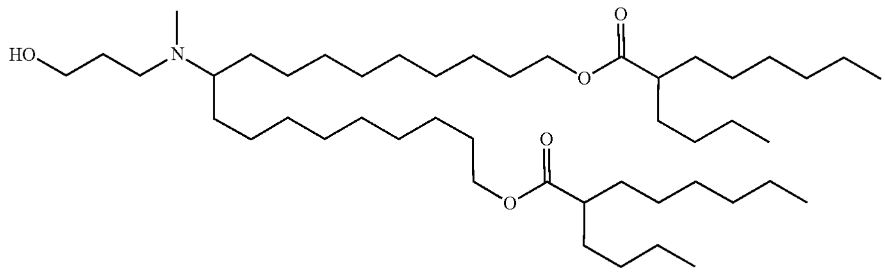 [SMILES: CCCCCCC(CCCC)C(=O)OCCCCCCCCCC(CCCCCCCCCOC(=O)C(CCCC)CCCCCC)N(C)CCCO] |
| VI-20 | 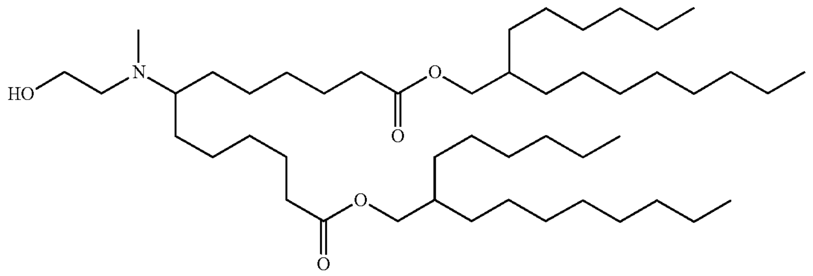 [SMILES: CCCCCCCCC(CCCCCC)COC(=O)CCCCCC(CCCCCC(=O)OCC(CCCCCC)CCCCCCCC)N(C)CCO] |
| VI-21 | 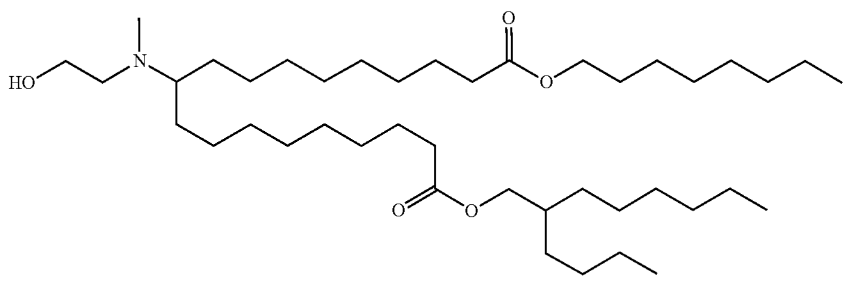 [SMILES: CCCCCCCCOC(=O)CCCCCCCCC(CCCCCCCCC(=O)OCC(CCCC)CCCCCC)N(C)CCO] |

TABLE 5-continued
| Representative cationic lipids of structure (VI) | |
|---|---|
| No. | Structure |
| VI-22 | 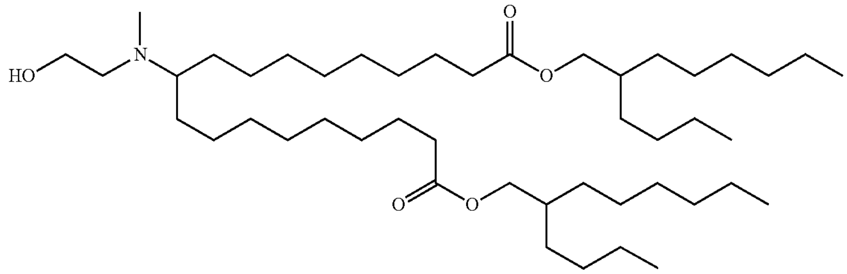 [SMILES: CCCCCCC(CCCC)COC(=O)CCCCCCCCC(CCCCCCCCC(=O)OCC(CCCC)CCCCCC)N(C)CCO] |
| VI-23 | 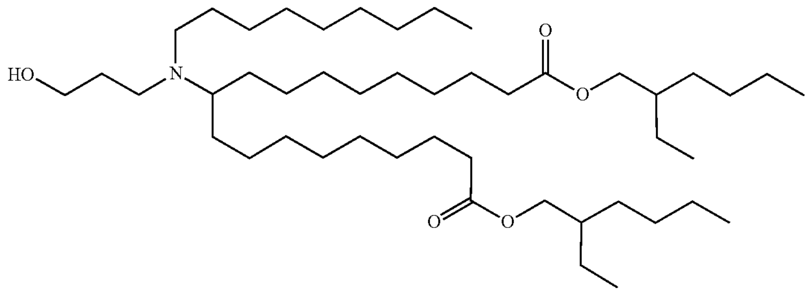 [SMILES: CCCCCCCCCN(CCCO)C(CCCCCCCCC(=O)OCC(CC)CCCC)CCCCCCCCC(=O)OCC(CC)CCCC] |
| VI-24 | 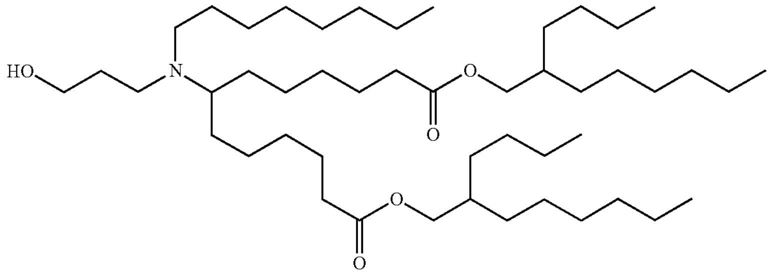 [SMILES: CCCCCCCCN(CCCO)C(CCCCCC(=O)OCC(CCCC)CCCCCC)CCCCCC(=O)OCC(CCCC)CCCCCC] |
| VI-25 | 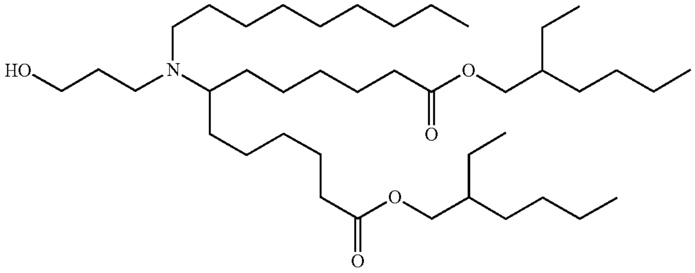 [SMILES: CCCCCCCCCN(CCCO)C(CCCCCC(=O)OCC(CC)CCCC)CCCCCC(=O)OCC(CC)CCCC] |
| VI-26 | 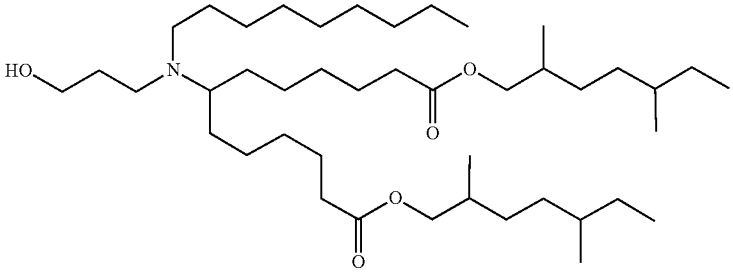 [SMILES: CCCCCCCCCN(CCCO)C(CCCCCC(=O)OCC(C)CCC(C)CC)CCCCCC(=O)OCC(C)CCC(C)CC] |

TABLE 5-continued
| Representative cationic lipids of structure (VI) | |
|---|---|
| No. | Structure |
| VI-27 | 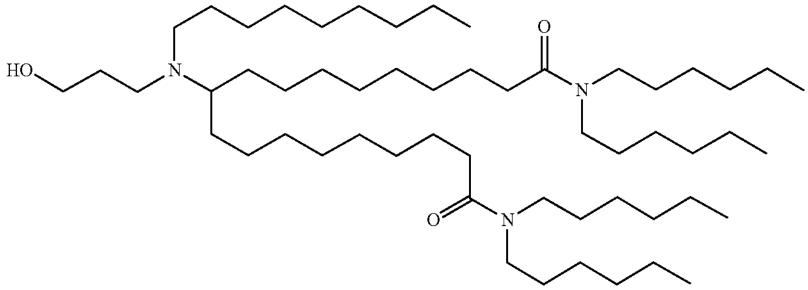 [SMILES: CCCCCCCCCN(CCCO)C(CCCCCCCCC(=O)N(CCCCCC)CCCCCC)CCCCCCCCC(=O)N(CCCCCC)CCCCCC] |
| VI-28 | 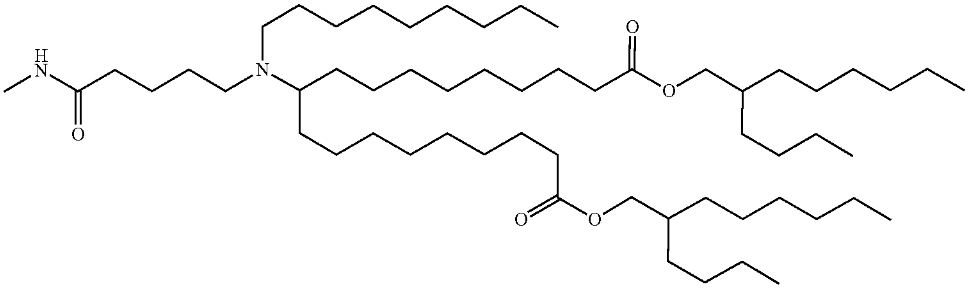 [SMILES: CCCCCCCCCN(CCCCC(=O)NC)C(CCCCCCCCC(=O)OCC(CCCC)CCCCCC)CCCCCCCCC(=O)OCC(CCCC)CCCCCC] |
| VI-29 | 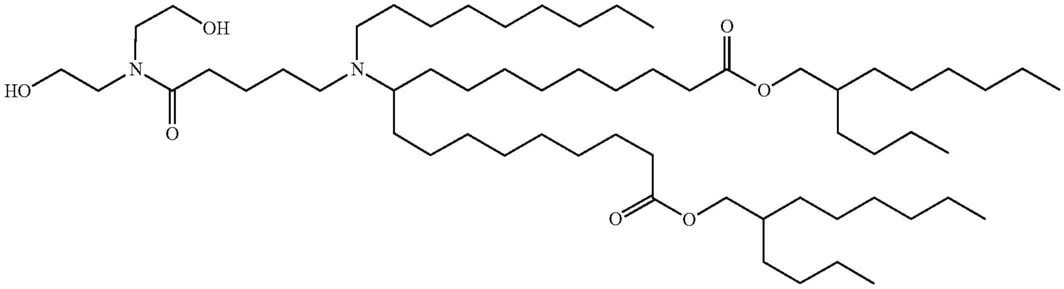 [SMILES: CCCCCCCCCN(CCCCC(=O)N(CCO)CCO)C(CCCCCCCCC(=O)OCC(CCCC)CCCCCC)CCCCCCCCC(=O)OCC(CCCC)CCCCCC] |
| VI-30 | 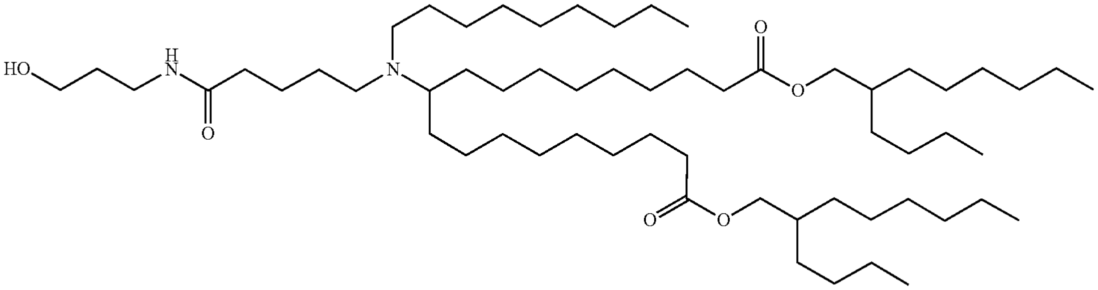 [SMILES: CCCCCCCCCN(CCCCC(=O)NCCCO)C(CCCCCCCCC(=O)OCC(CCCC)CCCCCC)CCCCCCCCC(=O)OCC(CCCC)CCCCCC] |
| VI-31 | 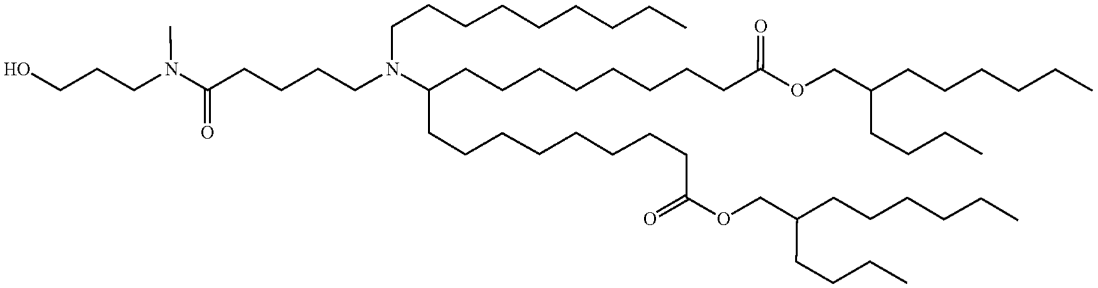 [SMILES: CCCCCCCCCN(CCCCC(=O)N(C)CCCO)C(CCCCCCCCC(=O)OCC(CCCC)CCCCCC)CCCCCCCCC(=O)OCC(CCCC)CCCCCC] |

TABLE 5-continued
| Representative cationic lipids of structure (VI) | |
|---|---|
| No. | Structure |
| VI-32 | 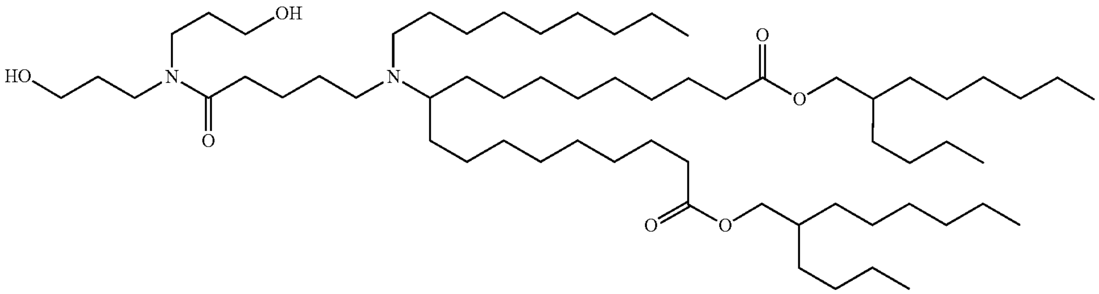 [SMILES: CCCCCCCCCN(CCCCC(=O)N(CCCO)CCCO)C(CCCCCCCCC(=O)OCC(CCCC)CCCCCC)CCCCCCCCC(=O)OCC(CCCC)CCCCCC] |
| VI-33 | 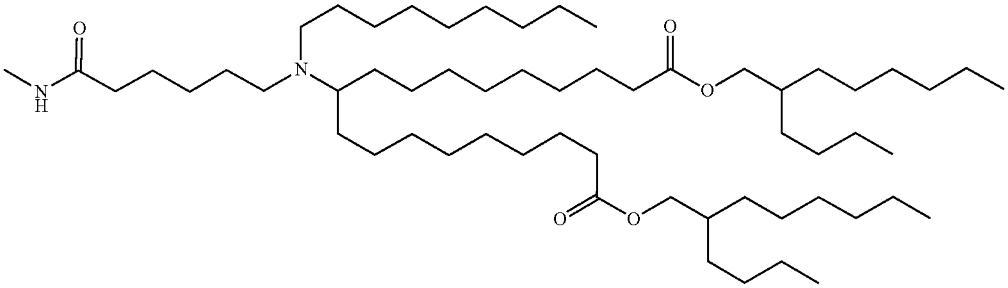 [SMILES: CCCCCCCCCN(CCCCCC(=O)NC)C(CCCCCCCCC(=O)OCC(CCCC)CCCCCC)CCCCCCCCC(=O)OCC(CCCC)CCCCCC] |
| VI-34 | 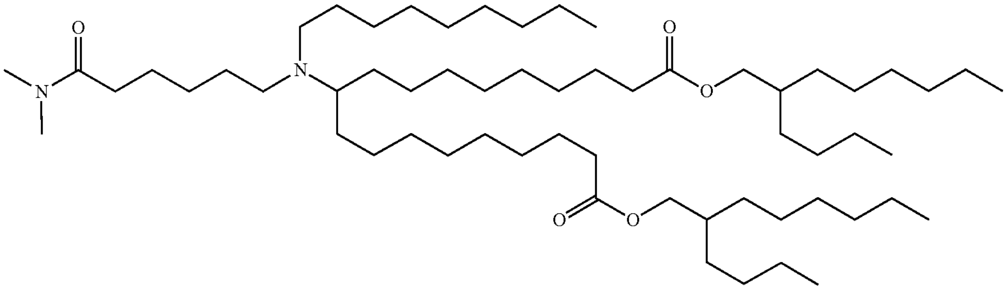 [SMILES: CCCCCCCCCN(CCCCCC(=O)N(C)C)C(CCCCCCCCC(=O)OCC(CCCC)CCCCCC)CCCCCCCCC(=O)OCC(CCCC)CCCCCC] |
| VI-35 | 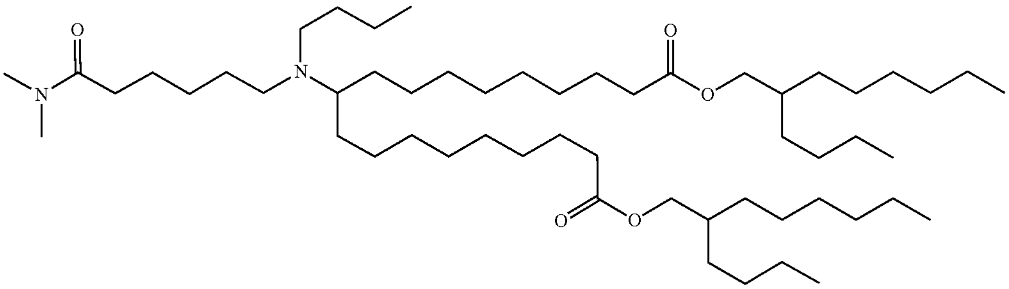 [SMILES: CCCCCCC(CCCC)COC(=O)CCCCCCCCC(CCCCCCCCC(=O)OCC(CCCC)CCCCCC)N(CCCC)CCCCCC(=O)N(C)C] |
| VI-36 | 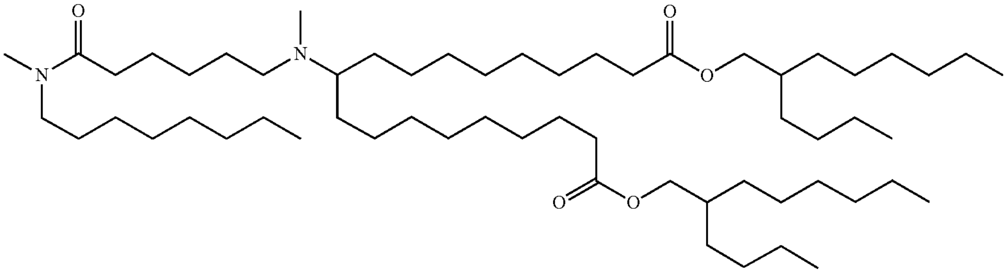 [SMILES: CCCCCCCCN(C)C(=O)CCCCCN(C)C(CCCCCCCCC(=O)OCC(CCCC)CCCCCC)CCCCCCCCC(=O)OCC(CCCC)CCCCCC] |

TABLE 5-continued

| Representative cationic lipids of structure (VI) | |
|---|---|
| No. | Structure |
| VI-37 | 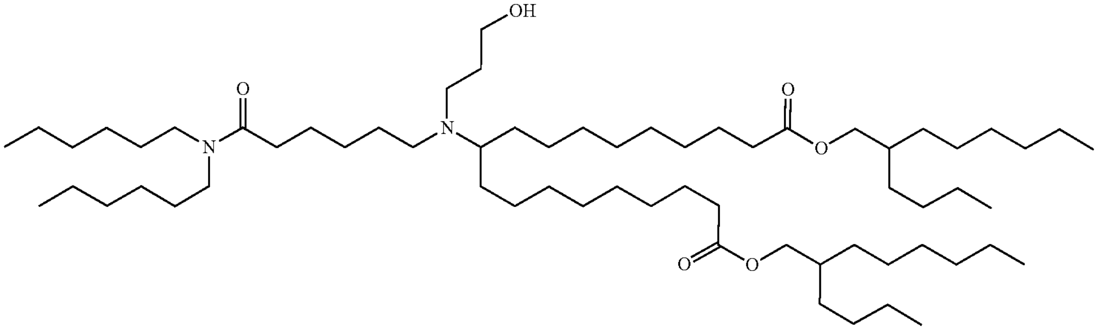 [SMILES: CCCCCCC(CCCC)COC(=O)CCCCCCCCC(CCCCCCCCC(=O)OCC(CCCC)CCCCCC)N(CCCO)CCCCCC(=O)N(CCCCCC)CCCCCC] |

In one embodiment, the cationic lipid is a compound having the following structure (VII):

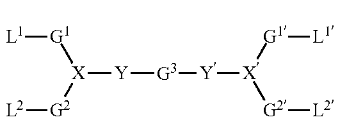

(VII)

or a pharmaceutically acceptable salt, prodrug or stereoisomer thereof, wherein:

X and X' are each independently N or CR;

Y and Y' are each independently absent, —O(C═O)—, —(C═O)O— or NR, provided that:

a) Y is absent when X is N;

b) Y' is absent when X' is N;

c) Y is —O(C═O)—, —(C═O)O— or NR when X is CR; and d) Y' is —O(C═O)—, —(C═O)O— or NR when X' is CR, $L^1$ and $L^{1'}$ are each independently —O(C═O)$R^1$, —(C═O)O$R^1$, —C(═O)$R^1$, —O$R^1$, —S(O)$_z$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ and $L^{2'}$ are each independently —O(C═O)$R^2$, —(C═O)O$R^2$, —C(═O)$R^2$, —O$R^2$, —S(O)$_z$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$; —N$R^d$C(═O)O$R^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ heteroalkylene or $C_2$-$C_{24}$ heteroalkenylene;

$R^a$, $R^b$, $R^d$ and $R^e$ are, at each occurrence, independently H, $C_1$-$C_{12}$ alkyl or $C_2$-$C_{12}$ alkenyl;

$R^c$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, heteroalkylene and heteroalkenylene is independently substituted or unsubstituted unless otherwise specified.

In other different embodiments of structure (VII):

X and X' are each independently N or CR;

Y and Y' are each independently absent or NR, provided that:

a) Y is absent when X is N;

b) Y' is absent when X is N;

c) Y is NR when X is CR; and d) Y' is NR when X' is CR, $L^1$ and $L^{1'}$ are each independently —O(C═O)$R^1$, —(C═O)O$R^1$, —C(═O)$R^1$, —O$R^1$, —S(O)$_z$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ and $L^{2'}$ are each independently —O(C═O)$R^2$, —(C═O)O$R^2$, —C(═O)$R^2$, —O$R^2$, —S(O)$_z$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$; —N$R^d$C(═O)O$R^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ alkyleneoxide or $C_2$-$C_{24}$ alkenyleneoxide;

$R^a$, $R^b$, $R^d$ and $R^e$ are, at each occurrence, independently H, $C_1$-$C_{12}$ alkyl or $C_2$-$C_{12}$ alkenyl;

$R^c$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, alkyleneoxide and alkenyleneoxide is independently substituted or unsubstituted unless otherwise specified.

In some embodiments of structure (VII), $G^3$ is $C_2$-$C_{24}$ alkyleneoxide or $C_2$-$C_{24}$ alkenyleneoxide. In certain embodiments, $G^3$ is unsubstituted. In other embodiments, $G^3$ is substituted, for example substituted with hydroxyl. In more specific embodiments $G^3$ is $C_2$-$C_{12}$ alkyleneoxide, for example, in some embodiments $G^3$ is $C_3$-$C_7$ alkyleneoxide or in other embodiments $G^3$ is $C_3$-$C_{12}$ alkyleneoxide.

In other embodiments of structure (VII), $G^3$ is $C_2$-$C_{24}$ alkyleneaminyl or $C_2$-$C_{24}$ alkenyleneaminyl, for example $C_6$-$C_{12}$ alkyleneaminyl. In some of these embodiments, $G^3$ is unsubstituted. In other of these embodiments, $G^3$ is substituted with $C_1$-$C_6$ alkyl.

In some embodiments of structure (VII), X and X' are each N, and Y and Y' are each absent. In other embodiments, X and X' are each CR, and Y and Y' are each NR. In some of these embodiments, R is H.

In certain embodiments of structure (VII), X and X' are each CR, and Y and Y' are each independently —O(C═O)— or —(C═O)O—.

In some of the foregoing embodiments of structure (VII), the compound has one of the following structures (VIIA), (VIIB), (VIIC), (VIID), (VIIE), (VIIF), (VIIG) or (VIIH):

(VIIA)

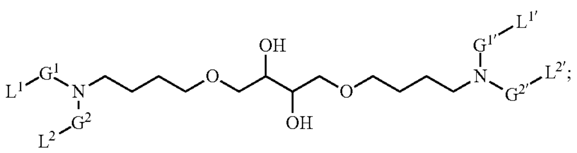

(VIIB)

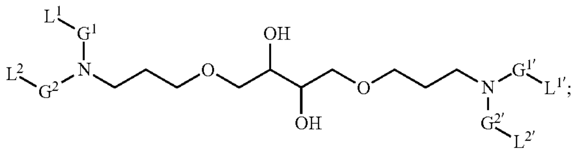

(VIIC)

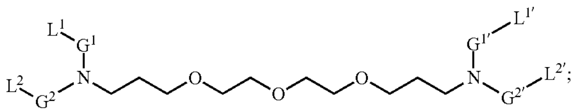

(VIID)

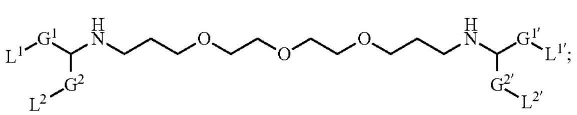

(VIIE)

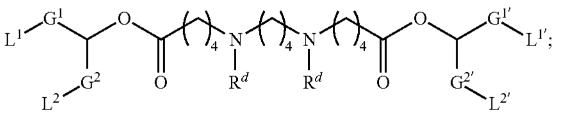

(VIIF)

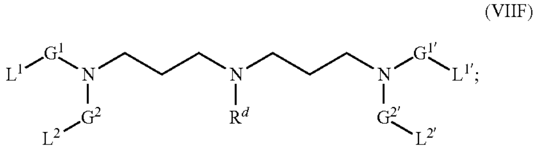

(VIIG)

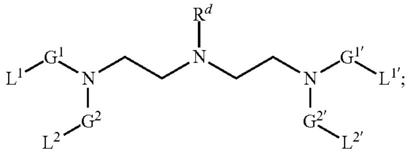 or (VIIH)

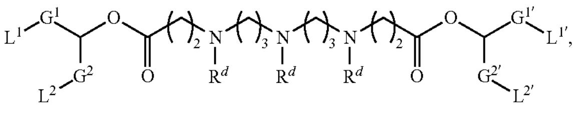

wherein $R^d$ is, at each occurrence, independently H or optionally substituted $C_1$-$C_6$ alkyl. For example, in some embodiments $R^d$ is H. In other embodiments, $R^d$ is $C_1$-$C_6$ alkyl, such as methyl. In other embodiments, $R^d$ is substituted $C_1$-$C_6$ alkyl, such as $C_1$-$C_6$ alkyl substituted with —O(C═O)R, —(C═O)OR, —NRC(═O)R or —C(═O)N(R)$_2$, wherein R is, at each occurrence, independently H or $C_1$-$C_{12}$ alkyl.

In some of the foregoing embodiments of structure (VII), $L^1$ and $L^{1'}$ are each independently —O(C═O)$R^1$, —(C═O)O$R^1$ or —C(═O)N$R^bR^c$, and $L^2$ and $L^2$ are each independently —O(C═O)$R^2$, —(C═O)O$R^2$ or —C(═O)N$R^eR^f$. For example, in some embodiments $L^1$ and $L^{1'}$ are each —(C═O)O$R^1$, and $L^2$ and $L^{2'}$ are each —(C═O)O$R^2$. In other embodiments $L^1$ and $L^{1'}$ are each —(C═O)O$R^1$, and $L^2$ and $L^{2'}$ are each —C(═O)N$R^eR^f$. In other embodiments $L^1$ and $L^{1'}$ are each —C(═O)N$R^bR^c$, and $L^2$ and $L^{2'}$ are each —C(═O)N$R^eR^f$.

In some embodiments of the foregoing, $G^1$, $G^{1'}$, $G^2$ and $G^{2'}$ are each independently $C_2$-$C_8$ alkylene, for example $C_4$-$C_8$ alkylene.

In some of the foregoing embodiments of structure (VII), $R^1$ or $R^2$, are each, at each occurrence, independently branched $C_6$-$C_{24}$ alkyl. For example, in some embodiments, $R^1$ and $R^2$ at each occurrence, independently have the following structure.

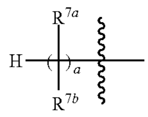 , wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (VII), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of structure (VII), $R^1$ or $R^2$, or both, at each occurrence independently has one of the following structures:

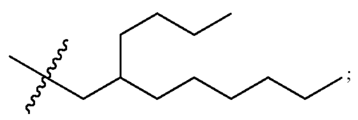

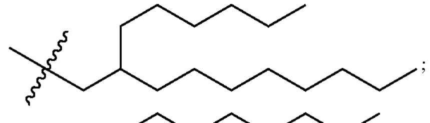

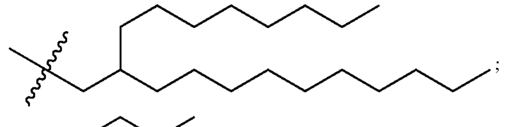

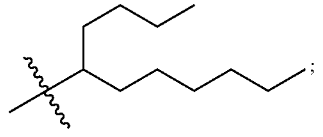

-continued

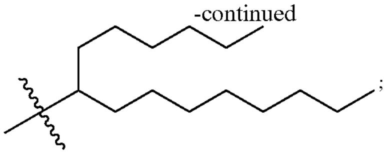
;

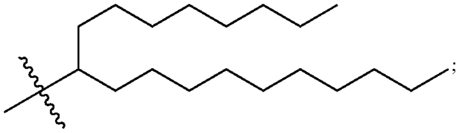
;

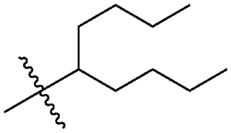
;

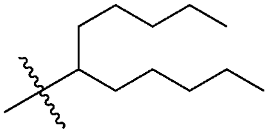
;

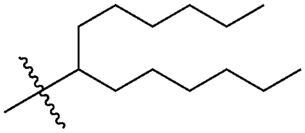
;

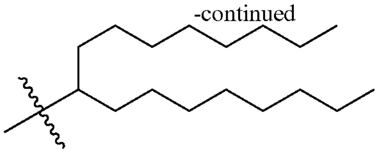
or

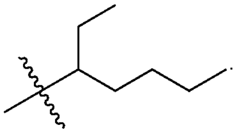
.

In some of the foregoing embodiments of structure (VII), $R^b$, $R^c$, $R^e$ and $R^f$, when present, are each independently $C_3$-$C_{12}$ alkyl. For example, in some embodiments $R^b$, $R^c$, $R^e$ and $R^f$, when present, are n-hexyl and in other embodiments $R^b$, $R^c$, $R^e$ and $R^f$, when present, are n-octyl.

In various different embodiments of structure (VII), the cationic lipid has one of the structures set forth in Table 6 below.

TABLE 6

Representative cationic lipids of structure (VII)

| No. | Structure |
|---|---|
| VII-1 | 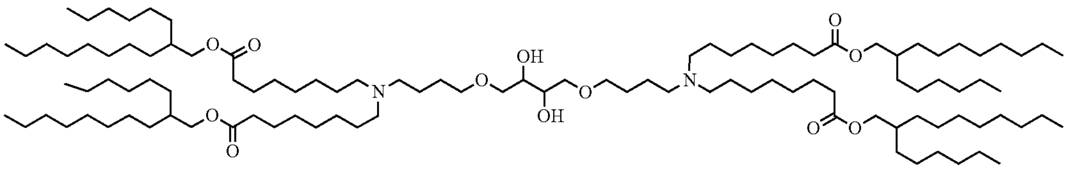 [SMILES: CCCCCCCCC(CCCCCC)COC(=O)CCCCCCCN(CCCCCCCC(=O)OCC(CCCCCC)CCCCCCCC)CCCCOCC(O)C(O)COCCCCN(CCCCCCCC(=O)OCC(CCCCCC)CCCCCCCC)CCCCCCCC(=O)OCC(CCCCCC)CCCCCCCC] |
| VII-2 | 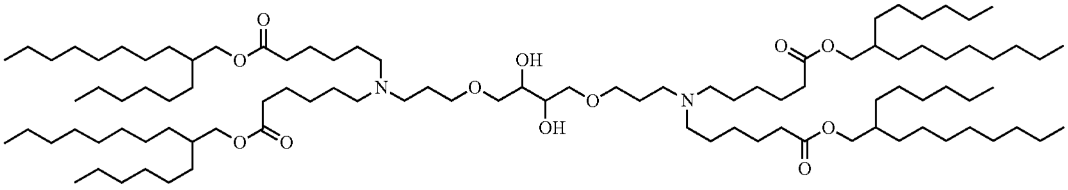 [SMILES: CCCCCCCCC(CCCCCC)COC(=O)CCCCCN(CCCCCC(=O)OCC(CCCCCC)CCCCCCCC)CCCOCC(O)C(O)COCCCN(CCCCCC(=O)OCC(CCCCCC)CCCCCCCC)CCCCCC(=O)OCC(CCCCCC)CCCCCCCC] |
| VII-3 | 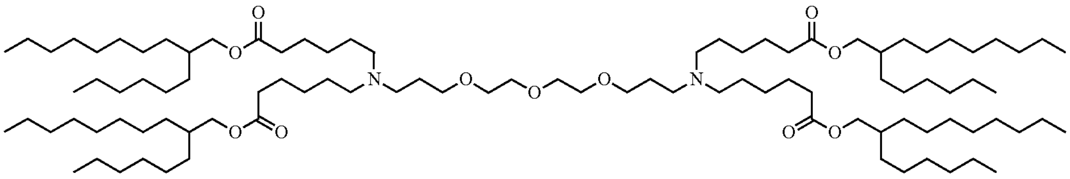 [SMILES: CCCCCCCCC(CCCCCC)COC(=O)CCCCCN(CCCCCC(=O)OCC(CCCCCC)CCCCCCCC)CCCOCCOCCOCCCN(CCCCCC(=O)OCC(CCCCCC)CCCCCCCC)CCCCCC(=O)OCC(CCCCCC)CCCCCCCC] |
| VII-4 | 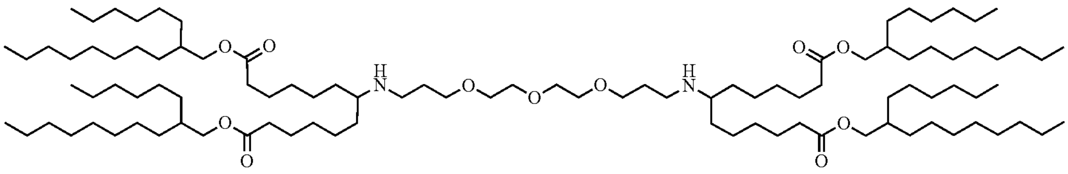 [SMILES: CCCCCCCCC(CCCCCC)COC(=O)CCCCCC(CCCCCC(=O)OCC(CCCCCC)CCCCCCCC)NCCCOCCOCCOCCCNC(CCCCCC(=O)OCC(CCCCCC)CCCCCCCC)CCCCCC(=O)OCC(CCCCCC)CCCCCCCC] |

TABLE 6-continued
Representative cationic lipids of structure (VII)
| No. | Structure |
| --- | --- |
| VII-5 | 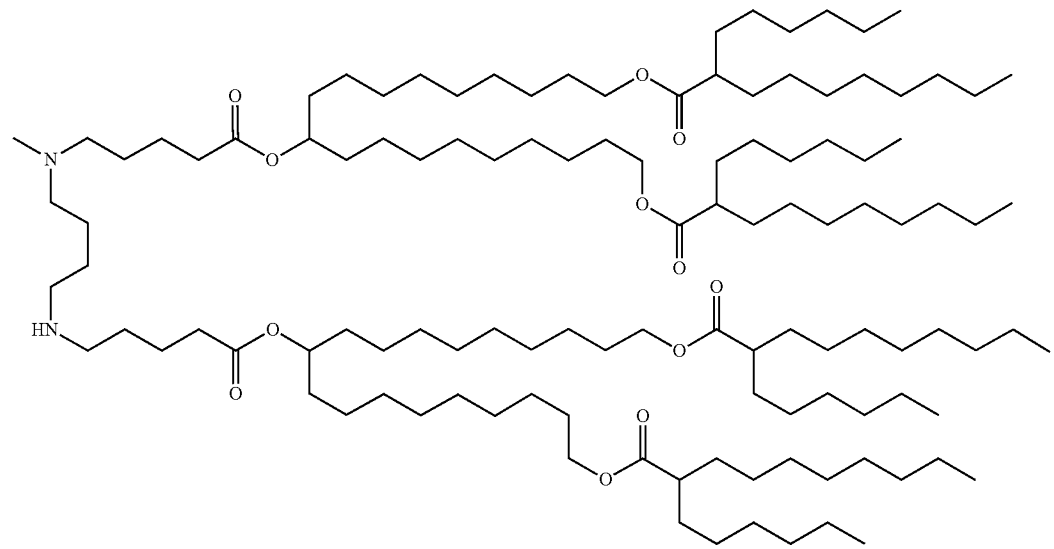 [SMILES: CCCCCCCCC(CCCCCC)C(=O)OCCCCCCCCCC(CCCCCCCCCOC(=O)C(CCCCCC)CCCCCCCC)OC(=O)CCCCNCCCCN(C)CCCCC(=O)OC(CCCCCCCCCOC(=O)C(CCCCCC)CCCCCCCC)CCCCCCCCCOC(=O)C(CCCCCC)CCCCCCCC] |
| VII-6 | 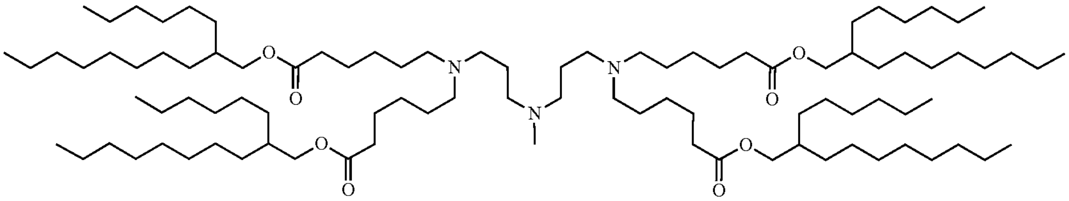 [SMILES: CCCCCCCCC(CCCCCC)COC(=O)CCCCCN(CCCCCC(=O)OCC(CCCCCC)CCCCCCCC)CCCN(C)CCCN(CCCCCC(=O)OCC(CCCCCC)CCCCCCCC)CCCCCC(=O)OCC(CCCCCC)CCCCCCCC] |
| VII-7 | 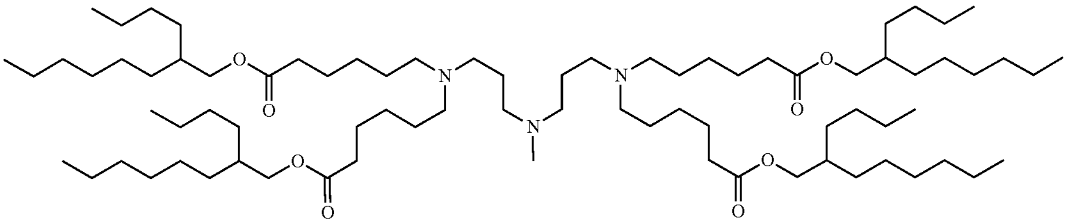 [SMILES: CCCCCCC(CCCC)COC(=O)CCCCCN(CCCCCC(=O)OCC(CCCC)CCCCCC)CCCN(C)CCCN(CCCCCC(=O)OCC(CCCC)CCCCCC)CCCCCC(=O)OCC(CCCC)CCCCCC] |
| VII-8 | 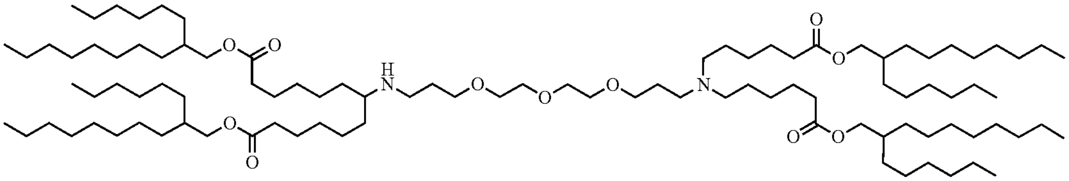 [SMILES: CCCCCCCCC(CCCCCC)COC(=O)CCCCCC(CCCCCC(=O)OCC(CCCCCC)CCCCCCCC)NCCCOCCOCCOCCCN(CCCCCC(=O)OCC(CCCCCC)CCCCCCCC)CCCCCC(=O)OCC(CCCCCC)CCCCCCCC] |
| VII-9 | 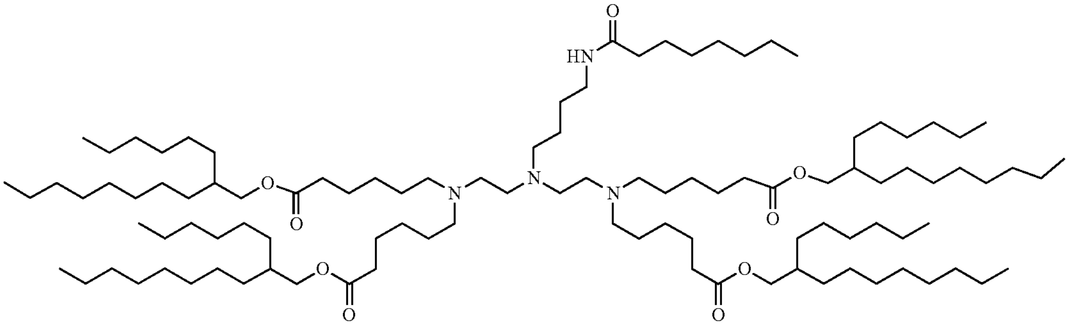 [SMILES: CCCCCCCCC(CCCCCC)COC(=O)CCCCCN(CCCCCC(=O)OCC(CCCCCC)CCCCCCCC)CCN(CCCCNC(=O)CCCCCCC)CCN(CCCCCC(=O)OCC(CCCCCC)CCCCCCCC)CCCCCC(=O)OCC(CCCCCC)CCCCCCCC] |

TABLE 6-continued

| Representative cationic lipids of structure (VII) | |
|---|---|
| No. | Structure |
| VII-10 | 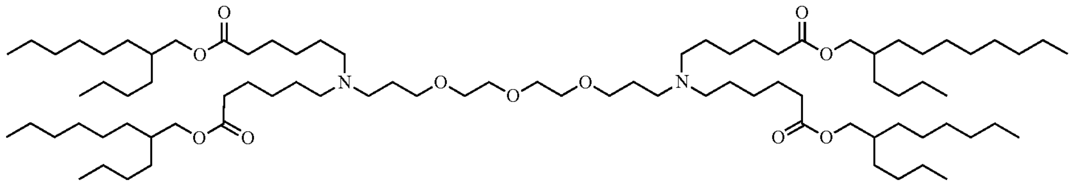 [SMILES: CCCCCCCCC(CCCC)COC(=O)CCCCCN(CCCCCC(=O)OCC(CCCC)CCCCCC)CCCOCCOCCOCCCN(CCCCCC(=O)OCC(CCCC)CCCCCC)CCCCCC(=O)OCC(CCCC)CCCCCC] |
| VII-11 | 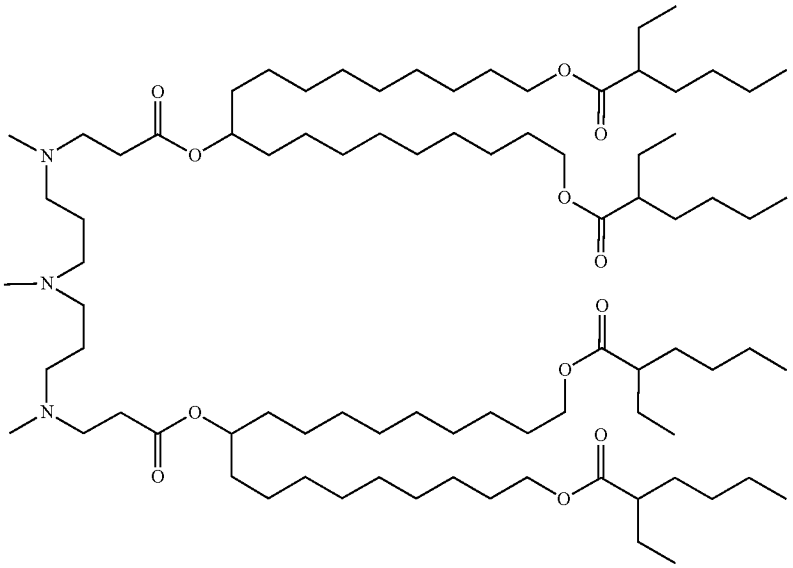 [SMILES: CCCCC(CC)C(=O)OCCCCCCCCCC(CCCCCCCCCOC(=O)C(CC)CCCC)OC(=O)CCN(C)CCCN(C)CCCN(C)CCC(=O)OC(CCCCCCCCCOC(=O)C(CC)CCCC)CCCCCCCCCOC(=O)C(CC)CCCC] |

In one embodiment, the cationic lipid is a compound having the following structure (VIII):

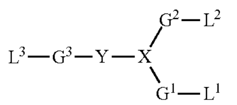

(VIII)

or a pharmaceutically acceptable salt, prodrug or stereoisomer thereof, wherein:

X is N, and Y is absent; or X is CR, and Y is NR;

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^bR^c$, —N$R^a$C(═O)N$R^bR^c$, —OC(═O)N$R^bR^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^eR^f$, —N$R^d$C(═O)N$R^eR^f$, —OC(═O)N$R^eR^f$; —N$R^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In more embodiments of structure (I):

X is N, and Y is absent; or X is CR, and Y is NR;

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^bR^c$, —N$R^a$C(═O)N$R^bR^c$, —OC(═O)N$R^bR^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^eR^f$, —N$R^d$C(═O)N$R^eR^f$, —OC(═O)N$R^eR^f$; —N$R^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In other embodiments of structure (I):

X is N and Y is absent, or X is CR and Y is NR;

$L^1$ is —O(C═O)$R^1$, —(C═O)O$R^1$, —C(═O)$R^1$, —O$R^1$, —S(O)$_x R^1$, —S—S$R^1$, —C(═O)S$R^1$, —SC(═O)$R^1$, —N$R^a$C(═O)$R^1$, —C(═O)N$R^b R^c$, —N$R^a$C(═O)N$R^b R^c$, —OC(═O)N$R^b R^c$ or —N$R^a$C(═O)O$R^1$;

$L^2$ is —O(C═O)$R^2$, —(C═O)O$R^2$, —C(═O)$R^2$, —O$R^2$, —S(O)$_x R^2$, —S—S$R^2$, —C(═O)S$R^2$, —SC(═O)$R^2$, —N$R^d$C(═O)$R^2$, —C(═O)N$R^e R^f$, —N$R^d$C(═O)N$R^e R^f$, —OC(═O)N$R^e R^f$; —N$R^d$C(═O)O$R^2$ or a direct bond to $R^2$ $L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently branched $C_6$-$C_{24}$ alkyl or branched $C_6$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In certain embodiments of structure (VIII), $G^3$ is unsubstituted. In more specific embodiments $G^3$ is $C_2$-$C_{12}$ alkylene, for example, in some embodiments $G^3$ is $C_3$-$C_7$ alkylene or in other embodiments $G^3$ is $C_3$-$C_{12}$ alkylene. In some embodiments, $G^3$ is $C_2$ or $C_3$ alkylene.

In other embodiments of structure (VIII), $G^3$ is $C_1$-$C_{12}$ heteroalkylene, for example $C_1$-$C_{12}$ aminylalkylene.

In certain embodiments of structure (VIII), X is N and Y is absent. In other embodiments, X is CR and Y is NR, for example in some of these embodiments R is H.

In some of the foregoing embodiments of structure (VIII), the compound has one of the following structures (VIIIA), (VIIIB), (VIIIC) or (VIIID):

(VIIIA)

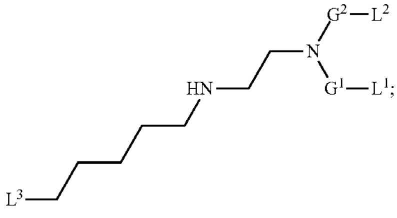

(VIIIB)

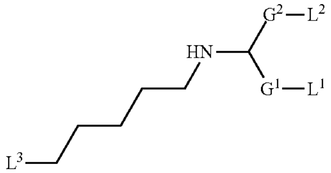

-continued (VIIIC)

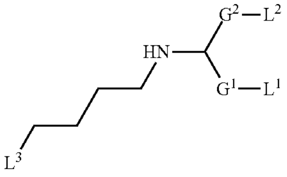

or (VIIID)

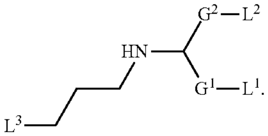

In some of the foregoing embodiments of structure (VIII), $L^1$ is —O(C═O)$R^1$, —(C═O)O$R^1$ or —C(═O)N$R^b R^c$, and $L^2$ is —O(C═O)$R^2$, —(C═O)O$R^2$ or —C(═O)N$R^e R^f$. In other specific embodiments, $L^1$ is —(C═O)O$R^1$ and $L^2$ is —(C═O)O$R^2$. In any of the foregoing embodiments, $L^3$ is —(C═O)O$R^3$.

In some of the foregoing embodiments of structure (VIII), $G^1$ and $G^2$ are each independently $C_2$-$C_{12}$ alkylene, for example $C_4$-$C_{10}$ alkylene.

In some of the foregoing embodiments of structure (VIII), $R^1$, $R^2$ and $R^3$ are each, independently branched $C_6$-$C_{24}$ alkyl. For example, in some embodiments, $R^1$, $R^2$ and $R^3$ each, independently have the following structure:

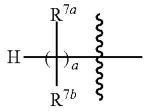

, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (VIII), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In some of the foregoing embodiments of structure (VIII), X is CR, Y is NR and $R^3$ is $C_1$-$C_{12}$ alkyl, such as ethyl, propyl or butyl. In some of these embodiments, $R^1$ and $R^2$ are each independently branched $C_6$-$C_{24}$ alkyl.

In different embodiments of structure (VIII), $R^1$, $R^2$ and $R^3$ each, independently have one of the following structures:

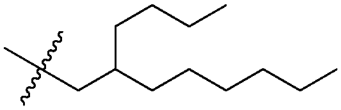

;

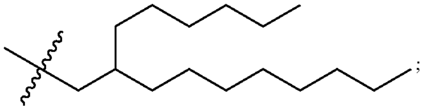

;

-continued

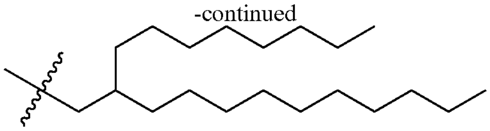
;

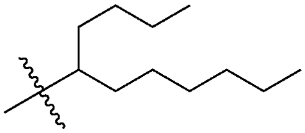
;

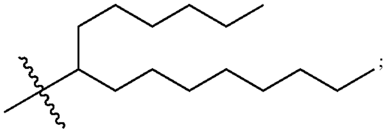
;

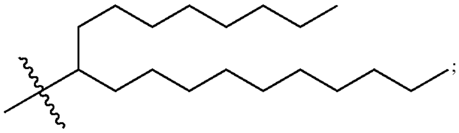
;

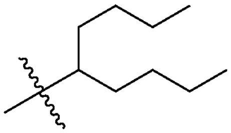
;

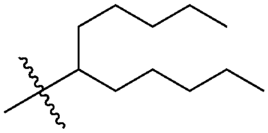
;

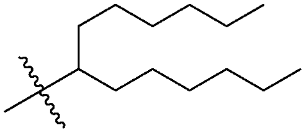
;

-continued

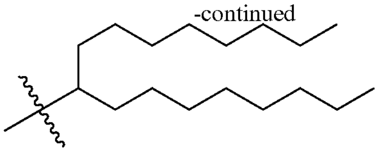
;

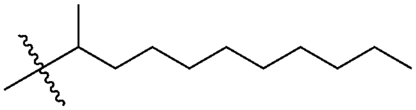
;

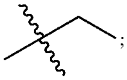
; 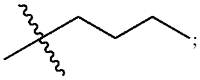
;

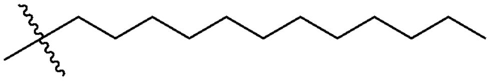
or

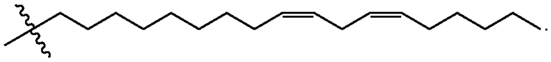
.

In certain embodiments of structure (VIII), $R^1$ and $R^2$ and $R^3$ are each, independently, branched $C_6$-$C_{24}$ alkyl and $R^3$ is $C_1$-$C_{24}$ alkyl or $C_2$-$C_{24}$ alkenyl.

In some of the foregoing embodiments of structure (VIII), $R^b$, $R^c$, $R^e$ and $R^f$ are each independently $C_3$-$C_{12}$ alkyl. For example, in some embodiments $R^b$, $R^c$, $R^e$ and $R^f$ are n-hexyl and in other embodiments $R^b$, $R^c$, $R^e$ and $R^f$ are n-octyl.

In various different embodiments of structure (VIII), the compound has one of the structures set forth in Table 7 below.

TABLE 7

Representative cationic lipids of structure (VIII)

| No. | Structure |
|---|---|
| VIII-1 | 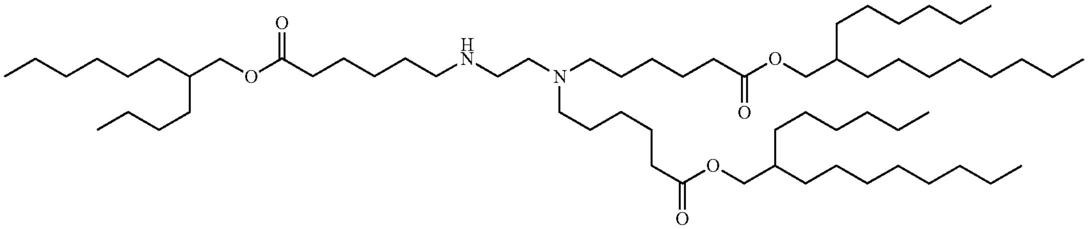 [SMILES: CCCCCCCCC(CCCCCC)COC(=O)CCCCCN(CCCCCC(=O)OCC(CCCCCC)CCCCCCCC)CCNCCCCCC(=O)OCC(CCCC)CCCCCC] |
| VIII-2 | 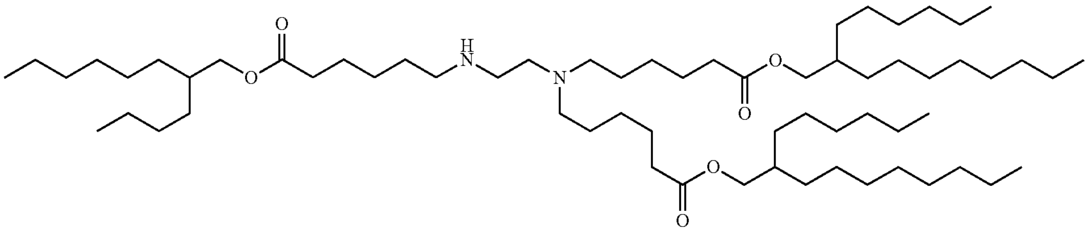 [SMILES: CCCCCCCCC(CCCCCC)COC(=O)CCCCCN(CCCCCC(=O)OCC(CCCCCC)CCCCCCCC)CCNCCCCCC(=O)OCC(CCCC)CCCCCC] |

TABLE 7-continued
| Representative cationic lipids of structure (VIII) | |
|---|---|
| No. | Structure |
| VIII-3 | 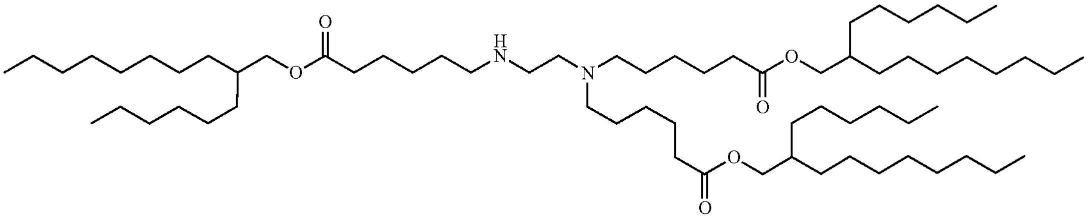 [SMILES: CCCCCCCCC(CCCCCC)COC(=O)CCCCCNCCN(CCCCCC(=O)OCC(CCCCCC)CCCCCCCC)CCCCCC(=O)OCC(CCCCCC)CCCCCCCC] |
| VIII-4 | 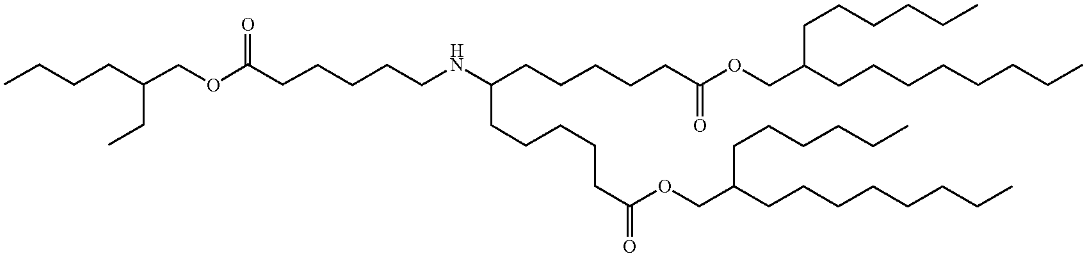 [SMILES: CCCCCCCCC(CCCCCC)COC(=O)CCCCCC(CCCCCC(=O)OCC(CCCCCC)CCCCCCCC)NCCCCCC(=O)OCC(CC)CCCC] |
| VIII-5 | 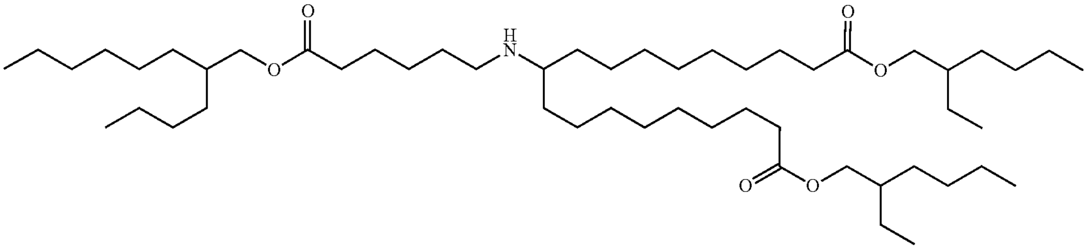 [SMILES: CCCCCCC(CCCC)COC(=O)CCCCCNC(CCCCCCCCC(=O)OCC(CC)CCCC)CCCCCCCCC(=O)OCC(CC)CCCC] |
| VIII-6 | 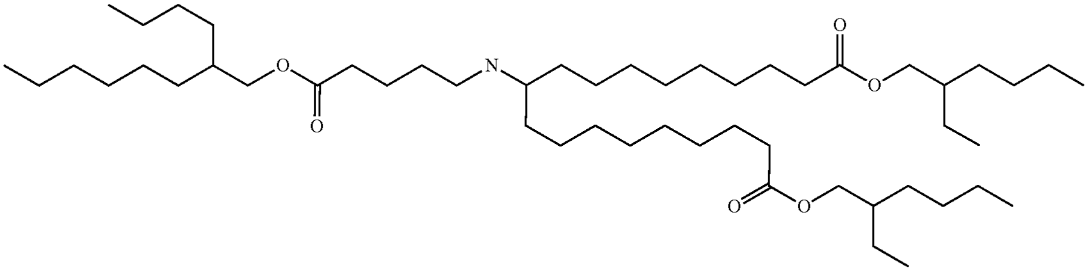 |
| VIII-7 | 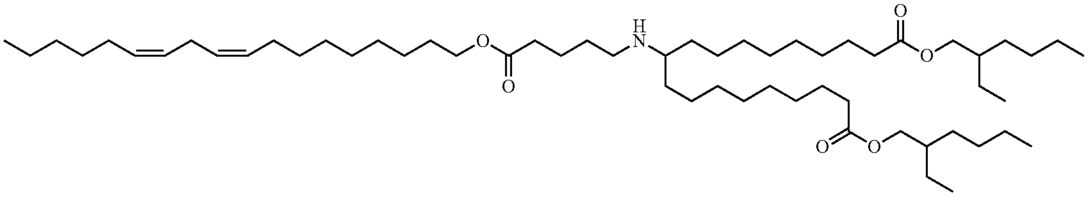 [SMILES: CCCCC/C=C\C/C=C\CCCCCCCCOC(=O)CCCCNC(CCCCCCCCC(=O)OCC(CC)CCCC)CCCCCCCCC(=O)OCC(CC)CCCC] |
| VIII-8 | 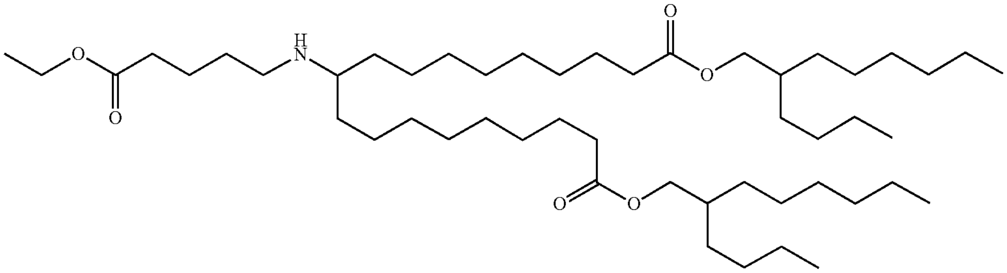 [SMILES: CCCCCCC(CCCC)COC(=O)CCCCCCCCC(CCCCCCCCC(=O)OCC(CCCC)CCCCCC)NCCCCC(=O)OCC] |

TABLE 7-continued

| Representative cationic lipids of structure (VIII) | |
|---|---|
| No. | Structure |
| VIII-9 | 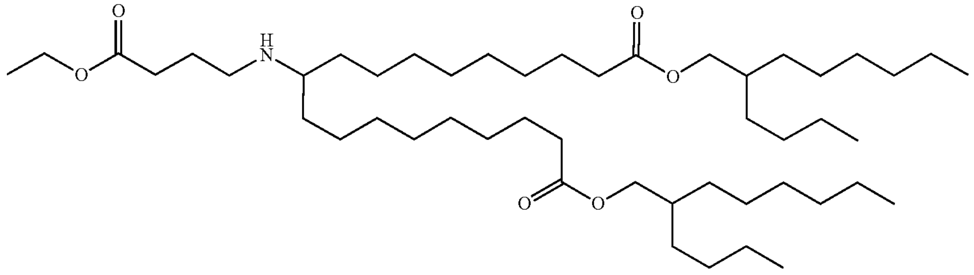 [SMILES: CCCCCCC(CCCC)COC(=O)CCCCCCCCC(CCCCCCCCC(=O)OCC(CCCC)CCCCCC)NCCCC(=O)OCC] |
| VIII-10 | 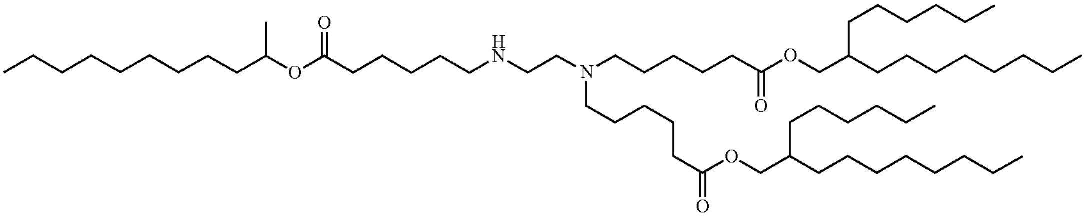 [SMILES: CCCCCCCCCC(C)OC(=O)CCCCCNCCN(CCCCCC(=O)OCC(CCCCCC)CCCCCCCC)CCCCCC(=O)OCC(CCCCCC)CCCCCCCC] |
| VIII-11 | 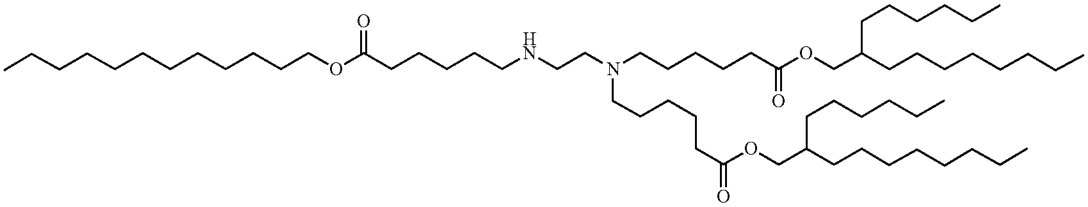 [SMILES: CCCCCCCCCCCCOC(=O)CCCCCNCCN(CCCCCC(=O)OCC(CCCCCC)CCCCCCCC)CCCCCC(=O)OCC(CCCCCC)CCCCCCCC] |
| VIII-12 | 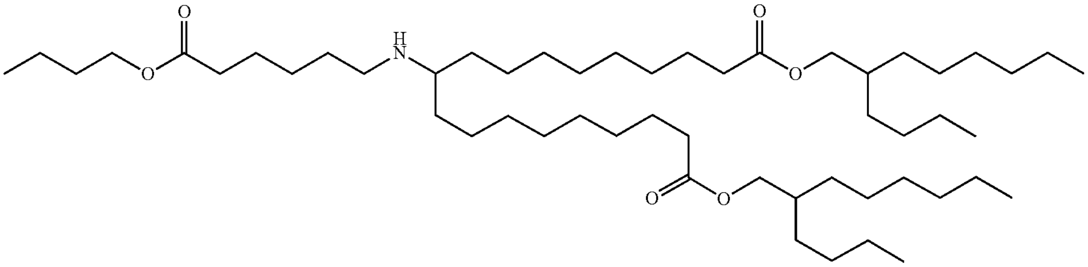 [SMILES: CCCCCCC(CCCC)COC(=O)CCCCCCCCC(CCCCCCCCC(=O)OCC(CCCC)CCCCCC)NCCCCCC(=O)OCCCC] |

In one embodiment, the cationic lipid is a compound having the following structure (IX):

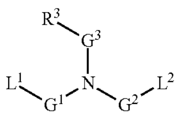

(IX)

or a pharmaceutically acceptable salt, prodrug or stereoisomer thereof, wherein:

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$, —N$R^d$C(═O)O$R^2$ or a direct bond to $R^2$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^3$ is —N($R^4$)$R^5$;

$R^4$ is $C_1$-$C_{12}$ alkyl;

$R^5$ is substituted $C_1$-$C_{12}$ alkyl; and x is 0, 1 or 2, and wherein each alkyl, alkenyl, alkylene, alkenylene, cycloalkylene, cycloalkenylene, aryl and aralkyl is independently substituted or unsubstituted unless otherwise specified.

In certain embodiments of structure (XI), $G^3$ is unsubstituted. In more specific embodiments $G^3$ is $C_2$-$C_{12}$ alkylene, for example, in some embodiments $G^3$ is $C_3$-$C_7$ alkylene or in other embodiments $G^3$ is $C_3$-$C_{12}$ alkylene. In some embodiments, $G^3$ is $C_2$ or $C_3$ alkylene.

In some of the foregoing embodiments of structure (IX), the compound has the following structure (IX A):

(IXA)

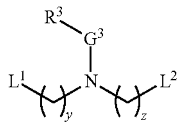

wherein y and z are each independently integers ranging from 2 to 12, for example an integer from 2 to 6, from 4 to 10, or for example 4 or 5. In certain embodiments, y and z are each the same and selected from 4, 5, 6, 7, 8 and 9.

In some of the foregoing embodiments of structure (IX), $L^1$ is —O(C═O)$R^1$, —(C═O)O$R^1$ or —C(═O)N$R^bR^c$, and $L^2$ is —O(C═O)$R^2$, —(C═O)O$R^2$ or —C(═O)N$R^eR^f$. For example, in some embodiments $L^1$ and $L^2$ are —(C═O)O$R^1$ and —(C═O)O$R^2$, respectively. In other embodiments $L^1$ is —(C═O)O$R^1$ and $L^2$ is —C(═O)N$R^eR^f$. In other embodiments $L^1$ is —C(═O)N$R^bR^c$ and $L^2$ is —C(═O)N$R^eR^f$.

In other embodiments of the foregoing, the compound has one of the following structures (IXB), (IXC), (IXD) or (IXE):

(IXB)

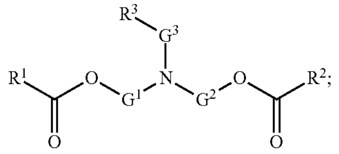

(IXC)

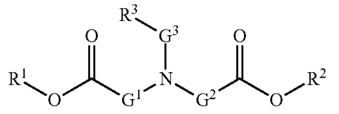

(IXD)

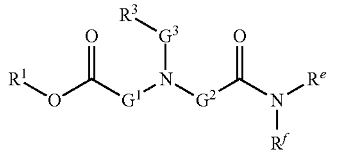

or (IXE)

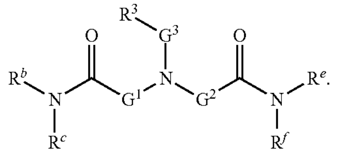

In some of the foregoing embodiments, the compound has structure (IXB), in other embodiments, the compound has structure (IXC) and in still other embodiments the compound has the structure (IXD). In other embodiments, the compound has structure (IXE).

In some different embodiments of the foregoing, the compound has one of the following structures (IXF), (IXG), (IXH) or (IXJ):

(IXF)

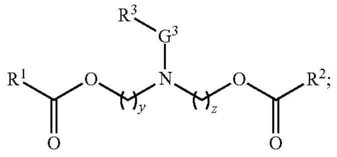

(IXG)

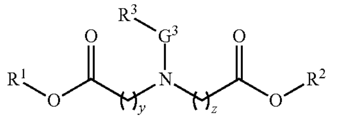

(IXH)

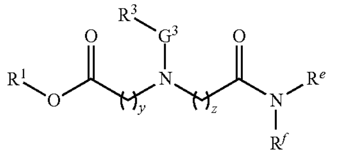

or (IXJ)

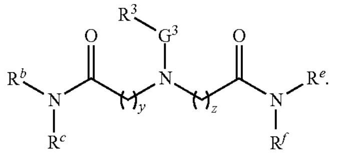

wherein y and z are each independently integers ranging from 2 to 12, for example an integer from 2 to 6, for example 4.

In some of the foregoing embodiments of structure (IX), y and z are each independently an integer ranging from 2 to 10, 2 to 8, from 4 to 10 or from 4 to 7. For example, in some embodiments, y is 4, 5, 6, 7, 8, 9, 10, 11 or 12. In some embodiments, z is 4, 5, 6, 7, 8, 9, 10, 11 or 12. In some embodiments, y and z are the same, while in other embodiments y and z are different.

In some of the foregoing embodiments of structure (IX), $R^1$ or $R^2$, or both is branched $C_6$-$C_{24}$ alkyl. For example, in some embodiments, $R^1$ and $R^2$ each, independently have the following structure:

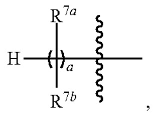

, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (IX), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of structure (IX), $R^1$ or $R^2$, or both, has one of the following structures:

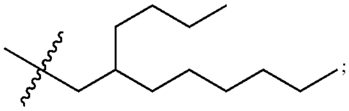
;
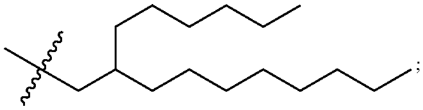
;
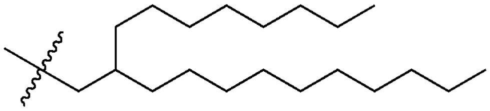
;
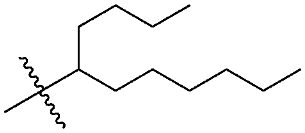
;
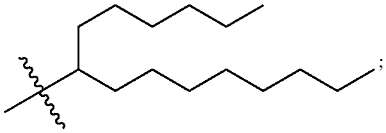
;
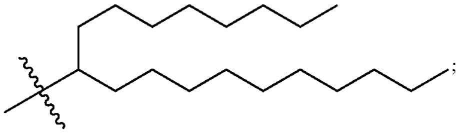
;
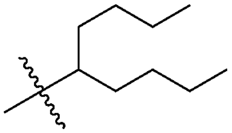
;
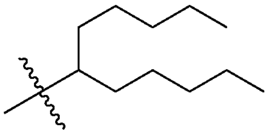
;
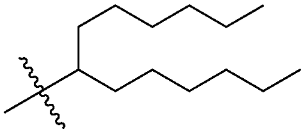
;
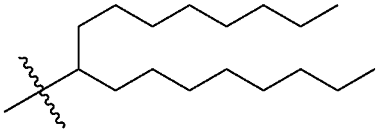
.

In some of the foregoing embodiments of structure (IX), $R^b$, $R^c$, $R^e$ and $R^f$ are each independently $C_3$-$C_{12}$ alkyl. For example, in some embodiments $R^b$, $R^c$, $R^e$ and $R^f$ are n-hexyl and in other embodiments $R^b$, $R^c$, $R^e$ and $R^f$ are n-octyl.

In any of the foregoing embodiments of structure (IX), $R^4$ is substituted or unsubstituted: methyl, ethyl, propyl, n-butyl, n-hexyl, n-octyl or n-nonyl. For example, in some embodiments $R^4$ is unsubstituted. In other $R^4$ is substituted with one or more substituents selected from the group consisting of —$OR^8$, —$NR^gC({=}O)R^h$, —$C({=}O)NR^gR^h$, —$C({=}O)R^h$, —$OC({=}O)R^h$, —$C({=}O)OR^h$ and —$OR^iOH$, wherein:

$R^g$ is, at each occurrence independently H or $C_1$-$C_6$ alkyl;

$R^h$ is at each occurrence independently $C_1$-$C_6$ alkyl; and $R^i$ is, at each occurrence independently $C_1$-$C_6$ alkylene.

In other of the foregoing embodiments of structure (IX), $R^5$ is substituted: methyl, ethyl, propyl, n-butyl, n-hexyl, n-octyl or n-nonyl. In some embodiments, $R^5$ is substituted ethyl or substituted propyl. In other different embodiments, $R^5$ is substituted with hydroxyl. In still more embodiments, $R^5$ is substituted with one or more substituents selected from the group consisting of —$OR^g$, —$NR^gC({=}O)R^h$, —$C(O)NR^gR^h$, —$C({=}O)R^h$, —$OC({=}O)R^h$, —$C({=}O)OR^h$ and —$OR^iOH$, wherein:

$R^g$ is, at each occurrence independently H or $C_1$-$C_6$ alkyl;

$R^h$ is at each occurrence independently $C_1$-$C_6$ alkyl; and $R^i$ is, at each occurrence independently $C_1$-$C_6$ alkylene.

In other embodiments of structure (IX), $R^4$ is unsubstituted methyl, and $R^5$ is substituted: methyl, ethyl, propyl, n-butyl, n-hexyl, n-octyl or n-nonyl. In some of these embodiments, $R^5$ is substituted with hydroxyl.

In some other specific embodiments of structure (IX), $R^3$ has one of the following structures:

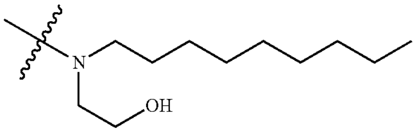
;
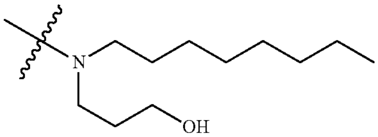
;
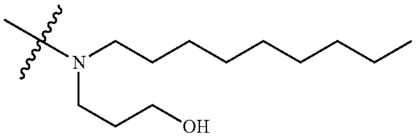
;
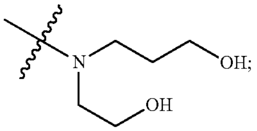
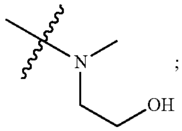
;
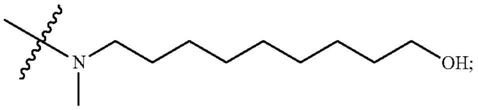
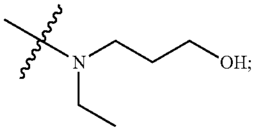
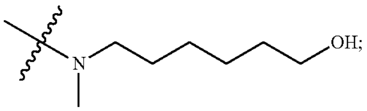
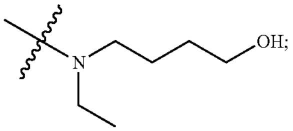

-continued
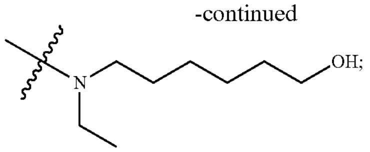
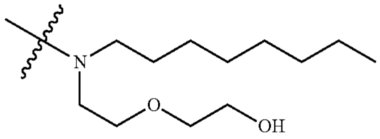
;
-continued
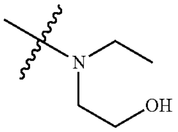
or
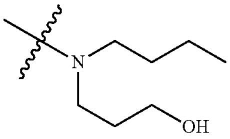
.
In various different embodiments of structure (IX), the cationic lipid has one of the structures set forth in Table 8 below.
TABLE 8
| Representative cationic lipids of structure (IX) | |
|---|---|
| No. | Structure |
| IX-1 | 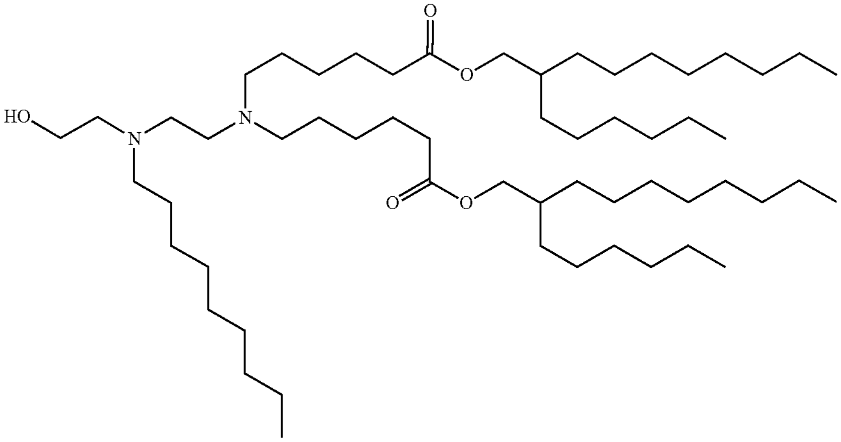 [SMILES: CCCCCCCCCN(CCO)CCN(CCCCCC(=O)OCC(CCCCCC)CCCCCCCC)CCCCCC(=O)OCC(CCCCCC)CCCCCCCC] |
| IX-2 | 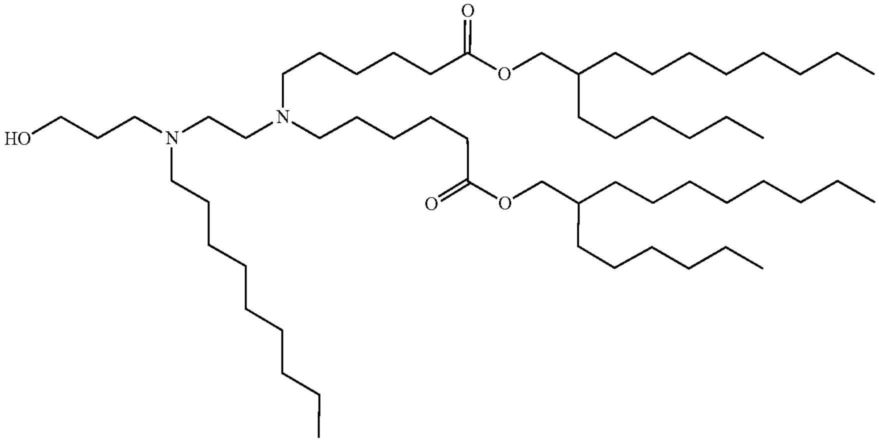 [SMILES: CCCCCCCCCN(CCCO)CCN(CCCCCC(=O)OCC(CCCCCC)CCCCCCCC)CCCCCC(=O)OCC(CCCCCC)CCCCCCCC] |
| IX-3 | 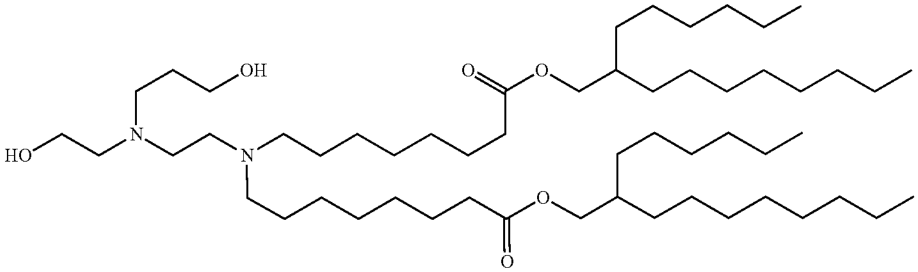 [SMILES: CCCCCCCCC(CCCCCC)COC(=O)CCCCCCCN(CCCCCCCC(=O)OCC(CCCCCC)CCCCCCCC)CCN(CCO)CCCO] |

TABLE 8-continued
Representative cationic lipids of structure (IX)
| No. | Structure |
|---|---|
| IX-4 | 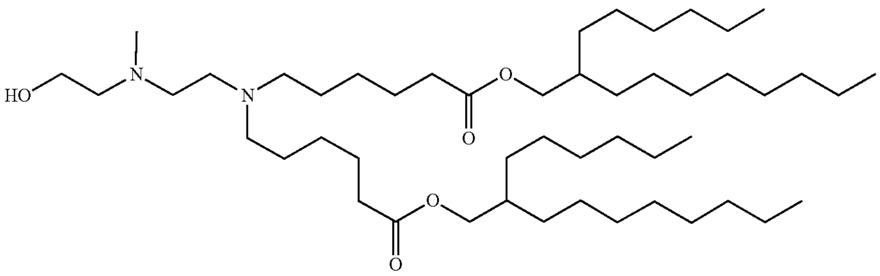 [SMILES: CCCCCCCCC(CCCCCC)COC(=O)CCCCCN(CCCCCC(=O)OCC(CCCCCC)CCCCCCCC)CCN(C)CCO] |
| IX-5 | 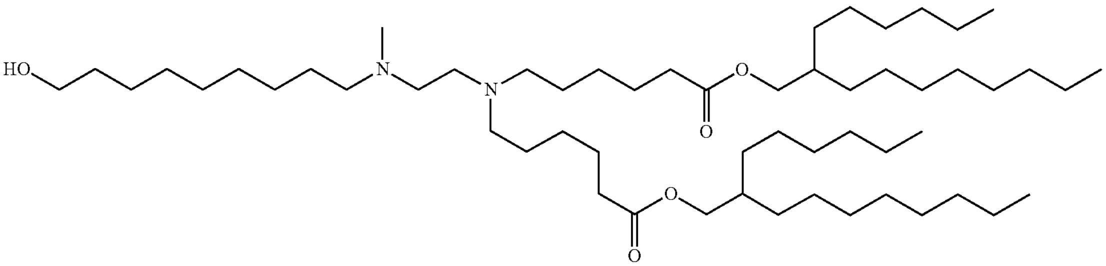 [SMILES: CCCCCCCCC(CCCCCC)COC(=O)CCCCCN(CCCCCC(=O)OCC(CCCCCC)CCCCCCCC)CCN(C)CCCCCCCCCO] |
| IX-6 | 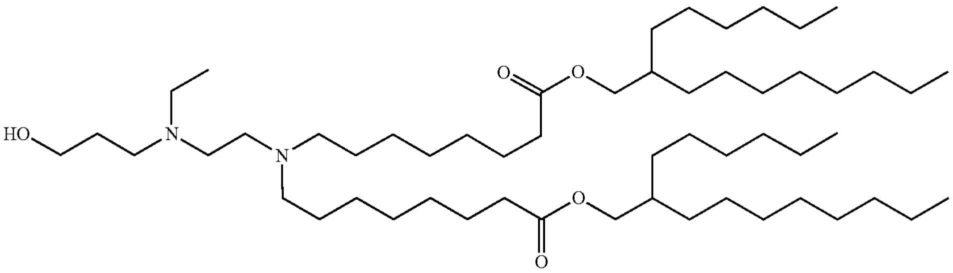 [SMILES: CCCCCCCCC(CCCCCC)COC(=O)CCCCCCCN(CCCCCCCC(=O)OCC(CCCCCC)CCCCCCCC)CCN(CC)CCCO] |
| IX-7 | 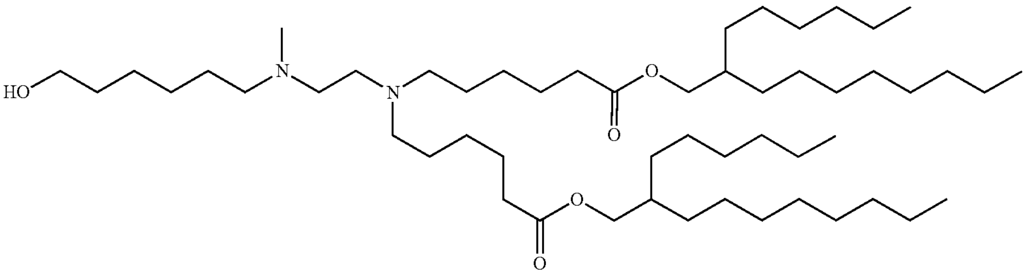 [SMILES: CCCCCCCCC(CCCCCC)COC(=O)CCCCCN(CCCCCC(=O)OCC(CCCCCC)CCCCCCCC)CCN(C)CCCCCCO] |
| IX-8 | 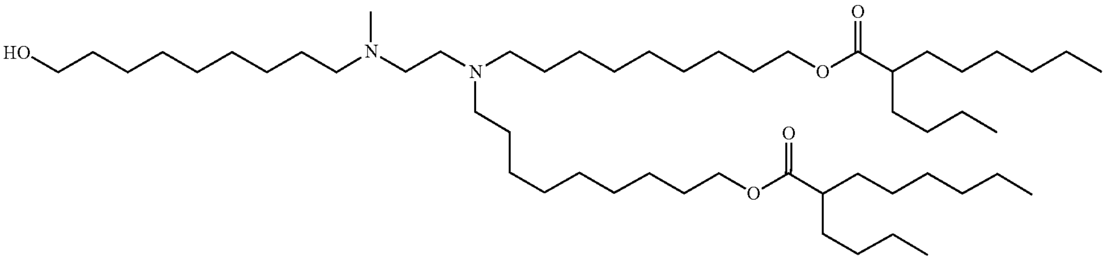 [SMILES: CCCCCCC(CCCC)C(=O)OCCCCCCCCCN(CCCCCCCCCOC(=O)C(CCCC)CCCCCC)CCN(C)CCCCCCCCCO] |

TABLE 8-continued
| Representative cationic lipids of structure (IX) | |
|---|---|
| No. | Structure |
| IX-9 | 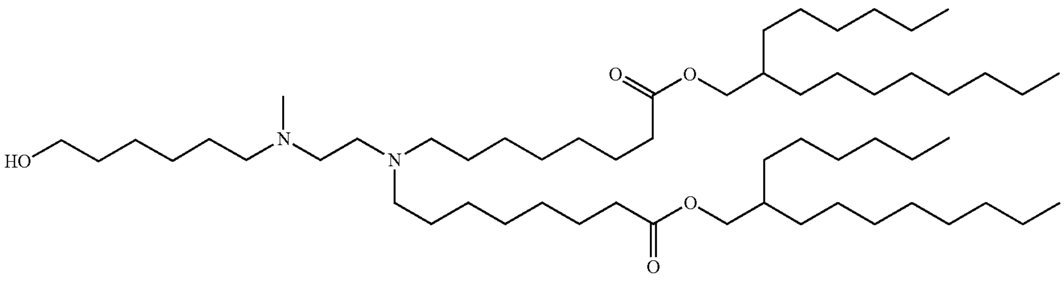 [SMILES: CCCCCCCCC(CCCCCC)COC(=O)CCCCCCCN(CCCCCCCC(=O)OCC(CCCCCC)CCCCCCCC)CCN(C)CCCCCCO] |
| IX-10 | 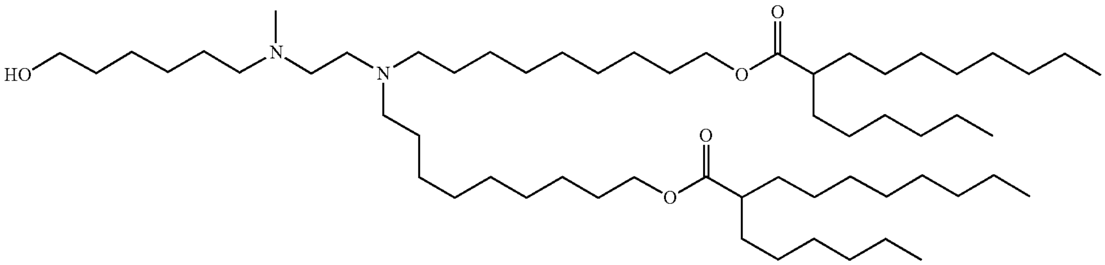 [SMILES: CCCCCCCCC(CCCCCC)C(=O)OCCCCCCCCCN(CCCCCCCCCOC(=O)C(CCCCCC)CCCCCCCC)CCN(C)CCCCCCO] |
| IX-11 | 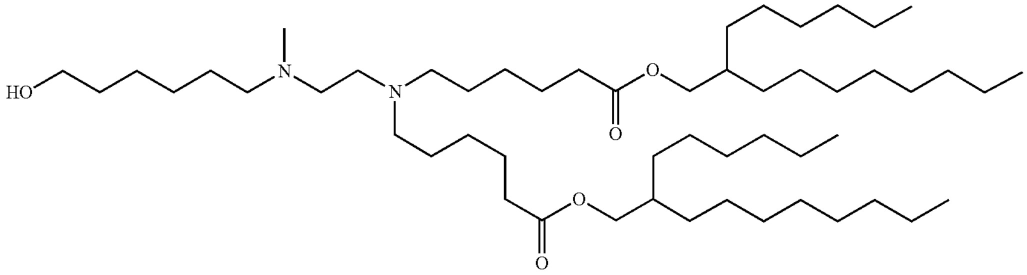 [SMILES: CCCCCCCCC(CCCCCC)COC(=O)CCCCCN(CCCCCC(=O)OCC(CCCCCC)CCCCCCCC)CCN(C)CCCCCCO] |
| IX-12 | 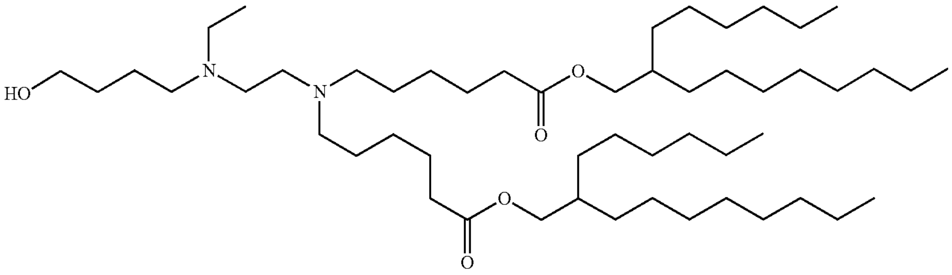 [SMILES: CCCCCCCCC(CCCCCC)COC(=O)CCCCCN(CCCCCC(=O)OCC(CCCCCC)CCCCCCCC)CCN(CC)CCCCO] |
| IX-13 | 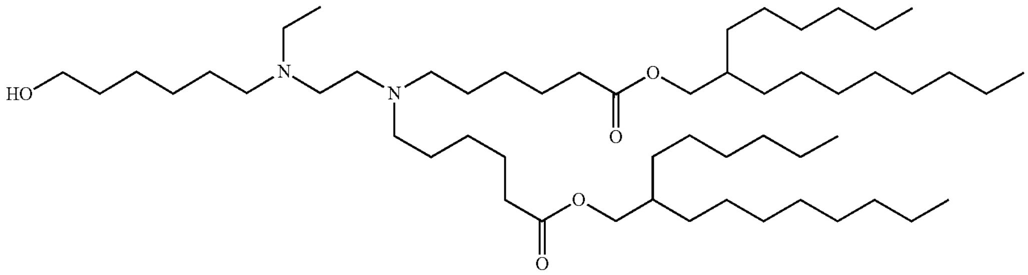 [SMILES: CCCCCCCCC(CCCCCC)COC(=O)CCCCCN(CCCCCC(=O)OCC(CCCCCC)CCCCCCCC)CCN(CC)CCCCCCO] |

TABLE 8-continued
| Representative cationic lipids of structure (IX) | |
|---|---|
| No. | Structure |
| IX-14 | 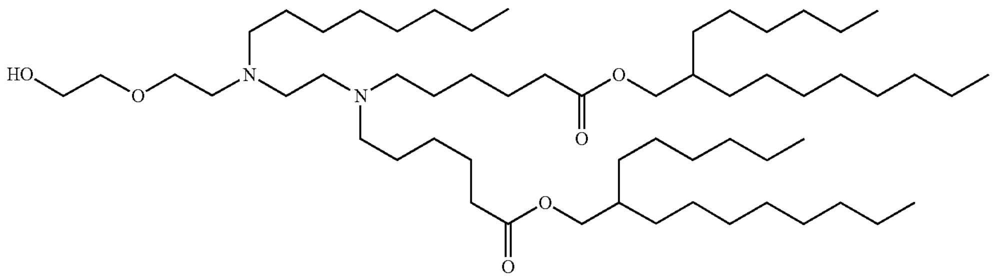 [SMILES: CCCCCCCCC(CCCCCC)COC(=O)CCCCCN(CCCCCC(=O)OCC(CCCCCC)CCCCCCCC)CCN(CCCCCCCC)CCOCCO] |
| IX-15 | 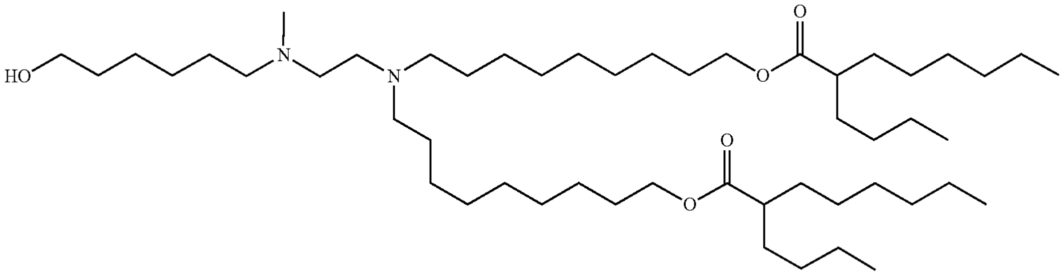 [SMILES: CCCCCCC(CCCC)C(=O)OCCCCCCCCCN(CCCCCCCCCOC(=O)C(CCCC)CCCCCC)CCN(C)CCCCCCO] |
| IX-16 | 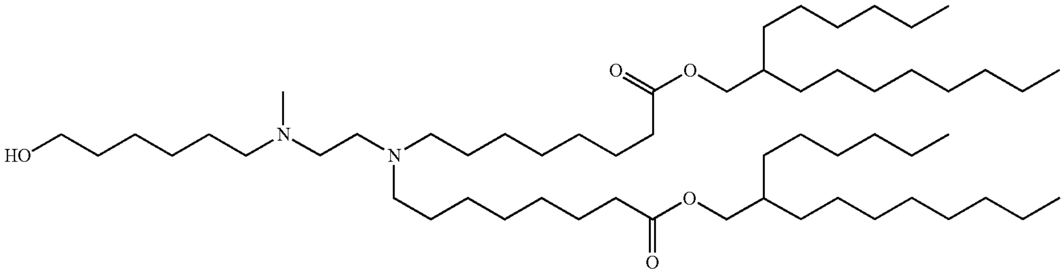 [SMILES: CCCCCCCCC(CCCCCC)COC(=O)CCCCCCCN(CCCCCCCC(=O)OCC(CCCCCC)CCCCCCCC)CCN(C)CCCCCCO] |
| IX-17 | 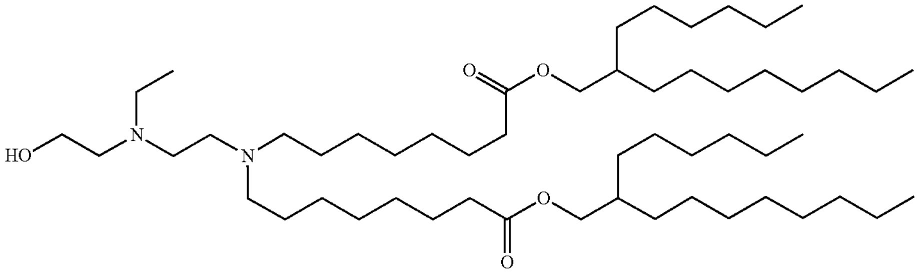 [SMILES: CCCCCCCCC(CCCCCC)COC(=O)CCCCCCCN(CCCCCCCC(=O)OCC(CCCCCC)CCCCCCCC)CCN(CC)CCO] |
| IX-18 | 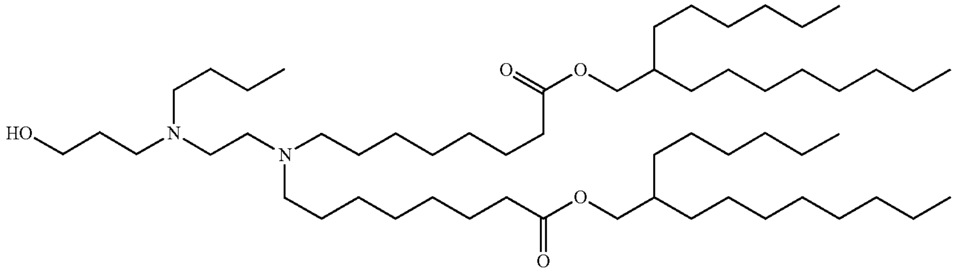 [SMILES: CCCCCCCCC(CCCCCC)COC(=O)CCCCCCCN(CCCCCCCC(=O)OCC(CCCCCC)CCCCCCCC)CCN(CCCC)CCCO] |

In one embodiment, the cationic lipid is a compound having the following structure (X):

(X)

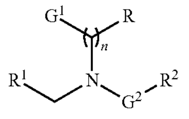

or a pharmaceutically acceptable salt, tautomer, prodrug or stereoisomer thereof, wherein:

$G^1$ is —OH, —$NR^3R^4$, —(C═O)$NR^5$ or —$NR^3$(C═O)$R^5$;

$G^2$ is —$CH_2$— or —(C═O)—;

R is, at each occurrence, independently H or OH;

$R^1$ and $R^2$ are each independently branched, saturated or unsaturated $C_{12}$-$C_{36}$ alkyl;

$R^3$ and $R^4$ are each independently H or straight or branched, saturated or unsaturated $C_1$-$C_6$ alkyl;

$R^5$ is straight or branched, saturated or unsaturated $C_1$-$C_6$ alkyl; and n is an integer from 2 to 6.

In some embodiments, $R^1$ and $R^2$ are each independently branched, saturated or unsaturated $C_{12}$-$C_{30}$ alkyl, $C_{12}$-$C_{20}$ alkyl, or $C_{15}$-$C_{20}$ alkyl. In some specific embodiments, $R^1$ and $R^2$ are each saturated. In certain embodiments, at least one of $R^1$ and $R^2$ is unsaturated.

In some of the foregoing embodiments of structure (X), $R^1$ and $R^2$ have the following structure:

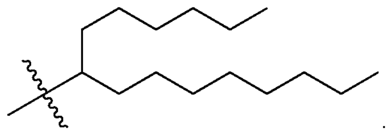 [SMILES: *C(CCCCCC)CCCCCCCC]

In some of the foregoing embodiments of structure (X), the compound has the following structure (XA):

(XA)

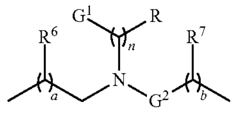

wherein:

$R^6$ and $R^7$ are, at each occurrence, independently H or straight or branched, saturated or unsaturated $C_1$-$C_{14}$ alkyl;

a and b are each independently an integer ranging from 1 to 15, provided that $R^6$ and a, and $R^7$ and b, are each independently selected such that $R^1$ and $R^2$, respectively, are each independently branched, saturated or unsaturated $C_{12}$-$C_{36}$ alkyl.

In some of the foregoing embodiments, the compound has the following structure (XB):

(XB)

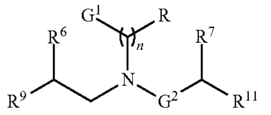

wherein:

$R^8$, $R^9$, $R^{10}$ and $R^{11}$ are each independently straight or branched, saturated or unsaturated $C_4$-$C_{12}$ alkyl, provided that $R^8$ and $R^9$, and $R^{10}$ and $R^{11}$, are each independently selected such that $R^1$ and $R^2$, respectively, are each independently branched, saturated or unsaturated $C_{12}$-$C_{36}$ alkyl. In some embodiments of (XB), $R^8$, $R^9$, $R^{10}$ and $R^{11}$ are each independently straight or branched, saturated or unsaturated $C_6$-$C_{10}$ alkyl. In certain embodiments of (XB), at least one of $R^8$, $R^9$, $R^{10}$ and $R^{11}$ is unsaturated. In other certain specific embodiments of (XB), each of $R_8$, $R^9$, $R^{10}$ and $R^{11}$ is saturated.

In some of the foregoing embodiments, the compound has structure (XA), and in other embodiments, the compound has structure (XB).

In some of the foregoing embodiments, $G^1$ is —OH, and in some embodiments $G^1$ is —$NR^3R^4$. For example, in some embodiments, $G^1$ is —$NH_2$, —$NHCH_3$ or —$N(CH_3)_2$. In certain embodiments, $G^1$ is —(C═O)$NR^5$. In certain other embodiments, $G^1$ is —$NR^3$(C═O)$R^5$. For example, in some embodiments $G^1$ is —NH(C═O)$CH_3$ or —NH(C═O)$CH_2CH_2CH_3$.

In some of the foregoing embodiments of structure (X), $G^2$ is —$CH_2$—. In some different embodiments, $G^2$ is —(C═O)—.

In some of the foregoing embodiments of structure (X), n is an integer ranging from 2 to 6, for example, in some embodiments n is 2, 3, 4, 5 or 6. In some embodiments, n is 2. In some embodiments, n is 3. In some embodiments, n is 4.

In certain of the foregoing embodiments of structure (X), at least one of $R^1$, $R^2$, $R^3$, $R^4$ and $R^5$ is unsubstituted. For example, in some embodiments, $R^1$, $R^2$, $R^3$, $R^4$ and $R^5$ are each unsubstituted. In some embodiments, $R^3$ is substituted. In other embodiments $R^4$ is substituted. In still more embodiments, $R^5$ is substituted. In certain specific embodiments, each of $R^3$ and $R^4$ are substituted. In some embodiments, a substituent on $R^3$, $R^4$ or $R^5$ is hydroxyl. In certain embodiments, $R^3$ and $R^4$ are each substituted with hydroxyl.

In some of the foregoing embodiments of structure (X), at least one R is OH. In other embodiments, each R is H.

In various different embodiments of structure (X), the compound has one of the structures set forth in Table 9 below.

TABLE 9
| Representative cationic lipids of structure (X) | |
|---|---|
| No. | Structure |
| X-1 | 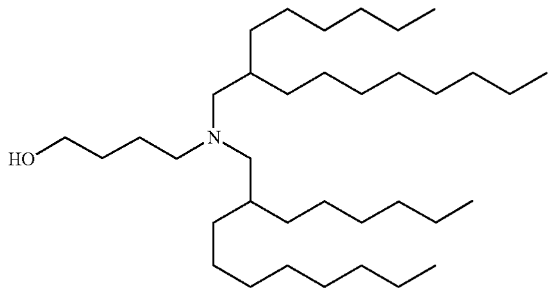 [SMILES: CCCCCCCCC(CCCCCC)CN(CCCCO)CC(CCCCCC)CCCCCCCC] |
| X-2 | 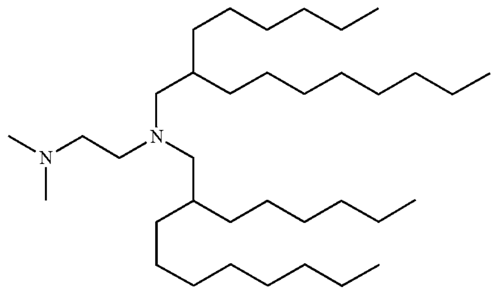 [SMILES: CCCCCCCCC(CCCCCC)CN(CCN(C)C)CC(CCCCCC)CCCCCCCC] |
| X-3 | 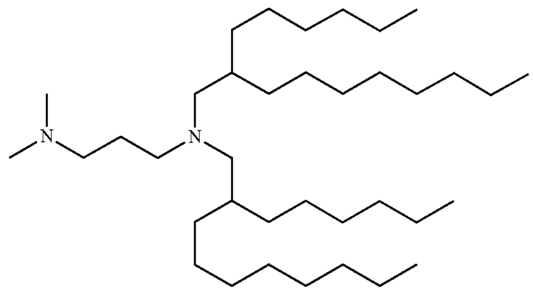 [SMILES: CCCCCCCCC(CCCCCC)CN(CCCN(C)C)CC(CCCCCC)CCCCCCCC] |
| X-4 | 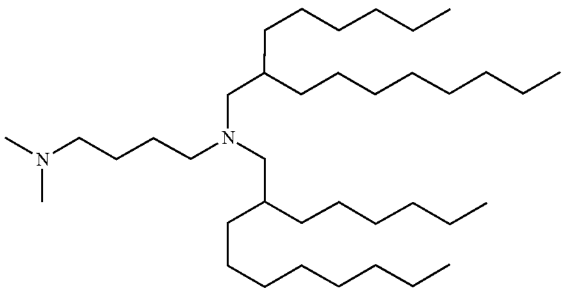 [SMILES: CCCCCCCCC(CCCCCC)CN(CCCCN(C)C)CC(CCCCCC)CCCCCCCC] |
| X-5 | 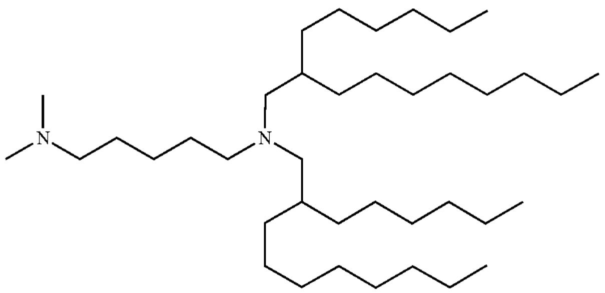 [SMILES: CCCCCCCCC(CCCCCC)CN(CCCCCN(C)C)CC(CCCCCC)CCCCCCCC] |

TABLE 9-continued
| Representative cationic lipids of structure (X) | |
|---|---|
| No. | Structure |
| X-6 | 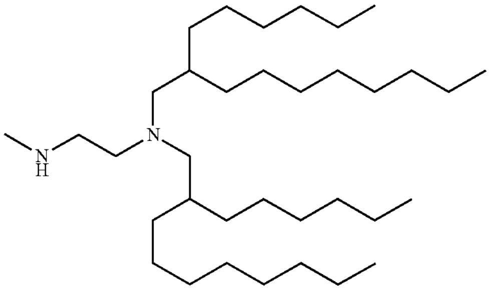 [SMILES: CCCCCCCCC(CCCCCC)CN(CCNC)CC(CCCCCC)CCCCCCCC] |
| X-7 | 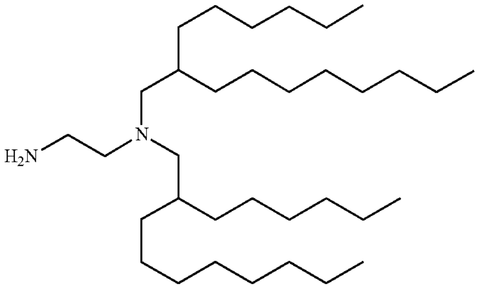 [SMILES: CCCCCCCCC(CCCCCC)CN(CCN)CC(CCCCCC)CCCCCCCC] |
| X-8 | 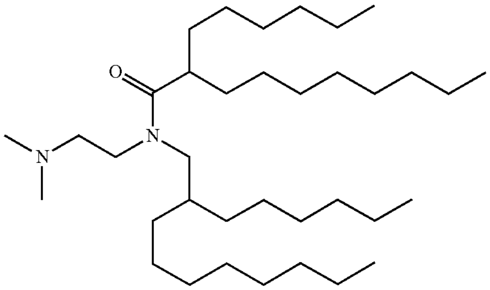 [SMILES: CCCCCCCCC(CCCCCC)CN(CCN(C)C)C(=O)C(CCCCCC)CCCCCCCC] |
| X-9 | 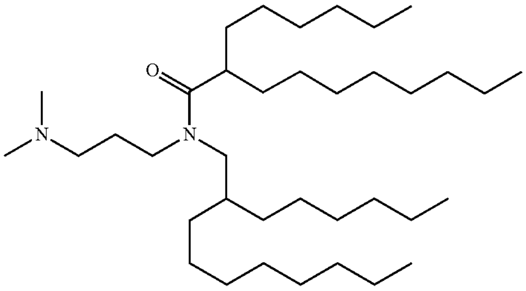 [SMILES: CCCCCCCCC(CCCCCC)CN(CCCN(C)C)C(=O)C(CCCCCC)CCCCCCCC] |
| X-10 | 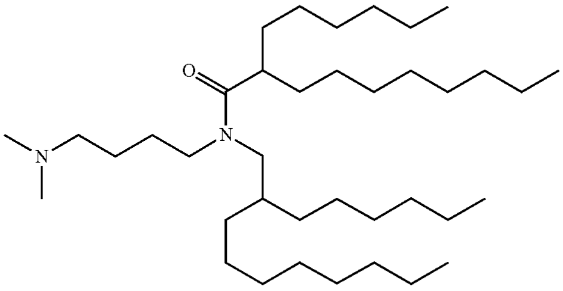 [SMILES: CCCCCCCCC(CCCCCC)CN(CCCCN(C)C)C(=O)C(CCCCCC)CCCCCCCC] |

TABLE 9-continued
| Representative cationic lipids of structure (X) | |
|---|---|
| No. | Structure |
| X-11 | 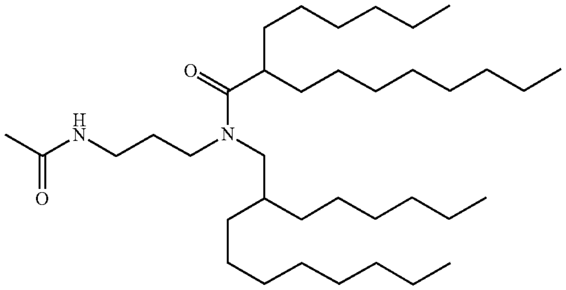 [SMILES: CCCCCCCCC(CCCCCC)CN(CCCNC(C)=O)C(=O)C(CCCCCC)CCCCCCCC] |
| X-12 | 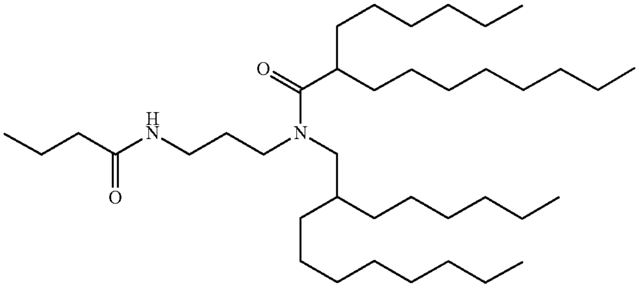 [SMILES: CCCCCCCCC(CCCCCC)CN(CCCNC(=O)CCC)C(=O)C(CCCCCC)CCCCCCCC] |
| X-13 | 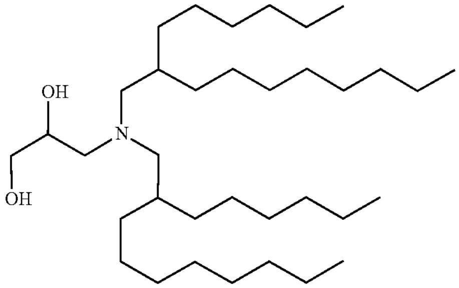 [SMILES: CCCCCCCCC(CCCCCC)CN(CC(O)CO)CC(CCCCCC)CCCCCCCC] |
| X-14 | 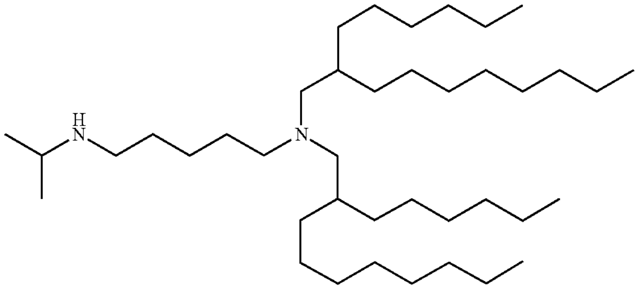 [SMILES: CCCCCCCCC(CCCCCC)CN(CCCCCNC(C)C)CC(CCCCCC)CCCCCCCC] |
| X-15 | 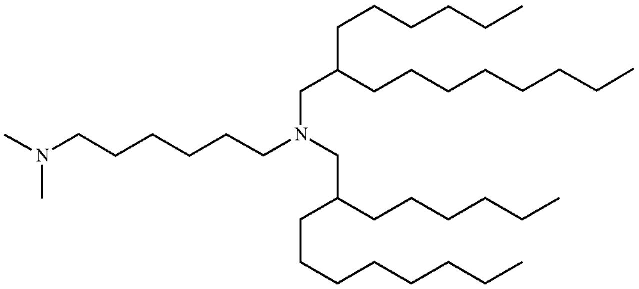 [SMILES: CCCCCCCCC(CCCCCC)CN(CCCCCCN(C)C)CC(CCCCCC)CCCCCCCC] |

TABLE 9-continued

| Representative cationic lipids of structure (X) | |
|---|---|
| No. | Structure |
| X-16 | 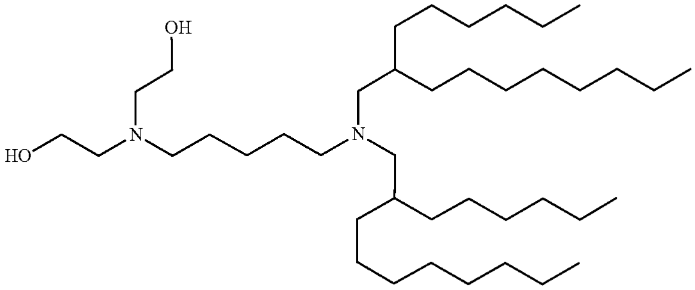 [SMILES: CCCCCCCCC(CCCCCC)CN(CCCCCN(CCO)CCO)CC(CCCCCC)CCCCCCCC] |
| X-17 | 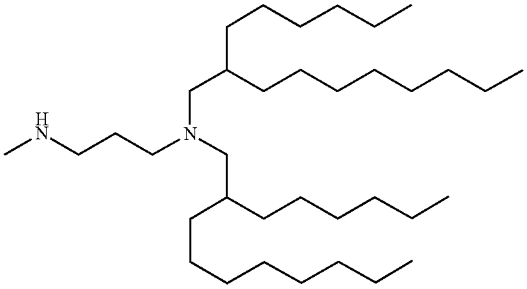 [SMILES: CCCCCCCCC(CCCCCC)CN(CCCNC)CC(CCCCCC)CCCCCCCC] |

In any of Embodiments 1, 2, 3, 4 or 5, the LNPs further comprise a neutral lipid. In various embodiments, the molar ratio of the cationic lipid to the neutral lipid ranges from about 2:1 to about 8:1. In certain embodiments, the neutral lipid is present in any of the foregoing LNPs in a concentration ranging from 5 to 10 mol percent, from 5 to 15 mol percent, 7 to 13 mol percent, or 9 to 11 mol percent. In certain specific embodiments, the neutral lipid is present in a concentration of about 9.5, 10 or 10.5 mol percent. In some embodiments, the molar ratio of cationic lipid to the neutral lipid ranges from about 4.1:1.0 to about 4.9:1.0, from about 4.5:1.0 to about 4.8:1.0, or from about 4.7:1.0 to 4.8:1.0. In some embodiments, the molar ratio of total cationic lipid to the neutral lipid ranges from about 4.1:1.0 to about 4.9:1.0, from about 4.5:1.0 to about 4.8:1.0, or from about 4.7:1.0 to 4.8:1.0.

Exemplary neutral lipids for use in any of Embodiments 1, 2, 3, 4 or 5 include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2-dielaidoyl-sn-glycero-3-phophoethanolamine (transDOPE). In one embodiment, the neutral lipid is 1,2-distearoyl-sn-glycero-3phosphocholine (DSPC). In some embodiments, the neutral lipid is selected from DSPC, DPPC, DMPC, DOPC, POPC, DOPE and SM. In some embodiments, the neutral lipid is DSPC.

In various embodiments of Embodiments 1, 2, 3, 4 or 5, any of the disclosed lipid nanoparticles comprise a steroid or steroid analogue. In certain embodiments, the steroid or steroid analogue is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In certain specific embodiments, the steroid is present in a concentration of 40, 41, 42, 43, 44, 45, or 46 molar percent.

In certain embodiments, the molar ratio of cationic lipid to the steroid ranges from 1.0:0.9 to 1.0:1.2, or from 1.0:1.0 to 1.0:1.2. In some of these embodiments, the molar ratio of cationic lipid to cholesterol ranges from about 5:1 to 1:1. In certain embodiments, the steroid is present in a concentration ranging from 32 to 40 mol percent of the steroid.

In certain embodiments, the molar ratio of total cationic to the steroid ranges from 1.0:0.9 to 1.0:1.2, or from 1.0:1.0 to 1.0:1.2. In some of these embodiments, the molar ratio of total cationic lipid to cholesterol ranges from about 5:1 to 1:1. In certain embodiments, the steroid is present in a concentration ranging from 32 to 40 mol percent of the steroid.

In some embodiments of Embodiments 1, 2, 3 4 or 5, the LNPs further comprise a polymer conjugated lipid. In various other embodiments of Embodiments 1, 2, 3 4 or 5, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy) propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy) ethyl-N-(2,3-di(tetradecanoxy)propyl)carbamate or 2,3-di (tetradecanoxy)propyl-N-(ω-methoxy(polyethoxy)ethyl) carbamate.

In various embodiments, the polymer conjugated lipid is present in a concentration ranging from 1.0 to 2.5 molar percent. In certain specific embodiments, the polymer conjugated lipid is present in a concentration of about 1.7 molar percent. In some embodiments, the polymer conjugated lipid is present in a concentration of about 1.5 molar percent.

In certain embodiments, the molar ratio of cationic lipid to the polymer conjugated lipid ranges from about 35:1 to about 25:1. In some embodiments, the molar ratio of cationic lipid to polymer conjugated lipid ranges from about 100:1 to about 20:1.

In certain embodiments, the molar ratio of total cationic lipid (i.e., the sum of the first and second cationic lipid) to the polymer conjugated lipid ranges from about 35:1 to about 25:1. In some embodiments, the molar ratio of total cationic lipid to polymer conjugated lipid ranges from about 100:1 to about 20:1.

In some embodiments of Embodiments 1, 2, 3 4 or 5, the pegylated lipid, when present, has the following Formula (XI):

(XI)

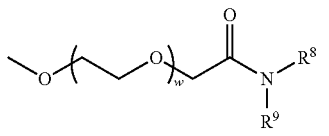

or a pharmaceutically acceptable salt, tautomer or stereoisomer thereof, wherein:

$R^{12}$ and $R^{13}$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60.

In some embodiments, $R^{12}$ and $R^{13}$ are each independently straight, saturated alkyl chains containing from 12 to 16 carbon atoms. In other embodiments, the average w ranges from 42 to 55, for example, the average w is 42, 43, 44, 45, 46, 47, 48, 49, 50, 51, 52, 53, 54 or 55. In some specific embodiments, the average w is about 49.

In some embodiments, the pegylated lipid has the following Formula (XIa):

(XIa)

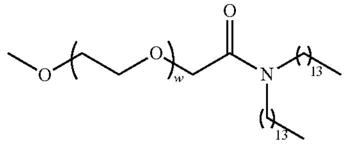

wherein the average w is about 49.

In some embodiments of Embodiments 1, 2, 3 4 or 5, the nucleic acid is selected from antisense and messenger RNA. For example, messenger RNA may be used to induce an immune response (e.g., as a vaccine), for example by translation of immunogenic proteins.

In other embodiments of Embodiments 1, 2, 3 4 or 5, the nucleic acid is mRNA, and the mRNA to lipid ratio in the LNP (i.e., N/P, were N represents the moles of cationic lipid and P represents the moles of phosphate present as part of the nucleic In an embodiment, the transfer vehicle comprises a lipid or an ionizable lipid described in US patent publication number 20190314524.

Some embodiments of the present invention provide nucleic acid-lipid nanoparticle compositions comprising one or more of the novel cationic lipids described herein as structures listed in Table 10, that provide increased activity of the nucleic acid and improved tolerability of the compositions in vivo.

In one embodiment, an ionizable lipid has the following structure (XII):

(XII)

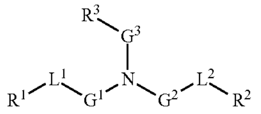

or a pharmaceutically acceptable salt, tautomer, prodrug or stereoisomer thereof, wherein:

one of $L^1$ or $L^2$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$+ or —$NR^aC$(═O)O—, and the other of $L^1$ or $L^2$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)$OR^4$, —OC(═O)$R^4$ or —$NR^5C$(═O)$R^4$;

$R^4$ is $C_1$-$C_{12}$alkyl;

$R^5$ is H or $C_1$-$C_6$ alkyl; and x is 0, 1 or 2.

In some embodiments, an ionizable lipid has one of the following structures (XIIA) or (XIIB):

(XIIA)

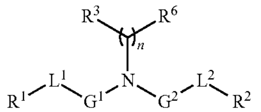

(XIIB)

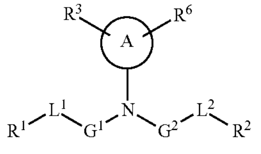

wherein:

A is a 3 to 8-membered cycloalkyl or cycloalkylene ring;

$R^6$ is, at each occurrence, independently H, OH or $C_1$-$C_{24}$ alkyl; and n is an integer ranging from 1 to 15.

In some embodiments, the ionizable lipid has structure (XIIA), and in other embodiments, the ionizable lipid has structure (XIIB).

In other embodiments, an ionizable lipid has one of the following structures (XIIC) or (XIID):

(XIIC)

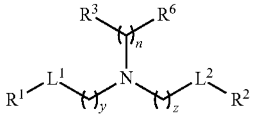

(XIID)

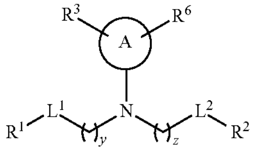

wherein y and z are each independently integers ranging from 1 to 12.

In some embodiments, one of $L^1$ or $L^2$ is —O(C═O)—. For example, in some embodiments each of $L^1$ and $L^2$ are —O(C═O)—. In some different embodiments of any of the foregoing, $L^1$ and $L^2$ are each independently —(C═O)O— or —O(C═O)—. For example, in some embodiments each of $L^1$ and $L^2$ is —(C═O)O—.

In some embodiments, an ionizable lipid has one of the following structures (XIIE) or (XIIF):

(XIIE)

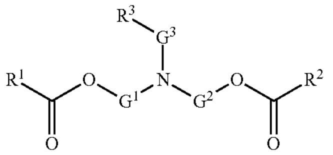

(XIIF)

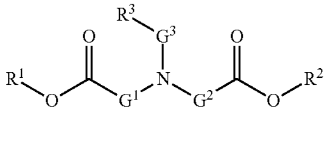

In some embodiments, an ionizable lipid has one of the following structures (XIIG), (XIIH), (XIII), or (XIIJ):

(XIIG)

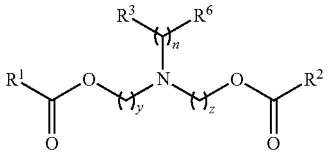

(XIIH)

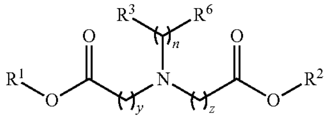

(XIII)

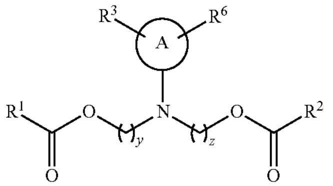

-continued (XIIJ)

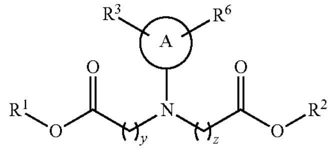

In some embodiments, n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some embodiments, y and z are each independently an integer ranging from 2 to 10. For example, in some embodiments, y and z are each independently an integer ranging from 4 to 9 or from 4 to 6.

In some embodiments, $R^6$ is H. In other embodiments, $R^6$ is $C_1$-$C_{24}$ alkyl. In other embodiments, $R^6$ is OH.

In some embodiments, $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some embodiments, $R^1$ or $R^2$, or both, is $C_6$-$C_{24}$ alkenyl. For example, in some embodiments, $R^1$ and $R^2$ each, independently have the following structure:

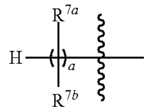

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms.

In some embodiments, a is an integer ranging from 5 to 9 or from 8 to 12.

In some embodiments, at least one occurrence of $R^{7a}$ is H. For example, in some embodiments, $R^{7a}$ is H at each occurrence. In other different embodiments, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments, $R^1$ or $R^2$, or both, has one of the following structures:

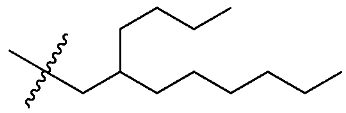

;

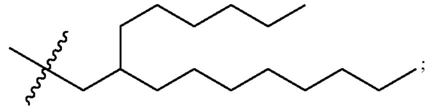

;

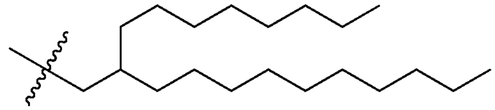

;

-continued

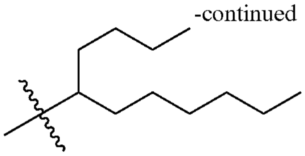;

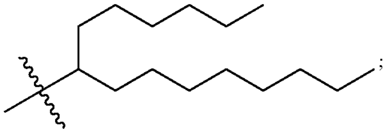;

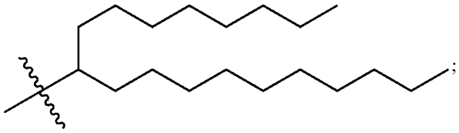;

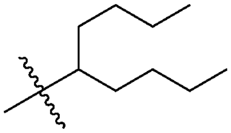;

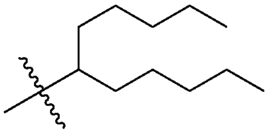;

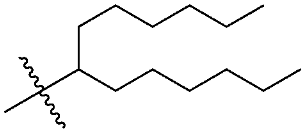;

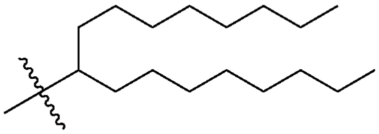.

In some embodiments, $R^3$ is —OH, —CN, —C(═O)OR$^4$, —OC(═O)R$^4$ or —NHC(═O)R$^4$. In some embodiments, $R^4$ is methyl or ethyl.

In some embodiments, an ionizable lipid is a compound of Formula (1):

Formula (1)

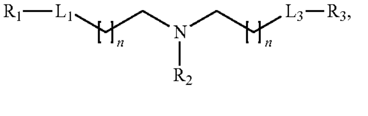

wherein:

each n is independently 1, 2, 3, 4, 5, 6, 7, 8, 9, 10, 11, 12, 13, 14, or 15; and $L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)amino carbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl.

In some embodiments, $R_1$ and $R_3$ are the same. In some embodiments, $R_1$ and $R_3$ are different.

In some embodiments, $R_1$ and $R_3$ are each independently a branched saturated $C_9$-$C_{20}$alkyl. In some embodiments, one of $R_1$ and $R_3$ is a branched saturated $C_9$-$C_{20}$ alkyl, and the other is an unbranched saturated $C_9$-$C_{20}$ alkyl. In some embodiments, $R_1$ and $R_3$ are each independently selected from a group consisting of:

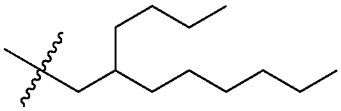,

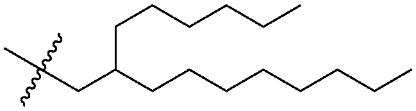,

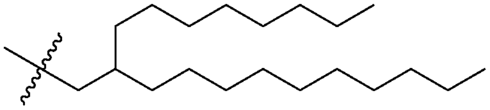,

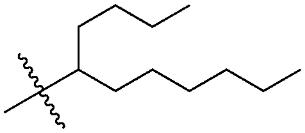,

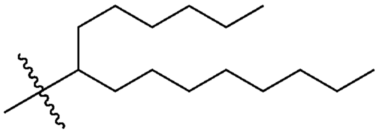,

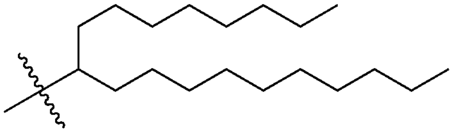,

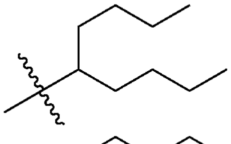, 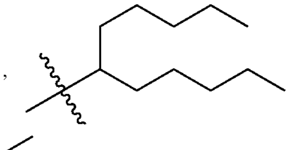,

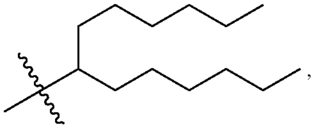,

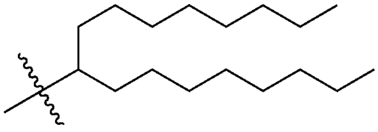, and

-continued

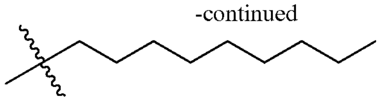

In various embodiments, $R_2$ is selected from a group consisting of:

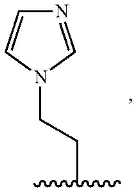 , 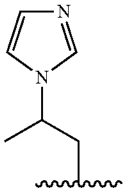 , 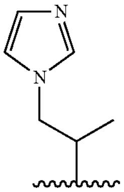 ,

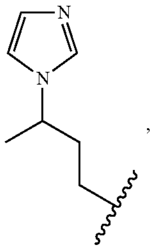 , 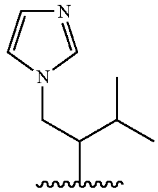 , 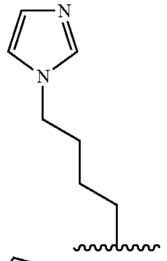 ,

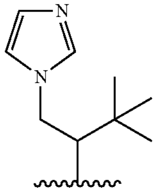 , 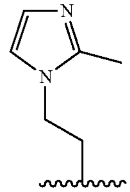 , 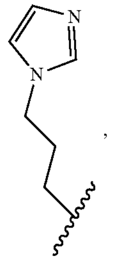 ,

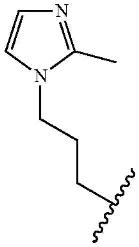 , 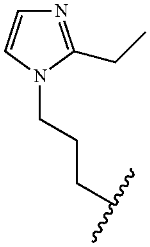 , 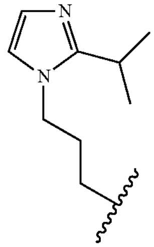 ,

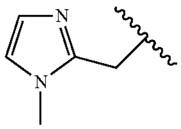 , 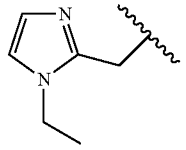 ,

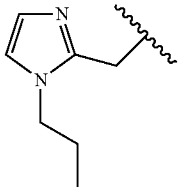 , 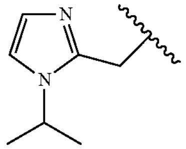 ,

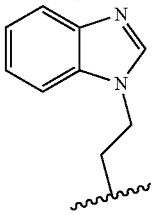 , 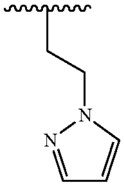 ,

-continued

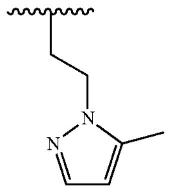 , and 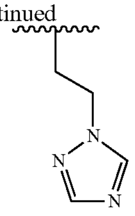 .

In some embodiments, $R_2$ may be as described in International Pat. Pub. No. WO2019/152848 A 1, which is incorporated herein by reference in its entirety.

In some embodiments, an ionizable lipid is a compound of Formula (1-1) or Formula (1-2):

Formula (1-1)

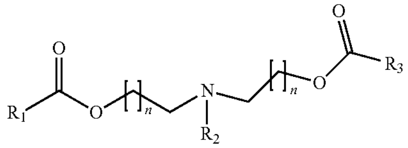

Formula (1-2)

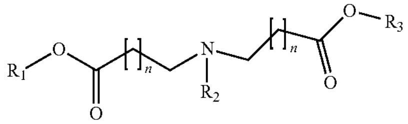

wherein n, $R_1$, $R_2$, and $R_3$ are as defined in Formula (1).

Preparation methods for the above compounds and compositions are described herein below and/or known in the art.

It will be appreciated by those skilled in the art that in the process described herein the functional groups of intermediate compounds may need to be protected by suitable protecting groups. Such functional groups include, e.g., hydroxyl, amino, mercapto, and carboxylic acid. Suitable protecting groups for hydroxyl include, e.g., trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino, and guanidine include, e.g., t-butoxycarbonyl, benzyloxycarbonyl, and the like. Suitable protecting groups for mercapto include, e.g., —C(O)—R" (where R" is alkyl, aryl, or arylalkyl), p-methoxybenzyl, trityl, and the like. Suitable protecting groups for carboxylic acid include, e.g., alkyl, aryl, or arylalkyl esters. Protecting groups may be added or removed in accordance with standard techniques, which are known to one skilled in the art and as described herein. The use of protecting groups is described in detail in, e.g., Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin, or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as prodrugs. All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can also be converted to their free base or acid form by standard techniques.

The following reaction scheme illustrates an exemplary method to make compounds of Formula (1):

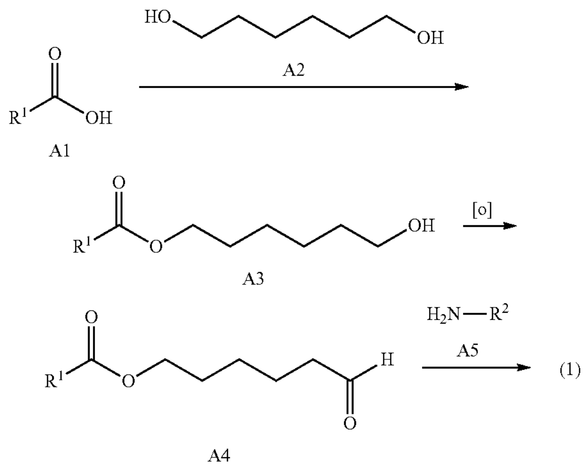

A1 are purchased or prepared according to methods known in the art. Reaction of A1 with diol A2 under appropriate condensation conditions (e.g., DCC) yields ester/alcohol A3, which can then be oxidized (e.g., with PCC) to aldehyde A4. Reaction of A4 with amine A5 under reductive amination conditions yields a compound of Formula (1).

The following reaction scheme illustrates a second exemplary method to make compounds of Formula (1), wherein $R_1$ and $R_3$ are the same:

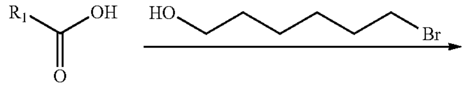

-continued

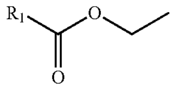

Modifications to the above reaction scheme, such as using protecting groups, may yield compounds wherein $R_1$ and $R_3$ are different. The use of protecting groups, as well as other modification methods, to the above reaction scheme will be readily apparent to one of ordinary skill in the art.

It is understood that one skilled in the art may be able to make these compounds by similar methods or by combining other methods known to one skilled in the art. It is also understood that one skilled in the art would be able to make other compounds of Formula (1) not specifically illustrated herein by using the appropriate starting materials and modifying the parameters of the synthesis. In general, starting materials may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

In some embodiments, an ionizable lipid is a compound of Formula (2):

Formula (2)

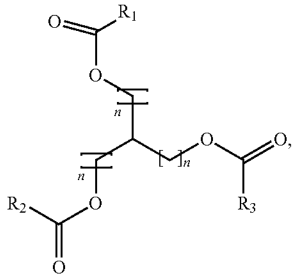

wherein each n is independently 1, 2, 3, 4, 5, 6, 7, 8, 9, 10, 11, 12, 13, 14, or 15.

In some embodiments, as used in Formula (2), $R_1$ and $R_2$ are as defined in Formula (1).

In some embodiments, as used in Formula (2), $R_1$ and $R_2$ are each independently selected from a group consisting of:

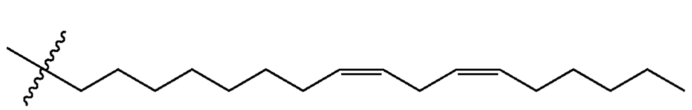

,

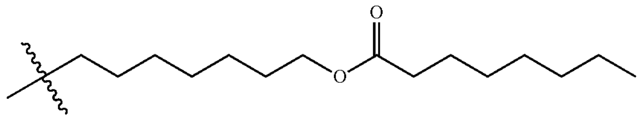

,

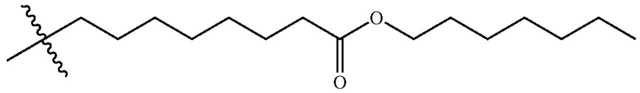

,

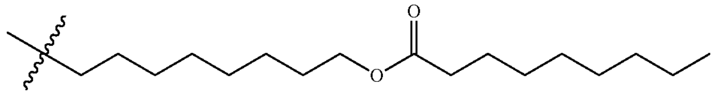

,

-continued
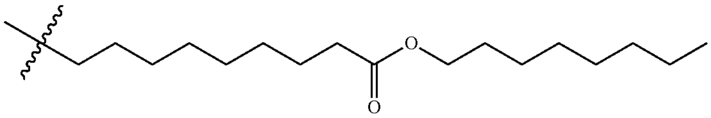,
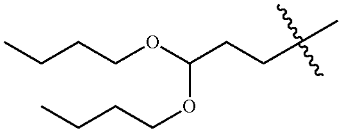,
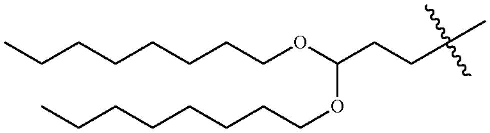,
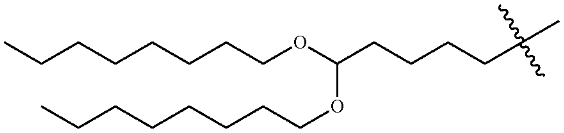,
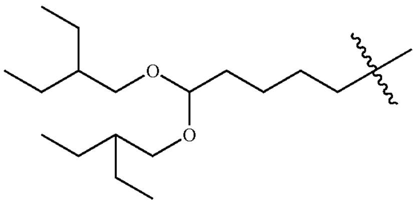,
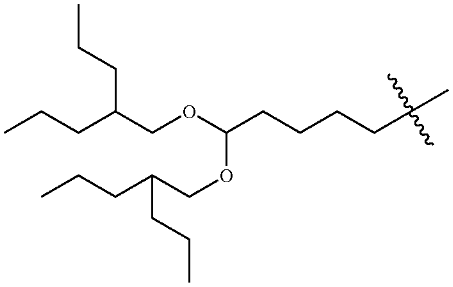,
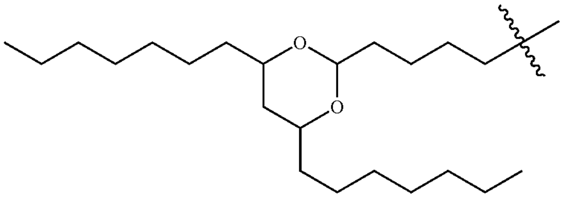,
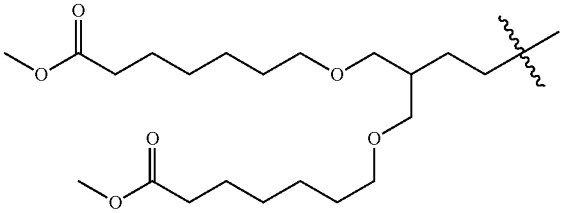,
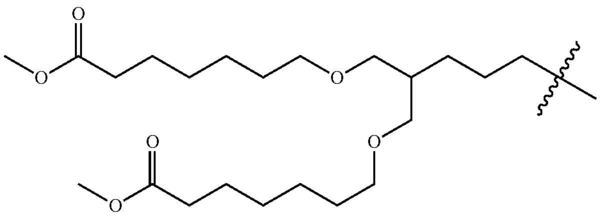,
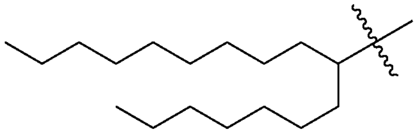,
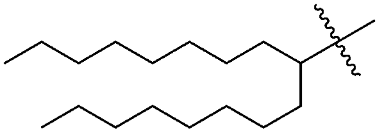,
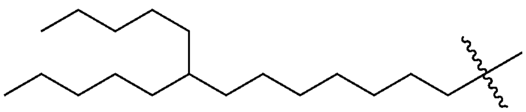,
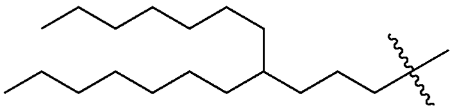,
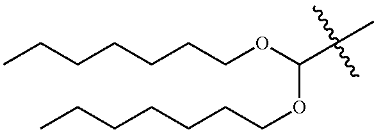,
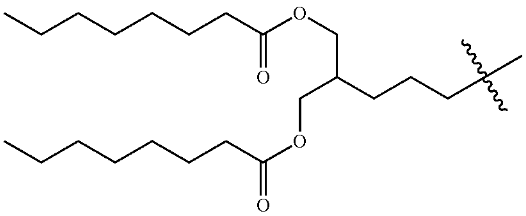, -continued

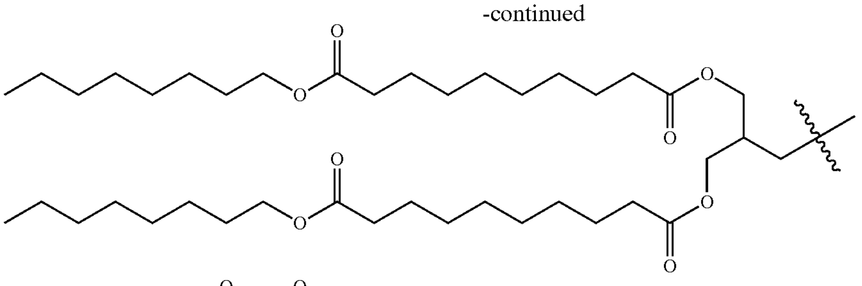

,

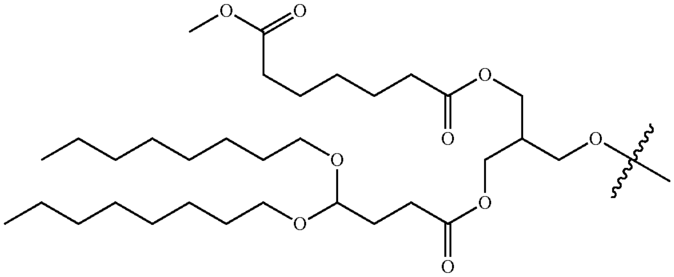

,

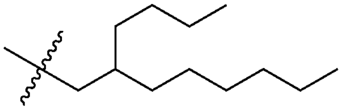

,

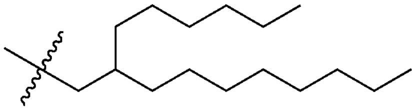

,

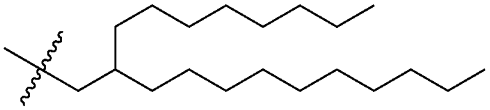

,

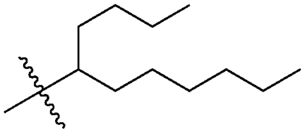

,

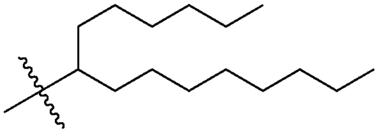

,

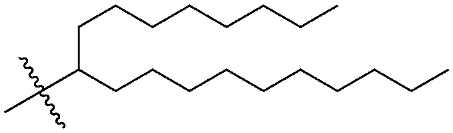

,

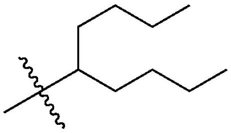

,

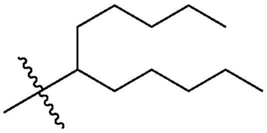

,

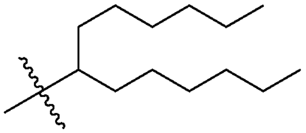

, and

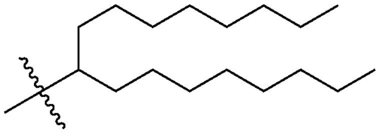

.

In some embodiments, $R_1$ and/or $R_2$ as used in Formula (2) may be as described in International Pat. Pub. No. WO2015/095340 A 1, which is incorporated herein by reference in its entirety. In some embodiments, $R_1$ as used in Formula (2) may be as described in International Pat. Pub. No. WO2019/152557 A 1, which is incorporated herein by reference in its entirety.

In some embodiments, as used in Formula (2), $R_3$ is selected from a group consisting of:

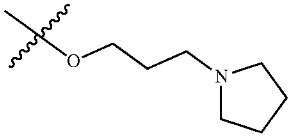

,

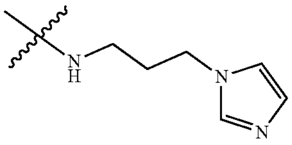

,

-continued

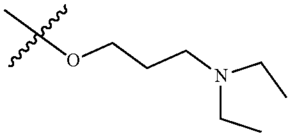

,

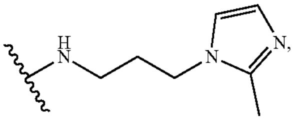

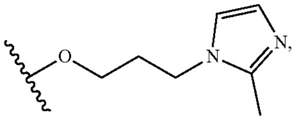

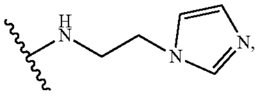

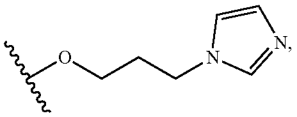

-continued

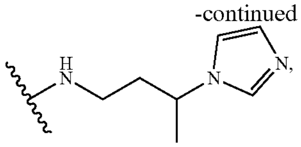,

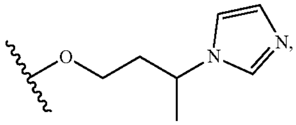,

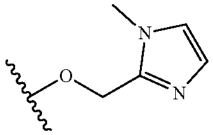,

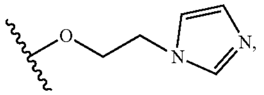, and

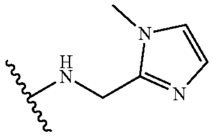.

In some embodiments, an ionizable lipid is a compound of Formula (3)

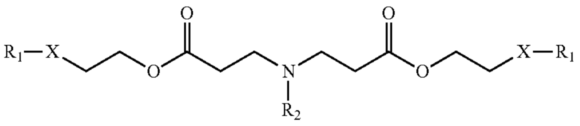

wherein X is selected from —O—, —S—, or —OC(O)—*, wherein * indicates the attachment point to $R_1$.

In some embodiments, an ionizable lipid is a compound of Formula (3-1):

(3-1)

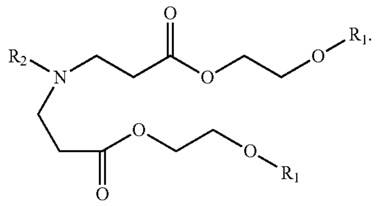

In some embodiments, an ionizable lipid is a compound of Formula (3-2):

(3-2)

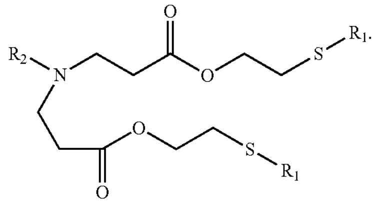

In some embodiments, an ionizable lipid is a compound of Formula (3-3):

(3-3)

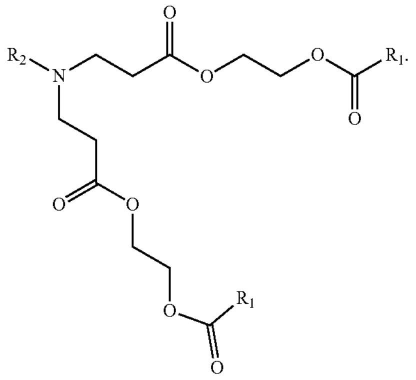

In some embodiments, as used in Formula (3-1), (3-2), or (3-3), each $R_1$ is independently a branched saturated $C_9$-$C_{20}$ alkyl. In some embodiments, each $R_1$ is independently selected from a group consisting of:

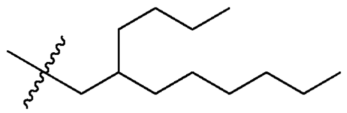,

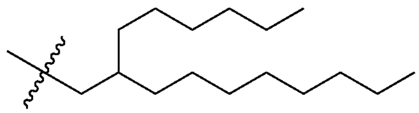,

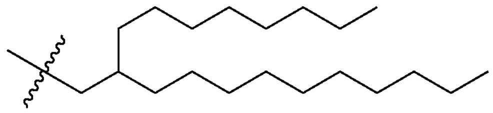,

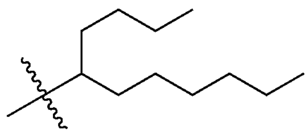,

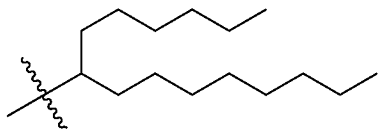,

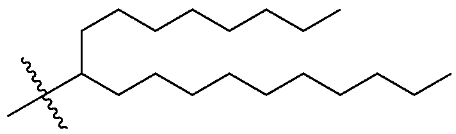,

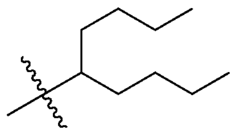, 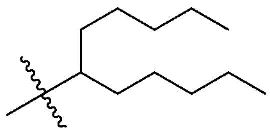,

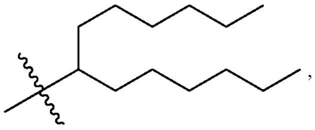

, and

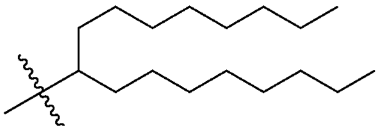

.

In some embodiments, each $R_1$ in Formula (3-1), (3-2), or (3-3) are the same.

In some embodiments, as used in Formula (3-1), (3-2), or (3-3), $R_2$ is selected from a group consisting of:

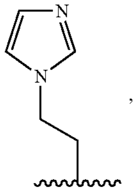

,

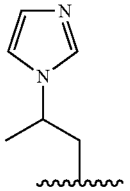

,

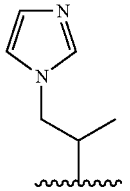

,

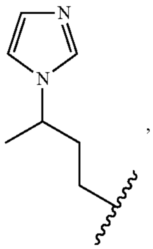

,

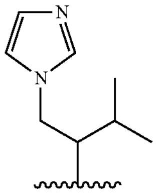

,

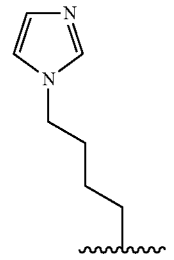

,

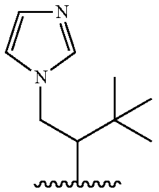

,

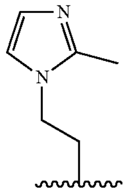

,

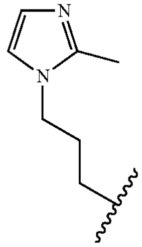

,

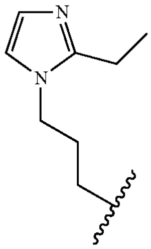

,

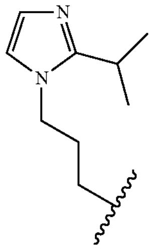

,

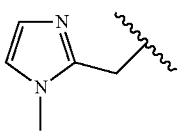

,

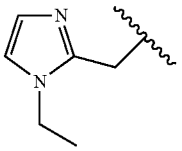

,

-continued

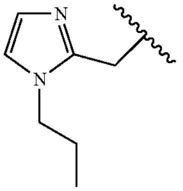

,

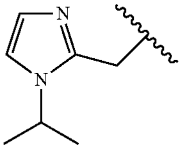

,

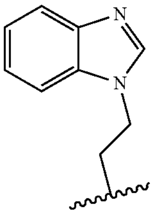

,

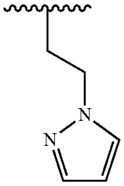

,

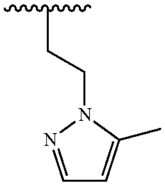

,

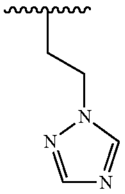

, and

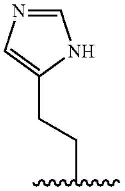

.

In some embodiments, $R_2$ as used in Formula (3-1), (3-2), or (3-3) may be as described in International Pat. Pub. No. WO2019/152848A1, which is incorporated herein by reference in its entirety.

In some embodiments, an ionizable lipid is a compound of Formula (5):

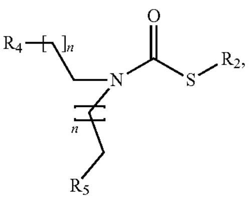

(5)

wherein:

each n is independently 1, 2, 3, 4, 5, 6, 7, 8, 9, 10, 11, 12, 13, 14, or 15; and $R_2$ is as defined in Formula (1).

In some embodiments, as used in Formula (5), $R_4$ and $R_5$ are defined as $R_1$ and $R_3$, respectively, in Formula (1). In some embodiments, as used in Formula (5), $R_4$ and $R_5$ may be as described in International Pat. Pub. No. WO2019/191780 A1, which is incorporated herein by reference in its entirety.

In some embodiments, an ionizable lipid of the disclosure is selected from Table 10a. In some embodiments, the ionizable lipid is Lipid 26 in Table 10a. In some embodiments, the ionizable lipid is Lipid 27 in Table 10a. In some embodiments, the ionizable lipid is Lipid 53 in Table 10a. In some embodiments, the ionizable lipid is Lipid 54 in Table 10a.

In some embodiments, an ionizable lipid of the disclosure is selected from the group consisting of:
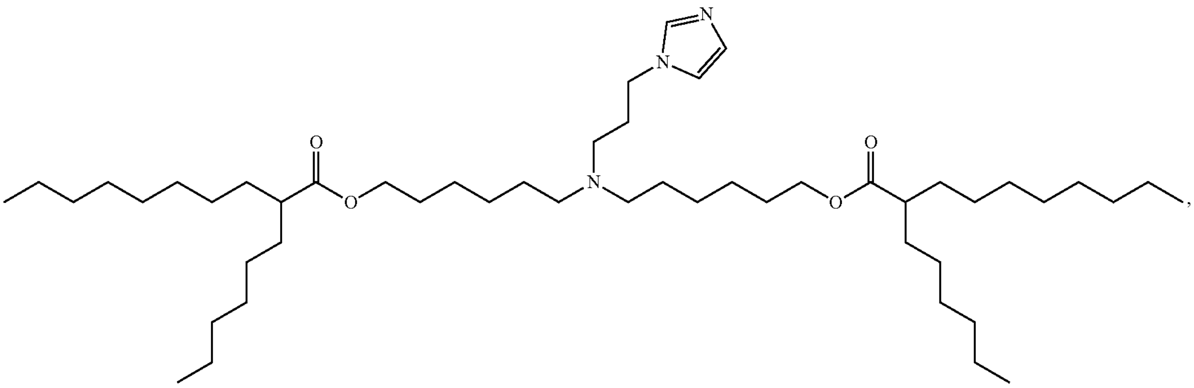
,
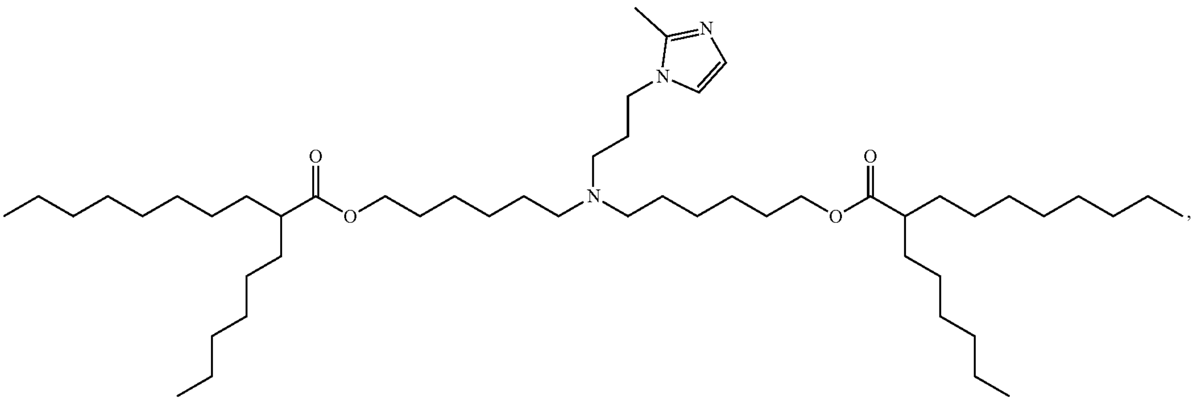
,
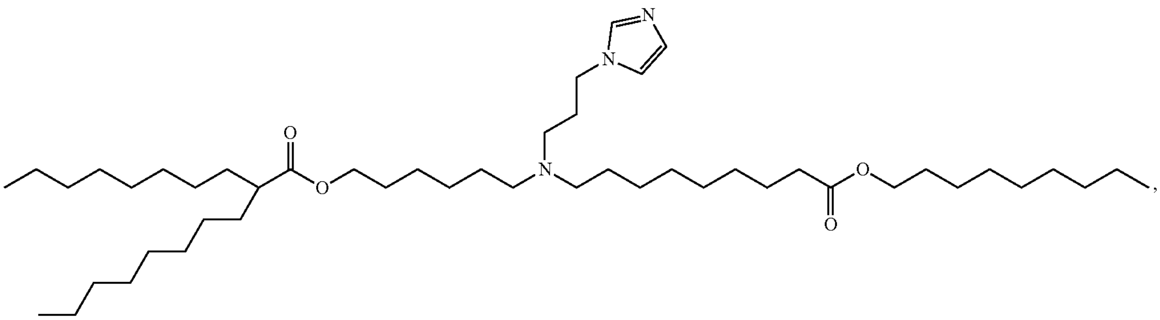
, and
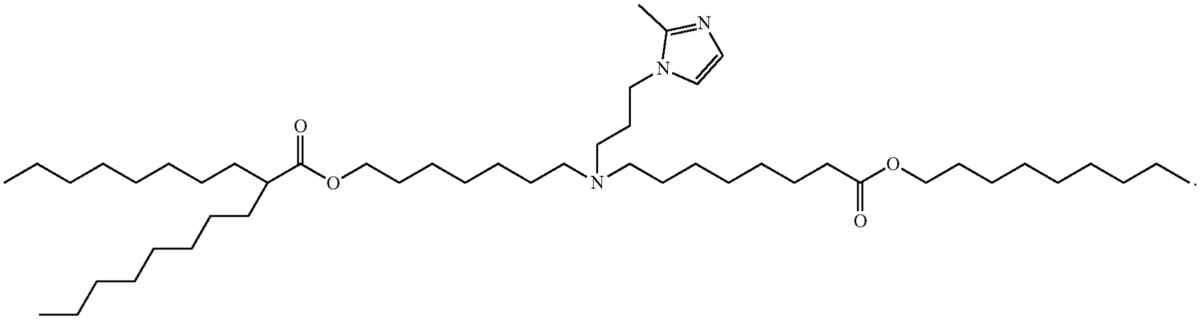
.

TABLE 10a
| Ionizable lipid number | Structure |
| --- | --- |
| 1 | 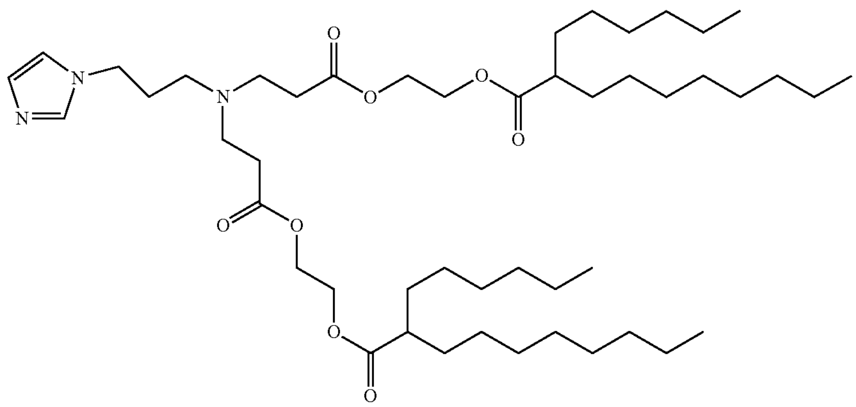 [SMILES: CCCCCCCCC(CCCCCC)C(=O)OCCOC(=O)CCN(CCCn1ccnc1)CCC(=O)OCCOC(=O)C(CCCCCC)CCCCCCCC] |
| 2 | 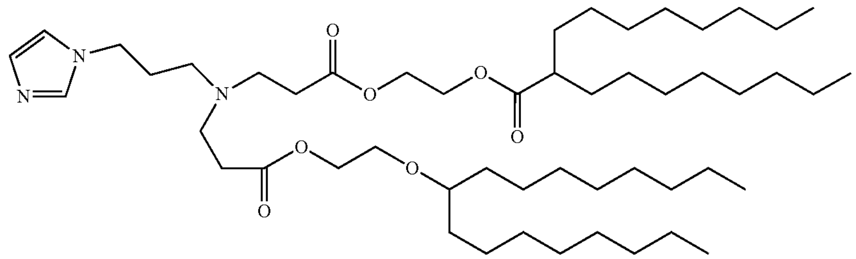 [SMILES: CCCCCCCCC(CCCCCCCC)OCCOC(=O)CCN(CCCn1ccnc1)CCC(=O)OCCOC(=O)C(CCCCCCCC)CCCCCCCC] |
| 3 | 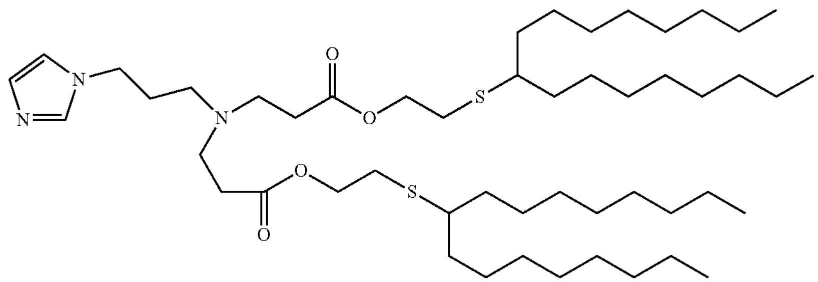 [SMILES: CCCCCCCCC(CCCCCCCC)SCCOC(=O)CCN(CCCn1ccnc1)CCC(=O)OCCSC(CCCCCCCC)CCCCCCCC] |
| 4 | 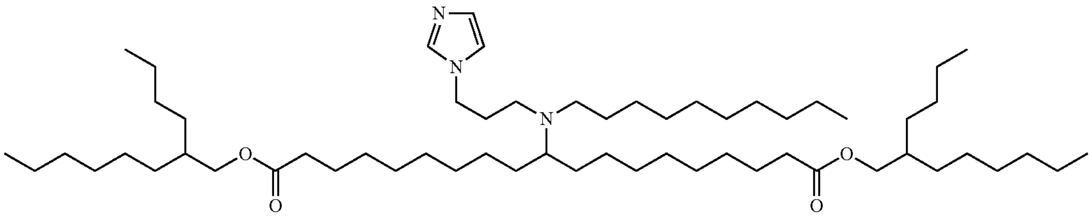 [SMILES: CCCCCCCCCCN(CCCn1ccnc1)C(CCCCCCCCC(=O)OCC(CCCC)CCCCCC)CCCCCCCCC(=O)OCC(CCCC)CCCCCC] |
| 5 | 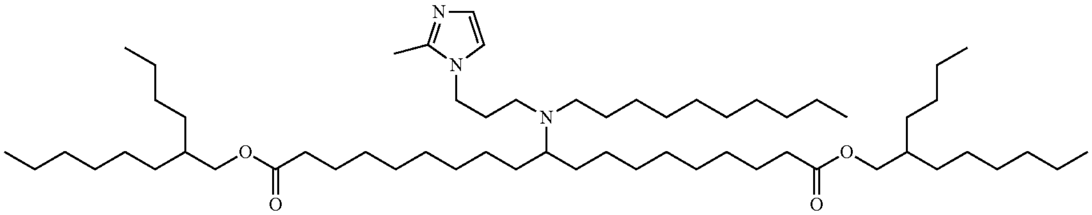 [SMILES: CCCCCCCCCCN(CCCn1ccnc1C)C(CCCCCCCCC(=O)OCC(CCCC)CCCCCC)CCCCCCCCC(=O)OCC(CCCC)CCCCCC] |

TABLE 10a-continued
| Ionizable lipid number | Structure |
|---|---|
| 6 | 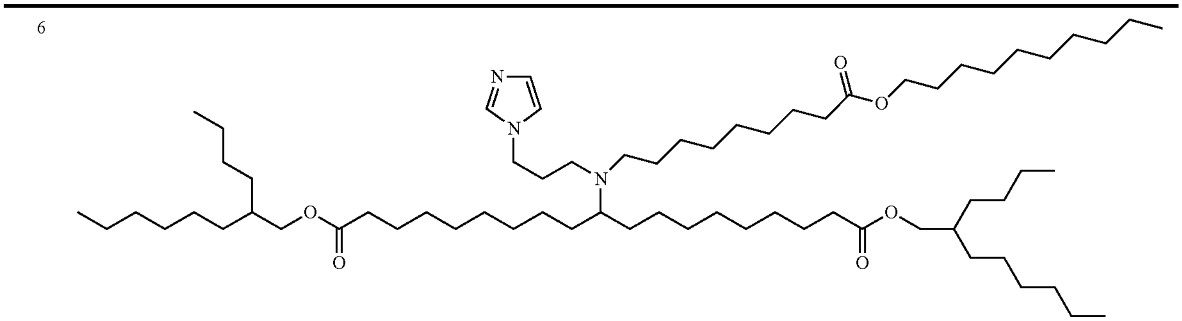 |
| 7 | 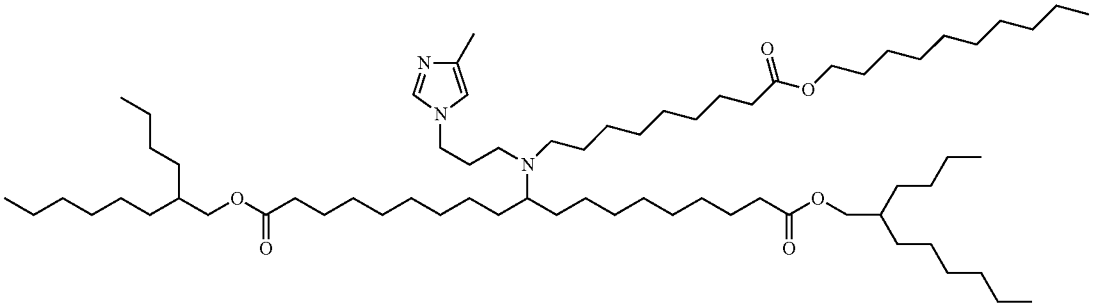 [SMILES: CCCCCCCCCCOC(=O)CCCCCCCCN(CCCn1cnc(C)c1)C(CCCCCCCCC(=O)OCC(CCCC)CCCCCC)CCCCCCCCC(=O)OCC(CCCC)CCCCCC] |
| 8 | 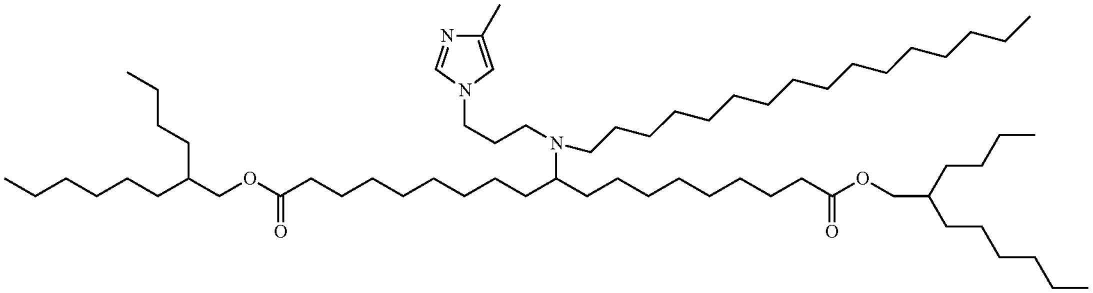 [SMILES: CCCCCCCCCCCCCCCCN(CCCn1cnc(C)c1)C(CCCCCCCCC(=O)OCC(CCCC)CCCCCC)CCCCCCCCC(=O)OCC(CCCC)CCCCCC] |
| 9 | 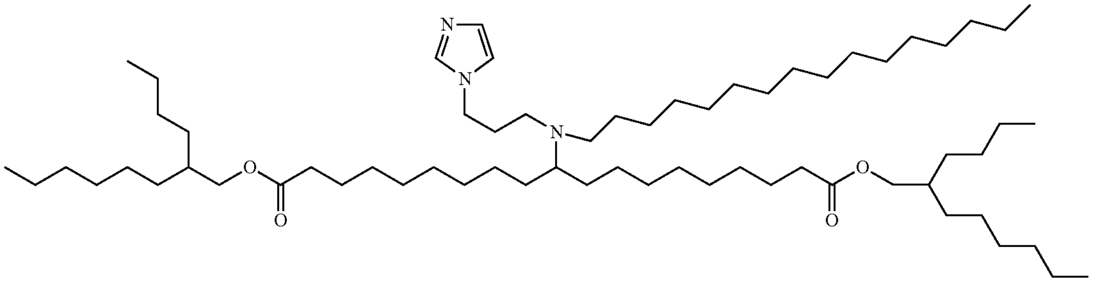 [SMILES: CCCCCCCCCCCCCCCCN(CCCn1ccnc1)C(CCCCCCCCC(=O)OCC(CCCC)CCCCCC)CCCCCCCCC(=O)OCC(CCCC)CCCCCC] |
| 10 | 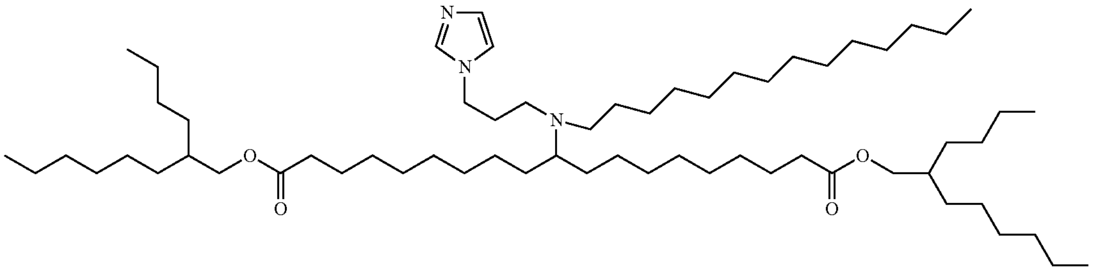 [SMILES: CCCCCCCCCCCCCCN(CCCn1ccnc1)C(CCCCCCCCC(=O)OCC(CCCC)CCCCCC)CCCCCCCCC(=O)OCC(CCCC)CCCCCC] |

TABLE 10a-continued
| Ionizable lipid number | Structure |
|---|---|
| 11 | 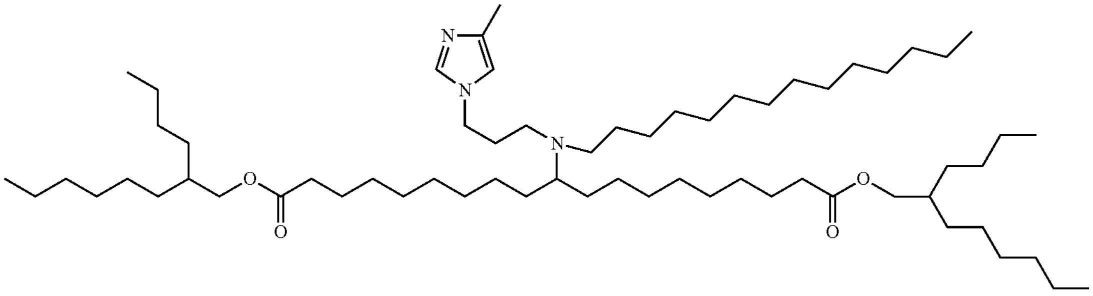 [SMILES: CCCCCCCCCCCCCCN(CCCn1cnc(C)c1)C(CCCCCCCCC(=O)OCC(CCCC)CCCCCC)CCCCCCCCC(=O)OCC(CCCC)CCCCCC] |
| 12 | 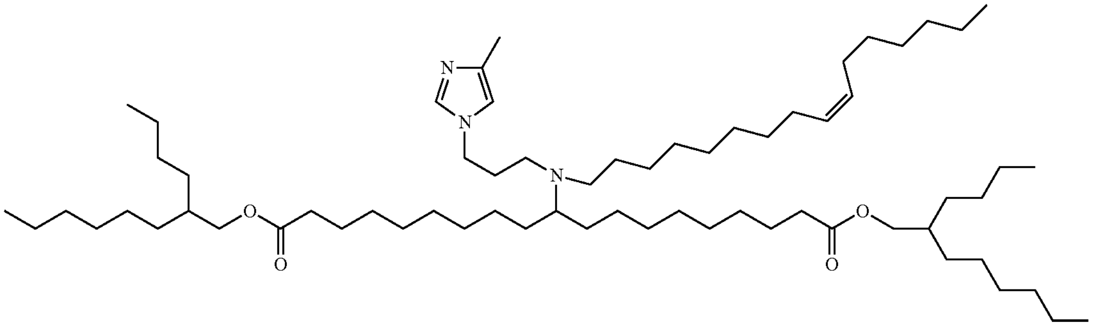 [SMILES: CCCCCC/C=C\CCCCCCCCN(CCCn1cnc(C)c1)C(CCCCCCCCC(=O)OCC(CCCC)CCCCCC)CCCCCCCCC(=O)OCC(CCCC)CCCCCC] |
| 13 | 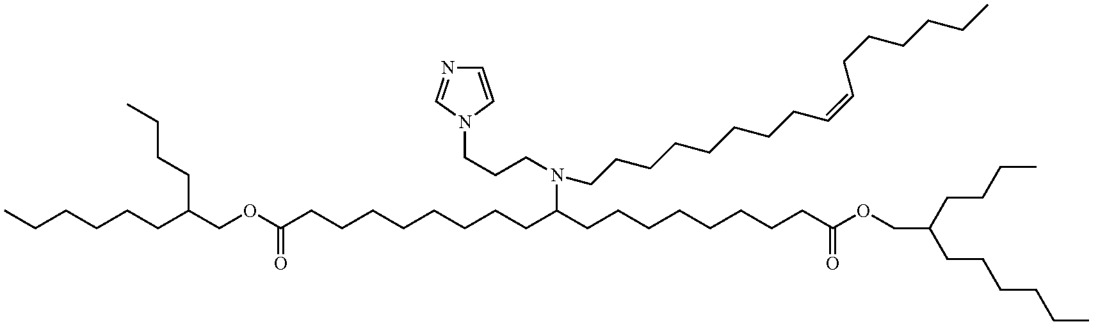 [SMILES: CCCCCC/C=C\CCCCCCCCN(CCCn1ccnc1)C(CCCCCCCCC(=O)OCC(CCCC)CCCCCC)CCCCCCCCC(=O)OCC(CCCC)CCCCCC] |
| 14 | 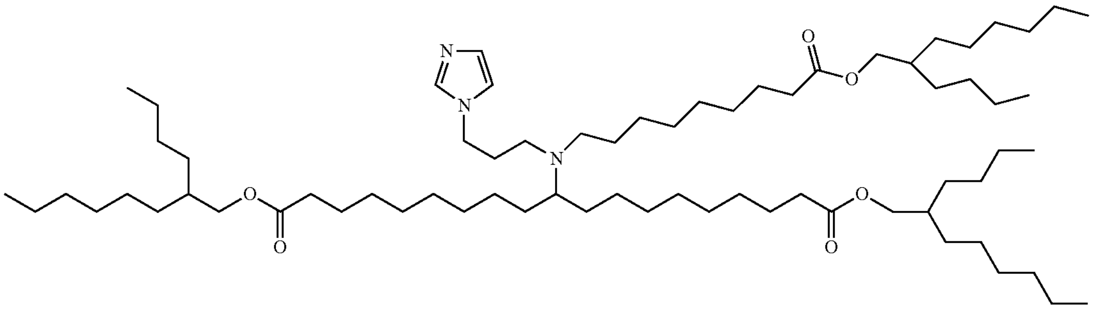 [SMILES: CCCCCCC(CCCC)COC(=O)CCCCCCCCC(CCCCCCCCC(=O)OCC(CCCC)CCCCCC)N(CCCCCCCCC(=O)OCC(CCCC)CCCCCC)CCCn1ccnc1] |

TABLE 10a-continued
| Ionizable lipid number | Structure |
|---|---|
| 15 | 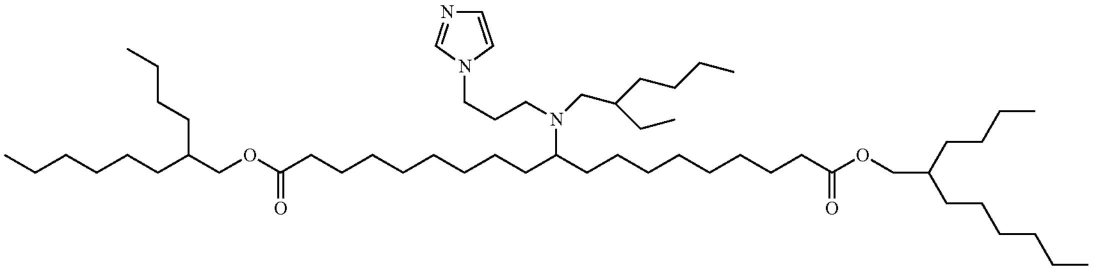 [SMILES: CCCCCCC(CCCC)COC(=O)CCCCCCCCC(CCCCCCCCC(=O)OCC(CCCC)CCCCCC)N(CCCn1ccnc1)CC(CC)CCCC] |
| 16 | 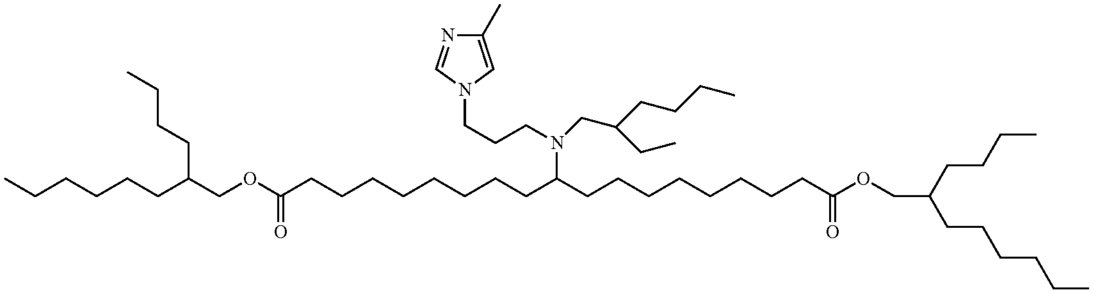 [SMILES: CCCCCCC(CCCC)COC(=O)CCCCCCCCC(CCCCCCCCC(=O)OCC(CCCC)CCCCCC)N(CCCn1cnc(C)c1)CC(CC)CCCC] |
| 17 | 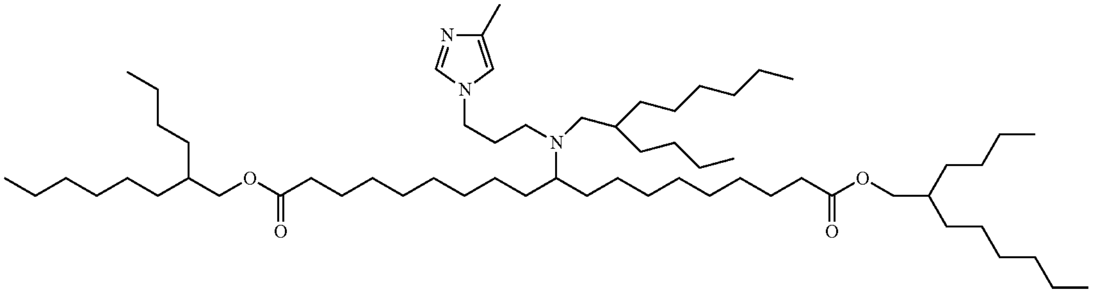 [SMILES: CCCCCCC(CCCC)COC(=O)CCCCCCCCC(CCCCCCCCC(=O)OCC(CCCC)CCCCCC)N(CCCn1cnc(C)c1)CC(CCCC)CCCCCC] |
| 18 | 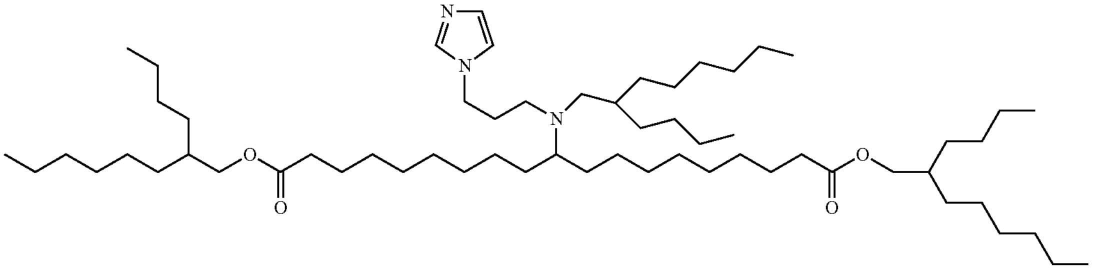 [SMILES: CCCCCCC(CCCC)COC(=O)CCCCCCCCC(CCCCCCCCC(=O)OCC(CCCC)CCCCCC)N(CCCn1ccnc1)CC(CCCC)CCCCCC] |
| 19 | 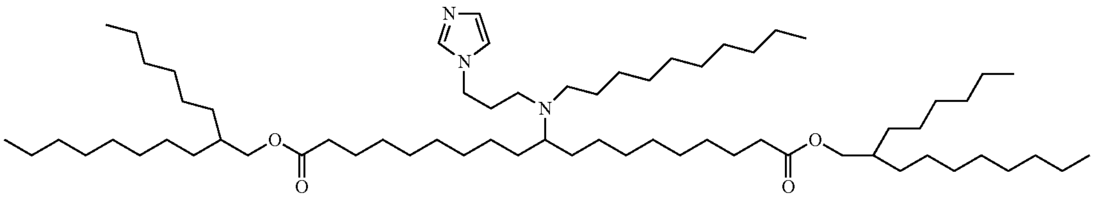 [SMILES: CCCCCCCCCCN(CCCn1ccnc1)C(CCCCCCCCC(=O)OCC(CCCCCC)CCCCCCCC)CCCCCCCCC(=O)OCC(CCCCCC)CCCCCCCC] |

TABLE 10a-continued
| Ionizable lipid number | Structure |
|---|---|
| 20 | 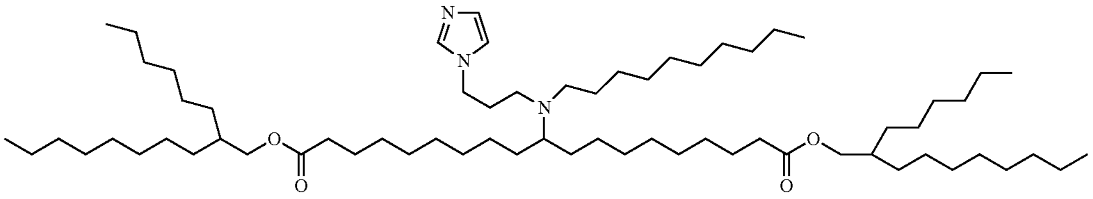 [SMILES: CCCCCCCCCCN(CCCn1ccnc1)C(CCCCCCCCC(=O)OCC(CCCCCC)CCCCCCCC)CCCCCCCCC(=O)OCC(CCCCCC)CCCCCCCC] |
| 21 | 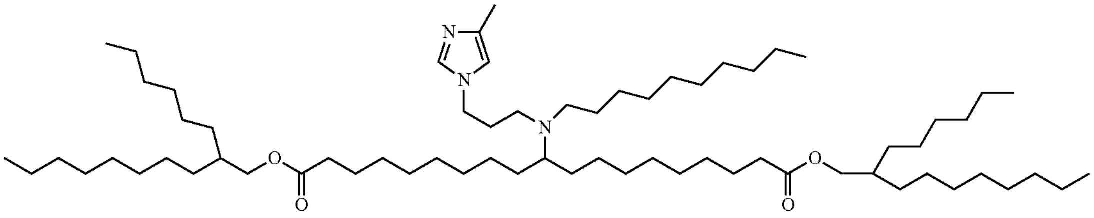 |
| 22 | 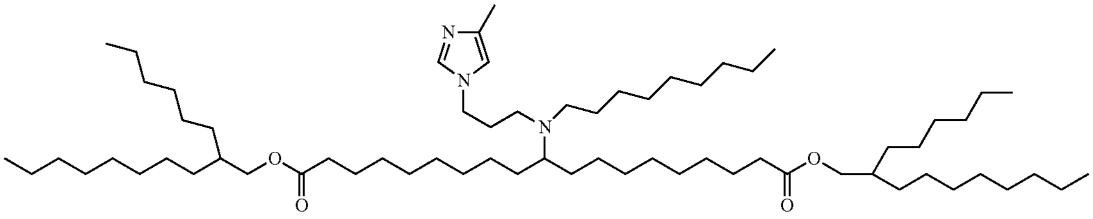 [SMILES: CCCCCCCCCN(CCCn1cnc(C)c1)C(CCCCCCCCC(=O)OCC(CCCCCC)CCCCCCCC)CCCCCCCCC(=O)OCC(CCCCCC)CCCCCCCC] |
| 23 | 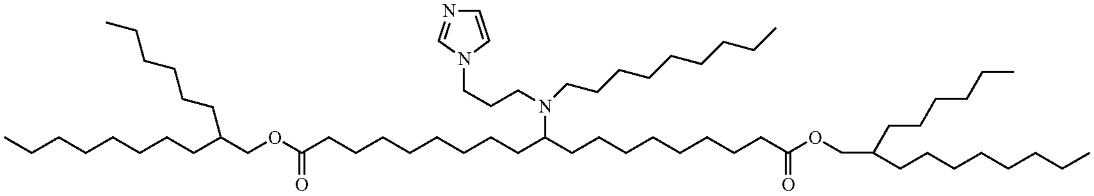 [SMILES: CCCCCCCCCN(CCCn1ccnc1)C(CCCCCCCCC(=O)OCC(CCCCCC)CCCCCCCC)CCCCCCCCC(=O)OCC(CCCCCC)CCCCCCCC] |
| 24 | 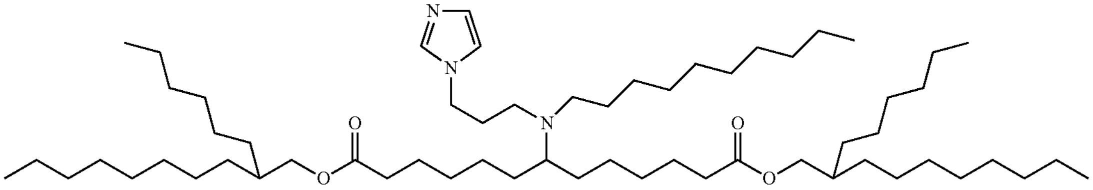 [SMILES: CCCCCCCCCCN(CCCn1ccnc1)C(CCCCCC(=O)OCC(CCCCCC)CCCCCCCC)CCCCCC(=O)OCC(CCCCCC)CCCCCCCC] |
| 25 | 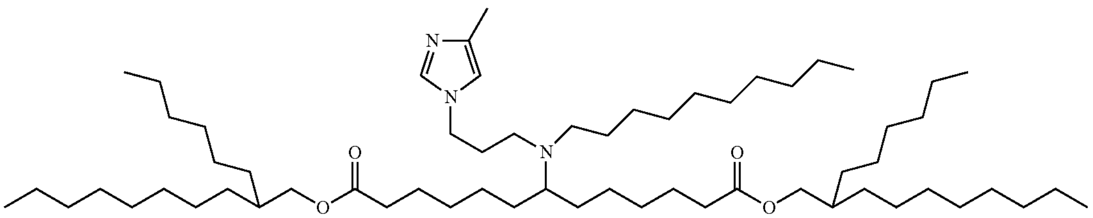 [SMILES: CCCCCCCCCCN(CCCn1cnc(C)c1)C(CCCCCC(=O)OCC(CCCCCC)CCCCCCCC)CCCCCC(=O)OCC(CCCCCC)CCCCCCCC] |

TABLE 10a-continued
| Ionizable lipid number | Structure |
|---|---|
| 26 | 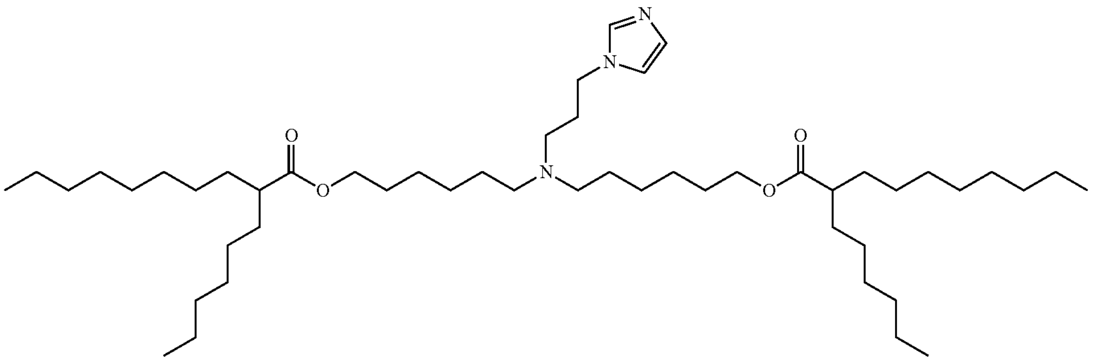 [SMILES: CCCCCCCCC(CCCCCC)C(=O)OCCCCCCN(CCCCCCOC(=O)C(CCCCCC)CCCCCCCC)CCCn1ccnc1] |
| 27 | 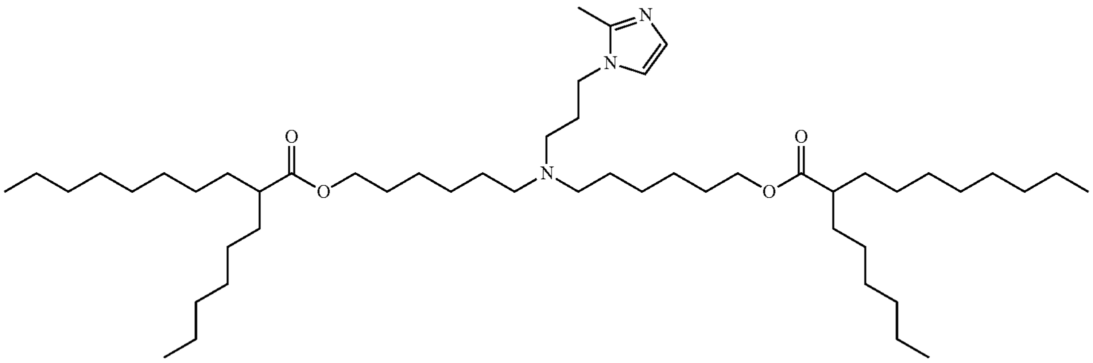 [SMILES: CCCCCCCCC(CCCCCC)C(=O)OCCCCCCN(CCCCCCOC(=O)C(CCCCCC)CCCCCCCC)CCCn1ccnc1C] |
| 28 | 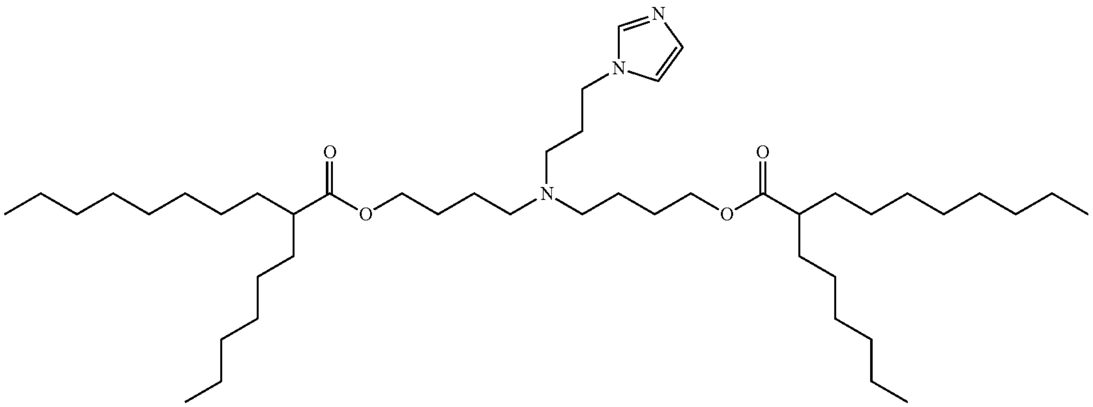 [SMILES: CCCCCCCCC(CCCCCC)C(=O)OCCCCN(CCCCOC(=O)C(CCCCCC)CCCCCCCC)CCCn1ccnc1] |

TABLE 10a-continued
| Ionizable lipid number | Structure |
| --- | --- |
| 29 | 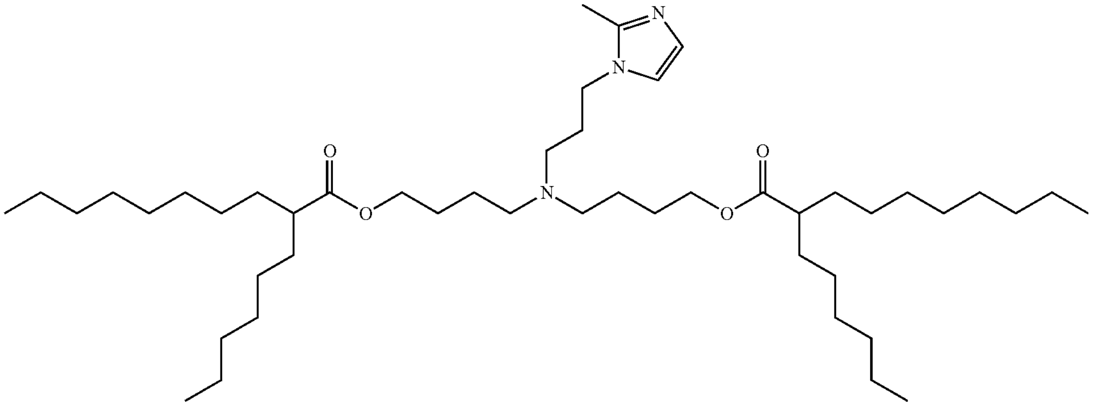 [SMILES: CCCCCCCCC(CCCCCC)C(=O)OCCCCN(CCCCOC(=O)C(CCCCCC)CCCCCCCC)CCCn1ccnc1C] |
| 30 | 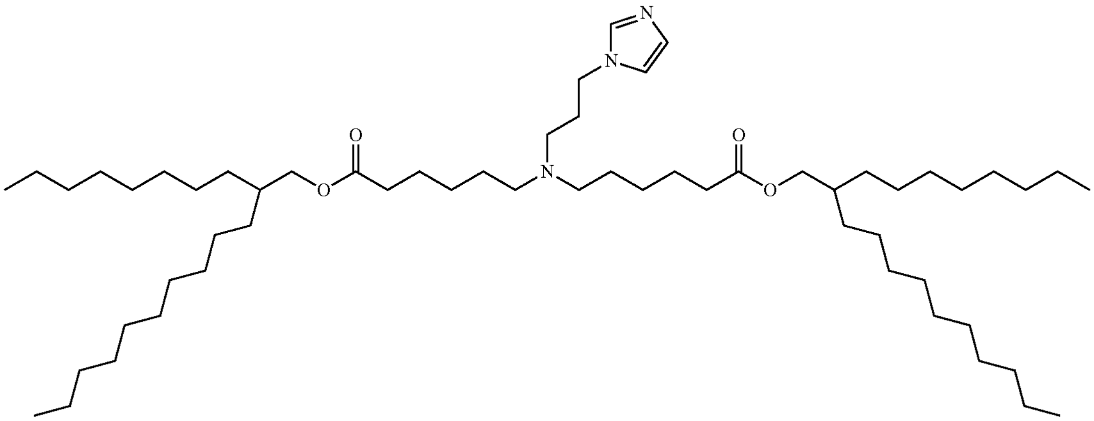 [SMILES: CCCCCCCCCCC(CCCCCCCC)COC(=O)CCCCCN(CCCCCC(=O)OCC(CCCCCCCC)CCCCCCCCCC)CCCn1ccnc1] |
| 31 | 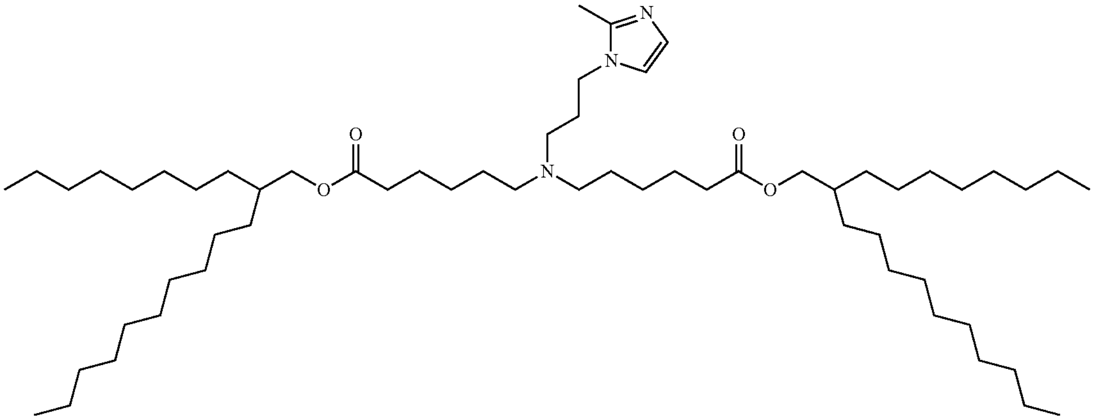 [SMILES: CCCCCCCCCCC(CCCCCCCC)COC(=O)CCCCCN(CCCCCC(=O)OCC(CCCCCCCC)CCCCCCCCCC)CCCn1ccnc1C] |

TABLE 10a-continued
| Ionizable lipid number | Structure |
|---|---|
| 32 | 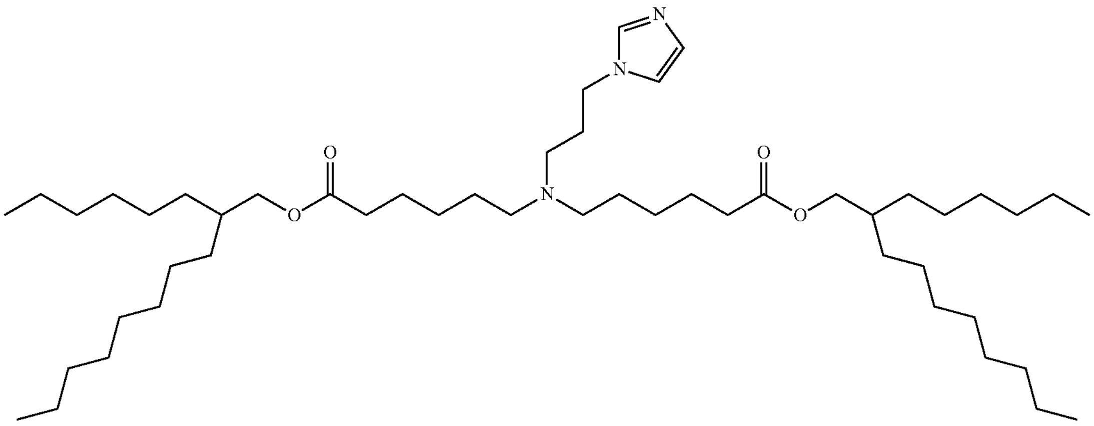 [SMILES: CCCCCCCCC(CCCCCC)COC(=O)CCCCCN(CCCCCC(=O)OCC(CCCCCC)CCCCCCCC)CCCn1ccnc1] |
| 33 | 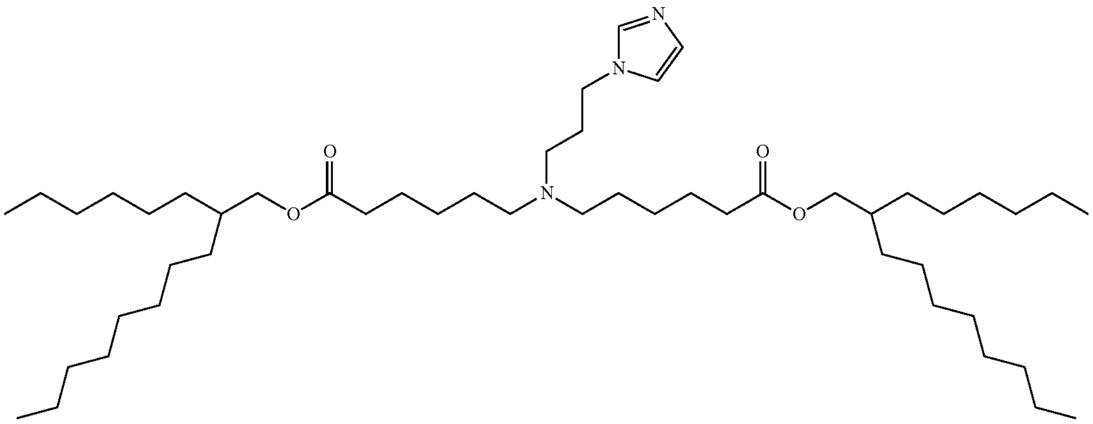 [SMILES: CCCCCCCCC(CCCCCC)COC(=O)CCCCCN(CCCCCC(=O)OCC(CCCCCC)CCCCCCCC)CCCn1ccnc1] |
| 34 | 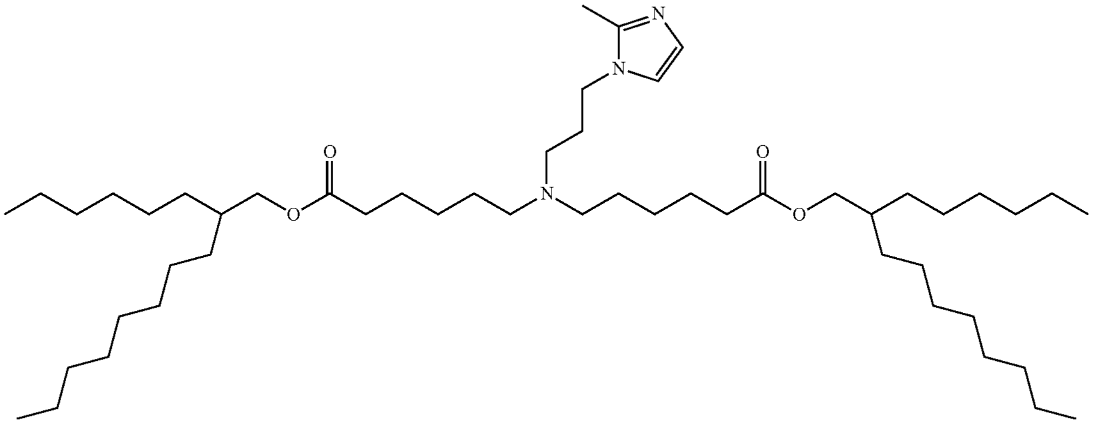 [SMILES: CCCCCCCCC(CCCCCC)COC(=O)CCCCCN(CCCCCC(=O)OCC(CCCCCC)CCCCCCCC)CCCn1ccnc1C] |

TABLE 10a-continued
| Ionizable lipid number | Structure |
| --- | --- |
| 35 | 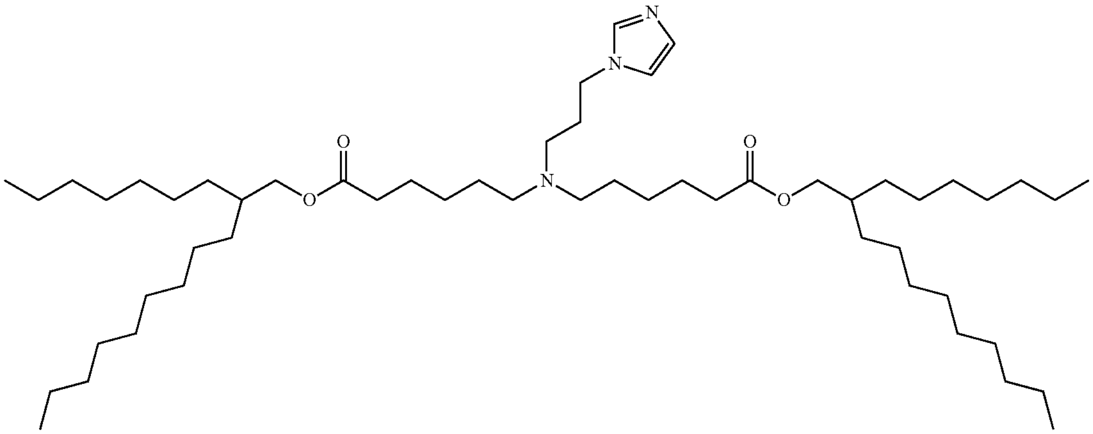 [SMILES: CCCCCCCCCC(CCCCCCC)COC(=O)CCCCCN(CCCCCC(=O)OCC(CCCCCCC)CCCCCCCCC)CCCn1ccnc1] |
| 36 | 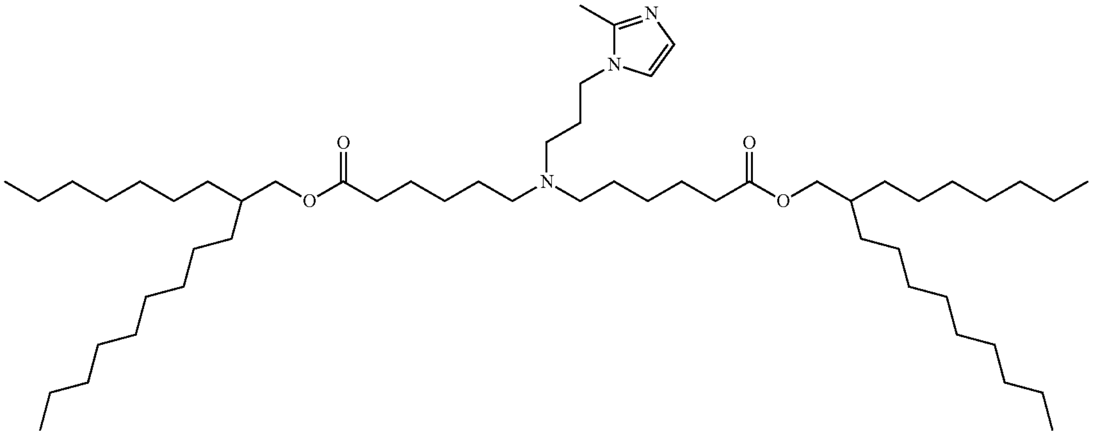 [SMILES: CCCCCCCCCC(CCCCCCC)COC(=O)CCCCCN(CCCCCC(=O)OCC(CCCCCCC)CCCCCCCCC)CCCn1ccnc1C] |
| 37 | 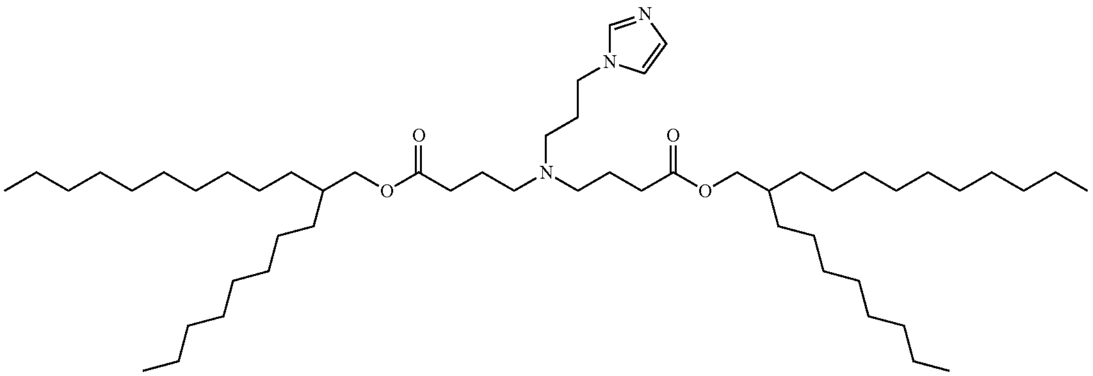 [SMILES: CCCCCCCCCCC(CCCCCCCC)COC(=O)CCCN(CCCC(=O)OCC(CCCCCCCC)CCCCCCCCCC)CCCn1ccnc1] |

TABLE 10a-continued
| Ionizable lipid number | Structure |
|---|---|
| 38 | 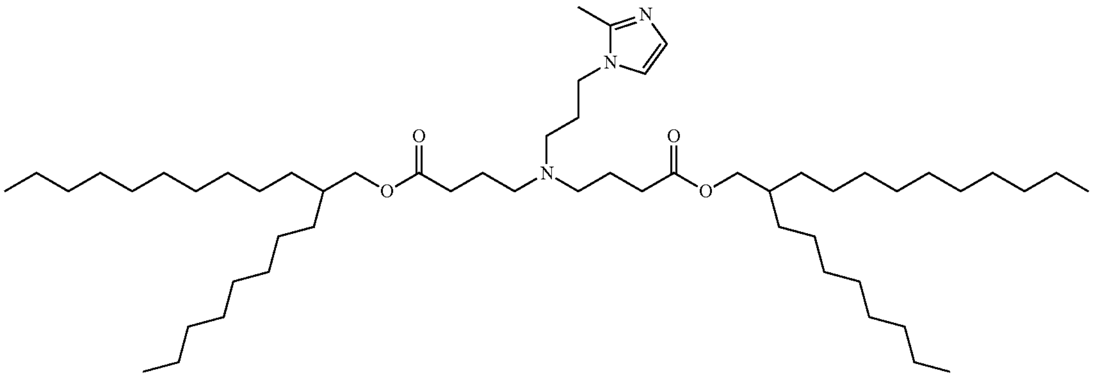 [SMILES: CCCCCCCCCCC(CCCCCCCC)COC(=O)CCCN(CCCC(=O)OCC(CCCCCCCC)CCCCCCCCCC)CCCn1ccnc1C] |
| 39 | 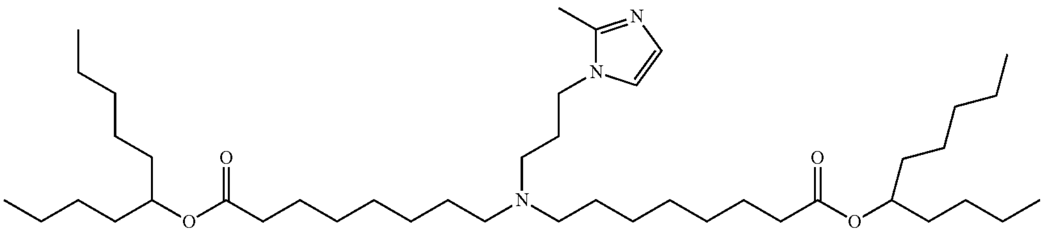 [SMILES: CCCCCC(CCCC)OC(=O)CCCCCCCN(CCCCCCCC(=O)OC(CCCC)CCCCC)CCCn1ccnc1C] |
| 40 | 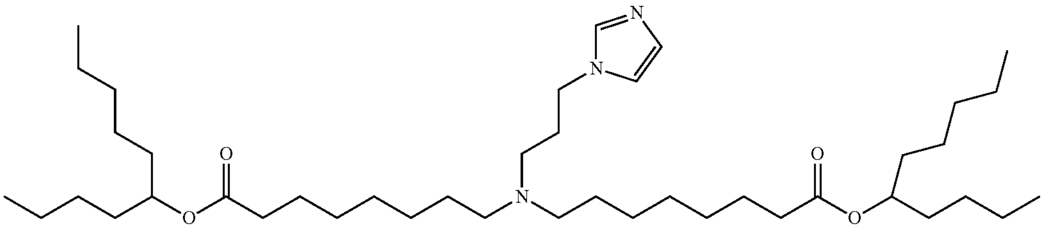 [SMILES: CCCCCC(CCCC)OC(=O)CCCCCCCN(CCCCCCCC(=O)OC(CCCC)CCCCC)CCCn1ccnc1] |
| 41 | 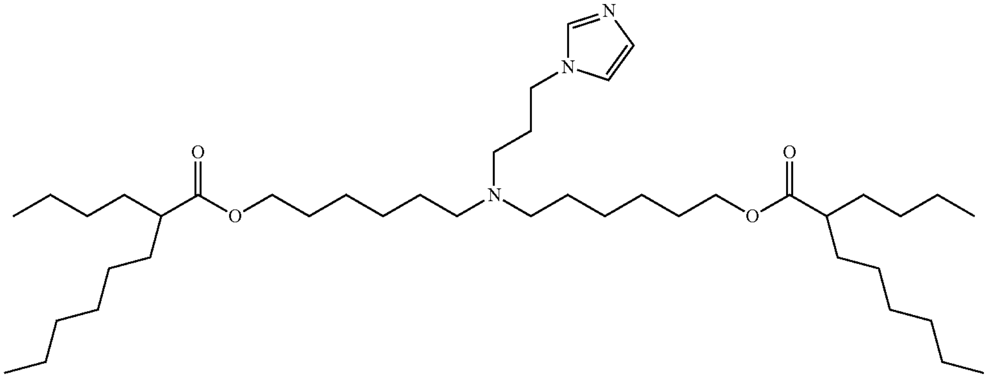 [SMILES: CCCCCCC(CCCC)C(=O)OCCCCCCN(CCCCCCOC(=O)C(CCCC)CCCCCC)CCCn1ccnc1] |

TABLE 10a-continued
| Ionizable lipid number | Structure |
| --- | --- |
| 42 | 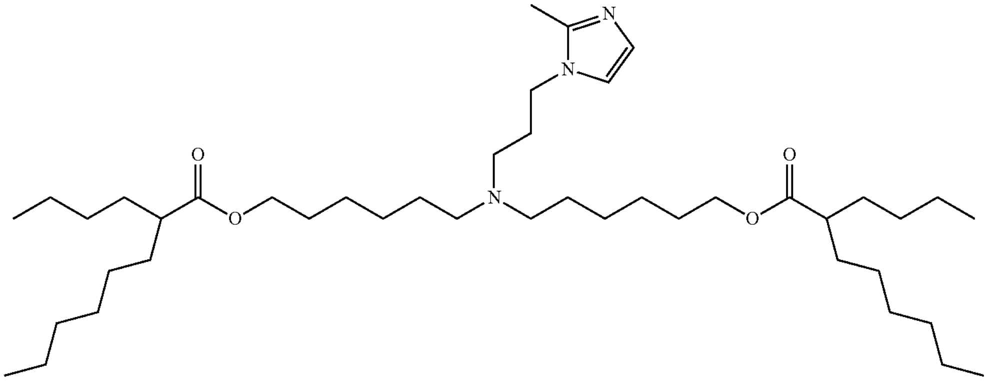 [SMILES: CCCCCCC(CCCC)C(=O)OCCCCCCN(CCCCCCOC(=O)C(CCCC)CCCCCC)CCCn1ccnc1C] |
| 43 | 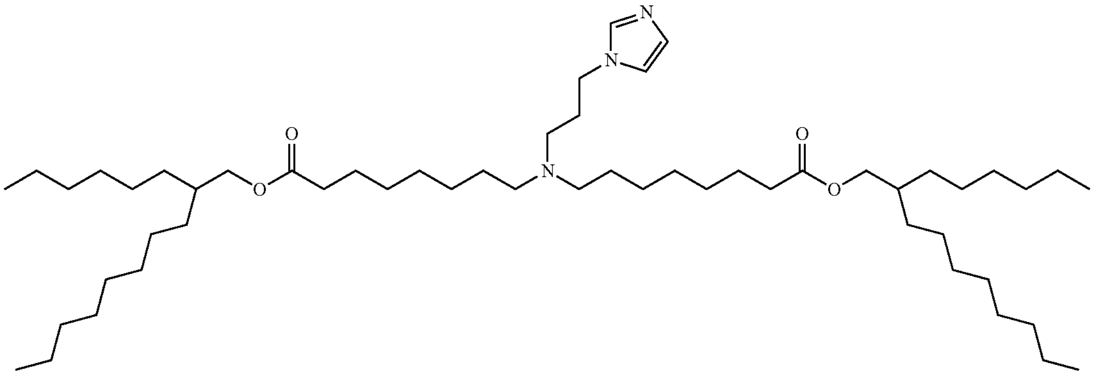 [SMILES: CCCCCCCCC(CCCCCC)COC(=O)CCCCCCCN(CCCCCCCC(=O)OCC(CCCCCC)CCCCCCCC)CCCn1ccnc1] |
| 44 | 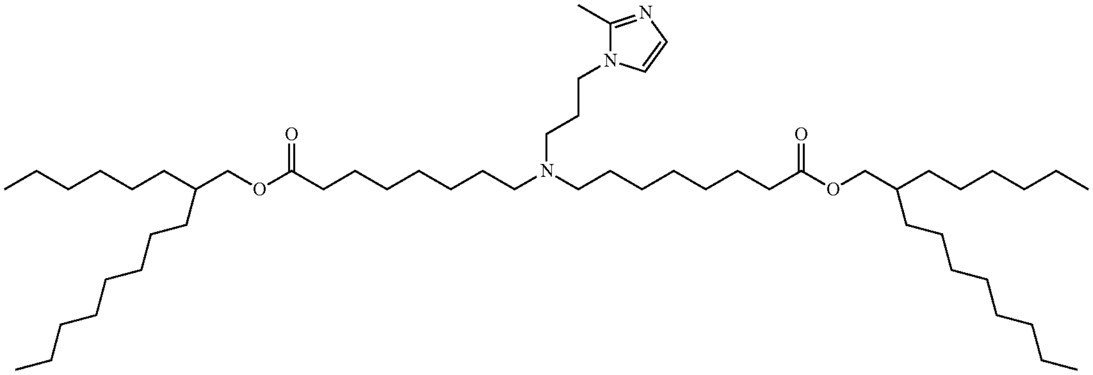 [SMILES: CCCCCCCCC(CCCCCC)COC(=O)CCCCCCCN(CCCCCCCC(=O)OCC(CCCCCC)CCCCCCCC)CCCn1ccnc1C] |
| 45 | 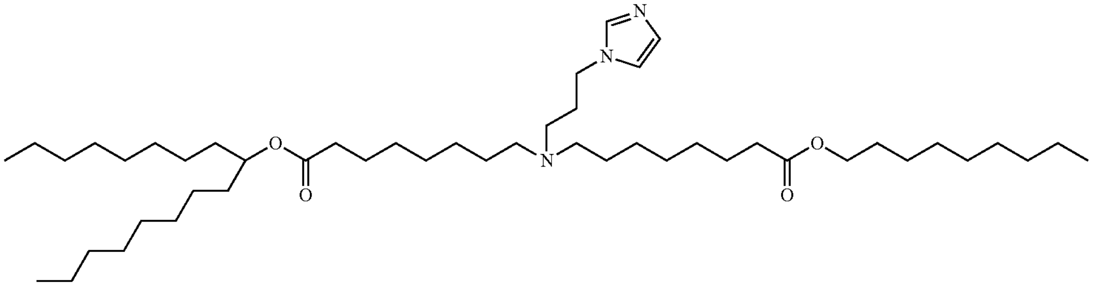 |

TABLE 10a-continued
| Ionizable lipid number | Structure |
|---|---|
| 46 | 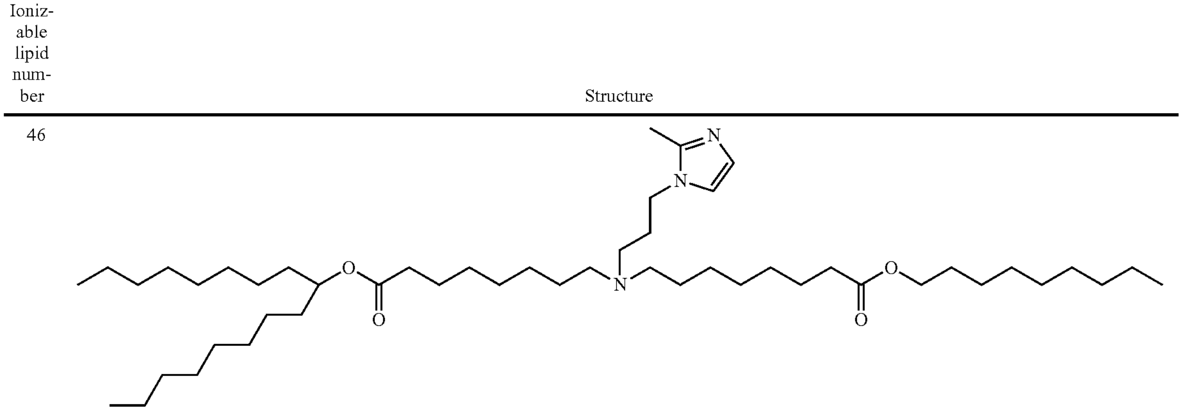 |
| 47 | 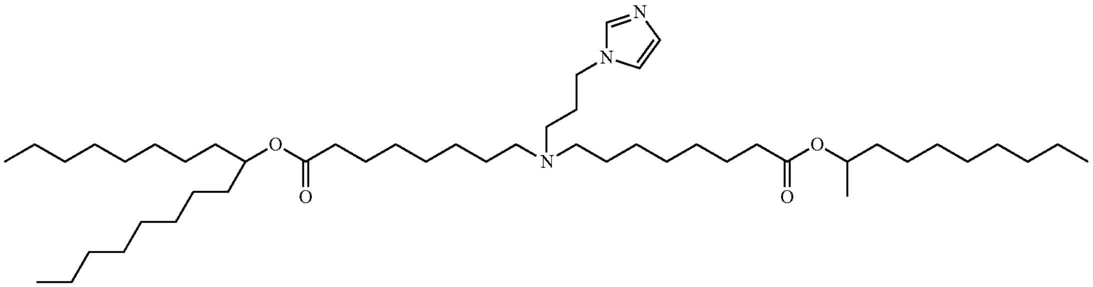 [SMILES: CCCCCCCCC(C)OC(=O)CCCCCCCN(CCCCCCCC(=O)OC(CCCCCCCC)CCCCCCCC)CCCn1ccnc1] |
| 48 | 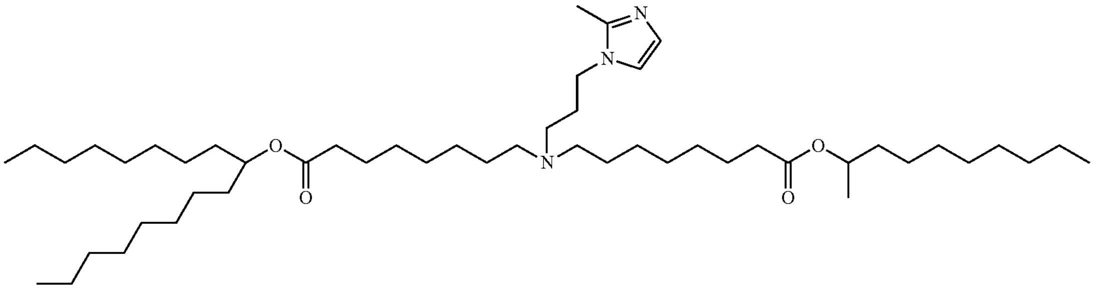 [SMILES: CCCCCCCCC(C)OC(=O)CCCCCCCN(CCCCCCCC(=O)OC(CCCCCCCC)CCCCCCCC)CCCn1ccnc1C] |
| 49 | 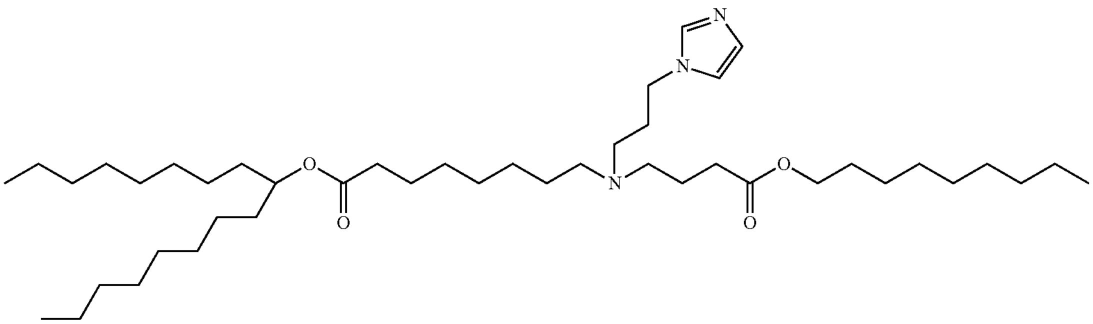 [SMILES: CCCCCCCCCOC(=O)CCCN(CCCCCCCC(=O)OC(CCCCCCCC)CCCCCCCC)CCCn1ccnc1] |
| 50 | 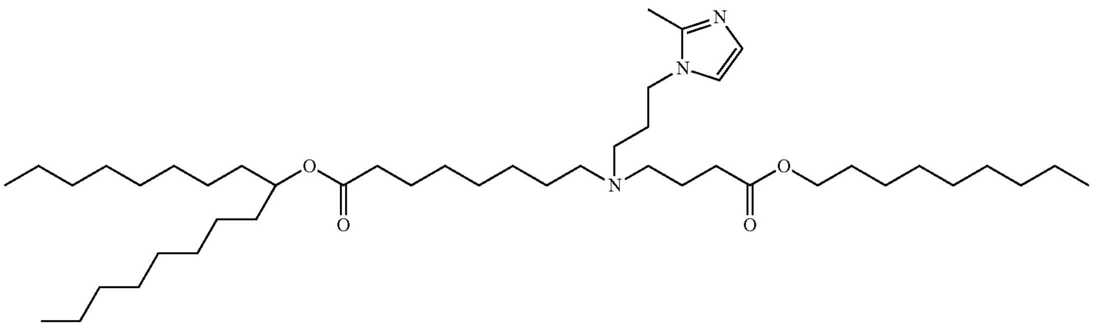 [SMILES: CCCCCCCCCOC(=O)CCCN(CCCCCCCC(=O)OC(CCCCCCCC)CCCCCCCC)CCCn1ccnc1C] |

TABLE 10a-continued
| Ionizable lipid number | Structure |
| --- | --- |
| 51 | 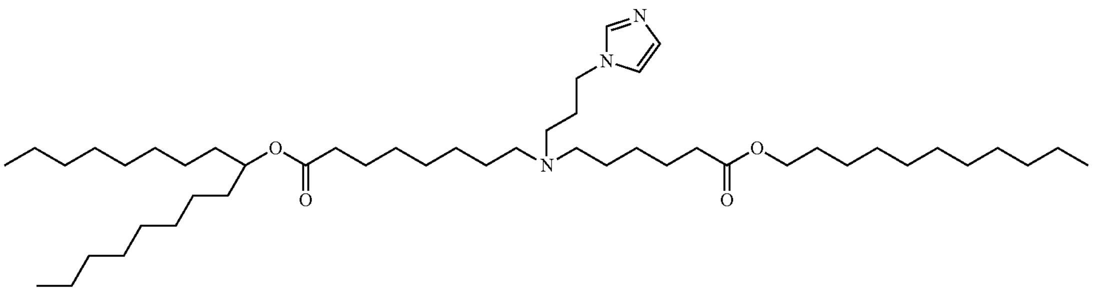 [SMILES: CCCCCCCCCCCOC(=O)CCCCCN(CCCCCCCC(=O)OC(CCCCCCCC)CCCCCCCC)CCCn1ccnc1] |
| 52 | 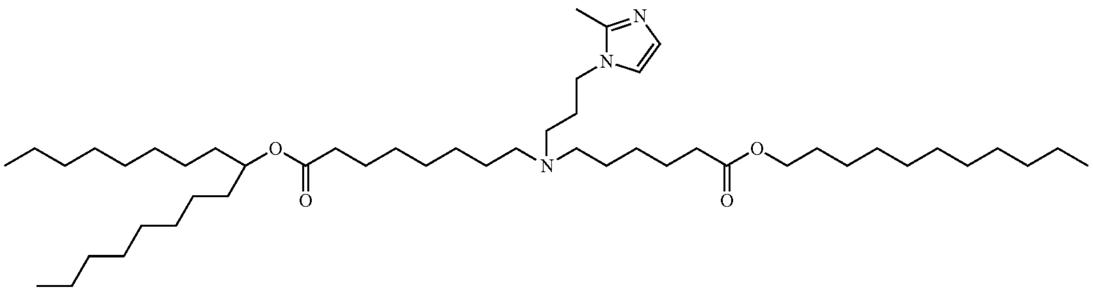 [SMILES: CCCCCCCCCCCOC(=O)CCCCCN(CCCCCCCC(=O)OC(CCCCCCCC)CCCCCCCC)CCCn1ccnc1C] |
| 53 | 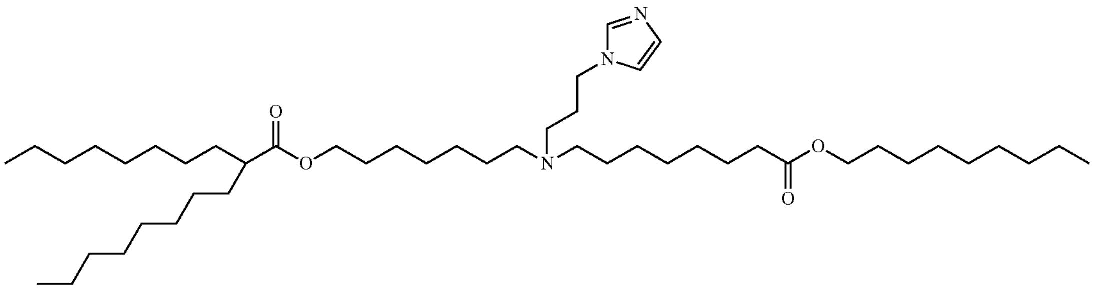 [SMILES: CCCCCCCCCOC(=O)CCCCCCCN(CCCCCCCOC(=O)C(CCCCCCCC)CCCCCCCC)CCCn1ccnc1] |
| 54 | 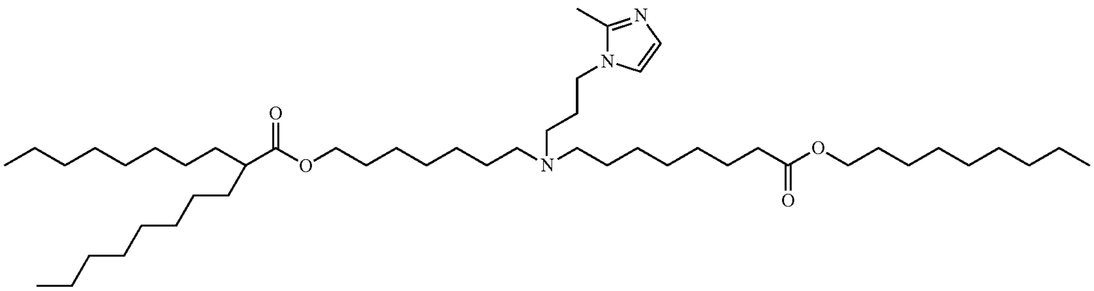 [SMILES: CCCCCCCCCOC(=O)CCCCCCCN(CCCCCCCOC(=O)C(CCCCCCCC)CCCCCCCC)CCCn1ccnc1C] |
| 55 | 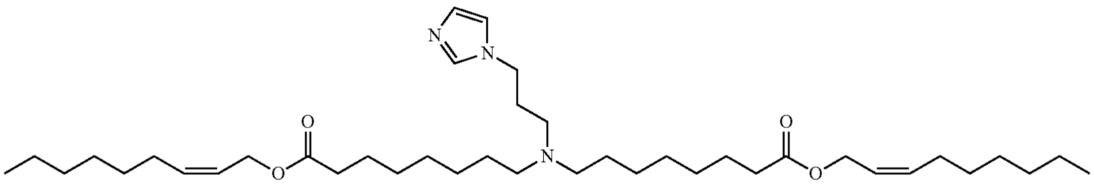 [SMILES: CCCCCC/C=C\COC(=O)CCCCCCCN(CCCCCCCC(=O)OC/C=C\CCCCCC)CCCn1ccnc1] |

TABLE 10a-continued
| Ionizable lipid number | Structure |
|---|---|
| 56 | 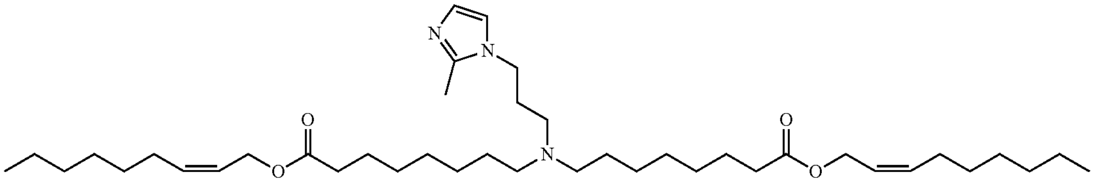 [SMILES: CCCCCC/C=C\COC(=O)CCCCCCCN(CCCCCCCC(=O)OC/C=C\CCCCCC)CCCn1ccnc1C] |
| 57 | 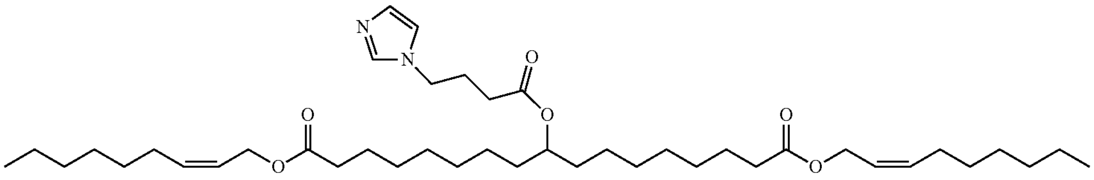 [SMILES: CCCCCC/C=C\COC(=O)CCCCCCCC(CCCCCCCC(=O)OC/C=C\CCCCCC)OC(=O)CCCn1ccnc1] |
| 58 | 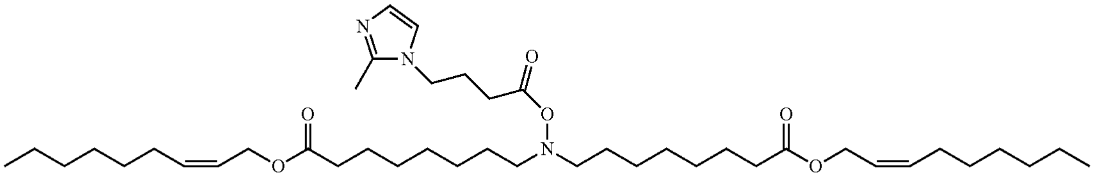 [SMILES: CCCCCC/C=C\COC(=O)CCCCCCCN(CCCCCCCC(=O)OC/C=C\CCCCCC)OC(=O)CCCn1ccnc1C] |
| 59 | 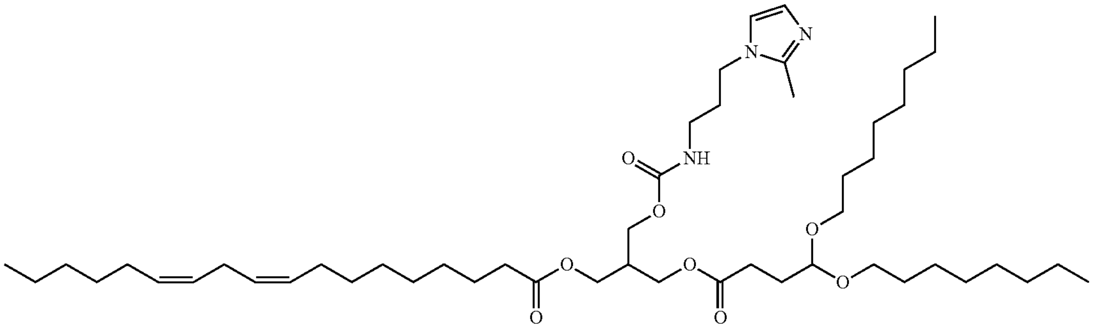 [SMILES: CCCCC/C=C\C/C=C\CCCCCCCC(=O)OCC(COC(=O)CCC(OCCCCCCCC)OCCCCCCCC)COC(=O)NCCCn1ccnc1C] |
| 60 | 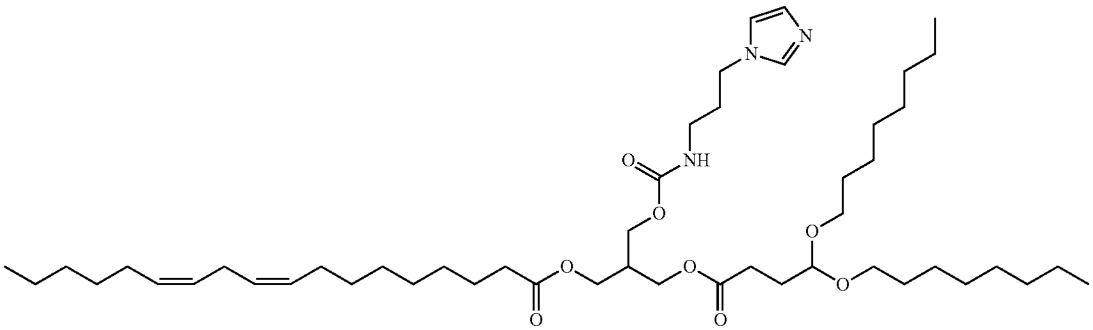 [SMILES: CCCCC/C=C\C/C=C\CCCCCCCC(=O)OCC(COC(=O)CCC(OCCCCCCCC)OCCCCCCCC)COC(=O)NCCCn1ccnc1] |

TABLE 10a-continued
| Ionizable lipid number | Structure |
|---|---|
| 61 | 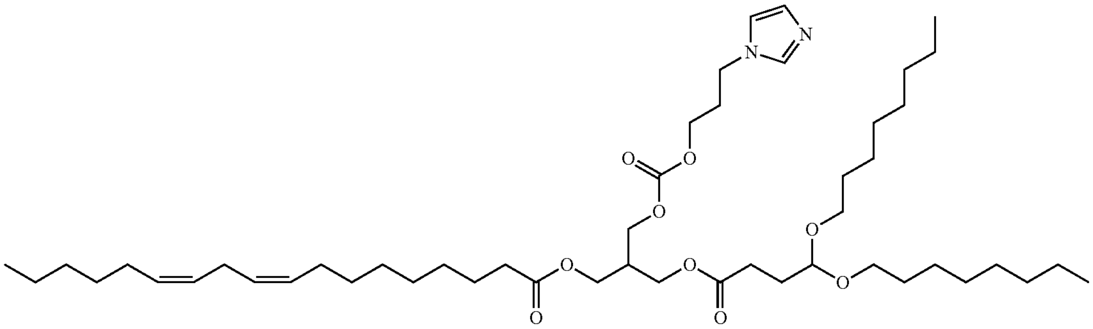 [SMILES: CCCCC/C=C\C/C=C\CCCCCCCC(=O)OCC(COC(=O)CCC(OCCCCCCCC)OCCCCCCCC)COC(=O)OCCCn1ccnc1] |
| 62 | 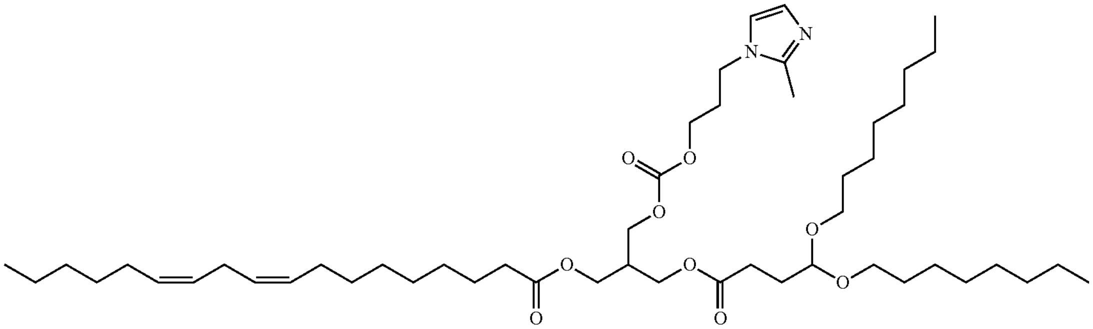 |
| 63 | 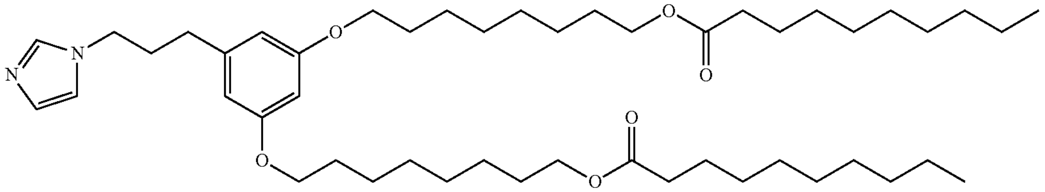 [SMILES: CCCCCCCCCC(=O)OCCCCCCCCOc1cc(CCCn2ccnc2)cc(OCCCCCCCCOC(=O)CCCCCCCCC)c1] |
| 64 | 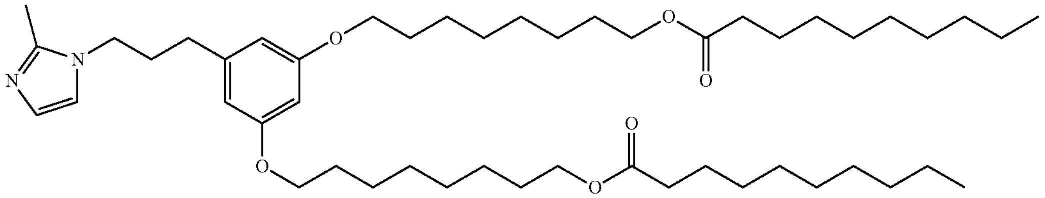 [SMILES: CCCCCCCCCC(=O)OCCCCCCCCOc1cc(CCCn2ccnc2C)cc(OCCCCCCCCOC(=O)CCCCCCCCC)c1] |
| 65 | 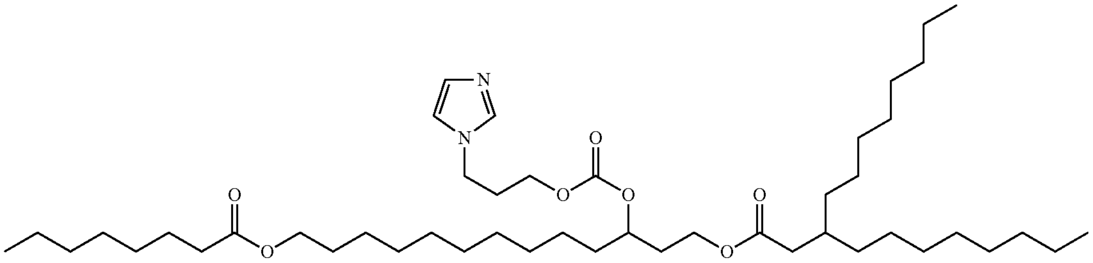 [SMILES: CCCCCCCCC(CCCCCCCC)CC(=O)OCCC(CCCCCCCCCCOC(=O)CCCCCCC)OC(=O)OCCCn1ccnc1] |

TABLE 10a-continued
| Ionizable lipid number | Structure |
|---|---|
| 66 | 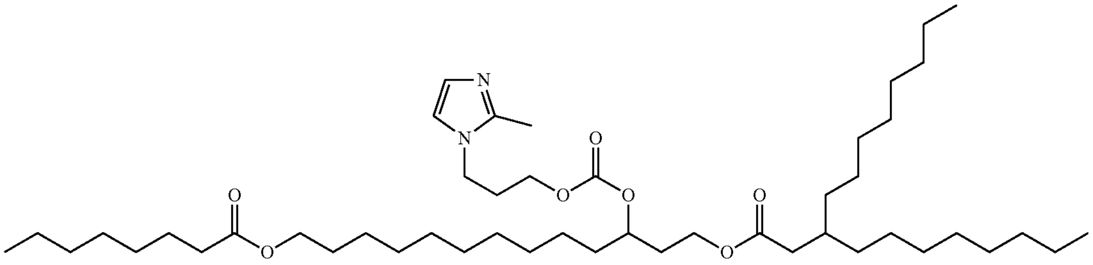 [SMILES: CCCCCCCCC(CCCCCCCC)CC(=O)OCCC(CCCCCCCCCCOC(=O)CCCCCCC)OC(=O)OCCCn1ccnc1C] |
| 67 | 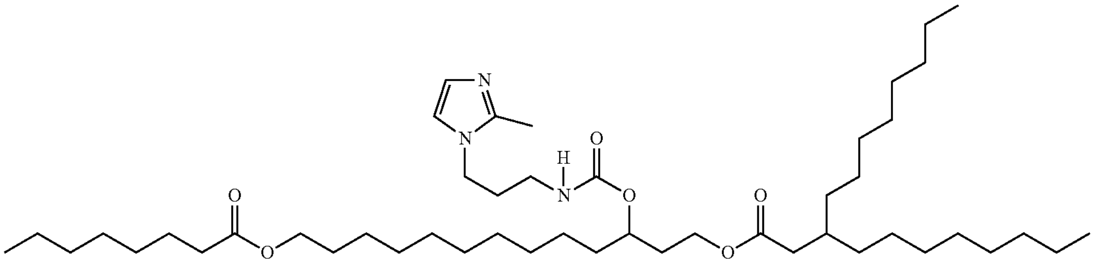 [SMILES: CCCCCCCCC(CCCCCCCC)CC(=O)OCCC(CCCCCCCCCCOC(=O)CCCCCCC)OC(=O)NCCCn1ccnc1C] |
| 68 | 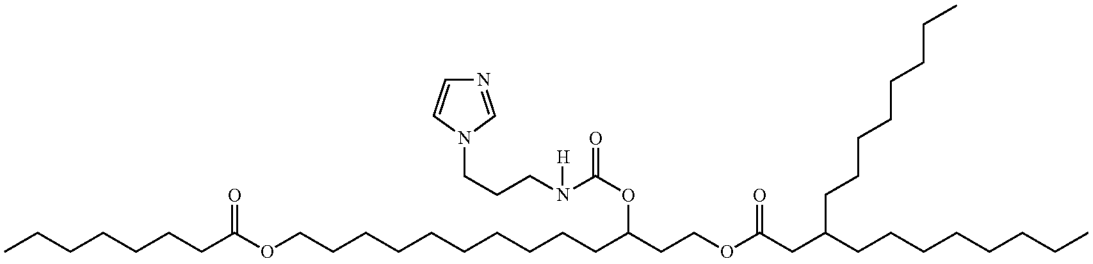 [SMILES: CCCCCCCCC(CCCCCCCC)CC(=O)OCCC(CCCCCCCCCCOC(=O)CCCCCCC)OC(=O)NCCCn1ccnc1] |
| 69 | 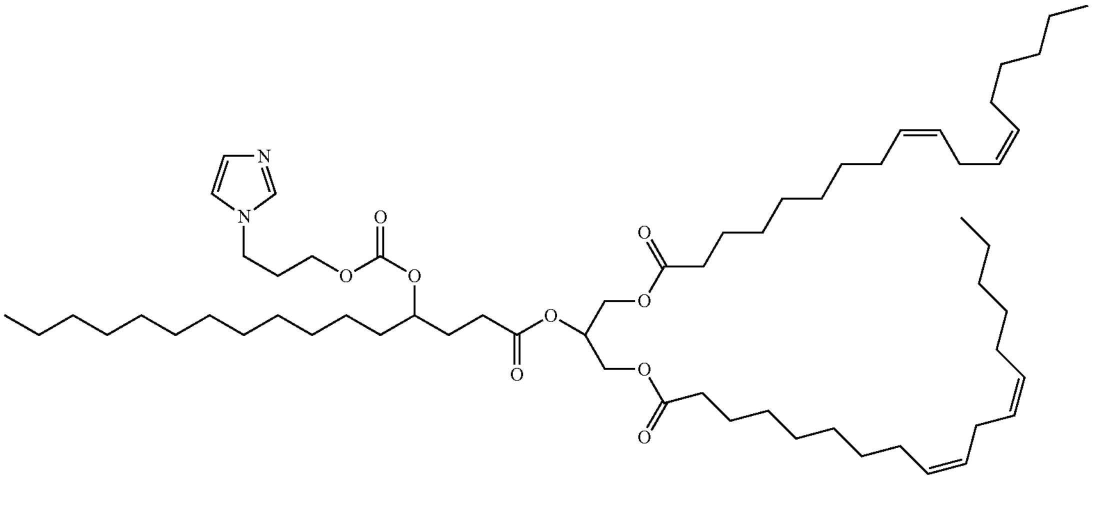 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCn1ccnc1] |

TABLE 10a-continued
| Ionizable lipid number | Structure |
| --- | --- |
| 70 | 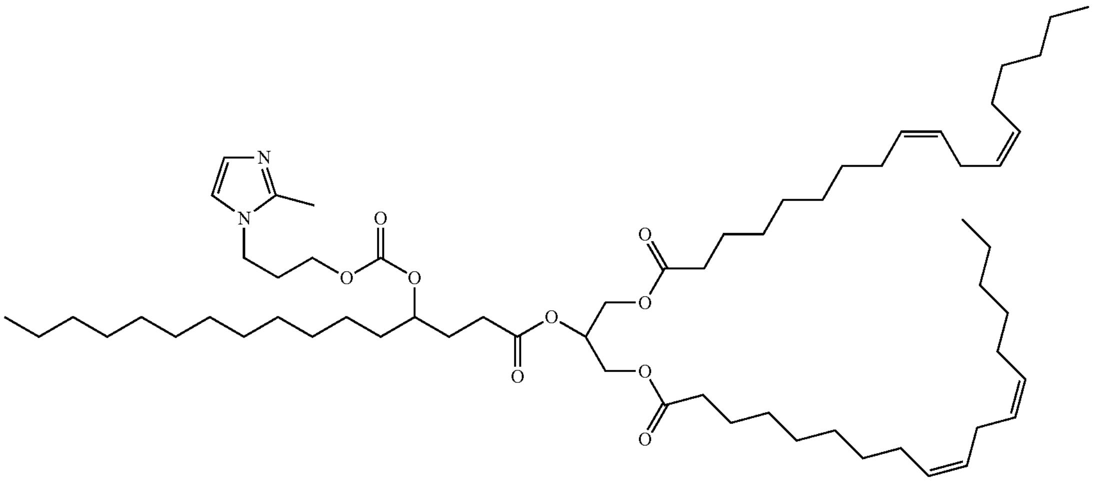 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCn1ccnc1C] |
| 71 | 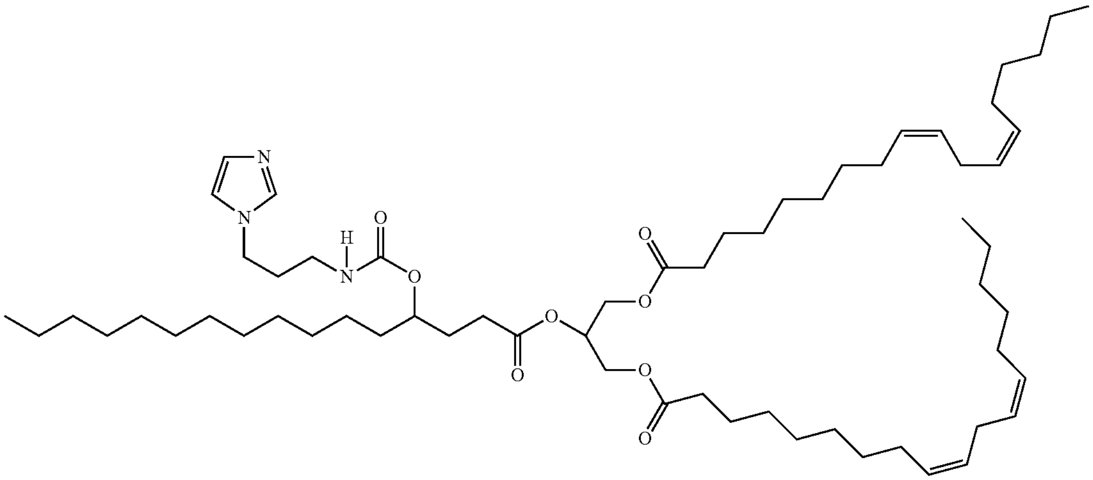 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCn1ccnc1] |
| 72 | 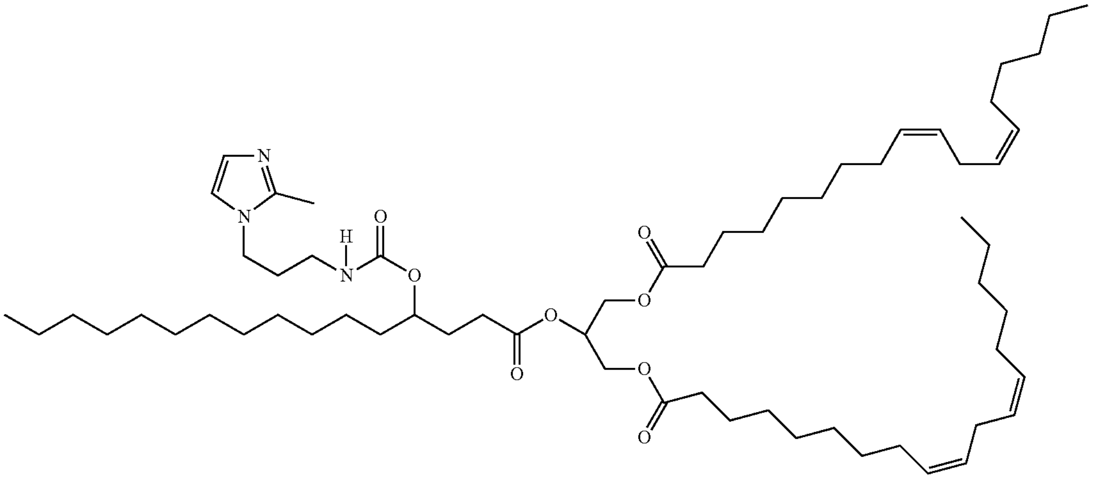 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCn1ccnc1C] |

TABLE 10a-continued
| Ionizable lipid number | Structure |
|---|---|
| 73 | 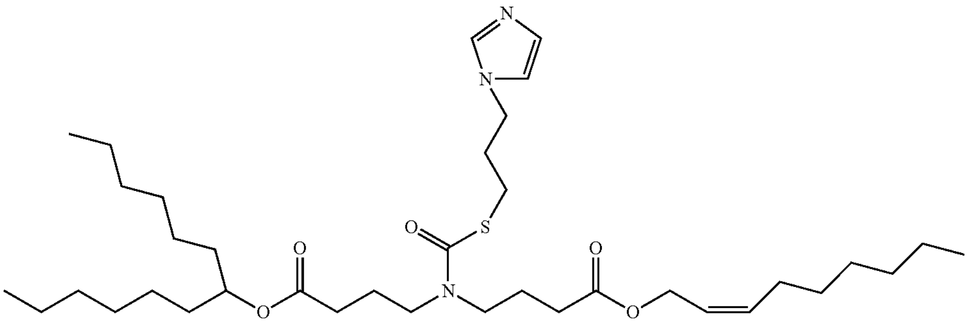 [SMILES: CCCCCC/C=C\COC(=O)CCCN(CCCC(=O)OC(CCCCCC)CCCCCC)C(=O)SCCCn1ccnc1] |
| 74 | 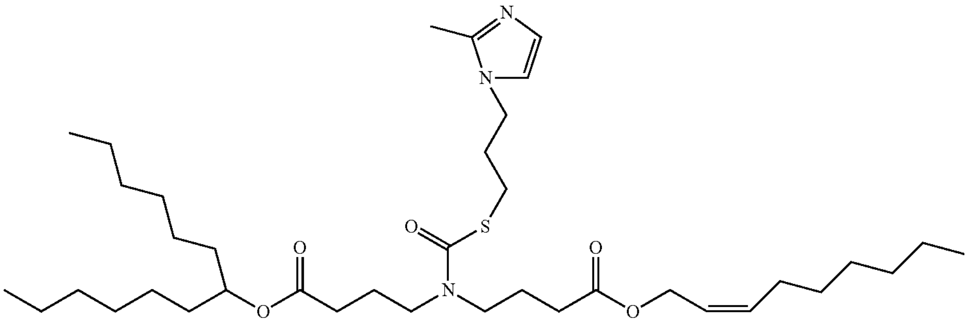 [SMILES: CCCCCC/C=C\COC(=O)CCCN(CCCC(=O)OC(CCCCCC)CCCCCC)C(=O)SCCCn1ccnc1C] |
| 75 | 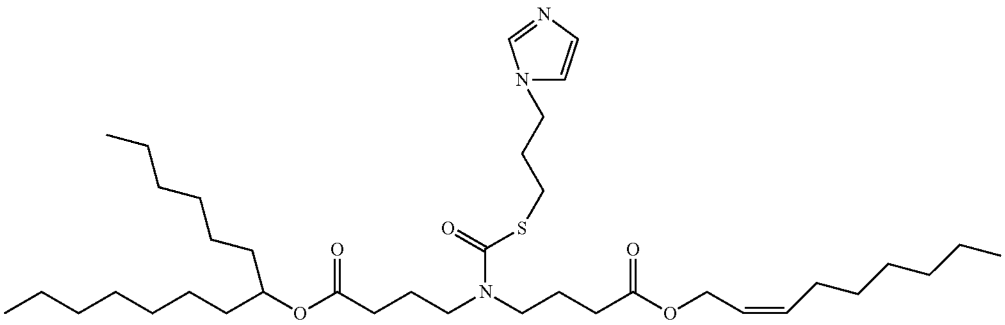 [SMILES: CCCCCC/C=C\COC(=O)CCCN(CCCC(=O)OC(CCCCCC)CCCCCCC)C(=O)SCCCn1ccnc1] |
| 76 | 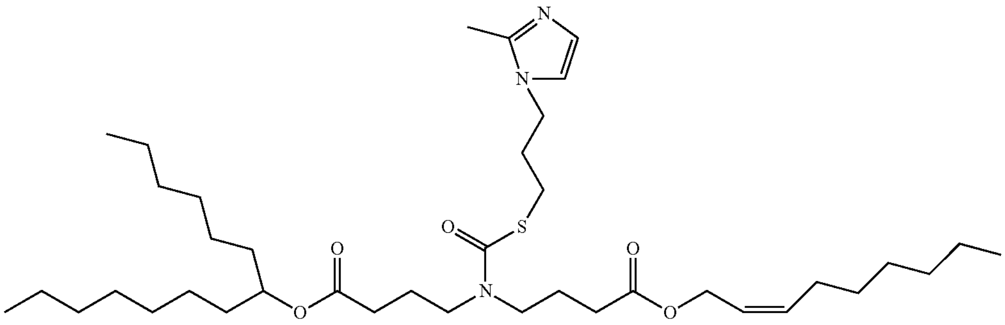 [SMILES: CCCCCC/C=C\COC(=O)CCCN(CCCC(=O)OC(CCCCCC)CCCCCCC)C(=O)SCCCn1ccnc1C] |

TABLE 10a-continued
| Ionizable lipid number | Structure |
|---|---|
| 77 | 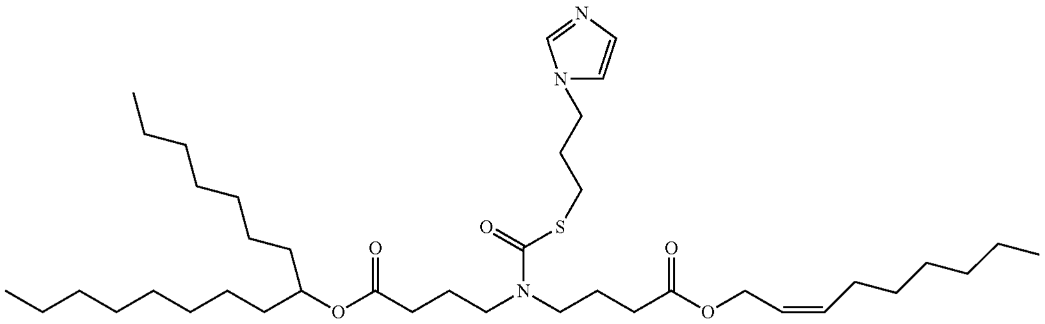 [SMILES: CCCCCC/C=C\COC(=O)CCCN(CCCC(=O)OC(CCCCCCC)CCCCCCCC)C(=O)SCCCn1ccnc1] |
| 78 | 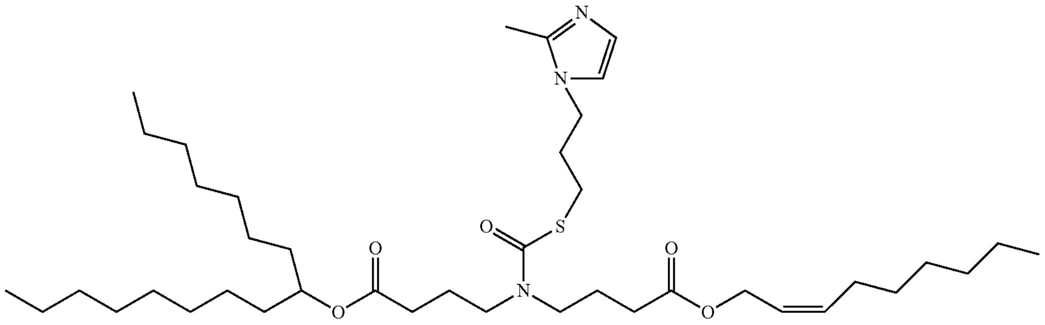 [SMILES: CCCCCC/C=C\COC(=O)CCCN(CCCC(=O)OC(CCCCCCC)CCCCCCCC)C(=O)SCCCn1ccnc1C] |
| 79 | 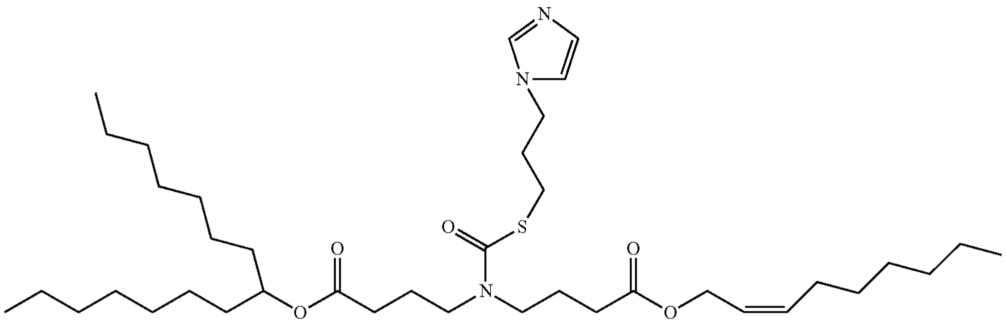 |
| 80 | 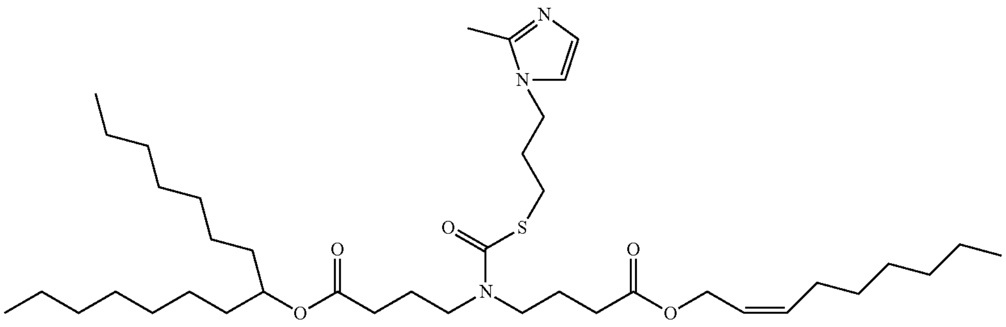 |

TABLE 10a-continued
| Ionizable lipid number | Structure |
|---|---|
| 81 | 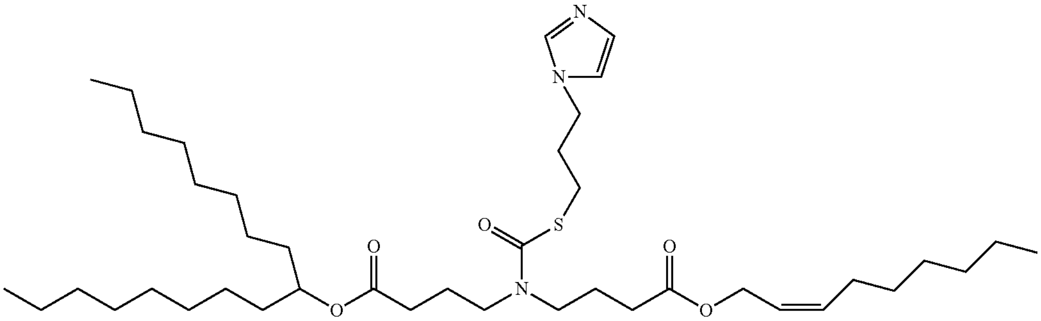 [SMILES: CCCCCC/C=C\COC(=O)CCCN(CCCC(=O)OC(CCCCCCCC)CCCCCCCC)C(=O)SCCCn1ccnc1] |
| 82 | 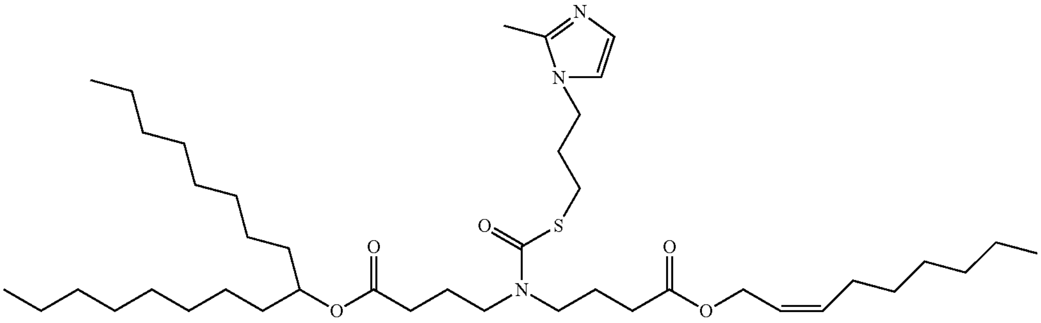 [SMILES: CCCCCC/C=C\COC(=O)CCCN(CCCC(=O)OC(CCCCCCCC)CCCCCCCC)C(=O)SCCCn1ccnc1C] |
| 83 | 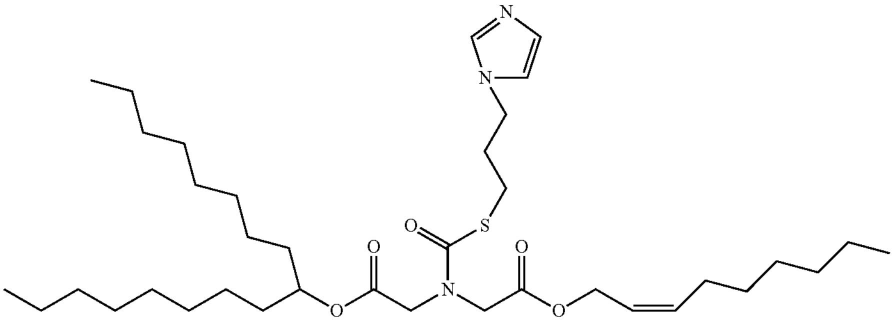 [SMILES: CCCCCC/C=C\COC(=O)CN(CC(=O)OC(CCCCCCCC)CCCCCCCC)C(=O)SCCCn1ccnc1] |
| 84 | 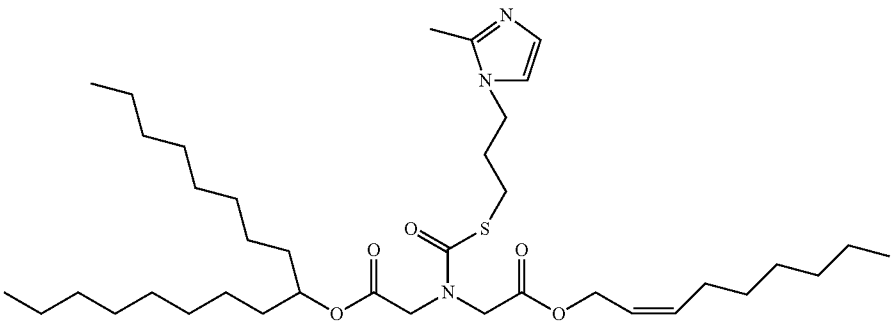 [SMILES: CCCCCC/C=C\COC(=O)CN(CC(=O)OC(CCCCCCCC)CCCCCCCC)C(=O)SCCCn1ccnc1C] |

TABLE 10a-continued
| Ionizable lipid number | Structure |
|---|---|
| 85 | 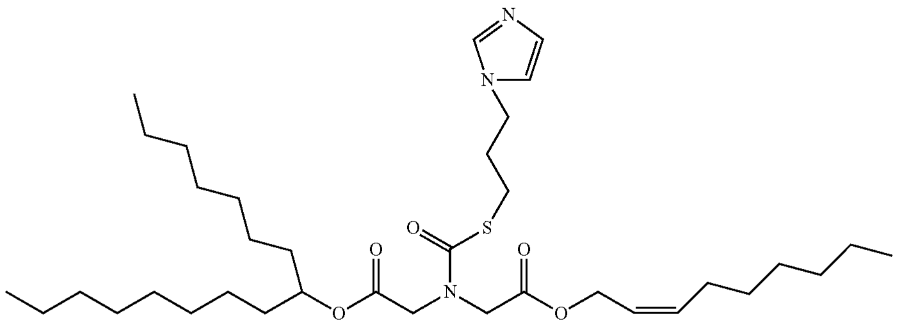 [SMILES: CCCCCC/C=C\COC(=O)CN(CC(=O)OC(CCCCCCC)CCCCCCCC)C(=O)SCCCn1ccnc1] |
| 86 | 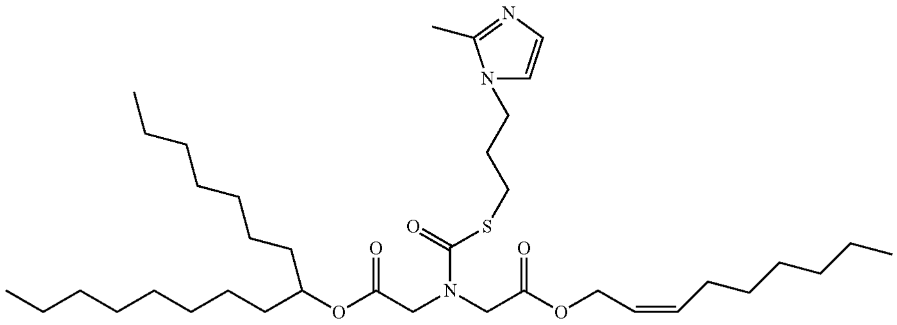 [SMILES: CCCCCC/C=C\COC(=O)CN(CC(=O)OC(CCCCCCC)CCCCCCCC)C(=O)SCCCn1ccnc1C] |
| 87 | 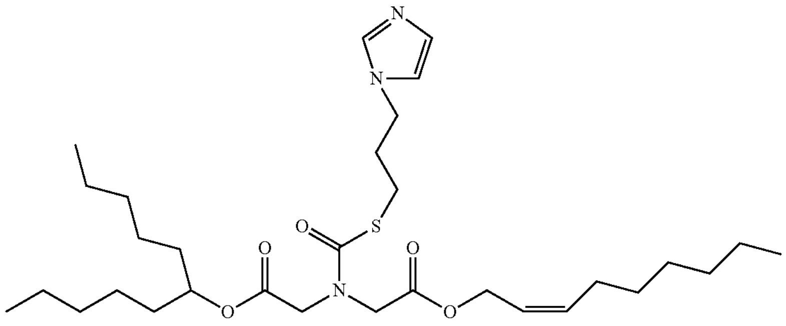 [SMILES: CCCCCC/C=C\COC(=O)CN(CC(=O)OC(CCCCC)CCCCC)C(=O)SCCCn1ccnc1] |
| 88 | 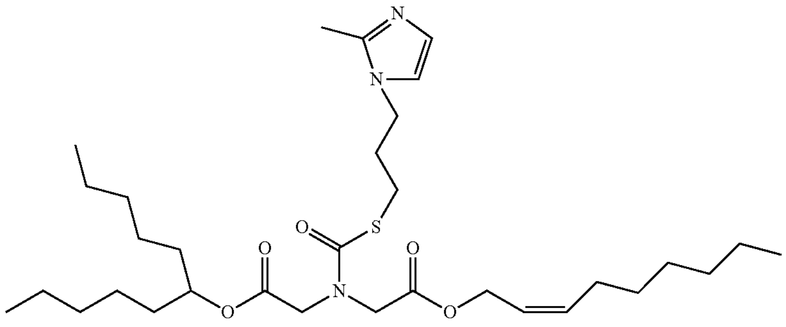 [SMILES: CCCCCC/C=C\COC(=O)CN(CC(=O)OC(CCCCC)CCCCC)C(=O)SCCCn1ccnc1C] |

TABLE 10a-continued
| Ionizable lipid number | Structure |
| --- | --- |
| 89 | 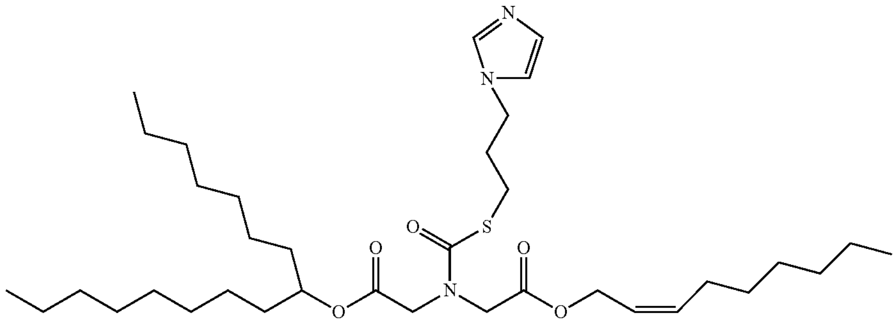 [SMILES: CCCCCC/C=C\COC(=O)CN(CC(=O)OC(CCCCCCC)CCCCCCCC)C(=O)SCCCn1ccnc1] |
| 90 | 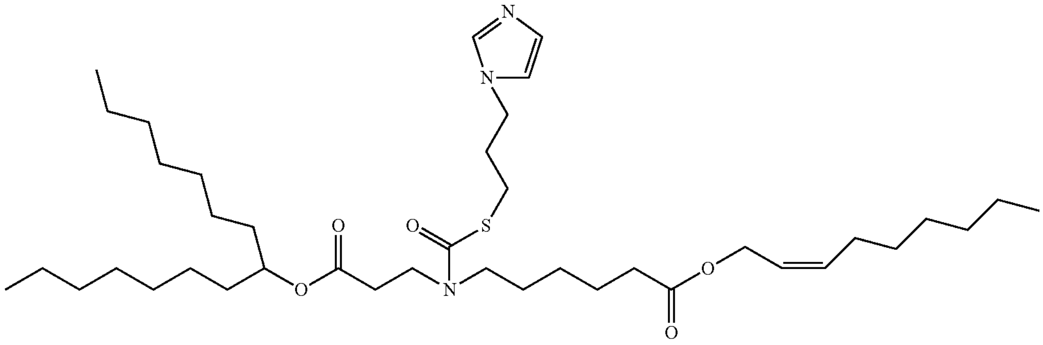 [SMILES: CCCCCC/C=C\COC(=O)CCCCCN(CCC(=O)OC(CCCCCCC)CCCCCCC)C(=O)SCCCn1ccnc1] |
| 91 | 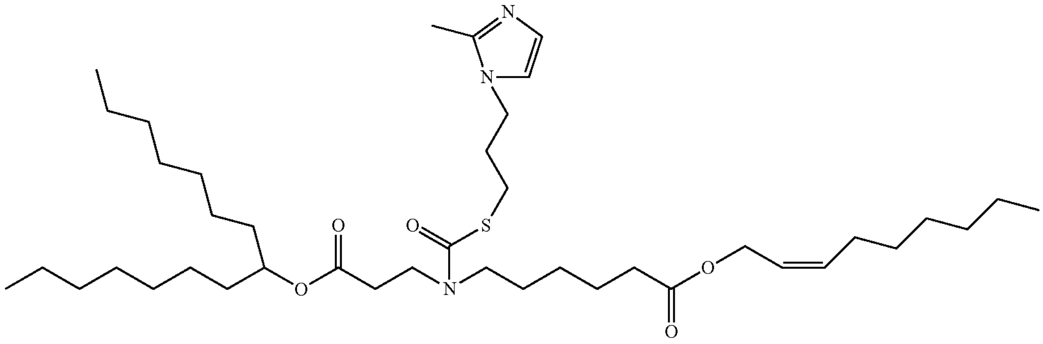 [SMILES: CCCCCC/C=C\COC(=O)CCCCCN(CCC(=O)OC(CCCCCCC)CCCCCCC)C(=O)SCCCn1ccnc1C] |
| 92 | 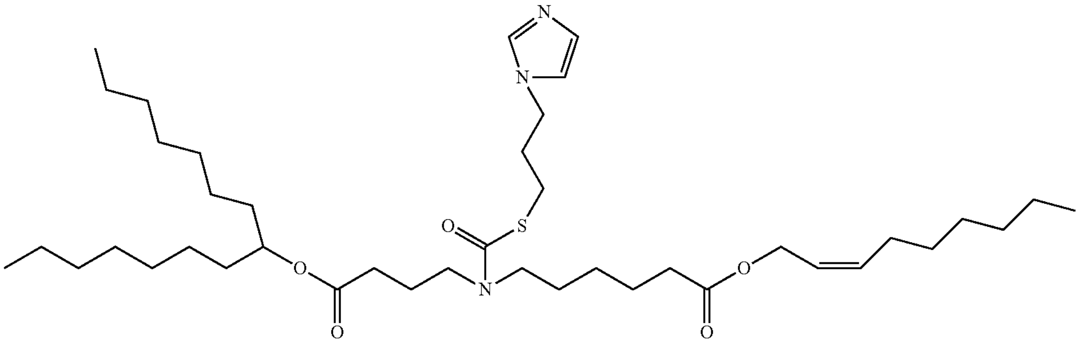 [SMILES: CCCCCC/C=C\COC(=O)CCCCCN(CCCC(=O)OC(CCCCCCC)CCCCCCC)C(=O)SCCCn1ccnc1] |

TABLE 10a-continued
| Ionizable lipid number | Structure |
|---|---|
| 93 | 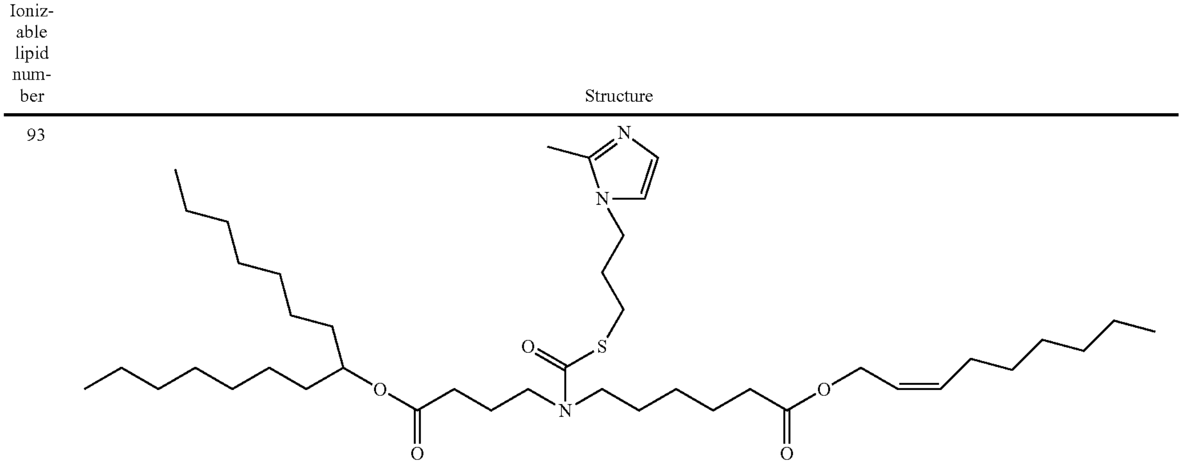 |
| 94 | 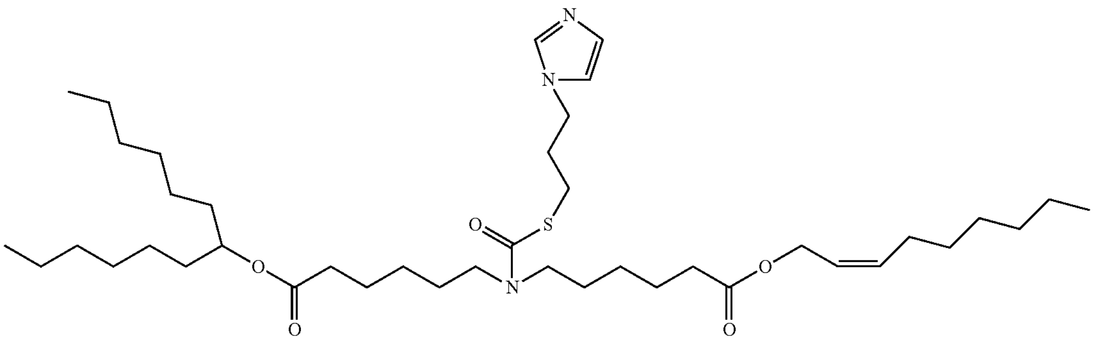 [SMILES: CCCCCC/C=C\COC(=O)CCCCCN(CCCCCC(=O)OC(CCCCCC)CCCCCC)C(=O)SCCCn1ccnc1] |
| 95 | 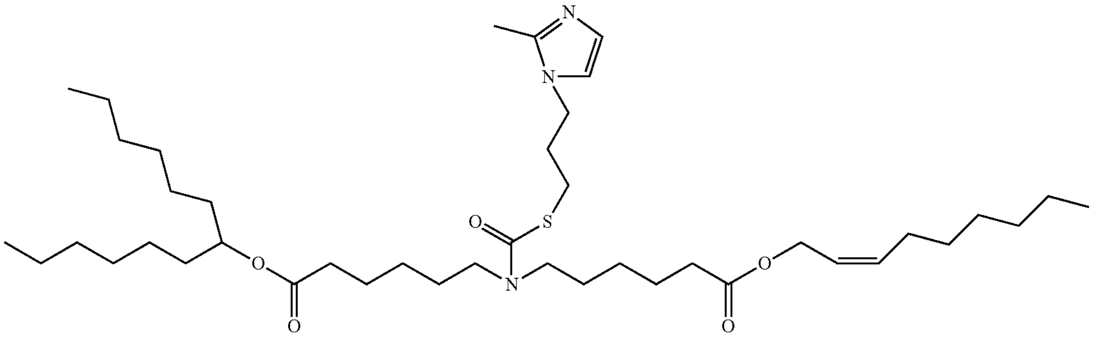 [SMILES: CCCCCC/C=C\COC(=O)CCCCCN(CCCCCC(=O)OC(CCCCCC)CCCCCC)C(=O)SCCCn1ccnc1C] |
| 96 | 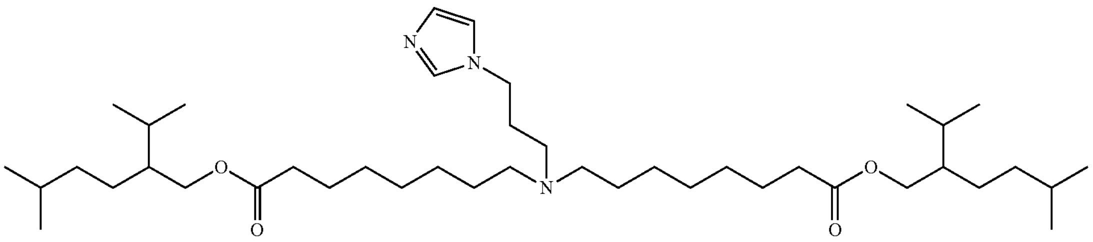 [SMILES: CC(C)CCC(COC(=O)CCCCCCCN(CCCCCCCC(=O)OCC(CCC(C)C)C(C)C)CCCn1ccnc1)C(C)C] |
| 97 | 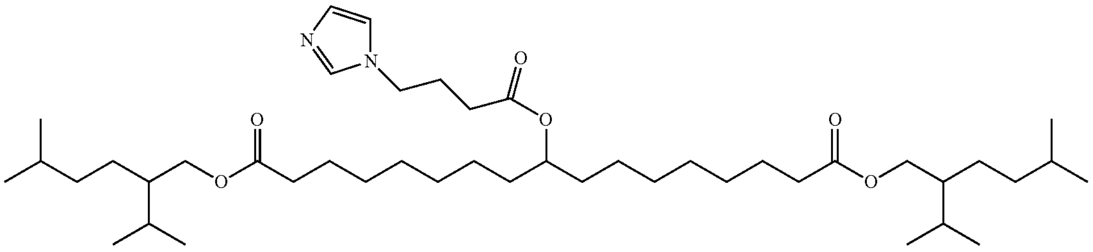 [SMILES: CC(C)CCC(COC(=O)CCCCCCCC(CCCCCCCC(=O)OCC(CCC(C)C)C(C)C)OC(=O)CCCn1ccnc1)C(C)C] |

TABLE 10a-continued
| Ionizable lipid number | Structure |
| --- | --- |
| 98 | 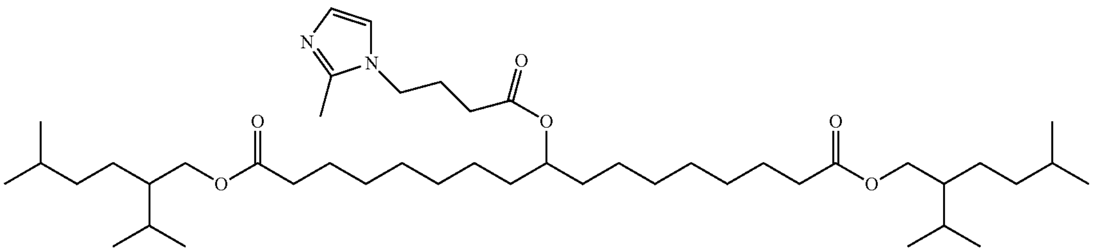 [SMILES: Cc1nccn1CCCC(=O)OC(CCCCCCCC(=O)OCC(CCC(C)C)C(C)C)CCCCCCCC(=O)OCC(CCC(C)C)C(C)C] |
| 99 | 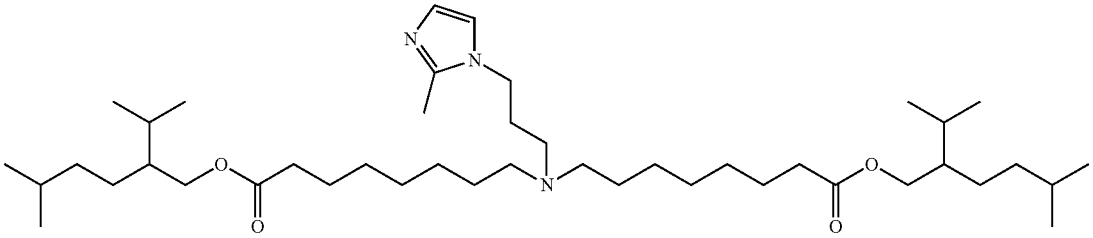 [SMILES: Cc1nccn1CCCN(CCCCCCCC(=O)OCC(CCC(C)C)C(C)C)CCCCCCCC(=O)OCC(CCC(C)C)C(C)C] |
| 100 | 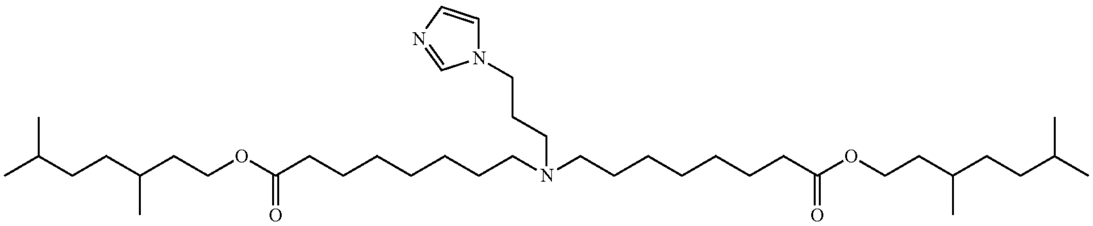 [SMILES: CC(C)CCC(C)CCOC(=O)CCCCCCCN(CCCCCCCC(=O)OCCC(C)CCC(C)C)CCCn1ccnc1] |
| 101 | 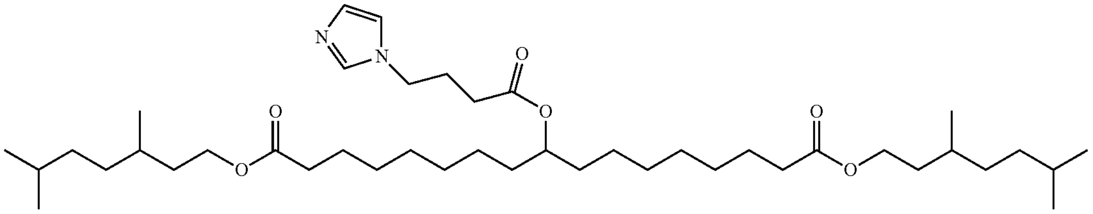 [SMILES: CC(C)CCC(C)CCOC(=O)CCCCCCCC(CCCCCCCC(=O)OCCC(C)CCC(C)C)OC(=O)CCCn1ccnc1] |
| 102 | 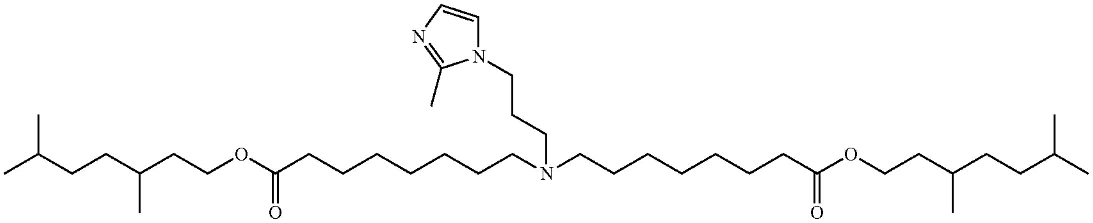 [SMILES: Cc1nccn1CCCN(CCCCCCCC(=O)OCCC(C)CCC(C)C)CCCCCCCC(=O)OCCC(C)CCC(C)C] |
| 103 | 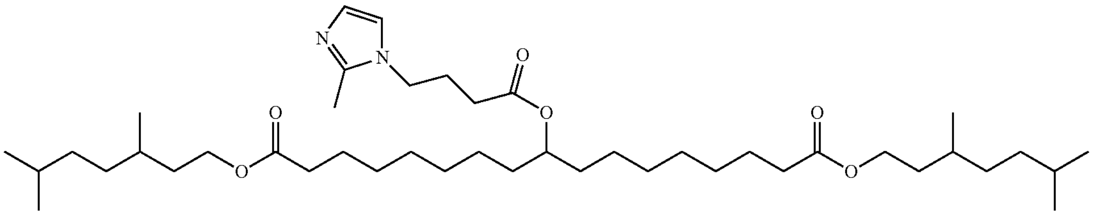 [SMILES: Cc1nccn1CCCC(=O)OC(CCCCCCCC(=O)OCCC(C)CCC(C)C)CCCCCCCC(=O)OCCC(C)CCC(C)C] |

TABLE 10a-continued
| Ionizable lipid number | Structure |
|---|---|
| 104 | 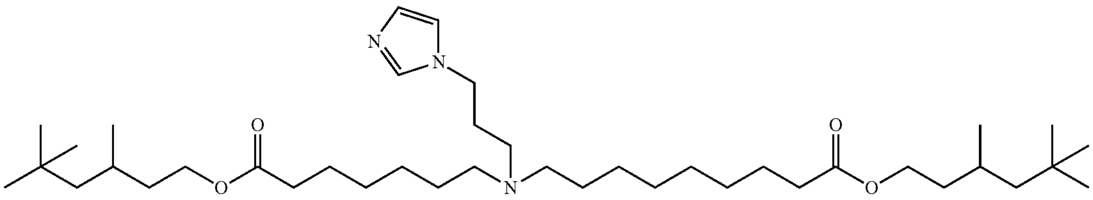 [SMILES: CC(CCOC(=O)CCCCCCCCN(CCCCCCC(=O)OCCC(C)CC(C)(C)C)CCCn1ccnc1)CC(C)(C)C] |
| 105 | 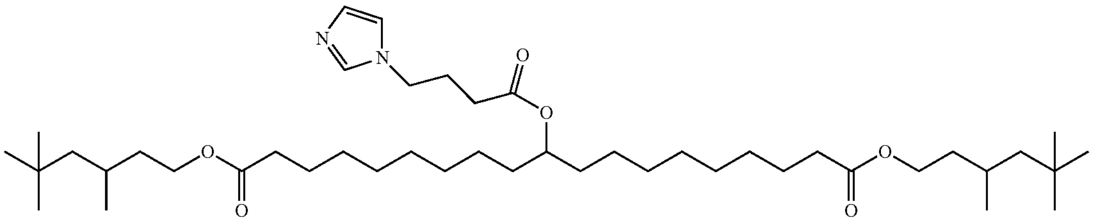 [SMILES: CC(CCOC(=O)CCCCCCCCC(CCCCCCCCC(=O)OCCC(C)CC(C)(C)C)OC(=O)CCCn1ccnc1)CC(C)(C)C] |
| 106 | 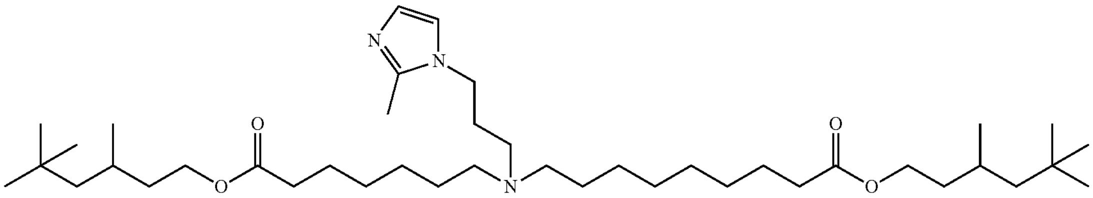 [SMILES: Cc1nccn1CCCN(CCCCCCCCC(=O)OCCC(C)CC(C)(C)C)CCCCCCC(=O)OCCC(C)CC(C)(C)C] |
| 107 | 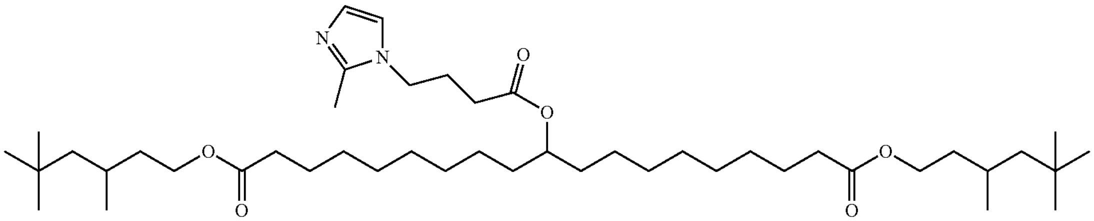 [SMILES: Cc1nccn1CCCC(=O)OC(CCCCCCCCC(=O)OCCC(C)CC(C)(C)C)CCCCCCCCC(=O)OCCC(C)CC(C)(C)C] |
| 108 | 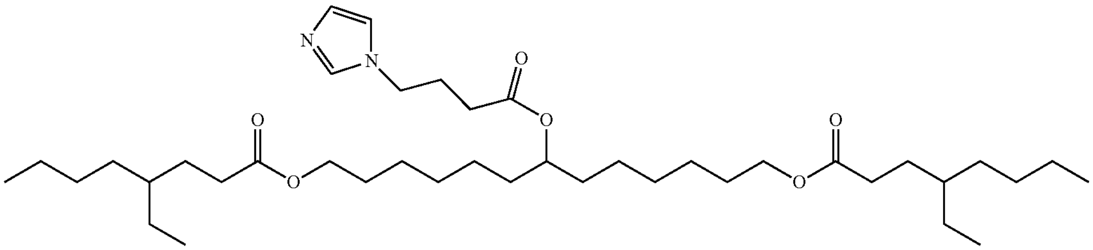 [SMILES: CCCCC(CC)CCC(=O)OCCCCCCC(CCCCCCOC(=O)CCC(CC)CCCC)OC(=O)CCCn1ccnc1] |
| 109 | 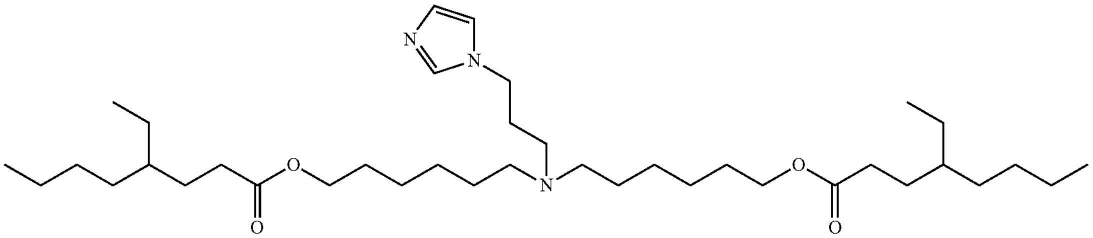 [SMILES: CCCCC(CC)CCC(=O)OCCCCCCN(CCCCCCOC(=O)CCC(CC)CCCC)CCCn1ccnc1] |

TABLE 10a-continued
| Ionizable lipid number | Structure |
|---|---|
| 110 | 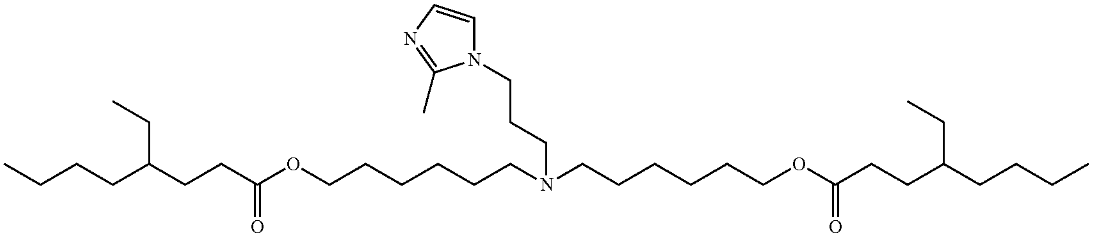 [SMILES: CCCCC(CC)CCC(=O)OCCCCCCN(CCCCCCOC(=O)CCC(CC)CCCC)CCCn1ccnc1C] |
| 111 | 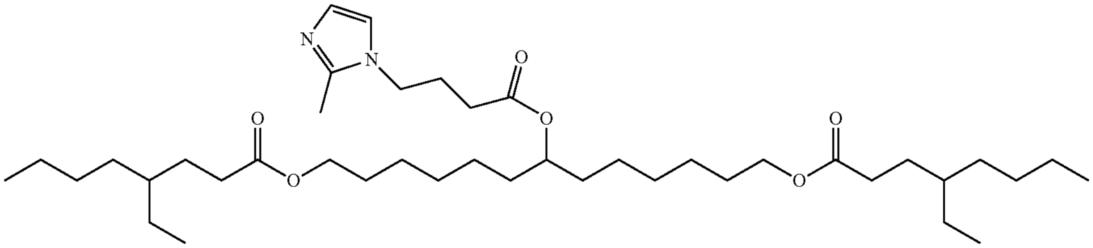 [SMILES: CCCCC(CC)CCC(=O)OCCCCCCC(CCCCCCOC(=O)CCC(CC)CCCC)OC(=O)CCCn1ccnc1C] |
| 112 | 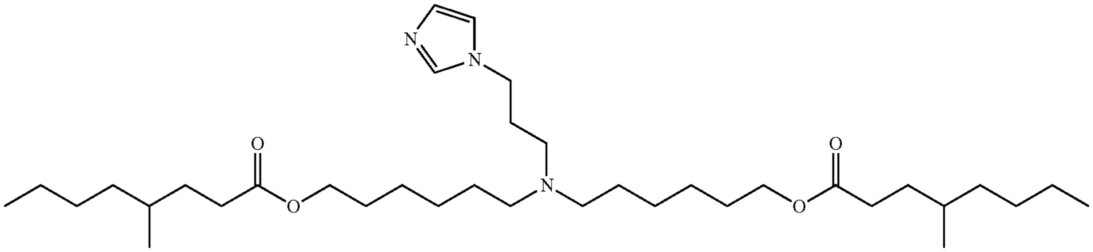 [SMILES: CCCCC(C)CCC(=O)OCCCCCCN(CCCCCCOC(=O)CCC(C)CCCC)CCCn1ccnc1] |
| 113 | 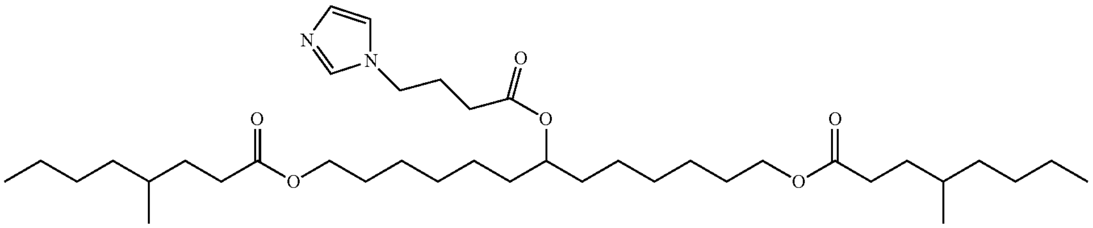 [SMILES: CCCCC(C)CCC(=O)OCCCCCCC(CCCCCCOC(=O)CCC(C)CCCC)OC(=O)CCCn1ccnc1] |
| 114 | 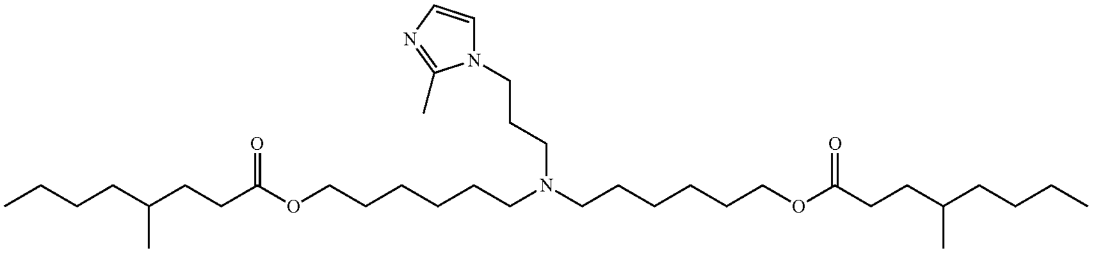 [SMILES: CCCCC(C)CCC(=O)OCCCCCCN(CCCCCCOC(=O)CCC(C)CCCC)CCCn1ccnc1C] |
| 115 | 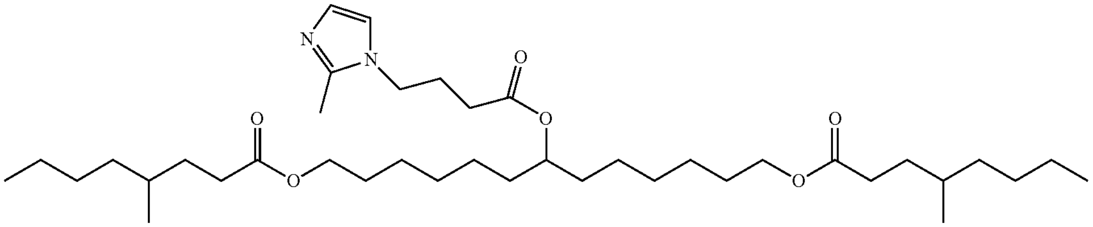 [SMILES: CCCCC(C)CCC(=O)OCCCCCCC(CCCCCCOC(=O)CCC(C)CCCC)OC(=O)CCCn1ccnc1C] |

TABLE 10a-continued
| Ionizable lipid number | Structure |
|---|---|
| 116 | 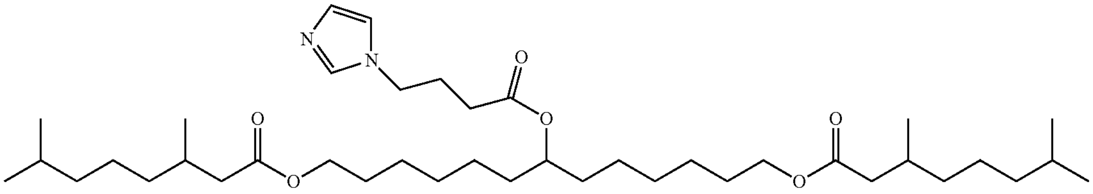 [SMILES: CC(C)CCCC(C)CC(=O)OCCCCCCC(CCCCCCOC(=O)CC(C)CCCC(C)C)OC(=O)CCCn1ccnc1] |
| 117 | 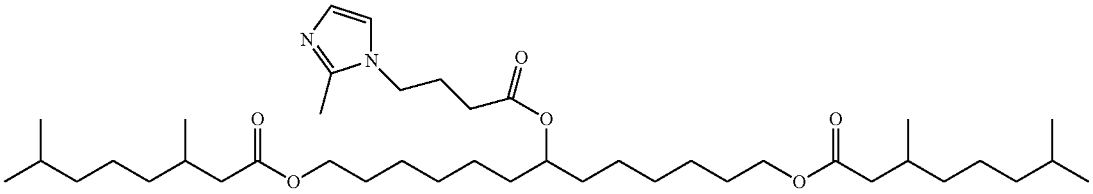 [SMILES: Cc1nccn1CCCC(=O)OC(CCCCCCOC(=O)CC(C)CCCC(C)C)CCCCCCOC(=O)CC(C)CCCC(C)C] |
| 118 | 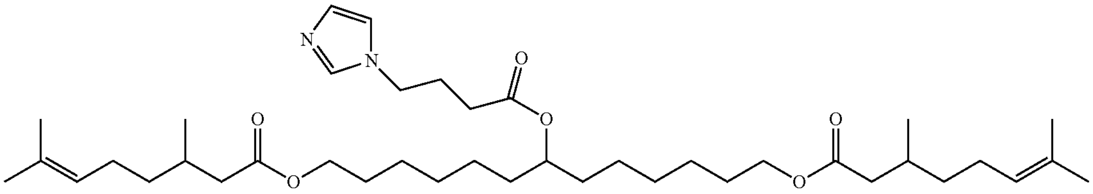 [SMILES: CC(C)=CCCC(C)CC(=O)OCCCCCCC(CCCCCCOC(=O)CC(C)CCC=C(C)C)OC(=O)CCCn1ccnc1] |
| 119 | 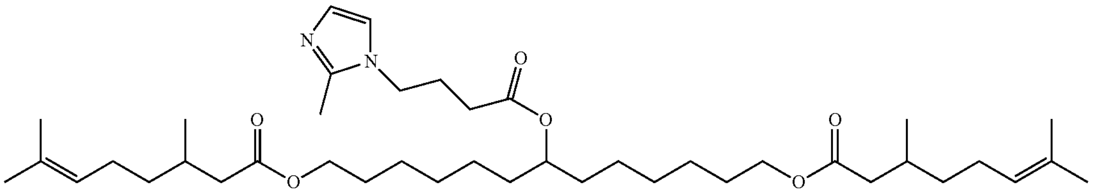 [SMILES: CC(C)=CCCC(C)CC(=O)OCCCCCCC(CCCCCCOC(=O)CC(C)CCC=C(C)C)OC(=O)CCCn1ccnc1C] |
| 120 | 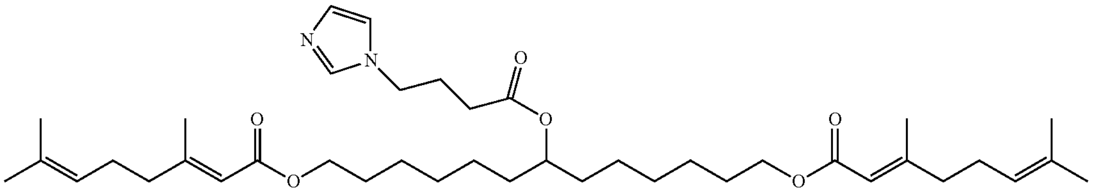 [SMILES: CC(C)=CCC/C(C)=C/C(=O)OCCCCCCC(CCCCCCOC(=O)/C=C(\C)CCC=C(C)C)OC(=O)CCCn1ccnc1] |
| 121 | 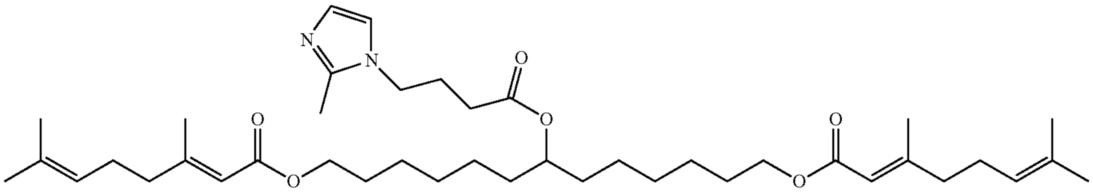 [SMILES: CC(C)=CCC/C(C)=C/C(=O)OCCCCCCC(CCCCCCOC(=O)/C=C(\C)CCC=C(C)C)OC(=O)CCCn1ccnc1C] |
| 122 | 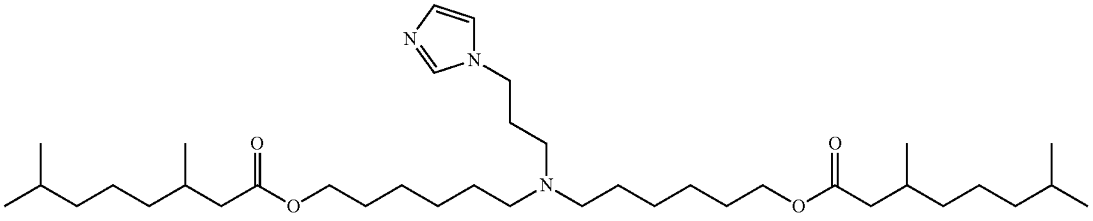 [SMILES: CC(C)CCCC(C)CC(=O)OCCCCCCN(CCCCCCOC(=O)CC(C)CCCC(C)C)CCCn1ccnc1] |

TABLE 10a-continued
| Ionizable lipid number | Structure |
| --- | --- |
| 123 | 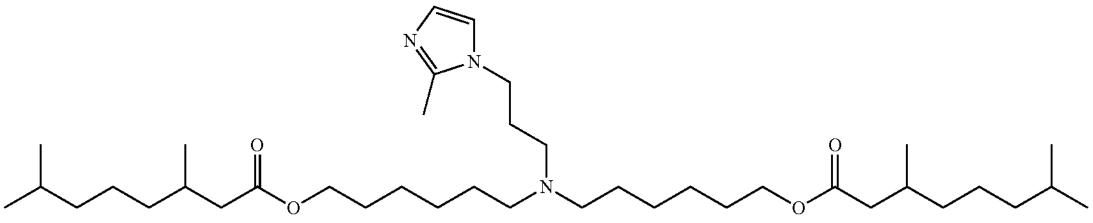 [SMILES: Cc1nccn1CCCN(CCCCCCOC(=O)CC(C)CCCC(C)C)CCCCCCOC(=O)CC(C)CCCC(C)C] |
| 124 | 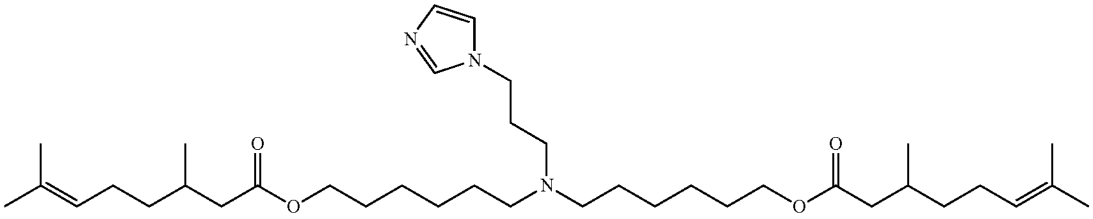 [SMILES: CC(C)=CCCC(C)CC(=O)OCCCCCCN(CCCCCCOC(=O)CC(C)CCC=C(C)C)CCCn1ccnc1] |
| 125 | 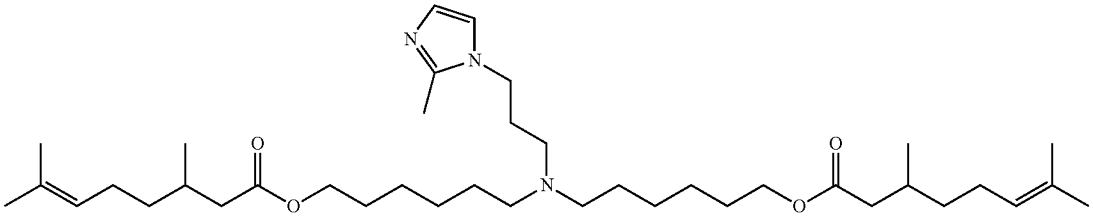 [SMILES: CC(C)=CCCC(C)CC(=O)OCCCCCCN(CCCCCCOC(=O)CC(C)CCC=C(C)C)CCCn1ccnc1C] |
| 126 | 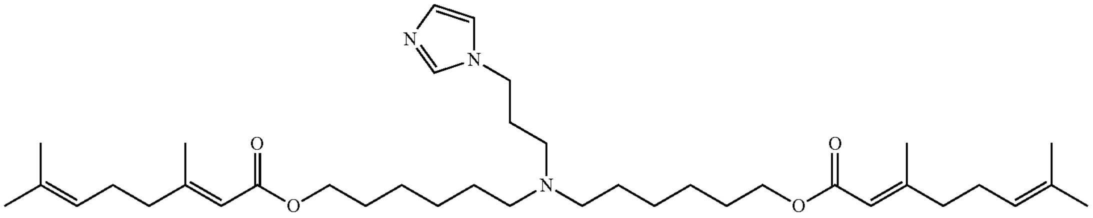 [SMILES: CC(C)=CCC/C(C)=C/C(=O)OCCCCCCN(CCCCCCOC(=O)/C=C(\C)CCC=C(C)C)CCCn1ccnc1] |
| 127 | 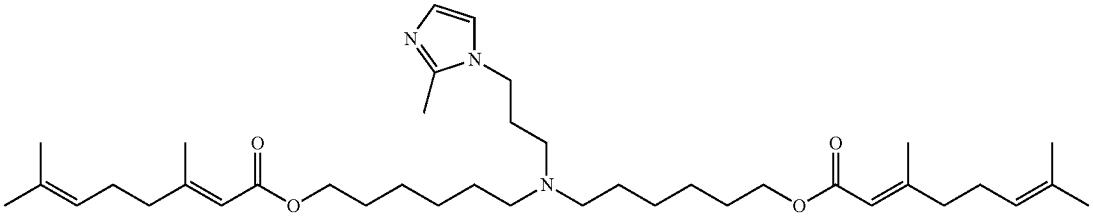 [SMILES: CC(C)=CCC/C(C)=C/C(=O)OCCCCCCN(CCCCCCOC(=O)/C=C(\C)CCC=C(C)C)CCCn1ccnc1C] |
| 128 | 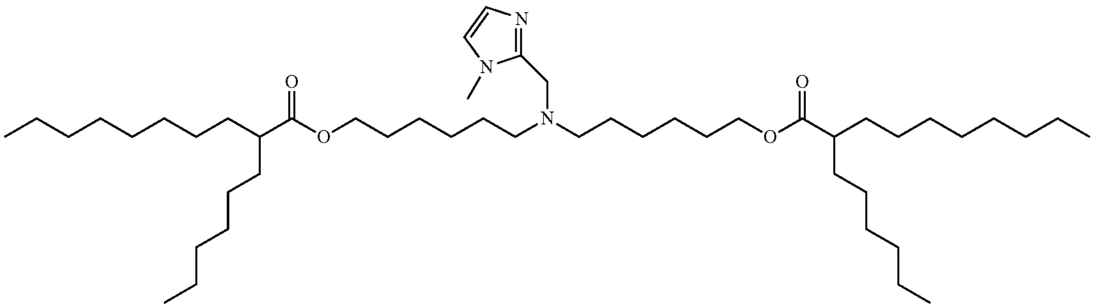 [SMILES: CCCCCCCCC(CCCCCC)C(=O)OCCCCCCN(CCCCCCOC(=O)C(CCCCCC)CCCCCCCC)Cc1nccn1C] |

TABLE 10a-continued
| Ionizable lipid number | Structure |
| --- | --- |
| 129 | 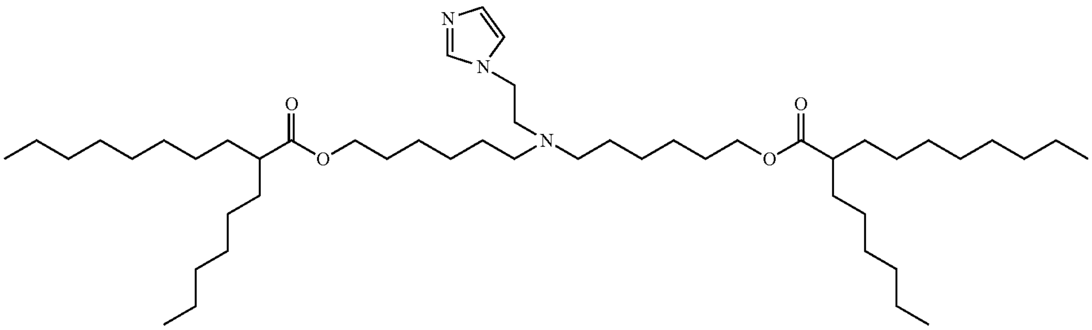 [SMILES: CCCCCCCCC(CCCCCC)C(=O)OCCCCCCN(CCCCCCOC(=O)C(CCCCCC)CCCCCCCC)CCn1ccnc1] |
| 130 | 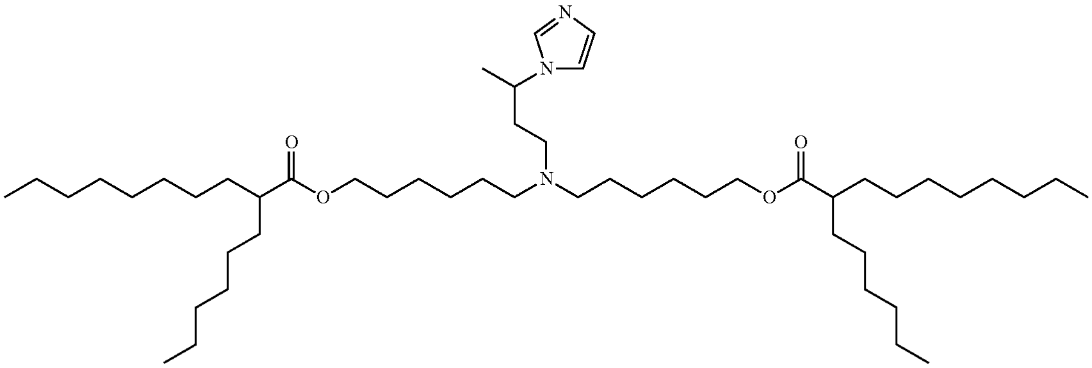 [SMILES: CCCCCCCCC(CCCCCC)C(=O)OCCCCCCN(CCCCCCOC(=O)C(CCCCCC)CCCCCCCC)CCC(C)n1ccnc1] |
| 131 | 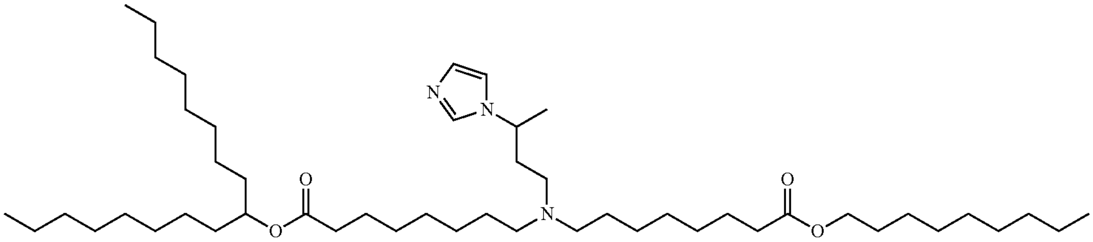 [SMILES: CCCCCCCCCOC(=O)CCCCCCCN(CCCCCCCC(=O)OC(CCCCCCCC)CCCCCCCC)CCC(C)n1ccnc1] |
| 132 | 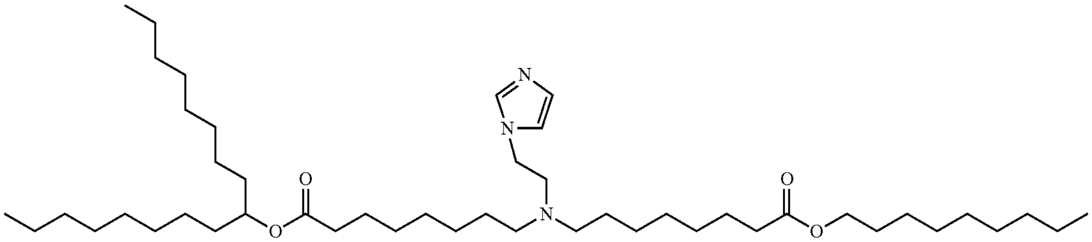 [SMILES: CCCCCCCCCOC(=O)CCCCCCCN(CCCCCCCC(=O)OC(CCCCCCCC)CCCCCCCC)CCn1ccnc1] |
| 133 | 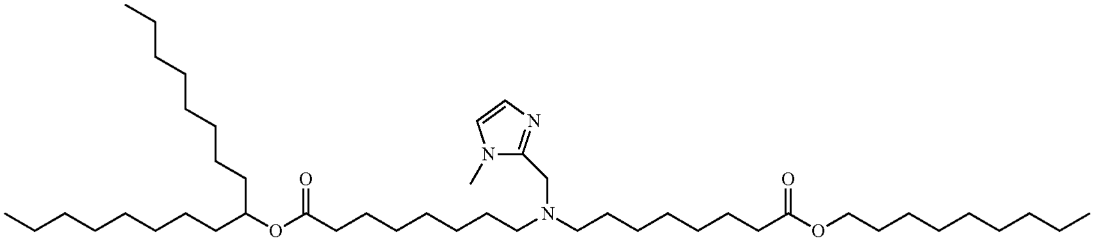 [SMILES: CCCCCCCCCOC(=O)CCCCCCCN(CCCCCCCC(=O)OC(CCCCCCCC)CCCCCCCC)Cc1nccn1C] |

TABLE 10a-continued
| Ionizable lipid number | Structure |
| --- | --- |
| 134 | 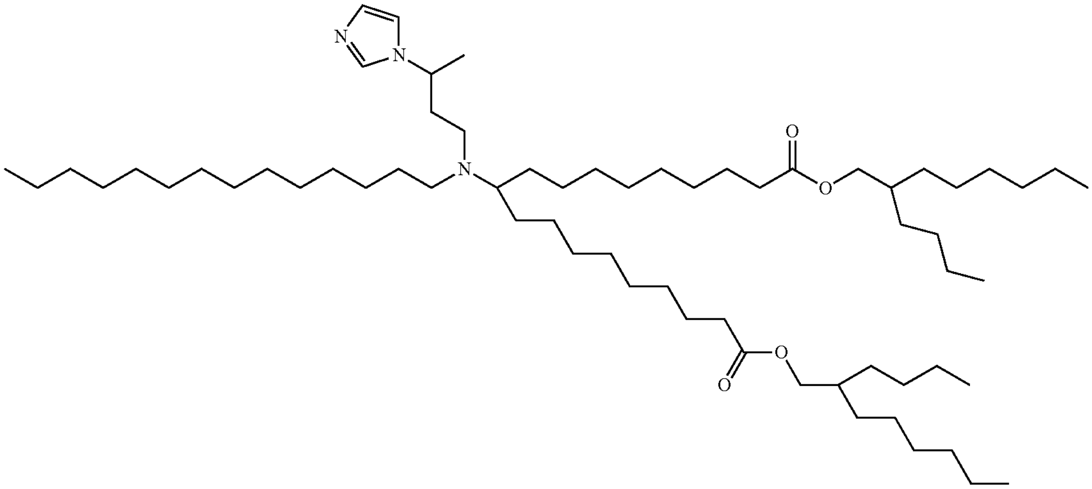 [SMILES: CCCCCCCCCCCCCCN(CCC(C)n1ccnc1)C(CCCCCCCCC(=O)OCC(CCCC)CCCCCC)CCCCCCCCC(=O)OCC(CCCC)CCCCCC] |
| 135 | 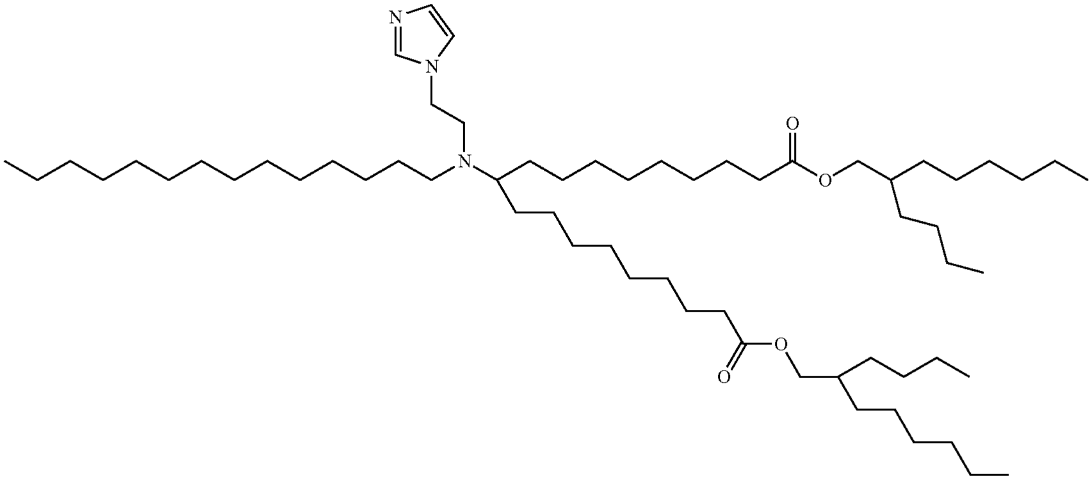 [SMILES: CCCCCCCCCCCCCCN(CCn1ccnc1)C(CCCCCCCCC(=O)OCC(CCCC)CCCCCC)CCCCCCCCC(=O)OCC(CCCC)CCCCCC] |
| 136 | 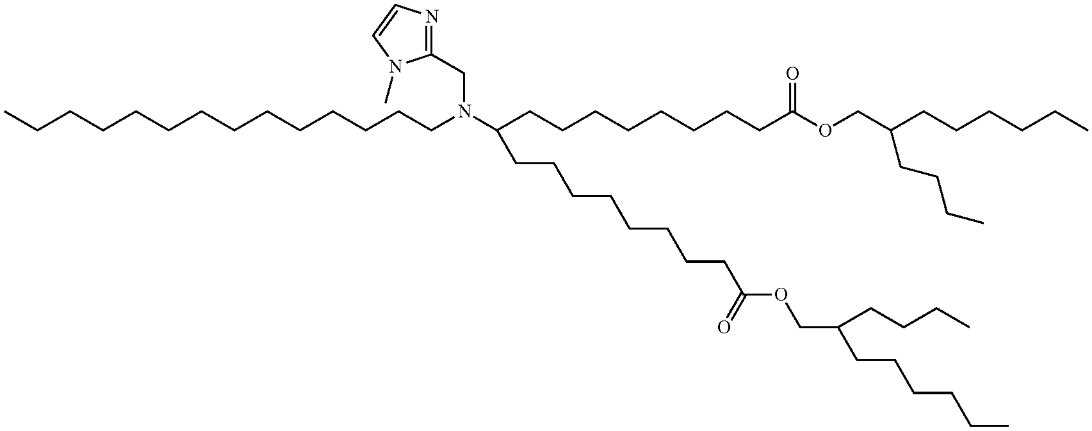 [SMILES: CCCCCCCCCCCCCCN(Cc1nccn1C)C(CCCCCCCCC(=O)OCC(CCCC)CCCCCC)CCCCCCCCC(=O)OCC(CCCC)CCCCCC] |

In some embodiments, the ionizable lipid has a beta-hydroxyl amine head group. In some embodiments, the ionizable lipid has a gamma-hydroxyl amine head group.

In some embodiments, an ionizable lipid of the disclosure is a lipid selected from Table 10b. In some embodiments, an ionizable lipid of the disclosure is Lipid 15 from Table 10b. In an embodiment, the ionizable lipid is described in US patent publication number US20170210697A1. In an embodiment, the ionizable lipid is described in US patent publication number US20170119904A1.

TABLE 10b

| Ionizable lipid number | Structure |
| --- | --- |
| 1 | 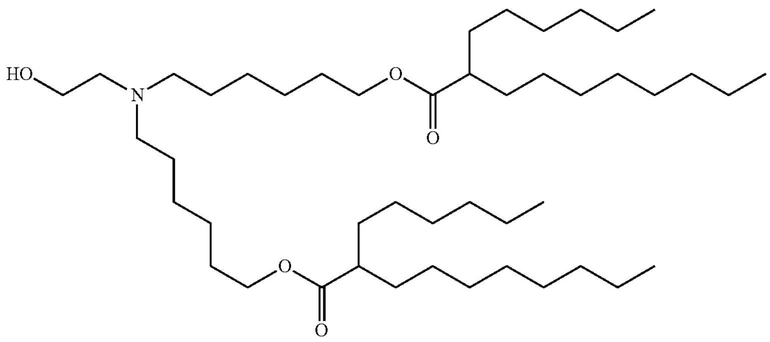 [SMILES: CCCCCCCCC(CCCCCC)C(=O)OCCCCCCN(CCO)CCCCCCOC(=O)C(CCCCCC)CCCCCCCC] |
| 2 | 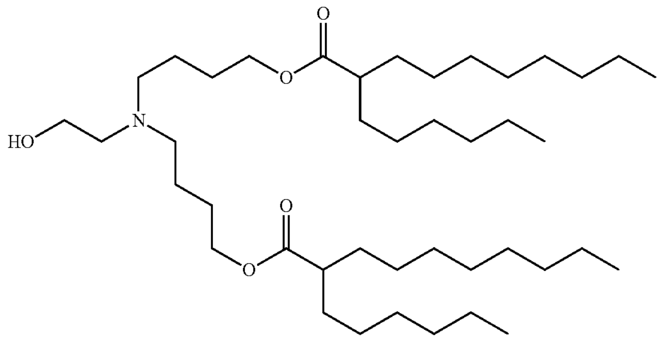 [SMILES: CCCCCCCCC(CCCCCC)C(=O)OCCCCN(CCO)CCCCOC(=O)C(CCCCCC)CCCCCCCC] |
| 3 | 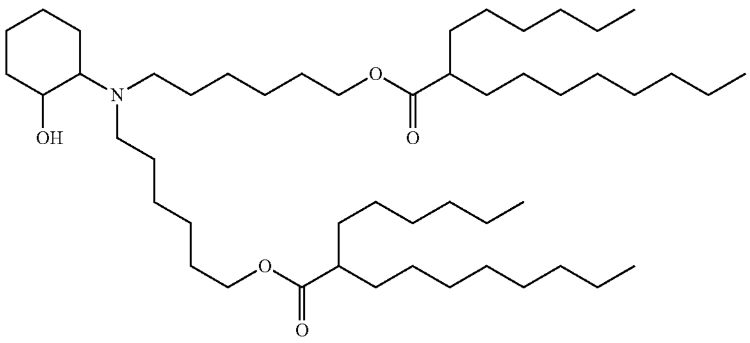 [SMILES: CCCCCCCCC(CCCCCC)C(=O)OCCCCCCN(CCCCCCOC(=O)C(CCCCCC)CCCCCCCC)C1CCCCC1O] |
| 4 | 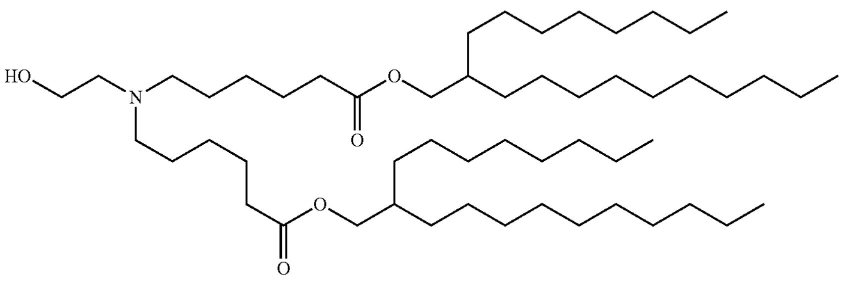 [SMILES: CCCCCCCCCCC(CCCCCCCC)COC(=O)CCCCCN(CCO)CCCCCC(=O)OCC(CCCCCCCC)CCCCCCCCCC] |

TABLE 10b-continued
| Ionizable lipid number | Structure |
| --- | --- |
| 5 | 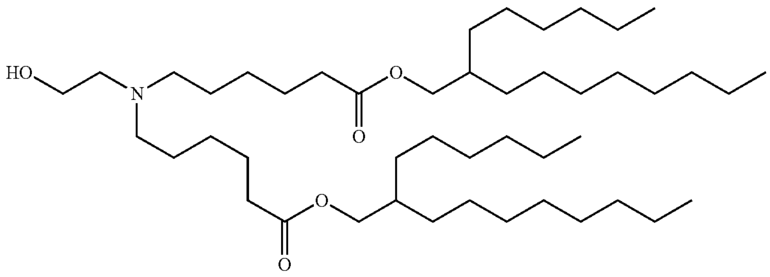 [SMILES: CCCCCCCCC(CCCCCC)COC(=O)CCCCCN(CCO)CCCCCC(=O)OCC(CCCCCC)CCCCCCCC] |
| 6 | 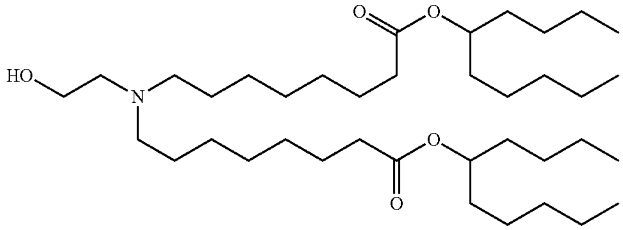 [SMILES: CCCCCC(CCCC)OC(=O)CCCCCCCN(CCO)CCCCCCCC(=O)OC(CCCC)CCCCC] |
| 7 | 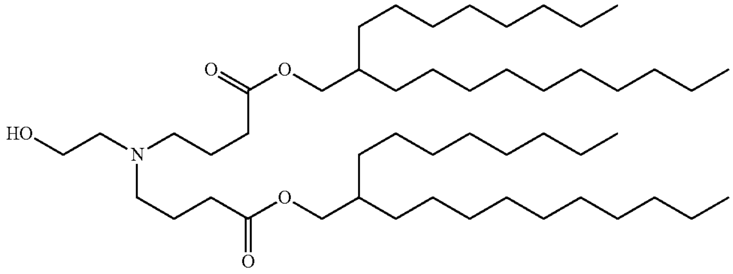 [SMILES: CCCCCCCCCCC(CCCCCCCC)COC(=O)CCCN(CCO)CCCC(=O)OCC(CCCCCCCC)CCCCCCCCCC] |
| 8 | 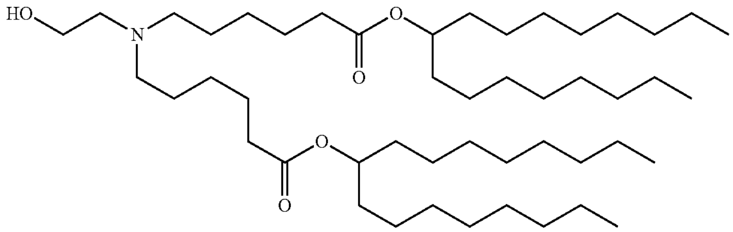 [SMILES: CCCCCCCCC(CCCCCCCC)OC(=O)CCCCCN(CCO)CCCCCC(=O)OC(CCCCCCCC)CCCCCCCC] |
| 9 | 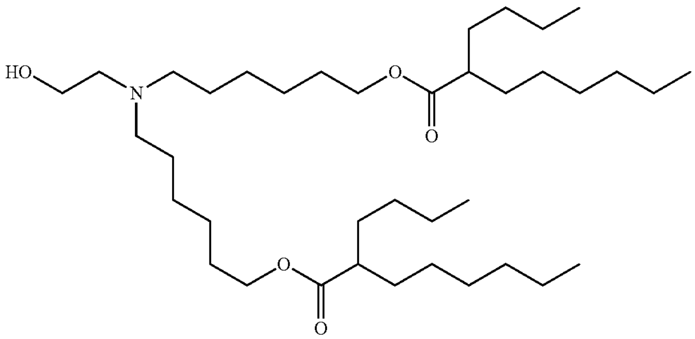 [SMILES: CCCCCCC(CCCC)C(=O)OCCCCCCN(CCO)CCCCCCOC(=O)C(CCCC)CCCCCC] |

TABLE 10b-continued
| Ionizable lipid number | Structure |
| --- | --- |
| 10 | 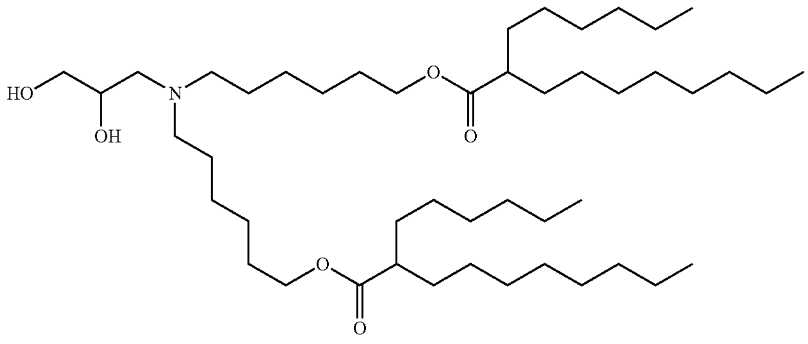 [SMILES: CCCCCCCCC(CCCCCC)C(=O)OCCCCCCN(CCCCCCOC(=O)C(CCCCCC)CCCCCCCC)CC(O)CO] |
| 11 | 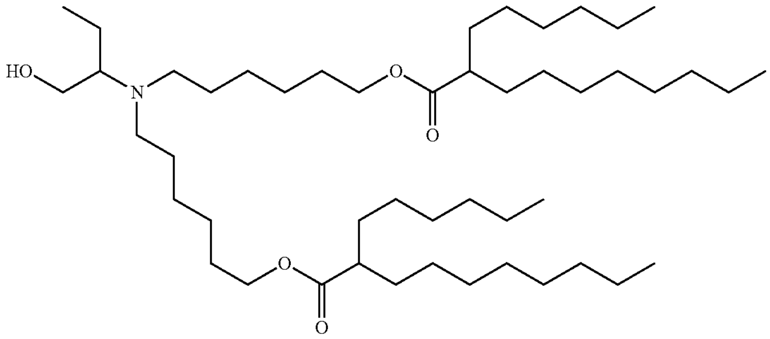 [SMILES: CCCCCCCCC(CCCCCC)C(=O)OCCCCCCN(CCCCCCOC(=O)C(CCCCCC)CCCCCCCC)C(CC)CO] |
| 12 | 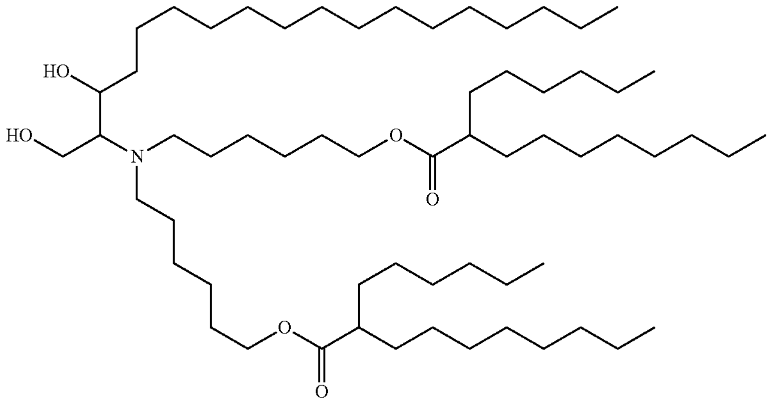 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| 13 | 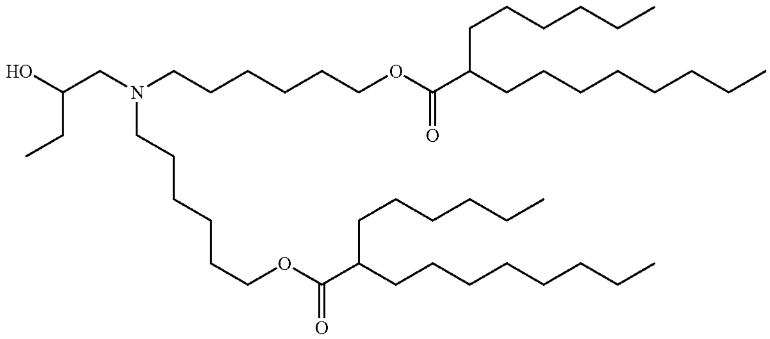 [SMILES: CCCCCCCCC(CCCCCC)C(=O)OCCCCCCN(CCCCCCOC(=O)C(CCCCCC)CCCCCCCC)CC(O)CC] |

TABLE 10b-continued
| Ionizable lipid number | Structure |
|---|---|
| 14 | 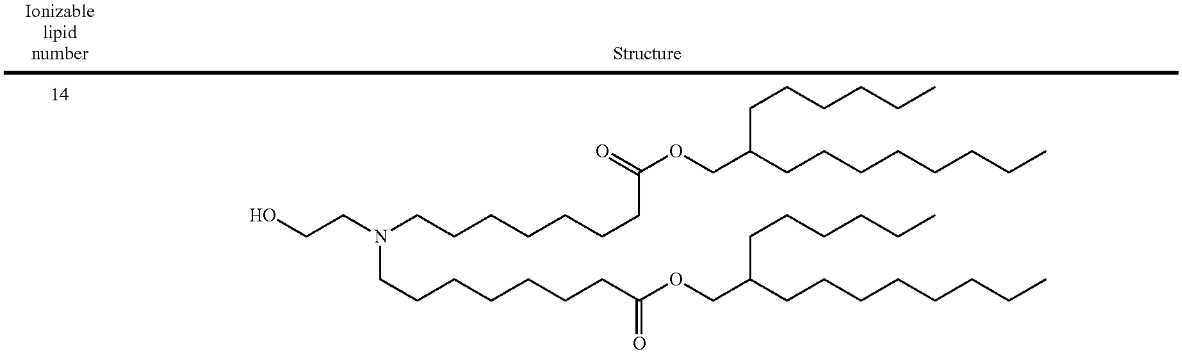 |
| 15 | 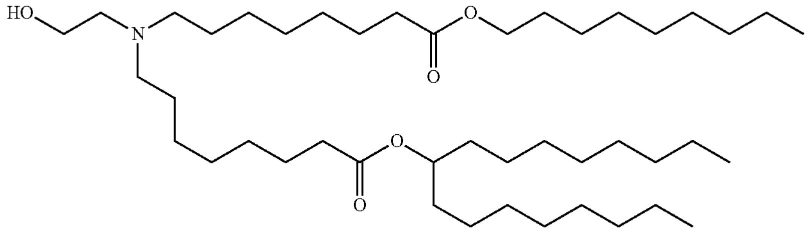 [SMILES: CCCCCCCCCOC(=O)CCCCCCCN(CCO)CCCCCCCC(=O)OC(CCCCCCCC)CCCCCCCC] |
| 16 | 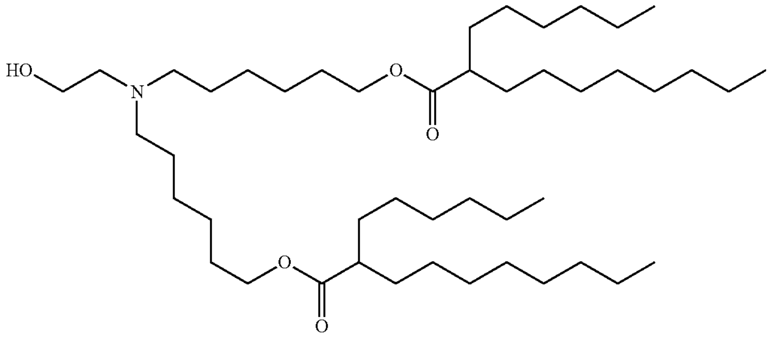 [SMILES: CCCCCCCCC(CCCCCC)C(=O)OCCCCCCN(CCO)CCCCCCOC(=O)C(CCCCCC)CCCCCCCC] |
| 17 | 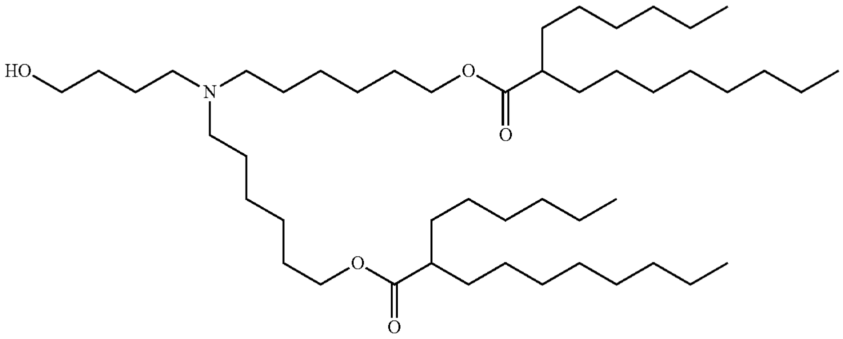 [SMILES: CCCCCCCCC(CCCCCC)C(=O)OCCCCCCN(CCCCO)CCCCCCOC(=O)C(CCCCCC)CCCCCCCC] |
| 18 | 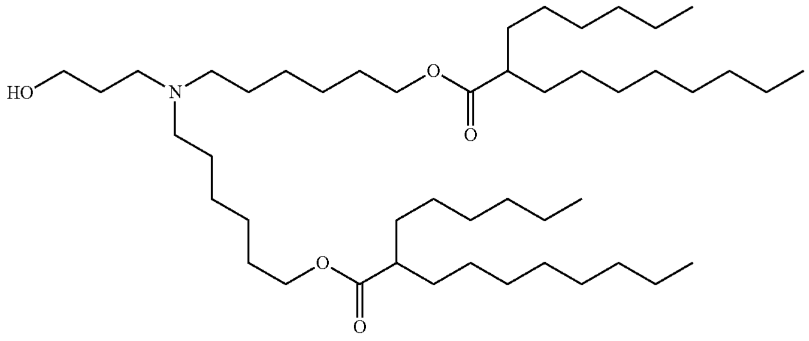 [SMILES: CCCCCCCCC(CCCCCC)C(=O)OCCCCCCN(CCCO)CCCCCCOC(=O)C(CCCCCC)CCCCCCCC] |

TABLE 10b-continued
| Ionizable lipid number | Structure |
|---|---|
| 19 | 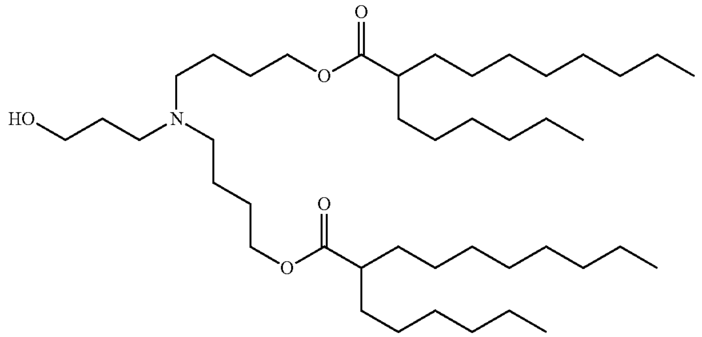 [SMILES: CCCCCCCCC(CCCCCC)C(=O)OCCCCN(CCCO)CCCCOC(=O)C(CCCCCC)CCCCCCCC] |
| 20 | 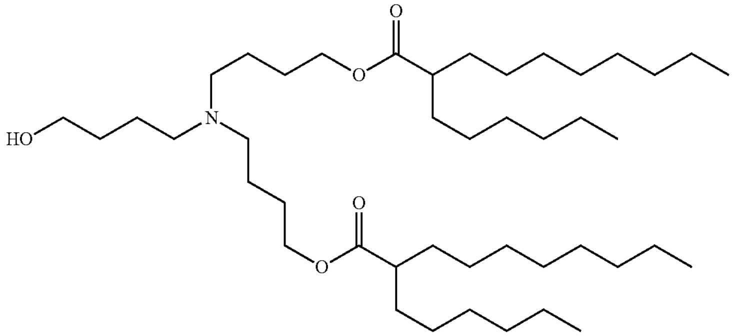 [SMILES: CCCCCCCCC(CCCCCC)C(=O)OCCCCN(CCCCO)CCCCOC(=O)C(CCCCCC)CCCCCCCC] |
| 21 | 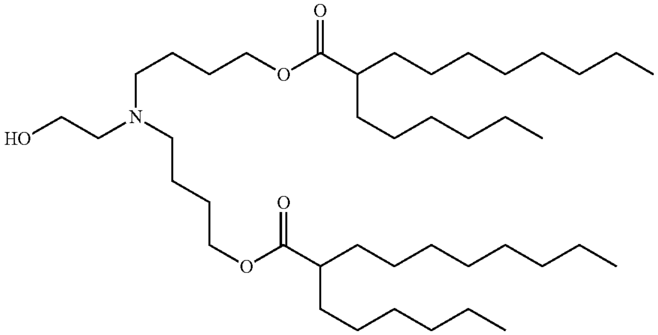 [SMILES: CCCCCCCCC(CCCCCC)C(=O)OCCCCN(CCO)CCCCOC(=O)C(CCCCCC)CCCCCCCC] |
| 22 | 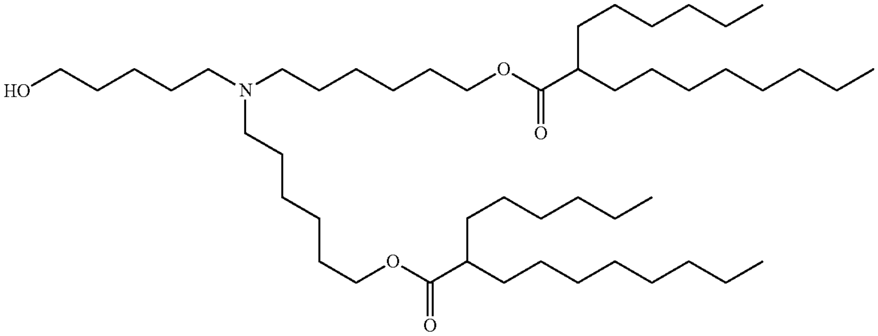 [SMILES: CCCCCCCCC(CCCCCC)C(=O)OCCCCCCN(CCCCCO)CCCCCCOC(=O)C(CCCCCC)CCCCCCCC] |

TABLE 10b-continued
| Ionizable lipid number | Structure |
|---|---|
| 23 | 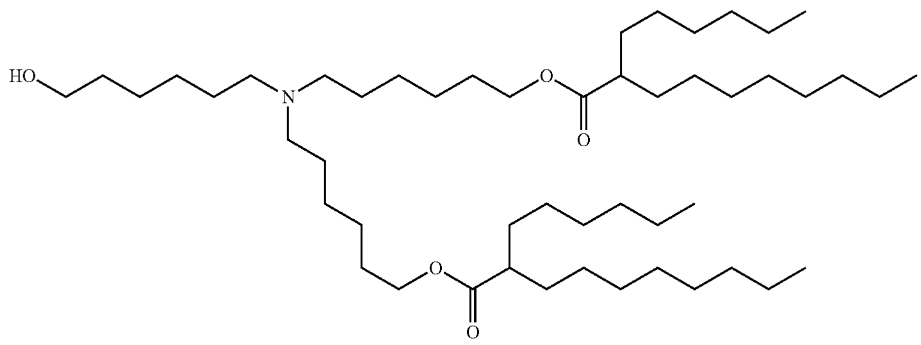 [SMILES: CCCCCCCCC(CCCCCC)C(=O)OCCCCCCN(CCCCCCO)CCCCCCOC(=O)C(CCCCCC)CCCCCCCC] |
| 24 | 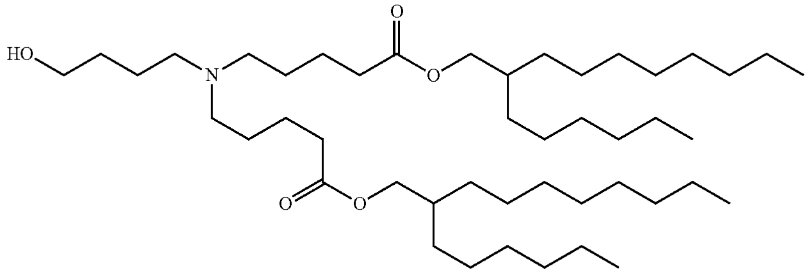 [SMILES: CCCCCCCCC(CCCCCC)COC(=O)CCCCN(CCCCO)CCCCC(=O)OCC(CCCCCC)CCCCCCCC] |
| 25 | 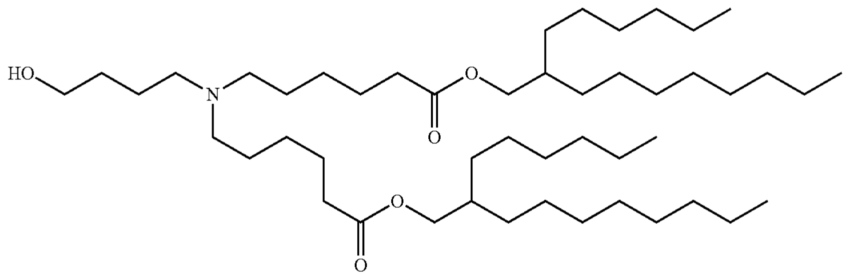 [SMILES: CCCCCCCCC(CCCCCC)COC(=O)CCCCCN(CCCCO)CCCCCC(=O)OCC(CCCCCC)CCCCCCCC] |
| 26 | 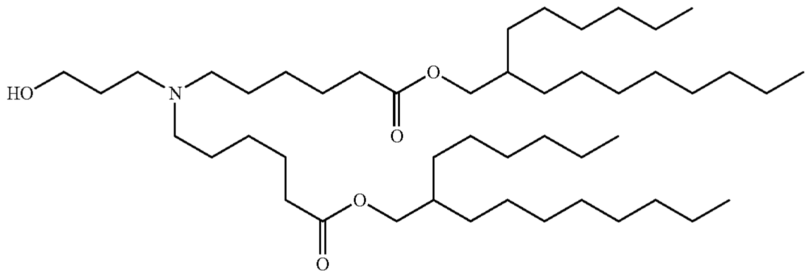 [SMILES: CCCCCCCCC(CCCCCC)COC(=O)CCCCCN(CCCO)CCCCCC(=O)OCC(CCCCCC)CCCCCCCC] |
| 27 | 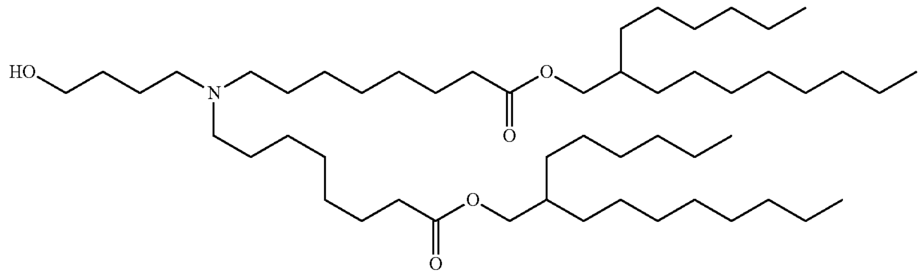 [SMILES: CCCCCCCCC(CCCCCC)COC(=O)CCCCCCCN(CCCCO)CCCCCCCC(=O)OCC(CCCCCC)CCCCCCCC] |

TABLE 10b-continued
| Ionizable lipid number | Structure |
|---|---|
| 28 | 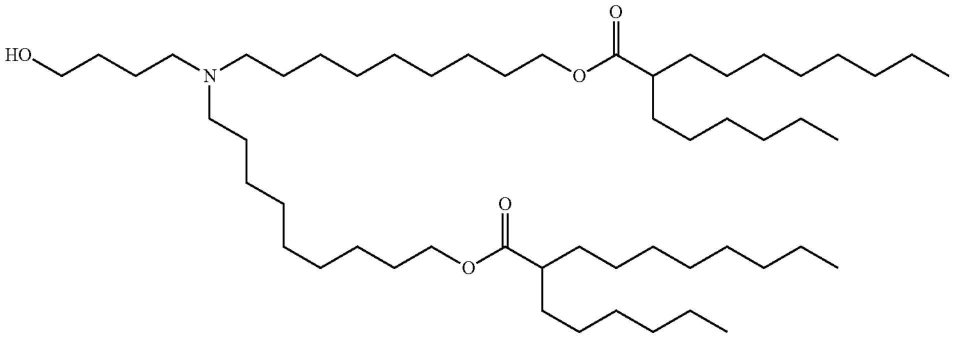 [SMILES: CCCCCCCCC(CCCCCC)C(=O)OCCCCCCCCCN(CCCCO)CCCCCCCCCOC(=O)C(CCCCCC)CCCCCCCC] |
| 29 | 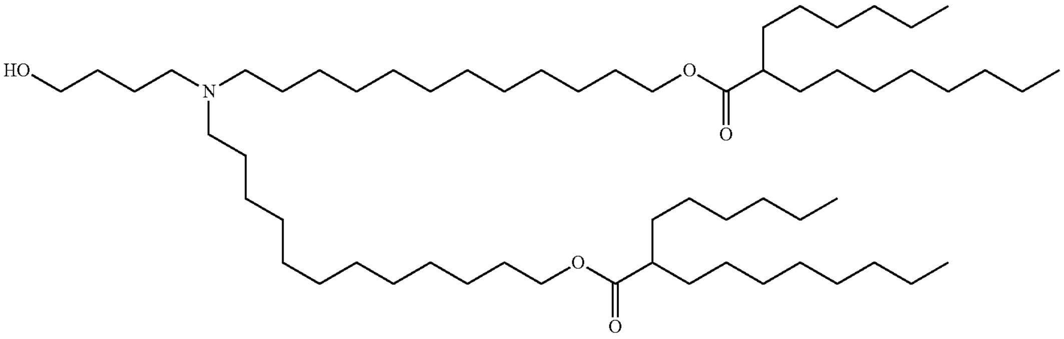 [SMILES: CCCCCCCCC(CCCCCC)C(=O)OCCCCCCCCCCCCN(CCCCO)CCCCCCCCCCCCOC(=O)C(CCCCCC)CCCCCCCC] |
| 30 | 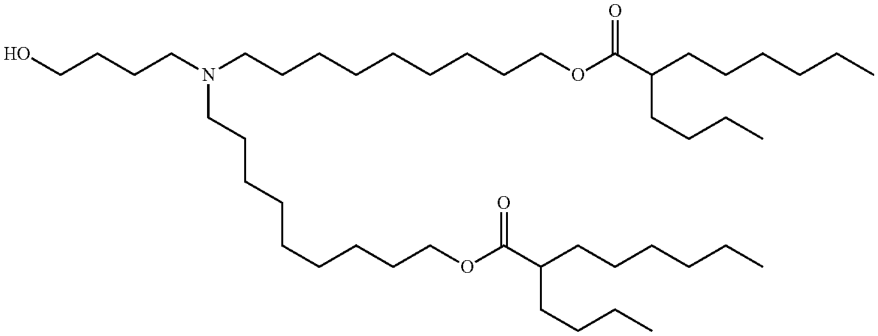 [SMILES: CCCCCCC(CCCC)C(=O)OCCCCCCCCCN(CCCCO)CCCCCCCCCOC(=O)C(CCCC)CCCCCC] |
| 31 | 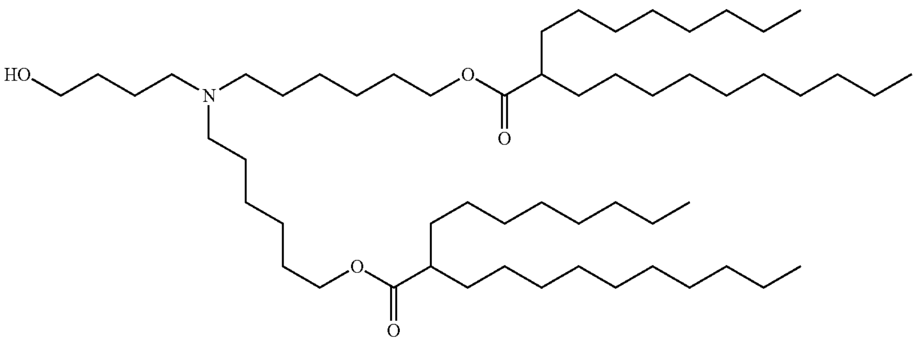 [SMILES: CCCCCCCCCCC(CCCCCCCC)C(=O)OCCCCCCN(CCCCO)CCCCCCOC(=O)C(CCCCCCCC)CCCCCCCCCC] |

TABLE 10b-continued
| Ionizable lipid number | Structure |
|---|---|
| 32 | 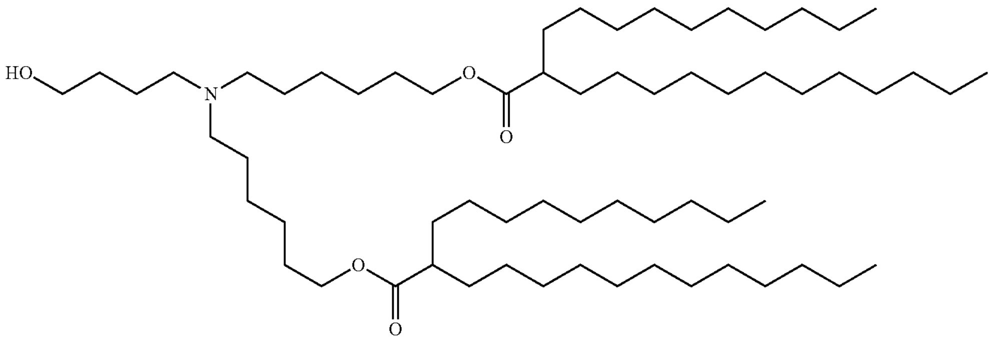 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| 33 | 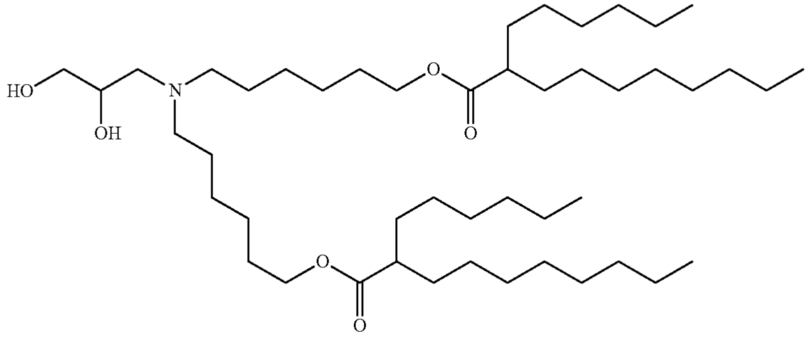 [SMILES: CCCCCCCCC(CCCCCC)C(=O)OCCCCCCN(CCCCCCOC(=O)C(CCCCCC)CCCCCCCC)CC(O)CO] |
| 34 | 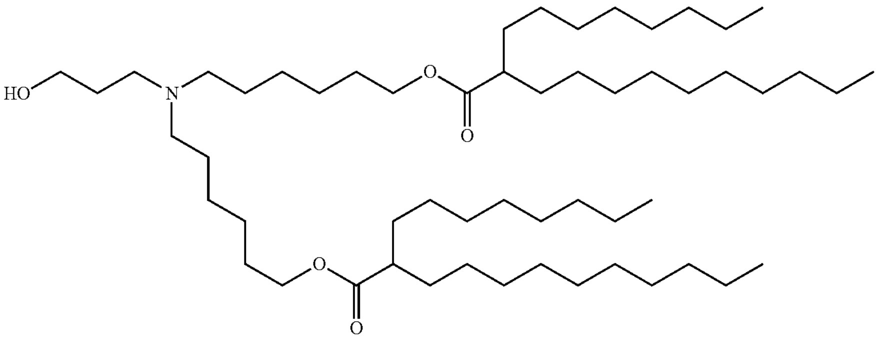 [SMILES: CCCCCCCCCCC(CCCCCCCC)C(=O)OCCCCCCN(CCCO)CCCCCCOC(=O)C(CCCCCCCC)CCCCCCCCCC] |
| 35 | 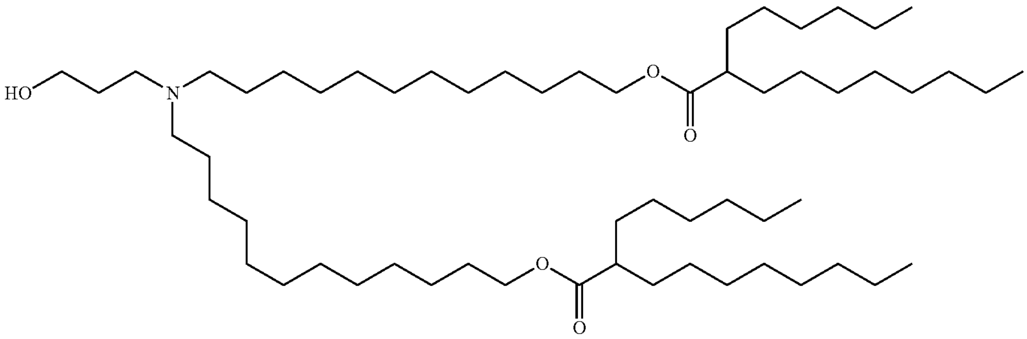 [SMILES: CCCCCCCCC(CCCCCC)C(=O)OCCCCCCCCCCCCN(CCCO)CCCCCCCCCCCCOC(=O)C(CCCCCC)CCCCCCCC] |

TABLE 10b-continued
| Ionizable lipid number | Structure |
|---|---|
| 36 | 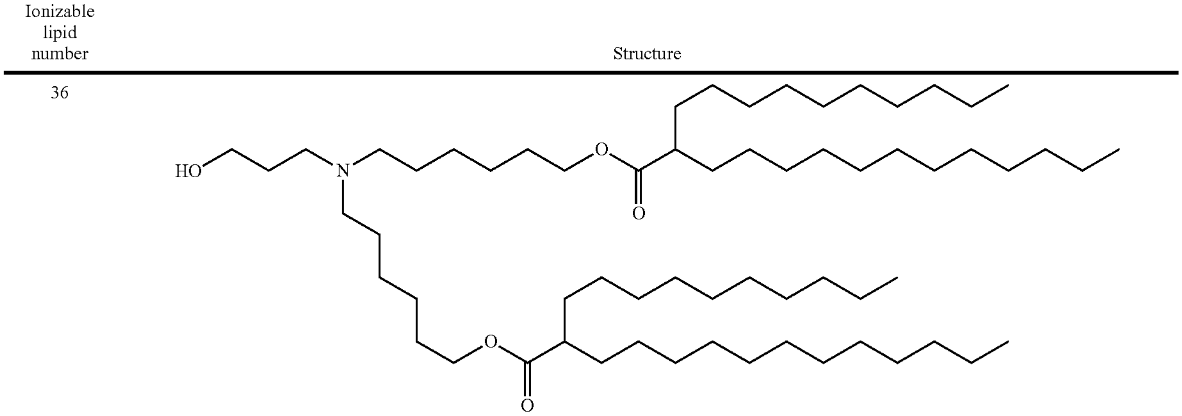 |
| 37 | 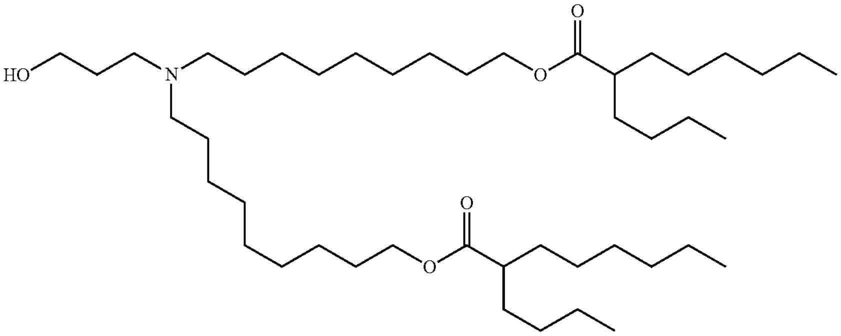 [SMILES: CCCCCCC(CCCC)C(=O)OCCCCCCCCCN(CCCO)CCCCCCCCCOC(=O)C(CCCC)CCCCCC] |
| 38 | 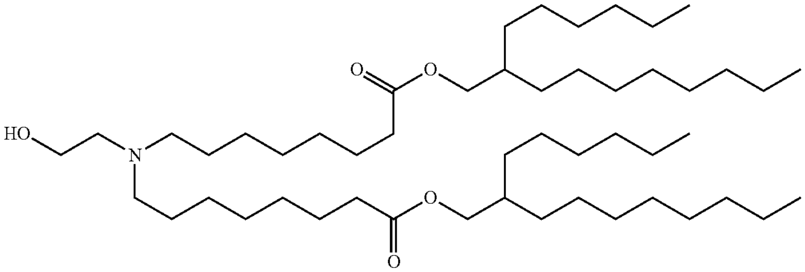 [SMILES: CCCCCCCCC(CCCCCC)COC(=O)CCCCCCCN(CCO)CCCCCCCC(=O)OCC(CCCCCC)CCCCCCCC] |
In some embodiments, an ionizable lipid has one of the structures set forth in Table 10 below.
TABLE 10
| Number | Structure |
|---|---|
| 1 | 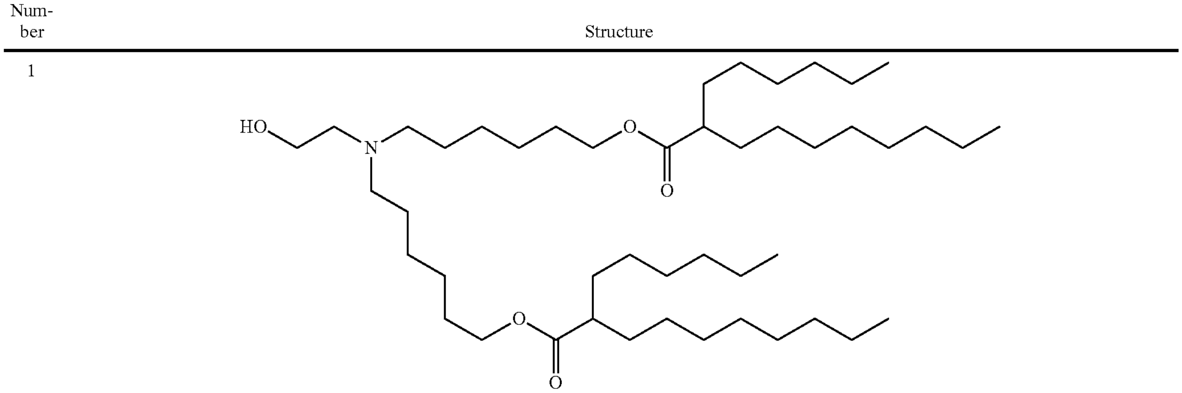 |

TABLE 10-continued
| Number | Structure |
| --- | --- |
| 2 | 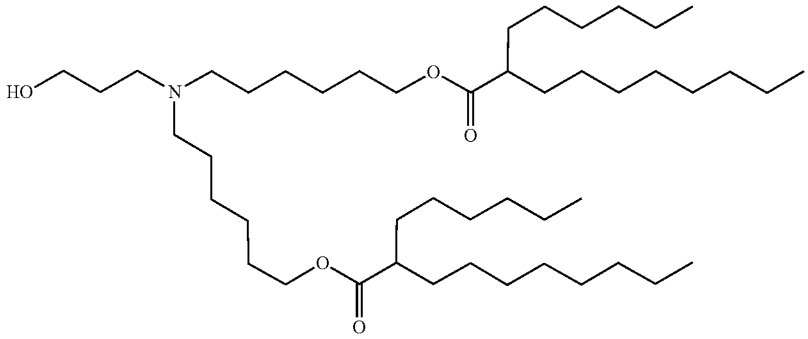 [SMILES: CCCCCCCCC(CCCCCC)C(=O)OCCCCCCN(CCCO)CCCCCCOC(=O)C(CCCCCC)CCCCCCCC] |
| 3 | 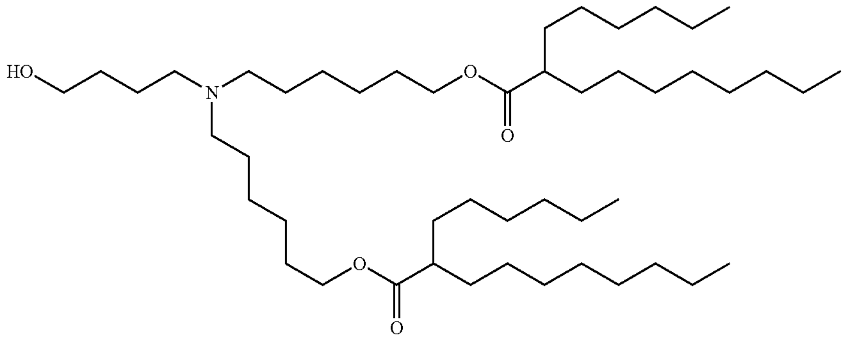 [SMILES: CCCCCCCCC(CCCCCC)C(=O)OCCCCCCN(CCCCO)CCCCCCOC(=O)C(CCCCCC)CCCCCCCC] |
| 4 | 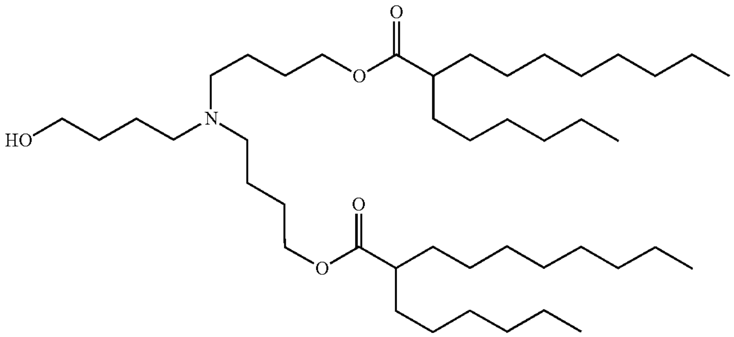 [SMILES: CCCCCCCCC(CCCCCC)C(=O)OCCCCN(CCCCO)CCCCOC(=O)C(CCCCCC)CCCCCCCC] |
| 5 | 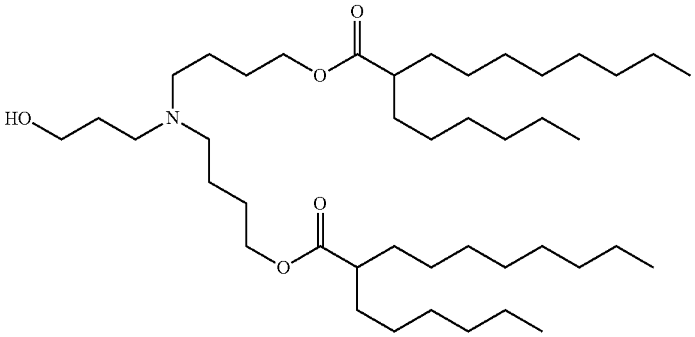 [SMILES: CCCCCCCCC(CCCCCC)C(=O)OCCCCN(CCCO)CCCCOC(=O)C(CCCCCC)CCCCCCCC] |

TABLE 10-continued
| Number | Structure |
| --- | --- |
| 6 | 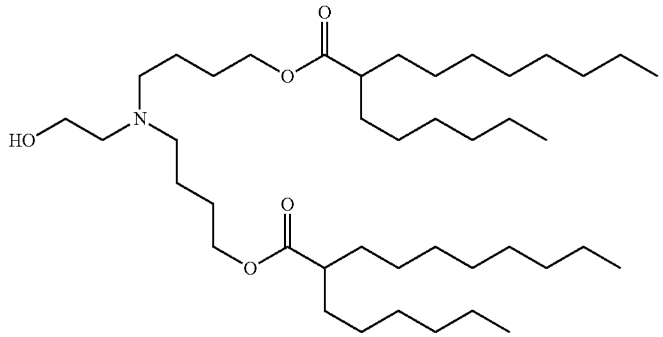 [SMILES: CCCCCCCCC(CCCCCC)C(=O)OCCCCN(CCO)CCCCOC(=O)C(CCCCCC)CCCCCCCC] |
| 7 | 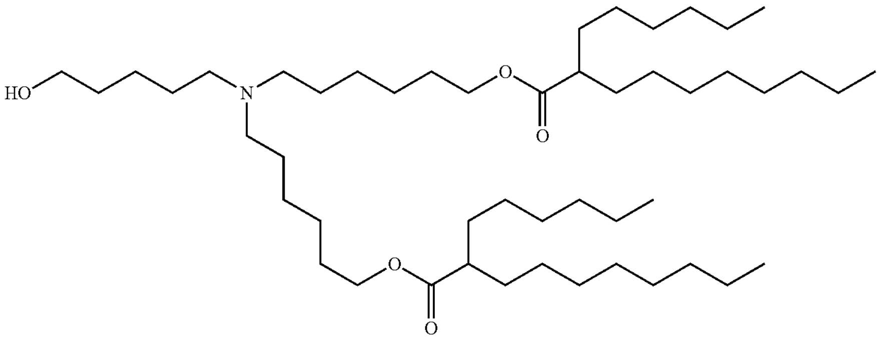 [SMILES: CCCCCCCCC(CCCCCC)C(=O)OCCCCCCN(CCCCCO)CCCCCCOC(=O)C(CCCCCC)CCCCCCCC] |
| 8 | 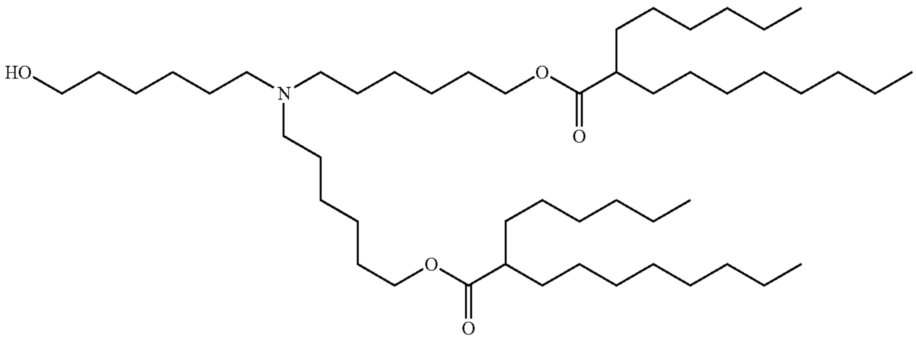 [SMILES: CCCCCCCCC(CCCCCC)C(=O)OCCCCCCN(CCCCCCO)CCCCCCOC(=O)C(CCCCCC)CCCCCCCC] |
| 9 | 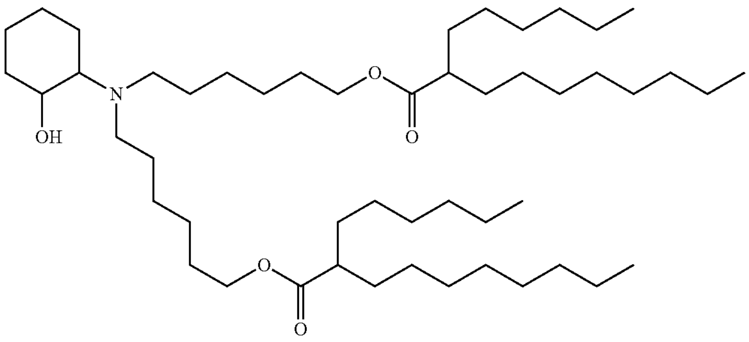 [SMILES: CCCCCCCCC(CCCCCC)C(=O)OCCCCCCN(CCCCCCOC(=O)C(CCCCCC)CCCCCCCC)C1CCCCC1O] |

TABLE 10-continued
| Number | Structure |
| --- | --- |
| 10 | 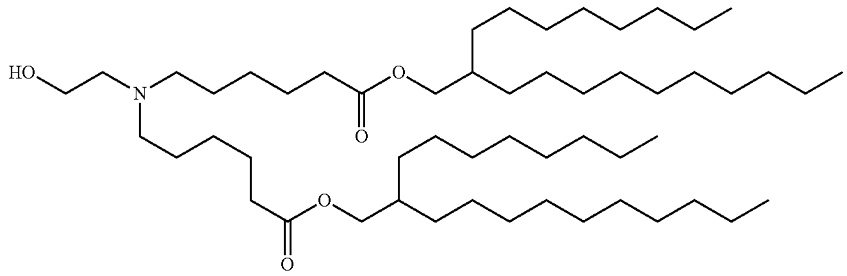 [SMILES: CCCCCCCCCCC(CCCCCCCC)COC(=O)CCCCCN(CCO)CCCCCC(=O)OCC(CCCCCCCC)CCCCCCCCCC] |
| 11 | 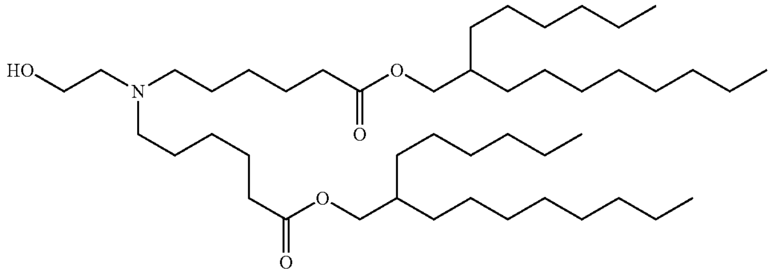 [SMILES: CCCCCCCCC(CCCCCC)COC(=O)CCCCCN(CCO)CCCCCC(=O)OCC(CCCCCC)CCCCCCCC] |
| 12 | 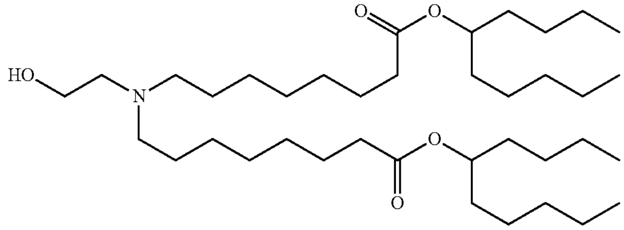 [SMILES: CCCCCC(CCCC)OC(=O)CCCCCCCN(CCO)CCCCCCCC(=O)OC(CCCC)CCCCC] |
| 13 | 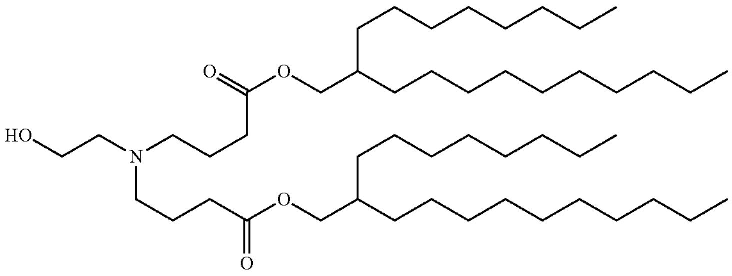 [SMILES: CCCCCCCCCCC(CCCCCCCC)COC(=O)CCCN(CCO)CCCC(=O)OCC(CCCCCCCC)CCCCCCCCCC] |
| 14 | 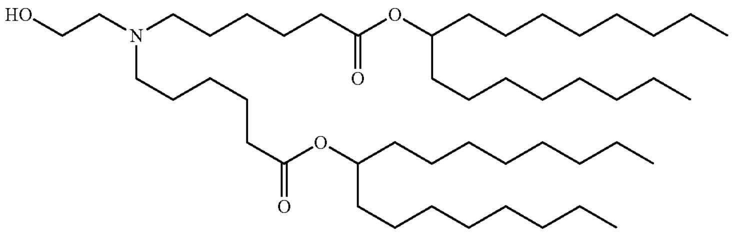 [SMILES: CCCCCCCCC(CCCCCCCC)OC(=O)CCCCCN(CCO)CCCCCC(=O)OC(CCCCCCCC)CCCCCCCC] |
| 15 | 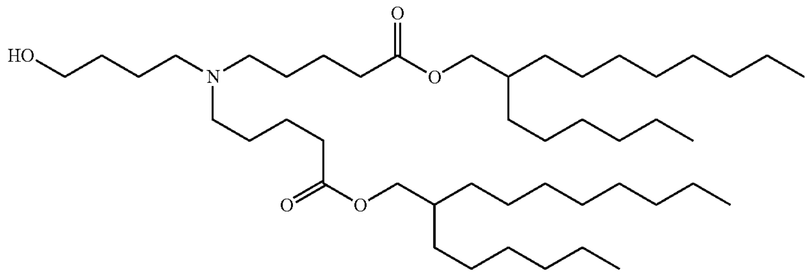 [SMILES: CCCCCCCCC(CCCCCC)COC(=O)CCCCN(CCCCO)CCCCC(=O)OCC(CCCCCC)CCCCCCCC] |

TABLE 10-continued
| Number | Structure |
| --- | --- |
| 16 | 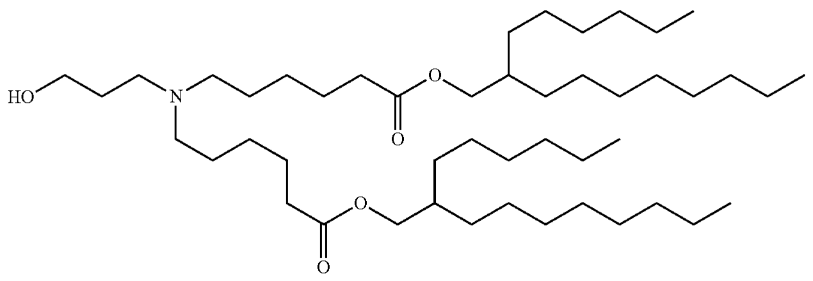 [SMILES: CCCCCCCCC(CCCCCC)COC(=O)CCCCCN(CCCO)CCCCCC(=O)OCC(CCCCCC)CCCCCCCC] |
| 17 | 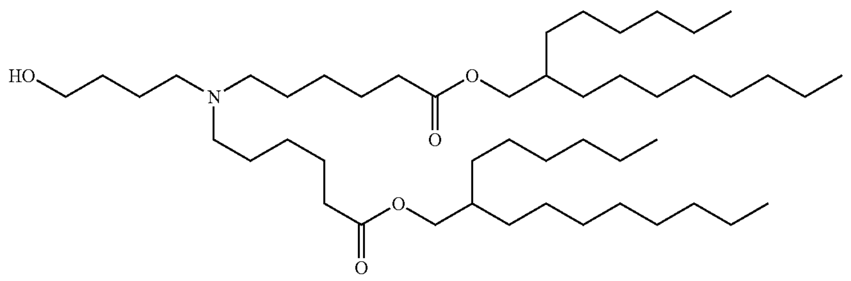 [SMILES: CCCCCCCCC(CCCCCC)COC(=O)CCCCCN(CCCCO)CCCCCC(=O)OCC(CCCCCC)CCCCCCCC] |
| 18 | 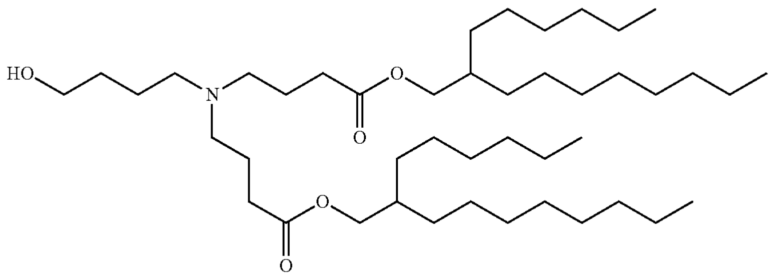 [SMILES: CCCCCCCCC(CCCCCC)COC(=O)CCCN(CCCCO)CCCC(=O)OCC(CCCCCC)CCCCCCCC] |
| 19 | 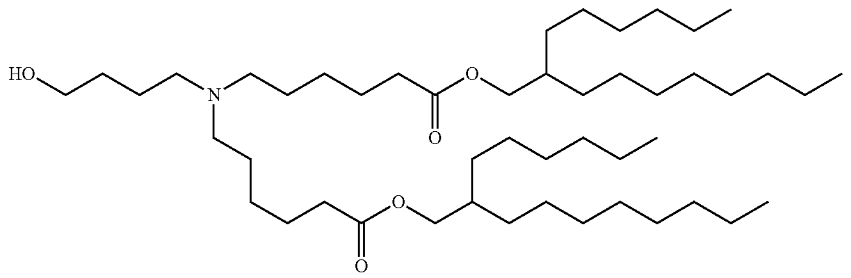 [SMILES: CCCCCCCCC(CCCCCC)COC(=O)CCCCCN(CCCCO)CCCCCC(=O)OCC(CCCCCC)CCCCCCCC] |
| 20 | 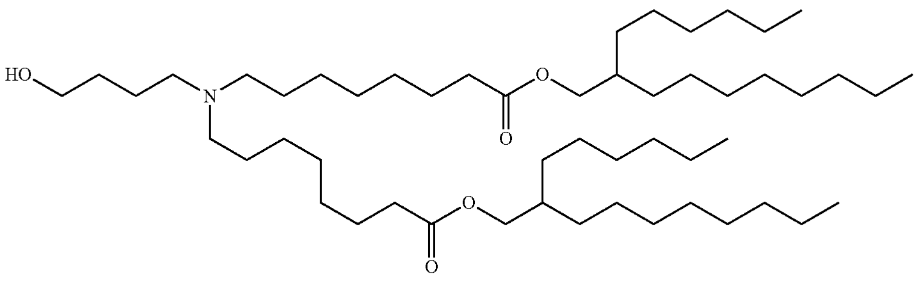 [SMILES: CCCCCCCCC(CCCCCC)COC(=O)CCCCCCCN(CCCCO)CCCCCCCC(=O)OCC(CCCCCC)CCCCCCCC] |

TABLE 10-continued
| Number | Structure |
|---|---|
| 21 | 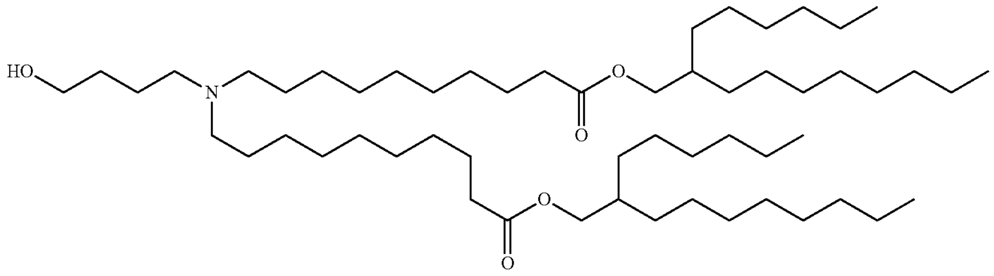 [SMILES: CCCCCCCCC(CCCCCC)COC(=O)CCCCCCCCCN(CCCCO)CCCCCCCCCC(=O)OCC(CCCCCC)CCCCCCCC] |
| 22 | 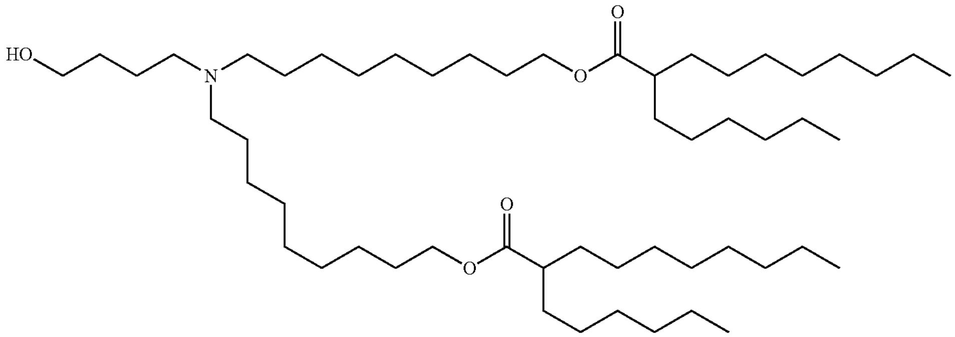 [SMILES: CCCCCCCCC(CCCCCC)C(=O)OCCCCCCCCCN(CCCCO)CCCCCCCCCOC(=O)C(CCCCCC)CCCCCCCC] |
| 23 | 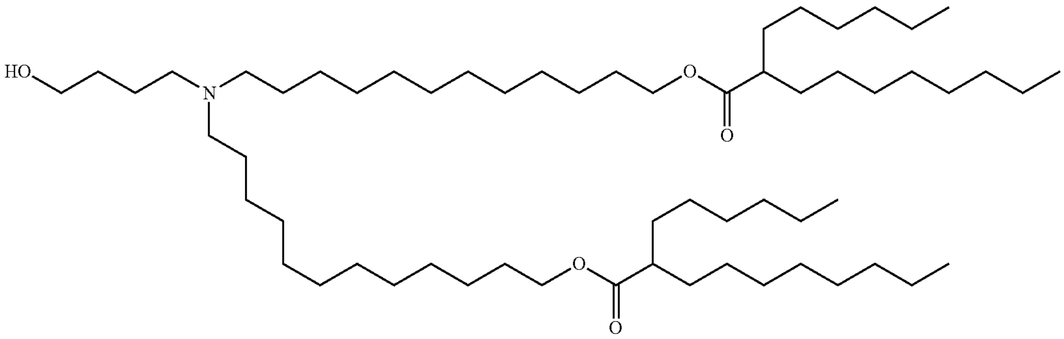 [SMILES: CCCCCCCCC(CCCCCC)C(=O)OCCCCCCCCCCCCN(CCCCO)CCCCCCCCCCCCOC(=O)C(CCCCCC)CCCCCCCC] |
| 24 | 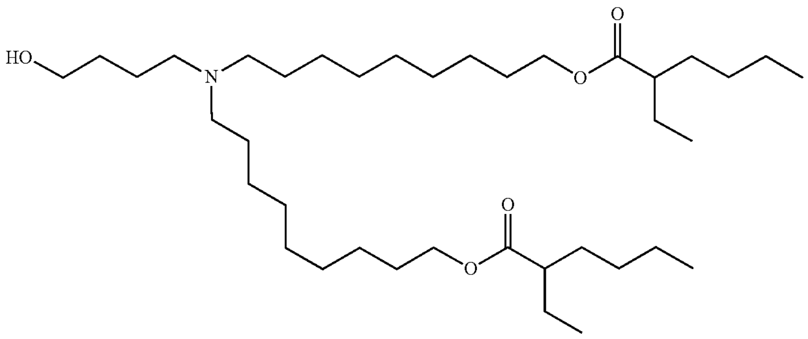 [SMILES: CCCCC(CC)C(=O)OCCCCCCCCCN(CCCCO)CCCCCCCCCOC(=O)C(CC)CCCC] |

TABLE 10-continued
| Number | Structure |
| --- | --- |
| 25 | 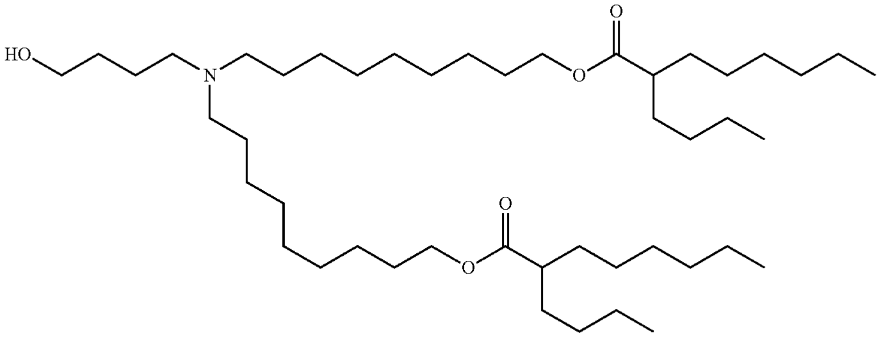 [SMILES: CCCCCCC(CCCC)C(=O)OCCCCCCCCCN(CCCCO)CCCCCCCCCOC(=O)C(CCCC)CCCCCC] |
| 26 | 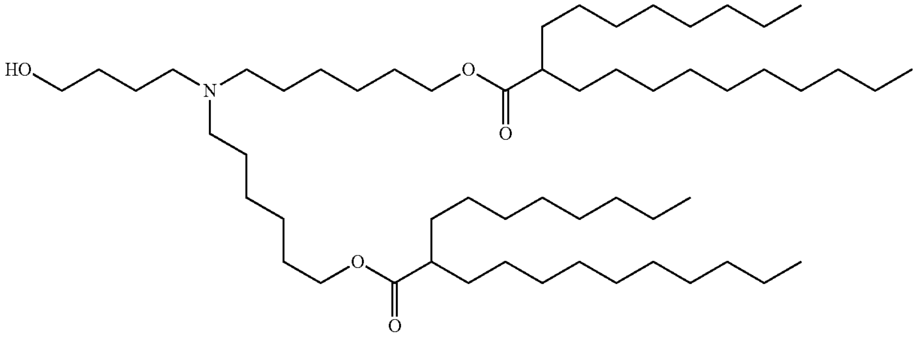 [SMILES: CCCCCCCCCCC(CCCCCCCC)C(=O)OCCCCCCN(CCCCO)CCCCCCOC(=O)C(CCCCCCCC)CCCCCCCCCC] |
| 27 | 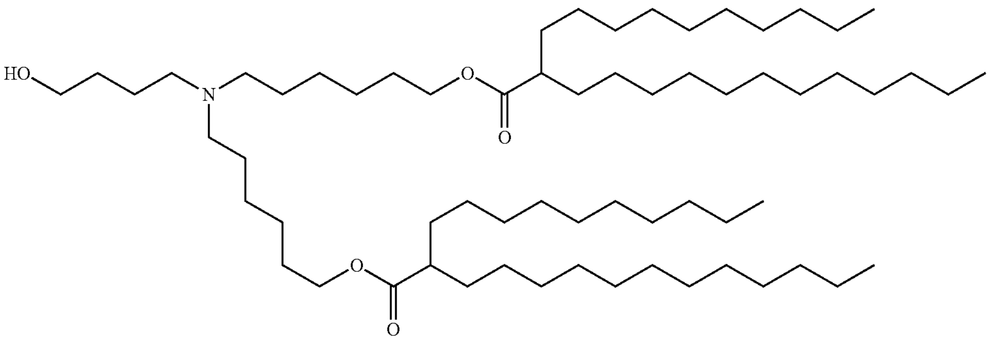 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| 28 | 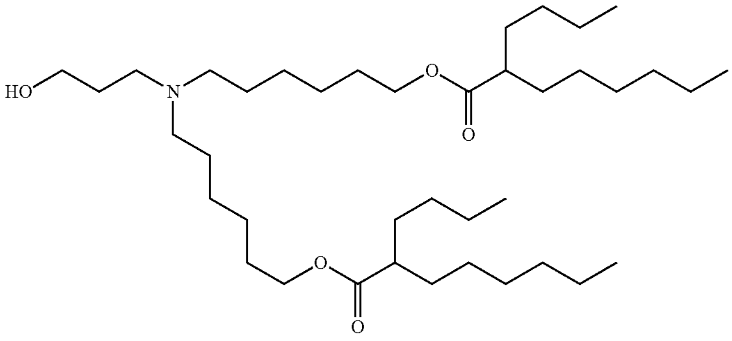 [SMILES: CCCCCCC(CCCC)C(=O)OCCCCCCN(CCCO)CCCCCCOC(=O)C(CCCC)CCCCCC] |

TABLE 10-continued
| Number | Structure |
|---|---|
| 29 | 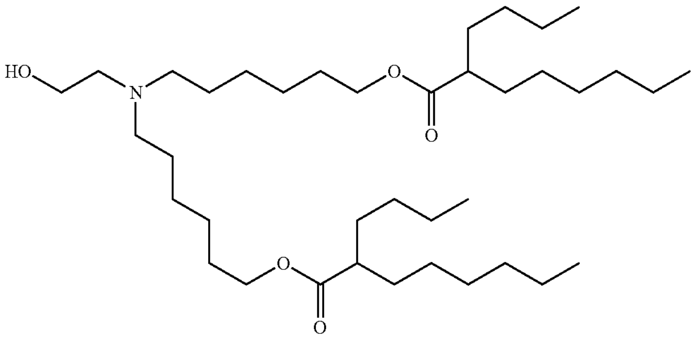 [SMILES: CCCCCCC(CCCC)C(=O)OCCCCCCN(CCO)CCCCCCOC(=O)C(CCCC)CCCCCC] |
| 30 | 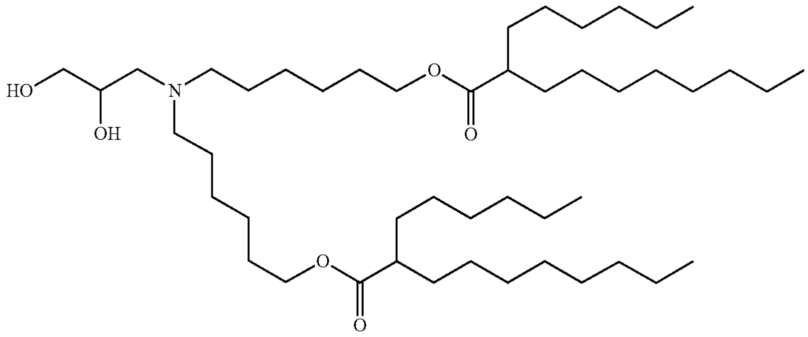 [SMILES: CCCCCCCCC(CCCCCC)C(=O)OCCCCCCN(CCCCCCOC(=O)C(CCCCCC)CCCCCCCC)CC(O)CO] |
| 31 | 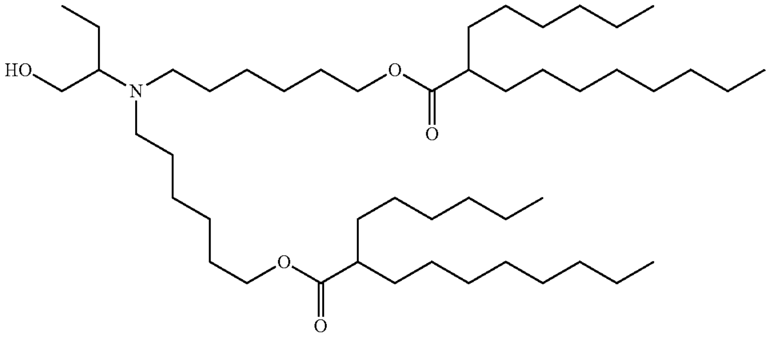 [SMILES: CCCCCCCCC(CCCCCC)C(=O)OCCCCCCN(CCCCCCOC(=O)C(CCCCCC)CCCCCCCC)C(CC)CO] |
| 32 | 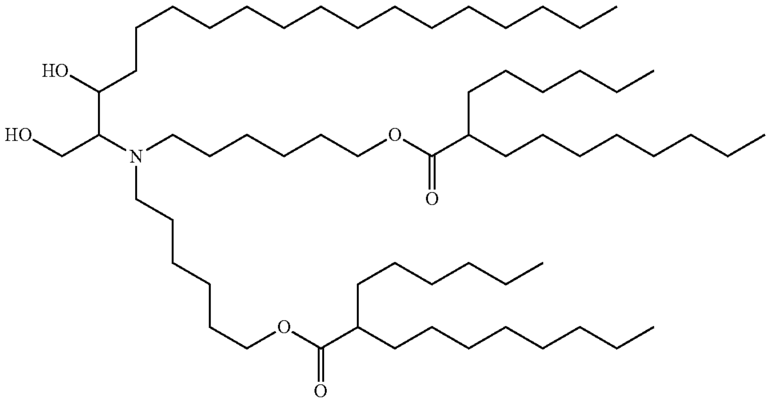 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |

TABLE 10-continued
| Number | Structure |
|---|---|
| 33 | 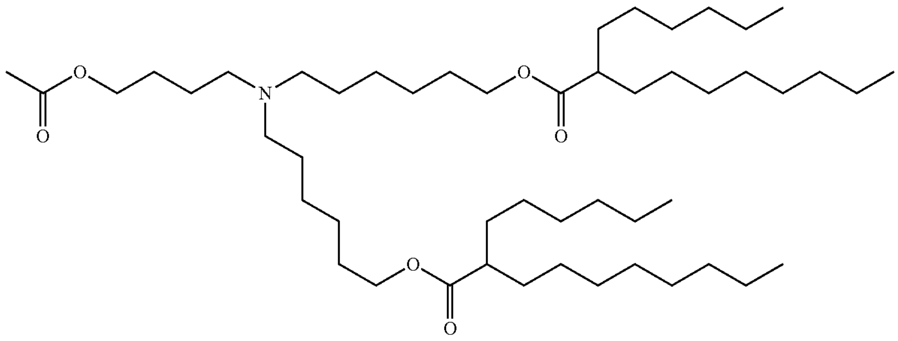 [SMILES: CCCCCCCCC(CCCCCC)C(=O)OCCCCCCN(CCCCCCOC(=O)C(CCCCCC)CCCCCCCC)CCCCOC(C)=O] |
| 34 | 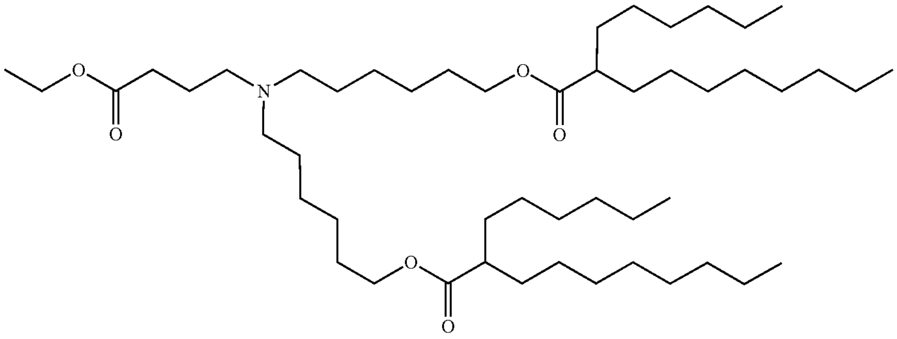 [SMILES: CCCCCCCCC(CCCCCC)C(=O)OCCCCCCN(CCCCCCOC(=O)C(CCCCCC)CCCCCCCC)CCCC(=O)OCC] |
| 35 | 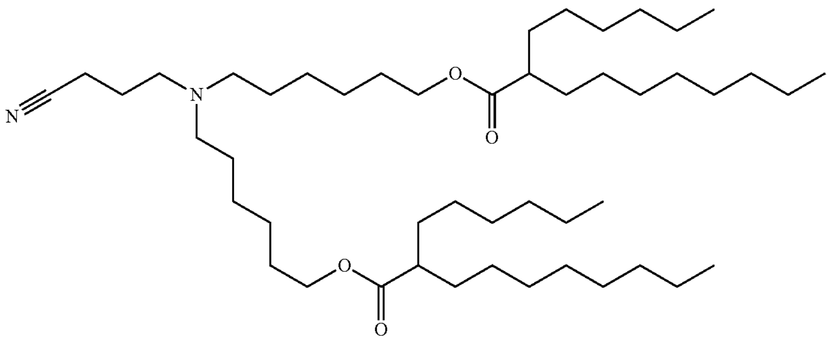 [SMILES: CCCCCCCCC(CCCCCC)C(=O)OCCCCCCN(CCCC#N)CCCCCCOC(=O)C(CCCCCC)CCCCCCCC] |
| 36 | 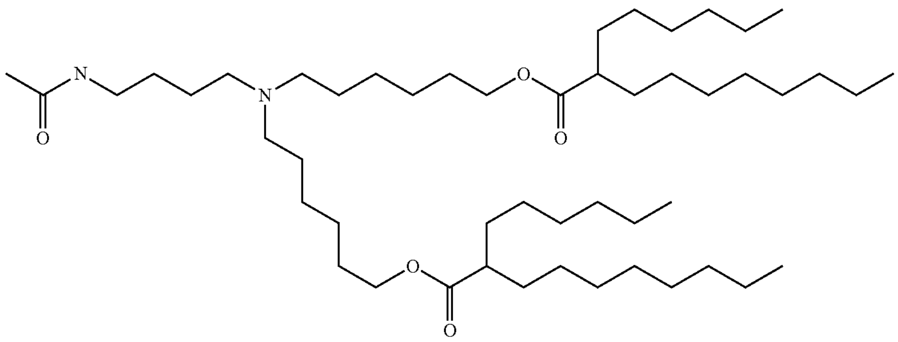 |

TABLE 10-continued
| Number | Structure |
|---|---|
| 37 | 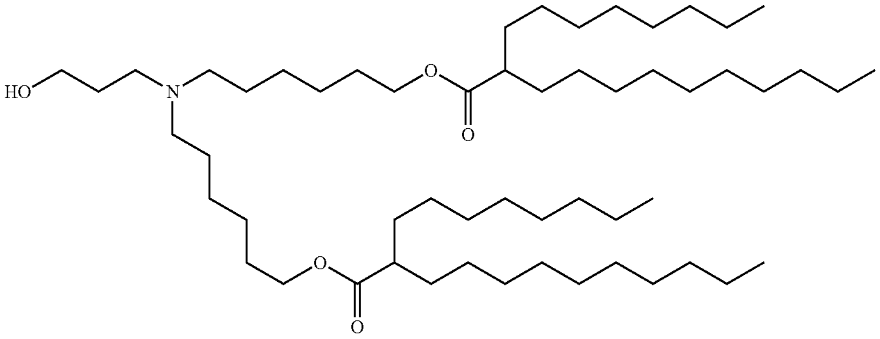 [SMILES: CCCCCCCCCCC(CCCCCCCC)C(=O)OCCCCCCN(CCCO)CCCCCCOC(=O)C(CCCCCCCC)CCCCCCCCCC] |
| 38 | 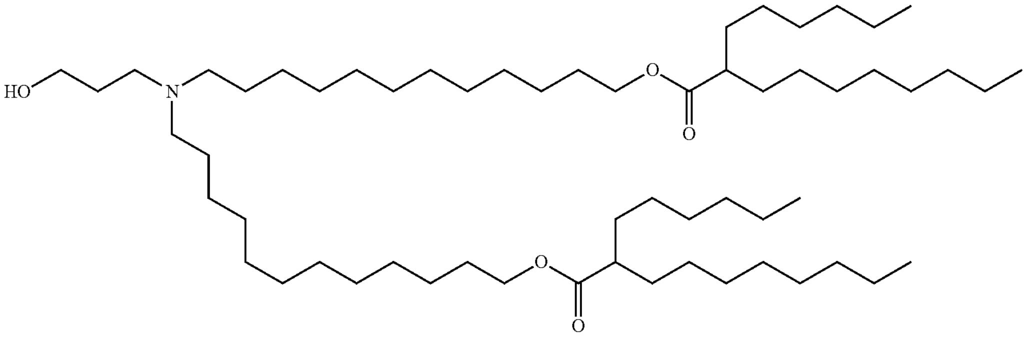 [SMILES: CCCCCCCCC(CCCCCC)C(=O)OCCCCCCCCCCCCN(CCCO)CCCCCCCCCCCCOC(=O)C(CCCCCC)CCCCCCCC] |
| 39 | 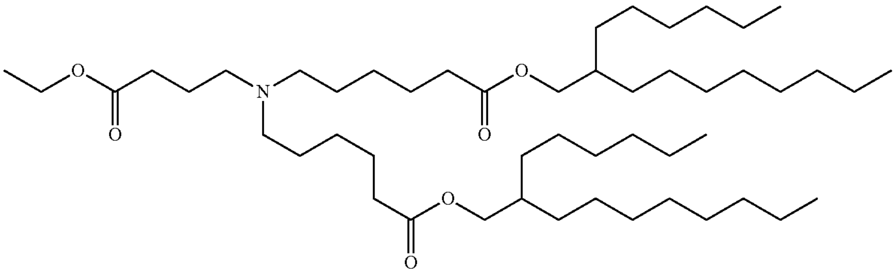 [SMILES: CCCCCCCCC(CCCCCC)COC(=O)CCCCCN(CCCCCC(=O)OCC(CCCCCC)CCCCCCCC)CCCC(=O)OCC] |
| 40 | 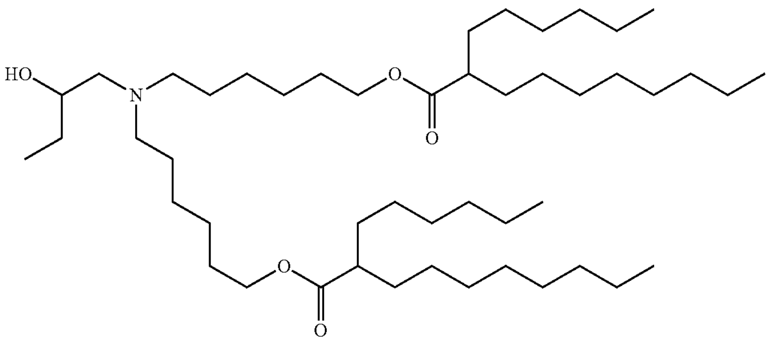 [SMILES: CCCCCCCCC(CCCCCC)C(=O)OCCCCCCN(CCCCCCOC(=O)C(CCCCCC)CCCCCCCC)CC(O)CC] |

TABLE 10-continued
| Number | Structure |
|---|---|
| 41 | 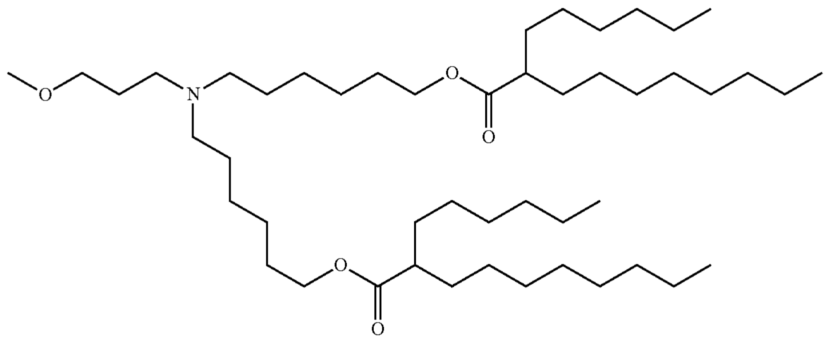 [SMILES: CCCCCCCCC(CCCCCC)C(=O)OCCCCCCN(CCCCCCOC(=O)C(CCCCCC)CCCCCCCC)CCCOC] |
| 42 | 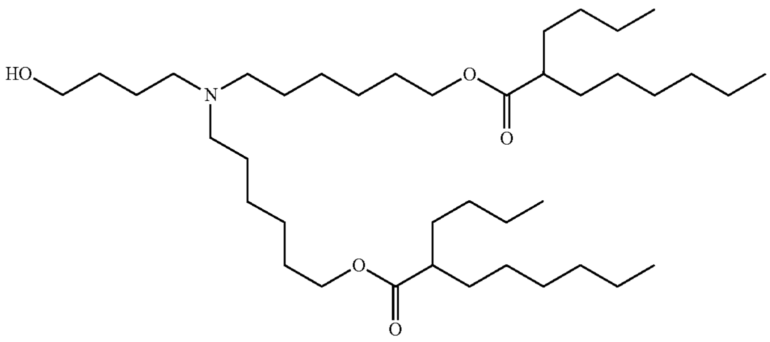 [SMILES: CCCCCCC(CCCC)C(=O)OCCCCCCN(CCCCO)CCCCCCOC(=O)C(CCCC)CCCCCC] |
| 43 | 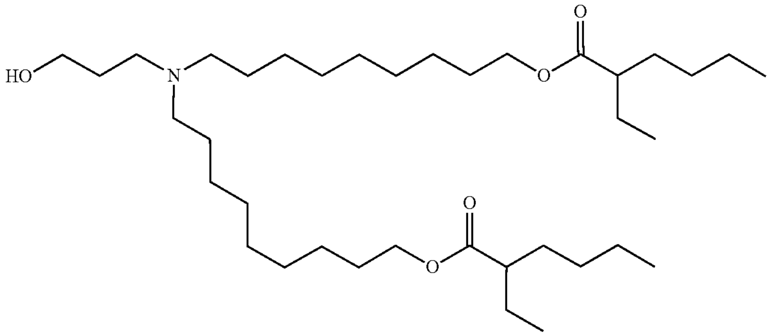 [SMILES: CCCCC(CC)C(=O)OCCCCCCCCCN(CCCO)CCCCCCCCCOC(=O)C(CC)CCCC] |
| 44 | 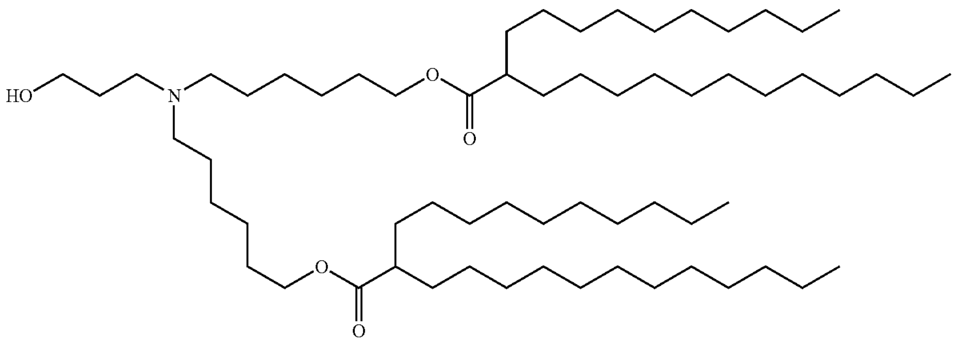 [SMILES: CCCCCCCCCCCCC(CCCCCCCCCC)C(=O)OCCCCCCN(CCCO)CCCCCCOC(=O)C(CCCCCCCCCC)CCCCCCCCCCCC] |

TABLE 10-continued
| Number | Structure |
| --- | --- |
| 45 | 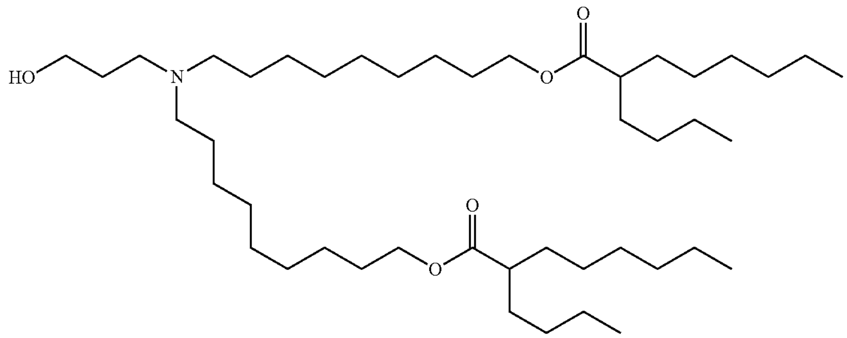 [SMILES: CCCCCCC(CCCC)C(=O)OCCCCCCCCCN(CCCO)CCCCCCCCCOC(=O)C(CCCC)CCCCCC] |
| 46 | 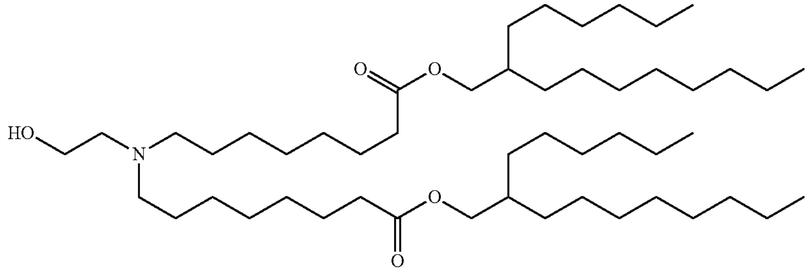 [SMILES: CCCCCCCCC(CCCCCC)COC(=O)CCCCCCCN(CCO)CCCCCCCC(=O)OCC(CCCCCC)CCCCCCCC] |
| 47 | 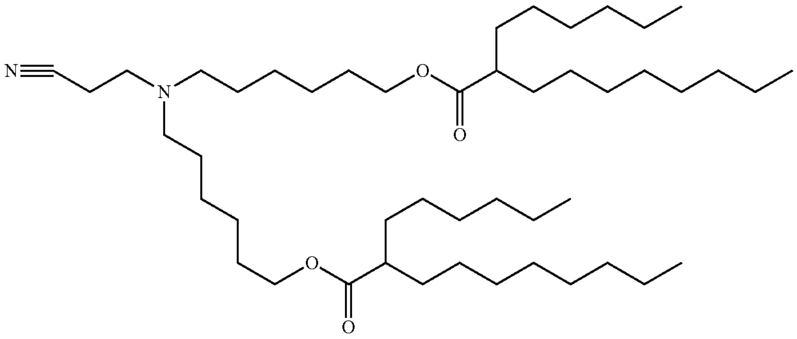 [SMILES: CCCCCCCCC(CCCCCC)C(=O)OCCCCCCN(CCC#N)CCCCCCOC(=O)C(CCCCCC)CCCCCCCC] |
| 48 | 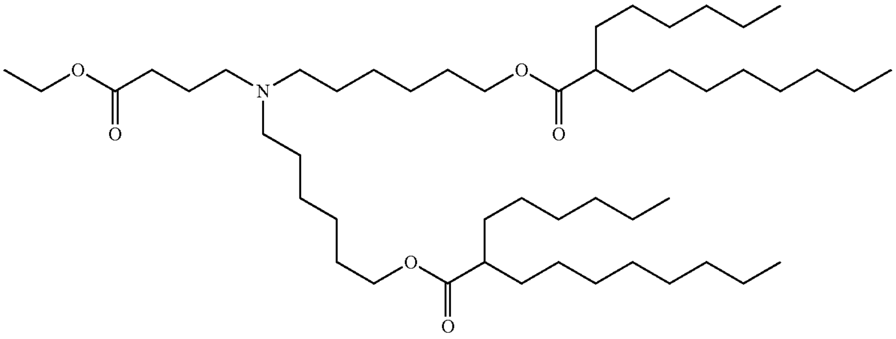 [SMILES: CCCCCCCCC(CCCCCC)C(=O)OCCCCCCN(CCCCCCOC(=O)C(CCCCCC)CCCCCCCC)CCCC(=O)OCC] |

TABLE 10-continued
| Number | Structure |
| --- | --- |
| 49 | 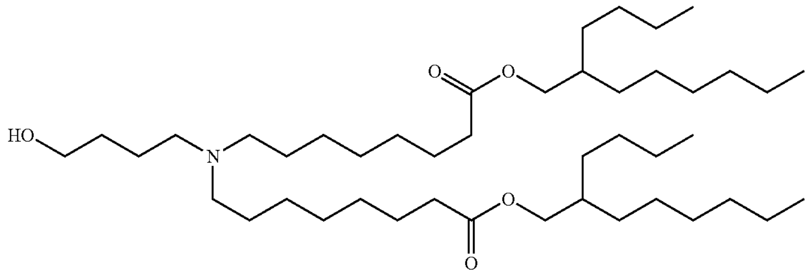 [SMILES: CCCCCCC(CCCC)COC(=O)CCCCCCCN(CCCCO)CCCCCCCC(=O)OCC(CCCC)CCCCCC] |
In some embodiments, the ionizable lipid has one of the structures set forth in Table 11 below. In some embodiments, the ionizable lipid as set forth in Table 11 is as described in international patent application PCT/US2010/061058.
TABLE 11
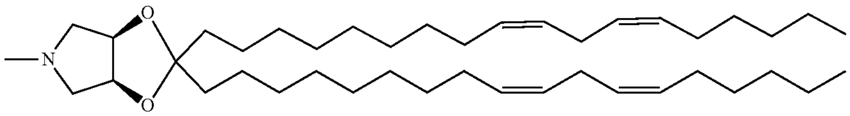
meso, cis
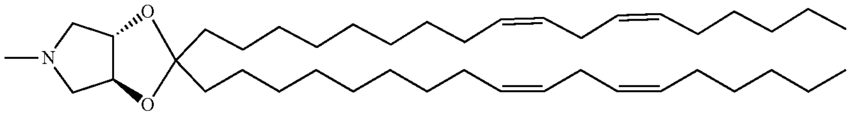 [SMILES: CCCCC/C=C\C/C=C\CCCCCCCCC1(CCCCCCCC/C=C\C/C=C\CCCCC)O[C@H]2CN(C)C[C@@H]2O1]
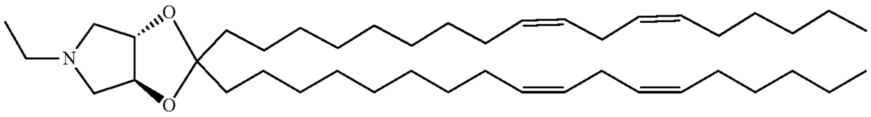 [SMILES: CCCCC/C=C\C/C=C\CCCCCCCCC1(CCCCCCCC/C=C\C/C=C\CCCCC)O[C@H]2CN(CC)C[C@@H]2O1]
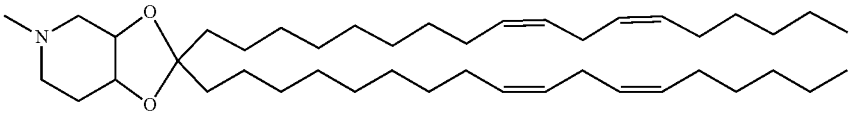
Racemic, cis
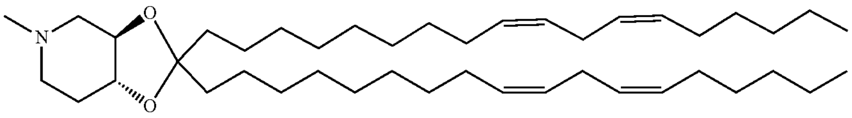
Racemic, trans
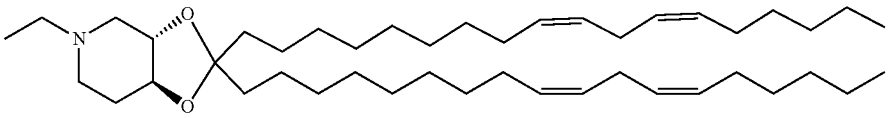 [SMILES: CCCCC/C=C\C/C=C\CCCCCCCCC1(CCCCCCCC/C=C\C/C=C\CCCCC)O[C@H]2CCN(CC)C[C@@H]2O1]
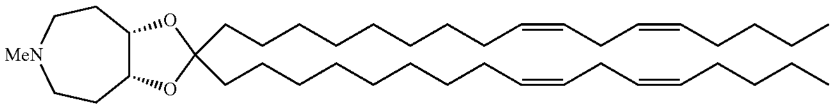 [SMILES: CCCC/C=C\C/C=C\CCCCCCCCC1(CCCCCCCC/C=C\C/C=C\CCCC)O[C@H]2CCN(C)CC[C@H]2O1]
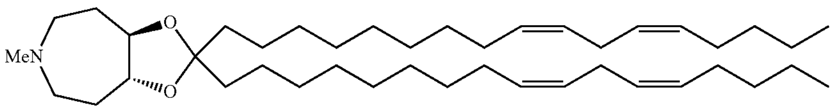 [SMILES: CCCC/C=C\C/C=C\CCCCCCCCC1(CCCCCCCC/C=C\C/C=C\CCCC)O[C@@H]2CCN(C)CC[C@H]2O1]

TABLE 11-continued
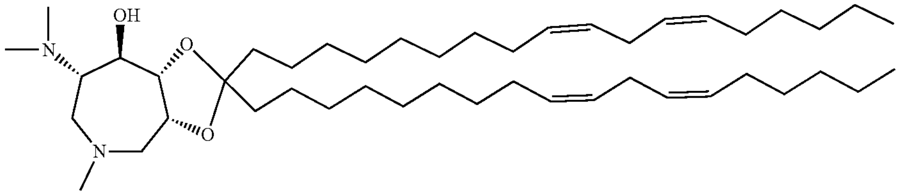 [SMILES: CCCCC/C=C\C/C=C\CCCCCCCCC1(CCCCCCCC/C=C\C/C=C\CCCCC)O[C@H]2[C@H](O)[C@@H](N(C)C)CN(C)C[C@H]2O1]
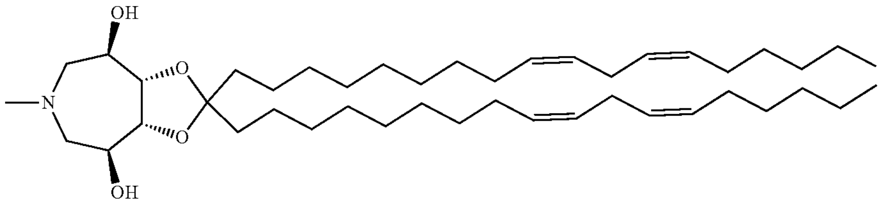 [SMILES: CCCCC/C=C\C/C=C\CCCCCCCCC1(CCCCCCCC/C=C\C/C=C\CCCCC)O[C@@H]2[C@H](O1)[C@@H](O)CN(C)C[C@H]2O]
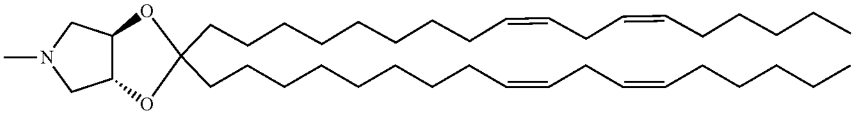
Racemic, trans
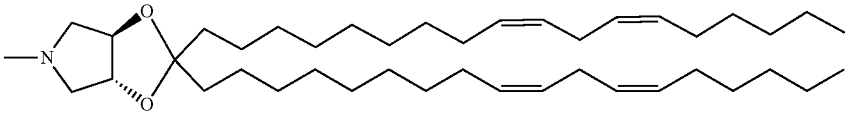 [SMILES: CCCCC/C=C\C/C=C\CCCCCCCCC1(CCCCCCCC/C=C\C/C=C\CCCCC)O[C@@H]2CN(C)C[C@H]2O1]
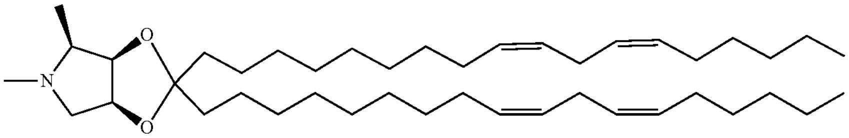 [SMILES: CCCCC/C=C\C/C=C\CCCCCCCCC1(CCCCCCCC/C=C\C/C=C\CCCCC)O[C@H]2[C@H](CN(C)[C@H]2C)O1]
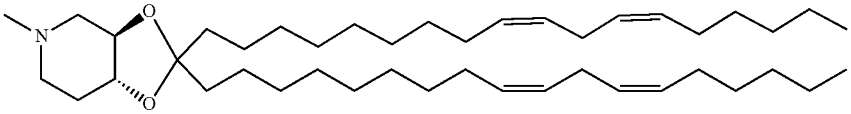 [SMILES: CCCCC/C=C\C/C=C\CCCCCCCCC1(CCCCCCCC/C=C\C/C=C\CCCCC)O[C@@H]2CCN(C)C[C@H]2O1]
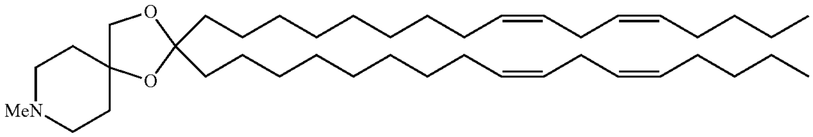 [SMILES: CCCC/C=C\C/C=C\CCCCCCCCC1(CCCCCCCC/C=C\C/C=C\CCCC)OCC2(CCN(C)CC2)O1]
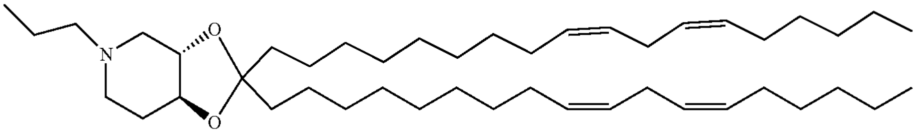 [SMILES: CCCCC/C=C\C/C=C\CCCCCCCCC1(CCCCCCCC/C=C\C/C=C\CCCCC)O[C@H]2CCN(CCC)C[C@@H]2O1]
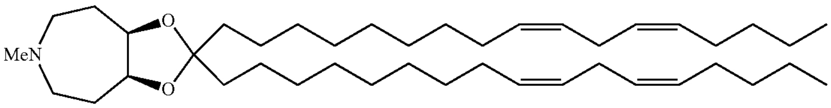 [SMILES: CCCC/C=C\C/C=C\CCCCCCCCC1(CCCCCCCC/C=C\C/C=C\CCCC)O[C@H]2CCN(C)CC[C@H]2O1]
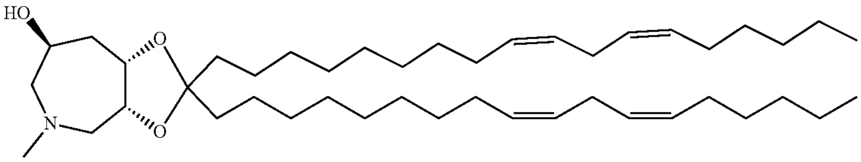 [SMILES: CCCCC/C=C\C/C=C\CCCCCCCCC1(CCCCCCCC/C=C\C/C=C\CCCCC)O[C@H]2C[C@H](O)CN(C)C[C@H]2O1]

TABLE 11-continued
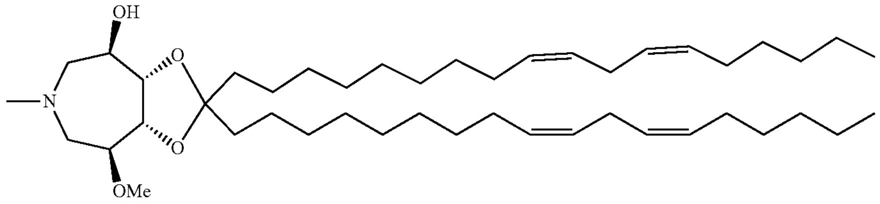 [SMILES: CCCCC/C=C\C/C=C\CCCCCCCCC1(CCCCCCCC/C=C\C/C=C\CCCCC)O[C@@H]2[C@H](O1)[C@@H](OC)CN(C)C[C@H]2O]
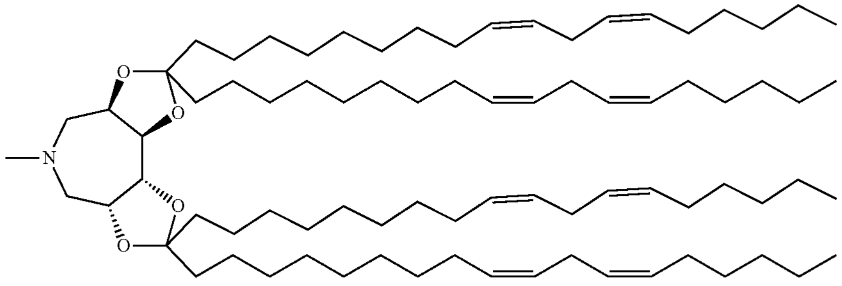 [SMILES: CCCCC/C=C\C/C=C\CCCCCCCCC1(CCCCCCCC/C=C\C/C=C\CCCCC)O[C@H]2[C@@H]3OC(CCCCCCCC/C=C\C/C=C\CCCCC)(CCCCCCCC/C=C\C/C=C\CCCCC)O[C@@H]3CN(C)C[C@H]2O1]
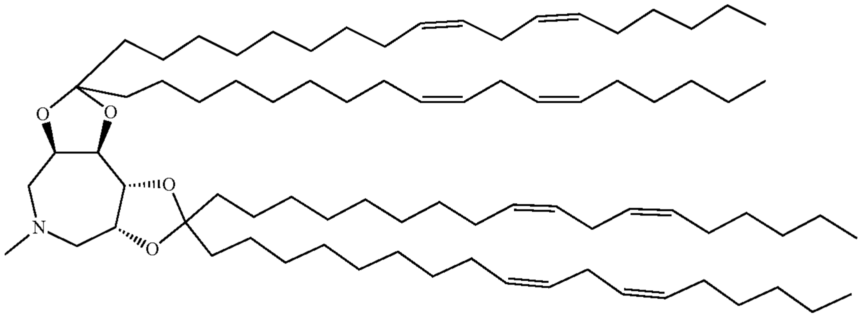 [SMILES: CCCCC/C=C\C/C=C\CCCCCCCCC1(CCCCCCCC/C=C\C/C=C\CCCCC)O[C@H]2[C@@H]3OC(CCCCCCCC/C=C\C/C=C\CCCCC)(CCCCCCCC/C=C\C/C=C\CCCCC)O[C@@H]3CN(C)C[C@H]2O1]
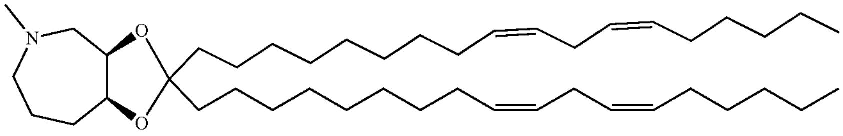
Racemic cis
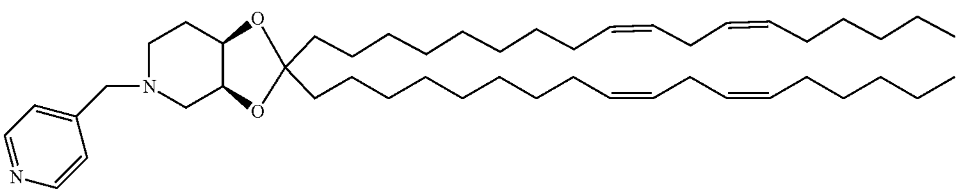 [SMILES: CCCCC/C=C\C/C=C\CCCCCCCCC1(CCCCCCCC/C=C\C/C=C\CCCCC)O[C@H]2CN(Cc3ccncc3)CC[C@H]2O1]
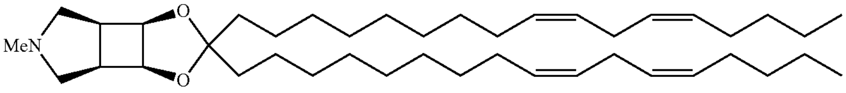 [SMILES: CCCC/C=C\C/C=C\CCCCCCCCC1(CCCCCCCC/C=C\C/C=C\CCCC)O[C@@H]2[C@@H]3CN(C)C[C@@H]3[C@@H]2O1]
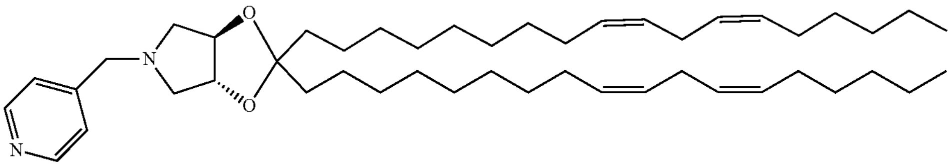 [SMILES: CCCCC/C=C\C/C=C\CCCCCCCCC1(CCCCCCCC/C=C\C/C=C\CCCCC)O[C@@H]2CN(Cc3ccncc3)C[C@H]2O1]
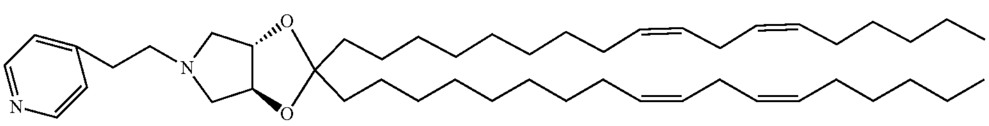 [SMILES: CCCCC/C=C\C/C=C\CCCCCCCCC1(CCCCCCCC/C=C\C/C=C\CCCCC)O[C@H]2CN(CCc3ccncc3)C[C@@H]2O1]

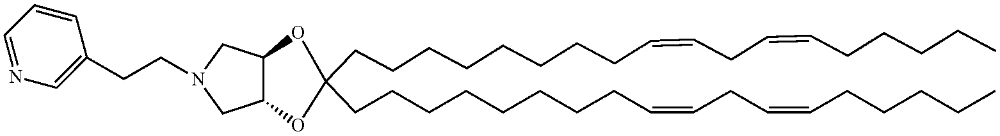 [SMILES: CCCCC/C=C\C/C=C\CCCCCCCCC1(CCCCCCCC/C=C\C/C=C\CCCCC)O[C@@H]2CN(CCc3cccnc3)C[C@H]2O1]
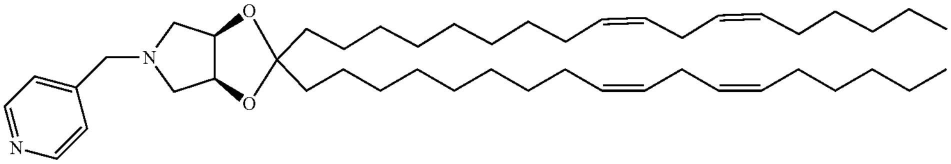 [SMILES: CCCCC/C=C\C/C=C\CCCCCCCCC1(CCCCCCCC/C=C\C/C=C\CCCCC)O[C@H]2CN(Cc3ccncc3)C[C@H]2O1]
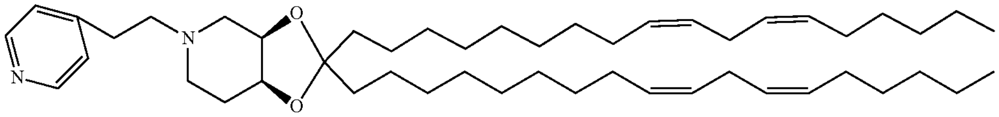 [SMILES: CCCCC/C=C\C/C=C\CCCCCCCCC1(CCCCCCCC/C=C\C/C=C\CCCCC)O[C@H]2CCN(CCc3ccncc3)C[C@H]2O1]
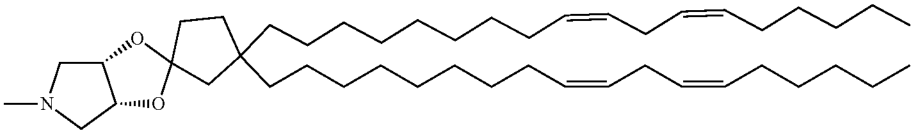
cis Racemic and optically pure
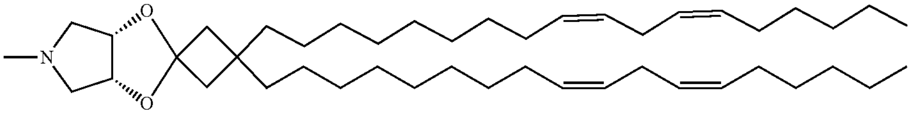
Racemic and optically pure
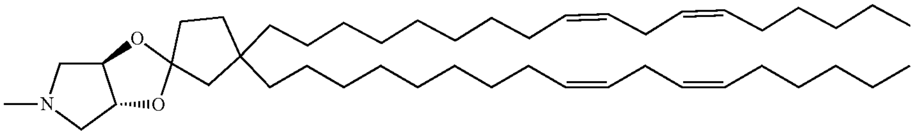 [SMILES: CCCCC/C=C\C/C=C\CCCCCCCCC1(CCCCCCCC/C=C\C/C=C\CCCCC)CCC2(C1)O[C@@H]1CN(C)C[C@H]1O2]
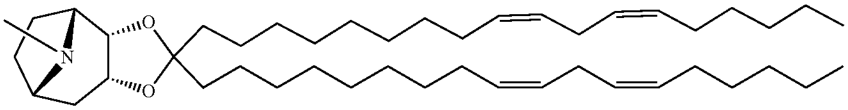 [SMILES: CCCCC/C=C\C/C=C\CCCCCCCCC1(CCCCCCCC/C=C\C/C=C\CCCCC)O[C@H]2[C@H]3CC[C@@H](C[C@H]2O1)N3C]
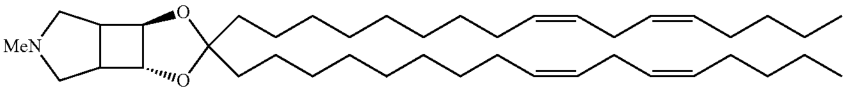 [SMILES: CCCC/C=C\C/C=C\CCCCCCCCC1(CCCCCCCC/C=C\C/C=C\CCCC)O[C@@H]2C3CN(C)CC3[C@H]2O1]
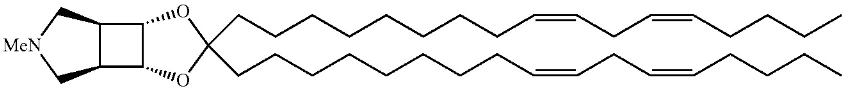
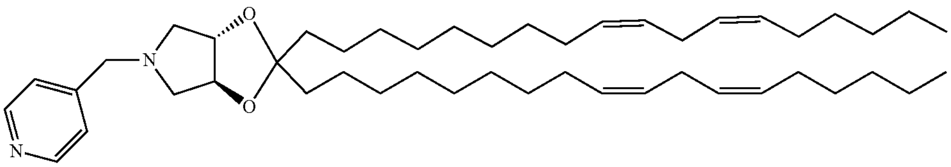 [SMILES: CCCCC/C=C\C/C=C\CCCCCCCCC1(CCCCCCCC/C=C\C/C=C\CCCCC)O[C@H]2CN(Cc3ccncc3)C[C@@H]2O1]
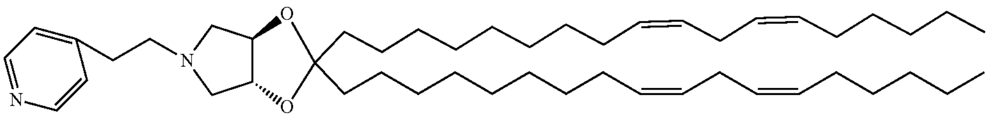 [SMILES: CCCCC/C=C\C/C=C\CCCCCCCCC1(CCCCCCCC/C=C\C/C=C\CCCCC)O[C@@H]2CN(CCc3ccncc3)C[C@H]2O1]

TABLE 11-continued
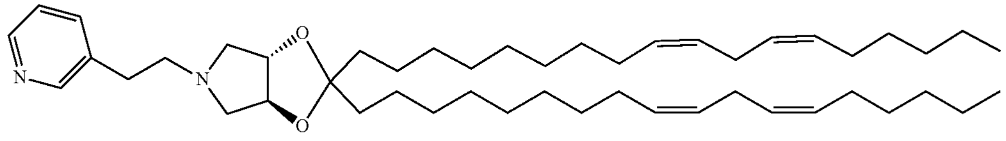 [SMILES: CCCCC/C=C\C/C=C\CCCCCCCCC1(CCCCCCCC/C=C\C/C=C\CCCCC)O[C@H]2CN(CCc3cccnc3)C[C@@H]2O1]
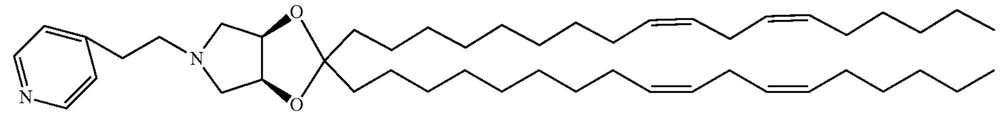 [SMILES: CCCCC/C=C\C/C=C\CCCCCCCCC1(CCCCCCCC/C=C\C/C=C\CCCCC)O[C@H]2CN(CCc3ccncc3)C[C@H]2O1]
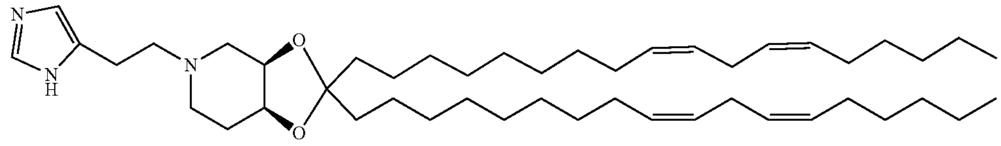 [SMILES: CCCCC/C=C\C/C=C\CCCCCCCCC1(CCCCCCCC/C=C\C/C=C\CCCCC)O[C@H]2CCN(CCc3cnc[nH]3)C[C@H]2O1]
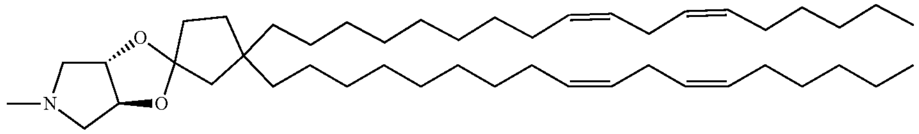 [SMILES: CCCCC/C=C\C/C=C\CCCCCCCCC1(CCCCCCCC/C=C\C/C=C\CCCCC)CCC2(C1)O[C@H]1CN(C)C[C@@H]1O2]
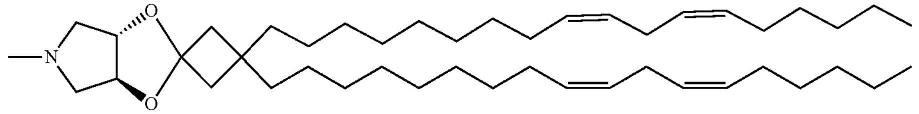 [SMILES: CCCCC/C=C\C/C=C\CCCCCCCCC1(CCCCCCCC/C=C\C/C=C\CCCCC)CC2(C1)O[C@H]1CN(C)C[C@@H]1O2]
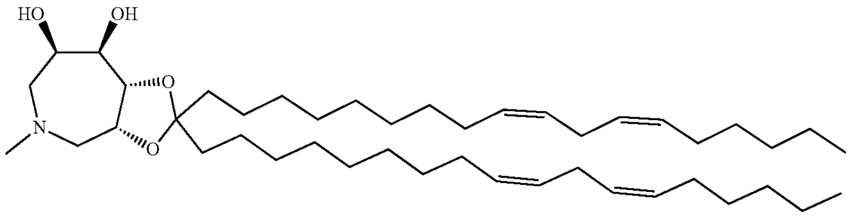 [SMILES: CCCCC/C=C\C/C=C\CCCCCCCCC1(CCCCCCCC/C=C\C/C=C\CCCCC)O[C@H]2[C@H](O)[C@H](O)CN(C)C[C@H]2O1]
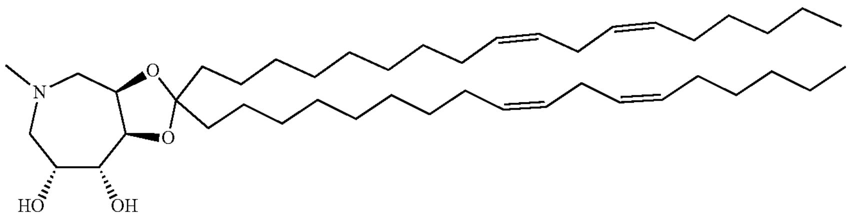 [SMILES: CCCCC/C=C\C/C=C\CCCCCCCCC1(CCCCCCCC/C=C\C/C=C\CCCCC)O[C@H]2[C@H](O)[C@H](O)CN(C)C[C@H]2O1]
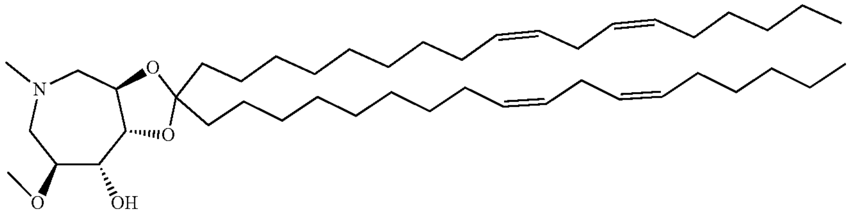 [SMILES: CCCCC/C=C\C/C=C\CCCCCCCCC1(CCCCCCCC/C=C\C/C=C\CCCCC)O[C@@H]2[C@H](O)[C@@H](OC)CN(C)C[C@H]2O1]

TABLE 11-continued
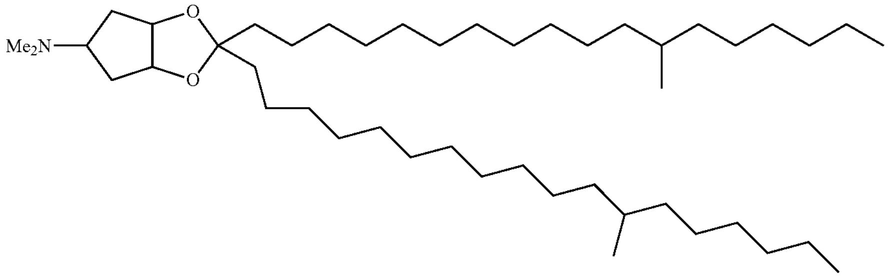 [SMILES: CCCCCCC(C)CCCCCCCCCCCC1(CCCCCCCCCCCC(C)CCCCCC)OC2CC(N(C)C)CC2O1]
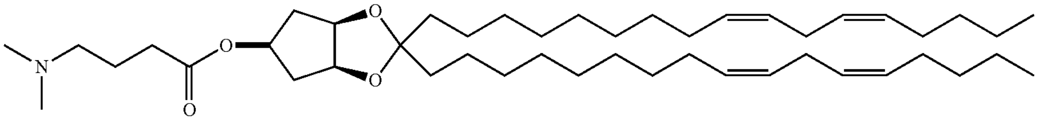 [SMILES: CCCC/C=C\C/C=C\CCCCCCCCC1(CCCCCCCC/C=C\C/C=C\CCCC)O[C@H]2C[C@@H](OC(=O)CCCN(C)C)C[C@H]2O1]
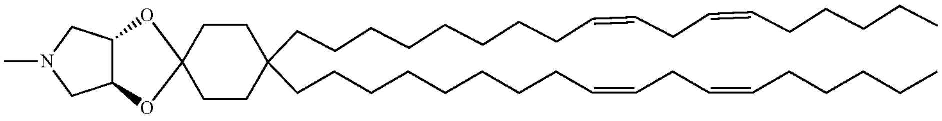 [SMILES: CCCCC/C=C\C/C=C\CCCCCCCCC1(CCCCCCCC/C=C\C/C=C\CCCCC)CCC2(CC1)O[C@H]1CN(C)C[C@@H]1O2]
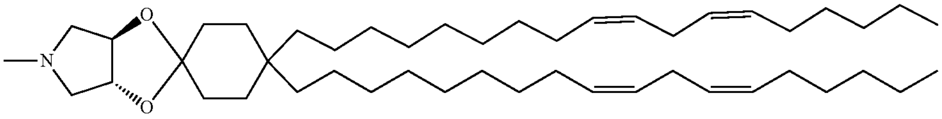 [SMILES: CCCCC/C=C\C/C=C\CCCCCCCCC1(CCCCCCCC/C=C\C/C=C\CCCCC)CCC2(CC1)O[C@@H]1CN(C)C[C@H]1O2]
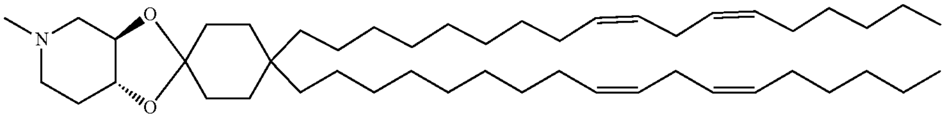 [SMILES: CCCCC/C=C\C/C=C\CCCCCCCCC1(CCCCCCCC/C=C\C/C=C\CCCCC)CCC2(CC1)O[C@@H]1CCN(C)C[C@H]1O2]
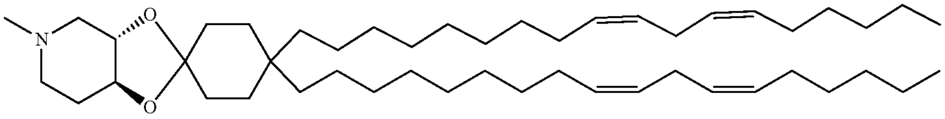 [SMILES: CCCCC/C=C\C/C=C\CCCCCCCCC1(CCCCCCCC/C=C\C/C=C\CCCCC)CCC2(CC1)O[C@H]1CCN(C)C[C@@H]1O2]
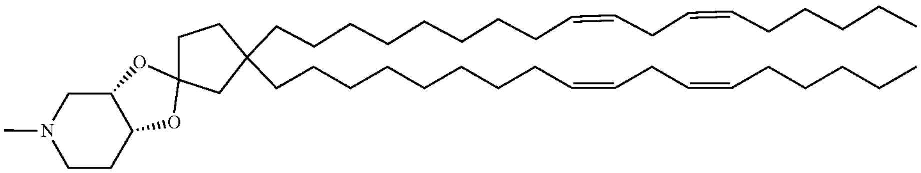
cis Racemic and optically pure
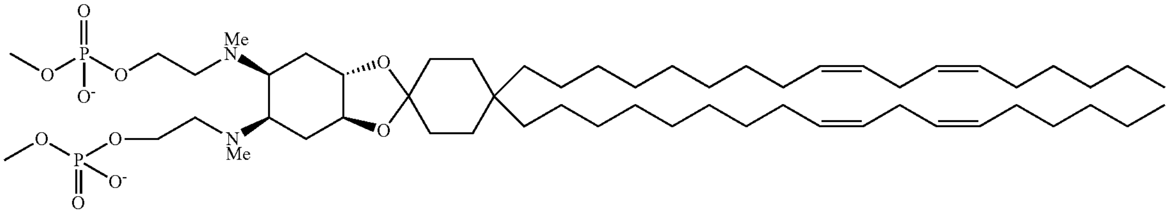 [SMILES: CCCCC/C=C\C/C=C\CCCCCCCCC1(CCCCCCCC/C=C\C/C=C\CCCCC)CCC2(CC1)O[C@H]1C[C@@H](N(C)CCOP(=O)([O-])OC)[C@@H](N(C)CCOP(=O)([O-])OC)C[C@@H]1O2]
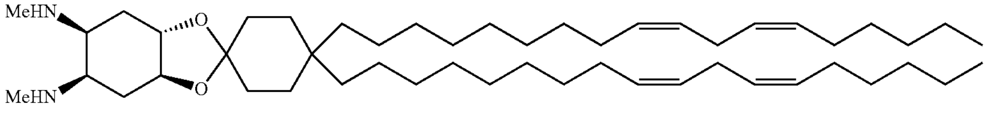 [SMILES: CCCCC/C=C\C/C=C\CCCCCCCCC1(CCCCCCCC/C=C\C/C=C\CCCCC)CCC2(CC1)O[C@H]1C[C@H](NC)[C@H](NC)C[C@@H]1O2]
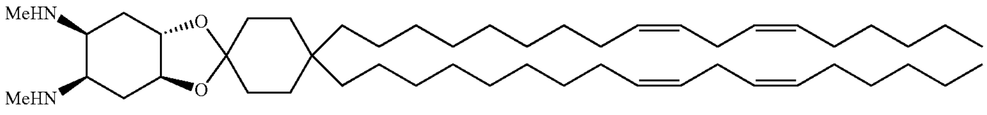 [SMILES: CCCCC/C=C\C/C=C\CCCCCCCCC1(CCCCCCCC/C=C\C/C=C\CCCCC)CCC2(CC1)O[C@H]1C[C@H](NC)[C@H](NC)C[C@@H]1O2]

TABLE 11-continued
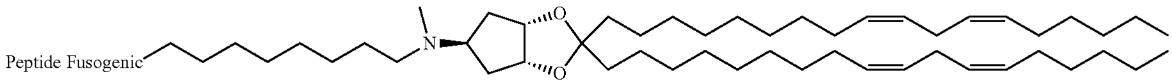
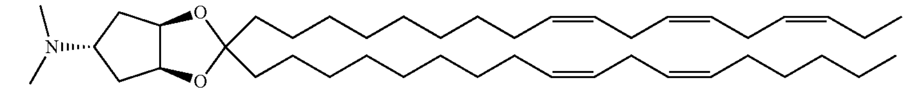
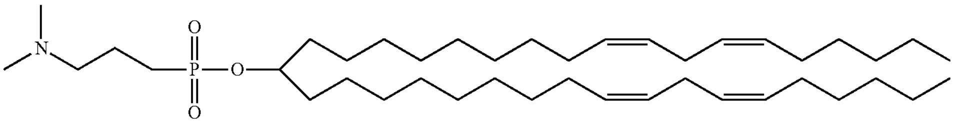
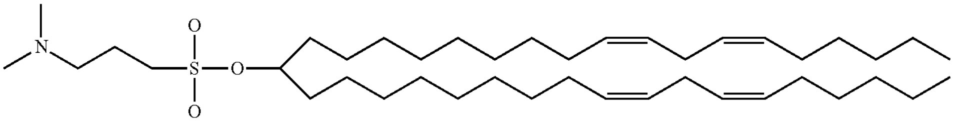
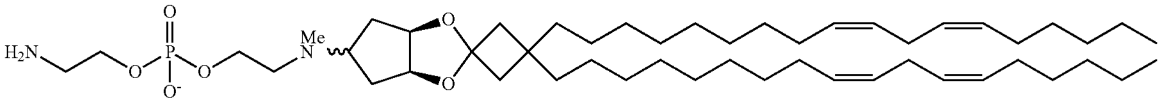 [SMILES: CCCCC/C=C\C/C=C\CCCCCCCCC1(CCCCCCCC/C=C\C/C=C\CCCCC)CC2(C1)O[C@H]1CC(N(C)CCOP(=O)([O-])OCCN)C[C@H]1O2]
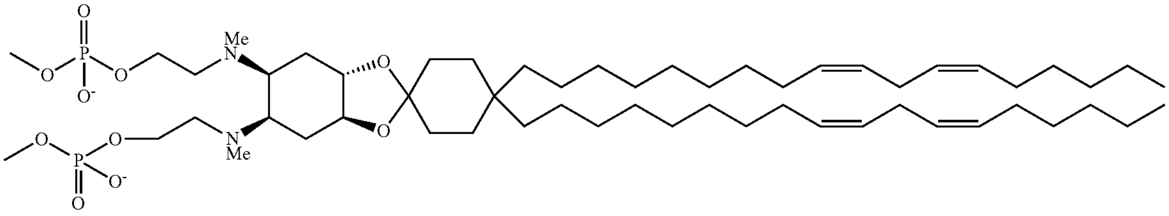 [SMILES: CCCCC/C=C\C/C=C\CCCCCCCCC1(CCCCCCCC/C=C\C/C=C\CCCCC)CCC2(CC1)O[C@H]1C[C@@H](N(C)CCOP(=O)([O-])OC)[C@@H](N(C)CCOP(=O)([O-])OC)C[C@@H]1O2]
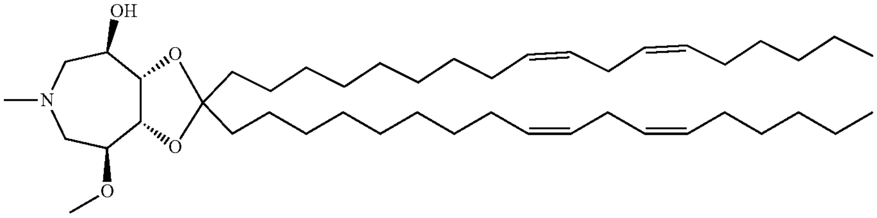 [SMILES: CCCCC/C=C\C/C=C\CCCCCCCCC1(CCCCCCCC/C=C\C/C=C\CCCCC)O[C@@H]2[C@H](O1)[C@@H](OC)CN(C)C[C@H]2O]
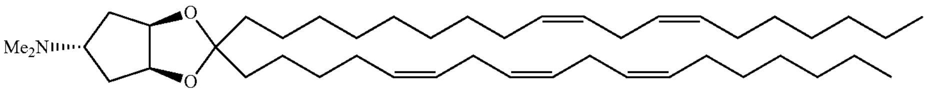
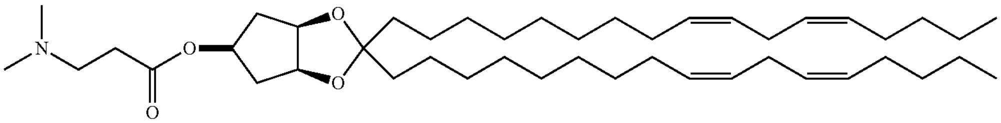 [SMILES: CCCC/C=C\C/C=C\CCCCCCCCC1(CCCCCCCC/C=C\C/C=C\CCCC)O[C@H]2C[C@@H](OC(=O)CCN(C)C)C[C@H]2O1]
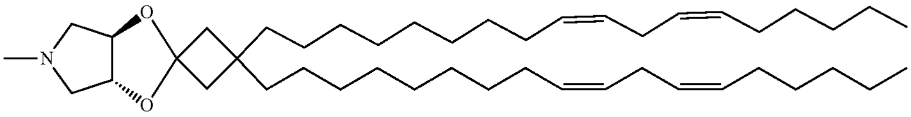 [SMILES: CCCCC/C=C\C/C=C\CCCCCCCCC1(CCCCCCCC/C=C\C/C=C\CCCCC)CC2(C1)O[C@@H]1CN(C)C[C@H]1O2]
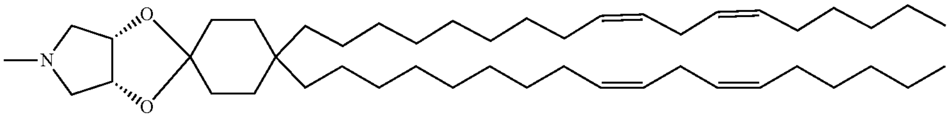
cis Racemic and optically pure TABLE 11-continued
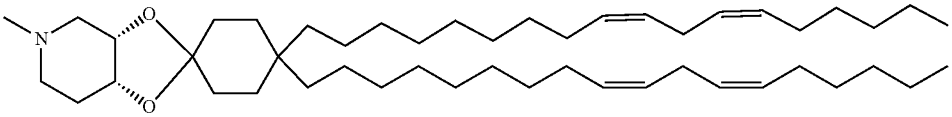
cis Racemic and optically pure
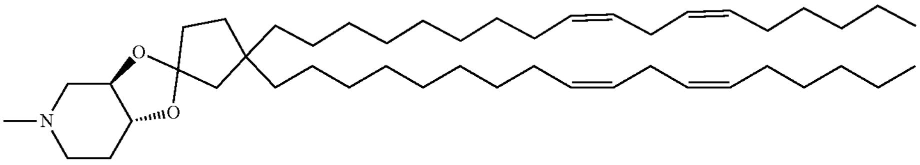
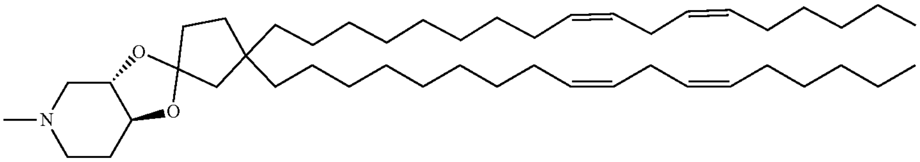
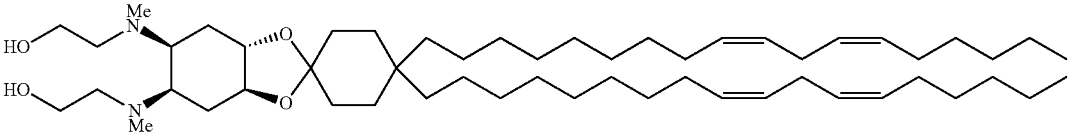
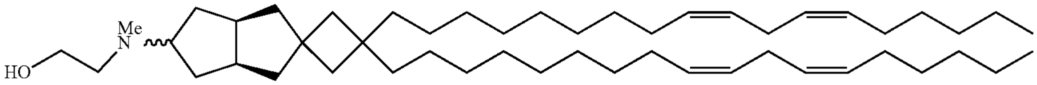 [SMILES: CCCCC/C=C\C/C=C\CCCCCCCCC1(CCCCCCCC/C=C\C/C=C\CCCCC)CC2(C[C@H]3CC(N(C)CCO)C[C@H]3C2)C1]
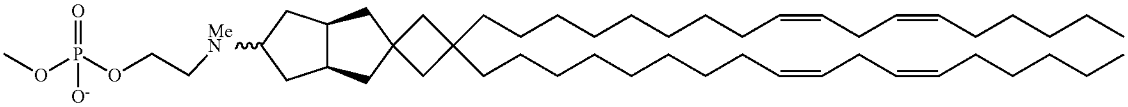 [SMILES: CCCCC/C=C\C/C=C\CCCCCCCCC1(CCCCCCCC/C=C\C/C=C\CCCCC)CC2(C[C@H]3CC(N(C)CCOP(=O)([O-])OC)C[C@H]3C2)C1]
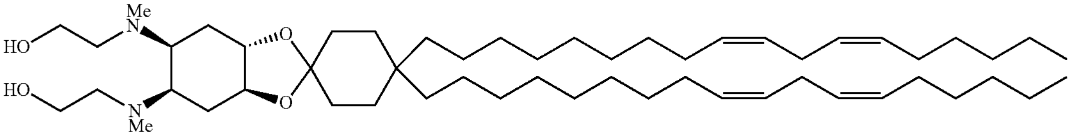
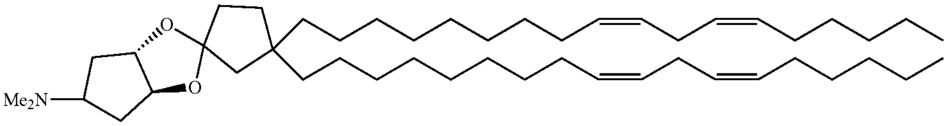 [SMILES: CCCCC/C=C\C/C=C\CCCCCCCCC1(CCCCCCCC/C=C\C/C=C\CCCCC)CCC2(C1)O[C@H]1CC(N(C)C)C[C@@H]1O2]
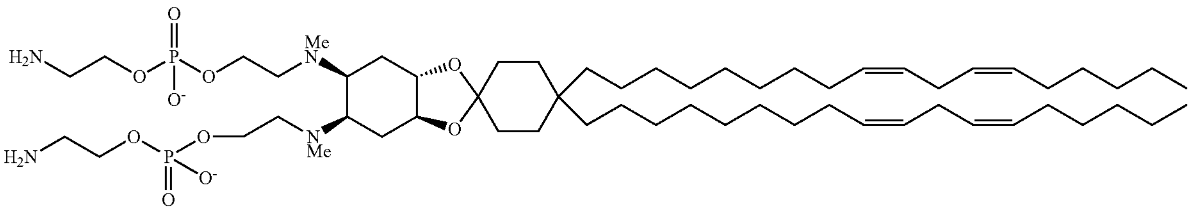
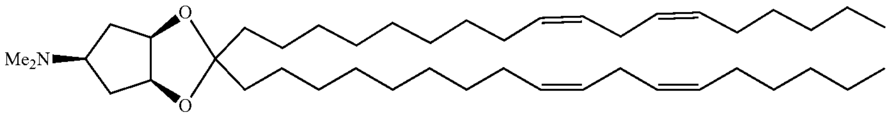
meso compound TABLE 11-continued
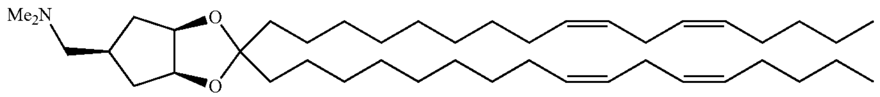 [SMILES: CCCC/C=C\C/C=C\CCCCCCCCC1(CCCCCCCC/C=C\C/C=C\CCCC)O[C@H]2C[C@@H](CN(C)C)C[C@H]2O1]
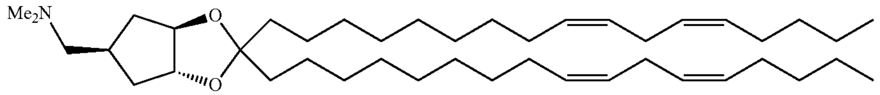
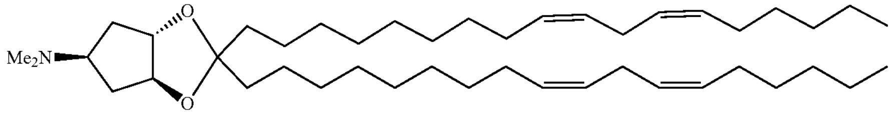
racemic compound
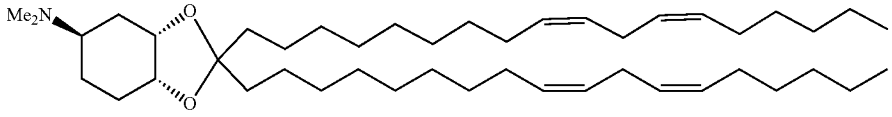
racemic compound
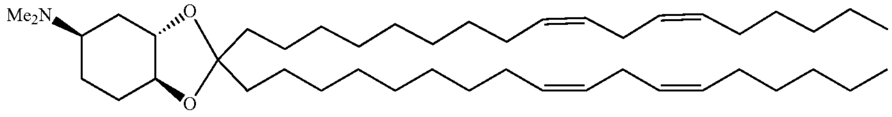
racemic compound
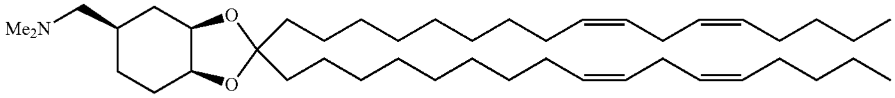 [SMILES: CCCC/C=C\C/C=C\CCCCCCCCC1(CCCCCCCC/C=C\C/C=C\CCCC)O[C@H]2CC[C@@H](CN(C)C)C[C@H]2O1]
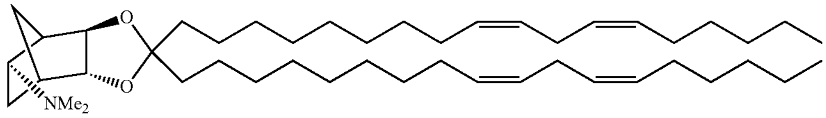
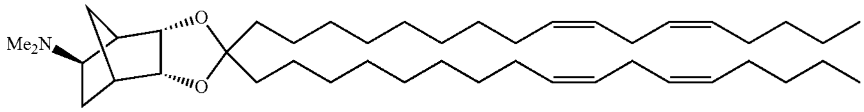 [SMILES: CCCC/C=C\C/C=C\CCCCCCCCC1(CCCCCCCC/C=C\C/C=C\CCCC)O[C@@H]2C3CC([C@H](N(C)C)C3)[C@@H]2O1]
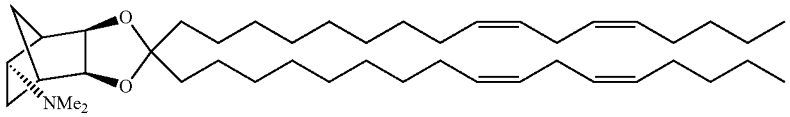
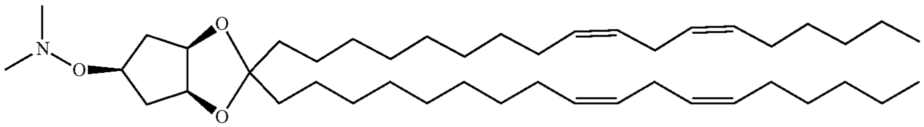 [SMILES: CCCCC/C=C\C/C=C\CCCCCCCCC1(CCCCCCCC/C=C\C/C=C\CCCCC)O[C@H]2C[C@@H](ON(C)C)C[C@H]2O1]
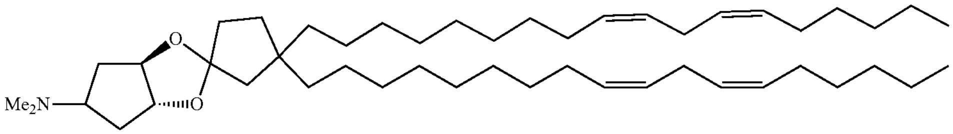 [SMILES: CCCCC/C=C\C/C=C\CCCCCCCCC1(CCCCCCCC/C=C\C/C=C\CCCCC)CCC2(C1)O[C@@H]1CC(N(C)C)C[C@H]1O2]

TABLE 11-continued
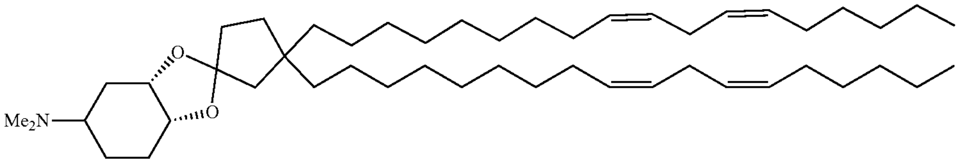
cis Racemic and optically pure
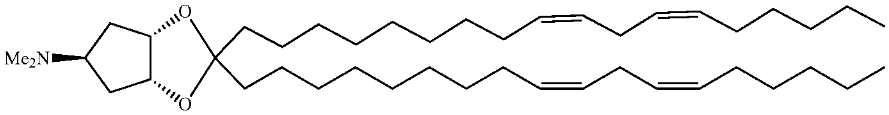
meso compound
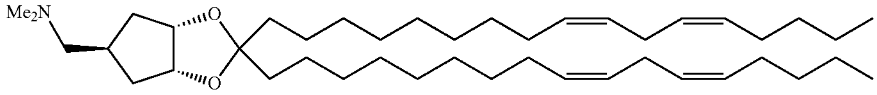 [SMILES: CCCC/C=C\C/C=C\CCCCCCCCC1(CCCCCCCC/C=C\C/C=C\CCCC)O[C@H]2C[C@H](CN(C)C)C[C@H]2O1]
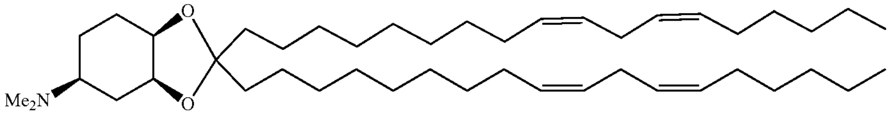 [SMILES: CCCCC/C=C\C/C=C\CCCCCCCCC1(CCCCCCCC/C=C\C/C=C\CCCCC)O[C@H]2C[C@@H](N(C)C)CC[C@H]2O1]
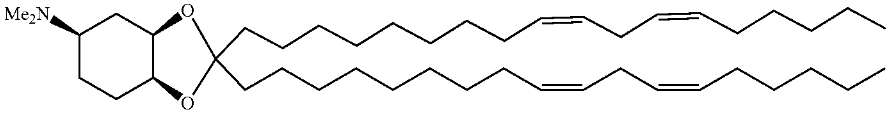
racemic compound
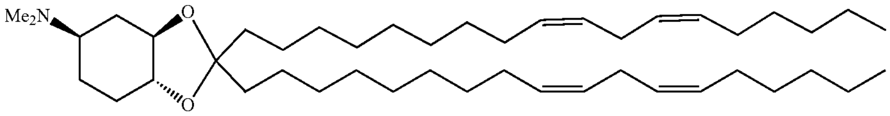
racemic compound
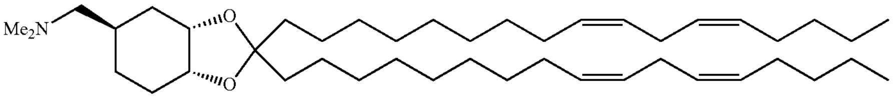
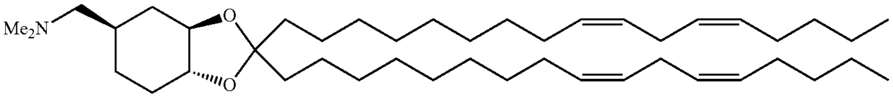 [SMILES: CCCC/C=C\C/C=C\CCCCCCCCC1(CCCCCCCC/C=C\C/C=C\CCCC)O[C@@H]2CC[C@@H](CN(C)C)C[C@H]2O1]
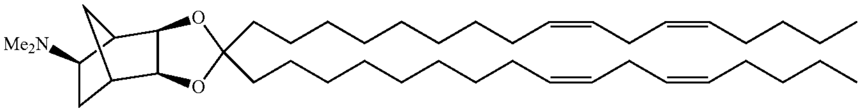 [SMILES: CCCC/C=C\C/C=C\CCCCCCCCC1(CCCCCCCC/C=C\C/C=C\CCCC)O[C@@H]2C3CC(C[C@H]3N(C)C)[C@@H]2O1]
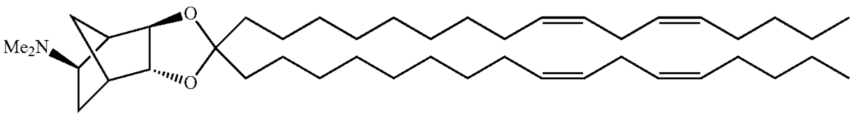 [SMILES: CCCC/C=C\C/C=C\CCCCCCCCC1(CCCCCCCC/C=C\C/C=C\CCCC)O[C@@H]2C3CC([C@H]2O1)[C@H](N(C)C)C3]
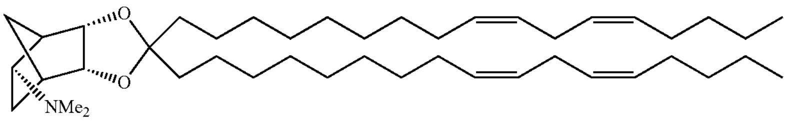 [SMILES: CCCC/C=C\C/C=C\CCCCCCCCC1(CCCCCCCC/C=C\C/C=C\CCCC)O[C@@H]2C3CC([C@@H]2O1)[C@@H](N(C)C)C3]

TABLE 11-continued
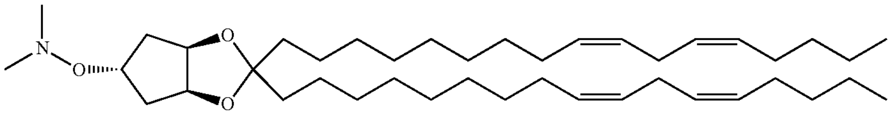 [SMILES: CCCC/C=C\C/C=C\CCCCCCCCC1(CCCCCCCC/C=C\C/C=C\CCCC)O[C@H]2C[C@H](ON(C)C)C[C@H]2O1]
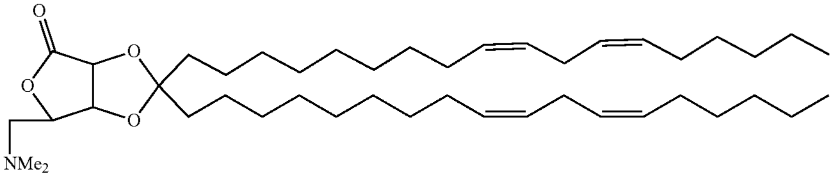 [SMILES: CCCCC/C=C\C/C=C\CCCCCCCCC1(CCCCCCCC/C=C\C/C=C\CCCCC)OC2C(=O)OC(CN(C)C)C2O1]
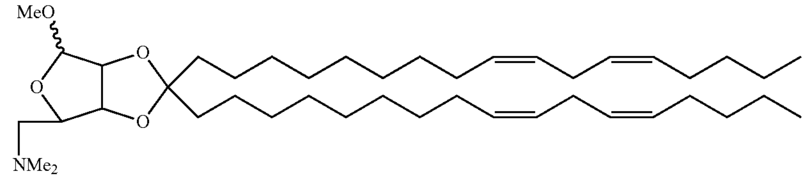 [SMILES: CCCC/C=C\C/C=C\CCCCCCCCC1(CCCCCCCC/C=C\C/C=C\CCCC)OC2C(CN(C)C)OC(OC)C2O1]
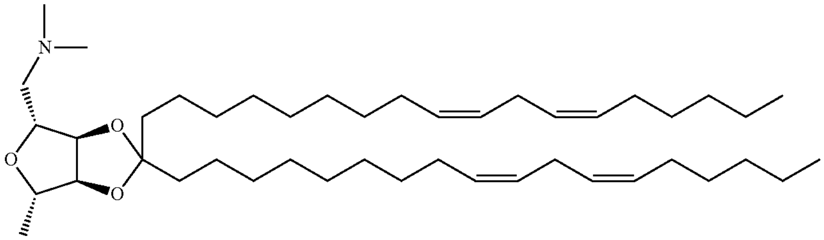 [SMILES: CCCCC/C=C\C/C=C\CCCCCCCCC1(CCCCCCCC/C=C\C/C=C\CCCCC)O[C@@H]2[C@H](O1)[C@@H](CN(C)C)O[C@H]2C]
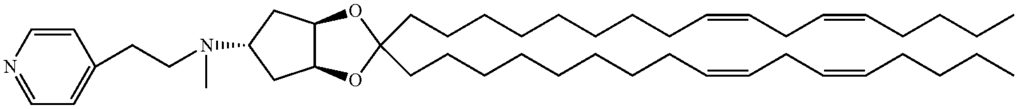 [SMILES: CCCC/C=C\C/C=C\CCCCCCCCC1(CCCCCCCC/C=C\C/C=C\CCCC)O[C@H]2C[C@H](N(C)CCc3ccncc3)C[C@H]2O1]
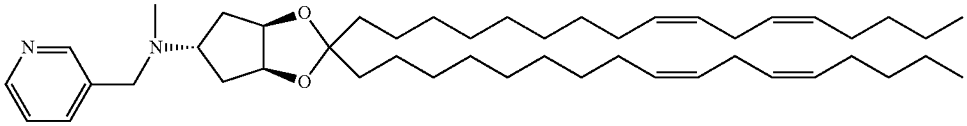 [SMILES: CCCC/C=C\C/C=C\CCCCCCCCC1(CCCCCCCC/C=C\C/C=C\CCCC)O[C@H]2C[C@H](N(C)Cc3cccnc3)C[C@H]2O1]
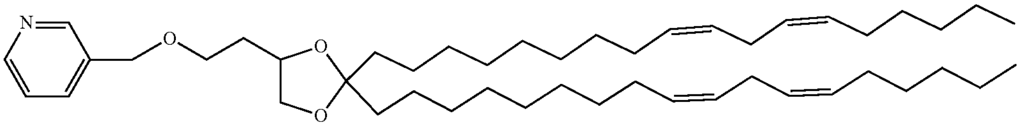 [SMILES: CCCCC/C=C\C/C=C\CCCCCCCCC1(CCCCCCCC/C=C\C/C=C\CCCCC)OCC(CCOCc2cccnc2)O1]
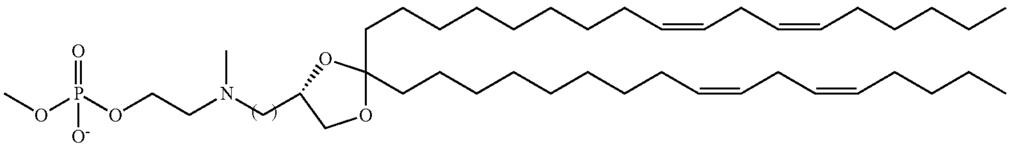
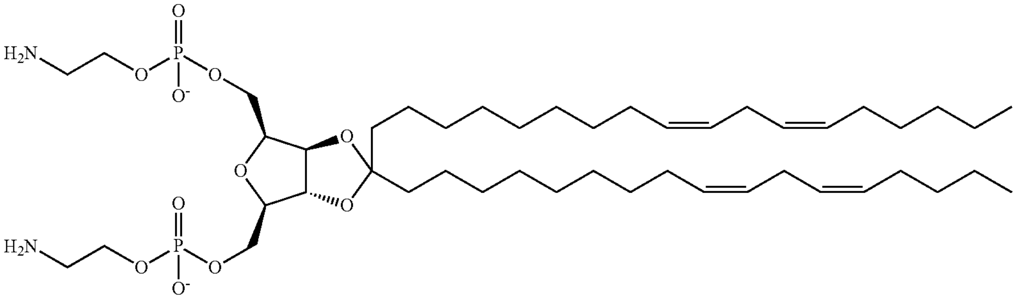

TABLE 11-continued
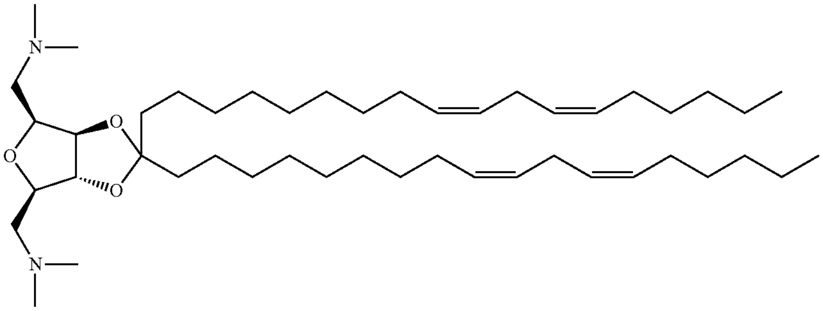 [SMILES: CCCCC/C=C\C/C=C\CCCCCCCCC1(CCCCCCCC/C=C\C/C=C\CCCCC)O[C@H]2[C@H](O1)[C@@H](CN(C)C)O[C@H]2CN(C)C]
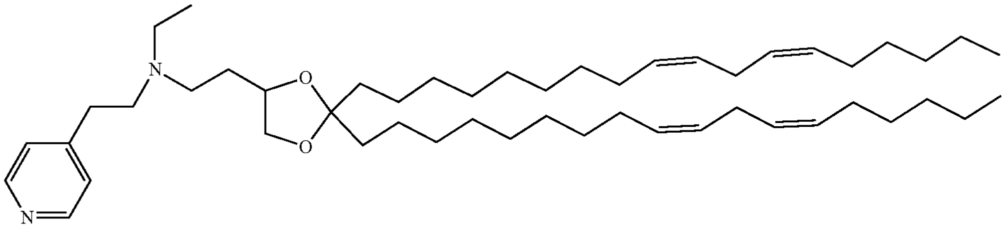 [SMILES: CCCCC/C=C\C/C=C\CCCCCCCCC1(CCCCCCCC/C=C\C/C=C\CCCCC)OCC(CCN(CC)CCc2ccncc2)O1]
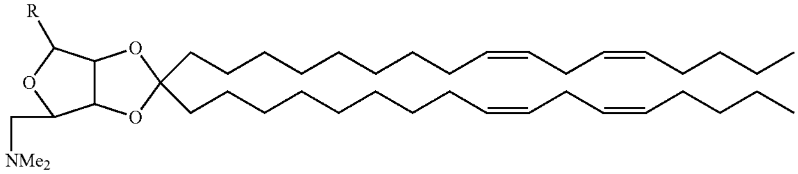
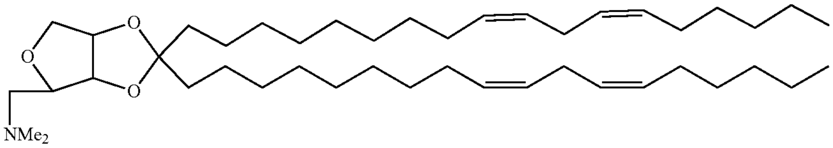 [SMILES: CCCCC/C=C\C/C=C\CCCCCCCCC1(CCCCCCCC/C=C\C/C=C\CCCCC)OC2COC(CN(C)C)C2O1]
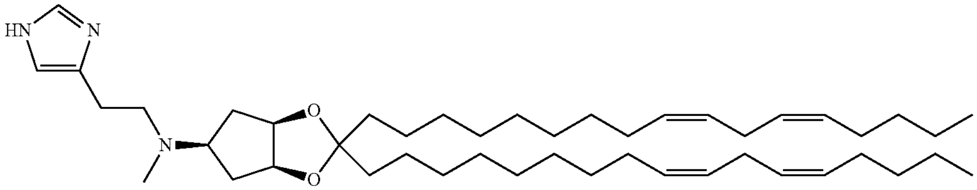 [SMILES: CCCC/C=C\C/C=C\CCCCCCCCC1(CCCCCCCC/C=C\C/C=C\CCCC)O[C@H]2C[C@@H](N(C)CCc3c[nH]cn3)C[C@H]2O1]
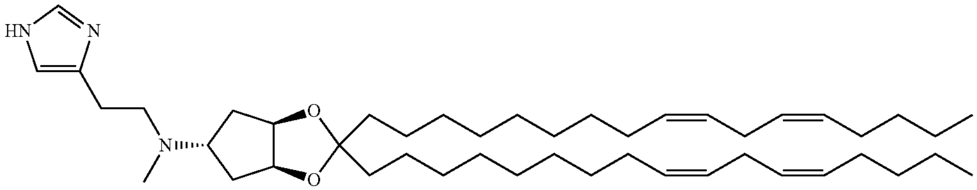 [SMILES: CCCC/C=C\C/C=C\CCCCCCCCC1(CCCCCCCC/C=C\C/C=C\CCCC)O[C@H]2C[C@H](N(C)CCc3c[nH]cn3)C[C@H]2O1]
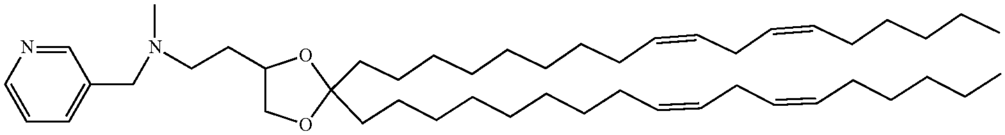 [SMILES: CCCCC/C=C\C/C=C\CCCCCCCCC1(CCCCCCCC/C=C\C/C=C\CCCCC)OCC(CCN(C)Cc2cccnc2)O1]
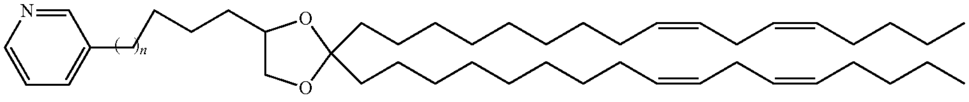
n = 1-10

TABLE 11-continued
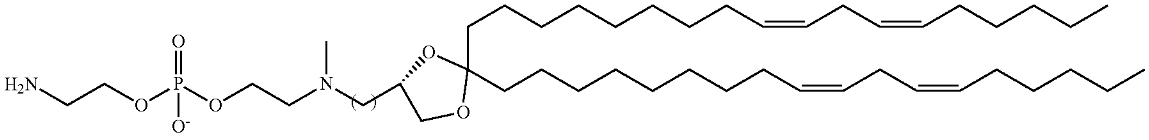
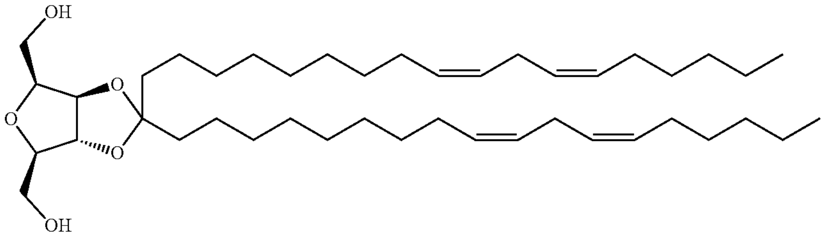 [SMILES: CCCCC/C=C\C/C=C\CCCCCCCCC1(CCCCCCCC/C=C\C/C=C\CCCCC)O[C@H]2[C@H](O1)[C@@H](CO)O[C@H]2CO]
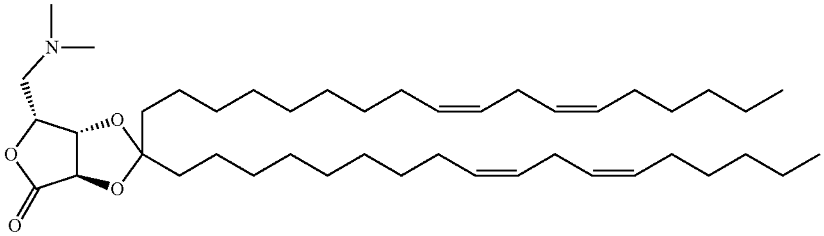 [SMILES: CCCCC/C=C\C/C=C\CCCCCCCCC1(CCCCCCCC/C=C\C/C=C\CCCCC)O[C@H]2[C@@H](CN(C)C)OC(=O)[C@@H]2O1]
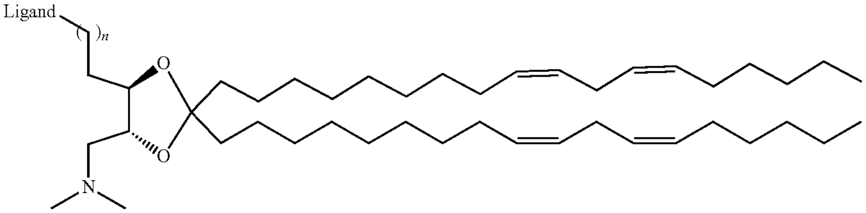
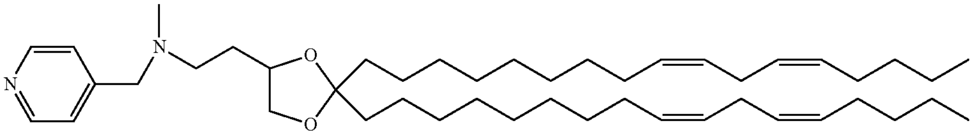 [SMILES: CCCC/C=C\C/C=C\CCCCCCCCC1(CCCCCCCC/C=C\C/C=C\CCCC)OCC(CCN(C)Cc2ccncc2)O1]
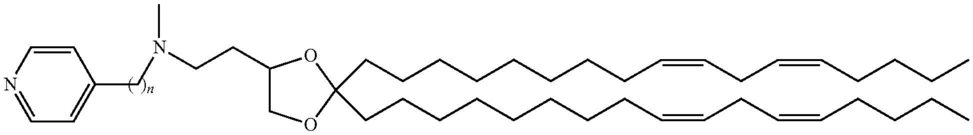 [SMILES: CCCC/C=C\C/C=C\CCCCCCCCC1(CCCCCCCC/C=C\C/C=C\CCCC)OCC(CCN(C)Cc2ccncc2)O1]
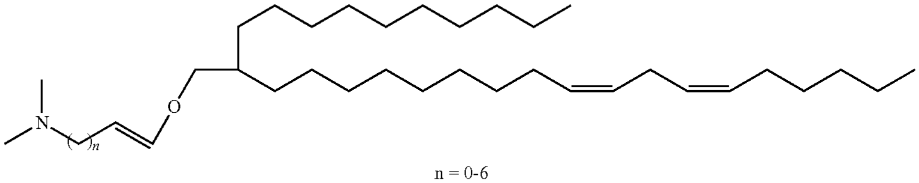
n = 0-6
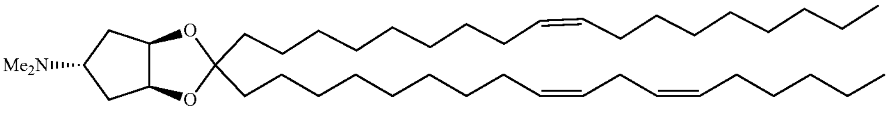
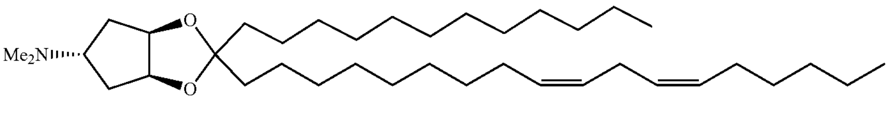

TABLE 11-continued
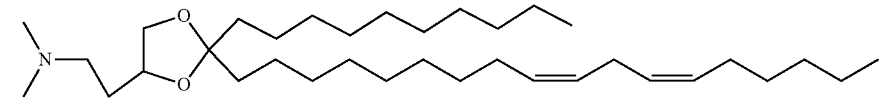 [SMILES: CCCCC/C=C\C/C=C\CCCCCCCCC1(CCCCCCCCCC)OCC(CCN(C)C)O1]
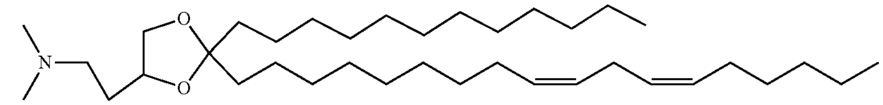 [SMILES: CCCCC/C=C\C/C=C\CCCCCCCCC1(CCCCCCCCCCCC)OCC(CCN(C)C)O1]
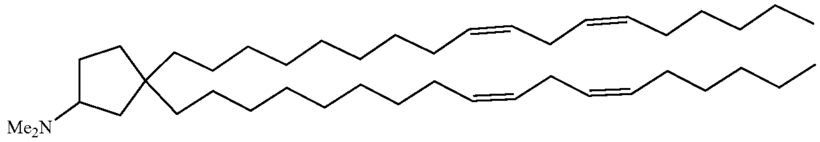
Racemic and optically pure
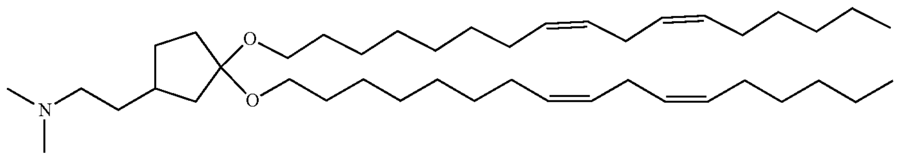 [SMILES: CCCCC/C=C\C/C=C\CCCCCCCOC1(OCCCCCCC/C=C\C/C=C\CCCCC)CCC(CCN(C)C)C1]
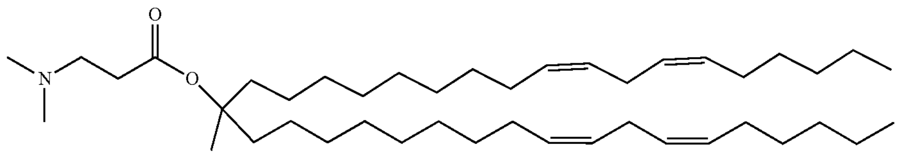 [SMILES: CCCCC/C=C\C/C=C\CCCCCCCCC(C)(CCCCCCCC/C=C\C/C=C\CCCCC)OC(=O)CCN(C)C]
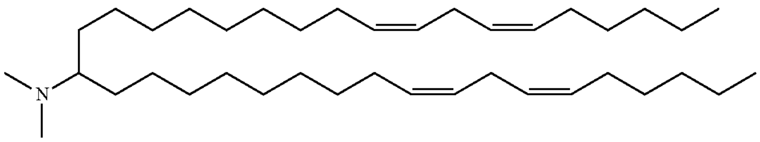 [SMILES: CCCCC/C=C\C/C=C\CCCCCCCCC(CCCCCCCC/C=C\C/C=C\CCCCC)N(C)C]
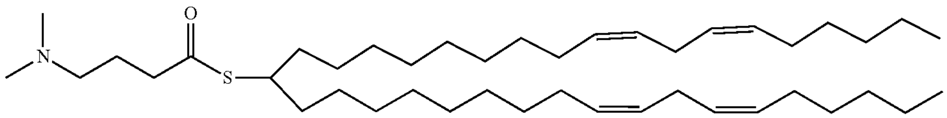 [SMILES: CCCCC/C=C\C/C=C\CCCCCCCCC(CCCCCCCC/C=C\C/C=C\CCCCC)SC(=O)CCCN(C)C]
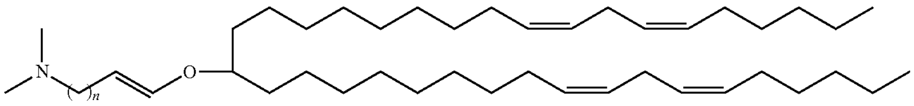
n = 0-6
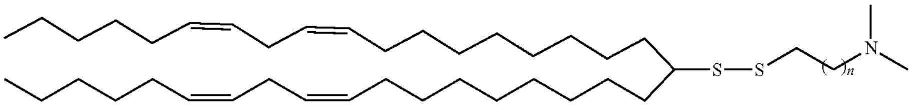
n = 0-6
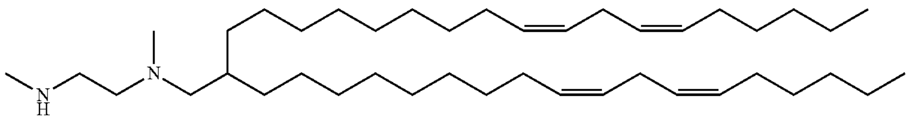 [SMILES: CCCCC/C=C\C/C=C\CCCCCCCCC(CCCCCCCC/C=C\C/C=C\CCCCC)CN(C)CCNC]
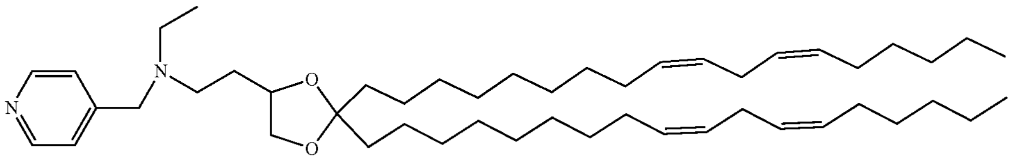 [SMILES: CCCCC/C=C\C/C=C\CCCCCCCCC1(CCCCCCCC/C=C\C/C=C\CCCCC)OCC(CCN(CC)Cc2ccncc2)O1]

TABLE 11-continued
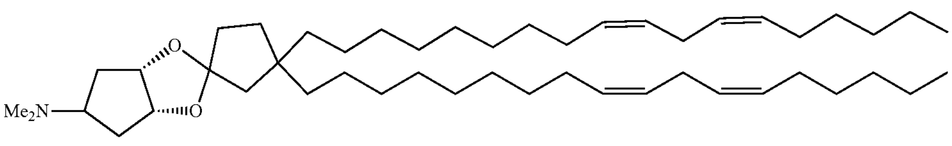
cis Racemic and optically pure
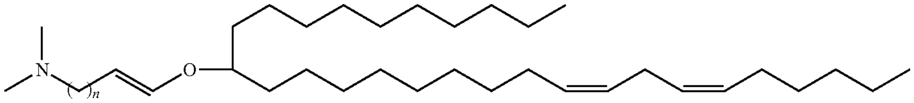
n = 0-6
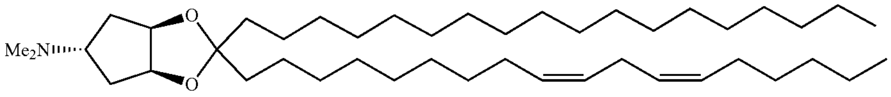
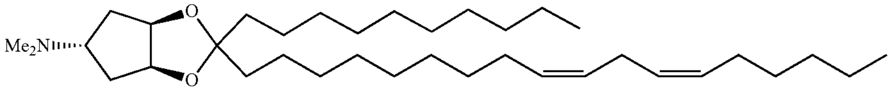
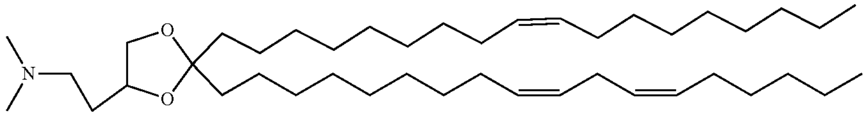 [SMILES: CCCCC/C=C\C/C=C\CCCCCCCCC1(CCCCCCCC/C=C\CCCCCCCC)OCC(CCN(C)C)O1]
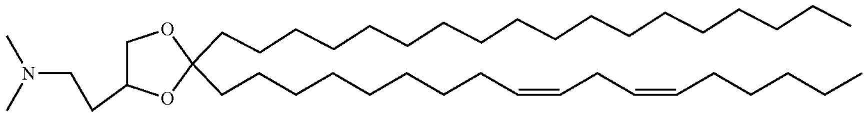 [SMILES: CCCCC/C=C\C/C=C\CCCCCCCCC1(CCCCCCCCCCCCCCCCCC)OCC(CCN(C)C)O1]
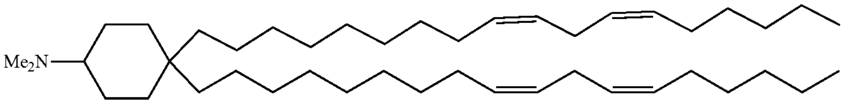
Racemic and optically pure
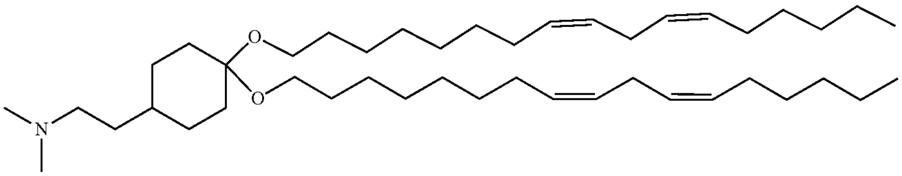 [SMILES: CCCCC/C=C\C/C=C\CCCCCCCOC1(OCCCCCCC/C=C\C/C=C\CCCCC)CCC(CCN(C)C)CC1]
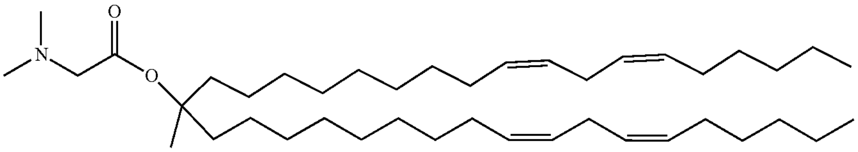 [SMILES: CCCCC/C=C\C/C=C\CCCCCCCCC(C)(CCCCCCCC/C=C\C/C=C\CCCCC)OC(=O)CN(C)C]
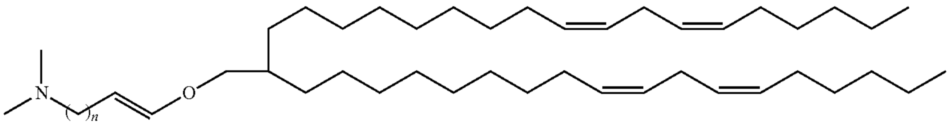
n = 0-6
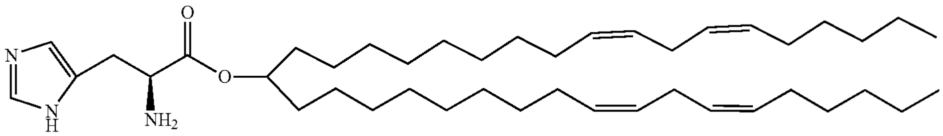 [SMILES: CCCCC/C=C\C/C=C\CCCCCCCCC(CCCCCCCC/C=C\C/C=C\CCCCC)OC(=O)[C@@H](N)Cc1cnc[nH]1]

TABLE 11-continued
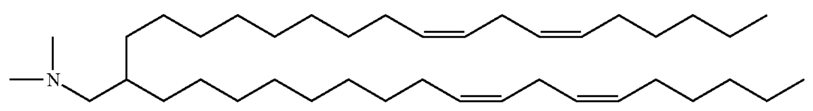 [SMILES: CCCCC/C=C\C/C=C\CCCCCCCCC(CCCCCCCC/C=C\C/C=C\CCCCC)CN(C)C]
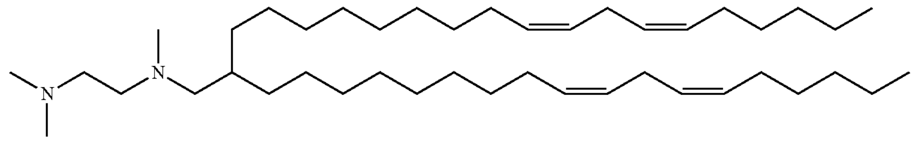
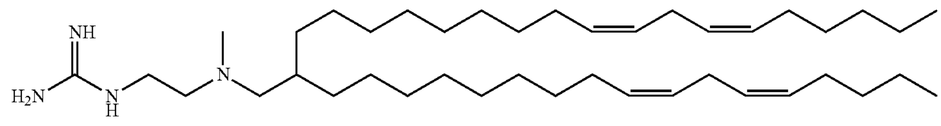 [SMILES: CCCC/C=C\C/C=C\CCCCCCCCC(CCCCCCCC/C=C\C/C=C\CCCCC)CN(C)CCNC(=N)N]
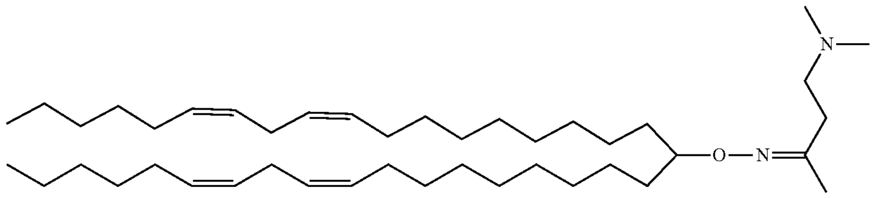 [SMILES: CCCCC/C=C\C/C=C\CCCCCCCCC(CCCCCCCC/C=C\C/C=C\CCCCC)ON=C(C)CCN(C)C]
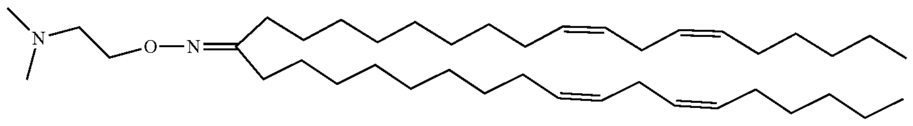 [SMILES: CCCCC/C=C\C/C=C\CCCCCCCCC(CCCCCCCC/C=C\C/C=C\CCCCC)=NOCCN(C)C]
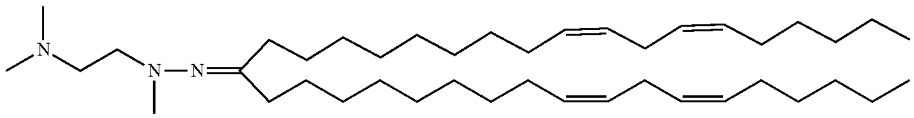 [SMILES: CCCCC/C=C\C/C=C\CCCCCCCCC(CCCCCCCC/C=C\C/C=C\CCCCC)=NN(C)CCN(C)C]
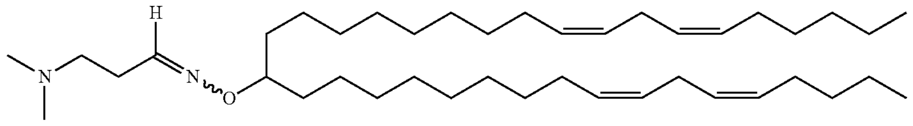 [SMILES: CCCC/C=C\C/C=C\CCCCCCCCC(CCCCCCCC/C=C\C/C=C\CCCCC)ON=CCCN(C)C]
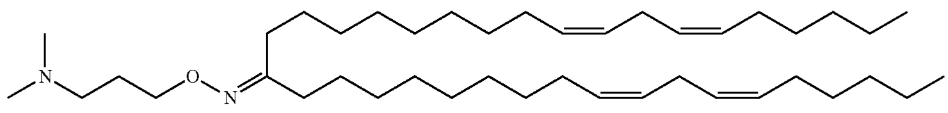
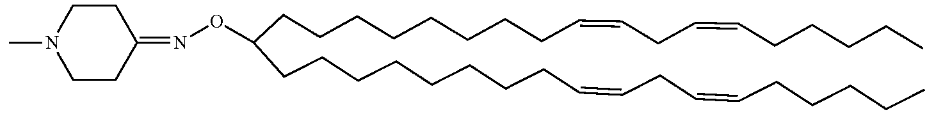 [SMILES: CCCCC/C=C\C/C=C\CCCCCCCCC(CCCCCCCC/C=C\C/C=C\CCCCC)ON=C1CCN(C)CC1]
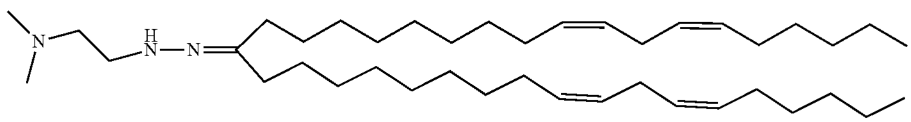 [SMILES: CCCCC/C=C\C/C=C\CCCCCCCCC(CCCCCCCC/C=C\C/C=C\CCCCC)=NNCCN(C)C]
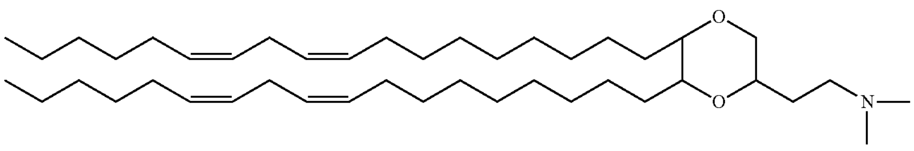 [SMILES: CCCCC/C=C\C/C=C\CCCCCCCCC1OCC(CCN(C)C)OC1CCCCCCCC/C=C\C/C=C\CCCCC]

TABLE 11-continued
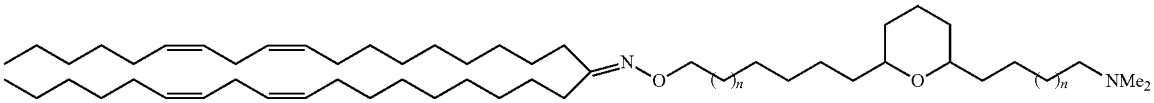
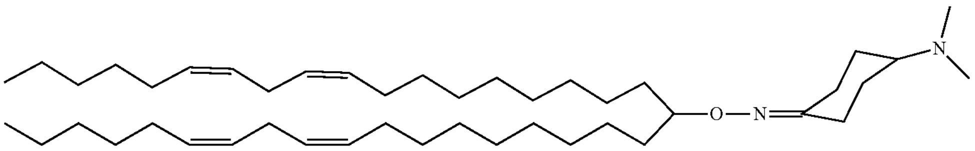 [SMILES: CCCCC/C=C\C/C=C\CCCCCCCCC(CCCCCCCC/C=C\C/C=C\CCCCC)ON=C1CCC(N(C)C)CC1]
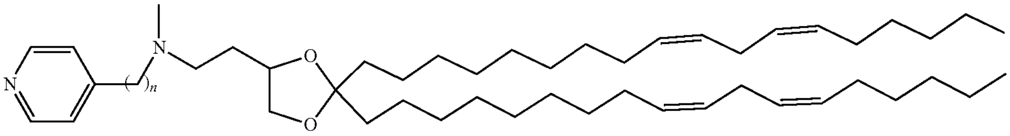
n = 0-6
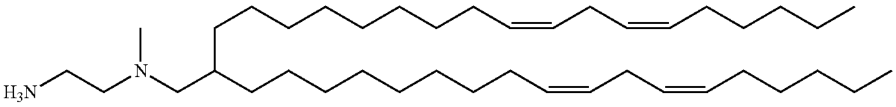
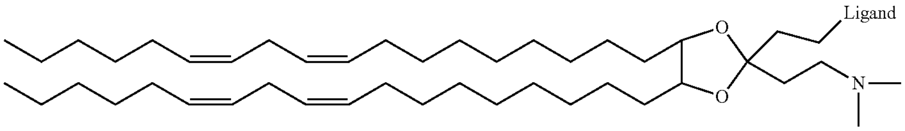
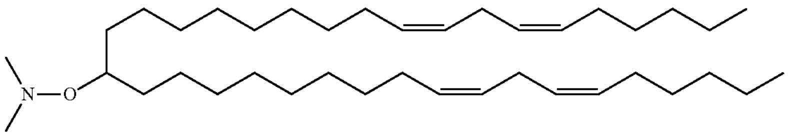 [SMILES: CCCCC/C=C\C/C=C\CCCCCCCCC(CCCCCCCC/C=C\C/C=C\CCCCC)ON(C)C]
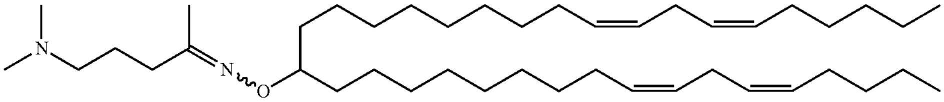 [SMILES: CCCC/C=C\C/C=C\CCCCCCCCC(CCCCCCCC/C=C\C/C=C\CCCCC)ON=C(C)CCCN(C)C]
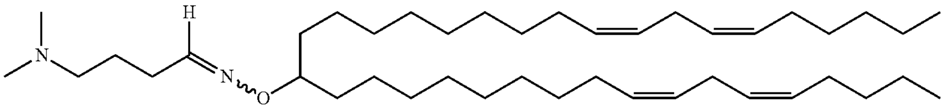 [SMILES: CCCC/C=C\C/C=C\CCCCCCCCC(CCCCCCCC/C=C\C/C=C\CCCCC)ON=CCCCN(C)C]
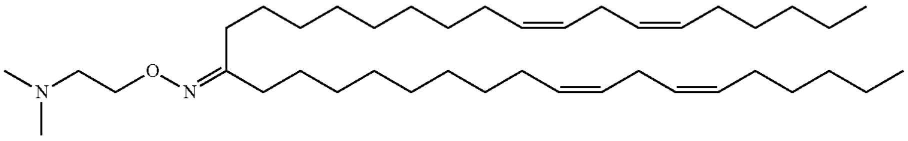
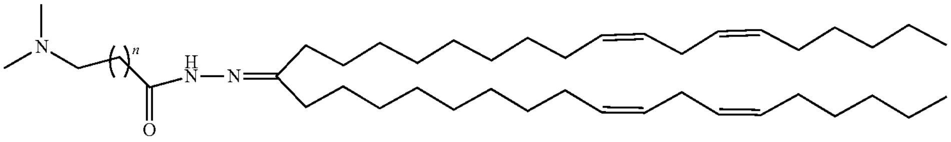
n = 0-6

TABLE 11-continued
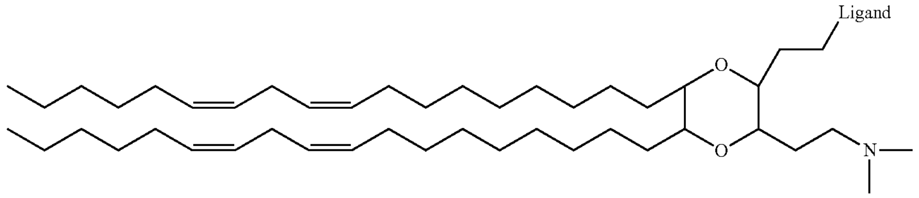
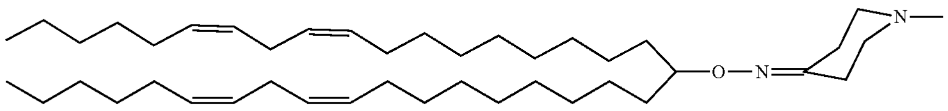 [SMILES: CCCCC/C=C\C/C=C\CCCCCCCCC(CCCCCCCC/C=C\C/C=C\CCCCC)ON=C1CCN(C)CC1]
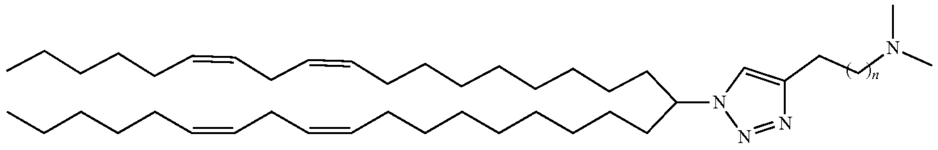
n = 0-6
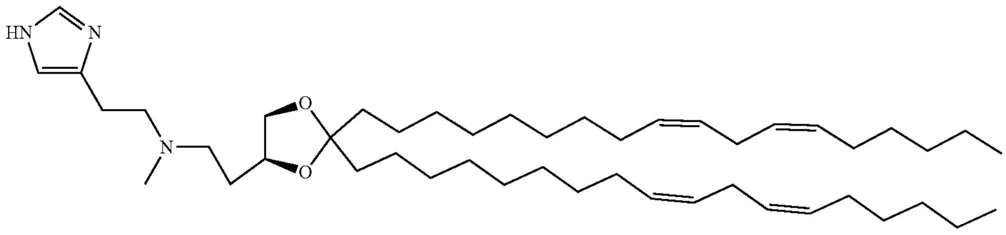
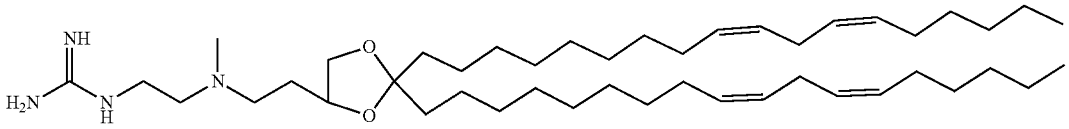 [SMILES: CCCCC/C=C\C/C=C\CCCCCCCCC1(CCCCCCCC/C=C\C/C=C\CCCCC)OCC(CCN(C)CCNC(=N)N)O1]
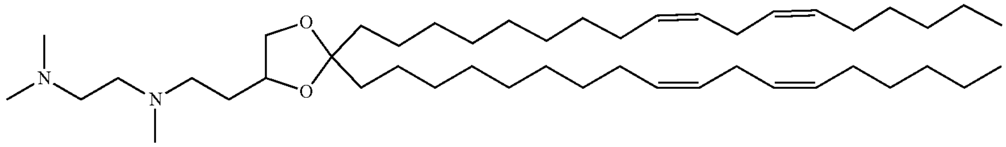 [SMILES: CCCCC/C=C\C/C=C\CCCCCCCCC1(CCCCCCCC/C=C\C/C=C\CCCCC)OCC(CCN(C)CCN(C)C)O1]
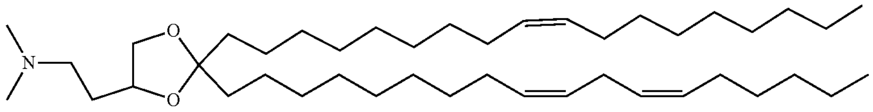 [SMILES: CCCCC/C=C\C/C=C\CCCCCCCCC1(CCCCCCCC/C=C\CCCCCCCC)OCC(CCN(C)C)O1]
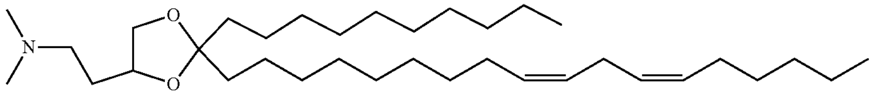 [SMILES: CCCCC/C=C\C/C=C\CCCCCCCCC1(CCCCCCCCCC)OCC(CCN(C)C)O1]
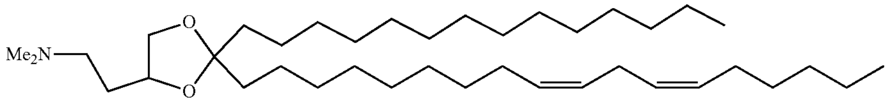 [SMILES: CCCCC/C=C\C/C=C\CCCCCCCCC1(CCCCCCCCCCCCCC)OCC(CCN(C)C)O1]
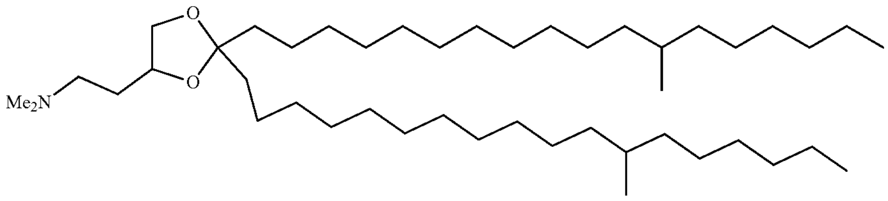 [SMILES: CCCCCCC(C)CCCCCCCCCCCC1(CCCCCCCCCCCC(C)CCCCCC)OCC(CCN(C)C)O1]

TABLE 11-continued
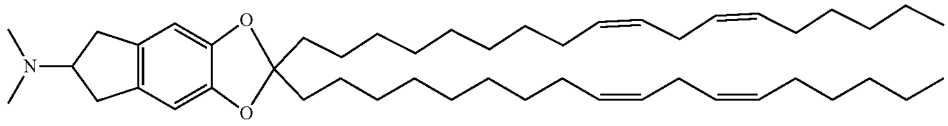 [SMILES: CCCCC/C=C\C/C=C\CCCCCCCCC1(CCCCCCCC/C=C\C/C=C\CCCCC)Oc2cc3c(cc2O1)CC(N(C)C)C3]
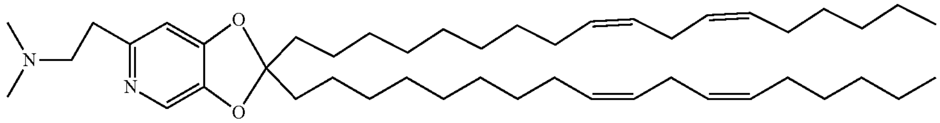 [SMILES: CCCCC/C=C\C/C=C\CCCCCCCCC1(CCCCCCCC/C=C\C/C=C\CCCCC)Oc2cnc(CCN(C)C)cc2O1]
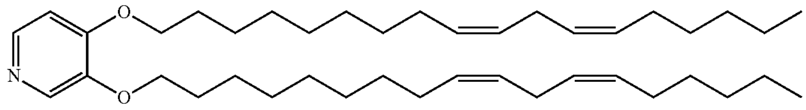 [SMILES: CCCCC/C=C\C/C=C\CCCCCCCCOc1ccncc1OCCCCCCCC/C=C\C/C=C\CCCCC]
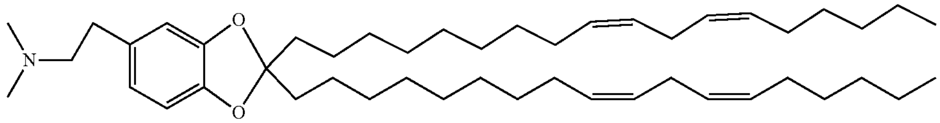 [SMILES: CCCCC/C=C\C/C=C\CCCCCCCCC1(CCCCCCCC/C=C\C/C=C\CCCCC)Oc2ccc(CCN(C)C)cc2O1]
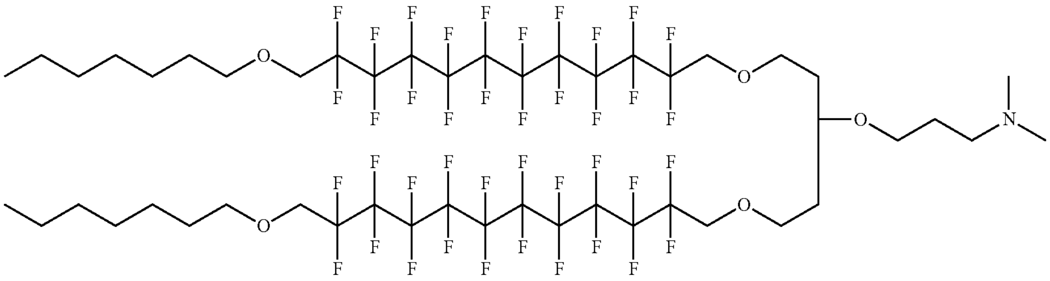 [SMILES: CCCCCCCOCC(F)(F)C(F)(F)C(F)(F)C(F)(F)C(F)(F)C(F)(F)C(F)(F)C(F)(F)C(F)(F)C(F)(F)COCCCC(CCOCC(F)(F)C(F)(F)C(F)(F)C(F)(F)C(F)(F)C(F)(F)C(F)(F)C(F)(F)C(F)(F)C(F)(F)COCCCCCCC)OCCCN(C)C]
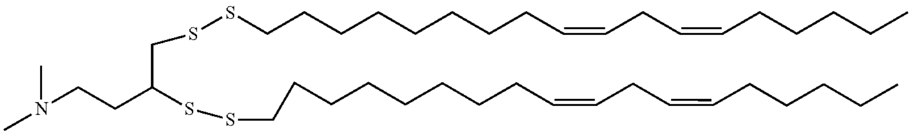 [SMILES: CCCCC/C=C\C/C=C\CCCCCCCCSSCC(CCN(C)C)SSCCCCCCCC/C=C\C/C=C\CCCCC]
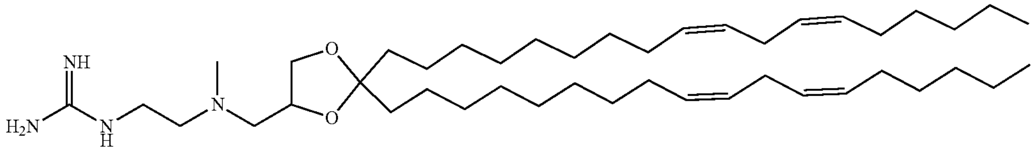 [SMILES: CCCCC/C=C\C/C=C\CCCCCCCCC1(CCCCCCCC/C=C\C/C=C\CCCCC)OCC(CN(C)CCNC(=N)N)O1]
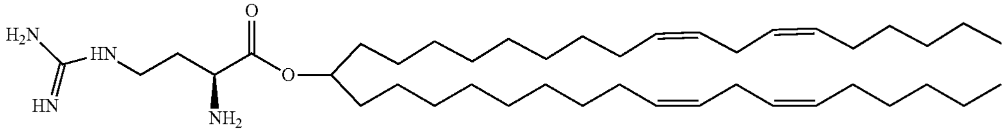 [SMILES: CCCCC/C=C\C/C=C\CCCCCCCCC(CCCCCCCC/C=C\C/C=C\CCCCC)OC(=O)[C@@H](N)CCNC(=N)N]
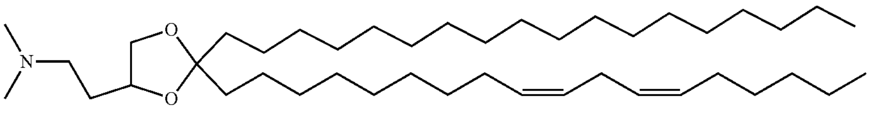 [SMILES: CCCCC/C=C\C/C=C\CCCCCCCCC1(CCCCCCCCCCCCCCCCCC)OCC(CCN(C)C)O1]
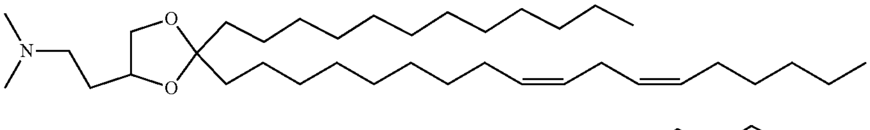
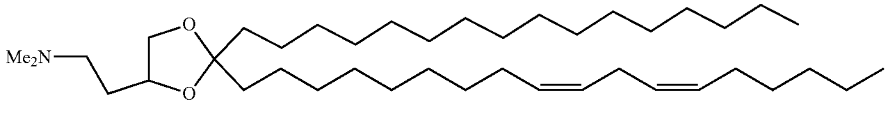 [SMILES: CCCCC/C=C\C/C=C\CCCCCCCCC1(CCCCCCCCCCCCCCCC)OCC(CCN(C)C)O1]

TABLE 11-continued
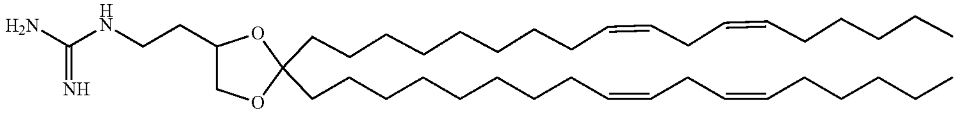 [SMILES: CCCCC/C=C\C/C=C\CCCCCCCCC1(CCCCCCCC/C=C\C/C=C\CCCCC)OCC(CCNC(=N)N)O1]
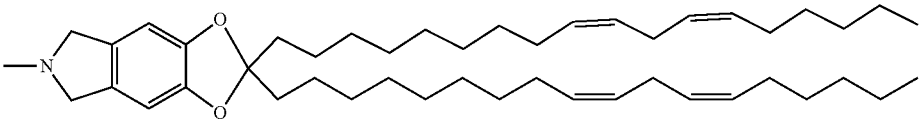 [SMILES: CCCCC/C=C\C/C=C\CCCCCCCCC1(CCCCCCCC/C=C\C/C=C\CCCCC)Oc2cc3c(cc2O1)CN(C)C3]
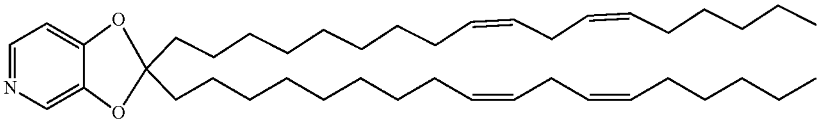 [SMILES: CCCCC/C=C\C/C=C\CCCCCCCCC1(CCCCCCCC/C=C\C/C=C\CCCCC)Oc2ccncc2O1]
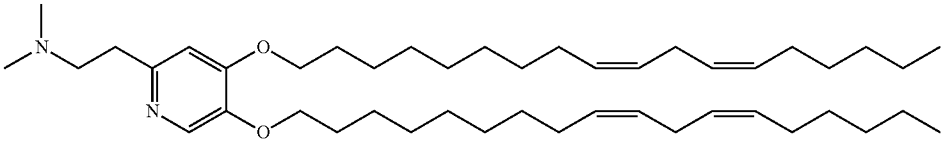 [SMILES: CCCCC/C=C\C/C=C\CCCCCCCCOc1cnc(CCN(C)C)cc1OCCCCCCCC/C=C\C/C=C\CCCCC]
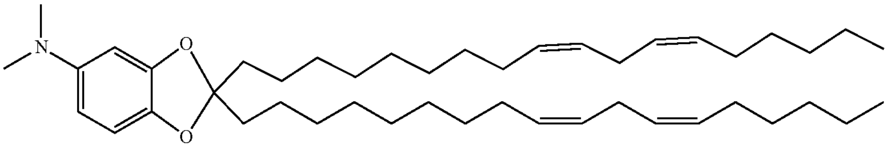 [SMILES: CCCCC/C=C\C/C=C\CCCCCCCCC1(CCCCCCCC/C=C\C/C=C\CCCCC)Oc2ccc(N(C)C)cc2O1]
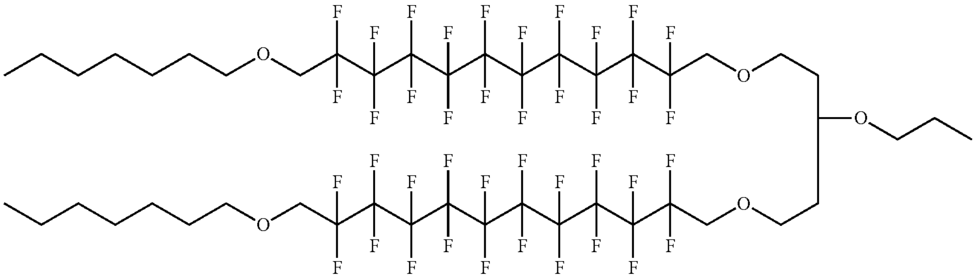 [SMILES: CCCCCCCOCC(F)(F)C(F)(F)C(F)(F)C(F)(F)C(F)(F)C(F)(F)C(F)(F)C(F)(F)C(F)(F)C(F)(F)COCCC(CCOCC(F)(F)C(F)(F)C(F)(F)C(F)(F)C(F)(F)C(F)(F)C(F)(F)C(F)(F)C(F)(F)C(F)(F)COCCCCCCC)OCCC]
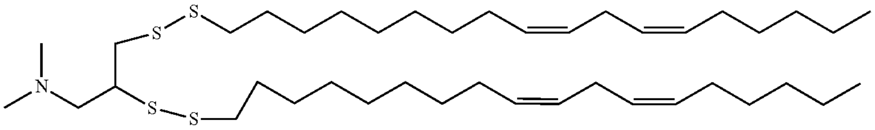 [SMILES: CCCCC/C=C\C/C=C\CCCCCCCCSSCC(CN(C)C)SSCCCCCCCC/C=C\C/C=C\CCCCC]
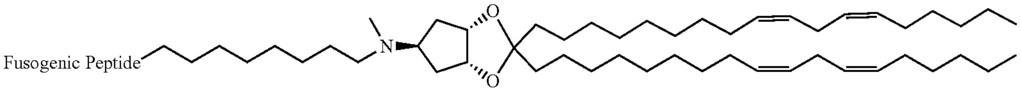
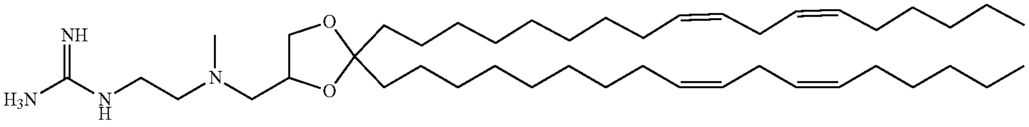 [SMILES: CCCCC/C=C\C/C=C\CCCCCCCCC1(CCCCCCCC/C=C\C/C=C\CCCCC)OCC(CN(C)CCNC(=N)N)O1]
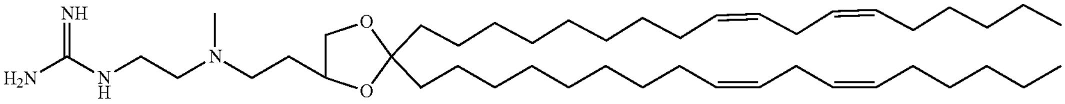 [SMILES: CCCCC/C=C\C/C=C\CCCCCCCCC1(CCCCCCCC/C=C\C/C=C\CCCCC)OCC(CCN(C)CCNC(=N)N)O1]
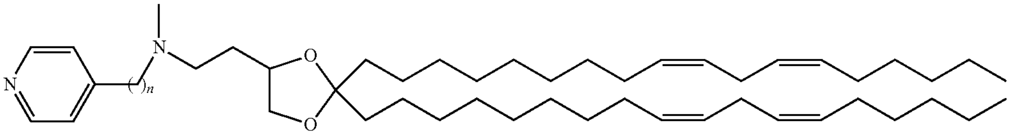 [SMILES: CCCCC/C=C\C/C=C\CCCCCCCCC1(CCCCCCCC/C=C\C/C=C\CCCCC)OCC(CCN(C)Cc2ccncc2)O1]

TABLE 11-continued
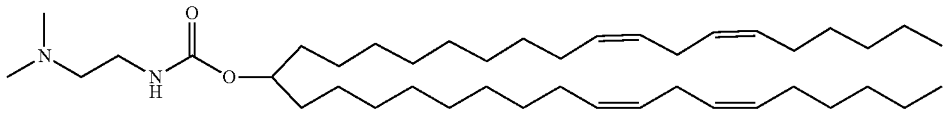 [SMILES: CCCCC/C=C\C/C=C\CCCCCCCCC(CCCCCCCC/C=C\C/C=C\CCCCC)OC(=O)NCCN(C)C]
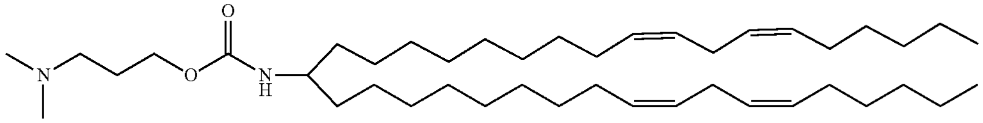 [SMILES: CCCCC/C=C\C/C=C\CCCCCCCCC(CCCCCCCC/C=C\C/C=C\CCCCC)NC(=O)OCCCN(C)C]
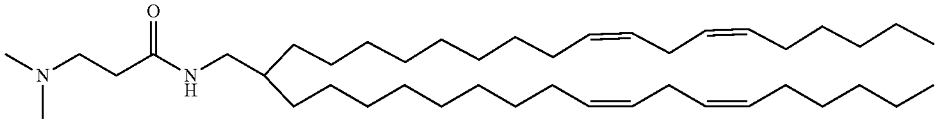 [SMILES: CCCCC/C=C\C/C=C\CCCCCCCCC(CCCCCCCC/C=C\C/C=C\CCCCC)CNC(=O)CCN(C)C]
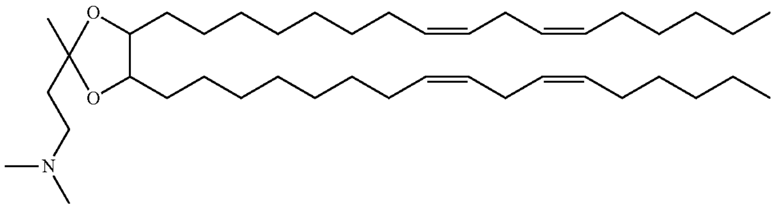
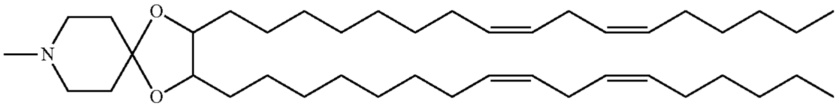 [SMILES: CCCCC/C=C\C/C=C\CCCCCCCC1OC2(CCN(C)CC2)OC1CCCCCCC/C=C\C/C=C\CCCCC]
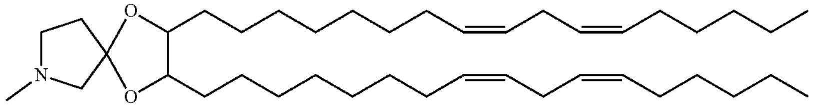 [SMILES: CCCCC/C=C\C/C=C\CCCCCCCC1OC2(CCN(C)C2)OC1CCCCCCC/C=C\C/C=C\CCCCC]
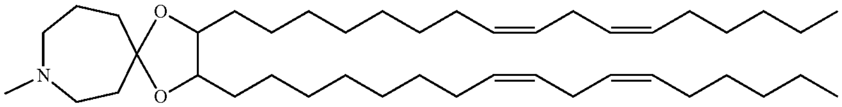 [SMILES: CCCCC/C=C\C/C=C\CCCCCCCC1OC2(CCCN(C)CC2)OC1CCCCCCC/C=C\C/C=C\CCCCC]
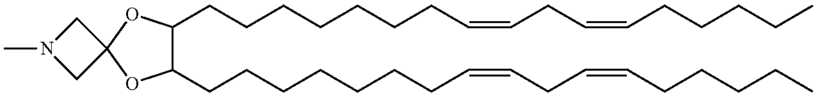 [SMILES: CCCCC/C=C\C/C=C\CCCCCCCC1OC2(CN(C)C2)OC1CCCCCCC/C=C\C/C=C\CCCCC]
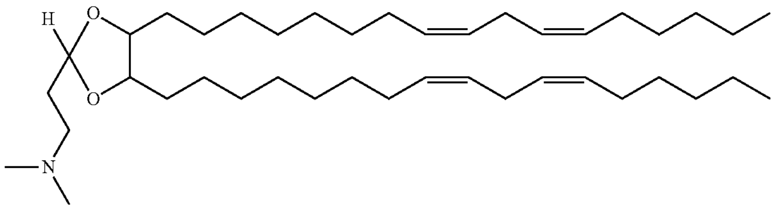 [SMILES: CCCCC/C=C\C/C=C\CCCCCCCC1OC(CCN(C)C)OC1CCCCCCC/C=C\C/C=C\CCCCC]
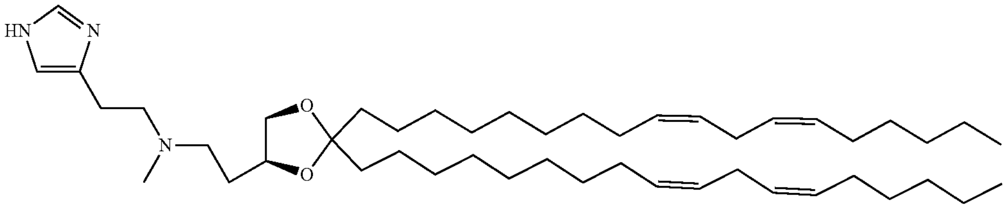

TABLE 11-continued
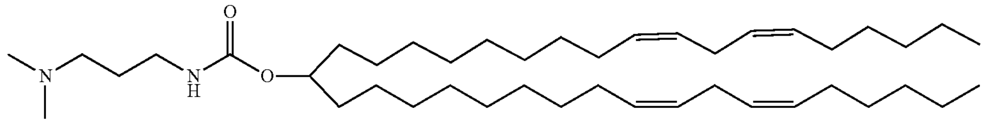 [SMILES: CCCCC/C=C\C/C=C\CCCCCCCCC(CCCCCCCC/C=C\C/C=C\CCCCC)OC(=O)NCCCN(C)C]
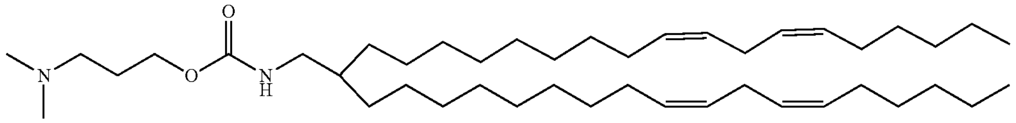 [SMILES: CCCCC/C=C\C/C=C\CCCCCCCCC(CCCCCCCC/C=C\C/C=C\CCCCC)CNC(=O)OCCCN(C)C]
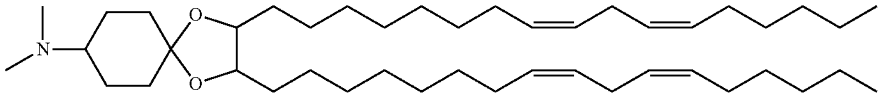 [SMILES: CCCCC/C=C\C/C=C\CCCCCCCC1OC2(CCC(N(C)C)CC2)OC1CCCCCCC/C=C\C/C=C\CCCCC]
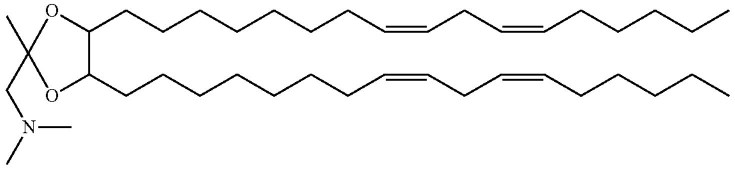 [SMILES: CCCCC/C=C\C/C=C\CCCCCCCC1OC(C)(CN(C)C)OC1CCCCCCC/C=C\C/C=C\CCCCC]
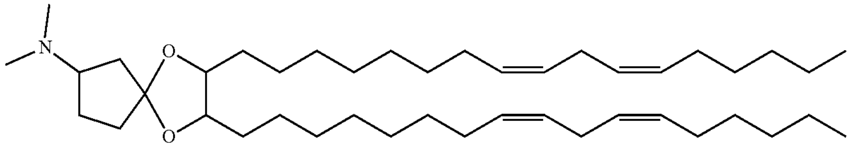 [SMILES: CCCCC/C=C\C/C=C\CCCCCCCC1OC2(CCC(N(C)C)C2)OC1CCCCCCC/C=C\C/C=C\CCCCC]
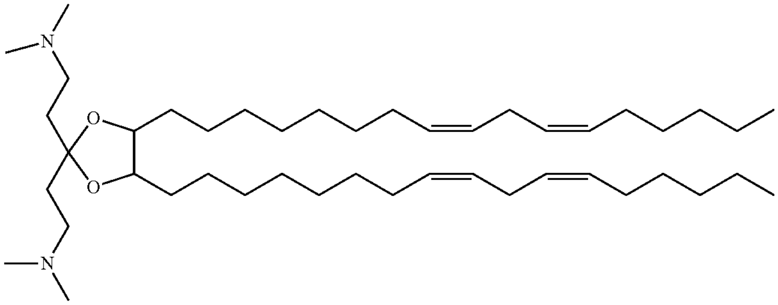 [SMILES: CCCCC/C=C\C/C=C\CCCCCCCC1OC(CCN(C)C)(CCN(C)C)OC1CCCCCCC/C=C\C/C=C\CCCCC]
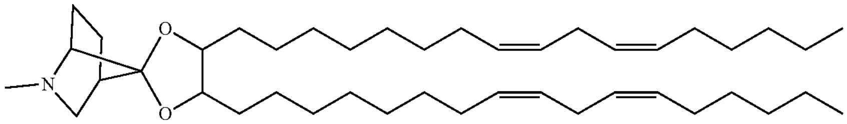 [SMILES: CCCCC/C=C\C/C=C\CCCCCCCC1OC2(OC1CCCCCCC/C=C\C/C=C\CCCCC)C1CCC2N(C)C1]
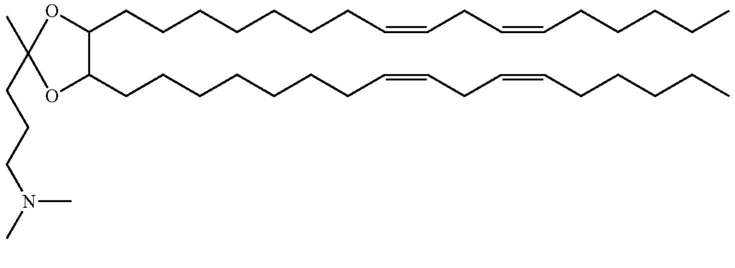 [SMILES: CCCCC/C=C\C/C=C\CCCCCCCC1OC(C)(CCCN(C)C)OC1CCCCCCC/C=C\C/C=C\CCCCC]

TABLE 11-continued
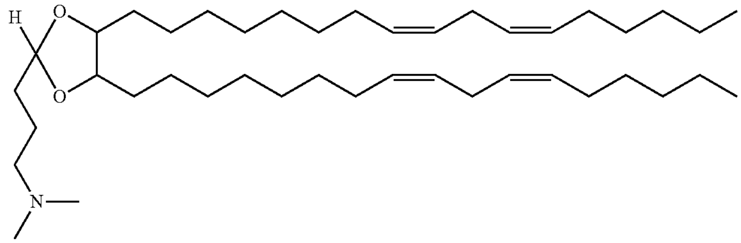 [SMILES: CCCCC/C=C\C/C=C\CCCCCCCC1OC(CCCN(C)C)OC1CCCCCCC/C=C\C/C=C\CCCCC]
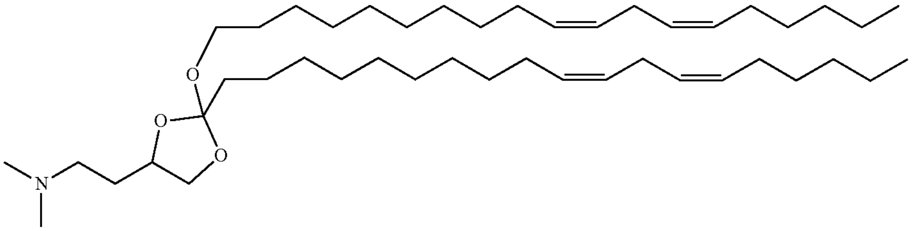 [SMILES: CCCCC/C=C\C/C=C\CCCCCCCCCOC1(CCCCCCCCC/C=C\C/C=C\CCCCC)OCC(CCN(C)C)O1]
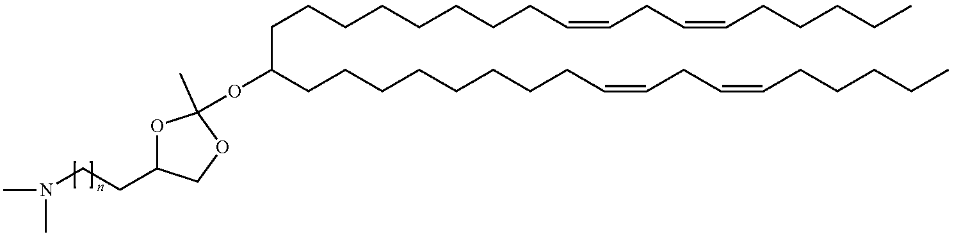
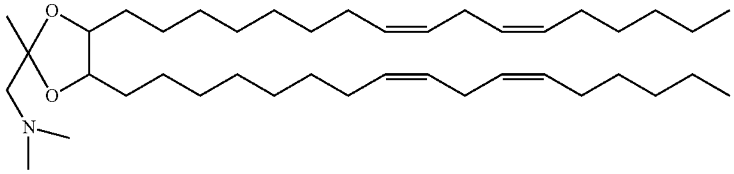 [SMILES: CCCCC/C=C\C/C=C\CCCCCCCC1OC(C)(CN(C)C)OC1CCCCCCC/C=C\C/C=C\CCCCC]
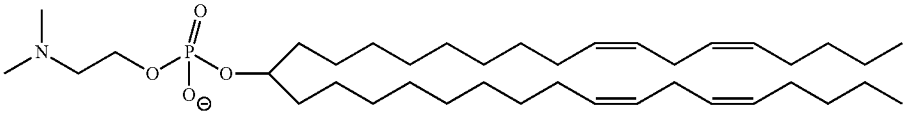 [SMILES: CCCC/C=C\C/C=C\CCCCCCCCC(CCCCCCCC/C=C\C/C=C\CCCC)OP(=O)([O-])OCCN(C)C]
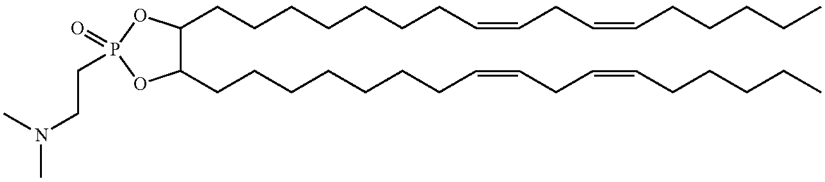 [SMILES: CCCCC/C=C\C/C=C\CCCCCCCC1OP(=O)(CCN(C)C)OC1CCCCCCC/C=C\C/C=C\CCCCC]
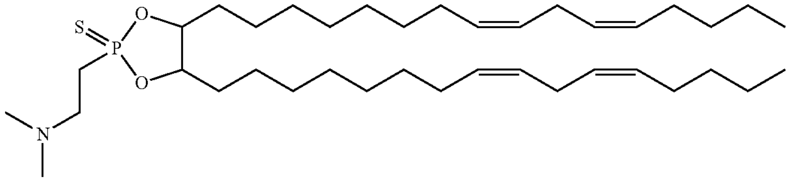 [SMILES: CCCC/C=C\C/C=C\CCCCCCCC1OP(=S)(CCN(C)C)OC1CCCCCCC/C=C\C/C=C\CCCC]
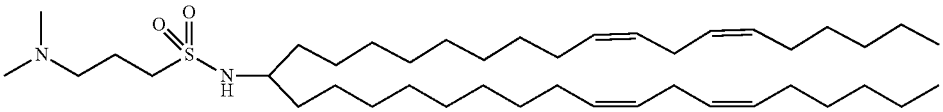 [SMILES: CCCCC/C=C\C/C=C\CCCCCCCCC(CCCCCCCC/C=C\C/C=C\CCCCC)NS(=O)(=O)CCCN(C)C]

TABLE 11-continued
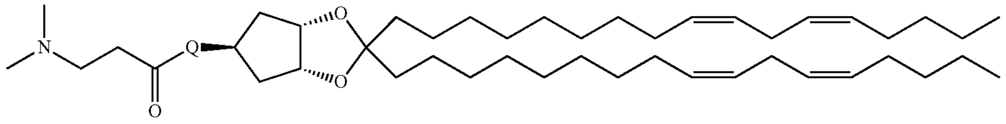
Q is O, NH, NMe
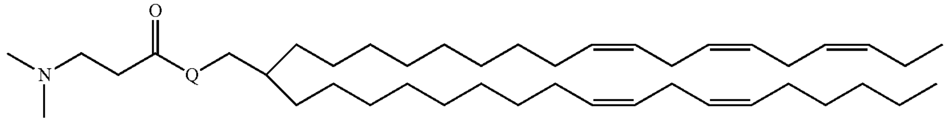
Q is O, NH, NMe
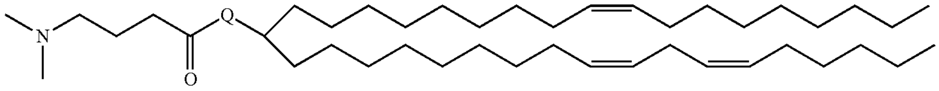
Q is O, NH, NMe
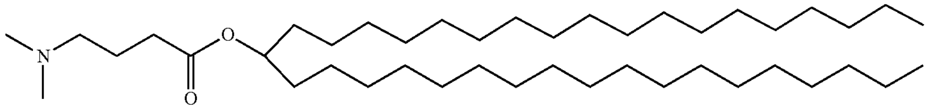 [SMILES: CCCCCCCCCCCCCCCCCCC(CCCCCCCCCCCCCCCCCC)OC(=O)CCCN(C)C]
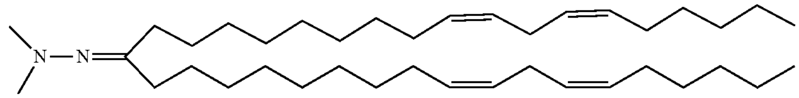 [SMILES: CCCCC/C=C\C/C=C\CCCCCCCCC(CCCCCCCC/C=C\C/C=C\CCCCC)=NN(C)C]
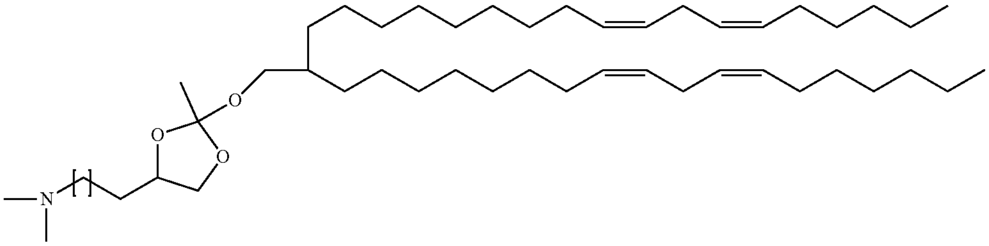
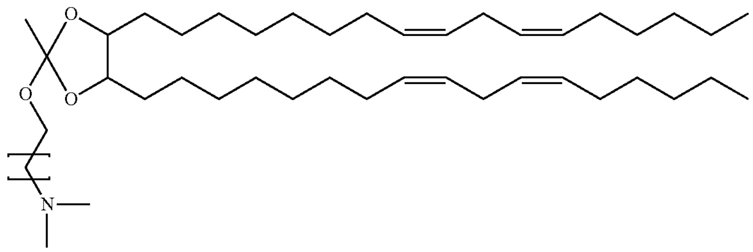
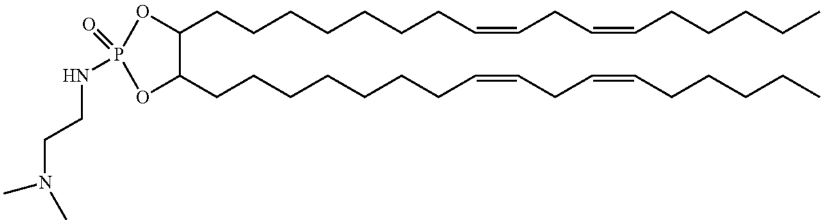 [SMILES: CCCCC/C=C\C/C=C\CCCCCCCC1OP(=O)(NCCN(C)C)OC1CCCCCCC/C=C\C/C=C\CCCCC]
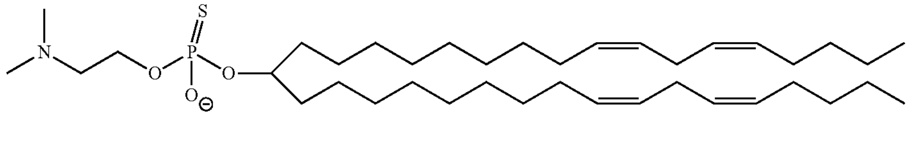 [SMILES: CCCC/C=C\C/C=C\CCCCCCCCC(CCCCCCCC/C=C\C/C=C\CCCC)OP([O-])(=S)OCCN(C)C]

TABLE 11-continued
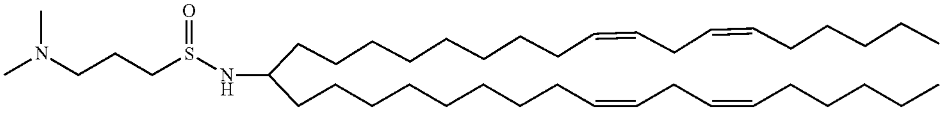 [SMILES: CCCCC/C=C\C/C=C\CCCCCCCCC(CCCCCCCC/C=C\C/C=C\CCCCC)NS(=O)CCCN(C)C]
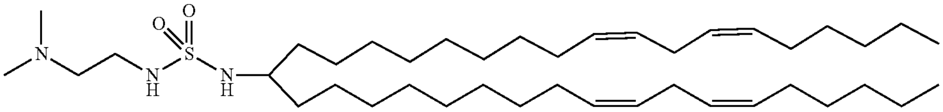 [SMILES: CCCCC/C=C\C/C=C\CCCCCCCCC(CCCCCCCC/C=C\C/C=C\CCCCC)NS(=O)(=O)NCCN(C)C]
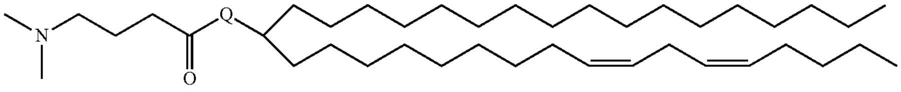
Q is O, NH, NMe
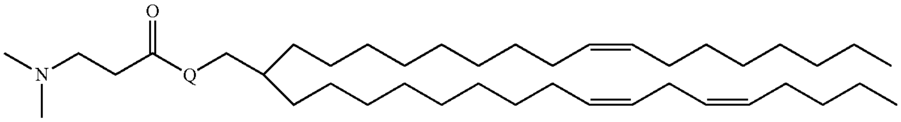
Q is O, NH, NMe
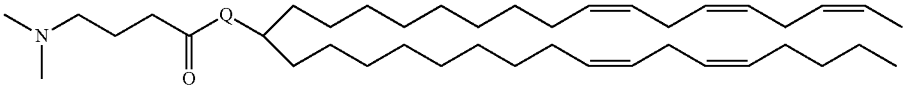
Q is O, NH, NMe
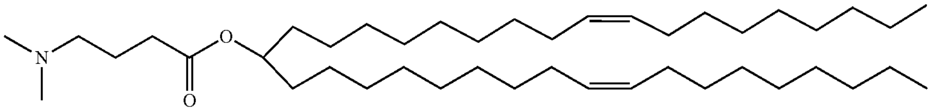 [SMILES: CCCCCCCC/C=C\CCCCCCCCC(CCCCCCCC/C=C\CCCCCCCC)OC(=O)CCCN(C)C]
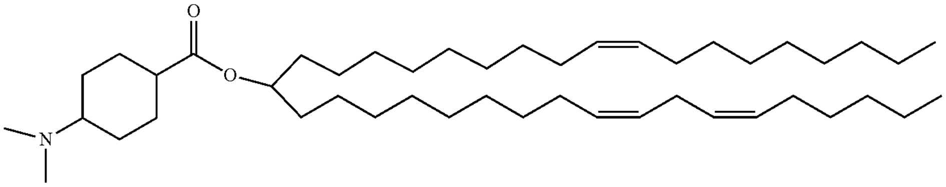 [SMILES: CCCCC/C=C\C/C=C\CCCCCCCCC(CCCCCCCC/C=C\CCCCCCCC)OC(=O)C1CCC(N(C)C)CC1]
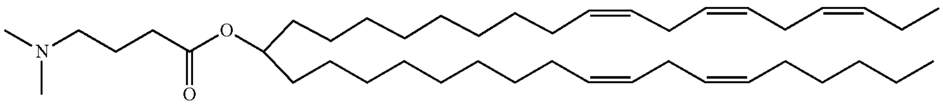 [SMILES: CC/C=C\C/C=C\C/C=C\CCCCCCCCC(CCCCCCCC/C=C\C/C=C\CCCCC)OC(=O)CCCN(C)C]
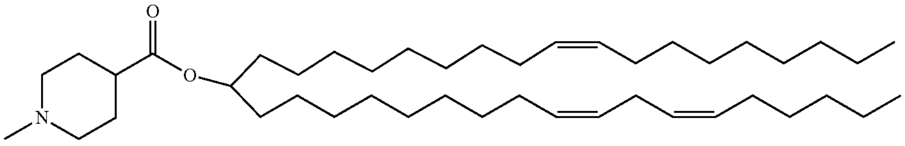 [SMILES: CCCCC/C=C\C/C=C\CCCCCCCCC(CCCCCCCC/C=C\CCCCCCCC)OC(=O)C1CCN(C)CC1]
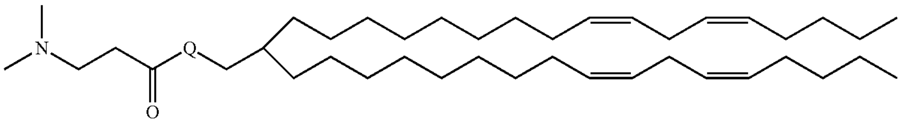
Q is O, NH, NMe
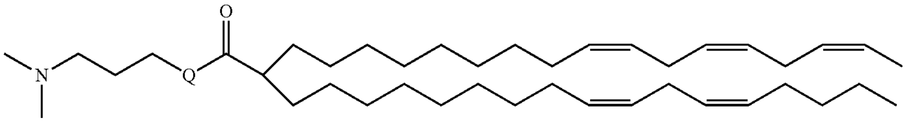
Q is O, NH, NMe TABLE 11-continued
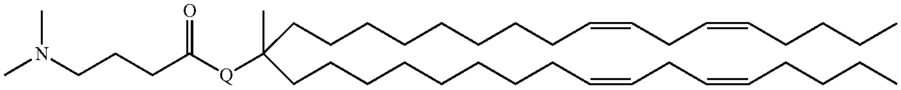
Q is O, NH, NMe
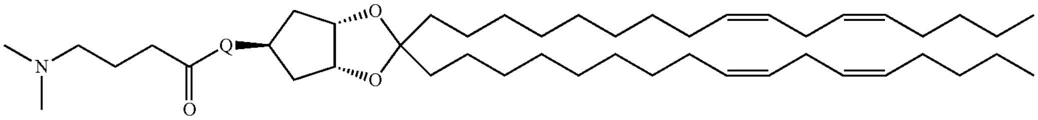
Q is O, NH, NMe
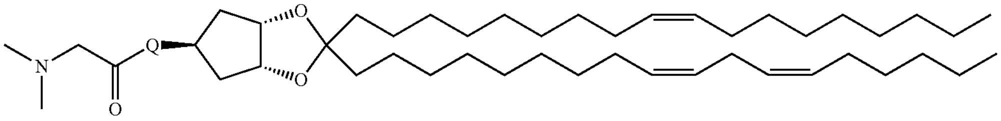
Q is O, NH, NMe
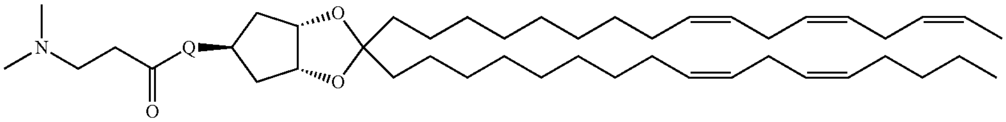
Q is O, NH, NMe
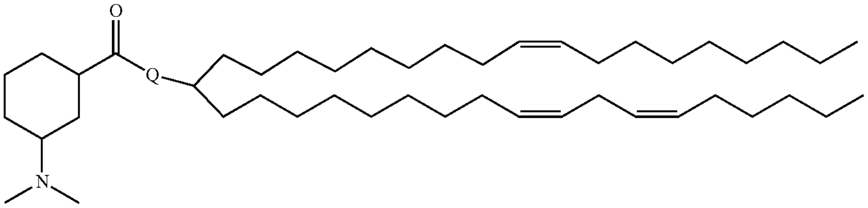
Q is O, NH, NMe
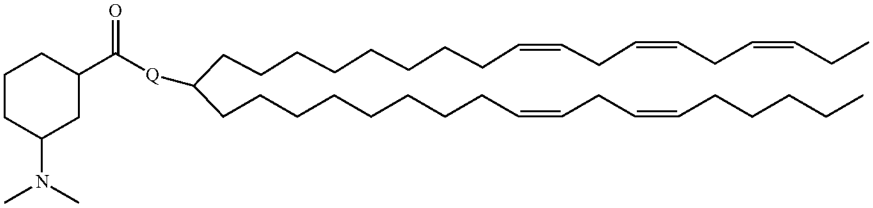
Q is O, NH, NMe
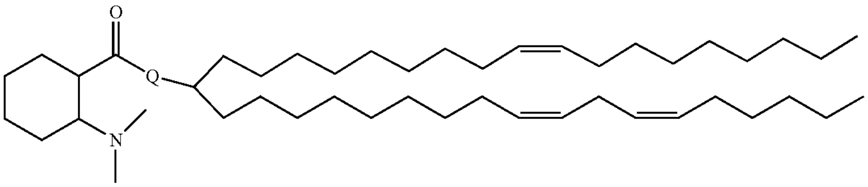
Q is O, NH, NMe
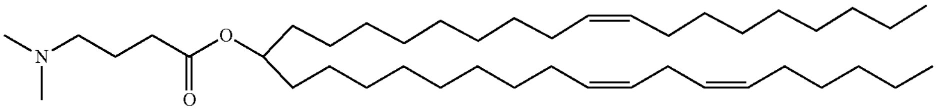 [SMILES: CCCCC/C=C\C/C=C\CCCCCCCCC(CCCCCCCC/C=C\CCCCCCCC)OC(=O)CCCN(C)C]

TABLE 11-continued
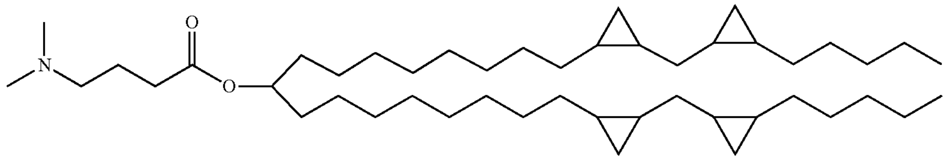 [SMILES: CCCCCC1CC1CC1CC1CCCCCCCCC(CCCCCCCCC1CC1CC1CC1CCCCC)OC(=O)CCCN(C)C]
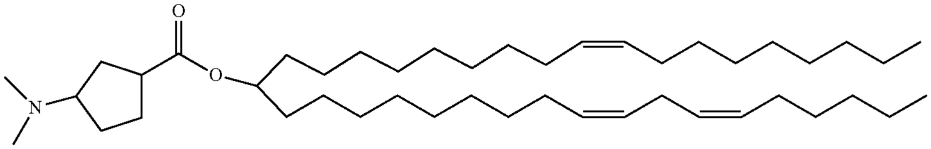 [SMILES: CCCCC/C=C\C/C=C\CCCCCCCCC(CCCCCCCC/C=C\CCCCCCCC)OC(=O)C1CCC(N(C)C)C1]
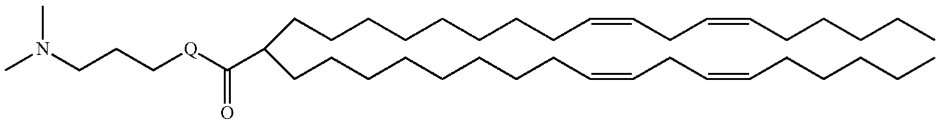
Q is O, NH, NMe
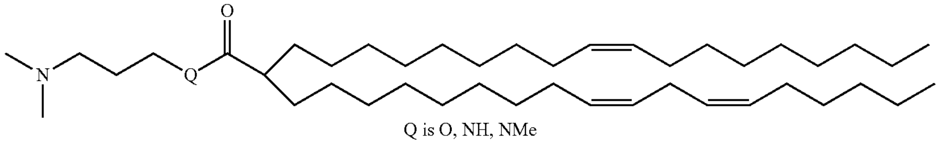
Q is O, NH, NMe
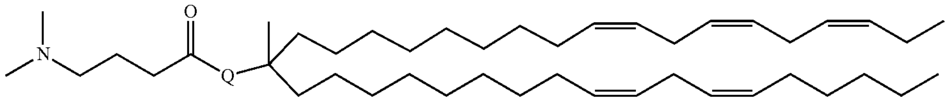
Q is O, NH, NMe
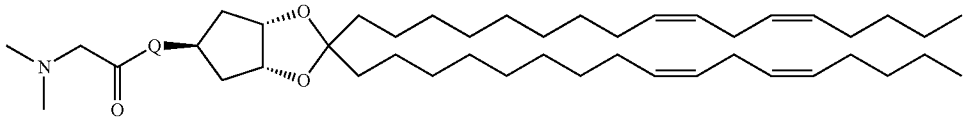
Q is O, NH, NMe
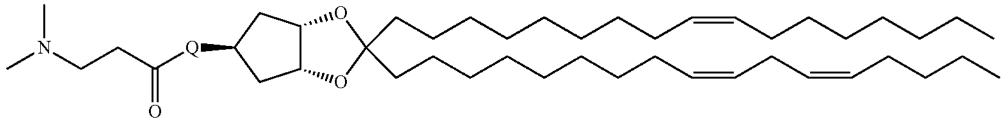
Q is O, NH, NMe
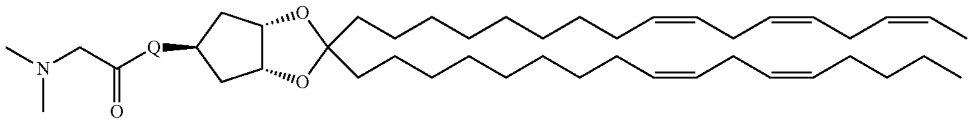
Q is O, NH, NMe
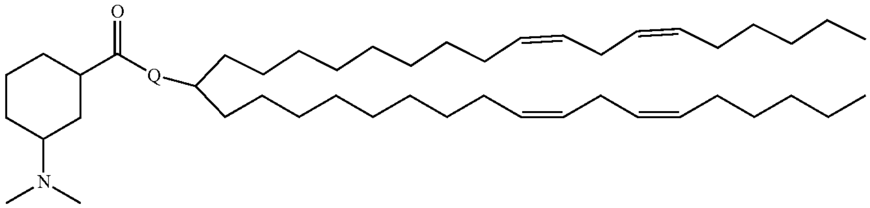
Q is O, NH, NMe TABLE 11-continued
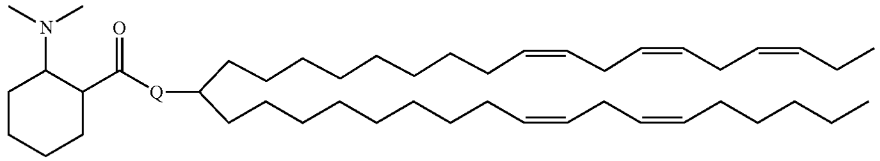
Q is O, NH, NMe
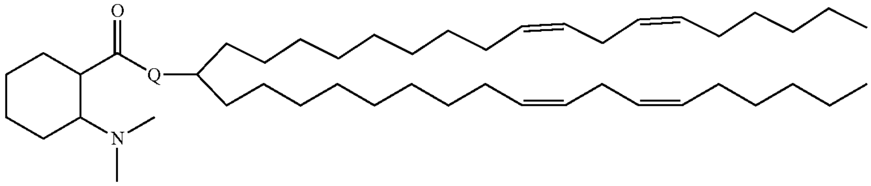
Q is O, NH, NMe
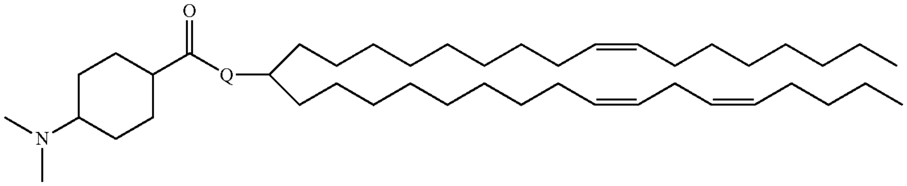
Q is O, NH, NMe
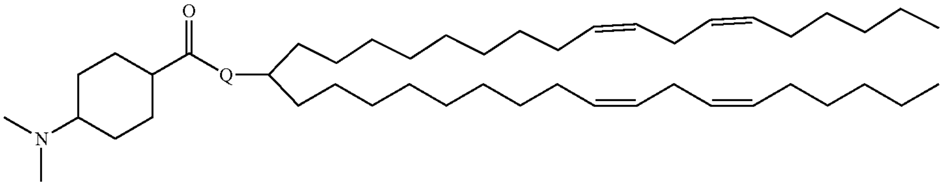
Q is O, NH, NMe
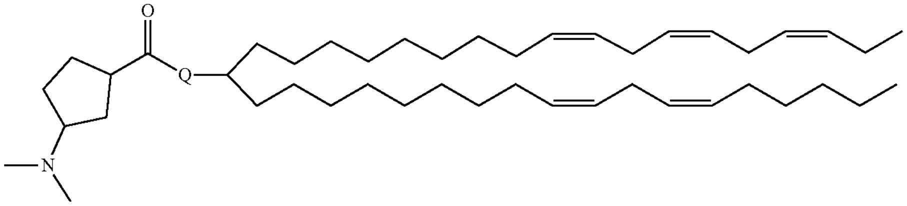
Q is O, NH, NMe
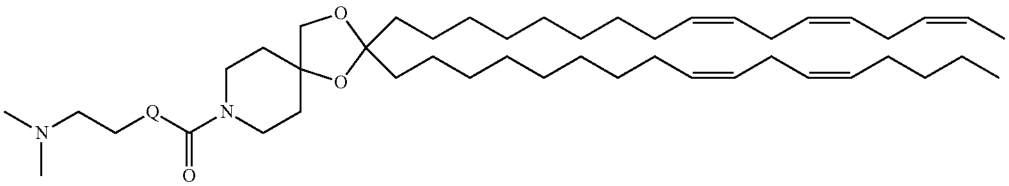
Q is O, NH, NMe
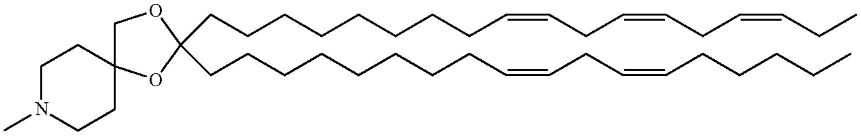 [SMILES: CC/C=C\C/C=C\C/C=C\CCCCCCCCC1(CCCCCCCC/C=C\C/C=C\CCCCC)OCC2(CCN(C)CC2)O1]

TABLE 11-continued
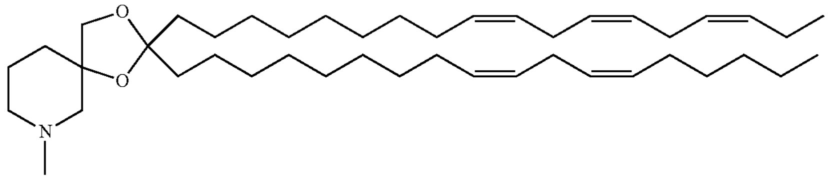 [SMILES: CC/C=C\C/C=C\C/C=C\CCCCCCCCC1(CCCCCCCC/C=C\C/C=C\CCCCC)OCC2(CCCN(C)C2)O1]
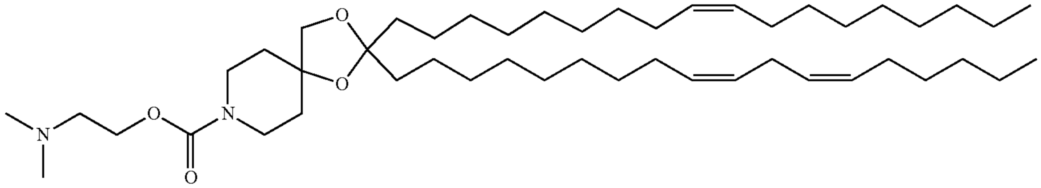 [SMILES: CCCCC/C=C\C/C=C\CCCCCCCCC1(CCCCCCCC/C=C\CCCCCCCC)OCC2(CCN(C(=O)OCCN(C)C)CC2)O1]
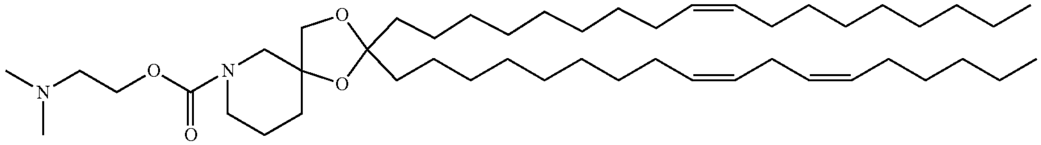
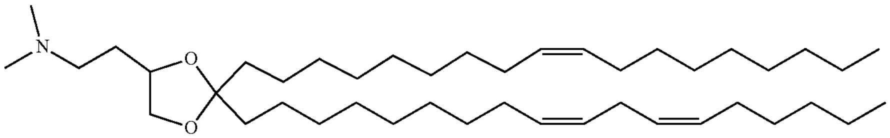 [SMILES: CCCCC/C=C\C/C=C\CCCCCCCCC1(CCCCCCCC/C=C\CCCCCCCC)OCC(CCN(C)C)O1]
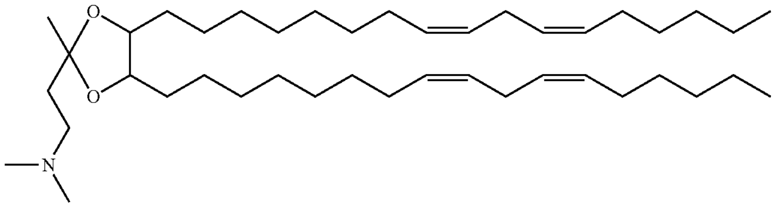
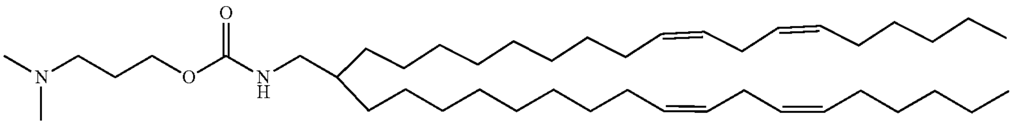 [SMILES: CCCCC/C=C\C/C=C\CCCCCCCCC(CCCCCCCC/C=C\C/C=C\CCCCC)CNC(=O)OCCCN(C)C]
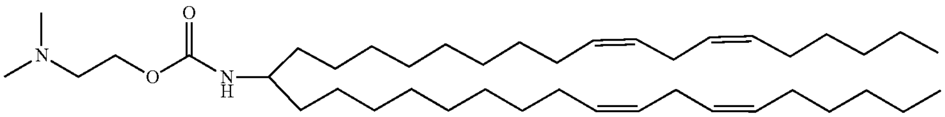 [SMILES: CCCCC/C=C\C/C=C\CCCCCCCCC(CCCCCCCC/C=C\C/C=C\CCCCC)NC(=O)OCCN(C)C]
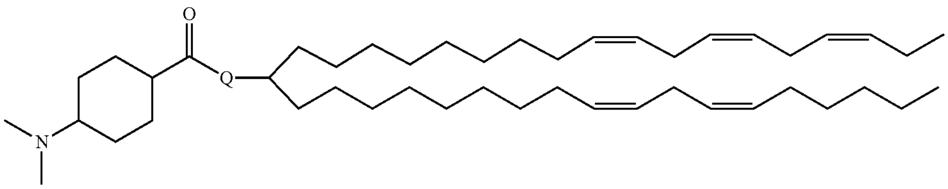
Q is O, NH, NMe
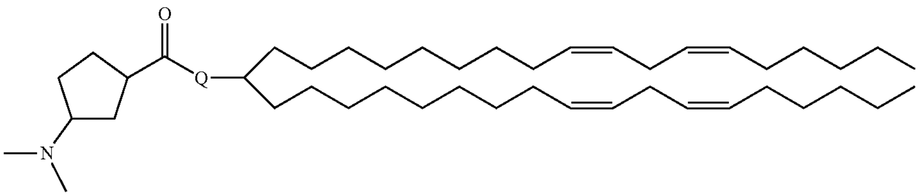
Q is O, NH, NMe TABLE 11-continued
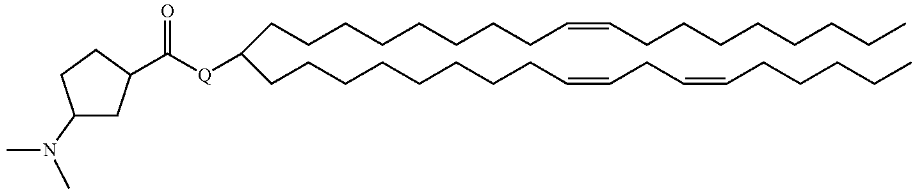
Q is O, NH, NMe
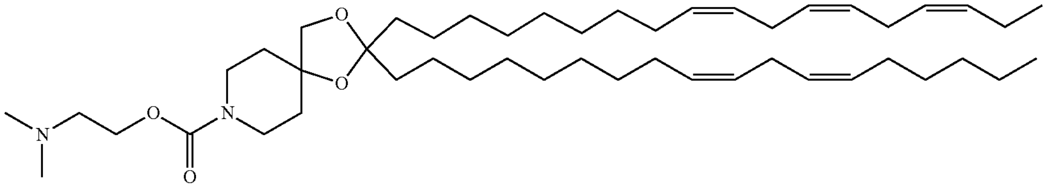 [SMILES: CC/C=C\C/C=C\C/C=C\CCCCCCCCC1(CCCCCCCC/C=C\C/C=C\CCCCC)OCC2(CCN(C(=O)OCCN(C)C)CC2)O1]
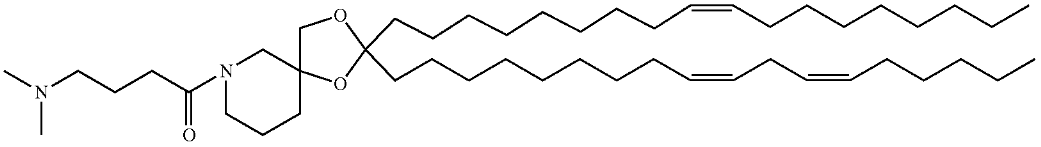 [SMILES: CCCCC/C=C\C/C=C\CCCCCCCCC1(CCCCCCCC/C=C\CCCCCCCC)OCC2(CCCN(C(=O)CCCN(C)C)C2)O1]
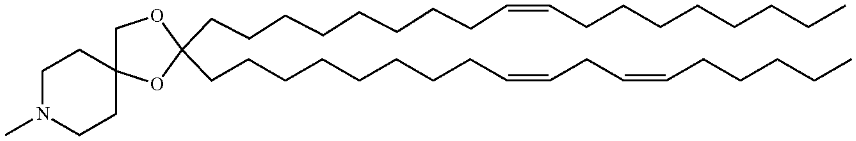 [SMILES: CCCCC/C=C\C/C=C\CCCCCCCCC1(CCCCCCCC/C=C\CCCCCCCC)OCC2(CCN(C)CC2)O1]
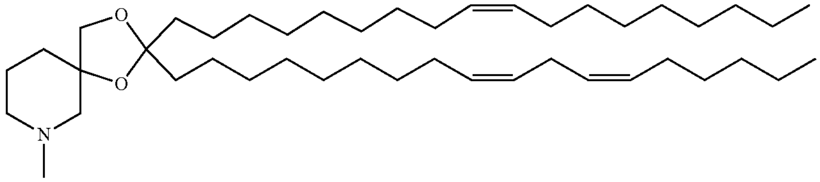 [SMILES: CCCCC/C=C\C/C=C\CCCCCCCCC1(CCCCCCCC/C=C\CCCCCCCC)OCC2(CCCN(C)C2)O1]
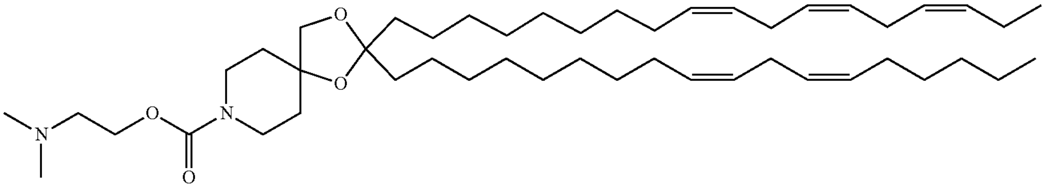 [SMILES: CC/C=C\C/C=C\C/C=C\CCCCCCCCC1(CCCCCCCC/C=C\C/C=C\CCCCC)OCC2(CCN(C(=O)OCCN(C)C)CC2)O1]
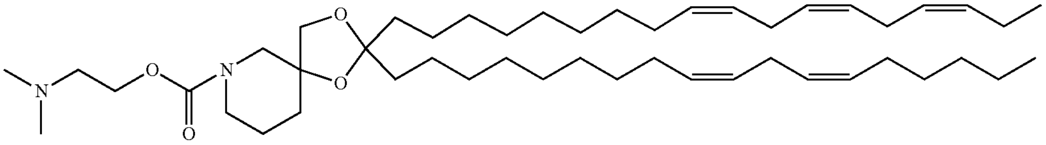 [SMILES: CC/C=C\C/C=C\C/C=C\CCCCCCCCC1(CCCCCCCC/C=C\C/C=C\CCCCC)OCC2(CCCN(C(=O)OCCN(C)C)C2)O1]
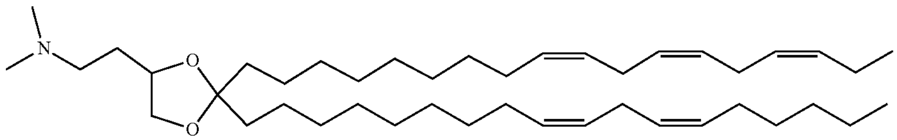 [SMILES: CC/C=C\C/C=C\C/C=C\CCCCCCCCC1(CCCCCCCC/C=C\C/C=C\CCCCC)OCC(CCN(C)C)O1]
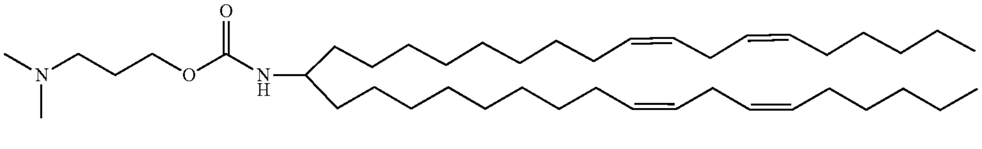 [SMILES: CCCCC/C=C\C/C=C\CCCCCCCCC(CCCCCCCC/C=C\C/C=C\CCCCC)NC(=O)OCCCN(C)C]

TABLE 11-continued
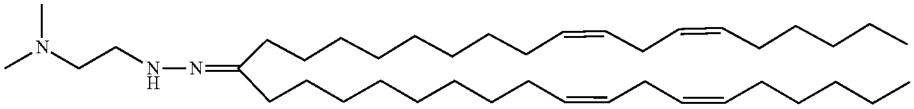 [SMILES: CCCCC/C=C\C/C=C\CCCCCCCCC(CCCCCCCC/C=C\C/C=C\CCCCC)=NNCCN(C)C]
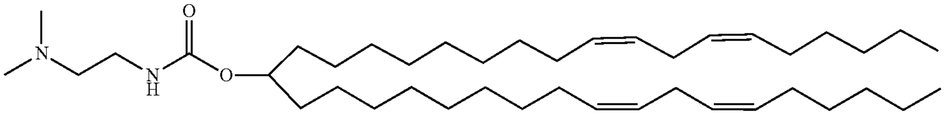 [SMILES: CCCCC/C=C\C/C=C\CCCCCCCCC(CCCCCCCC/C=C\C/C=C\CCCCC)OC(=O)NCCN(C)C]
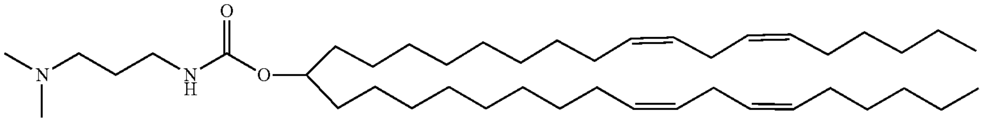 [SMILES: CCCCC/C=C\C/C=C\CCCCCCCCC(CCCCCCCC/C=C\C/C=C\CCCCC)OC(=O)NCCCN(C)C]
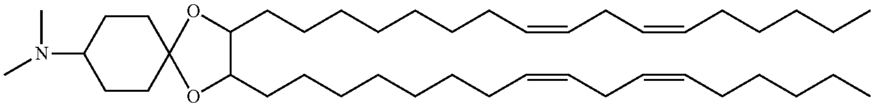 [SMILES: CCCCC/C=C\C/C=C\CCCCCCCC1OC2(CCC(N(C)C)CC2)OC1CCCCCCC/C=C\C/C=C\CCCCC]
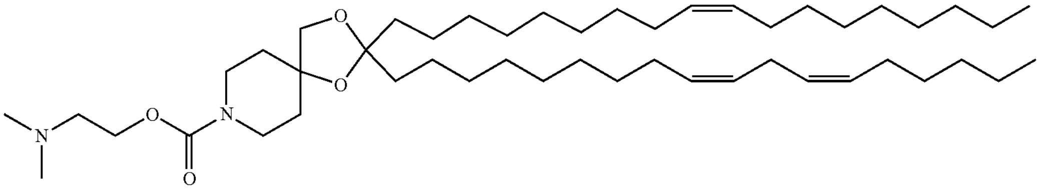 [SMILES: CCCCC/C=C\C/C=C\CCCCCCCCC1(CCCCCCCC/C=C\CCCCCCCC)OCC2(CCN(C(=O)OCCN(C)C)CC2)O1]
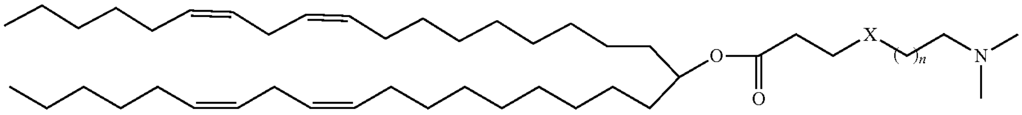
X = O, S, NH, NMe; n = 0-6
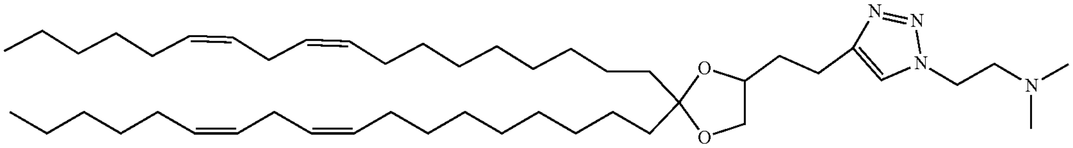 [SMILES: CCCCC/C=C\C/C=C\CCCCCCCCC1(CCCCCCCC/C=C\C/C=C\CCCCC)OCC(CCc2cn(CCN(C)C)nn2)O1]
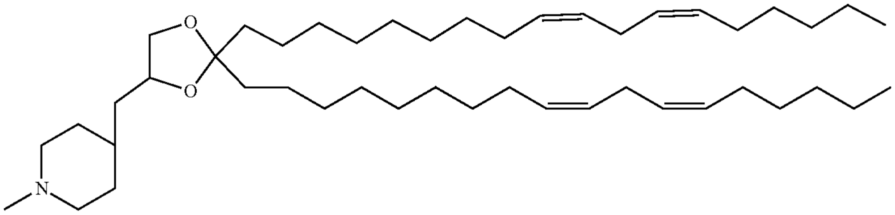 [SMILES: CCCCC/C=C\C/C=C\CCCCCCCCC1(CCCCCCCC/C=C\C/C=C\CCCCC)OCC(CC2CCN(C)CC2)O1]
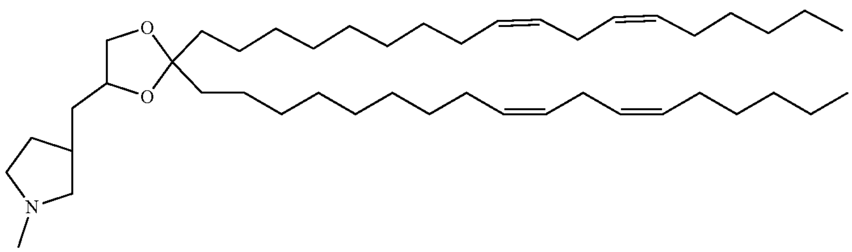 [SMILES: CCCCC/C=C\C/C=C\CCCCCCCCC1(CCCCCCCC/C=C\C/C=C\CCCCC)OCC(CC2CCN(C)C2)O1]

TABLE 11-continued
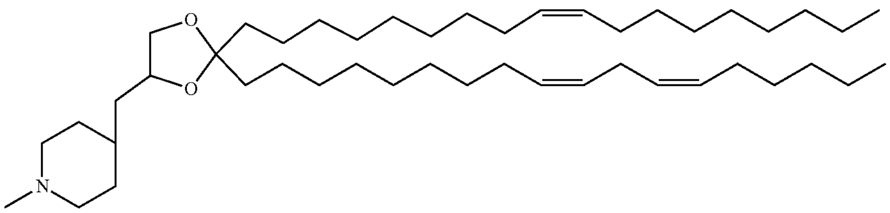 [SMILES: CCCCC/C=C\C/C=C\CCCCCCCCC1(CCCCCCCC/C=C\CCCCCCCC)OCC(CC2CCN(C)CC2)O1]
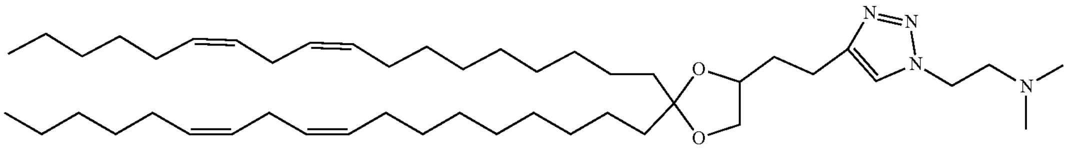 [SMILES: CCCCC/C=C\C/C=C\CCCCCCCCC1(CCCCCCCC/C=C\C/C=C\CCCCC)OCC(CCc2cn(CCN(C)C)nn2)O1]
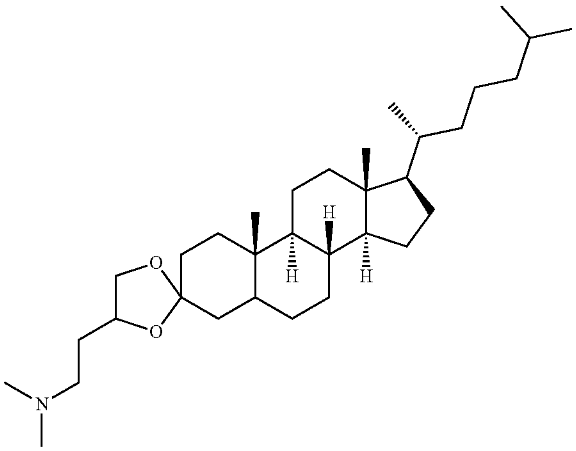
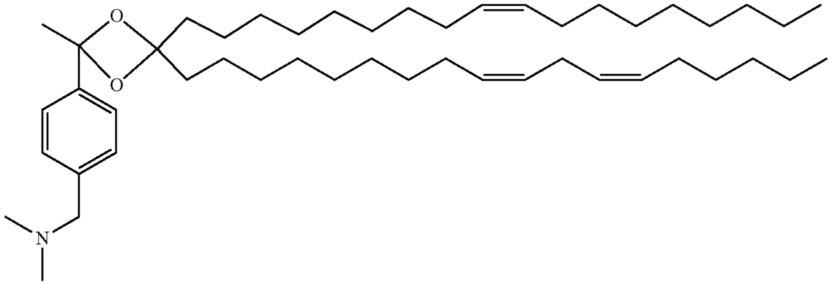 [SMILES: CCCCC/C=C\C/C=C\CCCCCCCCC1(CCCCCCCC/C=C\CCCCCCCC)OC(C)(c2ccc(CN(C)C)cc2)O1]
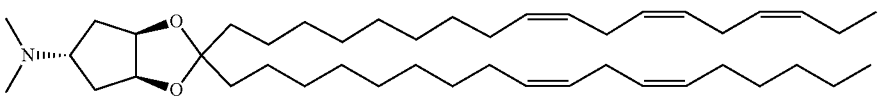
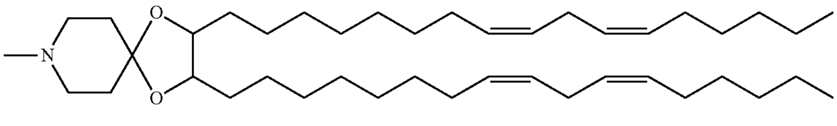 [SMILES: CCCCC/C=C\C/C=C\CCCCCCCC1OC2(CCN(C)CC2)OC1CCCCCCC/C=C\C/C=C\CCCCC]
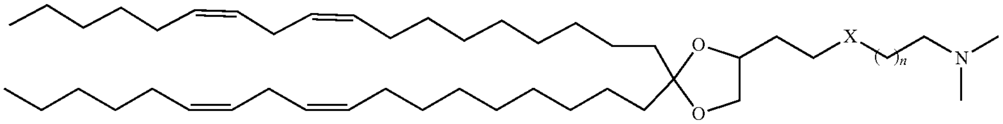
X = O, S, NH, NMe; n = 0-6

TABLE 11-continued
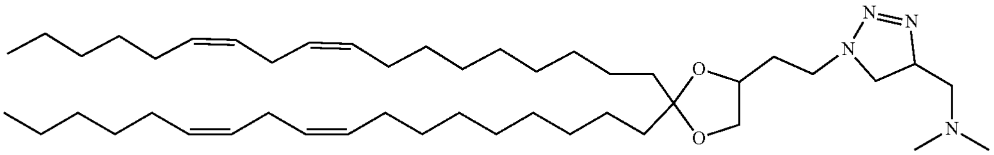 [SMILES: CCCCC/C=C\C/C=C\CCCCCCCCC1(CCCCCCCC/C=C\C/C=C\CCCCC)OCC(CCN2CC(CN(C)C)N=N2)O1]
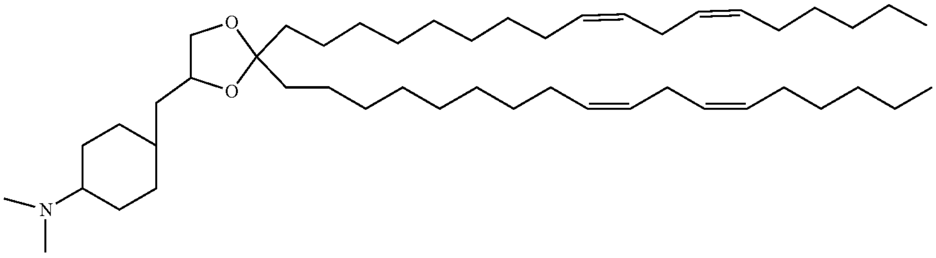 [SMILES: CCCCC/C=C\C/C=C\CCCCCCCCC1(CCCCCCCC/C=C\C/C=C\CCCCC)OCC(CC2CCC(N(C)C)CC2)O1]
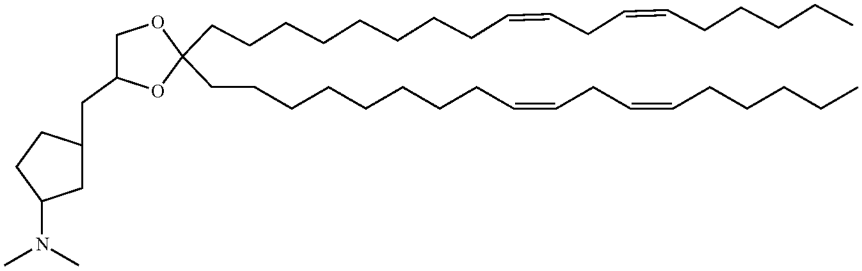 [SMILES: CCCCC/C=C\C/C=C\CCCCCCCCC1(CCCCCCCC/C=C\C/C=C\CCCCC)OCC(CC2CCC(N(C)C)C2)O1]
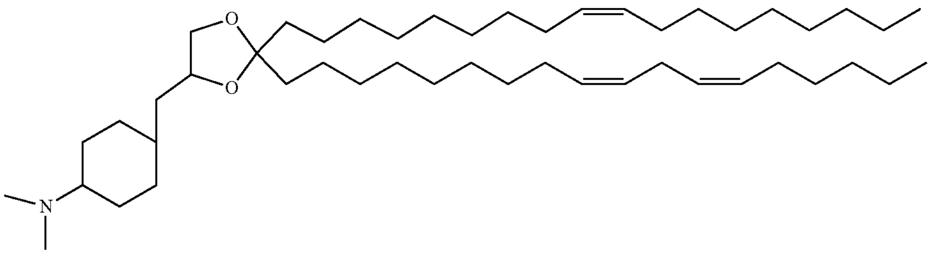 [SMILES: CCCCC/C=C\C/C=C\CCCCCCCCC1(CCCCCCCC/C=C\CCCCCCCC)OCC(CC2CCC(N(C)C)CC2)O1]
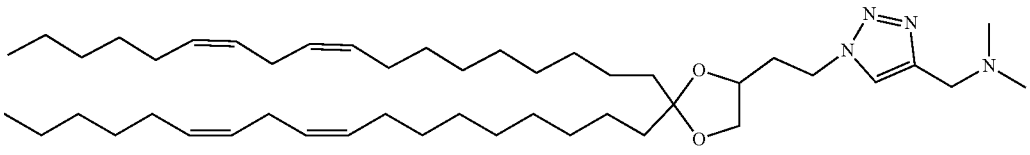 [SMILES: CCCCC/C=C\C/C=C\CCCCCCCCC1(CCCCCCCC/C=C\C/C=C\CCCCC)OCC(CCn2cc(CN(C)C)nn2)O1]
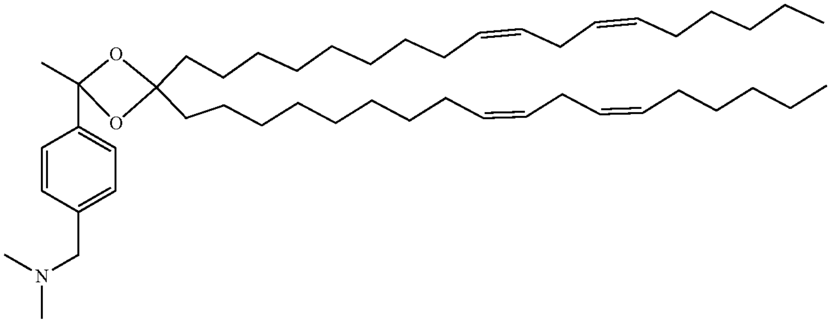 [SMILES: CCCCC/C=C\C/C=C\CCCCCCCCC1(CCCCCCCC/C=C\C/C=C\CCCCC)OC(C)(c2ccc(CN(C)C)cc2)O1]

TABLE 11-continued
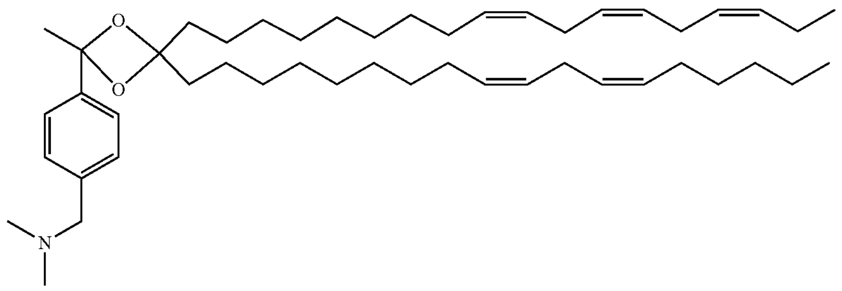 [SMILES: CC/C=C\C/C=C\C/C=C\CCCCCCCCC1(CCCCCCCC/C=C\C/C=C\CCCCC)OC(C)(c2ccc(CN(C)C)cc2)O1]
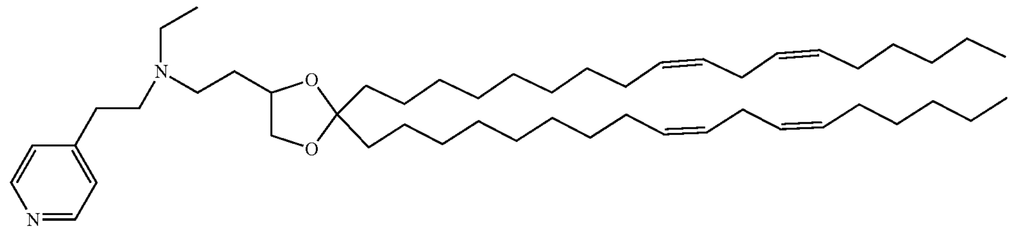 [SMILES: CCCCC/C=C\C/C=C\CCCCCCCCC1(CCCCCCCC/C=C\C/C=C\CCCCC)OCC(CCN(CC)CCc2ccncc2)O1]
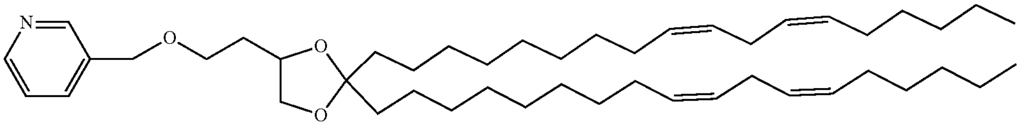 [SMILES: CCCCC/C=C\C/C=C\CCCCCCCCC1(CCCCCCCC/C=C\C/C=C\CCCCC)OCC(CCOCc2cccnc2)O1]
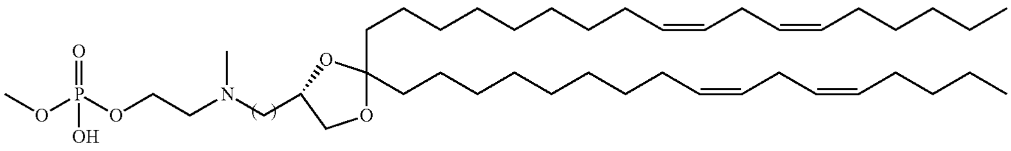
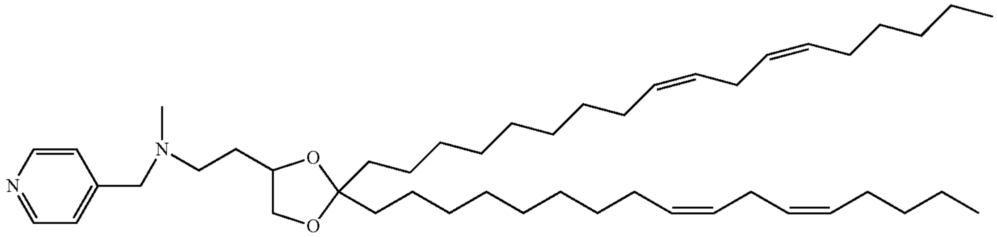 [SMILES: CCCC/C=C\C/C=C\CCCCCCCCC1(CCCCCCCC/C=C\C/C=C\CCCCC)OCC(CCN(C)Cc2ccncc2)O1]
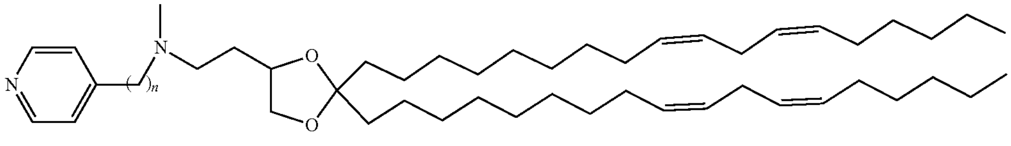
n = 0-6
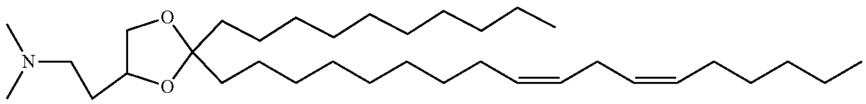 [SMILES: CCCCC/C=C\C/C=C\CCCCCCCCC1(CCCCCCCCCC)OCC(CCN(C)C)O1]
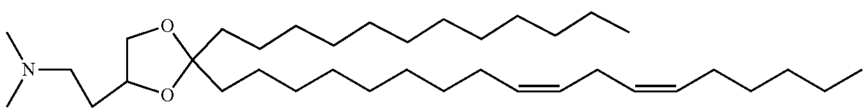 [SMILES: CCCCC/C=C\C/C=C\CCCCCCCCC1(CCCCCCCCCCCC)OCC(CCN(C)C)O1]

TABLE 11-continued
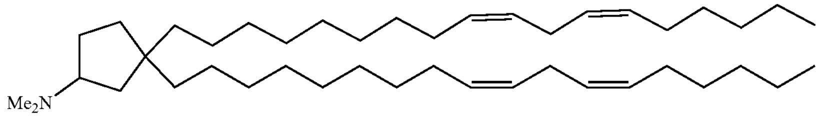
Racemic and optically pure
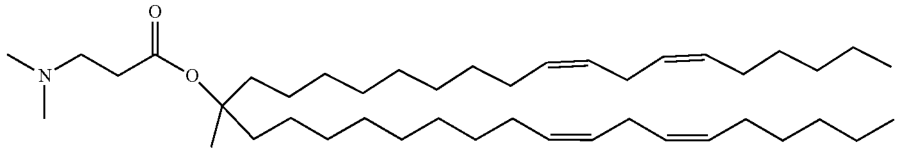 [SMILES: CCCCC/C=C\C/C=C\CCCCCCCCC(C)(CCCCCCCC/C=C\C/C=C\CCCCC)OC(=O)CCN(C)C]
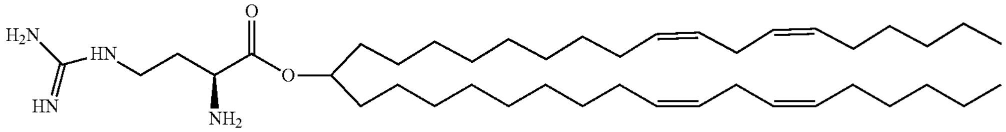
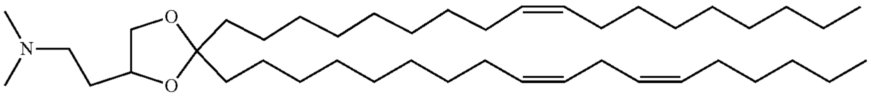 [SMILES: CCCCC/C=C\C/C=C\CCCCCCCCC1(CCCCCCCC/C=C\CCCCCCCC)OCC(CCN(C)C)O1]
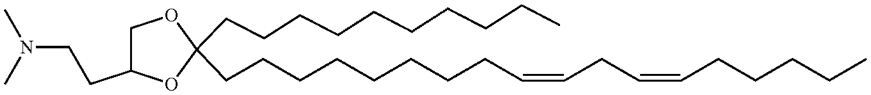 [SMILES: CCCCC/C=C\C/C=C\CCCCCCCCC1(CCCCCCCCCC)OCC(CCN(C)C)O1]
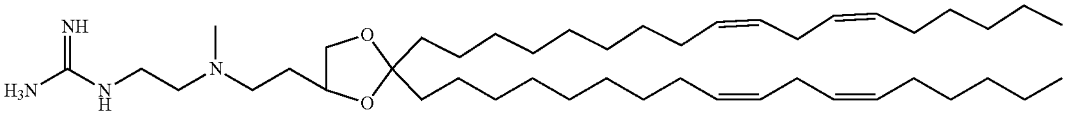 [SMILES: CCCCC/C=C\C/C=C\CCCCCCCCC1(CCCCCCCC/C=C\C/C=C\CCCCC)OCC(CCN(C)CCNC(=N)N)O1]
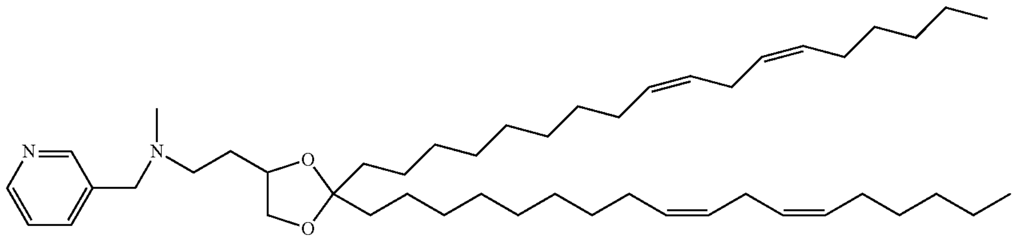 [SMILES: CCCCC/C=C\C/C=C\CCCCCCCCC1(CCCCCCCC/C=C\C/C=C\CCCCC)OCC(CCN(C)Cc2cccnc2)O1]
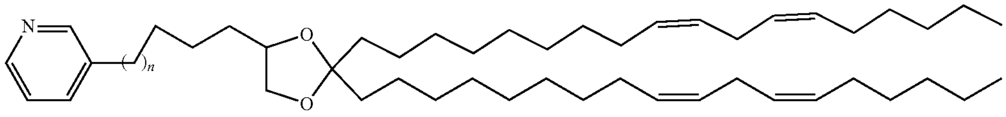
n = 1-10
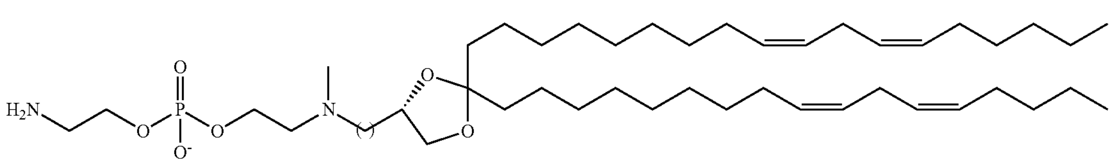
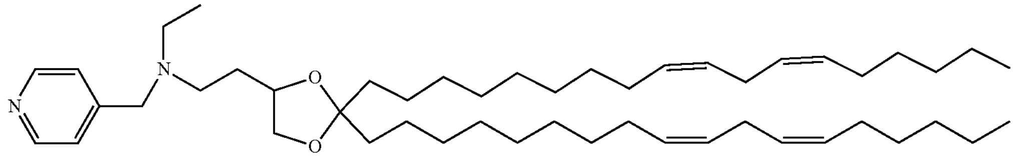 [SMILES: CCCCC/C=C\C/C=C\CCCCCCCCC1(CCCCCCCC/C=C\C/C=C\CCCCC)OCC(CCN(CC)Cc2ccncc2)O1]

TABLE 11-continued
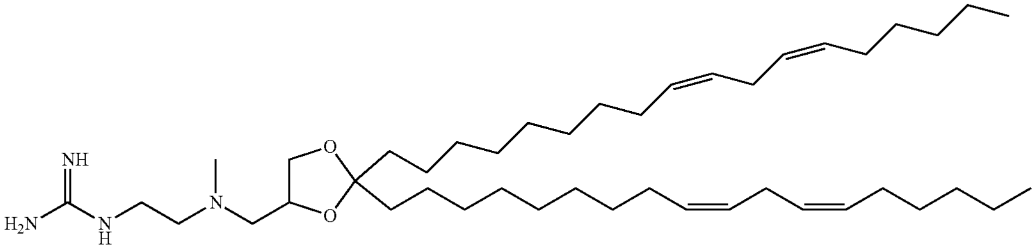 [SMILES: CCCCC/C=C\C/C=C\CCCCCCCCC1(CCCCCCCC/C=C\C/C=C\CCCCC)OCC(CN(C)CCNC(=N)N)O1]
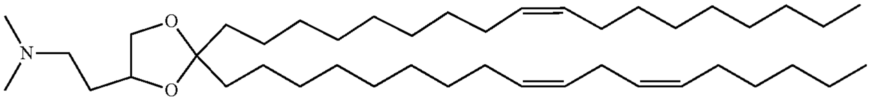 [SMILES: CCCCC/C=C\C/C=C\CCCCCCCCC1(CCCCCCCC/C=C\CCCCCCCC)OCC(CCN(C)C)O1]
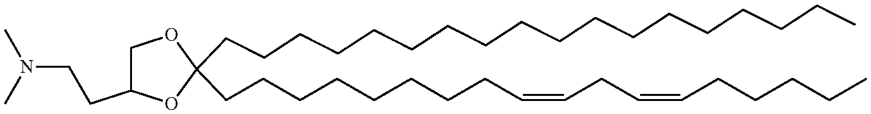 [SMILES: CCCCC/C=C\C/C=C\CCCCCCCCC1(CCCCCCCCCCCCCCCCCC)OCC(CCN(C)C)O1]
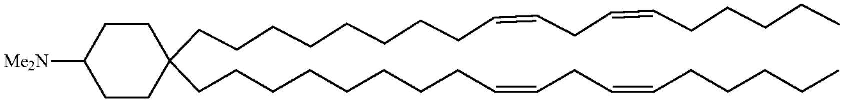
Racemic and optically pure
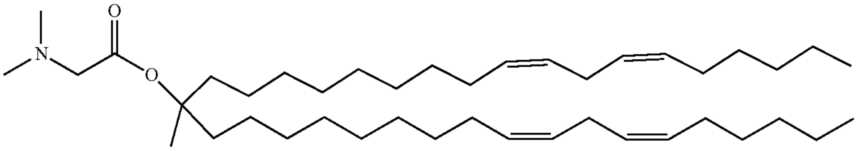 [SMILES: CCCCC/C=C\C/C=C\CCCCCCCCC(C)(CCCCCCCC/C=C\C/C=C\CCCCC)OC(=O)CN(C)C]
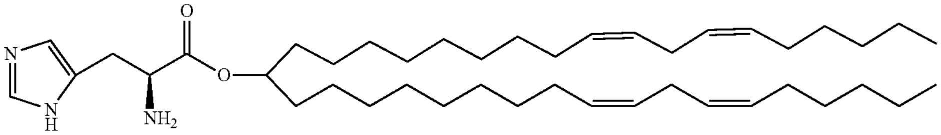 [SMILES: CCCCC/C=C\C/C=C\CCCCCCCCC(CCCCCCCC/C=C\C/C=C\CCCCC)OC(=O)[C@@H](N)Cc1cnc[nH]1]
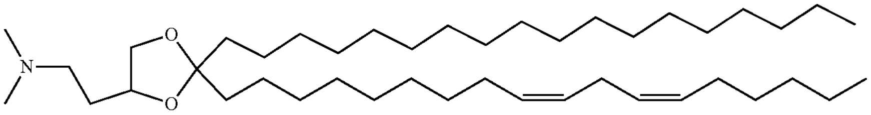 [SMILES: CCCCC/C=C\C/C=C\CCCCCCCCC1(CCCCCCCCCCCCCCCCCC)OCC(CCN(C)C)O1]
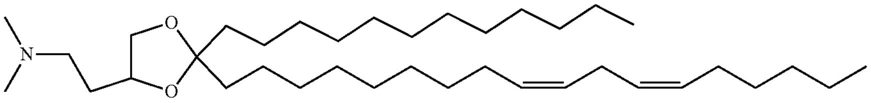 [SMILES: CCCCC/C=C\C/C=C\CCCCCCCCC1(CCCCCCCCCCCC)OCC(CCN(C)C)O1]
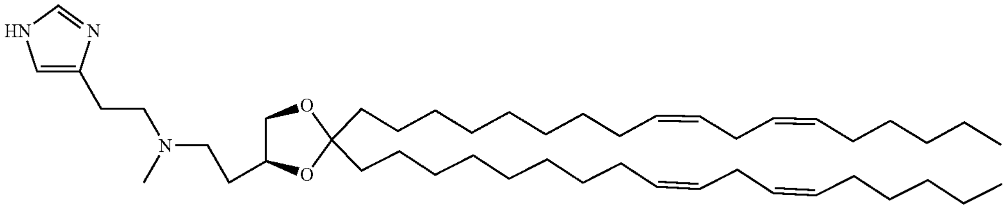
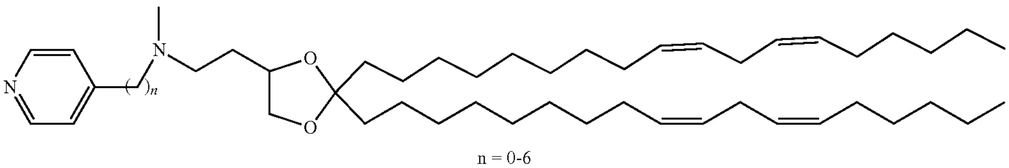
n = 0-6

TABLE 11-continued
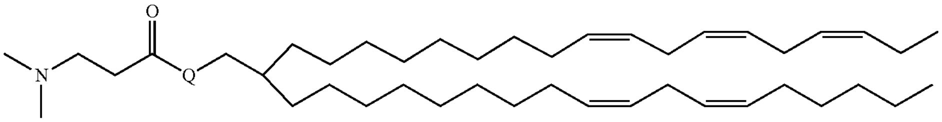
Q is O
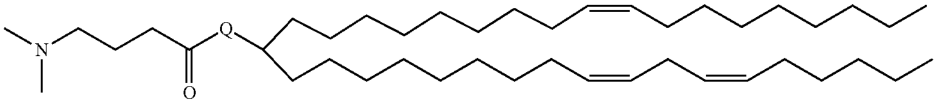
Q is O
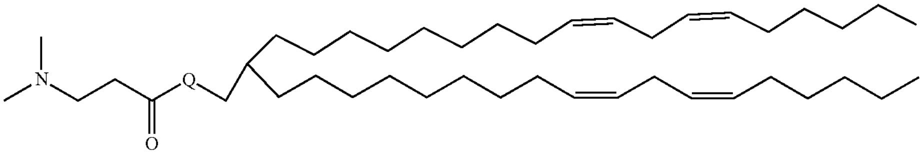
Q is O
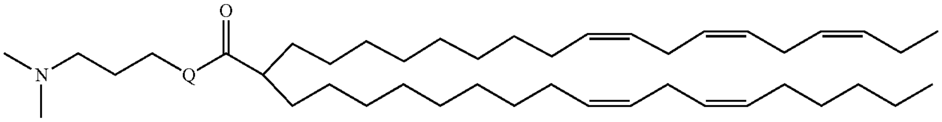
Q is O
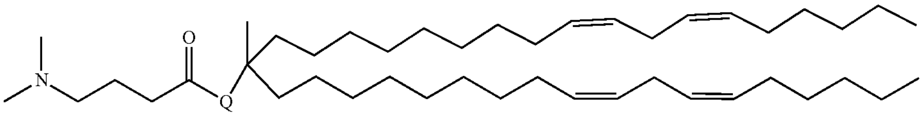
Q is O
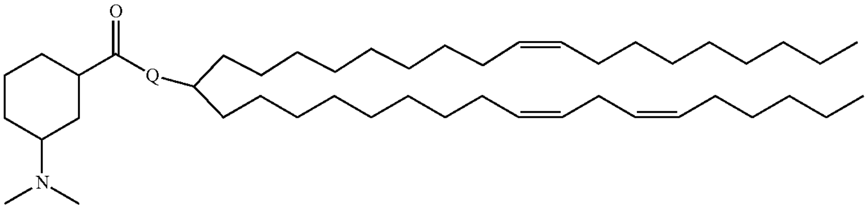
Q is O
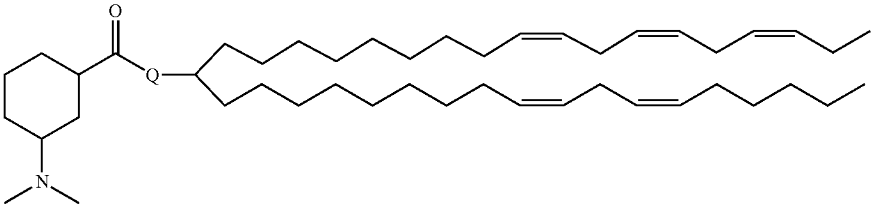
Q is O
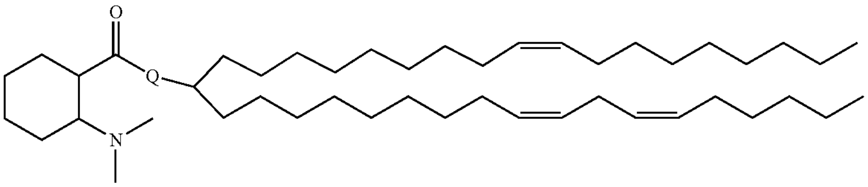
Q is O TABLE 11-continued
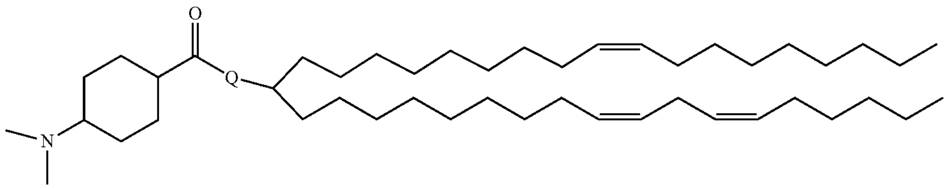
Q is O
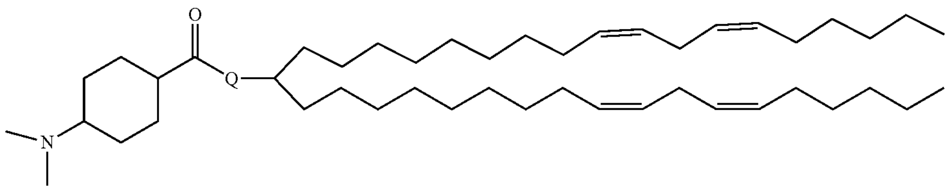
Q is O
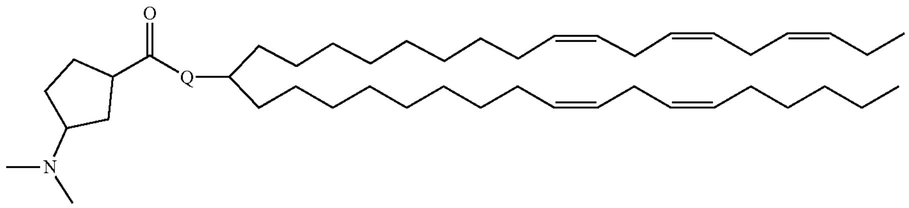
Q is O
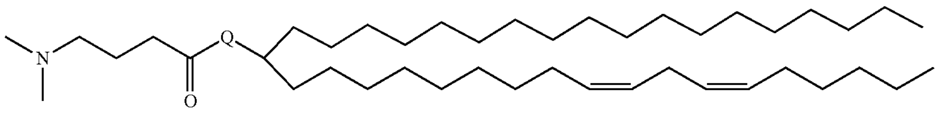
Q is O
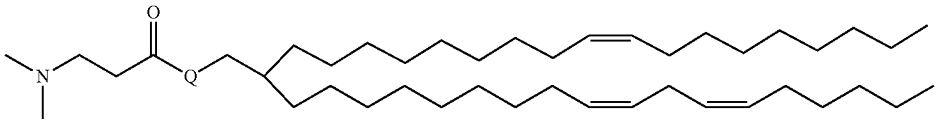
Q is O
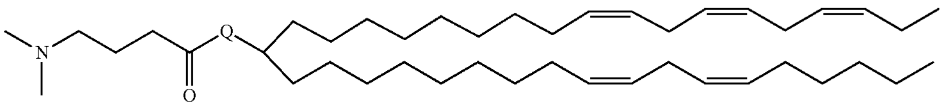
Q is O
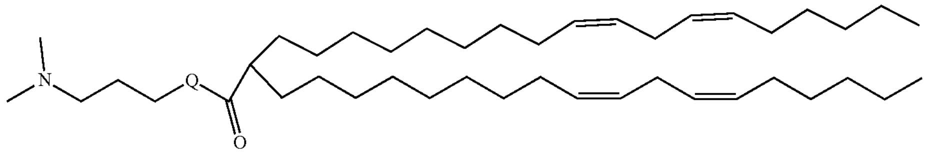
Q is O
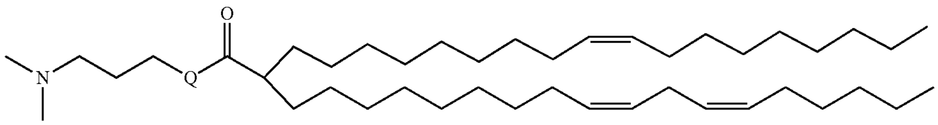
Q is O TABLE 11-continued
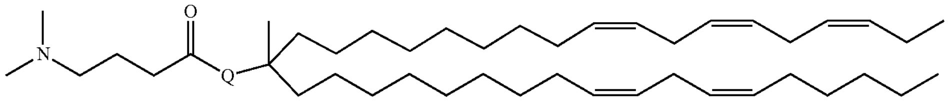
Q is O
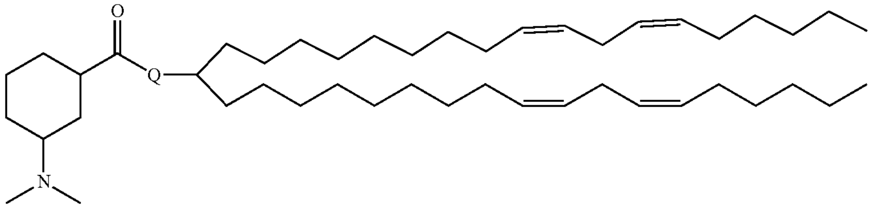
Q is O
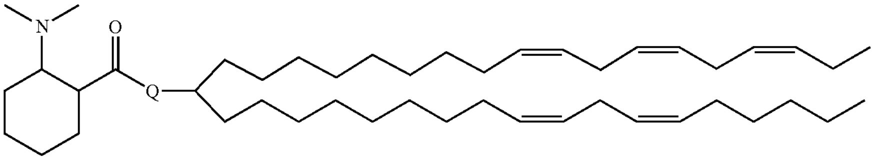
Q is O
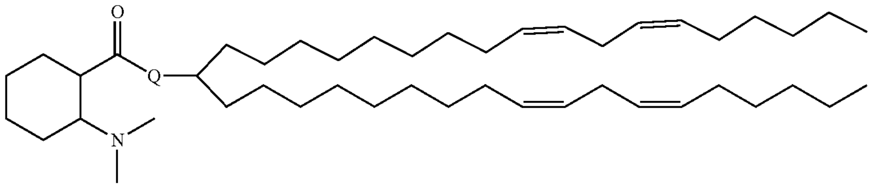
Q is O
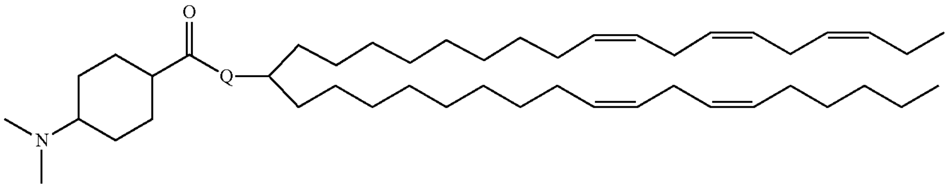
Q is O
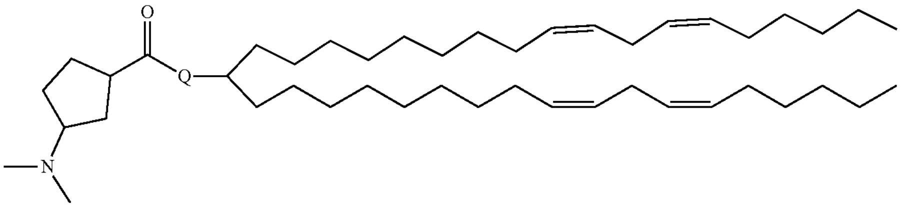
Q is O
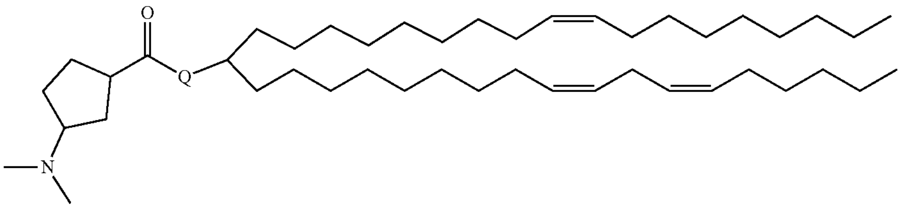
Q is O TABLE 11-continued
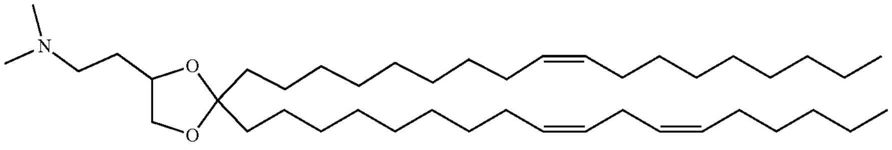 [SMILES: CCCCC/C=C\C/C=C\CCCCCCCCC1(CCCCCCCC/C=C\CCCCCCCC)OCC(CCN(C)C)O1]
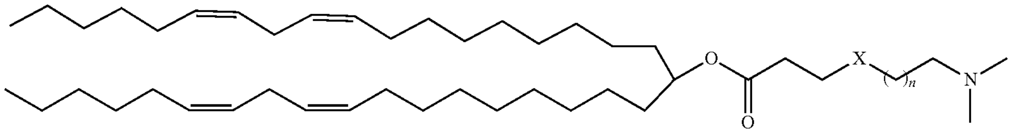
X = O, S, NH, NMe; n = 0-6
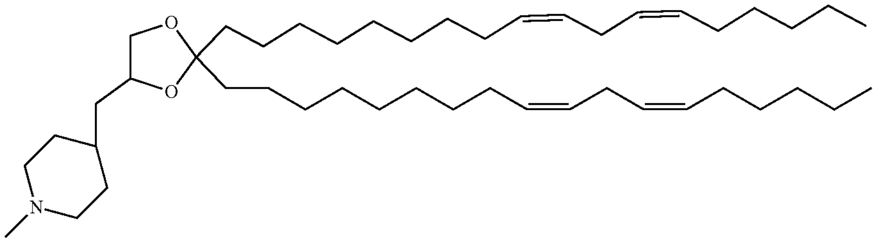 [SMILES: CCCCC/C=C\C/C=C\CCCCCCCCC1(CCCCCCCC/C=C\C/C=C\CCCCC)OCC(CC2CCN(C)CC2)O1]
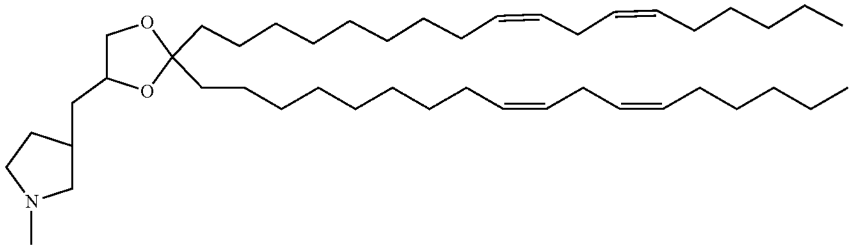 [SMILES: CCCCC/C=C\C/C=C\CCCCCCCCC1(CCCCCCCC/C=C\C/C=C\CCCCC)OCC(CC2CCN(C)C2)O1]
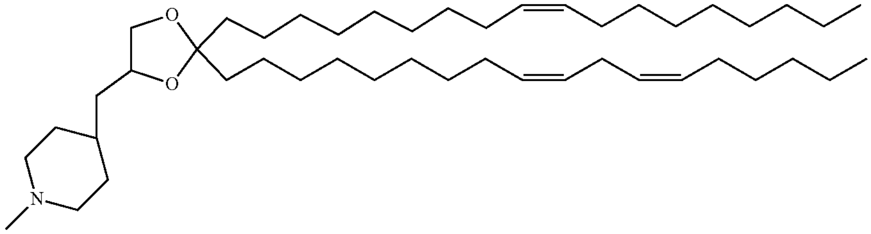 [SMILES: CCCCC/C=C\C/C=C\CCCCCCCCC1(CCCCCCCC/C=C\CCCCCCCC)OCC(CC2CCN(C)CC2)O1]
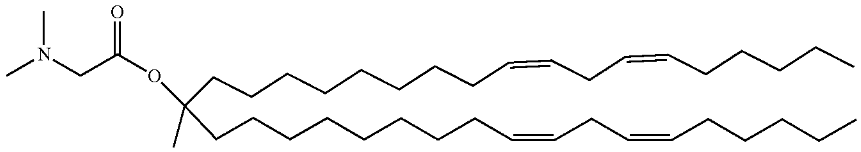 [SMILES: CCCCC/C=C\C/C=C\CCCCCCCCC(C)(CCCCCCCC/C=C\C/C=C\CCCCC)OC(=O)CN(C)C]
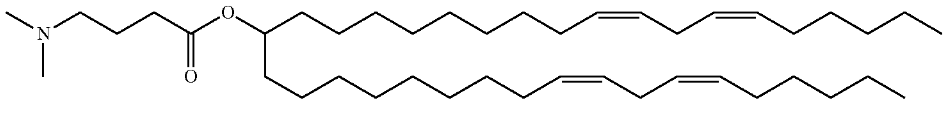
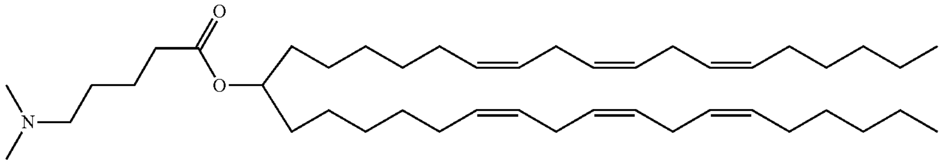 [SMILES: CCCCC/C=C\C/C=C\C/C=C\CCCCCC(CCCCC/C=C\C/C=C\C/C=C\CCCCC)OC(=O)CCCCN(C)C]
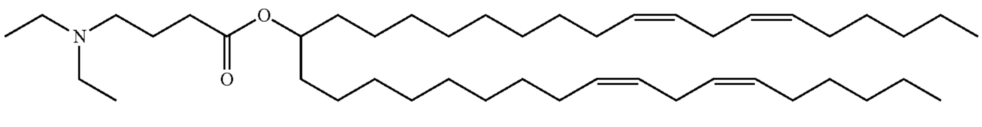 [SMILES: CCCCC/C=C\C/C=C\CCCCCCCCC(CCCCCCCC/C=C\C/C=C\CCCCC)OC(=O)CCCN(CC)CC]

TABLE 11-continued
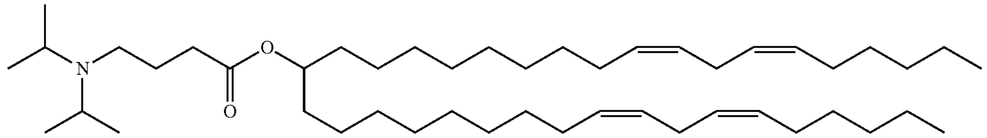 [SMILES: CCCCC/C=C\C/C=C\CCCCCCCCC(CCCCCCCC/C=C\C/C=C\CCCCC)OC(=O)CCCN(C(C)C)C(C)C]
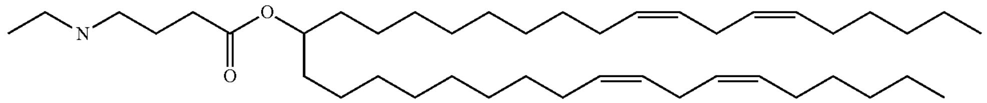 [SMILES: CCCCC/C=C\C/C=C\CCCCCCCCC(CCCCCCCC/C=C\C/C=C\CCCCC)OC(=O)CCCNCC]
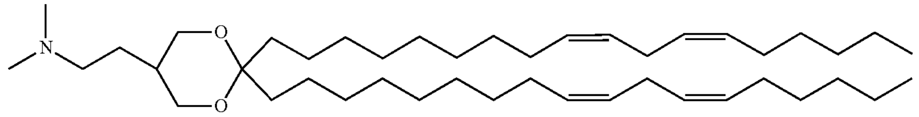 [SMILES: CCCCC/C=C\C/C=C\CCCCCCCCC1(CCCCCCCC/C=C\C/C=C\CCCCC)OCC(CCN(C)C)CO1]
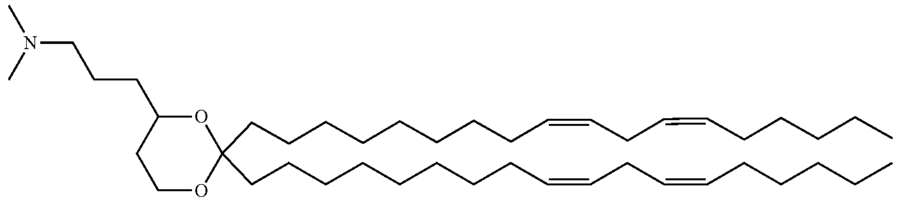 [SMILES: CCCCC/C=C\C/C=C\CCCCCCCCC1(CCCCCCCC/C=C\C/C=C\CCCCC)OCCC(CCCN(C)C)O1]
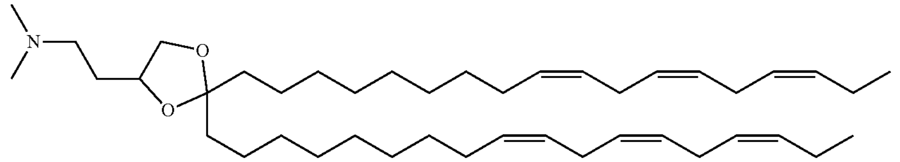 [SMILES: CC/C=C\C/C=C\C/C=C\CCCCCCCCC1(CCCCCCCC/C=C\C/C=C\C/C=C\CC)OCC(CCN(C)C)O1]
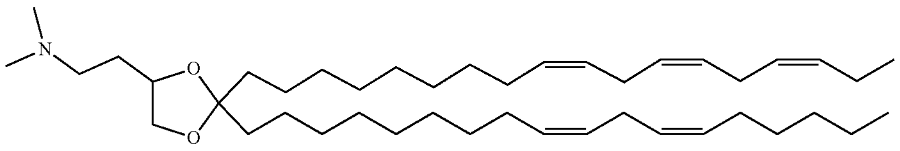 [SMILES: CC/C=C\C/C=C\C/C=C\CCCCCCCCC1(CCCCCCCC/C=C\C/C=C\CCCCC)OCC(CCN(C)C)O1]
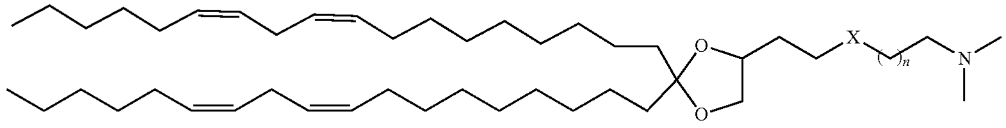
X = O, S, NH, NMe; n = 0-6
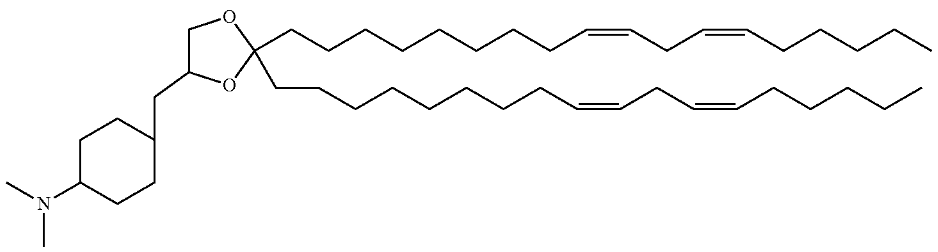 [SMILES: CCCCC/C=C\C/C=C\CCCCCCCCC1(CCCCCCCC/C=C\C/C=C\CCCCC)OCC(CC2CCC(N(C)C)CC2)O1]
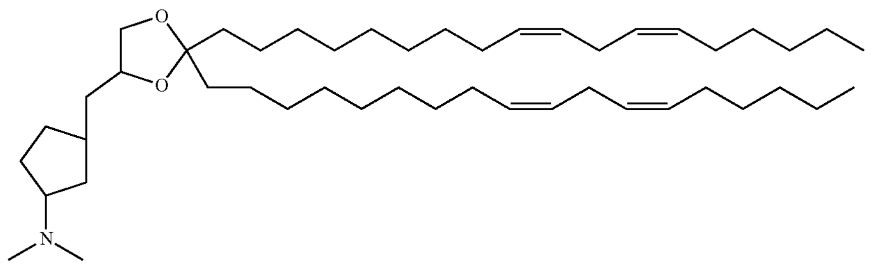 [SMILES: CCCCC/C=C\C/C=C\CCCCCCCCC1(CCCCCCCC/C=C\C/C=C\CCCCC)OCC(CC2CCC(N(C)C)C2)O1]

TABLE 11-continued
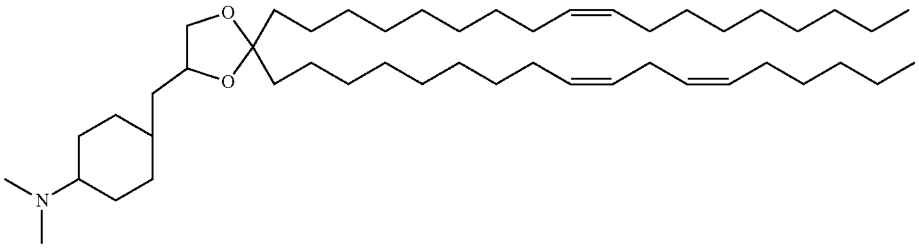 [SMILES: CCCCC/C=C\C/C=C\CCCCCCCCC1(CCCCCCCC/C=C\CCCCCCCC)OCC(CC2CCC(N(C)C)CC2)O1]
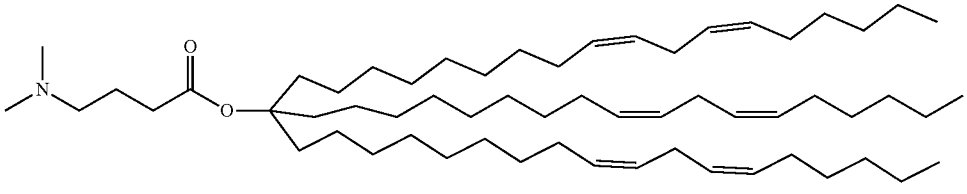 [SMILES: CCCCC/C=C\C/C=C\CCCCCCCCC(CCCCCCCC/C=C\C/C=C\CCCCC)(CCCCCCCC/C=C\C/C=C\CCCCC)OC(=O)CCCN(C)C]
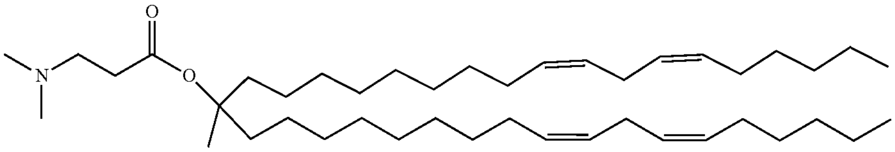 [SMILES: CCCCC/C=C\C/C=C\CCCCCCCCC(C)(CCCCCCCC/C=C\C/C=C\CCCCC)OC(=O)CCN(C)C]
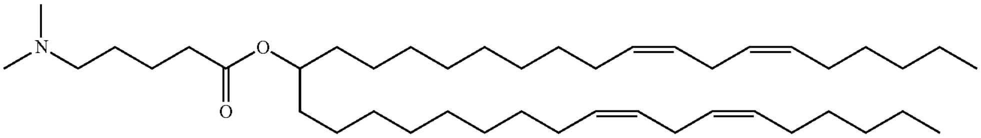 [SMILES: CCCCC/C=C\C/C=C\CCCCCCCCC(CCCCCCCC/C=C\C/C=C\CCCCC)OC(=O)CCCCN(C)C]
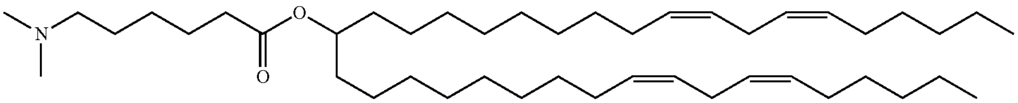 [SMILES: CCCCC/C=C\C/C=C\CCCCCCCCC(CCCCCCCC/C=C\C/C=C\CCCCC)OC(=O)CCCCCN(C)C]
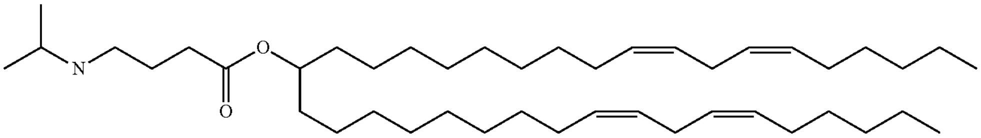
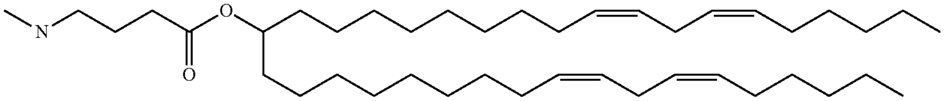
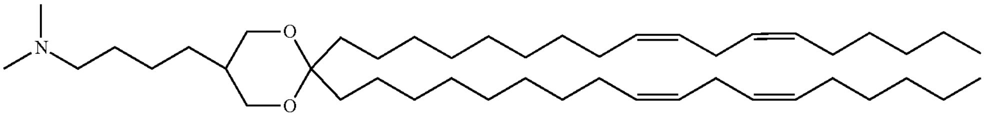 [SMILES: CCCCC/C=C\C/C=C\CCCCCCCCC1(CCCCCCCC/C=C\C/C=C\CCCCC)OCC(CCCCN(C)C)CO1]
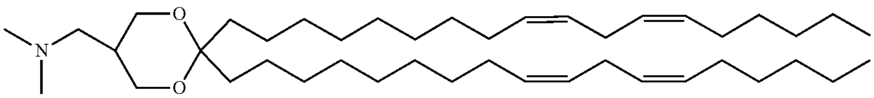 [SMILES: CCCCC/C=C\C/C=C\CCCCCCCCC1(CCCCCCCC/C=C\C/C=C\CCCCC)OCC(CN(C)C)CO1]
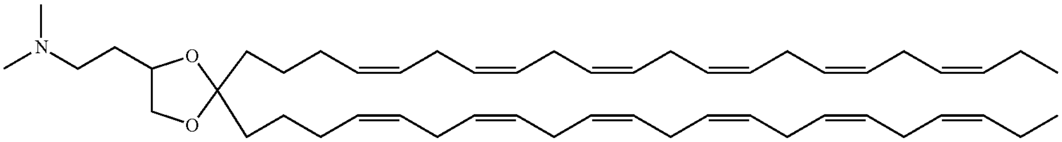 [SMILES: CC/C=C\C/C=C\C/C=C\C/C=C\C/C=C\C/C=C\CCCC1(CCC/C=C\C/C=C\C/C=C\C/C=C\C/C=C\C/C=C\CC)OCC(CCN(C)C)O1]

TABLE 11-continued
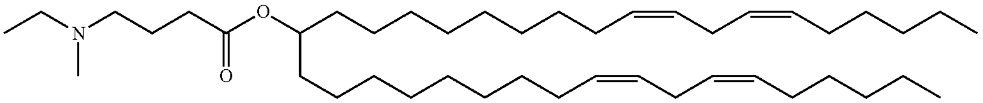 [SMILES: CCCCC/C=C\C/C=C\CCCCCCCCC(CCCCCCCC/C=C\C/C=C\CCCCC)OC(=O)CCCN(C)CC]
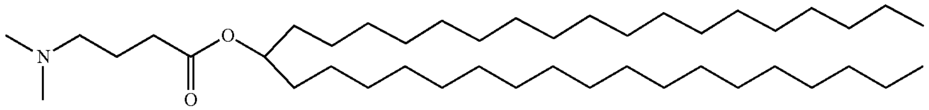 [SMILES: CCCCCCCCCCCCCCCCCCC(CCCCCCCCCCCCCCCCCC)OC(=O)CCCN(C)C]
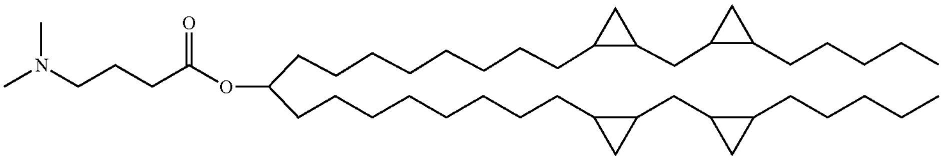 [SMILES: CCCCCC1CC1CC1CC1CCCCCCCCC(CCCCCCCCC1CC1CC1CC1CCCCC)OC(=O)CCCN(C)C]
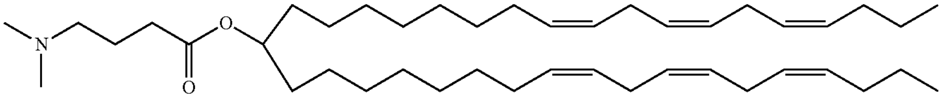 [SMILES: CCC/C=C\C/C=C\C/C=C\CCCCCCCC(CCCCCCC/C=C\C/C=C\C/C=C\CCC)OC(=O)CCCN(C)C]
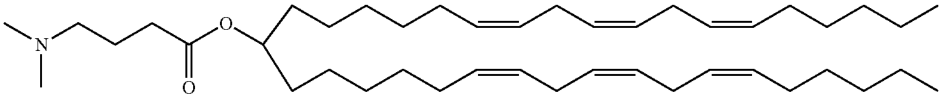 [SMILES: CCCCC/C=C\C/C=C\C/C=C\CCCCCC(CCCCC/C=C\C/C=C\C/C=C\CCCCC)OC(=O)CCCN(C)C]
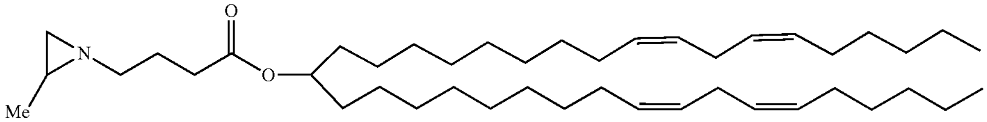 [SMILES: CCCCC/C=C\C/C=C\CCCCCCCCC(CCCCCCCC/C=C\C/C=C\CCCCC)OC(=O)CCCN1CC1C]
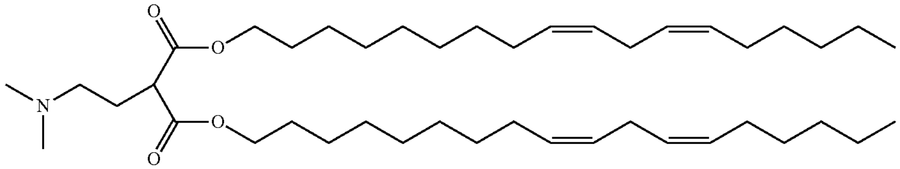 [SMILES: CCCCC/C=C\C/C=C\CCCCCCCCOC(=O)C(CCN(C)C)C(=O)OCCCCCCCC/C=C\C/C=C\CCCCC]
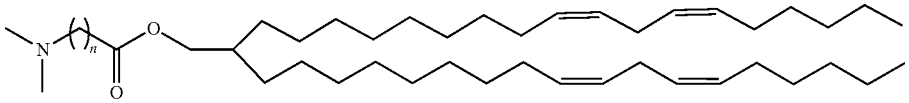
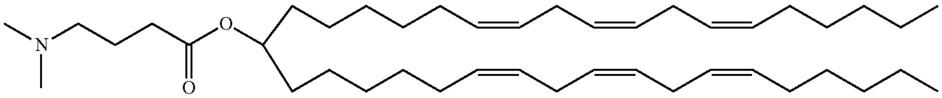 [SMILES: CCCCC/C=C\C/C=C\C/C=C\CCCCCC(CCCCC/C=C\C/C=C\C/C=C\CCCCC)OC(=O)CCCN(C)C]
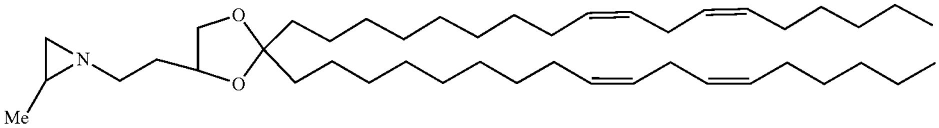 [SMILES: CCCCC/C=C\C/C=C\CCCCCCCCC1(CCCCCCCC/C=C\C/C=C\CCCCC)OCC(CCN2CC2C)O1]
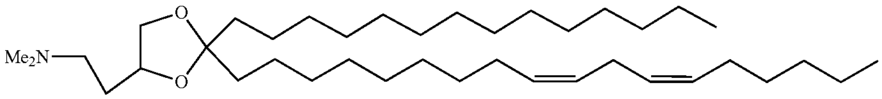 [SMILES: CCCCC/C=C\C/C=C\CCCCCCCCC1(CCCCCCCCCCCCCC)OCC(CCN(C)C)O1]

TABLE 11-continued
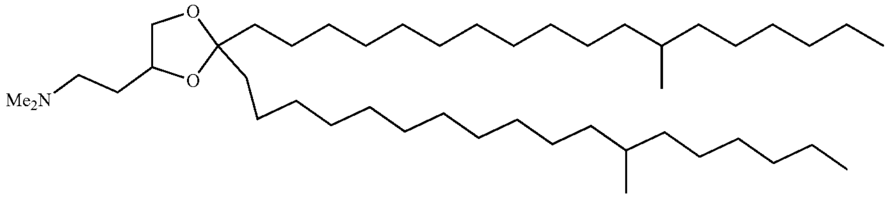 [SMILES: CCCCCCC(C)CCCCCCCCCCCC1(CCCCCCCCCCCC(C)CCCCCC)OCC(CCN(C)C)O1]
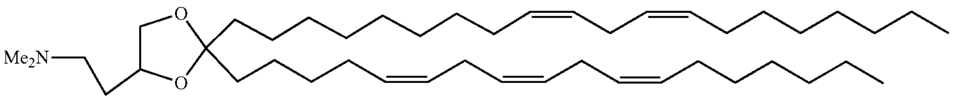 [SMILES: CCCCCC/C=C\C/C=C\C/C=C\CCCCC1(CCCCCCCC/C=C\C/C=C\CCCCCCC)OCC(CCN(C)C)O1]
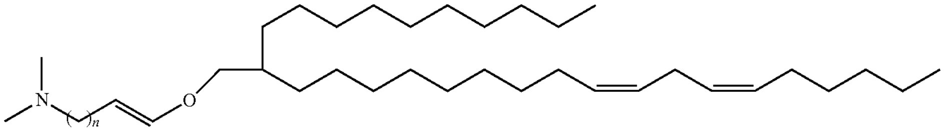
n = 0-6
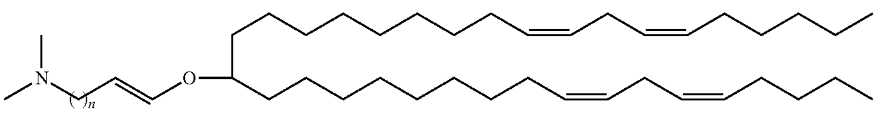
n = 0-6
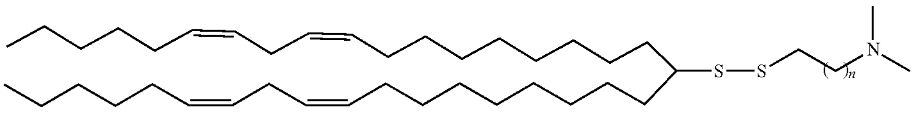
n = 0-6
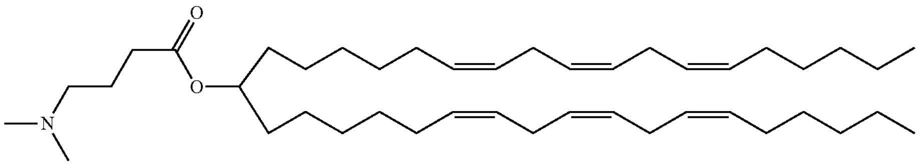 [SMILES: CCCCC/C=C\C/C=C\C/C=C\CCCCCC(CCCCC/C=C\C/C=C\C/C=C\CCCCC)OC(=O)CCCN(C)C]
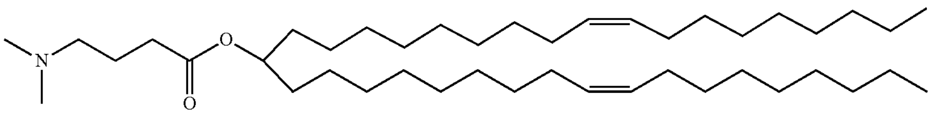 [SMILES: CCCCCCCC/C=C\CCCCCCCCC(CCCCCCCC/C=C\CCCCCCCC)OC(=O)CCCN(C)C]
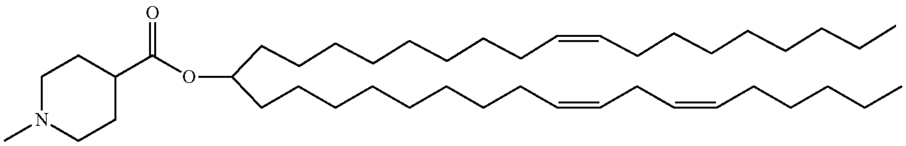 [SMILES: CCCCC/C=C\C/C=C\CCCCCCCCC(CCCCCCCC/C=C\CCCCCCCC)OC(=O)C1CCN(C)CC1]
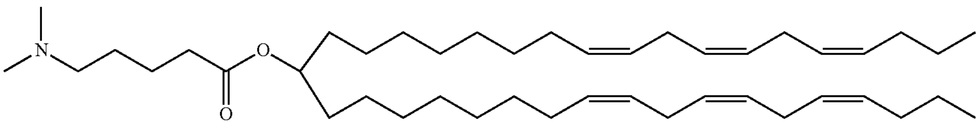 [SMILES: CCC/C=C\C/C=C\C/C=C\CCCCCCCC(CCCCCCC/C=C\C/C=C\C/C=C\CCC)OC(=O)CCCCN(C)C]
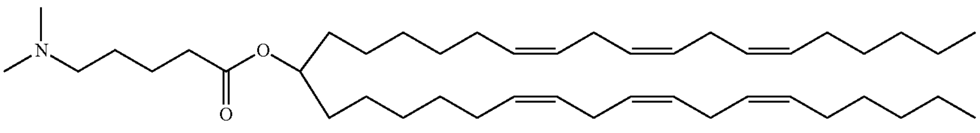 [SMILES: CCCCC/C=C\C/C=C\C/C=C\CCCCCC(CCCCC/C=C\C/C=C\C/C=C\CCCCC)OC(=O)CCCCN(C)C]

TABLE 11-continued
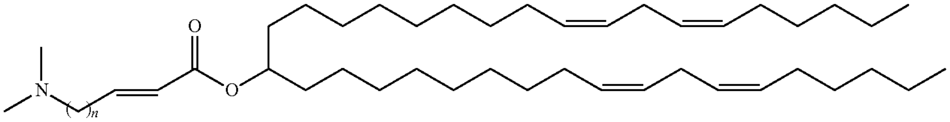
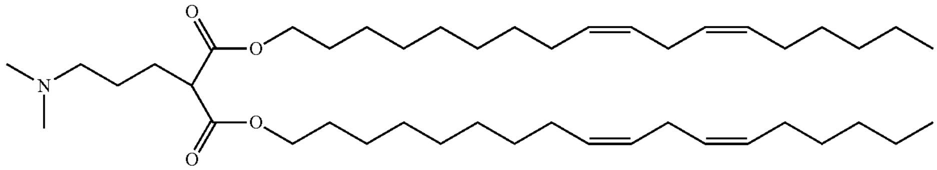 [SMILES: CCCCC/C=C\C/C=C\CCCCCCCCOC(=O)C(CCCN(C)C)C(=O)OCCCCCCCC/C=C\C/C=C\CCCCC]
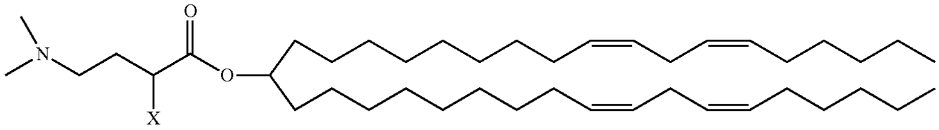
e.g., X = Me, OH, Cl, etc
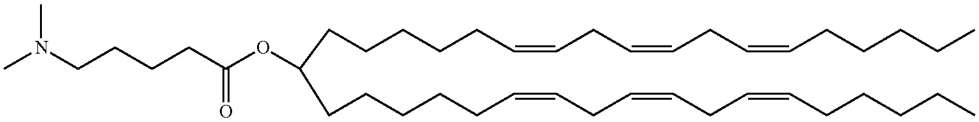 [SMILES: CCCCC/C=C\C/C=C\C/C=C\CCCCCC(CCCCC/C=C\C/C=C\C/C=C\CCCCC)OC(=O)CCCCN(C)C]
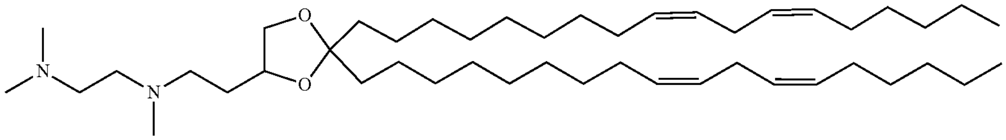 [SMILES: CCCCC/C=C\C/C=C\CCCCCCCCC1(CCCCCCCC/C=C\C/C=C\CCCCC)OCC(CCN(C)CCN(C)C)O1]
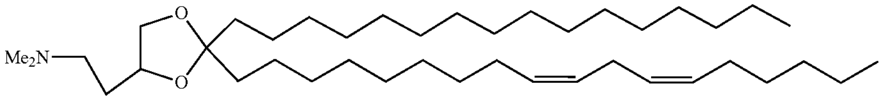
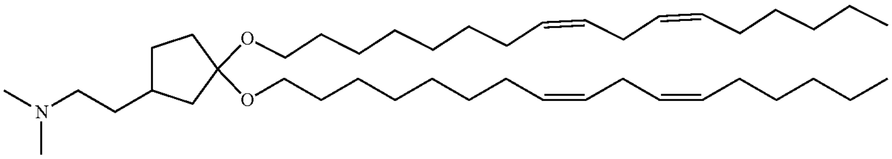 [SMILES: CCCCC/C=C\C/C=C\CCCCCCCOC1(OCCCCCCC/C=C\C/C=C\CCCCC)CCC(CCN(C)C)C1]
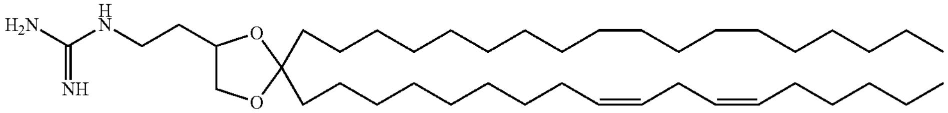 [SMILES: CCCCC/C=C\C/C=C\CCCCCCCCC1(CCCCCCCCCCCCCCCCCC)OCC(CCNC(=N)N)O1]
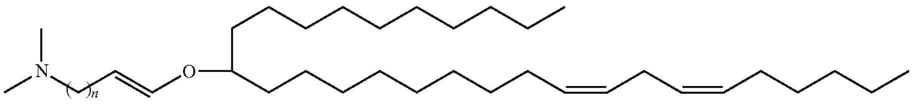
n = 0-6
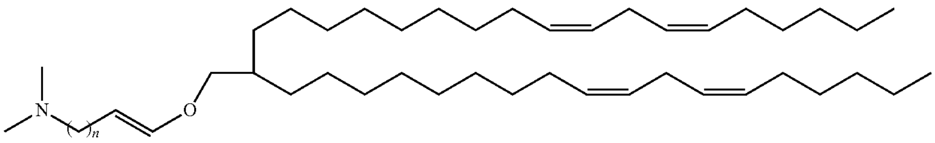
n = 0-6
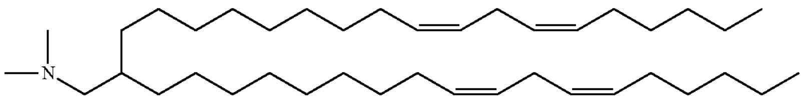

TABLE 11-continued
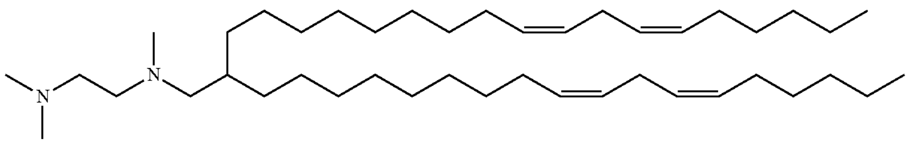 [SMILES: CCCCC/C=C\C/C=C\CCCCCCCCC(CCCCCCCC/C=C\C/C=C\CCCCC)CN(C)CCN(C)C]
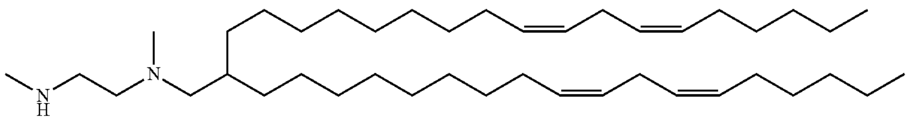 [SMILES: CCCCC/C=C\C/C=C\CCCCCCCCC(CCCCCCCC/C=C\C/C=C\CCCCC)CN(C)CCNC]
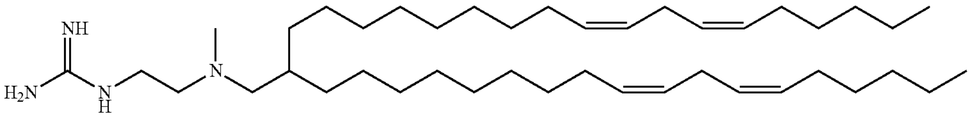 [SMILES: CCCCC/C=C\C/C=C\CCCCCCCCC(CCCCCCCC/C=C\C/C=C\CCCCC)CN(C)CCNC(=N)N]
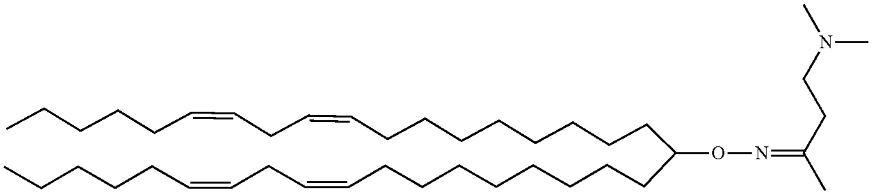 [SMILES: CCCCC/C=C\C/C=C\CCCCCCCCC(CCCCCCCC/C=C\C/C=C\CCCCC)ON=C(C)CCN(C)C]
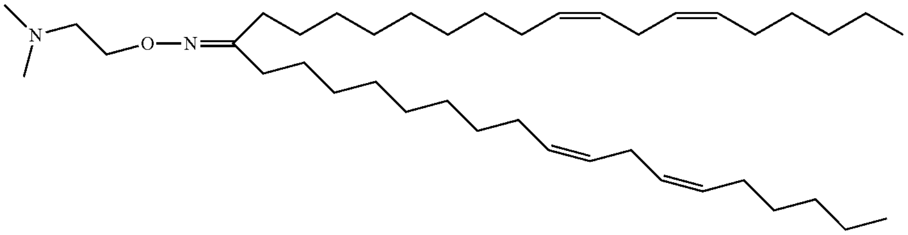 [SMILES: CCCCC/C=C\C/C=C\CCCCCCCCC(CCCCCCCC/C=C\C/C=C\CCCCC)=NOCCN(C)C]
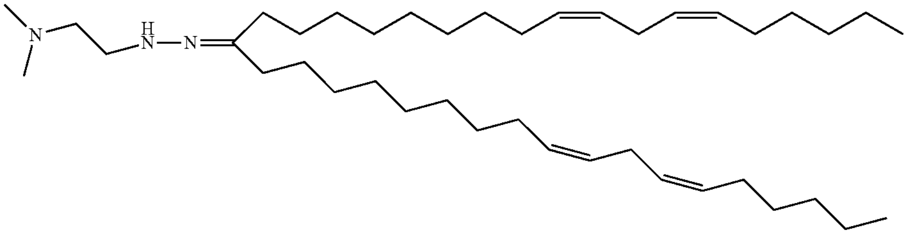
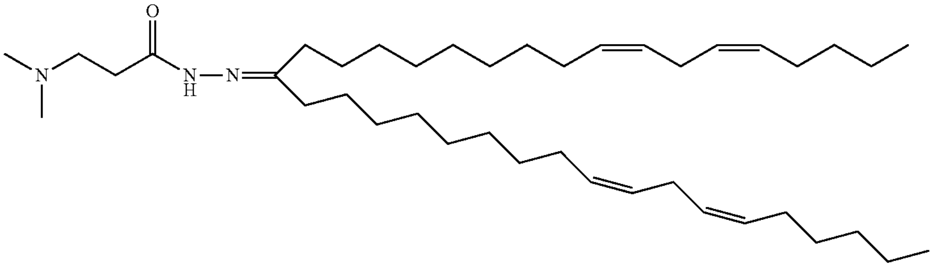 [SMILES: CCCC/C=C\C/C=C\CCCCCCCCC(CCCCCCCC/C=C\C/C=C\CCCCC)=NNC(=O)CCN(C)C]
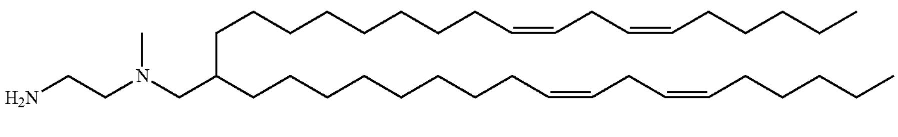 [SMILES: CCCCC/C=C\C/C=C\CCCCCCCCC(CCCCCCCC/C=C\C/C=C\CCCCC)CN(C)CCN]

TABLE 11-continued
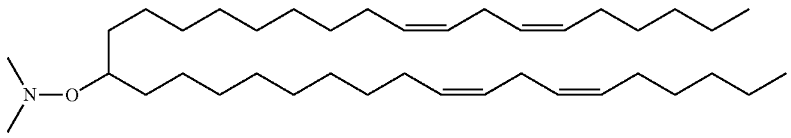 [SMILES: CCCCC/C=C\C/C=C\CCCCCCCCC(CCCCCCCC/C=C\C/C=C\CCCCC)ON(C)C]
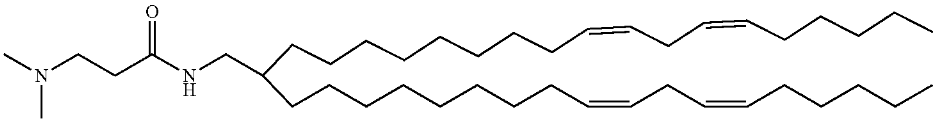 [SMILES: CCCCC/C=C\C/C=C\CCCCCCCCC(CCCCCCCC/C=C\C/C=C\CCCCC)CNC(=O)CCN(C)C]
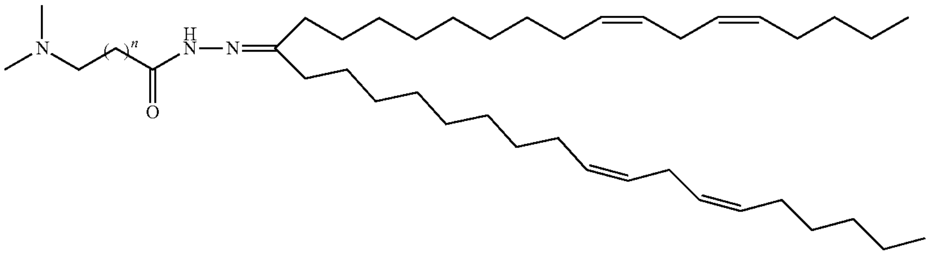
n = 0-6
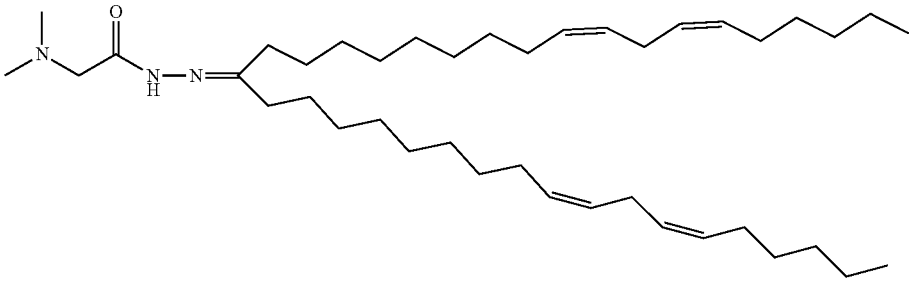 [SMILES: CCCCC/C=C\C/C=C\CCCCCCCCC(CCCCCCCC/C=C\C/C=C\CCCCC)=NNC(=O)CN(C)C]
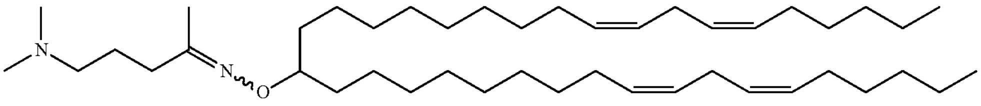 [SMILES: CCCCC/C=C\C/C=C\CCCCCCCCC(CCCCCCCC/C=C\C/C=C\CCCCC)ON=C(C)CCCN(C)C]
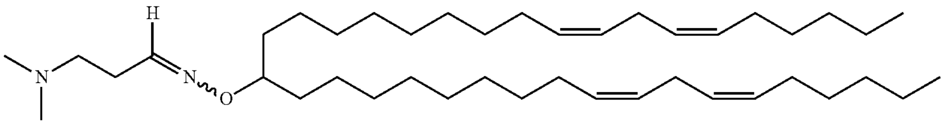 [SMILES: CCCCC/C=C\C/C=C\CCCCCCCCC(CCCCCCCC/C=C\C/C=C\CCCCC)ON=CCCN(C)C]
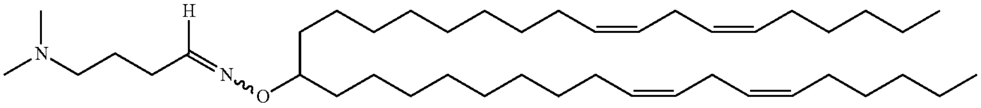 [SMILES: CCCCC/C=C\C/C=C\CCCCCCCCC(CCCCCCCC/C=C\C/C=C\CCCCC)ON=CCCCN(C)C]
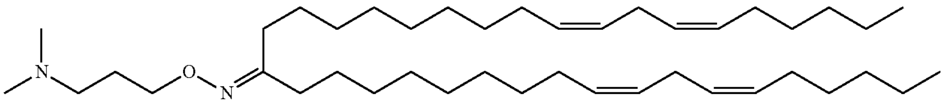 [SMILES: CCCCC/C=C\C/C=C\CCCCCCCCC(CCCCCCCC/C=C\C/C=C\CCCCC)=NOCCCN(C)C]
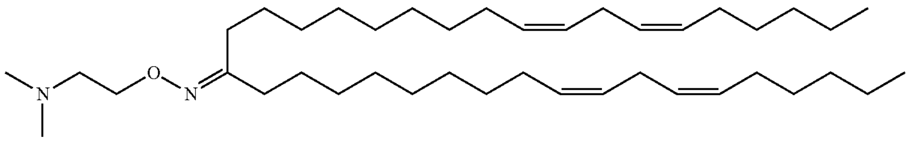

TABLE 11-continued
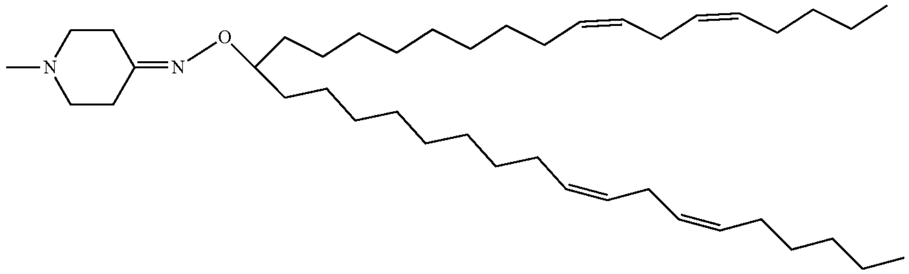 [SMILES: CCCC/C=C\C/C=C\CCCCCCCCC(CCCCCCCC/C=C\C/C=C\CCCCC)ON=C1CCN(C)CC1]
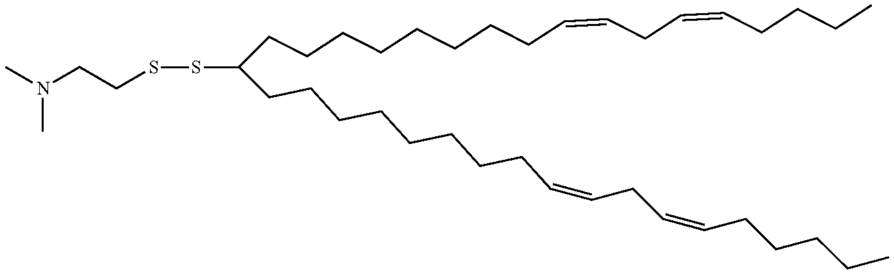 [SMILES: CCCC/C=C\C/C=C\CCCCCCCCC(CCCCCCCC/C=C\C/C=C\CCCCC)SSCCN(C)C]
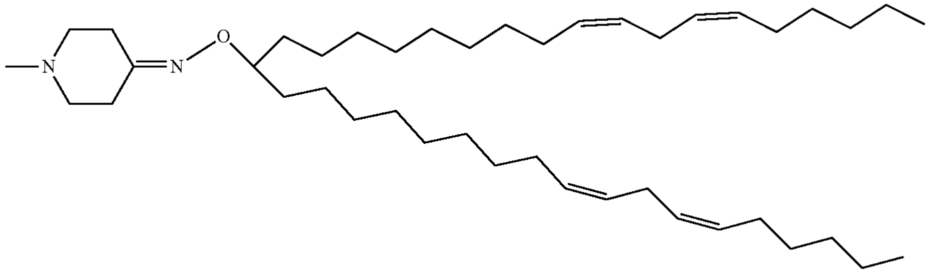 [SMILES: CCCCC/C=C\C/C=C\CCCCCCCCC(CCCCCCCC/C=C\C/C=C\CCCCC)ON=C1CCN(C)CC1]
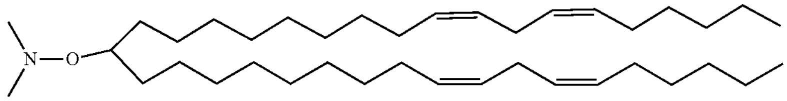 [SMILES: CCCCC/C=C\C/C=C\CCCCCCCCC(CCCCCCCC/C=C\C/C=C\CCCCC)ON(C)C]
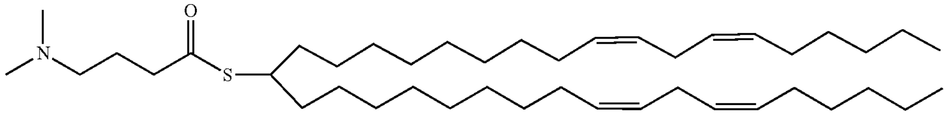
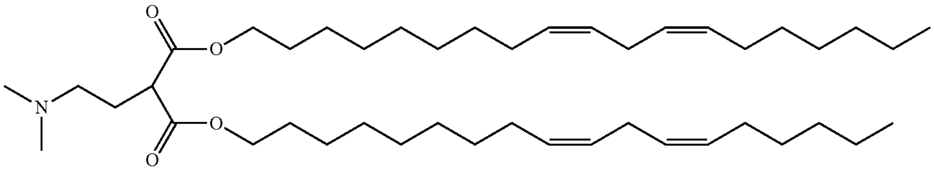 [SMILES: CCCCC/C=C\C/C=C\CCCCCCCCOC(=O)C(CCN(C)C)C(=O)OCCCCCCCC/C=C\C/C=C\CCCCCC]
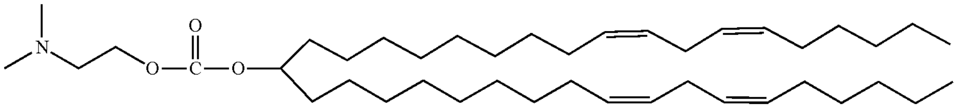 [SMILES: CCCCC/C=C\C/C=C\CCCCCCCCC(CCCCCCCC/C=C\C/C=C\CCCCC)OC(=O)OCCN(C)C]
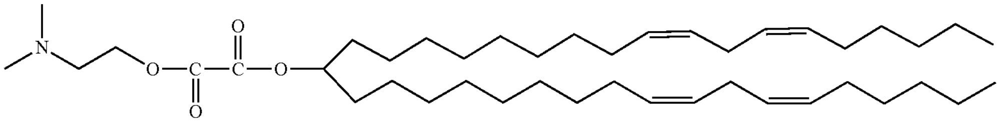 [SMILES: CCCCC/C=C\C/C=C\CCCCCCCCC(CCCCCCCC/C=C\C/C=C\CCCCC)OC(=O)C(=O)OCCN(C)C]

TABLE 11-continued
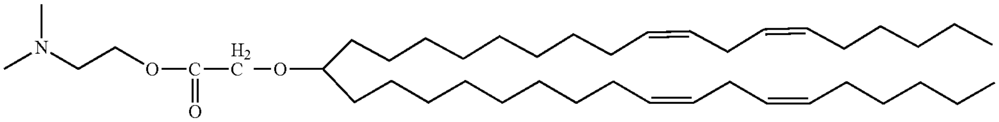 [SMILES: CCCCC/C=C\C/C=C\CCCCCCCCC(CCCCCCCC/C=C\C/C=C\CCCCC)OCC(=O)OCCN(C)C]
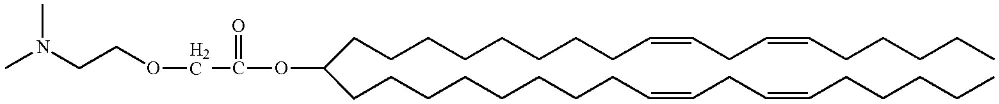 [SMILES: CCCCC/C=C\C/C=C\CCCCCCCCC(CCCCCCCC/C=C\C/C=C\CCCCC)OC(=O)COCCN(C)C]
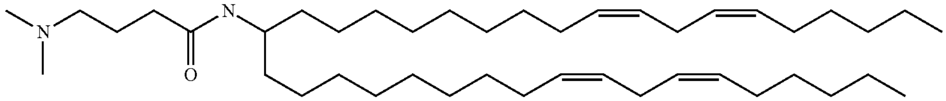 [SMILES: CCCCC/C=C\C/C=C\CCCCCCCCC(CCCCCCCC/C=C\C/C=C\CCCCC)NC(=O)CCCN(C)C]
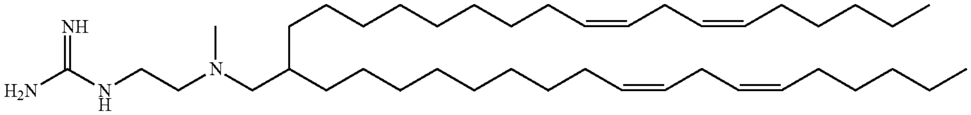 [SMILES: CCCCC/C=C\C/C=C\CCCCCCCCC(CCCCCCCC/C=C\C/C=C\CCCCC)CN(C)CCNC(=N)N]
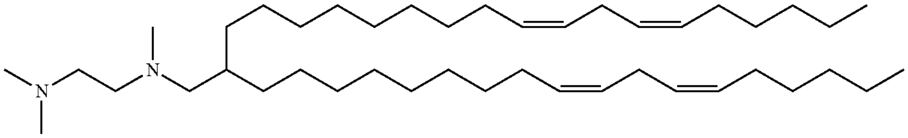
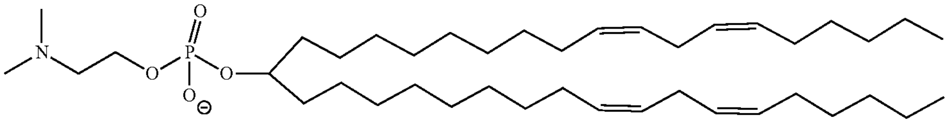 [SMILES: CCCCC/C=C\C/C=C\CCCCCCCCC(CCCCCCCC/C=C\C/C=C\CCCCC)OP(=O)([O-])OCCN(C)C]
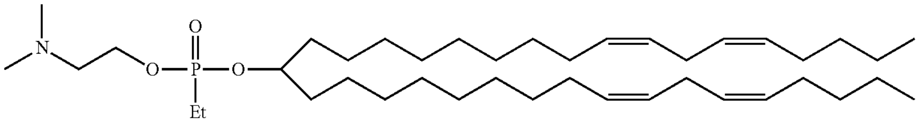 [SMILES: CCCC/C=C\C/C=C\CCCCCCCCC(CCCCCCCC/C=C\C/C=C\CCCC)OP(=O)(CC)OCCN(C)C]
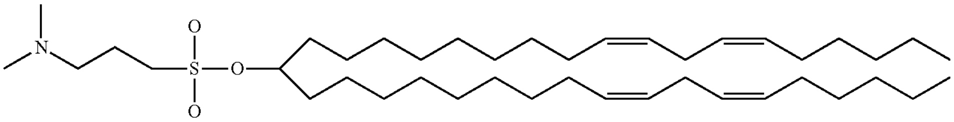 [SMILES: CCCCC/C=C\C/C=C\CCCCCCCCC(CCCCCCCC/C=C\C/C=C\CCCCC)OS(O)(O)CCCN(C)C]
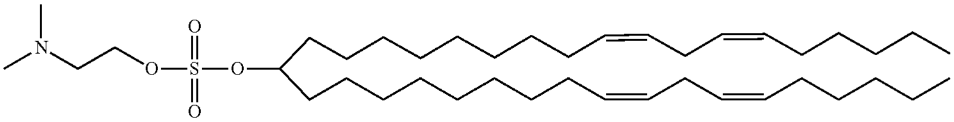 [SMILES: CCCCC/C=C\C/C=C\CCCCCCCCC(CCCCCCCC/C=C\C/C=C\CCCCC)OS(=O)(=O)OCCN(C)C]
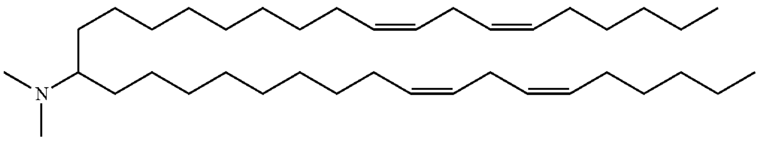 [SMILES: CCCCC/C=C\C/C=C\CCCCCCCCC(CCCCCCCC/C=C\C/C=C\CCCCC)N(C)C]
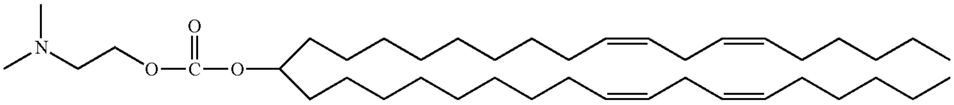 [SMILES: CCCCC/C=C\C/C=C\CCCCCCCCC(CCCCCCCC/C=C\C/C=C\CCCCC)OC(=O)OCCN(C)C]
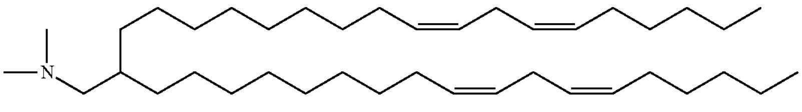 [SMILES: CCCCC/C=C\C/C=C\CCCCCCCCC(CCCCCCCC/C=C\C/C=C\CCCCC)CN(C)C]

TABLE 11-continued
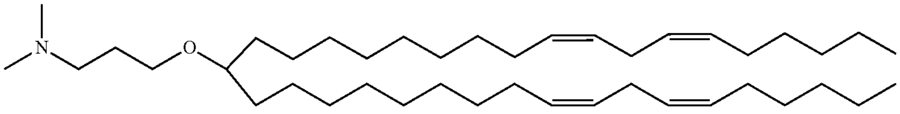 [SMILES: CCCCC/C=C\C/C=C\CCCCCCCCC(CCCCCCCC/C=C\C/C=C\CCCCC)OCCCN(C)C]
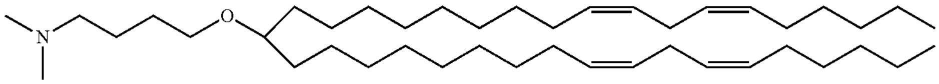 [SMILES: CCCCC/C=C\C/C=C\CCCCCCCCC(CCCCCCCC/C=C\C/C=C\CCCCC)OCCCCN(C)C]
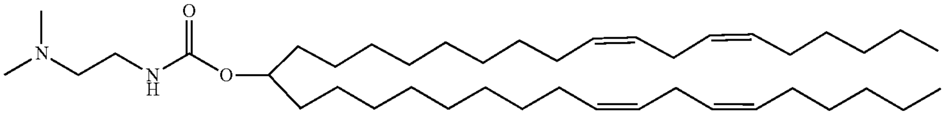 [SMILES: CCCCC/C=C\C/C=C\CCCCCCCCC(CCCCCCCC/C=C\C/C=C\CCCCC)OC(=O)NCCN(C)C]
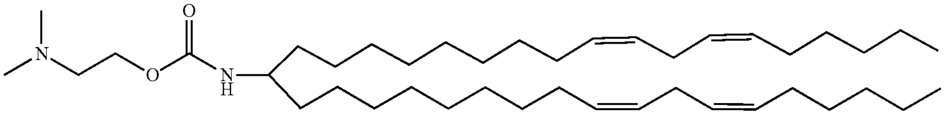 [SMILES: CCCCC/C=C\C/C=C\CCCCCCCCC(CCCCCCCC/C=C\C/C=C\CCCCC)NC(=O)OCCN(C)C]
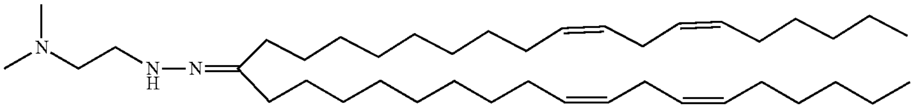
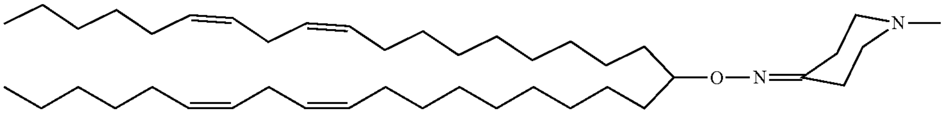 [SMILES: CCCCC/C=C\C/C=C\CCCCCCCCC(CCCCCCCC/C=C\C/C=C\CCCCC)ON=C1CCN(C)CC1]
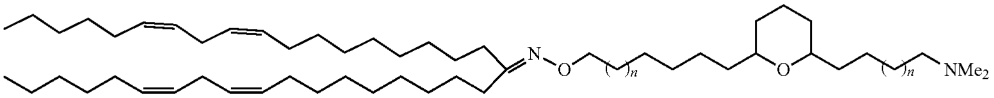
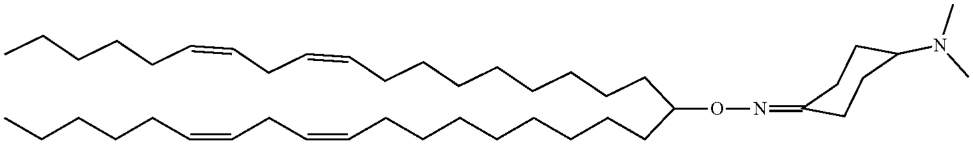 [SMILES: CCCCC/C=C\C/C=C\CCCCCCCCC(CCCCCCCC/C=C\C/C=C\CCCCC)ON=C1CCC(N(C)C)CC1]
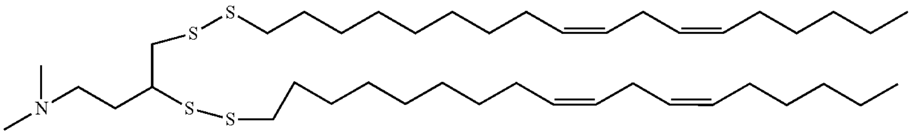 [SMILES: CCCCC/C=C\C/C=C\CCCCCCCCSSCC(CCN(C)C)SSCCCCCCCC/C=C\C/C=C\CCCCC]
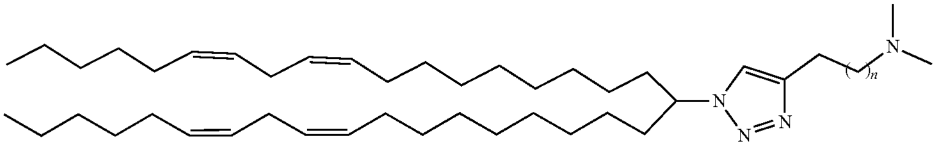
n = 0-6
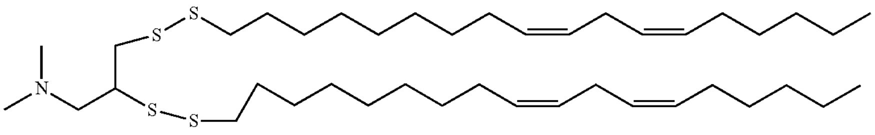 [SMILES: CCCCC/C=C\C/C=C\CCCCCCCCSSCC(CN(C)C)SSCCCCCCCC/C=C\C/C=C\CCCCC]
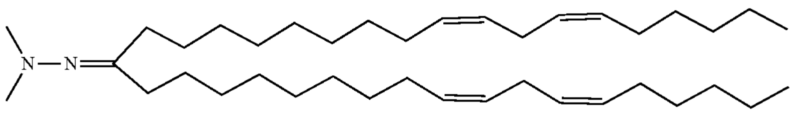 [SMILES: CCCCC/C=C\C/C=C\CCCCCCCCC(CCCCCCCC/C=C\C/C=C\CCCCC)=NN(C)C]

TABLE 11-continued
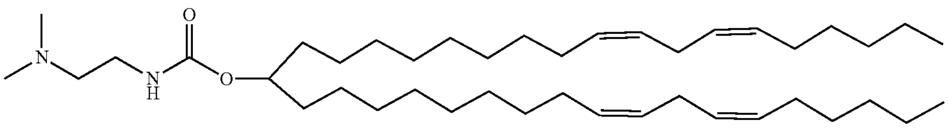 [SMILES: CCCCC/C=C\C/C=C\CCCCCCCCC(CCCCCCCC/C=C\C/C=C\CCCCC)OC(=O)NCCN(C)C]
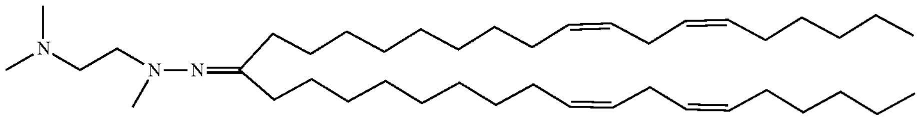 [SMILES: CCCCC/C=C\C/C=C\CCCCCCCCC(CCCCCCCC/C=C\C/C=C\CCCCC)=NN(C)CCN(C)C]
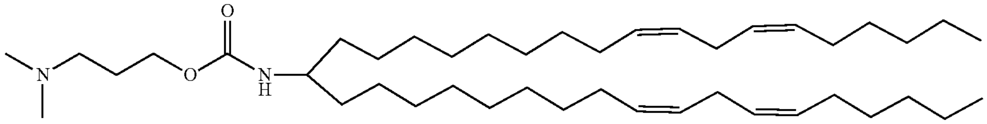 [SMILES: CCCCC/C=C\C/C=C\CCCCCCCCC(CCCCCCCC/C=C\C/C=C\CCCCC)NC(=O)OCCCN(C)C]
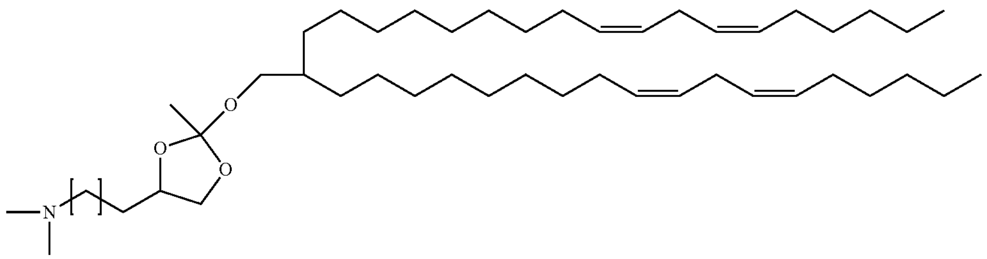
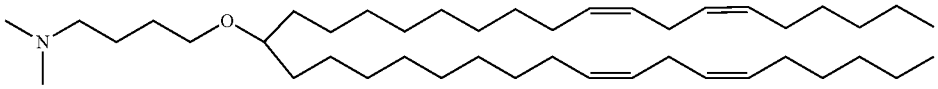 [SMILES: CCCCC/C=C\C/C=C\CCCCCCCCC(CCCCCCCC/C=C\C/C=C\CCCCC)OCCCCN(C)C]
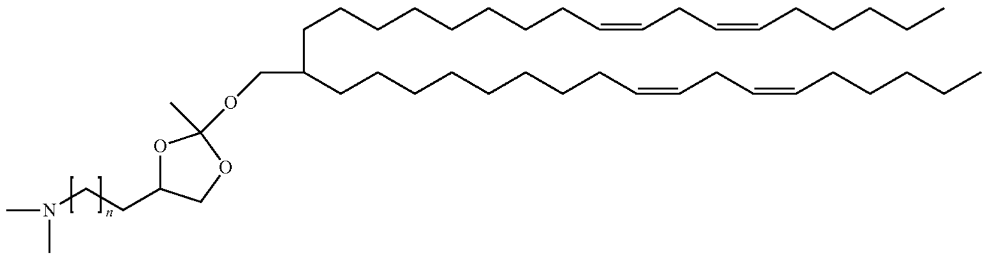
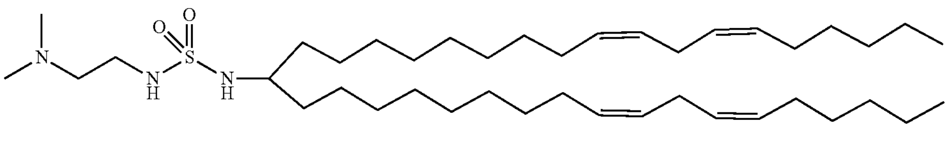 [SMILES: CCCCC/C=C\C/C=C\CCCCCCCCC(CCCCCCCC/C=C\C/C=C\CCCCC)NS(=O)(=O)NCCN(C)C]
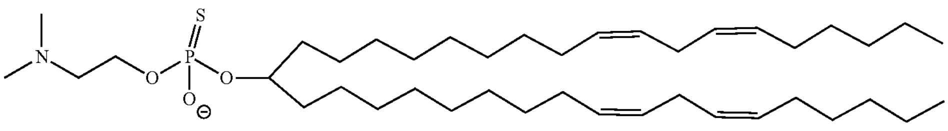
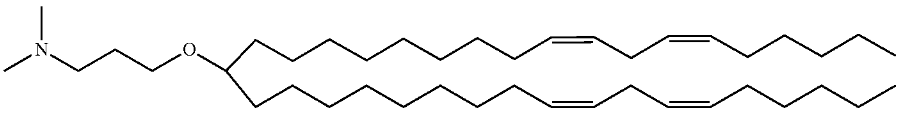 [SMILES: CCCCC/C=C\C/C=C\CCCCCCCCC(CCCCCCCC/C=C\C/C=C\CCCCC)OCCCN(C)C]

TABLE 11-continued
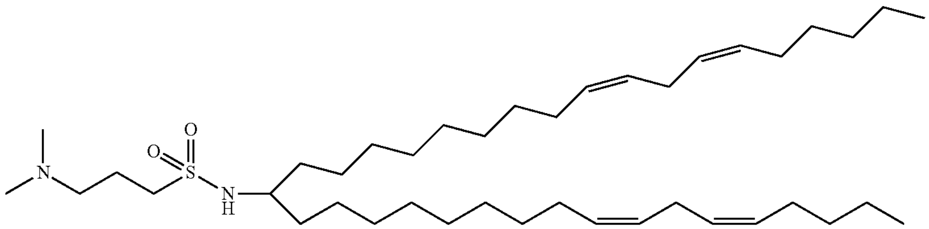 [SMILES: CCCC/C=C\C/C=C\CCCCCCCCC(CCCCCCCC/C=C\C/C=C\CCCCC)NS(=O)(=O)CCCN(C)C]
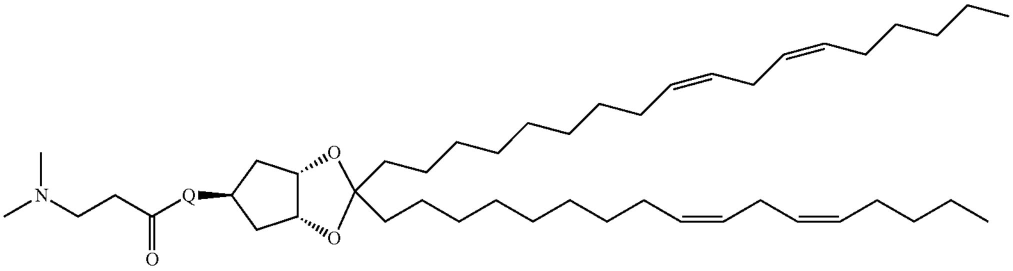
Q is NH, NMe
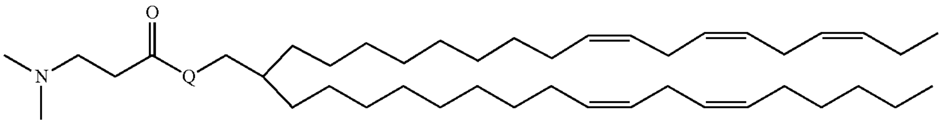
Q is NH, NMe
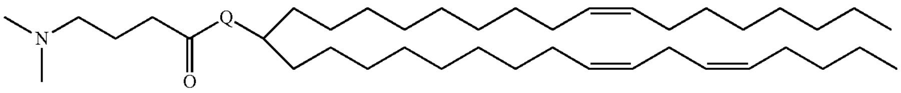
Q is NH, NMe
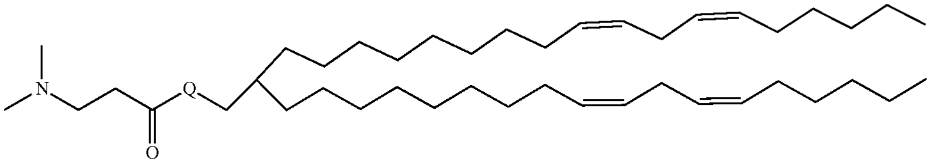
Q is NH, NMe
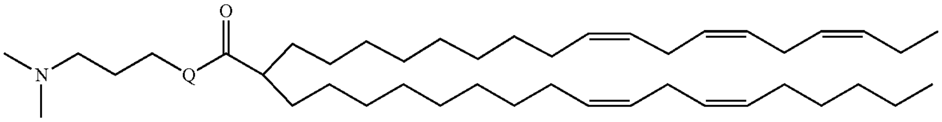
Q is NH, NMe
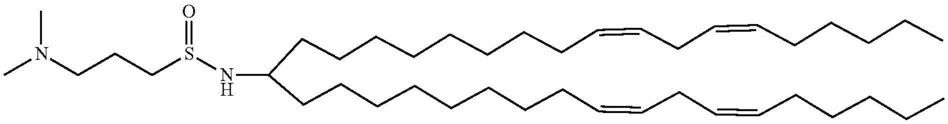 [SMILES: CCCCC/C=C\C/C=C\CCCCCCCCC(CCCCCCCC/C=C\C/C=C\CCCCC)NS(=O)CCCN(C)C]
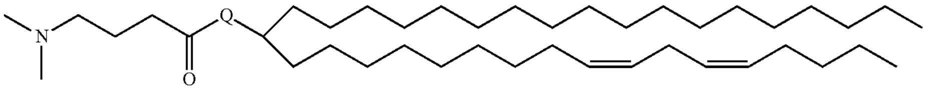
Q is NH, NMe TABLE 11-continued
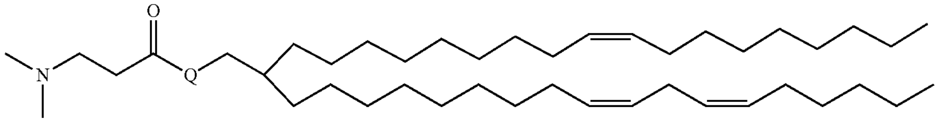
Q is NH, NMe
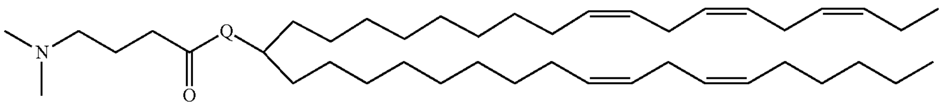
Q is NH, NMe
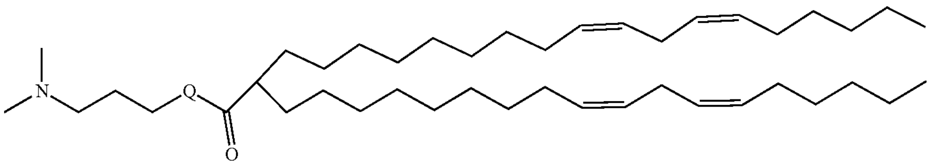
Q is NH, NMe
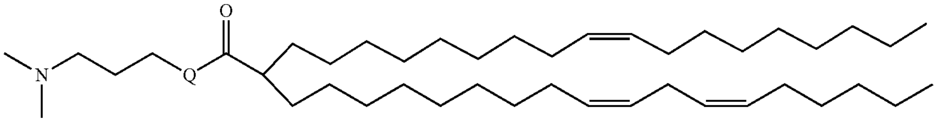
Q is NH, NMe
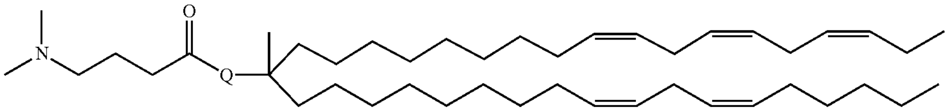
Q is NH, NMe
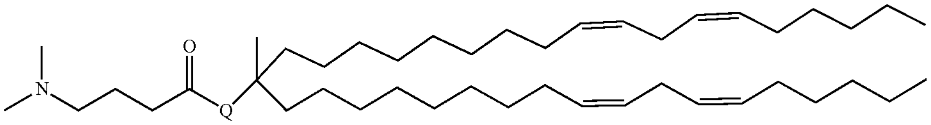
Q is NH, NMe
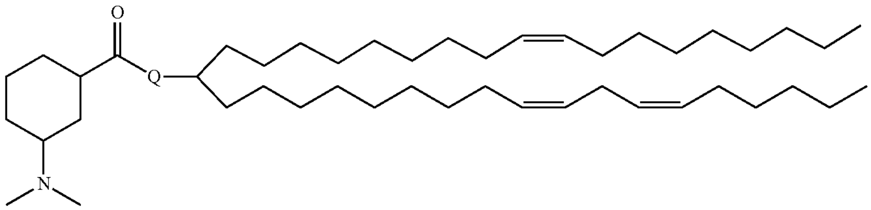
Q is NH, NMe
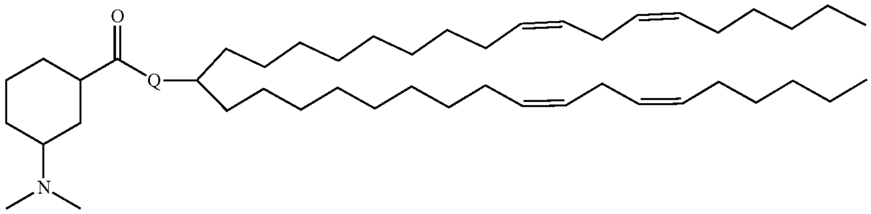
Q is NH, NMe TABLE 11-continued
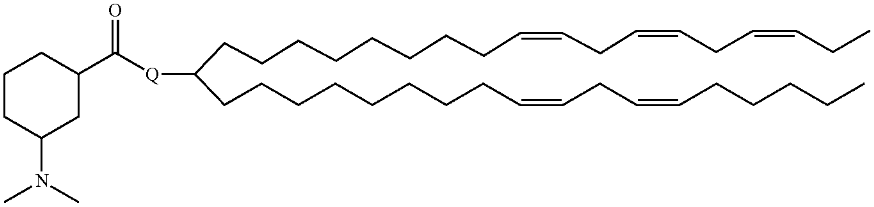
Q is NH, NMe
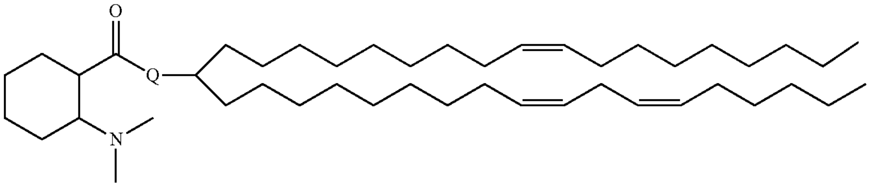
Q is NH, NMe
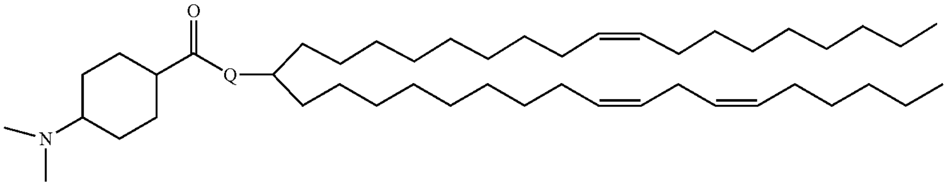
Q is NH, NMe
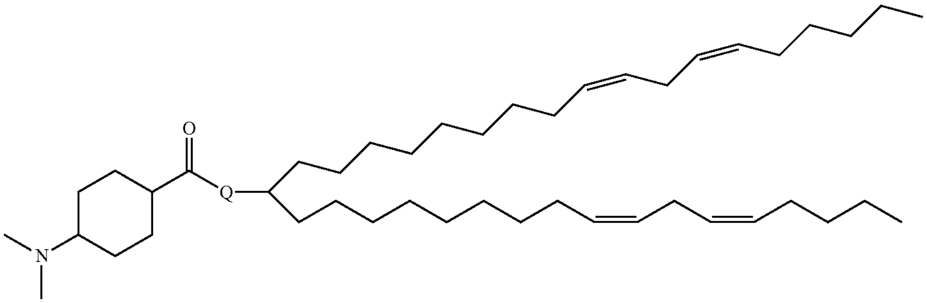
Q is NH, NMe
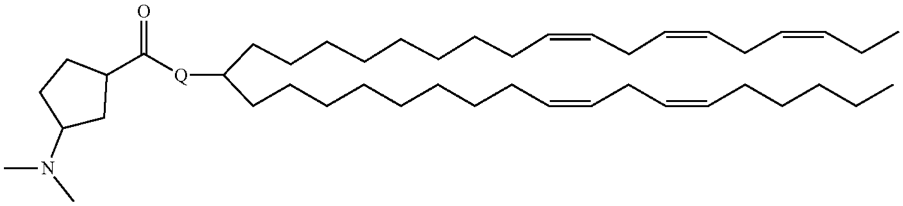
Q is NH, NMe
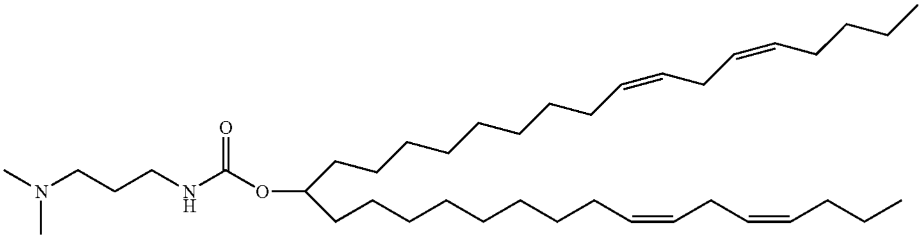 [SMILES: CCC/C=C\C/C=C\CCCCCCCCC(CCCCCCCC/C=C\C/C=C\CCCC)OC(=O)NCCCN(C)C]

TABLE 11-continued
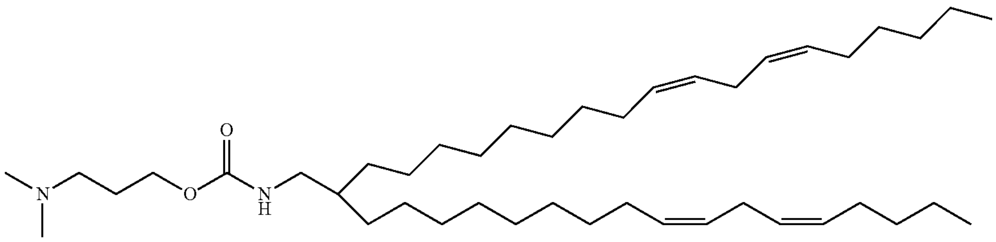 [SMILES: CCCC/C=C\C/C=C\CCCCCCCCC(CCCCCCCC/C=C\C/C=C\CCCCC)CNC(=O)OCCCN(C)C]
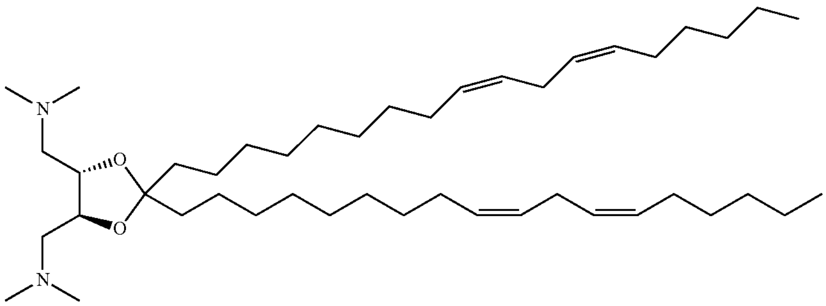 [SMILES: CCCCC/C=C\C/C=C\CCCCCCCCC1(CCCCCCCC/C=C\C/C=C\CCCCC)O[C@@H](CN(C)C)[C@H](CN(C)C)O1]
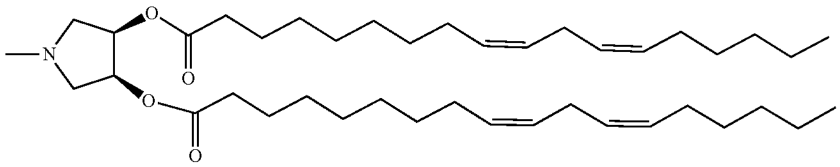 [SMILES: CCCCC/C=C\C/C=C\CCCCCCCC(=O)O[C@H]1CN(C)C[C@H]1OC(=O)CCCCCCC/C=C\C/C=C\CCCCC]
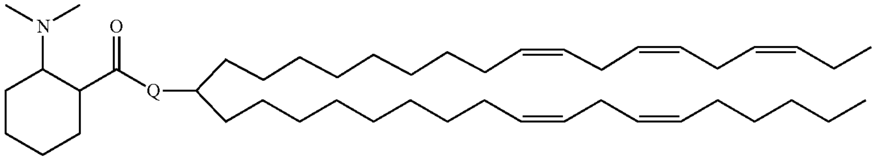
Q is NH, NMe
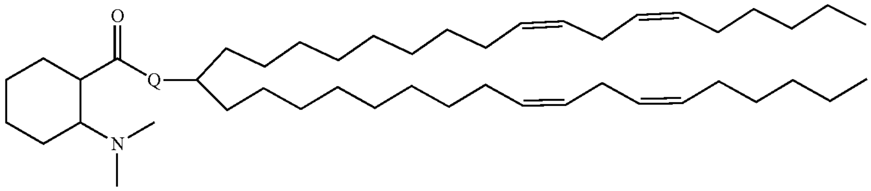
Q is NH, NMe
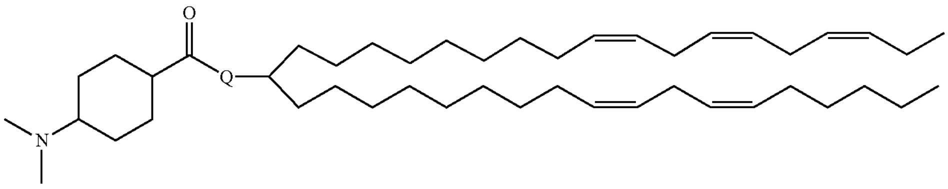
Q is NH, NMe TABLE 11-continued
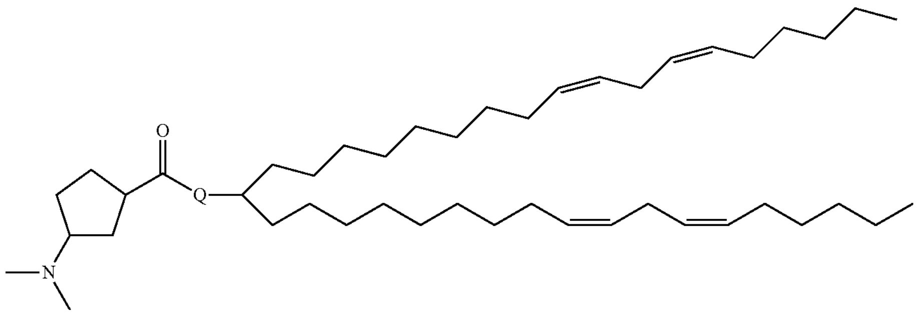
Q is NH, NMe
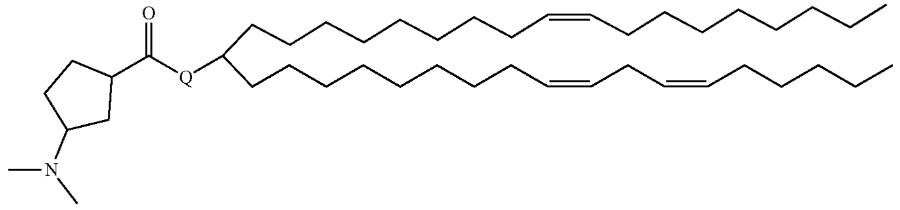
Q is NH, NMe
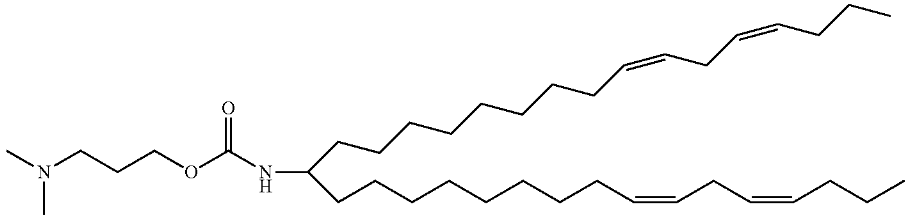 [SMILES: CCC/C=C\C/C=C\CCCCCCCCC(CCCCCCCC/C=C\C/C=C\CCC)NC(=O)OCCCN(C)C]
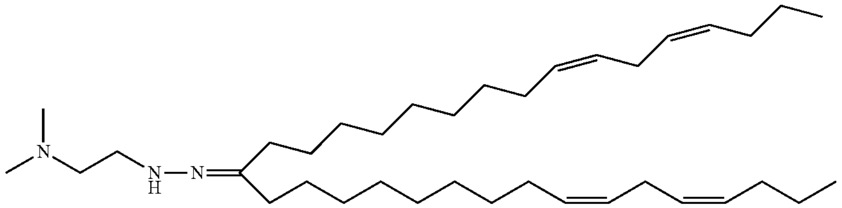 [SMILES: CCC/C=C\C/C=C\CCCCCCCCC(CCCCCCCC/C=C\C/C=C\CCC)=NNCCN(C)C]
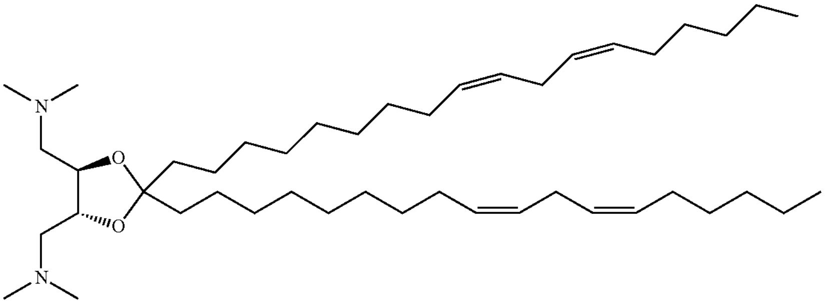 [SMILES: CCCCC/C=C\C/C=C\CCCCCCCCC1(CCCCCCCC/C=C\C/C=C\CCCCC)O[C@H](CN(C)C)[C@@H](CN(C)C)O1]
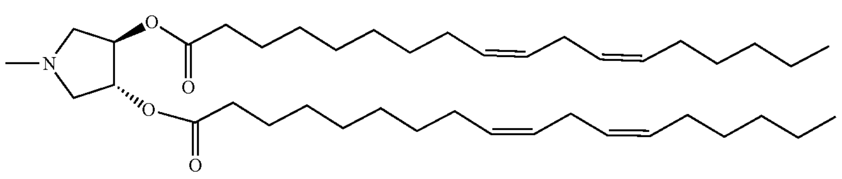 [SMILES: CCCCC/C=C\C/C=C\CCCCCCCC(=O)O[C@@H]1CN(C)C[C@H]1OC(=O)CCCCCCC/C=C\C/C=C\CCCCC]

TABLE 11-continued
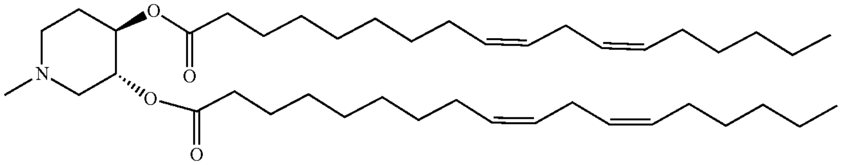 [SMILES: CCCCC/C=C\C/C=C\CCCCCCCC(=O)O[C@@H]1CCN(C)C[C@H]1OC(=O)CCCCCCC/C=C\C/C=C\CCCCC]
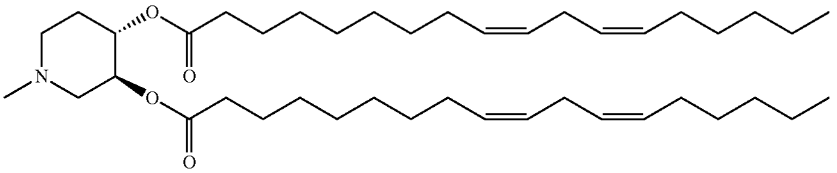 [SMILES: CCCCC/C=C\C/C=C\CCCCCCCC(=O)O[C@H]1CCN(C)C[C@@H]1OC(=O)CCCCCCC/C=C\C/C=C\CCCCC]
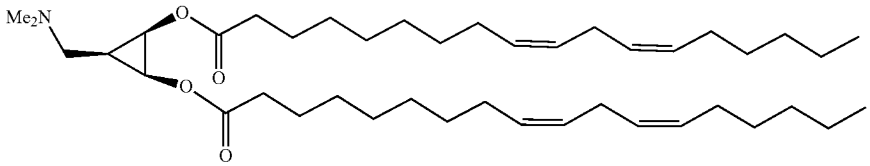 [SMILES: CCCCC/C=C\C/C=C\CCCCCCCC(=O)O[C@@H]1[C@H](CN(C)C)[C@@H]1OC(=O)CCCCCCC/C=C\C/C=C\CCCCC]
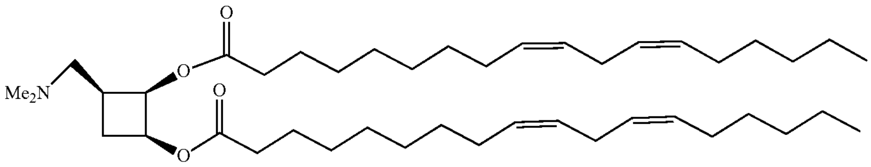 [SMILES: CCCCC/C=C\C/C=C\CCCCCCCC(=O)O[C@@H]1[C@H](CN(C)C)C[C@@H]1OC(=O)CCCCCCC/C=C\C/C=C\CCCCC]
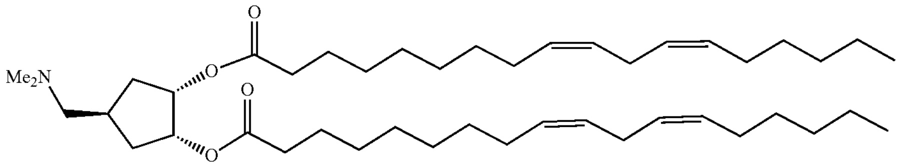 [SMILES: CCCCC/C=C\C/C=C\CCCCCCCC(=O)O[C@H]1C[C@H](CN(C)C)C[C@H]1OC(=O)CCCCCCC/C=C\C/C=C\CCCCC]
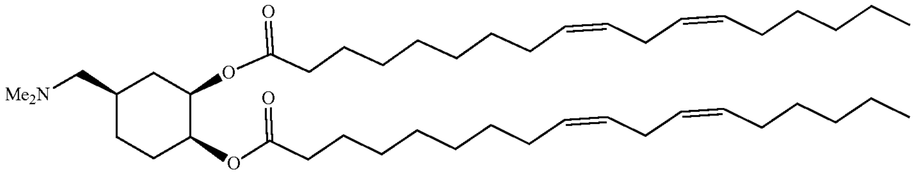 [SMILES: CCCCC/C=C\C/C=C\CCCCCCCC(=O)O[C@H]1CC[C@@H](CN(C)C)C[C@H]1OC(=O)CCCCCCC/C=C\C/C=C\CCCCC]
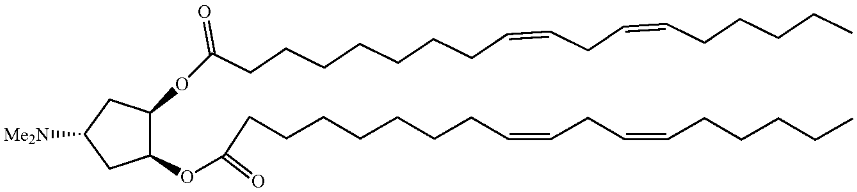 [SMILES: CCCCC/C=C\C/C=C\CCCCCCCC(=O)O[C@H]1C[C@H](N(C)C)C[C@H]1OC(=O)CCCCCCC/C=C\C/C=C\CCCCC]
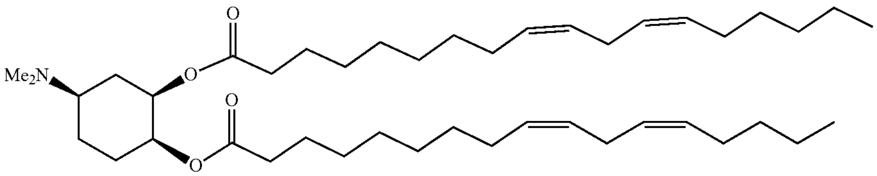 [SMILES: CCCC/C=C\C/C=C\CCCCCCCC(=O)O[C@H]1CC[C@@H](N(C)C)C[C@H]1OC(=O)CCCCCCC/C=C\C/C=C\CCCCC]
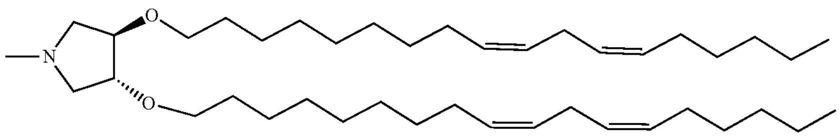 [SMILES: CCCCC/C=C\C/C=C\CCCCCCCCO[C@@H]1CN(C)C[C@H]1OCCCCCCCC/C=C\C/C=C\CCCCC]

TABLE 11-continued
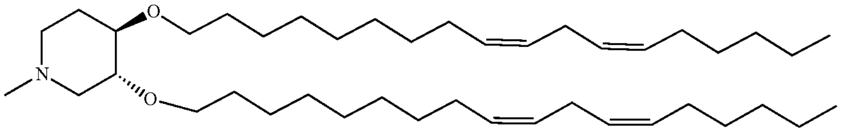 [SMILES: CCCCC/C=C\C/C=C\CCCCCCCCO[C@@H]1CCN(C)C[C@H]1OCCCCCCCC/C=C\C/C=C\CCCCC]
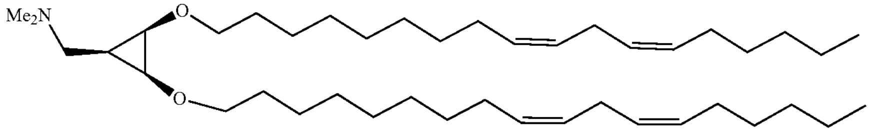 [SMILES: CCCCC/C=C\C/C=C\CCCCCCCCO[C@@H]1[C@H](CN(C)C)[C@@H]1OCCCCCCCC/C=C\C/C=C\CCCCC]
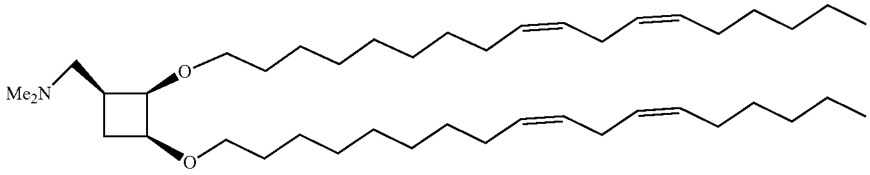 [SMILES: CCCCC/C=C\C/C=C\CCCCCCCCO[C@@H]1[C@H](CN(C)C)C[C@@H]1OCCCCCCCC/C=C\C/C=C\CCCCC]
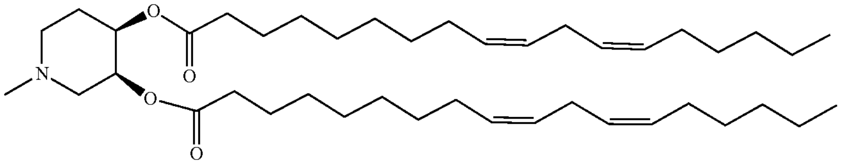 [SMILES: CCCCC/C=C\C/C=C\CCCCCCCC(=O)O[C@H]1CN(C)CC[C@H]1OC(=O)CCCCCCC/C=C\C/C=C\CCCCC]
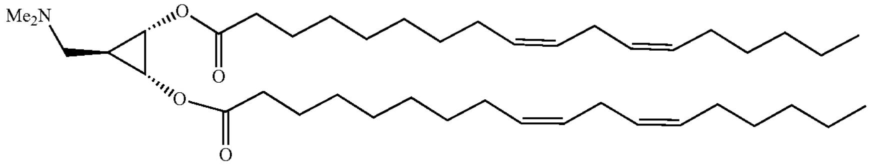 [SMILES: CCCCC/C=C\C/C=C\CCCCCCCC(=O)O[C@@H]1[C@@H](CN(C)C)[C@@H]1OC(=O)CCCCCCC/C=C\C/C=C\CCCCC]
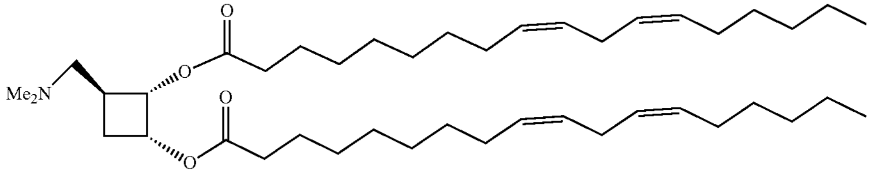 [SMILES: CCCCC/C=C\C/C=C\CCCCCCCC(=O)O[C@H]1[C@H](CN(C)C)C[C@H]1OC(=O)CCCCCCC/C=C\C/C=C\CCCCC]
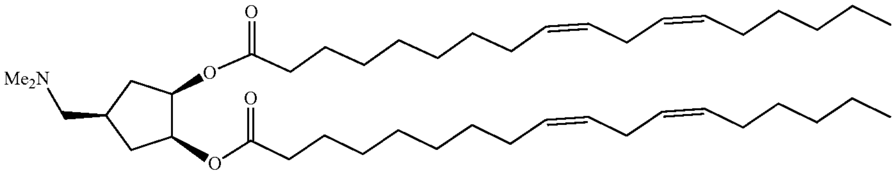 [SMILES: CCCCC/C=C\C/C=C\CCCCCCCC(=O)O[C@H]1C[C@@H](CN(C)C)C[C@H]1OC(=O)CCCCCCC/C=C\C/C=C\CCCCC]
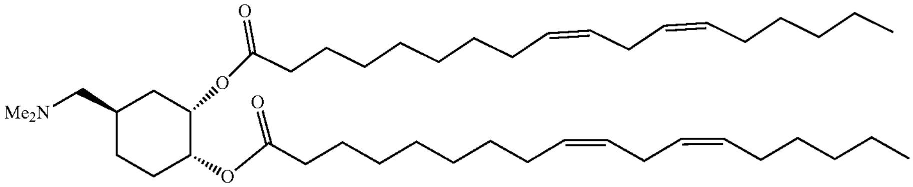 [SMILES: CCCCC/C=C\C/C=C\CCCCCCCC(=O)O[C@H]1C[C@H](CN(C)C)CC[C@H]1OC(=O)CCCCCCC/C=C\C/C=C\CCCCC]
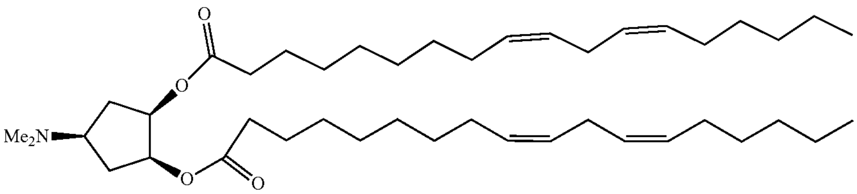 [SMILES: CCCCC/C=C\C/C=C\CCCCCCCC(=O)O[C@H]1C[C@@H](N(C)C)C[C@H]1OC(=O)CCCCCCC/C=C\C/C=C\CCCCC]

TABLE 11-continued
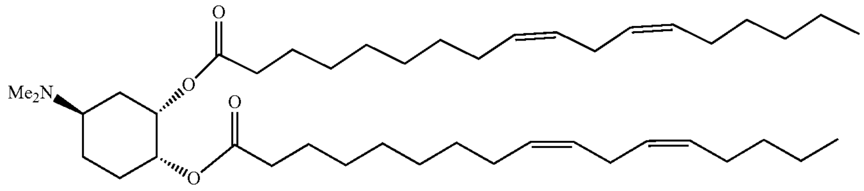 [SMILES: CCCC/C=C\C/C=C\CCCCCCCC(=O)O[C@@H]1CC[C@@H](N(C)C)C[C@@H]1OC(=O)CCCCCCC/C=C\C/C=C\CCCCC]
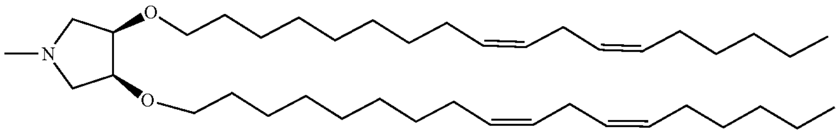
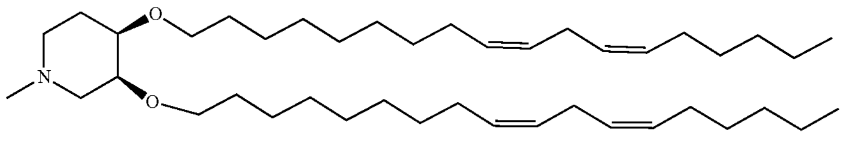 [SMILES: CCCCC/C=C\C/C=C\CCCCCCCCO[C@H]1CN(C)CC[C@H]1OCCCCCCCC/C=C\C/C=C\CCCCC]
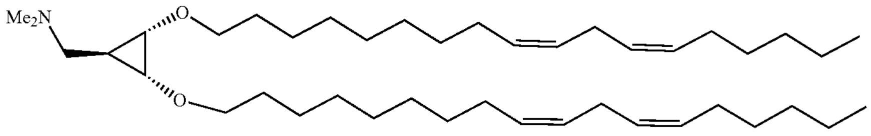 [SMILES: CCCCC/C=C\C/C=C\CCCCCCCCO[C@@H]1[C@@H](CN(C)C)[C@@H]1OCCCCCCCC/C=C\C/C=C\CCCCC]
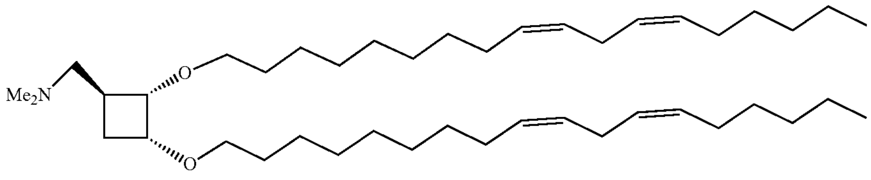 [SMILES: CCCCC/C=C\C/C=C\CCCCCCCCO[C@H]1[C@H](CN(C)C)C[C@H]1OCCCCCCCC/C=C\C/C=C\CCCCC]
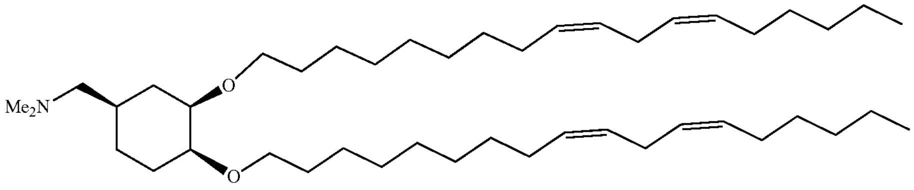 [SMILES: CCCCC/C=C\C/C=C\CCCCCCCCO[C@H]1CC[C@@H](CN(C)C)C[C@H]1OCCCCCCCC/C=C\C/C=C\CCCCC]
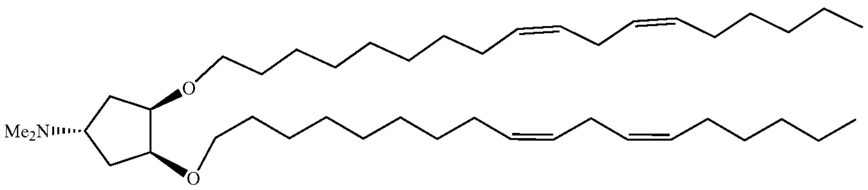 [SMILES: CCCCC/C=C\C/C=C\CCCCCCCCO[C@H]1C[C@H](N(C)C)C[C@H]1OCCCCCCCC/C=C\C/C=C\CCCCC]
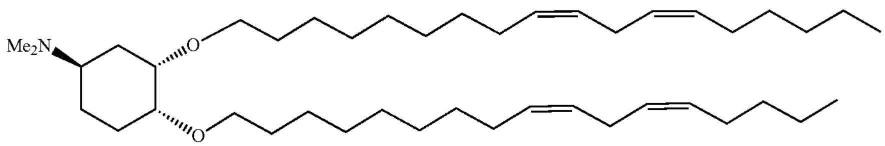 [SMILES: CCCC/C=C\C/C=C\CCCCCCCCO[C@@H]1CC[C@@H](N(C)C)C[C@@H]1OCCCCCCCC/C=C\C/C=C\CCCCC]
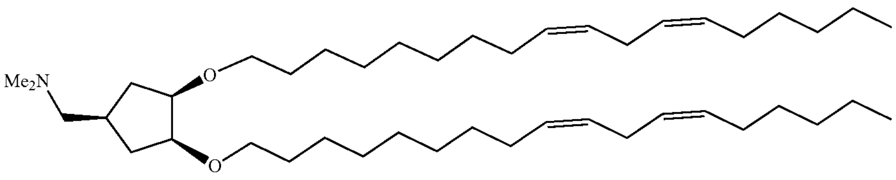 [SMILES: CCCCC/C=C\C/C=C\CCCCCCCCO[C@H]1C[C@@H](CN(C)C)C[C@H]1OCCCCCCCC/C=C\C/C=C\CCCCC]

TABLE 11-continued

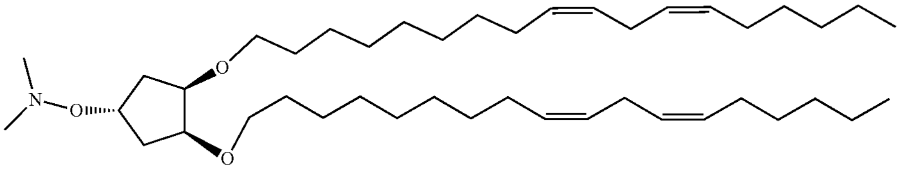 [SMILES: CCCCC/C=C\C/C=C\CCCCCCCCO[C@H]1C[C@H](ON(C)C)C[C@H]1OCCCCCCCC/C=C\C/C=C\CCCCC]

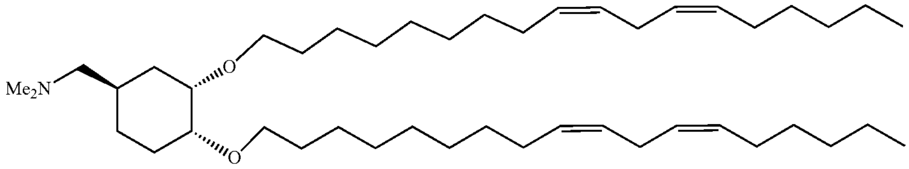 [SMILES: CCCCC/C=C\C/C=C\CCCCCCCCO[C@H]1C[C@H](CN(C)C)CC[C@H]1OCCCCCCCC/C=C\C/C=C\CCCCC]

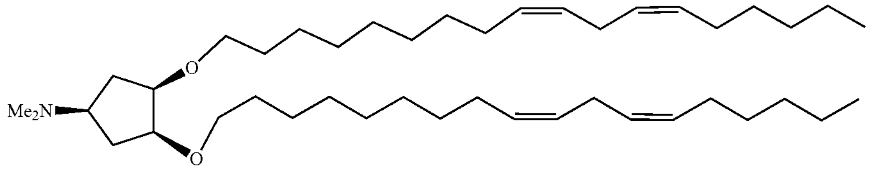 [SMILES: CCCCC/C=C\C/C=C\CCCCCCCCO[C@H]1C[C@@H](N(C)C)C[C@H]1OCCCCCCCC/C=C\C/C=C\CCCCC]

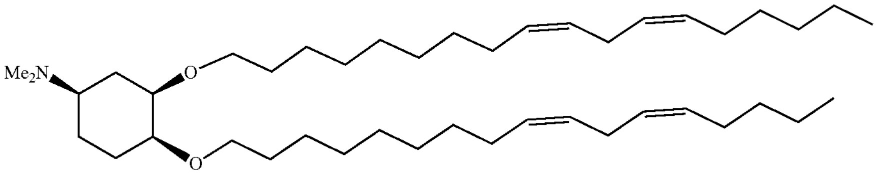 [SMILES: CCCC/C=C\C/C=C\CCCCCCCCO[C@H]1CC[C@@H](N(C)C)C[C@H]1OCCCCCCCC/C=C\C/C=C\CCCCC]

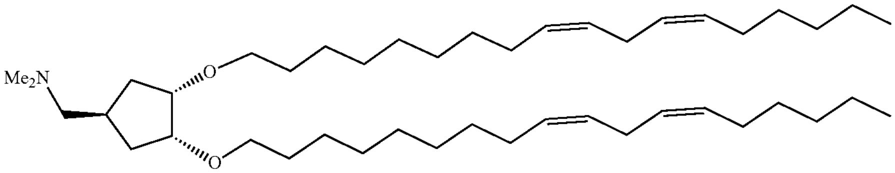 [SMILES: CCCCC/C=C\C/C=C\CCCCCCCCO[C@H]1C[C@H](CN(C)C)C[C@H]1OCCCCCCCC/C=C\C/C=C\CCCCC]

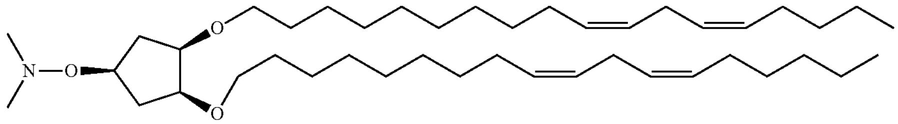 [SMILES: CCCC/C=C\C/C=C\CCCCCCCCCO[C@@H]1C[C@H](ON(C)C)C[C@@H]1OCCCCCCCC/C=C\C/C=C\CCCCC]

In some embodiments, the transfer vehicle comprises Lipid A, Lipid B, Lipid C, and/or Lipid D. In some embodiments, inclusion of Lipid A, Lipid B, Lipid C, and/or Lipid D improves encapsulation and/or endosomal escape. In some embodiments, Lipid A, Lipid B, Lipid C, and/or Lipid D are described in international patent application PCT/US2017/028981.

In some embodiments, an ionizable lipid is Lipid A, which is (9Z,12Z)-3-((4,4-bis(octyloxy)butanoyl)oxy)-2-((((3-(diethylamino)propoxy)carbonyl)oxy)methyl)propyl octadeca9,12-dienoate, also called 3-((4,44bis(octyloxy)butanoyl)oxy)-2-((((3-(diethylamino)propoxy)carbonyl)oxy)methyl)propyl (9Z,12Z)-octadeca-9,12-dienoate. Lipid A can be depicted as:

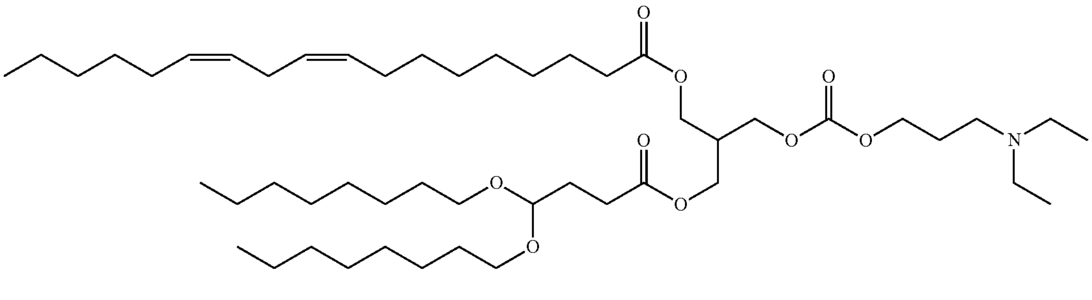 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid A may be synthesized according to WO2015/095340 (e.g., pp. 84-86), incorporated by reference in its entirety.

In some embodiments, an ionizable lipid is Lipid B, which is ((5-((dimethylamino)methyl)-1,3-phenylene)bis(oxy))bis(octane-8,1-diyl)b is (decanoate). Lipid B can be depicted as:

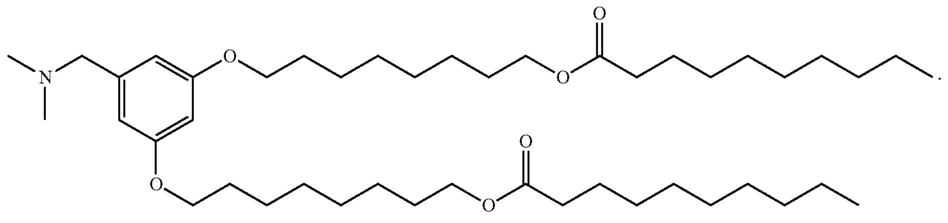 [SMILES: CCCCCCCCCC(=O)OCCCCCCCCOc1cc(CN(C)C)cc(OCCCCCCCCOC(=O)CCCCCCCCC)c1]

Lipid B may be synthesized according to WO2014/136086 (e.g., pp. 107-09), incorporated by reference in its entirety.

In some embodiments, an ionizable lipid is Lipid C, which is 2-((4-(((3-(dimethylamino)propoxy)carbonyl)oxy)hexadecanoyl)oxy)propane-1,3-diyl(9Z,9'Z,12Z,12'Z)-bis(octadeca-9,12-dienoate). Lipid C can be depicted as:

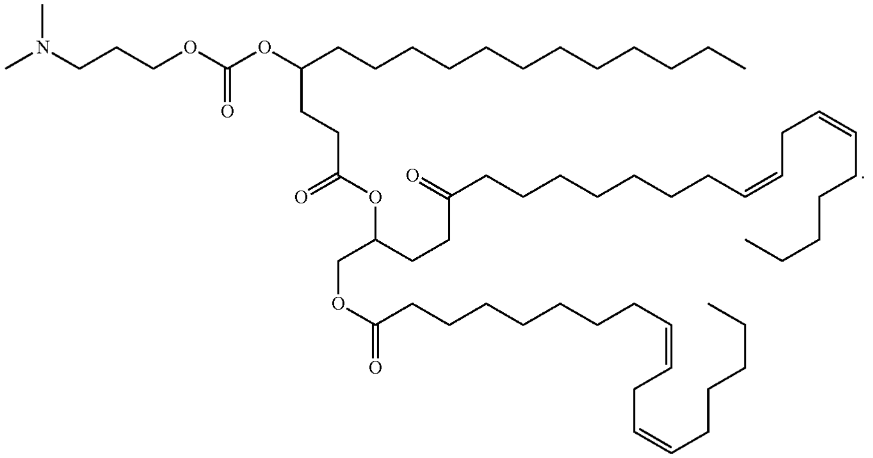 [SMILES: CCCCC/C=C\C/C=C\CCCCCCCC(=O)CCC(COC(=O)CCCCCCC/C=C\C/C=C\CCCCC)OC(=O)CCC(CCCCCCCCCCCC)OC(=O)OCCCN(C)C]

In some embodiments, an ionizable lipid is Lipid D, which is 3-(((3-(dimethylamino)propoxy)carbonyl)oxy)-13-(octanoyloxy)tridecyl 3-octylundecanoate. Lipid D can be depicted as:

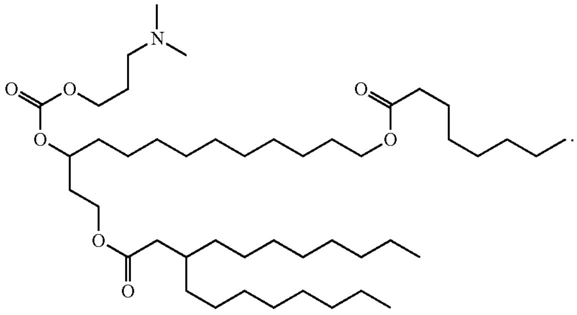 [SMILES: CCCCCCCCC(CCCCCCCC)CC(=O)OCCC(CCCCCCCCCCOC(=O)CCCCCCC)OC(=O)OCCCN(C)C]

Lipid C and Lipid D may be synthesized according to WO2015/095340, incorporated by reference in its entirety.

In some embodiments, an ionizable lipid is described in US patent publication number 20190321489. In some embodiments, an ionizable lipid is described in international patent publication WO 2010/053572, incorporated herein by reference. In some embodiments, an ionizable lipid is C12-200, described at paragraph [00225] of WO 2010/053572.

Several ionizable lipids have been described in the literature, many of which are commercially available. In certain embodiments, such ionizable lipids are included in the transfer vehicles described herein. In some embodiments, the ionizable lipid N-[1-(2,3-dioleyloxy)propyl]-N,N,N-trimethylammonium chloride or "DOTMA" is used. (Felgner et al. Proc. Nat'l Acad. Sci. 84, 7413 (1987); U.S. Pat. No. 4,897,355). DOTMA can be formulated alone or can be combined with a neutral lipid, dioleoylphosphatidylethanolamine or "DOPE" or other cationic or non-cationic lipids into a lipid nanoparticle. Other suitable cationic lipids include, for example, ionizable cationic lipids as described in U.S. provisional patent application 61/617,468, filed Mar. 29, 2012 (incorporated herein by reference), such as, e.g., (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002), $C_{12-200}$ (described in WO 2010/053572), 2-(2,2-di((9Z,12Z)-octadeca-9,12-dien-1-yl)-1,3-dioxolan-4-yl)-N,N-dimethylethanamine (DLinKC2-DMA)) (See, WO 2010/042877; Semple et al., Nature Biotech. 28:172-176 (2010)), 2-(2,2-di((9Z,2Z)-octadeca-9,12-dien-1-yl)-1,3-dioxolan-4-yl)-N, N-dimethylethanamine (DLin-KC2-DMA), (3S,10R,13R,17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate (ICE), (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), (15Z,18 Z)—N,N-dimethyl-6-((9Z,12Z)-octadeca-9,12-dien-1-yl)tetracosa-5,15,18-trien-1-amine (HGT5002), 5-carboxyspermylglycine-dioctadecylamide (DOGS), 2,3-dioleyloxy-N-[2(spermine-carboxamido)ethyl]-N,N-dimethyl-1-propanaminium (DOSPA) (Behr et al. Proc. Nat.'l Acad. Sci. 86, 6982 (1989); U.S. Pat. Nos. 5,171,678; 5,334,761), 1,2-Dioleoyl-3-Dimethylammonium-Propane (DODAP), 1,2-Dioleoyl-3-Trimethylammonium-Propane or (DOTAP). Contemplated ionizable lipids also include 1,2-distcaryloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylamninopropane (DLincarbDAP), 1,2-Dilinoleoylcarbamyl-3-dimethylaminopropane (DLinCDAP), 2,2-dilinoleyl-4-dimethylaminomethy1-[1,3]-dioxolane (DLin-K-DMA), 2,2-dilinoleyl-4-dimethylaminoethyl-[1,3]-dioxolane (DLin-K-XTC2-DMA) or GL67, or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). The use of cholesterol-based ionizable lipids to formulate the transfer vehicles (e.g., lipid nanoparticles) is also contemplated by the present invention. Such cholesterol-based ionizable lipids can be used, either alone or in combination with other lipids. Suitable cholesterol-based ionizable lipids include, for example, DC-Cholesterol (N,N-dimethyl-N-ethylcarboxamidocholesterol), and 1,4-bis(3-N-oleylamino-propyl)piperazine (Gao, et al., Biochem. Biophys. Res. Comm. 179, 280 (1991); Wolf et al. BioTechniques 23, 139 (1997); U.S. Pat. No. 5,744,335).

Also contemplated are cationic lipids such as dialkylamino-based, imidazole-based, and guanidinium-based lipids. For example, also contemplated is the use of the ionizable lipid (3S,10R,13R,17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate (ICE), as disclosed in International Application No. PCT/US2010/058457, incorporated herein by reference.

Also contemplated are ionizable lipids such as the dialkylamino-based, imidazole-based, and guanidinium-based lipids. For example, certain embodiments are directed to a composition comprising one or more imidazole-based ionizable lipids, for example, the imidazole cholesterol ester or "ICE" lipid, (3S,10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (XIII) below. In an embodiment, a transfer vehicle for delivery of circRNA may comprise one or more imidazole-based ionizable lipids, for example, the imidazole cholesterol ester or "ICE" lipid (3S,10R, 13R, 17R)-10, 13-dimethyl-17-((R)-6-methylheptan-2-yl)-2, 3, 4, 7, 9, 10, 11, 12, 13, 14, 15, 16, 17-tetradecahydro-1H-cyclopenta[a]phenanthren-3-yl 3-(1H-imidazol-4-yl)propanoate, as represented by structure (XIII).

(XIII)

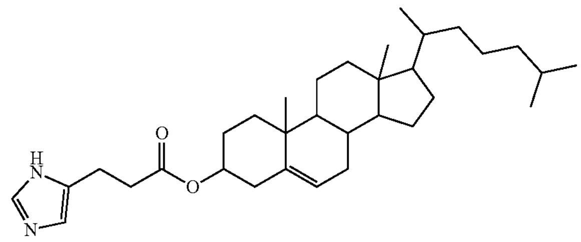

Without wishing to be bound by a particular theory, it is believed that the fusogenicity of the imidazole-based cationic lipid ICE is related to the endosomal disruption which is facilitated by the imidazole group, which has a lower pKa relative to traditional ionizable lipids. The endosomal disruption in turn promotes osmotic swelling and the disruption of the liposomal membrane, followed by the transfection or intracellular release of the nucleic acid(s) contents loaded therein into the target cell.

The imidazole-based ionizable lipids are also characterized by their reduced toxicity relative to other ionizable lipids.

In some embodiments, an ionizable lipid is described by US patent publication number 20190314284. In certain embodiments, the an ionizable lipid is described by structure 3, 4, 5, 6, 7, 8, 9, or 10 (e.g., HGT4001, HGT4002, HGT4003, HGT4004 and/or HGT4005). In certain embodiments, the one or more cleavable functional groups (e.g., a disulfide) allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells. For example, when a transfer vehicle (e.g., a lipid nanoparticle) comprises one or more of the lipids of structures 3-10, the phase transition in the lipid bilayer of the one or more target cells facilitates the delivery of the circRNA into the one or more target cells.

In certain embodiments, the ionizable lipid is described by structure (XIV), (XIV)

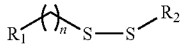

wherein:

$R_1$ is selected from the group consisting of imidazole, guanidinium, amino, imine, enamine, an optionally-substituted alkyl amino (e.g., an alkyl amino such as dimethylamino) and pyridyl;

$R_2$ is selected from the group consisting of structure XV and structure XVI;

XV

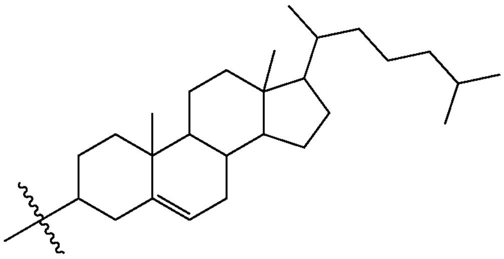

XVI

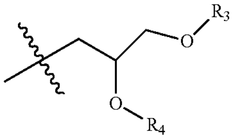

wherein $R_3$ and $R_4$ are each independently selected from the group consisting of an optionally substituted, variably saturated or unsaturated C6-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, $R_3$ and $R_4$ are each an optionally substituted, polyunsaturated C18 alkyl, while in other embodiments $R_3$ and $R_4$ are each an unsubstituted, polyunsaturated C18 alkyl. In certain embodiments, one or more of $R_3$ and $R_4$ are (9Z,12Z)-octadeca-9,12-dien.

Also disclosed herein are pharmaceutical compositions that comprise the compound of structure XIV, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is structure XV; and wherein n is zero or any positive integer. Further disclosed herein are pharmaceutical compositions comprising the compound of structure XIV, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is structure XVI; wherein $R_3$ and $R_4$ are each independently selected from the group consisting of an optionally substituted, variably saturated or unsaturated C6-C20 alkyl and an optionally substituted, variably saturated or unsaturated C6-C20 acyl; and wherein n is zero or any positive integer. In certain embodiments. $R_3$ and $R_4$ are each an optionally substituted, polyunsaturated C18 alkyl, while in other embodiments $R_3$ and $R_4$ are each an unsubstituted, polyunsaturated C18 alkyl (e.g., octadeca-9,12-dien).

In certain embodiments, the $R_1$ group or head-group is a polar or hydrophilic group (e.g., one or more of the imidazole, guanidinium and amino groups) and is bound to the $R_2$ lipid group by way of the disulfide (S—S) cleavable linker group, for example as depicted in structure XIV. Other contemplated cleavable linker groups may include compositions that comprise one or more disulfide (S—S) linker group bound (e.g., covalently bound) to, for example an alkyl group (e.g., $C_1$ to C10 alkyl). In certain embodiments, the $R_1$ group is covalently bound to the cleavable linker group by way of a $C_1$-$C_{20}$ alkyl group (e.g., where n is one to twenty), or alternatively may be directly bound to the cleavable linker group (e.g., where n is zero). In certain embodiments, the disulfide linker group is cleavable in vitro and/or in vivo (e.g., enzymatically cleavable or cleavable upon exposure to acidic or reducing conditions).

In certain embodiments, the inventions relate to the compound 5-(((10,13-dimethyl-17-(6-methylheptan-2-yl)-2,3,4,7,8,9,10,11,12,13,14,15,16,17-tetradecahydro-1H-cyclopenta[a]phenanthren-3-yl)disulfanyl)methyl)-1H-imidazole, having structure XVII (referred to herein as "HGT4001").

XVII

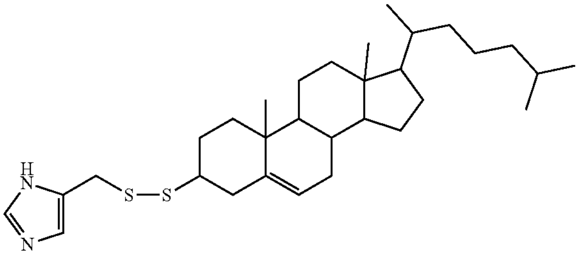

In certain embodiments, the inventions relate to the compound 1-(2-(((3S,10R, 13R)-10, 13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)ethyl)guanidine, having structure XVIII (referred to herein as "HGT4002").

XVIII

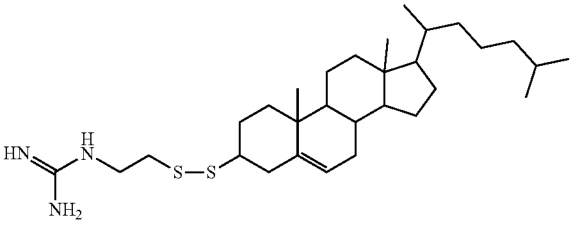

In certain embodiments, the inventions relate to the compound 2-((2,3-Bis((9Z,12Z)-octadeca-9,12-dien-1-yloxy)propyl)disulfanyl)-N,N-dimethylethanamine, having structure XIX (referred to herein as "HGT4003").

XIX

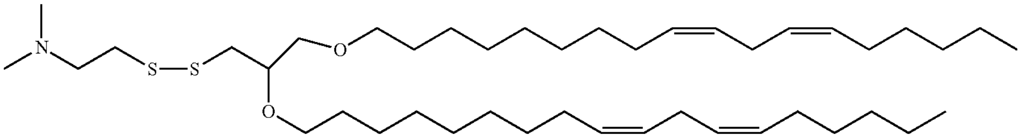

In other embodiments, the inventions relate to the compound 5-(((2,3-bis((9Z,12Z)-octadeca-9,12-dien-1-yloxy)propyl)disulfanyl)methyl)-1H-imidazole having the structure of structure XX (referred to herein as "HGT4004").

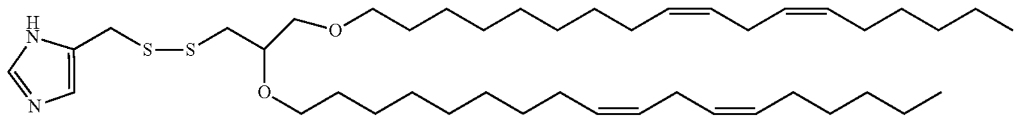

XX

In still other embodiments, the inventions relate to the compound 1-(((2,3-bis((9Z,12Z)-octadeca-9,12-dien-1-yloxy)propyl)disulfanyl)methyl)guanidine having structure XXI (referred to herein as "HGT4005").

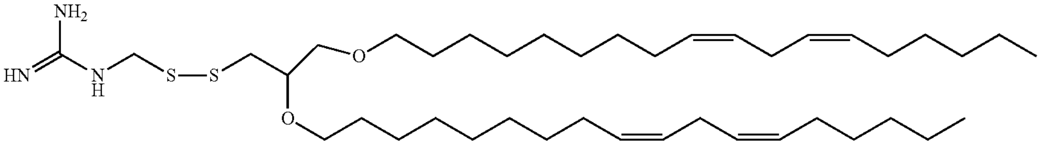

XXI

In certain embodiments, the compounds described as structures 3-10 are ionizable lipids.

The compounds, and in particular the imidazole-based compounds described as structures 3-8 (e.g., HGT4001 and HGT4004), are characterized by their reduced toxicity, in particular relative to traditional ionizable lipids. In some embodiments, the transfer vehicles described herein comprise one or more imidazole-based ionizable lipid compounds such that the relative concentration of other more toxic ionizable lipids in such pharmaceutical or liposomal composition may be reduced or otherwise eliminated.

The ionizable lipids include those disclosed in international patent application PCT/US2019/025246, and US patent publications 2017/0190661 and 2017/0114010, incorporated herein by reference in their entirety. The ionizable lipids may include a lipid selected from the following tables 12, 13, 14, or 15.

TABLE 12

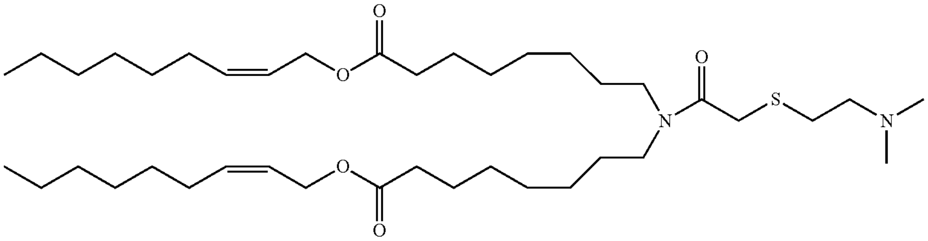

ATX-001

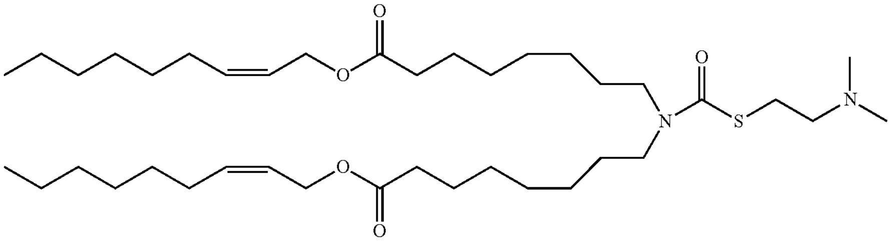

ATX-002

TABLE 12-continued
ATX-003
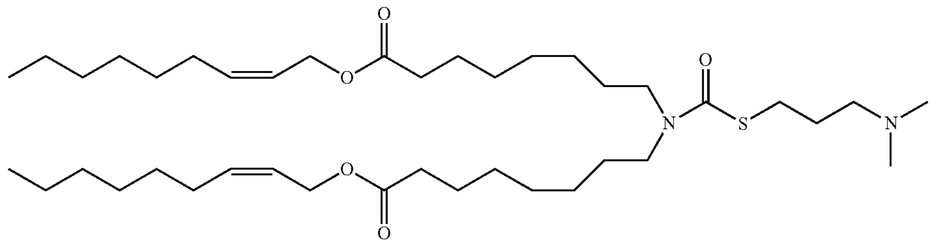 [SMILES: CCCCCC/C=C\COC(=O)CCCCCCCN(CCCCCCCC(=O)OC/C=C\CCCCCC)C(=O)CSCCN(C)C]
ATX-004
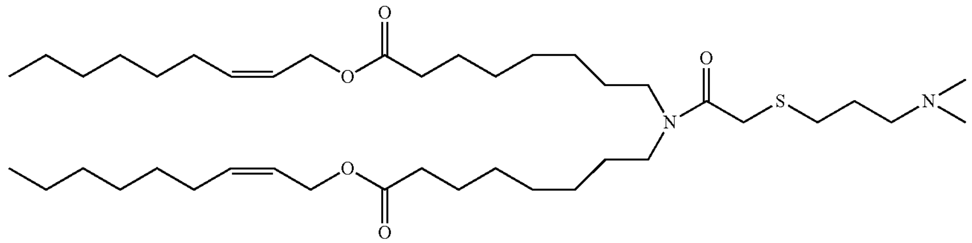 [SMILES: CCCCCC/C=C\COC(=O)CCCCCCCN(CCCCCCCC(=O)OC/C=C\CCCCCC)C(=O)CSCCCN(C)C]
ATX-005
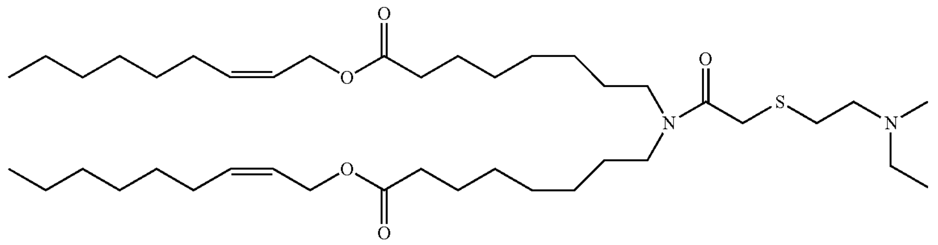 [SMILES: CCCCCC/C=C\COC(=O)CCCCCCCN(CCCCCCCC(=O)OC/C=C\CCCCCC)C(=O)CSCCN(C)CC]
ATX-006
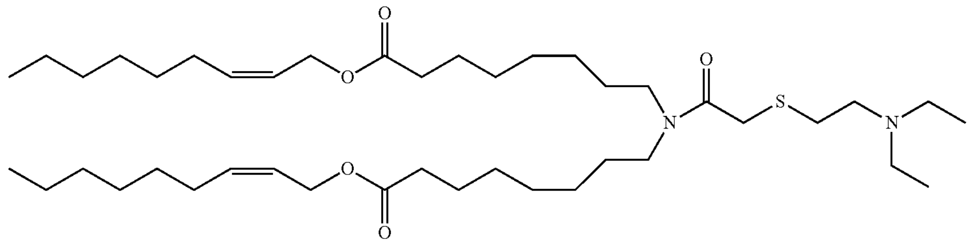 [SMILES: CCCCCC/C=C\COC(=O)CCCCCCCN(CCCCCCCC(=O)OC/C=C\CCCCCC)C(=O)CSCCN(CC)CC]
ATX-007
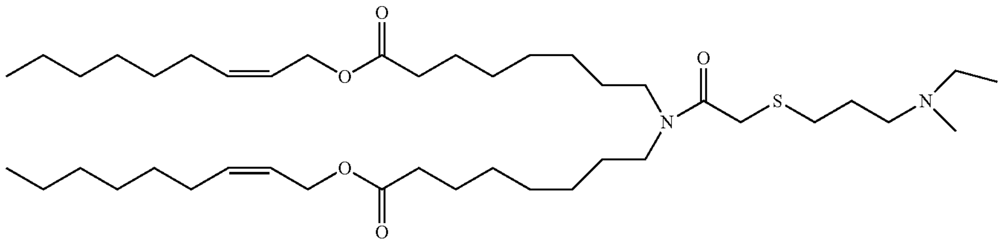 [SMILES: CCCCCC/C=C\COC(=O)CCCCCCCN(CCCCCCCC(=O)OC/C=C\CCCCCC)C(=O)CSCCCN(C)CC]
ATX-008
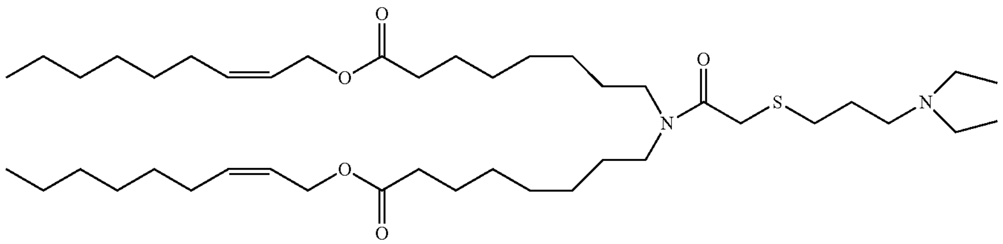 [SMILES: CCCCCC/C=C\COC(=O)CCCCCCCN(CCCCCCCC(=O)OC/C=C\CCCCCC)C(=O)CSCCCN(CC)CC]

TABLE 12-continued
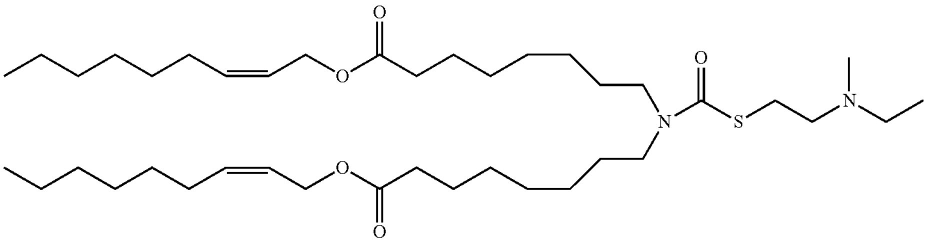 [SMILES: CCCCCC/C=C\COC(=O)CCCCCCCN(CCCCCCCC(=O)OC/C=C\CCCCCC)C(=O)SCCN(C)CC]
ATX-009
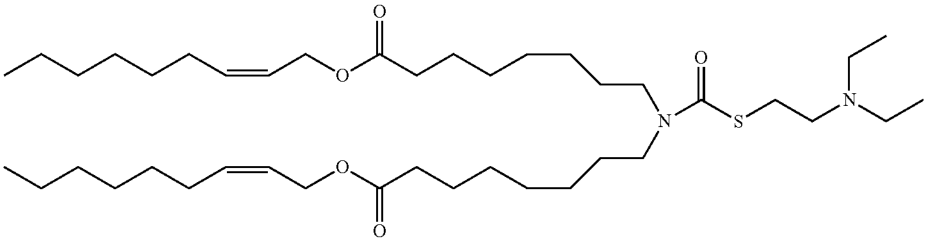 [SMILES: CCCCCC/C=C\COC(=O)CCCCCCCN(CCCCCCCC(=O)OC/C=C\CCCCCC)C(=O)SCCN(CC)CC]
ATX-010
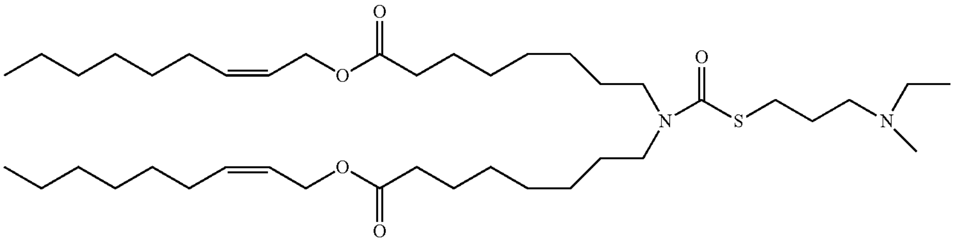 [SMILES: CCCCCC/C=C\COC(=O)CCCCCCCN(CCCCCCCC(=O)OC/C=C\CCCCCC)C(=O)SCCCN(C)CC]
ATX-011
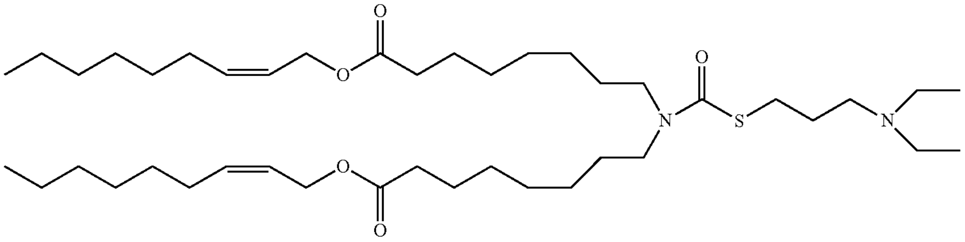 [SMILES: CCCCCC/C=C\COC(=O)CCCCCCCN(CCCCCCCC(=O)OC/C=C\CCCCCC)C(=O)SCCCN(CC)CC]
ATX-012
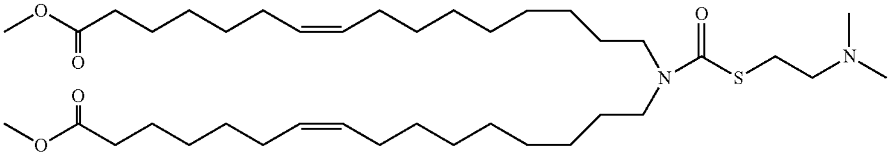
ATX-013
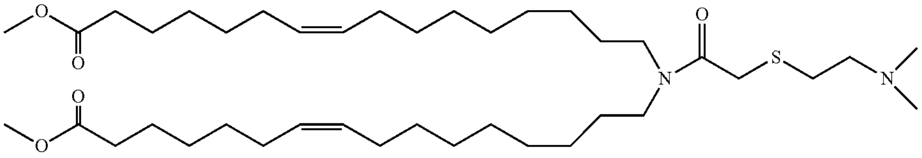
ATX-014
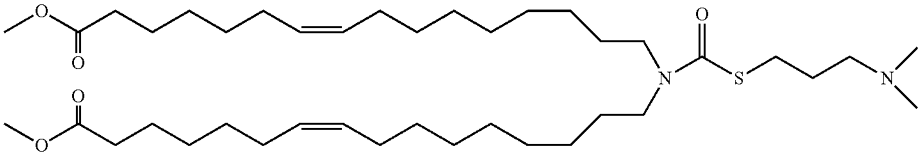
ATX-015

TABLE 12-continued
ATX-016
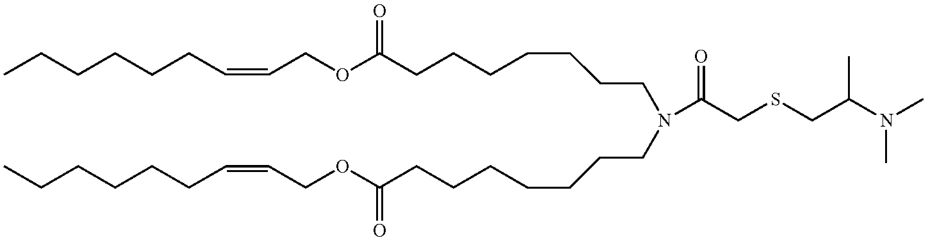 [SMILES: CCCCCC/C=C\COC(=O)CCCCCCCN(CCCCCCCC(=O)OC/C=C\CCCCCC)C(=O)CSCC(C)N(C)C]
ATX-017
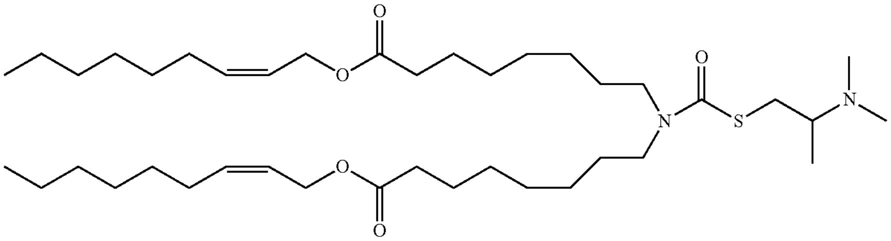 [SMILES: CCCCCC/C=C\COC(=O)CCCCCCCN(CCCCCCCC(=O)OC/C=C\CCCCCC)C(=O)SCC(C)N(C)C]
ATX-018
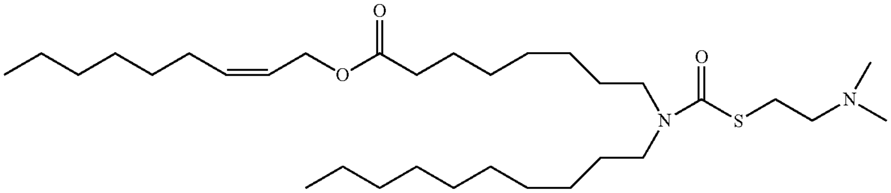 [SMILES: CCCCCC/C=C\COC(=O)CCCCCCCN(CCCCCCCCCC)C(=O)SCCN(C)C]
ATX-019
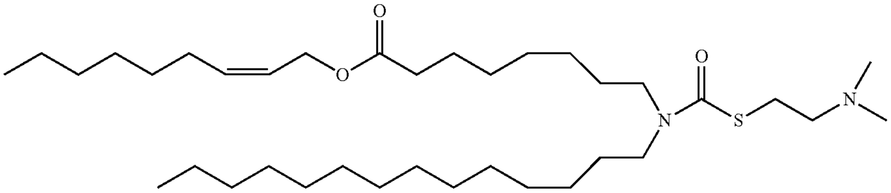 [SMILES: CCCCCC/C=C\COC(=O)CCCCCCCN(CCCCCCCCCCCCCC)C(=O)SCCN(C)C]
ATX-020
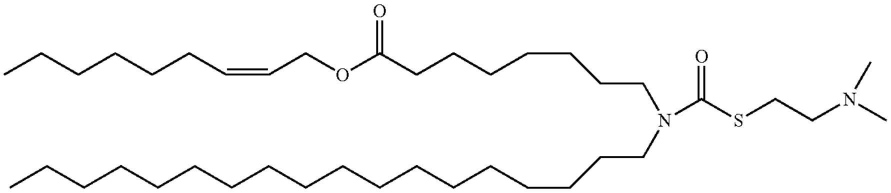 [SMILES: CCCCCC/C=C\COC(=O)CCCCCCCN(CCCCCCCCCCCCCCCCCC)C(=O)SCCN(C)C]
ATX-021
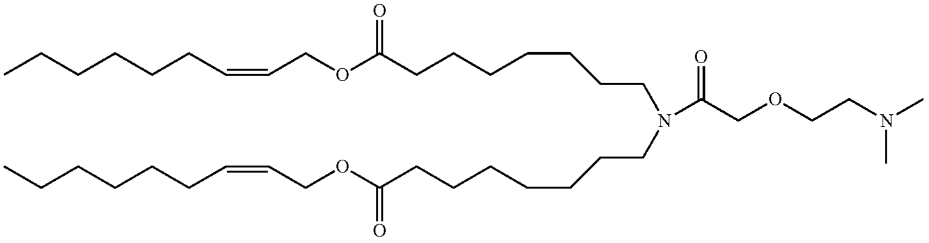 [SMILES: CCCCCC/C=C\COC(=O)CCCCCCCN(CCCCCCCC(=O)OC/C=C\CCCCCC)C(=O)COCCN(C)C]
ATX-022
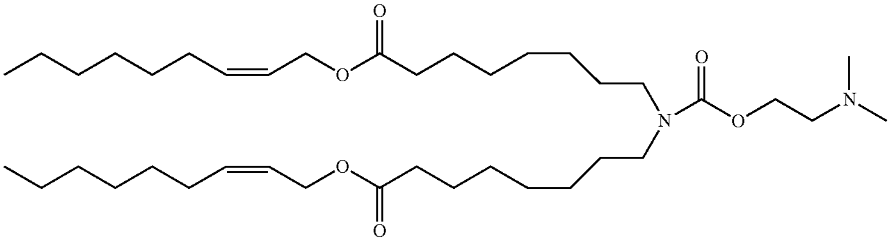

TABLE 12-continued
ATX-023
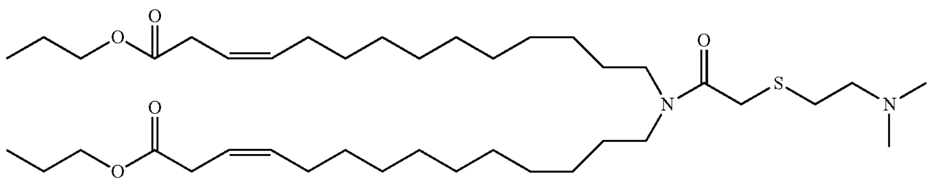 [SMILES: CCCOC(=O)C/C=C\CCCCCCCCCCN(CCCCCCCCCC/C=C\CC(=O)OCCC)C(=O)CSCCN(C)C]
ATX-024
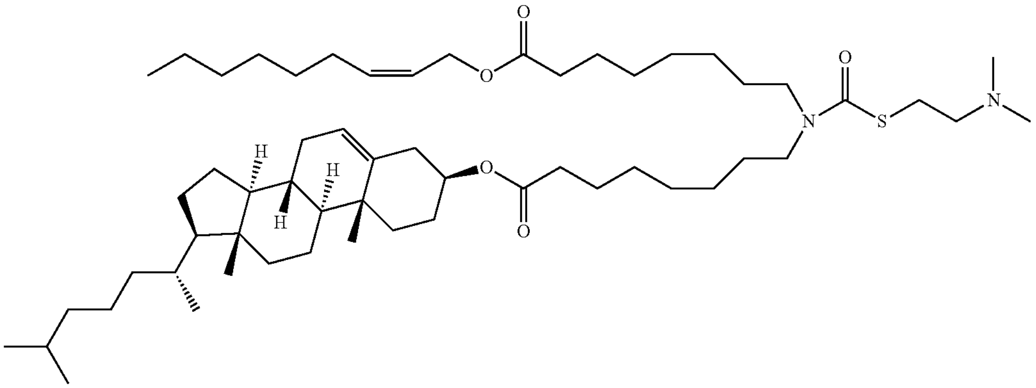
ATX-025
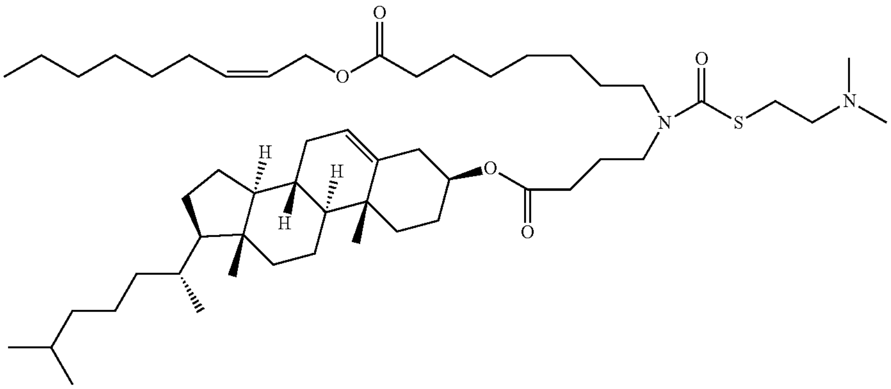
ATX-026
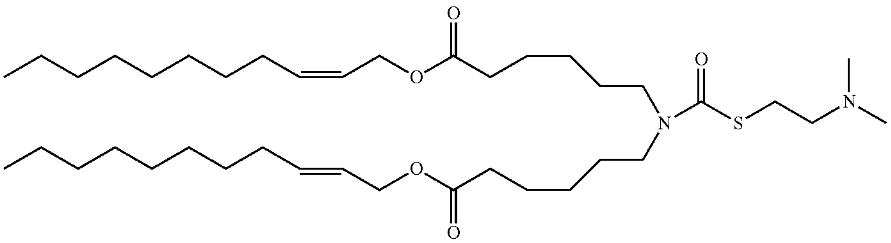 [SMILES: CCCCCCCC/C=C\COC(=O)CCCCCN(CCCCCC(=O)OC/C=C/CCCCCCCC)C(=O)SCCN(C)C]
ATX-027
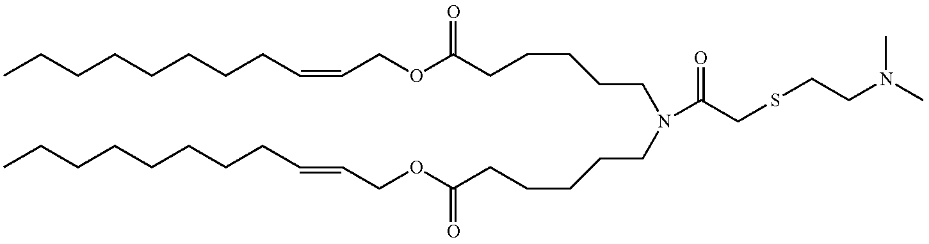 [SMILES: CCCCCCCC/C=C\COC(=O)CCCCCN(CCCCCC(=O)OC/C=C/CCCCCCCC)C(=O)CSCCN(C)C]

TABLE 12-continued
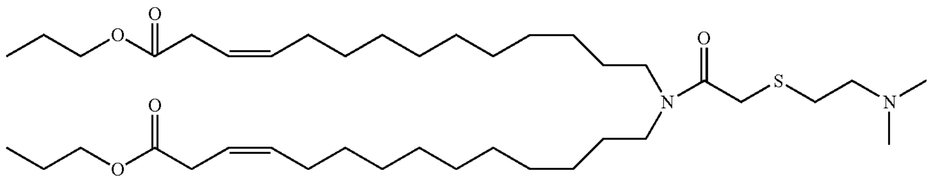 [SMILES: CCCOC(=O)C/C=C\CCCCCCCCCCN(CCCCCCCCCC/C=C\CC(=O)OCCC)C(=O)CSCCN(C)C]
ATX-028
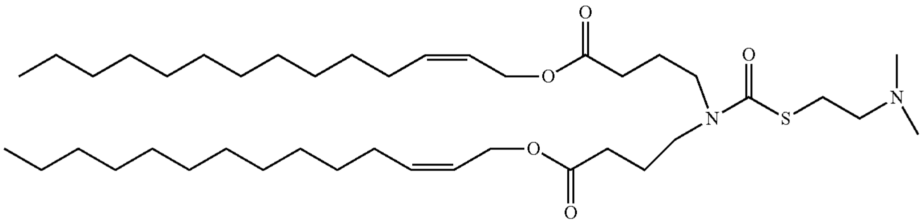 [SMILES: CCCCCCCCCCC/C=C\COC(=O)CCCN(CCCC(=O)OC/C=C\CCCCCCCCCCC)C(=O)SCCN(C)C]
ATX-029
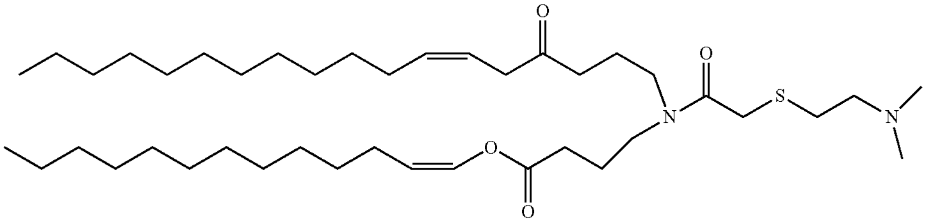 [SMILES: CCCCCCCCCCC/C=C\CC(=O)CCCN(CCCC(=O)O/C=C\CCCCCCCCCCC)C(=O)CSCCN(C)C]
ATX-030
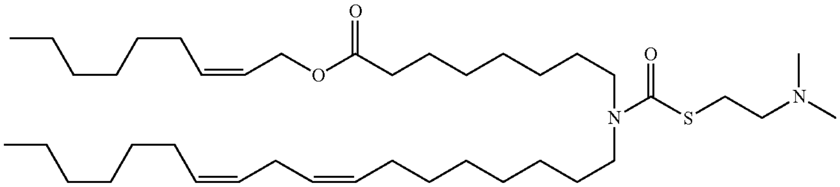 [SMILES: CCCCCC/C=C\C/C=C\CCCCCCCN(CCCCCCCC(=O)OC/C=C\CCCCCC)C(=O)SCCN(C)C]
ATX-031
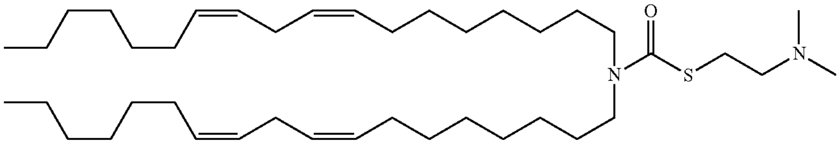 [SMILES: CCCCCC/C=C\C/C=C\CCCCCCCN(CCCCCCC/C=C\C/C=C\CCCCCC)C(=O)SCCN(C)C]
ATX-032
TABLE 13
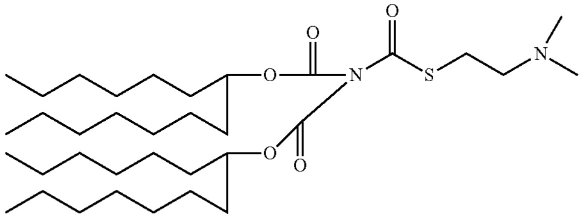 [SMILES: CCCCCCCC(CCCCCC)OC(=O)N(C(=O)OC(CCCCCC)CCCCCCC)C(=O)SCCN(C)C]
ATX-B-1
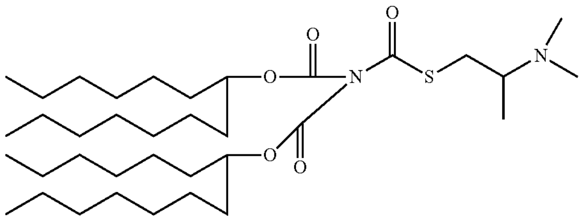 [SMILES: CCCCCCCC(CCCCCC)OC(=O)N(C(=O)OC(CCCCCC)CCCCCCC)C(=O)SCC(C)N(C)C]
ATX-B-2

TABLE 13-continued
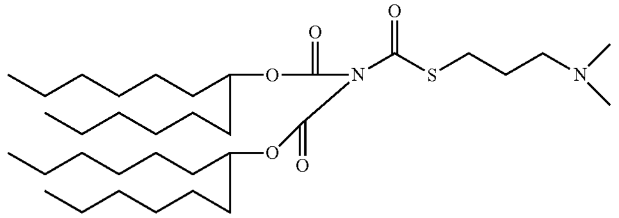 [SMILES: CCCCCCC(CCCCCC)OC(=O)N(C(=O)OC(CCCCCC)CCCCCC)C(=O)SCCCN(C)C]
ATX-B-3
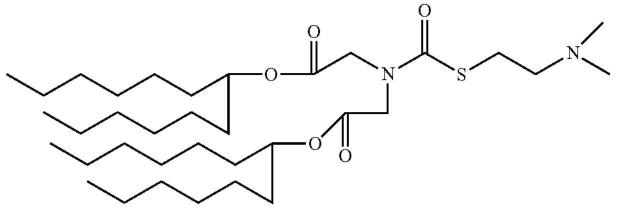 [SMILES: CCCCCCC(CCCCCC)OC(=O)CN(CC(=O)OC(CCCCCC)CCCCCC)C(=O)SCCN(C)C]
ATX-B-4
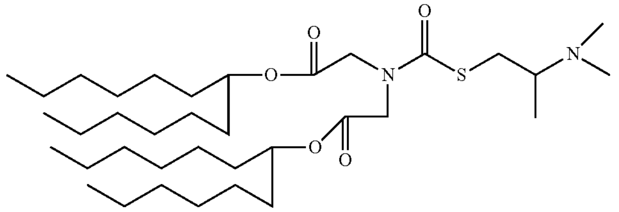 [SMILES: CCCCCCC(CCCCCC)OC(=O)CN(CC(=O)OC(CCCCCC)CCCCCC)C(=O)SCC(C)N(C)C]
ATX-B-5
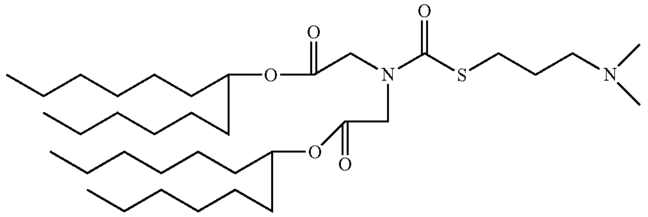 [SMILES: CCCCCCC(CCCCCC)OC(=O)CN(CC(=O)OC(CCCCCC)CCCCCC)C(=O)SCCCN(C)C]
ATX-B-6
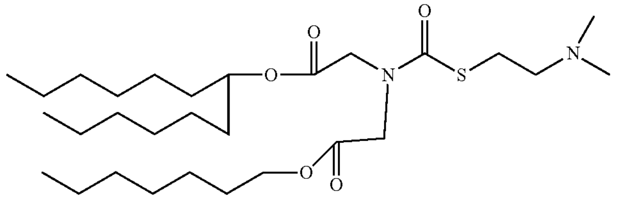 [SMILES: CCCCCCCOC(=O)CN(CC(=O)OC(CCCCCC)CCCCCC)C(=O)SCCN(C)C]
ATX-B-7
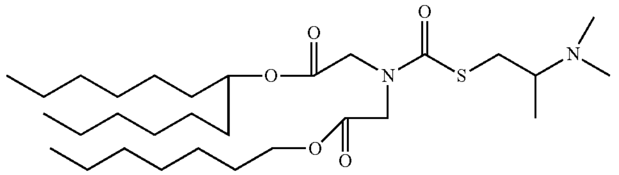 [SMILES: CCCCCCCOC(=O)CN(CC(=O)OC(CCCCCC)CCCCCC)C(=O)SCC(C)N(C)C]
ATX-B-8
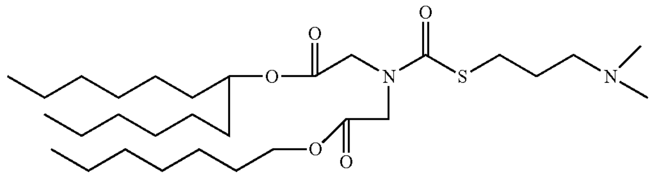 [SMILES: CCCCCCCOC(=O)CN(CC(=O)OC(CCCCCC)CCCCCC)C(=O)SCCCN(C)C]
ATX-B-9

TABLE 13-continued
| | |
|---|---|
| 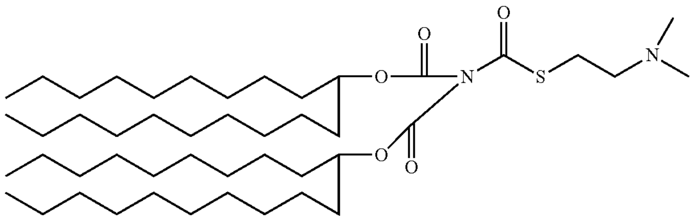 [SMILES: CCCCCCCCCCC(CCCCCCCCC)OC(=O)N(C(=O)OC(CCCCCCCCC)CCCCCCCCCC)C(=O)SCCN(C)C] | ATX-B-10 |
| 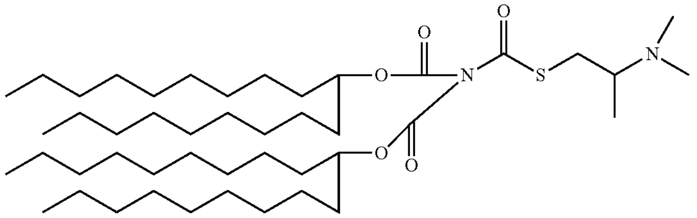 [SMILES: CCCCCCCCCC(CCCCCCCCC)OC(=O)N(C(=O)OC(CCCCCCCCC)CCCCCCCCC)C(=O)SCC(C)N(C)C] | ATX-B-11 |
| 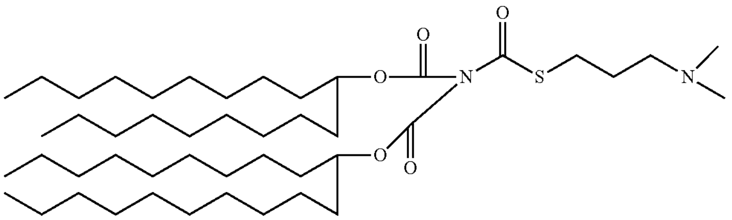 [SMILES: CCCCCCCCCCC(CCCCCCCCC)OC(=O)N(C(=O)OC(CCCCCCCCC)CCCCCCCCC)C(=O)SCCCN(C)C] | ATX-B-12 |
| Compound | ATX-# |
|---|---|
| 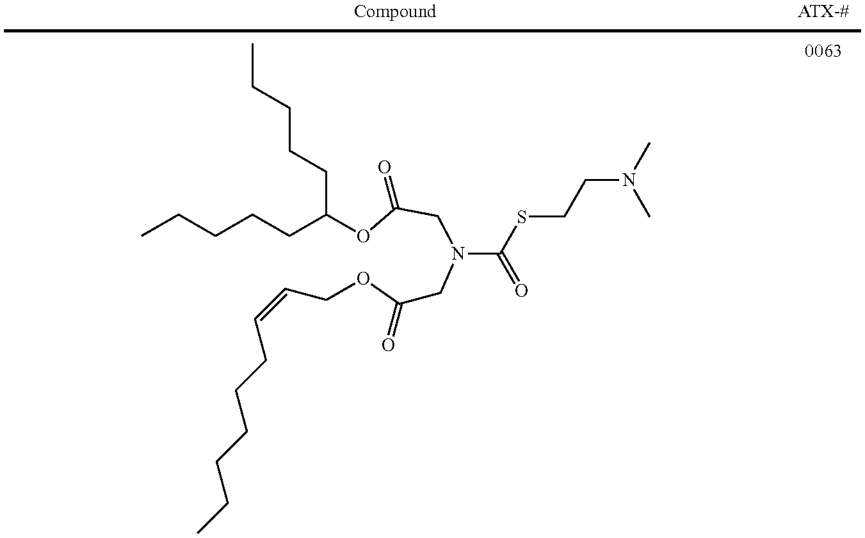 | 0063 |

-continued
| Compound | ATX-# |
|---|---|
| 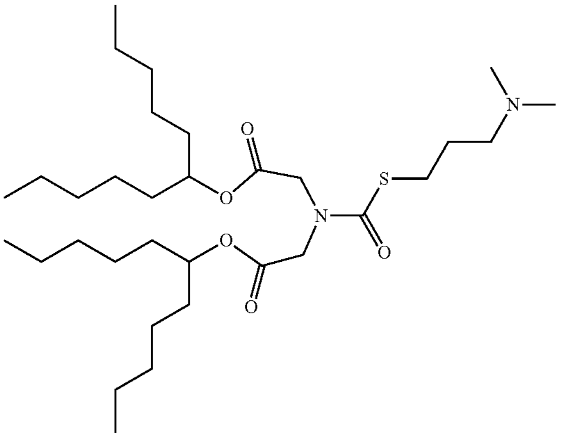 [SMILES: CCCCCC(CCCCC)OC(=O)CN(CC(=O)OC(CCCCC)CCCCC)C(=O)SCCCN(C)C] | 0130 |
| 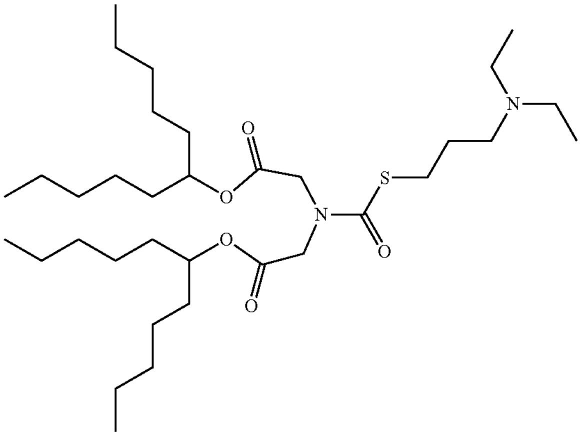 [SMILES: CCCCCC(CCCCC)OC(=O)CN(CC(=O)OC(CCCCC)CCCCC)C(=O)SCCCN(CC)CC] | 0131 |
| 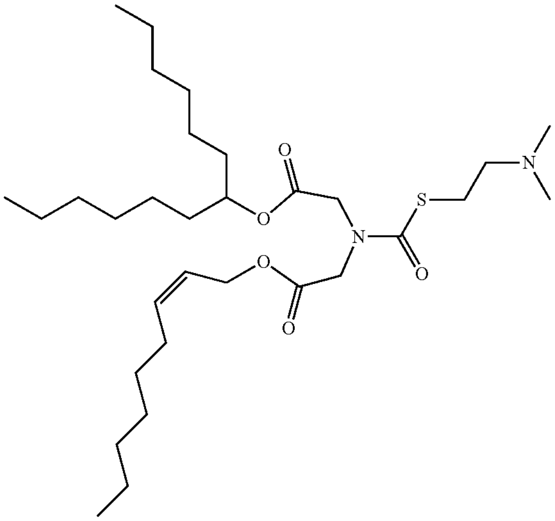 [SMILES: CCCCCC/C=C\COC(=O)CN(CC(=O)OC(CCCCCC)CCCCCC)C(=O)SCCN(C)C] | 0044 |

-continued
| Compound | ATX-# |
|---|---|
| 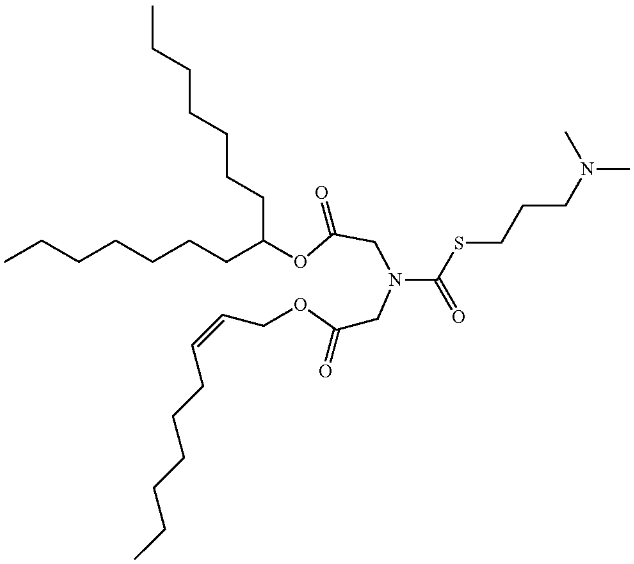 [SMILES: CCCCCC/C=C\COC(=O)CN(CC(=O)OC(CCCCCCC)CCCCCCC)C(=O)SCCCN(C)C] | 0111 |
| 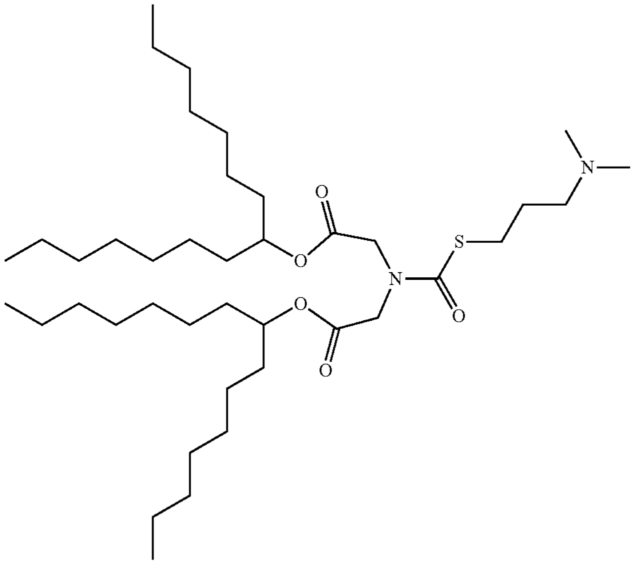 [SMILES: CCCCCCCC(CCCCCCC)OC(=O)CN(CC(=O)OC(CCCCCCC)CCCCCCC)C(=O)SCCCN(C)C] | 0132 |

-continued
| Compound | ATX-# |
| --- | --- |
| 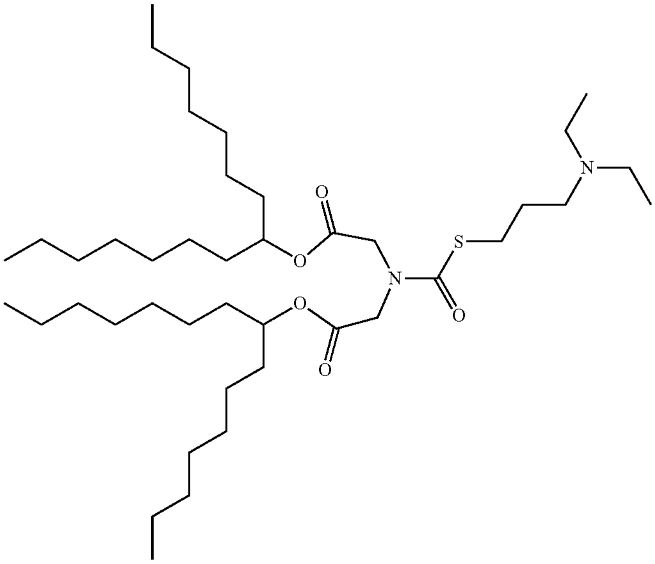 [SMILES: CCCCCCCC(CCCCCCC)OC(=O)CN(CC(=O)OC(CCCCCCC)CCCCCCC)C(=O)SCCCN(CC)CC] | 0134 |
| 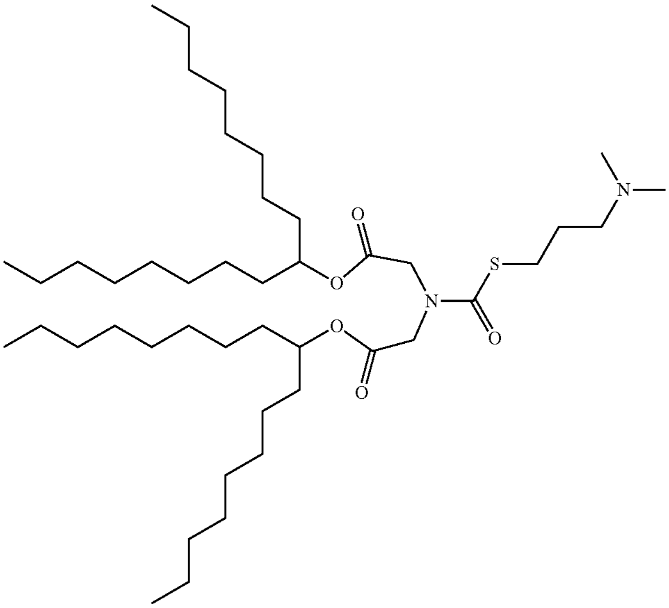 [SMILES: CCCCCCCCC(CCCCCCCC)OC(=O)CN(CC(=O)OC(CCCCCCCC)CCCCCCCC)C(=O)SCCCN(C)C] | 0133 |

-continued
| Compound | ATX-# |
|---|---|
| 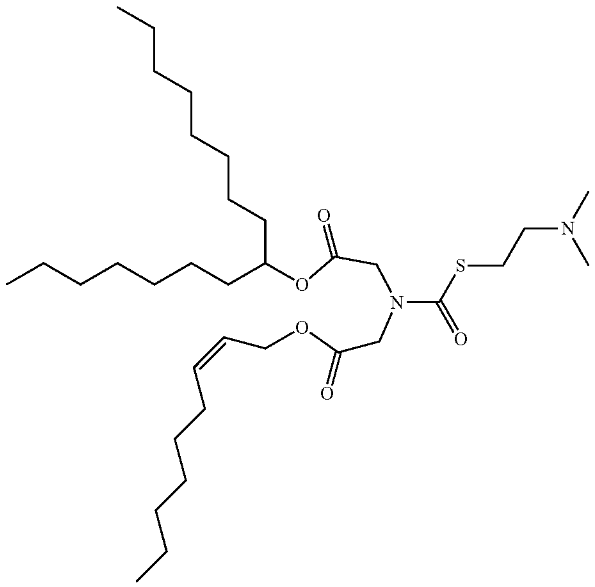 [SMILES: CCCCCC/C=C\COC(=O)CN(CC(=O)OC(CCCCCCC)CCCCCCCC)C(=O)SCCN(C)C] | 0064 |
| 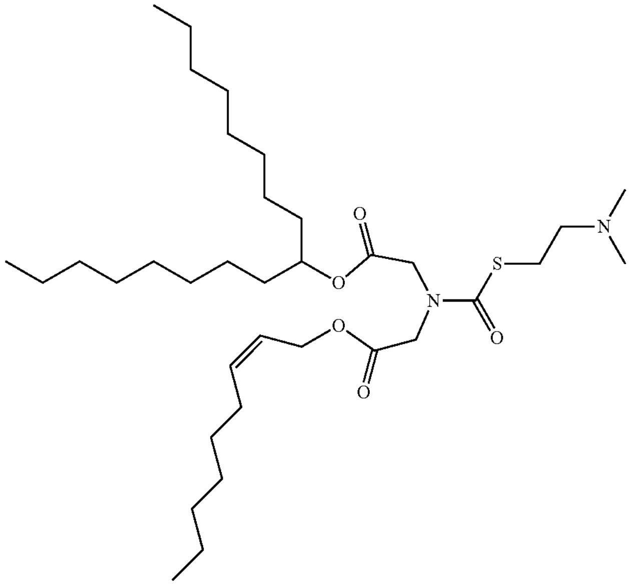 [SMILES: CCCCCC/C=C\COC(=O)CN(CC(=O)OC(CCCCCCCC)CCCCCCCC)C(=O)SCCN(C)C] | 0061 |

-continued
| Compound | ATX-# |
|---|---|
| 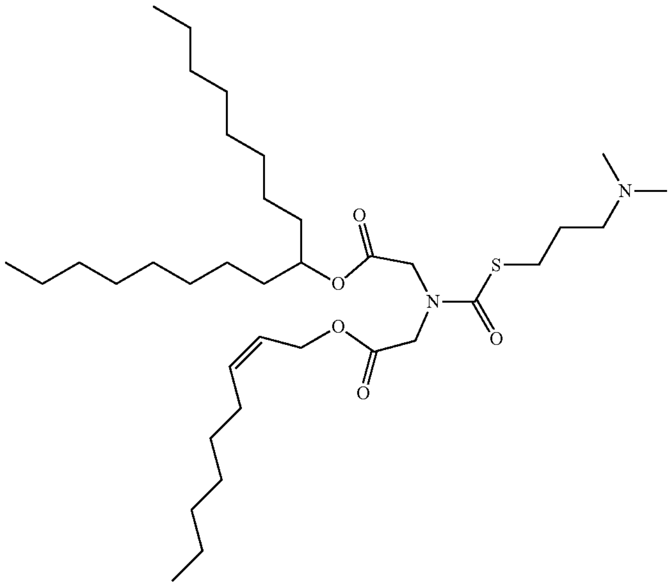 [SMILES: CCCCCC/C=C\COC(=O)CN(CC(=O)OC(CCCCCCCC)CCCCCCCC)C(=O)SCCCN(C)C] | 0100 |
| 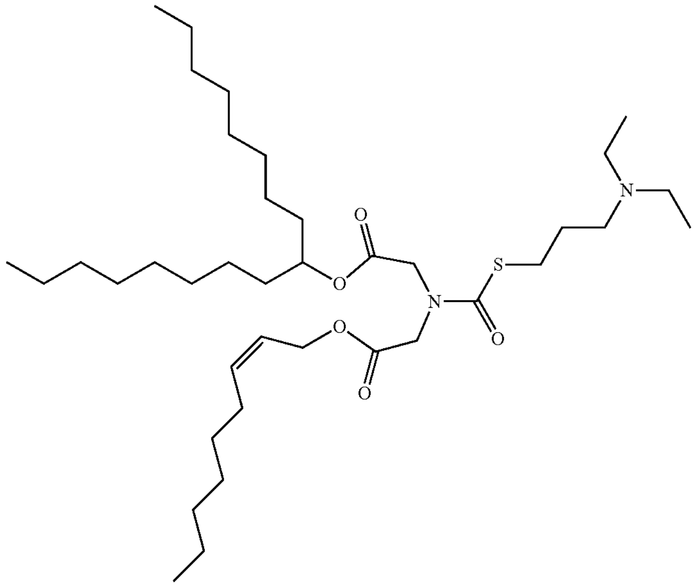 [SMILES: CCCCCC/C=C\COC(=O)CN(CC(=O)OC(CCCCCCCC)CCCCCCCC)C(=O)SCCCN(CC)CC] | 0117 |

-continued
| Compound | ATX-# |
|---|---|
| 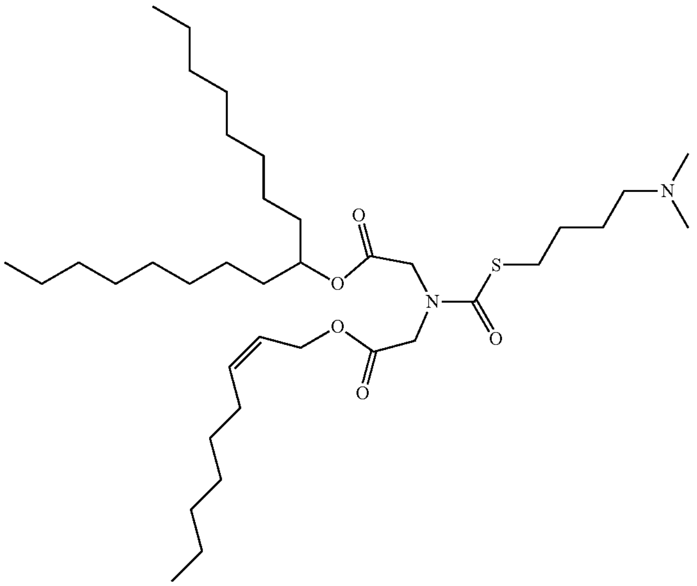 [SMILES: CCCCCC/C=C\COC(=O)CN(CC(=O)OC(CCCCCCCC)CCCCCCCC)C(=O)SCCCCN(C)C] | 0114 |
| 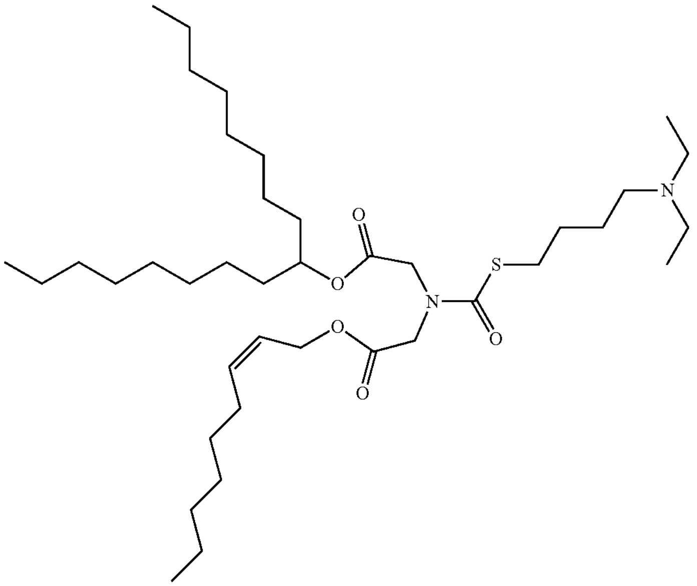 [SMILES: CCCCCC/C=C\COC(=O)CN(CC(=O)OC(CCCCCCCC)CCCCCCCC)C(=O)SCCCCN(CC)CC] | 0115 |

-continued
| Compound | ATX-# |
| --- | --- |
| 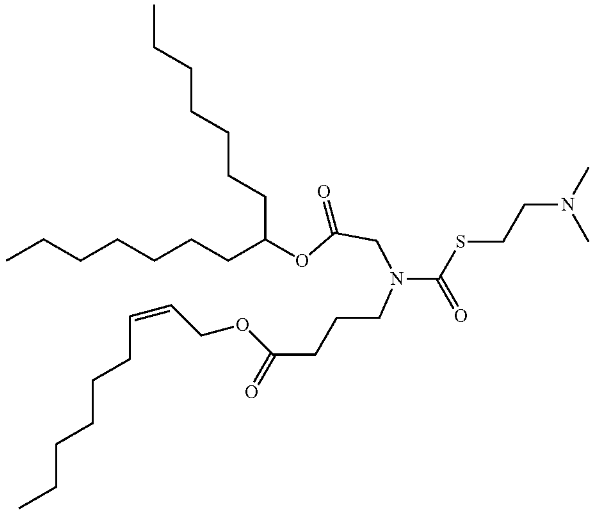 [SMILES: CCCCCC/C=C\COC(=O)CCCN(CC(=O)OC(CCCCCCC)CCCCCCC)C(=O)SCCN(C)C] | 0101 |
| 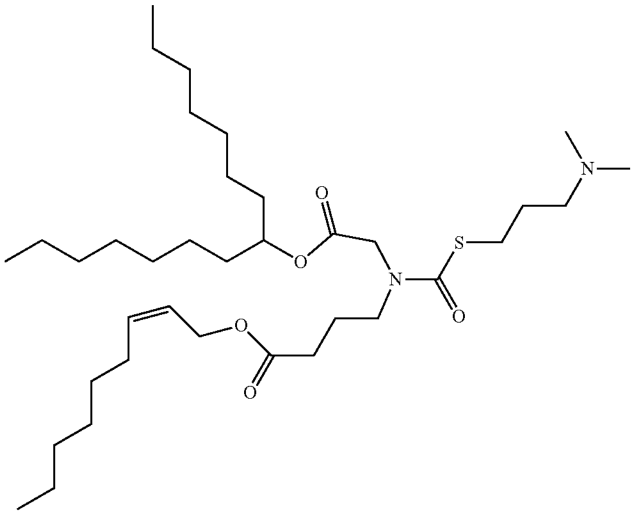 [SMILES: CCCCCC/C=C\COC(=O)CCCN(CC(=O)OC(CCCCCCC)CCCCCCC)C(=O)SCCCN(C)C] | 0106 |
| 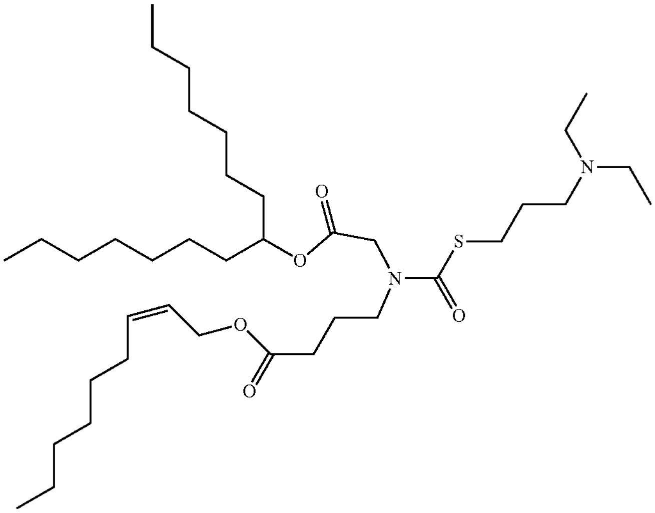 [SMILES: CCCCCC/C=C\COC(=O)CCCN(CC(=O)OC(CCCCCCC)CCCCCCC)C(=O)SCCCN(CC)CC] | 0116 |

-continued
| Compound | ATX-# |
|---|---|
| 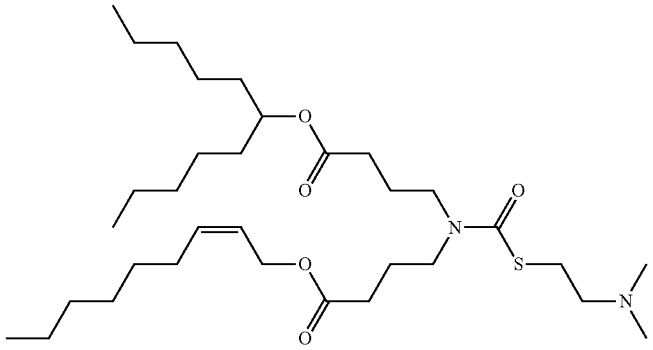 [SMILES: CCCCCC/C=C\COC(=O)CCCN(CCCC(=O)OC(CCCCC)CCCCC)C(=O)SCCN(C)C] | 0043 |
| 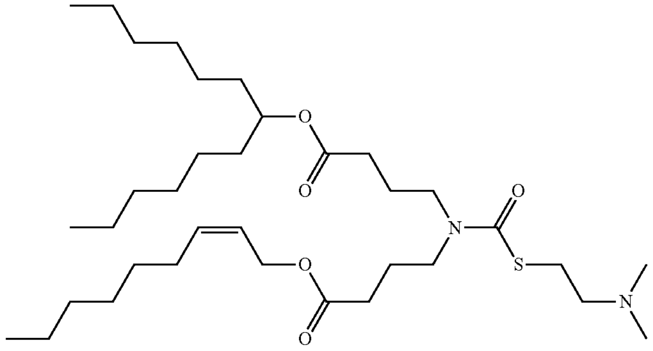 [SMILES: CCCCCC/C=C\COC(=O)CCCN(CCCC(=O)OC(CCCCCC)CCCCCC)C(=O)SCCN(C)C] | 0086 |
| 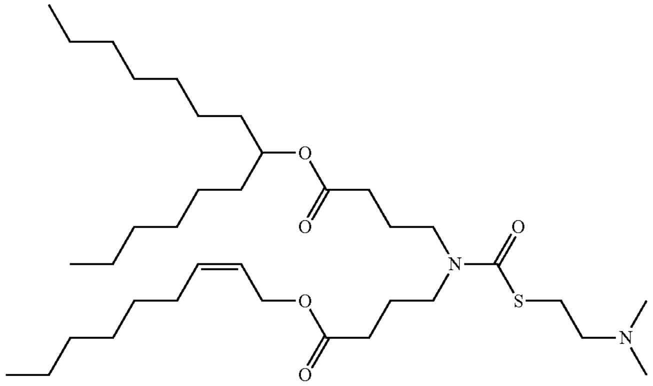 [SMILES: CCCCCC/C=C\COC(=O)CCCN(CCCC(=O)OC(CCCCCC)CCCCCCC)C(=O)SCCN(C)C] | 0058 |
| 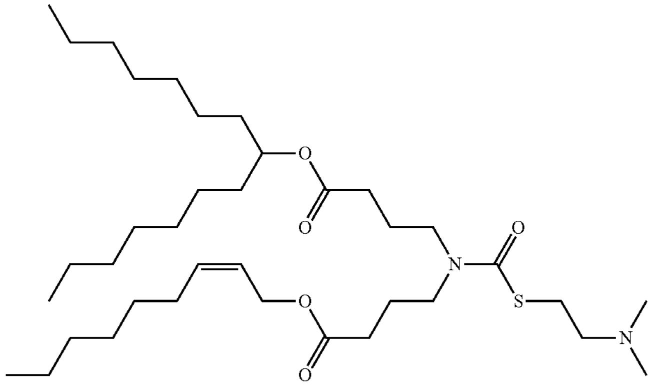 [SMILES: CCCCCC/C=C\COC(=O)CCCN(CCCC(=O)OC(CCCCCCC)CCCCCCC)C(=O)SCCN(C)C] | 0081 |

-continued
| Compound | ATX-# |
| --- | --- |
| 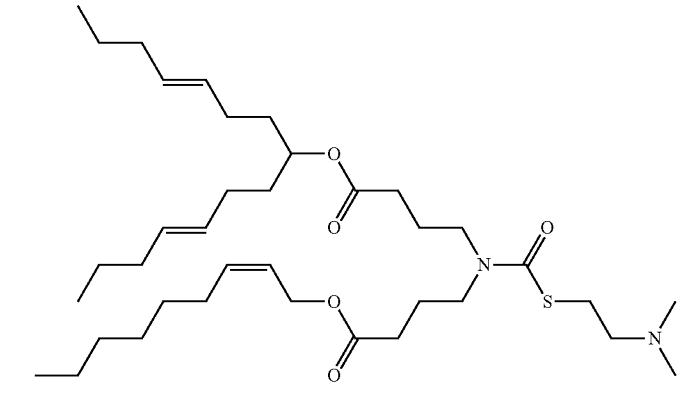 [SMILES: CCC/C=C/CCC(CC/C=C/CCC)OC(=O)CCCN(CCCC(=O)OC/C=C\CCCCCC)C(=O)SCCN(C)C] | 0123 |
| 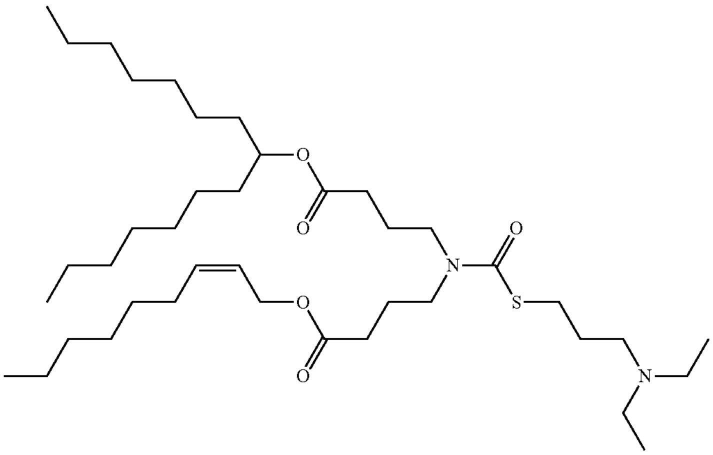 [SMILES: CCCCCC/C=C\COC(=O)CCCN(CCCC(=O)OC(CCCCCCC)CCCCCCC)C(=O)SCCCN(CC)CC] | 0122 |
| 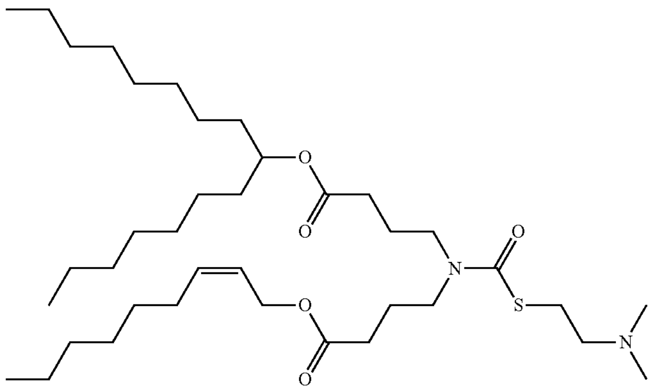 [SMILES: CCCCCC/C=C\COC(=O)CCCN(CCCC(=O)OC(CCCCCCC)CCCCCCCC)C(=O)SCCN(C)C] | 0057 |

-continued
| Compound | ATX-# |
| --- | --- |
| 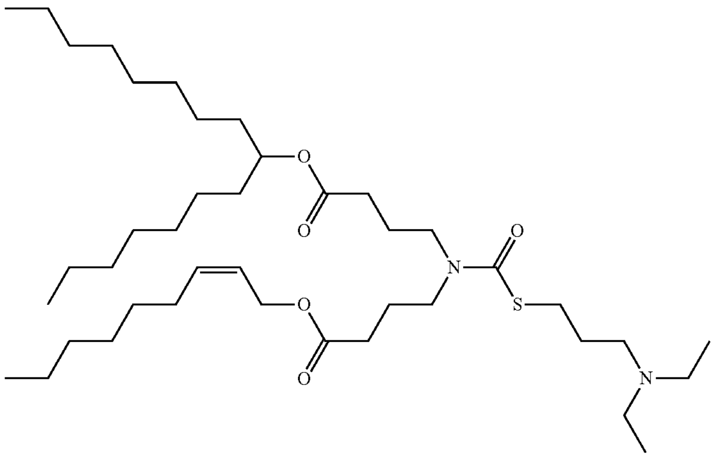 [SMILES: CCCCCC/C=C\COC(=O)CCCN(CCCC(=O)OC(CCCCCCC)CCCCCCCC)C(=O)SCCCN(CC)CC] | 0088 |
| 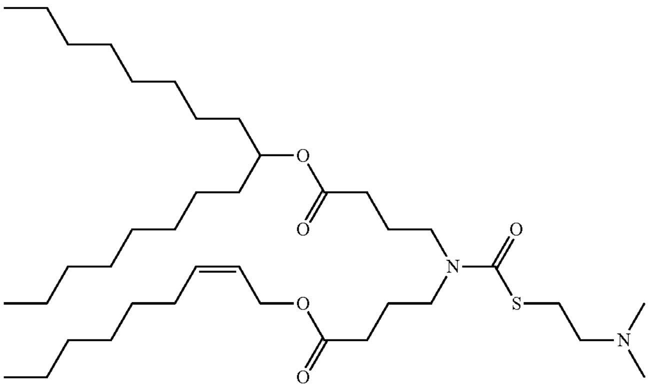 [SMILES: CCCCCC/C=C\COC(=O)CCCN(CCCC(=O)OC(CCCCCCCC)CCCCCCCC)C(=O)SCCN(C)C] | 0087 |
| 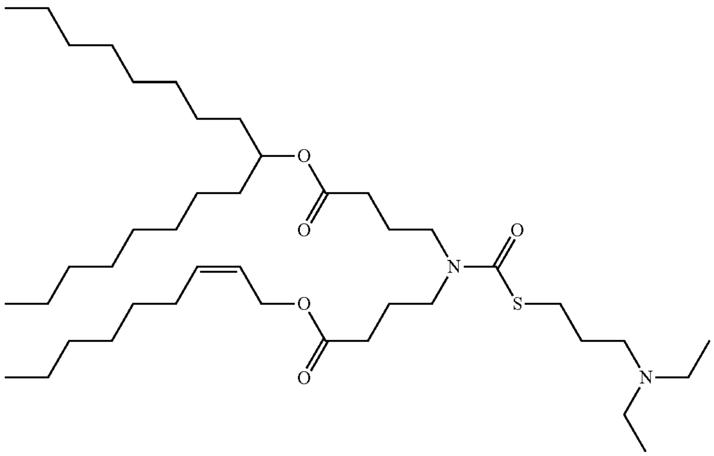 [SMILES: CCCCCC/C=C\COC(=O)CCCN(CCCC(=O)OC(CCCCCCCC)CCCCCCCC)C(=O)SCCCN(CC)CC] | 0124 |

-continued
| Compound | ATX-# |
|---|---|
| 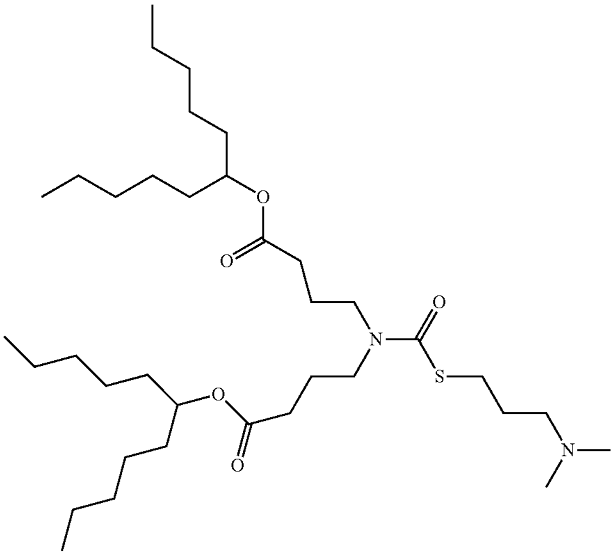 [SMILES: CCCCCC(CCCCC)OC(=O)CCCN(CCCC(=O)OC(CCCCC)CCCCC)C(=O)SCCCN(C)C] | 0128 |
| 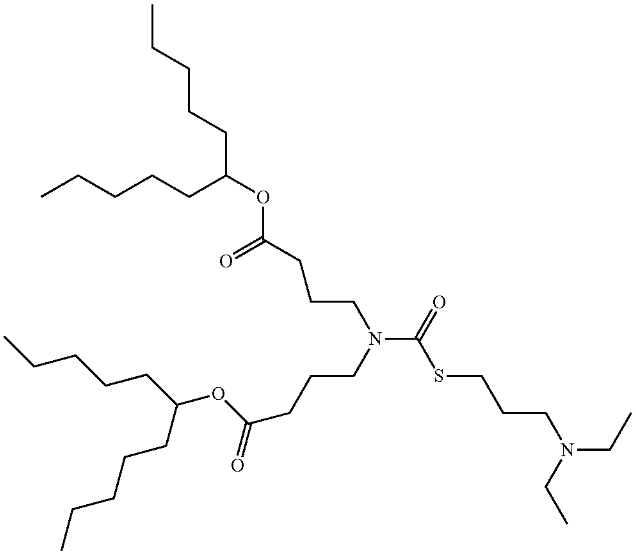 [SMILES: CCCCCC(CCCCC)OC(=O)CCCN(CCCC(=O)OC(CCCCC)CCCCC)C(=O)SCCCN(CC)CC] | 0127 |

-continued
| Compound | ATX-# |
| --- | --- |
| 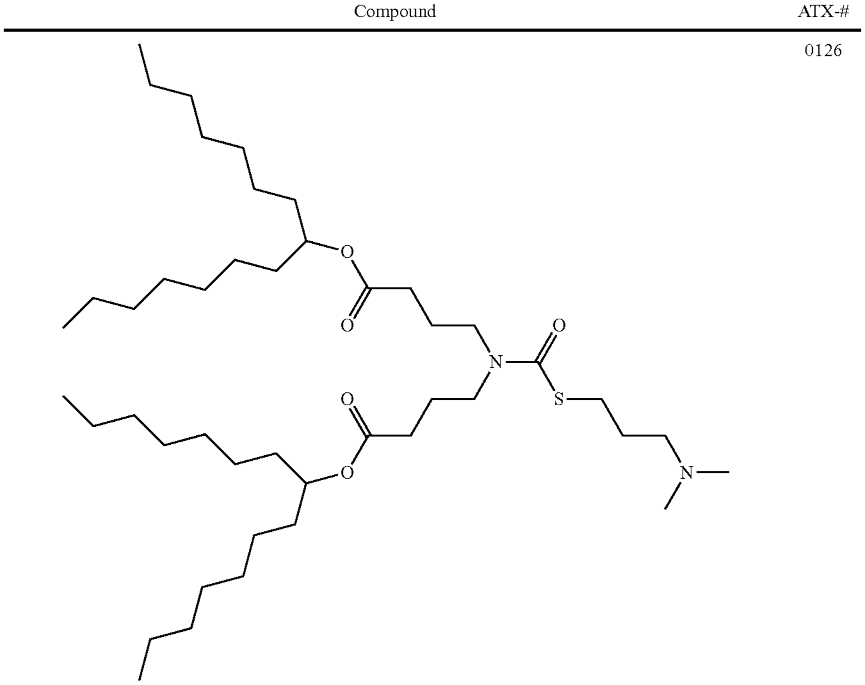 | 0126 |
| 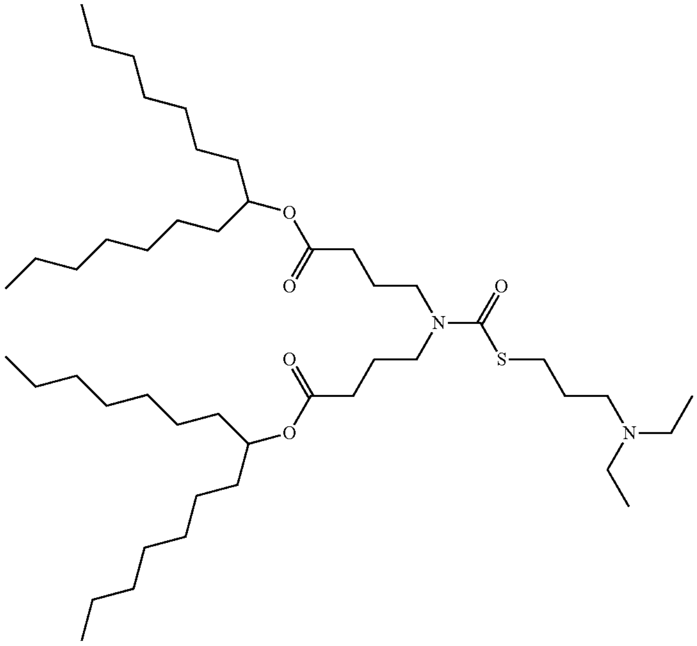 [SMILES: CCCCCCCC(CCCCCCC)OC(=O)CCCN(CCCC(=O)OC(CCCCCCC)CCCCCCC)C(=O)SCCCN(CC)CC] | 0129 |

-continued
| Compound | ATX-# |
|---|---|
| 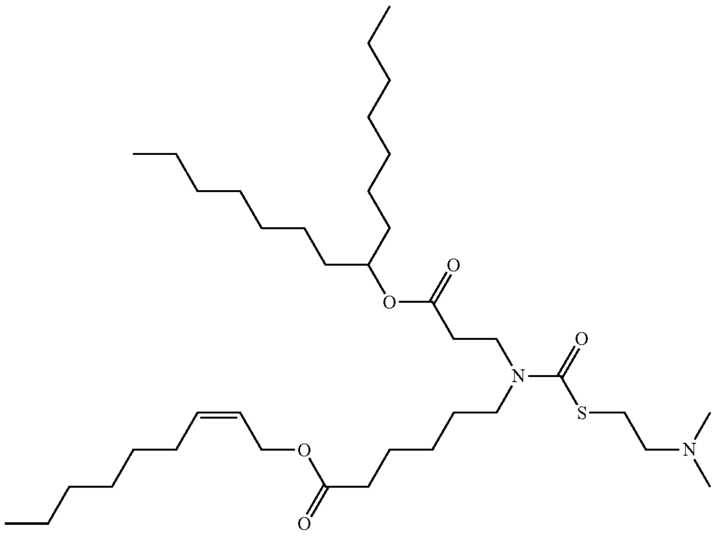 [SMILES: CCCCCC/C=C\COC(=O)CCCCCN(CCC(=O)OC(CCCCCCC)CCCCCCC)C(=O)SCCN(C)C] | 0082 |
| 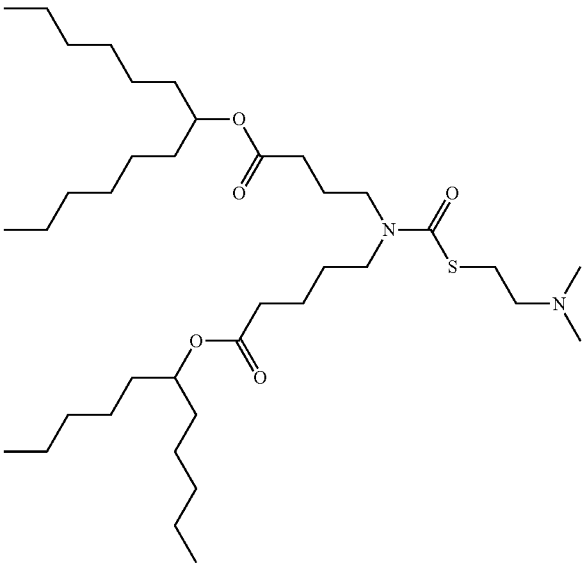 [SMILES: CCCCCCC(CCCCCC)OC(=O)CCCN(CCCCC(=O)OC(CCCCC)CCCCC)C(=O)SCCN(C)C] | 0085 |
| 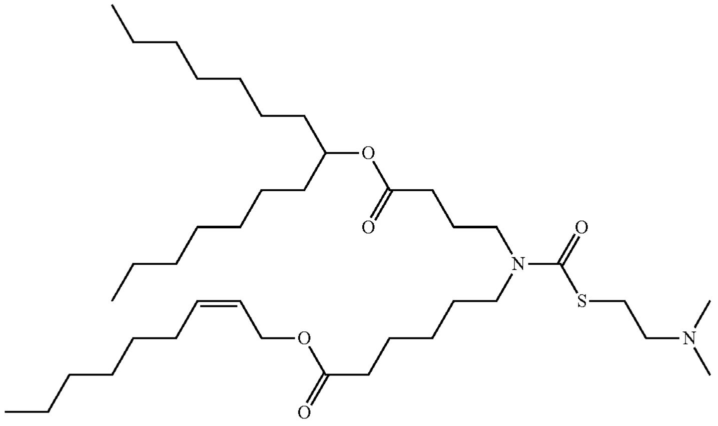 [SMILES: CCCCCC/C=C\COC(=O)CCCCCN(CCCC(=O)OC(CCCCCCC)CCCCCCC)C(=O)SCCN(C)C] | 0083 |

-continued
| Compound | ATX-# |
|---|---|
| 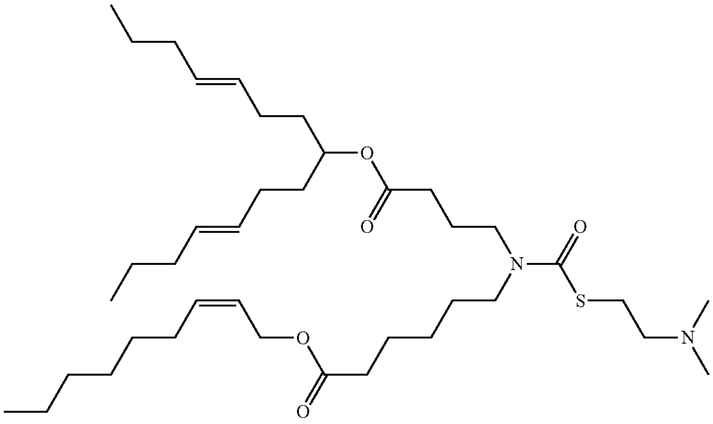 [SMILES: CCC/C=C/CCC(CC/C=C/CCC)OC(=O)CCCN(CCCCCC(=O)OC/C=C\CCCCCC)C(=O)SCCN(C)C] | 0121 |
| 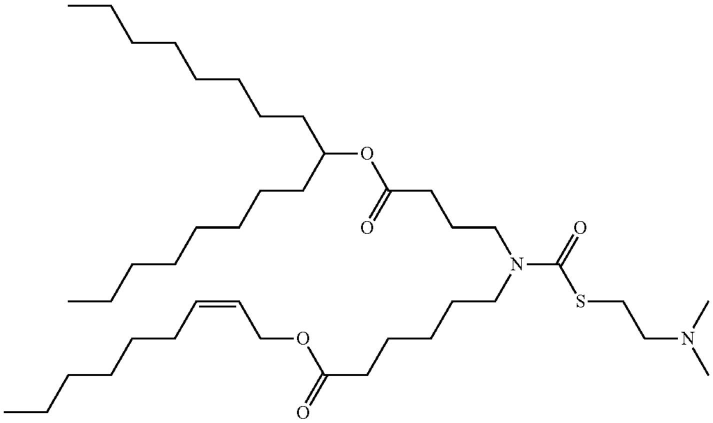 [SMILES: CCCCCC/C=C\COC(=O)CCCCCN(CCCC(=O)OC(CCCCCCCC)CCCCCCCC)C(=O)SCCN(C)C] | 0091 |
| 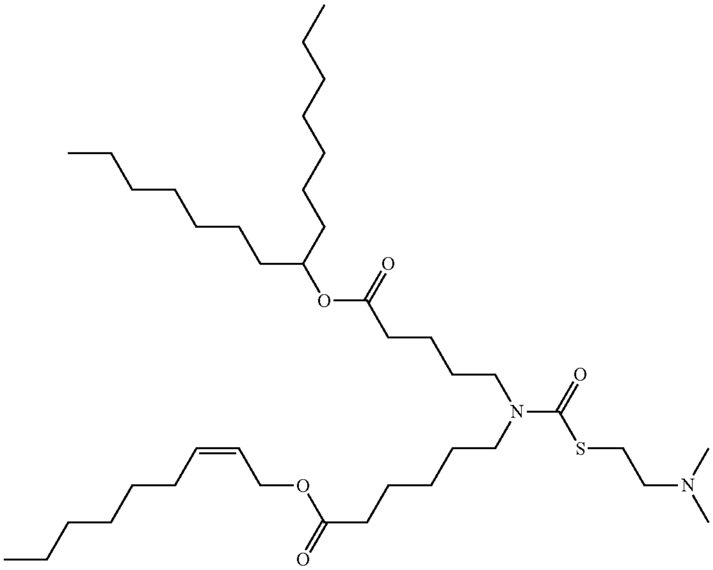 [SMILES: CCCCCC/C=C\COC(=O)CCCCCN(CCCCC(=O)OC(CCCCCCC)CCCCCCC)C(=O)SCCN(C)C] | 0102 |

-continued
| Compound | ATX-# |
| --- | --- |
| 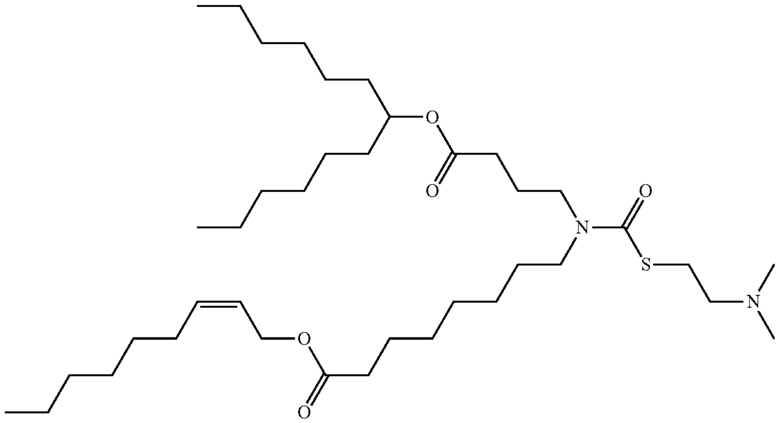 [SMILES: CCCCCC/C=C\COC(=O)CCCCCCCN(CCCC(=O)OC(CCCCCC)CCCCCC)C(=O)SCCN(C)C] | 0098 |
| 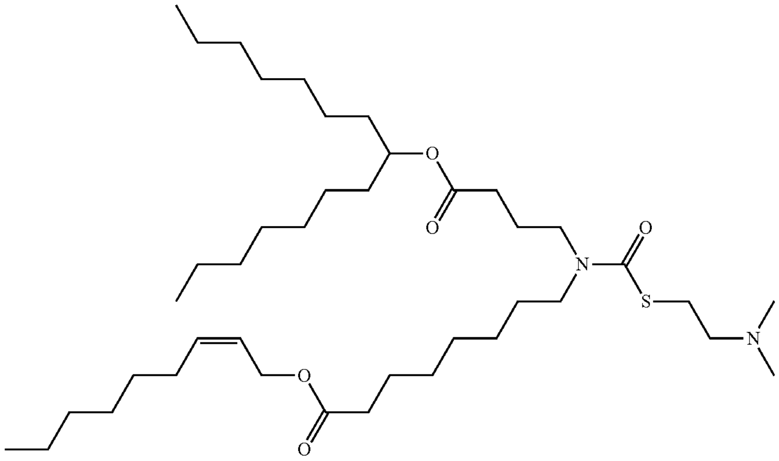 [SMILES: CCCCCC/C=C\COC(=O)CCCCCCCN(CCCC(=O)OC(CCCCCCC)CCCCCCC)C(=O)SCCN(C)C] | 0092 |
| 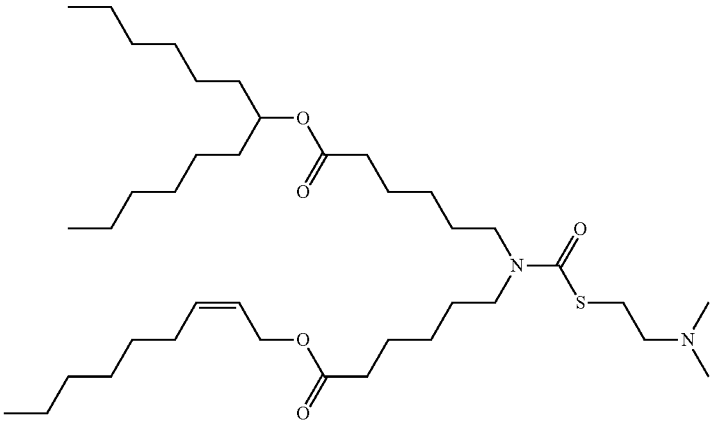 [SMILES: CCCCCC/C=C\COC(=O)CCCCCN(CCCCCC(=O)OC(CCCCCC)CCCCCC)C(=O)SCCN(C)C] | 0084 |

-continued
| Compound | ATX-# |
| --- | --- |
| 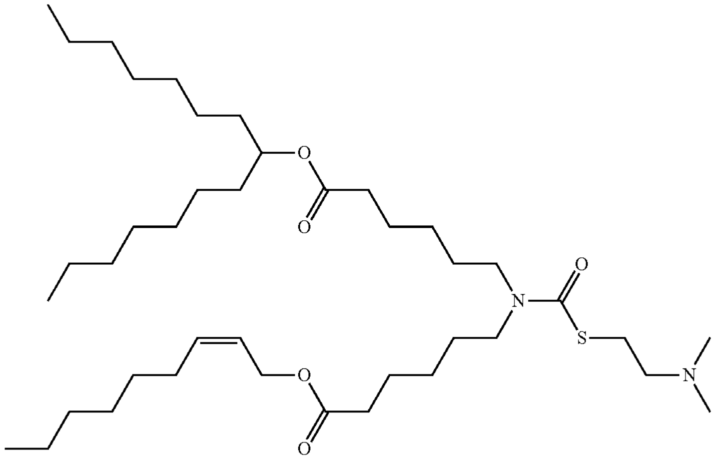 [SMILES: CCCCCC/C=C\COC(=O)CCCCCN(CCCCCC(=O)OC(CCCCCCC)CCCCCCC)C(=O)SCCN(C)C] | 0095 |
| 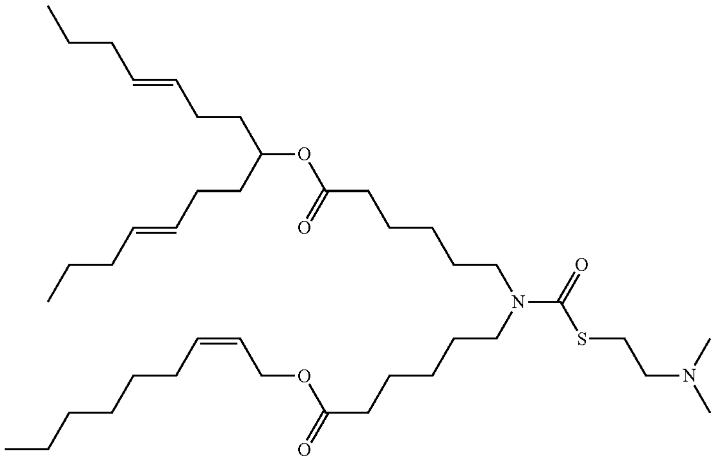 [SMILES: CCC/C=C/CCC(CC/C=C/CCC)OC(=O)CCCCCN(CCCCCC(=O)OC/C=C\CCCCCC)C(=O)SCCN(C)C] | 0125 |
| 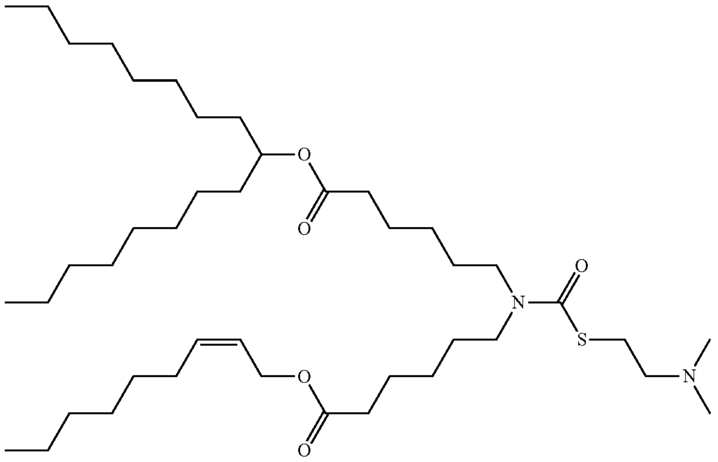 [SMILES: CCCCCC/C=C\COC(=O)CCCCCN(CCCCCC(=O)OC(CCCCCCCC)CCCCCCCC)C(=O)SCCN(C)C] | 0094 |

-continued
| Compound | ATX-# |
| --- | --- |
| 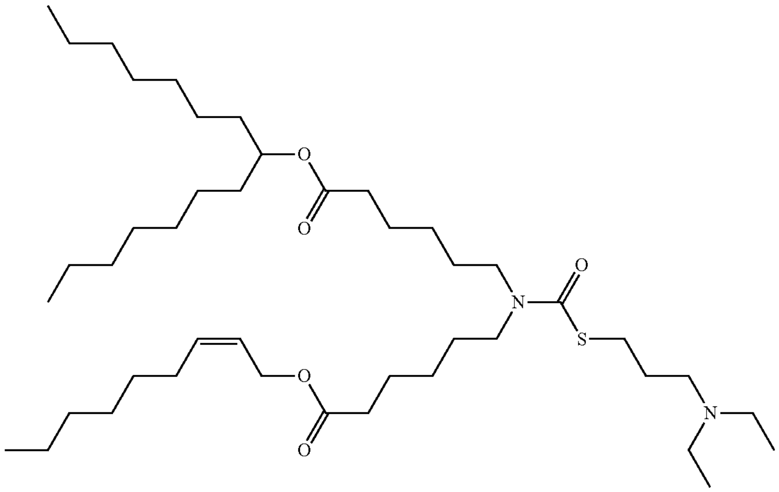 [SMILES: CCCCCC/C=C\COC(=O)CCCCCN(CCCCCC(=O)OC(CCCCCCC)CCCCCCC)C(=O)SCCCN(CC)CC] | 0109 |
| 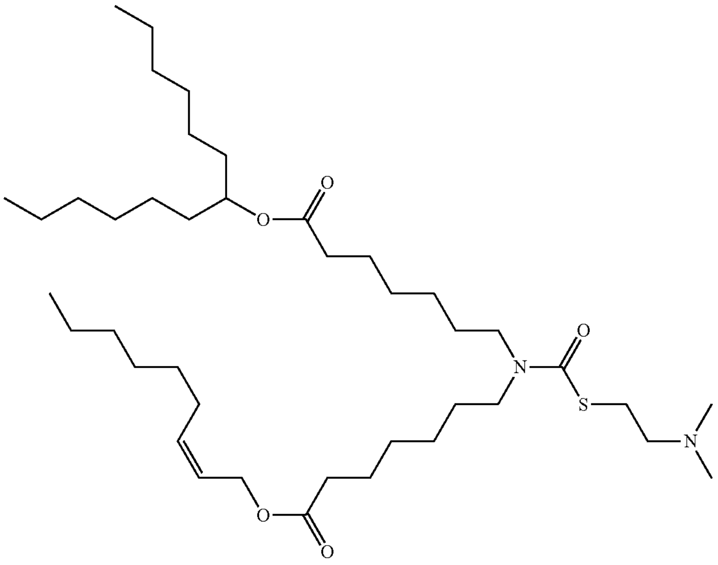 [SMILES: CCCCCC/C=C\COC(=O)CCCCCCN(CCCCCCC(=O)OC(CCCCCC)CCCCCC)C(=O)SCCN(C)C] | 0110 |

-continued
| Compound | ATX-# |
|---|---|
| 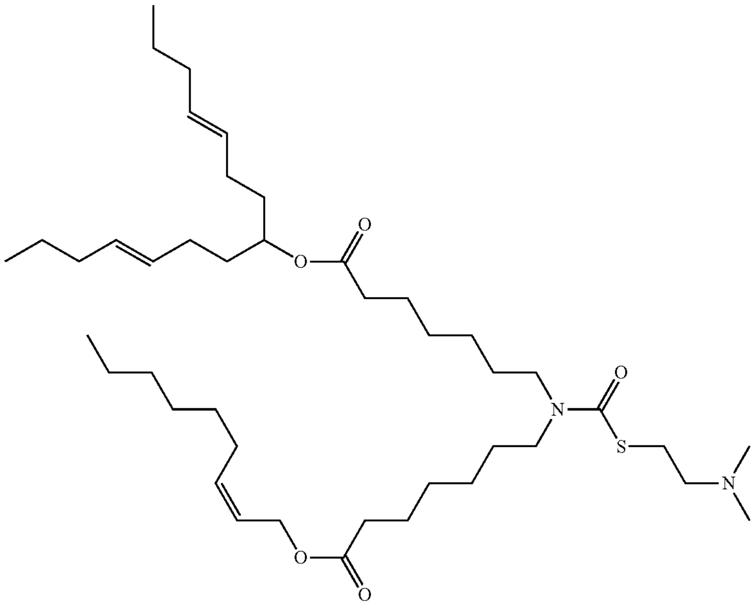 [SMILES: CCC/C=C/CCC(CC/C=C/CCC)OC(=O)CCCCCCN(CCCCCCC(=O)OC/C=C\CCCCCC)C(=O)SCCN(C)C] | 0118 |
| 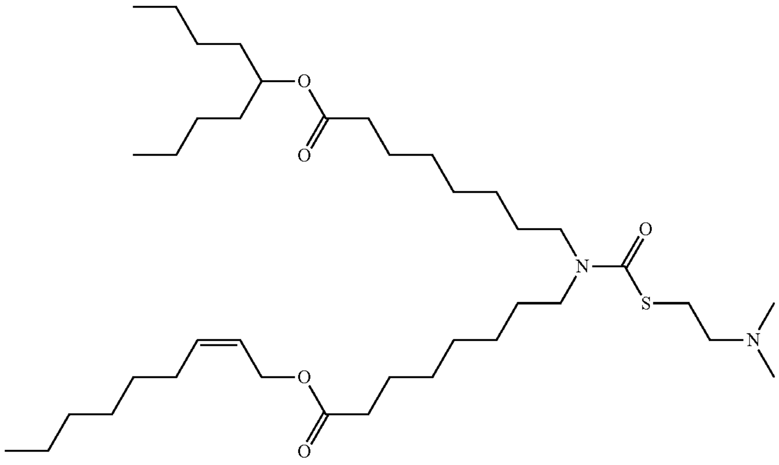 [SMILES: CCCCCC/C=C\COC(=O)CCCCCCCN(CCCCCCCC(=O)OC(CCCC)CCCC)C(=O)SCCN(C)C] | 0108 |
| 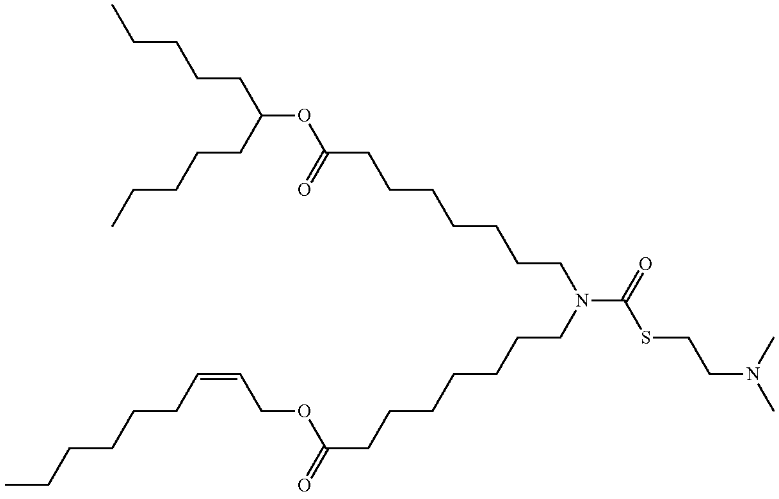 [SMILES: CCCCCC/C=C\COC(=O)CCCCCCCN(CCCCCCCC(=O)OC(CCCCC)CCCCC)C(=O)SCCN(C)C] | 0107 |

-continued
| Compound | ATX-# |
| --- | --- |
| 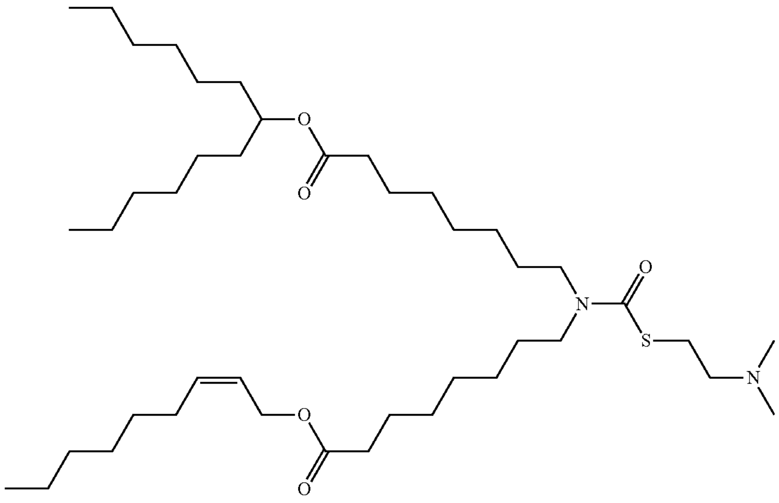 [SMILES: CCCCCC/C=C\COC(=O)CCCCCCCN(CCCCCCCC(=O)OC(CCCCCC)CCCCCC)C(=O)SCCN(C)C] | 0093 |
| 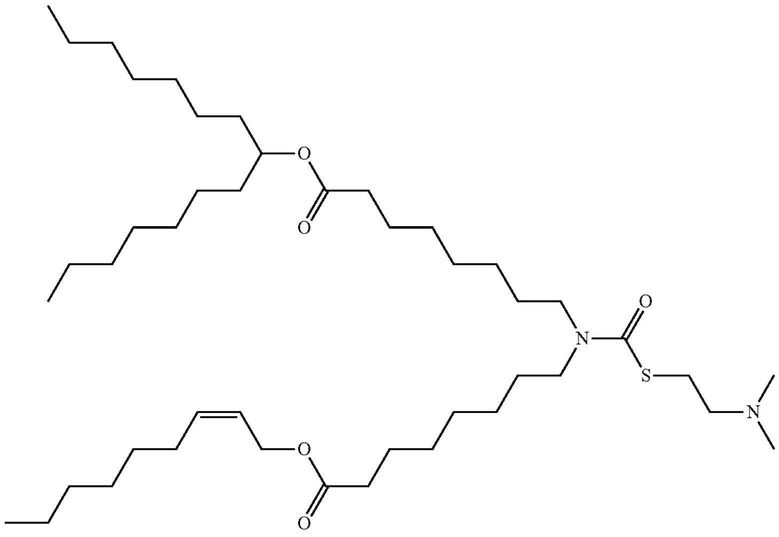 [SMILES: CCCCCC/C=C\COC(=O)CCCCCCCN(CCCCCCCC(=O)OC(CCCCCCC)CCCCCCC)C(=O)SCCN(C)C] | 0097 |
| 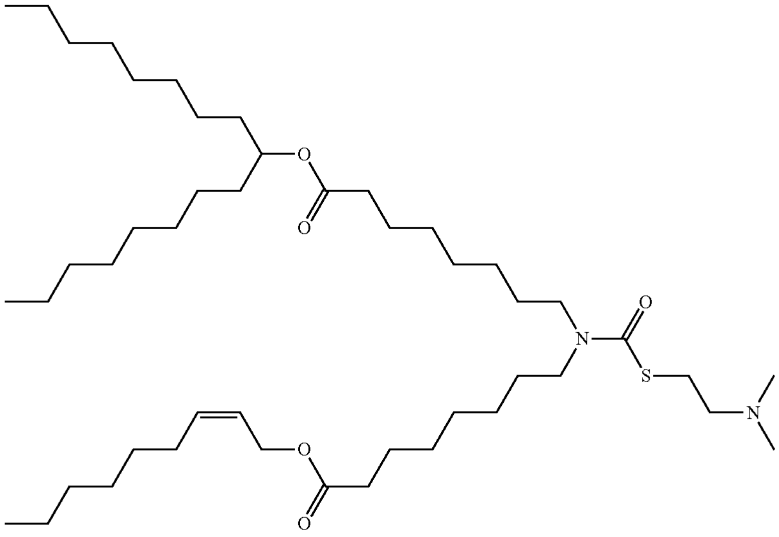 [SMILES: CCCCCC/C=C\COC(=O)CCCCCCCN(CCCCCCCC(=O)OC(CCCCCCCC)CCCCCCCC)C(=O)SCCN(C)C] | 0096 |

TABLE 15
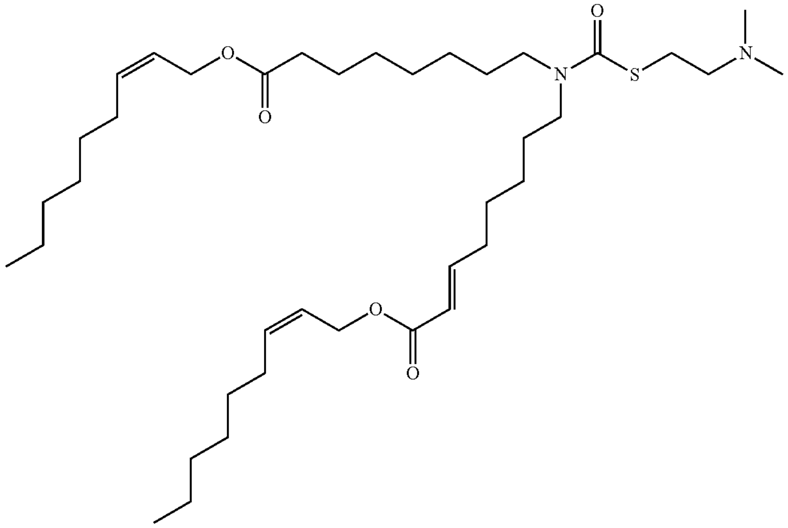 [SMILES: CCCCCC/C=C\COC(=O)/C=C/CCCCCN(CCCCCCCC(=O)OC/C=C\CCCCCC)C(=O)SCCN(C)C]
11
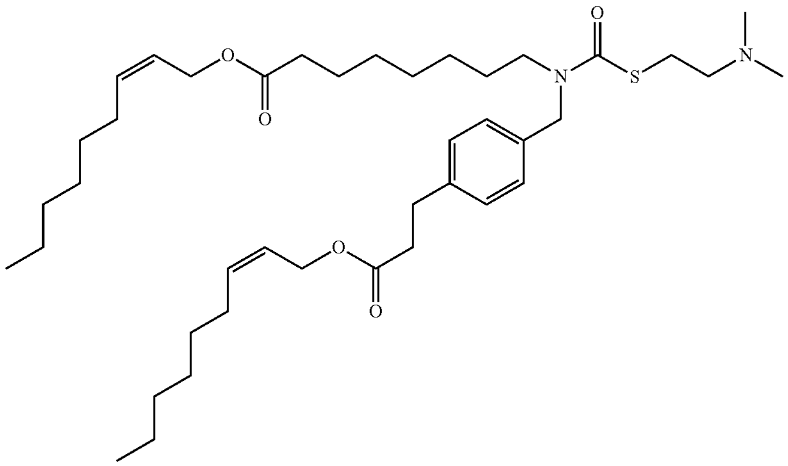 [SMILES: CCCCCC/C=C\COC(=O)CCCCCCCN(Cc1ccc(CCC(=O)OC/C=C\CCCCCC)cc1)C(=O)SCCN(C)C]
13
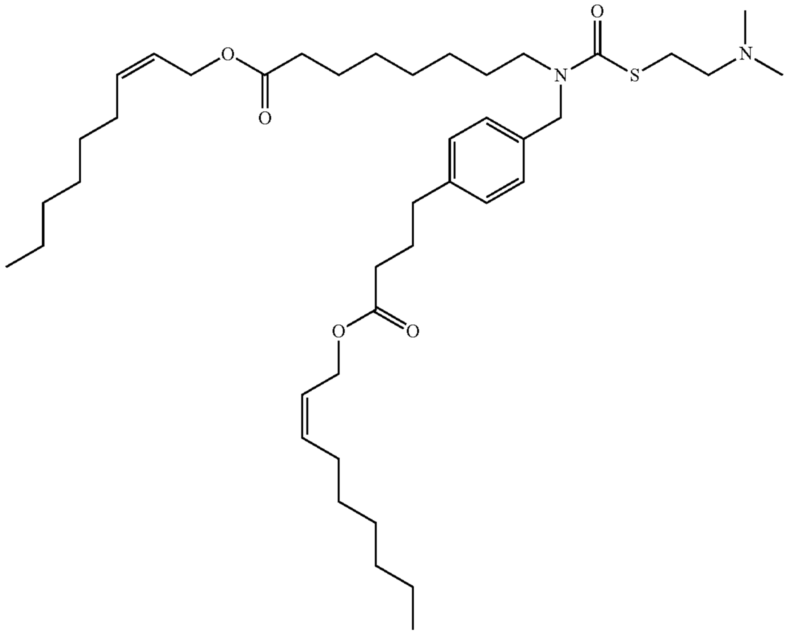 [SMILES: CCCCCC/C=C\COC(=O)CCCCCCCN(Cc1ccc(CCCC(=O)OC/C=C\CCCCCC)cc1)C(=O)SCCN(C)C]
14

TABLE 15-continued
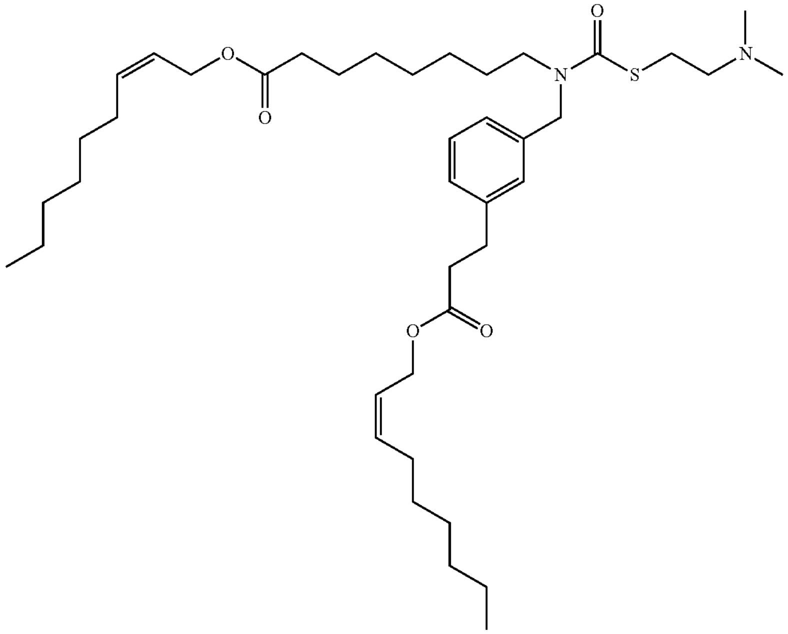 [SMILES: CCCCCC/C=C\COC(=O)CCCCCCCN(Cc1cccc(CCC(=O)OC/C=C\CCCCCC)c1)C(=O)SCCN(C)C]
15
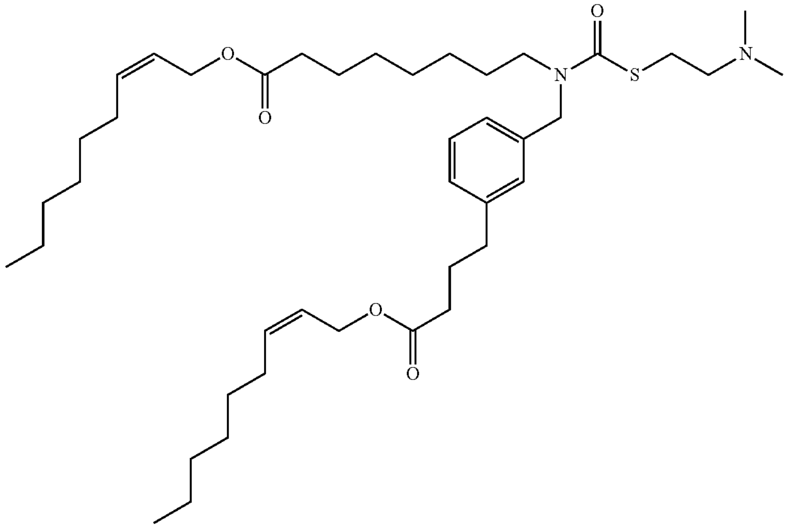 [SMILES: CCCCCC/C=C\COC(=O)CCCCCCCN(Cc1cccc(CCCC(=O)OC/C=C\CCCCCC)c1)C(=O)SCCN(C)C]
16
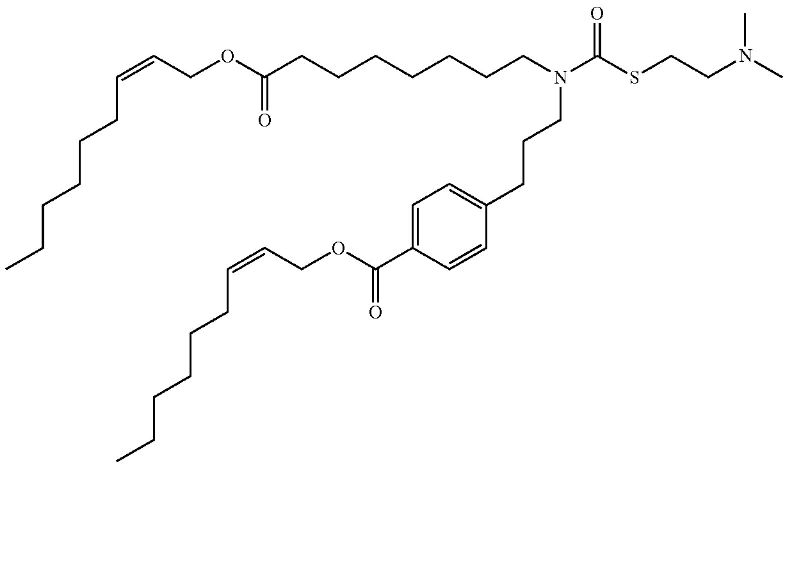 [SMILES: CCCCCC/C=C\COC(=O)CCCCCCCN(CCCc1ccc(C(=O)OC/C=C\CCCCCC)cc1)C(=O)SCCN(C)C]
17

TABLE 15-continued
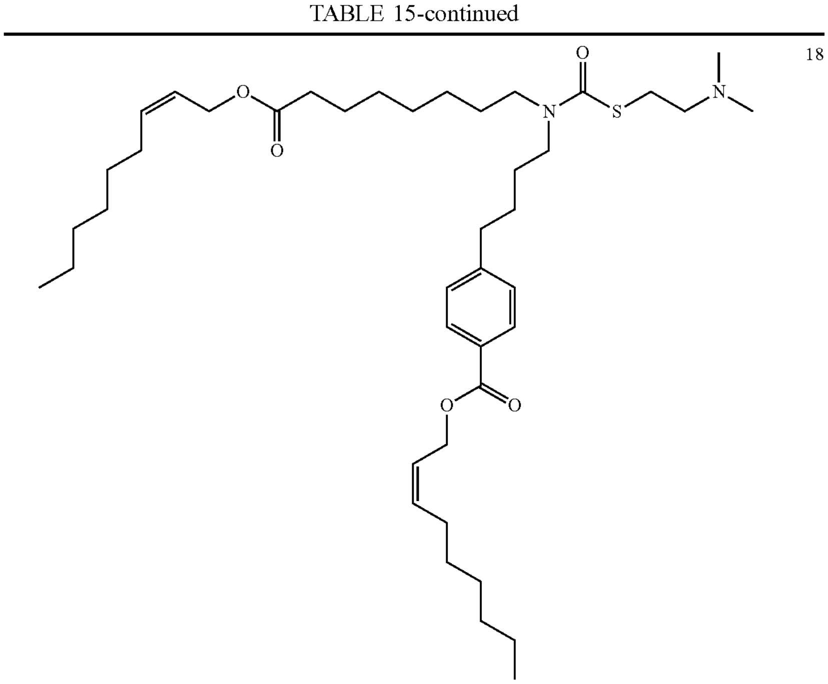
18
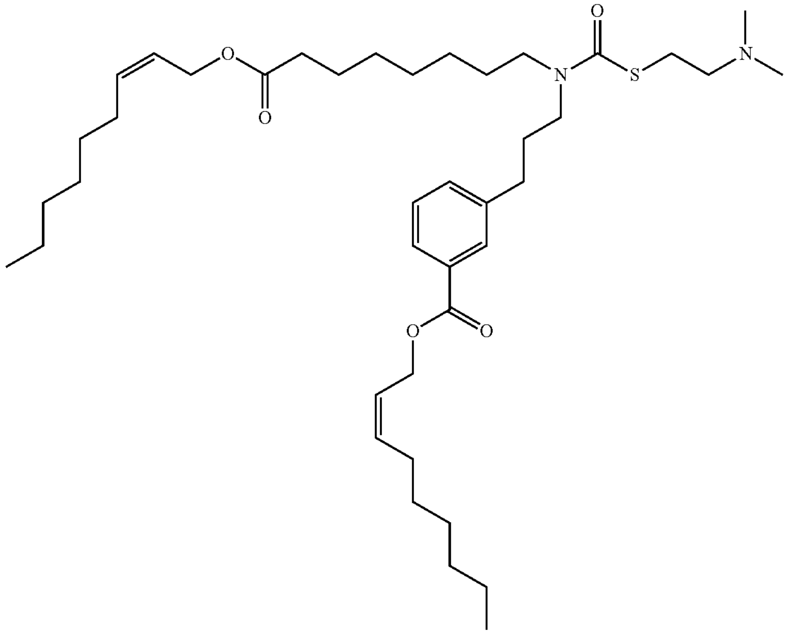 [SMILES: CCCCCC/C=C\COC(=O)CCCCCCCN(CCCc1cccc(C(=O)OC/C=C\CCCCCC)c1)C(=O)SCCN(C)C]
19

TABLE 15-continued
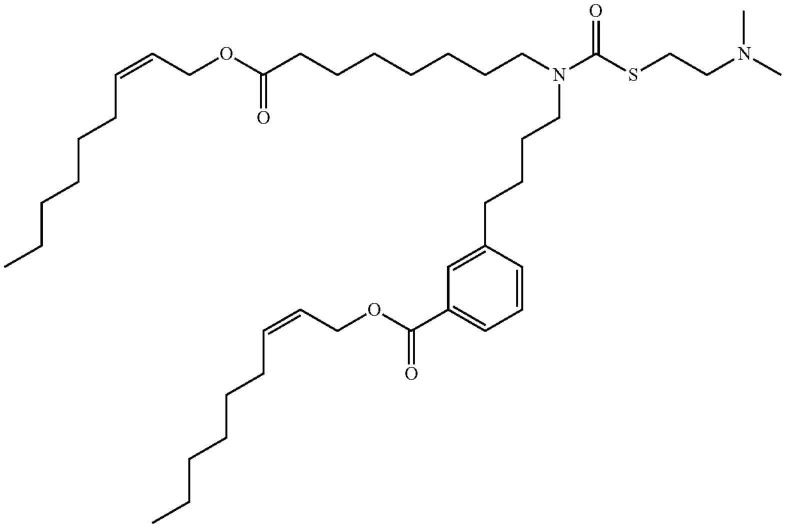 [SMILES: CCCCCC/C=C\COC(=O)CCCCCCCN(CCCCc1cccc(C(=O)OC/C=C\CCCCCC)c1)C(=O)SCCN(C)C]
In some embodiments, an ionizable lipid is as described in international patent application PCT/US2019/015913. In some embodiments, an ionizable lipid is chosen from the following:
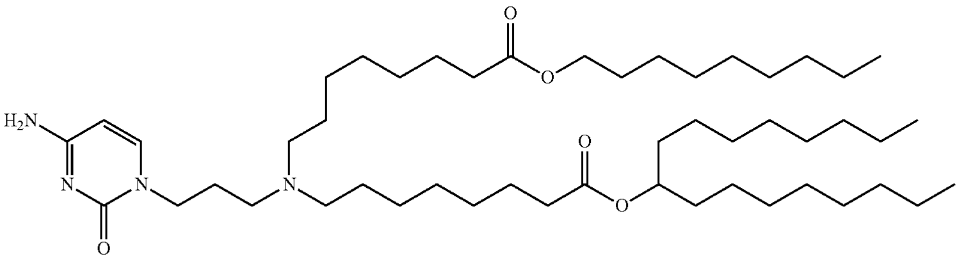
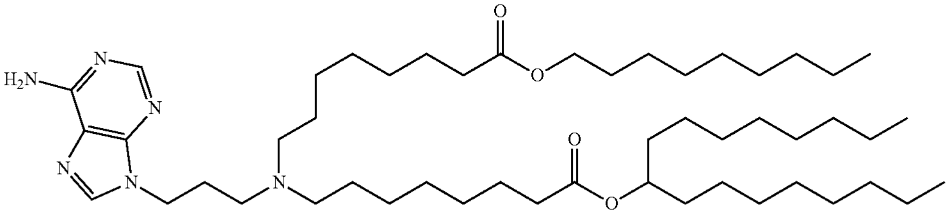
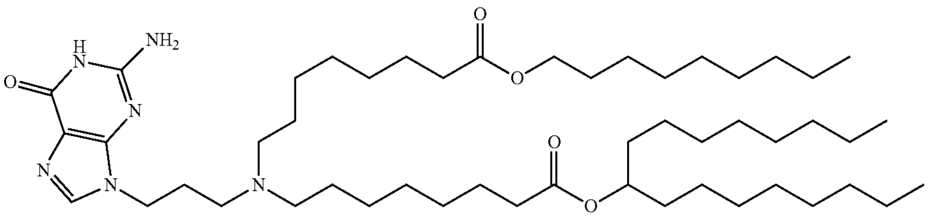
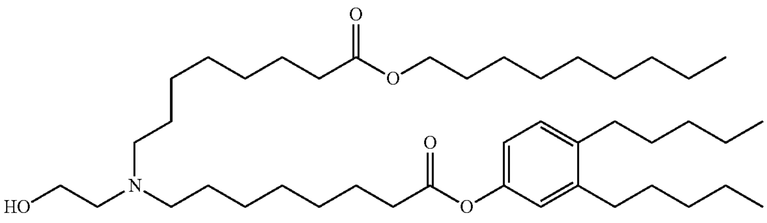

-continued
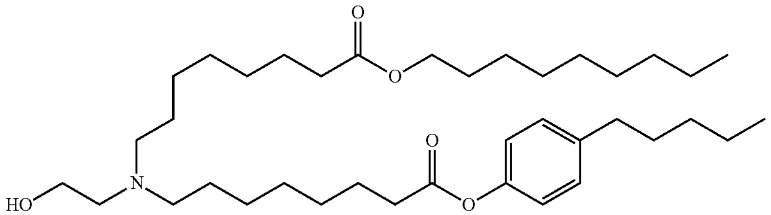
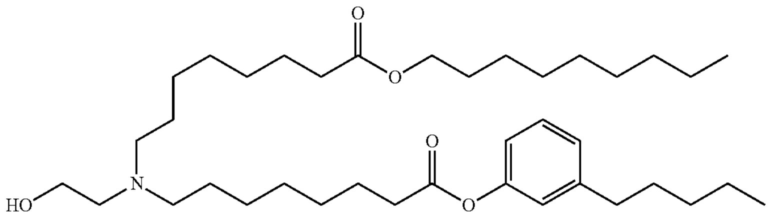
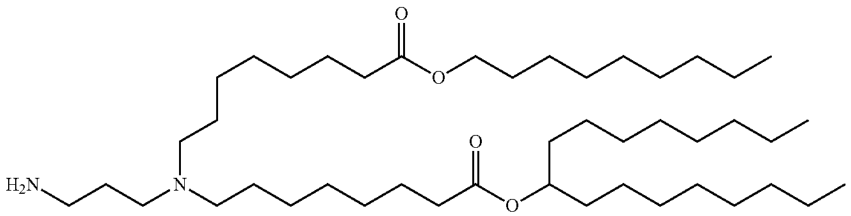
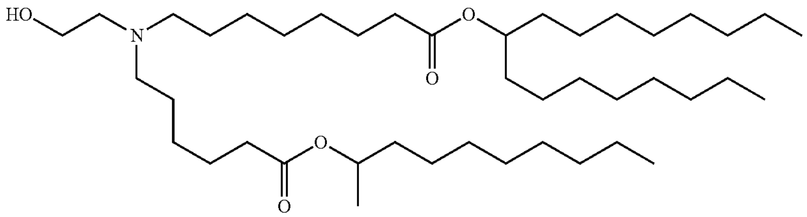
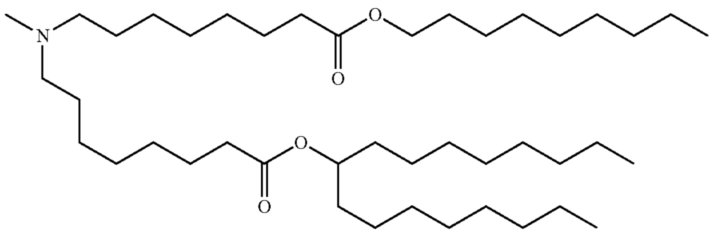
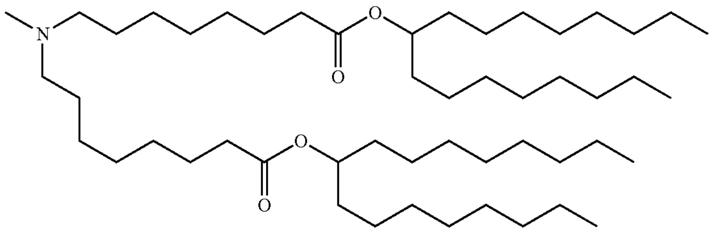
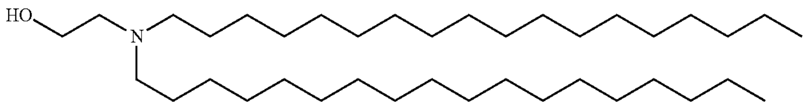
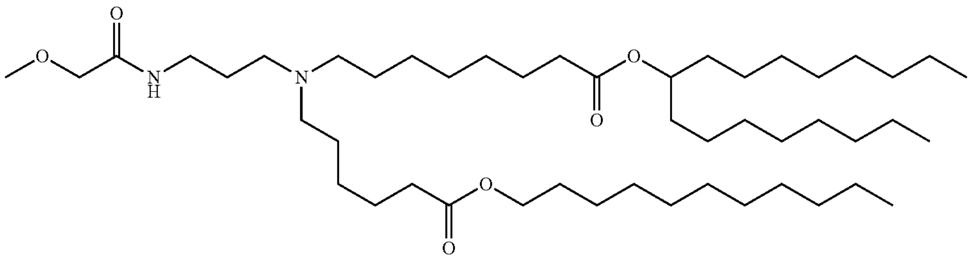

-continued
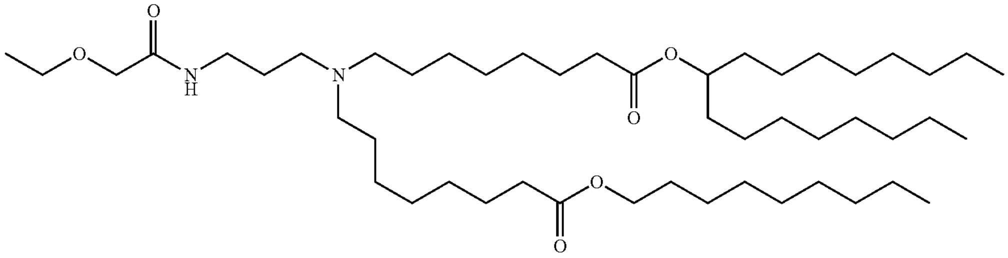
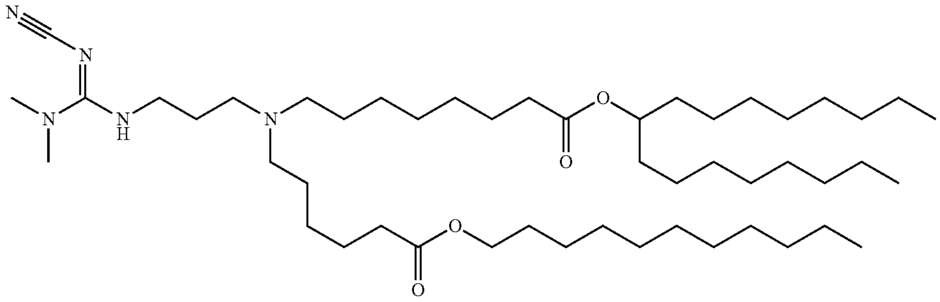
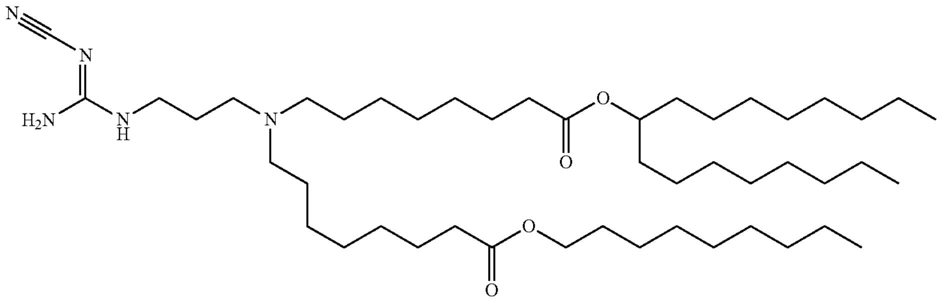
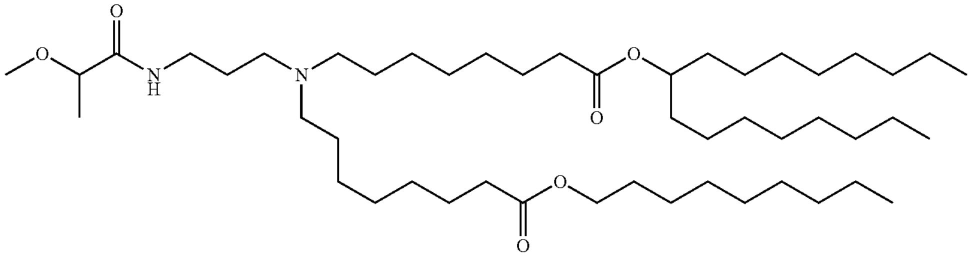
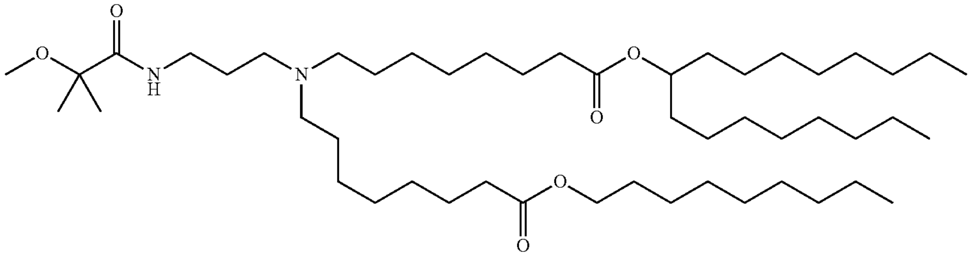
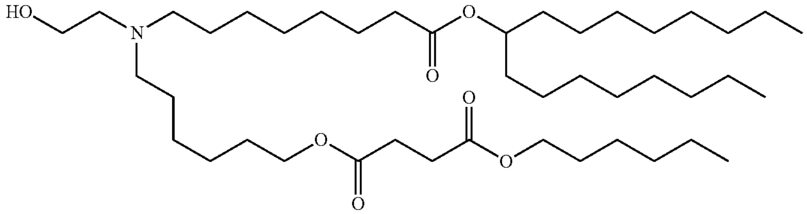

-continued
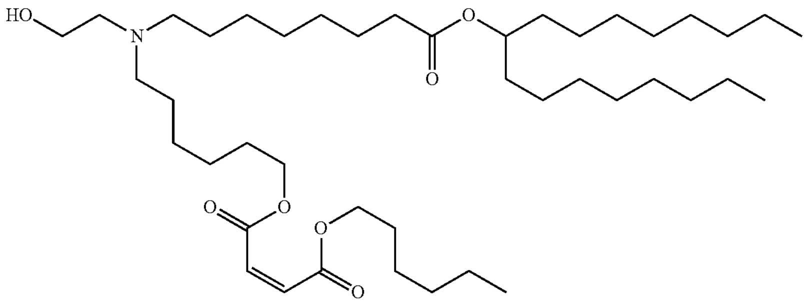
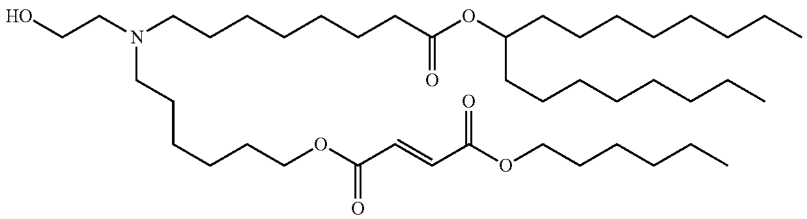
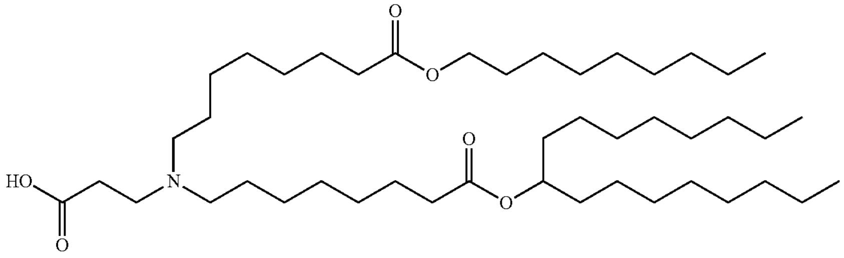
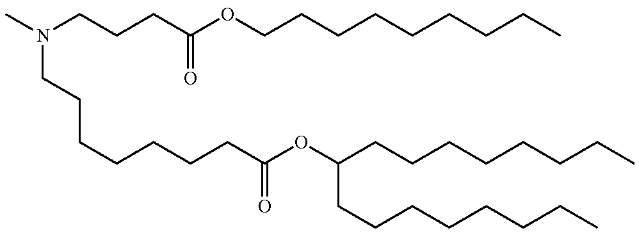
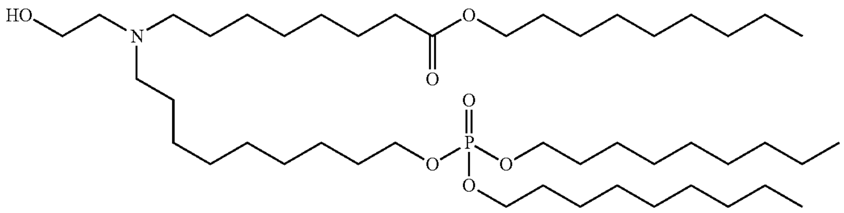
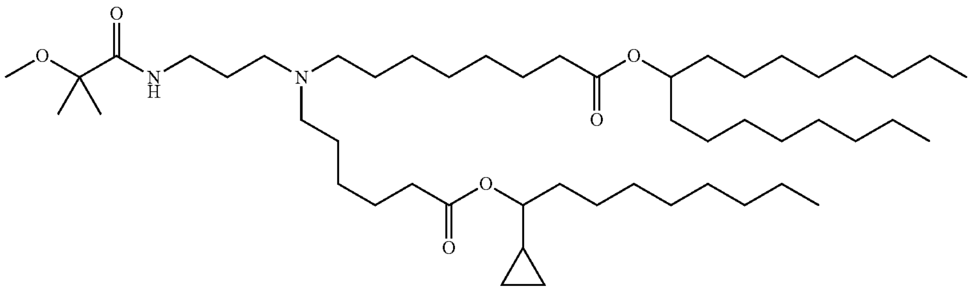

-continued
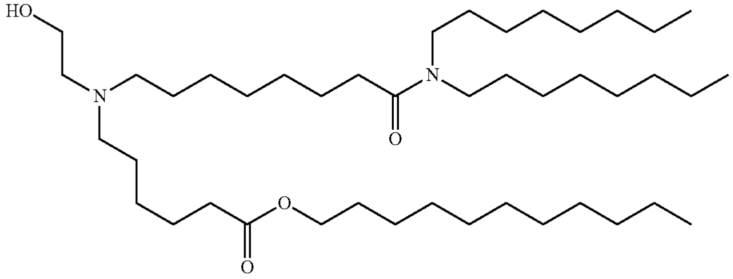
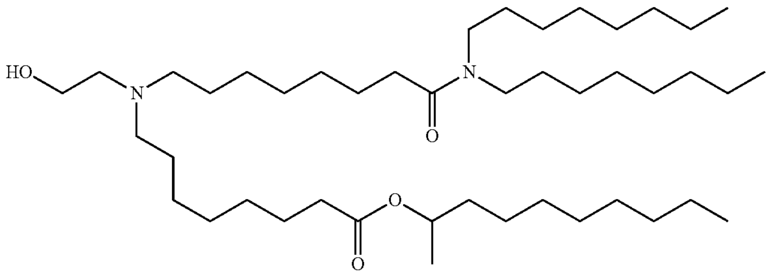
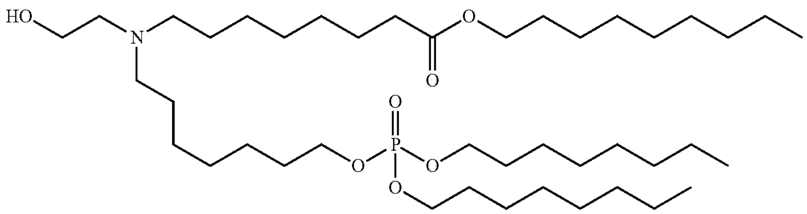
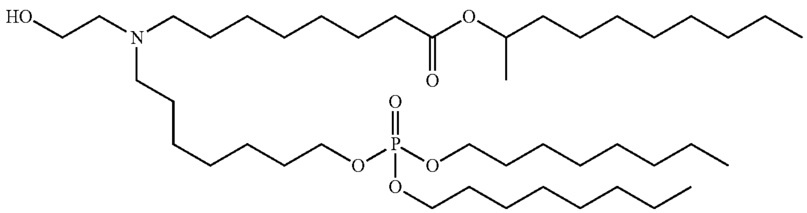
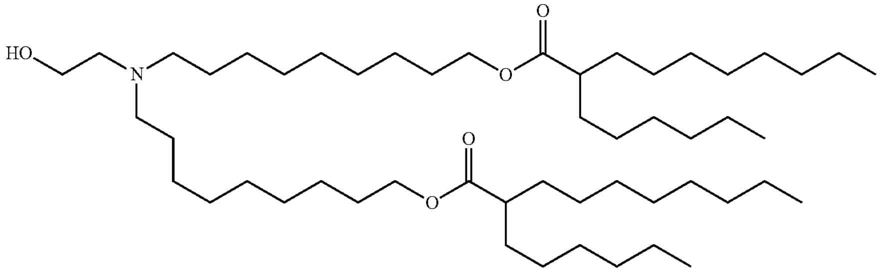
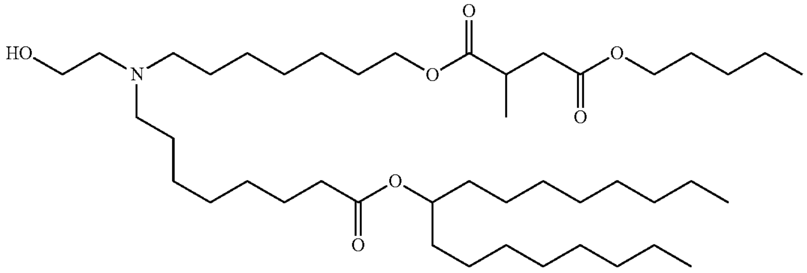

-continued
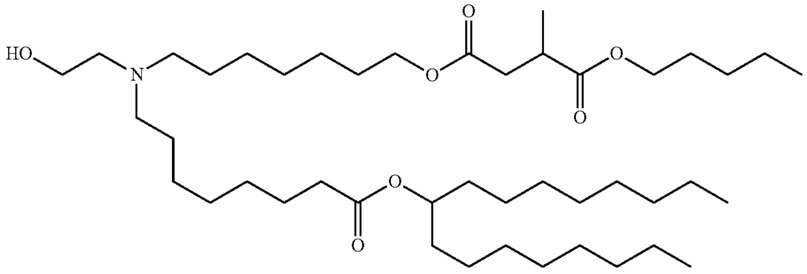
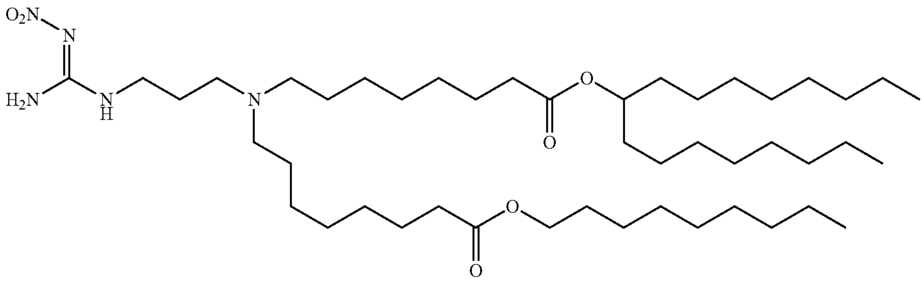
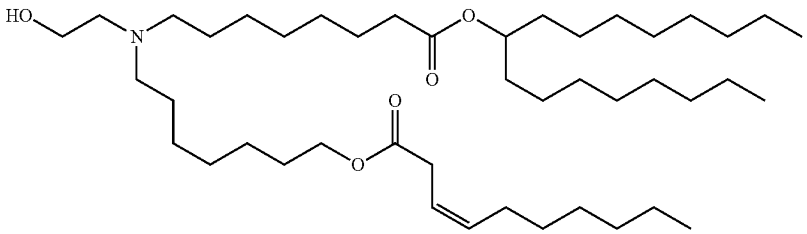
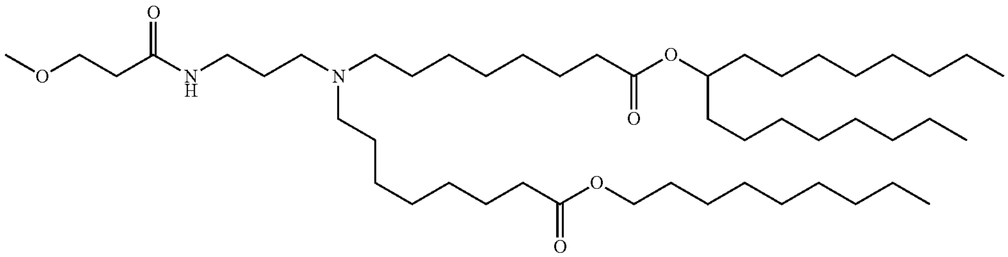
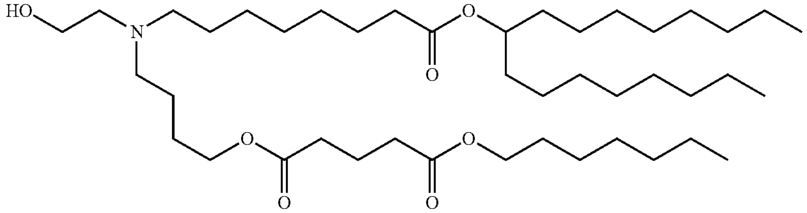
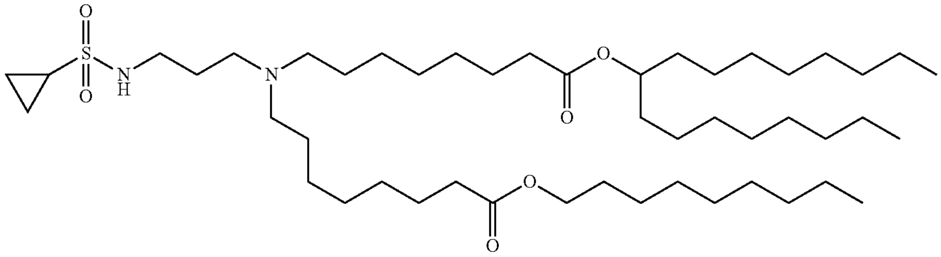

-continued
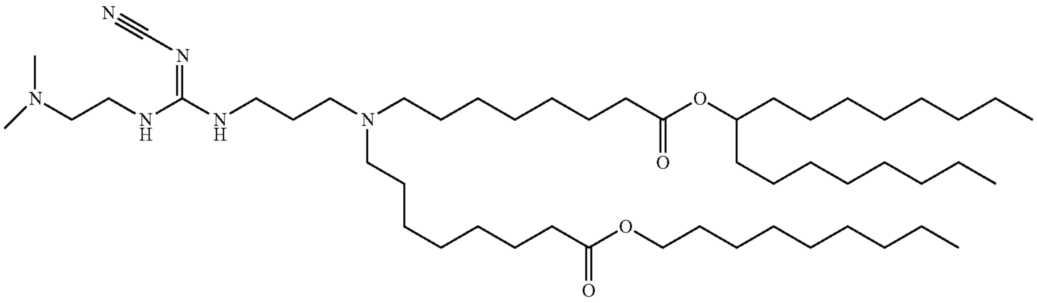
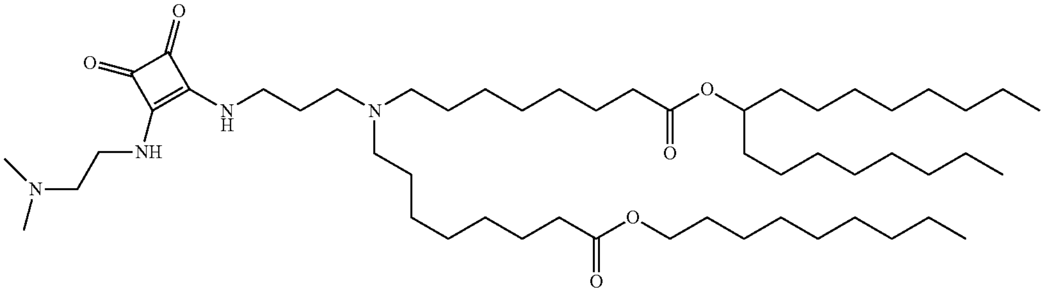
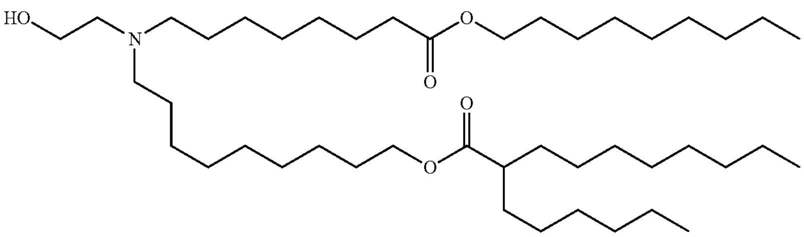
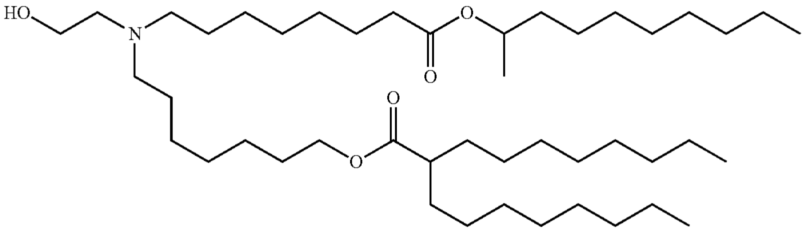
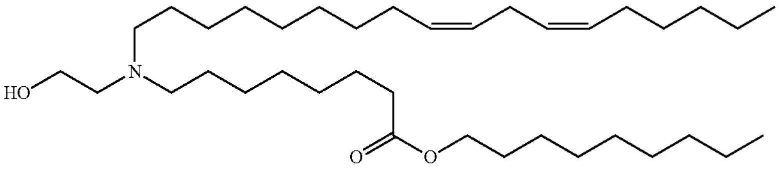
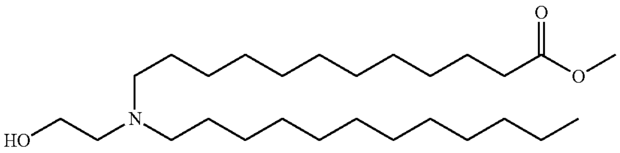
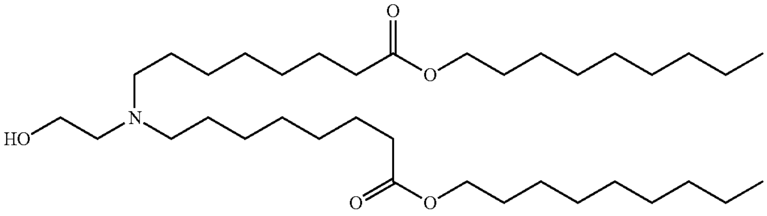

-continued
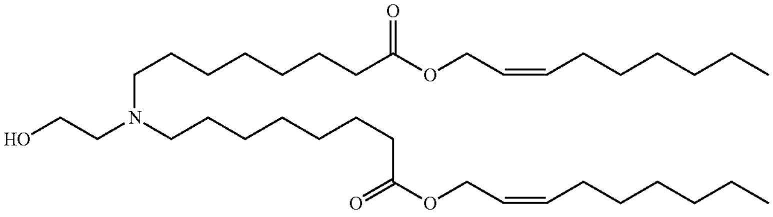
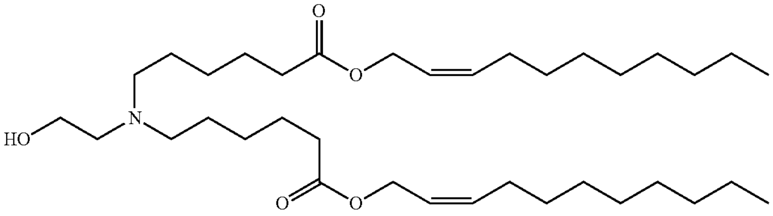
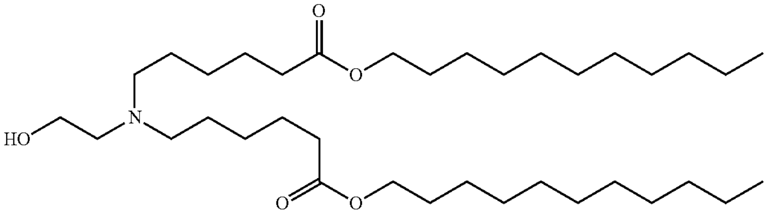
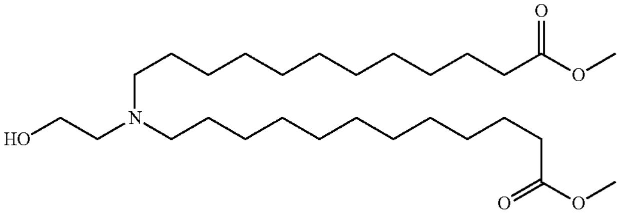
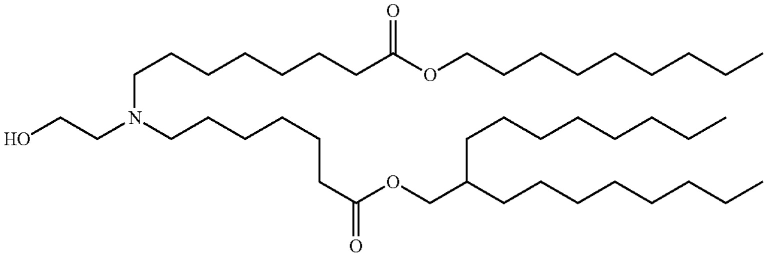
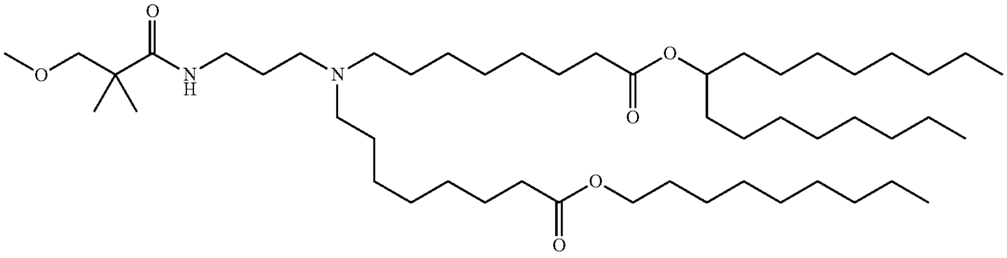
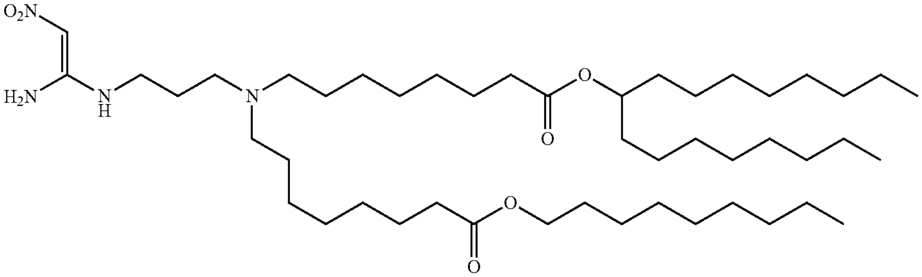

-continued
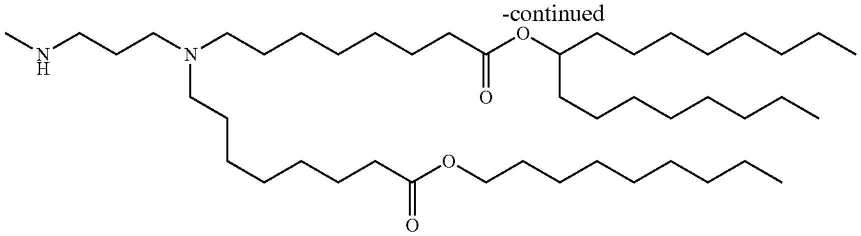
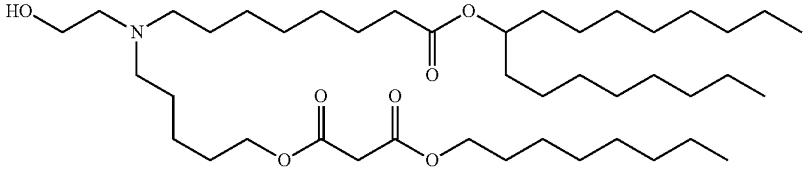
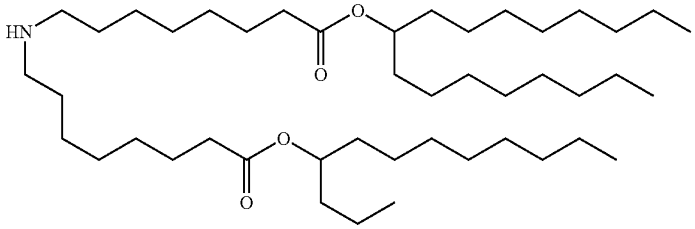
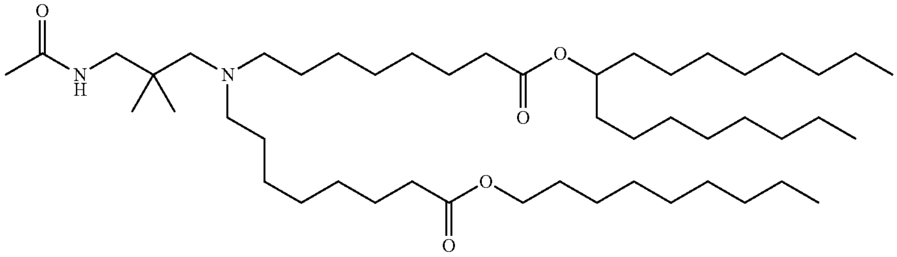
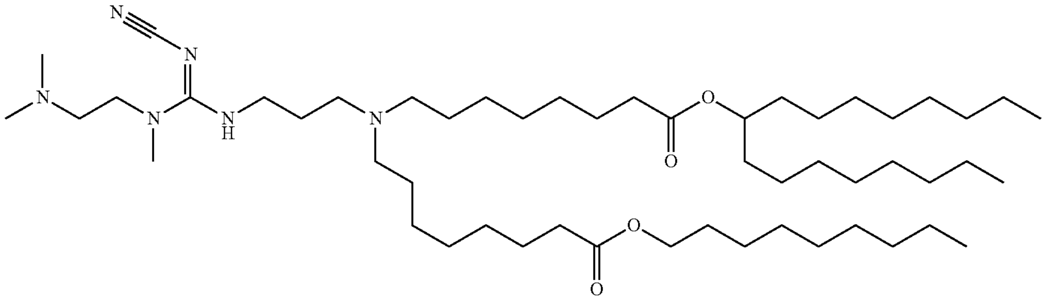
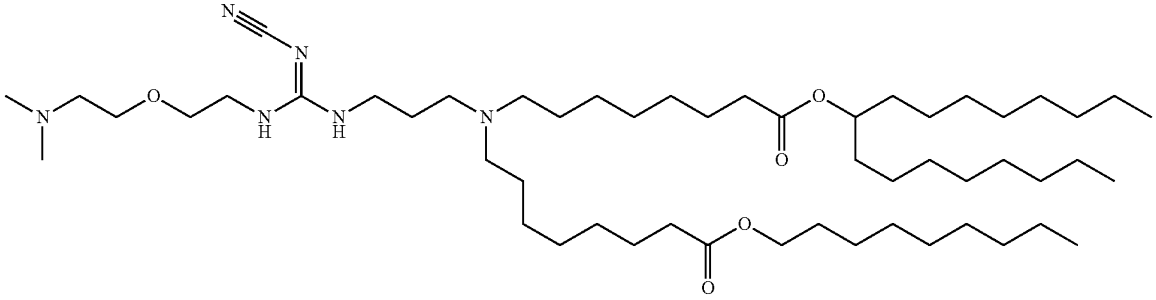
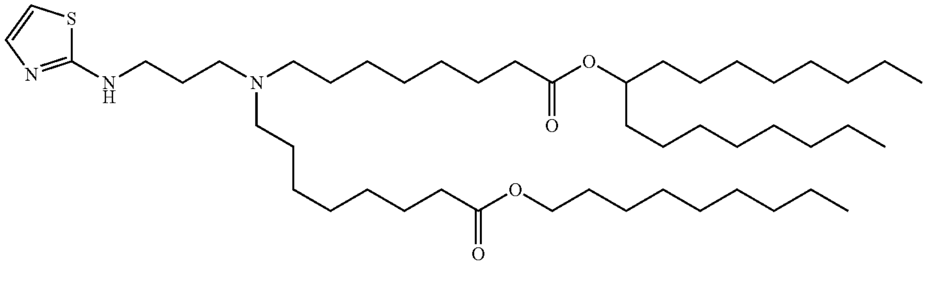

-continued
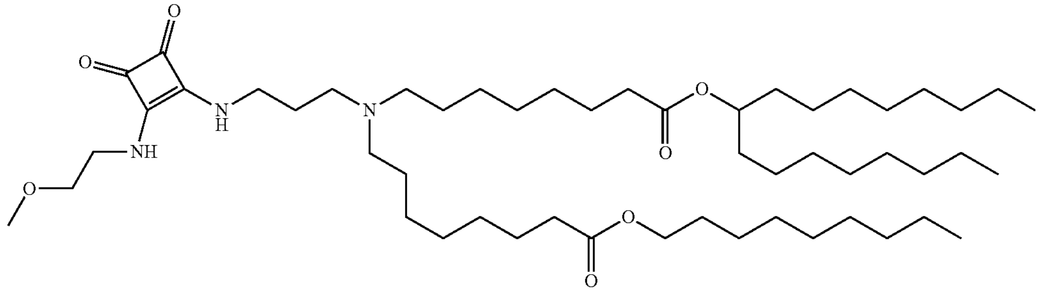
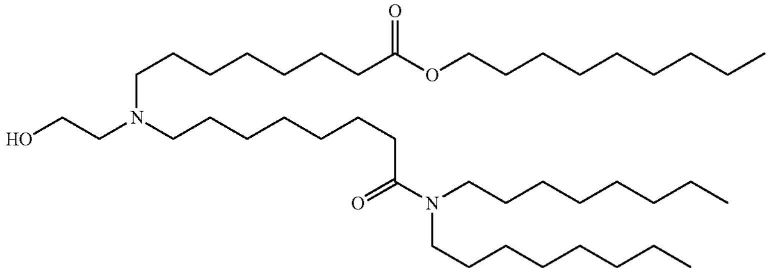
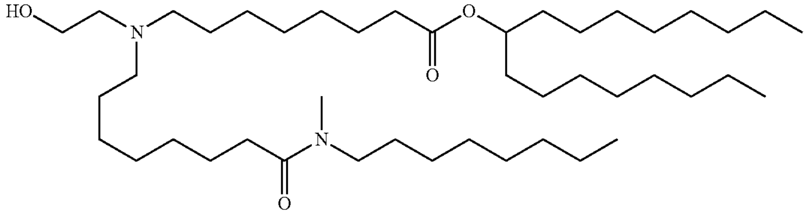
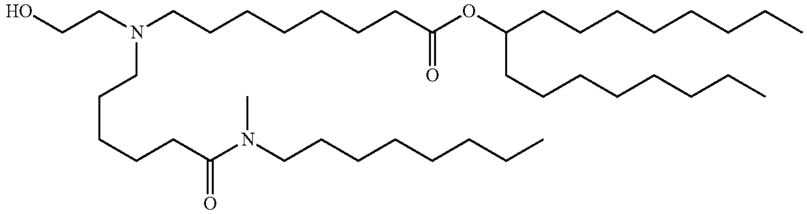
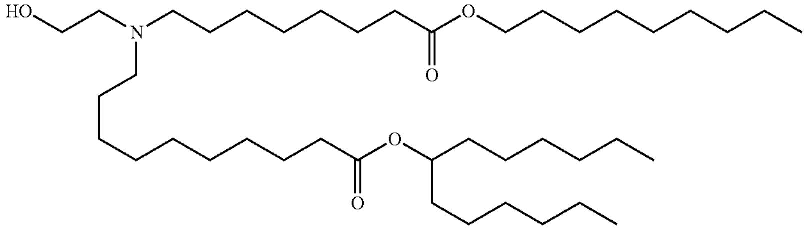
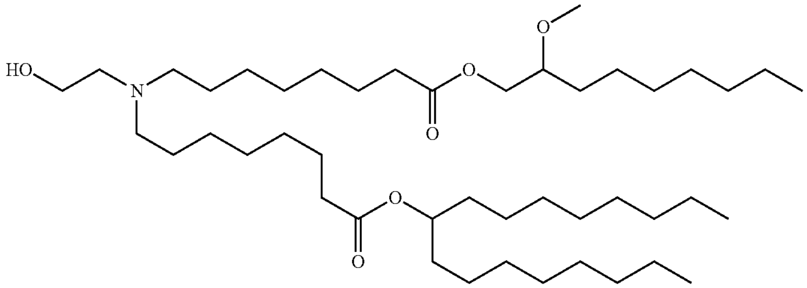
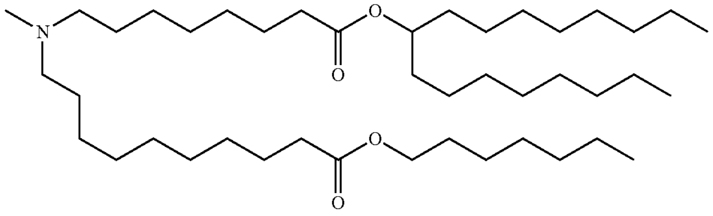

-continued
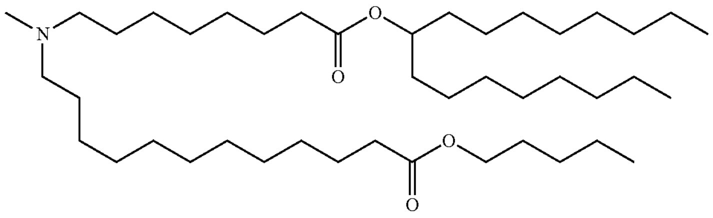
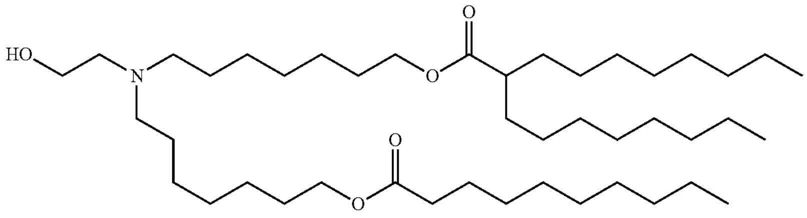
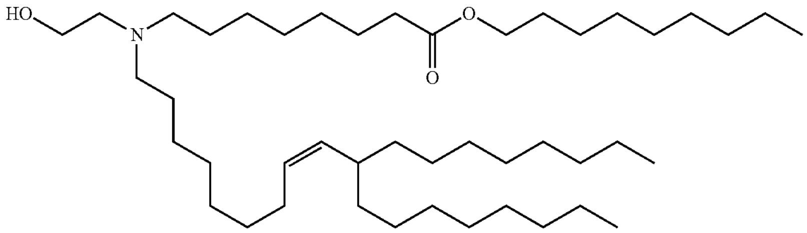
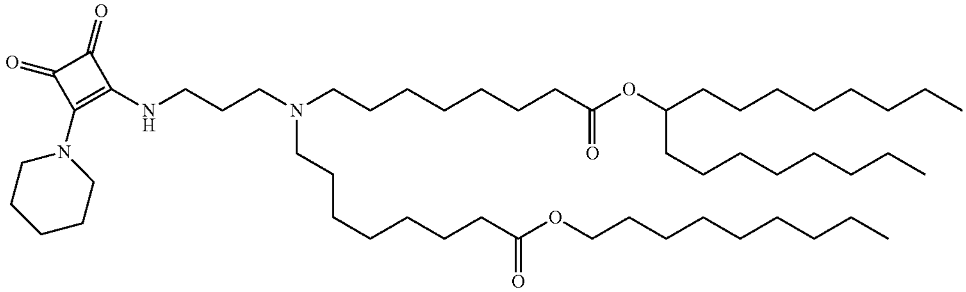
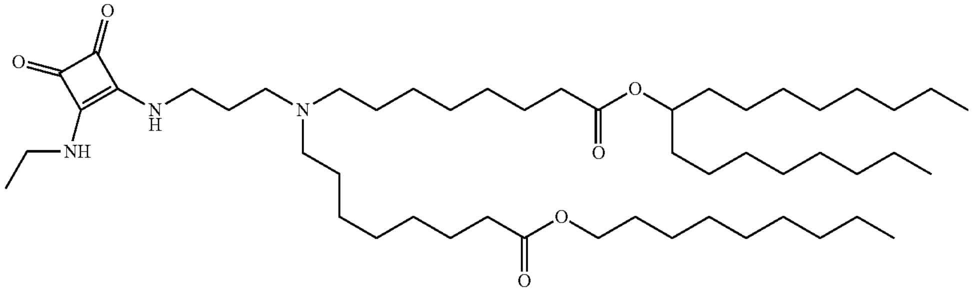
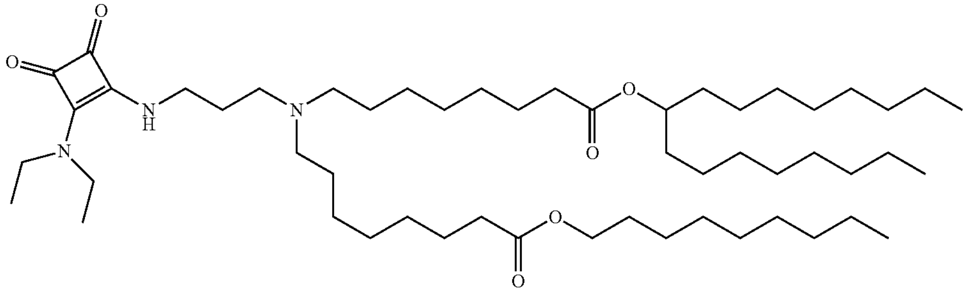

-continued
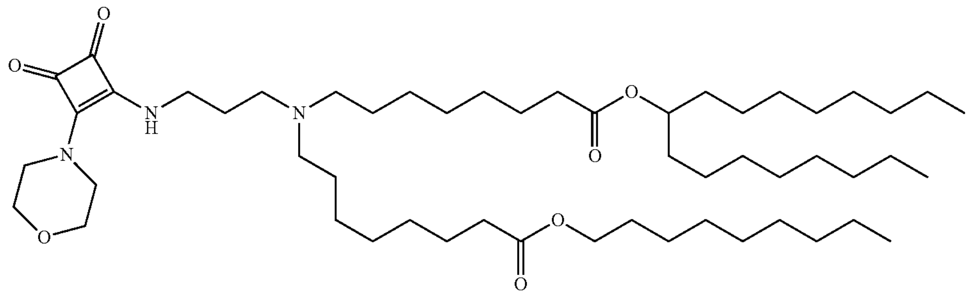
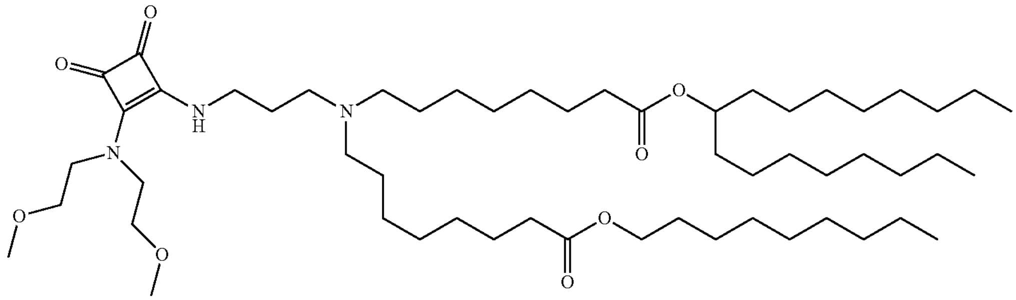
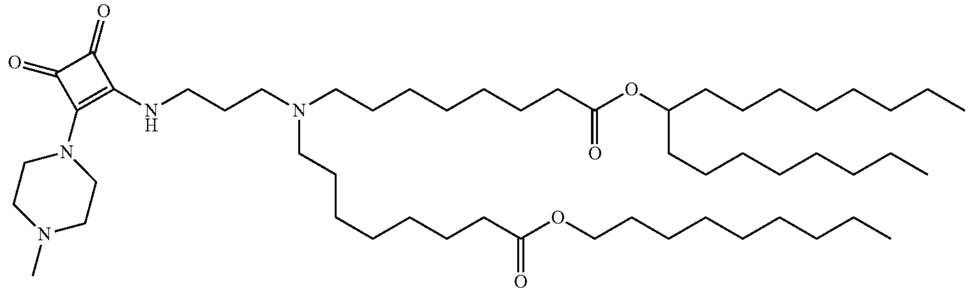
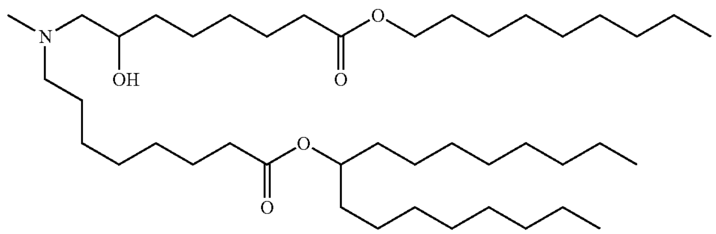
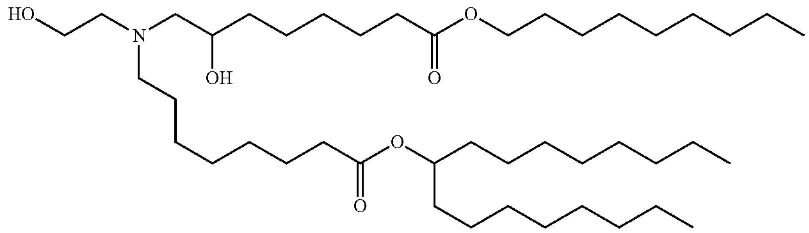
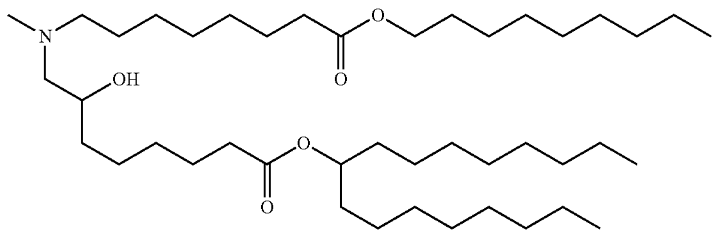

-continued
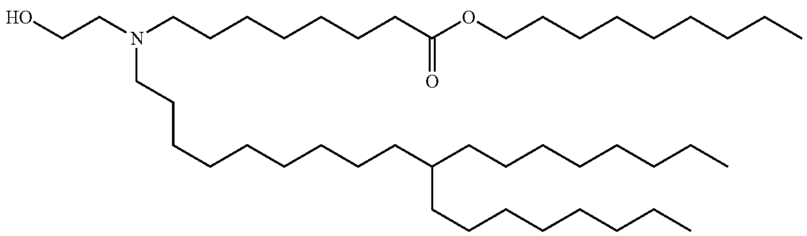
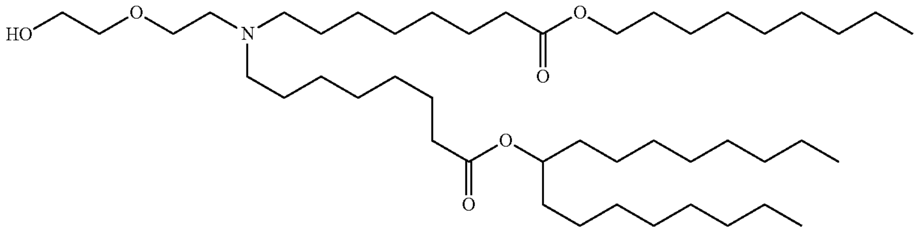
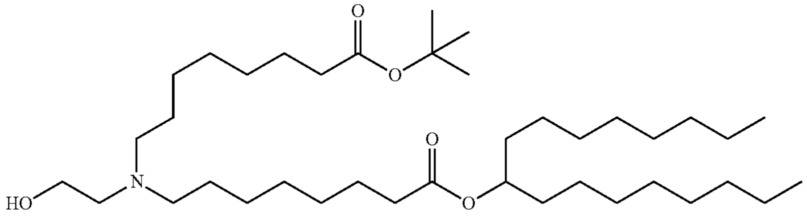
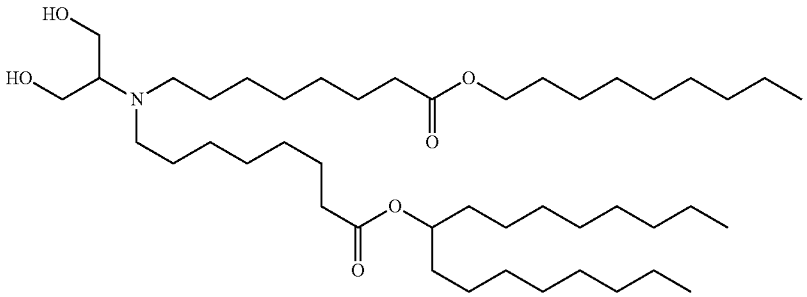
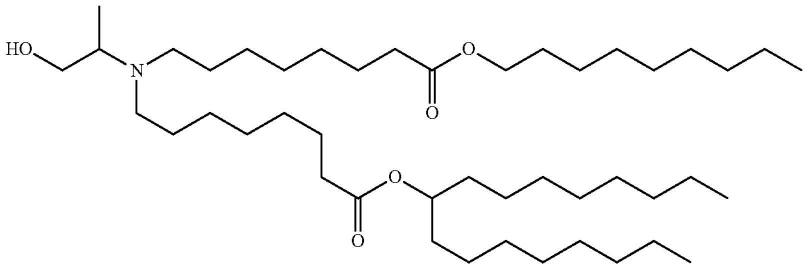
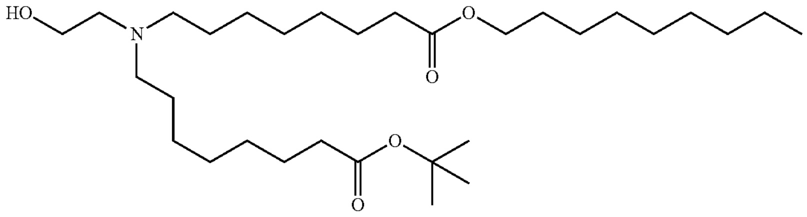

-continued
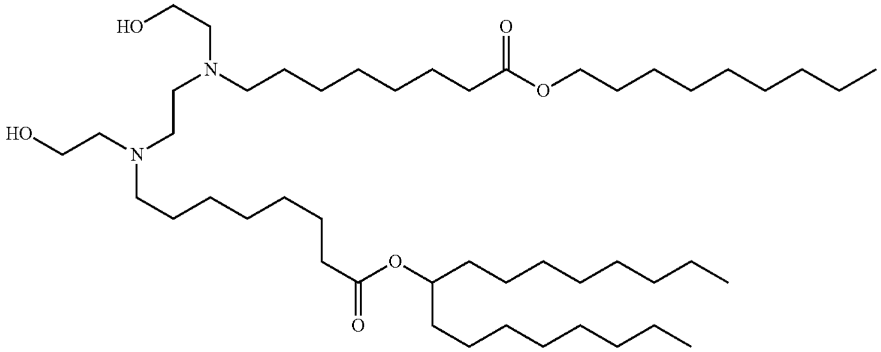
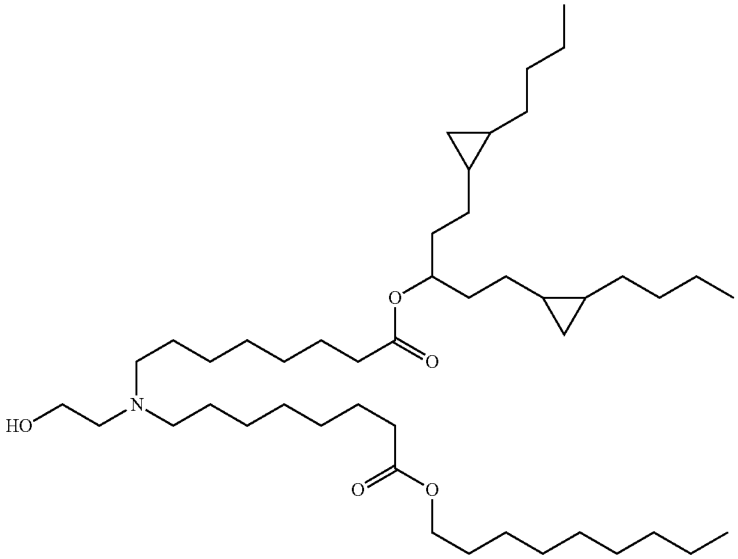
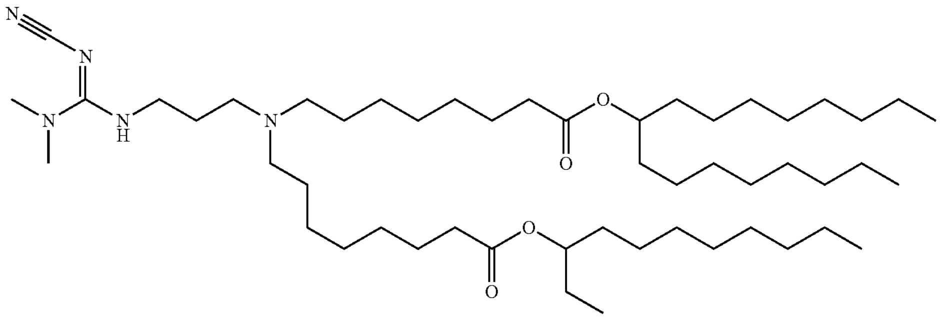
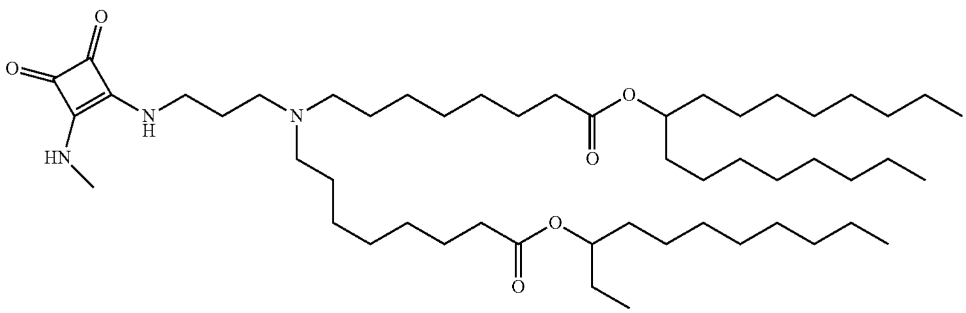

-continued
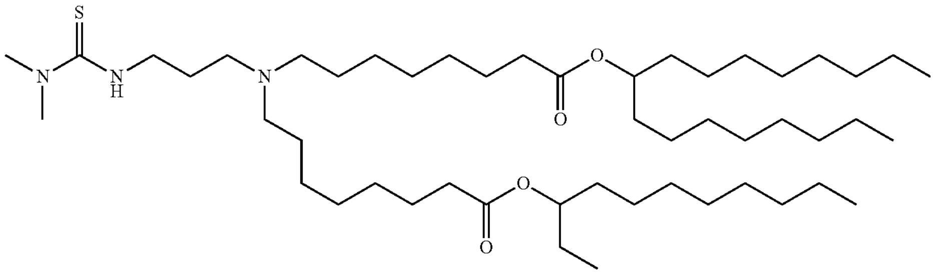
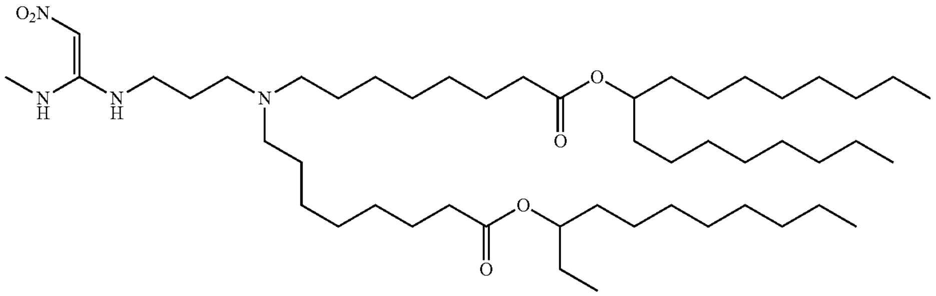
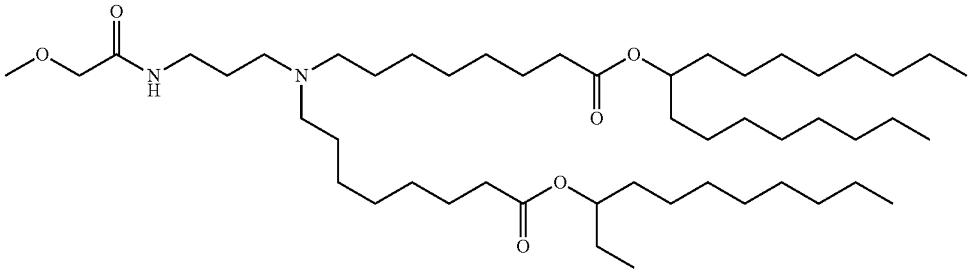
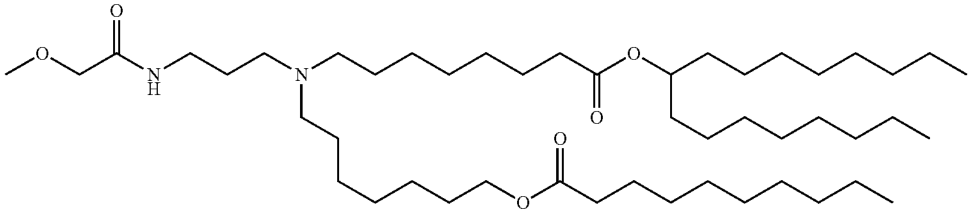
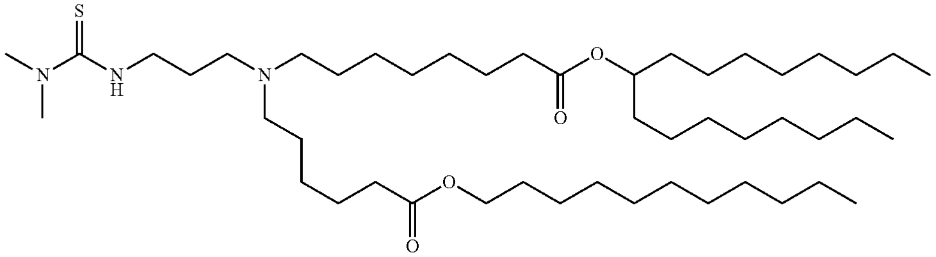
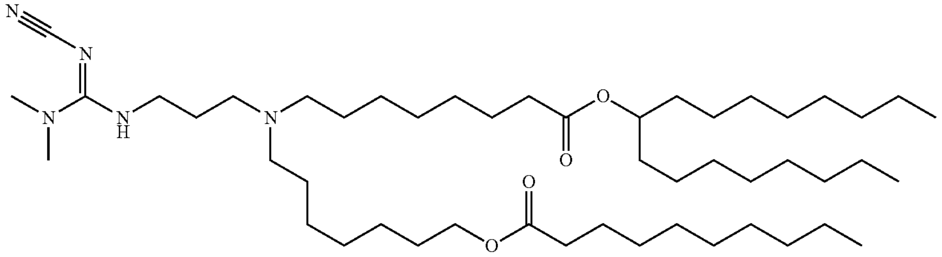

-continued
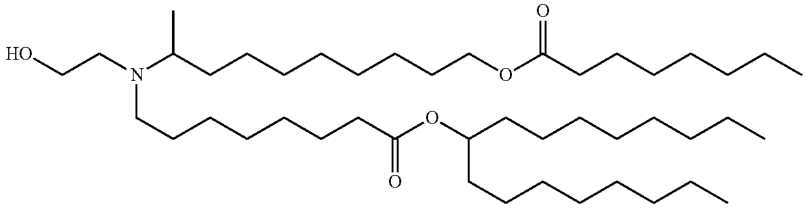
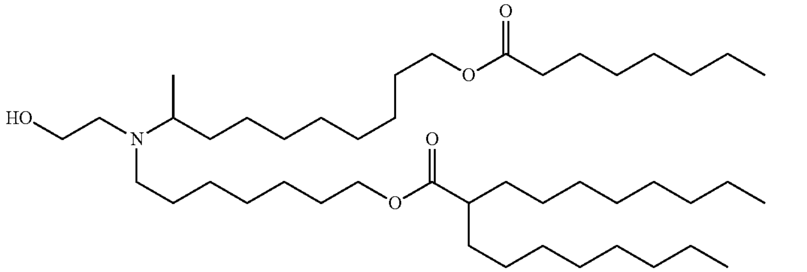
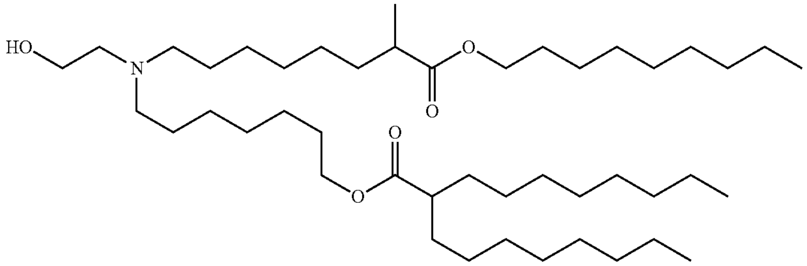
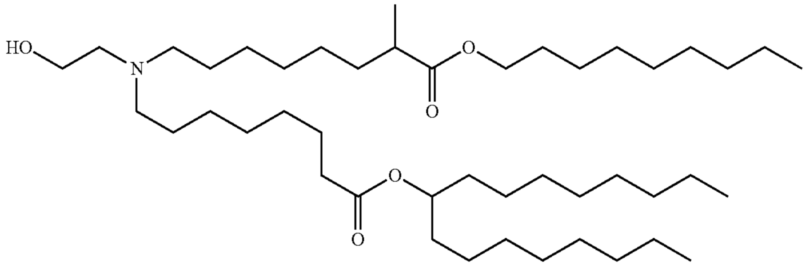
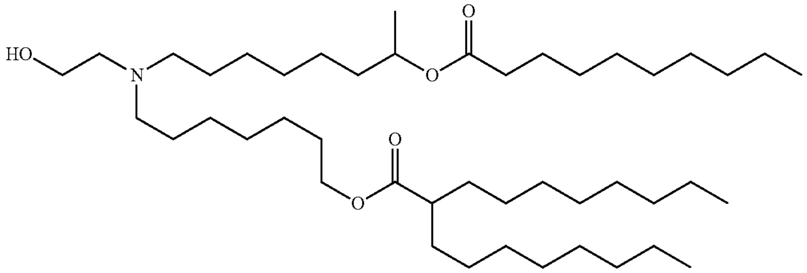
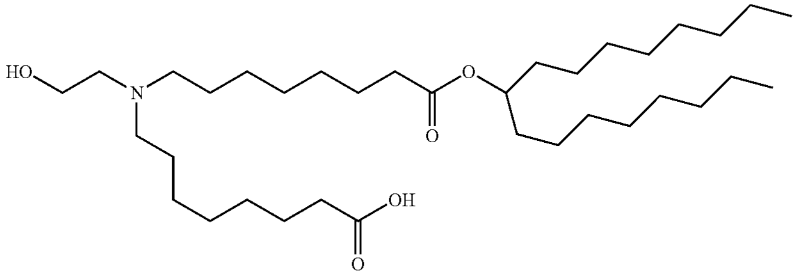

-continued
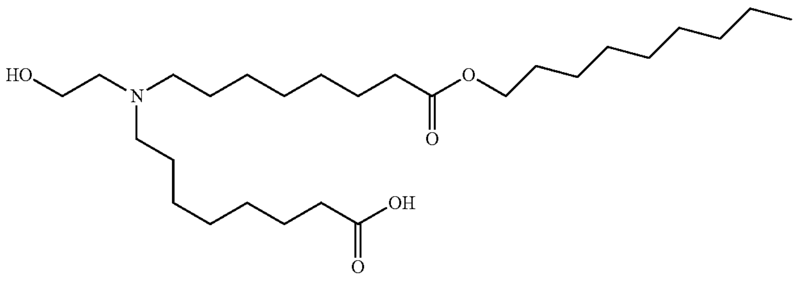
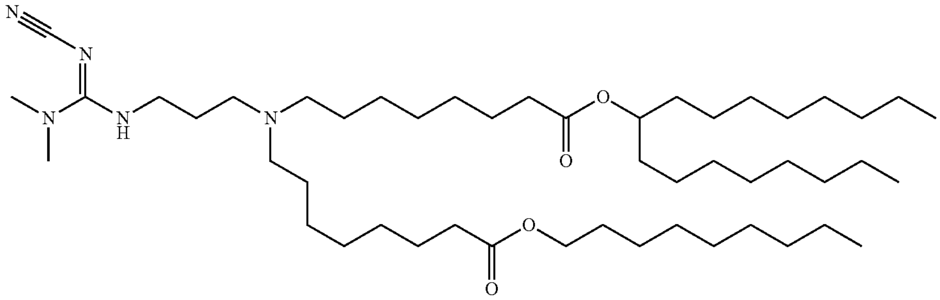
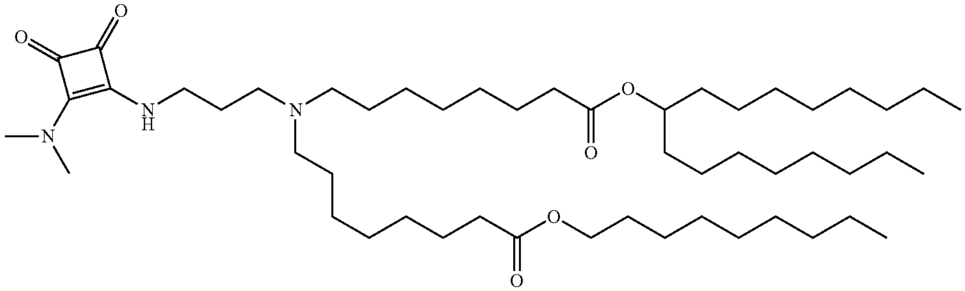
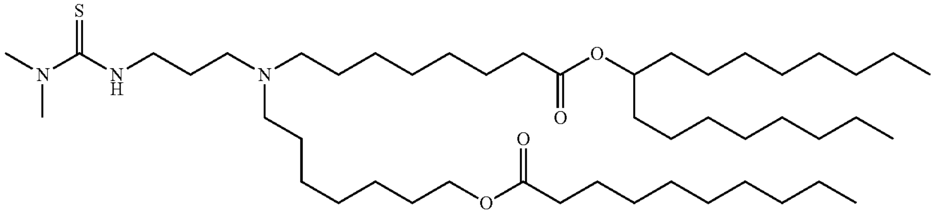
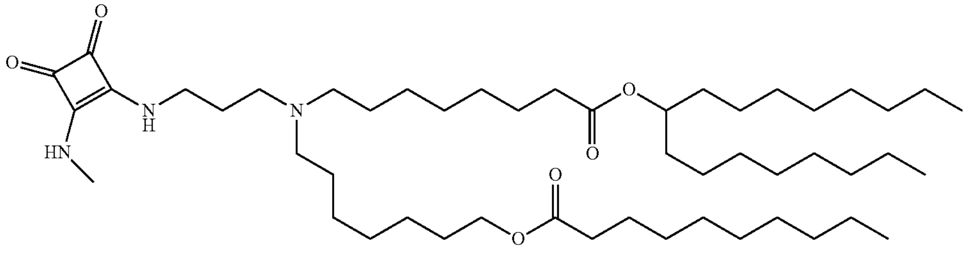
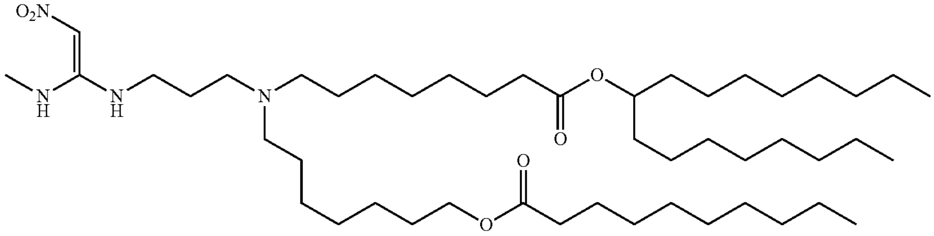

-continued
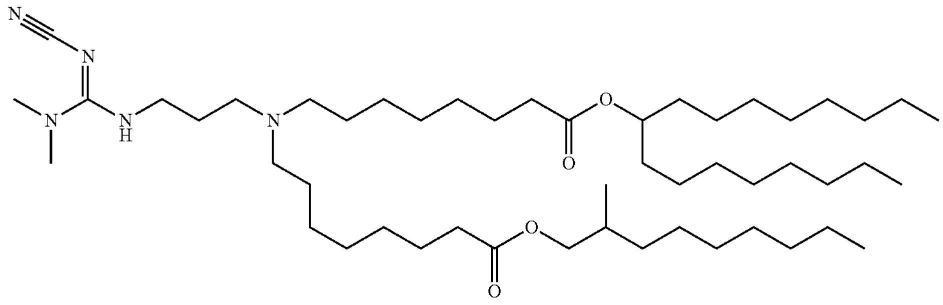
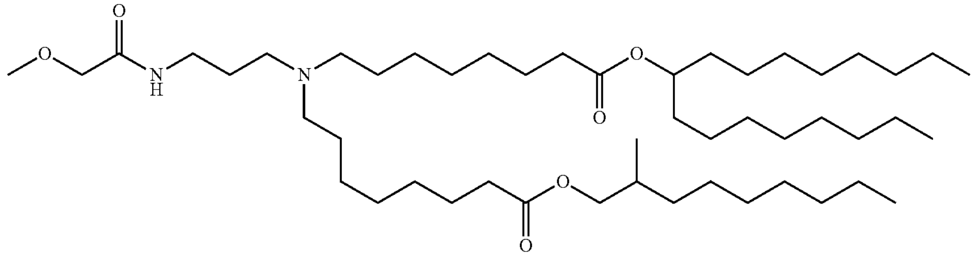
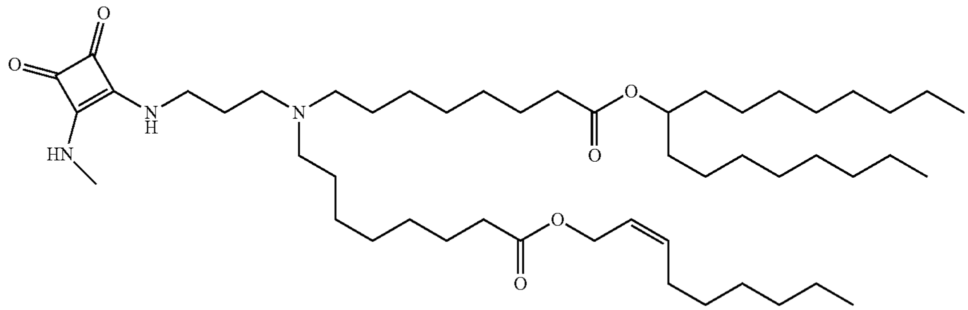
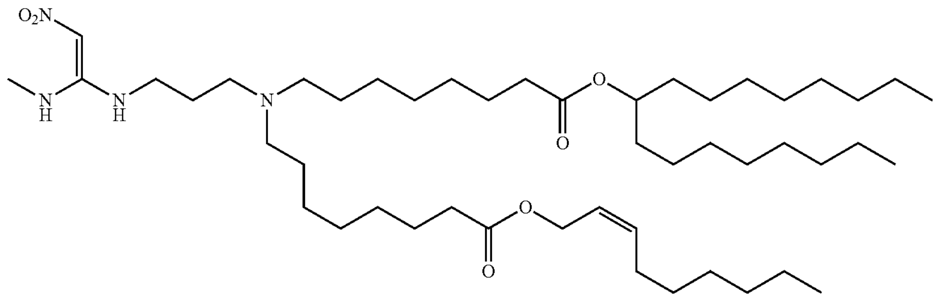
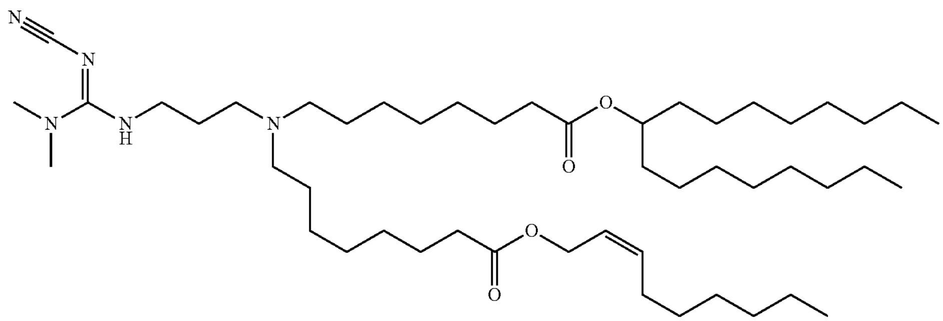

-continued
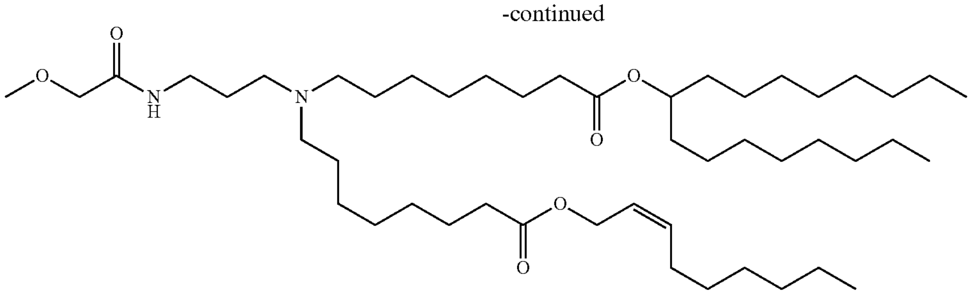
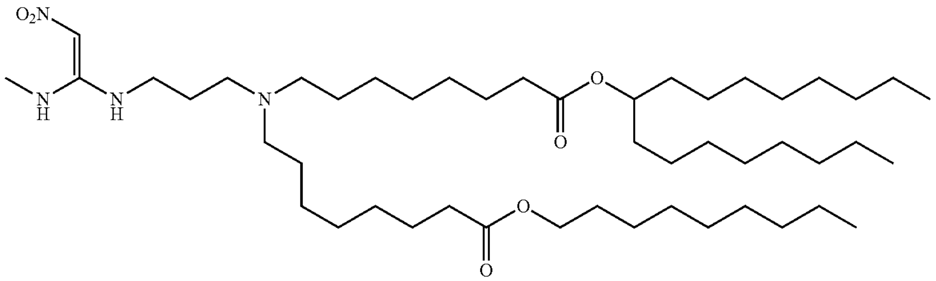
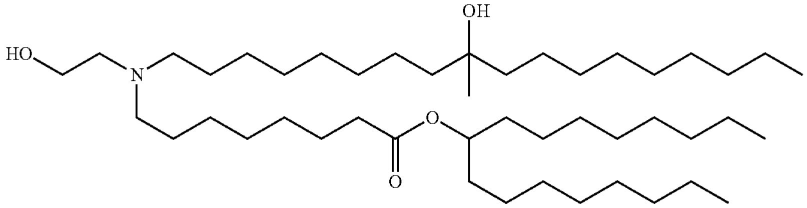
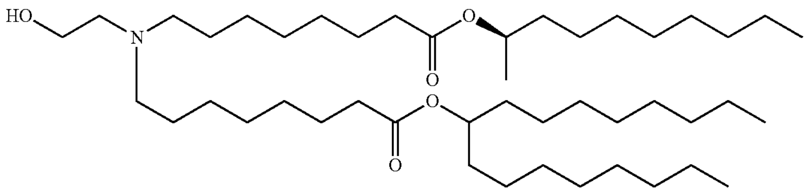
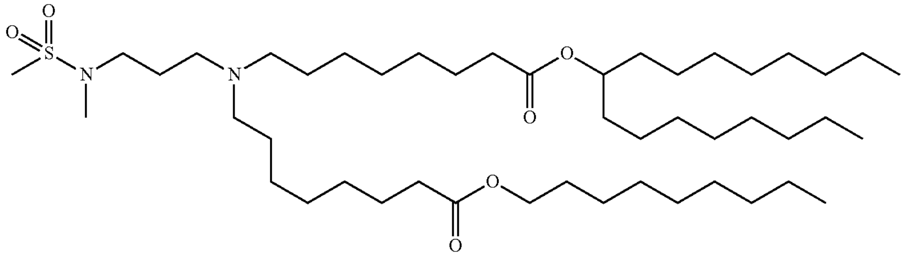
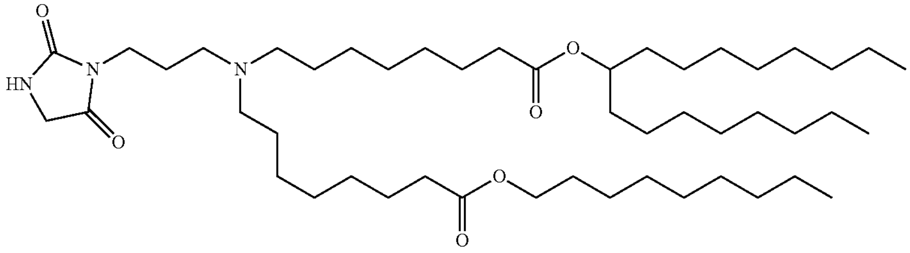
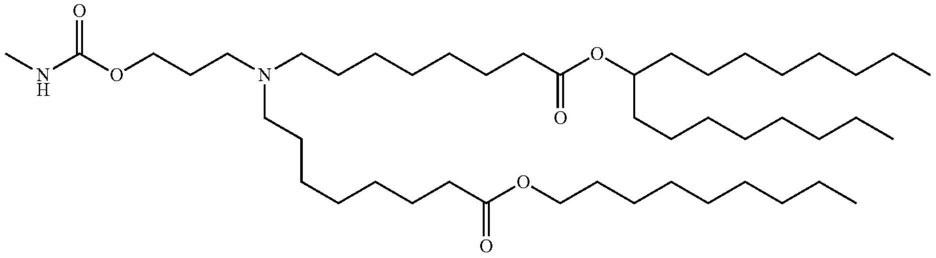

-continued
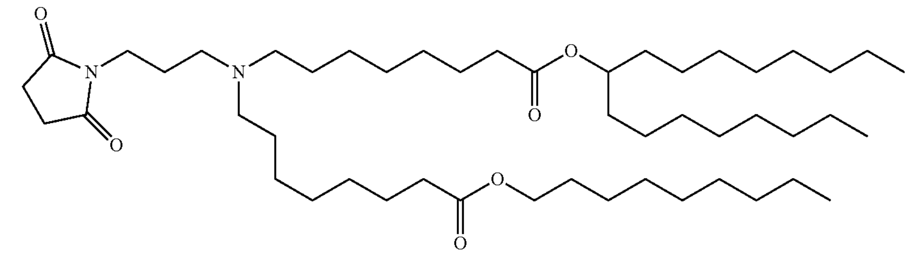
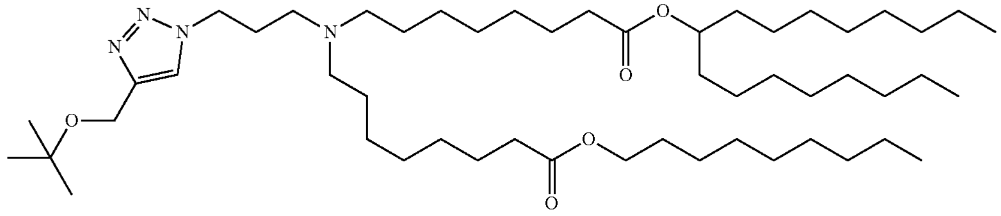
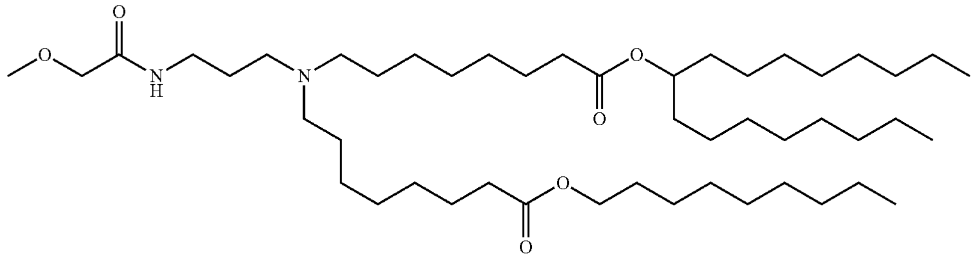
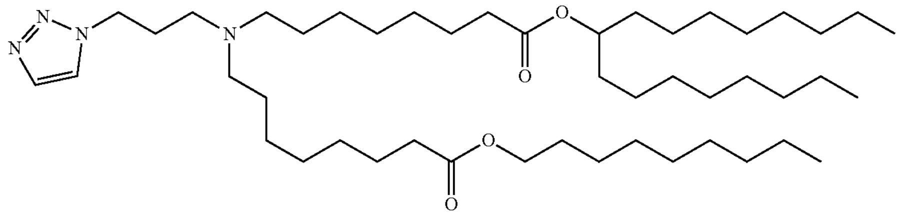
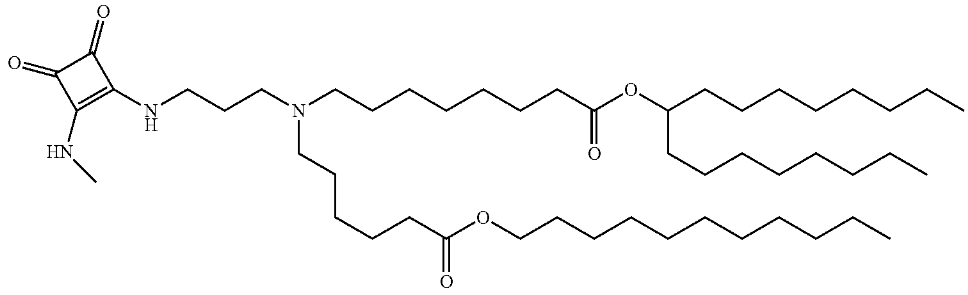
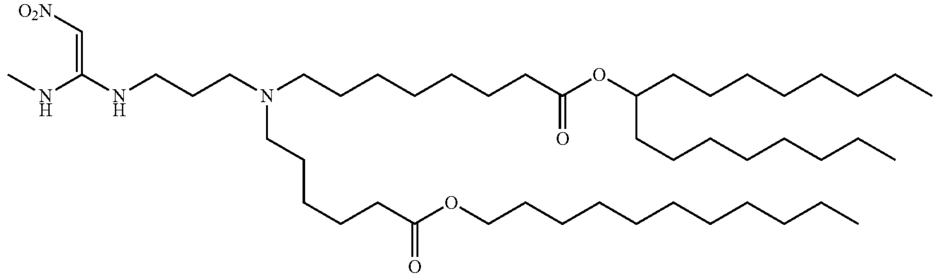

-continued
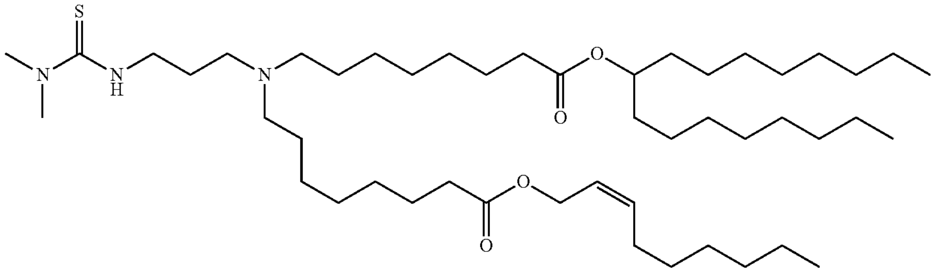
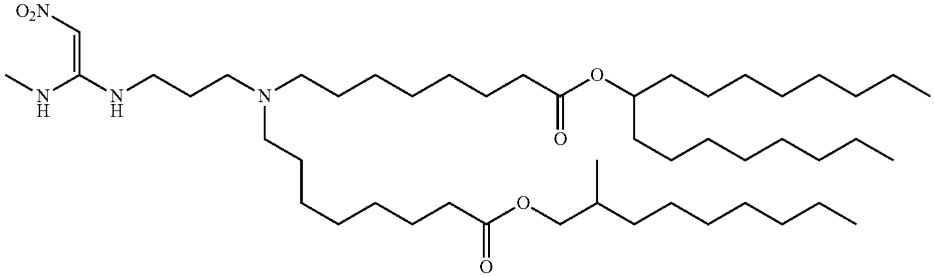
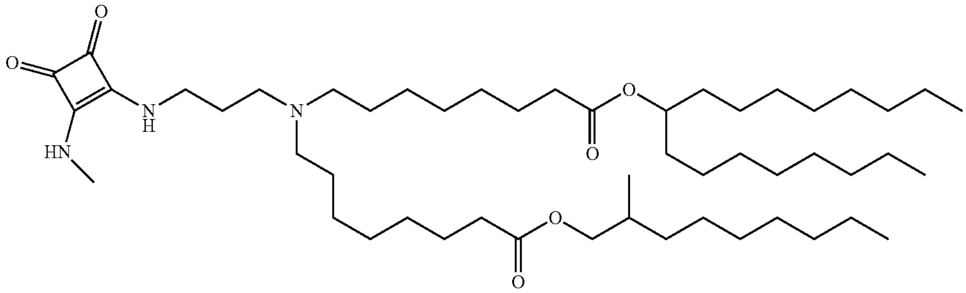
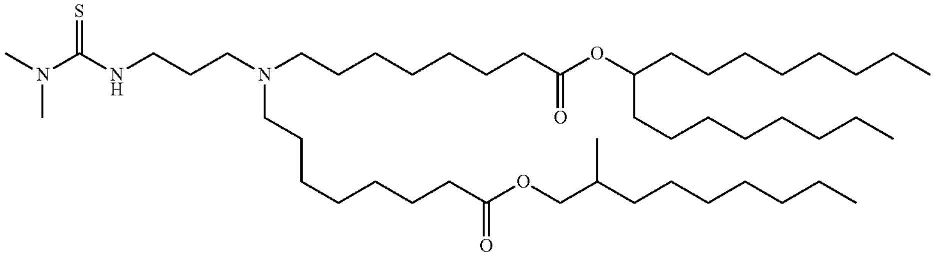
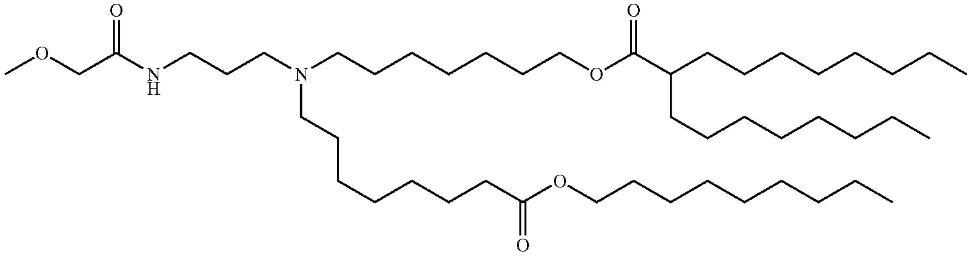
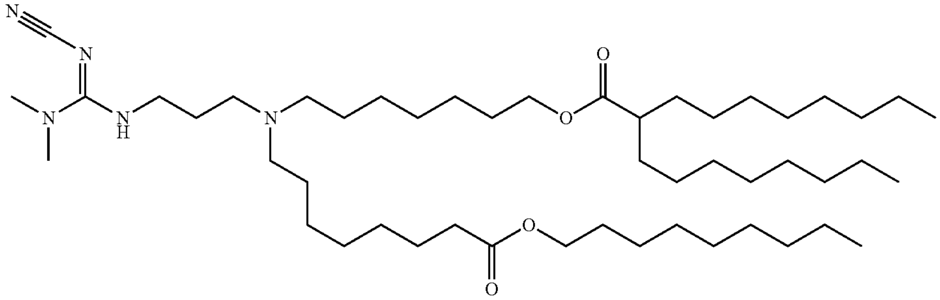

-continued
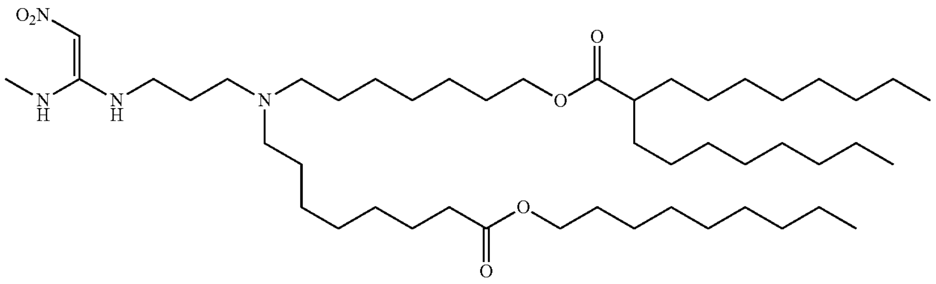
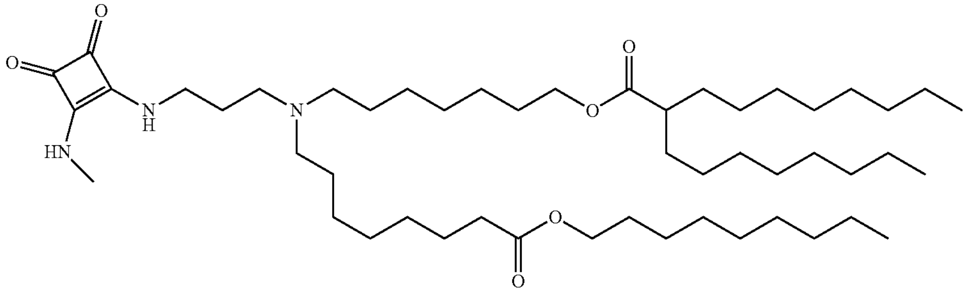
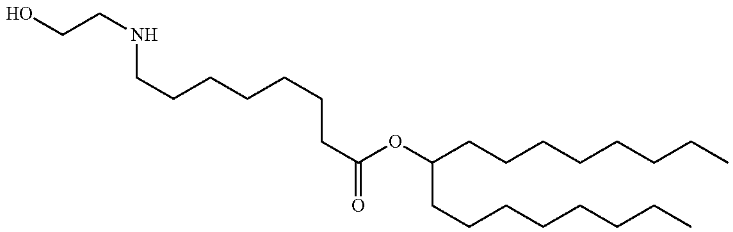
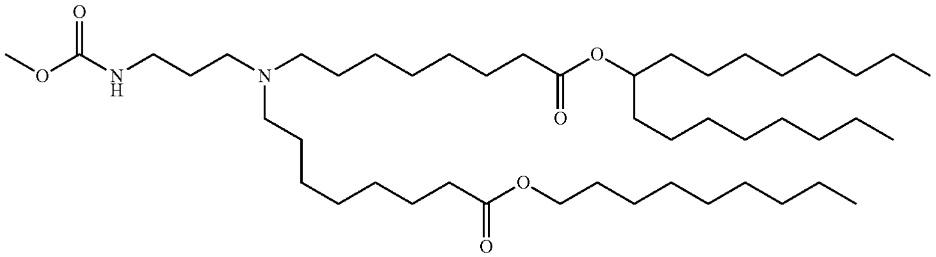
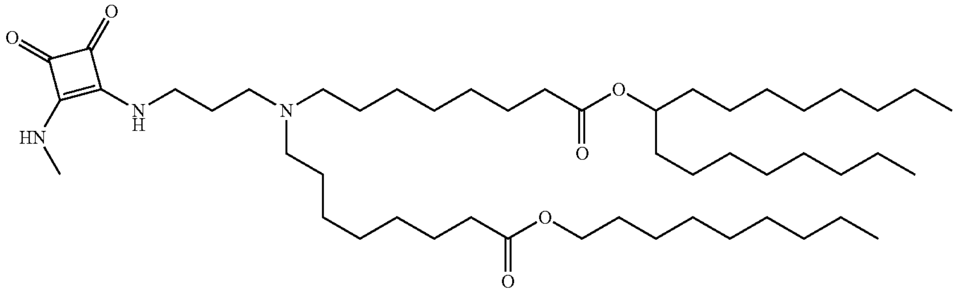
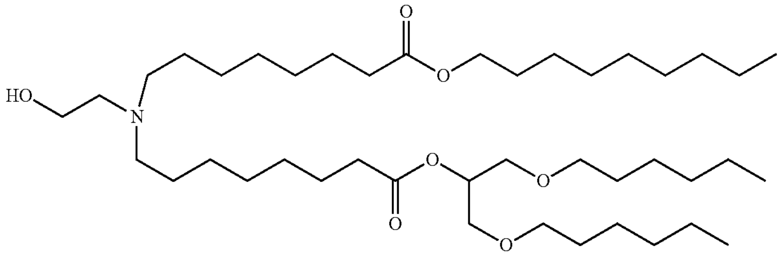

-continued
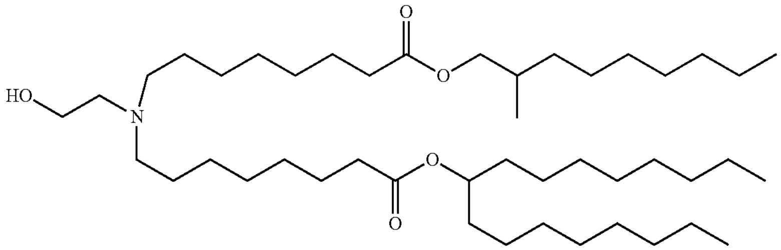
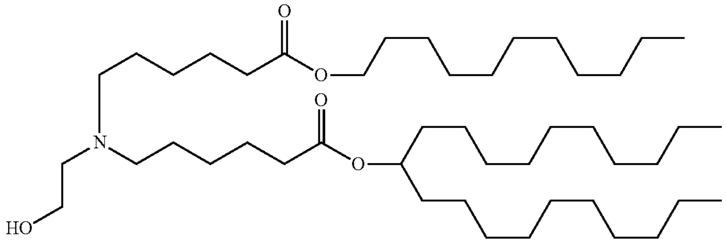
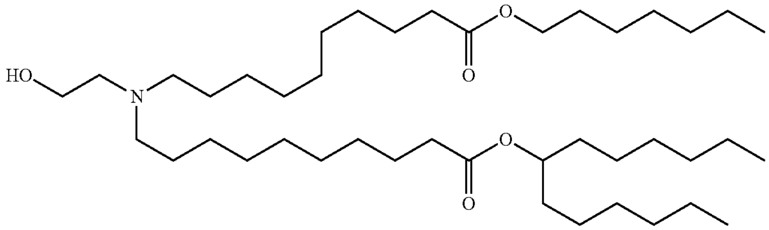
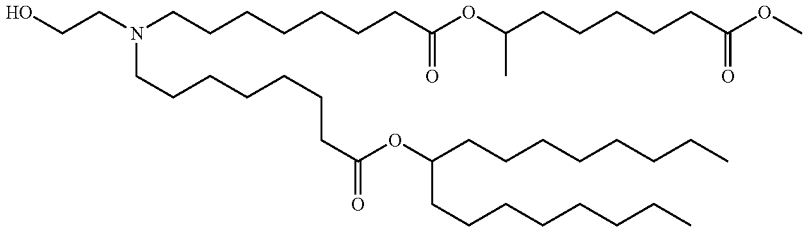
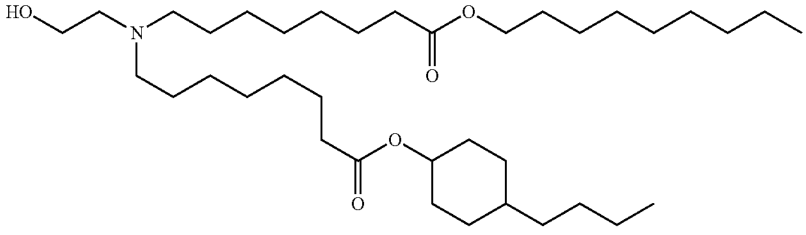
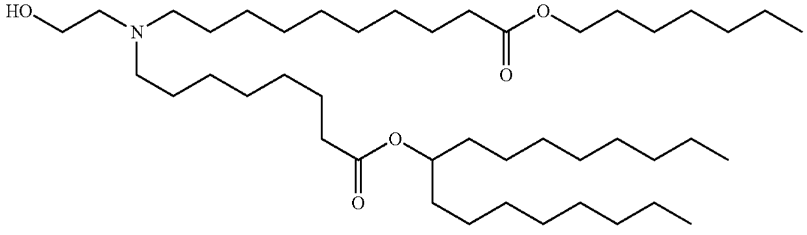
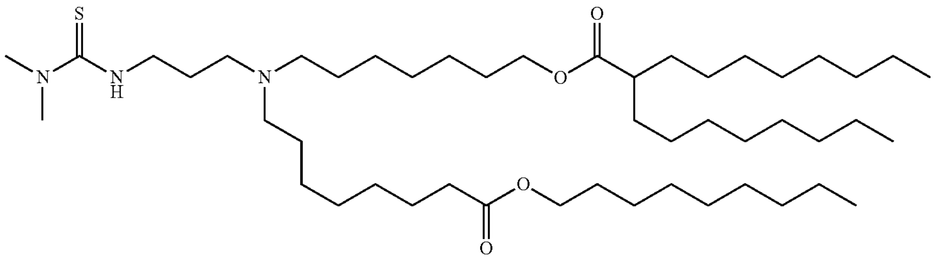

-continued
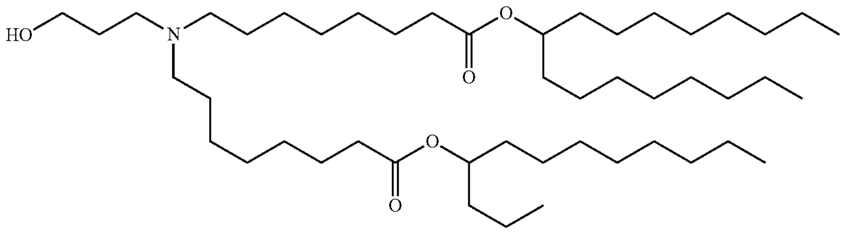
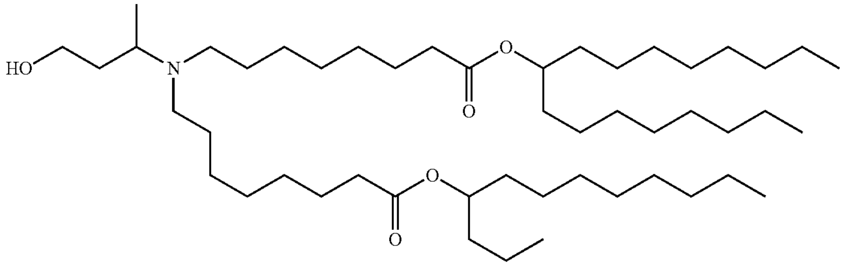
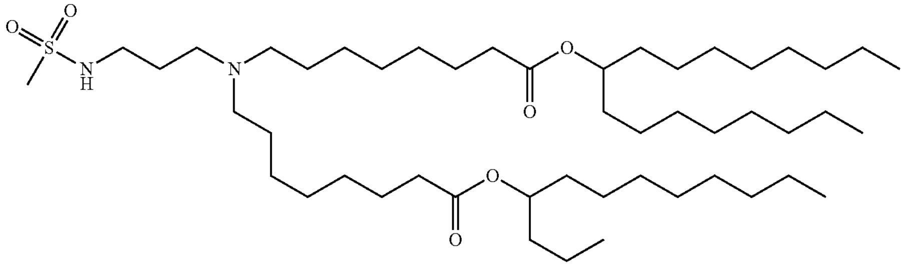
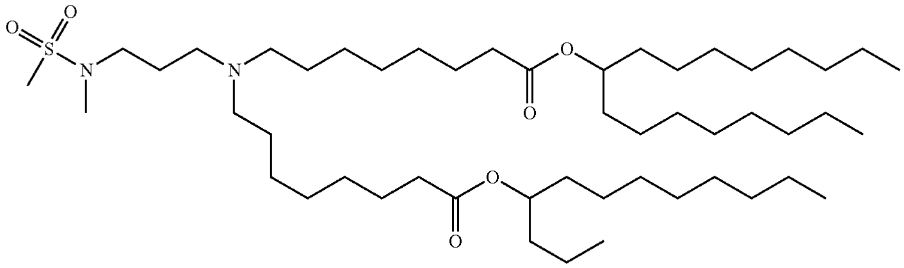
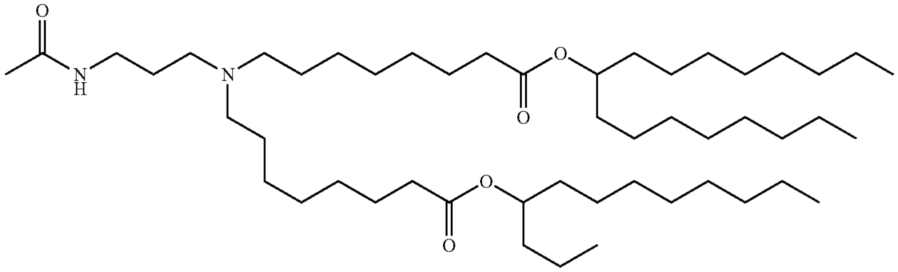
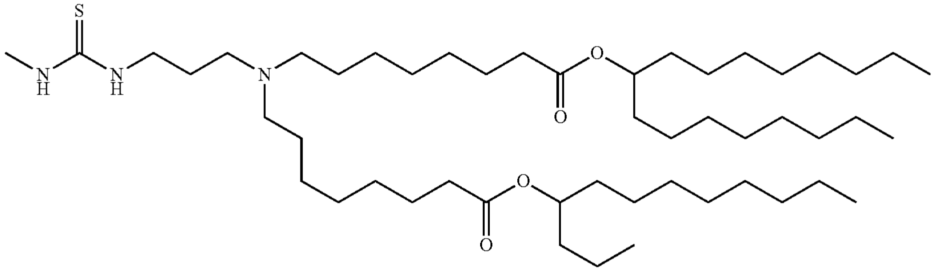

-continued
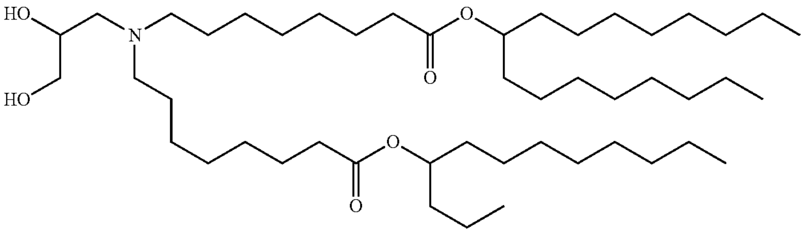
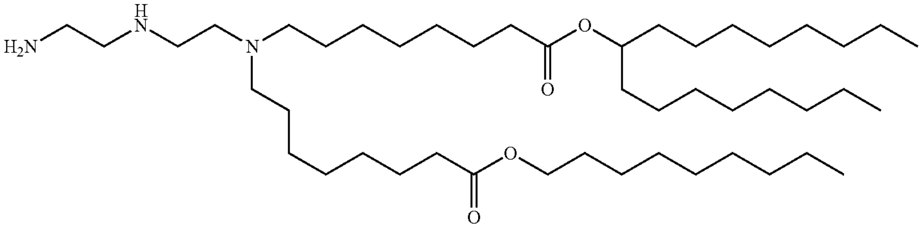
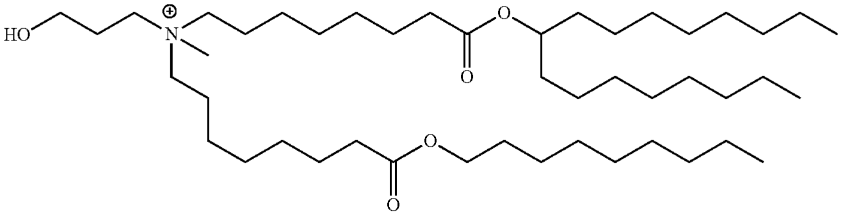
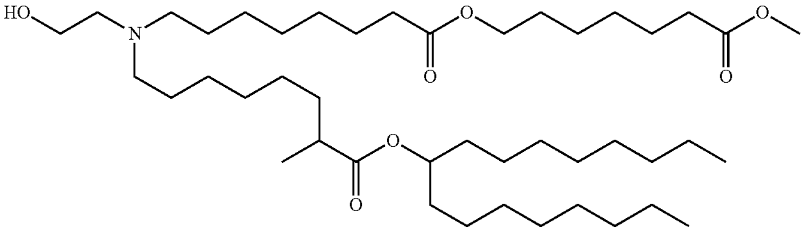
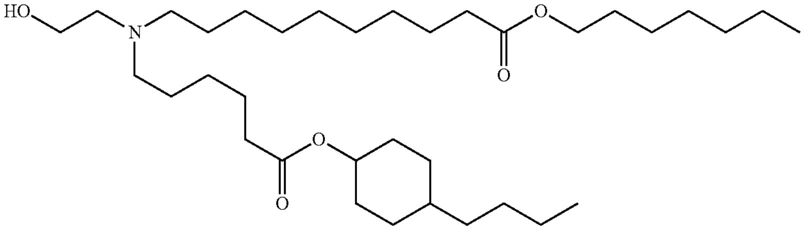
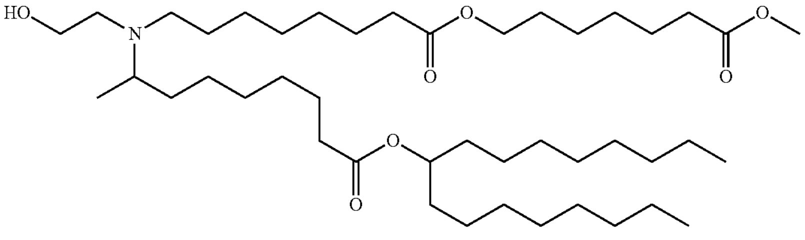
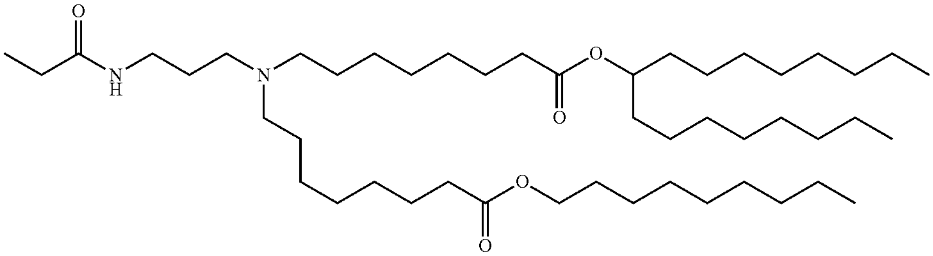

-continued
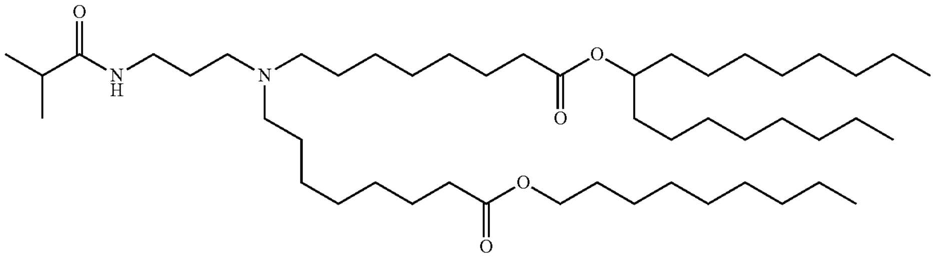
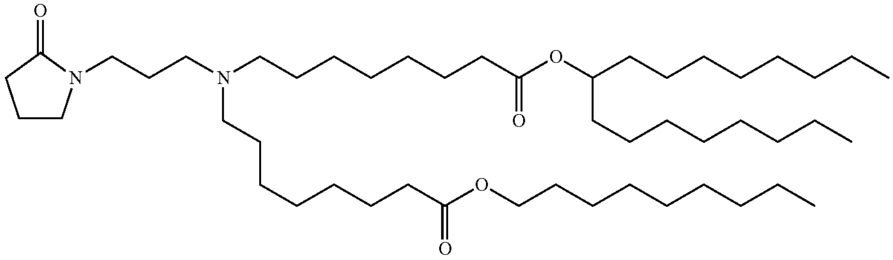
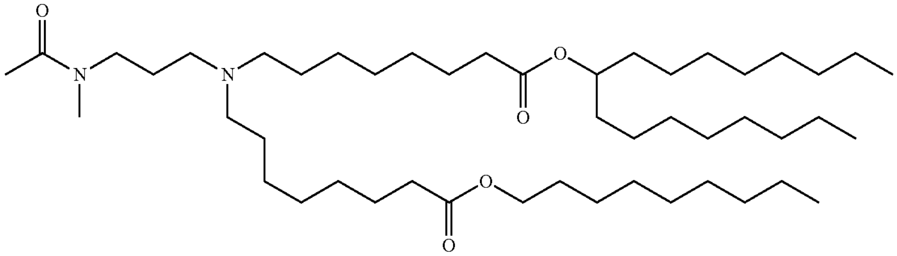
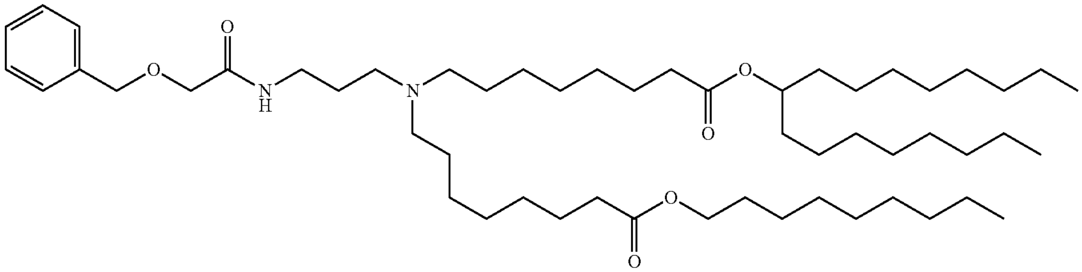
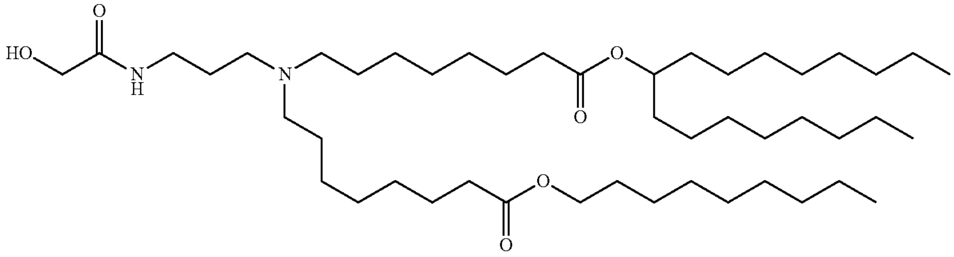
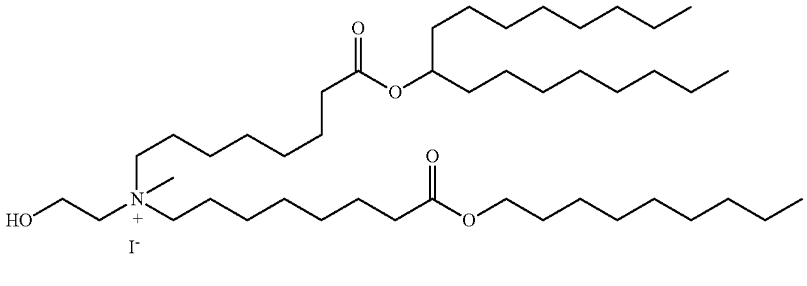

-continued
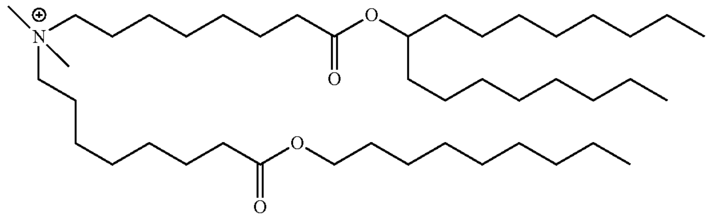
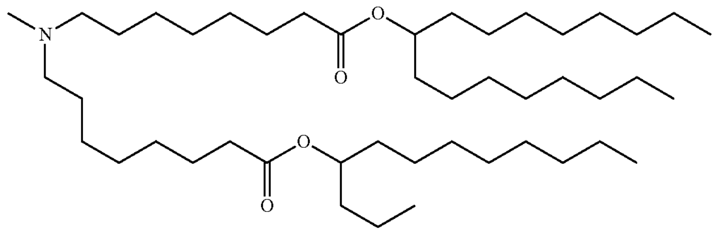
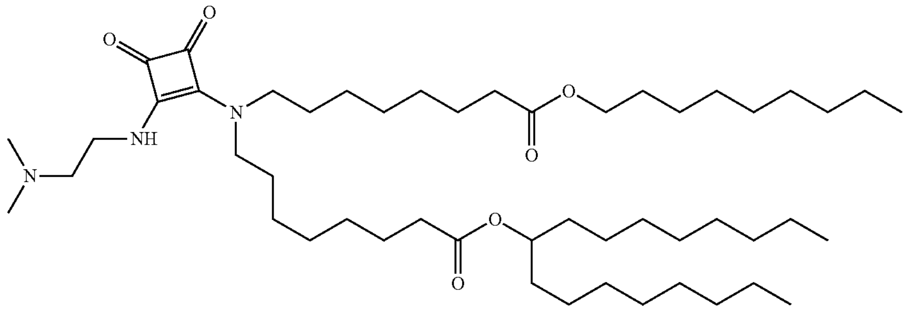
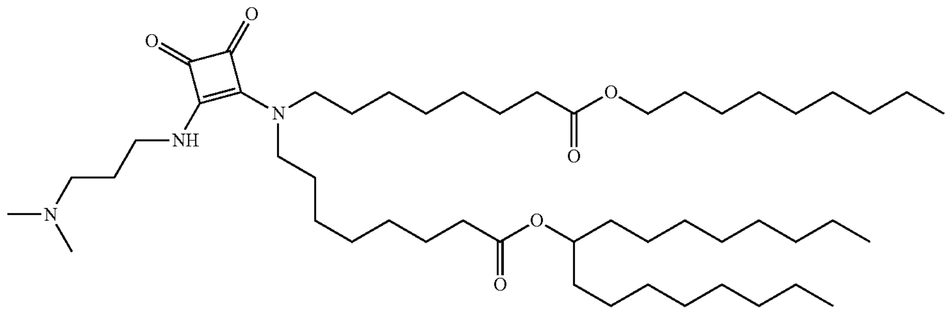
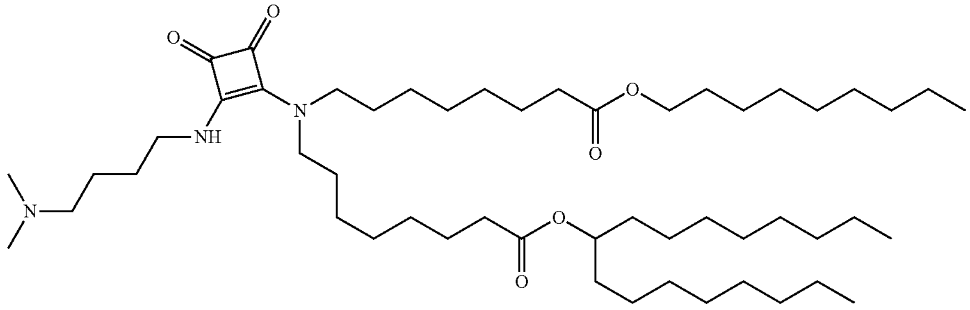
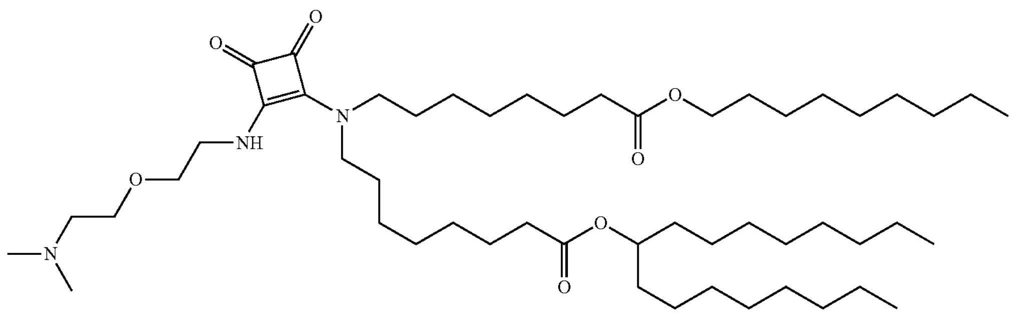

-continued
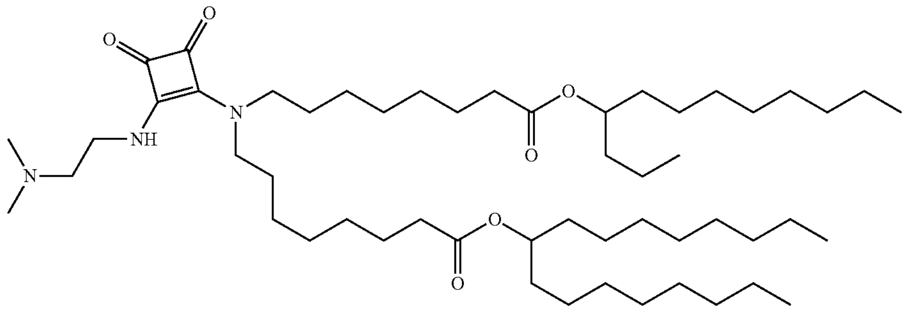
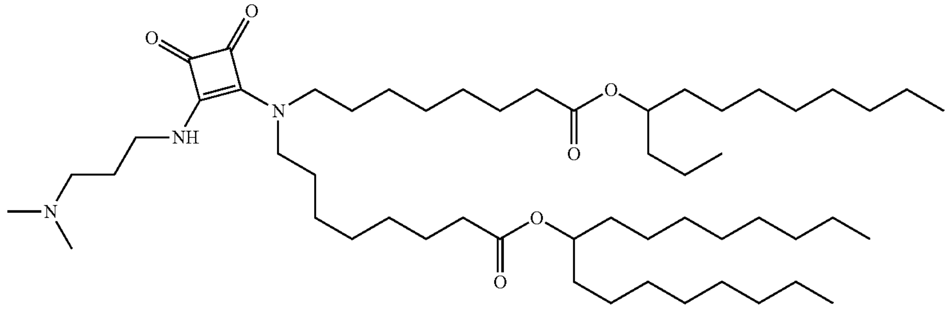
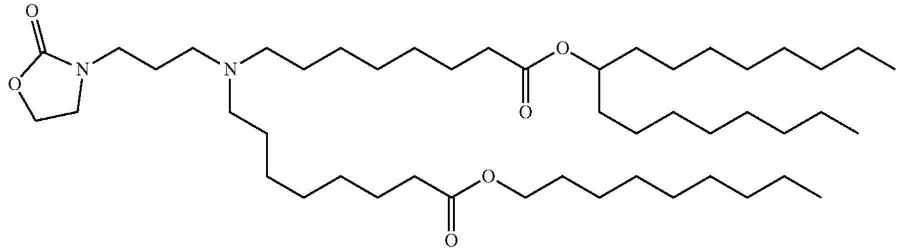
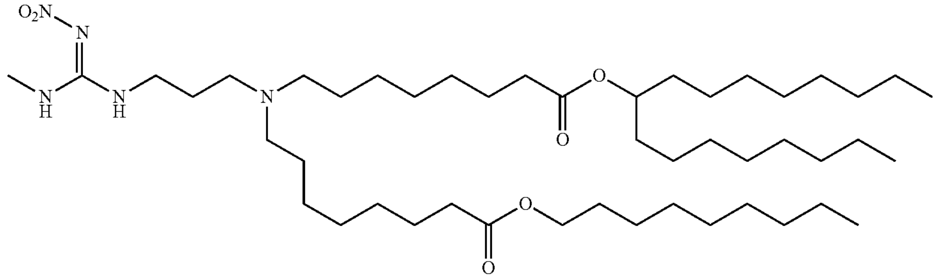
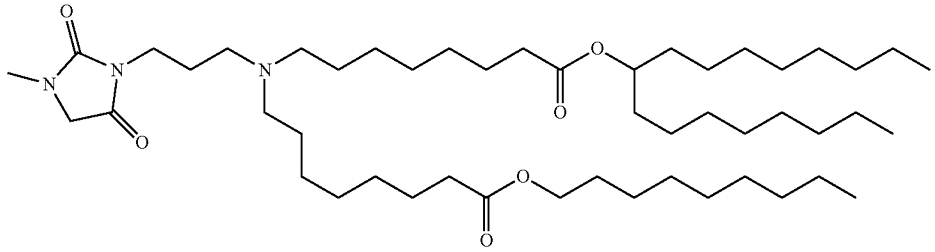
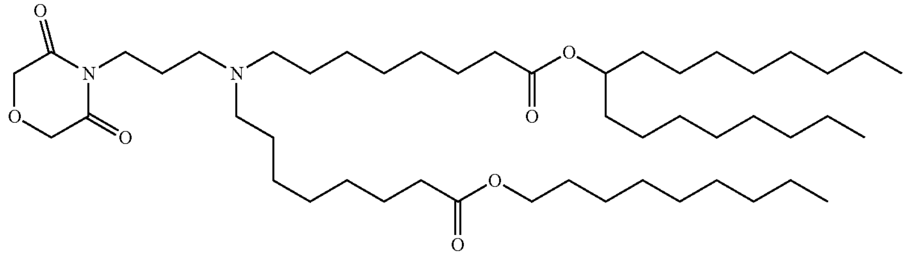

-continued
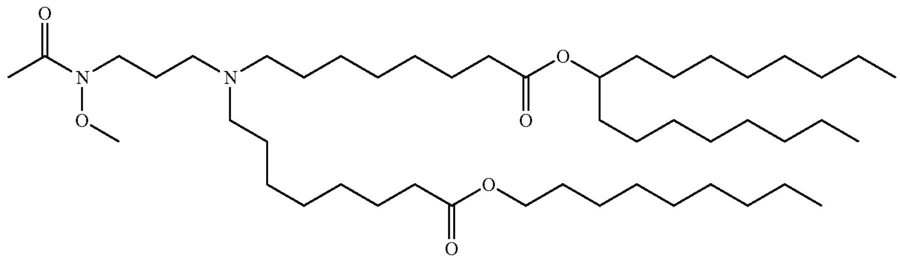
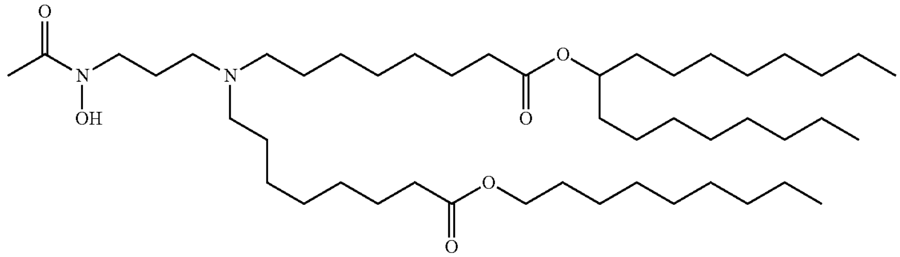
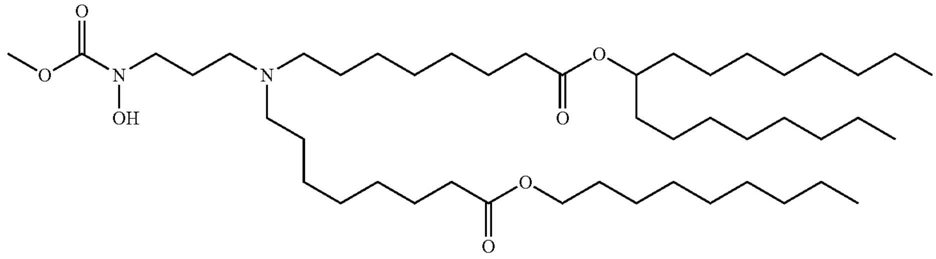
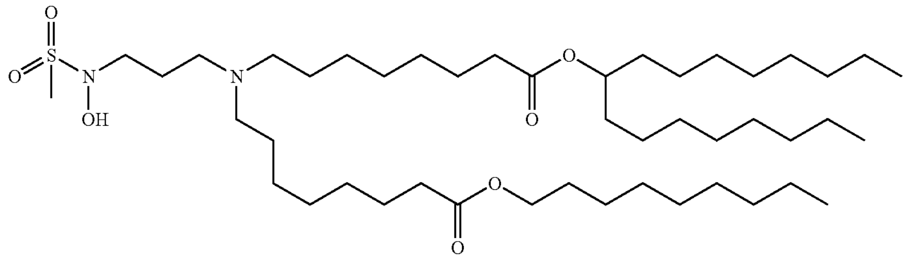
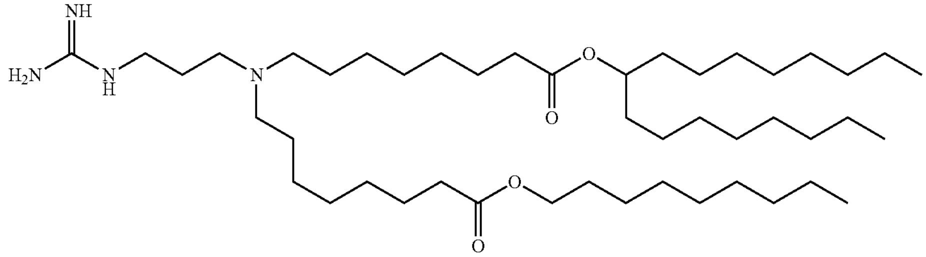
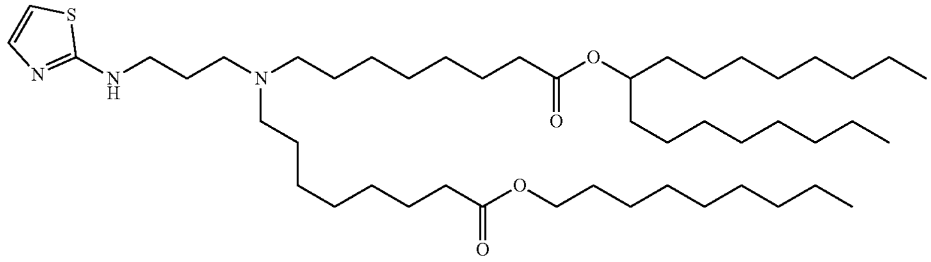

-continued
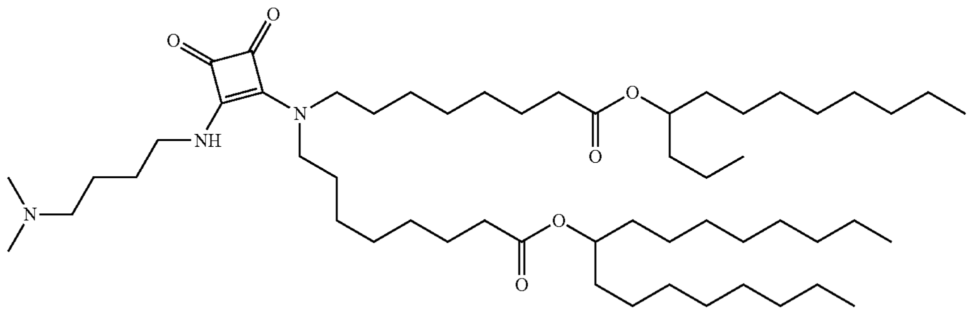
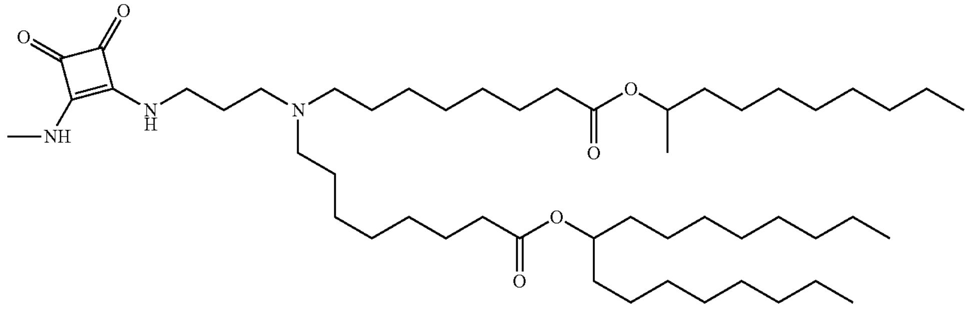
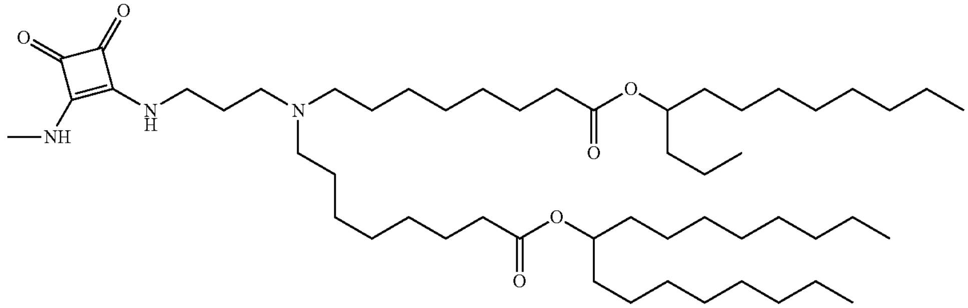
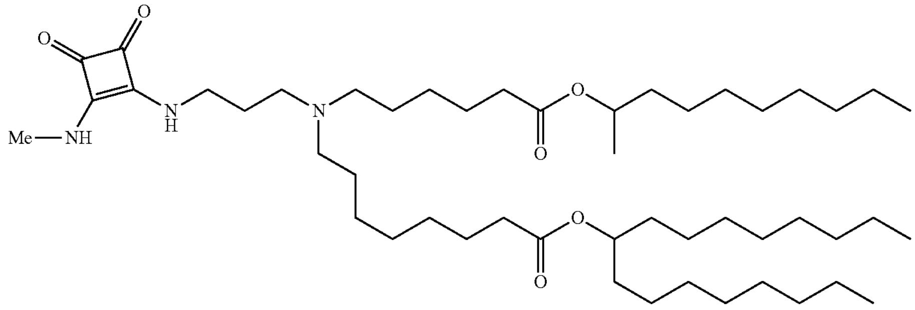
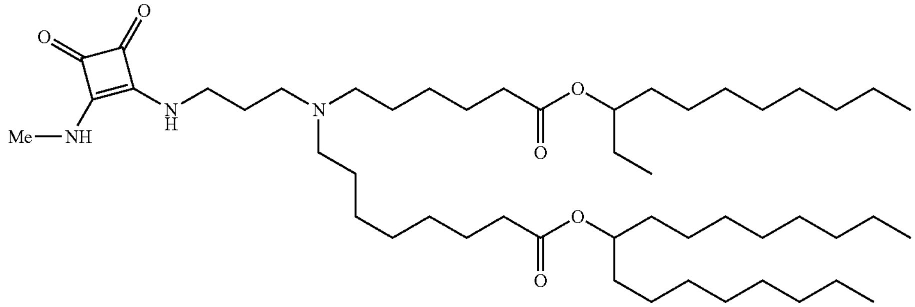

-continued
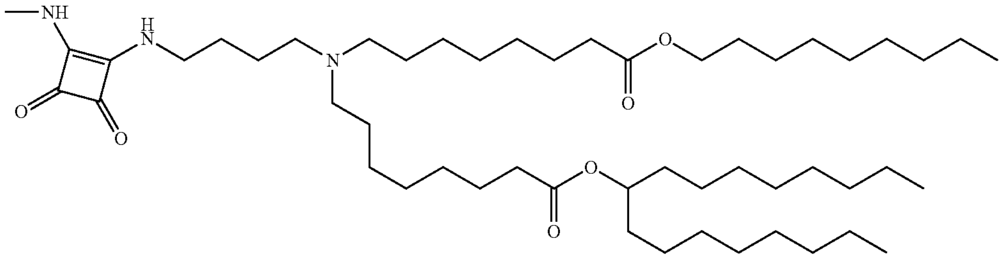
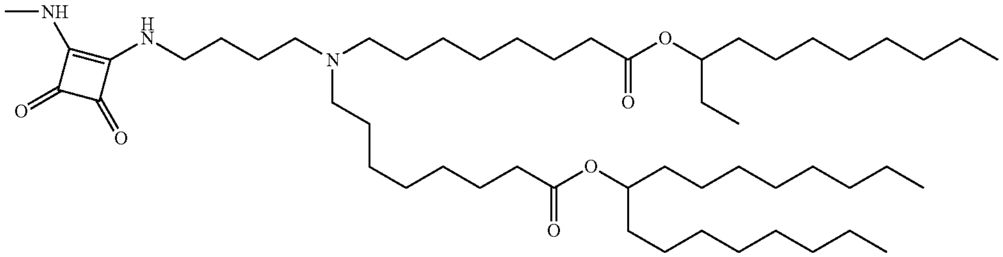
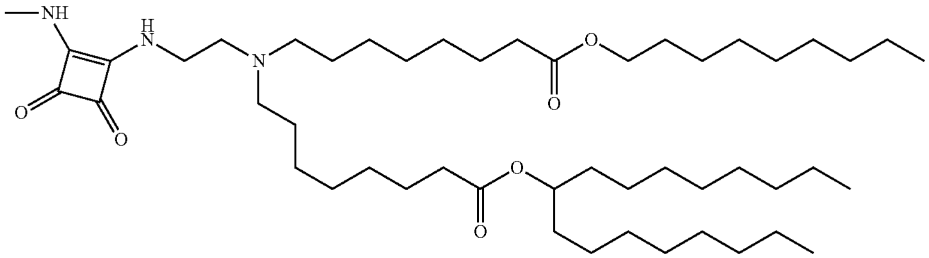
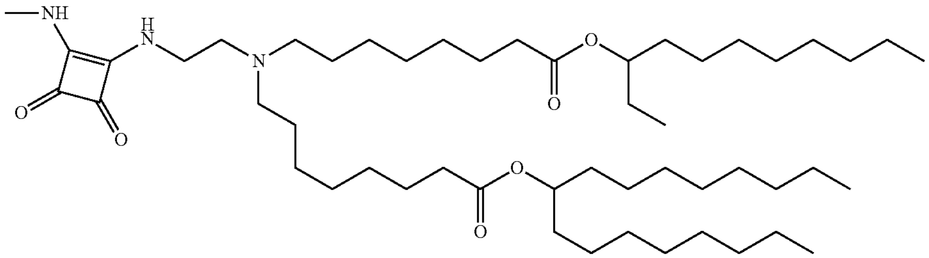
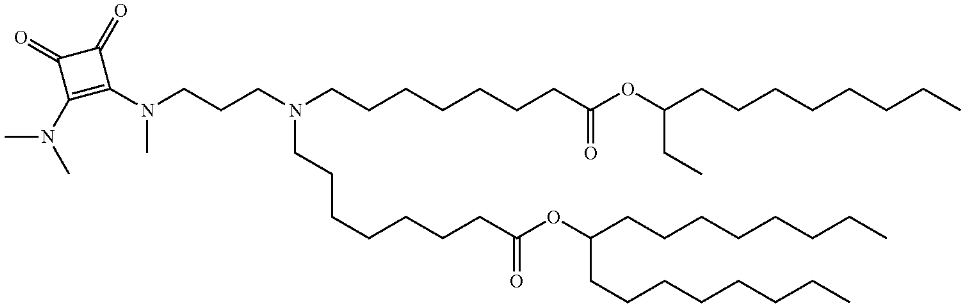
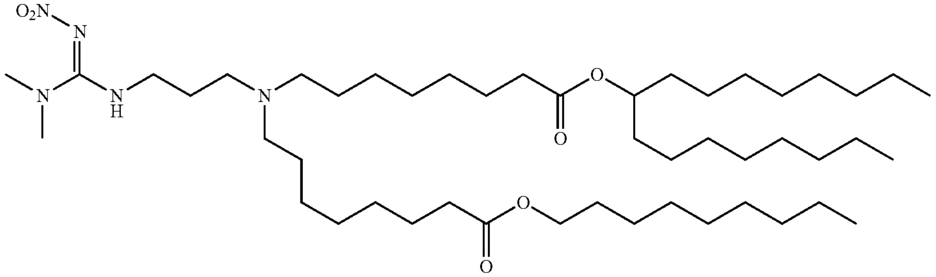

-continued
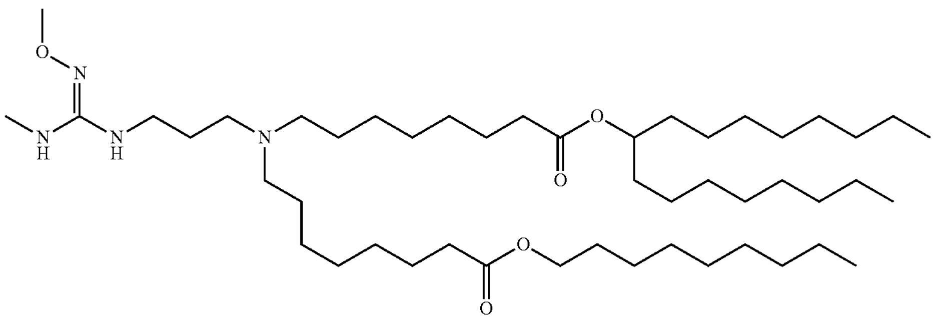
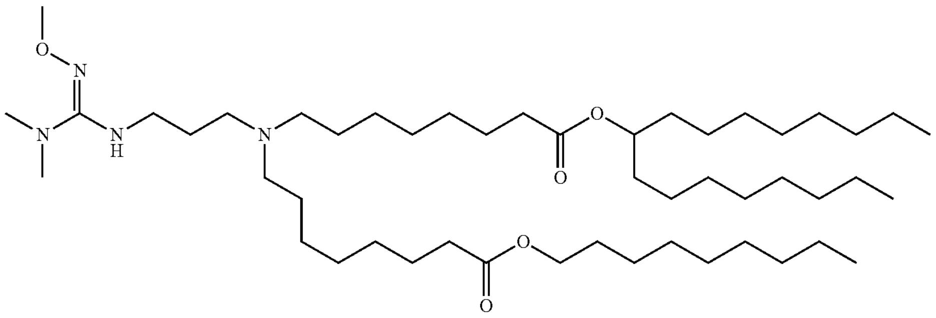
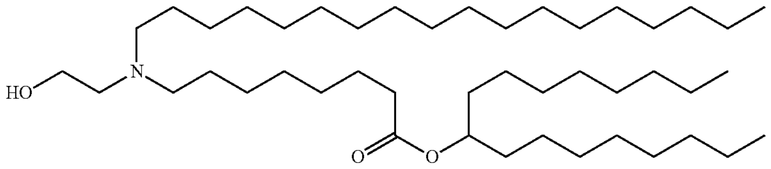
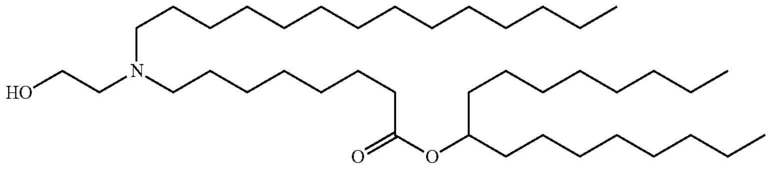
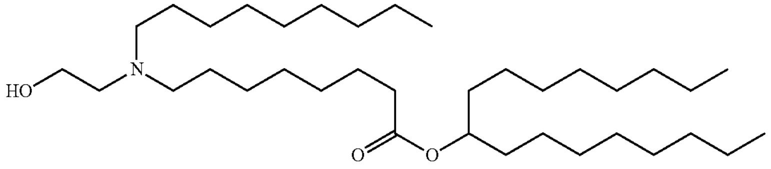
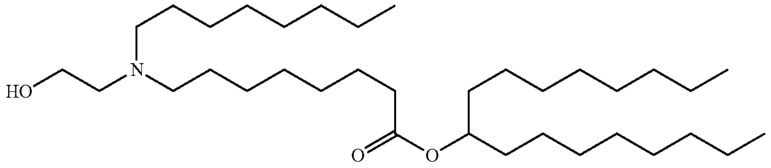
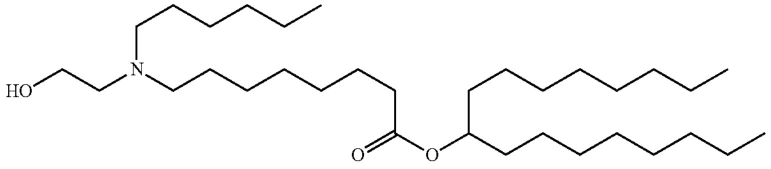
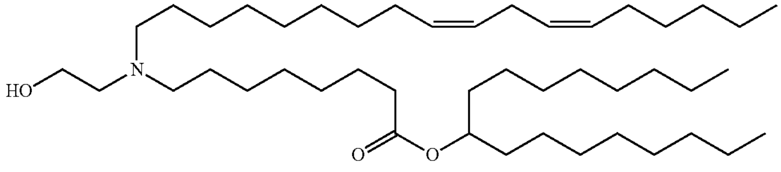

-continued
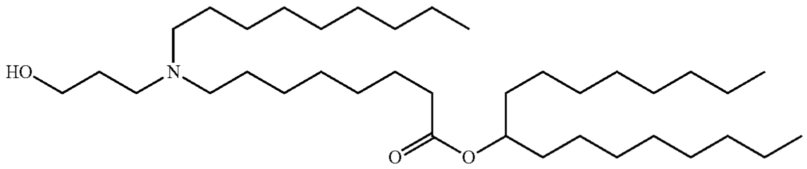
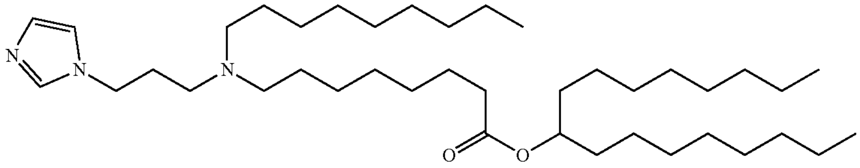
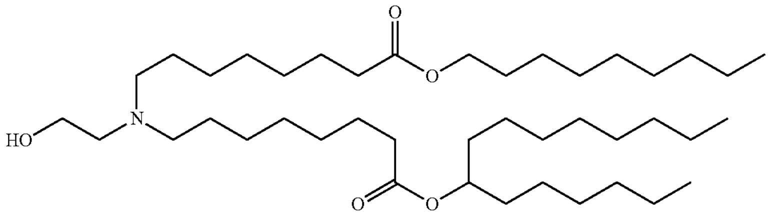
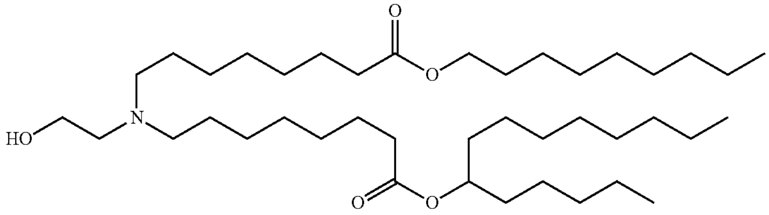
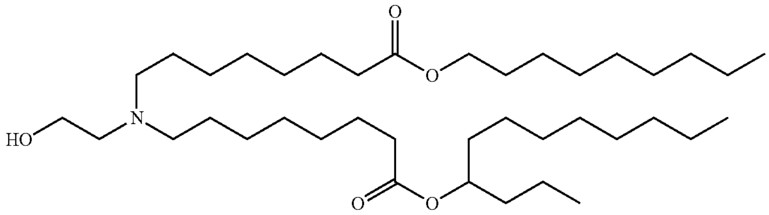
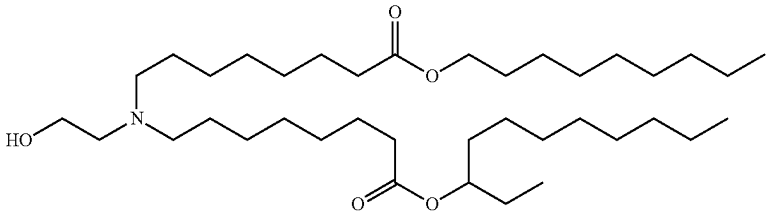
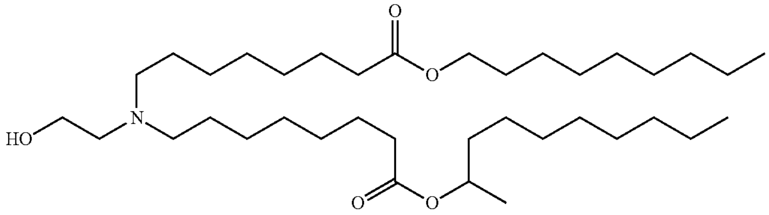
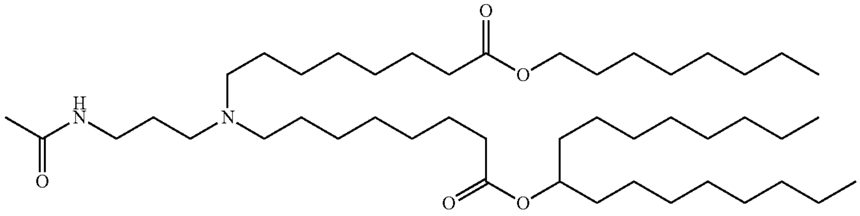

-continued
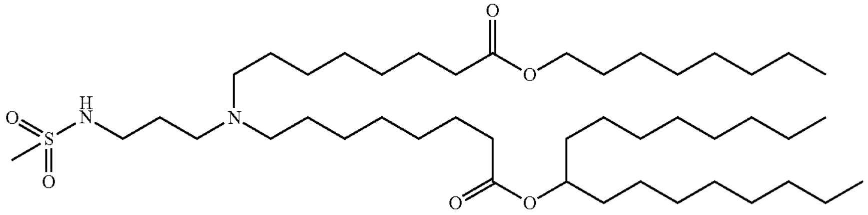
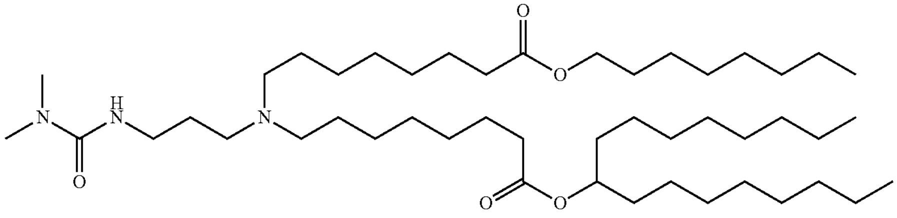
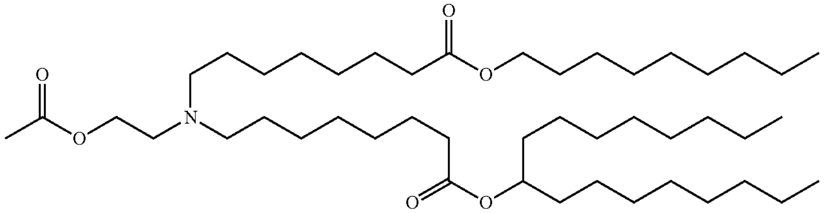
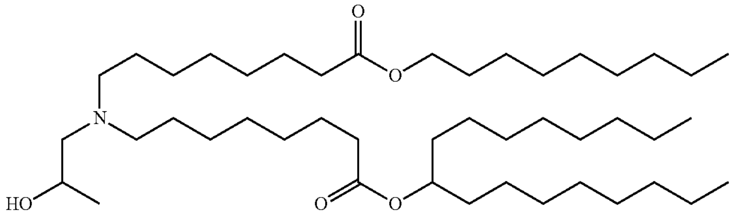
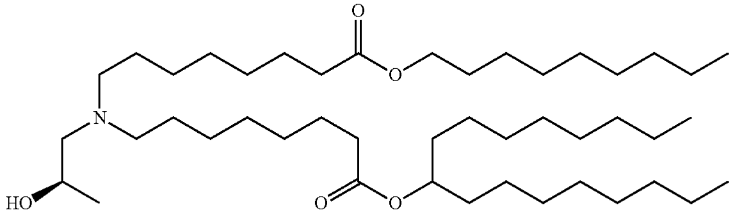
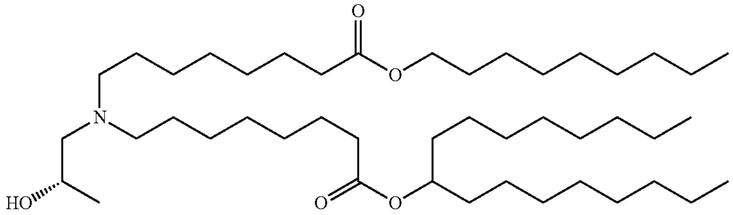
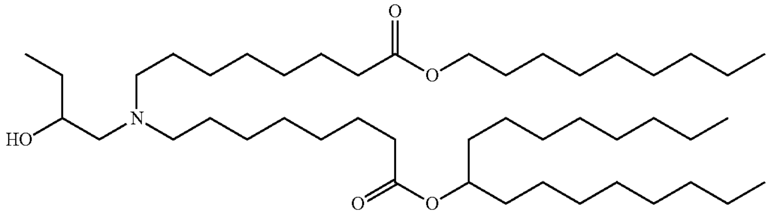
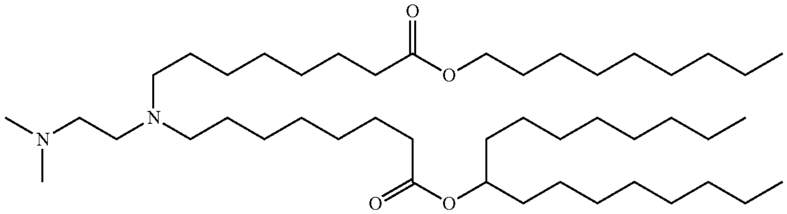

-continued
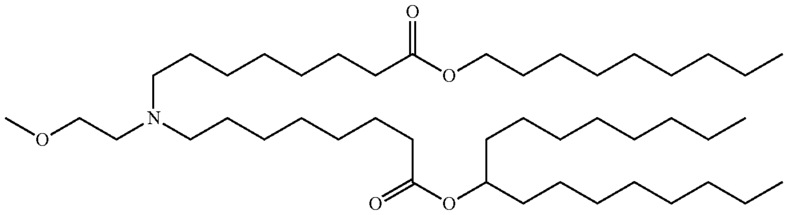
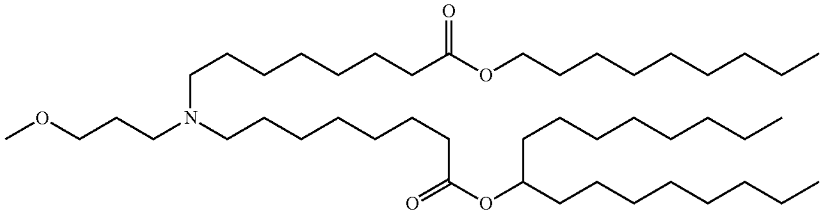
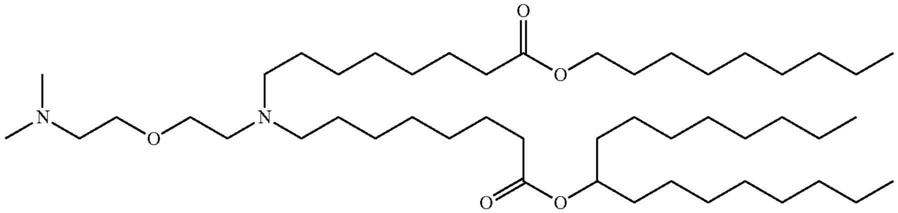
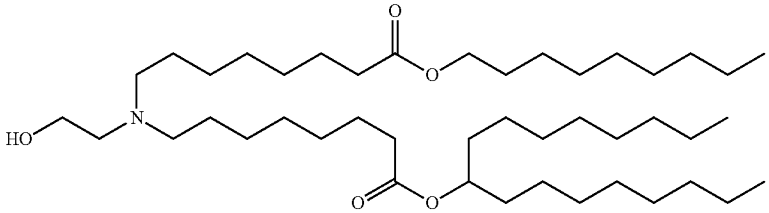
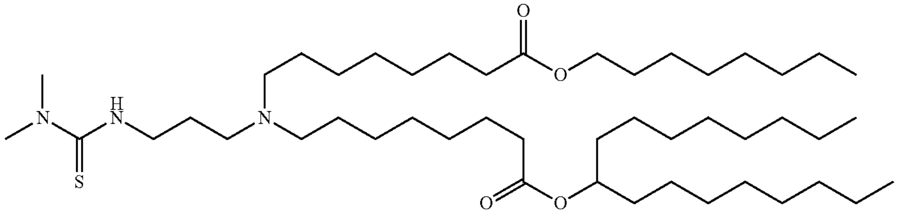
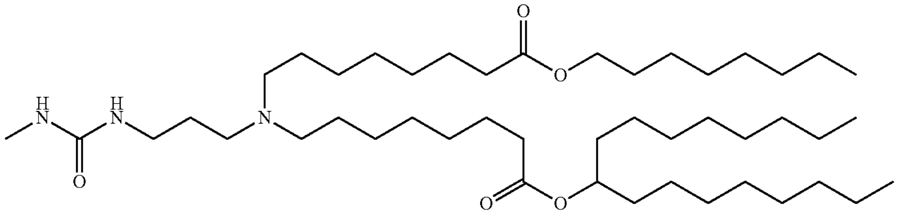
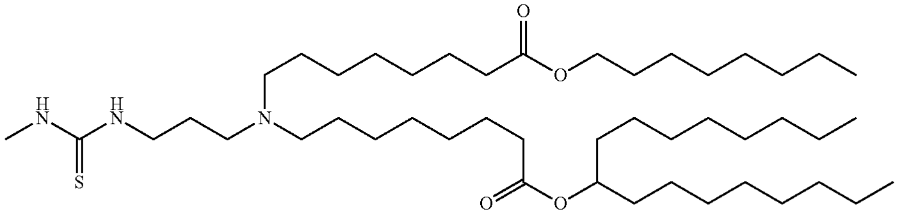
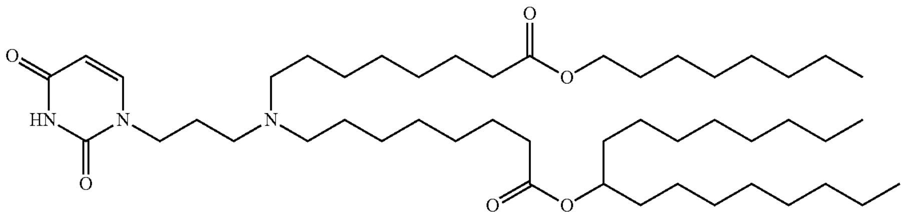

-continued
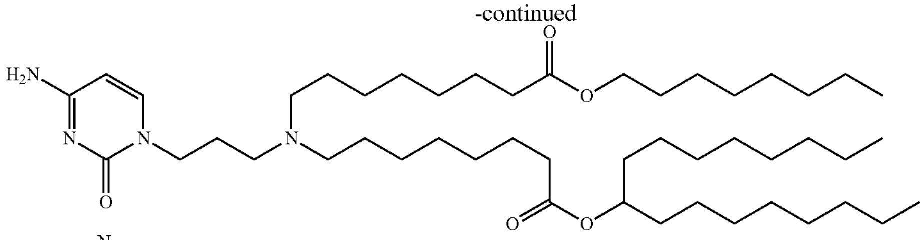
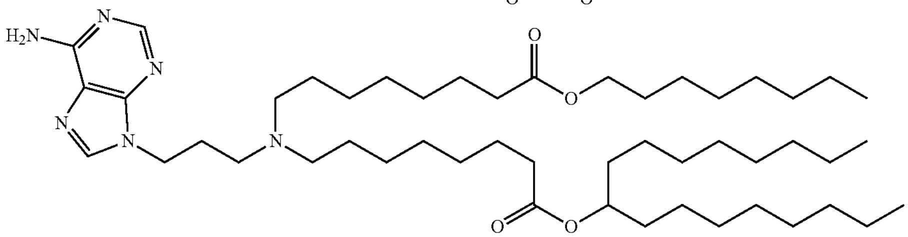
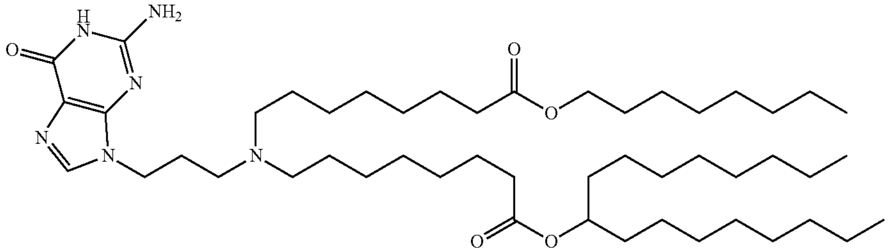
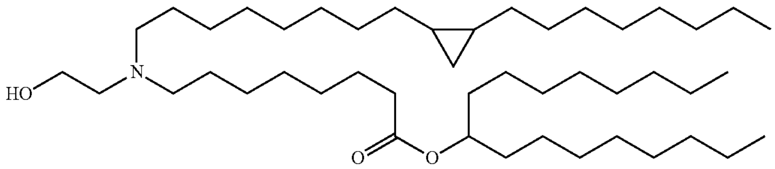
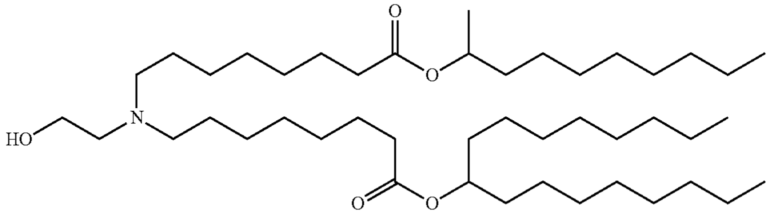
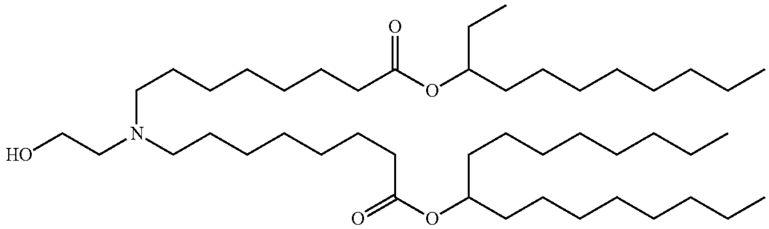
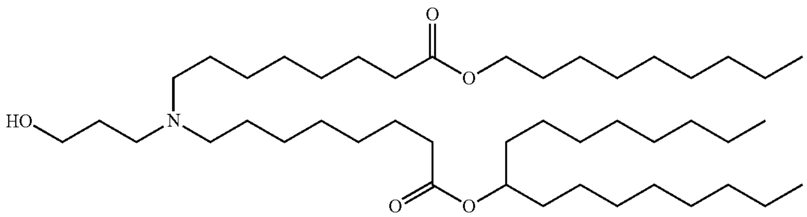
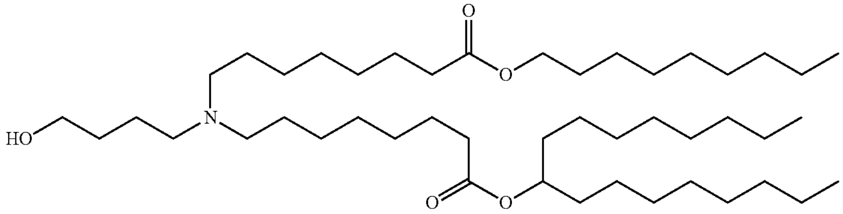

-continued
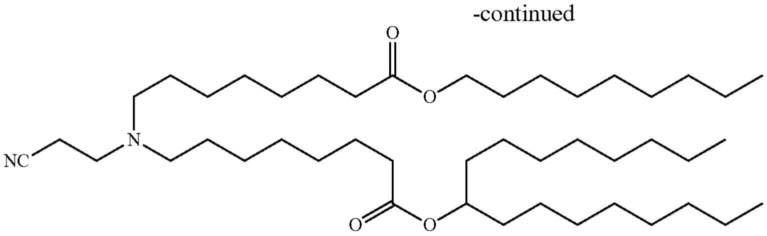
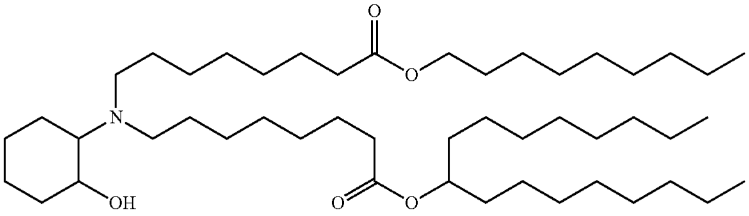
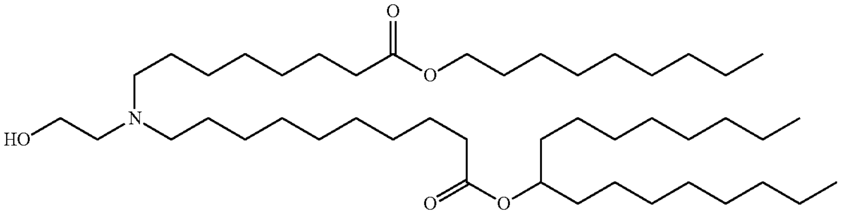
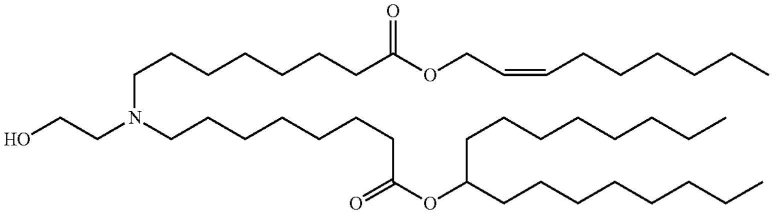
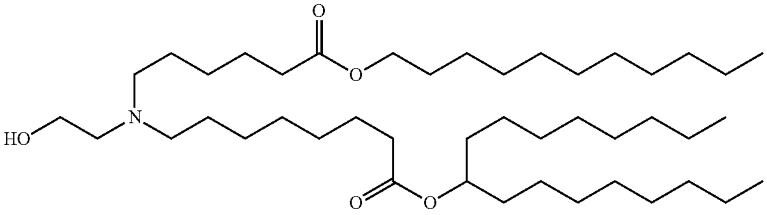
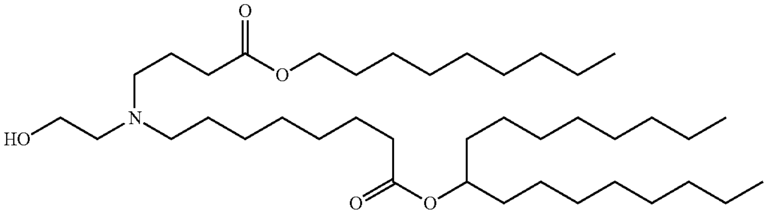
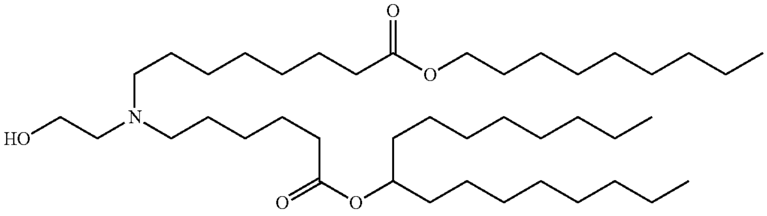
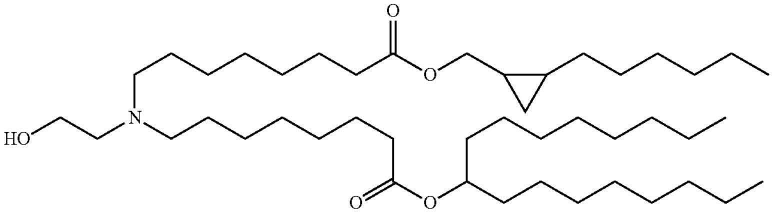

-continued
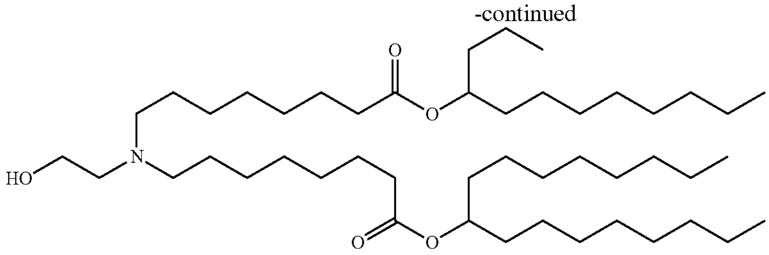
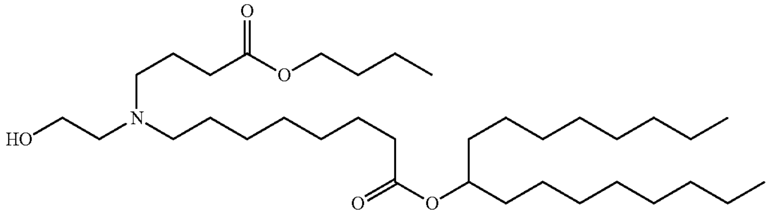
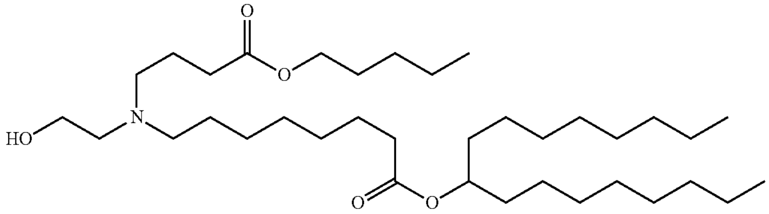
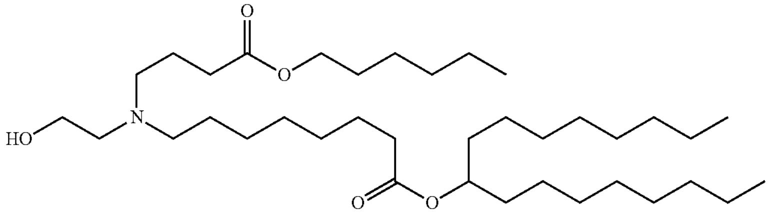
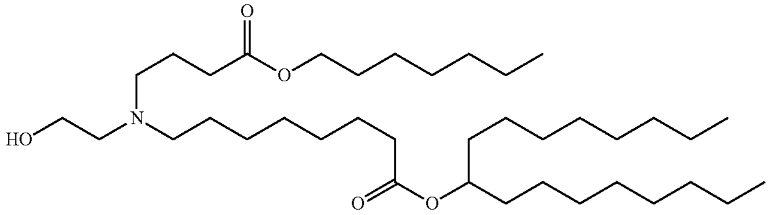
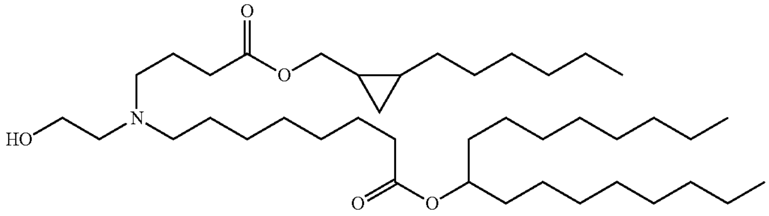
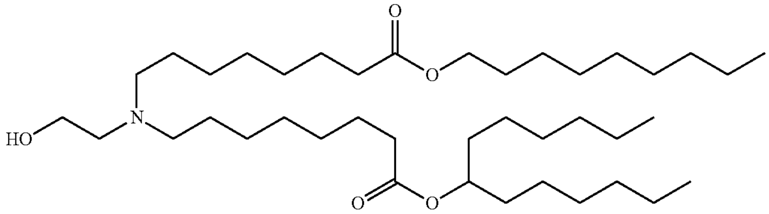
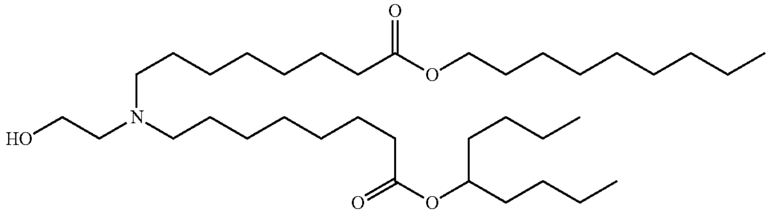

-continued
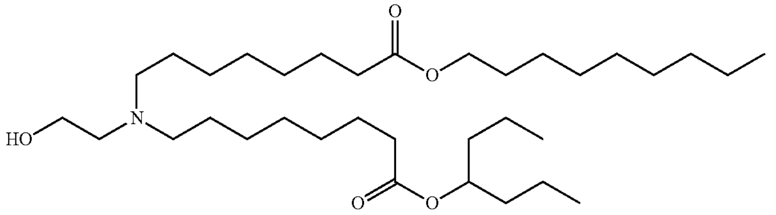
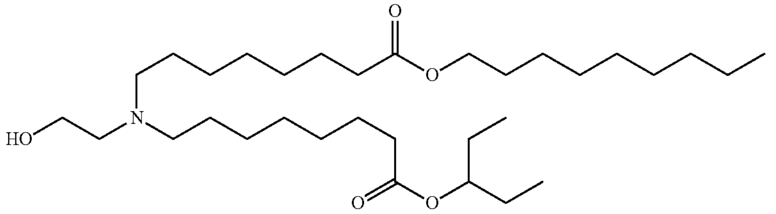
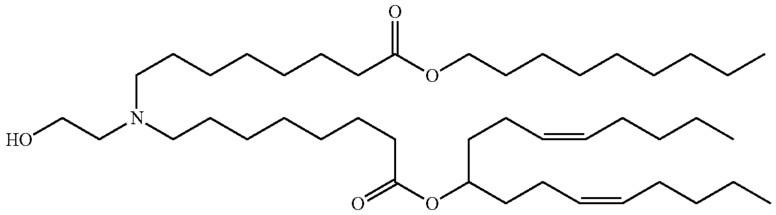
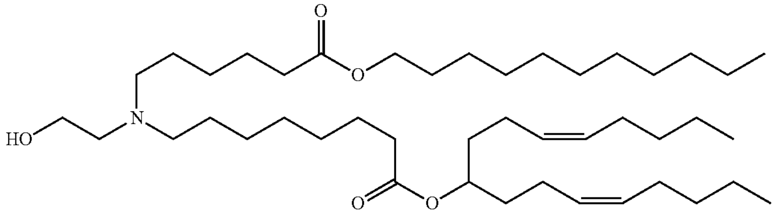
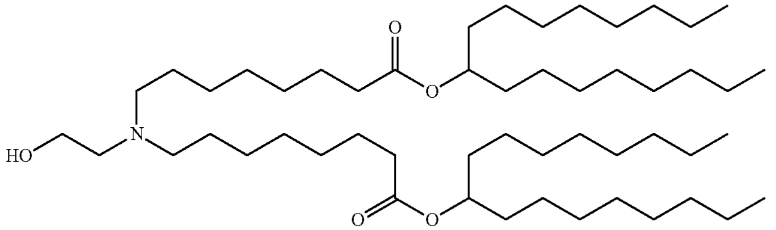
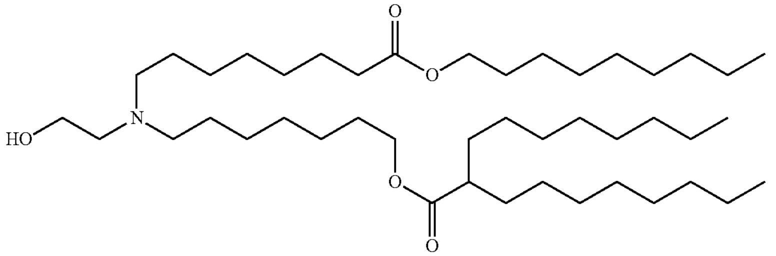
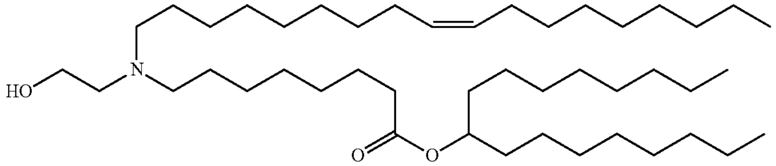
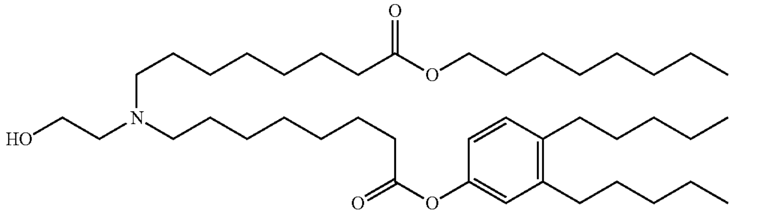

-continued
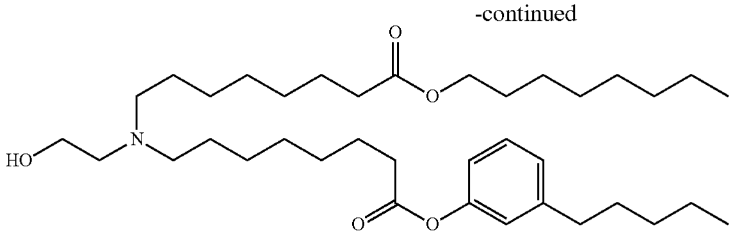
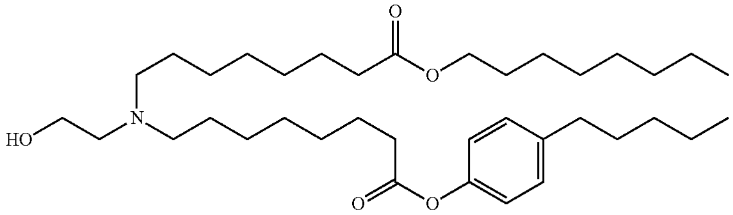
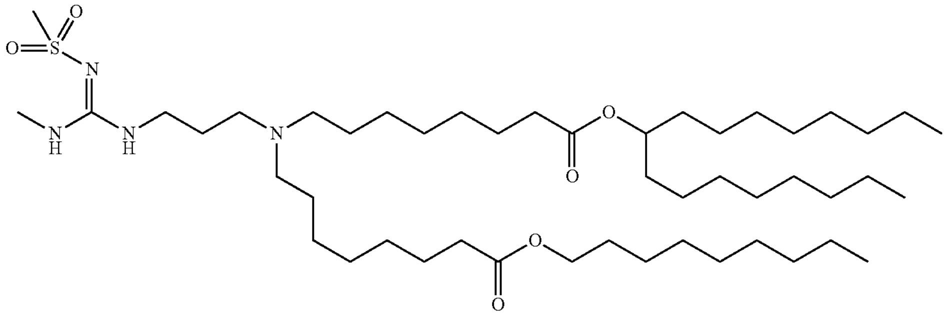
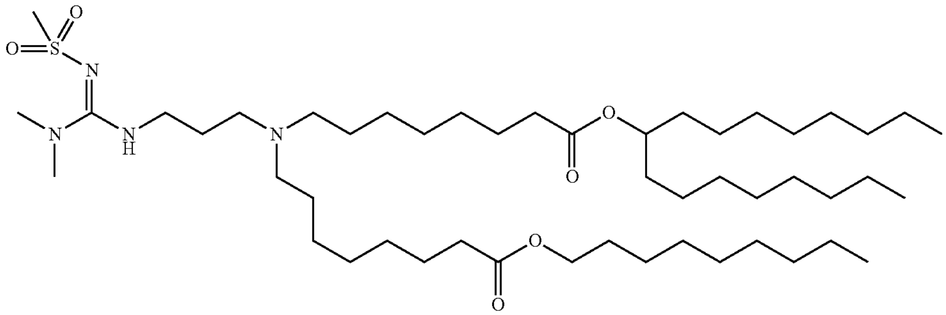
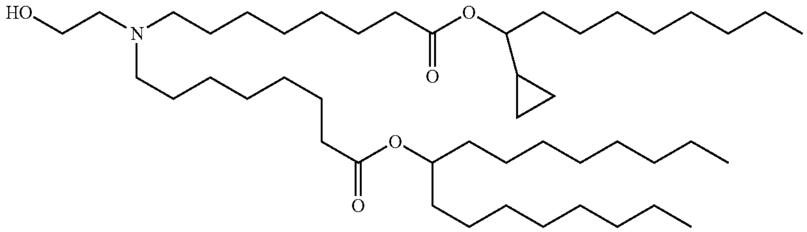
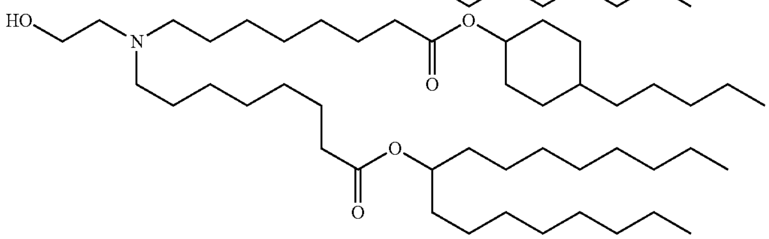

-continued
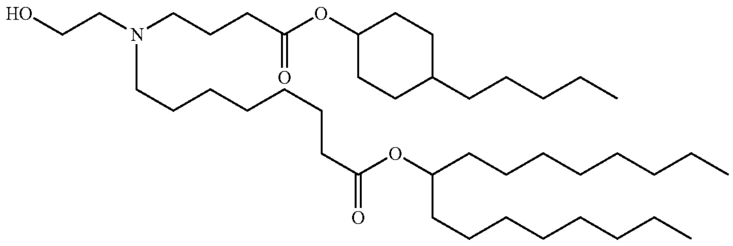
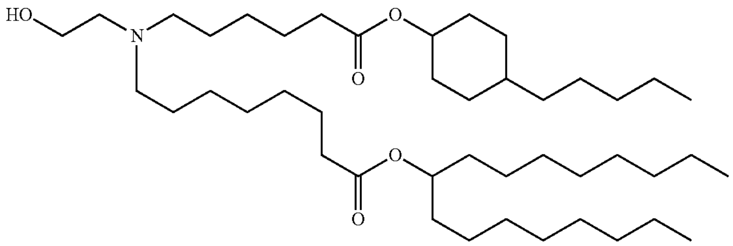
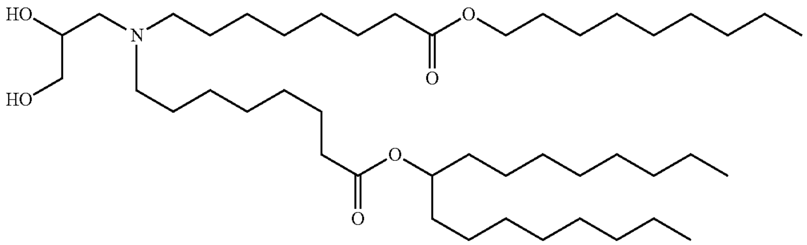
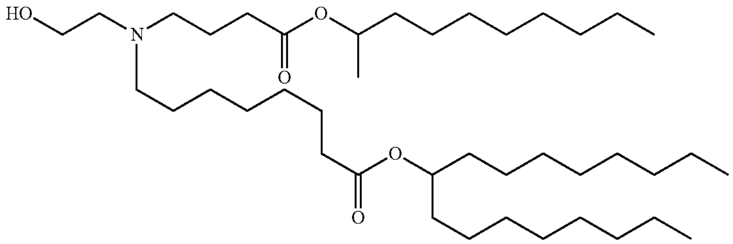
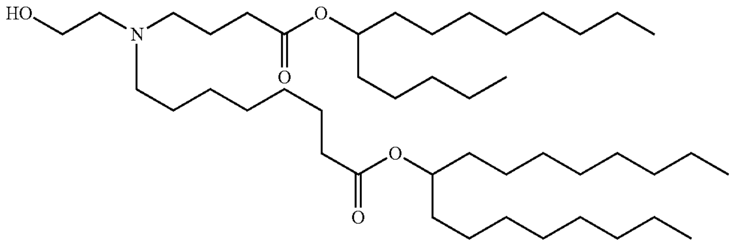
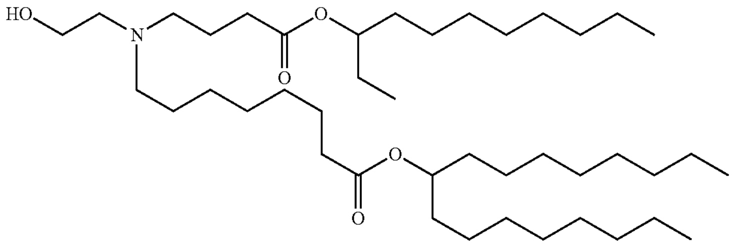
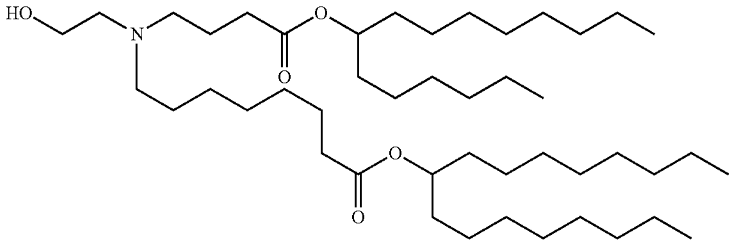

-continued
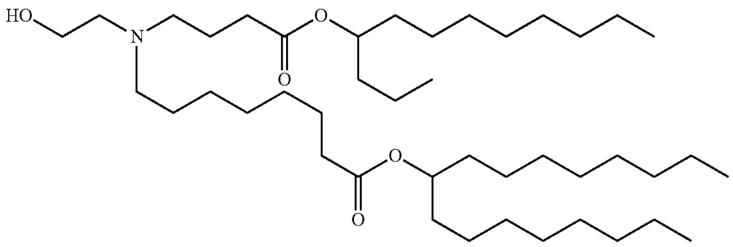
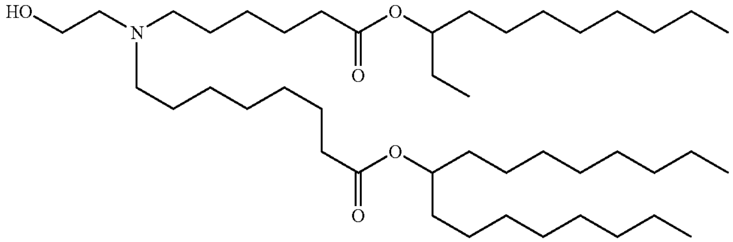
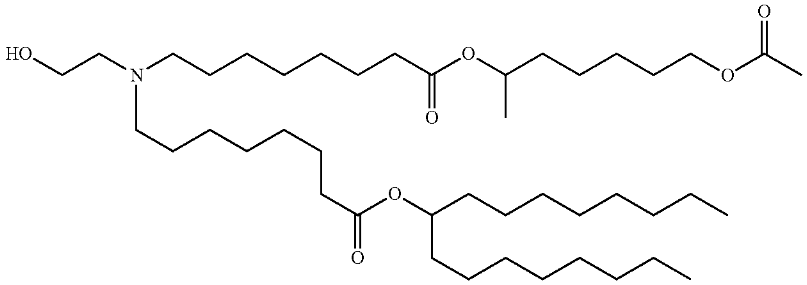
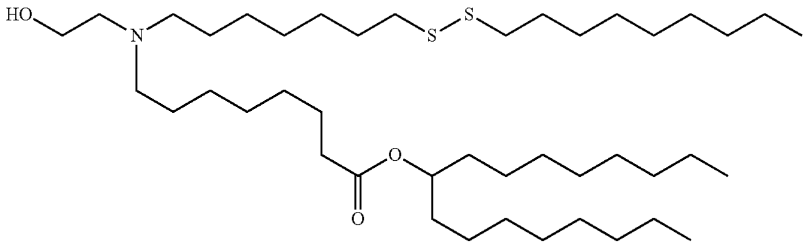
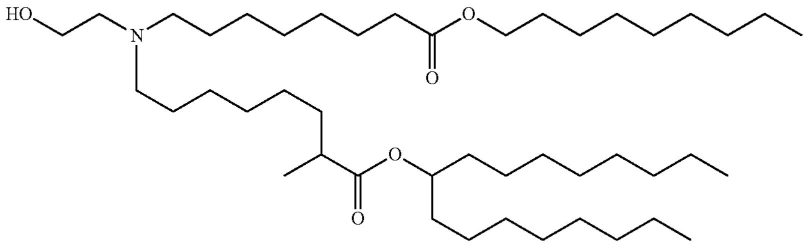
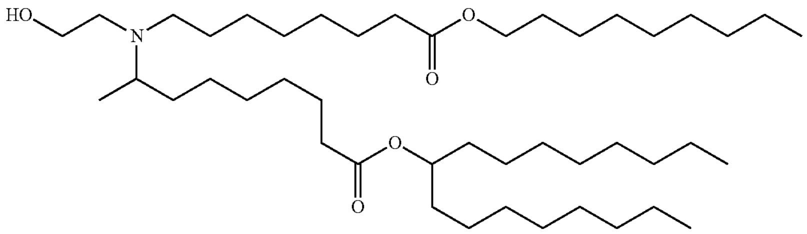
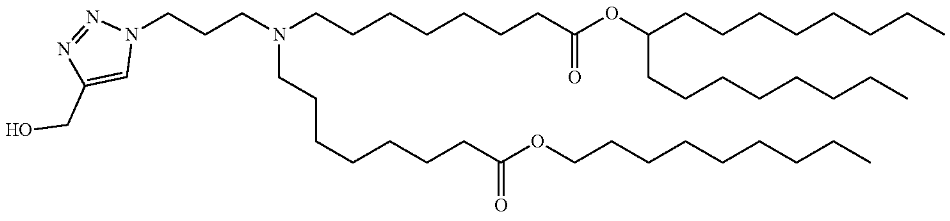

-continued
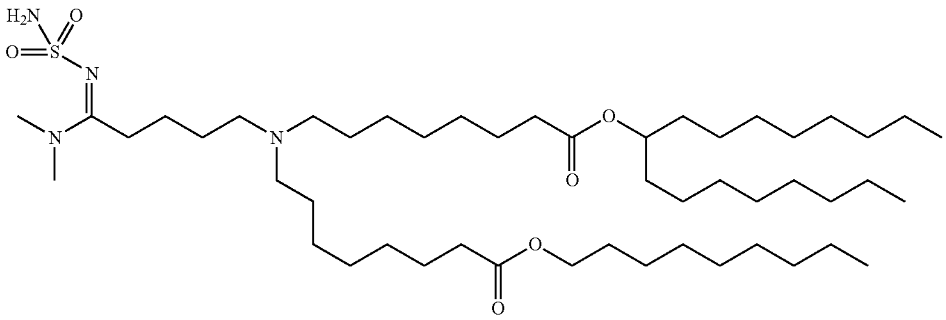
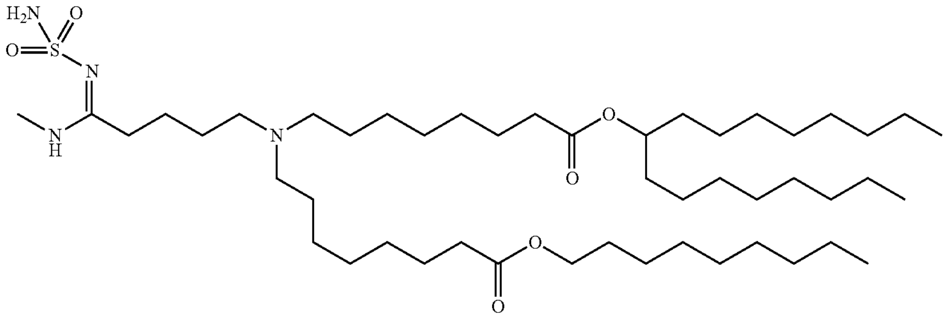
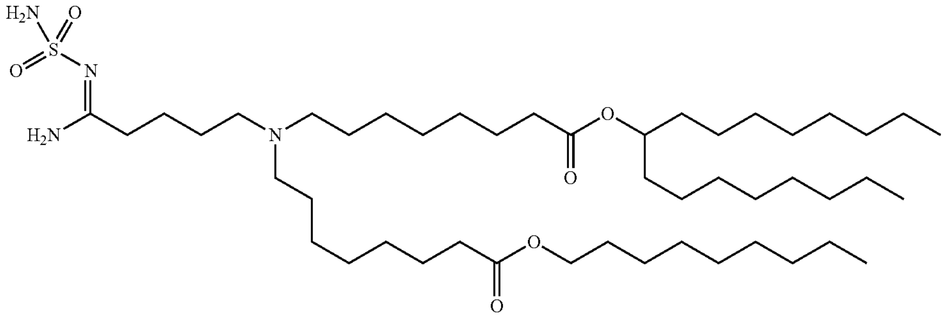
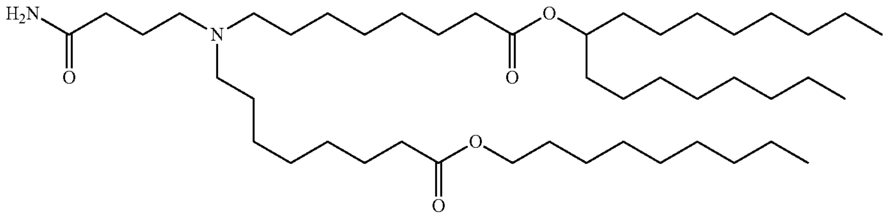
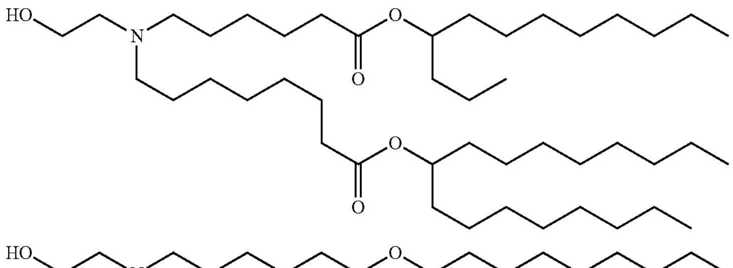
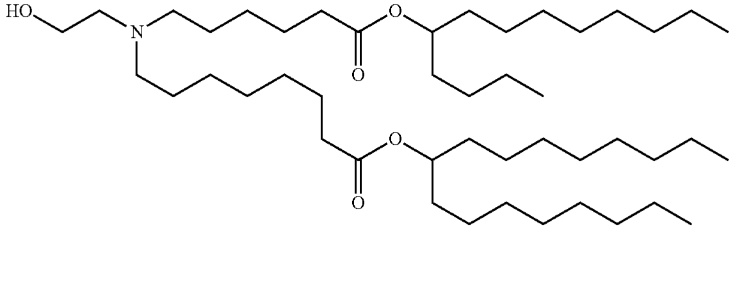

-continued
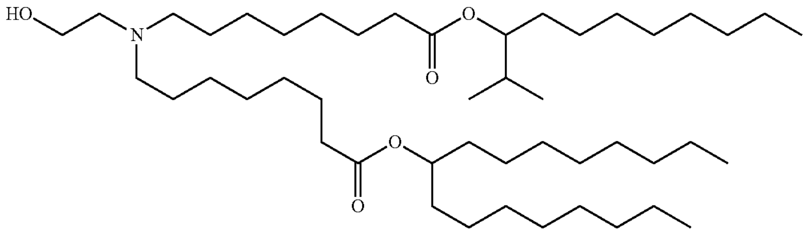
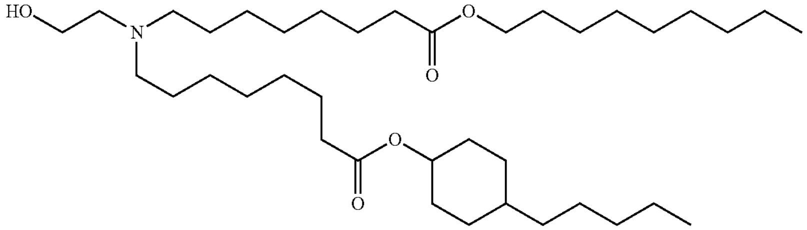
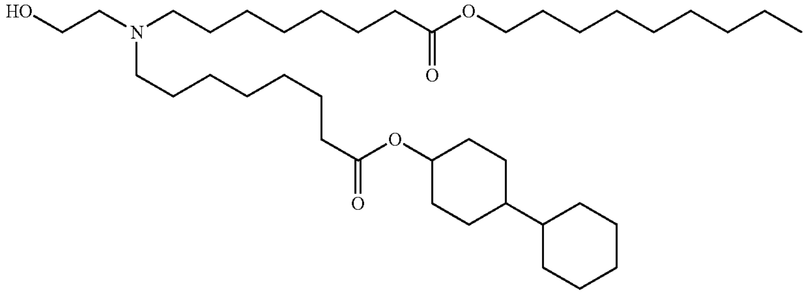
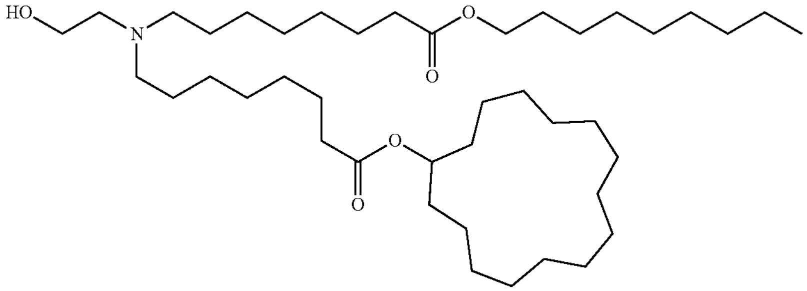
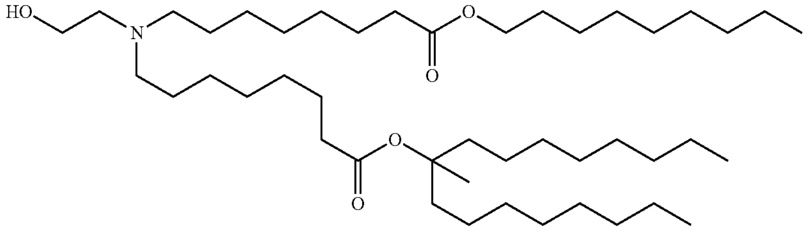
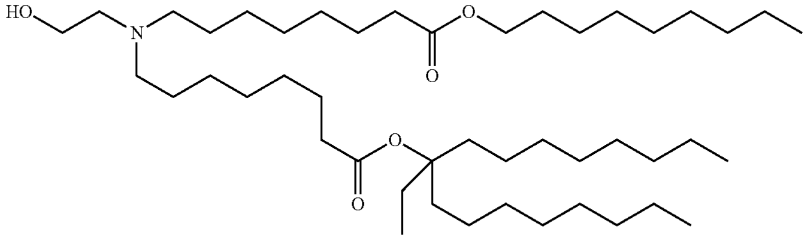

-continued
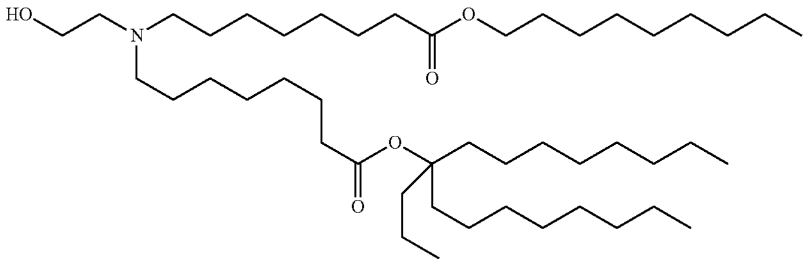
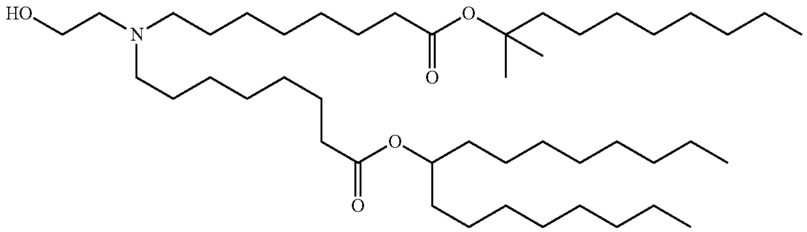
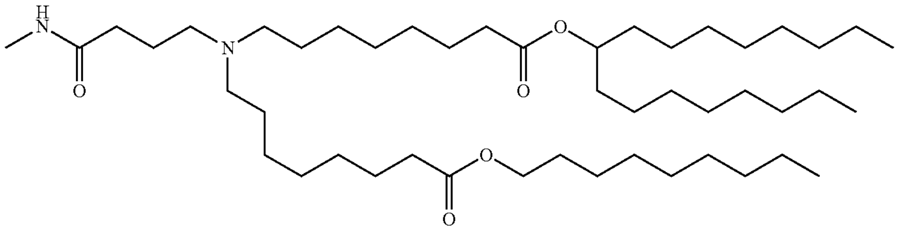
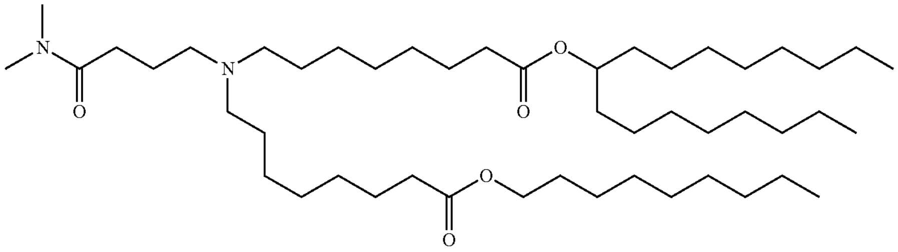
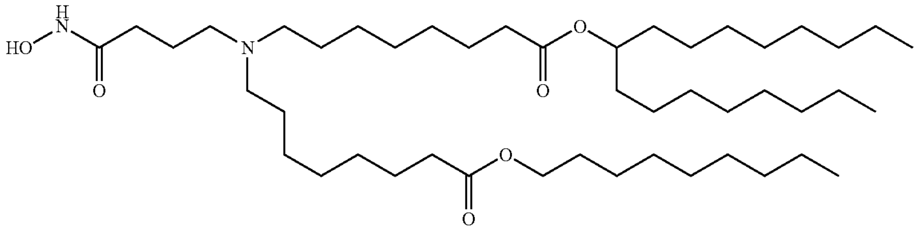
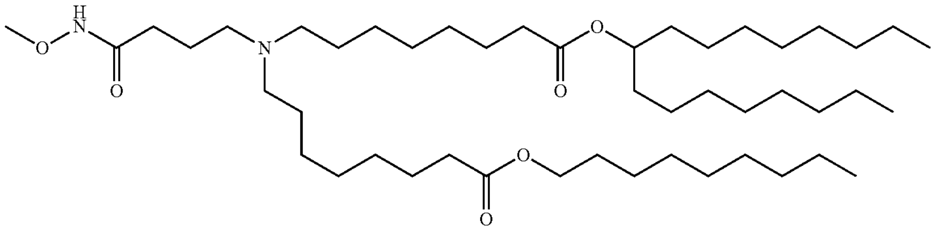
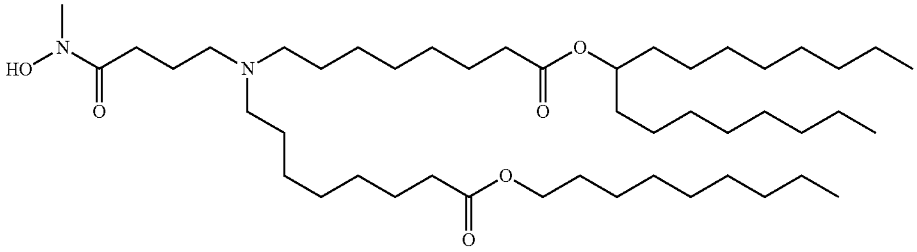

-continued
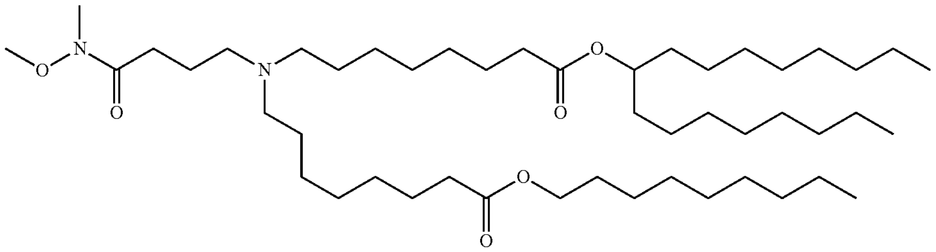
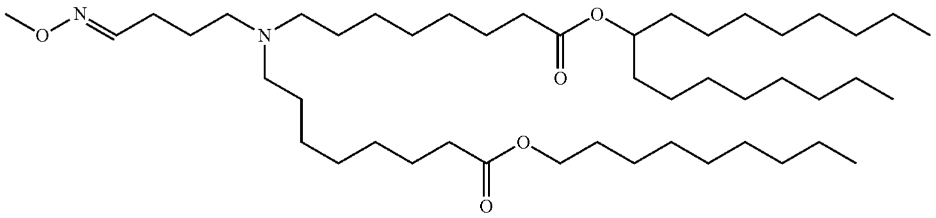
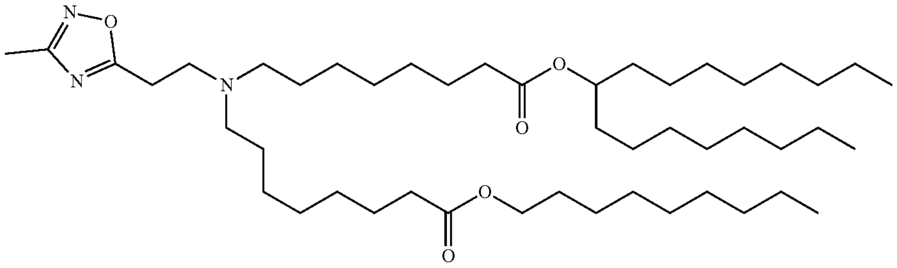
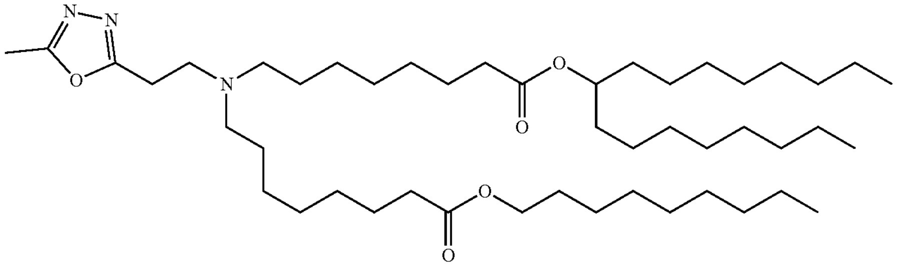
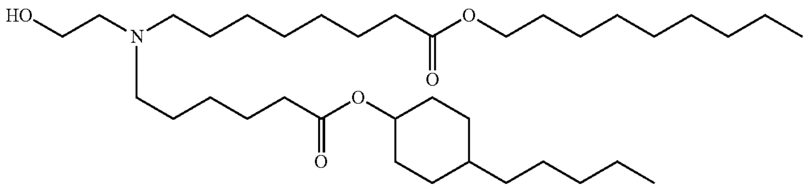
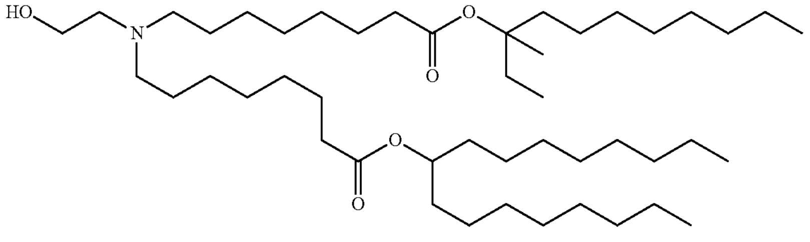
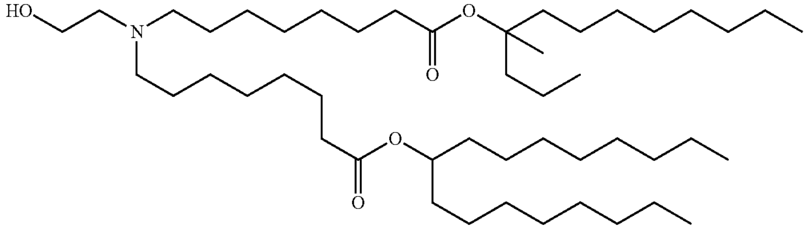

-continued
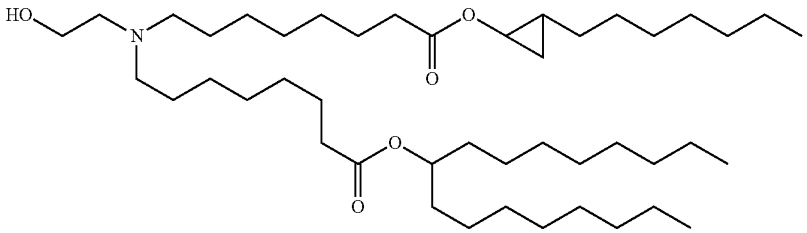
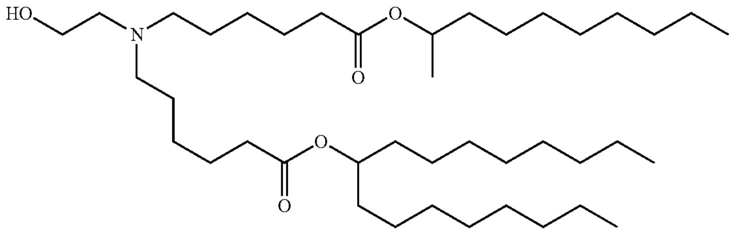
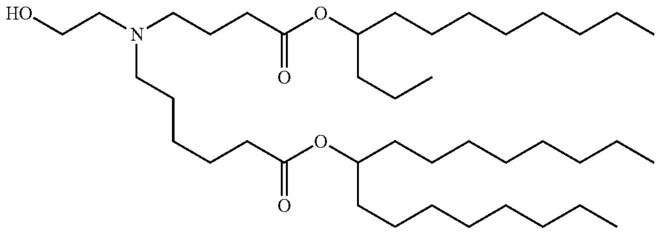
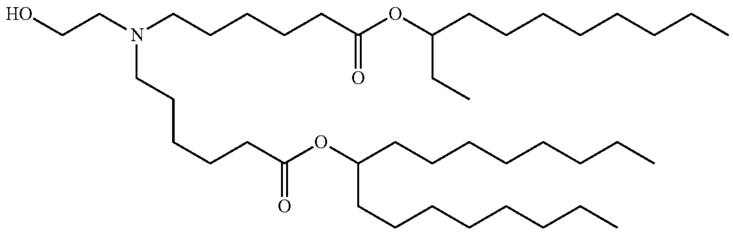
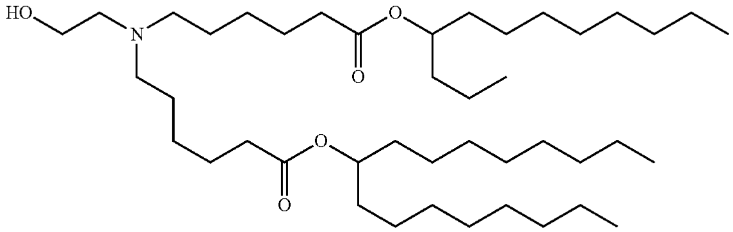
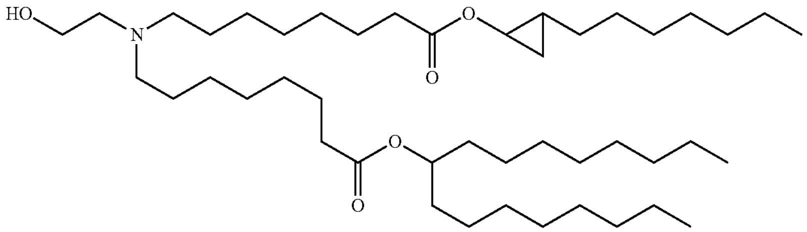
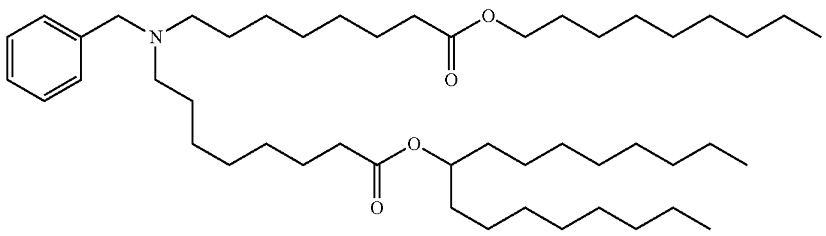

-continued
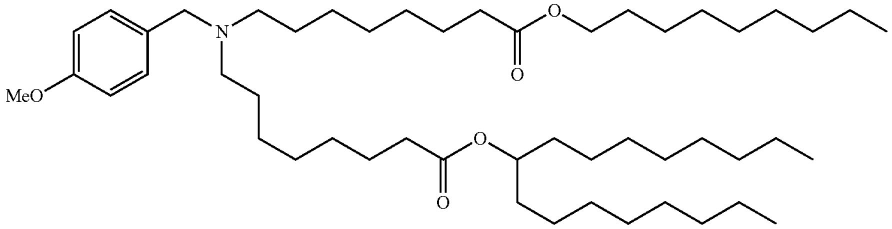
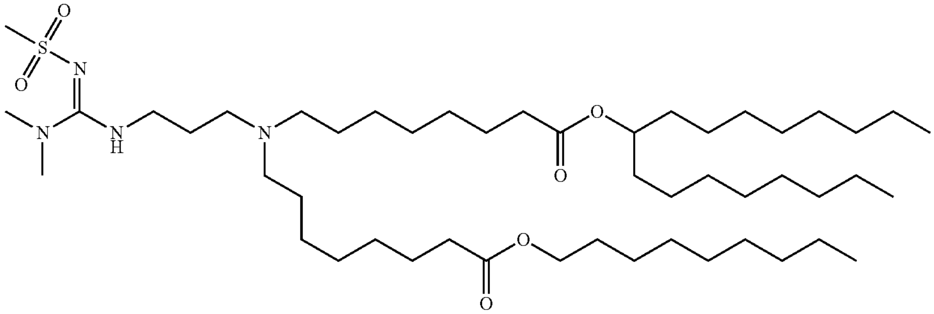
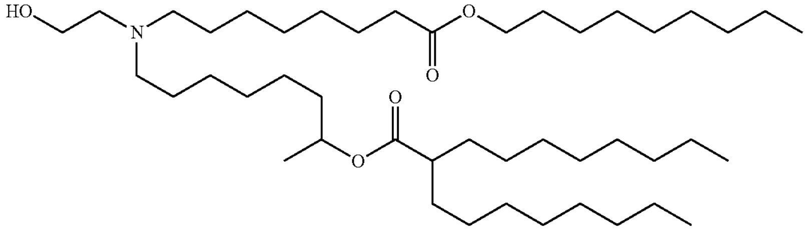
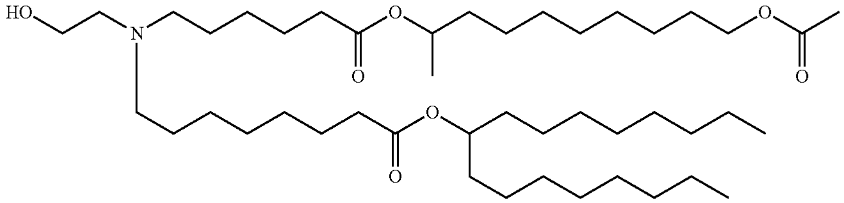
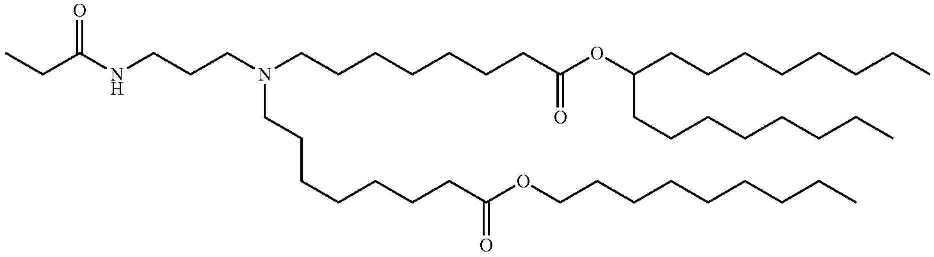
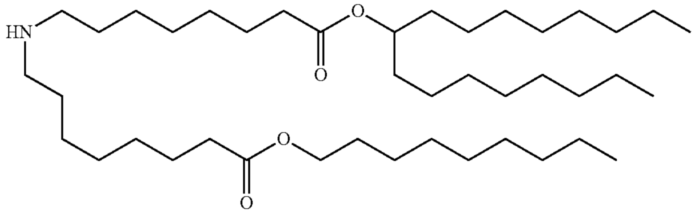
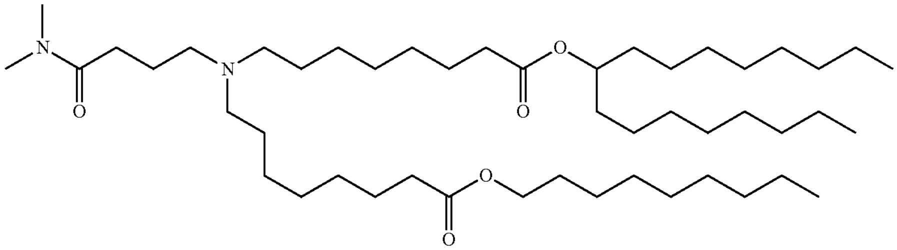

-continued
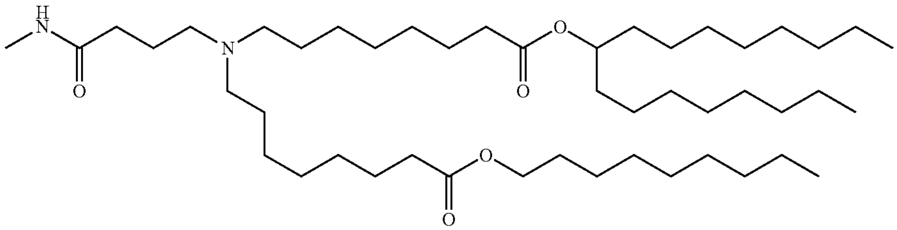
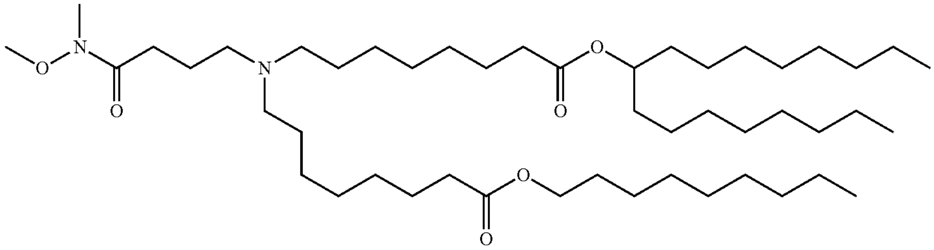
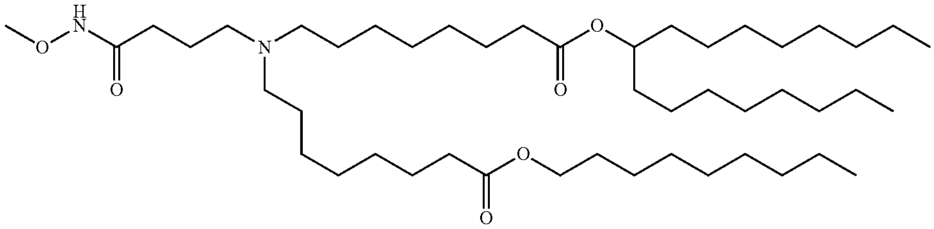
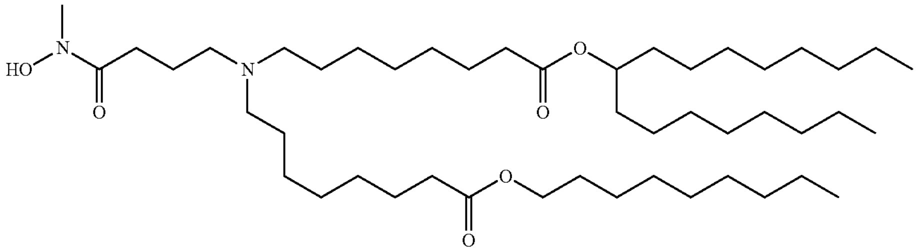
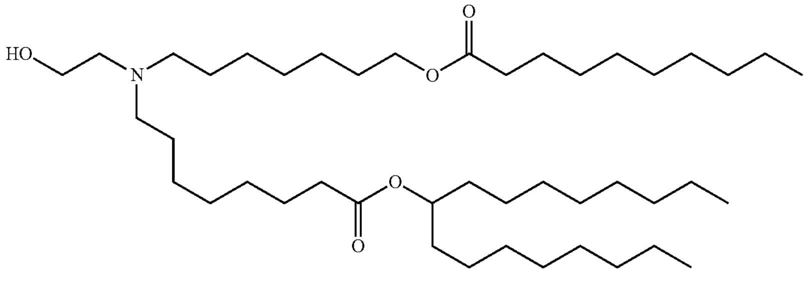
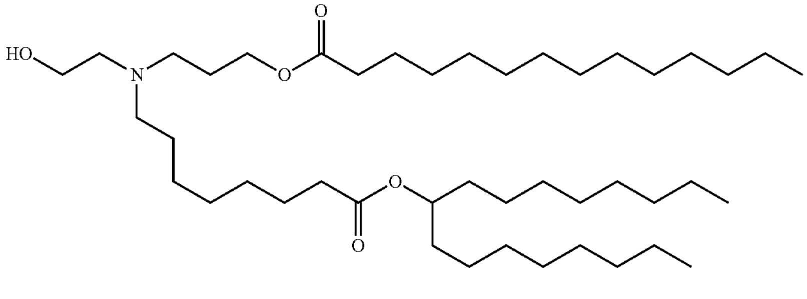

-continued
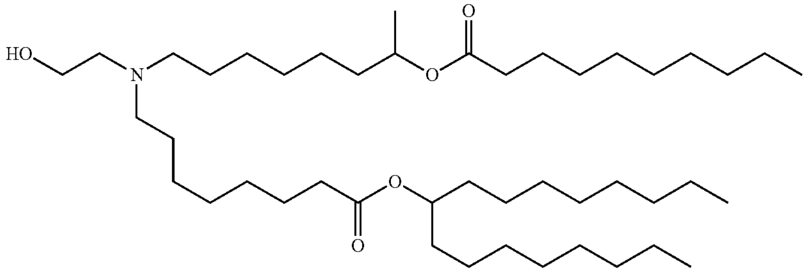
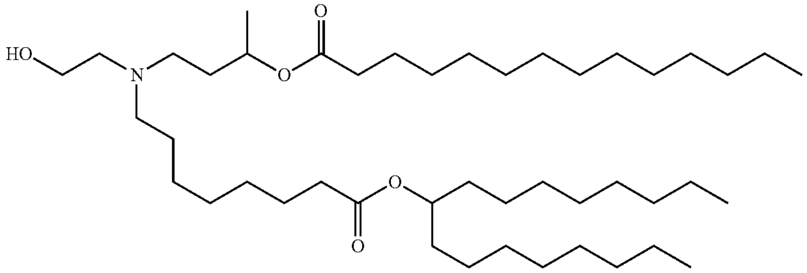
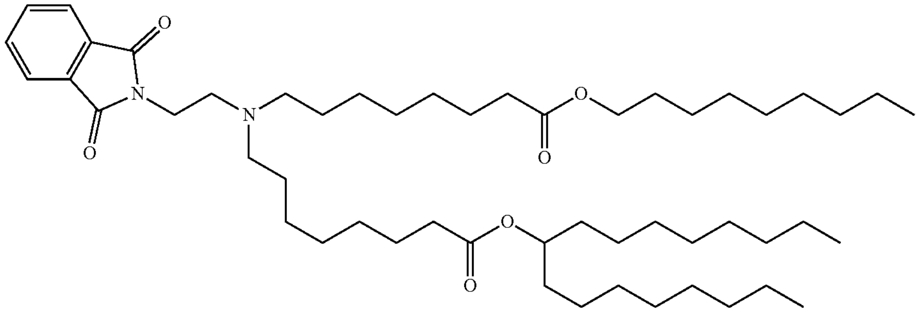
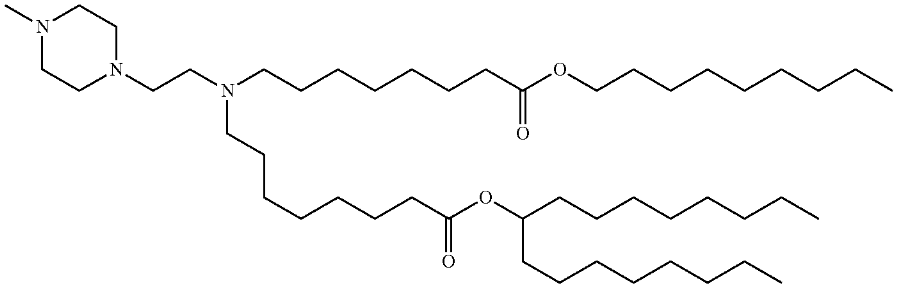
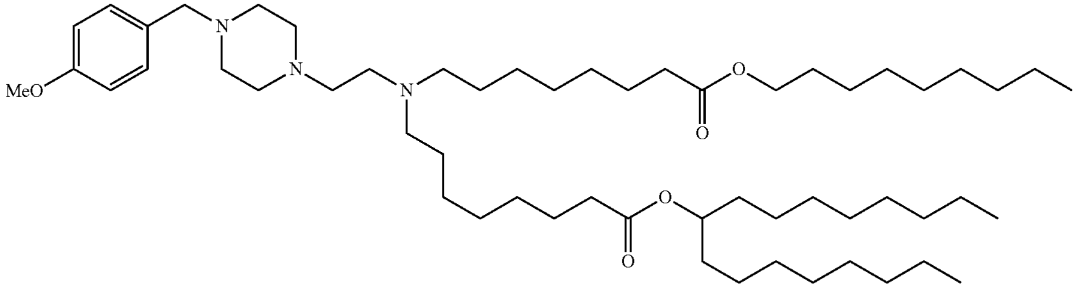
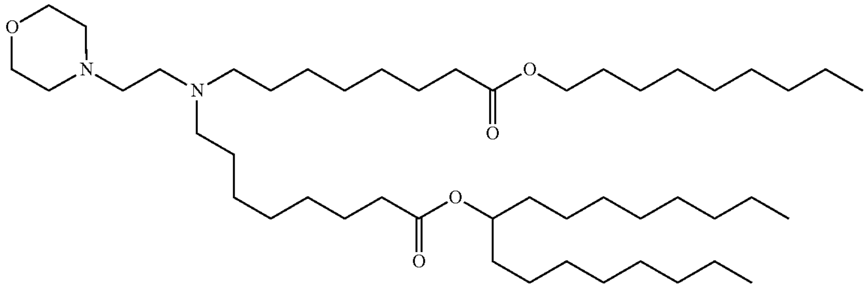

-continued
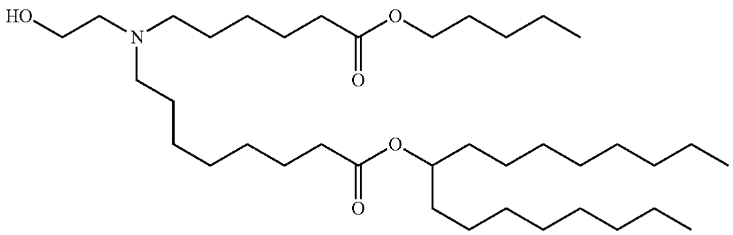
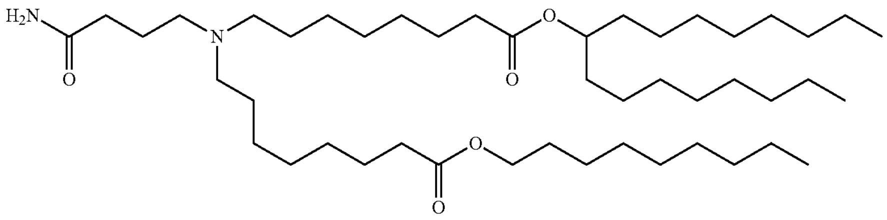
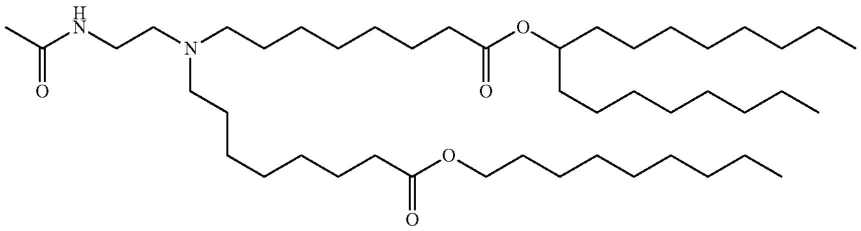
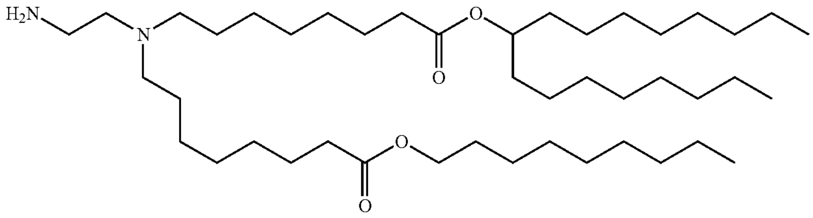
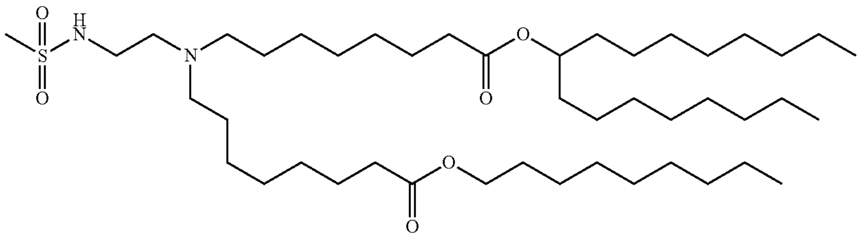
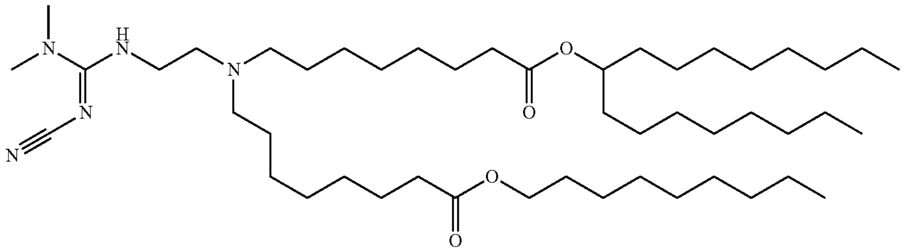
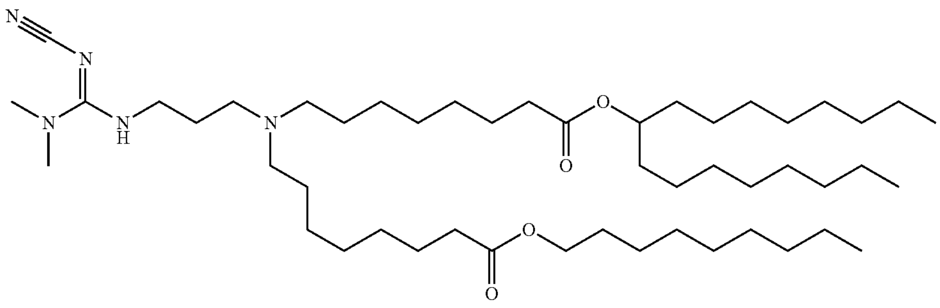

-continued
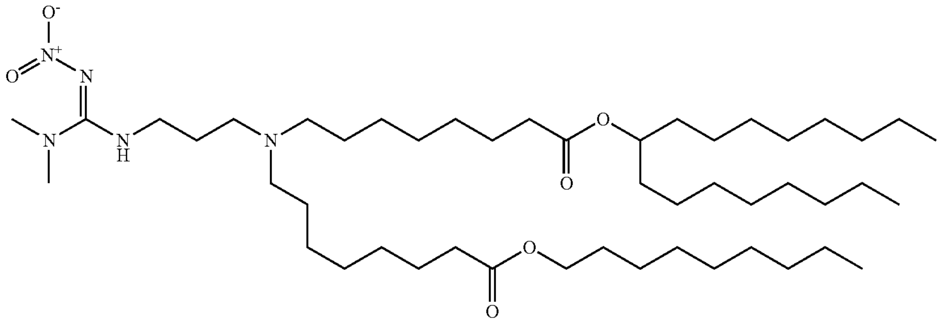
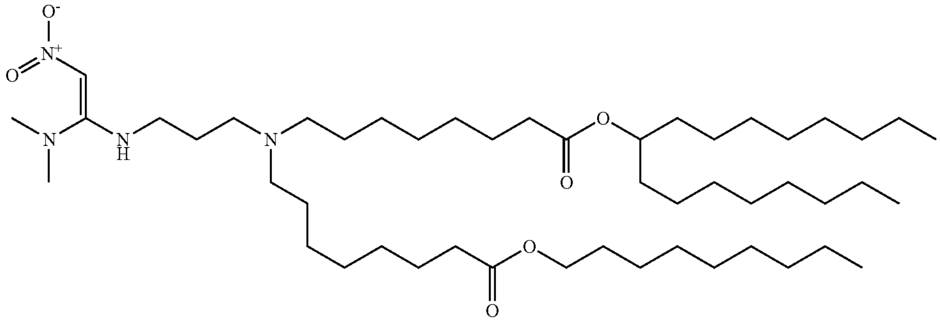
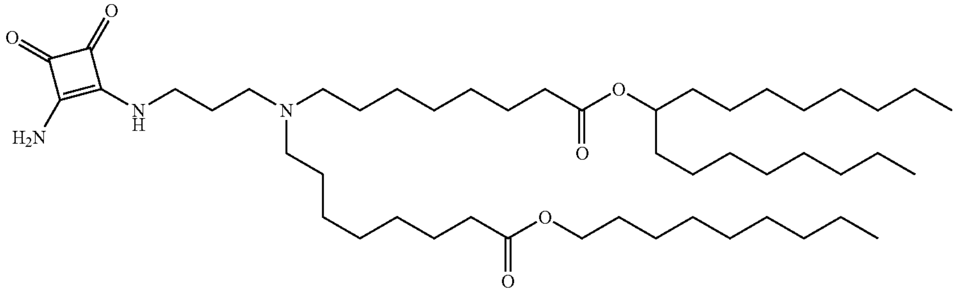
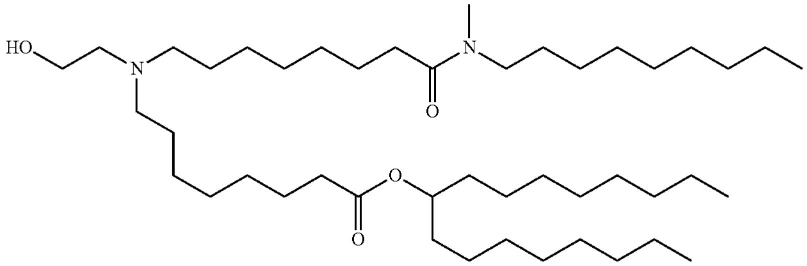
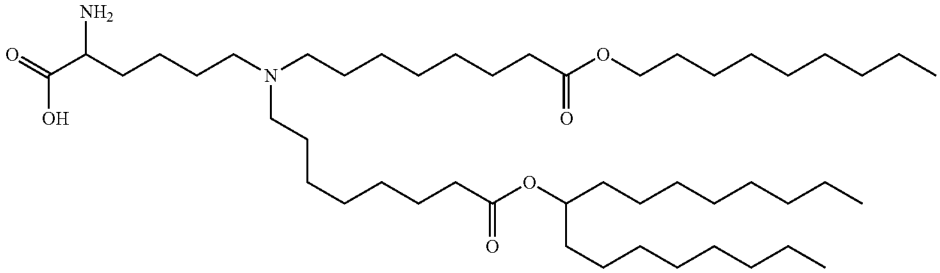
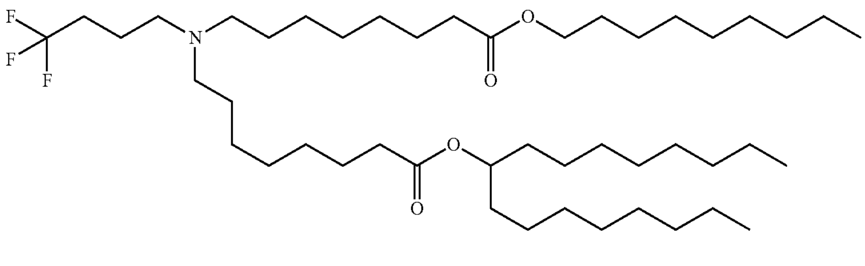

-continued
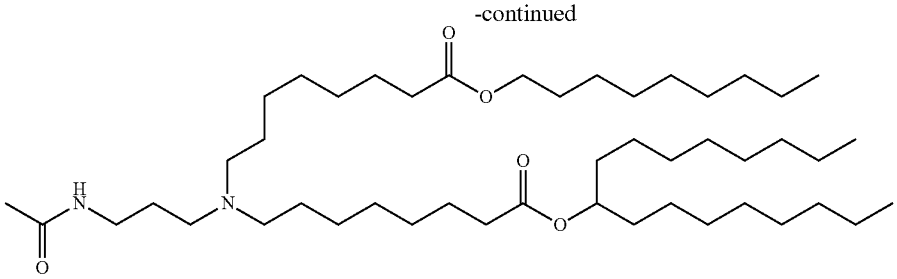
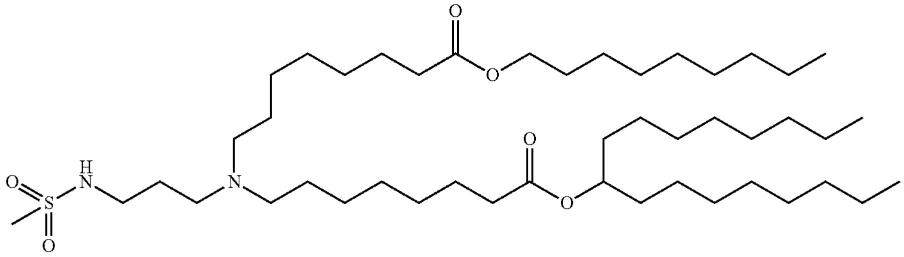
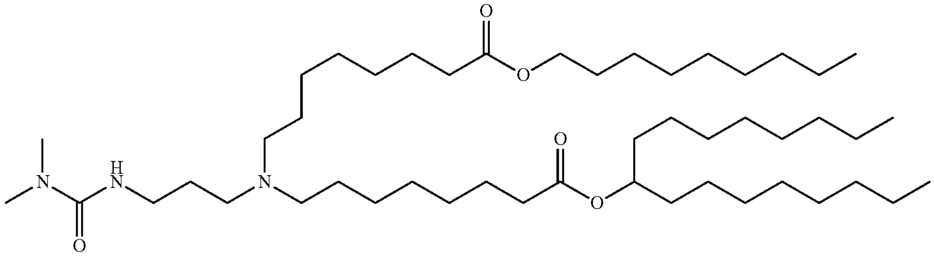
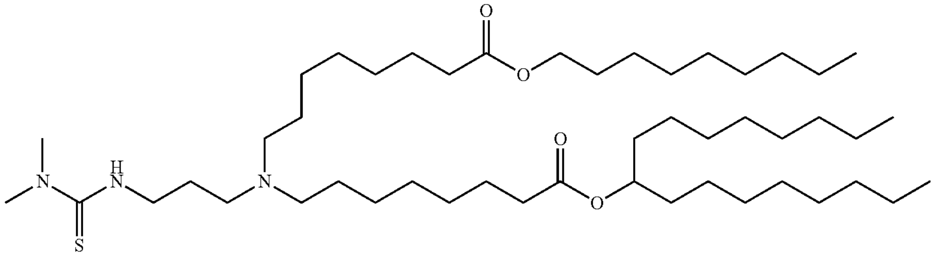
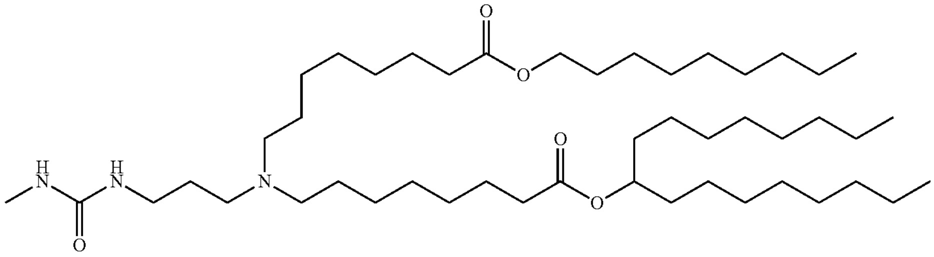
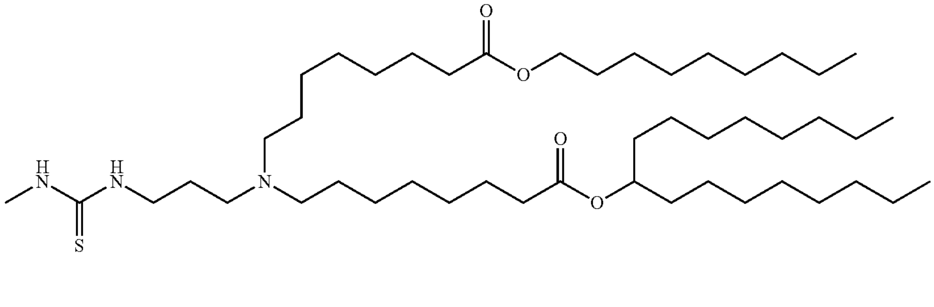

-continued
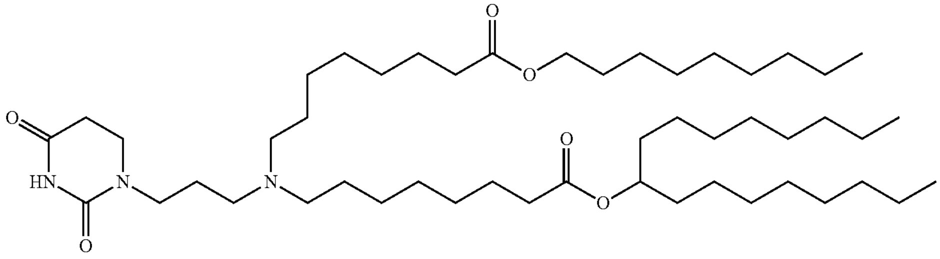
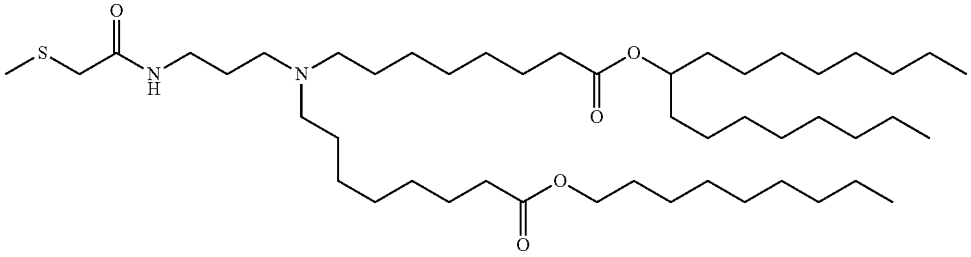
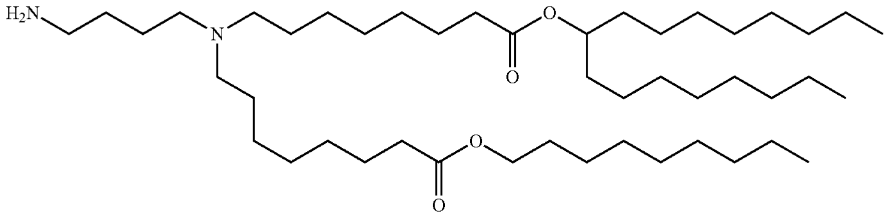
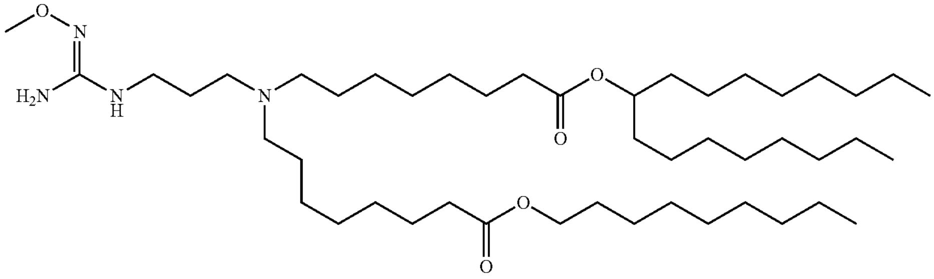
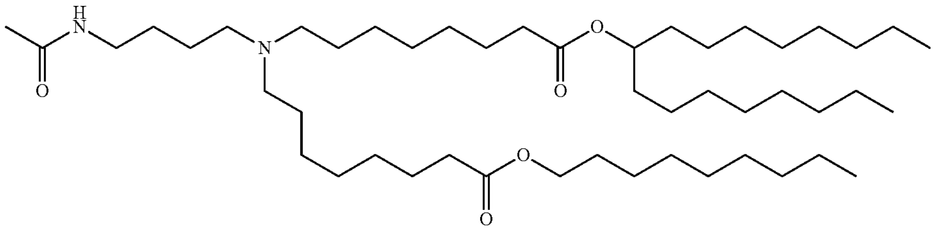
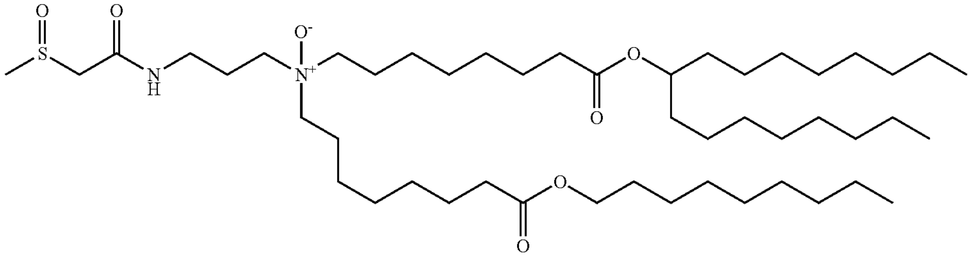

-continued

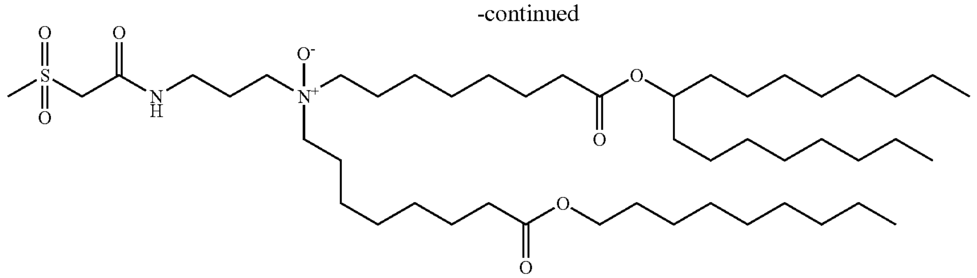

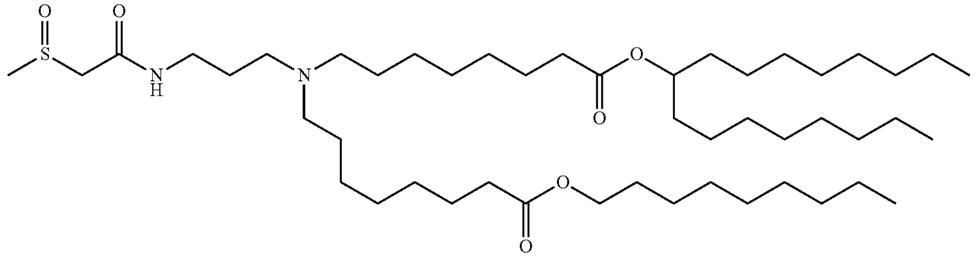

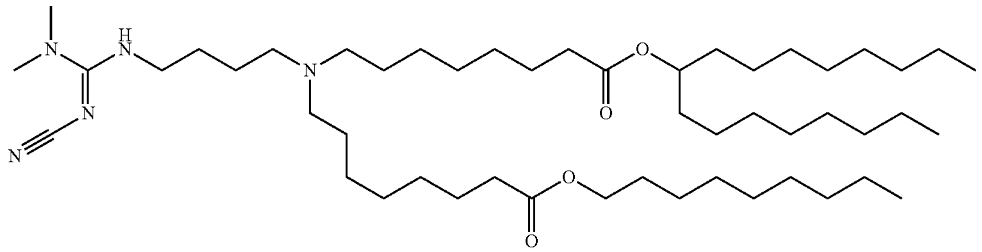

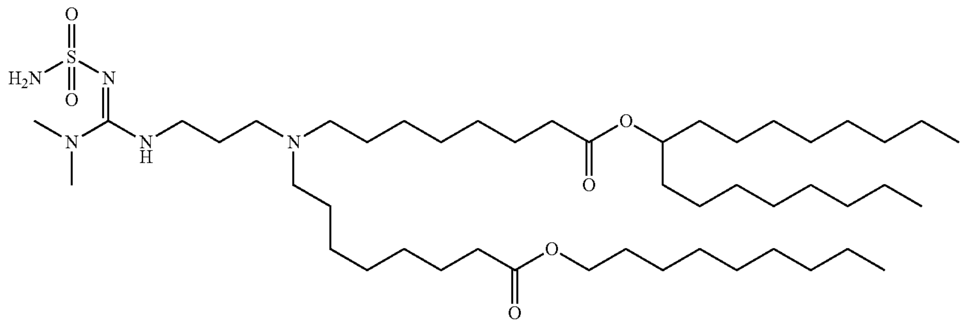

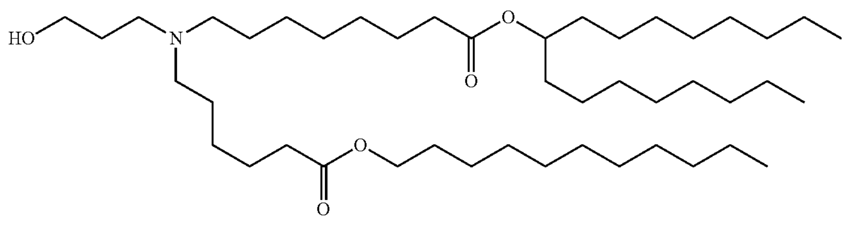

5.1 Amine Lipids

In certain embodiments, transfer vehicle compositions for the delivery of circular RNA comprise an amine lipid. In certain embodiments, an ionizable lipid is an amine lipid. In some embodiments, an amine lipid is described in international patent application PCT/US2018/053569.

In some embodiments, the amine lipid is Lipid E, which is (9Z,12Z)-3-((4,4-bis(octyloxy)butanoyl)oxy)-2-((((3-(diethylamino)propoxy)carbonyl)oxy)methyl)propyl octadeca-9,12-dienoate.

Lipid E can be depicted as:

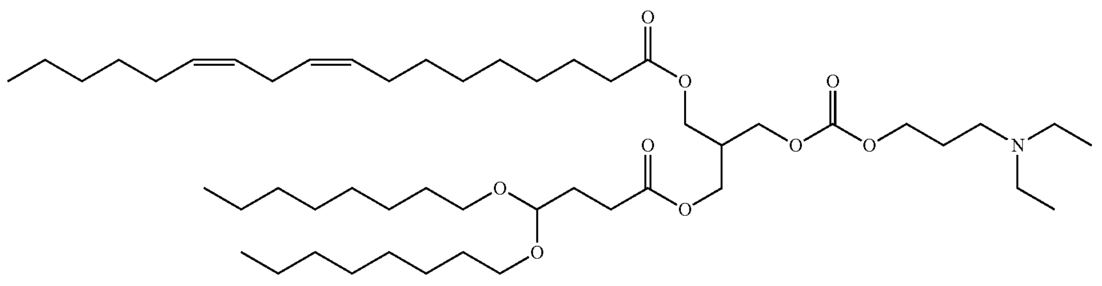 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid E may be synthesized according to WO2015/095340 (e.g., pp. 84-86). In certain embodiments, the amine lipid is an equivalent to Lipid E.

In certain embodiments, an amine lipid is an analog of Lipid E. In certain embodiments, a Lipid E analog is an acetal analog of Lipid E. In particular transfer vehicle compositions, the acetal analog is a C4-C12 acetal analog. In some embodiments, the acetal analog is a C5-C12 acetal analog. In additional embodiments, the acetal analog is a C5-C10 acetal analog. In further embodiments, the acetal analog is chosen from a C4, C5, C6, C7, C9, C10, C11 and C12 acetal analog.

Amine lipids and other biodegradable lipids suitable for use in the transfer vehicles, e.g., lipid nanoparticles, described herein are biodegradable in vivo. The amine lipids described herein have low toxicity (e.g., are tolerated in animal models without adverse effect in amounts of greater than or equal to 10 mg/kg). In certain embodiments, transfer vehicles composing an amine lipid include those where at least 75% of the amine lipid is cleared from the plasma within 8, 10, 12, 24, or 48 hours, or 3, 4, 5, 6, 7, or 10 days.

Biodegradable lipids include, for example, the biodegradable lipids of WO2017/173054, WO2015/095340, and WO2014/136086.

Lipid clearance may be measured by methods known by persons of skill in the art. See, for example, Maier, M. A., et al. Biodegradable Lipids Enabling Rapidly Eliminated Lipid Nanoparticles for Systemic Delivery of RNAi Therapeutics. Mol. Ther. 2013, 21(8), 1570-78.

Transfer vehicle compositions comprising an amine lipid can lead to an increased clearance rate. In some embodiments, the clearance rate is a lipid clearance rate, for example the rate at which a lipid is cleared from the blood, serum, or plasma. In some embodiments, the clearance rate is an RNA clearance rate, for example the rate at which an circRNA is cleared from the blood, serum, or plasma. In some embodiments, the clearance rate is the rate at which transfer vehicles are cleared from the blood, serum, or plasma. In some embodiments, the clearance rate is the rate at which transfer vehicles are cleared from a tissue, such as liver tissue or spleen tissue. In certain embodiments, a high rate of clearance leads to a safety profile with no substantial adverse effects. The amine lipids and biodegradable lipids may reduce transfer vehicle accumulation in circulation and in tissues. In some embodiments, a reduction in transfer vehicle accumulation in circulation and in tissues leads to a safety profile with no substantial adverse effects.

Lipids may be ionizable depending upon the pH of the medium they are in. For example, in a slightly acidic medium, the lipid, such as an amine lipid, may be protonated and thus bear a positive charge. Conversely, in a slightly basic medium, such as, for example, blood, where pH is approximately 7.35, the lipid, such as an amine lipid, may not be protonated and thus bear no charge.

The ability of a lipid to bear a charge is related to its intrinsic pKa. In some embodiments, the amine lipids of the present disclosure may each, independently, have a pKa in the range of from about 5.1 to about 7.4. In some embodiments, the bioavailable lipids of the present disclosure may each, independently, have a pKa in the range of from about 5.1 to about 7.4. For example, the amine lipids of the present disclosure may each, independently, have a pKa in the range of from about 5.8 to about 6.5. Lipids with a pKa ranging from about 5.1 to about 7.4 are effective for delivery of cargo in vivo, e.g., to the liver. Further, it has been found that lipids with a pKa ranging from about 5.3 to about 6.4 are effective for delivery in vivo, e.g., into tumors. See, e.g., WO2014/136086.

5.2 Lipids Containing a Disulfide Bond

In some embodiments, the ionizable lipid is described in U.S. Pat. No. 9,708,628.

The present invention provides a lipid represented by structure (XXII):

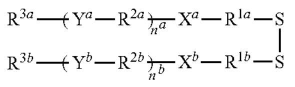

In structure (XXII), $X^a$ and $X^b$ are each independently $X^1$ or $X^2$ shown below.

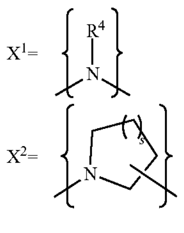

$R^4$ in $X^1$ is an alkyl group having 1-6 carbon atoms, which may be linear, branched or cyclic. The alkyl group preferably has a carbon number of 1-3. Specific examples of the alkyl group having 1-6 carbon atoms include methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like. $R^4$ is preferably a methyl group, an ethyl group, a propyl group or an isopropyl group, most preferably a methyl group.

The sin $X^2$ is 1 or 2. When s is 1, $X^2$ is a pyrrolidinium group, and when s is 2, $X^2$ is a piperidinium group. s is preferably 2. While the binding direction of $X^2$ is not limited, a nitrogen atom in $X^2$ preferably binds to $R^{1a}$ and $R^{1b}$.

$X^a$ may be the same as or different from $X^b$, and $X^a$ is preferably the same group as $X^b$.

$n^a$ and $n^b$ are each independently 0 or 1, preferably 1. When $n^a$ is 1, $R^{3a}$ binds to $X^a$ via $Y^a$ and $R^{2a}$, and when $n^a$ is 0, a structure of $R^{3a}$—$X^a$—$R^{1a}$—S— is taken. Similarly, when $n^b$ is 1, $R^{3b}$ binds to $X^b$ via $Y^b$ and $R^{2b}$, and when $n^b$ is 0, a structure of $R^{3b}$—$X^b$—$R^{1b}$—S— is taken.

$n^a$ may be the same as or different from $n^b$, and $n^a$ is preferably the same as $n^b$.

$R^{1a}$ and $R^{1b}$ are each independently an alkylene group having 1-6 carbon atoms, which may be linear or branched, preferably linear. Specific examples of the alkylene group having 1-6 carbon atoms include methylene group, ethylene group, trimethylene group, isopropylene group, tetramethylene group, isobutylene group, pentamethylene group, neopentylene group and the like. $R^{1a}$ and $R^{1b}$ are each preferably a methylene group, an ethylene group, a trimethylene group, an isopropylene group or a tetramethylene group, most preferably an ethylene group.

$R^{1a}$ may be the same as or different from $R^{1b}$, and $R^{1a}$ is preferably the same group as $R^{1b}$.

$R^{2a}$ and $R^{2b}$ are each independently an alkylene group having 1-6 carbon atoms, which may be linear or branched, preferably linear. Examples of the alkylene group having 1-6 carbon atoms include those recited as the examples of the alkylene group having 1-6 carbon atoms for $R^{1a}$ or $R^{1b}$. $R^{2a}$, and $R^{2b}$ are each preferably a methylene group, an ethylene group, a trimethylene group, an isopropylene group or a tetramethylene group.

When $X^a$ and $X^b$ are each $X^1$, $R^{2a}$, and $R^{2b}$ are preferably trimethylene groups. When $X^a$ and $X^b$ are each $X^2$, $R^{2a}$, and $R^{2b}$ are preferably ethylene groups.

$R^{2a}$, may be the same as or different from $R^{2b}$, and $R^{2a}$, is preferably the same group as $R^{2b}$ $Y^a$ and $Y^b$ are each independently an ester bond, an amide bond, a carbamate bond, an ether bond or a urea bond, preferably an ester bond, an amide bond or a carbamate bond, most preferably an ester bond. While the binding direction of $Y^a$ and $Y^b$ is not limited, when $Y^a$ is an ester bond, a structure of $R^{3a}$—CO—O–$R^{2a}$— is preferable, and when $Y^b$ is an ester bond, a structure of $R^{3b}$—CO—O—$R^{2b}$— is preferable.

$Y^a$ may be the same as or different from $Y^b$, and $Y^a$ is preferably the same group as $Y^b$.

$R^{3a}$ and $R^{3b}$ are each independently a sterol residue, a liposoluble vitamin residue or an aliphatic hydrocarbon group having 12-22 carbon atoms, preferably a liposoluble vitamin residue or an aliphatic hydrocarbon group having 12-22 carbon atoms, most preferably a liposoluble vitamin residue.

Examples of the sterol residue include a cholesteryl group (cholesterol residue), a cholestaryl group (cholestanol residue), a stigmasteryl group (stigmasterol residue), a β-sitosteryl group (β-sitosterol residue), a lanosteryl group (lanosterol residue), and an ergosteryl group (ergosterol residue) and the like. The sterol residue is preferably a cholesteryl group or a cholestaryl group.

As the liposoluble vitamin residue, a residue derived from liposoluble vitamin, as well as a residue derived from a derivative obtained by appropriately converting a hydroxyl group, aldehyde or carboxylic acid, which is a functional group in liposoluble vitamin, to other reactive functional group can be used. As for liposoluble vitamin having a hydroxyl group, for example, the hydroxyl group can be converted to a carboxylic acid by reacting with succinic acid anhydride, glutaric acid anhydride and the like. Examples of the liposoluble vitamin include retinoic acid, retinol, retinal, ergosterol, 7-dehydrocholesterol, calciferol, cholecalciferol, dihydroergocalciferol, dihydrotachysterol, tocopherol, tocotrienol and the like. Preferable examples of the liposoluble vitamin include retinoic acid and tocopherol.

The aliphatic hydrocarbon group having 12-22 carbon atoms may be linear or branched, preferably linear. The aliphatic hydrocarbon group may be saturated or unsaturated. In the case of an unsaturated aliphatic hydrocarbon group, the aliphatic hydrocarbon group generally contains 1-6, preferably 1-3, more preferably 1-2 unsaturated bonds. While the unsaturated bond includes a carbon-carbon double bond and a carbon-carbon triple bond, it is preferably a carbon-carbon double bond. The aliphatic hydrocarbon group has a carbon number of preferably 12-18, most preferably 13-17. While the aliphatic hydrocarbon group includes an alkyl group, an alkenyl group, an alkynyl group and the like, it is preferably an alkyl group or an alkenyl group. Specific examples of the aliphatic hydrocarbon group having 12-22 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, decadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group and the like. The aliphatic hydrocarbon group having 12-22 carbon atoms is preferably tridecyl group, tetradecyl group, heptadecyl group, octadecyl group, heptadecadienyl group or octadecadienyl group, particularly preferably tridecyl group, heptadecyl group or heptadecadienyl group.

In one embodiment, an aliphatic hydrocarbon group having 12-22 carbon atoms, which is derived from fatty acid, aliphatic alcohol, or aliphatic amine is used. When $R^{3a}$ (or $R^{3b}$) is derived from fatty acid, $Y^a$ (or $Y^b$) is an ester bond or an amide bond, and fatty acid-derived carbonyl carbon is included in $Y^a$ (or $Y^b$). For example, when linoleic acid is used, $R^{3a}$ (or $R^{3b}$) is a heptadecadienyl group.

$R^{3a}$ may be the same as or different from $R^{3b}$, and $R^{3a}$ is preferably the same group as $R^{3b}$.

In one embodiment, $X^a$ is the same as $X^b$, $n^a$ is the same as $n^b$, $R^{1a}$ is the same as $R^{1b}$, $R^{2a}$, is the same as $R^{2b}$, $R^{3a}$ is the same as $R^{3b}$, and $Y^a$ is the same as $Y^b$.

In one embodiment, $X^a$ and $X^b$ are each independently X1, $R^4$ is an alkyl group having 1-3 carbon atoms, $n^a$ and $n^b$ are each 1, $R^{1a}$ and $R^{1b}$ are each independently an alkylene group having 1-6 carbon atoms, $R^{2a}$, and $R^{2b}$ are each independently an alkylene group having 1-6 carbon atoms, $Y^a$ and $Y^b$ are each an ester bond or an amide bond, and $R^{3a}$ and $R^{3b}$ are each independently an aliphatic hydrocarbon group having 12-22 carbon atoms.

In one embodiment, $X^a$ and $X^b$ are each X1, $R^4$ is an alkyl group having 1-3 carbon atoms, $n^a$ and $n^b$ are each 1, $R^{1a}$ and $R^{1b}$ are each an alkylene group having 1-6 carbon atoms, $R^{2a}$, and $R^{2b}$ are each an alkylene group having 1-6 carbon atoms, $Y^a$ and $Y^b$ are each an ester bond or an amide bond, $R^{3a}$ and $R^{3b}$ are each an aliphatic hydrocarbon group having 12-22 carbon atoms, $X^a$ is the same as $X^b$, $R^{1a}$ is the same as $R^{1b}$, $R^{2a}$, is the same as $R^{2b}$, and $R^{3a}$ is the same as $R^{3b}$.

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$, and $R^{2b}$ are each a trimethylene group, $Y^a$ and $Y^b$ are each —CO—O—, and $R^{3a}$ and $R^{3b}$ are each independently an alkyl group or alkenyl group having 13-17 carbon atoms.

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$, and $R^{2b}$ are each a trimethylene group, $Y^a$ and $Y^b$ are each —CO—O—, $R^{3a}$ and $R^{3b}$ are each an alkyl group or alkenyl group having 13-17 carbon atoms, and $R^{3a}$ is the same as $R^{3b}$.

In one embodiment, $X^a$ and $X^b$ are each independently $X^1$, $R^4$ is an alkyl group having 1-3 carbon atoms, $n^a$ and $n^b$ are each 1, $R^{1a}$ and $R^{1b}$ are each independently an alkylene group having 1-6 carbon atoms, $R^{2a}$, and $R^{2b}$ are each independently an alkylene group having 1-6 carbon atoms, $Y^a$ and $Y^b$ are each an ester bond or an amide bond, and $R^{3a}$ and $R^{3b}$ are each independently a liposoluble vitamin residue (e.g., retinoic acid residue, tocopherol residue).

In one embodiment, $X^a$ and $X^b$ are each $X^1$, $R^4$ is an alkyl group having 1-3 carbon atoms, $n^a$ and $n^b$ are each 1, $R^{1a}$ and $R^{1b}$ are each an alkylene group having 1-6 carbon atoms, $R^{2a}$, and $R^{2b}$ are each an alkylene group having 1-6 carbon atoms, $Y^a$ and $Y^b$ are each an ester bond or an amide bond, $R^{3a}$ and $R^{3b}$ are each a liposoluble vitamin residue (e.g., retinoic acid residue, tocopherol residue), $X^a$ is the same as $X^b$, $R^{1a}$ is the same as $R^1$, $R^{2a}$, is the same as $R^{2b}$, and $R^{3a}$ is the same as $R^{3b}$.

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$, and $R^{2b}$ are each a trimethylene group, $Y^a$ and $Y^b$ are each —CO—O—, and $R^{3a}$ and $R^{3b}$ are each independently a liposoluble vitamin residue (e.g., retinoic acid residue, tocopherol residue).

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$, and $R^{2b}$ are each a trimethylene group, $Y^a$ and $Y^b$ are each —CO—O—, $R^{3a}$ and $R^{3b}$ are each a liposoluble vitamin residue (e.g., retinoic acid residue, tocopherol residue), and $R^{3a}$ is the same as $R^{3b}$.

In one embodiment, $X^a$ and $X^b$ are each independently $X^2$, t is 2, $R^{1a}$ and $R^{1b}$ are each independently an alkylene group having 1-6 carbon atoms, $R^{2a}$, and $R^{2b}$ are each independently an alkylene group having 1-6 carbon atoms, $Y^a$ and $Y^b$ are each an ester bond, and $R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms).

In one embodiment, $X^a$ and $X^b$ are each independently $X^2$, t is 2, $R^{1a}$ and $R^{1b}$ are each independently an alkylene group having 1-6 carbon atoms, $R^{2a}$, and $R^{2b}$ are each independently an alkylene group having 1-6 carbon atoms, $Y^a$ and $Y^b$ are each an ester bond, $R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms), $X^a$ is the same as $X^b$, $R^{1a}$ is the same as $R^1$, $R^{2a}$, is the same as $R^{2b}$, and $R^{3a}$ is the same as $R^{3b}$.

In one embodiment, $X^a$ and $X^b$ are each independently $X^2$, t is 2, $R^{1a}$ and $R^{1b}$ are each an ethylene group, $R^{2a}$, and $R^{2b}$ are each independently an alkylene group having 1-6 carbon atoms, $Y^a$ and $Y^b$ are each an ester bond, $R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms), $X^a$ is the same as $X^b$, $R^{2a}$, is the same as $R^{2b}$, and $R^{3a}$ is the same as $R^{3b}$.

In some embodiments, an ionizable lipid has one of the structures set forth in Table 15b below.
TABLE 15b
| Number | Structure |
| --- | --- |
| 1 | 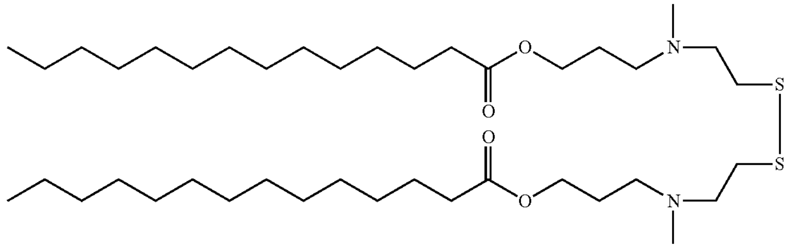 [SMILES: CCCCCCCCCCCCCC(=O)OCCCN(C)CCSSCCN(C)CCCOC(=O)CCCCCCCCCCCCC] |
| 2 | 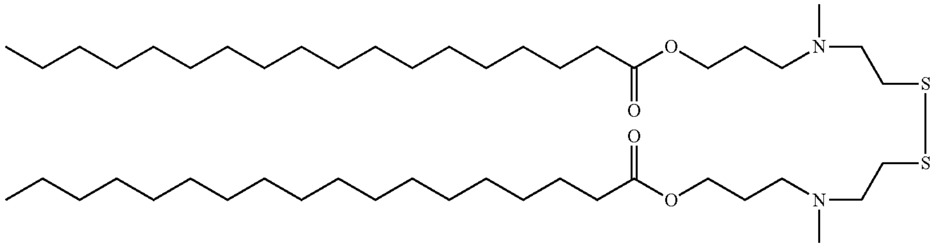 [SMILES: CCCCCCCCCCCCCCCCCC(=O)OCCCN(C)CCSSCCN(C)CCCOC(=O)CCCCCCCCCCCCCCCCC] |
| 3 | 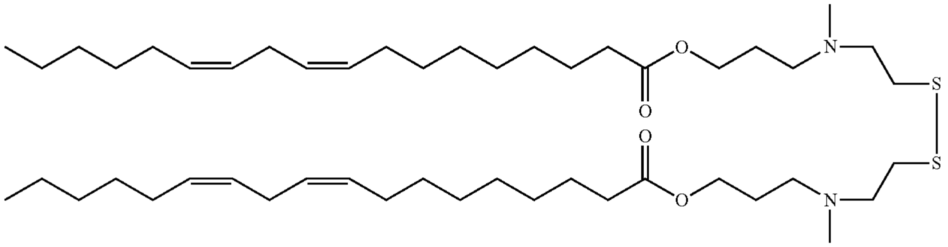 [SMILES: CCCCC/C=C\C/C=C\CCCCCCCC(=O)OCCCN(C)CCSSCCN(C)CCCOC(=O)CCCCCCC/C=C\C/C=C\CCCCC] |
| 4 | 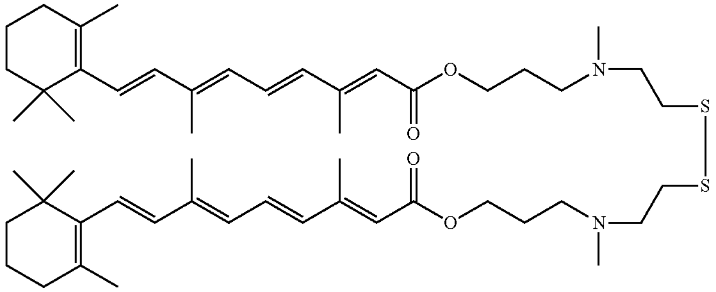 [SMILES: CC1=C(/C=C/C(C)=C/C=C/C(C)=C/C(=O)OCCCN(C)CCSSCCN(C)CCCOC(=O)/C=C(C)/C=C/C=C(C)/C=C/C2=C(C)CCCC2(C)C)C(C)(C)CCC1] |
| 5 | 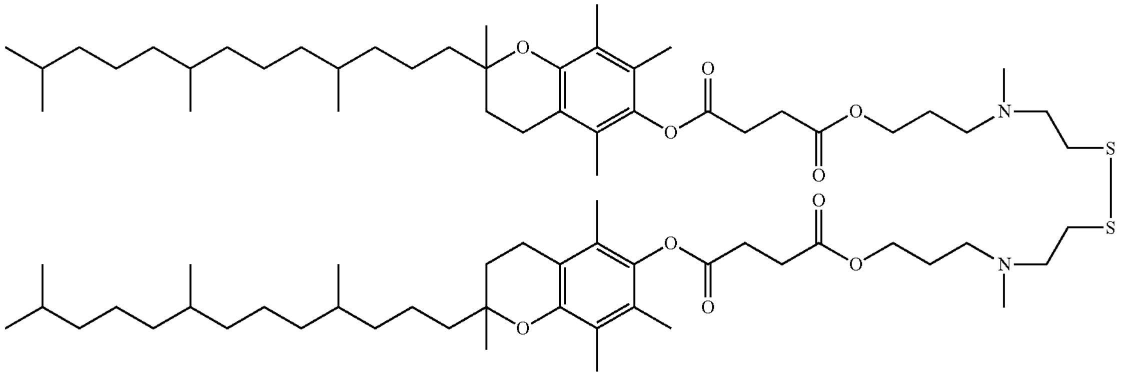 [SMILES: Cc1c(C)c2c(c(C)c1OC(=O)CCC(=O)OCCCN(C)CCSSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

TABLE 15b-continued
| Number | Structure |
|---|---|
| 6 | 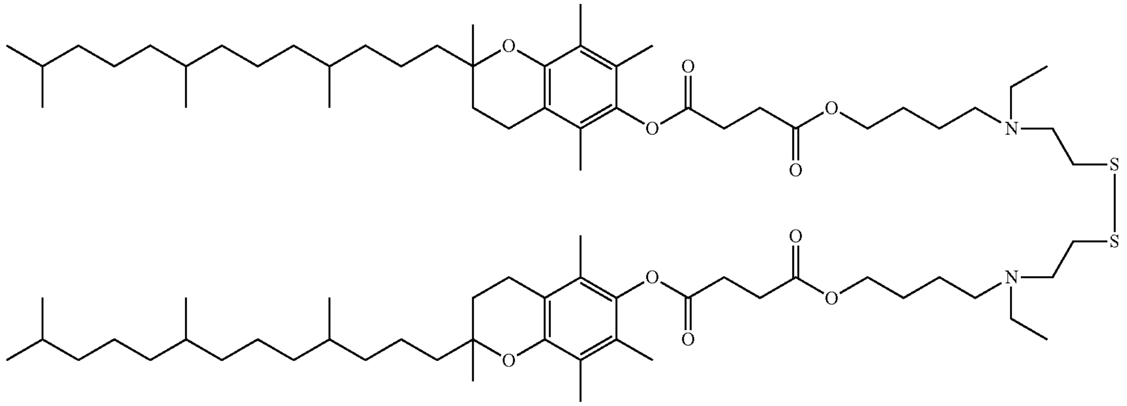 [SMILES: CCN(CCCCOC(=O)CCC(=O)Oc1c(C)c(C)c2c(c1C)CCC(C)(CCCC(C)CCCC(C)CCCC(C)C)O2)CCSSCCN(CC)CCCCOC(=O)CCC(=O)Oc1c(C)c(C)c2c(c1C)CCC(C)(CCCC(C)CCCC(C)CCCC(C)C)O2] |
| 7 | 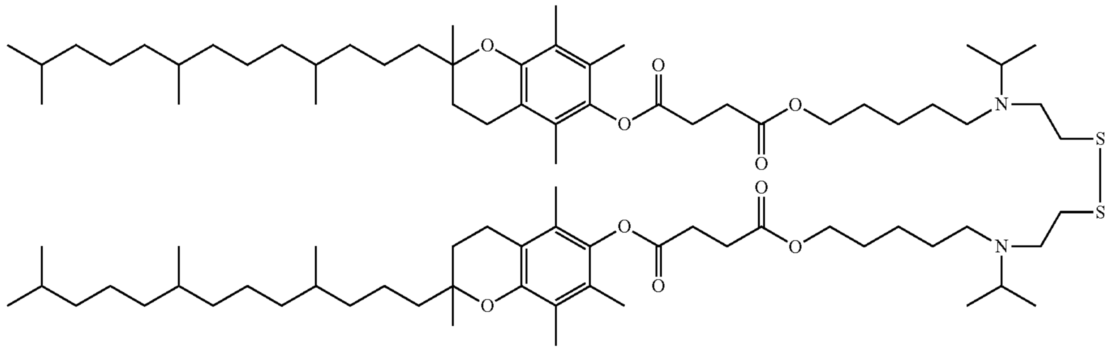 [SMILES: Cc1c(C)c2c(c(C)c1OC(=O)CCC(=O)OCCCCCN(CCSSCCN(CCCCCOC(=O)CCC(=O)Oc1c(C)c(C)c3c(c1C)CCC(C)(CCCC(C)CCCC(C)CCCC(C)C)O3)C(C)C)C(C)C)CCC(C)(CCCC(C)CCCC(C)CCCC(C)C)O2] |
| 8 | 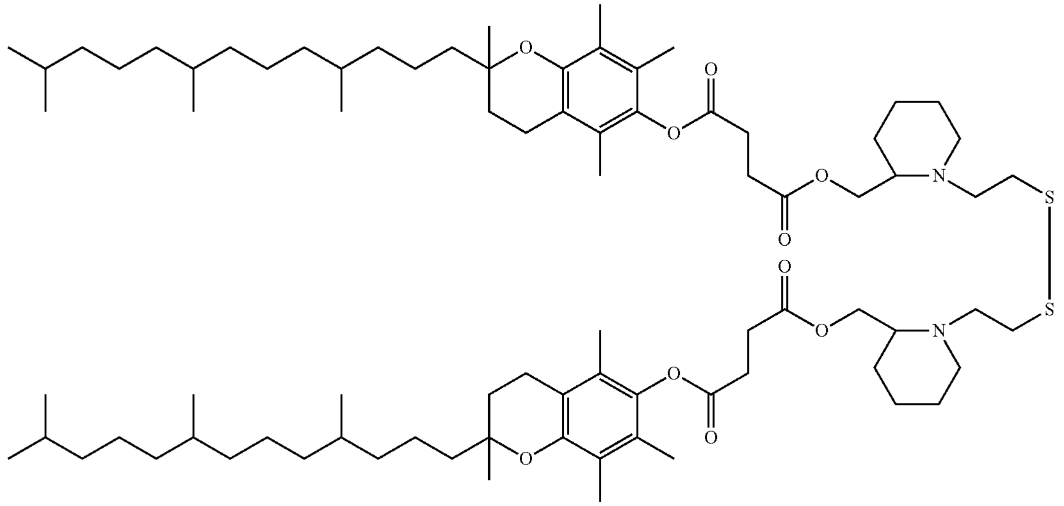 [SMILES: Cc1c(C)c2c(c(C)c1OC(=O)CCC(=O)OCC1CCCCN1CCSSCCN1CCCCC1COC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

TABLE 15b-continued
| Number | Structure |
| --- | --- |
| 9 | 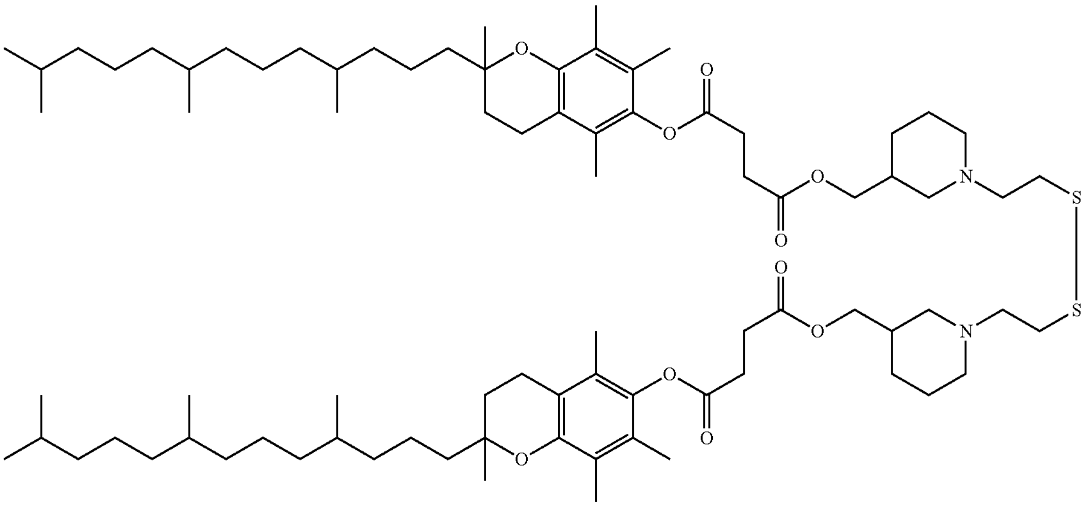 [SMILES: Cc1c(C)c2c(c(C)c1OC(=O)CCC(=O)OCC1CCCN(CCSSCCN3CCCC(COC(=O)CCC(=O)Oc4c(C)c(C)c5c(c4C)CCC(C)(CCCC(C)CCCC(C)CCCC(C)C)O5)C3)C1)CCC(C)(CCCC(C)CCCC(C)CCCC(C)C)O2] |
| 10 | 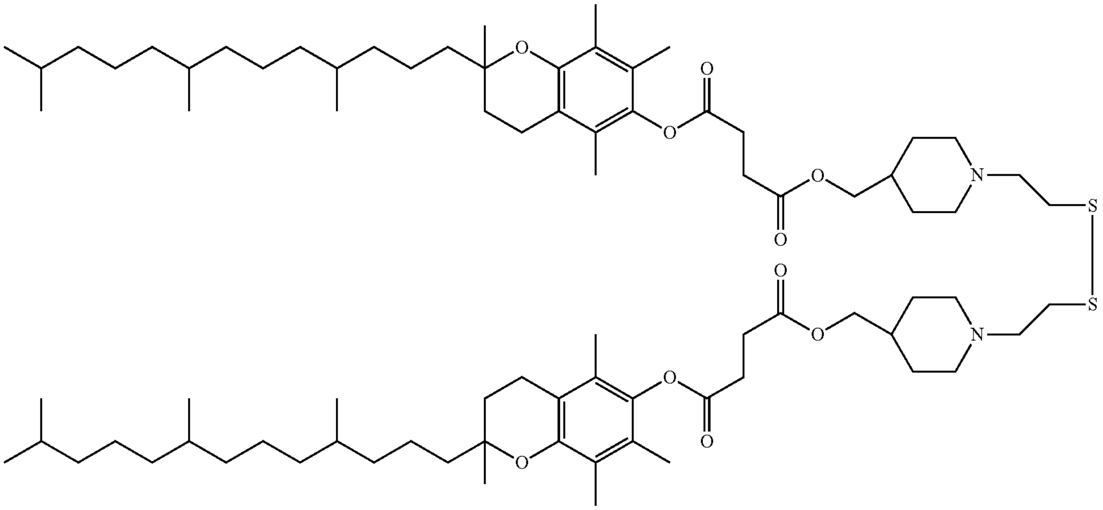 [SMILES: Cc1c(C)c2c(c(C)c1OC(=O)CCC(=O)OCC1CCN(CCSSCCN3CCC(COC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| 11 | 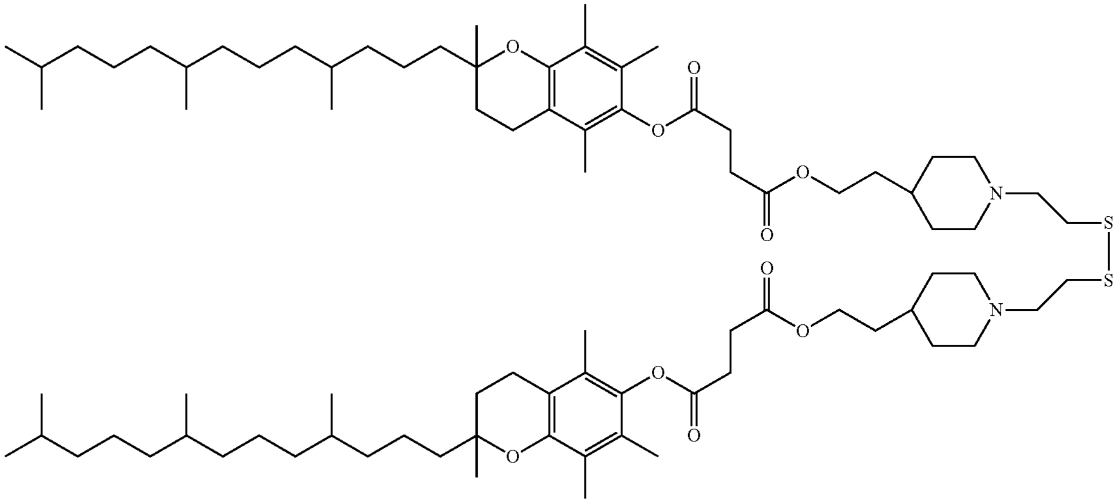 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |

TABLE 15b-continued
| Number | Structure |
| --- | --- |
| 12 | 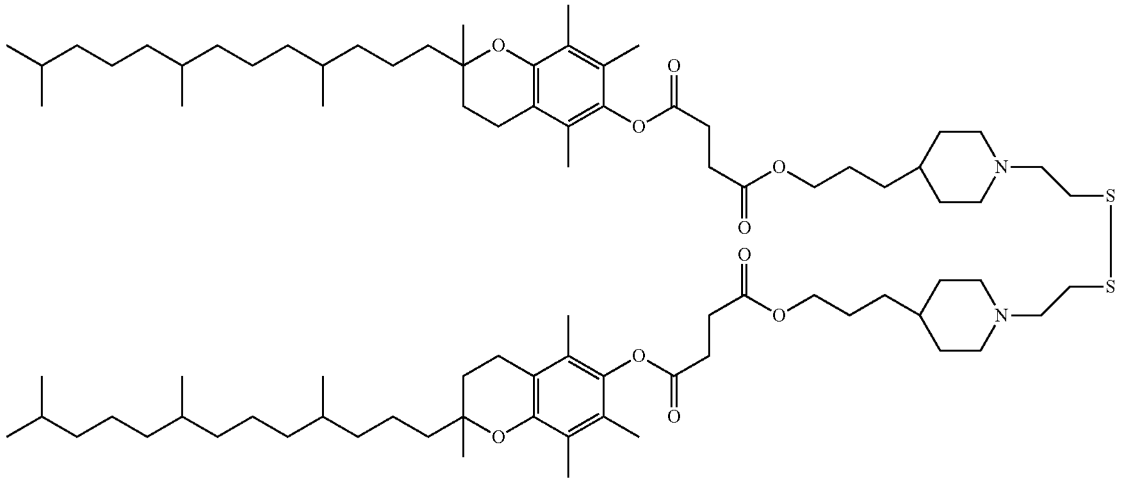 [SMILES: Cc1c(C)c2c(c(C)c1OC(=O)CCC(=O)OCCCC1CCN(CCSSCCN3CCC(CCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| 13 | 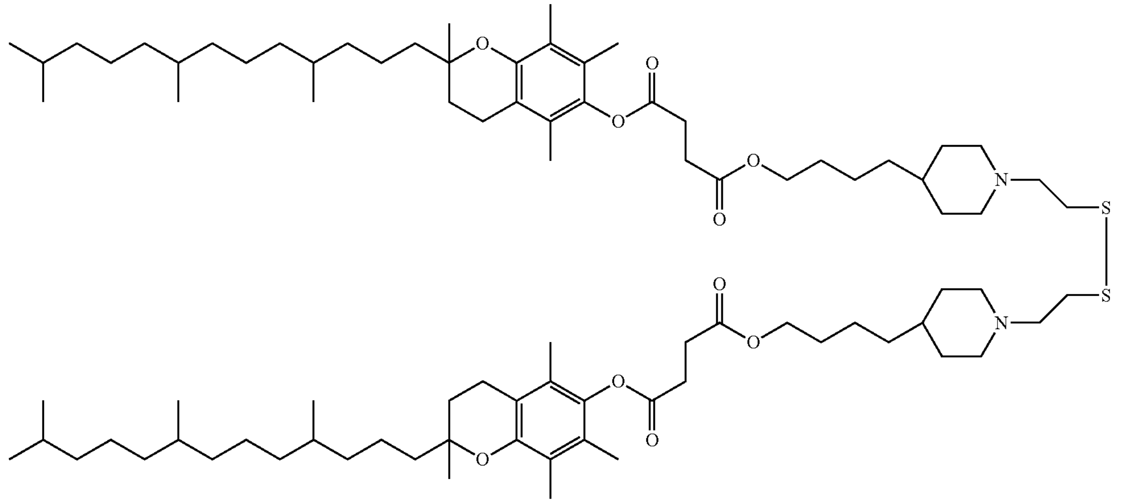 [SMILES: Cc1c(C)c2c(c(C)c1OC(=O)CCC(=O)OCCCCC1CCN(CCSSCCN3CCC(CCCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| 14 | 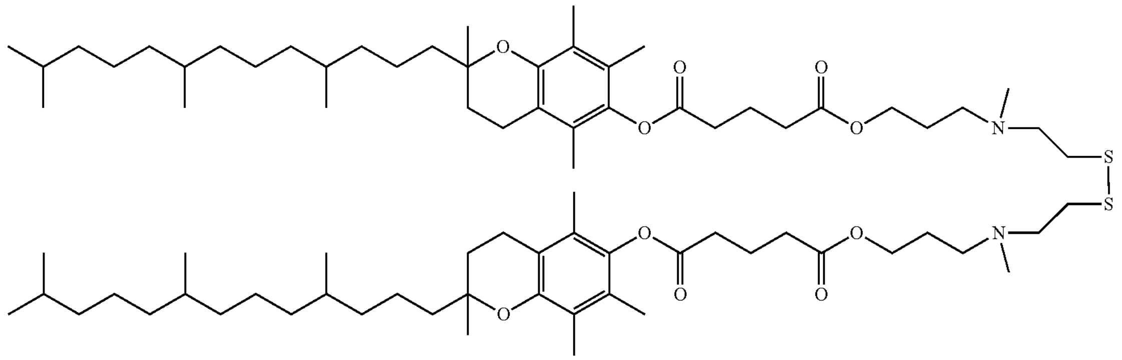 [SMILES: Cc1c(C)c2c(c(C)c1OC(=O)CCCC(=O)OCCCN(C)CCSSCCN(C)CCCOC(=O)CCCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

TABLE 15b-continued

| Number | Structure |
|---|---|
| 15 | 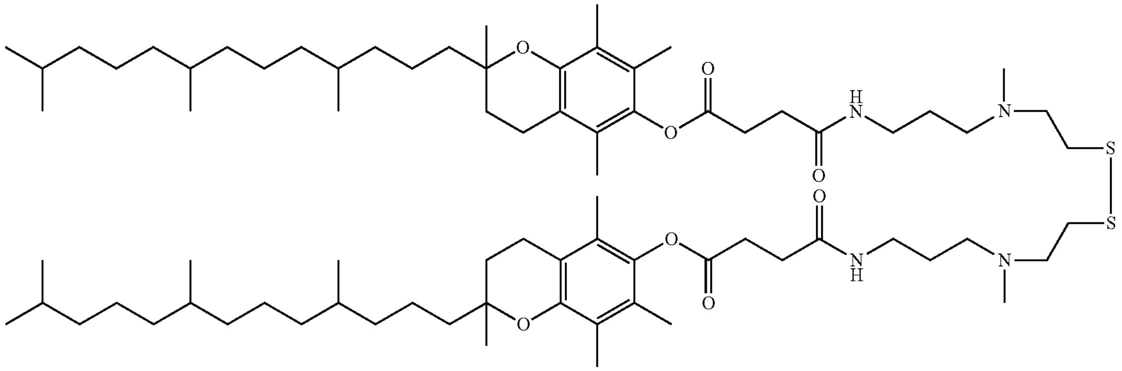 [SMILES: Cc1c(C)c2c(c(C)c1OC(=O)CCC(=O)NCCCN(C)CCSSCCN(C)CCCNC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

A lipid of the present invention may have an —S—S— (disulfide) bond. The production method for such a compound includes, for example, a method including producing $R^{3a}$—($Y^a$—$R^{2a}$)$n^a$-$X^a$—$R^{1a}$—SH, and $R^{3b}$—($Y^b$—$R^{2b}$)$n^b$-$X^b$—$R^{1b}$—SH, and subjecting them to oxidation (coupling) to give a compound containing —S—S—, a method including sequentially bonding necessary parts to a compound containing an —S—S— bond to finally obtain the compound of the present invention and the like. Preferred is the latter method.

A specific example of the latter method is shown below, which is not to be construed as limiting.

Examples of the starting compound include —S—S— bond-containing two terminal carboxylic acid, two terminal carboxylate, two terminal amine, two terminal isocyanate, two terminal alcohol, two terminal alcohol having a leaving group such as MsO (mesylate group) and the like, a two terminal carbonate having a leaving group such as pNP (p-nitrophenylcarbonate group) and the like.

For example, when a compound containing $X^1$ or $X^2$ for $X^a$ and $X^b$ is produced, two terminal functional groups of compound (1) containing an —S—S— bond are reacted with an NH group in compound (2) having the —NH— group and one functional group at the terminal, the functional group at the terminal in compound (2) which did not contribute to the reaction is reacted with a functional group in compound (3) containing $R^3$, whereby the compound of the present invention containing an —S—S— bond, $R^{1a}$ and $R^{1b}$, $X^a$ and $X^b$, $R^{2a}$ and $R^{2b}$, $Y^a$ and $Y^b$, and $R^{3a}$ and $R^{3b}$ can be obtained.

In the reaction of compound (1) and compound (2), an alkali catalyst such as potassium carbonate, sodium carbonate, potassium t-butoxide and the like may be used as a catalyst, or the reaction may be performed without a catalyst. Preferably, potassium carbonate or sodium carbonate is used as a catalyst.

The amount of catalyst is 0.1-100 molar equivalents, preferably, 0.1-20 molar equivalents, more preferably 0.1-5 molar equivalents, relative to compound (1). The amount of compound (2) to be charged is 1-50 molar equivalents, preferably 1-10 molar equivalents, relative to compound (1).

The solvent to be used for the reaction of compound (1) and compound (2) is not particularly limited as long as it is a solvent or aqueous solution that does not inhibit the reaction. For example, ethyl acetate, dichloromethane, chloroform, benzene, toluene and the like can be mentioned. Among these, toluene and chloroform are preferable.

The reaction temperature is −20 to 200° C., preferably 0 to 80° C., more preferably 20 to 50° C., and the reaction time is 1-48 hr, preferably 2-24 hr.

When the reaction product of compound (1) and compound (2) is reacted with compound (3), an alkali catalyst such as potassium carbonate, sodium carbonate, potassium t-butoxide and the like, or an acid catalyst such as PTS (p-toluenesulfonic acid), MSA (methanesulfonic acid) and the like may be used, like the catalyst used for the reaction of compound (1) and compound (2), or the reaction may be performed without a catalyst.

In addition, the reaction product of compound (1) and compound (2) may be directly reacted with compound (3) by using a condensing agent such as DCC (dicyclohexylcarbodiimide), DIC (diisopropylcarbodiimide), EDC (1-ethyl-3-(3-dimethylaminopropyl)carbodiimide hydrochloride) and the like. Alternatively, compound (3) may be treated with a condensing agent to be once converted to an anhydride and the like, after which it is reacted with the reaction product of compound (1) and compound (2).

The amount of compound (3) to be charged is 1-50 molar equivalents, preferably 1-10 molar equivalents, relative to the reaction product of compound (1) and compound (2).

The catalyst to be used is appropriately selected according to the functional groups to be reacted.

The amount of catalyst is 0.05-100 molar equivalents, preferably 0.1-20 molar equivalents, more preferably 0.2-5 molar equivalent, relative to compound (1).

The solvent to be used for the reaction of the reaction product of compound (1) and compound (2) with compound (3) is not particularly limited as long as it is a solvent or aqueous solution that does not inhibit the reaction. For example, ethyl acetate, dichloromethane, chloroform, benzene, toluene and the like can be mentioned. Among these, toluene and chloroform are preferable.

The reaction temperature is 0 to 200° C., preferably 0 to 120° C. more preferably 20 to 50° C., and the reaction time is 1 hr-48 hr, preferably 2-24 hr.

The reaction product obtained by the above-mentioned reaction can be appropriately purified by a general purification method, for example, washing with water, silica gel column chromatography, crystallization, recrystallization, liquid-liquid extraction, reprecipitation, ion exchange column chromatography and the like.

5.3 Structure XXIII Lipids

In some embodiments, an ionizable lipid is described in U.S. Pat. No. 9,765,022.

The present invention provides a compound represented by structure (XXIII):

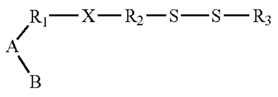

In structure XXIII, a hydrophilic and optionally positively charged head is

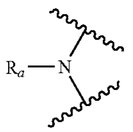
,
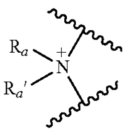
,
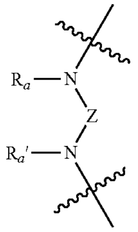
,
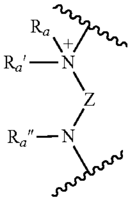
, or
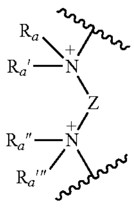

in which each of $R_a$, $R_a'$, $R_a''$, and $R_a'''$, independently, is H, a $C_1$-$C_{20}$ monovalent aliphatic radical, a $C_1$-$C_{20}$ monovalent heteroaliphatic radical, a monovalent aryl radical, or a monovalent heteroaryl radical, and Z is a $C_1$-$C_{20}$ bivalent aliphatic radical, a $C_1$-$C_{20}$ bivalent heteroaliphatic radical, a bivalent aryl radical, or a bivalent heteroaryl radical; B is a $C_1$-$C_{24}$ monovalent aliphatic radical, a $C_1$-$C_{24}$ monovalent heteroaliphatic radical, a monovalent aryl radical, a monovalent heteroaryl radical, or

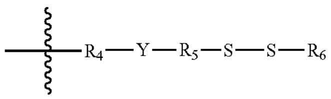

each of $R_1$ and $R_4$, independently, is a bond, a $C_1$-$C_{10}$ bivalent aliphatic radical, a $C_1$-$C_{10}$ bivalent heteroaliphatic radical, a bivalent aryl radical, or a bivalent heteroaryl radical; each of $R_2$ and $R_5$, independently, is a bond, a $C_1$-$C_{20}$ bivalent aliphatic radical, a $C_1$-$C_{20}$ bivalent heteroaliphatic radical, a bivalent aryl radical, or a bivalent heteroaryl radical; each of $R_3$ and $R_6$, independently, is a $C_1$-$C_{20}$ monovalent aliphatic radical, a $C_1$-$C_{20}$ monovalent heteroaliphatic radical, a monovalent aryl radical, or a monovalent heteroaryl radical; each of

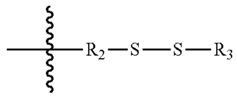

a hydrophobic tail, and

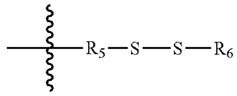

also a hydrophobic tail, has 8 to 24 carbon atoms; and each of X, a linker, and Y, also a linker, independently, is

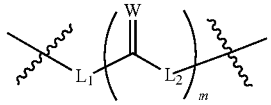
,
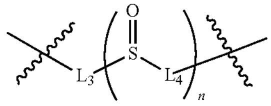
,
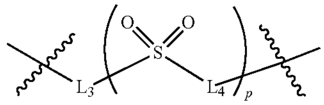
,
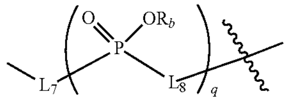
, or
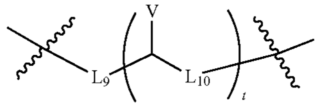
, in which each of m, n, p, q, and t, independently, is 1-6; W is O, S, or $NR_c$; each of $L_1$, $L_3$, $L_5$, $L_7$, and $L_9$, directly linked to $R_1$, $R_2$, $R_4$, or $R_5$, independently, is a bond, O, S, or $NR_d$; each of $L_2$, $L_4$, $L_6$, $L_8$, and $L_{10}$, independently, is a bond, O, S, or $NR_e$; V is $OR_f$, $SR_g$, or $NR_hR_i$; and each of $R_b$, $R_c$, $R_d$, $R_e$, $R_f$, $R_g$, $R_h$, and $R_i$, independently, is H, OH, $C_{1-10}$ oxyaliphatic radical, $C_1$-$C_{10}$ monovalent aliphatic radical, $C_1$-$C_{10}$ monovalent heteroaliphatic radical, a monovalent aryl radical, or a monovalent heteroaryl radical.

A subset of the above-described lipid-like compounds include those in which A is

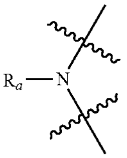
or
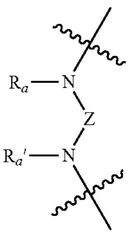
, each of $R^a$ and $R_a'$, independently, being a $C_1$-$C_{10}$ monovalent aliphatic radical, a $C_1$-$C_{10}$ monovalent heteroaliphatic radical, a monovalent aryl radical, or a monovalent heteroaryl radical; and Z being a $C_1$-$C_{10}$ bivalent aliphatic radical, a $C_1$-$C_{10}$ bivalent heteroaliphatic radical, a bivalent aryl radical, or a bivalent heteroaryl radical.

Some lipid-like compounds of this invention feature each of $R_1$ and $R_4$, independently, being $C_1$-$C_6$ (e.g., $C_1$-$C_4$) bivalent aliphatic radical or a $C_1$-$C_6$ (e.g., $C_1$-$C_4$) bivalent heteroaliphatic radical, the total carbon number for $R_2$ and $R_3$ being 12-20 (e.g., 14-18), the total carbon number of $R_5$ and $R_6$ also being 12-20 (e.g., 14-18), and each of X and Y, independently, is

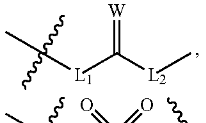,
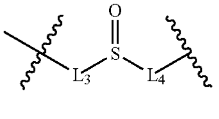,
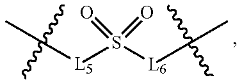,
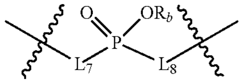, or
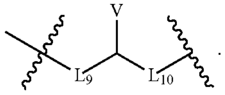.

Specific examples of X and Y include

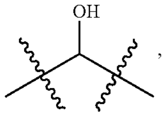,
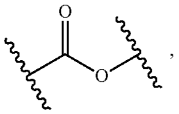,
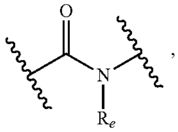,
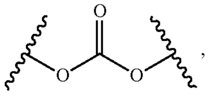,
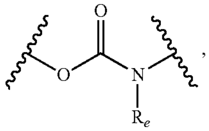,
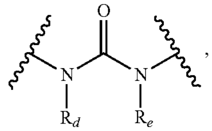, and
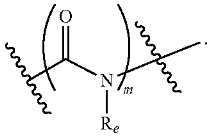.

m being 2-6.

Still within the scope of this invention is a pharmaceutical composition containing a nanocomplex that is formed of a protein and a bioreducible compound. In this pharmaceutical composition, the nanocomplex has a particle size of 50 to 500 nm; the bioreducible compound contains a disulfide hydrophobic moiety, a hydrophilic moiety, and a linker joining the disulfide hydrophobic moiety and the hydrophilic moiety; and the protein binds to the bioreducible compound via a non-covalent interaction, a covalent bond, or both.

In certain embodiments, the disulfide hydrophobic moiety is a heteroaliphatic radical containing one or more —S—S— groups and 8 to 24 carbon atoms; the hydrophilic moiety is an aliphatic or heteroaliphatic radical containing one or more hydrophilic groups and 1-20 carbon atoms, each of the hydrophilic groups being amino, alkylamino, dialkylamino, trialkylamino, tetraalkylammonium, hydroxyamino, hydroxyl, carboxyl, carboxylate, carbamate, carbamide, carbonate, phosphate, phosphite, sulfate, sulfite, or thiosulfate; and the linker is O, S, Si, $C_1$-$C_6$ alkylene,

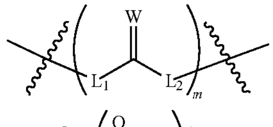,
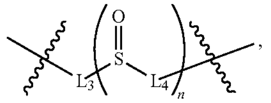,
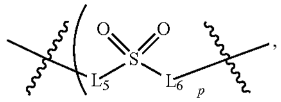,
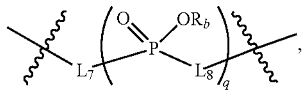, or
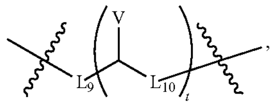, in which the variables are defined above.

Specific examples of X and Y include O, S, Si, $C_1$-$C_6$ alkylene,

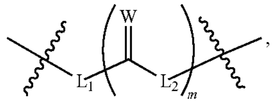,
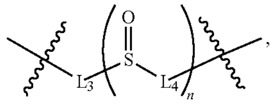,
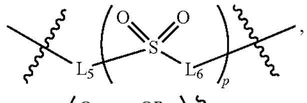,
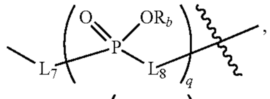, or
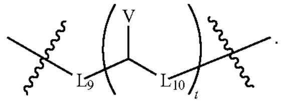.

In some embodiments, a lipid-like compound of this invention, as shown in structure XXIII above, includes (i) a hydrophilic head, A; (ii) a hydrophobic tail, $R_2$—S—S—$R_3$; and (iii) a linker, X. Optionally, these compounds contain a second hydrophobic tail, $R_5$—S—S—$R_6$ and a second linker, Y.

The hydrophilic head of structure XXIII contains one or more hydrophilic functional groups, e.g., hydroxyl, carbonyl, carboxyl, amino, sulfhydryl, phosphate, amide, ester, ether, carbamate, carbonate, carbamide, and phosphodiester. These groups can form hydrogen bonds and are optionally positively or negatively charged.

Examples of the hydrophilic head include:
1
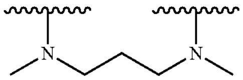
2
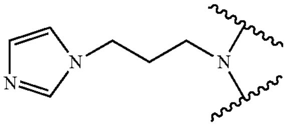
3
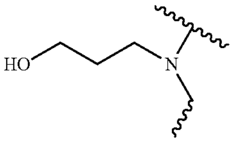
4
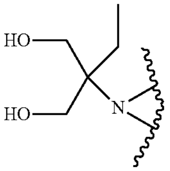
5
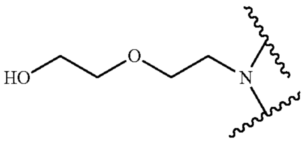
6
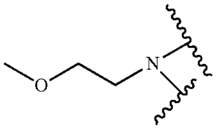
7
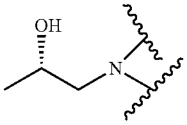
8
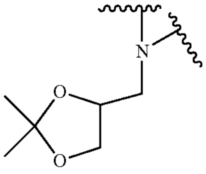
9
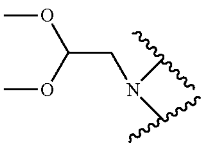
10
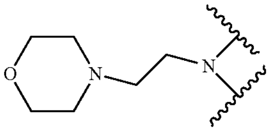
-continued
11
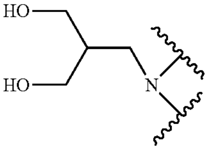
12
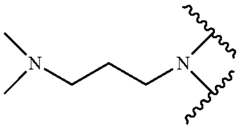
13
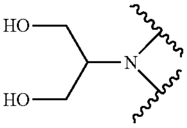
14
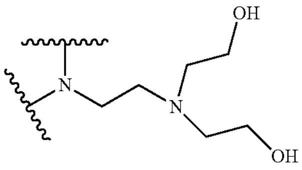
15
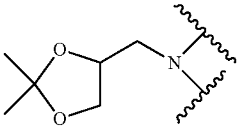
16
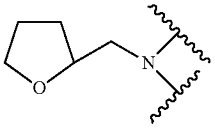
17
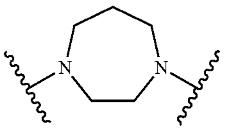
18
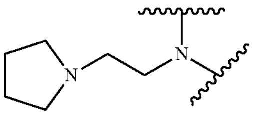
19
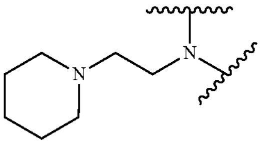
20
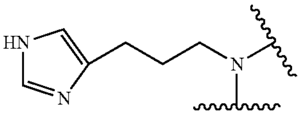
21
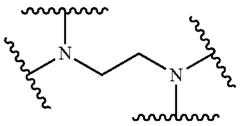

-continued

22

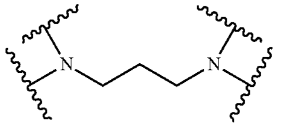

23

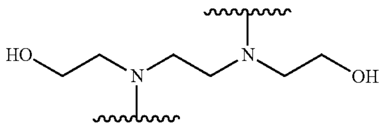

24

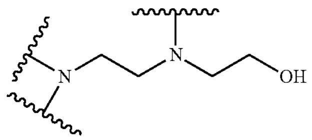

25

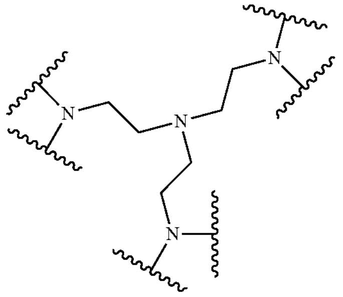

26

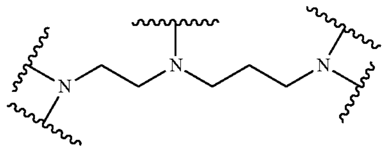

27

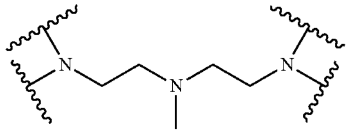

28

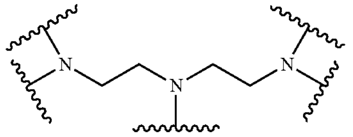

-continued

29

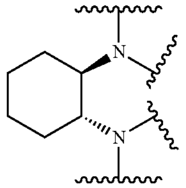

30

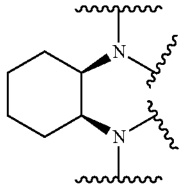

31

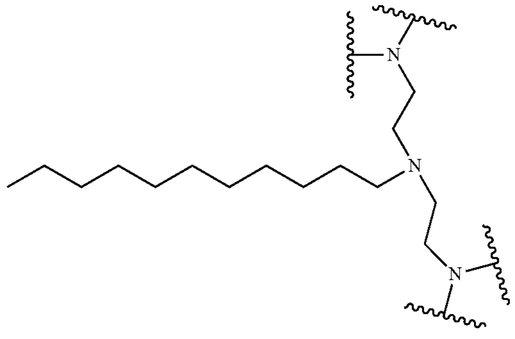

32

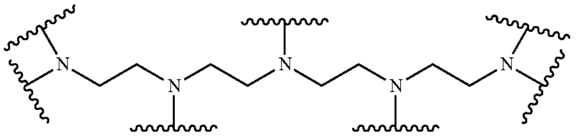

Other examples include those described in Akinc et al., Nature Biotechnology, 26, 561-69 (2008) and Mahon et al., US Patent Application Publication 2011/0293703.

The hydrophobic tail of structure XXIII is a saturated or unsaturated, linear or branched, acyclic or cyclic, aromatic or nonaromatic hydrocarbon moiety containing a disulfide bond and 8-24 carbon atoms. One or more of the carbon atoms can be replaced with a heteroatom, such as N, O, P, B, S, Si, Sb, Al, Sn, As, Se, and Ge. The tail is optionally substituted with one or more groups described above. The lipid-like compounds containing this disulfide bond can be bioreducible.

Examples include:

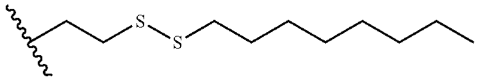

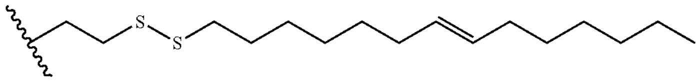

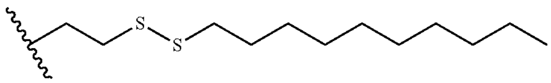

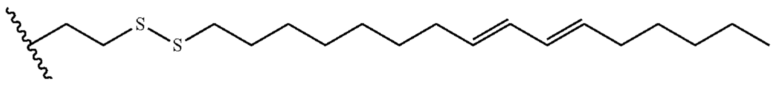

-continued

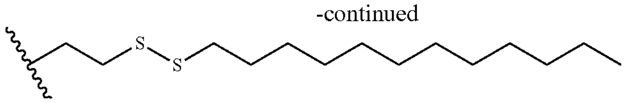

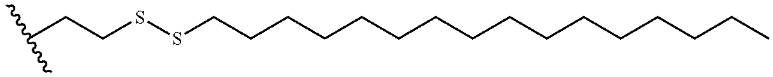

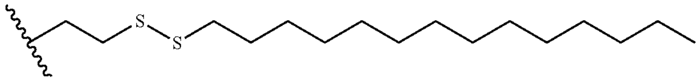

A linker of structure XXIII links the hydrophilic head and the hydrophobic tail.

The linker can be any chemical group that is hydrophilic or hydrophobic, polar or non-polar, e.g., O, S, Si, amino, alkylene, ester, amide, carbamate, carbamide, carbonate, phosphate, phosphite, sulfate, sulfite, and thiosulfate. Examples include:

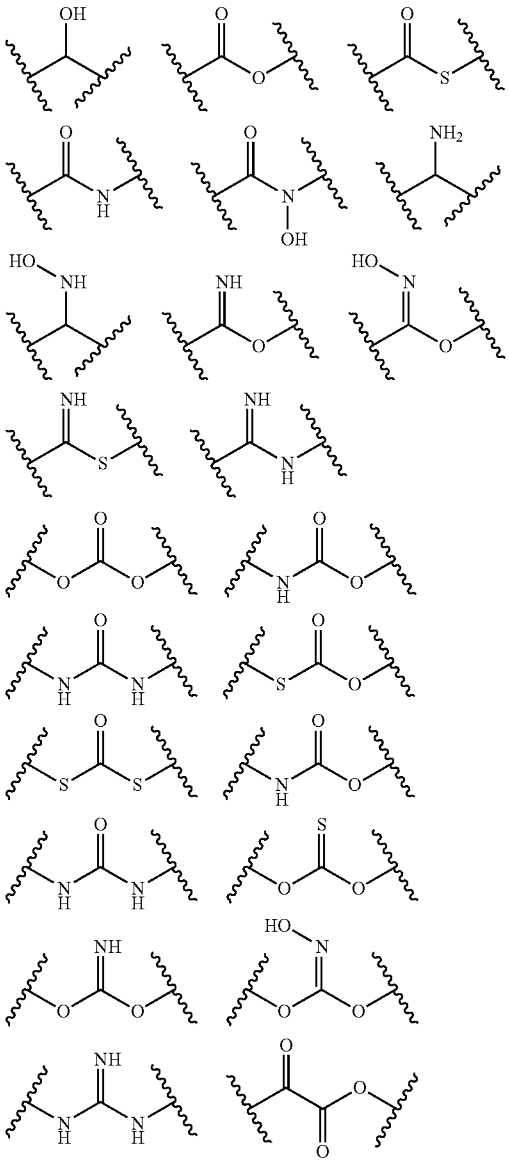

-continued

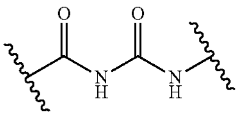

Shown below are exemplary lipid-like compounds of this invention:

80-O14B

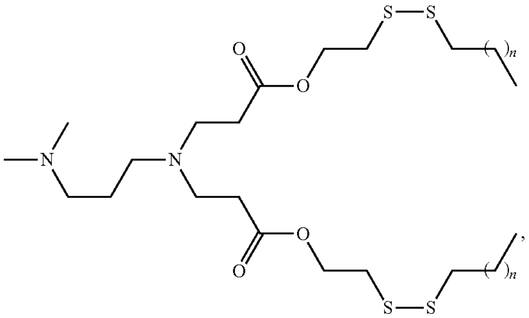

$n = 8$

80-O16B

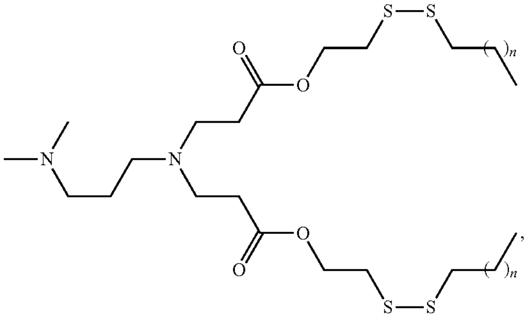

$n = 10$

-continued
80-O18B
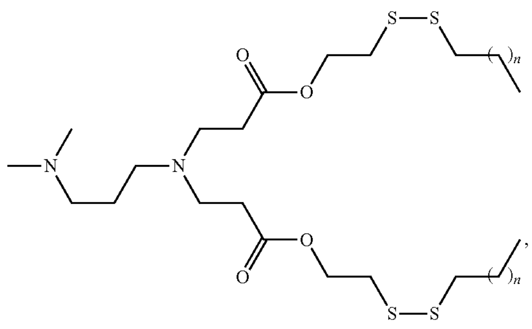
$n = 12$
87-O14B
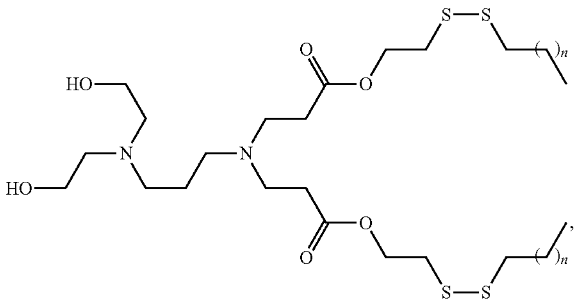
$n = 8$
87-O16B
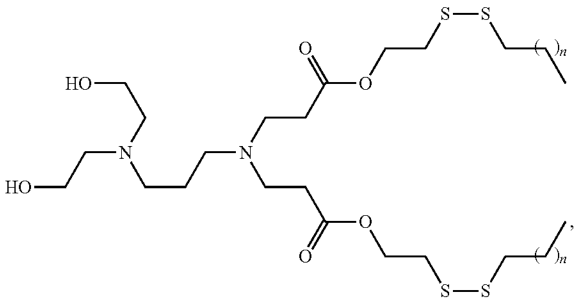
$n = 10$
87-O18B
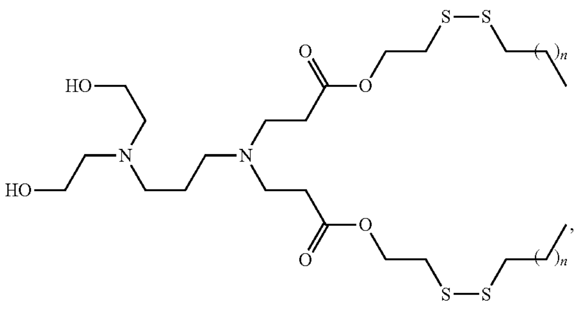
$n = 12$
-continued
1-O16B
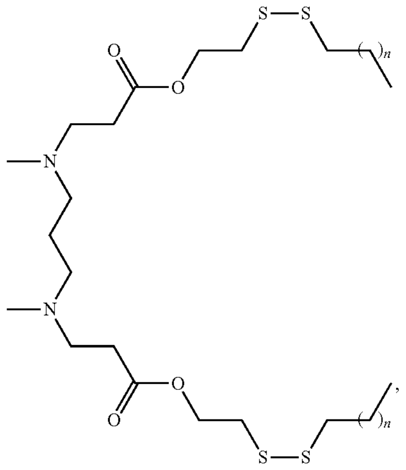
$n = 10$
1-O18B
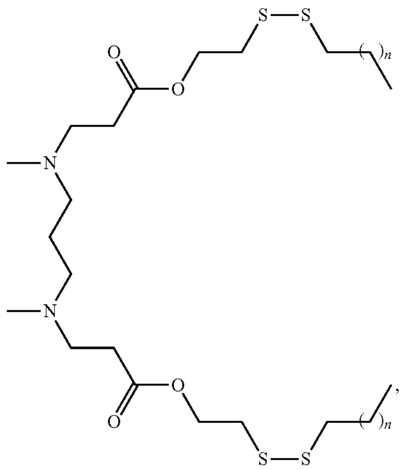
$n = 12$
The lipid-like compounds of structure XXIII can be prepared by methods well known the art. See Wang et al., ACS Synthetic Biology, 1, 403-07 (2012); Manoharan, et al., International Patent Application Publication WO 2008/042973; and Zugates et al., U.S. Pat. No. 8,071,082. The route shown below exemplifies synthesis of these lipid-like compounds:
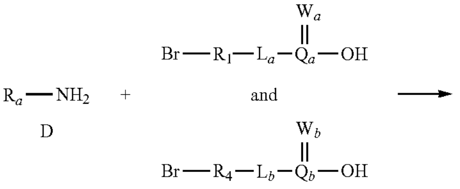
D
and
E1 and E2

-continued

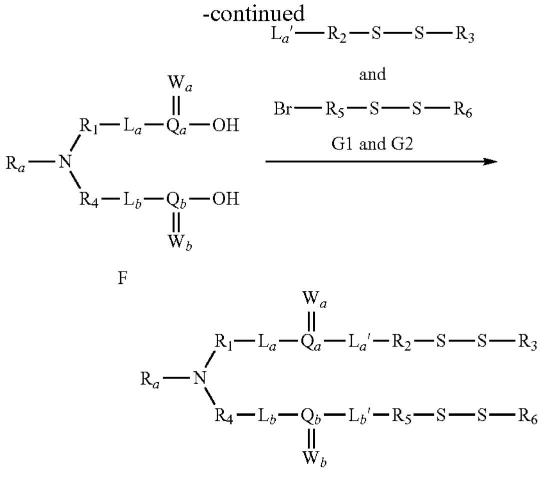

F

H

Each of $L_a$, $L_a'$, L, and L' can be one of $L_1$-$L_{10}$; each of $W_a$ and $W_b$, independently, is W or V; and $R_a$ and $R_1$-$R_6$ are defined above, as well as $L_1$-$L_{10}$, W, and V.

In this exemplary synthetic route, an amine compound, i.e., compound D, reacts with bromides E1 and E2 to form compound F, which is then coupled with both G1 and G2 to afford the final product, i.e., compound H. One or both of the double bonds in this compound (shown above) can be reduced to one or two single bonds to obtain different lipid-like compounds of structure XXIII.

Other lipid-like compounds of this invention can be prepared using other suitable starting materials through the above-described synthetic route and others known in the art. The method set forth above can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2nd ed., John Wiley and Sons 2009) and subsequent editions thereof. Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

As mentioned above, these lipid-like compounds are useful for delivery of pharmaceutical agents. They can be preliminarily screened for their efficacy in delivering pharmaceutical agents by an in vitro assay and then confirmed by animal experiments and clinic trials. Other methods will also be apparent to those of ordinary skill in the art.

Not to be bound by any theory, the lipid-like compounds of structure XXIII facilitate delivery of pharmaceutical agents by forming complexes, e.g., nanocomplexes and microparticles. The hydrophilic head of such a lipid-like compound, positively or negatively charged, binds to a moiety of a pharmaceutical agent that is oppositely charged and its hydrophobic moiety binds to a hydrophobic moiety of the pharmaceutical agent. Either binding can be covalent or non-covalent.

The above described complexes can be prepared using procedures described in publications such as Wang et al., ACS Synthetic Biology, 1, 403-07 (2012). Generally, they are obtained by incubating a lipid-like compound and a pharmaceutical agent in a buffer such as a sodium acetate buffer or a phosphate buffered saline ("PBS").

5.4 Hydrophilic Groups

In certain embodiments, the selected hydrophilic functional group or moiety may alter or otherwise impart properties to the compound or to the transfer vehicle of which such compound is a component (e.g., by improving the transfection efficiencies of a lipid nanoparticle of which the compound is a component). For example, the incorporation of guanidinium as a hydrophilic head-group in the compounds disclosed herein may promote the fusogenicity of such compounds (or of the transfer vehicle of which such compounds are a component) with the cell membrane of one or more target cells, thereby enhancing, for example, the transfection efficiencies of such compounds. It has been hypothesized that the nitrogen from the hydrophilic guanidinium moiety forms a six-membered ring transition state which grants stability to the interaction and thus allows for cellular uptake of encapsulated materials. (Wender, et al., Adv. Drug Del. Rev. (2008) 60: 452-472.) Similarly, the incorporation of one or more amino groups or moieties into the disclosed compounds (e.g., as a head-group) may further promote disruption of the endosomal/lysosomal membrane of the target cell by exploiting the fusogenicity of such amino groups. This is based not only on the pKa of the amino group of the composition, but also on the ability of the amino group to undergo a hexagonal phase transition and fuse with the target cell surface, i.e. the vesicle membrane. (Koltover, et al. Science (1998) 281: 78-81.) The result is believed to promote the disruption of the vesicle membrane and release of the lipid nanoparticle contents into the target cell.

Similarly, in certain embodiments the incorporation of, for example, imidazole as a hydrophilic head-group in the compounds disclosed herein may serve to promote endosomal or lysosomal release of, for example, contents that are encapsulated in a transfer vehicle (e.g., lipid nanoparticle) of the invention. Such enhanced release may be achieved by one or both of a proton-sponge mediated disruption mechanism and/or an enhanced fusogenicity mechanism. The proton-sponge mechanism is based on the ability of a compound, and in particular a functional moiety or group of the compound, to buffer the acidification of the endosome. This may be manipulated or otherwise controlled by the pKa of the compound or of one or more of the functional groups comprising such compound (e.g., imidazole). Accordingly, in certain embodiments the fusogenicity of, for example, the imidazole-based compounds disclosed herein (e.g., HGT4001 and HGT4004) are related to the endosomal disruption properties, which are facilitated by such imidazole groups, which have a lower pKa relative to other traditional ionizable lipids. Such endosomal disruption properties in turn promote osmotic swelling and the disruption of the liposomal membrane, followed by the transfection or intracellular release of the polynucleotide materials loaded or encapsulated therein into the target cell. This phenomenon can be applicable to a variety of compounds with desirable pKa profiles in addition to an imidazole moiety. Such embodiments also include multi-nitrogen based functionalities such as polyamines, poly-peptide (histidine), and nitrogen-based dendritic structures.

Exemplary ionizable and/or cationic lipids are described in International PCT patent publications WO2015/095340, WO2015/199952, WO2018/011633, WO2017/049245, WO2015/061467, WO2012/040184, WO2012/000104, WO2015/074085, WO2016/081029, WO2017/004, 143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO20, 12/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US patent publications US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/0090372, US2013/0274523, US2013/0274504, US2013/0274504, US2009/0023673, US2012/0128760, US2010/0324120, US2014/0200257, US2015/0203446, US2018/0005363, US2014/0308304, US2013/0338210, US2012/0101148, US2012/0027796, US2012/0058144, US2013/0323269, US2011/0117125, US2011/0256175, US2012/0202871, US2011/0076335, US2006/0083780, US2013/0123338, US2015/0064242, US2006/0051405, US2013/0065939, US2006/0008910, US2003/0022649, US2010/0130588, US2013/0116307, US2010/0062967, US2013/0202684, US2014/0141070, US2014/0255472, US2014/0039032, US2018/0028664, US2016/0317458, and US2013/0195920, the contents of all of which are incorporated herein by reference in their entirety. International patent application WO 2019/131770 is also incorporated herein by reference in its entirety.

6. PEG Lipids

The use and inclusion of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of C6-C20 length. In some embodiments, the PEG-modified lipid employed in the compositions and methods of the invention is 1,2-dimyristoyl-sn-glycerol, methoxypolyethylene Glycol (2000 MW PEG) "DMG-PEG2000." The addition of PEG-modified lipids to the lipid delivery vehicle may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

In an embodiment, a PEG-modified lipid is described in International Pat. Appl. No. PCT/US2019/015913, which is incorporated herein by reference in their entirety. In an embodiment, a transfer vehicle comprises one or more PEG-modified lipids.

Non-limiting examples of PEG-modified lipids include PEG-modified phosphatidylethanolamines and phosphatidic acids, PEG-ceramide conjugates (e.g., PEG-CerC14 or PEG-CerC20), PEG-modified dialkylamines and PEG-modified 1,2-diacyloxypropan-3-amines. In some further embodiments, a PEG-modified lipid may be, e.g., PEG-c-DOMG, PEG-DMG, PEG-DLPE, PEG-DMPE, PEG-DPPC, or a PEG-DSPE.

In some still further embodiments, the PEG-modified lipid includes, but is not limited to, 1,2-dimyristoyl-sn-glycerol methoxypolyethylene glycol (PEG-DMG), 1,2-distearoyl-sn-glycero-3-phosphoethanolamine-N-[amino(poly ethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In various embodiments, a PEG-modified lipid may also be referred to as "PEGylated lipid" or "PEG-lipid."

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, such as from about $C_{14}$ to about $C_{16}$. In some embodiments, a PEG moiety, for example a mPEG-$NH_2$, has a size of about 1000, about 2000, about 5000, about 10,000, about 15,000 or about 20,000 daltons. In one embodiment, the PEG-lipid is PEG2k-DMG.

In one embodiment, the lipid nanoparticles described herein can comprise a lipid modified with a non-diffusible PEG. Non-limiting examples of non-diffusible PEGs include PEG-DSG and PEG-DSPE.

PEG-lipids are known in the art, such as those described in U.S. Pat. No. 8,158,601 and International Pat. Publ. No. WO2015/130584 A2, which are incorporated herein by reference in their entirety.

In various embodiments, lipids (e.g., PEG-lipids), described herein may be synthesized as described International Pat. Publ. No. PCT/US2016/000129, which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG-DMG. PEG-DMG has the following structure:

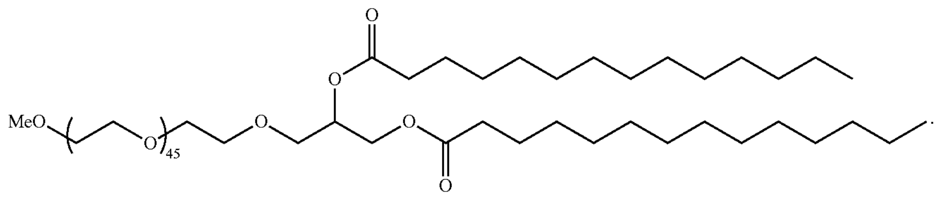

In some embodiments the PEG-modified lipids are a modified form of PEG-C18, or PEG-1. PEG-1 has the following structure

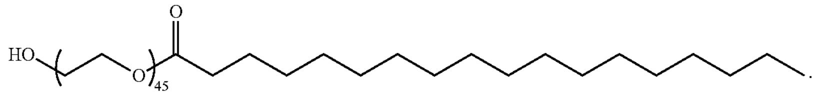

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In some embodiments, the PEG lipid is a compound of Formula (P1):

(P1)

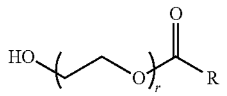

or a salt or isomer thereof, wherein:

r is an integer between 1 and 100;

R is $C_{10-40}$ alkyl, $C_{10-40}$ alkenyl, or $C_{10-40}$ alkynyl; and optionally one or more methylene groups of R are independently replaced with $C_{3-10}$ carbocyclylene, 4 to 10 membered heterocyclylene, $C_{6-10}$ arylene, 4 to 10 membered heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(═N$R^N$)—, —C(═N$R^N$)N($R^N$)—, —N$R^N$C(═N$R^N$)—, —N$R^N$C(═N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —$OS(O)_2$—, —$S(O)_2O$—, —$OS(O)_2O$—, —N($R^N$)S(O)—, —S(O)N($R^N$)—, —N($R^N$)S(O)N($R^N$)—, —OS(O)N($R^N$)—, —N($R^N$)S(O)O—, —S(O)2-, —N($R^N$)S(O)2-, —$S(O)_2$N($R^N$)—, —N($R^N$)$S(O)_2$N($R^N$)—, —$OS(O)_2$N($R^N$)—, or —N($R^N$)$S(O)_2O$—; and each instance of $R^N$ is independently hydrogen, $C_{1-6}$ alkyl, or a nitrogen protecting group.

For example, R is C17 alkyl. For example, the PEG lipid is a compound of Formula (P1-a):

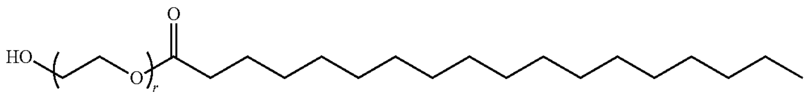

or a salt or isomer thereof, wherein r is an integer between 1 and 100.

For example, the PEG lipid is a compound of the following formula:

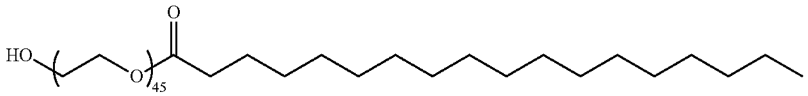

7. Helper Lipids

In some embodiments, the transfer vehicle (e.g., LNP) described herein comprises one or more non-cationic helper lipids. In some embodiments, the helper lipid is a phospholipid. In some embodiments, the helper lipid is a phospholipid substitute or replacement. In some embodiments, the phospholipid or phospholipid substitute can be, for example, one or more saturated or (poly)unsaturated phospholipids, or phospholipid substitutes, or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the helper lipid is a 1,2-distearoyl-177-glycero-3-phosphocholine (DSPC) analog, a DSPC substitute, oleic acid, or an oleic acid analog.

In some embodiments, a helper lipid is a non-phosphatidyl choline (PC) zwitterionic lipid, a DSPC analog, oleic acid, an oleic acid analog, or a DSPC substitute.

In some embodiments, a helper lipid is described in PCT/US2018/053569. Helper lipids suitable for use in a lipid composition of the disclosure include, for example, a variety of neutral, uncharged or zwitterionic lipids. Such helper lipids are preferably used in combination with one or more of the compounds and lipids disclosed herein. Examples of helper lipids include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoylsn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC),1-paimitoyl-2-myristoyl phosphatidylcholine (PMPC),1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), paimitoyioieoyl phosphatidylcholine (POPC), lysophosphatidyl choline, dioleoyl phosphatidylethanol amine (DOPE) dilinoleoylphosphatidylcholine distearoylphosphatidylethanolamine (DSPE), dimyristoyl phosphatidylethanolamine (DMPE), dipalmitoylp hosphatidylethanolamine (DPPE), palmitoyloleoyl phosphatidylethanolamine (POPE), lysophosphatidylethanolamine and combinations thereof. In one embodiment, the helper lipid may be distearoylphosphatidylcholine (DSPC) or dimyristoyl phosphatidyl ethanolamine (DMPE). In another embodiment, the helper lipid may be distearoylphosphatidylcholine (DSPC). Helper lipids function to stabilize and improve processing of the transfer vehicles. Such helper lipids are preferably used in combination with other excipients, for example, one or more of the ionizable lipids disclosed herein. In some embodiments, when used in combination with an ionizable lipid, the helper lipid may comprise a molar ratio of 5% to about 90%, or about 10% to about 70% of the total lipid present in the lipid nanoparticle.

8. Structural Lipids

In an embodiment, a structural lipid is described in international patent application PCT/US2019/015913.

The transfer vehicles described herein comprise one or more structural lipids. Incorporation of structural lipids in the lipid nanoparticle may help mitigate aggregation of other lipids in the particle. Structural lipids can include, but are not limited to, cholesterol, fecosterol, ergosterol, bassicasterol, tomatidine, tomatine, ursolic, alpha-tocopherol, and mixtures thereof. In certain embodiments, the structural lipid is cholesterol. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

The transfer vehicles described herein comprise one or more structural lipids. Incorporation of structural lipids in a transfer vehicle, e.g., a lipid nanoparticle, may help mitigate aggregation of other lipids in the particle. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. Structural lipids can include, but are not limited to, sterols (e.g., phytosterols or zoosterols).

In certain embodiments, the structural lipid is a steroid. For example, sterols can include, but are not limited to, cholesterol, β-sitosterol, fecosterol, ergosterol, sitosterol, campesterol, stigmasterol, brassicasterol, ergosterol, tomatidine, tomatine, ursolic acid, or alpha-tocopherol.

In some embodiments, a transfer vehicle includes an effective amount of an immune cell delivery potentiating lipid, e.g., a cholesterol analog or an amino lipid or combination thereof, that, when present in a transfer vehicle, e.g., an lipid nanoparticle, may function by enhancing cellular association and/or uptake, internalization, intracellular trafficking and/or processing, and/or endosomal escape and/or may enhance recognition by and/or binding to immune cells, relative to a transfer vehicle lacking the immune cell delivery potentiating lipid. Accordingly, while not intending to be bound by any particular mechanism or theory, in one embodiment, a structural lipid or other immune cell delivery potentiating lipid of the disclosure binds to C1q or promotes the binding of a transfer vehicle comprising such lipid to C1q. Thus, for in vitro use of the transfer vehicles of the disclosure for delivery of a nucleic acid molecule to an immune cell, culture conditions that include C1q are used (e.g., use of culture media that includes serum or addition of exogenous C1q to serum-free media). For in vivo use of the transfer vehicles of the disclosure, the requirement for C1q is supplied by endogenous C1q.
In certain embodiments, the structural lipid is cholesterol. In certain embodiments, the structural lipid is an analog of cholesterol. In some embodiments, the structural lipid is a lipid in Table 16:
TABLE 16
| CMPD No. S— | Structure |
|---|---|
| 1 | 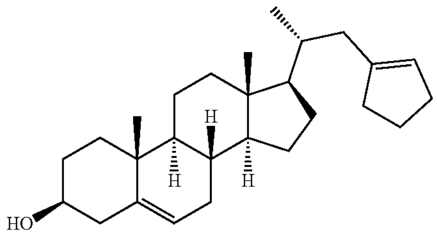 |
| 2 | 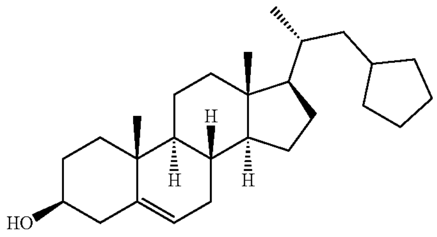 |
| 3 | 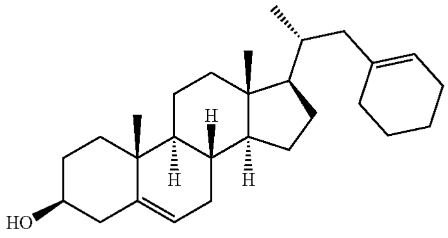 |
| 4 | 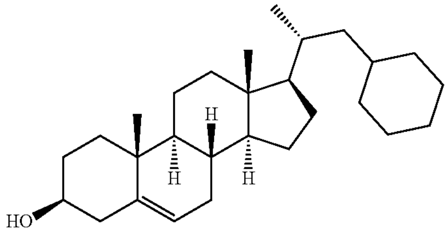 |
| 5 | 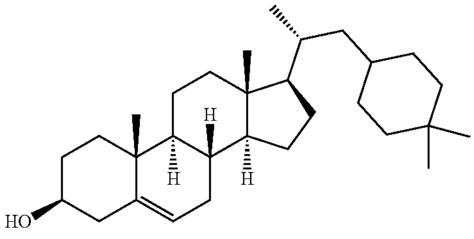 |

TABLE 16-continued
| CMPD No. S— | Structure |
|---|---|
| 6 | 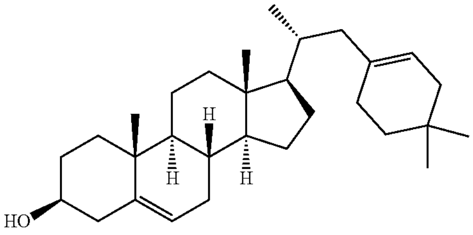 |
| 7 | 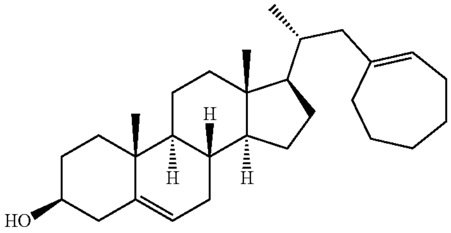 |
| 8 | 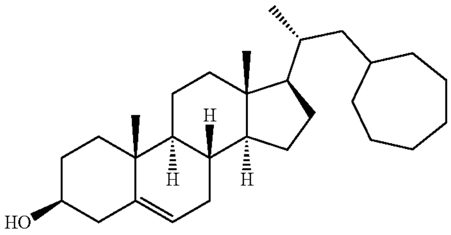 |
| 9 | 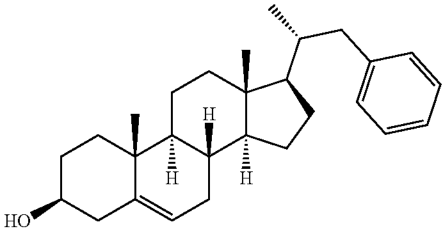 |
| 10 | 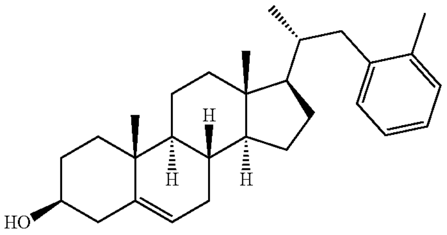 |
| 11 | 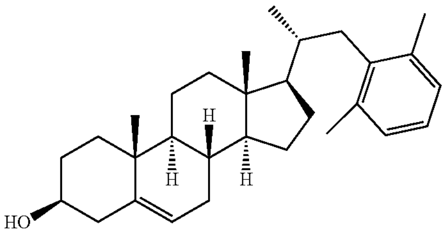 |

TABLE 16-continued
| CMPD No. S— | Structure |
|---|---|
| 12 | 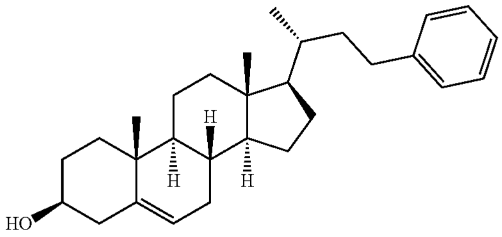 |
| 13 | 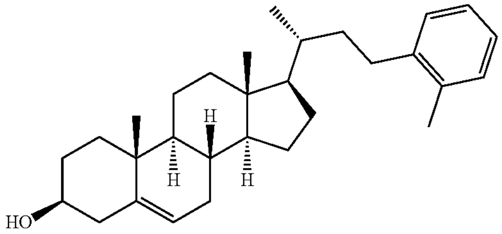 |
| 14 | 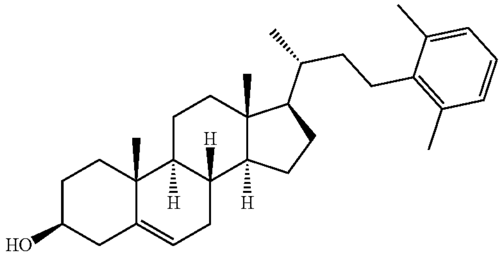 |
| 15 | 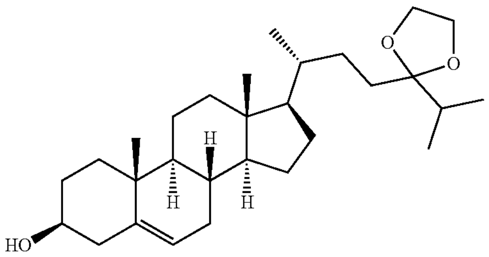 |
| 16 | 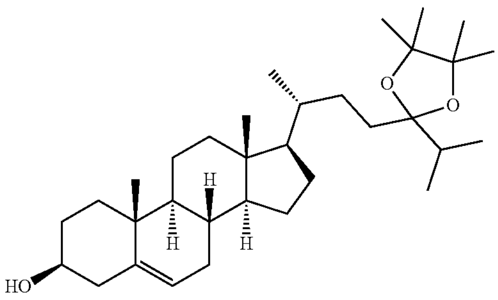 |

TABLE 16-continued
| CMPD No. S— | Structure |
|---|---|
| 17 | 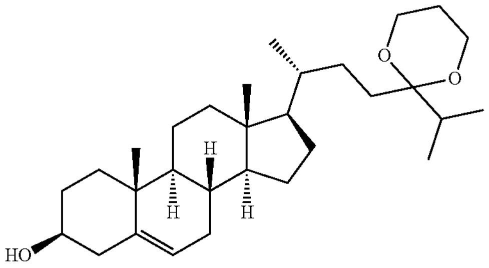 |
| 18 | 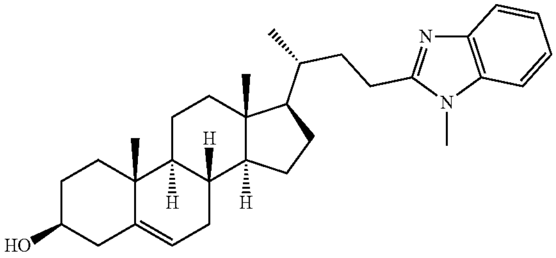 |
| 19 | 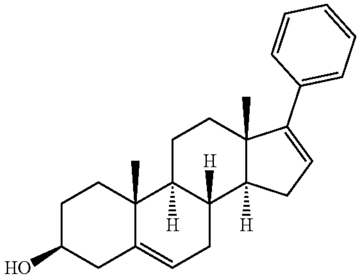 |
| 20 | 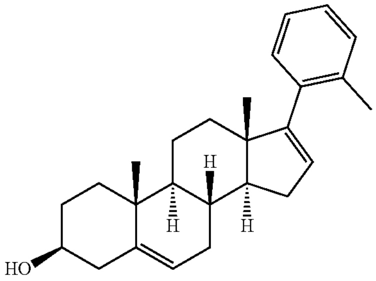 |
| 21 | 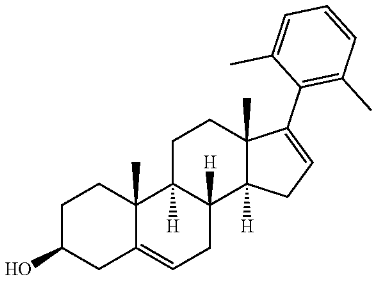 |

TABLE 16-continued
| CMPD No. S— | Structure |
| --- | --- |
| 150 | 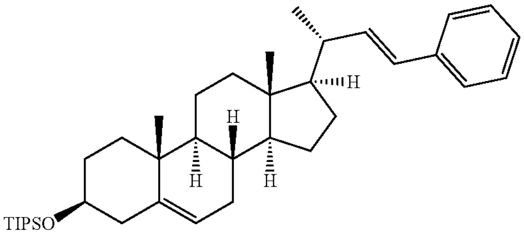 |
| 154 | 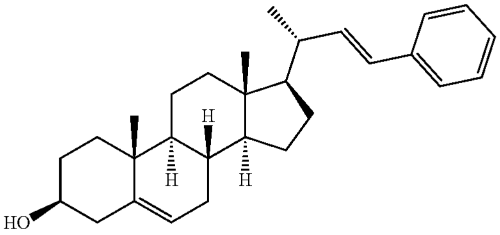 |
| 162 | 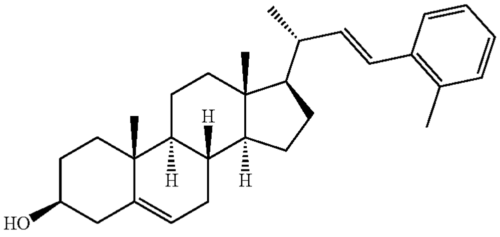 |
| 163 | 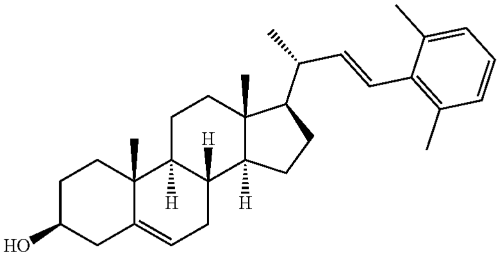 |
| 164 | 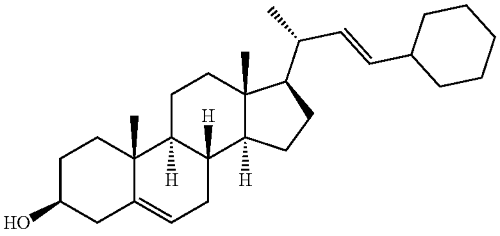 |
| 184 | 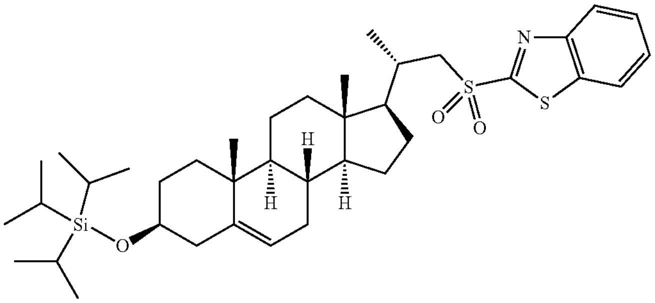 |

TABLE 16-continued
| CMPD No. S— | Structure |
| --- | --- |
| 22 | 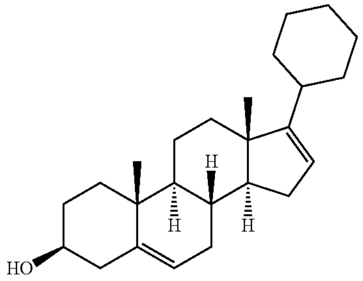 |
| 23 | 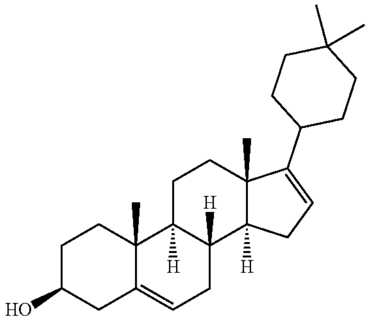 |
| 24 | 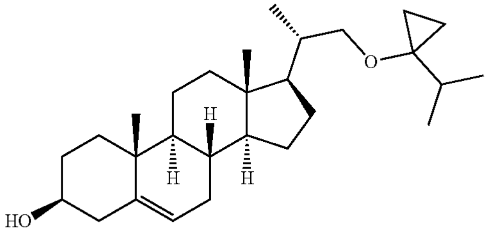 |
| 25 | 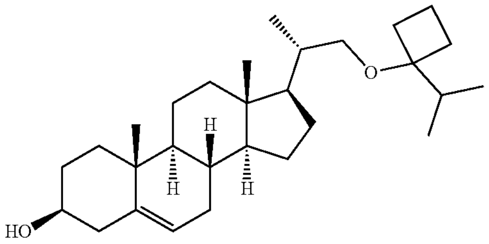 |
| 26 | 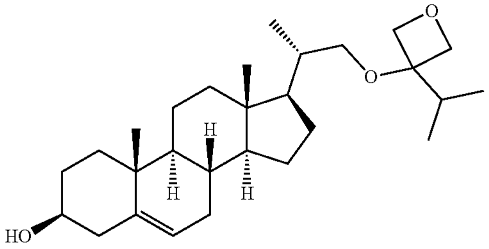 |

TABLE 16-continued
| CMPD No. S— | Structure |
| --- | --- |
| 27 | 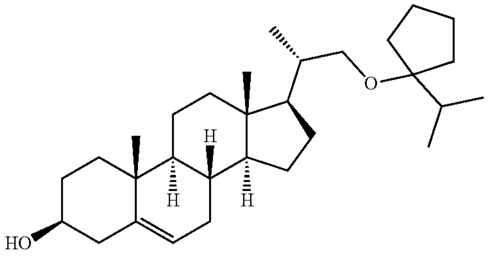 |
| 28 | 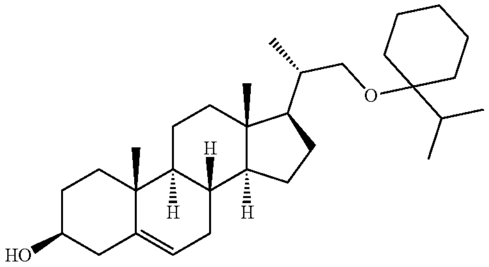 |
| 29 | 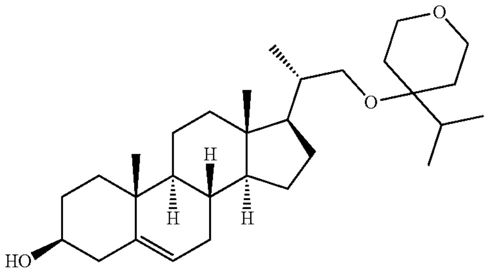 |
| 30 | 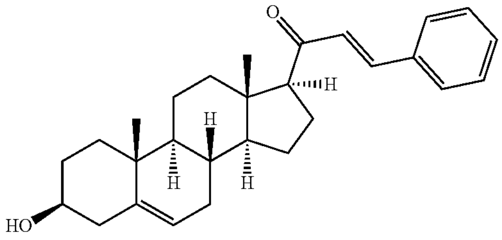 |
| 31 | 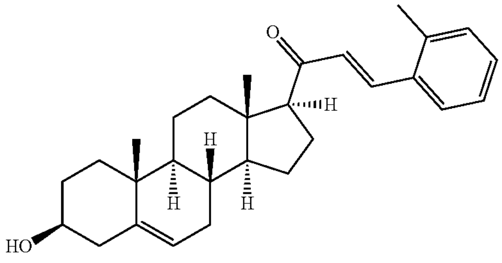 |

TABLE 16-continued
| CMPD No. S— | Structure |
|---|---|
| 32 | 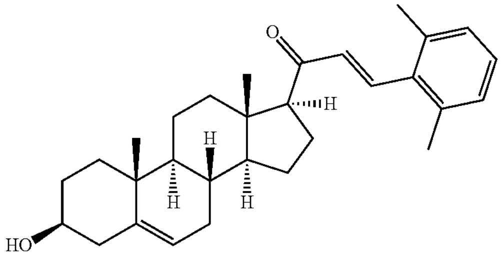 |
| 33 | 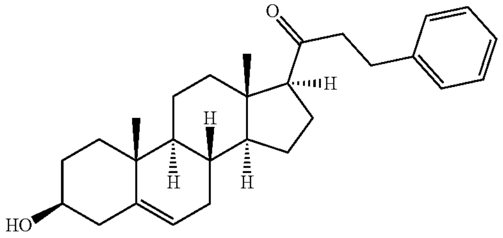 |
| 34 | 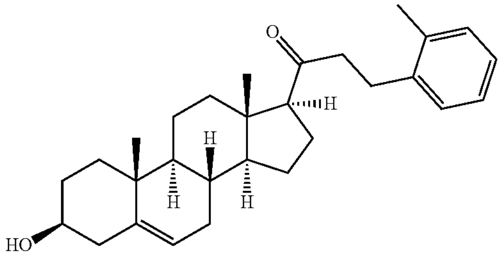 |
| 35 | 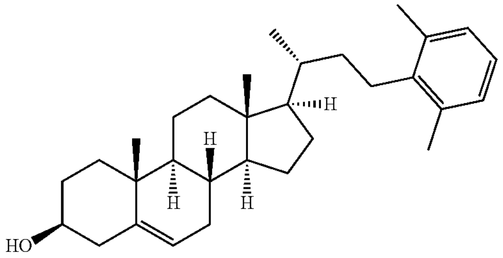 |
| 36 | 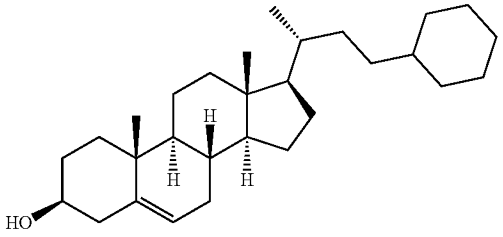 |
| 37 | 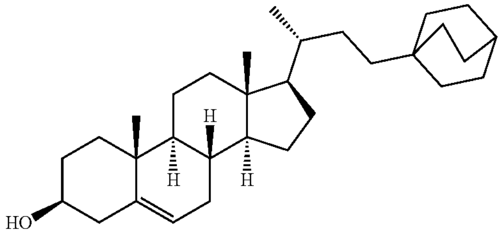 |

TABLE 16-continued
| CMPD No. S— | Structure |
|---|---|
| 38 | 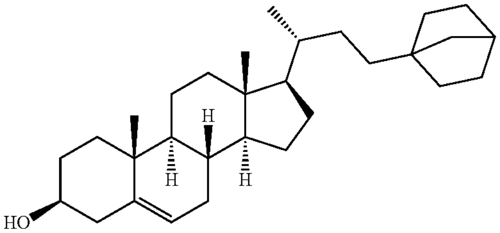 |
| 39 | 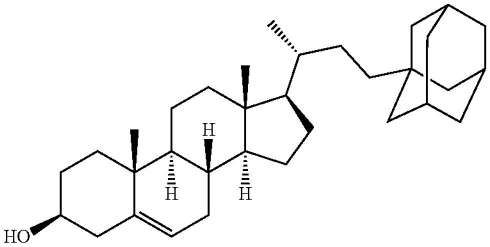 |
| 40 | 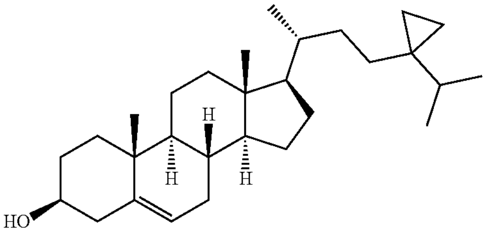 |
| 41 | 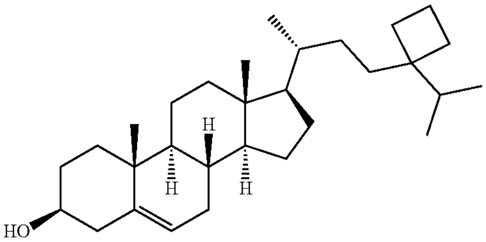 |
| 42 | 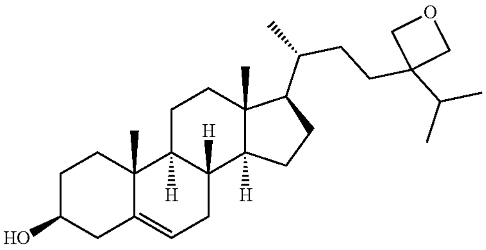 |
| 165 | 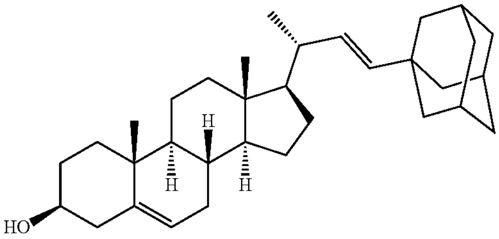 |

TABLE 16-continued
| CMPD No. S— | Structure |
| --- | --- |
| 169 | 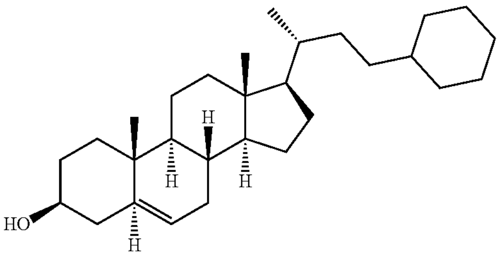 |
| 170 | 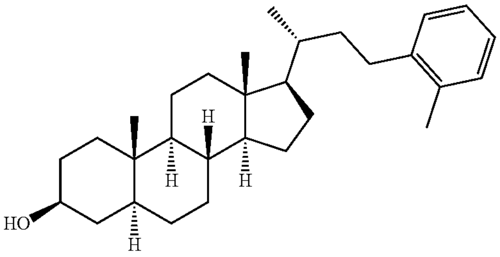 |
| 171 | 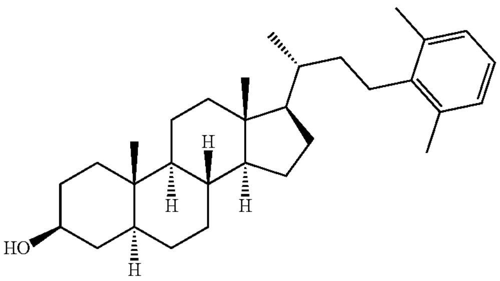 |
| 172 | 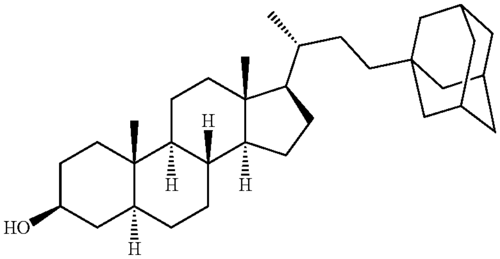 |
| 43 | 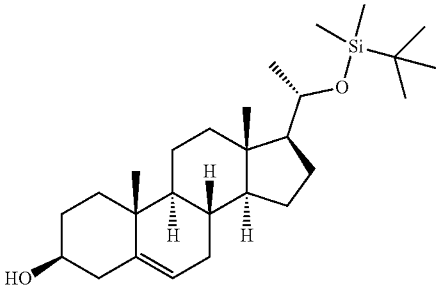 |

TABLE 16-continued
| CMPD No. S— | Structure |
| --- | --- |
| 44 | 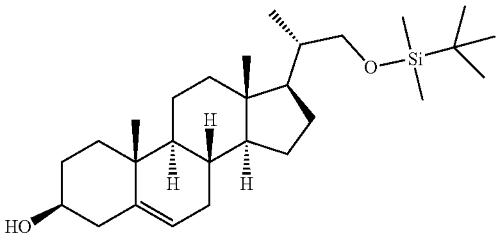 |
| 45 | 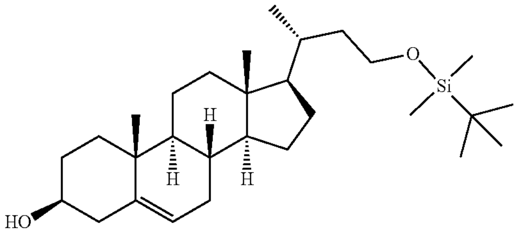 |
| 46 | 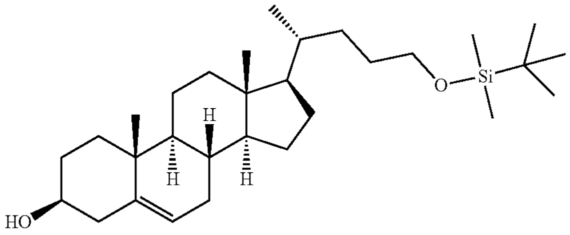 |
| 175 | 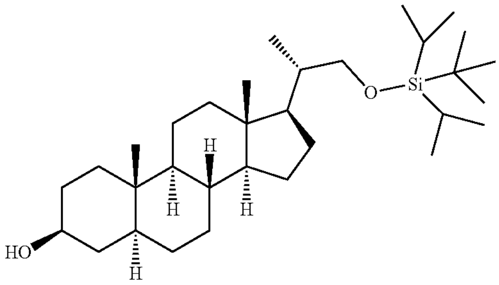 |
| 176 | 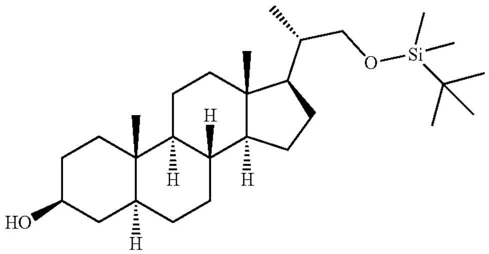 |
| 51 | 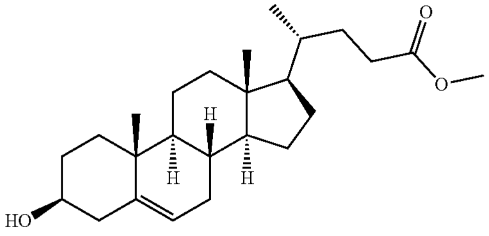 |

TABLE 16-continued
| CMPD No. S— | Structure |
| --- | --- |
| 52 | 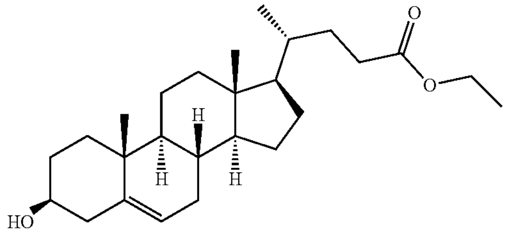 |
| 53 | 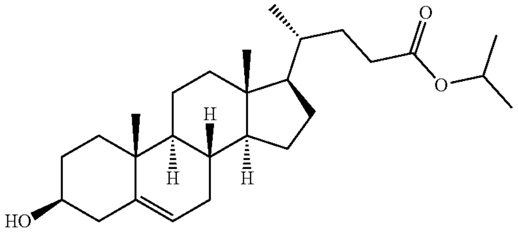 |
| 54 | 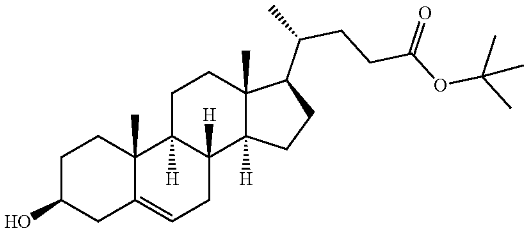 |
| 55 | 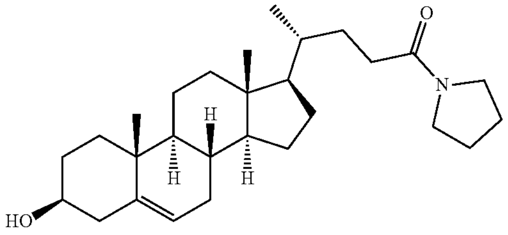 |
| 56 | 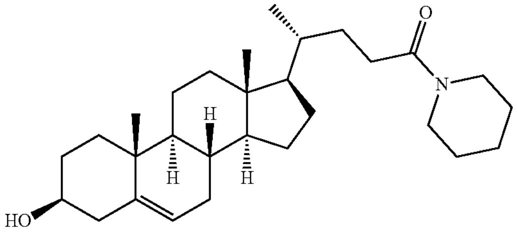 |
| 57 | 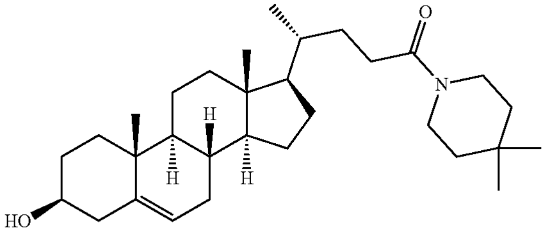 |

TABLE 16-continued
| CMPD No. S— | Structure |
|---|---|
| 58 | 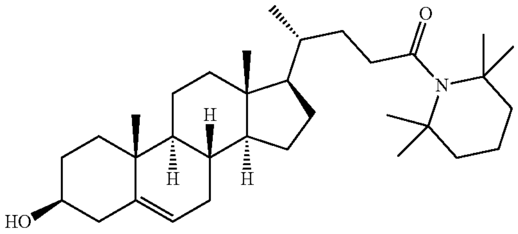 |
| 59 | 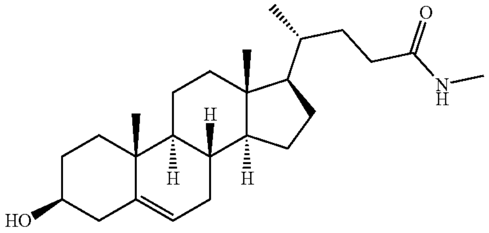 |
| 153 | 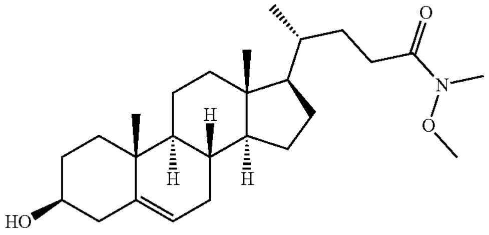 |
| 47 | 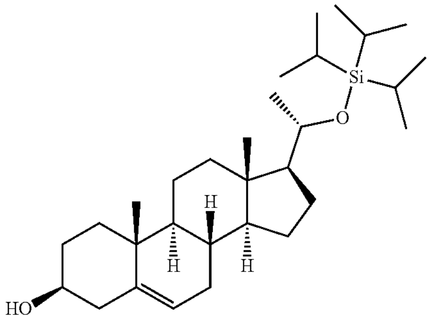 |
| 48 | 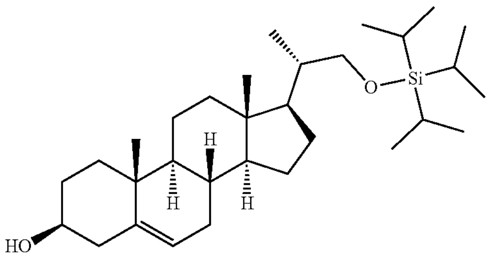 |

TABLE 16-continued
| CMPD No. S— | Structure |
|---|---|
| 49 | 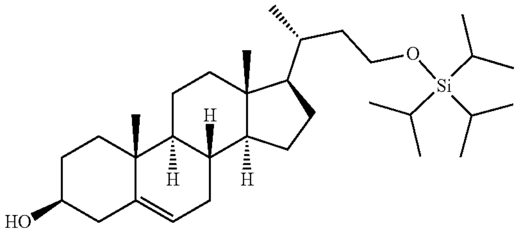 |
| 50 | 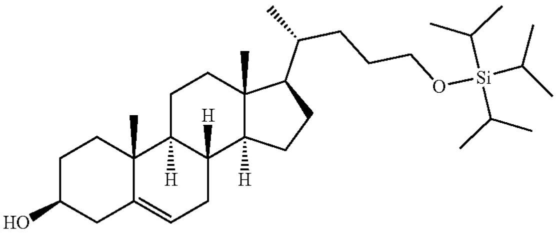 |
| 177 | 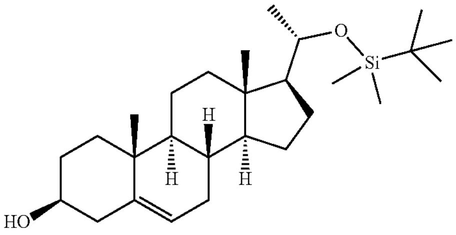 |
| 178 | 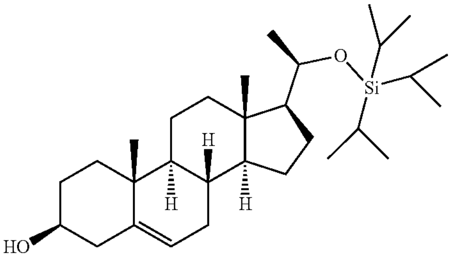 |
| 60 | 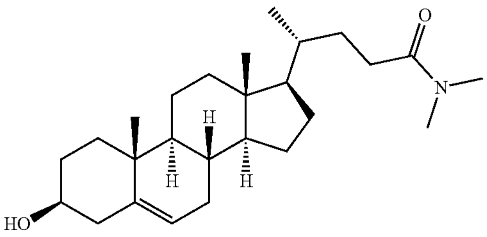 |
| 61 | 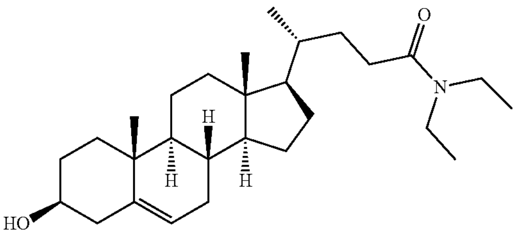 |

TABLE 16-continued
| CMPD No. S— | Structure |
|---|---|
| 62 | 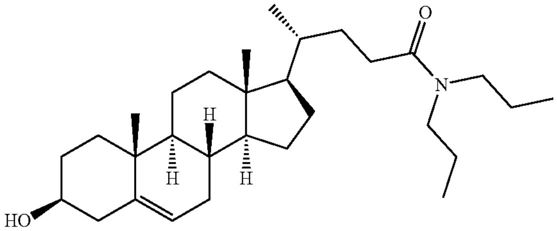 |
| 63 | 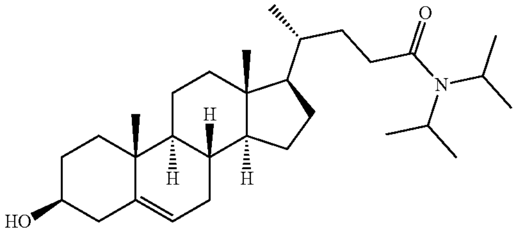 |
| 64 | 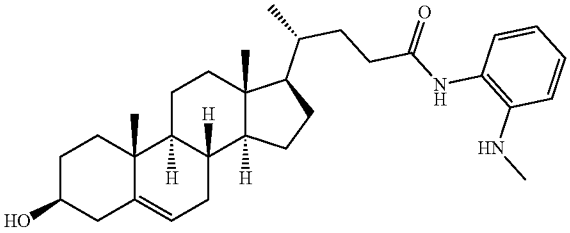 |
| 65 | 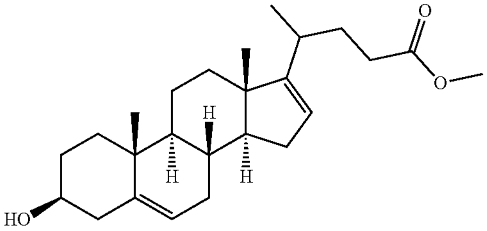 |
| 66 | 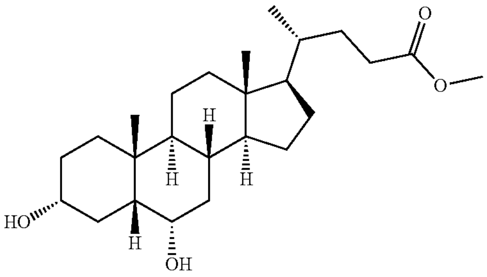 |

TABLE 16-continued
| CMPD No. S— | Structure |
|---|---|
| 67 | 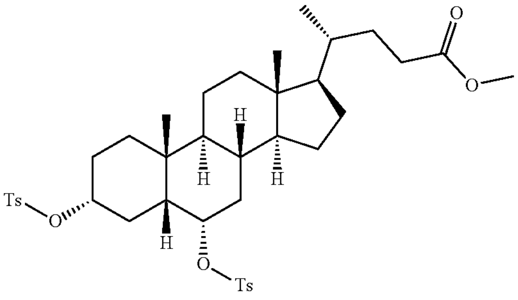 |
| 149 | 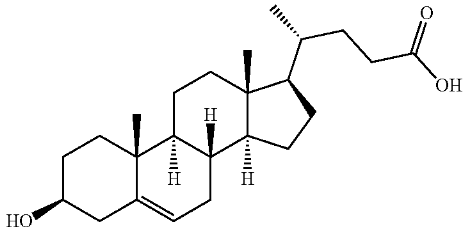 |
| 68 | 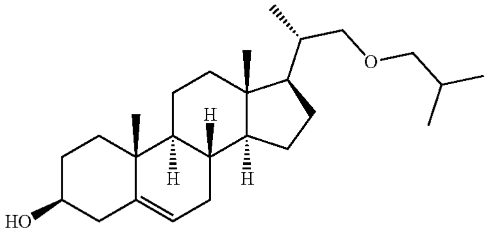 |
| 69 | 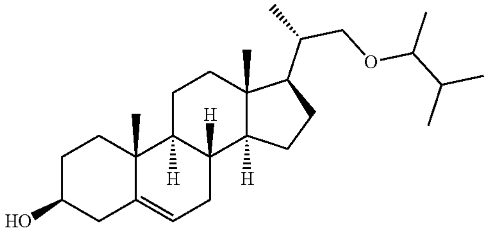 |
| 70 | 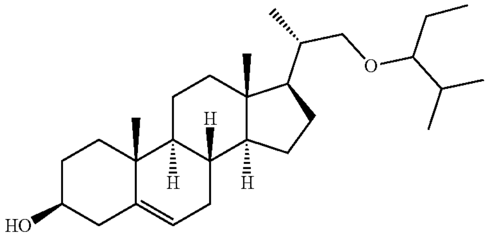 |
| 71 | 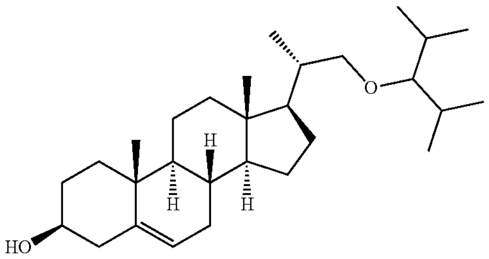 |

TABLE 16-continued
| CMPD No. S— | Structure |
|---|---|
| 72 | 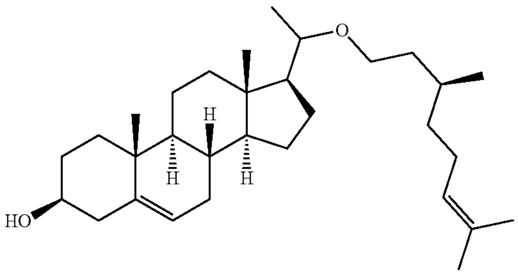 |
| 73 | 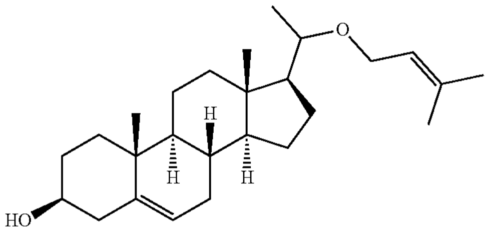 |
| 74 | 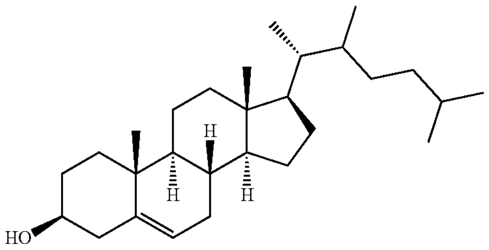 |
| 75 | 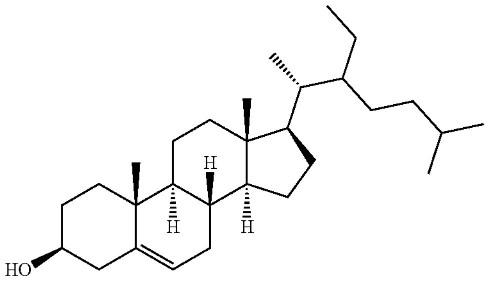 |
| 76 | 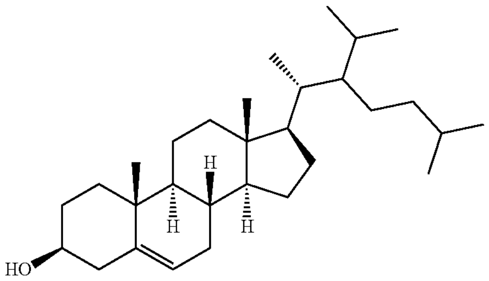 |

TABLE 16-continued
| CMPD No. S— | Structure |
| --- | --- |
| 77 | 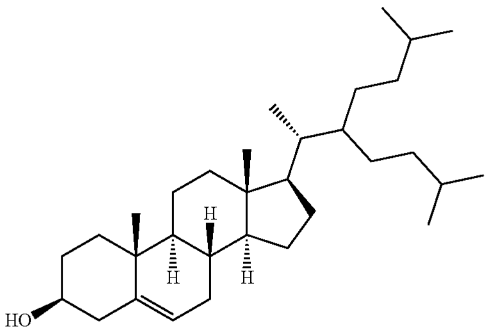 |
| 78 | 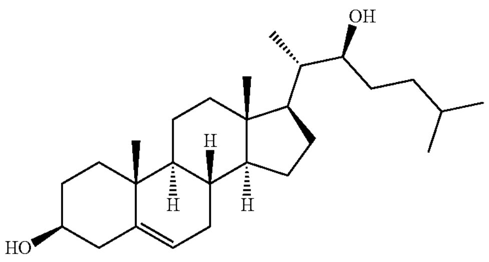 |
| 79 | 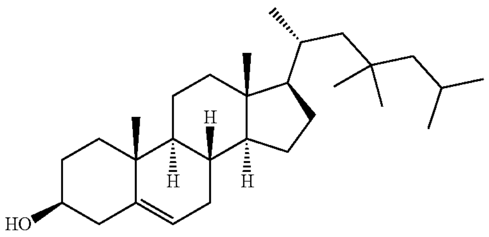 |
| 80 | 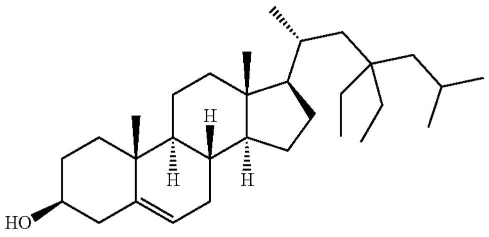 |
| 81 | 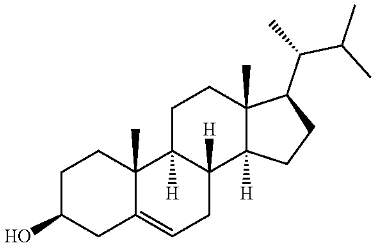 |

TABLE 16-continued
| CMPD No. S— | Structure |
|---|---|
| 82 | 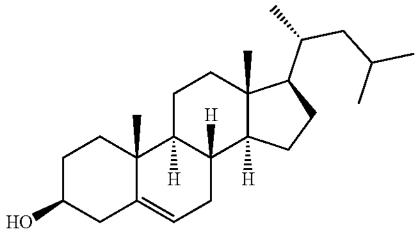 |
| 83 | 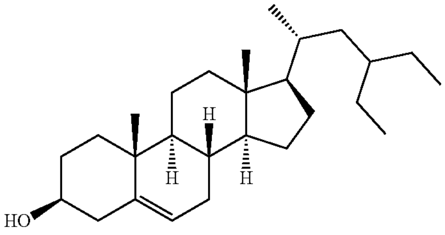 |
| 84 | 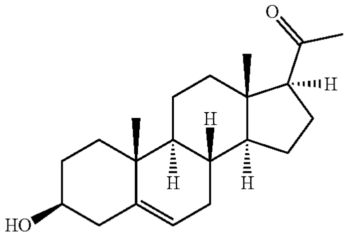 |
| 85 | 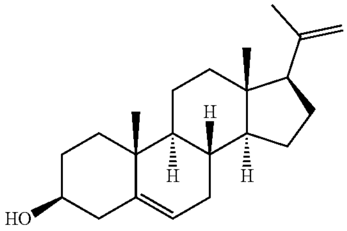 |
| 86 | 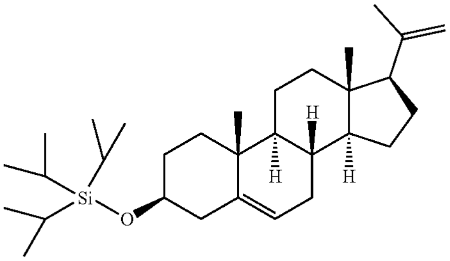 |
| 87 | 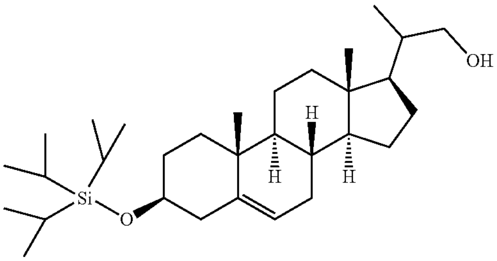 |

TABLE 16-continued
| CMPD No. S— | Structure |
| --- | --- |
| 152 | 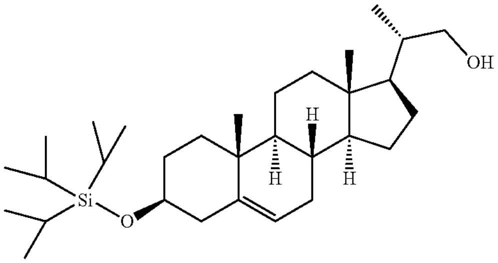 |
| 157 | 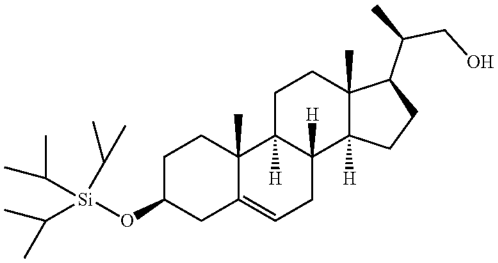 |
| 88 | 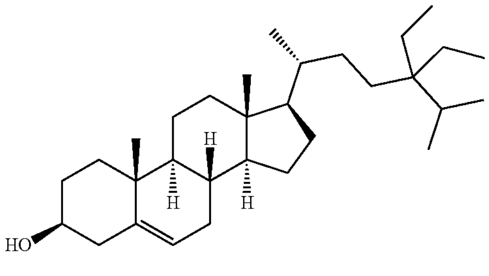 |
| 89 | 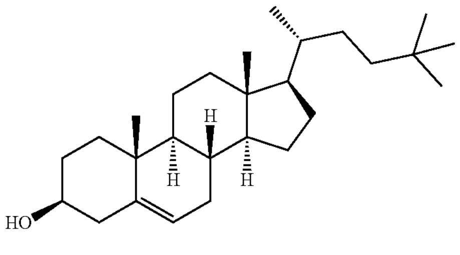 |
| 90 | 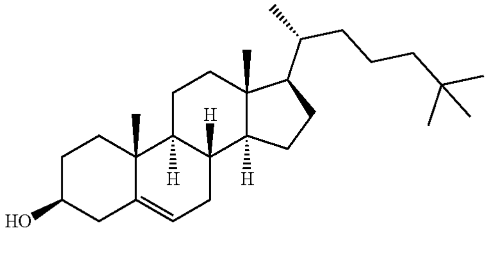 |

TABLE 16-continued
| CMPD No. S— | Structure |
| --- | --- |
| 91 | 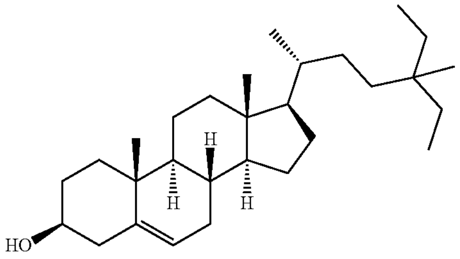 |
| 93 | 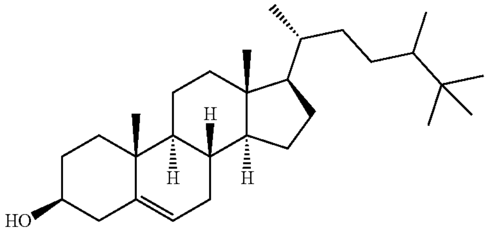 |
| 94 | 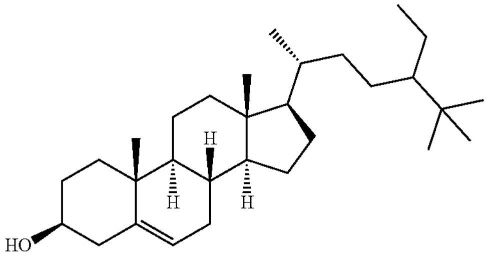 |
| 95 | 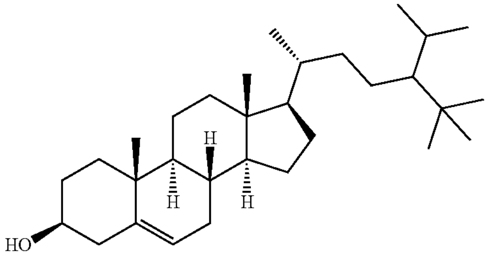 |
| 96 | 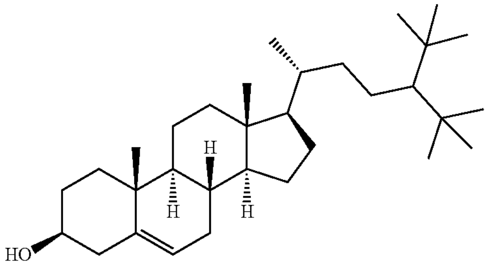 |

TABLE 16-continued
| CMPD No. S— | Structure |
| --- | --- |
| 92 | 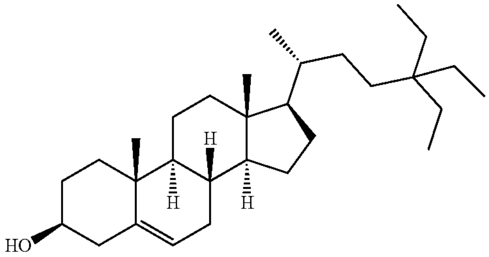 |
| 98 | 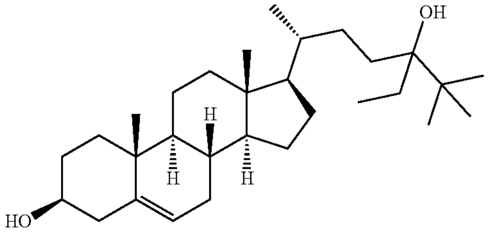 |
| 99 | 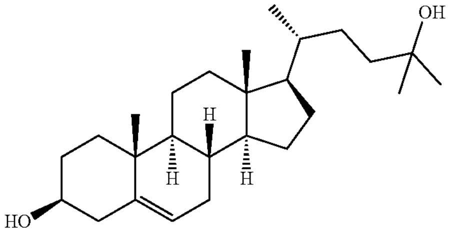 |
| 100 | 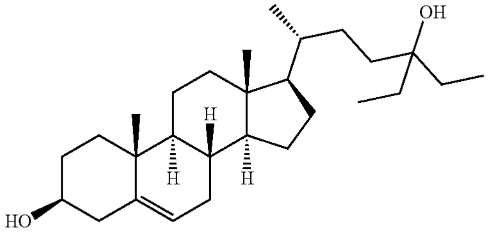 |
| 101 | 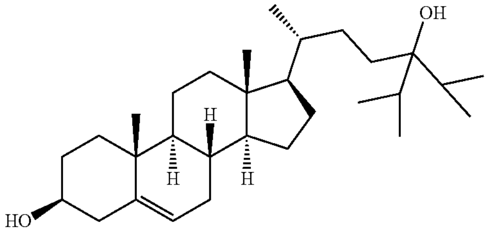 |
| 97 | 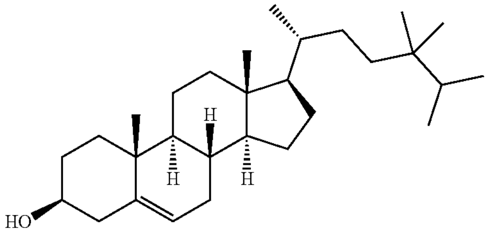 |

TABLE 16-continued
| CMPD No. S— | Structure |
|---|---|
| 102 | 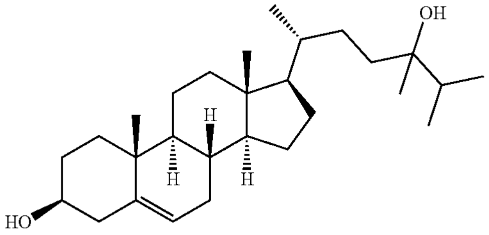 |
| 103 | 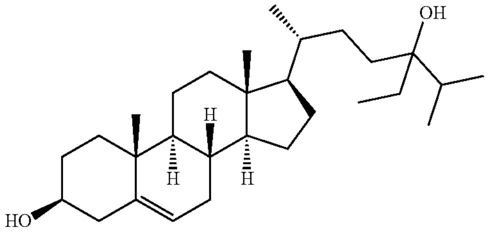 |
| 104 | 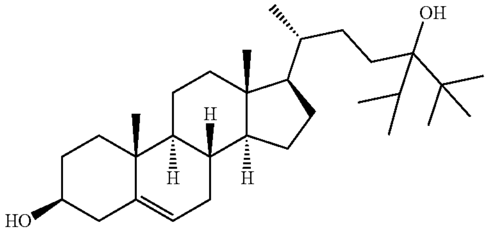 |
| 105 | 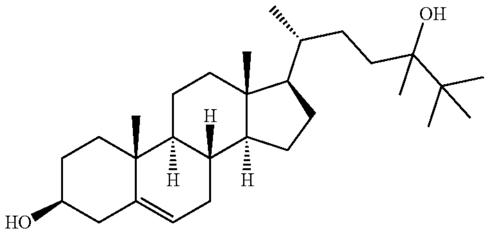 |
| 180 | 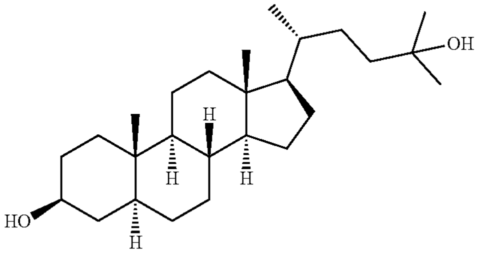 |
| 181 | 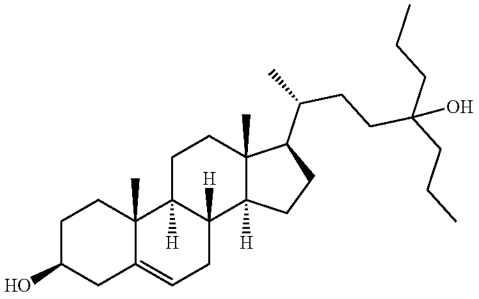 |

TABLE 16-continued
| CMPD No. S— | Structure |
|---|---|
| 182 | 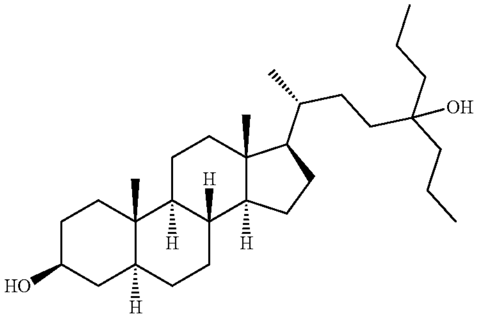 |
| 106 | 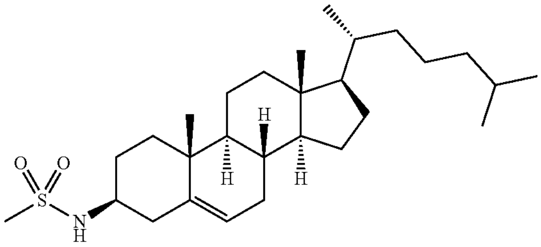 |
| 107 | 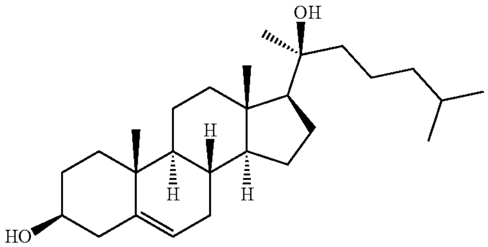 |
| 108 | 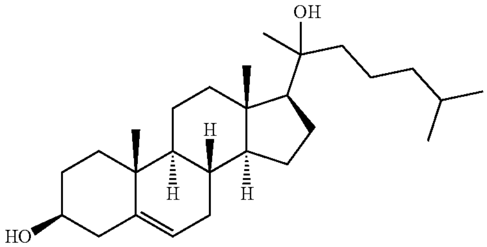 |
| 109 | 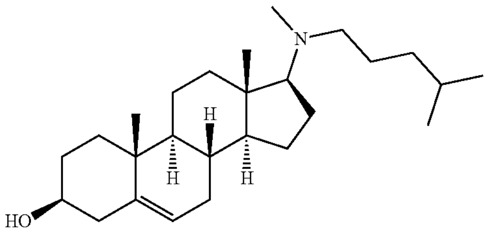 |

TABLE 16-continued
| CMPD No. S— | Structure |
|---|---|
| 110 | 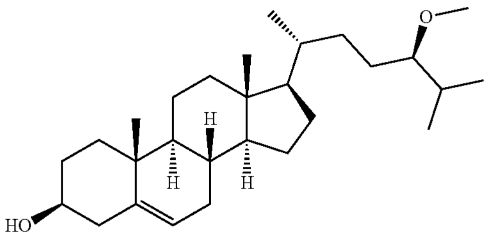 |
| 111 | 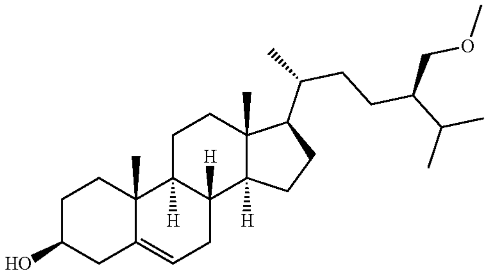 |
| 112 | 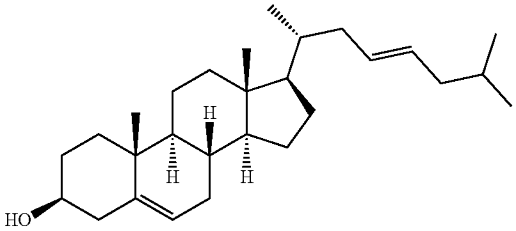 |
| 113 | 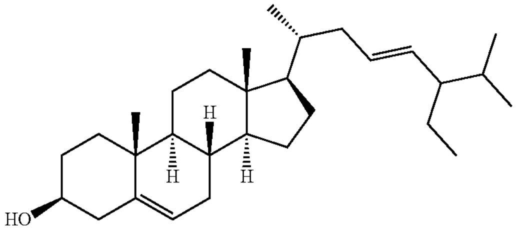 |
| 114 | 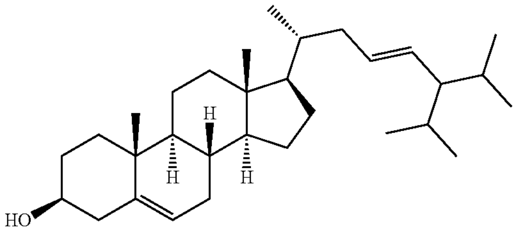 |
| 115 | 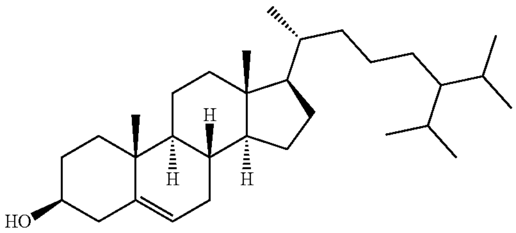 |

TABLE 16-continued
| CMPD No. S— | Structure |
|---|---|
| 116 | 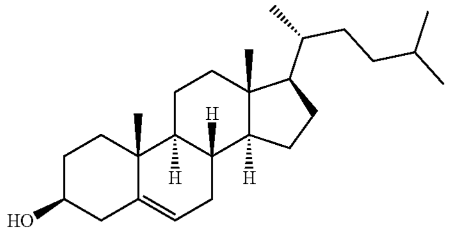 |
| 117 | 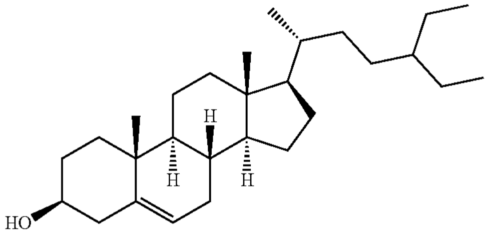 |
| 118 | 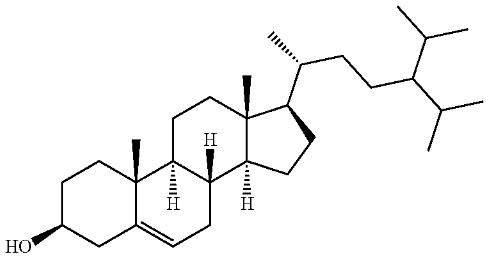 |
| 119 | 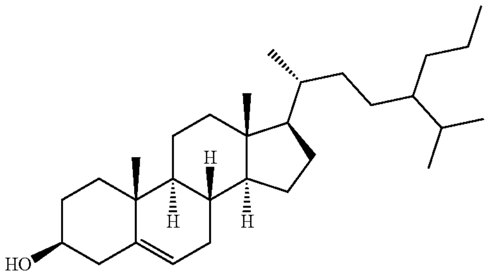 |
| 120 | 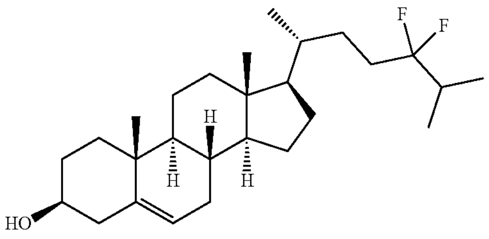 |
| 156 | 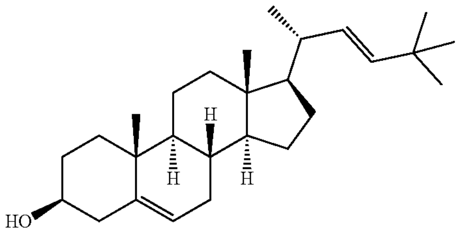 |

TABLE 16-continued
| CMPD No. S— | Structure |
|---|---|
| 158 | 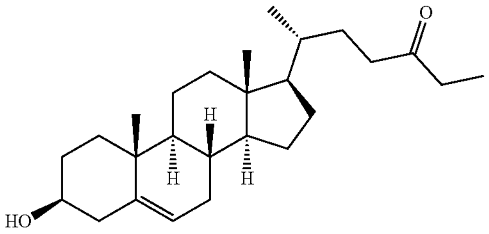 |
| 160 | 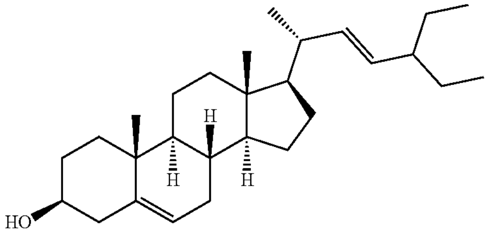 |
| 161 | 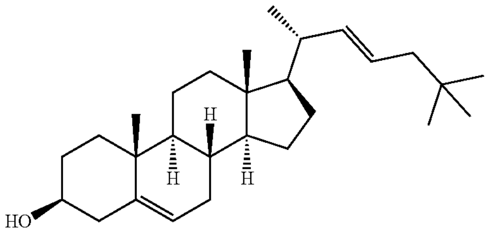 |
| 166 | 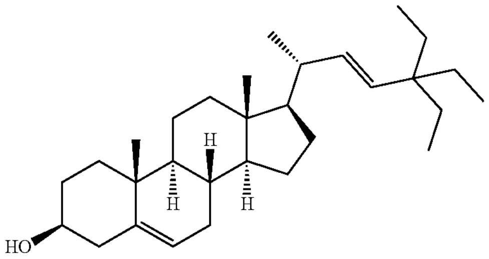 |
| 121 | 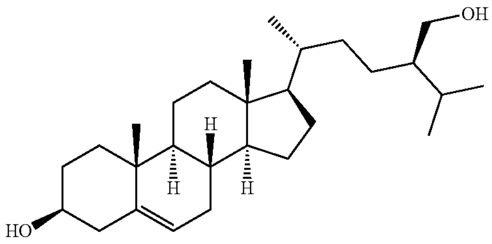 |
| 122 | 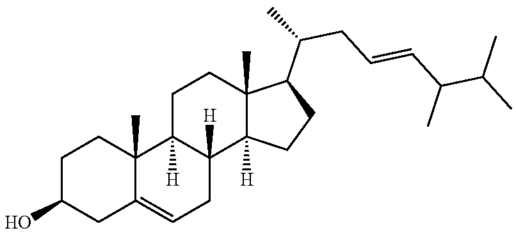 |

TABLE 16-continued
| CMPD No. S— | Structure |
| --- | --- |
| 123 | 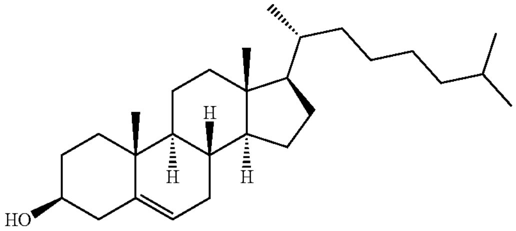 |
| 124 | 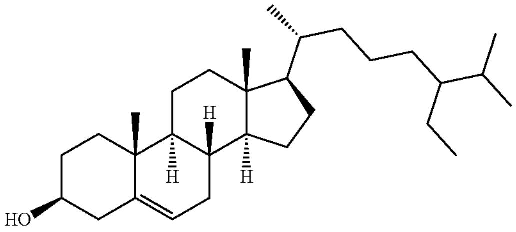 |
| 125 | 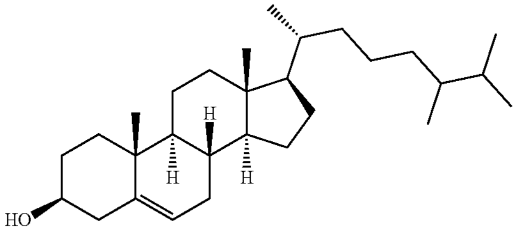 |
| 126 | 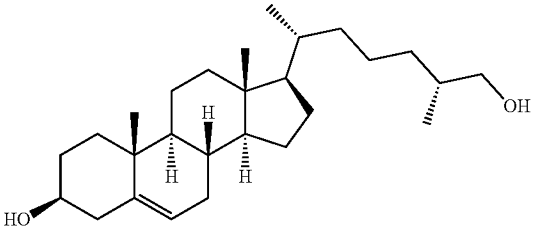 |
| 127 | 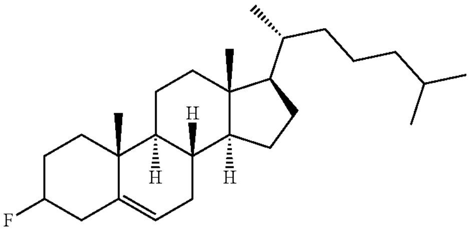 |
| 128 | 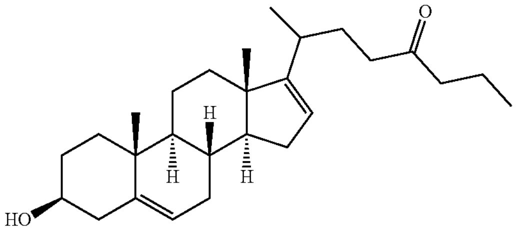 |

TABLE 16-continued
| CMPD No. S— | Structure |
| --- | --- |
| 129 | 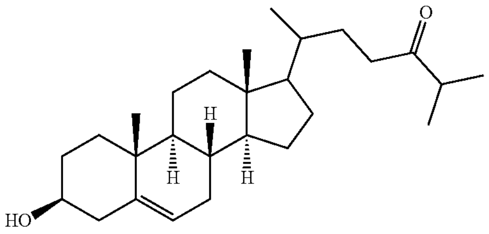 |
| 130 | 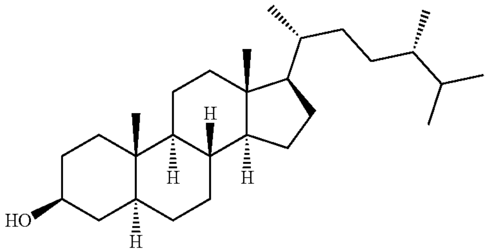 |
| 155 | 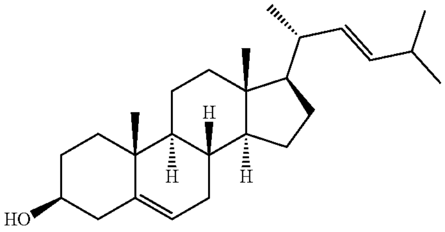 |
| 167 | 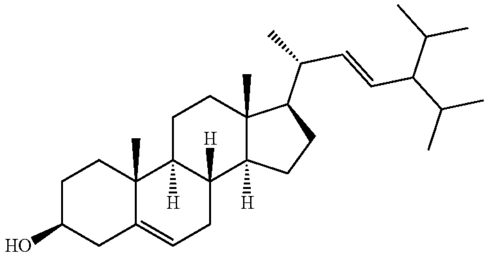 |
| 168 | 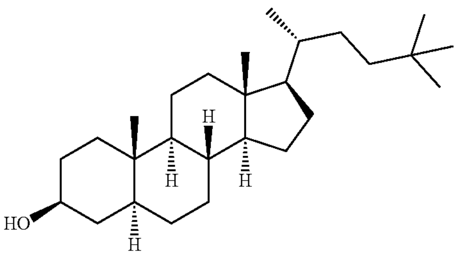 |

TABLE 16-continued
| CMPD No. S— | Structure |
| --- | --- |
| 173 | 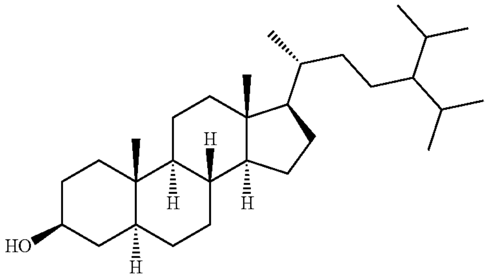 |
| 174 | 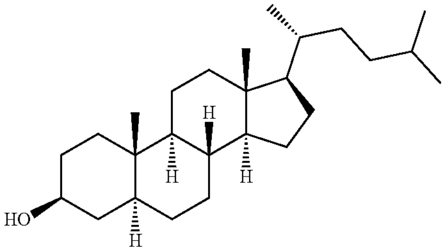 |
| 179 | 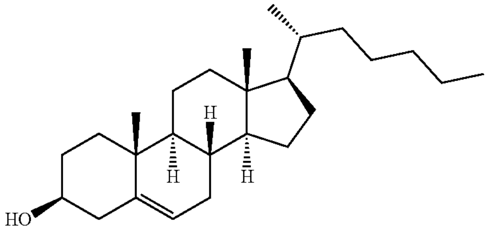 |
| 131 | 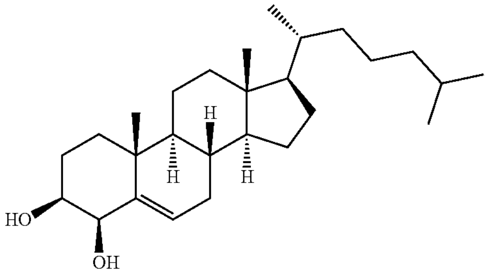 |
| 132 | 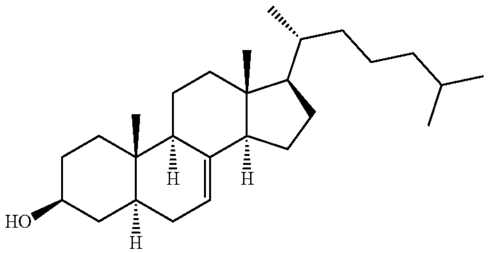 |

TABLE 16-continued
| CMPD No. S— | Structure |
|---|---|
| 133 | 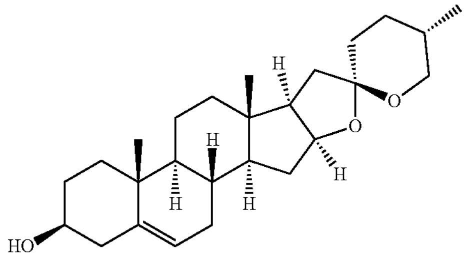 |
| 134 | 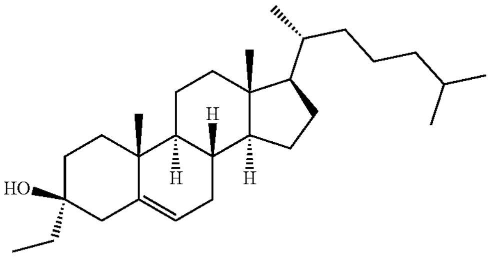 |
| 135 | 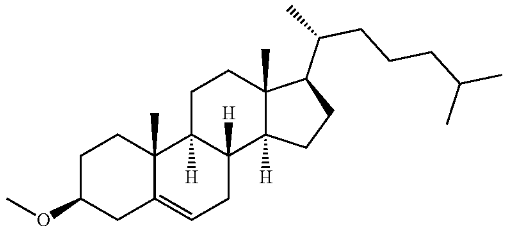 |
| 136 | 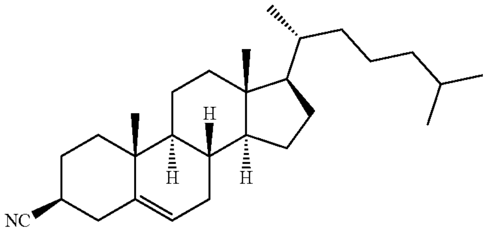 |
| 137 | 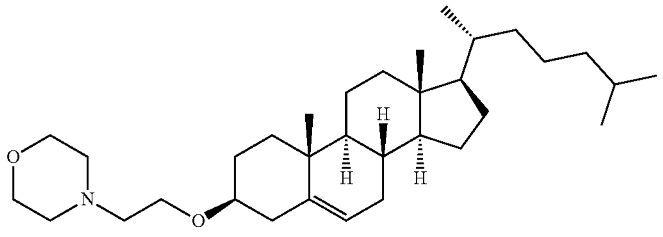 |
| 138 | 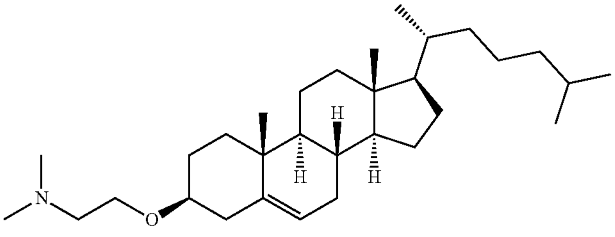 |

TABLE 16-continued
| CMPD No. S— | Structure |
|---|---|
| 139 | 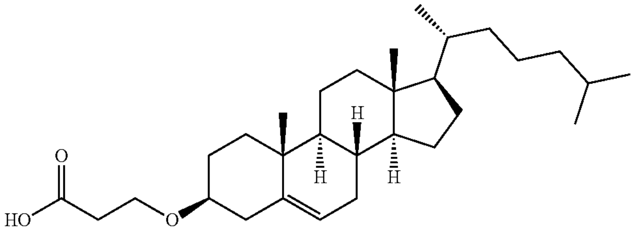 |
| 140 | 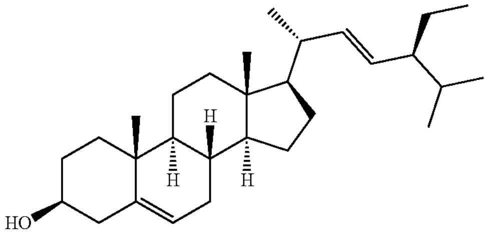 |
| 141 | 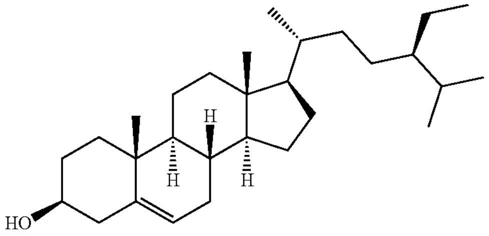 |
| 159 | 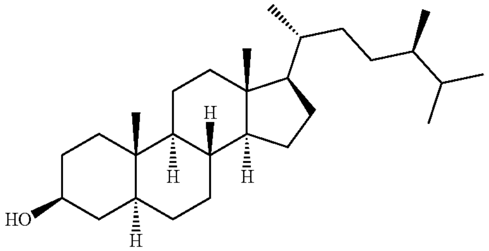 |
| 142 | 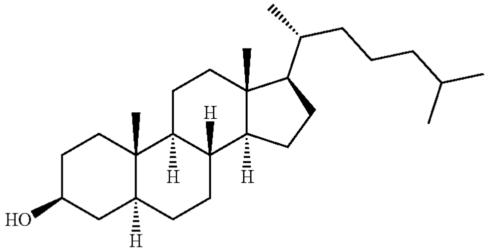 |
| 143 | 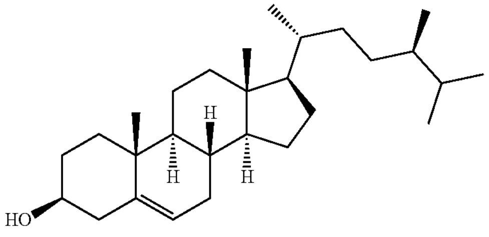 |

TABLE 16-continued
| CMPD No. S— | Structure |
|---|---|
| 144 | 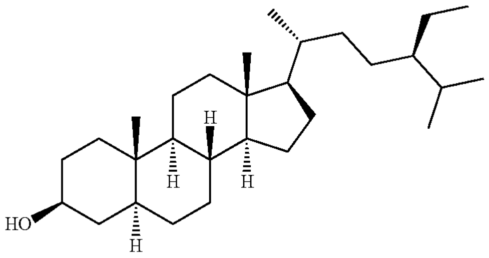 |
| 145 | 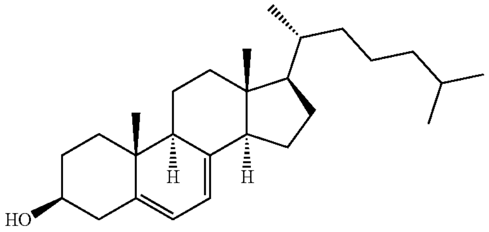 |
| 146 | 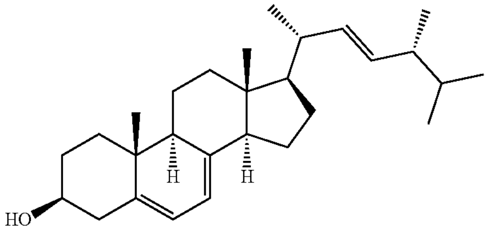 |
| 147 | 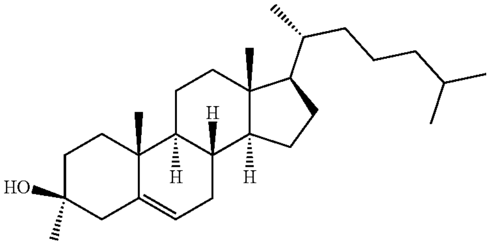 |
| 148 | 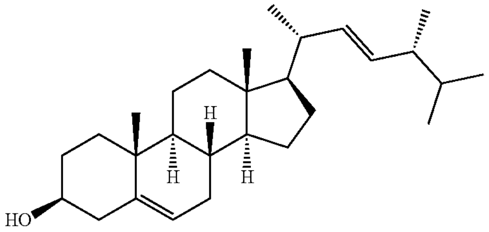 |
| 151 | 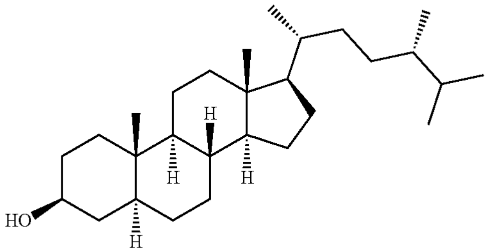 |

TABLE 16-continued

| CMPD No. S— | Structure |
|---|---|
| 183 | 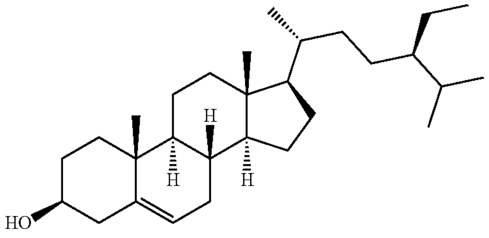<br>Compound 141<br>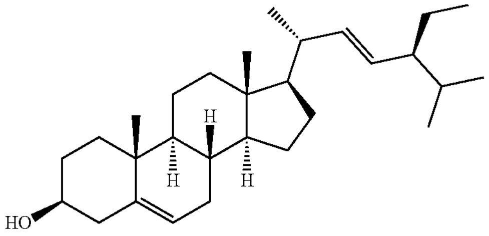<br>compound 140<br>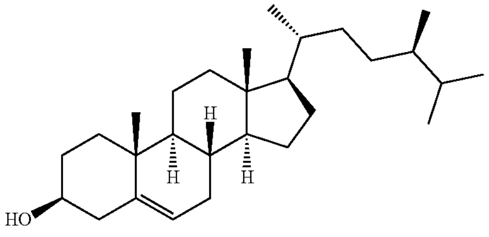<br>Compound 143<br>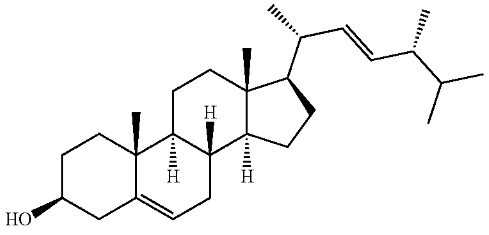<br>Compound 148 |

9. LNP Formulations

The formation of a lipid nanoparticle (LNP) described herein may be accomplished by any methods known in the art. For example, as described in U.S. Pat. Pub. No. US2012/0178702 A1, which is incorporated herein by reference in its entirety. Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21, 1570-1578 (the contents of each of which are incorporated herein by reference in their entirety).

In one embodiment, the LNP formulation may be prepared by, e.g., the methods described in International Pat. Pub. No. WO 2011/127255 or WO 2008/103276, the contents of each of which are herein incorporated by reference in their entirety.

In one embodiment, LNP formulations described herein may comprise a polycationic composition. As a non-limiting example, the polycationic composition may be a composition selected from Formulae 1-60 of U.S. Pat. Pub. No. US2005/0222064 A1, the content of which is herein incorporated by reference in its entirety.

In one embodiment, the lipid nanoparticle may be formulated by the methods described in U.S. Pat. Pub. No. US2013/0156845 A1, and International Pat. Pub. No. WO2013/093648 A2 or WO2012/024526 A2, each of which is herein incorporated by reference in its entirety.

In one embodiment, the lipid nanoparticles described herein may be made in a sterile environment by the system and/or methods described in U.S. Pat. Pub. No. US2013/0164400 A1, which is incorporated herein by reference in its entirety.

In one embodiment, the LNP formulation may be formulated in a nanoparticle such as a nucleic acid-lipid particle described in U.S. Pat. No. 8,492,359, which is incorporated herein by reference in its entirety.

A nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

In some embodiments, the lipid nanoparticles described herein may be synthesized using methods comprising microfluidic mixers. Exemplary microfluidic mixers may include, but are not limited to, a slit interdigitial micromixer including, but not limited to, those manufactured by Precision Nanosystems (Vancouver, BC, Canada), Microinnova (Allerheiligen bei Wildon, Austria) and/or a staggered herringbone micromixer (SHM) (Zhigaltsev, I. V. et al. (2012) Langmuir. 28:3633-40; Belliveau, N. M. et al. Mol. Ther. Nucleic. Acids. (2012) 1:e37; Chen, D. et al. J. Am. Chem. Soc. (2012) 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Pat. Pub. Nos. US2004/0262223 A1 and US2012/0276209 A1, each of which is incorporated herein by reference in their entirety.

In one embodiment, the lipid nanoparticles may be formulated using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut fur Mikrotechnik Mainz GmbH, Mainz Germany). In one embodiment, the lipid nanoparticles are created using microfluidic technology (see, Whitesides (2006) Nature. 442: 368-373; and Abraham et al. (2002) Science. 295: 647-651; each of which is herein incorporated by reference in its entirety). As a non-limiting example, controlled microfluidic formulation includes a passive method for mixing streams of steady pressure-driven flows in micro channels at a low Reynolds number (see, e.g., Abraham et al. (2002) Science. 295: 647651; which is herein incorporated by reference in its entirety).

In one embodiment, the circRNA of the present invention may be formulated in lipid nanoparticles created using a micromixer chip such as, but not limited to, those from Harvard Apparatus (Holliston, Mass.), Dolomite Microfluidics (Royston, UK), or Precision Nanosystems (Van Couver, BC, Canada). A micromixer chip can be used for rapid mixing of two or more fluid streams with a split and recombine mechanism.

In one embodiment, the lipid nanoparticles may have a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm. In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. Each possibility represents a separate embodiment of the present invention.

In some embodiments, a nanoparticle (e.g., a lipid nanoparticle) has a mean diameter of 10-500 nm, 20-400 nm, 30-300 nm, or 40-200 nm. In some embodiments, a nanoparticle (e.g., a lipid nanoparticle) has a mean diameter of 50-150 nm, 50-200 nm, 80-100 nm, or 80-200 nm.

In some embodiments, the lipid nanoparticles described herein can have a diameter from below 0.1 μm to up to 1 mm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, less than 975 μm.

In another embodiment, LNPs may have a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm. Each possibility represents a separate embodiment of the present invention.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.1, 1, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20. Each possibility represents a separate embodiment of the present invention.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −20 mV to about +20 mV, from about −20 mV to about +15 mV, from about −20 mV to about +10 mV, from about −20 mV to about +5 mV, from about −20 mV to about 0 mV, from about −20 mV to about −5 mV, from about −20 mV to about −10 mV, from about −20 mV to about −15 mV from about −20 mV to about +20 mV, from about −20 mV to about +15 mV, from about −20 mV to about +10 mV, from about −20 mV to about +5 mV, from about −20 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV. Each possibility represents a separate embodiment of the present invention.

The efficiency of encapsulation of a therapeutic agent describes the amount of therapeutic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic agent in a solution containing the nanoparticle composition before and after breaking up the nanoparticle composition with one or more organic solvents or detergents. Fluorescence may be used to measure the amount of free therapeutic agent (e.g., nucleic acids) in a solution. For the nanoparticle compositions described herein, the encapsulation efficiency of a therapeutic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%. Each possibility represents a separate embodiment of the present invention. In some embodiments, the lipid nanoparticle has a polydiversity value of less than 0.4. In some embodiments, the lipid nanoparticle has a net neutral charge at a neutral pH. In some embodiments, the lipid nanoparticle has a mean diameter of 50-200 nm.

The properties of a lipid nanoparticle formulation may be influenced by factors including, but not limited to, the selection of the cationic lipid component, the degree of cationic lipid saturation, the selection of the non-cationic lipid component, the degree of noncationic lipid saturation, the selection of the structural lipid component, the nature of the PEGylation, ratio of all components and biophysical parameters such as size. As described herein, the purity of a PEG lipid component is also important to an LNP's properties and performance.

10. Methods

In one embodiment, a lipid nanoparticle formulation may be prepared by the methods described in International Publication Nos. WO2011127255 or WO2008103276, each of which is herein incorporated by reference in their entirety. In some embodiments, lipid nanoparticle formulations may be as described in International Publication No. WO2019131770, which is herein incorporated by reference in its entirety.

In some embodiments, circular RNA is formulated according to a process described in U.S. patent application Ser. No. 15/809,680. In some embodiments, the present invention provides a process of encapsulating circular RNA in transfer vehicles comprising the steps of forming lipids into pre-formed transfer vehicles (i.e. formed in the absence of RNA) and then combining the pre-formed transfer vehicles with RNA. In some embodiments, the novel formulation process results in an RNA formulation with higher potency (peptide or protein expression) and higher efficacy (improvement of a biologically relevant endpoint) both in vitro and in vivo with potentially better tolerability as compared to the same RNA formulation prepared without the step of preforming the lipid nanoparticles (e.g., combining the lipids directly with the RNA).

For certain cationic lipid nanoparticle formulations of RNA, in order to achieve high encapsulation of RNA, the RNA in buffer (e.g., citrate buffer) has to be heated. In those processes or methods, the heating is required to occur before the formulation process (i.e. heating the separate components) as heating post-formulation (post-formation of nanoparticles) does not increase the encapsulation efficiency of the RNA in the lipid nanoparticles. In contrast, in some embodiments of the novel processes of the present invention, the order of heating of RNA does not appear to affect the RNA encapsulation percentage. In some embodiments, no heating (i.e. maintaining at ambient temperature) of one or more of the solutions comprising the pre-formed lipid nanoparticles, the solution comprising the RNA and the mixed solution comprising the lipid nanoparticle encapsulated RNA is required to occur before or after the formulation process.

RNA may be provided in a solution to be mixed with a lipid solution such that the RNA may be encapsulated in lipid nanoparticles. A suitable RNA solution may be any aqueous solution containing RNA to be encapsulated at various concentrations. For example, a suitable RNA solution may contain an RNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable RNA solution may contain an RNA at a concentration in a range from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

Typically, a suitable RNA solution may also contain a buffering agent and/or salt. Generally, buffering agents can include HEPES, Tris, ammonium sulfate, sodium bicarbonate, sodium citrate, sodium acetate, potassium phosphate or sodium phosphate. In some embodiments, suitable concentration of the buffering agent may be in a range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM.

Exemplary salts can include sodium chloride, magnesium chloride, and potassium chloride. In some embodiments, suitable concentration of salts in an RNA solution may be in a range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM.

In some embodiments, a suitable RNA solution may have a pH in a range from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5.

Various methods may be used to prepare an RNA solution suitable for the present invention. In some embodiments, RNA may be directly dissolved in a buffer solution described herein. In some embodiments, an RNA solution may be generated by mixing an RNA stock solution with a buffer solution prior to mixing with a lipid solution for encapsulation. In some embodiments, an RNA solution may be generated by mixing an RNA stock solution with a buffer solution immediately before mixing with a lipid solution for encapsulation.

According to the present invention, a lipid solution contains a mixture of lipids suitable to form transfer vehicles for encapsulation of RNA. In some embodiments, a suitable lipid solution is ethanol based. For example, a suitable lipid solution may contain a mixture of desired lipids dissolved in pure ethanol (i.e. 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. In some embodiments, a suitable lipid solution may contain a mixture of desired lipids at a total concentration in a range from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml.

11. Targeting

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide a means to passively direct the delivery of the compositions to such target cells.

Alternatively, the present invention contemplates active targeting, which involves the use of targeting moieties that may be bound (either covalently or non-covalently) to the transfer vehicle to encourage localization of such transfer vehicle at certain target cells or target tissues. For example, targeting may be mediated by the inclusion of one or more endogenous targeting moieties in or on the transfer vehicle to encourage distribution to the target cells or tissues. Recognition of the targeting moiety by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a moiety capable of enhancing affinity of the composition to the target cell. Targeting moieties may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. No. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more moieties (e.g., peptides, aptamers, oligonucleotides, a vitamin or other molecules) that are capable of enhancing the affinity of the compositions and their nucleic acid contents for the target cells or tissues. Suitable moieties may optionally be bound or linked to the surface of the transfer vehicle. In some embodiments, the targeting moiety may span the surface of a transfer vehicle or be encapsulated within the transfer vehicle. Suitable moieties and are selected based upon their physical, chemical or biological properties (e.g., selective affinity and/or recognition of target cell surface markers or features). Cell-specific target sites and their corresponding targeting ligand can vary widely. Suitable targeting moieties are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). As an example, the use of galactose as a targeting moiety would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting moieties that have been conjugated to moieties present in the transfer vehicle (e.g., a lipid nanoparticle) therefore facilitate recognition and uptake of the compositions of the present invention in target cells and tissues. Examples of suitable targeting moieties include one or more peptides, proteins, aptamers, vitamins and oligonucleotides.

In particular embodiments, a transfer vehicle comprises a targeting moiety. In some embodiments, the targeting moiety mediates receptor-mediated endocytosis selectively into a specific population of cells. In some embodiments, the targeting moiety is capable of binding to a T cell antigen. In some embodiments, the targeting moiety is capable of binding to a NK, NKT, or macrophage antigen. In some embodiments, the targeting moiety is capable of binding to a protein selected from the group CD3, CD4, CD8, PD-1, 4-1BB, and CD2. In some embodiments, the targeting moiety is an single chain Fv (scFv) fragment, nanobody, peptide, peptide-based macrocycle, minibody, heavy chain variable region, light chain variable region or fragment thereof. In some embodiments, the targeting moiety is selected from T-cell receptor motif antibodies, T-cell α chain antibodies, T-cell β chain antibodies, T-cell γ chain antibodies, T-cell δ chain antibodies, CCR7 antibodies, CD3 antibodies, CD4 antibodies, CD5 antibodies, CD7 antibodies, CD8 antibodies, CD11b antibodies, CD11c antibodies, CD16 antibodies, CD19 antibodies, CD20 antibodies, CD21 antibodies, CD22 antibodies, CD25 antibodies, CD28 antibodies, CD34 antibodies, CD35 antibodies, CD40 antibodies, CD45RA antibodies, CD45RO antibodies, CD52 antibodies, CD56 antibodies, CD62L antibodies, CD68 antibodies, CD80 antibodies, CD95 antibodies, CD117 antibodies, CD127 antibodies, CD133 antibodies, CD137 (4-1BB) antibodies, CD163 antibodies, F4/80 antibodies, IL-4Rα antibodies, Sca-1 antibodies, CTLA-4 antibodies, GITR antibodies GARP antibodies, LAP antibodies, granzyme B antibodies, LFA-1 antibodies, transferrin receptor antibodies, and fragments thereof. In some embodiments, the targeting moiety is a small molecule binder of an ectoenzyme on lymphocytes. Small molecule binders of ectoenzymes include A2A inhibitors CD73 inhibitors, CD39 or adesines receptors A2aR and A2bR. Potential small molecules include AB928.

In some embodiments, transfer vehicles are formulated and/or targeted as described in Shobaki N, Sato Y, Harashima H. Mixing lipids to manipulate the ionization status of lipid nanoparticles for specific tissue targeting. Int J Nanomedicine. 2018; 13:8395-8410. Published 2018 Dec. 10. In some embodiments, a transfer vehicle is made up of 3 lipid types. In some embodiments, a transfer vehicle is made up of 4 lipid types. In some embodiments, a transfer vehicle is made up of 5 lipid types. In some embodiments, a transfer vehicle is made up of 6 lipid types.

12. Target Cells

Where it is desired to deliver a nucleic acid to an immune cell, the immune cell represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, T cells, B cells, macrophages, and dentritic cells.

In some embodiments, the target cells are deficient in a protein or enzyme of interest. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The compositions of the invention may be prepared to preferentially distribute to target cells such as in the heart, lungs, kidneys, liver, and spleen. In some embodiments, the compositions of the invention distribute into the cells of the liver or spleen to facilitate the delivery and the subsequent expression of the circRNA comprised therein by the cells of the liver (e.g., hepatocytes) or the cells of spleen (e.g., immune cells). The targeted cells may function as a biological "reservoir" or "depot" capable of producing, and systemically excreting a functional protein or enzyme. Accordingly, in one embodiment of the invention the transfer vehicle may target hepatocytes or immune cells and/or preferentially distribute to the cells of the liver or spleen upon delivery. In an embodiment, following transfection of the target hepatocytes or immune cells, the circRNA loaded in the vehicle are translated and a functional protein product is produced, excreted and systemically distributed. In other embodiments, cells other than hepatocytes (e.g., lung, spleen, heart, ocular, or cells of the central nervous system) can serve as a depot location for protein production.

In one embodiment, the compositions of the invention facilitate a subject's endogenous production of one or more functional proteins and/or enzymes. In an embodiment of the present invention, the transfer vehicles comprise circRNA which encode a deficient protein or enzyme. Upon distribution of such compositions to the target tissues and the subsequent transfection of such target cells, the exogenous circRNA loaded into the transfer vehicle (e.g., a lipid nanoparticle) may be translated in vivo to produce a functional protein or enzyme encoded by the exogenously administered circRNA (e.g., a protein or enzyme in which the subject is deficient). Accordingly, the compositions of the present invention exploit a subject's ability to translate exogenously- or recombinantly-prepared circRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of circRNA encoding a deficient protein or enzyme avoids the need to deliver the nucleic acids to specific organelles within a target cell. Rather, upon transfection of a target cell and delivery of the nucleic acids to the cytoplasm of the target cell, the circRNA contents of a transfer vehicle may be translated and a functional protein or enzyme expressed.

In some embodiments, a circular RNA comprises one or more miRNA binding sites. In some embodiments, a circular RNA comprises one or more miRNA binding sites recognized by miRNA present in one or more non-target cells or non-target cell types (e.g., Kupffer cells or hepatic cells) and not present in one or more target cells or target cell types (e.g., hepatocytes or T cells). In some embodiments, a circular RNA comprises one or more miRNA binding sites recognized by miRNA present in an increased concentration in one or more non-target cells or non-target cell types (e.g., Kupffer cells or hepatic cells) compared to one or more target cells or target cell types (e.g., hepatocytes or T cells). miRNAs are thought to function by pairing with complementary sequences within RNA molecules, resulting in gene silencing.

13. Pharmaceutical Compositions

In certain embodiments, provided herein are compositions (e.g., pharmaceutical compositions) comprising a therapeutic agent provided herein. In some embodiments, the therapeutic agent is a circular RNA polynucleotide provided herein. In some embodiments the therapeutic agent is a vector provided herein. In some embodiments, the therapeutic agent is a cell comprising a circular RNA or vector provided herein (e.g., a human cell, such as a human T cell). In certain embodiments, the composition further comprises a pharmaceutically acceptable carrier. In some embodiments, the compositions provided herein comprise a therapeutic agent provided herein in combination with other pharmaceutically active agents or drugs, such as anti-inflammatory drugs or antibodies capable of targeting B cell antigens, e.g., anti-CD20 antibodies, e.g., rituximab.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the therapeutic agent(s) and one which has no detrimental side effects or toxicity under the conditions of use.

The choice of carrier will be determined in part by the particular therapeutic agent, as well as by the particular method used to administer the therapeutic agent. Accordingly, there are a variety of suitable formulations of the pharmaceutical compositions provided herein.

In certain embodiments, the pharmaceutical composition comprises a preservative. In certain embodiments, suitable preservatives may include, for example, methylparaben, propylparaben, sodium benzoate, and benzalkonium chloride. Optionally, a mixture of two or more preservatives may be used. The preservative or mixtures thereof are typically present in an amount of about 0.0001% to about 2% by weight of the total composition.

In some embodiments, the pharmaceutical composition comprises a buffering agent. In some embodiments, suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

In some embodiments, the concentration of therapeutic agent in the pharmaceutical composition can vary, e.g., less than about 1%, or at least about 1%, 2%, 3%, 4%, 5%, 6%, 7%, 8%, 9% 10%, 15%, 20%, 25%, 30%, 35%, 40%, 45%, or about 50% or more by weight, and can be selected primarily by fluid volumes, and viscosities, in accordance with the particular mode of administration selected.

The following formulations for oral, aerosol, parenteral (e.g., subcutaneous, intravenous, intraarterial, intramuscular, intradermal, intraperitoneal, and intrathecal), and topical administration are merely exemplary and are in no way limiting. More than one route can be used to administer the therapeutic agents provided herein, and in certain instances, a particular route can provide a more immediate and more effective response than another route.

Formulations suitable for oral administration can comprise or consist of (a) liquid solutions, such as an effective amount of the therapeutic agent dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the therapeutic agent with a flavorant, usually sucrose, acacia or tragacanth. Pastilles can comprise the therapeutic agent with an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In some embodiments, the therapeutic agents provided herein can be administered in a physiologically acceptable diluent in a pharmaceutical carrier, such as a sterile liquid or mixture of liquids, including water, saline, aqueous dextrose and related sugar solutions, an alcohol such as ethanol or hexadecyl alcohol, a glycol such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutical adjuvants.

Oils, which can be used in parenteral formulations in some embodiments, include petroleum, animal oils, vegetable oils, or synthetic oils. Specific examples of oils include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in certain embodiments of parenteral formulations include fatty alkali metal, ammonium, and triethanolamme salts, and suitable detergents include (a) cationic detergents such as, for example, dimethyl dialkyl ammonium halides. and alkyl pyridinium halides, (b) anionic detergents such as, for example, alkyl, aryl, and olefin sulfonates, alky, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

In some embodiments, the parenteral formulations will contain, for example, from about 0.5% to about 25% by weight of the therapeutic agent in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and high molecular weight adducts of ethylene oxide with a hydrophobic base, formed by the condensation of propylene oxide with propylene glycol. The parenteral formulations can be presented in unit-dose or multi-dose sealed containers, such as ampoules or vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In certain embodiments, injectable formulations are provided herein. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed, pages 622-630 (1986)).

In some embodiments, topical formulations are provided herein. Topical formulations, including those that are useful for transdermal drug release, are suitable in the context of certain embodiments provided herein for application to skin. In some embodiments, the therapeutic agent alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

In certain embodiments, the therapeutic agents provided herein can be formulated as inclusion complexes, such as cyclodextrin inclusion complexes, or liposomes. Liposomes can serve to target the therapeutic agents to a particular tissue. Liposomes also can be used to increase the half-life of the therapeutic agents. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

In some embodiments, the therapeutic agents provided herein are formulated in time-released, delayed release, or sustained release delivery systems such that the delivery of the composition occurs prior to, and with sufficient time to cause, sensitization of the site to be treated. Such systems can avoid repeated administrations of the therapeutic agent, thereby increasing convenience to the subject and the physician, and may be particularly suitable for certain composition embodiments provided herein. In one embodiment, the compositions of the invention are formulated such that they are suitable for extended-release of the circRNA contained therein. Such extended-release compositions may be conveniently administered to a subject at extended dosing intervals. For example, in one embodiment, the compositions of the present invention are administered to a subject twice day, daily or every other day. In an embodiment, the compositions of the present invention are administered to a subject twice a week, once a week, every ten days, every two weeks, every three weeks, every four weeks, once a month, every six weeks, every eight weeks, every three months, every four months, every six months, every eight months, every nine months or annually.

In some embodiments, a protein encoded by an inventive polynucleotide is produced by a target cell for sustained amounts of time. For example, the protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments the polypeptide is expressed at least at a therapeutic level for more than one, more than four, more than six, more than 12, more than 24, more than 48, or more than 72 hours after administration. In some embodiments, the polypeptide is detectable at a therapeutic level in patient serum or tissue (e.g., liver or lung). In some embodiments, the level of detectable polypeptide is from continuous expression from the circRNA composition over periods of time of more than one, more than four, more than six, more than 12, more than 24, more than 48, or more than 72 hours after administration.

In certain embodiments, a protein encoded by an inventive polynucleotide is produced at levels above normal physiological levels. The level of protein may be increased as compared to a control. In some embodiments, the control is the baseline physiological level of the polypeptide in a normal individual or in a population of normal individuals. In other embodiments, the control is the baseline physiological level of the polypeptide in an individual having a deficiency in the relevant protein or polypeptide or in a population of individuals having a deficiency in the relevant protein or polypeptide. In some embodiments the control can be the normal level of the relevant protein or polypeptide in the individual to whom the composition is administered. In other embodiments the control is the expression level of the polypeptide upon other therapeutic intervention, e.g., upon direct injection of the corresponding polypeptide, at one or more comparable time points.

In certain embodiments, the levels of a protein encoded by an inventive polynucleotide are detectable at 3 days, 4 days, 5 days, or 1 week or more after administration. Increased levels of secreted protein may be observed in the serum and/or in a tissue (e.g., liver or lung).

In some embodiments, the method yields a sustained circulation half-life of a protein encoded by an inventive polynucleotide. For example, the protein may be detected for hours or days longer than the half-life observed via subcutaneous injection of the protein or mRNA encoding the protein. In some embodiments, the half-life of the protein is 1 day, 2 days, 3 days, 4 days, 5 days, or 1 week or more.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems: wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

In some embodiments, the therapeutic agent can be conjugated either directly or indirectly through a linking moiety to a targeting moiety. Methods for conjugating therapeutic agents to targeting moieties is known in the art. See, for instance, Wadwa et al., J, Drug Targeting 3:111 (1995) and U.S. Pat. No. 5,087,616.

In some embodiments, the therapeutic agents provided herein are formulated into a depot form, such that the manner in which the therapeutic agent is released into the body to which it is administered is controlled with respect to time and location within the body (see, for example, U.S. Pat. No. 4,450,150). Depot forms of therapeutic agents can be, for example, an implantable composition comprising the therapeutic agents and a porous or non-porous material, such as a polymer, wherein the therapeutic agents are encapsulated by or diffused throughout the material and/or degradation of the non-porous material. The depot is then implanted into the desired location within the body and the therapeutic agents are released from the implant at a predetermined rate.

14. Therapeutic Methods

In certain aspects, provided herein is a method of treating and/or preventing a condition, e.g., cancer.

In certain embodiments, the therapeutic agents provided herein are coadministered with one or more additional therapeutic agents (e.g., in the same pharmaceutical composition or in separate pharmaceutical compositions). In some embodiments, the therapeutic agent provided herein can be administered first and the one or more additional therapeutic agents can be administered second, or vice versa. Alternatively, the therapeutic agent provided herein and the one or more additional therapeutic agents can be administered simultaneously.

In some embodiments, the subject is a mammal. In some embodiments, the mammal referred to herein can be any mammal, including, but not limited to, mammals of the order Rodentia, such as mice and hamsters, or mammals of the order Logomorpha, such as rabbits. The mammals may be from the order Carnivora, including Felines (cats) and Canines (dogs). The mammals may be from the order Artiodactyla, including Bovines (cows) and Swines (pigs), or of the order Perssodactyla, including Equines (horses). The mammals may be of the order Primates, Ceboids, or Simoids (monkeys) or of the order Anthropoids (humans and apes). Preferably, the mammal is a human.

15. Sequences

TABLE 17

IRES sequences.

| SEQ ID NO | IRES | Sequence |
|---|---|---|
| 1 | EMCV-A | cccccctctccctcccccccctaacgttactggccgaagccgcttggaataaggccggtgtgcgttt<br>gtctatatgttattttccaccatattgccgtcttttggcaatgtgagggcccggaaacctggccctgtct<br>tcttgacgagcattcctaggggtctttcccctctcgccaaaggaatgcaaggtctgttgaatgtcgtg<br>aaggaagcagttcctctggaagcttcttgaagacaaacaacgtctgtagcgaccctttgcaggcag<br>cggaaccccccacctggcgacaggtgcctctgcggccaaaagccacgtgtataagatacacctg<br>caaaggcggcacaaccccagtgccacgttgtgagttggatagttgtggaaagagtcaaatggctc<br>tcctcaagcgtattcaacaaggggctgaaggatgcccagaaggtaccccattgtatgggatctgat<br>ctggggcctcggtgcacatgctttacatgtgtttagtcgaggttaaaaaacgtctaggccccccgaa<br>ccacggggacgtggttttcctttgaaaaacacgatgataatatggccacaacc |
| 2 | EMCV-B | ctcccccctcccccccccttactatactggccgaagccacttggaataaggccggtgtgcgtttgtcta<br>catgctattttctaccgcattaccgtcttatggtaatgtgagggtccagaacctgaccctgtcttcttga<br>cgaacactcctaggggtctttcccctctcgacaaaggagtgtaaggtctgttgaatgtcgtgaagga<br>agcagttcctctggaagcttcttaaagacaaacaacgtctgtagcgaccctttgcaggcagcggaa<br>ccccccacctggtgacaggtgcctctgcggccaaaagccacgtgtataagatacacctgcaaag<br>gcggcacaaccccagtgccacgttgtgagttggatagttgtggaaagagtcaaatggctctcctca<br>agcgtattcaacaaggggctgaaggatgcccagaaggtaccccattgtatgggatctgatctggg<br>gcctcggtgcacgtgctttacacgtgttgagtcgaggtgaaaaaacgtctaggccccccgaacca<br>cggggacgtggttttcctttgaaaaccacgattacaat |
| 3 | EMCV-Bf | ttgccagtctgctcgatatcgcaggctgggtccgtgactacccactcccccttcaacgtgaaggct<br>acgatagtgccagggcgggtactgccgtaagtgccaccccaaacaacaacaacaaaacaaactc<br>cccctcccccccccttactatactggccgaagccacttggaataaggccggtgtgcgtttgtctacat<br>gctattttctaccgcattaccgtcttatggtaatgtgagggtccagaacctgaccctgtcttcttgacg |

TABLE 17-continued

IRES sequences.

| SEQ ID NO | IRES | Sequence |
|---|---|---|
| | | aacactcctaggggtctttcccctctcgacaaaggagtgtaaggtctgttgaatgtcgtgaaggaag<br>cagttcctctggaagcttcttaaagacaaacaacgtctgtagcgaccctttgcaggcagcggaacc<br>ccccacctggtgacaggtgcctctgcggccaaaagccacgtgtataagatacacctgcaaaggc<br>ggcacaaccccagtgccacgttgtgagttggatagttgtggaaagagtcaaatggctctcctcaag<br>cgtattcaacaaggggctgaaggatgcccagaaggtaccccattgtatgggatctgatctggggc<br>ctcggtgcacgtgctttacacgtgttgagtcgaggtgaaaaaacgtctaggccccccgaaccacg<br>gggacgtggttttcctttgaaaaccacgattacaat |
| 4 | EMCV-Cf | ttgccagtctgctcgatatcgcaggctgggtccgtgactacccactcccccttcaacgtgaaggct<br>acgatagtgccagggcgggtactgccgtaagtgccaccccaaaacaacaacaacccccctctc<br>cctccTccccccctaacgttactggccgaagccgcttggaataaggccggtgtgcgtttgtctatat<br>gttattttccaccatattgccgtcttttggcaatgtgagggcccggaaacctggccctgtcttcttgac<br>gagcattcctaggggtctttcccctctcgccaaaggaatgcaaggtctgagaatgtcgtgaaggaa<br>gcagttcctctggaagcttcttgaagacaaacaacgtctgtagcgaccctttgcaggcagcggaac<br>cccccacctggcgacaggtgcctctgcggccaaaagccacgtgtataagatacacctgcaaagg<br>cggcacaaccccagtgccacgttgtgagttggatagttgtggaaagagtcaaatggctctcctcaa<br>gcgtattcaacaaggggctgaaggatgcccagaaggtaccccattgtatgggatctgatctgggg<br>cctcggtgcacatgctttacatgtgtttagtcgaggttaaaaaacgtctaggccccccgaaccacgg<br>ggacgtggttttcctttgaaaaacacgatgataat |
| 5 | EMCV pEC9 | cccccccccctaacgttactggccgaagccgcttggaataaggccggtgtgcgtttgtctatatgttat<br>tttccaccatattgccgtcttttggcaatgtgagggcccggaaacctggccctgtcttcttgacgagc<br>attcctaggggtctttcccctctcgccaaaggaatgcaaggtctgttgaatgtcgtgaaggaagcag<br>ttcctctggaagcttcttgaagacaaacaacgtctgtagcgaccctttgcaggcagcggaacccccc<br>cacctggcgacaggtgcctctgcggccaaaagccacgtgtataagatacacctgcaaaggcggc<br>acaaccccagtgccacgttgtgagttggatagttgtggaaagagtcaaatggctctcctcaagcgt<br>attcaacaaggggctgaaggatgcccagaaggtaccccattgtatgggatctgatctggggcctc<br>ggtgcacatgctttacatgtgtttagtcgaggttaaaaaacgtctaggccccccgaaccacgggga<br>cgtggttttcctttgaaaaacacgatgataat |
| 6 | Picobir-navirus | gtaaattaaatgctatttacaaaatttaaacagaaaggagagatgttatgaaccggttttacaaggttt<br>catacatcgaaaatagcactacctggggcagccgacacactaacatcgtctgtttaaccagaagtg<br>ttactgaaaggaggttattta |
| 7 | HCV QC64 | acctgcccctaataggggcgacactccgccatgaatcactcccctgtgaggaactactgtcttcac<br>gcagaaagcgtctagccatggcgttagtatgagtgtcgtacagcctccaggccccccctcccgg<br>gagagccatagtggtctgcggaaccggtgagtacaccggaattgccgggaagactgggtcctttc<br>ttggataaacccactctatgcccggacatttgggcgtgcccccgcaagactgctagccgagtagc<br>gttgggttgcgaaaggccttgtggtactgcctgatagggtgcttgcgagtgccccgggaggtctcg<br>tagaccgtgcatc |
| 8 | Human Cosavirus E/D | ctacaagctttgtgtaaacaaacttttgtttggcttttctcaagcttctctcacatcaggccccaaagat<br>gtcctgaaggtaccccgtgtatctgaggatgagcaccatcgactacccggacctgcaaaattttgc<br>aaacgcatgtggtatcccagcccctcctctcggggagggggctttgctcactcagcacaggatct<br>gatcaggagatccacctccggtgctttacaccggggcgtggatttaaaaattgcccaaggcctggc<br>gcacaacctaggggactaggttttccttatattttaaagctgtcaat |
| 9 | Human Cosavirus F | gtcttaggacgacgcatgtggtatcccagcccccgcctacattggcgggggcttttgaagcacca<br>gacactggatctgatcaggaggagggtagctgctttacagcccctcttaaaaattgcccaaggtcc<br>ggccacccaacctaggggactaggttttccttttatttttaaattgtcatt |
| 10 | Human Cosavirus JMY | acatgggggagactgcatgtggcagtcttgaaacgtgtggtttgacgtctaccttatatggcagtgg<br>gtggagtactgcaaagatgtcaccgtgattacacggtttttgaaccccacaccggctgtttgacgct<br>cgtagggcagcaggtttattttcattaaaattcttactttctagctgcatgagttctattcatgcagacg<br>gagtgatactcccgttccttcttggacaggttgcctccacgccctttgtggatcttaaggtgaccaagtc<br>actggtgttggaggtgaagatagagagtcctcttgggaatgtcatgtggctgtgccaggggttgta<br>gcgatgccattcgtgtgtgcggatttcctctcgtggtgacacgagcctcacaggccaaaagccccg<br>tccgaaaggacccgaatggtggagtgaccctgactccccccctgcatagttttgtgattaggaacttg<br>aggaatttctgtcataaatctctatcacatcaggccccaaagatgtcctgaaggtaccctgtgtatctg<br>aggatgagcaccaccgactacccggacttgcattagcagacacatgtggttgcccagccccacct<br>cttcagaggtggggctttgctcactcagcacaggatctgatcaggagccccgctcgtgtgctttaca<br>ctcgacgcggggttaaaaattgcccaaggcctggcacaacaacctaggggactaggttttcctattt<br>ttgtaaattatgtcaat |
| 11 | Rhino-virus NAT001 | gtgacaatcagccagattgttaacggtcaagcacttctgtttccccggtacccttgtatacgcttcacc<br>cgaggcgaaaagtgaggttatcgttatccgcaaagtgcctacgagaagcctagtagcacttttgaa<br>gcctatggctggtcgctcaactgtttacccagcagtagacctggcagatgaggctagatgttcccc<br>accagcgatggtgatctagcctgcgtggctgcctgcacactctattgagtgtgaagccagaaagtg<br>gacaaggtgtgaagagcctattgtgctcactttgagtcctccggcccctgaatgtggctaatcctaa<br>ccccgtagctgttgcatgtaatccaacatgtctgcagtcgtaatgggcaactatgggatggaaccaa<br>ctactttgggtgtccgtgtttcttgtttttctttatgcttgcttatggtgacaactgtagttattacatt<br>tgttacc |

TABLE 17-continued

IRES sequences.

| SEQ ID NO | IRES | Sequence |
|---|---|---|
| 12 | HRV14 | ttaaaacagcggatgggtatcccaccattcgacccattgggtgtagtactctggtactatgtacctttg<br>tacgcctgtttctccccaaccacccttccttaaaattcccacccatgaaacgttagaagcttgacatta<br>aagtacaataggtggcgccatatccaatggtgtctatgtacaagcacttctgtttcccaggagcgag<br>gtataggctgtacccactgccaaaagcctttaaccgttatccgccaaccaactacgtaacagttagt<br>accatcttgttcttgactggacgttcgatcaggtggattttccctccactagtttggtcgatgaggcta<br>ggaattccccacgggtgaccgtgtcctagcctgcgtggcggccaacccagcttatgctgggacgc<br>ccttttaaggacatggtgtgaagactcgcatgtgcttggttgtgagtcctccggcccctgaatgcgg<br>ctaaccttaaccctagagccttatgccacgatccagtggagtaaggtcgtaatgagcaattccggg<br>acgggaccgactactttgggtgtccgtgtttctcatttttcttcatattgtcttatggtcacagcatata<br>tatacatatactgtgatc |
| 13 | HRV89 | ttaaaactgggagtgggttgttcccactcactccacccatgcggtgttgtactctgttattacggtaac<br>tttgtacgccagtttttcccacccttccccataatgtaacttagaagtttgtacaatatgaccaataggt<br>gacaatcatccagactgtcaaaggtcaagcacttctgtttccccggtcaatgaggatatgctttaccc<br>aaggcaaaaaccttagagatcgttatccccacactgcctacacagagcccagtaccatttttgatat<br>aattgggttggtcgctccctgcaaacccagcagtagacctggcagatgaggctggacattcccca<br>ctggcgacagtggtccagcctgcgtggctgcctgctcacccttcttgggtgagaagcctaattattg<br>acaaggtgtgaagagccgcgtgtgctcagtgtgcttcctccggcccctgaatgtggctaaccttaa<br>ccctgcagccgttgcccataatccaatgggtttgcggtcgtaatgcgtaagtgcgggatgggacca<br>actactttgggtgtccgtgtttcctgtttttcttttgattgcattttatggtgacaatttatagtgtata<br>gattgtcatc |
| 14 | HRVC-02 | ttaaaactgggtacaggttgttcccacctgtatcacccacgtggtgtggtgctcttgtattccggtaca<br>cttgcacgccagtttgccacccctcacccgtcgtaacttagaagctaacaactcgaccaacaggcg<br>gtggtaaaccataccacttacggtcaagcactcctgtttccccggtatgcgaggaatagactcctac<br>agggttgaagcctcaagtatcgttatccgcattggtactacgcaaagcttagtagtgccttgaaagtc<br>ccttggttggtcgctccgctagtttcccctagtagacctggcagatgaggcaggacactccccact<br>ggcgacagtggtcctgcctgcgtggctgcctgcgcacccttaggggtgcgaagccaagtgacag<br>acaaggtgtgaagagccccgtgtgctaccaatgagtcctccggcccctgaatgcggctaatccaa<br>ccccacagctattgcacacaagccagtgtgtatgtagtcgtaatgagcaattgtgggacggaaccg<br>actactttgggtgtccgtgtttccttttattcttatcattctgcttatggtgacaatactgtgaaatagt<br>gttgttacc |
| 15 | HRV-A21 | taaaactggatccaggttgttcccacctggatctcctattgggagttgtactctattattccggtaatttt<br>gtacgccagttttatcttcccccctccccaattgtaacttagaaggttatcaatacgaccaataggtggt<br>agttagccaaactaccaaaggtcaagcacttctgtttccccggtcaaagttgatatgctccaacagg<br>gcaaaaacaactgagatcgttatccgcaaagtgcctacgcaaagcctagtaacacctttgaagattt<br>atggttggtcgttccgctatttcccatagtagacctggcagatgaggctagaaatcccccactggcg<br>acagtgctctagcctgcgtggctgcctgcgcaccccttgggtgcgaagccatacattggacaagg<br>tgtgaagagccccgtgtgctcactttgagtcctccggcccctgaatgtggctaaccttaaccctgca<br>gctagtgcatgtaatccaacatgttgctagtcgtaatgagtaattgcgggacgggaccaactactttg<br>ggtgtccgtgtttcactttttccttttaatattgcttatggtgacaatatatatagctatatatattgac<br>acc |
| 16 | Salivirus A SH1 | ttcccctgcaaccattacgcttactcgcatgtgcattgagtggtgcatgtgttgaacaaacagctaca<br>ctcacatgggggcgggttttcccgccctacggcttctcgcgaggcccacccctcccctttctcccat<br>aactacagtgctttggtaggtaagcatcctgatcccccgcggaagctgctcacgtggcaactgtgg<br>ggacccagacaggttatcaaaggcacccggtctttccgccttcaggagtatccctgctagcgaatt<br>ctagtagggctctgcttggtgccaacctcccccaaatgcgcgctgcgggagtgctcttccccaact<br>caccctagtatcctctcatgtgtgtgcttggtcagcatatctgagacgatgttccgctgtcccagacc<br>agtccagtaatggacgggccagtgtgcgtagtcgtcttccggcttgtccggcgcatgtttggtgaac<br>cggtggggtaaggttggtgtgcccaacgcccgtactcaggggatacctcaaggcacccaggaat<br>gccagggaggtaccccgcttcacagcgggatctgaccctggggtaaatgtctgcgggggggtcttc<br>ttggcccacttctcagtacttttcagg |
| 17 | Salivirus FHB | acatgggggtctgcggacggcttcggcccacccgcgacaagaatgccgtcatctgtcctcatta<br>cccgtattccttcccttcccccgcaaccaccacgcttactcgcgcacgtgttgagtggcacgtgcgt<br>tgtccaaacagctacacccacacccttcggggcgggtttgtcccgccctcgggttcctcgcggaa<br>ccccccccctccctctctctctttctatccgccctcacttcccataactacagtgctttggtaggtgagc<br>accctgaccccccgcggaagctgctaacgtggcaactgtggggatccaggcaggttatcaaagg<br>cacccggtctttccgccttcaggagtatctctgccggtgaattccggtagggctctgcttggtgcca<br>acctcccccaaatgcgcgctgcgggagtgctcttccccaactcatcttagtaacctctcatgtgtgtg<br>cttggtcagcatatctgaggcgacgttccgctgtcccagaccagtccagcaatggacgggccagt<br>gtgcgtagtcgctttccggttttccggcgcatgtttggcgaaacgctgaggtaaggttggtgtgccc<br>aacgcccgtaatttggtgatacctcaagaccacccaggaatgccagggaggtaccccacttcggt<br>gggatctgaccctgggctaattgtctacggtggttcttcttgcttccacttctctttttttctggcatg |
| 18 | Salivirus NG-J1 | tatggcaggcgggcttgtggacggcttcggcccacccacagcaagaatgccatcatctgtcctca<br>cccccaattttccctttttcttcccctgcaaccattacgcttactcgcatgtgcattgagtggtgcatgtg<br>ttgaacaaacagctacactcacatgggggcgggttttcccgccctacggcctctcgcgaggcccac<br>cccttccctccccttataactacagtgctttggtaggtaagcatcctgatcccccgcggaagctgctc<br>acgtggcaactgtggggacccagacaggttatcaaaggcacccggtctttccgccttcaggagtat<br>ccctactagtgaattctagcggggctctgcttggtgccaacctcccccaaatgcgcgctgcgggag |

TABLE 17-continued

| IRES sequences. | | |
|---|---|---|
| SEQ ID NO | IRES | Sequence |
| | | tgctcttccccaactcaccctagtatcctctcatgtgtgtgcttggtcagcatatctgagacgatgttcc gctgtcccagaccagtccagtaatggacgggccagtgcgtgtagtcgtcttccggcttgtccggg gcatgtttggtgaaccggtggggtaaggttggtgtgcccaacgcccgtactttggtgacacctcaa gaccacccaggaatgccagggaggtaccccacctcacggtgggatctgaccctgggctaattgt ctacggtggttcttcttgcttccacttctttcttctgttcacg |
| 19 | Human Parecho-virus 1 | tttgaaaggggtctcctagagagcttggccgtcggccttataccccgacttgctgagtttctctagg agagcccttttcccagccctgaggcggctggtcaataaaagcctcaaacgtaactaacacctaaga agatcatgtaaaccctatgcctggtctccactattcgaaggcaacttgcaataagaagagtgggatc aagacgcttaaagcatagagacagttttcttttctaacccacatttgtgtggggtggcagatggcgtg ccataactctaatagtgagataccacgcttgtggaccttatgctcacacagccatcctctagtaagttt gtgagacgtctggtgacgtgtgggaacttattggaaacaacatttgctgcaaagcatcctactgcc agcggaaaaacacctggtaacaggtgcctctggggccaaaagccaaggtttaacagaccctttag gattggttctaaacctgagatgttgtggaagatatttagtacctgctgatctggtagttatgcaaacact agttgtaaggcccatgaaggatgcccagaaggtacccgtaggtaacaagtgacactatggatctg atttggggccagatacctctatcttggtgatctggttaaaaaacatctaatgggccaaacccggggg ggatccccggtttcctcttattctatcaatgccact |
| 20 | Crohivirus B | gtataagagacaggtgtttgccttgtcttcggactggcatcttgggaccaaccccccttttccccagc catgggttaaatggcaataaaggacgtaacaactttgtaaccattaagctttgtaattttgtaaccact aagctttgtgcacataatgtaaccatcaagcttgttagtcccagcaggaggtttgcatgcttgtagcc gaaatggggctcgacccccccatagtaggatacttgattttgcattccattgtggacctgcaaactcta cacatagaggctttgtcttgcatctaaacacctgagtacagtgtgtacctagaccctatagtacggga ggaccgtttgtttcctcaataaccctacataataggctaggtgggcatgcccaatttgcaagatccca gactgggggtcggtctgggcagggttagatccctgttagctactgcctgatagggtggtgctcaac catgtgtagtttaaattgagctgttcatatacc |
| 21 | Yc-3 | actgaagatcctacagtaactactgccccaatgaacgccacagatgggtctgctgatgactacctat cttagtgctagttgaggtttgaagtgagccggtttttagaagaaccagtttctgaacattatcatcccc agcatctattctatacgcacaagatagatagtcatcagcagacacatctgtgctactgcttgatagag ttgcggctggtcaacttagattggtataaccagttgagtggcaa |
| 22 | Rosavirus M-7 | tatgcatcactggacggcctaacctcggtcgtggcttcttgccgatttcagcgctaccaggctttctg gtctcgccaggcgttgattagtaggtgcactgtctaagtgaagacagcagtgctctctgtgaaaagt tgatgacactcttcaggtttgtagcgatcactcaaggctagcggatttccccgtgtggtaacacacg cctctaggcccagaaggcacggtgttgacagcaccccttgagtggctggtcttccccaccagcac ctgatttgtggattcttcctagtaacggacaagcatggctgctcttaagcattcagtgcgtccggggc tgaaggatgcccagaaggtacccgcaggtaacgataagctcactgtggatctgatctggggctgc gggctgggtgtctttccacccagccaaaacccgtaaaacggtagtcgcagttaaaaaacgtctag gccccacccccccagggatggggggttcccttaaaccctcacaagttcaac |
| 23 | Shanbavirus A | tgaaaagggggcgcagggtggtggtggttactaaatacccaccatcgccctgcacttccctttcc cctgtggctcagggtcacttagccccctctttgggttaccagtagttttctacccctgggcacagggt taactatgcaagacggaacaacaatctcttagtccccctcgccgatagtgggctcgacccccatgt gtaggagtggataagggacggagtgagccgatacggggaagagtgtgcggtcacaccttaattc catgagcgctgcgaagaaggaagctgtgaacaatggcgacctgaaccgtacacatggagctcca caggcatggtactcgttagactacgcagcctggttgggagtgggtataccctgggtgagccgcca gtgaatgggttgttcactggttaacacacactgcctgatagggtcagggcctcctgtccccgccgta atgaggtagaccatatgcc |
| 24 | Pasivirus A | gcggctggatattctggccgtgcaactgcttttgaccagtggctctgggtaacttagccaaagtgtc cttctccctttccctattatatgttttatggctttgtctggtcttgtttagtttatatataagatccttt ccgccgatatagacctcgacagtctagtgtaggaggattggtgatattaatttgccccagaagagtgacc gtgacacatagaaaccatgagtacatgtgtatccgtggaggatcgcccgggactggattccatatccc attgccatcccaacaagcggagggtatacccactatgtgcacgtctgcagtgggagtctgcagatt tagtcatactgcctgatagggtgtgggcctgcactctggggtactcaggctgtttatatataat |
| 25 | Pasivirus A2 | gctggactttctggctgcgcaactgcttttaaccagtggctctgggttacttagccaaaaccccccttc cccgtaccctagtttgtgtgtgtattattattttgttgttgttttgtaaatttttatataagatcctttc cgccgatatagacctcgacagtctagtgtaggaggattggtgatattaatatgccccagaagagtgaccg tgacacatagaaaccatgagtacatgtgtatccgtggaggatcgcccgggactggattccatatccca ttgccatcccaacaaacggagggtatacccgctatgtgcgcgtctacagtgggaatctgtagattta gtcatactgcctgatagggtgtgggcctgcactctggggtactcaggctgtttatataat |
| 26 | Echovirus E14 | ttaaaacagcctgtgggttgttcccatccacagggcccactgggcgccagcactctggtattgcgg taccttagtgcgcctgttttatatacccgtcccccaaacgtaacttagacgcatgtcaacgaagacca atagtaagcgcagcacaccagctgtgttccggtcaagcacttctgttaccccggaccgagtatcaa taagctactcacgtggctgaaggagaaaacgttcgttacccgaccaattacttcaagaaacctagta acaccatgaaggttgcgcagtgtttcgctccgcacaaccccagtgtagatcaggtcgatgagtcac cgcattccccacgggtgaccgtggcggtggctgcgctggcggcctgcccatggggaaacccat gggacgcttcaatactgacatggtgcgaagagtctattgagctaattggtagtcctccggcccctga atgcggctaatcctaactgcggagcagatacccacacaccagtgggcagtctgtcgtaacgggca actctgcagcggaaccgactactttgggtgtccgtgtttctctttatccttatactggctgcttatggtg acaattgagagattgttaccatatagctattggattggccatccggtgacaaatagagcaattgtgtat |

TABLE 17-continued

IRES sequences.

| SEQ ID NO | IRES | Sequence |
|---|---|---|
| | | ttgtttgttggtttcgtgccattaaattacaaggttctaaacacccttaatcttattatagcattcaacacaacaaa |
| 27 | Human Parecho-virus 5 | gtacattagatgcgtcatctgcaactttagtcaataaattacctccaatgtcattaccaacattccctaccttttcactaacacctaagacaacaagtacctatgcctggtctccactattcgaaggcaacttgcaataagaagagtggaattaagacgcttaaagcatagagctagttatcttttctaacccacaaagttttgtggggtggcagatggcgtgccataactctattagtgagataccatgcttgtggatcttatgctcacacagccatcctctagtaagttgataaggtgtctggtgatatgtgggaactcacatgaaccattaatttaccgtaaggtatcctatagccagcggaatcacatctggtgacagatgcctctggggccgaaagccaaggtttaacagaccctataggattggtttcaaaacctgaattgatgtggattgtgtatagtacctgttgatctggtaacagtgtcaacactagttgtaaggcccacgaaggatgcccagaaggtacccgtaggtaacaagtgacactatggatctgatctggggccagctacctctatcatggtgagttggttaaaaaacgtctagtgggccaaacccagggggatccctggtttccttttacctaatcaaagccact |
| 28 | Aichi Virus | tttgaaaaggggtgggggggcctcggcccctcaccctcttttccggtggtctggtcccggaccaccgttactccattcagcttcttcggaacctgttcggaggaattaaacgggcacccatactccccccacccccttttgtaactaagtatgtgtgctcgtgatcttgactcccacggaacggaccgatccgttggtgaacaaacagctaggtccacatcctcccttcccctgggagggcccccgccctcccacatcctccccccagcctgacgtatcacaggctgtgtgaagcccccgcgaaagctgctcacgtggcaattgtgggtccccccttcatcaagacaccaggtctttcctccttaaggctagccccggcgtgtgaattcacgttgggcaactagtggtgtcactgtgcgctcccaatctcggccgcggagtgctgttccccaagccaaacccctggcccttcactatgtgcctggcaagcatatctgagaaggtgttccgctgtggctgccaacctggtgacaggtgccccagtgtgcgtaaccttcttccgtctccggacggtagtgattggttaagatttggtgtaaggttcatgtgccaacgccctgtgcgggatgaaacctctactgccctaggaatgccaggcaggtaccccacctccgggtgggatctgagcctgggctaattgtctacgggtagtttcatttccaatcctttttatgtcggagtc |
| 29 | Hepatitis A Virus HA16 | ttcaagaggggtctccggagttttccggaacccctcttggaagtccatggtgaggggacttgatacctcaccgccgtttgcctaggctataggctaaatttccctttccctgtccttcccctatttccctttgttttgtttgtaaatattaattcctgcaggttcagggttctttaatctgtttctctataagaacactcaattttttcacgctttctgtctcctttcttccagggctctccccttgccctaggctctggccgttgcgcccggcggggtcaactccatgattagcatggagctgtaggagtctaaattggggacgcagatgtttgggacgtcgccttgcagtgttaacttggctttcatgaacctctttgatcttccacaaggggtaggctacgggtgaaacctcttaggctaatacttcaatgaagagatgccttggatagggtaacagcggcggatattggtgagttgttaagacaaaaaccattcaacgccggaggactggctctcatccagtggtgcattgagggattgattgtcagggctgtctctaggtttaatctcagacctctctgtgcttagggcaaacactatttggccttaaatgggatcctgtgagaggggggtccctccattgacagctggactgttctttggggccttatgtggtgtttgcctctgaggtactcaggggcatttaggtttttcctcattcttaaataata |
| 30 | Phopivirus | gggagtaaacctcaccaccgtttgccgtggtttacggctacctattttttggatgtaaatattaattcctgcaggttcaggtctcttgaattatgtccacgctagtggcactctcttacccataagtgacgccttagcggaacctttctacacttgatgtggttaggggttacattatttccctgggccttctttggccctttttcccctgcactatcattctttcttccgggctctcagcatgccaatgttccgaccggtgcgcccgccggggttaactccatggttagcatggagctgtaggccctaaaagtgctgacactggaactggactattgaagcatacactgttaactgaaacatgtaactccaatcgatcttctacaaggggtaggctacgggtgaaacccccttaggttaatactcatattgagagatacttctgataggttaaggttgctggataatggtgagtttaacgacaaaaaccattcaacagctgtgggccaacctcatcaggtagatgcttttggagccaagtgcgtaggggtgtgtgtggaaatgcttcagtggaaggtgccctcccgaaaggtcgtaggggtaatcaggggcagttaggtttccacaattacaatttgaa |
| 31 | CVA10 | gctcttccgatctgggttgttcccacccacagggcccactgggcgccagcactctgattccacggaatctttgtgcgcctgttttacaacccttcccaatttgtacgtagaagcaatacacactactgatcaatagtaggcatggcgcgccagtcatgtcatgatcaagcacttctgttcccccggactgagtatcaatagactgctcacgcggttgaaggagaaaacgttcgttacccggctaactacttcgagaaacctagtagcaccatggaagctgcggagtgtttcgctcagcactttccccgtgtagatcaggtcgatgagtcactgcaatccccacgggcgaccgtggcagtggctgcgttggcggcctgcctatggggcaacccataggacgctaatcctaactgcggagcacatgccttcaacccaggaggtggtgtgtcgtaacgggtaactctggctaatcctaactgcggagcacatgccttcaacccaggaggtggtgtgtcgtaacgggtaactctgcagcggaaccgactactttgggtgtccgtgtttccttttatccttatattggctgcttatggtgacaatcacggaattgttgccatatagctattggattggccatccggtgtctaacagagctattgtatacctatttgttggatttactcccctatcatacaaatctctgaacactttgtgctttatactgaacttaaacacacgaaa |
| 32 | Entero-virus C | ttaaaacagctctggggttgttcccaccccagaggcccacgtggcggccagtacaccggtaccacggtacccttgtacgcctgttttatactcccccctccccgtaaactagaagcacgaaacacaagttcaatagaaggggggtacagaccagtaccaccacgaacaagcacttctgttcccccggtgaggtcacatagactgtccccacggtcaaaagtgactgatccgttatccgctcacgtacttcggaaagcctagtaccaccttggaatctacgatgcgttgcgctcagcactcgaccccggagtgtagcttaggctgatgagtctggacgttccccactggtgacagtggtccaggctgcgttggcggcctacctgtggtccaaaaccacaggacgctagtagtgaacaaggtgtgaagagcccactgagctacctgagaatcctccggcccctgaatgcggctaatcccaaccacggagcaggtaatcgcaaaccagcggtcagcctgtcgtaacgcgtaagtctgtggcggaaccgactactttgggtgtccgtgtttccttttatttttatggtggctgcttatggtgacaatcatagattgttatcataaagcaaattggattggccatccggagtgagctaaactatctatttctctgagtgttggattcgtttcacccacattctgaacaatcagcctcattagtgttaccctgttaataagacgatatcatcacg |

TABLE 17-continued

IRES sequences.

| SEQ ID NO | IRES | Sequence |
|---|---|---|
| 33 | Entero-virus D | ttaaaacagctctggggttgttcccaccccagaggcccacgtggcggctagtactccggtacccc<br>ggtacccttgtacgcctgttttatactccctttcccaagtaactttagaagaaataaactaatgttcaac<br>aggaggggtacaaaccagtaccaccacgaacacacacttctgtttccccggtgaagttgcatag<br>actgtacccacggttgaaagcgatgaatccgttacccgcttaggtacttcgagaagcctagtatcat<br>cttggaatcttcgatgcgttgcgatcagcactctaccccgagtgtagcttgggtcgtgagtctgga<br>caccccacaccggcgacgtggtccaggctgcgttggcggcctaccctggctagcaccatggga<br>cgctagttgtgaacaaggtgcgaagagcctattgagctacctgagagtcctccggcccctgaatgc<br>ggctaatcccaaccacggagcaaatgctcacaatccagtgagtggtttgtcgtaatgcgcaagtct<br>gtggcggaaccgactactttgggtgtccgtgtttccttttattttattatggctgcttatggtgacaat<br>ctgagattgttatcatatagctattggattagccatccggtgatatcttgaaattttgccataactttttt<br>cacaaatcctacaacattacactacactttctcttgaataattgagacaactcata |
| 34 | Entero-virus J | ttaaaatagcctcagggttgttccaccctgagggcccacgtggtgtagtactctggtattacggtac<br>ctttgtacgcctattttataccccttccccaagtaatttagaagcaagcacaaaccagttcagtagta<br>agcagtacaatccagtactgtaatgaacaagtacttctgttaccccggaagggtctatcggtaagct<br>gtacccacggctgaagaatgacctaccgttaaccggctacctacttcgagaagcctagtaatgccg<br>ttgaagttttattgacgttacgctcagcacactaccccgtgtgtagttttggctgatgagtcacggcac<br>tccccacgggcgaccgtggccgtggctgcgttggcggccaaccaaggagtgcaagctccttgga<br>cgtcatattacagacatggtgtgaagagcctattgagctaggtggtagtcctccggcccctgaatgc<br>ggctaatcctaactccggagcatatcggtgcgaaccagcacttggtgtgttgtaatacgtaagtctg<br>gagcggaaccgactactttgggtgtccgtgtttcctgttttaactttatggctgcttatggtgacaatt<br>taacattgttaccatatagctgagggttggccatccggattttgttataaaaccatttcctcgtgccttg<br>acctttaacacatttgtgaacttctttaaatcccttttattagtccttaaatactaaga |
| 35 | Human Pegivirus 2 | aactgttgttgtagcaatgcgcatattgctacttcggtacgcctaattggtaggcgcccggccgacc<br>ggccccgcaagggcctagtaggacgtgtgacaatgccatgagggatcatgacactggggtgag<br>cggaggcagcaccgaagtcgggtgaactcgactcccagtgcgaccacctggcttggtcgttcatg<br>gagggcatgcccacgggaacgctgatcgtgcaaagggatgggtccctgcactggtgccatgcg<br>cggcaccactccgtacagcctgatagggtggcggcgggcccccccagtgtgacgtccgtggag<br>cgcaac |
| 36 | GBV-C GT110 | tgacgtgggggggttgatTTTccccccccggcactgggtgcaagccccagaaaccgacgcct<br>atctaagtagacgcaatgactcggcgccgactcggcgaccggccaaaaggtggtggatgggtga<br>tgacagggttggtaggtcgtaaatcccggtcatcctggtagccactataggtgggtcttaagagaa<br>ggtcaagattcctcttacgcctgcggcgagaccgcgcacggtccacaggtgttggccctaccggt<br>gtgaataagggcccgacatcaggc |
| 37 | GBV-C K1737 | gacgtgggggggttgatccccccccTTTggcactgggtgcaagccccagaaaccgacgccta<br>tttaaacagacgttaagaaccggcgccgacccggcgaccggccaaaaggtggtggatgggtgat<br>gccagggttggtaggtcgtaaatcccggtcatcttggtagccactataggtgggtcttaagggttgg<br>ttaaggtccctctggcgcttgtggcgagaaagcgcacggtccacaggtgttgccctaccggtgt<br>gaataagggcccgacgtcaggctcgtcgttaaaccgagcccactacccacctgggcaaacaacg<br>cccacgtacggtccacgtcgcccttcaatgtctctcttgaccaataggcttagccggcgagttgaca<br>aggaccagtgggggctgggcggtaggggaaggacccctgccgctgcccttcccggtggagtg<br>ggaaatgc |
| 38 | GBV-C Iowa | tgacgtgggggggttgatccGccccccccggcactCggtgcaagccccataaaccgacgccta<br>tctaagtagacgcaatgactcggcgccgactcggcgaccggccaaaaggtggtggatgggtggt<br>gacagggttggtaggtcgtaaatcccggtcatcctggtagccactataggtgggtcttaagagaag<br>gtcaagactcctcttgtgcctgcggcgagaccgcgcacggtccacaggtgctggccctaccggtg<br>tgaataagggcccgacgtcaggctcgtcgttaaaccgagcccgtcacccacctgggcaaacgac<br>gcccacgtacggtccacgtcgcccttca |
| 39 | Pegivirus A 1220 | tgtagcaatgcgcatattgctacttcggtacgcctaattggtaggcgcccggccgaccggccccgc<br>aagggcctagtaggacgtgtgacaatgccatgcgggatcatgacactggggtgagcggaggca<br>gcaccgaagtcgggtgaactcgactcccagtgcgaccacctggcaggtcgttcatggagggcat<br>gcccacgggaacgctgatcgtgcaaagggatgggtccctgcactggtgccatgcgcggcacca<br>ctccgtacagcctgatagggtggcggcgggcccccccagtgtgacgtccgtggagcgcaac |
| 40 | Pasivirus A3 | attttctggccgtgtagctgcttttgaccagtggctctgggttacttagccaaatccccccttccttcacc<br>cttttaaatttgatggtctgtgttgtttgttttgtcttgtctaaataatatataagatccttcccgccga<br>tacagacctcgacagtctggtgtaggagggttggtgttattaatttgccccagaagagtgaccgtgacac<br>atagaaaccatgagtacatgtgtatccgtggaggatcgcccgggactggattccatatcccattgcc<br>atcccaacaagcggagggtatacccactatgtgcgcgtttgcagtgggaatctgcaaatttagtcat<br>actgcctgatagggtgtgggcctgcactctggggtactcaggctgacatataat |
| 41 | Sapelovirus | cccctccacccttaaggtggttgtatcccacataccccaccctcccttccaaagtggacggacaact<br>ggattttgactaacggcaagtctgaatggtatgatttggatacgtttaaacggcagtagcgtggcga<br>gctatggaaaaatcgcaattgtcgatagccatgttagtgacgcgcttcggcgtgctcctttggtgatt<br>cggcgactggttacaggagagtaggcagtgagctatgggcaaacctctacagtattacttagagg<br>gaatgtgcaattgagacttgacgagcgtctctttgagatgtggcgcatgctcttggcattaccatagt<br>gagcttccaggagggaaacctggactgggcctatactacctgatagggtcgcggctggccgcct<br>gtaactagtatagtcagttgaaacccccc |

TABLE 17-continued

IRES sequences.

| SEQ ID NO | IRES | Sequence |
|---|---|---|
| 42 | Rosavirus B | gtctctttagtgtctatgcttcagagagcggtgaactgacaccgttgcttcttgcacagcccttcgtgc<br>cggtctttccggttctcgacagcgttgggcatcatggctagttaggctaagatagtggatgatctagt<br>gaacagttttggattgtttggagttttgtagcgatgctagtagtgtgtgtggacctccccacgtggtaa<br>cacgtgccccacaggccaaaagccaaggtgttgaaagcacccctactagtcccagactcacccat<br>ctgggaactcctctcatgaaaaatcttagtaacttttgattcggctattcatcaacctctctagtcaagg<br>gctgaaggatgcccggaaggtacccgcaggtaacgataagctcactgtggatctgatccggggc<br>tttggtgcgaccgtctgtccggcgtagccagagttaaaaaacgtctaggcccttccaccccaaggg<br>attggggtttccccaatcatttgaaagttcact |
| 43 | Bakunsa Virus | ttttgaacgccacctcggagcgatatccggggacccccctccccttttttccttcctaccttcttcccaaa<br>tttccctcttcccttgttattttggtttggatttcctggacatgactcggacggatctatctcatttgct<br>ttgtgtctgctccaccagtggcatggtcgaaagatcatcaacactggacgtgtactgtaatggccaaacg<br>tgcccacaggggaaaccatgccggtcgctgtagcggcgggtggacgtggtggacccctctccct<br>gctcataaactttgggtaggtgaagggttcaagcgacgcttgccgtgagggcgcatccggatggt<br>gggaaccaacaaactaggctgtaatggccgacctcaggtggatgagctagggctgctgcaccaa<br>aagggactcgattcgatatcccggcctggtagcctagtgcagtggactcgtagttgggaatctacg<br>actggcctagtacagggtgatagccccgtttcccacgcccacctgttgtagggacacccccccc |
| 44 | Tremovirus A | tttgaaagaggcctccggagtgtccggaggctctctttcgacccaacccatactgggggggtgtgtg<br>ggaccgtacctggagtgcacggtatatatgcattcccgcatggcaagggcgtgctaccttgcccct<br>tgacgcatggtatgcgtcatcatttgccttggttaagccccatagaaacgaggcgtcacgtgccga<br>aaatccctttgcgtttcacagaaccatcctaaccatgggtgtagtatgggaatcgtgtatggggatga<br>ttaggatctctcgtagagggataggtgtgccattcaaatccagggagtactctggctctgacattgg<br>gacatttgatgtaaccggacctggttcagtatccgggttgtcctgtattgttacggtgtatccgtcttgg<br>cacactgaaagggtattttttgggtaatcctttcctactgcctgatagggtggcgtgcccggccacga<br>gagattaagggtagcaatttaaac |
| 45 | Swine Pasivirus 1 | gcttttgaccagtggctctgggttacttagccaagtccctttctcttattttcactagtttatgttgtgt<br>gttgtctgttttgttttgtttaaattgtatacaagatccttcccgccgacacagacctcgacagtctggt<br>gtaggagggttggtgatattaatttgccccaaaagagtgaccgtgatacgtggaaaccatgagtacatgt<br>gtatccgtggaggatcgcccgggactggattccatatcccattgccatcccaacaaacggagggt<br>atacccaccacgtgcgcgtttgcagtgggaatctgcaaatttagtcatactgcctgatagggtgtgg<br>gcctgcactttggggtactcaggctgttcatataat |
| 46 | PLV-CHN | acatggggtatgttgtctgtcctgttttgagaaacaatatataagatcctttccgccgatatagacctc<br>gacagtctagtgtaggaggattggtgatagtaacttgccccagaagagtgaccgtgacacataga<br>aaccatgagtacatgtgtatccgtggaggatcgcccgggactggattccatatcccattgccatccc<br>aacaaacggagggtatacccactatgtgcgcgtttgcagtgggagcctgcaaatttagtcatactg<br>cctgatagggtgtgggcctgcactctggggtactcaggctgtttatataat |
| 47 | Pasivirus A (longer) | tgaaaaagtggttgtgcagctggattttccggctgtgcaactgcttttgaccagtggctctgggttact<br>tagccaaattcctttcccttatccctattggtttgtgttgtgtgttgtttgttttgttttgtcttaacta<br>tatacaagatccttcccgccgatacagacctcgacagtctggtgtaggagggttggtgttattaatttgc<br>cccaaaagagtgaccgtgacacgtggaaaccatgagtacatgtgtatccgtggaggatcgcccgggact<br>ggattccatatcccattgccatcccaacaaacggagggtatacccaccacgtgcgcgtttgcagtg<br>ggaatctgcaaatttagtcatactgcctgatagggtgtgggcctgcactttggggtactcaggctgtt<br>tatataat |
| 48 | Sicinivirus | gtgtcattaaggtgtgtttggaagttcgaattagctggtttgtggtgattagtagacccccctggaggta<br>cccaattcggatctgaccagggacccgtgactataccgctccggtaattcgggtttaaaacaatga<br>acgtcaccacacaattacttttctcattttattttcatcattgtcttcctatttaccgattacactcgat<br>ttccttggatgttcctggagatttccctggttacctggaccctcattattgttgttgatcacccagcgag<br>ctgtcccaattgcttattatttgcgcttacaacacgtcctaatatttttctggagatcgggagattgagc<br>tcccgggctatcctgccattcaac |
| 49 | Hepacivirus K | gggaacaatggtccgtccgcggaacgactctagccatgagtctagtacgagtgcgtgccacccat<br>tagcacaaaaaccactgactgagccacacccctcccggaatcctgagtacaggacattcgctcgg<br>acgacgcatgagcctccatgccgagaaaattgggtatacccacgggtaaggggtggccacccag<br>cgggaatctgggggctggtcactgactatggtacagcctgatagggtgctgccgcagcgtcagtg<br>gtatgcggctgttcatggaac |
| 50 | Hepacivirus A | acctccgtgctaggcacggtgcgttgtcagcgttttgcgcttgcatgcgctacacgcgtcgtccaac<br>gcggagggaacttcacatcaccatgtgtcactcccccctatggagggttccaccccgcttacacgga<br>aatgggttaaccatacccaaagtacgggtatgcgggtcctcctagggcccccccggcaggtcga<br>gggagctggaattcgtgaattcgtgagtacacgaaaatcgcggcttgaacgtctttgaccttcgga<br>gccgaaatttgggcgtgccccacgaaggaaggcgggggcggtgttgggccgccgcccccccttat<br>cccacggtctgataggatgcttgcgagggcacctgccggtctcgtagaccataggac |
| 51 | BVDV1 | gtatacgagaatttgcctaggacctcgtttacaatatgggcaatctaaaattataattaggcctaagg<br>gacaaatcctcctcagcgaaggccgaaaagaggctagccatgcccttagtaggactagcaaaata<br>agggggtagcaacagtggtgagttcgttggatggctgaagccctgagtacagggtagtcgtcag |

TABLE 17-continued

IRES sequences.

| SEQ ID NO | IRES | Sequence |
|---|---|---|
| | | tggttcgacgcttcggaggacaagcctcgagataccacgtggacgagggcatgcccacagcaca<br>tcttaacctggacgggggtcgttcaggtgaaaacggtttaaccaaccgctacgaatacagcctgat<br>agggtgctgcagaggcccactgtattgctactgaaaatctctgctgtacatggcac |
| 52 | Border Disease Virus | gtatacgggagtagctcatgcccgtatacaaaattggatattccaaaactcgattgggttagggagc<br>cctcctagcgacggccgaaccgtgttaaccatacacgtagtaggactagcagacgggaggacta<br>gccatcgtggtgagatccctgagcagtctaaatcctgagtacaggatagtcgtcagtagttcaacg<br>caggcacggttctgccttctagatgctacgtggacgagggcatgcccaagacttgctttaatctcgg<br>cgggggtcgccgaggtgaaaacacctaacggtgttggggttacagcctgatagggtgctgcaga<br>ggcccacgaataggctagtataaaaatctctgctgtacatggcac |
| 53 | BVDV2 | gtatacgagattagctaaagtactcgtatatggattggacgtcaacaaatttttaattggcaacgtagg<br>gaaccttcccctcagcgaaggccgaaaagaggctagccatgccccttagtaggactagcaaaagt<br>agggggactagcggtagcagtgagttcgttggatggccgaacccctgagtacaggggagtcgtc<br>aatggttcgacactccattagtcgaggagtctcgagatgccatgtggacgagggcatgcccacgg<br>cacatcttaacccatgcgggggttgcatgggtgaaagcgctaatcgtggcgttatggacacagcct<br>gatagggtgtagcagagacctgctattccgctagtaaaaaactctgctgtacatggcac |
| 54 | CSFV-PK15C | gtatacgaggttagttcattctcgtatgcattattggacaaatcaaaatttcaatttggttcagggcctc<br>cctccagcgacggccgaactgggctagccatgcccatagtaggactagcaaacggagggacta<br>gccgtagtggcgagctccctgggtgttctaagtcctgagtacaggacagtcgtcagtagttcgacg<br>tgagcagaagcccacctcgagatgctatgtggacgagggcatgcccaagacgcaccttaaccct<br>agcgggggtcgctagggtgaaatcacaccacgtgatgggagtccgacctgatagggtgctgcag<br>aggctcactattaggctagtataaaaatctctgctgtacatggcac |
| 55 | SF573 Dicistro-virus | aaaaccgaccccagagatcagaaagtcgttgacgcgatcttttattagaggacgttgcgctggcgc<br>gagctttaattagcagacgccaaaaataaacaacaaaatgctgatcgcgagacttaattgtcagac<br>gattggccaaatccgatgtgatctttgctgctcccagattgccgaaataggagtagtag |
| 56 | Hubei Picorna-like Virus | ccccaaaaccccccccttaaactcaacactgtagtggattcattttccgttgcaaaacaaaacattac<br>tacccgcatttatgtaggctctgtgttttctatgcgaccgttacattaatctctactctgacccactagt<br>ttataaaaccgaagacctgaatgaaacgattttccttcttttcaacctctaacgaacctctgacggcttg<br>agaaacctgaagttagtaattatgtttaaaagaaaggaaagtcaaacgcgatgactcttacatccctat<br>tccataccgttgctccacaatgtgagcgatgcgaggtcgggactgcagtattaggggaacgagct<br>acatggagagttaattatctctcccctcctacgggagtctcatgtgagctgtagaaagcggttggca<br>cctctcgttacctcgcctgtacatgatcc |
| 57 | CRPV | aaaagcaaaaatgtgatcttgcttgtaaatacaattttgagaggttaataaattacaagtagtgctatttt<br>tgtatttaggttagctatttagctttacgttccaggatgcctagtggcagccccacaatatccaggaag<br>ccctctctgcggtttttcagattaggtagtcgaaaaacctaagaaatttacct |
| 58 | Salivirus A BN5 | tttcctcctttcgaccgccttacggcaggcgggtccgcggacggcttcggcctacccgcgacaag<br>aatgccgtcatctgtccttatcacccatattctttcccttcccccgcaaccatcacgcttactcgcgca<br>cgtgttgagtggcacgtgcgttgtccaaacagttacactcacacccttggggcgggtttgtcccgcc<br>ctcgggttcctcgcggaaccctccctcttctctctccctttctatccgccttcactttccataactacagt<br>gctttggtaggtaagcatcctgacccccgcggaagctgccaacgtggcaactgtggggatccag<br>gcaggttatcaaaggcacccggtctttccgccttcaggagtatccctgccggtgaattccgacagg<br>gctctgcttggtgccaacctcccccaaatgcgcgctgcgggagtgctcttccccaactcatcttagt<br>aacctctcatgtgtgtgcttggtcagcatatctgaggcgacgttccgctgtcccagaccagtccagc<br>aatggacgggccagtgtgcgtagtcgctttccggtttcccggcgcatgtttggcgaaacgctgagg<br>taaggttggtgtgcccaatgcccgtaatttggtgacacctcaagaccacccaggaatgccaggga<br>ggtaccccacttcggtgggatctgaccctgggctaattgtctacggtggttcttcttgcttccacttctc<br>tttttctggcatg |
| 59 | Salivirus A BN2 | tatggcaggcgggcttgtggacggcttcggcccacccacagcaagaatgccatcatctgtcctca<br>cccccatgtttcccctttctttccctgcaaccgttacgcttactcgcaggtgcatttgagtggtgcacgt<br>gttgaataaacagctacactcacatgggggcgggttttcccgccctgcggcctctcgcgaggccc<br>acccctccccttcctcccataactacagtgctttggtaggtaagcatcctgatcccccgcggaagct<br>gctcacgtggcaactgtggggacccagacaggttatcaaaggcacccggtctttccgccttcagg<br>agtatccctgctagtgaattctagtagggctctgcttggtgccaacctcccccaaatgcgcgctgcg<br>ggagtgctcttccccaactcaccctagtatcctctcatgtgtgtgcttggtcagcatatctgagacgat<br>gttccgctgtcccagaccagtccagtaatggacgggccagtgtgcgtagtcgtcttccggcttttcc<br>ggcgcatgtttggtgaaccggtggggtaaggttggtgtgcccaacgcccgtactttggtgatacct<br>caagaccacccaggaatgccagggaggtaccccgcttcacagcgggatctgaccctgggctaat<br>tgtctacggtggttcttcttgcttccacttctttctactgttc |
| 60 | Salivirus A 02394 | tttcgaccgccttatggcaggcgggcttgtggacggcttcggcccacccacagcaagaatgccat<br>catctgtcctcacccccatttctcccctccttcccctgcaaccattacgcttactcgcatgtgcattgag<br>tggtgcacgtgttgaacaaacagctacactcacgtgggggcgggttttcccgcccttcggcctctc<br>gcgaggcccacccttccccttcctcccataactacagtgctttggtaggtaagcatcctgatccccc<br>gcggaagctgctcgcgtggcaactgtggggacccagacaggttatcaaaggcacccggtctttcc<br>gcctccaggagtatccctgctagtgaattctagtggggctctgcttggtgccaacctcccccaaatg<br>cgcgctgcgggagtgctcttccccaactcaccctagtatcctctcatgtgtgtgcttggtcagcatat<br>ctgagacgatgttccgctgtcccagaccagtccagcaatggacgggccagtgtgcgtagtcgtctt |

TABLE 17-continued

| IRES sequences. | | |
|---|---|---|
| SEQ ID NO | IRES | Sequence |
| | | ccggcttgtccggcgcatgtttggtgaaccggtggggtaaggttggtgtgcccaacgcccgtacttt ggtgacaactcaagaccacccaggaatgccagggaggtaccccgcctcacggcgggatctga ccctgggctaattgtctacggtggttcttcttgcttccatttctttcttctgttc |
| 61 | Salivirus A GUT | tatggcaggcgggcttgtggacggtttcggcccacccacagcaagaatgccatcatctgtcctcac ccccaattttccctttcttcccctgcaatcatcacgcttactcgcatgtgcattgagtggtgcatgtgtt gaacaaacagctacactcacatgggggcgggttttcccgccctacggcctctcgcgaggcccac ccttcccctccccttataactacagtgctttggcaggtaagcatcctgatccccgcggaagctgct cacgtggcaactgtggggacccagacaggttatcaaaggcacccggtctttccgccttcaggagc atccccactagtgaattctagtggggctctgcttggtgccaacctcccccaaatgcgcgctgcggg agtgctcttccccaacccatcctagtatcctctcatgtgtgtgcttggtcagcatatctgagacgacgt tccgctgtcccagaccagtccagtaatggacgggccagtgtgcgtagtcgtcttccggcttgtccg gcgcatgtttggtgaaccggtggggtaaggaggtgtgcccaacgcccgtactttggtgacacctc aagaccacccaggaatgccagggaggtaccccgcctcacggcgggatctgaccctgggctaatt gtctacggtggttcttcttgcttccacttctttctt |
| 62 | Salivirus A CH | ttctcctgcaaccattacgcttaatcgcatgtgcattgagtggtgcatgtgttgaacaaacagctaca atcacatgggggcgggttttcccgccccacggcttctcgcgaggcccatccctccctttttctcccat aactacagtgctttggtaggtaagcatcccgatctcccgcggaagctgctcacgtggcaactgtgg ggacccagacaggttatcaaaggcacccggtctttccgccttcaggagtatccctgctagcgaatt ctagtagggctctgcttggtgccaacctctcccaaatgcgcgctgcgggagtgctcttccccaaatc accccagtatcctctcatgtgtgtgcctggtcagcatatctgagacgatgttccgctgtcccagacca gtccagtaatggacgggccagtgtgcgtagtcgtcctccggcttgtccggcgcatgtttggtgaac cggtggggtaaggttggtgtgcccaacgcccgtaatcaggggatacctcaaggcacccaggaat gccagggaggtatcccgcctcacagcgggatctgaccctggggtaaatgtctgcggggggtcct cttggcccaattctcagtaattttcagg |
| 63 | Salivirus A SZ1 | tctgtcctcaccccatcttcccttctttcctgcaccgttacgcttactcgcatgtgcattgagtggtgca cgtgcttgaacaaacagctacactcacatgggggcgggttttcccgccctgcggcctctcgcgag gcccacccctccccttcctcccataactacagtgctttggtaggtaagcatcctgatccccgcgga agctgctcacgtggcaactgtggggacccagacaggttatcaaaggcacccggtctttccgccttc aggagtatccctgctagtgaattctagtagggctctgcttggtgccaacctcccccaaatgcgcgct gcgggagtgctcttccccaactcaccctagtatcctctcatgtgtgtgcttggtcagcatatctgaga cgatgttccgctgtcccagaccagtccagtaatggacgggccagtgtgcgtagtcgtcttccggctt gtccggcgcatgtttggtgaaccggtggggtaaggttggtgtgcccaacgcccgtactttggtgat acctcaagaccacccaggaatgccagggaggtaccccgcttcacagcgggatctgaccctggg ctaattgtctacggtggttcttcttgcttccacttctttctactgttcatg |
| 64 | Salivirus FHB | acatggggggtctgcggacggcttcggcccacccgcgacaagaatgccgtcatctgtcctcatta cccgtattccttcccttcccccgcaaccaccacgcttactcgcgcacgtgttgagtggcacgtgcgt tgtccaaacagctacacccacacccttcggggcgggtttgtcccgccctcgggttcctcgcggaa cccccccctccctctctctctttctatccgccctcacttcccataactacagtgctttggtaggtgagc accctgacccccgcggaagctgctaacgtggcaactgtggggatccaggcaggttatcaaagg cacccggtctttccgccttcaggagtatctctgccggtgaattccggtagggctctgcttggtgcca acctcccccaaatgcgcgctgcgggagtgctcttccccaactcatcttagtaacctctcatgtgtgtg cttggtcagcatatctgaggcgacgttccgctgtcccagaccagtccagcaatggacgggccagt gtgcgtagtcgctttccggttttccggcgcatgtttggcgaaacgctgaggtaaggttggtgtgccc aacgcccgtaatttggtgatacctcaagaccacccaggaatgccagggaggtaccccacttcggt gggatctgaccctgggctaattgtctacggtggttcttcttgcttccacttctcttttttctggcatg |
| 65 | CVB3 | ttaaaacagcctgtgggttgatcccacccacaggcccattgggcgctagcactctggtatcacggt acctttgtgcgcctgttttataccccctcccccaactgtaacttagaagtaacacacaccgatcaaca gtcagcgtggcacaccagccacgttttgatcaagcacttctgttaccccggactgagtatcaataga ctgctcacgcggttgaaggagaaagcgttcgttatccggccaactacttcgaaaaacctagtaaca ccgtggaagttgcagagtgtttcgctcagcactaccccagtgtagatcaggtcgatgagtcaccgc attccccacgggcgaccgtggcggtggctgcgttggcggcctgcccatggggaaacccatggg acgctctaatacagacatggtgcgaagagtctattgagctagttggtagtcctccggcccctgaatg cggctaatcctaactgcggagcacacaccctcaagccagagggcagtgtgtcgtaacgggcaac tctgcagcggaaccgactactttgggtgtccgtgtttcattttattcctatactggctgcttatggtgac aattgagagatcgttaccatatagctattggattggccatccggtgactaatagagctattatatatcc ctttgttgggtttataccacttagcagaaagaggttaaaacattacaattcattgttaagttgaatacag caaa |
| 66 | CVB1 | ttaaaacagcctgtgggttgttcccacccacaggcccattgggcgctagcactctggtatcacggta cctttgtgcgcctgttttacatcccctccccaaattgtaatttagaagtttcacacaccgatcattagca agcgtggcacaccagccatgttttgatcaagcacttctgttaccccggactgagtatcaatagaccg ctaacgcggttgaaggagaaaacgttcgttacccggccaactacttcgaaaaacctagtaacacca tggaagttgcggagtgtttcgctcagcactaccccagtgtagatcaggtcgatgagtcaccgcgttc cccacgggcgaccgtggcggtggctgcgttggcggcctgcctacggggaaacccgtaggacg ctctaatacagacatggtgcgaagagtctattgagctagttggtaatcctccggcccctgaatgcgg ctaatcctaactgcggagcacatacccctcaaaccaggggggcagtgtgtcgtaacgggcaactctg cagcggaaccgactactttgggtgtccgtgtttcattttattcctatactggctgcttatggtgacaatt |

TABLE 17-continued

IRES sequences.

| SEQ ID NO | IRES | Sequence |
|---|---|---|
| | | gacaggttgttaccatatagttattggattggccatccggtgactaacagagcaattatatatctctttg<br>ttgggtttataccacttagcttgaaagaggttaaaacactacatctcatcattaaactaaatacaacaa<br>a |
| 67 | Echovirus 7 | ttaaaacagcctgtgggttgttcccacccacagggcccattgggcgtcagcaccctggtatcacgg<br>tacctttgtgcgcctgttttatatcccttcccccaattgtaacttagaagaaacacacaccgatcaaca<br>gcaagcgtggcacaccagccatgttttggtcaagcacttctgttaccccggactgagtatcaataga<br>ctgctcacgcggttgaaggagaaagcgtccgttatccggccagctacttcgagaaacctagtaac<br>accatggaagttgcggagtgtttcgctcagcactaccccagtgtagatcaggtcgatgagtcaccg<br>ctttccccacgggcgaccgtggcggtggctgcgttggcggcctgcctatgggggaacccatagg<br>acgctctaatacagacatggtgcgaagagtctattgagctagctggtattcctccggcccctgaatg<br>cggctaatcctaactgtggagcacatgcccctaatccaaggggtagtgtgtcgtaatgagcaattcc<br>gcagcggaaccgactactttgggtgtccgtgtttcctcttattcttgtactggctgcttatggtgacaat<br>tgagagattgttaccatatagctattggattggccatccggtgactaatagagctattgtgtatctcttt<br>gttggatttgtaccacttaatttgaaagaaatcaggacactacgctacattttactattgaacaccgca<br>aa |
| 68 | CVB5 | ttaaaacagcctgtgggttgtacccacccacagggcccactgggcgctagcactctggtatcacg<br>gtacctttgtgcgcctgttttatgccccttcccccaattgaaacttagaagttacacacaccgatcaa<br>cagcgggcgtggcataccagccgcgtcttgatcaagcactcctgtttccccggaccgagtatcaat<br>agactgctcacgcggttgaaggagaaaacgttcgttacccggctaactacttcgagaaacctagta<br>gcatcatgaaagttgcgaagcgtttcgctcagcacatccccagtgtagatcaggtcgatgagtcac<br>cgcattccccacgggcgaccgtggcggtggctgcgttggcggcctgcctacggggcaacccgt<br>aggacgcttcaatacagacatggtgcgaagagtcgattgagctagttagtagtcctccggcccctg<br>aatccggctaatcctaactgcggagcacataccctcaacccaggggggcattgtgtcgtaacgggt<br>aactctgcagcggaaccgactactttgggtgtccgtgtttccttttattcttataatggctgcttatggtg<br>acaattgaaagattgttaccatatagctattggattggccatccggtgtctaacagagctattatatac<br>ctctttgttggatttgtaccacttgatctaaaggaagtcaagacactacaattcatcatacaattgaaca<br>cagcaaa |
| 69 | EVA71 | ttaaaacagcctgtgggttgcacccactcacagggcccactgggcgcaagcactctggcacttcg<br>gtacctttgtgcgcctgttttatatcccctcccccaatgaaatttagaagcagcaaaccccgatcaata<br>gcaggcataacgctccagttatgtcttgatcaagcacttctgtttccccggactgagtatcaatagac<br>tgctcacgcggttgaaggagaaaacgttcgttatccggctaactacttcggaaagcctagtaacac<br>catggaagttgcggagagtttcgttcagcacttccccagtgtagatcaggtcgatgagtcaccgcat<br>tccccacgggcgaccgtggcggtggctgcgttggcggcctgcccatggggtaacccatgggac<br>gctctaatacggacatggtgtgaagagtctactgagctagttagtagtcctccggcccctgaatgcg<br>gctaatcccaactgcggagcacacgcccacaagccagtgggtagtgtgtcgtaacgggcaactct<br>gcagcggaaccgactactttgggtgtccgtgtttccttttattcttatgttggctgcttatggtgacaatt<br>aaagagttgttaccatatagctattggattggccatccggtgtgcaacagagcgatcgtttacctattt<br>attggttttgtaccattgacactgaagtctgtgatcacccttaattttatcttaaccctcaacacagccaa<br>ac |
| 70 | CVA3 | ttaaaacagcctgtgggttgtacccacccacagggcccactgggcgctagcacactggtattacg<br>gtacctttgtgcgcctgttttatacccccccaacctcgaaacttagaagtaaagcaaacccgatca<br>atagcaggtgcggcgcaccagtcgcatcttgatcaagcacttctgtaaccccggaccgagtatcaa<br>tagactgctcacgcggttgaaggagaaaacgttcgttacccggctaactacttcgagaaacccagt<br>agcatcatgaaagttgcagagtgtttcgctcagcactacccccgtgtagatcaggccgatgagtca<br>ccgcacttccccacgggcgaccgtggcggtggctgcgttggcggcctgcctatggggcaaccca<br>taggacgctctaatacggacatggtgcgaagagtctattgagctagttagtagtcctccggcccctg<br>aatgcggctaatcctaactgcggagcacatacccttaatccaaagggcagtgtgtcgtaacgggta<br>actctgcagcggaaccgactactttgggtgtccgtgtttccttttaattttactggctgcttatggtgac<br>aattgaggaattgttgccatatagctattggattggccatccggtgactaacagagctattgtgttcca<br>atttgttggatttaccccgctcacactcacagtcgtaagaacccttcattacgtgttatttctcaactcaa<br>gaaa |
| 71 | CVA12 | ttaaaacagcctgtgggttgtacccacccacagggcccactgggcgctagcactctggtactacg<br>gtacctttgtgtgcctgttttaagcccctacccccactcgtaacttagaaggcttctcacactcgatc<br>aatagtaggtgtggcacgccagtcacaccgtgatcaagcacttctgttaccccggtctgagtacca<br>ataagctgctaacgcggctgaaggggaaaacgatcgttatccggctaactacttcgagaaaccca<br>gtaccaccatgaacgttgcagggtgtttcgctcggcacaaccccagtgtagatcaggtcgatgagt<br>caccgtattccccacgggcgaccgtggcggtggctgcgttggcggcctgcccatggggtgaccc<br>atgggacgctctaatactgacatggtgcgaagagtctattgagctagttagtagtcctccggcccct<br>gaatgcggctaatcctaactgcggagcacatacccttaatccaaagggcagtgtgtcgtaacggg<br>caactctgcagcggaaccgactactttgggtgtccgtgtttccttttattcttacattggctgcttatggt<br>gacaattgaaaagttgttaccatatagctattggattggccatccggtgacaaatagagctattgtata<br>tctttttgttggttacgtaccccttaattacaaagtggtttcaactttgaaatacatcctaacactaaattg<br>tagaaa |
| 72 | EV24 | ttaaaacagcctgtgggttgcacccacccacagggcccacagggcgctagcactctggtatcacg<br>gtacctttgtgcgcctgttttattaccccttccccaattgaaaattagaagcaatgcacaccgatcaac<br>agcaggcgtggcgcaccagtcacgtctcgatcaagcacttctgtttccccggaccgagtatcaata<br>gactgctcacgcggttgaaggagaaagtgttcgttatccggctaaccacttcgagaaacccagtaa<br>caccatgaaagttgcagggtgtttcgctcagcacttccccagtgtagatcaggtcgatgagtcacc |

TABLE 17-continued

| IRES sequences. | | |
|---|---|---|
| SEQ ID NO | IRES | Sequence |
| | | gcgttccccacgggcgaccgtggcggtggctgcgttggcggcctgcctatgggttaacccatag<br>gacgctctaatacagacatggtgcgaagagtttattgagctggttagtatccctccggcccctgaat<br>gcggctaatcctaactgcggagcacgtgcctccaatccaggggggttgcatgtcgtaacgggtaac<br>tctgcagcggaaccgactactttgggtgtccgtgtttccttttattcttatactggctgcttatggtgaca<br>atcgaggaattgttaccatatagctattggattggccatccggtgtctaacagagcgattatatacctc<br>tttgttggatttatgcagctcaataccaccaactttaacacattgaaatatatcttaaagttaaacacag<br>caaa |
| 348 | AP1.0 | attctcgggctacggccctggagccactccggctcctaaagatttagaagtttgagcacacccgcc<br>cactagggcccccccatccagggggggcaacgggcaagcacttctgtttccccggtatgatctgata<br>ggctgtaaccacggctgaaacagagattatcgttatccgcttcactacttcgagaagcctagtaatg<br>atgggtgaaattgaatccgttgatccggtgtctcccccacaccagaaactcatgatgagggttgcca<br>tcccggctacggcgacgtagcgggcatccctgcgctggcatgaggcctcttaggaggacggatg<br>atatggatcttgtcgtgaagagcctattgagctagtgtcgactcctccgcccccgtgaatgcggcta<br>atcctaaccccggagcaggtgggtccaatccagggcctggcctgtcgtaatgcgtaagtctggga<br>cggaaccgactactttcgggaaggcgtgtttccatttgttcattatttgtgtgtttatggtgacaactctg<br>ggtaaacgttctattgcgtttattgagagattcccaacaattgaacaaacgagaactacctgttttatta<br>aatttacacagagaagaattaca |
| 349 | CK1.0 | gtggccacgcccgggccaccgatacttcccttcactccttcgggactgttggggaggaacacaac<br>agggctcccctgttttcccattccttccccctttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctactgctgacaactcactgactatccact<br>tgctctgTcacG |
| 350 | PV1.0 | aacaaaaggctacaccacttgggctacggcccgcgccaccttgtggcgcaaagacattagaaga<br>atagcataccgcccactagggccctgcagccagcagggtaacgggcaagcacttctgtctcccc<br>ggtagaacggtataggctgtacccacggccgaaaactgaactatcgttacccgactccgtacttcg<br>caaagcttagtaggaaactggaaagttcgagttattgacccggagtgttcccccactccagaaac<br>gcgtgatgagggttgccaccccgaccatggcgacatggtgggcatccctgcgctggcacgcgg<br>cctctaagaggataactcgctcctactggtaaccgaagagccccgtgagctacggtttattcctccg<br>cctccctgaatgcggctaatcctaacccatgagcagttgccatagatccatatggtggactgtcgta<br>acgcgtaagttgtgggcggaaccgactactttgggatggcgtgtttccttgttttctccatttgttgttgt<br>atggtgacaagttatagatctcgatctatagcgtttcttgagagatttccaaacatttattcaagtcgta<br>caattcttgtgtttaagcagtacagtgtaacc |
| 351 | SV1.0 | tctgtcctcaccccatcttcccttctttcctgcaccgttacgcttactcgcatgtgcattgagtggtgca<br>cgtgcttgaacaaacagctacactcacatgggggcgggttttcccgccctgcggcctctcgcgag<br>gcccacccctccccttcctcccataactacagtgctttggtaggtaagcatcctgatcccccgcgga<br>agctgctcacgtggcaactgtggggacccagacaggttatcaaaggcacccggtctttccgccttc<br>aggagtatccctgctagtgaattctagtagggctctgcttggtgccaacctcccccaaatgcgcgct<br>gcgggagtgctcttccccaactcaccctagtatcctctcatgtgtgtgcttggtcagcatatctgaga<br>cgatgttccgctgtcccagaccagtccagtaatggacgggccagtgtgcgtagtcgtcttccggctt<br>gtccggcgcatgtttggtgaaccggtggggtaaggttggtgtgcccaacgcccgtactttggtgat<br>acctcaagaccacccaggaatgccagggaggtaccccgcttcacagcgggatctgaccctggg<br>ctaattgtctacggtggttcttcttgcttccacttctttctactgttcgccacc |
| 352 | Caprine Kobuvirus 5Δ40 | gtggccacgcccgggccaccgatacttcccttcactccttcgggactgttggggaggaacacaac<br>agggctcccctgttttcccattccttccccctttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctactgctgacaactcactgactatc<br>cacttgctctcttgtgcctttctgctctggttcaagttccttgattgtttttgactgcttttcactgctt<br>ttcttctcacaatccttgctcagttcaaagtc |
| 353 | Caprine Kobuvirus 5Δ40/3Δ122 | gtggccacgcccgggccaccgatacttcccttcactccttcgggactgttggggaggaacacaac<br>agggctcccctgttttcccattccttccccctttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactaaagtc |

TABLE 17-continued

IRES sequences.

| SEQ ID NO | IRES | Sequence |
|---|---|---|
| 354 | Caprine Kobuvirus 5Δ40/3Δ86_ Distal | gtggccacgcccgggccaccgatacttcccttcactccttcgggactgttggggaggaacacaac<br>agggctcccctgttttcccattccttccccctttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgaccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttccttttttcttttcacacaactctactgctgacaactcactgactatccact<br>tgctctaaagtc |
| 355 | Caprine Kobuvirus 5Δ40/3Δ 122_Kozak | gtggccacgcccgggccaccgatacttcccttcactccttcgggactgttggggaggaacacaac<br>agggctcccctgttttcccattccttcccctttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttccttttttcttttcacacaactgccacc |
| 356 | Caprine Kobuvirus 5Δ440/3Δ86 Proximal | gtggccacgcccgggccaccgatacttcccttcactccttcgggactgttggggaggaacacaac<br>agggctcccctgttttcccattccttccccctttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcttggtaagtggggtgtgcccaatccctacaaaggttg<br>attctttcaccaccttaggaatgctccggaggtaccccagcaacagctgggatctgaccggaggct<br>aattgtctacgggtggtgtttccttttttcttttcacacaactttcactgcttttcttctcacaatccttgc<br>tcagttcaaagtc |
| 357 | Parabovirus | tgaaccgttacgcaccactcagttggtgtttggtggcaccaatgatggaacaaaaggctacaccac<br>ttgggctacggcccgcgccaccttgtggcgcaaagacattagaagaatagcataccgcccactag<br>ggccctgcagccagcagggtaacgggcaagcacttctgtctccccggtagaacggtataggctgt<br>acccacggccgaaaactgaactatcgttacccgactccgtacttcgcaaagcttagtaggaaactg<br>gaaagttcgagttattgacccggagtgttcccccactccagaaacgcgtgatgagggttgccacc<br>ccgaccatggcgacatggtgggcatccctgcgctggcacgcggcctctaagaggataactcgct<br>cctactggtaaccgaagagccccgtgagctacggtttattcctccgcctccctgaatgcggctaatc<br>ctaacccatgagcagttgccatagatccatatggtggactgtcgtaacgcgtaagttgtgggcgga<br>accgactactttgggatggcgtgtttccttgttttctccatttgttgttgtatggtgacaagttatagatct<br>cgatctatagcgtttcttgagagatttccaaacatttattcaagtcgtacaattcttgtgtttaagcagta<br>cagtgtaagg |
| 358 | Parabovirus 5Δ48 | aacaaaaggctacaccacttgggctacggcccgcgccaccttgtggcgcaaagacattagaaga<br>atagcataccgcccactagggccctgcagccagcagggtaacgggcaagcacttctgtctcccc<br>ggtagaacggtataggctgtacccacggccgaaaactgaactatcgttacccgactccgtacttcg<br>caaagcttagtaggaaactggaaagttcgagttattgacccggagtgttcccccactccagaaac<br>gcgtgatgagggttgccaccccgaccatggcgacatggtgggcatccctgcgctggcacgcgg<br>cctctaagaggataactcgctcctactggtaaccgaagagccccgtgagctacggtttattcctccg<br>cctccctgaatgcggctaatcctaacccatgagcagttgccatagatccatatggtggactgtcgta<br>acgcgtaagttgtgggcggaaccgactactttgggatggcgtgtttccttgttttctccatttgttgttgt<br>atggtgacaagttatagatctcgatctatagcgtttcttgagagatttccaaacatttattcaagtcgta<br>caattcttgtgtttaagcagtacagtgtaagg |
| 359 | Parabovirus 5Δ67 | tgggctacggcccgcgccaccttgtggcgcaaagacattagaagaatagcataccgcccactag<br>ggccctgcagccagcagggtaacgggcaagcacttctgtctccccggtagaacggtataggctgt<br>acccacggccgaaaactgaactatcgttacccgactccgtacttcgcaaagcttagtaggaaactg<br>gaaagttcgagttattgacccggagtgttcccccactccagaaacgcgtgatgagggttgccacc<br>ccgaccatggcgacatggtgggcatccctgcgctggcacgcggcctctaagaggataactcgct<br>cctactggtaaccgaagagccccgtgagctacggtttattcctccgcctccctgaatgcggctaatc<br>ctaacccatgagcagttgccatagatccatatggtggactgtcgtaacgcgtaagttgtgggcgga<br>accgactactttgggatggcgtgtttccttgttttctccatttgttgttgtatggtgacaagttatagatct<br>cgatctatagcgtttcttgagagatttccaaacatttattcaagtcgtacaattcttgtgtttaagcagta<br>cagtgtaagg |
| 360 | Parabovirus 3Δ60 | tgaaccgttacgcaccactcagttggtgtttggtggcaccaatgatggaacaaaaggctacaccac<br>ttgggctacggcccgcgccaccttgtggcgcaaagacattagaagaatagcataccgcccactag<br>ggccctgcagccagcagggtaacgggcaagcacttctgtctccccggtagaacggtataggctgt<br>acccacggccgaaaactgaactatcgttacccgactccgtacttcgcaaagcttagtaggaaactg<br>gaaagttcgagttattgacccggagtgttcccccactccagaaacgcgtgatgagggttgccacc<br>ccgaccatggcgacatggtgggcatccctgcgctggcacgcggcctctaagaggataactcgct<br>cctactggtaaccgaagagccccgtgagctacggtttattcctccgcctccctgaatgcggctaatc<br>ctaacccatgagcagttgccatagatccatatggtggactgtcgtaacgcgtaagttgtgggcgga<br>accgactactttgggatggcgtgtttccttgttttctccatttgttgttgtatggtgacaagttatagatct<br>cgatctatagcgtttgtaagg |

TABLE 17-continued

| IRES sequences. | | |
|---|---|---|
| SEQ ID NO | IRES | Sequence |
| 361 | Apodemus Picornavirus | tttgaaaggggtgcggatatcatggcgtttctcgccatgatatccgcacattgcaaacccatattgca<br>tacccactgggtatgcattatggggaggcccctttcacccctcccccccaattaccttttcccccctct<br>agtaaccatacgctttactcagcgtaactactccgggttacgtgatgaagaagaggctacggagatt<br>ctcgggctacggccctggagccactccggctcctaaagatttagaagtttgagcacacccgccca<br>ctagggcccccatccagggggggcaacgggcaagcacttctgtttccccggtatgatctgatagg<br>ctgtaaccacggctgaaacagagattatcgttatccgcttcactacttcgagaagcctagtaatgatg<br>ggtgaaattgaatccgttgatccggtgtctcccccacaccagaaactcatgatgagggttgccatcc<br>cggctacggcgacgtagcgggcatccctgcgctggcatgaggcctcttaggaggacggatgata<br>tggatcttgtcgtgaagagcctattgagctagtgtcgactcctccgcccccgtgaatgcggctaatc<br>ctaaccccggagcaggtgggtccaatccagggcctggcctgtcgtaatgcgtaagtctgggacg<br>gaaccgactactttcgggaaggcgtgtttccatttgttcattatttgtgtgtttatggtgacaactctgg<br>gtaaacgttctattgcgtttattgagagattcccaacaattgaacaaacgagaactacctgttttattaa<br>atttacacagagaagaattaca |
| 362 | Apodemus Picornavirus 5Δ105 | cccctcccccccccaattaccttttcccccctctagtaaccatacgctttactcagcgtaactactccggg<br>ttacgtgatgaagaagaggctacggagattctcgggctacggccctggagccactccggctccta<br>aagatttagaagtttgagcacacccgcccactagggcccccatccagggggggcaacgggcaa<br>gcacttctgtttccccggtatgatctgataggctgtaaccacggctgaaacagagattatcgttatcc<br>gcttcactacttcgagaagcctagtaatgatgggtgaaattgaatccgttgatccggtgtctcccca<br>caccagaaactcatgatgagggttgccatcccggctacggcgacgtagcgggcatccctgcgct<br>ggcatgaggcctcttaggaggacggatgatatggatcttgtcgtgaagagcctattgagctagtgtc<br>gactcctccgcccccgtgaatgcggctaatcctaaccccggagcaggtgggtccaatccagggc<br>ctggcctgtcgtaatgcgtaagtctgggacggaaccgactactttcgggaaggcgtgtttccatttgt<br>tcattatttgtgtgtttatggtgacaactctgggtaaacgttctattgcgtttattgagagattcccaaca<br>attgaacaaacgagaactacctgttttattaaatttacacagagaagaattaca |
| 363 | Apodemus Picornavirus 5Δ201 | attctcgggctacggccctggagccactccggctcctaaagatttagaagtttgagcacacccgcc<br>cactagggcccccatccagggggggcaacgggcaagcacttctgtttccccggtatgatctgata<br>ggctgtaaccacggctgaaacagagattatcgttatccgcttcactacttcgagaagcctagtaatg<br>atgggtgaaattgaatccgttgatccggtgtctcccccacaccagaaactcatgatgagggttgcca<br>tcccggctacggcgacgtagcgggcatccctgcgctggcatgaggcctcttaggaggacggatg<br>atatggatcttgtcgtgaagagcctattgagctagtgtcgactcctccgcccccgtgaatgcggcta<br>atcctaaccccggagcaggtgggtccaatccagggcctggcctgtcgtaatgcgtaagtctggga<br>cggaaccgactactttcgggaaggcgtgtttccatttgttcattatttgtgtgtttatggtgacaactctg<br>ggtaaacgttctattgcgtttattgagagattcccaacaattgaacaaacgagaactacctgttttatta<br>aatttacacagagaagaattaca |
| 364 | Kobuvirus SZAL6 | ttcacaccctctttccggtggtccggacccagaccaccgttactccattcagctacttcggtacctg<br>ttcggaggaattaaacgggcaccctacccaagggttacatgggaccatattcctcctcccctgtaac<br>tttaagtttgtgcccgtattcttgactccaggcggatgttgtgtcgcccgtcctgtgaacaaacagct<br>agacactttcctcccctccctctgggctgctccggcagtccactccctcccccccagcgtaacatgcc<br>ccgctggagtgatgcacctggaagtcgtggacgtgggttagtaacttcggtgaaaacccactataa<br>tgacaactggttgacccccacactcaaaggactcgagtctttctcccttaaggctagcccggccac<br>atgaatttgcagctggcaactagtgagtccaccatgtcccgcaacctcggctgcggagtgctgttc<br>cccaagcgtatgccttccttctgtaagagtgcgcctggcaagcacatctgagaagtcgttccgctgc<br>gtcgtgccaacctggcgacaggtgacccagtgtgcgtagacttcttccggattcgtccggctcttct<br>ctaggaaacatgcgtgtaaggttcatgtgccaaagccctgcgcgcggtgttcttctactgccctagg<br>aatgtgccgcaggtacccctacttcggtagggatctgagcggtagctaattgtctacgggtagtttc<br>atttccatcttctcttcaggtcgacatc |
| 365 | Kobuvirus SZAL6 5Δ158 | ttgactccaggcggatgttgtgtcgcccgtcctgtgaacaaacagctagacactttcctcccctccct<br>ctgggctgctccggcagtccactccctcccccccagcgtaacatgccccgctggagtgatgcacct<br>ggaagtcgtggacgtgggttagtaacttcggtgaaaacccactataatgacaactggttgaccccc<br>acactcaaaggactcgagtctttctcccttaaggctagcccggccacatgaatttgcagctggcaac<br>tagtgagtccaccatgtcccgcaacctcggctgcggagtgctgttccccaagcgtatgccttccttc<br>tgtaagagtgcgcctggcaagcacatctgagaagtcgttccgctgcgtcgtgccaacctggcgac<br>aggtgacccagtgtgcgtagacttcttccggattcgtccggctcttctctaggaaacatgcgtgtaa<br>ggttcatgtgccaaagccctgcgcgcggtgttcttctactgccctaggaatgtgccgcaggtaccc<br>ctacttcggtagggatctgagcggtagctaattgtctacgggtagtttcatttccatcttctcttcaggt<br>cgacatc |
| 366 | Kobuvirus SZAL6 5Δ76 | gaattaaacgggcaccctacccaagggttacatgggaccatattcctcctcccctgtaactttaagtt<br>ttgtgcccgtattcttgactccaggcggatgttgtgtcgcccgtcctgtgaacaaacagctagacact<br>ttcctcccctccctctgggctgctccggcagtccactccctcccccccagcgtaacatgccccgctg<br>gagtgatgcacctggaagtcgtggacgtgggttagtaacttcggtgaaaacccactataatgacaa<br>ctggttgacccccacactcaaaggactcgagtctttctcccttaaggctagcccggccacatgaatt<br>tgcagctggcaactagtgagtccaccatgtcccgcaacctcggctgcggagtgctgttccccaag<br>cgtatgccttccttctgtaagagtgcgcctggcaagcacatctgagaagtcgttccgctgcgtcgtg<br>ccaacctggcgacaggtgacccagtgtgtgtagacttcttccggattcgtccggctcttctctagga<br>aacatgcgtgtaaggttcatgtgccaaagccctgcgcgcggtgttcttctactgccctaggaatgtg<br>ccgcaggtacccctacttcggtagggatctgagcggtagctaattgtctacgggtagtttcatttcca<br>tcttctcttcaggtcgacatc |

TABLE 17-continued

IRES sequences.

| SEQ ID NO | IRES | Sequence |
| --- | --- | --- |
| 367 | Kobuvirus SZAL6 3Δ37 | tttcacaccctcttttccggtggtccggacccagaccaccgttactccattcagctacttcggtacctg<br>ttcggaggaattaaacgggcaccctacccaagggttacatgggaccatattcctcctcccctgtaac<br>tttaagttttgtgcccgtattcttgactccaggcggatgttgtgtcgcccgtcctgtgaacaaacagct<br>agacactttcctcccctccctctgggctgctccggcagtccactccctccccccagcgtaacatgcc<br>ccgctggagtgatgcacctggaagtcgtggacgtgggttagtaacttcggtgaaaacccactataa<br>tgacaactggttgacccccacactcaaaggactcgagtctttctcccttaaggctagcccggccac<br>atgaatttgcagctggcaactagtgagtccaccatgtcccgcaacctcggctgcggagtgctgttc<br>cccaagcgtatgccttccttctgtaagagtgcgcctggcaagcacatctgagaagtcgttccgctgc<br>gtcgtgccaacctggcgacaggtgacccagtgtgcgtagacttcttccggattcgtccggctcttct<br>ctaggaaacatgcgtgtaaggttcatgtgccaaagccctgcgcgcggtgttcttctactgccctagg<br>aatgtgccgcaggtacccctacttcggtagggatctgagcggtagctaattggacatc |
| 368 | Salivirus SZ1 | tctgtcctcaccccatcttcccttctttcctgcaccgttacgcttactcgcatgtgcattgagtggtgca<br>cgtgcttgaacaaacagctacactcacatgggggcgggttttcccgccctgcggcctctcgcgag<br>gcccacccctccccttcctcccataactacagtgctttggtaggtaagcatcctgatcccccgcgga<br>agctgctcacgtggcaactgtggggacccagacaggttatcaaaggcacccggtctttccgccttc<br>aggagtatccctgctagtgaattctagtagggctctgcttggtgccaacctcccccaaatgcgcgct<br>gcgggagtgctcttccccaactcaccctagtatcctctcatgtgtgtgcttggtcagcatatctgaga<br>cgatgttccgctgtcccagaccagtccagtaatggacgggccagtgtgcgtagtcgtcttccggctt<br>gtccggcgcatgtttggtgaaccggtggggtaaggttggtgtgcccaacgcccgtactttggtgat<br>acctcaagaccacccaggaatgccagggaggtaccccgcttcacagcgggatctgaccctggg<br>ctaattgtctacggtggttcttcttgcttccacttctttctactgttcatg |
| 369 | Crohivirus B | gtataagagacaggtgtttgccttgtcttcggactggcatcttgggaccaaccccccttttccccagc<br>catgggttaaatggcaataaaggacgtaacaactttgtaaccattaagctttgtaattttgtaaccact<br>aagctttgtgcacataatgtaaccatcaagcttgttagtcccagcaggaggtttgcatgcttgtagcc<br>gaaatggggctcgacccccccatagtaggatacttgattttgcattccattgtggacctgcaaactcta<br>cacatagaggctttgtcttgcatctaaacacctgagtacagtgtgtacctagaccctatagtacggga<br>ggaccgtttgtttcctcaataaccctacataataggctaggtgggcatgcccaatttgcaagatccca<br>gactgggggtcggtctgggcagggttagatccctgttagctactgcctgatagggtggtgctcaac<br>catgtgtagtttaaattgagctgttcatatacc |
| 370 | Crohivirus B 5Δ51 | ccccccttttccccagccatgggttaaatggcaataaaggacgtaacaactttgtaaccattaagctt<br>tgtaattttgtaaccactaagctttgtgcacataatgtaaccatcaagcttgttagtcccagcaggagg<br>tttgcatgcttgtagccgaaatggggctcgacccccccatagtaggatacttgattttgcattccattgt<br>ggacctgcaaactctacacatagaggctttgtcttgcatctaaacacctgagtacagtgtgtacctag<br>accctatagtacgggaggaccgtttgtttcctcaataaccctacataataggctaggtgggcatgcc<br>caatttgcaagatcccagactgggggtcggtctgggcagggttagatccctgttagctactgcctg<br>atagggtggtgctcaaccatgtgtagtttaaattgagctgttcatatacc |
| 371 | CVB3 | ttaaaacagcctgtgggttgatcccacccacagggcccattgggcgctagcactctggtatcacgg<br>tacctttgtgcgcctgttttataccccctcccccaactgtaacttagaagtaacacacaccgatcaac<br>agtcagcgtggcacaccagccacgttttgatcaagcacttctgttaccccggactgagtatcaatag<br>actgctcacgcggttgaaggagaaagcgttcgttatccggccaactacttcgaaaaacctagtaac<br>accgtggaagttgcagagtgtttcgctcagcactaccccagtgtagatcaggtcgatgagtcaccg<br>cattccccacgggcgaccgtggcggtggctgcgttggcggcctgcccatggggaaacccatgg<br>gacgctctaatacagacatggtgcgaagagtctattgagctagaggtagtcctccggcccctgaat<br>gcggctaatcctaactgcggagcacacaccctcaagccagagggcagtgtgtcgtaacgggcaa<br>ctctgcagcggaaccgactactttgggtgtccgtgtttcattttaacctatactggctgcttatggtga<br>caattgagagattgttaccatatagctattggattggccatccggtgaccaatagagctattatatatct<br>ctttgttgggtttataccacttagcttgaaagaggttaaaacattacaattcattgttaagttgaatacag<br>caaa |
| 372 | CVB3 3Δ91 | ttaaaacagcctgtgggttgatcccacccacagggcccattgggcgctagcactctggtatcacgg<br>tacctttgtgcgcctgttttataccccctcccccaactgtaacttagaagtaacacacaccgatcaac<br>agtcagcgtggcacaccagccacgttttgatcaagcacttctgttaccccggactgagtatcaatag<br>actgctcacgcggttgaaggagaaagcgttcgttatccggccaactacttcgaaaaacctagtaac<br>accgtggaagttgcagagtgtttcgctcagcactaccccagtgtagatcaggtcgatgagtcaccg<br>cattccccacgggcgaccgtggcggtggctgcgttggcggcctgcccatggggaaacccatgg<br>gacgctctaatacagacatggtgcgaagagtctattgagctagttggtagtcctccggcccctgaat<br>gcggctaatcctaactgcggagcacacaccctcaagccagagggcagtgtgtcgtaacgggcaa<br>ctctgcagcggaaccgactactttgggtgtccgtgtttcattttattcctatactggctgcttatggtga<br>caattgagagattgttaccatatagctattggattggccatccggtgaagcaaa |
| 373 | SAFV | cacttatttaattcggccttttgtgacaagcccctcggtgaaagaacctctctcttttcgacgtggttgg<br>aattgccatcatttccgacgaaagtgctatcatgcctccccgattatgtgatgttttctgccctgctgg<br>gcggagcattctcgggttgagaaaccttgaatctttttctttggaaccttggttcccccggtctaagcc<br>gcttggaatatgacagggttattttcttgatcttatttctacttttgcgggttctatccgtaaaaagggtac<br>gtgctgccccttccttctctggagaattcacacggcggtctttccgtctctcaacaagtgtgaatgca<br>gcatgccggaaacggtgaagaaaacagttttctgtggaaatttagagtgcacatcgaaacagctgt<br>agcgacctcacagtagcagcggactcccctcttggcgacaagagcctctgcggccaaaagcccc<br>gtggataagatccactgctgtgagcggtgcaaccccagcaccctggttcgatgatcattctctatgg |

TABLE 17-continued

IRES sequences.

| SEQ ID NO | IRES | Sequence |
|---|---|---|
| | | aaccagaaaatggttttctcaagccctccggtagagaagccaagaatgtcctgaaggtaccccgc<br>gtgcgggatctgatcaggagaccaattggcggtgctttacactgtcactttggtttaaaaattgtcac<br>agcttctccaaaccaagtggtcttggttttccaattttgttga |
| 374 | SAFV 5Δ46 | cctctctcttttcgacgtggttggaattgccatcatttccgacgaaagtgctatcatgcctccccgatta<br>tgtgatgttttctgccctgctgggcggagcattctcgggttgagaaaccttgaatctttttctttggaac<br>cttggttcccccggtctaagccgcttggaatatgacagggttattttcttgatcttatttctacttttgcgg<br>gttctatccgtaaaaagggtacgtgctgccccttccttctctggagaattcacacggcggtctttccgt<br>ctctcaacaagtgtgaatgcagcatgccggaaacggtgaagaaaacagttttctgtggaaatttaga<br>gtgcacatcgaaacagctgtagcgacctcacagtagcagcggactcccctcttggcgacaagag<br>cctctgcggccaaaagccccgtggataagatccactgctgtgagcggtgcaaccccagcaccct<br>ggttcgatgatcattctctatggaaccagaaaatggttttctcaagccctccggtagagaagccaag<br>aatgtcctgaaggtaccccgcgtgcgggatctgatcaggagaccaattggcggtgctttacactgt<br>cactttggtttaaaaattgtcacagcttctccaaaccaagtggtcttggttttccaattttgttga |
| 375 | SAFV 5Δ93 | gtgctatcatgcctccccgattatgtgatgttttctgccctgctgggcggagcattctcgggttgaga<br>aaccttgaatctttttctttggaaccttggttcccccggtctaagccgcttggaatatgacagggttattt<br>tcttgatcttatttctacttttgcgggttctatccgtaaaaagggtacgtgctgccccttccttctctgga<br>gaattcacacggcggtctttccgtctctcaacaagtgtgaatgcagcatgccggaaacggtgaaga<br>aaacagttttctgtggaaatttagagtgcacatcgaaacagctgtagcgacctcacagtagcagcg<br>gactcccctcttggcgacaagagcctctgcggccaaaagccccgtggataagatccactgctgtg<br>agcggtgcaaccccagcaccctggttcgatgatcattctctatggaaccagaaaatggttttctcaa<br>gccctccggtagagaagccaagaatgtcctgaaggtaccccgcgtgcgggatctgatcaggaga<br>ccaattggcggtgctttacactgtcactttggtttaaaaattgtcacagcttctccaaaccaagtggtct<br>tggttttccaattttgttga |
| 376 | SAFV 3Δ47 | cacttatttaattcggccttttgtgacaagcccctcggtgaaagaacctctctcttttcgacgtggttgg<br>aattgccatcatttccgacgaaagtgctatcatgcctccccgattatgtgatgttttctgccctgctgg<br>gcggagcattctcgggttgagaaaccttgaatctttttctttggaaccttggttcccccggtctaagcc<br>gcttggaatatgacagggttattttcttgatcttatttctacttttgcgggttctatccgtaaaaagggtac<br>gtgctgccccttccttctctggagaattcacacggcggtctttccgtctctcaacaagtgtgaatgca<br>gcatgccggaaacggtgaagaaaacagttttctgtggaaatttagagtgcacatcgaaacagctgt<br>agcgacctcacagtagcagcggactcccctcttggcgacaagagcctctgcggccaaaagcccc<br>gtggataagatccactgctgtgagcggtgcaaccccagcaccctggttcgatgatcattctctatgg<br>aaccagaaaatggttttctcaagccctccggtagagaagccaagaatgtcctgaaggtaccccgc<br>gtgcgggatctgatcaggagaccaattggcggtgctttacactgtcactttggtttaatgttga |
| 377 | SAFV Kozak | cacttatttaattcggccttttgtgacaagcccctcggtgaaagaacctctctcttttcgacgtggttgg<br>aattgccatcatttccgacgaaagtgctatcatgcctccccgattatgtgatgttttctgccctgctgg<br>gcggagcattctcgggttgagaaaccttgaatatttctttggaaccttggttcccccggtctaagcc<br>gcttggaatatgacagggttattttcttgatcttatttctacttttgcgggttctatccgtaaaaagggtac<br>gtgctgccccttccttctctggagaattcacacggcggtctttccgtctctcaacaagtgtgaatgca<br>gcatgccggaaacggtgaagaaaacagttttctgtggaaatttagagtgcacatcgaaacagctgt<br>agcgacctcacagtagcagcggactcccctcttggcgacaagagcctctgcggccaaaagcccc<br>gtggataagatccactgctgtgagcggtgcaaccccagcaccctggttcgatgatcattctctatgg<br>aaccagaaaatggttttctcaagccctccggtagagaagccaagaatgtcctgaaggtaccccgc<br>gtgcgggatctgatcaggagaccaattggcggtgctttacactgtcactttggtttaaaaattgtcac<br>agcttctccaaaccaagtggtcttggttttccaattttgttgaccgcc |
| 378 | GLuc CK dCTG1 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTctgacaactcactgactatcca<br>cttgctctaaagtc |
| 379 | GLuc CK dCTG1_2 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTcGTacaactcactgactatcc<br>acttgctctaaagtc |
| 380 | GLuc CK dCTG1_2_3 | gtggccacgcccgggccaccgatacttcccttcactccttcgggactgttggggaggaacacaac<br>agggctcccctgttttcccctttccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc |

TABLE 17-continued

IRES sequences.

| SEQ ID NO | IRES | Sequence |
| --- | --- | --- |
| | | ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTcGTacaactcacGTactat<br>ccacttgctctaaagtc |
| 381 | GLuc CK dAll | gtggccacgcccgggccaccgatacttcccttcactccttcgggactgttggggaggaacacaac<br>agggctcccctgttttcccattccttccccctttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctcGTcGTacaactcacGTactaC<br>TcactGTctctaaagtc |
| 382 | CK SZ1-L1S | gggggtggggggggcctcggcccccctcaccctcttttccggtggccacgcccgggccaccgat<br>acttcccttcactccttcgggactgttggggaggaacacaacagggctcccctgttttcccattcctt<br>ccccctttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgtcttccaggtcctcctggttggcgttgtccagaa<br>ctgcttcaggtaagtggggtgtgcccaatccctacaaaggttgaaccacccaggaatgccaggga<br>ggtaccccgcttcacagcgggatctgaccctgggctaattgtctacggtggttcttcttgcttccactt<br>ctttctactgttcgccacc |
| 383 | CK Aichi Scan (AV-S) | gggggtggggggggcctcggcccccctcaccctcttttccggtggccacgcccgggccaccgat<br>acttcccttcactccttcgggactgttggggaggaacacaacagggctcccctgttttcccattcctt<br>ccccctttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgtcttccaggtcctcctggttggcgttgtccagaa<br>ctgcttcaggtaagtggggtgtgcccaatccctacaaaggttgattctttcaccaccttaggaatgct<br>ccggaggtaccccagcaacagctgggatctgaccggaggctaattgtctacgggtggtgtttcatt<br>tccaatccttttatgtcggagtc |
| 384 | CK Aichi Loop (AV-L1) | gggggtggggggggcctcggcccccctcaccctcttttccggtggccacgcccgggccaccgat<br>acttcccttcactccttcgggactgttggggaggaacacaacagggctcccctgttttcccattcctt<br>ccccctttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgtcttccaggtcctcctggttggcgttgtccagaa<br>ctgcttcaggtaagtggggtgtgcccaatccctacaaaggttgaactgccctaggaatgccaggca<br>ggtaccccacctccgggtgggatctgagcctgggctaattgtctacgggtagtttcctttttcttttca<br>cacaactctactgctgacaactcactgactatccacttgctctcttgtgcctttctgctctggttcaagtt<br>ccttgattgtttttgactgcttttcactgcttttcttctcacaatccttgctcagttcaaagtc |
| 385 | CK SZ1-L2 | gggggtggggggggcctcggcccccctcaccctcttttccggtggccacgcccgggccaccgat<br>acttcccttcactccttcgggactgttggggaggaacacaacagggctcccctgttttcccattcctt<br>ccccctttcccaaccccaaccgccgtatctggtggcggcaagacacacgggtctttccctctaaa<br>aagcctgtccaacgcctgatcccccgcggaagctgctcacgtggcaactgtggggacccagaca<br>ggttatcaaaggcacccggtctttccgccttcaggagtatccctgctagtgaattctagtagggctct<br>gcttgcgttgtccagaaactgcttcaggtaagtggggtgtgcccaatccctacaaaggttgattcttt<br>caccaccttaggaatgctccggaggtaccccagcaacagctgggatctgaccggaggctaattgt<br>ctacgggtggtgtttcctttttcttttcacacaactctactgctgacaactcactgactatccacttgctc<br>tcttgtgcctttctgctctggttcaagttccttgattgtttttgactgcttttcactgctttcttctcaca<br>atccttgctcagttcaaagtc |
| 386 | CK Aichi TriLoop (AV-L2) | gggggtggggggggcctcggcccccctcaccctcttttccggtggccacgcccgggccaccgat<br>acttcccttcactccttcgggactgttggggaggaacacaacagggctcccctgttttcccattcctt<br>ccccctttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcatgtgcctggcaagcatatctgagaaggtgttccgctgtggctgccaacct<br>ggtgacaggtgccccagtgtgcgtaaccttcttccgtctccggacggtgcgttgtccagaaactgct<br>tcaggtaagtggggtgtgcccaatccctacaaaggttgattctttcaccaccttaggaatgctccgg<br>aggtaccccagcaacagctgggatctgaccggaggctaattgtctacgggtggtgtttcctttttcttt<br>tcacacaactctactgctgacaactcactgactatccacttgctctcttgtgcctttctgctctggttcaa<br>gttccttgattgtttttgactgcttttcactgcttttcttctcacaatccttgctcagttcaaagtc |
| 387 | CK Scan Deletion (ΔS) | gggggtggggggggcctcggcccccctcaccctcttttccggtggccacgcccgggccaccgat<br>acttcccttcactccttcgggactgttggggaggaacacaacagggctcccctgttttcccattcctt<br>ccccctttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgatcttccaggtcctcctggttggcgttgtccagaaa |

TABLE 17-continued

IRES sequences.

| SEQ ID NO | IRES | Sequence |
|---|---|---|
| | | ctgcttcaggtaagtggggtgtgcccaatccctacaaaggttgattctttcaccaccttaggaatgct<br>ccggaggtaccccagcaacagctgggatctgaccggaggctaattgtctacgggtggtg |
| 388 | CK Loop Deletion (ΔL1) | gggggtgggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgatcttccaggtcctcctggttggcgttgtccagaaa<br>ctgcttcaggtaagtggggtgtgcccaatccctacaaaggttgatttcctttttcttttcacacaactct<br>actgctgacaactcactgactatccacttgctctcttgtgcctttctgctctggttcaagttccttgattgt<br>tttgactgcttttcactgcttttcttctcacaatccttgctcagttcaaagtc |
| 389 | CK Triloop Deletion (ΔL2) | gggggtgggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgcgttgtccagaaactgcttcaggtaagtggggtgtgcccaatccctacaa<br>aggttgattctttcaccaccttaggaatgctccggaggtaccccagcaacagctgggatctgaccg<br>gaggctaattgtctacgggtggtgtttcctttttcttttcacacaactctactgctgacaactcactgact<br>atccacttgctctcttgtgcctttctgctctggttcaagttccttgattgtttttgactgcttttcactgc<br>ttttcttctcacaatccttgctcagttcaaagtc |
| 413 | RhPV | gataaaagaacctataatcccttcgcacaccgcgtcacaccgcgctatatgctgctcattaggaatt<br>acggctcctttttttgtggatacaatctcttgtatacgatatacttattgttaatttcattgacctttacgcaa<br>tcctgcgtaaatgctggtatagggtgtacttcggatttccgagcctatattggttttgaaaggaccttta<br>agtccctactatactacattgtactagcgtaggccacgtaggcccgtaagatattataactattttatta<br>tattttattcacccccccacattaatcccagaaaagctttataactataagtaagccgtgccgaaacgtt<br>aatcggtcgctagttgcgtaacaactgttagtttaattttccaaaaattatttttcacaatttttagttaaga<br>ttttagcttgccttaagcagtctttatatcttctgtatattattttaaagtttatag-<br>gagcaaagttcgcttta<br>ctcgcaatagctattttatttattttaggaatattatcacctcgtaattatttaattataacattagcttta<br>tctatttata |
| 414 | Halastaviarva (1x mut) | cttgattctaaccttgccgtatggtgccctaacgggttcatttaatcatgcgatgagggttgctatacc<br>gcatccattctaaggcgattcaatgcttcatttaggaattagttgacgattaaaaggtacccccacaa<br>aaacaaaaccaatcttacttgatttcgttttaactgaccactgcgatcccaaattttcgccttcttatca<br>aagtatgttgtgttctttgggtgtacaacctgagaacttgtctacaactacatattactcgaggaagaa<br>attcggtttaagccgtgccttctcacgtttagtatatctatctGgacacaccttcttcatcttctaatccc<br>catctagtctcctgatcagagacgtcgttattaacaaataaccccccttgttaataagagacaaagta<br>caatcaagctaagttctcttggagttcctgtaggaacttagccattgtgatagagtcataagtctatgt<br>gcatagacagctctagctcaccatttccttcccaacccatcttttcatcagcttaactctatgaatccga<br>tgcaaaaaccattctaacatcttatggtgctttccaagccaaatgagagctcactcttttgagccgcta<br>tttaatggacaataaacgttttatagtgtacatcatattgtaaaaacaaa |
| 415 | Oscivirus | cctcggtccctctttccgtcgccgcccacgacgttaaatgcggtgttgtggtgcttaggtgccacac<br>cactgctatttgggtccccctttcccctatatatgtttgtttgtttatttcaatttcttgaggattggcac<br>ctccttatgccaaatctaaatcgtggaggatcccaggctttctggtctttaacagaactccacgtccaggt<br>catagaaactggttggtaggctgcctgagtagtccatttgctagtagtcccttgtgaacagggtggct<br>cccgtttactgctggtattcccggtgtaggtcgccatggtggtaacaccatcctgcattgtgtgtgaa<br>ccagtaccgcaaggatagcaaggtatgaacacttgtggacgaaatggtaagtgatcaattcactttc<br>atggccggaaggtcacgtggcaatcatgccacccaggtaccctcctcgggaggatctgagggt<br>gggctaagcagaccctgccatgtggctgaacttttcccttattgttttactttgtaacatttatagttgtgt<br>tagtgatttgtgtgttgtgcccttgtgagctatatccagtataagttcgcagctagaagttaatccttcg<br>acatcggctgtattggaa |
| 416 | Cadicivirus B | caccaaccccttgacctgtaatgtcagtggacagagtgctcctctgttcccggttaccgtgttccagg<br>acacgattgtaatcctgcgcctcaccagcgctgcgtgcacgtctgcataaggaaacgtgccttccc<br>catgtctctatcaattctttggtgagtgaccgccctagttgctcatcctatgggattcttctctcatgggt<br>tctttgtggcatgcgaatgtcaccttaattggaggtctttaattagatatcctttcttcatctttgatatg<br>agtgtcggaatttgattcctagtctctgcaaaacaaccccacttgatgaattcaacttttcaaccgcacaa<br>acataatcaggtttttaaattgaatgtttctaaattctaaatttagtttatttaagtagtttgccatcttga<br>ctcgatgtaaaattgtcatacaagtcttcttttcttttcttttacactttgaagtttgcacttagcagtcgttc<br>tgcacagctttcgagttttgtttgatcgacatcgcaacttccacccacctctctttttctagtgttgaatgcg<br>gctaatcctaacccgagagcaataaacccaggtttattgtcgtaacgcgcaagtcttggacggaac<br>cgactatacacacacctctttaccctttagtacacccttggtacg |
| 417 | PSIV (2x mut for XbaI) | gcaaaatgggtacgtagttaaccactgcgtatcaggattgcaggccacgaagggtatttgcatatct<br>ttctatgcggtattacggcttaaaacccgttgtatcttgtTgtttgactgcctgtatcactagtggccatt<br>ttatttaggttagagacccctgatagtaggagagttacaaactctttaaaaattgttgaccccggaaa<br>agatggtgacccctgtaagtagttgatcAagaagatctatgcgctggcatagtaatccagtgtttcc<br>tgttttaggatgacctctgaaagtagatgaccgtggaaagtcacgtagtgccccaatagcacgttt<br>gggcagcgtgcgctatcacaaggcttgatctccgaggagccccttgttttagctggctggaagcca |

TABLE 17-continued

IRES sequences.

| SEQ ID NO | IRES | Sequence |
|---|---|---|
| | | atgatcttaagtagataagtgctgttgcttgtagttcaacagaaagctttgagtacgtctttcttgcgag aaagaacacatgcattcttatgctctcaattctattatttttattttgggcgaaaggaaagctctcacgc gagtacgaatagccaacccttttat |
| 418 | PSIV IGR | GCTGACTATGTGATCTTATTAAAATTAGGTTAAATTTCGAG GTTAAAAATAGTTTTAATATTGCTATAGTCTTAGAGGTCTT GTATATTTATACTTACCACACAAGATGGACCGGAGCAGCCC TCCAATATCTAGTGTACCCTCG |
| 419 | PV Mahoney | ATGAGTCTGGACATCCCTCACCGGTGACGGTGGTCCAGGCT GCGTTGGCGGCCTACCTATGGCTAACGCCATGGGACGCTAG TTGTGAACAAGGTGTGAAGAGCCTATTGAGCTACATAAGA ATCCTCCGGCCCCTGAATGCGGCTAATCCCAACCTCGGAGC AGGTGGTCACAAACCAGTGATTGGCCTGTCGTAACGCGCA AGTCCGTGGCGGAACCGACTACTTTGGGTGTCCGTGTTTCC TTTTATTTTATTGTGGCTGCTTATGGTGACAATCACAGATTG TTATCATAAAGCGAATTGGATTGGCC |
| 420 | REV A | GGGGTCGCCGTCCTACACATTGTTGTGACGTGCGGCCCAGA TTCGAATCTGTAATAAAAGCTTTTTCTTCTATATCCTCAGAT TGGCAGTGAGAGGAGATTTTGTTCGTGGTGTTGGCTGGCCT ACTGGGTGGGGTAGGGATCCGGACTGAATCCGTAGTATTTC GGTACAACATTTGGGGGCTCGTCCGGGATTCCTCCCCATCG GCAGAGGTGCCTACTGTTTCTTCGAACTCCGGCGCCGGTAA GTAAGTACTTGATTTTGGTACCTCGCGAGGGTTTGGGAGGA TCGGAGTGGCGGGACGCTGCCGGGAAGCTCCACCTCCGCT CAGCAGGGGACGCCCTGGTCTGAGCTCTGTGGTATCTGATT GTTGTTGAACCGTCTCTAAGACGGTGATACTATAAGTCGTG GTTTGTGTGTTTGTTTGTTACCTTGTGTTTGTTCGTCACTTGT CGACAGCGCCCTGCGAATTGGTGTACCCACACCGCGCGGCT TGCGAATAATACTTTGGAGAGTCTTTTGCCTCCAGTGTCTTC CGTTTGTACTCGTCCTCCTCTCCCTCTCCGGCCGGGATGGG |
| 421 | Tropivirus A | tgtcgcatgttgccaacatcaaaattctgggagagtcgcgaactccttaacactgccttgcctcgac ggagccgttgttatagtgtcgacgggatacaaacattaaactaaacccacttgcctcgacggaacc ccttaccttttatttttttatatagtatgaaagtgaatcttgtatgaatgttcatagaaaactgcaaatgagt accacgtctaacatgagagaatgatactggagaaatccaagtttagaagtcactacgaatcccagc ggaaacaagggaattctgagcttctaataggcgtttaagactatttgcaaaattctggtgcgtaagtg atattttcattgcgtagaacgctggtaaccactccggctagtataagcattgttagtcacttattatgaa actccacactatcctttctggagaagcacacaaacttacatggtaaagctagaccattatcttaagcg gtgagtacactgcaaccttgtaacaatgcttgtatgactactttttgtatatcttgagcaatattgttgag gtggacatgtccaaaggtaatgttgttgggaatggaggggtccattttcccgtgcacgtagtgtact agtattgggtgatagccttgcggcggatcaaccatgtattttaatccgttgactttcac |
| 422 | Symapivirus A | ttgggaaatccccaatgcttctttcaacaccgcctgactatgcggtggcgcttcggctcaaacaact agtcacttccccctcttaactactacccaagacttctaactacccttacctacttatttgtctaaatttcaa acttttattctcacgcgtcttataaacatcttttctatttgttatggtatgttttgtgatttgtgtggtgtat ttcatttaatgggatctagtggaccgtgccccggttgggtatccgctccctttaaatgtttgcaagcactct tgacattataacctatcatttagtttacttgtttgtatgatcgtatttctgaatcgtaacatttatgcaattc tttctcgccgagacttgtctaggagataaagttcctgcatatttagtgttacggttgtataatggagactta gatagcttcacactgaggacgctttttcgctatcctttttgacctgattcaggccagtgtggagttaatg attgtatggatgggccctacaatttgtctaagacttggtgatagcctcgcggccgctcgccatttata caactgaatagcggttgaaactctct |
| 423 | Sakobuvirus A FFUP1 (1x mut) | tcacgcgcttttccggtggtcacccaccgttagggagcgccagcgttcgcgcttccgctaccaggt gacacactcctttcccctcccccattcccgttcccatcctctggactggtttctcctcacgattgacca gcagctgggagctgttaccagacgttggacagtaagtcccggatgcactatagggctggtggcta gtgcttggtaagcactcaacgccatacctaatgtgtacctcggcttgccctcctggtcgtggtgacc ggctgtttctcttcccttggctcCagacggctggtgtcctaccaccaccgttgcatgcagacctcc ccctgcgcactcgaacgccctgtcccagcagggttagtatgtgctgtgcagatctgcatgtgacac cccatccactggtagagcaggaagttgccctagctaacgcggcaagtattactttccgctacacgt ccttgagattcctcggacctctggaactagggtgactgtgggcttgggaaaacccaccttggtcctg tactgcctgatagggtcgcggctggccgaccagtggatgtagccagttgttttgggat |
| 424 | Rosavirus C NFSM6F | cagggagatctccatgaataatcttttccaccctctttagcgtctatgctattgaggacgggttggag ccccgttgacccagcgtcagagtgtgtcggtagcaggctttctgctctcgccccatgccggccaca cctcccattagtgatgtgaaggttgtaagttacatgtgaaaaggtttctaataattgagctgaatgtag cgattacctaaggtgagcggattcccccacgtggtaacacgtgcctctcaggccaaaagccaagg tgttaaaagcaccccttaggtaggccactaccccgtggcctcagttctcttagaagattcacttagta gtgtgtgcactggcaactcttaagcagagctagtgagtgggctaaggatgccctgaaggtacccg caggtaacgttaagacactgtggatctgatcaggggctcgagtgctgaagctttacagaggtagct cgagttaaaaaacgtctatgccccctcccccacgggagtgggggacccccacaccaattttagatt gcact |

TABLE 17-continued

IRES sequences.

| SEQ ID NO | IRES | Sequence |
|---|---|---|
| 425 | Rosavirus 2 GA7403 | ccaggcatggcgttaaacatgcattcccttcccctagtaacctcccttcgccccttccccacgttgta ccccctccgagatggctgctaaggcgcttgctgctacagcagtctcgtgtttcgggtgttataagtg ctttcttttccactccactccctgcctatggggagcggaacggccttgtctcggtcgttgcttcttgca gatcttcaccccctccaggctttctggactcgccaggggtggagtagtaggcgcactgtctaagtga aggtagcagtgttgttggcgaagagttgtggacctactttgagtttgtagcgatcatccagagctag cggatctccccacgcggtaacgcgtgcctctaggcccaaaaggcacggtgttcacagcacccttt ggatggcgggggtgccccccctccgcacttaaagtagaaaaacagcttagtagtcaaataacatgg ctttcctcaagcattcagtgctcatgggactgaaggatgcccagaaggtacccgcaggcaacga taagctcactgtggatctgatctggggccctgggccaggtgctatacacctggttaaaaccaaatct ggtagtcagggttaaaaaacgtctaagtcccaccccccgggggacggggggttcccttaaaccct caactgacacc |
| 426 | Rhimavirus A | cgaattccggacatctcctttcgggggcgagcgtcaccgtgcccctcatggaggcaactgtgcctc taatcggtgacccactgagaaaattttctttctacgtggctaaacaatgcaactttataataacacaaa tttaatgcttaatcttaacaccaaagatttgaacatatgtttggaaagtggcacacttcaaacattgcat agttgctaggggtgaagtccctttaaggggttgcagaggatctttcctctttatgagcggctaggagt atcttcttgatattatgtggtcgtgcaactcacttcccagatgtatgacggtgtactaagcgattggaa ctagtcataacctctttgaattttggtattgcgagtctagcagggggatatttaccgctaaagggtgac acactcgtgagggtggcctttggtgtggtgtatatttattccgcccatcttgcatggggtgctaaaattct aatgctgtgaaataaccattttctgaatacattctctacatttggagtcaaatatgaggaatgccactca ggtacccttgacatgatcttggatctgagagtgggctaattatctaattatttggcgactttctaaaatct tctgtttttagtggtgacaatttatggttataaa |
| 427 | Rafivirus LPXYC222841 | gtgtccgggaagcgactcaagcttttgactgagtctctacaccttcatccgtaacatctttaagtttatg tgcctatggacctctagtgcactgccatcaccggggggtgtattggactggtttttccacaatccattca tcctgaggaattttggctttgttactaggatggtcccaccacacgcttatctgtgcctattgtgtcaacc atgttcttaagtagttgtgcccgtgggtgagtagataaccacaacaatccgataaagcatctcgcaa ggatgtgagtaatggagtgtatgtgctacagagacccacaacctgaaccaagagagacacagtg aggattgtaaaggggggaactctttgaaagggcatgtcccgcaattcctactgactgacaccgggg gttggtgtcggtggattttagcaaatcctgttactgggtgatagccttgtgcacttcacttggttcttgta taagtgctgta |
| 428 | Rafivirus WHWGGF74766 | tgcgaatttattcgcacagtctcttttcccccatcttgtgtgtgtgatggggtaagccgcagagtaata cctactctgctgcaaacacactcactcttttctatctactttatatcatgtaataataagtagggaacata ttcaattcatattgttcatctcactgaacccgcatgaaggactgcattgcatatcctggacgaagtgac gtggaatatttggacatttatggattggacaccattacgctttgtgcctctacggagatgtaaccataa tcttaagtagtagtaccccagcacaagaggataaagtggcatacacgacaacgggtgttgctcgc accttagtaatgtggatgttcacccttggagcgtgctgaaactctgtgggtaaagacacacattagta caaatgtgggggaactcactgaaagggcatgtcccgtgtactggtgtgccggaaagtgggggtc gctttctggagaacttagtagttcttgttattgggtgatagccttgcggcggatcaactcacagttttaa tccgttgttttgcat |
| 429 | Poecivirus BCCH-449 | actacacaatcgcaacacgcgcaagtttgtagtttgattggcgtgcaaatgtcaaatcaagcatata acacaatttggtggctgttggtgtttgttataggaattttggttgtgttgaaattgtggatgtgtaggaaa tatgcacaattacgtcagcgtcaggagtttttataacctggcgcaacaccaaaatggtcttcgcgcttt aacatcaccagcgaggtgtaaacaaattgaagttgaattagatcgtgtataggccagggaaccatc cctcccaacgccacatcttgtggggaagttgggataatggtgggtctatatgaattggtctgtagac ccacagtgaagagtgaatagtatgcttgcggttccatttgttaatggtctagcatgggtgggggcgg caaccccgtgaggggttccccactggccaaaagcccaggggttagtcatttcaaccaaggaagct ggtaacctggtgacctgaacttgagtggtgagacccccttgctagagtgtgtaaaccgattgtaagc attttgtttgcttagtatctgtggtataagcagtcaattttgtataggctcaaggctgtggtagttagtag atgcccggaaggttattactgatccggggaccgtgactatacattaggtaaaccggtttaaaaacc |
| 430 | Megirivirus ALY | ttcgggacactggatgggcgacttggtggggctgccactctatcttgacctttcgttactgactttcg gatctctgactcctccttgtctcttgcgtttggtccacggacggactaattggaatgtttactggctaag cctcgttctgaaataccctagccaatgggttgtagtaggatcctggtgtttccattaaacctcttccga ccatagtagctagagttatggctgtgtaggatgtgggtaagaccgctttttgcgtatctcccacaaga caccggattatggatgtgtccgctggataaggctcgaaacctcccaactgaaggtggtgctgaaat attgcaagcctaggttgtgtagaggcaagtagatgcctgccgcgacattcgtcttccgccctttttgg gttagtagtgtacctacatggacgtggggctgggaatccccaccttgcataacactggttgatagac ctgcggctggtcaagttactatggtataaccagttgaaatggct |
| 431 | Megirivirus E | gcttggcaacctcatatcgttactctgccgaccagtctgggtcgtgtggccacacaatgggattcgtt ctgttgtgtagagtcacatggcattactgggctgatcggtggggatccgttgccacccctaaaccct tacatttactggactgcttttcttggccccggaatgattcgctcacccgcgatgaggactgttgttctta ttatggcaggattacgcgtctggtccgcgtaaggactaattcctatgtttatacgttactaccttgttct gaacggtgggcgccaccccgcctagtaggatcctggcttatcgtgtagacctctagggaccacatt agctagagtgtaggctgctatggatggagtagtgacccctttttgggtatcactctctaagactccgg aatgtgtcatagtacgctggaaatccttacttgtttttccatgagggggaggtggtgctgaaatattgc aagccacccctcggttaaaacagtttggtgccgcttatgccatattaccgccccttgtagttgggctg tttttgcagctccgggttagtagagtaccatagtggacgcggtgttgggaatcaccgccttggctgc acactgcttgatagagctgcggctggtcaagctaattgtggtataaccagttgatttggcat |

TABLE 17-continued

IRES sequences.

| SEQ ID NO | IRES | Sequence |
|---|---|---|
| 432 | Megirivirus C | ttcccgaccggtctggcaaaccggacggttatcctggttagatgtctgatggttgctggaacgtggt<br>ggctactgctgccaccttctggcttcctttaatgggcatctagctgggttctttgccacaatccatctta<br>ctctcttacccattttctattacccagacttgttgaaactggtaaagttgacctactggcttcgttttgag<br>actattctggtgttggtggacactctttccacaagtagattgtatggagttcatgctcgttttgaaccgg<br>gaatggcacaacccgtagtaggatcttgcctctgccatactaatctgcgcctgttgcttttagactatg<br>ggctgctaaggatgacattggaacccctttttggatattccatgtcaagtcaactgtttcatctggtgta<br>cgctggaaatccttgttccgaggtcttgtctggaggtggtgctgaaatattgcaagccacaggcagt<br>tccttggacttggtgccgctatcagatgctacaccctctatgggcaaatgttgaaccttagtggacgc<br>gtgagatgggaatccacgccggccatagactggctgataagctcgcggctgatcgagttgcaaca<br>gtaatcagttgatttgccact |
| 433 | Ludopivirus | tagacccccacctagcccttttccccgtcagtgggggggcttactcactgggcatctgttaatctggc<br>ctaactagattgacaccactcccttggaacgtaactccacgctaactcactggctctacgcacagac<br>acacggtctttctgctatccccggggaagataccagatggcgaccggctgtcccagcggcctagt<br>agctactcgggttgagtacccaccacggttttgacgcctgctaaaattcaagagacagaggtaggg<br>gtgcttagtgtgtgggggaagttcccacaagcgaggcaaagcattgctccctcgcgtcaccgggt<br>gcaaggtaaattggctggacttccgctctacccttgctactcgccctcttcggagggttcgaagtga<br>cactaggtatacgcatggttgggaaaccatgcctggcctactactgggtgatagcctggcggcgg<br>gtccgtctcttggcttatacccgttgatttgggat |
| 434 | Livupivirus | tatctacatggggatccaggctgtatggaatgtctgtcttaacaagcactataccagaaagatccac<br>ccaaagtggtgggactgggactgtgaggtgagaaatcccgaaaccagccttctcaagcgtcgga<br>cgatctttctgttttagtgaacaccttgccttttaaatggatgacaacaccccttcagcaaatcgcaatc<br>tgaaatcccaaaagactgtttagccgaactctggtaatcactccggagagaagtaggatacgcagccc<br>ctgtggactcttgatttcaggactcaaggtagctagagctggaacttcatggaatgacaaaggaata<br>tatgcacattgtgcgctttcctggccttgtagcccgtcgtgaggatatgtcgttgggaatcgacatctt<br>agtccagtactgcttgatagagtgtcggctggcacagttacctgagaataagtcagttgtacttaaca<br>tgaacaaaaaaaataactaccacaactaccacaatctaccaatacttgaattatgctgaatctcgtac<br>agtaaaaacgttccgtggaaggacaagtattgaagtgcggttacatcatccgatacgcgctggatc<br>cctca |
| 435 | Aichivirus A FSS693 | cacccatacaccccccacccccttttctgtaactcaagtatgtgtgctcgtaatcttgactcccacgga<br>atggatcgatccgctggagaacaaactgctagatccacatcctccctccccttgggaggacctcgg<br>tcctcccacatcctccctccagcctgacgtatcacaggctgtgtgaagcccccgcgaaagctgctc<br>acgtggcaattgtgggtcccccttcatcaagacaccaggtctttcctccttaaggctagccccgat<br>gtgtgaattcacattgggcaactagtggtgtcactgtgcgctcccaatctcggccgcggagtgctgt<br>tccccaagccaaacccctggcccttcactatgtgcctggcaagcatatctgagaaggtgttccgct<br>gtggctgccagcctggtaacaggtgccccagtgtgcgtaaccttcttccgtctccggacggtagtg<br>attggttaagatttggtgtaaggttcatgtgccaacgccctgtgcgggatgaaacctctactgcccta<br>ggaatgccaggcaggtaccccaccttcgggtgggatctgagcctgggctaattgtctacgggtag<br>tttcatttccaattcttttatgctggagtc |
| 436 | Aichivirus KVGH | tactccattcagcttcttcggaacctgttcggaggaattaaacgggcacccatactccccccaccc<br>ccctttttgtaactaagtatgtgtgctcgtgaccttgactcccacggaacggaccgatccgttggtgaa<br>caaacagctaggtccacatcctcctttcccctgggagggtccccgccctcccacatcccccccca<br>gcctgacgtgtcacaggctgtgtgaagcccccgcgaaagctgctcacgtggcaattgtgggtccc<br>cccttcatcaagacaccaggtctttcctccttaaggctagccccggcgtgtgaactcacgttgggca<br>actagtggtgtcactgtgcgctcccaatctcggccgcggagtgctgttccccaagccaaacccctg<br>gcccttcactatgtgcctggcaagcacacctgagaaggtgttccgctgtggctgccagcctggtaa<br>caggtgccccagtgtgcgtaaccttcttccgtcttcggacggtggtgattggttaagatttggtgtaa<br>ggttcatgtgccaacgccctgtgcgggatgaaacctctactgccctaggaatgccaggcaggtac<br>cccaccttcgggtgggatctgagcctgggctaattgtctacgggtggtttcatttccaattctttcatgt<br>cggagtc |
| 437 | Aichivirus DV | tactccattcagcttcttcggaacctgttcggaggaattaaacgggcacccatacaccccccaccccc<br>ttttctgcaacttaagtatgtgtgctcgtaatcttgactcccacggaacggatcgatccgctggagaa<br>caaactgctagatccacatcctcccttcccctgggaggaccccggtcctcccacatcctcccccca<br>gcctgacgtaacacaggctgtgtgaagtccccgcgaaagctgctcacgtggcaattgtgggtccc<br>cccttcaccaagacaccaggtctttcctccttaaggctagccccgatgtgtgaattcacattgggca<br>actagtggtgtcactgtgcgctcccaatctcggccgcggagtgctgttccccaagccaaacccctg<br>gcccttcactatgtgcctggcaagcatatctgagaaggtgttccgctgtggctgccagcctggtaac<br>aggtgccccagtgtgcgtaaccttcttccgtctccggacggtagtgattggttaagatttggtgtaag<br>gttcatgtgccaacgccctgtgcgggatgaaacctctactgccctaggaatgccaggcaggtacc<br>ccaccttcgggtgggatctgagcctgggctaattgtctacgggtagtttcatttccaattcttttatgtc<br>ggagtc |
| 438 | Murine Kobuvirus 1 | gtaacttcaagtgtgtgtgctcgtaatcttgactcctgccggaatgccgcccggttcagtgaacaaa<br>cagctaggcaagtccctcccttcccctgtggtcggttctcaccggccaccatccctcccccagcct<br>gacgtgttacaggctgtgcaaagcccccgcgaaagctgctcacgtggcaattgtgggtcccccctt<br>tgtcaagacaccgagtctttctcccttaaggctagcccggtcccacgaacgtggaactggcaacta<br>gtggtgtcactacacgcctccgacctcggacgcggagtgctgttccccaagctgtaaccctgacc<br>caagactgtgctgcctggcaagcaccgtctgggaagatgttccgctgtggctgccaaacctggta<br>acaggtgccccagtgtgtgtagtcttcctccagtctccggactggcagtcttgtgtaaagatgcagt |

TABLE 17-continued

IRES sequences.

| SEQ ID NO | IRES | Sequence |
|---|---|---|
| | | gtaaggttcaagtgccaaatccctggaaggagtgaccctctactgccctaggaatgctgtgcaggt acccccaacttcggttggggatctgagcacaggctaattgtctacgggtagtttcatttcccatcctct ctttttggcatc |
| 439 | Porcine Kobuvirus K-30 | tttgaaaaggggggtggggggcctcggcccccctcaccctcttttccggtggccacccgcccggg ccaccgttactccactccactccttcgggactggtttggaggaacataacagggcttcccatccctg tttacccttactccactcacccctccccttgaccaaccctatccacaccccactgactgactcctttgg atcttgacctcggaatgcctacttgacctcccacttgcctctcccttttcggattgccggtggtgcctg gcggaaaaagcacaagtgtgttgttggctaccaaactcctacccgacaaaggtgcgtgtccgcgt gctgagtaatgggataggagatgccaataacaggctcgcccatgagtagagcatggactgcggt gcatgtgacttcggtcaccaggggcatagcattgctcacccctgaatcaagtcatcgagatttctct gacctctgaagtgcactgtggttgcgtggctgggaatccacgcttgaccatgtactgcttgatagag tcgcggctggccgactcatgggttaaagtcagttgacaagacac |
| 440 | Porcine Kobuvirus XX | ccaccgttacttcactccactccctcgggactggtttggaggagcataacagggcttcccatccctg ttcaccctcaataccacccaccctttccctcaaccatccctatccacaccccactgactgattcccttg gattttgacctcagaacgcctacttgacctcccacttgcctttcccttctcggattgccggtggtgcct ggcggaaaaagcacaagtgtgttgcaggctaccaaactcctacccgacaaaggtacgtgtccgc gtgctgagtaatgggataggagatgcctacaacaggctcgcccatgagtagagcatggactgcg gtgcatgtgacttcggtcaccacgggcatagcattgctcacccgtgaatcaagtcattgagattcct ctgacctctgaagtgcactgtggttgcgtggctgggaatccacgcttgaccatgtactgcttgatag agtcgcggctggccgactcatgggttaaagtcagttgataagacac |
| 441 | Caprine Kobuvirus 12Q108 | gggggtgggggggcctcggcccccctcaccctcttttccggtggccacgcccgggccaccgat acttcccttcactccttcgggactgttggggaggaacacaacagggctcccctgttttcccattcctt ccccctttcccaaccccaaccgccgtatctggtggcggcaagacacacgggtctttccctctaaa gcacaattgtgtgtgtgtcccaggtcctcctgcgtacggtgcgggagtgctcccacccaactgttgt aagcctgtccaacgcgtcgtcctggcaagactatgacgtcgcatgttccgctgcggatgccgacc gggtaaccggttccccagtgtgtgtagtgcgatcttccaggtcctcctggttggcgttgtccagaaa ctgcttcaggtaagtggggtgtgcccaatccctacaaaggttgattctttcaccaccttaggaatgct ccggaggtaccccagcaacagctgggatctgaccggaggctaattgtctacgggtggtgtttcctt tttcttttcacacaactctactgctgacaactcactgactatccacttgctctcttgtgcctttctgctctg gttcaagttccttgattgtttttgactgcttttcactgcttttcttctcacaatccttgctcagttcaaagtc |
| 442 | Rabbit Kobuvirus | gggctataaatatgggcattcctcttccccccttccccttttgaagatgagtgcgcatattcttgactccg cctggattggccgcccaaggcgtgaacaagcagctaggccaccatgacactgcggtggtgtccg aacccgcgggtgccttcacgggcacctgtggtatgtaggactcccaccgtggtcttccctttccccc tcaatctttccccctggttcgactaacgggaccagtgctggaacctgtccggtgaacggtatagca ggcccccccggcagaaacacccggtgcttaccccttaaggctagcccccacctttgaatttggttg gggcaactagtgggtgtacagttggcgtgaaccctccggtctaggagtgctcttgcccaatcctct gtgtgtgccttgcagtagggactggcaatccttcgcgtaggtgatccgctgtgccatgccatcctgg cgacaggaggcccagtgtgcgcaacctacgtcccttctgggtgctgcattgcattacctttggagta agcttggtgtgccgaaaccccagggtttacgtaccactcgtggtgtgaggaatgtgccgcaggtac cccatccttgaggtgggatctgagcggtagctaattgtctagcaccactttcttcctttttttctttgctgg tcacg |
| 443 | Aalivirus | ttgaaaggggggtgctcagggtagctccctgagctcttccctccttccctcatcaacgtctggcccac gatacgggccacctttcaatcttaactaactatccctttaatctatttggattttctggtttagaataatttg gaacacataattggattatcttttaggattgtggataggatttgttcgggatatcactcccttcctgtgct aacacatattctaattccctcctttgtctattatctcttggaggtggtgctgaaatattgcaagccacttg agtgtatagatgaagtaggctcaagatgaatgttgtgttactcaaggcaagtgtagctatcactaaga tattggtaacgtgaaacggattaccggtagtagcgtgatcttccgtcttagtgctctagtgactagag gacaacgacatggcatcacatatcttaaccctccagttttggcatccgggacagaatgggctggat atccgctttctttctggggtatgtgatgggtggtattggggtaaccaccttgaccatgacgctcgata agagtgaccgcctgatcattgaaacctctagtataaaattcaggctgaaatc |
| 444 | Grusopivirus A | tgcctgagtaggattgtgaatttaggtatgagagggttagccaacccattctgaaccataatagatac gtcaatctgaatccatctaaatctatctcttaggcagtggtgctgaaatattgcaagctactagggata gacgtgatctgattcaagaacctatctaatgtggtgatgagaaggctaggtttatccatagtaatccct tgttctgaacaggcaatgcacatgctctagtaggatctcgggctctgcgattggctctaaaccgacc aatccaggtagaggcactaagtgtaggacttgccaaaatgtattacatgctggtaccgactcactag tctggaaactccacactgaaagtgactgggggggggccccatcacatttgtgctactgcttgataga gttgcggctggtcaacttggattggtataaccagttgaa |
| 445 | Grusopivirus B | gccatccgtaggttctggtaaggttccatcaactgttggggcgctagttgctatgaccgcattcacg gacggatgatttatagtatcacccaatccgggcacaacttctttagccacttcttccacattactaagg gctctcttgccgagtttcaacgtctagtccacgacacggaccttcctacttttctatcttcttattttctct actaaattggtatctggtactgaagatatgcggattgtgattttgtgcctgtctaaactaaccctattcta gggttaggtgggtaccatatactaatggtgaacaggattacctatgtatccattagtccctatggatct ggcgacccacaaactcatgttcatagagaggctaagctgagtgctcgccgaataagcattgcttca ggtgccgactattgtctggaaaccactcagtgatagctatagggggggccccgtagcatctgcct tactgcctgatagggtggcggctggtccatgaacatgcagtaaccagttgacttgac |

TABLE 17-continued

IRES sequences.

| SEQ ID NO | IRES | Sequence |
|---|---|---|
| 446 | Yancheng osbecks grenadier anchovy picornavirus | ccttagggtctggaatgcgtcctttctgggcacttccacaatcctaaggtaattttcaacgccagcga<br>tggagcgatatccaaagaacctttatgttttagttcgtcttgtatgtttataaaatataaaattgggatta<br>gcaacccacaaaaacatttttgttattctcaccacatgagagggtggttaaacctcttcgtaacctatc<br>ttgcttgattggctacttgggctagatttaggacaacctctttagcaagcctaaattactcctcgtaca<br>gcacctggtaacaggcgtacctggaggttacggtggcgctaacttggacttctcgttaattcgtgca<br>agtttaaatgatgcctattttgaatacaagaaagtatgatagtaacttagggcgtgaagttccgcttaa<br>cataaggcagtataagtactaagataaggtgtaagacctaccttaataactgttgtcttttctcatggtc<br>tttccgtgggagcccttgctaggggtaaagttaagtattctcaaataatttttcattcaaactctttctctc<br>tgtttt |
| 447 | Turkey Gallivirus M176 | ccactcgcacttcctggatagtgcgttagatatgcccgacatatcgcttccaggaccaaagccccc<br>cttttctctttcccaaccagcttcgccactcaagctgtaattccatgtccggtctttccggccttagtatc<br>atggaaatgtggtcgtgctcaaatgaaattgagttgacattgatcaatgaaagttgcactgaactttg<br>ctaaactggctagcgccacctggtgtgtgccgttggtctcctcacatggtaacatgtgccaacggg<br>cccgaaaggctagtgggcaattaccgctccaagggaggggtacccaccccgacctgaacagcg<br>gtaatgaagctcacctcccaggctctgaccccgagaagtttagttatttagtaggtgtaattagtactt<br>gtgattggtcaatagatagtagatgaaacgttatggatgaatgagtagacccccctgaaggtacccc<br>attacatgggatctgatcagggccacattctgcgtgtctccccgcacttgtggttaaaaccatgaaa<br>gttcatcccaaacaatcttttcctcttctttttcttttagtggtgacaacctactggattggtgattaccaat<br>ctgtactagtgttgtattaagacttgttgtgtggagaaaatggactctttcaagaagatttttg |
| 448 | Falcovirus A1 | taaaaggggacgcggtgtggcagctttggctgtcatgccgtgttctccttttaccccaaggactagc<br>cttgggggttttccaaattcctttccctgtaggctttacttctctttatctatcttttctgtaactaagtttt<br>gcctattctaaaaatatttagaatgtgtttggatgtaactaagtttgtgcctgccctaaaaatattttaggg<br>cttgtttggataacctcgtcccttgtgttcagtgccgcacaatttgctaggcactgttcacttcctttgtttg<br>tccattatgtatgctaaggtatgaattccatcatatgcttagcctctacatgcataatcttattccctccct<br>ggtgcaaactacgcccccaacatatgtgaatcttttaagcatattcctgaccccacacatatatatgtg<br>ttctcgtgaattcccccaccgtgaggtggtcacttggacgtggtgtgtgtcacacagcatatatatga<br>tgcaggatgttgtttttaagataagcatatgtccttagtgctttgcatcatttcctccacaccccgtgaat<br>gcggctaatcttaaccctgttgggtccgtgggtaaaccaacccattaaccacaggacggaaccga<br>ctactttcgggagtgtgtgtttctttttcttcttttgtcact |
| 449 | Tremovirus B | ttcaaatggcccctgggttgatacccagtggtcatttggacactttggtaaggaggtgtaattatcctt<br>cccatgtggaacctagtgcttaggtttactttatatgttctttgtttgtcctttgtactttctatcgggcaat<br>cttgttgttcaatacaatatgtatttgaactgcctaagataaattcagttttcaaccaacccctctcttgg<br>ggttgtgtctttctttctttcttatatcctcttaagctgacttacttgctaatccgactcctcgtcaacggg<br>agggtaaagcagtatcactagggtattgtgatgtaggagaaaaagtaagtagagatagtgcatgta<br>acgaaagtgacttggtactttaaactctcttaatcccaaagtgtggtattggtcatgttggagtaggct<br>acgggtgaaactccttcacatttagtaatgtgttcacacgctaacgctacggtagatgacagactag<br>gtcttattctcaacgtagggggacgggtgtatgttcatgattagccacatattaaggttttgaggggct<br>gagtcatataagtatgtgcattaatttctggtactggtccctggggactggcccttttctaggttgatttt<br>agtttccccaatttttaaaaactaatgagatttacgac |
| 450 | Didelphis aurita HAV | tctttggtctggggaactaaaataccagacccgcgtttgcctagcgatataggctttaattgttgtttgt<br>cattgtgcgtttgatatgtgttttaatgtaaataataattctagcaggttctagacttgatcatgtcctcttt<br>aaggcactcatttcaacttgctatctttcttttcttccttggttctccctacaccaaatgcactggccgct<br>gcgcccggcggggtcaaccacatgattagcatgtggctgtaggtgttgaaggctgggacatgaac<br>atcaatggaatagtgcgcatgcttactggggtccattgaagtagtgggatctttctattggggtaggc<br>tacgggtgaaaccccttaggttaatactcatattgagagataccttggataggttaactgtgctggat<br>atggttgagtttaacgacaaaaagccatcaacagctgtggacagaacctcatccttagattgctcac<br>tatggatatgtgctctgggcgtgtttcttgcatgatggccattggtcaattcatgcctgggccaatgta<br>ggattagccttaaattacttttaaaagtagcctcatttagctggactaatggtggggcgtatgatcctg<br>catttggcctctggggtaatcaggggcatttaggtttccacataatagcaaat |
| 451 | Hepatovirus G1 | gcaaggggtggttttaaccttgcacgcgtttaccgtgcgttaacggttttccatgtttgtatgtcttgttt<br>gtattatgtgttttgtaaatattaattcctgcaggttcagggttctttaatcatgttgggctgtacccacac<br>tcaacttttggccataagtgagtttcttaacgaaccttttaacacaggatgttattagggcccaatatttt<br>ccctgaggccttctttggcctctatttttccccttttctatctccttgtattccgggctcacgtgatgcca<br>atggactgacccatgcgcccgtgggggttaactactggagtagccagtagctgtaggtgctaaaa<br>gtcacgtacgtgtaagactggacgagacctctcagctataactgaaagtagtaagtatgtctgaact<br>tcttgaaggggtaggctacgggtgaaaccccttaggttaatactcatattgagagatacctctgatag<br>gtgaaggtttccggtagaggtgagtttaacgacaaagcctctcaacggatgtgggcccacctcatc<br>agcaagatgctttcatacccaataccgtaggggctgggttgttgagacagtcccaagcgtccctcc<br>cgcaaggttgtaggggtactcaggggcatttaggtttccacaattaaacaaataca |
| 452 | Hepatovirus D | ctttggatgcccatagtgcgggggtataaataccgcactccctttagctgttccgagggtatcggaa<br>cctatatgtttgttttctgtctgtctgtcagctttatgtgtgctcgtcccctttagggcactcatttcagctt<br>gctttcattcttttcttccccggttctcaccttaccggaggcactggccgttgcgcccggcggggtca<br>acctagtgattagcactaggctgtaggtgtctaaagtggtgacattaagacttggtaactgatttcag<br>cactgttaactgatgttggggatgacttgattgatcttctggaaggggtaggctacgggtgaaaccc<br>cttatcttaataccactatgtagagatagattcagtaggttaagggcagtggataaggttgagttcattt<br>tggacaataaaccttcaacactggtggacccaatctcactgaccagatgctttcttgactgatccttc<br>agaggggtgattcttctgaataggttgccttgacactgatgcctgagacccattgggtcgggcctta |

TABLE 17-continued

IRES sequences.

| SEQ ID NO | IRES | Sequence |
|---|---|---|
| | | aatcatggaactccactggactttcatggcctagcttctgccttagacagactctggggccccacga<br>ccctctgggcccttcggggtactcaggggcatttaggtttttccacaattaaaagagtta |
| 453 | Hepatovirus H2 | gtcatgtttctctttaagaacactcaattttggccataagtgagactcttgtcgaacctttcatgtcagg<br>accatgttagggccattatccttttccctggggcattcttcttgcccctgtttcatctttctatcatcttt<br>cttccgggctctcacaatgccaatggagcgaccgatgcgcacgtcggggttaacccatggattagcc<br>atgggctgtagctgctaaaagttgtgactcctgaagcatactatcaatggtagtagatgtaactgaaa<br>cactgaagcttctctgatcttgaaagaagggtaggctacgggtgaaacccttcaggttaatactcat<br>attgagagatacctttggtaggttaacgttggcggataatgttgagtttaacgacaataaacattcaac<br>gcctgtgggcgaacctcaccaatttcatgctttgaagtgaatgtgcgtagggtctctatcggagatg<br>ctatgtggatggtgccctccctggaaacaggttgtaggggtactcaggtgcacttaggtttccacatt<br>ttaaagatttttc |
| 454 | Hepatovirus I | ggctgcctgtgtctcaggggtaagtactggggccgcgttgaccgtgcggtacggttatgcttttaga<br>ttaggatgtccgtctgtccggcactctcttttgcttaaaatggccttaaatccatgggaggcgtaacca<br>tgggccctttgttacctagacatgattgcattgggggccgtccttggggcttaggccccagccatttc<br>tcttgactcgtctaagagtttacttcatcctttttctttactttattttccaggctctcagcatgccgacggct<br>ctgaccactgcgcccggtggggttaactgcatgattagcatgcagctgtaggagttaaaagtgctg<br>acaggccaattctgacgtaagtccactctatattaacttgatcaagtaaggttgattgatctttgtgaga<br>gggtaggctacgggtgaaaccctctaggttaatactcatattgagagatacctccagaaggtgaag<br>gttggcggatattggtgagttcttttaggacaaaaacctttcaacgcctgtgggcccacctcactggc<br>acaatgctttcatccccaattgtgatgggtagtttggactgaaatcaggagtaacctgccctacgagt<br>ttaggggtagttcaggggtatttaggcttccacatttgatagagtttatgagagtgagcc |
| 455 | Hepatovirus C | ttcaaaagccccagcggggtttcattaccccgctgtggcttttggacttccctaggatggggaagta<br>aattaccatcctcgcgtttgccgtgcgttaacggctacttttcttctagctgtagaagtaaaattcagca<br>tgttttatgtttgtttgtcttgtttgttatatacttttatacactcctacaaatgcacatgaagaacagttt<br>gtagagattaacaaacgcttagctgaacctaggtggtgaatctagtagtaagataagtagaggaagct<br>ataccttaagttggttgggccctcgtgtttgctctataaacaaaaccaagtgagtagagtggatgaac<br>agtactaaatccctgagtacagggaacctcacaggtgtgatacacttatgtctatgtgacctggttgg<br>aggttgggcgtgccctatgatactggagtgggagatcttttggggaacccacgttttcacactgcct<br>gatagggtcttgccgagagactcacttgtttcggctgtacttgtaac |
| 456 | Fipivirus A | tgcgggtaaactcccgcatgtgtgaatgaggcgatgtcccaggaactaactgccgatcctggtttta<br>actacgatccgtatttgttactaatgcgatatccccccattgtttgcctccatgttgttttcaacgcttttg<br>gccttgagtgttatcaagtgttttagcgacatagtgggaagctacggctgcgtccccatttttgagtg<br>gcgacccagttttagtggccactctgtccctgaactgcgctataatgtgaatttatgttcacaaaaac<br>ggactgatgtaactgttaatgactaaggaatagtacctcactgaagtatcaagaccccgttcgagcg<br>gtgtacatatatggatggaaaccagtctgagtcatctcgaatactaatcaatgagggatgtcgagta<br>agcatatcatgaaccacatagaatagtggggtttcggggttagaggctctctgcagcaatgtatctct<br>aacaccatggccgaaatgagagatagagaccacgatgtttgtgtgtaagtaatgatgtgtggaaag<br>aaaattctgaatgttggtatgatatcagtctaaggggagtggctcacctaagagctacccaaacattt<br>cacagcagacaacataacgtactgagagtagttggaaggttccagaaatcagt |
| 457 | Fipivirus C | cgcggttaaacccgcgccaaccttctttcagccgcgtctgagtagcgcggttagtcctgatacacagt<br>ttcctgttgggtactgtgtcttcgggtgaatgctcttgtgtgaatgttttaggctgtttaagggaagcgtt<br>tccccgtgcgctgtgagggtttctcacgctctttcggggtgcagtctcttctgttgttcattaagatgta<br>tggatgcactgttgtgaaggatttgtgaactggggatcgacaccccgtgaggggtgccccagtgtc<br>cataggagtttgctggagaggtgtgttgctgtagtgactatccgtgacctggcattctaaggtgttga<br>ccccaacctgtgagggtctggatcgcagtgttgaagtgctttggagggttcaatggggtttctgtagt<br>ggatattatgtgcttgacgactactggtacgagtgtattgggggtctacatgtgtga |
| 458 | Fipivirus E | ctcttccgatcttgggggttcgcccccatgtctcatttcaactagccgtgtgtctagttaacgcaccgc<br>ctcaccctggtcgttatcgggtcggttcttgcgaccgttagatcgtgagcgtttctgaggatcagttc<br>gtataagttctccggtgtggcgaccgtaaaatcgtcacgtcccatgcaatagatgacgttaaactcg<br>tttgccagttacataaaggaatgttgttacttttaaattgtctgttacatttaacatcttgccagtatgatg<br>ctactgtacactacgggtgtaggaaccttgtagtgtgacgtatcactcatatgtggatgggtgctcca<br>gacctttatggaagctctcagttagtagtgatccttgacttcattgagccctggtaacagtggaagtc<br>aagatgtatatgttgctcaacacacttcggtgctacgaagctgtttgtggaagtactggcgaggttca<br>ttctgaatcatatgtttgtcacatagtcagggagtgccgtcgcttacgacggacccttttttctttataatt<br>acaaatctgtgtctcaagtgttgttggctggtttttcttcttctgttttcattgttcatatatatacgtcaga<br>gtgaaagactcggtatatacaaaactgatccaga |
| 459 | Aquamavirus | ttcaaaggtggcgggagagttggcctcacgctgtttagcgtgagagctggctctcctgccccttcc<br>cctgagccggggatcttggctcattcccctcttttctatcctccctcattggactttacggatgacccg<br>gcataaacttgacaaccgatgttggatttcccttgtggctgtgatggaggacataccctcgggtgta<br>gttgtgtgcgtgtcgctctgcgactcgagcttcaaagtggtgctgaaatattgcaagcgtcgttgctc<br>gattaacggagtggtacaatcctatgaacccaagtgcattcatgcgaaagccccggaggggtgag<br>tagcatggactcgaatcagaagagctggagctcgcttggtacggcacgtagcattgctttgcctaa<br>agaccaagggggtatggctataggtgggggcctatagcttgtccagtgctggttgacagactcgtg<br>ctacgcgtctggttcgagtataagtagctgcaactcact |
| 460 | Avisivirus A | ttcactcgctttcccccccctctctatagggggcggtcttttaattcttattaatttcctactttactatcaaa<br>tttcttctaagtagggactgaggtcacttagccctccctctcctgggctttccagggttatagaggttcta |

TABLE 17-continued

IRES sequences.

| SEQ ID NO | IRES | Sequence |
|---|---|---|
| | | aagctaagccatgtgtcttgagctacacttagtacaaaggtttagtaatgattgtacatgccagtaac<br>cttctagtgcccatggattaaagagtggtaacactctccatggggcccgaaaggctagtgggcata<br>gttggcatcaaggaaggggtccccaccccaacctgaattgctggctagaagctcaccttagaaga<br>agtgctgggtgacaacgtgtccaatcgtgaacgactgatggaaacgtgtggagatggatatgtgg<br>gggttcactgagtagatgccctgaaggagaaatctgatcaggggcccgtgactatacgctaggta<br>aaccgggtataaaaaccatgaaaggtggcccaaaatcttttcctttttattttatttctatgttggtgaca<br>gtcaag |
| 461 | Avisivirus B | cacccccctactgccctaacccccaaagttagttatagggtggctccctacccttactccacggggta<br>agccctaacccggttgaatctcaagatcagccttagcgaggactattagtaccgctcaaacccctttg<br>cctgtagtgcccaggggtcacagaggggtgaccctctccctggggcccaaaaggctaggtggca<br>agacagggtccaagtgaggggctactctaagtagccccaagctgaacatcctgtctgaagccacc<br>cttgcagggccaggtttgattggggaaactagacaccagctttgtcctgggattggggggatatcg<br>agttagtccaggaggtgcgagtagatgcccccgaaggtaccccaggcacatctgggatctgatcg<br>ggggcccgtgactatacaataggtaaaccgggttaaaaaacatgaaagcgcctctctctttcctact<br>tcttttattgactggtgacaaaaatagcagt |
| 462 | Crohivirus A | gttgaagtccatttcttgcttgcccccgatgaatcctgttaaggcctcacggccctaagggtgaaact<br>cggttatcccctcctgtacttcgagaagattagtacaacactatgaaatctacatcttgtgatccggga<br>taaccccaatcccagaaacctgtgatgggcgtcaccacccctcttatggtaacataagggtgtcgc<br>cgcgttggcacaggaccctttgggctggatgtttttagtaatggtgtcgaaggtcctattgagctaca<br>ggagtttcctccgccctggtgaatgcggctaatcttatccctgagcctaaggttgcgatccagcaac<br>ttgatggtcgtaatgcgtaagttgggggcggaaccgactactttccagaaggcgtgtttctttgttttg<br>tctgttactatggtgcatgatatagatattgaatatttgatctttttgagctgtttcttatcttattgcta<br>catcctttcaggtgttggatttacattttggttaataag |
| 463 | Kunsagivirus B | gattttctggttatccccttttggacttggtaggggcccacgtgcccacccacctctgtgtgtgttgattt<br>ctaatcgatgcctggcagtggcggccacctctccttactggtaaacctccggtgagtgaagttgtca<br>agctacaggtaccgtgcaggatgaaatgcgcacatgtgaacaaactaggagtcatacaccgggtc<br>aaactctggaaacggagtccgggactctgaccaggagggtgagctcgaggcatcacattgatgg<br>acgcgattcgctatccttccctagtaggaccttgtggtgtaccccctggttgggaatccagggctggt<br>cgggtgcagggtgacagcctgttctccacctcaaccattgtaggagaaatcaacccct |
| 464 | Limnipivirus A | ttctttggatatccatttaacgtgtaccctatacgataattggggtggattctggatgcctagttccagt<br>gattggttaagaactcgtttactacgtatagtatgattagcaaagtgctcgattgatcacgtaatgatct<br>atgtggttaaaaacccagtagtatggtatatactcagtagtgtacactgtgagtacaactcttggcgta<br>gagagaacaattcacccgaatccgtggcgtatccatggaaataagtttacctaattgtatgttacaag<br>gcatatgagacatttatgagatatggtttattttgactaaacgagtgtagaggtggtggagtctatcca<br>acttcaagccatgcaattgttgtgttgattgatatcattgaccatttttgtggattgtgtacacatacaatt<br>tgaaaattaacccccctcaagaataagacatgggaccattcgtggtagataccgtgctcggatgcttg<br>agattagatgggttagactagttttggaatgagattgccgagaaagtcccgctagacatgttttacaa<br>gtcgtggtattccgctagactttttcgcagacacatggaagggtccatgtgttgtgcaattgcagggt<br>gacagcccaactgcagagttttccttactagaataaaaatctgttgtcaatttt |
| 465 | Limnipivirus C | gtttctgagcactggtaagagcttagacaaacgtttttaaaatttattttctctgcaacttttgtttgtg<br>tttatttttatttgttaattttgcgcctaagcatttgttgcgaagtatttgattcattagtaatattact<br>tattgtttatttagatggtattcaaagtggtgggagtatcgaacccaagcgtcgtatgctatctccttga<br>acaatttttaatcattgcgaagtgatcattgaaaaggataggtgtttaagaactcaaagagtgttaataa<br>tgttgggtgacaggtgtccccatagaatttattaacatgtttaggactggttatctagtaagaagaacca<br>tcgaacgcacgagcgagcattgcttgcggggcagttaccctgcgtcgatgtaagtgtgtaccggggggtg<br>cacatgttgattctttatggcctgatagggtgcgtcattcgcgcctagataattagtataatgcgaatg<br>gaataaatttac |
| 466 | Orivirus | ggtcccaggccaatattcttcgtaaggcttggttccaattttccaccactcgtgtttgggttctggccta<br>tggtacccagaggggcggtttgggggaattaactcccccctcccctgtggtcctataccaccccaca<br>cctctgtgggctttctttactatcttcttgttttccgacttttaaacactaggcaggcgcgcctagtcata<br>caccgcccggctggtctttccagcttttgtgggcggtgcgcgctggtccatcgtgcccagcgacat<br>agcaccttgtggacacctccgaacgccctcccctgtatggggtggtgcccaggggtttcagtgtgg<br>tgacacactccctggggcccgaaaggctagtgtgcaacaggtgaggtacagccagctgcccccg<br>tggctggagggaccaagcttgtgaagcacacctcaccacttgggggtgggctagtaagtggtga<br>aagcatagtgtccgtgtcgctggccaacactttgggtcaagtccagccactcagtgagtagatgcc<br>caggaggtacccctagtggatctgacttggggcctgttacttaatgcaggttaaaaactatgaaagc<br>tgagtagtgtagcccggctggtggcttctcttccttattcattctattttatggtgacaaacgcaactga<br>agcc |
| 467 | HAV FH1 | cttgatacctcaccgccgtttgcctaggctataggctaaatttccctttccctgtcctttccctatttcctt<br>ttgttttgtttgtaaatattaattcctgcaggttcagggttctttaatctgtttctctataagaacactcaa<br>ttttcacgctttctgtctcctttcttccagggctctccccttgccctaggctctggccgttgcgcccggcg<br>gggtcaactccatgattagcatggagctgtaggagtctaaattggggacgcagatgtttgggacgt<br>cgccttgcagtgttaacttggctttcatgaacctctttgatcttccacaaggggtaggctacgggtga<br>aacctcttaggctaatacttctatgaagagatgccttggatagggtaacagcggcggatattggtga<br>gttgttaagacaaaaaccattcaacgccgaaggactggctctcatccagtggatgcattgagggaa |

TABLE 17-continued

| IRES sequences. | | |
|---|---|---|
| SEQ ID NO | IRES | Sequence |
| | | ttgattgtcagggctgtctctaggtttaatctcagacctctctgtgcttagggcaaacactatttggcct taaatgggatcctgtgagaggggggtccctccattgacagctggactgactttggggccttatgtggt gtttgcctctgaggtactcaggggcatttaggtttttcctcattcttaaacaata |
| 468 | HAV HM175 | cgccgtttgcctaggctataggctaaatttttcccttttcccttttcccctttcctattccctttgcttgcttgta aatattgatttgtaaatattgattcctgcaggttcagggttcttaaatctgtttctctataagaacactcatt tcacgctttctgtcttctttcttccagggctctccccttgccctaggctctggccgttgcgcccggcgg ggtcaactccatgattagcatggagctgtaggagtctaaattggggacacagatgtttggaacgtca ccttgcagtgttaacttggctttcatgaatctctttgatcttccacaaggggtaggctacgggtgaaac ctcttaggctaatacttctatgaagagatgccttggatagggtaacagcggcggatattggtgagttg ttaagacaaaaaccattcaacgccggaggactgactctcatccagtggatgcattgagtggattga ctgtcggggctgtctttaggcttaattccagacctctctgtgcttggggcaaacatcatttggccttaa atgggattctgtgagaggggggatccctccattgccagctggactgttctttggggccttatgtggtgttt gccgctgaggtactcaggggcatttaggtttttcctcattcttaaataata |
| 469 | Parechovirus F | ggtcggggagatgtgttcatgatcggttaacaccatcatggatcatctctccccgacctctttttgacc cagctatgggttaaatagtactttctttctctttctctttgctttctttgtgtttgtttgattgcaacatataa caagcattttatcagtattagtgtctgcaactgtataacaagcaaggtggagcaatcatgcgagtatatct caattgaattgtgacacacaagtgtgcactatgtggaataaatgccattttggccaaacctggttagc cagaccagtagtaggacaatttggcacccttagtgggcgcgacctagatgctagggatgagcaaa cctatttcccctgagtacaggggctctccttcacctctacttttaggacctctttttgagtatcctcgata gaaggtgaagtgacggtgtaccggatggttaattgatctcattgctgggtgacagcccgctaggac caggcagcatctttgtatggacctgtacatgtaac |
| 470 | Parechovirus D | acatggggcaggtgtgctgtgccaagagcaacactacggtggccgagccgatggttcgtcacca cgtagtaggactccgtagtgcttggttacggcggacgtaagtcagttgagtgatgtctaagtggcaa accatgagtacatggtaaccttgtgtggactcgcgggacggaatttcctatcccattgactccttgta gcaaggtgggtatacccaaccacaatggcagcaccctgggtgggaacccaggggcctggatta gtatccagtcacacagcctgatagggtggcggctcagccactgaccagcgtctctaaataattgtg agctgttcatgcacc |
| 471 | Parechovirus C | cggtcatcccccttttccccacagccggtgtgggttctaatcggctcctactaaacacctaagcatca ctgcgcctctatctctcctatccacaggtctaagacgcttggaataagacatgtgggtgcaatagga agattagctagtccaatctctccttccagctacgcttctcccttcgatgagcgtaggggggggccccc acctccctcatctctggatagggctcttgctacggggctttcccgtctggaccagcaggcccactg gtgcgcttccattcaagtttagtgtgcattactgtctgaaatattgctttgctaggatctagtgtagcga cctgcatattgccagcggacttccccacatggtaacatgtgcctctgggcccaaaaggcatgtcttt gaccgtatgcagtacaaccccagtataggtcctttctatggcagtatggatctcagtgatgagtctat acagaatatggaagtggttcggatatgtcagcccgaaggatgcccagaaggtacccgcagataa ccttaagagactgtggatctgatctggggcccaccaccttcgggtgggtagaagctaaccatgcct tgggttaaaaaacgtctaagggctgaccagacccgggggatccgggttttccctatcttgacctact ctaatc |
| 472 | Ljungan Virus 87-012 | ctcattgcccacacctggttggttcccaggttcatacaataaccatcaataaacttttaacatctaagat agtattatcccatactagactggacgaagccgcttggaataagtctagtcttatcttgtatgtgtcctg cactgaacttgtttctgtctctggagtgctctacacttcagtaggggctgtacccgggcggtcccact cttcacaggaatctgcacaggtggctttcacctctggacagtgcattccacacccgctccacggta gaagatgatgtgtgtctttgcttgtgaaaagcttgtgaaaatcgtgtgtaggcgtagcggctacttga gtgccagcggattacccctagtggtaacactagcctctgggcccaaaaggcatgtcatttgaccac tcaggtacacaaccccagtgatgcacacgcttagtaatggcttagtaacaaacattgattgatcattt gaaagctgttaggaggtttaggtatgacgggctgaaggatgccctgaaggtacccataggtaacct taagcgactatggatctgatcaggggcccaccatgtaacacatgggtagaagtcttcggaccttgg gttaaaaaacgtctaggcccgccccccacagggatgtggggtttcccttataaccccaatattgtat a |
| 473 | Parechovirus A2 | gccgtcgggccttacaccccgacttgctgagtttctctaggagagtccctttcccagccagaggtg gctggtcaaacaataccaaacgtaactaaacatctaagataacatagccctatgcctggtctccacc agttgaaggcatcttgcaataaaatgggtggattaagacgcttaaagcatggagtcaattatcttttct aactagtgatcttcactgggtggcagatggcgtgccataactctattagtgggataccacgctcgtg gatcttatgcccacacagccatcctctagtaagtttgcaaggtgtctgatgaggcgtgggaacttatt ggaaataattacttgctgcgaagcatcctactgccagcggatcaacacctggtaacaggtgcccct ggggccaaaagccacggtttaacagaccctttaggattggttaaaacctgagtaattatggaagata cttagtacctaccaacttggtaacagtgcaaacactagttgtaaggcccacgaaggatgcccagaa ggtacccgcaggtaacaagagacactgtggatctgatctggggccacctacctctatcctggtgag gtggttaaaaaacgtctagtgggccaaacccagggggggatccctggtttccttattttagtgtaaatg tcatt |
| 474 | Parechovirus A3 | agagtccttttcccagccagaggtggctggttaaataatacctactgtaacaaaacatctaagatgta acaaccacacacctggtctccactggccgaaggcaactagcaataaggcaggtgggttcagacg cttaaagtgtgttgtacatattcttttctaacctgtgttttacacagggtggcagatggcgtgccataac tctaacagtgagataccacgcttgtggaccttatgctcacacagccatcctctagtaagtttgtaagat gtctgatgacgtgtgggaacctgttggagataacagtttgctgcaaagcatcccactgccagcgga tctacatctggtaacagatgcctctggggccaaaagccaaggtttaacagaccctttgggattggtt caaacctgaactgttatggaagacatttagtacctgctgatttggtagtaatgcaaacactagttgtaa |

TABLE 17-continued

| SEQ ID NO | IRES | Sequence |
|---|---|---|
| | | ggcccacgaaggatgcccagaaggtacccgtaggtaacaagtggcactatggatctgatctggg gccagctacctctatcttggtgagttggttaaaaaacgtctagtgggccaaacccaggggggatcc tggtttctttttaatttaagtaatcact |
| 475 | Parechovirus A8 | gggccttataccccgacttgctgagtttctctaggagagtccctttcccagccctgaggcggctgga taataaaggcctcacatgtaacaaacatctaagacaaaataatttgccttgcacctggtccccactag ttgaaggcatctagcaataagatgagtggaacaaggacgcttaaagtgcaatgatagttatcttttct aacccactatttatagtggggtggtggatggcgcaccataattctaatagtgagataccacgcttgtg gaccttatgctcacacagccatcctctagtaagtttgtgagacgtctggtgacgtgtgggaacttact ggaaacaatgctttgccgtaaggctttcattagccagcggaccaccacctggtaacaggtgcctct ggggccaaaagccaaggtttaatagaccctaatggaatggttcaaacctggagcattgtggaaagt acttagtacctgctgatctggtagtaatgcaaacactagttgtacggcccacgaaggatgcccaga aggtacccgtaggtaacaagtgacactatggatctgatctggggccaactacctctatcttggtgag aggttaaaaaacgtctagtgggccaaacccaggggggatccctggtttcctttttatttacttttgtcaa t |
| 476 | Parechovirus A17 | ctctattagtgagataccacgcttgtggaccttatgctcacacagccatcctctagtaagtttgtaaga cgtctggtgacgtgtgggaacttgtgggaatcaatattttgctttaaagcatccattagccagcggat aaaacacctggtaacaggtgcctctggggccaaaagccaaggtttaacagaccctagtggattgg tttcaaaacctgaaatattgtggaacacactcagtacctactgatctggtagtaatgcaagcactagtt gtaaggcccacgaaggatgcccagaaggtacctgtagggaacaagagacactatagatctgatct ggggctggctacctctattttggtgagtcagttaaaaaacgtctagtgggccaaacccagggggga ccctggtttccatttattttacaaaggcact |
| 477 | Potamipivirus A | cacatggaaagcttttcgcttccatgtttacgcacacactctctttgacaccctgttgtatggtgttaaa ctacaacatttgtctgtctataatcgttttattttgtttaccctatatgtacccaagtatttgattgcttgac tcacataagcatcggtaacccatactgttttatgagctactacctctgctgtctacatacattttatatgaat ggtttgagctctgcctcaggatcaaacatggtaacatgttcctttggtcagttagaatcttattgtataat ctaaggtgtctattagtacgtagaaagttgtaacacatatggggcctgatagccgctatctctgatgg atgtaaggtaaccttctttaggtctgatacattctgcacaggatccaattttcggtgccctgtacgagt gcactcttatgcacgaggacgagatatgctacaacccactgcaaatttaaacccaaactttaaca |
| 478 | Potamipivirus B | tttcaacgtcgtggctgacgttaaaaagccacaattccacttaccttttaccttttatgtttaatgtttgtta gttttgtgatctttaacaaatagatctaaataatttgttggtaaccaatctcggatgtttcggctgcattgt agtttatttatttcattttagttgtaggtggccactacgtcctggaatcatacatggtaacatgtacctcg gcggttatccactattacgctaatctaagaatatttaaatgaaaatgtaagtgttacggctgactttgg gcctgatagttaaatgctcgcactgacagatagtaccctcctttaggatcgattctgttacatgggatc cattttggtgccccactgattcaacctctttgagaaaaagagttagcatactacaaatttccaaacaa aaaccctttttaatgactacaacttatgatatttgaattttactgctcttgaaaaagatattttgacattga tcgctgtactgtttcagacattcattgcatccattttgttggctactcctcacaaactcaaaacttttcca cacgagaaaccttgtttattgaatttgcctttatttttaggaacttgttgttggatttattgtttgcttaat tattgacctcacacctgttttaaacactacaat |
| 479 | Beihai Conger Picornavirus | gggacaaccccacagctggtacaaccattgtgggttggtctccaccctttttcaaccgtggcaactt cggttaaagttgcaaatccccccctctccctattccacctcccttactacactccccatatatggtccca gattttattctacctctttatatttttatttagtacagtggtggtgaattactcccagcataaactttgctgg atcagtgttcatcaagcatactaattactaatgtactgagctatactattatctggcatctcacctggat aaccggtgtgaccatatttcctaggttgcctccctatgtattttgtagcacctgtgcatctgcacgttgg ggcgacaaattgtaggtttcctggcacgggtaagaattgtggaaagctagtatgcagttaatgcaa gggcgcgtttttcgctaccccgacactgctaaagtttttgggaggggtcccttaaacatttctagtatt gagtgatagctttgcggcaggtcaccacaaccttactataaataaacctgttgaatctcac |
| 480 | Porcine Sapelovirus JD2011 | tacgcatgtattccacactcatttccccctccacccttaaggtggttgtatccccataccttaccctcc cttccacaatggacggacaaatggatttgacctcacggcaaacacatatggtatgatttcggataca ccttaacggcagtagcgtggcgagctatggaaaaatcgcaattgtcgatagccatgttagtgacgc gcttcggcgtgctcctttggtgattcggcgactggttacaggagagtaggcagtgagctatgggca aacctctacagtattacttagagggaatgtgcaattgagacttgacgagcgtctcctcggagatgtg gcgcatgctcttggcattaccatagtgagcttccaggttgggaaacctggactgggcctatactacc tgatagggtcgcggctggccgcctgtaactagtatagtcagttgaaaccccccc |
| 481 | Porcine Sapelovirus A2 | ttgaaatgggtgtggggtacatgcgtattacggtacgcatatattccacactcatttcccccccctcca cccttaaggtggttgtatccccataccttaccctcccttctaaaacagatggacaaatggatttgaact tatggcaagtgaatatggtatgactttggatacactttaacggcagtagcgtggcgagctatggaaa aatcgcaattgtcgatagccatgttagtgacgcgcttcggcgtgctcctttggtgattcggcgactgg ttacaggagagtaggcagtgagctatgggcaaacctctacagtattacttagagggaatgtgcaatt gagacttgacgagcgtctcttagagatgtggcgcatgctcttggcattaccatagtgagcttccagg ttgggaaacctggactgggcctatactacctgatagggtcgcggctggccgcctgtaactagtata gtcagttgaaaccccccc |
| 482 | Simian Sapelovirus 1 | ccaaggatctgttgcataggcgttgtatcccctaaccttttacctacccatcccaataggactggtatt tcggttttgattgagtaatggatactgattctatacctgttacccattcaggggaaaaatggagtttcttt catggatctgacttgatatgaccaagagtcaacactttgcgtgttggccgtatggaatgctttaaggtt tattctttggattatgacttcagggttggccgcccaggataaaaggcaattgtggtaagtgatgttagt cattggtggttgaaacctgcctaagacgtcctaggtctacgctgtgcgggccgaagtaagcttagg |

TABLE 17-continued

IRES sequences.

| SEQ ID NO | IRES | Sequence |
|---|---|---|
| | | aataacagggagtatgccattttctgctttcacccaacacgaccgtacacgaaagagctagaggca<br>ctttggggcaaagggaaaagctttgcttagcccgaatgttcatttgagtccttgacgaatgcgtccc<br>gtctgtcccgacggtgaggcgtatggcgcatgctcatggcattacccaatggtgtatctgtgaggg<br>gggggctcctcacacttagtctagtgctacctgacagggccgcggctggtcgtttgtgtatggtata<br>accagtagtaatcccccatggattgctttaacttcccctcctcccttaccaagacattctctaag |
| 483 | Simian<br>Sapelovirus<br>2 | ttttaacttgttatgacattcaaggaaaaaatgtctttttcattatgggactgacctgtttatgaacatgag<br>cagcggcactgctccacgggctatccgtgtaagaaatattgattattcttatggatcatgatttcagg<br>gttggccgcccagtctaaaaggcaattgtggtaagctatgtaagtagttggctgttgaaaggagcc<br>aagtacatcctaggtctacgctgtgcgggccgaagtaagacttggaacaactctgagtaggcagtt<br>tttctctttagcccaacacgaccgcatactgaagagctagaggcactttggggcaaaggtaaaagc<br>attgcttagaccgaatgttcaatgagaccttgacgagtgctgtcacagtgtcccctgatggcagtatg<br>gcgcatgctcttggcattacccatatgtgtatctatagggggggggcccccctatacttagtctagtgc<br>tacctgacagggccgcggctggtcgtcggtgtgtggtataaccagtagtaatcccccatggattgc<br>tttaactccccctcctccctcaacaaaactttctctaag |
| 484 | Rabovirus<br>C | ccgggtataacccggagttttggggcaggtccaagccccacataggaacatacgatccacggatc<br>gtgtgttcttttatgctttctaaccttaccctttgtaaccattacgctttacgccgcatggtgtttggcggc<br>accatgacgtggacaagaggttacgccattacgatatgtaccctccctttaggggagagaccgac<br>caattatggtacagtatccaactgtattgtggtcaagtttcactgtttccccggtgatgcgggataggc<br>tgtacccacggccaaaacctgctgatccgttacccgactcacatctacgaggaggctagtaaaag<br>gcatgaagttcaagagtatgatccaaccagatccccactggtaaactagtgatgagggttcccgac<br>cgaacatggcaacatgtgggttccctgcgttggcactaggccccttccgaggggtgctctgaagat<br>ggattgttgatgaagaccaatttgtgcatgtgtttatcctccggccctctga |
| 485 | Rabovirus<br>A<br>NYC-B10 | ccgaccccactggtcgaaggccacttggcaataagactggtggaacaaggtcgcctgtagttgatt<br>ggaaccttctttctaatgacttatgtcagcggtgctactcacaccgtaactctcctaccctatccccac<br>gcttgtggaactaggaggggatgagtgattcaagtaagtactgtcagaatggtgaaaataatctgat<br>tctgaaacgctatggatccatcgaaagatggggctacacgcctgcggaacaacacatggtaacat<br>gtgccccaggggccgaaagccacggtgataggatcacccgtgtagtttgagatcatatcaatgttc<br>atagtctagtaagatgatttgaaatctaactggtctgatggctaactgcttgtcttattgcggcctaagg<br>atgtcctgcaggtacctttagagaaccattagagactattgatctgagcaggagccaaggtggtcttt<br>cccagccttggttaaaaagcgtctaagccgcggcaggggggcgggaggcccccctttcctcccaaa<br>ctataatatagattgt |
| 486 | Parabovirus<br>C | gatgtatccccatcccccagtgtgtatgccatactgcatagctcgcctatgccctatggattcacaac<br>cctttcatataccctccctacccaaccccgtaaccacatgctttactccgcttggggttttgcggcccc<br>atgttgtgacgaaatggctacgcaatcaatgcggctaatggggcctgccgcttttaagtggcccca<br>gttagaagtttatgcacacccgcccattaggaggccaccagccaggtggtcagagggcaagcac<br>ttctgtttccccggtgaagtttgataagctgtgcccacggctgaagcagacagatccgttacccgcc<br>tcactactacgagacggctagtagtgtgtaatatccgaatttcattgatccgggtgttccccccaccc<br>agaaacgtgtgatgaggagcggcacccctcctatggcaacatagggcctctcctgcgctggcac<br>acgggctctatgagcatgaaatcaggagaaagtcacacgaagaccaattgtgctagtgagattcc<br>tccgccccccctgaatgcggctaatcccaactccggagcgcccgctggcaaacccgccagaaga<br>gcgtcgtaatgcgtaagtctggagcggaaccgactactttgggtgtggcgtgtttcctttatttccttt<br>gtatttgtat |
| 487 | Parabovirus<br>B | aacccataatccattgtccatcaatgttttatggggggacccttttctcccctcccccctccaaatacct<br>tttacccctctgtaaccaagagtgtgcaaaatctatttactagcccagaattgcggcttctggggagg<br>tttattcctcatgcctaacaagatgttacgcaaactccgggctacggccctgggcttttgccctaaag<br>atttagaagtttacactatcgtccaacaggaggacaacaaaccagttgttctaaggacaagcacact<br>gtttccccggtgagactggatagactgtacccacggttgaaactggttgatccgttacccgactcac<br>tacttcgagaagattagtaggaaactgtgaaactgattccattgatccggatactttccccgtatcca<br>gaaactactgatgagggttgacttcccgactacggcgacgtagtgtcatccctgcgctggcagtag<br>gcctctttgaggatggaagatgtggatcggtaaccgaaggtcctattgagctagtgtttatacctccg<br>gcctcctgaatgcggctaatcctaacccatgatctagtgctcacaaaccagtgagtagctagtcgta<br>acgcgtaagtcgtgggcggaaccgactactttggagtgaccgtgtttcctattttacttttgtttg |
| 488 | Parabovirus<br>A3 | accgttacgcaccactcagttggtgtttggtggcaccaatgatggaacaaaaggctacaccacttg<br>ggctacggcccgcgccaccttgtggcgcaaagacattagaagaatagcataccgcccactaggg<br>ccctgcagccagcagggtaacgggcaagcacttctgtctccccggtagaacggtataggctgtac<br>ccacggccgaaaactgaactatcgttacccgactccgtacttcgcaaagcttagtaggaaactgga<br>aagttcgagttattgacccggagtgttccccccactccagaaacgcgtgatgagggttgccacccc<br>gaccatggcgacatggtgggcatccctgcgctggcacgcggcctctaagaggataactcgctcct<br>actggtaaccgaagagccccgtgagctacggtttattcctccgcctccctgaatgcggctaatccta<br>acccatgagcagttgccatagatccatatggtggactgtcgtaacgcgtaagttgtgggcggaacc<br>gactactttgggatggcgtgtttccttgttttctccatttgttgttgtatggtgacaagttatagatctcga<br>tctatagcgtttcttgagagtttaccaaacatttattcaagtcgtacaattcttgtgtttaagcagtacagt<br>gtaagg |
| 489 | Felipivirus<br>127F | gatgtcggatgacggctggccaccggggaaaaacggcaaatgtgcaccacctctgcaacccac<br>gccgaccacgtttaaccatggcgttagtaggagtggaccactgcagtgggctctggtgtgcgaca<br>gtcagtggtagagtagacagtcctgactgggcaatgggaccgcgttgcgtatccctaggtggcat |

TABLE 17-continued

IRES sequences.

| SEQ ID NO | IRES | Sequence |
|---|---|---|
| | | cgagattcctctgctacccaccagcgtggactcctatgggggggccccataggctaggtctatac<br>tgcctgatagggtcgcggctggtcgaccactgactgtataaccagttgtaactcact |
| 490 | Boosepivirus A | ttgaaagacctcggcatatatcgttgtcacaacggtatatgtcgagatctttctccccaccccctcca<br>attccctttttcccccctcttgcaacttagaagtagtttcacacagggcaataggatacgtgatccagcc<br>aggacacgtgagctcaagcacttctgtttccccgtccccttcacgtactacgggaatgttagtaattt<br>gtgtgcactttagtaaggttgatccgggattaaccccaaatcccagaaactggtgatgagcgttacc<br>acccccgccgggcgaccggaaggtttcgctgcgaggcaccagggcttcggcaccagaaaaag<br>gtaaagcaaatgaaggcgctactgtgctacgagaagtttcctccaggcccctgaatgcggctaatc<br>ctaaccagtgatccaccggtgcaaaaccatgtactaggtggtcgtaacgcgcaagtcgctggcgg<br>aaccgactactttgggtgtcctgtgtttccatatttattttattcaattttatggtgacaagagtaaagag<br>atacagatttgcagcc |
| 491 | Boosepivirus B | ttttctcccctcccccctccaactaccctttccccctcttgtaacgctagaagtttgtgcaaaccgcctgt<br>agggtactgcaatccagcagtgcataggctaagcttttcttgttaccccaccccacattatactgagg<br>aggattgtgaaattgtgttagtatgggttagtagcggtgacccgggtaaccccaacccagaaactc<br>acggatgagatgaacaggaccccacatggtaacgtgtgtgttcgtctgccccgcaaggtgaggcc<br>gtgagagctttgcacgcgaaaaccttgaaaacccaaaagtaccttgagctcttcgctattttgtgtttc<br>ctccaggaccctgaatgcggctaaacctaacccgcgatccgcacgtagcaacccagctagagtgt<br>ggtcgtaatgcgcaagttgcgggcggtaccgactactttggtgttcctgtgtttcctttattttattttga<br>atttttatggtgacaacagctagaaaataagagtgaac |
| 492 | Phacovirus Pf-CHK1 | gtgtgtcatttctcccctcccccctcccaaaccttttccccctctaatcggattgattaacccggttaaag<br>atgattaatggtttgtgagttgatatgatggcccggcattgaatccgggaattcttaagtaatggaatt<br>gcatccaatatgaaagtgagtgtggcaagctcacaagtagtacttggctctgcccattatttgagga<br>caactcttcttgactacaatgtgtttaaagtaaactggaccacattgtgtatccagacaactccatttg<br>ataatgtacgctggaaacgttttcagtgcatagggtcctaaagtggtgctgaaatattgcaagctcaa<br>tgggatactgaacgctgaaaaccgccgctgttatcatatgggcccctagtgggtaaatgttggcttt<br>aggcatatactgcttgggaatgcagtactggttgtagacagggtgatagcctaccggctggcgtag<br>ttgagaggtatagccagttgattgccat |
| 493 | HRVC3 QPM | ttaaagctggatcatggttgttcccaccatgattacccacgcggtgcagtggtcttgtattacggtac<br>atttccataccagttttatacaccccaccccgaaactcatagaagtttgtacacaatgaccaataggt<br>ggtggccatccaggtcgctaatggtcaagcacttctgtttccccggcacccttgtatacgcttcaccc<br>gaggcgaaaaatgaggttgtcgttatccgcaaagtgcctacgaaaagcctagtaacactttgaaaa<br>cccatggttggtcgctcagctgatacccaacagtagacctggcagatgaggctagacattcccca<br>ccagcgatggtggtctagcctgcgtggctgcctgcacaccctgccgggtgtgaagccagaaagt<br>ggacaaggtgtgaagagcctattgtgctcactttgagtcctccggcccctgaatgtggctaaccct a<br>accccgtagctgttgcatgtaacccaacatgtatgcagtcgtaatgggcaactatgggatgggacc<br>aactactttgggtgtccgtgtttcctgttttactttttcattgcttatggtgacaattgtatctgatacact<br>tgttacc |
| 494 | HRVB27 | ttaaaacagcggatgggtatcccaccatccgacccacagggtgtagtgctctggtattttgtaccttt<br>gcacgcctgtttccccattgtacccctccttaaatttcctccccaagtaacgttagaagtttaaggaaa<br>caaatgtacaataggaagcatcacatccagtggtgttatgtacaagcacttctgtttccccggagcg<br>aggtataagtggtacccaccgccgaaagcctttaaccgttatccgccaatcaactacgtaatggcta<br>gtattaccatgtttgtgacttggtgttcgatcaggtggacccccccactagtttggtcgatgaggctag<br>gaactccccacgggtgaccgtgtcctagcctgcgtggcggccaacccagcttttgctgggacgcc<br>tttttacagacatggtgtgaagacctgcatgtgcttgattgtgagtcctccggcccctgaatgcggct<br>aaccttaaccccggagccttgcaacataatccaatgttgttgaggtcgtaatgagtaattctgggatg<br>ggaccgactactttgggtgtccgtgtttccttttattctttatattgtcttatggtcacagcatatatagcat<br>atatactgtgatc |
| 495 | HRVA73 | ttaaaactgggtttgggttgttcccacccaaaccacccacgcggtgttgtacactgttattccggtaa<br>ccttgtacgccagttttatatcccttccccccccttgtaacttagaagacatgcgaatcgaccaatagca<br>ggcaatcaaccagattgtcaccggtcaagcacttctgtttccccggctctcgttgatatgctccaaca<br>gggcaaaaacaattggagtcgttacccgcaagatgcctacgcaaaacctagtagcatcttcgaag<br>atttttggttggtcgctcagttgctaccccagcaatagacctggcagatgaggctagaaatacccca<br>ctggtgacagtgttctagcctgcgtggctgcctgcacacccacacgggtgtgaagccaaagattg<br>gacaaggtgtgaagagtcacgtgtgctcatcttgagtcctccggcccctgaatgcggctaacctta<br>accccgtagccattgctcgcaatccagcgagtatatggtcgtaatgagtaattacgggatgggacc<br>gactactttgggtgtccgtgtttcacttttttacttatcaatttgcttatggtgacaatatatatagatatat<br>attgacacc |
| 496 | EV L | acatgggccagcccaccacacccactgggtgtagtagtctggttctatggaacctttctacgcctctt<br>ttgcttccctcccccatttctccttcgattgctccacctgtgatctttgcaacttagaagaaataatgaac<br>ccgcacaatagcgggcgctgagccacagcgtcaatgtgcaagcacttctgtttccccggaatggg<br>cccataggctgtacccacggctgaaaggaccggcccgttacccgccttggtactgcgagaatgt<br>tagtaactccctcgatagctttaggcgttacgctcagccctttgagcccgaagggtagttcgggtcg<br>atgaggctcgtcattccccactggcgacagtgtgacttgcctgcgttggcggcccggggtggggg<br>gcaaccccccatccacgcctactgaaggacagggtgtgaaggcgctattgcgctactaaggagtcc<br>tccggcccctgaatgcggctaacccgaaccccgagcccacggtggtaaacccgccacaagtgg<br>gtcgtaatgagtaatttggggcagggaccgactactttgggtgtccgtgtttcctgtttttccatacgat<br>ggctgcttatggtgacaaccataagcaattggattggccatccggtgttcatattgcgaat |

TABLE 17-continued

IRES sequences.

| SEQ ID NO | IRES | Sequence |
|---|---|---|
| 497 | EV K | tcagcctgacgcaagtgcctccattggagtctctccaagccctccggggcttggagggcgccgac<br>cccctgcctagggggagcccacgacacggctggagtccattggcacaccgcagccacgattca<br>agccagaattgaaagcgggaagcacttctgtctccccggtgtggatcatacgctgtacccacggc<br>gaaaagtgaagcatcgttacccgactcggtacttcgagaagcccagtacagttgtggatctctgca<br>gggtatacgctcagcgtgacccctacgtagttccttgagatggctgagagaacaccccacgggcg<br>accgtgtctctcggcgcgtggctcaaggccgggccttcagtggctcggtgccttgcagagtgaag<br>cctccgaacagcctattgagctaccgtttagcctccgccctcttgaatgcggctaatcctaaccatg<br>gagcgcccgcccacagtccagtgggtagagcgtcgtaacgcgcaagtccgtggcggaaccgac<br>tactttagagtggcgtgtttccaatttatcctttataaagttgcttatggtgacaccacaagagatccac<br>gatttcttgtttcttatcactgagacacaagtcatattcatcaatctttattgcggaattaacttggtgcgt<br>ccaaacacatcagc |
| 498 | EV J 1631 | caccctgagggcccacgtggcgtagtactctggtatcaaggtacctttgtacgcctattttatttccct<br>tcccccacagtaacttagaagcttatctcatagttcaacagtagggtcactaaccaagtggctcagc<br>gaacaagcacttctgtttccccggtcctagtacctgtgaagctgtacccacggcggaaggggaaa<br>aagatcgttatccggcccctacttcggaaagcctagtaacaccattgaagcaatcgagtgttgcg<br>ctcagcacagtaacccctgtgtagctttggttgatgagtctgggcactccccactggcgacagcgg<br>cccaggctgcgttggcggccaaccgactcgggcaacccgggtcggacgctcgtttgtggacatgg<br>tgtgaagagcctactgagctagagggtagtcctccggcccctgaatgcggataatcctaaccccg<br>gagcacccacactcaatccagagtgcaggatgtcgtaacgcgtaagtctgggacggaaccgact<br>actttgggtgtccgtgtttcctgttttacttactttggctgcttatggtgacaatctagtgttgttaccatat<br>agctattggattggccatccggtgttttgaattgtgtgtttatactaattcttttacatatcacagacaacc<br>aaat |
| 499 | EV J N125 | cggtacctttgtacgcctattttaccccttccccttgtaacttagaagcaaagcaaaccagttcaata<br>gtaagcaacacaacccagtgttgtgacgaacaagtacttctgtttccccgggagggtctgacggta<br>agctgtacccacggctgaagtatgacctaccgttaaccggctacctacttcgagaagtctagtaata<br>ccattgaagttttgttggcgttacgctcaacacactaccccgtgtgtagttttggctgatgagtcacgg<br>cattccccacgggcgaccgtggccgtggctgcgttgcggccaaccaaggggcgcaagctccttg<br>gacgtcacttaacagacatggtgtgaagaacctattgagctaggtagtagtcctccggcccctgaat<br>gcggctaatcctaactccggagcacatcagtgcaacccagcatttggtgtgttgtaatacgcaagtc<br>tggagcggaaccgactactttgggtgtccgtgtttcctgttttaccttatttggctgcttatggtgacaa<br>tttgatattgttaccatatagctgttggattggccatccggattttgaaagagacccaaaactttcttct<br>ctacttcagattcaagtgcgaagttttccttttcatatattacttactaatttgaagtaccaaag |
| 500 | EV I | ttagtactttctcacggggatagtggtatccctccctagtaatttagaagacttgaaaaaccgaccaat<br>aggcacctcgcatccagcggggtaaaggtcaagcacttctgtttccccgggtcgagtagcgatag<br>actgtgcccacggtcgaaggtgaaacaacccgttatccgactttgtacttcgggaagcctagtacc<br>accaaagattatgcttggggtttcgctcagcacgaccctggtgtagatcaggccgatggatcaccg<br>cattcctcacggcgactgtggcggtggtcgcgtggcagcctgccgatggggcaacccatcgga<br>cgccaagcatatgacagggtgtgaagagcctactgagctacaaagtattcctccggcccctgaat<br>gcggctaatcccaacccacggagcatttgctaccaaaccaggtagtggaatgtcgtaacgggtaac<br>tctgtggcggaaccgactactttgggtgtccgtgtttccttttaatttatcattctgtatatggtgacaact<br>atagtgctatctcgatttgcattactattgttgagattaaaactttattacattgttgcattttaccctttg<br>agtgagttttcacctgaacagattaatttactcatcctgtttatatattacaagcagaaatacttgcaaag |
| 501 | EV F1<br>BEV 261 | gcaatgctgcaccagtgcactggtacgctagtaccttttcacggagtagatggtatcccttaccccg<br>gaacctagaagattgcacacaaaccgaccaataggcgcaccgcatccagccgtgcagcggtca<br>agcacttctgtctccccggtctgtaaagatcgttatccgcccgacccactacgaaaagcctagtaac<br>tggccaagtgaacgcgaagttgcgctccgccacaaccccagtggtagctctggaagatggggct<br>cgcaccacccccgtggtaacacggttgcctgcccgcgtgtgcttccgggttcggtctcgtgccgtt<br>cacttcaacttcacgcaaccagccaagagcctattgtgctgggacggttttcctccggggccgtga<br>atgctgctaatcccaacctccgagcgtgtgcgcacaatccagtgttgctacgtcgtaacgcgtaagt<br>tggaggcggaacagactactttcggtaccccgtgtttcctctcattttatttaatattttatggtgacaat<br>tgttgagatttgcgctcttgcaacgttgccattgaatattggcttatactatttggttgccttttacaaaac<br>ctctgatatacccagttcttacattgatctgcttgtttttctcaatttgaagtatagactacaaatagcaaa |
| 502 | EV D94 | cgtggcggccagtactctggtatcacggtacctttgtacgcctgttttatatccccttcccccgcaact<br>tagaagaaaacaaatcaagttcactaggaggggtacaaaccagtaccaccacgaacaagcact<br>tctgtttccccggtgatgtcgtatagactgtaaccacggttgaaaacgattgatccgttatccgctctt<br>gtacttcgaaaagcccagtatcaccttggaatcttcgatgcgttgcgctcagcactcaaccccagag<br>tgtagcttaggtcgatgagtctggacactcctcaccggcgacggtggtccaggctgcgttggcgg<br>cctacctgtggtccaaagccacaggacgctagttgtgaacaaggtgtgaagagcctattgagctac<br>aagagaatcctccggcccctgaatgcggctaatcctaaccacggagcaagggtacacaaaccag<br>tgtatatcttgtcgtaacgcgcaagtctgtggcggaaccgactactttgggtgtccgtgtttccttttgt<br>ttttatcatggctgcttatggtgacaatctaagattgttatcatatagctgttggattggccatccggtaa<br>tttattgagatttgagcatttgcttgtttcttcaacaatttcacctattcattgcatttcagcagtcaaa |
| 503 | PV3 | tacctttgtacgcctgttttatactccctcccccgcaacttagaagcatacaattcaagctcaatagga<br>gggggtgcaagccagcgcctccgtgggcaagcactactgtttccccggtgaggccgcatagact<br>gttcccacggttgaaagtggccgatccgttatccgctcatgtacttcgagaagcctagtatcgctctg<br>gaatcttcgacgcgttgcgctcagcactcaaccccggagtgtagcttgggccgatgagtctggac<br>agtccccactggcgacagtggtccaggctgcgctggcggcccacctgtggcccaaagccacgg |

TABLE 17-continued

IRES sequences.

| SEQ ID NO | IRES | Sequence |
| --- | --- | --- |
| | | gacgctagttgtgaacagggtgtgaagagcctattgagctacatgagagtcctccggcccctgaat<br>gcggctaatcctaaccatggagcaggcagctgcaacccagcagccagcctgtcgtaacgcgcaa<br>gtccgtggcggaaccgactactttgggtgtccgtgtttccttttattcttgaatggctgcttatggtgac<br>aatcatagattgttatcataaagcgagttggattggccatccagtgtgaatcagattaattactcccttg<br>tttgttggatccactcccgaaacgttttactccttaacttattgaaattgtttgaagacaggatttcagtgt<br>caca |
| 504 | EV C102 | ctttgtacgcctgttttacatcccctcccccacgtaactttagaagcaattcaacaagttcaatagagg<br>gggtacaaaccagtatcaccacgaacaagcacttctgtttccccggtgattttacataagctgtgcc<br>cacggctgaaagtgaatgatccgttacccgctcgagtacttcgaaaagcctagtatcgctttgggat<br>cttcgacgcgttgcgctcagcactctaccccgagtgtagcttaggctgatgagtctgggcattcccc<br>atcggcgacgatggcccaggctgcgttggcggcctacccatggctaacgccatgggacgctagt<br>tgtgaacaaggtgtgaagagcctattgagctactcgagagtcctccggcccctgaatgcggctaat<br>cccaaccacggatcaggtgcctccaacccaggaggtggcctgtcgtaacgcgcaagtctgtggc<br>ggaaccgactactttgggtgtccgtgtttccttttatcttttaaatggctgcttatggtgacaatcataga<br>ttgttatcataaagcgaattggattggccatccggtgaaatacaaacacattatttacttgtttgttggat<br>ttactccgctcacacagcttactcctaagataatatttattgtattgctggtaaggagacactattata |
| 505 | EV 30 | aagcaaggcaaacctgaccaatagtaggtgtggcacaccagccgcattttggtcaagcacttctgt<br>ttccccggaccgagtatcaataagctgctcacgcggctgaaggagaaaccgttcgttacccgacc<br>agctacttcgagaaacctagtaacactatgaacgttgcggagtgtttcgttcagcacttccccgtgt<br>agatcaggtcgatgagtcaccgcattcctcacgggtgaccgtggcggtggctgcgttggcggcct<br>gcctacgggttcgcccgtaggacgctctaataccgacatggtgtgaagagtccattgagctagctg<br>gtagtcctccggcccctgaatgcggctaatcctaactgcggagcaggtgctcacagaccagtgag<br>tagcctgtcgtaacgggcaactctgcagcggaaccgactactttgggtgtttttcctttttttcttctctta<br>tattggctgcttatggtgacaattaaagaattgttaccatatagctattggattggccatccggtgacg<br>agcagagccattgtttacctctttgttggatttgtacctttgaaccacaaagtcttgaataccattcatct<br>cattttaaagttcaactcagctaaaagaaa |
| 506 | SA5 | agtacttggtattccggtacctttgtacacctatttacaaaccctaccccttgtaaccttagaagcaatt<br>atttaaccgctcactaggggtgtgctatccaagcacatcaagagcaagcacttctgtctccccgg<br>gaggggctaatggtacgctgtgcccacggcggaaatgagccctaccgttaaccggcagtctactt<br>cgggaagcccagtaactacattgaaactttgaggcgttacactcagcacataaccccaatgtgtagt<br>tctggtcgatgagccttggcatcccccacaggcgactgtggccaaggctgcgttggcggccagc<br>ctgcggaccaaaagtccgtaggacgcctaattgtggacatggtgtgaagagcctactgagctaga<br>ctgtagtcctccggcccctgaatgcggctaatcctaaccctggagcatccgcgtgcaacccagtac<br>gtagggtgtcgtaatgcgtaagtctgggatggaaccgactactttgggtgtccgtgtttcttgtttttca<br>tactgggtcgcttatggttacaactaattgttgtaatcattggcagtgcgcgctgaccacgcgattatt<br>gatatttccatttgttggatactccaatagtgtcaactcatatacacaacttttaccactgatcaagataa<br>aa |
| 507 | EV A114 | tgtgcgcctgttttgaaacccccctcccccaactcgaaacgtagaagtaatgtacactactgatcagta<br>gcaggcgtggcgcaccagccatgtctcgatcaagcacttctgtttccccggactgagtatcaatag<br>actgctcacgcggttgaaggtgaaaacgtccgttacccggctaactacttcgagaaacctagtagc<br>accatagaaactgcagagtgtttcgctcagcacttccccgtgtagatcaggtcgatgagtcactgc<br>aatccccacgggtgaccgtggcagtggctgcgttggcggcctgcctatggggcaacccatagga<br>cgctctaaggtggacatggtgtgaagagtctattgagctagttagtagtcctccggcccctgaatgc<br>ggctaatcctaactgtggagcgcatactcccaaaccagggagcagtgcgtcgtaacgggcaactc<br>cgcagcggaaccgactactttgggtgtccgtgtttccttttattcctatactggctgcttatggtgacaa<br>ttgagagattgttaccatatagctattggattggccatccagtgtgtaatagagcaatcatttaccaatt<br>tgttggatttactccattaacccacacgtctctcaacacactacatttcatcttactactgaacactaga<br>aa |
| 508 | Mobovirus A | tattctcccacaaaccttcttgtaactctgttaagccttttacatccatgtaatttaattttctccacctaaa<br>aggatttcccccatggtcctttttggctcgaacaaatgctacatagggtcttgttttctccccctggctc<br>tcttgccagggttccataccccaattcctctatttccatgattttcatcatggtttatttttactgtcttct<br>tattttctgaggtgaccaactcctaagccgactgggtcgcggaagcccggactcctcgcatcactagg<br>gtgcgtagcgatgtaggcgaaaatattggttgctagatgcatacatatagtgaattgatactacacca<br>aactctgttctttttgaaactagctattttctaagtaaggtaggctacgggtgaaaccttaccattgcag<br>gtacgtgaaccgcaacggacatttggccgaagactggtgtacccacgtcagttataggacctcttc<br>aacgttggtggacggcatgtcactgattagttaggctagtgaatttaagttcagggggtatcttttagc<br>ttaagcgtgtattctagtaggacttgcagagcctccccacctaggaggatctctgtttatagccccttt<br>tccttgttccgttagttttccacacttttacaatatttgatgatttgtt |
| 509 | Burpengary Virus | ctcccccccccttccccttcccgagtaggagattggcatgtatgctctacatgcccgattctctcttgct<br>cactctcttaaatcctggtggcggtctcggattaaacatttatgtcgtatctgggatcgtcttacttggt<br>ggtaattcctctgttgcctagggacctccggactgccggattaaaggtctcaacagagggcaatgt<br>acaaggaagtcattatacgctaattaagtatttgatgaatgactagtgtgacagggctgaggaactc<br>cccccgggtaaccggtgcctcagcgtccgaaagacacgtggataggatccaccctgttataccca<br>gcacgatgtaatagtcaaatacctctgatttgtgtaggatgtataaattgtgcattgtaaattttgggcg<br>tagagatgctccgaaggtaccccgttttacgggatctgatcggaggctaattacccaatgcgcccta<br>aataacttcatataatttctttttcttattcaaa |

TABLE 17-continued

IRES sequences.

| SEQ ID NO | IRES | Sequence |
| --- | --- | --- |
| 510 | Hunnivirus A1 | taacgtttggcaagaaccctcacctgtcaattgggaccaccactttcagtgaccccatgcgaagtag<br>tgagagagaataagctttcttacccttcatttgtgaacccttcagtcgaagccgcttggaataagata<br>ggaggaaaagttcattctaaatggagtgaaacatgtacttcagaatttctagcacgcgctgggctttc<br>ttgcgtgtgacggcactgtcttgccggagctctccacactgacaccccacgcttgtggaccttggtg<br>gcagatgacaacactgcagctggaattgagtgtctggtacactctgtgtaacagtgaaaacaatgt<br>gatcacttcggtgagctagtagcctgtggaccaacaactggtaacagttgcctcaggggccaaaa<br>gccacggtgtttacagcaccctactggtttgattggagcaatccaagatgtcacagagttagtaattg<br>ccaagcagtccgtactggtatcttgacataccgtgcagttttggatagtgaaggatgccctgacggt<br>acccataggtaacaagtgacactatggatctaagcaggggctcactctacgctgctttacagctgg<br>ctgtgagttaaaaaacgtctagctatccacaacctaggggactaggttttccttttatttagattacaatt<br>at |
| 511 | Hunnivirus A2 | acagtttttgacaaggaccctcacctgtcaatcgggaccaccactttcagtgaccccgtgcgaagt<br>gttgagagaaagtgagctttcttacccttcatttgtgaacccttcagtcgaagccgcttggaataagat<br>ggaaggaaatgttcattctaaatggagtgaaacatatacttaatttccagtgtttagtggtctttccact<br>agacaacggcactgtcttgccggaactctacacaccaacattccacgcttgtgggactcaaatgttg<br>gatgacacagttgtagctggaactgagtgtttagtgcactctgtgtaacagtgaaaacaatgtgatca<br>cttcggtgggctagtagcctgtggactaacaactggtaacagttgcctcaggggccaaaagccac<br>ggtgttaacagcaccctactagtttgattggagcaatccatgatgttacagagttagtaactgccaaa<br>cagattgtactggtatcttggcataccgtgcaacttaggatagtgaaggatgccctggcggtaccca<br>taggtaacaagtgacactatggatctaaacaggggctcactctacgttgctttacaactagctgtga<br>gttaaaaaacgtctaactatccacaacctaggggactaggttttccttttattttatacacaacta |
| 512 | Ia Io | ggtgtccgggtgtgtgggatagacccagatgtgcagtggatgcgagcatttgagtcagagtagga<br>gcaagcccaggggcaaagggaccacattgtgtatcccgaatgaaggatcgagatttctctcctcat<br>tacccggtgtcttgtcactgaggggggggcccaacagtcttagtcctatactgcctgatagggtcgc<br>ggctggccggactcaagtgctatagtcagttgattttcactc |
| 513 | Taura Syndrome Virus | ctttaaaagtcgtgcgtggcttcaccacgcacgatcagtactatcagttaaccactcttgaatatgctc<br>aatgaccctattcaacactggtgtctcttagtacattattttagcacttaacgtgcatgagttttgcccat<br>ttctttcaaaaaaatgagtattcgaggagacgtcccgctccccgtcttatttcaaccgtagactcgac<br>atctattggtggacatttaattccagtcgccgtaagttgcttctgccccgcgctatatttcttatacttat<br>ggttctataggtctggtttaaaacgtaaatagacggcccacaaactatagaacgcgtacccggaac<br>gccaatcccggataagtccctggatatatagatgcaccgcaatataagcctgcagactgtctcatat<br>act |
| 514 | ABPV | cccgtcaaaataacaacttataacacgatgttacccgaagaaaccattttagtgtaacatttaagatta<br>gaagtagttcatctaatagagataggcactattagaaggaggccttttctaaaggagccgttagtca<br>gcccagacaagcgcagtactttagaagagagaagttccccgatagcgaccgaaaagacgcgtttt<br>ccgtgctaactaatttaaatgtgggaacgaatattattattgaaattatgtgagccacgtagcaatcaa<br>gtcatgtttttgtcactacgtttactcatctaatgtagataattttgtttaagtacctatttaggtgtcatc<br>ccaccagagaagaaataatacgtaccggaacccagagtacaccccttattttaagccttactgggcttc<br>tctgttagttagtaatctggcccacgttttgcgttgagtggggtcccaacagtaggaattcgacggac<br>aagtagcaagcgagtcggtaccaattggtttagcatcgaaattactctgggcaggaagttactaaa<br>cgagaactttctgcttaaatcccaacgcacaaacaaatagagtaaataaataattata |
| 515 | BRAV-2 | tttgttttgcggctttgccgttgttcgggttttacctgttttcacacagcaaaacaggccttctagtttcgt<br>gcttaaacgagatcatgctcgaactagaactacatagctggtcactggactcataccacaccttgtg<br>gagctttatgggaaaggtggctagtgggctgtggaagtgactctgaccacatgcctctcaagtgtg<br>ggaaatcacggatcggtgtagcgacgacaacaggccttgggacaccctctccagtaatggagac<br>ccaaggggccaaaagccacgcctcgtgccctgttgttcacaaccccagtgcgacccgtgttagta<br>cctatttgcgagaactgtgtctggacagctaaacacaaccctagtgggagactaaggatgcccag<br>gaggtacccggaggtaacaagtgacactctggatctgacctggggagagagggcttgctttacag<br>gcgcctctctttaaaaagcttctatgtctcatcaggcaccggaggccgggcctttttcctttaaaatta<br>cactta |
| 516 | BRBV-1 | ccccccctacttaaagatgtacggttttgctgctttcacagagtaaagcagatagaggttctgaactg<br>gcaaactttacctcgaaacacgcccgtttttctgctgtgtctcacagactgtcctgtcacacttgtggc<br>ggcttgtgacactgtgaacatagtgagaccgaccaagacaacagatcaagtgtttgaacatcgaac<br>gtctaaactggatccgtaactggacatgttagggcaaggacttccccccctggtaacaggagcctgg<br>ctggccaaaagccccgctcattgagcctagcatgttgtcgaccctggactgttcagatttgttagtac<br>atggaattcacttgtcacggttcttctgaactcggtctctagtatgacagcctaaggatgccctccag<br>gtaccccggggtaacaagtgacacccgggatctgaggaggggactactttacgtagtttaaaaaa<br>cgtctaagctgttatggtgaccagaggctggcacctttcacttttaaaattacactactgactacaatt<br>gaagtgataacggttttacaggctttcaaactagttacacaagcactgttttcctgacacacacacttt |
| 517 | ERAV-1U188 | aatattggcgcgcgcatttgcgcgcccccccccatttcagcccccctgtcattgactggtcgaaggc<br>gttcgcaataagactggtcgtcacttggctgactatcgatcaggattagcgcgccctcgcgcggc<br>gggccgtcaagcccgtgcgctgtatagcgccaggtaaccggacagcggcttgctggattacccg<br>gtgccattgctctggatggtgtcaccaagctgacaaatgcggactgaacctcacaaagcgacaca<br>cctgtggtagcgctgcccaaaagggagcggaactcccccgccgcgaggcggtcctctctggcc<br>aaaagcccagcgttaatagcgccttttgggatgcaggagccccacctgccaggtgtgaagtggag<br>tgagtggatctccaatttggtctgttctgaactacaccatctactgctgtgaagaatgccctggaggc |

TABLE 17-continued

IRES sequences.

| SEQ ID NO | IRES | Sequence |
|---|---|---|
| | | aagctggttacagccctgaccaggggccctgcccgtgactctcgatcggcgcagggtcaaaatt<br>gtctaagcagcagcaggaacgcgggagcgtttcttttccctttgtatcgac |
| 518 | GFTV | atggggaagggtatgacgtgccccttccttcttcggagaactcgctctagtggtctttccacttctgg<br>aaaagagtgagtgcacgtgatcaggaccgtcgaagacgacaaatacctggtgctctatctcatag<br>acgtttcacagctgtagcgacccctcagtagcagcggaagcccctcctggtgacaggagcctct<br>gcggccaaaagccacgtggataagatccactgctgagggcggtgcgaccctagcaccctgtgat<br>gcatactagttgtagcgtgccggactattggtctgtcataagacacctgatagagagaccaagaat<br>gtcctggaggtaccccgcgtgcgggatctgaccaggagaccattgcccaatgctttacaacgggt<br>ctatggtttaaaaactgtcgcagtctctccaaaccaagtggtcttggttttcaattactttgaatatttca<br>ct |
| 519 | SAFV V13C | ttttcgacgtggttggaattgccatcatttccgacgaaagtgctatcatgcctccccgattatgtgatgt<br>tttctgccctgctgggcggagcattctcgggttgagaaaccttgaatctttttctttggaaccttggttc<br>ccccggtctaagccgcttggaatatgacagggttatttcttgatcttatttctacttttgcgggttctatc<br>cgtaaaaagggtacgtgctgccccttccttctctggagaattcacacggcggtctttccgtctctcaa<br>caagtgtgaatgcagcatgccggaaacggtgaagaaaacagttttctgtggaaatttagagtgcac<br>atcgaaacagctgtagcgacctcacagtagcagcggactcccctcttggcgacaagagcctctgc<br>ggccaaaagccccgtggataagatccactgctgtgagcggtgcaaccccagcaccctggttcgat<br>gatcattctctatggaaccagaaaatggttttctcaagccctccggtagagaagccaagaatgtcct<br>gaaggtaccccgcgtgcgggatctgatcaggagaccaattggcggtgctttacactgtcactttgg<br>tttaaaaattgtcacagcttctccaaaccaagtggtcttggttttccaattttgttgaatggcaat |
| 520 | SAV P-113 | ggagatctaagtcaaccgactccgacgaaactaccatcatgcctccccgattatgtgatgctttctg<br>ccctgctgggtggagcatcctcgggttgagaaaaccttcttcctttttccttggaccccggtcccccg<br>gtctaagccgcttggaataagacagggttatcttcacctcttccttcttctacttcatagtgttctatact<br>atgaaagggtatgtgtcgccccttccttctttggagaacacgcgcggcggtctttccgtctctcgaaa<br>agcgcgtgtgcgacatgcagagaaccgtgaagaaagcagtttgcggactagctttagtgcccaca<br>agaaaacagctgtagcgaccacacaaaggcagcggaccccccctcctggcaacaggagcctct<br>gcggccaaaagccacgtggataagatccacctttgtgtgcggcacaaccccagtgccctggtttct<br>tggtgacacttcagtgaaaacgcaaatggcgatctgaagcgcctctgtaggaaagccaagaatgt<br>ccaggaggtaccccttccctcgggaagggatctgacctggagacacatcacatgtgctttacacct<br>gtgcttgtgtttaaaaattgtcacagctttcccaaaccaagtggtcttggttttcactctttaaactgattt<br>cact |
| 521 | VHEV | aattccttcttcctttctccttggacctcggtcccccggtctaagccgctcggaatatgacagggttatt<br>ttcacctcttctctcttctacttcatagtgttctatactatgaaagggtatgtgtcgccccttccttcttgga<br>gaacgtgcgtggcggtctttccgtctctcgaaaaacgtgcgtgcgacatgcagagtaacgcaaag<br>aaagcagttcttggtctagctctggtgcccacaagaaaacagctgtagcgaccacacaaaggcag<br>cggaaacccccctcctggtaacaggagcctctgcggccaaaagccacgtggataagatccacctttt<br>gtgtgcggtgcaaccccagcaccctggtttcttggtgacaccttagtgaaccctcgaatggcaatct<br>caagcgcctctgtaggaaagccaagaatgtccaggaggtaccccttcctcatggagggatctgac<br>ctggagacacatcacacgtgctatacacttgtgcttgtgtttaaaaattgtcacagctttcccaaacca<br>agtggtcttggttttcccttaacttcgaaaagtcactatggcctgcaaacatggatacccagacgtgt<br>gccct |
| 522 | TRV NGS910 | atgcgacgtggttggagattaaaccgactccgacgaaagtgctatcatgcctccccgattatgtgat<br>gttttctgccctgctgggcggagcattctcgggttgatacaccttgaatccttcatccttggacctcag<br>gtcccccggtctaagccgcttggaatacgacagggttattttccaatcttctcctttctactttcatgag<br>tcctattcatgaaaagggtctgtgctgccccttccttcttggagaatctgcgcggcggtctttccgtct<br>ctcgaaaagcgcagatgcagcatgctggaaccggtgaagaaaacagttctttgtggaaacttaga<br>gcagacatcgaaacagctgtagtgacctcacagtagcagcggaacccccctcctggtaacaggag<br>cctctgcggccaaaagccccgtggataagatccactgctgtgagcggtgcaaccccagcaccct<br>ggttcgatggttgttctctgtggaaccagagaatggtctttctcaagccctccagtagagaagccaa<br>gaatgtcctgaaggtaccccgcatgcgggatctgatcaggagaccaatcgtcagtgctttacactg<br>gcgctttggtttaaaaactgtcacagcttctccaaaccaagtggtcttggttttcacttttatcaaactgt<br>ttc |
| 523 | EMCV2 RD1338 | aaatactggtcgaaaccgcttgggataagaccggggtttgttaatgtctcaatgttattctccaccca<br>attgacgtcttttgtcaattggagggcagtgaaaccttgcccttgcttcttgcagaggattcccagtgg<br>tctttccgctctcgacaagggaattcatgatccaccaaaagttgtgaagagagcaggtcccatgga<br>agctttctgacgactgatgatgactgtagcgaccctttgcaggcagcggacccccccacctggtga<br>caggtgcctctgcggccaaaagccacgtgtttaacagacacctgcaaaggcggcacaaccccag<br>tgcctcatcaaaagtctgatgactgtggaaatagtcaaccggcttttcttaagcaaatttggtgtcgg<br>ggctgaaggatgcccggaaggtaccacactggttgtgatctgatccggggccacagtacatgtgc<br>tttacacatgtagctgcggttaaaaaacgtctaggcccccgaaccacggggacgtggttttccttt<br>gaaaaccacgattacaat |
| 524 | EMCV1 JZ1203 | gtctgctcgatatcgcaggctgggtccgtgactacccactcccccttcaacgtgaaggctacgata<br>gtgccagggcgggtactgccgtaagtgccaccccaaaacaacaacaaacccccctaacattact<br>ggccgacgccgcttggaataaggccggtgtgcgtttgtctatatgttatttcccaccacattgccgtc<br>ttttggcaatgtgtgggcccggaaacctggccctgtcttcttgacgagcattcctaggggtctttccc<br>ctctcgccaaaggaatgcaaggtctgttgaatgtcgtgaaggaagcagttcctctggaagcttcttg<br>aagacaaacaacgtctgtagcggccctttgcaggcagcggaacccccacctggcgacaggtg |

TABLE 17-continued

| IRES sequences. | | |
|---|---|---|
| SEQ ID NO | IRES | Sequence |
| | | cctctgcggccaaaagccacgtgtataagatacacctgcaaaggcggcacaaccccagtgccac gttgtgagttggatagttgtggaaagagtcaaatggctctcctcaagcgtattcaacaaggggctga aggatgcccagaaggtaccccattgtatgggatctgatctggggcctcggtgcacatgctttacatg tgtttagtcgaggttaaaaaacgtctaggccccccgaaccacggggacgtggttttcctttgaaaaa cacgatgataat |
| 525 | EMCV1 AnrB-3741 | atgtggtcgaagccacttggaataagaccggcgtgcgcttgtctatatgttacttccaccacattgcc gtcttttggcaatgtgagggcccggaacctggccctgtcttcttgacgaacattcctaggggactttc ccctctcgccaaaggaatgtaaggtctgttgaatgtcgtgaaggaagcagttcctctggaagcttctt gaagacaaacagcgtctgtagcgaccctttgcaggcagcggaaccccccacctggtaacaggtg cctctgcggccgaaagccacgtgtataagatacacctgcaaaggcggcacaaccccagtgccac gttgtgcgttggatagttgtggaaagagtcaaatggctttccccaagcgtattcaacaaggggctga aggatgcccagaaggtaccccactggttgggatctgatctggggcctcggtgcaggtgctttacac ctgttgagtcgaggaaaaaaaacgtctaggccccccgaaccacggggacgtggttttcctagaaaa ccactatgacaat |
| 526 | Cosavirus D1 | cgtgctttacacggtttttgaaccccacaccggctgtttggcgcagcaggacagtaggtatattttctt tcatttctcttttctagccgcgtaggttctatctacgcgggcggagtgatactcccgctccttcttggac aggcggcctccacgctctttgtggatcttaaggctgccaagtcactggtgtttgaagtgaagaatgg agagacactagggcgtttcatgtggctttgccagggattgtagcgatgctgtgtgtgtgtgcggattt cccctcgtggcgacacgagcctcacaggccaaaagccctgtccgaaaggacccacacagtggg gttgccccgaccccctcccttcaaagctttgtgtaaacaaacttttgtttagactttcttaagcttctctca catcaggccccaaagatgtcctgaaggtaccctgtgtatctgaggatgagcaccaccaactaccc ggacttgtgggacgtgtcccacagacgcatgtggtattccagcccccctcctttgaggagggggct tttgctcgctcagcacaggatctgatcaggagattcatctctggtgctttacaccagagcatggattta aaaattgcccaaggcctggcaaacaacctaggggactaggttttctctattttaaaagatgtcaat |
| 527 | Cosavirus B1 | cgtgctttacacggtttttgaaccccacaccggctgtttggcgcttgcaggacagcaggtttattttctt ttaactctctctttctagccacacacgatctatgtgtgtgggcggagtgatactcccgttccttcttgga caggcggcctccacgccctttgtggatcttaaggctaccaagtcactggtgttggaaagtgaagag aaaggagttccttgggaactacatgtggcattgacagaggttgtagcgatgctgtgtgtgtgtgcgg attaccccccgtggcgacacggaccccacaggccaaaagccctgtccgaaaggacccacacagt ggagcaaccccagctcccctcttcaatgttttgtgttagcaaccttggtattattttctctcaagcttc caatacaccgggccccaaagatgtcctgaaggtaccccgtgtatctgaggatgagcaccatcaacta cccggacttgttctttcgagaacagacgcatgtggtaacccagccccgatcctaaggggtcgggg cttttgctcactcagcacaggatctgatcaggagacctcccccccctgctttacaggggggcggggg tttaaaaattgcccaaggcctggcaaataacctaggggactaggttttcctttttattttaaagttg tcaat |
| 528 | Cosavirus A SH1 | ccgtgctttacacggtttttgaaccccacaccggctgtttggcgcttgcaggacagcaggtttattttc ttatgctctttatttctagccaacagggttctatcctgttgggcggagtgatactcccgttccttcttg gacagattgcctccacgatctttgtggatctcaaggtgatcaagtcactggtaaatagagcgaaggttg aggaaacctgaggaatttccatgtggttttgccaggagttgtagcgatgctgtgtgtgtgtgcggatt tcccctcatggcaacatgagcctcacaggccaaaagccctgtccgaaaggacccacacagtgga gcaatcccagctccctcctacaaagctttgtgagaatgaactcacgtttattcttctttattctctgtt tacatcaggccccaaagatgtcctgaaggtaccttgtgtatctgggcatgagcaccatcaactacccgg acttgcatttcggtgcagacacatgtggttacccagcccctctgctttggcagaggggctttttgctcg ctcagcacgagatctgatcaggagccctttcccagtgtgctttacacctggcggggggttaaaaatt gcccaaggcctggcaaaataacctaggggactaggttttccttttattaacaatgtctgtcatt |
| 529 | Malagasivirus B | ctttatttcttatgtaactcttcttttaagttttatttgcctacttgtgagcttatgcgggaccactgt cttagacaaccccacatttgtcatgagtaagtacacgcaaccattacgattactttttaaccgtctgacctt ttgataacaactgaagttaggcgtgaaacatgcatttataccaaagtagccccgcatttccccactacg gtggggggggctaccctactggctaggaactgtagccattatgtgttgcctggctttcaggatctcac aacacaacagttctctcacaatggaatatgggtgagattgcagtgacatgaacaagtatctagtagt acatagactcaagcctagttgcctgcggaacaacatgtggtaacacatgccccagggtccaaaag acaagggttaacagccccactaggtgtctgtgtgtgaagaatacatagtagtagtgagaatgatctcac ctgttagtacagaatgagtatggcaggtgaaggatgtcctacaggtacccattatatggatctgagt aggagaccactagtggtggctttaccgccaggtgagtggataaaaagcgtctagccaagccaac agcactagggatagtgctttctattttattttattttcagtgtat |
| 530 | Mosavirus A2 SZAL6 | cccccccctcaaattgcaacgatatagctaatggcgagattgagatgctatatcacctccttctaagtt atagacctcatctgattgataaggacgtaatttggtcgaaaccgcttggaataagaccgatgcgcgt agtcatgatgatgatgtaagatctaggaacttatccaatctgcttatgtctatgtaagtagaggggca ggcctcattgccctaattctttctaccgagtatctgctagggtttctagcggcagaatacaggattga gggatacaagatactactgatcgattgtcgattgggaaacagtagatacttcaaagctaccagtag cgtggactcacagccagcggactacccctcatggtaacatgagcctctgggcccacaaggcacg tcgcaagacctgtgagacggcaaccccagcctagctttgttgaggaaacaagcgataacatgaca tgagagaccggaaggattcttgtattgtgagccgaaggatggcctctaggtacctcattttatgagat ctgaggaggtgctcttgagttggtgctttacactgcacaacacagagttaaaaagcgtctaagctcac ccggaaattgggaaatttccgttatttccattttgtttgcaaagtcgttc |
| 531 | SVV | ctgggccctcatgcccagtccttcctttccccttccgggggtaaaccggctgtgtttgctagaggc acagaggagcaacatccaacctgctttttgtggggaacggtgcggctccaattcctgcgtcgccaa |

TABLE 17-continued

IRES sequences.

| SEQ ID NO | IRES | Sequence |
| --- | --- | --- |
| | | aggtgttagcgcacccaaacggcgcatctaccaatgctattggtgtggtctgcgagttctagcctac<br>tcgtttctcccctatccactcactcacgcacaaaaagtgtgctgtaattacaagatttagccctcgcac<br>gagatgtgcgataaccgcaagattgactcaagcgcggaaagcgctgtaaccacatgctgttagtc<br>ccttcatggctgcgagatggctatccacctcggatcactgaactggagctcgaccctccttagtaag<br>ggaaccgagaggccttcttgcaacaagctccgacacagagtccacgtgattgctaccaccatgag<br>tacatggttctcccctctcgacccaggacttctttttgaatatccacggctcgatccagagggtgggg<br>catgatcccccctagcatagcgagctacagcgggaactgtagctaggccttagcgtgcttaggatac<br>tgcctgatagggcgacggcctagtcgtgtcggttctataggtagcacatacaaat |
| 532 | PTV A | actagtccttggacttttgttgtgtttaaacacagaaatttaattacctggccatgaattcattggattaa<br>ccccttctgaaagacttgctctggcgcgagctaaagcgcaattgtcaccaggtattgcaccagtggt<br>ggcgacagggtacagaagagcaagtactcctgaccgggcaatgggactgcattgcatatcccta<br>ggcacctattgagatttctctggggcccaccggcgtggagttcctgtatgggaatgcaggactgga<br>cttgtgctgcctgacagggtcgcggctggccgtctgtactttgtatagtcagttgaaactcacc |
| 533 | PTV B | cttccttttaattcgtaactgataagtgatagtccttggaagctaggttttagttacgctagttttggat<br>tatcttgtgcccaacatttgttttcgaacatatgttgtgtttaaacacagaaatctagtttctttggttat<br>gagtttaatggaatatccttttgaaagacttgccttggcgcgggctagagcgcaattgtcaccaggtatt<br>gcaccaatggtggcgacagggtacagaagagcaagtactcctgactgggtaatgggactgcattgca<br>tatccctaggcatctattgagatttctctggagcccaccagcatggagacctgtatgggaatgcagg<br>actggacttgtgctgcctgacagggtcgcggctggccgtctgtactttgtatagtcagttgaaactca<br>tt |
| 534 | Tottorivirus | cccctttacgtaactgcaacttaaagagtaccctactgcattggatgtgtggtaaacttttacgcacac<br>atttgtagtagtgttagttatgttctacctaatgagtatgcatgcacccgtcgaaacacgcttgtgataa<br>gataggtgagtccatgtgactaatctcattaagataaataagcaccctacaacgcacggcacgctc<br>gtgtcttccgtgcggggccgggacaacagcggcctaaatcttctaggtgaccaccatgcttttggg<br>actatggcaccactgtggacgtgagtacctggcagtaagtctgtgaaaagatggaaggtgtccca<br>agctatggggcgtatgcatatagcctgcggaacaaacaacggcgacgttgtccccagggcccaa<br>aaggcacgtggataagatccacctatatgtttaccccatagtgtaagtcactggaagtcctagtaatg<br>gatgtctggagtaaggctcacggggtagggcgaaggatgcccagaaggtacccgtaggtaacct<br>taagagactatggatctgatctggggaccggatggcgccatcaccatgacgtggaggccggttta<br>aaaaacgtctaagcccgaccaacaacctaggggactaggttttcctttttttattcatgtatgacgtt |
| 535 | Posavirus 1 | acatttccttgcgtgcgcacccgaaaatttattgaacttggcttgaatcataagtaatgcttcttatagc<br>ggacactttgagaatataatgatgtatggattaatgtatactgttttaaataacaaacctagacacgc<br>agttgcgttgatggttgtatcaatcacatataagtgttgaactcgtgttaatcctcgatcgctatatgttt<br>gccgcctacttccaataaaatagattacatgcgcgtcatgcctttgtgggttacctattggcctctgac<br>aaaaacaagtcgtaagatttgtagcttcccggtgtaaaaagctgggcgcggtctggctctcgtagg<br>gtggaaaggtccaccaatggctggttgagtgtaagctccggtgtcctggttgtcgcaattccaggc<br>gtcgtaataacctatattgcatctgactctaactcttgtggctctactgtatctagttcttgttctactaa<br>ctctaataatactactggctctaatactgaaaaacttacatatgttaatatagataatatccttgatcctg<br>atatccctcacgtcactgaagttcgccgaaaacgaatttcagatcatatcattgaatctcaaggatgtac<br>ttgctctgaacctactataactcctcatgcgttttcattttctactcttggc |
| 536 | A105-675 | ccacccacagcaagaatgccatcatctgtcctcacccccatttctcccctccacccctgcaaccatt<br>acgcttactcgcatgtgcattgagtggtgcacgtgttgaacaaacagctacactcacgtgggggcg<br>ggttttcccgccatcggcctctcgcgaggcccaccatccctttcctcccataactacagtgctttg<br>gtaggtaagcatcctgatcccccgcggaagctgctcgcgtggcaactgtggggacccagacagg<br>ttatcaaaggcacccggtctttccgcctccaggagtatccctgctagtgaattctagtggggctctgc<br>ttggtgccaacctcccccaaatgcgcgctgcgggagtgctcttccccaactcaccctagtatcctct<br>catgtgtgtgcttggtcagcatatctgagacgatgttccgctgtcccagaccagtccagcaatggac<br>gggccagtgtgcgtagtcgtcttccggcttgtccggcgcatgtttggtgaaccggtggggtaaggt<br>tggtgtgcccaacgcccgtactttggtgacaactcaagaccacccaggaatgccagggaggtacc<br>ccgcctcacggcgggatctgaccctgggctaattgtctacggtggacttcttgcaccatttctttctt<br>ctgttc |
| 537 | A110-675 | acctttgtgcgcctgttttataccccctcccccaactgtaacttagaagtaacacacaccgatcaaca<br>gtcagcgtggcacaccagccacgttttgatcaagcacttctgttaccccggactgagtatcaataga<br>ctgctcacgcggttgaaggagaaagcgttcgttatccggccaactacttcgaaaaacctagtaaca<br>ccgtggaagttgcagagtgtttcgctcagcactaccccagtgtagatcaggtcgatgagtcaccgc<br>attccccacgggcgaccgtggcggtggctgcgttggcggcctgcccatggggaaacccatggg<br>acgctctaatacagacatggtgcgaagagtctattgagctagttggtagtcctccggcccctgaatg<br>cggctaatcctaactgcggagcacacaccctcaagccagagggcagtgtgtcgtaacgggcaac<br>tctgcagcggaaccgactactttgggtgtccgtgtttcattttattcctatactggctgcttatggtgac<br>aattgagagatcgttaccatatagctattggattggccatccggtgactaatagagctattatatatcc<br>ctttgttgggtttataccacttagcttgaaagaggttaaaacattacaattcattgttaagttgaatacag<br>caaa |
| 538 | 18-675 | cccacagcaagaatgccatcatctgtcctcacccccaattttccctttcttcccctgcaaccattacg<br>cttactcgcatgtgcattgagtggtgcatgtgttgaacaaacagctacactcacatgggggcgggtt<br>ttcccgccctacggcctctcgcgaggcccacccccttccctccccttataactacagtgctttggtag<br>gtaagcatcctgatcccccgcggaagctgctcacgtggcaactgtggggacccagacaggttatc<br>aaaggcacccggtctttccgccttcaggagtatccctactagtgaattctagcggggctctgcttggt |

TABLE 17-continued

IRES sequences.

| SEQ ID NO | IRES | Sequence |
|---|---|---|
| | | gccaacctcccccaaatgcgcgctgcgggagtgctcttccccaactcaccctagtatcctctcatgt gtgtgatggtcagcatatctgagacgatgttccgctgtcccagaccagtccagtaatggacgggc cagtgcgtgtagtcgtcttccggcttgtccggggcatgtttggtgaaccggtggggtaaggttggtg tgcccaacgcccgtactttggtgacacctcaagaccacccaggaatgccagggaggtaccccac ctcacggtgggatctgaccctgggctaattgtctacggtggttcttcttgcttccacttctttcttctg ttcacg |
| 539 | A115-675 | acctttgtgcgcctgttttataccccccccaacctcgaaacttagaagtaaagcaaacccgatcaata gcaggtgcggcgcaccagtcgcatcttgatcaagcacttctgtaaccccggaccgagtatcaata gactgctcacgcggttgaaggagaaaacgttcgttacccggctaactacttcgagaaacccagta gcatcatgaaagttgcagagtgtttcgctcagcactaccccgtgtagatcaggccgatgagtcac cgcacttccccacgggcgaccgtggcggtggctgcgttggcggcctgcctatggggcaacccat aggacgctctaatacggacatggtgcgaagagtctattgagctagttagtagtcctccggcccctg aatgcggctaatcctaactgcggagcacatacccttaatccaaagggcagtgtgtcgtaacgggta actctgcagcggaaccgactactttgggtgtccgtgtttccttttaatttttactggctgcttatggtgac aattgaggaattgttgccatatagctattggattggccatccggtgactaacagagctattgtgttcca atttgaggatttaccccgctcacactcacagtcgtaagaacccttcattacgtgttatttctcaactcaa gaaa |
| 540 | A73-675 | ttactccattcagcttcttcggaacctgttcggaggaattaaacgggcacccatactccccccaccc ccctttttgtaactaagtatgtgtgctcgtgatcttgactcccacggaacggaccgatccgttggtgaa caaacagctaggtccacatcctcccttcccctgggagggcccccgccctcccacatcctcccccc agcctgacgtatcacaggctgtgtgaagcccccgcgaaagctgctcacgtggcaattgtgggtcc cccctcatcaagacaccaggtctttcctccttaaggctagccccggcgtgtgaattcacgttgggc aactagtggtgtcactgtgcgctcccaatctcggccgcggagtgctgttccccaagccaaacccct ggcccttcactatgtgcctggcaagcatatctgagaaggtgttccgctgtggctgccaacctggtga caggtgccccagtgtgcgtaaccttcttccgtctccggacggtagtgattggttaagatttggtgtaa ggttcatgtgccaacgccctgtgcgggatgaaacctctactgccctaggaatgccaggcaggtac cccacctccgggtgggatctgagcctgggctaattgtctacgggtagtttcatttccaatccttttat gtcggagtc |
| 541 | Kobuvirus 16317 | ttactccattcagcttcttcggaacctgttcggaggaattaaacgggcacccatacacccccatccc ctttctgcaacttaagtatgtgtgctcgtgatcttgactcccacggaatggatcgatccgctggagaa caaactgctagatccacatcctcccttcccctgggaggaccttggtcctcccacatcctcccccag cctgacgtaccacaggctgtgtgaagcccccgcgaaagctgctcacgtggcaattgtgggtcccc ccttcatcaagacaccaggtctttcctccttaaggctagccccgatgtgtgaattcacattgggcaac tagtggtgtcactgtgcgctcccaatctcggccgcggagtgctgttccccaagccaaacccctggc ccttcactatgtgcctggcaagcatacctgagaaggtgaccgctgtggctgccagcctggtaaca ggtgccccagtgtgcgtaaccttcttccgtcttcggacggtagtgattggttaagatttggtgtaaggt ccatgtgccaacgccctgtgcgggatgaaacctctactgccctaggaatgccaggcaggtacccc acccccgggtgggatctgagcctgggctaattgtctacgggtagtttcatttccaattcttttatgtcg gagtc |
| 542 | Aichivirus Chshc7 | ttactccattcagcttcttcggaacctgttcggaggaattaaacgggcacccatacatccccatcccc tttctgtaacttaagtatgtgtgcttgtaatcttgactcccacggaatggatcgatccgctggagaaca aactgctagatccacatcctcccttcccctgggaggaccttggtcctcccacatcctcccccagcc tgacgtaccacaggctgtgtgaagcccccgcgaaagctgctcacgtggcaattgtgggtcccccc ttcatcaagacaccaggtctttcctccttaaggctagccccgatgtgtgaattcacattgggcaacta gtggtgtcactgtgcgctcccaatctcggccgcggagtgctgttccccaagccaaacccctggcc cttcactatgtgcctggcaagcatatctgagaaggtgttccgctgtggctgccagcctggtaacagg tgccccagtgtgcgtaaccttcttccgtctccggacggtagtgattggttaagatttggtgtaaggttc atgtgccaacgccctgtgcgggatgaaatctctactgccctaggaatgccaggcaggtaccccac cctcgggtgggatctgagcctgggctaattgtctacgggtagtttcatttccaatccttttatgtcgga gtc |
| 543 | Aichivirus Goiania | actccattcagcttcttcggaacctgttcggaggaattaaacgggcacccatacacccccatcccct tttttgcaacttaagtatgtgtgctcgtaatcttgactcccacggaatggatcgatccgctggagaaca aactgctagatccacatcctccctcccccctgggaggacctcggtcctcccacatcctcccccag cctgacgtatcacaggctgtgtgaagcccccgcgaaagctgctcacgtggcaattgtgggtcccc ccttcatcaagacaccaggtctttcctccttaaggctagtcccgatgtgtgaattcacatcgggcaac tagtggtgtcactgtgcgctcccaatctcggccgcggagtgctgttccccaagccaaacccctggc ccttcactatgtgcctggcaagcatatctgagaaggcgttccgctgtggctgccagcctggtaaca ggtgccccagtgtgcgtaaccttcttccgtccccggacggtagtgattggttaagacttggcgtaag gttcatgtgccaacgccctgtgcgggatgaaacctctactgccctaggaatgccaggcaggtacc ccaccttcgggtgggatctgagcctgggctaattgtctacgggtagtttcatttctaattctttcatgtc ggagtc |
| 544 | Aichivirus ETHP4 | ttactccattcagcttcttcggaacctgttcggaggaattaaacgggcacccatacacccccacccc ctttttgcaacttaagtatgtgtgctcgtgatcttgactcccacggaatggatcgatccgctggagaa caaactgctagatccacatcctcccacccttgggaggacctcggtcctcccacatcctccccccag cctgacgtaccacaggctgtgtgaagcccccgcgaaagccgctcacgtggcaattgtgggtccc cccttcattaagacaccaggtctttcctccttaaggctagtcccgatgtgtgaattcacattgggcaac tagtggtgtcactgtgcgctcccaatctcggccgcggagtgctgttccccaagccaaacccctggc ccttcactatgtgcctggcaagcatatctgagaaggtgttccgctgtggctgccagcctggtaacag |

TABLE 17-continued

IRES sequences.

| SEQ ID NO | IRES | Sequence |
|---|---|---|
| | | gtgccccagtgtgcgtaaccttcttccgtcttcggacggtagtgattggttaagatttggcgtaaggtt catgtgccaacgccctgtgcgggatgaaacctctactaccctaggaatgccaggcaggtacccca ccctcgggtgggatctgagcctgggctaattgtctacgggtagtttcatttccaattcttctatgtcgg agtc |
| 545 | Aichivirus DVI2169 | tactccattcagcttcttcggaacctgttcggaggaattaaacgggcacccatacacccccaccccc ttttctgcaacttaagtatgtgtgctcgtaatcttgactcccacggaatggatcgatccgctggagaac aaactgctagatccacatcctcccttcccctgggaggaccccggtcctcccacatcctccccccag cctgacgtatcacaggctgtgtgaagtccccgcgaaagctgctcacgtggcaattgtgggtccccc cttcatcaagacaccaggtctttcctccttaaggctagccccgatgtgtgaattcacattgggcaact agtggtgtcactgtgcgctcccaatctcggccgcggagtgctgttccccaagccaaacccctggc ccttcactatgtgcctggcaagcatatctgagaaggtgttccgctgtggctgccagcctggtaacag gtgccccagtgtgcgtaaccttcttccgtctccggacggtagtgattggttaagatttggtgtaaggtt catgtgccaacgccctgtgcgggatgaaacctctactgccctaggaatgccaggcaggtacccca ccttcgggtgggatctgagcctgggctaattgtctacgggtagtttcatttccaattcattttatgtcgga gtc |
| 546 | Aichivirus DVI2321 | gcttcttcggaacctgttcggaggaattaaacgggcacccatacacccccaccccccttttctgcaac ttaagtatgtgtgctcgtaatcttgactcccacggaatggatcgatccgctggagaacaaactgcta gatccacatcctcccttcccctgggaggaccccggtcctcccacatcctccccccagcctgacgta tcacaggctgtgtgaagtccccgcgaaagctgctcacgtggcaattgtgggtccccccttcatcaa gacaccaggtctttcctccttaaggctagccccgatgtgtgaattcacattgggcaactagtggtgtc actgtgcgctcccaatctcggccgcggagtgctgttccccaagccaaacccctggcccttcactat gtgcctggcaagcatatctgagaaggtgttccgctgtggctgccagcctggtaacaggtgcccca gtgtgcgtaaccttcttccgtctccggacggtagtgattggttaagatttggtgtaaggttcatgtgcc aacgccctgtgcgggatgaaacctctactgccctaggaatgccaggcaggtaccccaccacggg tgggatctgagcctgggctaattgtctacgggtagtttcatttccaattcttttatgtcggagtc |
| 547 | Aichivirus rat08 | tactccattcagcttcttcggaacctgttcggaggaattaaacgggcacccactttcctgtcctctccc cttttctgtaactccaagtgtgtgctcgtaatcttgactcccgcggattgaccgctccgctggtgaaca aactgctaggtcatctcctccccacccttgggcgtccttccgggcgtccacaccctcccccagcc tgacgtgtcacaggctgtacaaagaccccgcgaaagctgctaacgtggcaattgtgggtcccccc tttgtaaaggaaccgagtctttctcccttaaggctagacccctgtgtgaattcacaggtggcaactag tggaccactgcatgctcccgacctcggccgcggagtgctgttccccaagtcgtaacactgaccac acttatgtgcctggcaagcatatctgagaagatgttccgctgtggctgccaaacctggtaacaggtg ccccagtgtgcgtagtcttcttccgtcttcggacggtaggtgttaggtaaagatgcggcgtaaggtt caagtgccaacgccctggaagggatgacccttctactgccctaggaatgccgcgcaggtacccc aggttcgcctgggatctgagcgcgggctaattgtctacgggtagtttcatttccctcttcttccactgg catc |
| 548 | Aichivirus Rt386 | actccattcagcttcttcggaacctgttcggaggaattaaacgggcacccactttcctgtcctctccc cctttctgcaactcaagtgtgtgctcgtaatcctgactcccacgggagaccgccccgttggtgaac aaacagctaggtcattccctccctaccctgggcgccatttcagtggcgttcatatcctccccccag cctgacgtgtcacaggctgtgcaaagtccccgcgaaagctgctcacgtggcaattgtgggtcccc cctttgtgaaggaaccgagtctttctcccttaaggctagacccctgtgtgaactcacaggtggcaac tagtggttccactgcatgctcccgacctcggccgcggagtgctgttccccaagtcgtgacactgac ctccacttatgtgcctggcaagcatatctgagaagatgttccgctgtggctgccaaacctggtaaca ggtgccccagtgcgtgtagtcttcttccgtctccggacggtaagtgtgtggtaaagatgcggcgtaa ggttcaagtgccaacgccctggaagggatgacccttctactgccctaggaatgccgcgcaggtac cccaggttcgcctgggatctgagcgcgggctaattgtctacgggtagtttcatttccctctcttttc actggcatc |
| 549 | Norway Rat Pestivirus | gtataagggttgggaaccttgtaccaagctacctctgccattcagtatttgggagtagaagtagatgt gtttacaaactcacacgtgtgggggcggggatagactgtgccagcggtcgtgtaccagcacctac gcatacgtgtggactgcgaaccaggagagcacctaggtctgacaagctgtgagaacacagtagt cgtcagtgagtcagctggtaaggatcacccacctggatactcacgtggacgagggagtttcccag tcagaaacctacaccagaggaggggtcctctggagacatggatggtctgagtaacagactatcta ctggggtgtgctgcctgacagggtctcggctgatagcctggctagcagtataaaaatcagttgaatt ggcatatgagttgtgaacatctagtaaacaatgaaagacaaaaacaaaaaatgagcataataaaaa aattgtacaatccactactcaggtgtggctgcagactt |
| 550 | Porcine Kobuvirus GS2 | tttgaaaagggggtgggggggcctcggccccctcaccctcttttccggtggccattcgcccgggc caccgttactccactccactccttcgggactggtttggaggaacacaacagggcttcccatccctgt ttaccctttattccatcatcctttccccaagtttaccctatccacaccccactgactgactcctttggattt tgacctcagaatgcctatttgacctcccactcgcctctcccttttcggattgccggtggtgcctggcg gaaaaagcacaagtgtgttgcaggctaccaaactcctacccgacaaaggtgcgtgtccgcgtgct gagtaatgggataggagatgcctacaacaggctcgcccatgagtagagcatggactgcggtgca tgtgacttcggtcaccacgggcatagcattgctcacccgtgaatcaagtcatcgagatttctctgacc tctgaagtgcactgtggagcgtggctgggaatccacgcttgaccatgtactgcttgatagagtcgc ggctggccgactcatgggttaaagtcagttgacaagacac |
| 551 | Kobuvirus SZAL6 | cctacccaagggttacatgggaccatattcctcctcccctgtaactttaagttttgtgcccgtattcag actccaggcggatgttgtgtcgcccgtcctgtgaacaaacagctagacactttcctcccctccctct gggctgctccggcagtccactccctccccccagcgtaacatgccccgctggagtgatgcacctgg |

TABLE 17-continued

IRES sequences.

| SEQ ID NO | IRES | Sequence |
|---|---|---|
| | | aagtcgtggacgtgggttagtaacttcggtgaaaacccactataatgacaactggttgaccccccac actcaaaggactcgagtctttctcccttaaggctagcccggccacatgaatttgcagctggcaacta gtgagtccaccatgtcccgcaacctcggctgcggagtgctgttccccaagcgtatgccttccttctg taagagtgcgcctggcaagcacatctgagaagtcgttccgctgcgtcgtgccaacctggcgacag gtgacccagtgtgcgtagacttcttccggattcgtccggctcttctctaggaaacatgcgtgtaaggt tcatgtgccaaagccctgcgcgcggtgttcttctactgccctaggaatgtgccgcaggtacccctac ttcggtagggatctgagcggtagctaattgtctacgggtagtttcatttccatcttctcttcaggtcgac atc |
| 552 | Kobuvirus sheep TB3 | gaccttctggtacttcttcgcctgggtcacaaaagcgaagaacctgcctctctaacgccagacgag cggcattaaacttgaacttctggcactctccactctccctttttccctgtccctttccccactgcgctctc aaggtcgcgcaatcctgggactagcccagttttaaaagttcctggcacccttgcccctctaggccc ttaaggtaggaactgaccttgtgctgtgatctcggtgcgggagtgctaccacgtagtcatcgtaagc ctcgtttctggactgccctggcaaggctacagagtaccgtgttccgctgtggatgccatccgggta accggaccccccagtgtgtgtagcggtatgttcacggtccgccgtgttcaccagattcctgacctgg ctttgctagaaatggtgtgtgcccaatccctgtgaccagtatcaattacatcacctaggaatgctagg aaggtaccccagtcctgagctgggatctgatcctaggctaattgtctacggtgatgctccttttatttc ttacaactgctattgactgtctgattgctgattctgctcttgtgctcttctgctctggctcattctcaa gggttctctttgtccaagatcctttggttctctccttgttccacttgccactgccaacgcttgtc |
| 553 | Pronghorn antelope pestivirus | gtatacgcagttagttcatcctgtgtatacagattggagactctaaaaacaacgattcggaataggg gcccgcggcgaagaccgaagacaggctaaccatgccgttagtagggctagcaccaaaacgcg ggaactagacacttaggagagtggtctggctactctaagaggtgagtacaccttaaccgtcaagg gttctactcctcagagaggactagagatgccctgtggacgggggcatgcccaagagttagcttag ccggggcgggggttgttccggtgaaagtagcaatattgaccacactgcctgatagggcggagca ggccccctaggtagtctagtataaaatgtctgctgtacatggcac |
| 554 | Porcine pestivirus isolate Bungowannah | tacgcggggtataacgacagtagacaagtgtcgttatgcatcattggccataacaaattatctaattt ggaatagggacctgcgacctgtacgaaggccgagcgtcggtagccattccgactagtaggacta gtacaaataggtcaactggttgagcaggtgagtgtgctgcagcggctaagcggtgagtacaccgt attcgtcaacaggtgctactggaaaggatcacccactagcgatgcctgtgtggacgaggacatgtc caagccaatgttatcagtagcgggggtcgttactgagaaagctgcccagaatgggtagttgcacat acagtctgataggatgccggcggatgccctgtatttgaccagtataaatattatccgttgtaaagcat |
| 555 | Porcine pestivirus 1 | gcagatatcggtggtggacctgggggttgggctcaccgtgccccttcatggggtagacctcactg cttgatagagtgccggcggatgcctcaggtaagagtataaaatccgttgttcactaac |
| 556 | Pestivirus giraffe-1 | gtatacgagtttagctcaatcctcgtatacaatattgggcgtcaccaaatatagatttggcataggca acaccccgatgcgaaggccgaaaagggctaaccatgcccttagtaggactagcaaaaaatcggg gactagcccaggtggtgagcttcctggatgaccgaagccctgagtacagggcagtcgtcaacagt tcaacacgcagaataggtttgcgtcttgatatgctgtgtggacgagggcatgcccacggtacatctt aacctatccggggggtcggataggcgaaagtccagtattggactgggagtacagcctgatagggtg ttgcagagacccatctgataggctagtataaaaaactctgctgtacatggcac |
| 557 | Classical swine fever virus | gtatacgaggttagttcattctcgtatgcatgattggacaaattaaaatacaatttggatcagggcctc cctccagcgacggccgaactgggctagccatgcccacagtaggactagcaaacggagggacta gccgtagtggcgagctccctgggtggtctaagtcctgagtacaggacagtcgtcagtagttcgac gtgagcagaagcccacctcgatatgctatgtggacgagggcatgcccaagacacaccttaaccct agcgggggtcgctagggtgaaatcacaccacgtgatgggagtacgacctgatagggtgctgcag aggcccactattaggctagtataaaaatctctgctgtacatggcac |
| 558 | Human pegivirus isolate JD2B1I | tcagggttggtaggtcgtaaatcccggtcaccttggtagccactataggtgggtcttaagagaaggt taagattcctcttgtgcctgcggcgagaccgcgcacggtccacaggtgttggccctaccggtggg aataagggcccgacgtcaggctcgtcgttaaaccgagcccgtcacccacctgggcaaacgacgc ccacgtacggtccacgtcgcccttca |
| 559 | Human pegivirus isolate GBV-C-ZJ | cccggcactgggtgcaagccccagaaaccgacgcctatttaaacagacgttatgaaccggcgcc gacccggcgaccggccaaaaggtggtggatgggtgatgccagggttggtaggtcgtaaatcccg gtcatcttggtagccactataggtgggtttaaagggaggtcaaggtccctctggcgcttgtggcga gaaagcgcacggtccacaggtgttggccctaccggtgtgaataagggcccgacgtcaggctcgt cgttaaaccgagcccattacccacctgggcaaacaacgcccacgtacggtccacgtcgccctaca atgtctctcagaccaataggctttgccggcgagagacaaggaccagtgggggctgggcgacgg gggtcgtataggaagaaaaatgccacccgccctcacccgaaggttcttgggctaccccggctgca ggccgccgcggagctggggtagcccaagaaccttcgggtgagggcgggtggcatttttcttccta taccgatc |
| 560 | Human pegivirus isolate JD2B8C | tggtcaccttggtagccactataggtgggtcttaagagaaggaaagattcctcttgtgcctgcggcg agaccgcgcacggtccacaggtgttggccctaccggtgtgaataagggcccgacgtcaggctcg tcgttaaaccgagcccatttcccgcctgggcaaacgacgcccacgtacggtccacgtcgccctttt aatgtctctcttgaccaataggttcatccggcgagagacaaggaccagtgggggccgggggtca cagggatggaccctgggccctgcccttcccggcggggtggggaaagcatggggccacccagct ccgcggcggcctgcagccggggtagcccaagaaccttcgggtgagggcgggtggcatttttctt cctataccgatc |

TABLE 17-continued

IRES sequences.

| SEQ ID NO | IRES | Sequence |
|---|---|---|
| 561 | Hepatitis GB virus A | gccgggtggaaggcccggaaccgccccaccacctcaactaggtggtaagggtacgtctatcggt ccggctggcccgaaaggcggtggatcctgtgtgttagggttcgtaggtggtaaatcccagcacag gtggtaatcgctatagggcaggcttatcccggtgaccgcttccctggatcctggagcgggtcgtgg cggcacggtccacaggagtggggcctccggtgtgaataagccctcgtctggagcatcagacgtt aaactgagacgtcccgaagagatcggaacgacgccccacgtatggcaacgccgcttaaaaccct tcggggacagctatgcgggttgacaatgccagtgggggccgggcccactattgagtgggctcc gagttcctctagggatggccgaaaggcagccatggggccacccaggcggcgccgtgctacagg cggcaaggggaaaaatccttcgggtgaccccgggtggcattccctcccttagcagcatgagtgtg gtggtagctgcaacc |
| 562 | Simian pegivirus | ggggaatctcacccccccgtccggttccggaagaatcggaaaccgacaccctgaccaatcattctt gatcatagagtggatgaagtgaaagccagacgaaagccggcggatgggtggtgacagggttgg taggtcgtaaatcccggccaccctggtacccggtataagttgggcggaagctgactgaagctccg tgctcttttctgtgcgttcttggtgcacggtccacaggtgacgcctataccggtgtgaataataggcc gactcgagcggagtcgttaaactgagaacctccatacggatggcaacttggcttgcgtacgggga cgccgctaaagtcacagtgggttaagtccggcgggttgacaaccccagcaaggcgagggggtc ctattgttggactctgccagacccggtggaggtaggcatggggtggcccagctccgcggcgcgc tacagccggggtagcccaaaatccgaaaggtgagggcgggccacatgtccgaaatttagtcaag c |
| 563 | Pegivirus I | agaatggtctaagtggttgccaccgtggtccgaaggggaggaggacctacgctgccagggttgg caggtcgtaaatcccgggtgtaggagatccctccttgttaggactgctggtagctgggggtcggt gaccccctgggcaaccgccaaacccggacgaccgggtggcggctccatgttggcacggtccac aggtgtgaaccctaccggtgtgaataagggttggtggttgcggtccaccttaaacgtagtatgcatt gggcttggtaaaacaccgctcgtagtacggaacgccgcctttaaagacacagtaggcgtagccg gcgggttgacaatccatacgggggtggggtgtggtcatggatctgtccacaccaccttcatgcg gccctctaagcaagccataccgggggaggcgcgcggcaccgcactgccgggcaaggggaa gaaccttcgggtgacccccccccaaccaccgtccgatcaatgctaatgttgcgtttaggcgtgaca ccggcaca |
| 564 | Pegivirus K | agaatggtgtgatccgtcgccgctccagcggaaagcgggcgggatctagtggttagggttgttcg cgtaaatcccacactagtggtacgctcgtataacgtgggagcagccggTggggtcgaccccccc Acctggcggctgctgagcaccggacgaagcgcgggggggtgaacgctaacccgcggcccggg ctgccaacgttaggcacgtcaggctggaagacgttaaacacagggcccccctcaaccctgatc cgaggccagagaccaaggtacgccgcccctttaaaggcgttactcgtccaataggatctctccgg cgggttgtcaaaccttgctggccctggtgatggttacgggagggggtggggcggggagtagaag ccccgcccggcatgggggtaccaagctcggcacgcccagcacgcgtggcgtaggggaaaaat ccttcgggtgacccctggtaccataaagtaattaacatgagcatgccgctagggtgtgctttttcttcc ttccttgggaaggcggtggcacc |
| 565 | Theiler's disease-associated virus | tgataccgtgtcccggtacgacctcgcgcgtccccaagctcgccctgagggggggagcgtaaggg cgcgtagtggggtagccccccaaaccgagccaccctagtgagtgactttagaatggttagggaga ctaccgccttcgctgtttggggacctaatgatccgcgtgccagggttcttcgggtaaatcccggcgc ggtgttttgggttcagggcagtaggggcagacgggccagcagtcgctggttcctggtaccaccac cctatccggacgacctccctcacgaaaggtcgccacggtctgtggctcgacgacgcctataattca gtccgaggggcgcagccctcgttaaacttaggcaaggttcctcgccattgatttggccaggggttt aagtgaacgccgcccttttaatgtttaatagggttctttcccggcgggttgacaaacacttccctggg ctcttcgttggcctcggttccttgatgcttcggcacccatgagcgcacagggggggaccctgcga cagtccgccaagaggaaaatccttcgggtgacctcgtgcgcaacccaatcccttcttcttccacatg gcgtgtctgtggtgcatgctgtg |
| 566 | Rodent pegivirus | ggacttcggtccccctgttactctgcgagccaccgcagagccagggttggtacgcccgaggtgtt agaccccggccgaaagctcctaaccatggggttagtaggacgtggtaaatgccactgaggggtt ggagagctggtagagcgagtaagtcggcgtaaggcccgagtacgggcctcccagcccgggtca gcctaaacctggctgtgatacccggtgcatggagggcgtgtcccaacgctcgatcgctgtagggt gggtccctgcagttgggtgtggctaccctgctcgtactgcttgatagagtcccggcggacggacc agctctcgtcagtccgtggagttgcac |
| 567 | Human pegivirus 2 | aactgttgttgtagcaatgcgcatattgctacttcggtacgcctaattggtaggcgcccggccgacc ggccccgcaagggcctagtaggacgtgtgacaatgccatgagggatcatgacactggggtgag cggaggcagcaccgaagtcgggtgaactcgactcccagtgcgaccacctggcttggtcgttcatg gagggcatgcccacgggaacgctgatcgtgcaaagggatgggtccctgcactggtgccatgcg cggcaccactccgtacagcctgatagggtggcggcgggccccccagtgtgacgtccgtggag cgcaac |
| 568 | GB virus C/Hepatitis G virus | cccccggcactgggtgcaagccccagaaaccgacgcctatctaagtagacgcaatgactcggcg ccgactcggcgaccggccaaaaggtggtggatgggtgatgacagggttggtaggtcgtaaatcc cggtcaccttggtagccactataggtgggtcttaagagaaggttaagattcctcttgtgcctgcggc gagaccgcgcacggtccacaggtgttggccctaccggtgggaataagggcccgacgtcaggct cgtcgttaaaccgagcccgttacccacctgggcaaacgacgcccacgtacggtccacgtcgccct tcaatgtctctcttgaccaataggcgtagccggcgagttgacaaggaccagtgggggccggggg cttggagagggactccaagtcccgcccttcccggtgggccgggaaatgc |

TABLE 17-continued

IRES sequences.

| SEQ ID NO | IRES | Sequence |
|---|---|---|
| 569 | Equine Pegivirus 1 | agaatggggagttaactcctggcactggcccgaagcatgaactgatcgcggtggcagggttcttc gggtaaatcccggccgcgtgttgtgattgtgttagggcaggtgacagtcggcagggtcgacccccc tgcttcaggaccactgtcttcctggacgaccgttgctgaaaaagggccgccacggtctgtagctcg ccgacgcttctaattcaggccggaggaccacgctccgtaatcgagcccaagtactcaaaccccag gacaaagggcgcagggttacctggtactacgagcttgggtgtccctgggagtaatcccagggtgc c |
| 570 | Culex theileri flavivirus | atataaatcccagtttggttaaacctatttcaaggcttaagttgtttattattttatcgccgctcgtga ctataaagttgcctagcggagagagataaagaagaaggagttcaaggctcagggcagggcgcaagtt ccctggtccctaggccgctcgcaggaaggaggagtgaagaagaagaaagagaaggagaggac caccgccgaaagaaggcaggtgcctcacaagagggccaaccagcgtgttggaccagtggcca acgccggacggcgtggtggcctgctgggacgcctggggattggatggagtgccttcctacagga agacatcgttcaagccatc |
| 571 | Bussuquara virus | agtatttcttctgcgtgagaccattgcgacagttcgtaccggtgagttttgacttaacgcagtgagaa aagttttcgaggaaagacgagaagcgaattctctga |
| 572 | Zika Virus | agttgttgatctgtgtgagtcagactgcgacagttcgagtctgaagcgagagctaacaacagtatca acaggtttatttggatttggaaacgagagtttctggtc |
| 573 | Yokose virus | agtaaattttgcgtgctagtcgctgagcgtcagaccgcaaagtgagtttttagtgatctaaagtgagg agttattcttactgtcatcaaacactacaaataaacacgttgaaattatttccggaagaacaactgtcc ggaataaagacg |
| 574 | Wesselsbron virus | agtatattctgcgtgctaatcgttcgacgttagtccgtggagtgagcttctattagagtcgttaacacg tttgaataatttctactgaaaggagtagaagaaaggagattcattccca |
| 575 | Equine hepacivirus | acctccgtgctatgcacggtgcgagtcagcgttttgcgcagctttgcgctacacgcgtcgtccaac gcggagggattcttccacattaccatgtgtcactcccccctatggagggaccaccccgcccacacg gaaataggttaaccatacctatagtacgggtgagcgggtcctcctagggcccccccggcaggtcg agggagctgaaattcgtgaatccgtgagtacacggaaatcgcggcttgaacgtcatacgtgacctt cggagccgaaatttgggcgtgccccacgaaggaaggcgggggcggtgttgggccgccgcccc ctttatcccacggtctgataggatgcttgcgagggcacctgccggtctcgtagaccataggac |
| 576 | Hepacivirus B | accacaaacactccagtttgttacactccgctaggaatgctcctggagcaccccccctagcagggc gtgggggatttcccctgcccgtctgcagaagggtggagccaaccaccttagtatgtaggcggcgg gactcatgacgctcgcgtgatgacaagcgccaagcttgacttggatggccctgatgggcgttcatg ggttcggtggtggtggtggcgctttaggcagcctccacgcccaccacctcccagatagagcggcggc actgtagggaagaccggggaccggtcactaccaaggacgcagacctctttttgagtatcacgcct ccggaagtagttgggcaagcccacctatatgtgttgggatggttggggaagccatccataccgta ctgcctgatagggtccttgcgaggggatctgggagtctcgtagaccgtagcac |
| 577 | Hepacivirus I | cagggtttcgaccctggcccggatacctatcgccttacgccgaaaggtaacgagtaggagtcggg tccccaggcccttaccgccaccaagccaggtggggaggtatgggagccgggggggtgcagctg gtagctccatgggggacgccccgtgagcggatgctgcatcgataccgggttagctctctgggaga gcggcacttgacaccacgaatccgggaaccggacaatcgccggcgtgggacgcgttgcctccg tggccgagcaatttggcatgcccgtggtgaagagtgatggtgggggggggcccccccttccagta ccgtactgcctgatagggtcttgcctcaagcccagagagtcgaggctgaaaaccgccatc |
| 578 | Hepacivirus J | gccgctcccgaaagggagtccggcgcgtcatcccactccgaggagtggggtggcgtccccgtg tgccggggaaccatgaagcctaagggcatccacattttagaatgaacttgaagcacgtttcgctgg ccggaaagtcctgggttcccatggccagggttccgcaggtgggtaaatcccggtggggttccatc caggatatacggcaggcgggcgtagtccggcggttcggacgacgtgtgggtcgcctacggtgg attgttcacaggatgggcactccggtgtgaatagg ccccgtcagggtgcgctgacgttaaactcag gccttgcctggtgttcggggaggattgcagggccacgccgcctctaagggccgtatggcacagta cttcttcgggcgggttgtcaaggccctccaacgcgacaccagtgcctcggcaggcatggggcca cccagctcggcgtcccgcacacagacggcgtaggggaaaatcagcaatgtgaccccgggtggc attttccttctctctacttccatgcatgatcaaccgcaatc |
| 579 | Hepacivirus K | gggaacaatggtccgtccgcggaacgactctagccatgagtctagtacgagtgcgtgccacccat tagcacaaaaaccactgactgagccacacccctcccggaatcctgagtacaggacattcgctcgg acgacgcatgagcctccatgccgagaaaattgggtatacccacgggtaaggggtggccacccag cgggaatctgggggctggtcactgactatggtacagcctgatagggtgctgccgcagcgtcagtg gtatgcggctgttcatggaac |
| 580 | Icavirus | cgaagtttaagctaagcaccctcgggcgttcccggattatgtgatcacatcaatttgatggctggtca ccacgcaacgcctggagagatactcttacttttctcttaagatccccggtcatttgacgcttgtaggat gatagggttattttccactataaatactttcatactcttggatgttctatatccaagacgggaggaccta ccccgtaccccttagaggtgagatgccaagaacaggccctttctgttctctcgacaatggcatcata ggcaacaagcatcacaccaagattgctaagttttgttaagagttcttcaagctatagggtggctgtag cgaccttctgatgcctgcggatacccccttcggagcgatccgtgccacaggggccaaaagccacg gctaacgcccatcaggagcggcacttaccccgtgccccacccttgaaacttgaatgttcacactgg cttctctcggctttctgaactgtctgcagttggggccccgaaggatgccctggaggtaccccattta |

TABLE 17-continued

| SEQ ID NO | IRES | Sequence |
|---|---|---|
| | | tgggatctgaccaggggacacctcagctctctaagttgctggtgtttaaaaaacgtctaagggccc ccaccccttaggtggagggatccacctttcctttattttttaaaactcttttatggtcacaattgttt |
| 581 | Antarctic penguin virus A | ctaggagactacgcagtgggataagatgactatgatgtcgtacgggcagaagccagtacagtcga agtcgagaccgacgtcgaggatttgactctgcctgacctagtgccatc |
| 582 | Forest pouched giant rat arterivirus | tattggatccgcctccgggcaaaggttactttcttgtacctcggcttagccacagggtgaccccttgt acgtaggggccccgacgtagcactggtctgacaacaccttctcggcatttcaccttctgcccgctct tccgggcggtggtgtcaagaagcagcagtgctcttctcttttcttcctgcagttcaccgagccctacg gggggtaggtg |
| 583 | Avisivirus Pf-CHK1 | cattcccctttccccagccatgggttaaatggcccctcaccaggttcggtgctgtctaggcttccagt aaagaagtcaaccgagcattgaacaaaacctcagtgggtatggtagttaaccccgtccactggac aactttgtcctcttaaaagtggatcaatccaccccaactcccccccctagccacctgagccatggtgg atagcagtgacgaaactagggaccccaatacctctagtgccaagagaattcccccctcgcgagag gtgctcttgggcccgaaaggctagttggcagggtgaagtgaaggaagctgctagcgtggcaacc ttaagcgtagcccgaagctgaccttagaggttaaccctagtggaccactggatgaagctgtggag gtggtggataggaaagttggccacttgtgagtagatgcccagaaggcataaggctgatctggggc cagtgactataccgttccggtaaacctggtataaaaaccatgaaagcaagtgggtttaaaatttcttct aattccttcatttcagtagtgataactggcaga |
| 584 | Avian paramyxovirus penguin | accaaacaaggactagataacccacgtgaccgttaactggaaaataagatgttgtaggggcgacc tagttggaattcgaccccggctccgaaacctctaattgtggttattggcagtctagtctacttctaacg |
| 585 | Newcastle disease virus | accaaacagagaatctgtgaggtacgataaaaggcgaagaagcaatcgagatcgtacgggtaga aggtgtgaaccccgagcgcgaggccgaagctcgaacctgagggaaccttctaccgat |
| 586 | Bat Hp-betacoro-navirus | ttaagcttcggcttgttgcataggaccggaaaggtactatctaccctaactcttgtagttagactctcta aacgaactttaaaactggttgtgtccttcagtagtctgtatggccattggaggcacaccggtaattatc aaatactaagaagattcatagtacatccttgtctagcttttggttggcagtgagcctacggtttcgtcc gtgtcgctcacaattatccacacagtaggtttcgtccgctgtggttgagttgctagtccgttgctgtttc gtcagccatctacaactcgacacc |
| 587 | Basella alba endonavirus | ggaatatggctaatcggcttattctaatcaaacgcaaaagacttatgacacagaccggacctgaac gaggtgataaaacacctcgttcaggttcaaaacgtagaagattcattcctccgattagaaatacaact acgtctaagcacgatagagatggtatcaagatcggttttagaccacgagaaaatcggcaaatgaaa gtacaagttgggtggtttaaattaccaagaacagtaacattcaagaacaacggcaacccgtttgtta cctcatttcgtaaattgtttagaagtaacaaagataaattatttaatggtgggaagaacctaagtacag taccagccagaagtagtgaaatgacagaaatgtttatgttcatgtccacgctagagggccaattgtc aatccaagatcgagatccaaaaataatcaataagtctatatacatgatagaggta |
| 588 | Ball python nidovirus | ccccttcacccataggcactaggagaacaggataacccctaacggggcatcctgcctgtgaccttt cagattcgctagttagatatcttcacagactctgctaggcttctgacccagtccgttcccaaagtccgt taccgcccgagtagcgcttaggcgcgaaagggacggaagtacctccagtaagcgaaagctgaa gtaagggaaatacggcaagactaacttgttagtcttacagtgtggataacctggtagttccccga tcccccaacgggcctccaaggaatcgagaaccaaccctcattccacgtctgtagtaagcaaaaa caggggcgatcttcaccgacacctctcaccacagagcacaccaacctctgtgaagccaatttcctc gtccaaggacaggttattgagggtcaactttcttccgaccagaagaagggatttcctaccaaaaga aaaaccaaatccaccaacaccacaaggtaaaacaacaacttgtgaagccaatacttagtcaaaga ctaactattgagggtcaactttctcttcaatagagaagggatttcctggtaaaacaaataacaacaac taacatcagcaact |
| 589 | Bat sapelovirus | gacaggtgttttggagggcggatgacgatatctggctggccaccagggaataacggcaaatgtct gatcatacggttcacaagtctaccggcgatagtggttcaacaccatgtgtagcagggattcttgcgt atgtgaaggcgacagtgc |
| 590 | Bat Picornavirus | taagcggaaagcattcttgtcccccggtcagtaacctataggctgttcccacggctgaaagggtga acatccgttacccgcctcagtacttcgagaaacctagtacgcctgatgattccaaattggtatgatcc ggtcaaccccagaccagaaactgtggatgggggtcaccattcctagtatggcaacatacaggtgt ccccgcgtgtgtcacaggcccttacgggtgccatttcggatgagtctggccgaagagtctattgag ctactgttgatacctccggccccctgaatgcggctaatctcaaccccggagccactgggtggtgaa ccaaccacttggtggtcgtaatgagcaattctgggacggaaccgactactttggggtgtccgtgttt cttttgttcatattaaactgttttatggtcacaacacaacttggtacgatttgtgattattcactgctcac ttgtcacagtaaatatacacaatcatc |
| 591 | Bat Picornavirus 2 | gggttttacgaaacccgtatacaccagaccttttctcccctccccctccacctaccttttcccccctcttt ggaccgaaacaaggacacgtaagtggaaacgcgattttatatgtggttggccaccacggaataac ggcaattgtctacatgtgggaagtgcaacctccctgccgataacccctgaccgggtgtgtaggat aggaaaggtgcccactgtgggcgacaggttatggtagagtggatacctagccaggggcaatggg |

TABLE 17-continued

| IRES sequences. | | |
|---|---|---|
| SEQ ID NO | IRES | Sequence |
| | | actgctttgcatatccctaatgaagtattgagatttctctgctcattacccggtgatggttgtgtggggg gggccccatacactagatccatactgcctgatagggtcgcggctggccgaccataacctgtatagt cagttgaattcagccaag |
| 592 | Bat Picornavirus 1 | gaaacccgtatacaccggaccttttctcccctccctctccacttaccttttttcccctcttcggcatgaaa caaggattattcaagtggaaacgcgatttaatatgcggctggccaccgcggaataacggcaattgt gtatctgctggaagccaagcctgcctagccgatagcccttgaccgggtgtgtaggatagcccagg aaccagcaatacgcgacaggttatggtagagtagatacctagccaggggcaatgggactgcattg catatccctaatgaaccattgagatactctggtcattacccggtgatggttactagaggggggcctc tagtactagatctatactgcctgatagggtcgcggctggccgaccatgacctgtatagtcagttgatt tgagcaat |
| 593 | Bat Iflavirus | acgaatcggtatacgcttcggtacctattgagcaagttcgaccctattacgatttgcctgcccgaatt tgactcaaacaattgtgacatactatgtctctgatgaaagcactacacgagtagcgcccagcatgta tgttttcaagtatagtataagtctgcctctatagtggattattgaccttaaagccagtcaaccatcct atatgctgcatcgagacttgatgtcaatctgcctctactacgcaaatgtctagtaattagttataaggtt ttactattaccctcataccaatatagtagtagtgtatgtgagtatcattcttactccgactgttaagaga aaccaatttatagtcgttaaatatgataaatggaatgaatgatggtgtcatataaaaacactcactcta taggcgtaagcattctcgctcttagagtcgtaaagaagaaatgccgtgtctatcagtatgttatgcga tttattttctgccacgcgatctagtgcaatctagttgacatacagacattgcctaccactcgcgaggg tcgaccggtagtgtaaggagtaagtgatgataccgcttattctgtaccattgcctggtgaggacag atcctgactaatataaatataaatgaacactagatccaag |
| 594 | Bat dicibavirus | gtatagcaccggaatggtatatactactccaagtatacgtactaggagttaaaccctgtaatttacag gggatttagtgactatatccgtaaaagtcgattggacgttaatcggtaacgaggccaagtaccgtg aaccaatttaaaaacgtattactcatgtggtagaaccaacttggaaatagcatggcatataggagat aggg |
| 595 | Betacoro-navirus HKU24 | gataaagtgtgaatcgatccgtagcatcgcaccctcgatctatgttagatctaatctaatctaaactt tataaaaacactaggtccctgctagcctatgcctgagggataggcgttgcatactagtgtcttagga atttgactgataacacttccctgctaacggcgtgagcactctcagtctaagcctcccacccatagga ggtatc |
| 596 | Betacoro-navirus England 1 | atttaagtgaatagcaggctatctcacttcccctcgttctcttgcagaactttgatataacgaacttaaa taaaagccctgagatagcgtattgagcacttgtctggtgggattgtggcattaatttgcctgctcatc taggcagtggacatatgctcaacactgggtataattctaattgaatactattatcagttagagcgtcgt gtctcttgtacgtctcggtcacaatacacggatcgtccggtgcgtggcaattcggggcacatc |
| 597 | Boone cardiovirus 1 | tacgatcgctgtacattccactactgccaattagctccccatcccgttgctcccctctataaggaga gccactcttgcaaaggtgaagccttcacccccggtcgaagccgcttggaataagacagggttattt tctcctctcctcggcgcttgcctcactaagctgaataggactatctattcaggcggatggtctggtcc gttccacttggacagagtgtgtatctgggattccggatctcgaccacacactcaccagagctcagg agtgattaagtcaaggcccgatctgcggcgaaaaggaaatgaagtattttgcagctgtagcgacct ctcaaggccagcggataccccacctggtgacaggtgcctctggggccaaaagccacgtgttaat agcacccttgagagcggtggtaccccaccaccctgcaaattatggatttgacttagtaactaaaaga ttgacttggcatacctcaacctgagcggcggctaaggatgccctgaaggtacccgtgttgaaatcg cttcggcgaccatggatctgatcaggggccctgcctggagtggttctatcccacacagcgtagggt taaaaaacgtctaaccgccccacaaagaccccggcagggatgccggtaccatttaccaattcttg acact |
| 598 | Breda virus | atcacctagtacttacaagcgggtcaaaccgccctccggaacggtcataaccccctcccgaacgt gcgcttgacgtgactggtattcagtctagctactgagaaatactccggggttgtaacccaccatat gacctttggtcagtaggtaacactccaaccaaacagcatctgacccacctccagcttgctgcaggc catttggacCaaacgggttcagatatcagtggctaaacctctgacccacctccagatactgcagg ccttttggactaaacgggtAcagactctagtggttagtattaactacccactgatagccgccaacc tgatttttattgttacaaaattagtgatacacattattacttacggaggcagtagtaggagatgcaca gtttttgctgataccaattatactgtgatttggtgattcggctaaggctgatttcacatacttagatgct tgaagtaaccacacaacatctgattgataggtactaaggtaaagagatcaggaaaaaacatagg cgcccatcagtggtgtctagattaattaatctggcaaacaagtatcaagtcatcgactccctaggag tgagacttacgagtaccaattcgcctattaggccatccatataaaa |
| 599 | Bovine viral diarrhea virus 3 | gtatacgcccagttagttcaggtggacgtgtacgattgggtatcccaaattaataataggataggga ctaaatcccctggcgaaggccgaaacaggttaaccataccatagtaggacgagcataatggggg actagtggtggcagtgagctccctggatcaccgaagccccgagtacggggtagtcgtcaatggtt cgacgcatcaaggaatgcctcgagatgccatgtggacgagggcgtgcccacggtgtatcttaacc caggcgggggccgcttgggtgaaatagggagttatacaagccatgggagtacagcctgatagg gtgttgcagagacctgctacaccactagtataaaaactctgctgtacatggcac |
| 600 | Bovine rhinitis A virus | ttttgcggctctgccgccgttcgggattacctgattcacagagcaaaacaggacctctagatcgtg cttaaacgagatcatgctcgaactagaactataacgctggtcactggacccgtgccgcgccttgcg gatctttgcgggaatggtggctagtgggctgtggaagtgactctaaccacacgcccctcaagtgtg ggaaaacacgaactggtgtagcgacgacgataggccagggacaccctctccagtgatggagac ccaaggggccaaaagccacgccttgtgccctgtcgttcacaaccccagtgcagttcgtgccagta cctgcttttgggaagtgtgctaggacagctgaaaacagtcctagtgggagactaaggatgcccag |

TABLE 17-continued

IRES sequences.

| SEQ ID NO | IRES | Sequence |
|---|---|---|
| | | gaggtacccggaggtaacaagtgacactctggatctgacttggggagagcgggtctgctttacag acgccactctttaaaaacttctatgtctcgtcaggcaccggaggccgggccattcattaaaacaa tacacttt |
| 601 | Bovine picornavirus isolate TCH6 | ttggatctgagcaggggcccccctagggttgattacaactcaactggggttaaaaaacgtctaac ccgacacgccagagggatctggtaccattatttcattactcaccactggatgcagattgacgataa acgttgttgtttgtgactattgacttgatctgatctacgggatactacactgttatacttcttgctttgat ggtgttcactgtactttgtctccttctacatttcaca |
| 602 | Bovine nidovirus TCH5 | caccaatagattagtcaagctgtctataggcataaactaacccccaaccccattaccccggggcca ggtgggccgccgccttcgggcaaacccgtgcgctggtataatcaaggttcacagccagattcact gccggttagctagtggggcggtagcctggcaaaacccgaagaggttggaaagggaacttcagg gtagtttatcctaggctagcgtagctacagttcggtcaagataaccgtcctggtgctagggctagta gagacagtggtaacttggacaagggtccagggccactttagggaataccctacggaaggctagg tccgtaaggaagacccccgcagagtccgcggttgagcagagctcctgcgtagacaaaaggcaa aaagtggattacattcgcctgcaggaaaaggcaaacgtcgaggagtcggagctaaagtactgga cgattgataccacgcctgctgcggtagataaa |
| 603 | Bovine hepacivirus | ccatcgacactccaggctcacggattaagttaggttccgccgaagcgggctaaccaggcccctag taggaggcgcctatcccgtgagccattccccacggattgagtggagctggagctgggaaggac cgagtacggtccaatcgagaagaaccctgatgaacattccaggcctatcggtagataggatatat ccaccagtgaaggcggggtcgtgggtacaggcccccctagtccacacagcctgatagggtcctgc cgcaggatccgtgggtgcggctgtacatgtacc |
| 604 | Botrytis cinerea mitovirus 4 RdRp | gccccgccgaccacctatttatactaaataggaaggtcccgactagtcggataattcggataacg aattatggttagatctattaaagttaaaatagattgaatactactcatcctccttattcctatactaggga gtaaatgacaaatgtctatcctcaaaccgaaatggcttaagtgatgaatttgaaagaaaggtaggat taagaatataaggcatcaatatattatacccttgaatgttaagtgaccacggcgtgacgattagggct atcttaggatagacagccatctaacgcgacagcagtggaaatcagcttagcatctcaagatcatgta taatatatacataaccttacaattataaaaccaaaccaaaacacactataatatatataaattatagaa gtatcggacctggacggtacctactattaactgatagtagccaaatgcaggaagctc |
| 605 | Botrytis cinerea mitovirus 2 RdRp | ggaacttttcagttccagaagtggattattaagcatcaaagatacactttgaacctgcgattaattcc ccatagtgactcttgttactgtgaattaggaatagagtagttcaacttctaatgaggtgaacaatataa taactcatcttattaaccctatacgtagacaattgtccaaagagacagaggaattctgccaatctgga atgtttggtacgcgtagaagataataagagaccctctattcccctgcctcatgactaagtcatggccc ggggtgtaatagagatacttttatatattatacaatc |
| 606 | Canine picodicis-trovirus strain 209 | cgctctttatacaaatctgtcaaccctagtataactctaagccgaacaattatagctaggctattattat ataacattaattaggcattagcgagtcgccaatctcaggtaatcctaaggataccatcctgagacta agatgaagcgccttcggttaccgatgcccggtgtccacgaagccatcgtggtcggccgcgtcccc cacctctcccaacttggactccatgattcagtaggtgtaatgattagtattattgattctgctcgttcaat gtgtttatcttcacgatctgggacccaacacatgcttcactcatgataaatgaggaccctcattaga agacacccaaaccatagagtgcgagaatgaggatactacttccattctggtaacagaaatgaattc ctgcgtgtgtctcgtaaatggaatattaagaacttcagataaatcgaacaatacactaatacaagag ttttctaccaacatgacaatgcggctaatctgaccgtggagctgtgaagcgctcaaacccgagtga gtatacagtcgtaatgcgtaagtccatgaggaaccgactactgttacctctgaggtgtgtactcatt CCtctcttttattattatttgttattgcaaatactacaactttgatcaac |
| 607 | Canine distemper virus | accagacaaagaggctaaggatagttaaattattgaatatatattaaaaacttagggtcaatgatcct accttaaagaacaaggctagggttcagacctaccaat |
| 608 | Canine kobuvirus | tttaagtgagtgcccaatctcttgactcctgctggaaccaccgaccagtagtgtccaaaatgccagg tggaaaatcctccatcccctctgggcttcatgcccggcatcctccccccagcctgacgtgccaca ggctgtgcaaagaccccgcgaaagctgccaaaagtggcaattgtgggtccccccctagtcaaggc gtcgagtctttctcccttaaggctagtcctgtcagtgaactctgtcgggcaactagtgacgccactgc atgcctccgacctcggccgcggagtgctgcccccccaagtcatgcccctgaccacaagagtgctg tctggcaaacattgtctgtgagaatgaccgctgtggctgccaagcctggtaacaggctgccccagt gtgcgtaaactcatccagacacggtctggcaacagctgaaagacatggcgtaaggggcgtgtg ccaacgccctggaacgagtgtccactctaataccccgaggaatgctacgcaggtacccctggctc gccagggatctgagcgtaggctaattgtctaagggtattacatacccaccctcacacttgacata |
| 609 | Camel alphacoro-navirus | cttaagtgtcaatctatctatagatagaaaagtcgctattagactagtgtctactcactcaactaaac gaaatttttgctacggccggcatctctgatgctggagtcgtggcgtaattgaaatttcatttgggttgc aacagtttggaaataagtgctgtgcgtcctagtctaagggactgtgttctgtcacgggattccattct acaaacgccaactcgaggactgtctcgtgatgtgtggaagcaaagactgtcatgtggaaaccag taactgttccta |
| 610 | Cripavirus | gcaaaatcggtagtacgaaaacgtacgaccaccgatgagactgaaatgacactagagagattatt tcaatatcctagtgaataaagtcaatatagaggagatcgatcgtcaatcgatggcgctgacagcc ggaaagacggcaataataaaaaccaagatttagtattaagattgattgaattgcaaaagctatcag aatagacaatcaaaatattaagtaaagcaaaagcacttaaagaagacaatataaattagttagtaac caaacctcatcgtgcccctaagggaaaccggaacgtaaaagcgtagaggtattaaggtcactgc |

TABLE 17-continued

IRES sequences.

| SEQ ID NO | IRES | Sequence |
|---|---|---|
| | | ggagacctaaaatccgcaatatatgattgtaatgattagaatagacttagatgtaactataagagat<br>ataaatacttgtttcaagatttatagacaagatctgatcctatggattttagataaccttcatgttagtgg<br>atagtgtgtgtacctatctaaacgcataaggctcaatacatatttaaagtaggactatgtattacggc<br>gcatctaacggtaacgttagtcaagaccggagaatctcggaatgaatatagtaaacccaaatttata |
| 611 | Human coxsackie-virus A2 | acctagtgcgcctgattatatccccaccccgagtaaacgttagaagttacgcaaccccgatcaata<br>gtaggtgtagcactccagctgcatcgagatcaagcacactgtctccccggaccgagtatcaatag<br>actgctaacgcggagaaggagaaaacgacgttacccggccaattacacgagaagcccagtagt<br>gccgtgaaagagcggagtgatcgctcagcacaccccccgtgtagatcaggctgatgagtcaccg<br>cgatccccacaggtgactgtggcggtggctgcgttggcggcctgcctatggggcaacccatagg<br>acgctctaatacagacatggtgcgaagagcctattgagctaaaggtagtcctccggcccctgaatg<br>cggctaatcctaactgcggagcacatgccctcaaaccaggggggtggtgtgtcgtaacgggtaact<br>ctgcagcggaaccgactactagggtgtccgtgatctattattcaataatggctgcttatggtgacaa<br>ttaaagaattgaaccatatagctaaggattggccatccggtgactaacaaatcgctcatataccagt<br>ttgttggttttgttcccttatcacatacagctcataacaccctcaatatttactacaattgaatagcaaga<br>a |
| 612 | Coronavirus AcCoV-JC34 | agaaacaagtagtgttttaaaaaccacaaattagtgcctgtaacatcatgcaatgaaagtagcgctc<br>actagcctctatgcaaagaatgaaaaagaaatacgaagcatttaaagaatacaatctatctaggata<br>ggtacaaactcctccccctcagacacggtcaactcaactcaactaaacgaaatcccccagcatg<br>gttccgacccgtgtaaggagtgtatacgtgcagtcgagcccttactagtgtaagcgtaacggcatc<br>taggtttgcacgtcaggaggaaacggtgtgtacgtactagtgatacgccgtatcggttccggccc<br>gataggtattgcattagacgtcctgggtggactgcctgcccttgtgtgattcggctgaccgtcagttt<br>ggtcacctcacacgtccttaagac |
| 613 | Chicken picornavirus 3 | gggtatggtggaaaccccgtccactgggcatcatgccctctcagaagtggatcaatccaccccaa<br>ctcccccccctggaacctgagccacagtggactccggtgacgaagctagggaccccaatacctca<br>agtgccaagagagtccccccctcgcgagaggtgctcagggcccaaaaggctagttggcagagt<br>gaagtgaaggaagctgctaacgtggtgaccttaagcgtaattcgaagctgacctttgaggttaacc<br>ctagtggaccactggaggaatctgtggaggtggtggttaggaaagttggccacttgtgagtagatg<br>cccagaaggcataaggctgatctggggccagtgactataccgaccggtaaacctggtataaaaa<br>ccatgaaagcaagtgggtgaaattactctattatccacattcagcagagatattggcaaa |
| 614 | Chicken picornavirus 1 | gtggccgacagcagaacacctaccgaaccaccacctcacccccataactccaccctctacacct<br>tccgctatggtggaaccactgcatattgccagactgagaatggccacccccctcgacacctgcccc<br>ctactgccccaccgcgcaaccattgcagtccactcggaggagaggcatgggggccccgacat<br>atccccagtccagaggtgaccacccccctccccgtccggtagatggtccagagggctagccgac<br>gccctctatgatgcagcagtctacctccgtcagcgcgagcatgcacagtcgagcccacggaaa<br>cacagcctagcattgcactctcaccctgcgtaccctgggcgccaccgctcgagattcgcatgac<br>gacaccctggcgtccccccaccgctacgtgatatactcgtggcatacaccgccctggcgacagt<br>acattccactgcctaatagggtggcctccctcaatctcccgcacccccccattgcgcacgtcatcac<br>cgccgccgctaacgcgatccggcgcggactcactggcactgtcccctcgtccgccgggtacca<br>ctcatggttggcttttcacttaactggaactggtgaccatcctacacatgatggtcgccatgaccat<br>gac |
| 615 | Chicken orivirus 1 | aaaccctcacgagtgcagtggtaggtcccaggccaatattcacgtaaggcaggaccaattacca<br>ccactcgtgtagggactggcctatggtacccagaggggcggtagggggaattaactccccctcc<br>cctgtggtcctataccaccccacacctctgtgggcatcatactatcacttgattccgactataaaca<br>ctaggcaggcgcgcctagtcatacaccgcccggctggtctaccagctcagtgggcggtgcgcg<br>ctggtccatcgtgcccagcgacatagcaccagtggacacctccgaacgccctcccctgtatggg<br>gtggtgcccaggggatcagtgtggtgacacactccctggggcccgaaaggctagtgtgcaacag<br>gtgaggtacagccagctgcccccgtggctggagggaccaagcagtgaagcacacctcaccact<br>tgggggtgggctagtaagtggtgaaagcatagtgtccgtgtcgctggccaacactagggtcaagt<br>ccagccactcagtgagtagatgcccaggaggtacccctagtggatctgacaggggcctgttactt<br>aatgcaggttaaaaactatgaaagctgagtagtgtagcccggctggtggcactcaccaattcattc<br>tatttt |
| 616 | Chicken gallivirus 1 | ggttaacttgataaccaaggcaccgtgcagggcagcacgttaggagacatgagattcatgctcc<br>aatgcccaaaactagtgtgatgatatgtctacccaaagtacccccaaggatcggtactcaaacct<br>taattcctagtcccatcattgggccaagtatctaggaaatgtacccgtgccagacgaacgtaagaa<br>agctgtcttttattgaacggactaatgaactaagtataactggctcgcgccacctggtgtgtgccga<br>ggaattcccccatggtaacatggtccaacgggcccgaaaggctagtgggcaatcggtcctccaa<br>ggaaggggacccaccccgacctgaacaggatagatgaagctcacctcccaggctcctaacccc<br>aaggaagttttacttatagtaattagaaatagtatgtaattgctggcaatcagctagtagtcaggaacg<br>ttatgaccaaatgagtagacccccagaaggtaccccattatatgggatctgatctgggcctcatact<br>gtgtgtctccccacatatgaggaaaaaccatgaaagtaggtccaaaatattataccattatcattct<br>ttagtggtgacgccattatatcagcagtagctg |
| 617 | Chicken calicivirus | ggtgcatcatcactgaacaccctcgggcagagatgcaagggtggaagtcactcctgccccctgg<br>caacatgcaggtgcccgatcccaagcttagactgacacctctcctgggtggtgcaacactccaag<br>gttgatgaacaaacctggagggacctctgggcaacctggtctctcgaggatctccggcgcatctcc<br>acagactacctcatgctcccggaacctgagaagaacactgatgcctatgatggctggctgatggtc<br>ggcgagatgagaccatgccggtctcattggctgggagg |

TABLE 17-continued

IRES sequences.

| SEQ ID NO | IRES | Sequence |
|---|---|---|
| 618 | Carp picornavirus 1 | agctacaggaaagagagagataatcacagcacataaatacaactacagaagagagccatccctg agcactatttacagcaaaccacgctgggaaaagtggtagcatgacccacttacgggaacttagtat aggattttaatatcttcgattcatattactatcaaactaagacgcccggacatatccgtgattatata gtttaagcaaaattgagtaactaagtattaacctgccaaatggtgagaagtaactctgtgaaaatacc atttgtgcatgaaattgtcagaaaactcaaggcattggggggtcccactgctgatggaggactatt gacagactctattgtagagagtagtgactaatgataacgatagcgtattacgcaatgggctgtacc cgttagatttagtatgccggggggaggggtcccactggattgcactatgtaacctgacagggcgtc tgccgacgcactacaatgaggataagatcggctgatttata |
| 619 | Falcon picornavirus | cgcttggaataagagagaggaattatgcatgctagagtgatgatacaactaattgactaatccaa gtgaagctcacgcaggggcggcacgacacagccgtaattcactaccgtccctccacaccagtg gatgaagggccggatgtgtggcctctggctaacccctctctctggggtgatgctactggatgatta ctcctagaccaaatcacatgaactcctcagatccacacggtggggctatgagcctgcggattaata gctggcgacagctaccccaggggccaaaagccacggtgaagcagcaccctcatagtctgatgc ccaagggctgatgttgggagctagtagtgtgtgtctggcctatgatagacactggccaagcgca gaggagtggggctgaaggatgcccagaaggtacccgtaggtaaccttaagagactatggatctg atctggggcccccctcacgtggcataccacgtgaggggggaaaaaaacgtctaggccccaccagc ccacgggagtgggctacccaaaaaagcccaacaatatttatggtgacaattcactgatcactagc aatttttgtattcaggactccaattattgatgcagatatagtggacattcagattcaaatacaaa |
| 620 | Equine rhinitis B virus 1 | cgacaggcacaggtcgctccgagactagtagtgtgggaacttgaactactgatgaaacgaggta gtgacactcagtacctgcgaacgaggtcggggccctcccacaccacacccaactacactatcgt tccactttagcaggggtcactactatccccctggcggcattggaactagccgtcgcgtcaaacgc gcagccctgaaggccccacaccagtggatcagccgtgggtatgatctggcatgtgatctcaagc ctgcaaccgaagccgaacagccacatgaacagatgagcgtggtagcgctgtgtgagttggcggt ggatccccctcgtggtaacacgagccccccgtggccaaaagcccagtgatacagcacctctcaca tccaggacgaccccatcctggcgctcactcaagtagtatggcttagtacgcattaggtggtaagcc gagactccctcggccagactgaatgcacacatgtctaggggctaaggatgtcctacaggtaccc gcacgtaaccttcagagagtgcggatctgagtaggagaccgtggtgcactgcatacagatgcag cccggataaaaagcgtctatgcccctacagggtagcggtgggccgcgcccatccattaaaacta cttgttct |
| 621 | Equine rhinitis A virus | aagggaactgctcgtaatgagagcacatgacattagccaagatacctggcaattgtcacgggag agaggagcccgactcgggcacttactctcaaacaatgaggcgcgcctcggcgcgcccccccat ttcagccccctgtcattgactggtcgaaggcgctcgcaataagactggtcgagcaggcttactatt gtttcaggcatagcgcgcccagcgcggcgggccgtcaagcccgtgtgctgtacagcaccaggt aaccggacagcggcagctggattacccggtgccattgctctggatggtgtcaccaagctggcag atgcggagtgaaccaacgaagcgacacacctgtggtagcgctgcccagaagggagcggagct cccccgccgcgaggcggtcctctctggccaaaagcccagcgttaatagcgccactgggatgca ggaaccccacctgccaggtgtgaagtggactaagtggatctccaataggcctgttctgaactacac catctactgctgtgaagaatgtcctgaaggcaagctggaacagccctgatcaggagccccgctcg tgactctcgatcgacgcggggtcaaaaactgtctaagcagcagcagaaacgcgggagcgatcat ttcctcatttgtttc |
| 622 | Equine arteritis virus | gctcgaagtgtgtatggtgccatatacggctcaccaccatatacactgcaagaattactattcagtg ggcccctctcggtaaatcctagagggctacctctcgttattgcgagattcgtcgttagataacggca agttccctttcttactatcctattttcatcttgtggcttgacgggtcactgccatcgtcgtcgatctcta tcaactacccttgcgact |
| 623 | Enterovirus sp. isolate CPML | actctggtatcacggtaccatgcacgcctatatatacccccaccccatcgtaacttagaagcaacaa acaaactgcccaatagcagcacaacacccagagtgaaggggcaagcacactgatccccggaa gggtctgacggtatgctgtacccacggcagaagtatgacctaccgttaaccggccatgtacttcga gaagcctagtaccattatgaaggagattgatgaacgctccccagcaaccccagctggtagactg gtcgatgagtctcggcattccccacgggcgaccgtggccgaggctgcgaggcggccagcctac accatacggtgtaggacgtcaagatactgacatggtgtgaagagcctattgagctacgtggtagtc ctccggcccctgaatgcggctaatcctaactccggagcatccgccagtaagcccactggaagggt gtcgtaatgcgaaagtctggagcggaaccgactactagggtgtccgtgtacctgattacttattga tggctgcttatggtgacaacttatagttatcatcataagctacaggtcagccaaccggagaattata ggttatttgttggtttcataaacctacagtcgtattacctgtcaattaattgactcaaaattaacaaca |
| 624 | Enterovirus AN12 | taccgctgcaccagtgagctggtacgctagtaccacgcacggagtagatggcatcccccacccc gtaacttagaagcaaagtacacatctggccaatagtggcgctgcatccagccgcgcaacggtcaa gcacttctgtttccccggtccgcaagggtcgttatccgcccagtccactacggaaagcctactaacc attgaagctatcgagaggagcgctcggccacgaccccggtggtagctctgagtgatggggctcg caaacaccccccgtggtaacacggatgcagcccgcgcgtgcactcgggacagcctattggttgtt cacctcaacatagtgtaaatggccaagagcctactgtgctggattggattcctccggagccgtgaa tgctgctaatcccaacctccgagcgtgtgcgcacaatccagtgagctacgtcgtaacgcgtaaga ggaggcggaacagactactacggtactccgtgatcattgattatatgaatatatggtgacaattgc tgagatagcgaattagcgactctaccgctgaacattgccctgtactacctaatcgcatacacaaaa cctcagagataccaagctcaacattgatctgcagattcctgaatctcaaatataaattggaacaagc aaa |
| 625 | Dolphin morbillivirus | accagacaaagctggctaggggtagaataacagataatgataaattatcatacttaggattaatgat cctatcaaaggcacaggataggataaaggacacagtc |

TABLE 17-continued

| IRES sequences. | | |
|---|---|---|
| SEQ ID NO | IRES | Sequence |
| 626 | Dianke virus | tgttttcaaccataatactactactacaagtataaaaccccgtccgtctgtcggagacgctaaactctg accaccaatctagccacatcagagcttaaagaacctcagagacactctcccacttaacatcattag gaatcttcgatgctacaacaacaggctagtgaacaataaatccgtacaattcacagagtaagagg ccataggtccagactagaaaggtagtactattgaacaaatacttagattaacagaggctataaata gtgctcatcacgaaacagagtaaccagtgcaatagtatgagcagagtaaaacgtcagatacgac acc |
| 627 | Guereza hepacivirus | cactcaatactacactccgcataggggagaagcgctggcgacgcggaaccgcgttaaccatac gcgtagtacgagtgcgacagaccccggtgctactggtggtagcgagacacgagccgaagtctgt ggggggaactccacttagagggcatgcccgggcgtaggcttctgagagggatgggccccaact tggcccctgagtggggggtgttacgacctgatagggtgcgggctggcgcctaccactaccagt cgtacatgagtc |
| 628 | Grapevine associated narnavirus-1 | gcccggggggtgcagtcctgtgaaagggtctgcaccatactatatatgtatatgattacatcccaaa aggcgacttcgttcaggattaaatctgacgtaggtccagtaaataagcatgtcaaaacatgtaagat atcctgtaatctactctcataagatgagataagatgatattgcagacccatgtaaataaatccattatg aattcattcatataaggtagaagtggtaactatggagaaacattaatataaaacggtcattagcatga acgtcattaaggaactggcataccaatgtctatttagtgactatgatatttagagtatcccttatattaat taacaattattccattagcatatcatccgacaacaaatataaaagaagaaatattactcattaaaa |
| 629 | Goat torovirus | gtacttacaagcgggttaaaccgccctccggaacggttacaacccccctcccgaacgtgcgcttga cgtgactggactcagtctggctactgagaaatactccagggagtatcccaccatcttgacctctgg tcattaggtaacaccataaccaaacaaactctacacacctaacccacctccagcttgctgcaggcc ttttggactaaacgggataggtgattgtgaccaactcgtctacccacctccagattactgcaggcct ttttggactaaacggCatagacttagtggttagtattaactacccactgatagccgccaacctgatt ttcattgagtaaaattagtgatatacactattacatacggaggcagtagtaggagatgcacagttt ttgagataccaattatactgtgatttagtgtattctgctaaggctgtatatacatacttagtaggaga agcaattatacaacatttatattgatttgatactaaggtaaagagtcttaggaaacaccatagacgcc attcttgtggtgtctagaccaactaatctggcaaacaagtaccaagtcattgactcactaggagtga gacttacgagtaccaatttgcctatttcggacatccatataaag |
| 630 | Foot-and-mouth disease virus O isolate | acaagcttgacaccgcctgtcccggcgttaaagggaagtaaccacaagcttacaaccgcctaccc cggtgttaatgggatgtaaccacaagatacaccttcacccggaagtaaaacggcaaattcacaca gttttgcccgtattcatgagaaacgggacgtctgcgcacgaaacgcgccgtcgcttgaggaggac ttgtacaaacacgatctaaacaggtaccccaactgacatacaccgtgcaatttgaaactccgcctg gtctttccaggtctagaggggtaacactagtactgtgcttgactccacgctcggtccactggcgagt gttagtaacagcactggtgcttcgtagcggagcatggtggccgtgggaactcctccttggtaacaa ggacccacggggccgaaagccacgtcctgacggacccaccatgtgtgcaaccccagcacggc aacttttctgtgaaactcactctaaggtgacactgatactggtattcaagtactggtgacaggctaag gatgcccttcaggtaccccgaggtaacacgcgacactcgggatctgagaaggggactggggctt ctgtaaaagcgcccagataaaaagatctatgcctggataggtgaccggaggccggcgccatcc attataactactgacttt |
| 631 | Feline infectious peritonitis virus | acttttaaagtaaagtgagtgtagcgtggctataactatcattactttaactagccagtgctagatttg tcttcggacaccaactcgaactaaacgaaatatagtctctctatgaaaccatagaagacaagcgag attatttcaccagtaggcaatcactcctaggaacggggagagagaacggcgcaccagggaccg tccctgtaggtaagtcgtctagtattagctgcggcggaccgcccgtcgtagttgggtagaccgggt tccgtcctgtgatctccctcgccggccgccaggaga |
| 632 | Farmington virus | acgacgcataagcagagaaacataagagactatgacatagtcaccctgtattcattattgactatat gacctattattagaccatcacgggtaaatccactcatgcagactcgccaagtacctccaaagtca gaacg |
| 633 | Avian infectious bronchitis virus | acttaagatagatattaatatatatctattacactagccagcgctagattataacttaacaaaacggac ttaaatacctacagctggtcctcataggtgaccattgcagtgcacttttagtgccctggatggcacctg gccacctgtcaggtattgttattaaaatcttattgagctggtatcactgcttgattgccgtgtctcacttt atacatctgagcagggctacctagtgtccagcgtcctacgggcgtcgtggctggttcgagtgcga ggaacctctggttcatctagcggtaggcgggtgtgtggaagtagcacttcagacgtaccggttctgt tgtgtgaaatacggggtcacctccccccacatacctctaagggcattgagcctagcgagggctac gttctcgcataaggtcggctatacgacgtagtagggggtagtgccaaacaacccctgaggtgaca ggttctggtggtgatagtgagcagacatacaatagacagtgacaac |
| 634 | Human rhinovirus 1 | ttaaaactgggtgtgggttgacccacccacaccacccaatgggtgagtactctgttattccggtaac tttgtacgccagtattccctcccctccccatccattacgtaacttagaagattaaatacaagaccaat agtaggcaactctccaggagtctaaggtcaagcacttctgatccccggttgatgagatatgctcca acagggcaaaaacaacagataccgttatccgcaaagtgcctacacagagcttagtaggattctga aagatctaggaggtcgttcagctgcatacccagcagtagaccagcagatgaggctggacattcc ccactggtaacagtggtccagcctgcgtggctgcctgcgcacctctcatgaggtgtgaagccaaa gatcggacagggtgtgaagagccgcgtgtgctcactttgagtcctccggcccctgaatgcggcta accttaaacctgcagccatggctcataagccaatgagatatggtcgtaacgagtaattgcgggatg ggaccgactactagggtgtccgtgatcactattcattattaattgcttatggtgacaatatatatattg atatatattggcatc |

TABLE 17-continued

IRES sequences.

| SEQ ID NO | IRES | Sequence |
|---|---|---|
| 635 | EV22 | ccttataacccgacttgctgagatctataggaaaaaccattcccagccaggggtggctggtcaa<br>taaaaaccccatagtaaccaacacctaagacaatttgatcaaccctatgcctggtccccactattc<br>gaaggcaacttgcaataagaagagtggaacaaggatgcttaaagcatagtgtaaatgatatacta<br>acctgtattatgtacagggtggcagatggcgtgccataaatctattagtgggataccacgcttgtgg<br>accttatgcccacacagccatcctctagtaagtagtaaaatgtctggtgagatgtgggaacttattgg<br>aaacaacaatttgcttaatagcatcctagtgccagcggaacaacatctggtaacagatgcctctggg<br>gccaaaagccaaggatgacagacccattaggattggatcaaaacctgaattgagtggaagatatt<br>cagtacctatcaatctggtagtggtgcaaacactagagtaaggcccacgaaggatgcccagaag<br>gtacccgcaggtaacaagagacactgtggatctgatctggggccaactacctctatcaggtgagtt<br>agttaaaaaacgtctagtgggccaaacccagggggatccctggtaccattattgttaatattgaca<br>tt |
| 636 | Human TMEV-like cardiovirus | tccgacgtggaggaattaacatcattccgacgaaagtgctattatgcctccccgattgtgtgatgctt<br>tctgccctgctgggcggagcgtcctcgggttgagaaaccttgaatcattcctaggagccttggctc<br>ccccggtctaagccgcaggaatatgacagggttattaccaaactattatactactacatgggact<br>atccatgaaaagggtatgtgagcccatccactaggagaatctgcgcggcggtctttccgtctctc<br>aacaggcgtggatgcaacatgccggaaacggtgaagaaaacagattctgtggaaatttagagtg<br>gacatcgaaacagctgtagcgacctcacagtagcagcggattcccctcaggcgacaagagcctc<br>tgcggccaaaagccccgtggataagatccactgctgtgagcggtgcaaccccagcaccctggttc<br>gatggccattctctatggaaccagaaaatggattctcaagccctccggtagagaagccaagaatgt<br>cctgaaggtaccccgcgcgcgggatctgatcaggagaccaattggcagtgattacgctgccactt<br>tggtttaaaaactgtcacagatctccaaaccaagtggtcaggattccaattagttgactgacaat |
| 637 | Human coronavirus 229E | acttaagtaccttatctatctacagatagaaaagagctattagactagtgtctactatctcaactaaac<br>gaaatttttgctatggccggcatattgatgctggagtcgtagtgtaattgaaatttcatttgggttgca<br>acagtttggaagcaagtgctgtgtgtcctagtctaagggatcgtgaccgtcacgagattccattcta<br>caaacgccttactcgaggaccgtctcgtgatgtgtggaagcaaagactgtattgtggaaaccagt<br>aactgttccta |
| 638 | Hubeizha-ovirus-like virus 1 | gtgcaggatggcctttcccatcttaagtggtagtaggatttcgtgggtccataccccccgatttcttg<br>gtacgtattccatgcacggagaatacgaccaaaactcttatttcaaaaaatattattattactcagtgg<br>gctgagtgcgacccaccagaccagcttagcaacctggaagttgaggagatttatggaaccaaatt<br>acacatgcgtggagtgccgccactccgtatctgacactcattacgcgattaagactgcgacgaga<br>cgagcgaa |
| 639 | Hubeitombus-like virus 9 | ggaccatccaggcaggtgtaggctagtaccctcacctgacctgtcgcgatgatggctttgtgagg<br>cttgtgggaggatcccaggcccatgcattgctgctgtcatcgtgaaaaatgagtatgctcgcacct<br>ggcgtggaggaaacggcatttgacggatgctaaggaggatttgaaggtcctcaactcccatgcctt<br>attacaagtcccattcatcaagcttcgagcccacgtctgtgacgagcagaggtgaggaggagtc<br>aagaggagtcctattcaagctgacgcagcaagaaccataaaactacattgctcaatgggcaaga<br>gcggctaaggctcggactcgtagcacgacagtgtgagcggagccctgtaaatgtcgcggccctt<br>catcggtggatgcatcggagataagaaaattggcatgaacttgctccaggatcgtacgtgatcgat<br>gaggagttgaacttagtaggaaccaacgtatgagcgtatggtgtccgaaactaagaagcaattcc<br>gtcatcgggcacgtatggaatactacaacgagaaaaaatgccttgaaaagatccactaggaacgc |
| 640 | Hubeitombus-like virus 32 | ttcgggatacccgcgtaagcggccacactgactggagtcggtgagaatttgtataccagatgagg<br>agacgttaccaccgtctcggcagtgctacgtctgggaaaggactgtgatagtggacagtcctacc<br>gtctttagatacattgcgagtgtatagcccgggagggattaactaatagcaacgcaatgcacacgg<br>cggttcggatttgcttgactgatggaaagacatctaagactaattgaacc |
| 641 | Hubeisobemo-like virus 3 | gagatgatgcgtgggccgttgcgctgcgggcggcccacctccctacggggaccgtgagacacc<br>gctggggaaggcccccacccccggccaaggggatcctgccgagaggcaggagaaagaggcc<br>cagccctctggggcgcattaggggTgcctgggagggaagtacccgagccgggcggccggtc<br>gggtgcggctgtgcagttcgaggctaaccgtaaggaaggcctgagctgcctcggcttgtcggaa<br>aggaagacgaaggcacttatcaaggattcaggaagcaggagcgcaattacagcgcgcgccgt<br>gcggcctggattaaccgcatttggccg |
| 642 | Hubeipicorna-like virus 2 | agcaacttctactgaaaactagctagagttcgacgatctctctggctaatgacaaataaccaatcaa<br>aaagtcaaatgttcatgtatatatatatttagtagtgacctttatttagaaaaactttagatgatttatcgtc<br>aagttgccctagtgaagcgatcagctattatatcgatcatttagtatacgtcttaattgacgagtaag<br>tacgttttgcatacctcacattgaggatagtatcgtacctgactaagaagttaaactagtctaccaata<br>gcaaccatataggatatagattgataaacaaggataatctgatcaatgctcagcttacggtgatta<br>tgtatagaaaaGtattataaaaactacataattgtcaaaagaaaaagcgttacgtactgacgcataa<br>tgttcacagtgtgacacaaaccactatattagattgtaaaataggctagcctgaccatttatcaaata<br>caaactgatcaaacgcctctccgagccataaggccgacgcgaatcgacataacagggtgagat<br>acagctgcagagcagccgaggatccacttatagagagagaattactcaaacgaaattagaagtc<br>acttctacacagaaagtctgagtaggcgttatccaaacgtaaa |
| 643 | Hepacivirus P | acatgggggggggctgacagtgagtacactgtgccaagcaggtgctacgctatgcctaggtgct<br>gctgtaggccaaggacatgtcccagtcatcccaggtgagggggggggacccctcaccgctgcc<br>actgcctgatagggtcctgccggagggtctcggtgtccggctgtac |
| 644 | Harrier picornavirus | gatgtgtgacggtgtaattactttccggatcccactttcctattataactctttcatcccaaggttaggg<br>aaagaacctggctcggtaccaccagaccctccgccacgctagtggactctccggagataacggt |

TABLE 17-continued

IRES sequences.

| SEQ ID NO | IRES | Sequence |
|---|---|---|
| | 1 | acccccctagtagtcacctgtgctggtgaagaaccacctagtattgcagggtgcgtgccgcctagct<br>tccatttcttctggagcactgtgcaatgaggtaccccacaggtaacaagtgcctcaggtcccgcaa<br>ggatactgtggggtggtgtgaccgcagggagctgtctccacggctcctctaatgttacgccgctat<br>ccacaggccagtgcgtgtcatcgatcccggatgacagagctagtattgcgaacccccaagtaaga<br>aaagtggctagtaacctgatagctggtgaagagggtgggtcagttgagtagatgccctagaggta<br>cccgaaaggatctgactagggacccgtgactatacattaggtaaaccgggtataaaaaccatgaa<br>aaactgaccactatcattaacctcactactattatgtgtgaaagtgattgagtaggactgtaccag<br>cccgcctttcttggattttctctatcgctcttcttacacctactgttatcaaggcactctttagagata |
| 645 | Kunsagivirus 1 | tttcaaatcggactccggtagttataccggagcccggtaggacgcagggccgcgttaacagccc<br>cccaccccatcccactgactgatactcggattggactcatagcattgctaactctgattctggatac<br>cccgtttatgtcgtcgcggtcggaagtgcacgtacacgacgagatctgatggcgatgtaccagg<br>ggggaggtggcggcagaaacgcccccgccgtaaacacggcgggccacgcctgtcaagccact<br>ccctggggccgagcgcctgaggtgatacagagagataagcacactgggcgctgacaacgcccg<br>ggacctcagtgagaagagcagtagggccgtgatatgggactccattggatatcccccgcagtcg<br>gaactcacggctactccgggagggaagcccgcgactggtactgtactgggtgatagcctggtgc<br>cttccctctcactgagtatgaaggctgaaaacccccct |
| 646 | Kagoshima-2-24-KoV | tatagtagcctgatctcgcaccgttaccgctcgacgggaatgtgaaactggcacccctcctctccc<br>ctaccaccctactccacgcccccattcataatttacaacgccgcacacagcggcggccgccaag<br>ggctagcctggcggaataaaaggaacctgggtctaccctcacaagccaaaaggtaggaccctg<br>tgtccctgaatgctcggtgaggaatgctgcaccgtaacgctagtgaagtgtttgcaagttctggccc<br>ggcaagcctacagagtgctgtgatccgctgcggacgccatcctggtaacaggacccccagtgtg<br>cgcaacagtatgacagacacggatgacacagcatcatggaccattgcgcgaaagtgcgtgcg<br>ccatatccctgtacacaggtgtgcactctggaccctaggaatgctgcgaaggtaccccgatcggc<br>gggatctgatcgcaggctaattgtctatgggacagtaccatacatactccacaattgactgcttaa<br>ctgactctggatcagtgcaccactgctctactgctctcaaaacggcacacttaccaactctcacca<br>tcgaccaacaccatttacacactaactatacgactcactgactcctggcaggtgaagac |
| 647 | Kashmirbee virus | tacgtacaattagacgcacgacatgcaacaatgaactcacatgtggcgctcggtagtaaccagag<br>gggcgtcattcccccgtatggagtggagaatataagctaccgactcgagctgtagaataattcagc<br>aacttataacgaacacgaatatagtcgacgaaaccatatagccataaactatgatagattataatg<br>ataaacagctcatgtaactgtctaaactacataaatacaactggattacgaaccataagtaactatca<br>agatgaagtctagtagtctcccaatataccgtgaaaagaatgagggacgagatagctctatttaaa<br>gacgtgaggcataaaactgataaatacattacctgagaaacctccataggagaagaatagaaaa<br>gattagtacctatacttaatagaaataaatatgaaataatgctgaagacaagtatacgattattaacct<br>ctatatactatataaagtatctgtgagtctcagtggacatcacagtaaggtcgcagaaacagtaatc<br>ttttcattcctgtgtcggagcagtggtaatggagccggacgatacgccaaaac |
| 648 | Jingmen picorna-like virus | tgtgtttttgtcaagataattgttctgtgattaacagtgattgtggttcgtgtaatgcgacgcagtcaaat<br>gctagttttgatgaagtgtatgagagagtggaaaacttatctcataagaagattgaagagtgtgtaga<br>tcaggctattgatcgagcttctaagcttcgtgattacaagcttaatgttcacaatggctcccgacggg<br>aatcatctgatcctctctttatttcgccccattcgttgttatcgcttggggtatctaagtttgttgcgtttga<br>gcagcatcacagtttcgcttcagttgagtctctgaagttgcttgctctgtct |
| 649 | Mumps virus | accaaggggaaaatgaagatgggatgaggtagaacaaatagtgtaagaaacagtaagcccgga<br>agtggtgttttgcgatacgaggccgggctcgatcctcaccatcattgtcgataggggacattttgac<br>actacctggaaa |
| 650 | Mouse Mosavirus | gaagttgatcatgaacttggttattggtggaacgcacatgaactcccaacaatgatcttgaagacac<br>agcgtggtaacaattaccatgcccagtggctgcccaagacattgatggctattgggtgatttatgat<br>gac |
| 651 | Miniopterus schreibersii picornavirus 1 | gttgtcgacccgttgatggataagcatgaggtggattcccccgattatgtctacccgttactatggc<br>gggcggtcgatcagggtgatctactgaggactgcaccaagtattatcattattctcagatctccgg<br>ctgtttgacgcagtaggacagcaggactattactcttaatctattctacccactagggtcctatccta<br>gtggagggagggtgccacccatctctattagagagtgcgcctggcggtctaccgtctctggaaa<br>aaggagcacatggcatgctacaattggcacaagaaaacaagctagcggattattctagtactaga<br>ggaagctgtagcgaccctgtatggcgagcggactcccctctcggcgacgagagcctctcgggcc<br>aaaagccaagtgttaatagcacccatacaggcggcagtaccccactgccctactcaacatacaat<br>gactgatgaaccactgaggatactgacacctagtagtaggattccaaggaatgtcctgaaggtac<br>cctgttagcttacgcgcaggatctgatcaggagtctattacagtgctgtacactgtgcaagggatta<br>aaaattgtttgaggaatccccgagatagtggtctatctatcctattagattacagacacg |
| 652 | Linda virus | gtatagcagcagtagctcaaggctgctatacgattggacataccaaattccaattggtgttagggac<br>cacctaggtgaaggccgacgacaggtagccattcctgttagtaggacgaaccgttatggtggact<br>ggttgctcaggtgagcaggctgcaatgcgtaagtggtgagtacaccacagccgtcaaaggtgcc<br>actggtaaggatcacccactggcgatgccttgtggacgggggcgtgcccaacgcaatgttagcg<br>gtggcgggggctgccatcgtgaaagctaggtcttgatggaccttgttgcctgtacagtctgatagg<br>atgccggcggatgccctgtgacagccagtataaagaatatccgagtgattgcac |
| 653 | Lesavirus 2 | tctttctttattttcttatgtaactcactattaagattattagcctacttgtgagcttatgcgggaccactg<br>tcttagacaaccccacatagtcatgagtaagtacacgcaaccattacgattactattaaccgtctga<br>ccttttgataacaactgaagttaggcgtgaaacatgcatttataccaaagtagccccgcatttcccca |

TABLE 17-continued

IRES sequences.

| SEQ ID NO | IRES | Sequence |
| --- | --- | --- |
| | | ctacggtggggggctaccctactggctaggaactgtagccattatgtgagcctggctttcaggat ctcacaacacaacagactctcacaatggaatatgggtgagattgcagtgacatgaacaagtatcta gtagtacatagactcaagcctagttgcctgcggaacaacatgtggtaacacatgccccagggtcca aaagacaagggttaacagcccatctaggtgtctgtgtgtgaagaatactttagtagtgttgttatgat ctcacctgttagtacagaatgagtatggcaggtgaaggatgtcctacaggtacccattatatggatc tgagtaggagaccactagtggtggctttaccgccaggtgagtggtttaaaaagcgtctagccaagc caacagcactagggatagtgctactatatatatattacagtgtatatggtgacaa |
| 654 | Lesavirus 1 | gtaactaataagcaagattactgcctgcaaactgcttcaatgggaccaccgcttcggcgacccatt gttgagtttgtatgtttttaagtaatattgcaaccatacgattatatagccgcctctctataatgatcagt tatagtgggacgtgaaacattggatactcacacacgtccggtcacccgggcgtgtgacttccgta agtcctatccacataccatcgtgggtaggccagcatgatgcacaggctgtgacagtgtgggtggg ctttccacctctcaacaacacactgaattgcaatgcactcacggaggaaatgacaataggttatagt tttgaactgtgctagtaatttattcacattaagccatgagcctgcggaatcacatgtggtaacacatg cctcagggcccaaaaggcacgggttagcagccccttcatggtgtgttagaagtgaaaacacatag tatgagctataatatattgagtatctctgtagtgtaccccgccaaatgtaaggatgcccagcaggt acccatatatggatctgagctggggattgatagtgtatctataaatgcactgatcaatttaaaaagcg tctaagtaggcacaaacactggggacagtgatttcattattatttatttgatta |
| 655 | Phopivirus strain NewEngland | gggagtaaacctcaccaccgtagccgtggatacggctacctatattggatgtaaatattaattcctg caggttcaggtctcttgaattatgtccacgctagtggcactctcttacccataagtgacgccttagcg gaacctactacacttgatgtggttaggggttacattataccctgggccactaggccattacccctg cactatcattattcaccgggctctcagcatgccaatgaccgaccggtgcgcccgccggggttaa ctccatggttagcatggagctgtaggccctaaaagtgctgacactggaactggactattgaagcat acactgttaactgaaacatgtaactccaatcgatcactacaaggggtaggctacgggtgaaacccc ttaggttaatactcatattgagagatacactgataggttaaggagctggataatggtgagtttaacga caaaaaccattcaacagctgtgggccaacctcatcaggtagatgcttaggagccaagtgcgtagg ggtgtgtgtggaaatgcttcagtggaaggtgccctcccgaaaggtcgtaggggtaatcaggggca gttaggtttccacaattacaatttgaa |
| 656 | Pestivirus strain Aydin | gtatacgagattagctcatactcgtgtacaaattggacgtagcaaatttaaaaattcggatagggtcc ccatccagcgacggccgaacggggttaaccatacctctagtaggactagcagacggatggacta gccacagtggtgagctccctgggaggtctaagttctgagtacagaacagtcgtcagtagttcaacg ctggtaaaccccagccttgagatgctacgtggacgagggcatgcccaagacacaccttaacctgg acgggggtcgtccaggtgaaagtacccatctagggtgctgggagtacagcctgatagggcgctg cagaggcccactgacaggctagtataaaaatctctgctgtacatggaac |
| 657 | Quail picornavirus QPV1 | tttgcatcagttcgcccctcccctcaccataccatttcccctattaggactgatacttggttatgatga gcagaggatttcgcaagttatgatcttgataaaaagtaattcacgaatcatgggattatagcctgga agtgaacactcatgtggcaagtgggttagtagctctccatgacccatgtgcagtggactgacaaca gtgagttcggggagtgtagtaaagggaaagtattacttacccgcacctgctatacgtggtgtacgta ggatacgagttagtagtgcttagcaactttaaactggtgctgaaatattgcaaggtcactgaagttgt gaacgcgaacgctccgccactgccatgtatagcgtgcaatgcataaatggtgcactacatgatacg agggaatgggaaaccctccatggccgaatgcagggtgacagcctgccggcggatgcctgttgtt agtataatccgttgatgccac |
| 658 | Porcine sapelovirus 1 | acactcatttccccccctccacccttaaggtggttgtatcccctacaccctaccctcccttccacatagg acgaataaacggacttgagattaaggcaagtacataaggtatggataggatacacttaaatggca gtagcgtggcgagctatggaaaaatcgcaattgtcgatagccatgttagcgacgcgcttcggcgtg ctcctaggtgattcggcgactggttacaggagagtagacagtgagctatgggcaaaccccctacag tattacttaggggaatgtgcaattgagacttgacgagcgtctctttgagatgtggcgcatgctcttgg cattaccatagtgagatccaggagggaaacctggactgggtctatactgcctgatagggtcgcg gctggccgcctgtaactagtatagtcagttgaaaacccccc |
| 659 | Porcine reproductive and respiratory syndrome virus 2 | atgacgtataggtgaggctctatgccaggcatagtattgtcaggagctgtgaccattggcacagc ccaaaacttgctgcacagaaacaccatctgtgatagcctccttcaggggagcttagggatgtccct agcaccttgcaccggagttgcactgattacggtctctccacccattaacc |
| 660 | Porcine enterovirus 9 | Gaaccttagaagatacacaaacaaagaccaataggagtccaacacccagaggattgcggtcaa gcacttctgatccccggacctagtagtgataggctgtacccacggccgaagatgaacccgtccgtt atccggctacctacttcgggaagcctagtaacattctgaagtctctgaggcgatcgctcagcacga ccccggtgtagatcgggctgatgggtctccgcataccccacgggcgaccgtggcggaggccgc gttggcggcccgcctatggcgaaagccataggacgcctcttagatgacagggtgtgaagagcct actgagctgggtagtagtcctccggcccctgaatgcggctaatcctaaccacggagcgtccacca gcaatccagctggcagggcgtcgtaacgggcaactctgtggcggaaccgactactagggtgtcc gtgtttccattgatcctattaggctgcttatggtgacaacgataagagttatcataaagctcttgggtt ggccacctggaaaaagttatcagtgatgatattgacggctctcacgcctaccaataagacaagcc ctatatttacttgagcatatactcgtcagaagaaatcacagagtatcataggatagttactcacatta aggacaag |

TABLE 17-continued

IRES sequences.

| SEQ ID NO | IRES | Sequence |
|---|---|---|
| 661 | Pigeon picornavirus B | tttatttagctgttaagattatttgtgccgagAccccatagtaggatcaggtgaccacattaagctct<br>Cccgaccacacatccaaacgataggcggtgtaagggctccctggctaagtgatactcattgctag<br>ggaagtgagcgacccgttaccagtaggaatacaggaggtcttagttgcctaaccagataaagtgg<br>tgctgaaatattgcaagctcaatgtctggcgaacgacggactaccgttgaactattgttaacgcccg<br>cgtgtgtaggcaacacacgggttagtaggtcacttacattgacatccgtgccgggaaagcggatct<br>gagctatcgattgcctgatagggtgccggcgggcgcggtacgtgtggtatagtccgctgtcttggg<br>gtatggcgtctactcggattgagtcgattggaatgtcccatgtcggagatgtcgttaccggtgtttg<br>ctttacttgtgcacgaataagaaaacagagtaggagattggaagttaatggataacatcaagtacc<br>attgcgacctcgtgcatataggccagaaaatcgaccacaaaatcgaga |
| 662 | Picornavirus HK21 | aaacgggaggatcggctaggcttatcctcttaatagtctacaaaactgggctgactggtggggga<br>gctactagatccgggagaggactagttaccccgcgtaacttccattagtcactccctccacctacc<br>catccctgtcccttagactcttaagtaggtgtgcaggcctggcccccggaaatgggcaaatcgg<br>acgtttgcgtgtagggtcgactgaaaggtggggcccactccaccgtagtaggatcacctgatcac<br>gtttaaacctctccgggcaggtatcgctagacactaggctgtataggatggcacgcacttaggatc<br>gcaccacctagtgcgccaagatcccgcattgagctcaagtacatggactagtaagatgtctaacc<br>agaggaggtggtgctgaaatattgcaagccactctggcgaacgtccactgcattgcctggaacag<br>gctctctagcgccctccactggtagcgcggtggtgggttagtaggatacctatatggacaggggat<br>gcgggaatacccctcactagctagtgactggttgatcgactggcggcggatccagtgatacttgca<br>taatccgcagacttgggag |
| 663 | Picorna-virales Tottori-HG1 | agccatgaactagtgtgcgattcccacagtgaggtcgaaagccccgcactgtctactcgcatattt<br>gactccagtccaccgcagccagcggttaggactggttaaagtgcattatgtgcacggcgccacg<br>cagaactgccagaaatggtaagctgcgcccaacgccaacggtagtgtatcccgttagtcacacgt<br>ttacagctgttcgttaacagtagggttttgtcgacccggaccccttaatgcgcgcgaattcaaccgc<br>gcctagtcggcaatggtatcatttaatcccatgcactacgggagaaatttgagaccaaagaattcct<br>gagggccactgcttgctctaagtgcaatgcctcgggagacttctgtcaggagcctagcggctttca<br>accgcgacagctaactcctgcgggatgtttggtgtccatacttactggcgtcctcacaacgctaagt<br>ggatgttgtccacaggtaggcaaacaccgagccccacattcaggagacctgtatgaacgatcctat<br>cagcattagagttggaattgggtgtgctaacgtccgcataagtgcaccccgtggtaacgctgggaa<br>actatccagcgcaacgtactgtcctcaatgtctagggaaggaccgccctaagcgtacaaccgggc<br>catgtgtcgagc |
| 664 | Rodent hepatovirus | ttcaaagaggggtccgggattttcctggtccccctctttgggcacccttggctcgggggtgtgaata<br>ccgtgctcgcgtttgccgtgcgttaacggcttcatttatgtttgtttgtctgttttattatgttGgtttgtct<br>gtttgttatgttggtattgttcgtgtttaatgttatgaccacattacactccagccaatgaagaacagatg<br>gtgcggttattgctggcggaattcctaacgtcctggatccgttggtacgcatcacaaaacaatttgca<br>gagagagtggtgaaacggcttgggaatccctgagtacagggaaatcacactgatagctcatcttg<br>gctgttttcagtcatggaccttatgcagtgtaatttgggtgtaccccccatagcttaggaggaatgttc<br>tgtcttggcactagagtgggacgctgatgcctccgtgtctaggatggtctaagggacagaatgggg<br>tgcctctgatgccatactacctgatagggtgctctcacggcctctgcatcttagtgagaagttcaattt<br>t |
| 665 | Rinderpest virus | accaaacaaagttgggtaaggatcggtctatcaatgattatgatttagcacacttaggattcaagatc<br>ctatcgactggagcaggcttaaggtaaaggttctttaaa |
| 666 | Rabovirus A | ctacggatatttgcatgacccgctttctatcgccccaacaatcccctttgtaaccacaagctttactca<br>ggctagcagcccgactagctgtttggaagaaaaggctagggcacacaccaacaacaccgaccc<br>cactggtcgaaggccgcttggcaataagactggtggaacagggtcgcctgtagttgtttggaacat<br>tctttctaatgactttgtcagcggtgctactcacaccgtaactcttctaccctatccccacgcttgtgga<br>actaggaggggatgagtgattcaagtaagtactgtcagaatggtgaaaatgatctgattctgaaacg<br>ctatggatccatcgaaagatggggctacacgcctgcggaacaacacatggtaacatgtgccccag<br>gggccgaaagccacggtgataggatcacccgtgtagtttgagatcatatcaatgttcatagtctagt<br>aagatgatttgaaatctaactgagctgatggctaactgcttgtcttattgcggcctaaggatgtcctgc<br>aggtaccttagataaccttaagagactattgatctgagcaggagccaaagtggtctttcccagcttt<br>ggttaaaaaacgtctaagccgcggcagggggcgggaggccccctttcctcccaaaacttaatatt<br>gattgt |
| 667 | Shingleback nidovirus 1 | ctgtgagtaccgacaggctcgaagtctattatgaggcgtcgaaacagaaaacctgtaacaactccg<br>gtttcatctatcactgccgtcaagaggcagaagaggacgaccacgtgtcaccagatcacttgtatct<br>gtttcagtcaggaagtcaacttttcgacgaagttcgaccattcatcgacccgctgaaaagcgtagaa<br>tcgagctcgtgaatttcgagctgaaacaacaaatcaacgagaacgagtggtacggttattataatta<br>cgacaaccaaaactgcaaagttcagttgccagtcacatgtcgaatcgaggacgtaacctgggatc<br>aggtttacgtg |
| 668 | Seneca valley virus | tttgaaatggggggctdgggccctgatgcccagtccttccctttccccttccggggggttaaccggctg<br>tgtttgctagaggcacagaggggcaacatccaacctgcttttgcggggaacggtgcggctccgatt<br>cctgcgtcgccaaaggtgttagcgcacccaaacggcgcacctaccaatgttattggtgtggtctgc<br>gagttctagcctactcgtttctcccccgaccattcactcacccacgaaaagtgtgttgtaaccataag<br>atttaacccccgcacgggatgtgcgataaccgtaagactggctcaagcgcggaaagcgctgtaac<br>cacatgctgttagtccctttatggctgcaagatggctacccacctcggatcactgaactggagctcg<br>accctccttagtaagggaaccgagaggccttcgtgcaacaagctccgacacagagtccacgtga<br>ctgctaccaccatgagtacatggttctcccctctcgacccaggacttctttttgaatatccacggctcg |

TABLE 17-continued

IRES sequences.

| SEQ ID NO | IRES | Sequence |
|---|---|---|
| | | atccagagggtggggcatgacccctagcatagcgagctacagcgggaactgtagctaggcctta gcgtgccttggatactgcctgatagggcgacggcctagtcgtgtcggttctataggtagcacatac aaat |
| 669 | Sclerotinia sclerotiorum dsRNA mycovirus-L | ttgaattaatcttttacgtttacgcgcataaaatcaggacacatctcttgtatactttagtatatcaatgat gtttttgttttatgcgattaatcgtaagagaacttctttccatccgcctgtatgggcgggataataagttc accgccttggtcgaggcgcaaacttgtatgtgcaaaggtgagctatatgctcgaaatagtcgtaact aacacacagccactacctgtagagctctattgatccggaatcctttagtgggaatgcagagctca ccggacctgcgggttcttcggcgttagggacttctgtttcagccttgaatcatttacctttataccttct ctgaggcgcctgggccgggcgcgatattaagtacaagtcaaggacatcgcgggtagtggtctaat cagccgctagtcctgctggagagttccaacttagttgggtgtggtgcatactagctggatagagtag gtatgtattgctaacgtatgccggaggctatccgtcctcggtagaacgtgccgaggagtagtctctg cagacccccgaacgcgtggggtctttacttaaatgtaggcggagggagcgctcgtaggtggaac gactgcctcccagtcgaatgcaagatttttgcacgcggaccagtctgcccggcaattcccgggtg |
| 670 | Yak enterovirus | ctccggcacagccgcaccagtgcactggtacgctagtaccttttcacggggtagtcggtatccccc cccgtaacttagaagcatgtaacaaaccgaccaataggtgcgcggcagccagctgcgttgcggtc aagcacttctgtctccccggtccgcaaggatcgttacccgcccactccactacgaggagcctagta actggccaagtgattgcggagttgcgttcagccacaaccccagtggtagctctggaagatggggc tcgcacatcccccgtggtaacacggttgcttgcccgcgtgtgcttccgggttcagtctccgactgttc acttcaacatcacgcaaccagccaagagccgattgtgctggagtggtcttcctccggggccgtga atgctgctaatcctaacctccgagcgtgtgcgcacaatccagtgttgctacgtcgtaacgcgtaagt tggaggcggaacagactactttcggcaccccgtgtttcctttattttattcttattttatggtgacaattg cagagatttgtgatattgcgactttaccgttaaacatagcactgcattacctggttgcattccacaaaa cttcagagattcctagttcctacattgacctacttgtttatttgaatcttaaatacaaacttgagcaagtg aa |
| 671 | Wobbly possum disease virus | cggctgtgagtgcttagcatatgctagagtactacagccgggtgttggagtcatatgcactggttgc ctgtataatagtcgggatctgtctgacctacattatctttgggagttgcttatcacgacaattctcgaag tgtctgtcgacagcttaccccccgattcgacaaggccccttgtccaccgcagacctatcgattttcaac gagaacactatcagaggtttaaatttaaaactcaccaaca |
| 672 | Avian orthoreovirus segment S1 | gctttttcaatcccttgtgtcgatgttcccgtatgtcatctggttcatgtaacggtgcaacttctatttg gtaacgttcactgtcaggcagcgcaaaactcggcgggtggtgatcttcaagcgacttcctctcttgtt gcttattggccctacttggctgcgggcggtggtctgctcgttgttattattataattgttggcgctgtttg ttgttgcaaggctaaggttaaagcggacgcagcccgaaacgttttctaccgagagctgttcgcactt aattcgggtaaaagtgatgcaggacctccgatttaccaggtttagtgtacgacgatttgagttttcac ctttcgtcttagaggagtgcactactccatctttcacgactataactaataccgatccggctctctactt taacattgagtttccgtcaagtcatcgtctctccccccttcattccagaactgttgtctcagccttgtacc gttcacgtttcattgattcggagattcgctctctgtgcaaccttatctagtatttgtgaatacgactgtgc gctactgccatccatcaacgctattacgacgatccctacaccaggtgcgtcatcatctctgattgttc attggg |
| 673 | Caprine Kobuvirus d10 | ggggcctcggcccccctcaccctcttttccggtggccacgcccgggccaccgatacttcccttcact ccttcgggactgttggggaggaacacaacagggctcccctgttttcccattccttccccccttttccca accccaaccgccgtatctggtggcggcaagacacacgggtctttccctctaaagcacaattgtgtg tgtgtcccaggtcctcctgcgtacggtgcgggagtgctcccacccaactgttgtaagcctgtccaa cgcgtcgtcctggcaagactatgacgtcgcatgttccgctgcggatgccgaccgggtaaccggtt ccccagtgtgtgtagtgcgatcttccaggtcctcctggttggcgttgtccagaaactgcttcaggtaa gtggggtgtgcccaatccctacaaaggttgattctttcaccaccttaggaatgctccggaggtaccc cagcaacagctgggatctgaccggaggctaattgtctacgggtggtgtttcctttttcttttcacacaa ctctactgctgacaactcactgactatccacttgctctcttgtgcctttctgctctggttcaagttccttg attgtttttgactgcttttcactgcttttcttctcacaatccttgctcagttcaaagtc |
| 674 | Caprine Kobuvirus d20 | ccccctcaccctcttttccggtggccacgcccgggccaccgatacttcccttcctccttcgggact gttggggaggaacacaacagggctcccctgttttcccattccttccccccttttcccaaccccaaccg ccgtatctggtggcggcaagacacacgggtctttccctctaaagcacaattgtgtgtgtgtgtcccagg tcctcctgcgtacggtgcgggagtgctcccacccaactgttgtaagcctgtccaacgcgtcgtcct ggcaagactatgacgtcgcatgttccgctgcggatgccgaccgggtaaccggttccccagtgtgt gtagtgcgatcttccaggtcctcctggttggcgttgtccagaaactgcttcaggtaagtggggtgtg cccaatccctacaaaggttgattctttcaccaccttaggaatgctccggaggtaccccagcaacag ctgggatctgaccggaggctaattgtctacgggtggtgtttcctttttcttttcacacaactctactgct gacaactcactgactatccacttgctctcttgtgcctttctgctctggttcaagttccttgattgtttttga ctgcttttcactgcttttcttctcacaatccttgctcagttcaaagtc |
| 675 | Caprine Kobuvirus d30 | ctcttttccggtggccacgcccgggccaccgatacttcccttcactccttcgggactgttggggagg aacacaacagggctcccctgttttcccattccttccccccttttcccaaccccaaccgccgtatctggt ggcggcaagacacacgggtctttccctctaaagcacaattgtgtgtgtgtgtcccaggtcctcctgcgt acggtgcgggagtgctcccacccaactgttgtaagcctgtccaacgcgtcgtcctggcaagactat gacgtcgcatgttccgctgcggatgccgaccgggtaaccggttccccagtgtgtgtagtgcgatct tccaggtcctcctggttggcgttgtccagaaactgcttcaggtaagtggggtgtgcccaatccctac |

TABLE 17-continued

IRES sequences.

| SEQ ID NO | IRES | Sequence |
| --- | --- | --- |
| | | aaaggttgattctttcaccaccttaggaatgctccggaggtaccccagcaacagctgggatctgac<br>cggaggctaattgtctacgggtggtgtttccttttttctttttcacacaactctactgctgacaactcactg<br>actatccacttgctctcttgtgcctttctgctctggttcaagttccttgattgtttttgactgcttttcact<br>gcttttcttctcacaatccttgctcagttcaaagtc |
| 676 | Caprine Kobuvirus d40 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctactgctgacaactcactgactatccact<br>tgctctcttgtgcctttctgctctggttcaagttccttgattgtttttgactgcttttcactgcttttcttc<br>tcacaatccttgctcagttcaaagtc |
| 677 | Caprine Kobuvirus d50 | ccgggccaccgatacttcccttcactccttcgggactgttggggaggaacacaacagggctcccc<br>tgttttcccattccttcccccttttcccaaccccaaccgccgtatctggtggcggcaagacacacgg<br>gtctttccctctaaagcacaattgtgtgtgtgtcccaggtcctcctgcgtacggtgcgggagtgctcc<br>cacccaactgttgtaagcctgtccaacgcgtcgtcctggcaagactatgacgtcgcatgttccgctg<br>cggatgccgaccgggtaaccggttccccagtgtgtgtagtgcgatcttccaggtcctcctggttgg<br>cgttgtccagaaactgcttcaggtaagtggggtgtgcccaatccctacaaaggttgattctttcacca<br>ccttaggaatgctccggaggtaccccagcaacagctgggatctgaccggaggctaattgtctacg<br>ggtggtgtttcctttttcttttcacacaactctactgctgacaactcactgactatccacttgctctcttgt<br>gcctttctgctctggttcaagttccttgattgtttttgactgcttttcactgcttttcttctcacaatcctt<br>gctcagttcaaagtc |
| 678 | Picorna-virales sp. isolate RtMruf-PicoV | tttgctcagcgtaacttctccgggttacgtggagaccaaaaggctacggagactcgggctacggc<br>cctggagcacctaggtgctcctaaagacgttagaagttgtacaaactcgcccaatagggcccccc<br>aaccagggggggtagcgggcaagcacttctgtttccccggtatgatctcataggctgtacccacgg<br>ctgaaagagagattatcgttacccgcctcactacttcgagaagcccagtaatggttcatgaagttgat<br>ctcgttgacccggtgtttcccccacaccagaaacctgtgatgggggtggtcatcccggtcatggcg<br>acatgacggacctccccgcgccggcacagggcctcttcggaggacgagtgacatggattcaacc<br>gtgaagagcctattgagctagtgttgattcctccgcccccgtgaatgcggctaatcccaactccgga<br>gcaggcgggcccaaaccagggtctggcctgtcgtaacgcgaaagtctggagcggaaccgacta<br>ctttcgggaaggcgtgtttcctttgttccttttatcaagttttatggtgacaactcctggtagacgtttt<br>attgcgtttattgagagatttccaacaattgaacagactagaaccacttgttttatcaaaccctcacagaa<br>taagataaca |
| 679 | Apodemus agrarius picornavirus strain Longquan-Aa118 | ttactcagcgtaactactccgggttacgtgatgaagaagaggctacggagattctcgggctacggc<br>cctggagccactccggctcctaaagatttagaagtttgagcacacccgcccactagggcccccca<br>tccagggggggcaacgggcaagcacttctgtttccccggtatgatctgataggctgtaaccacggct<br>gaaacagagattatcgttatccgcttcactacttcgagaagcctagtaatgatgggtgaaattgaatc<br>cgttgatccggtgtctcccccacaccagaaactcatgatgagggttgccatcccggctacggcga<br>cgtagcgggcatccctgcgctggcatgaggcctcttaggaggacggatgatatggatcttgtcgtg<br>aagagcctattgagctagtgtcgactcctccgcccccgtgaatgcggctaatcctaaccccggagc<br>aggtgggtccaatccagggcctggcctgtcgtaatgcgtaagtctgggacggaaccgactactttc<br>gggaaggcgtgtttccatttgttcattatttgtgtgtttatggtgacaactctgggtaaacgttctattgc<br>gtttattgagagattcccaacaattgaacaaacgagaactacctgttttattaaatttacacagagaag<br>aattaca |
| 680 | Niviventer confucianus picornavirus | ccctttcataacccccccccttttaacccaacccttcgtaaccgtacgcttcactcgcctttgggtatag<br>cggcccaatgtgctgaagaaaaggatacgctataaggggccaacgggtggtggcccttaagacc<br>acccaacctagaagcttgtacactcgggcaatagtgaggcccacatccagtgggtcaagcccaaa<br>gcattcttgaccccggtatgatctcataagctgtacccacggctgaaagagtgattatcgttatccca<br>ctcagtacttcggagagcctagtacaccacttggaaatggaagtctgtgatccggggttgaccctg<br>aaccccagaaactcatgatgaggctaaccttcccgaacacggcgacgtgtggttagcctgcgctg<br>gcatgaggcctctttgtaggcagactgaaatggaagggtgacgaagagccgactgagctactgttt<br>tattcctccggcccccctgaatgcggctaatcctaactcctggtccagtacttgtaacccaacaggtg<br>gctggtcgtaatgcgtaagccgggagcggaaccgactactttggggcgtccgtgtttctcaatatta<br>ttcatttctagcttatggtgacaatttatgattgcagagattgtgctgtatttgtgtctgagagaagaagt<br>aacaat |
| 681 | Bat picornavirus isolate BtRs-PicoV | tttcaaaaggccctgggcatacggcgttattcgtaacgtcgtatgtccagggcggtagcatcaggc<br>caaggcctgatgctaccacgtgtggactaaaccacacactcttcttgtgacacgttgtgtcacctatc<br>cctttcttggtaacttagaagcttgtacacttacgcacgtaggtgccccacatccagtggggtttgtg<br>caaagcaatcttgttccccggtaaaccctgataggctgtaaccacggccgaaacaaggtttgtcgtt<br>acccgactcactactacacaaagcctagtaaagacaatgaaagtgcgcagcgtgatccggtcaaa<br>accccttgaccagaaacacatgatgagggtcaccaacccccactggcgacagtgtggtgtccct<br>gcgttggcatgtggcctcgtagaggcgagcaatctggatttgctccgaagagccccgtgtgctagt<br>gtttatacctccggccccttgaatgcggctaatcctaacccccgagcatgtacacacaagccagtgt<br>gtagcatgtcgtaatgagcaatttggggatggaaccgactactttagggtgtccgtgtttctcattatt<br>ctttgtttgatgtttt |

TABLE 17-continued

IRES sequences.

| SEQ ID NO | IRES | Sequence |
|---|---|---|
| 682 | Rhinolophus picornavirus strain Guizhou-Rr100 | ttttttttctcaggcggtagcatccagccaaggcctgatgctaccaacgtgtgactaaaccacactct<br>ctttttgtgatacattgtgtcacctatccctttcttggtaacttagaagcttgtacacccacgcacgtag<br>gtaccccacatccagtggggttgtgcaaagcattcttgttccccggtaaaccctgataggctgtaa<br>ccacggctgaaacaaggtttgtcgttacccgactcactactacgcaaagcctagtaaagttcaatga<br>aagtgcgcagcgtgatccggtcaaaaccccttgaccagaaacacatgatgagggtcaccaacc<br>cccactggcgacagtgtggtgtccctgcgttggcatgtggcctcatagaggcgttgcaatctggatt<br>tgctccgaagagccccgtgtgctagtgtttatacctccggccccttgaatgcggctaatcctaaccc<br>ccgagcatgtacacacacgccagtgtgcagcatgtcgtaatgagcaatttggggatggaaccgac<br>tacatttgggtgtccgtgtttctcattattctttgtttgatgttttatggtgacaaca |
| 683 | Rhinolophus picornavirus strain Henan-Rf265 | cggaacgttgtatgctcagggcgtaggcaccacccacgggtggtgcctacacgtgtggactaaac<br>cacacactcttttcagcacttagtgctgctatctctttttgtaacttagaagtttgtacacaatgcgttag<br>ggccacacatccagtgtggtatcgcaaagcacttctgtttccccggtgctagtaggagggtggctg<br>ctccacggccacttgccgaacccatcgttacccgactcattacttcgcaaagcctagtaacccagtt<br>gaagcaagcccggcgtgttccggtcaggaaaaaccccccctggccagaaacatgtgatgagggt<br>gggctatccccactggtgacagtgagccctccctgcgttggcacatggcccgatctgggcgtggtt<br>cttgtggatgctgccgaagagccccgtgagctagtgtttataccgccggcctcgtgaatgcggcta<br>accctaaccccggagcagaggctactgaagccacagtagtcgctgtcgtaacgagtaattctggg<br>atgggaccgactactttcgagtgtccgtgtttcctttattcttttattgttgtttatggtgacaaac |
| 684 | Human enterovirus C105 | cccctaggatccactggatgtcagtacactggtatcgtggtacctttgtacgcctgttttatacccctt<br>ccccgcaactttagaagcatcaaaagcaccgctcaatagtcaccacaccccccagtgtggtttcgag<br>caagcacttctgttttcccggttgcgtcccatatgctgtgcaaacggcaaaaagggacaatatcgtta<br>cccgcttgtatactacgggaaacctagtaccaccattgattgtgttgagagttgcgctcatcacctttc<br>cccggtgtagctcaggccgatgaggctcagaatcccccacaggtgactgtgtctgagcctgcgtt<br>ggcggcctgccctcgccttatggcgtgggacgcttgatacatgacatggtgcgaagagtctactgt<br>gctatgcaagagtcctccggcccctgaatgtggctaatcctaaccactgatcccacgcacgcaaac<br>cagtgtgtagtgggtcgtaacgcgcaagtcggtggcggaaccaactactttgggtgaccgtgtttc<br>ctttattacttattgaatgtttatggtgacaattgtttgattcagttgttgccattctctacattcattt<br>acccagcatcaaaccaattgaactgttaca |
| 685 | Human poliovirus 1 strain NIE1116623 | agtctggacatccctcaccggcgacggtggtccaggctgcgctggcggcctacctgtggtccaaa<br>gccacgggacgctacatgtgaacaaggtgtgaagagcctattgagctacaaaagagtcctccgg<br>cccctgaatgcggctaatcccaaccacggatcaagggtgcacaaaccagtgtacaccttgtcgta<br>acgcgcaagtctgtggcggaaccgactactttgggtgtccgtgtttcctttttaatttgatggctgctt<br>atggtgacaatcatagattgttatcataaagctaattggattggccatccggtgagagtgaaatatatt<br>gtttacctccctgttgggtttactctaactaacttctccatttataaacttgtcatcacagttttaatat<br>tagaagtgcagtttaca |
| 686 | Human enterovirus 109 | tttaaaacagcctggggggttgttcccaccccccagggcccactgggcgttagtactctggtatcgcg<br>gtaccttagtatgcctgttttatgtctcctttcccccgcaactttagaagtaatcaagttatggctcaaca<br>gtcgccacaccccccagtgtggttccgagcaagcacttctgttccccggttgcgtcttatatgctgtgt<br>gaacggcagaaagggacaatatcgttatccgctcaactactacgggaagcctagtaccaccatgg<br>attgacctgaaagttgcgttcagcgcacccccagcgcagctcaggccgatgaggctccgaatacc<br>ccacgggcgaccgtgtcggagcctgcgttggcggcctgcccacgttgcaaaacgtgggacgctc<br>atttcatgacatggtgcgaagagcctactgtgctagttgagagtcctccggcccctgaatgtggata<br>atcctaaccactgaacctacgggcgcaaaccagcgtctggtaggccgtaacgcgcaagtcggtg<br>gcggaaccaactactttgggtgtccgtgtttccttttatctttttgaatgtttatggtgacaattgttgt<br>gtacagttgttaccatagtttgcattcagaaataaacctaacactttccaattatttgttaca |
| 687 | Human poliovirus 2 strain NIE0811460 | ttgtgcgcctgttttatattcccccccgcaacttagaagcacgaaaccaagttcaatagaagggg<br>tacaaaccagtaccaccacgaacaagcacttctgtttccccggtgacattgcatagactgctcacgc<br>ggttgaaagtgatcgatccgttacccgcttgtgtacttcgaaaagcctagtattgccttggaatcttcg<br>acgcgttgcgctcagcacccgaccccggggtgtagcttaggctgatgagtctggacattcctcacc<br>ggtgacggtggtccaggctgcgttggcggcctacctatggctaatgccataggacgctagatgtg<br>aacaaggtgtgaagagcctattgagctacataagagtcctccggcccctgaatgcggctaatccta<br>accacggagcaggcggtcgcaaaccagtgactagcttgtcgtaacgcgcaagtctgtggcggaa<br>ccgactactttgggtgtccgtgtttcctgttatttttattatggctgcttatggtgacaatcagagattg<br>ttatcataaagcgaaaggattggccatccggtgagtgttgtgtcaggtatacaactgtttgttggaacc<br>actgtgttagtttaacctctctttcaaccaattagtcaaaaacaatacgaagatagaacaacaatacta<br>ca |
| 688 | Bovine picornavirus | ttttctcccctcccccctccaactaccttttccccctcttgtaacgctagaagtttgtgcaaaccgcctgt<br>agggtactgcaatccagcagtgcataggctaagcttttcagaaccccaccccacattatactgagg<br>aggattgtgaaattgtgttagtatgggttagtagcggtgacccgggtaaccccaacccagaaactc<br>acggatgagatgaacaggaccccacatggtaacgtgtgtgttcgtctgccccgcaaggtgaggcc<br>gtgagagctttgcacgcgaaaaccttgaaaacccaaaagtaccttgagctcttcgctattttgtgtttc<br>ctccaggaccctgaatgcggctaaacctaacccgcgatccgcacgtagcaacccagctagagtgt<br>ggtcgtaatgcgcaagttgcgggcggtaccgactactttggtgttcctgtgtttcctttattttattttga<br>atttttatggtgacaacagctagaaaataagagtgaac |
| 689 | Human poliovirus 1 strain | acccttgtacgcctgttttatactcccctccccgtaacttagaagaaacaaaataagttcaataggag<br>ggggtacaaaccagtaccaccacgaacaagcacttctgtctccccggtgacattgcatagactgtc<br>cccacggttgaaagcaattgatccgttacccgctcttgtacttcgagaagcctagtaccatcttggaa |

TABLE 17-continued

IRES sequences.

| SEQ ID NO | IRES | Sequence |
|---|---|---|
| | EQG1419328 | tcatcgatgcgttgcgctccacactcagtcccagagtgtagcttaggctgatgagtctggacattcct caccggcgacggtggtccaggctgcgttggcggcctacctgtggcccaaagccacaggacgct agatgtgaacaaggtgtgaagagcctattgagctataagagagtcctccggcccctgaatgcggc taatcccaaccacggatcaagggtgcacgaaccagtgtataccttgtcgtaacgcgcaagtccgtg gcggaaccgactactttgggtgaccgtgtttccttttattatttcaatggctgcttatggtgacaatcatt gattgttatcataaagcgaattggactggccatccggtgaaagtgaaacatattgtttgcctcctcgtt gggtctacttcaaccaatctttacttacaatcttaccactacagttttgctggttagaagtgtgtttcacg |
| 690 | Human poliovirus 2 isolate IS_061 | ttgtgcgcctgttttatactcccctcccgcaacttagaagcacgaaaccaagttcaatagaagggg tacaaaccagtaccactacgaacaagcacttctgtttccccggtgacattgcatagactgctcacgc ggttgaaagtgatcgatccgttacccgcttgtgtacttcgaaaagcctagtatcgccttggaatcttc gacgcgttgcgctcagcacccgaccccggggtgtagcttaggccgatgagtctggacattcctca ccggtgacggtggtccaggctgcgttggcggcctacctatggctaacgccataggacgttagatg tgaacaaggtgtgaagagcctattgagctacataagagtcctccggcccctgaatgcggctaatcc taaccacggagcaggcggtcgcgaaccagtgactggcttgtcgtaacgcgcaagtctgtggcgg aaccgactactttgggtgtccgtgtttcctgttatttttatcatggctgcttatggtgacaatcagagatt gttatcataaagcgaattggattggccatccggtgagtgttgtgtcaggtatacaactgtttgttggaa ccactgtgttagctttgcttctcatttaaccaattaatcaaaaacaatacgaggataaaacaacaatac taca |
| 691 | Coxsackie-virus B5 | cctttgtgcgcctgttttatgccccttcccccaattgaaacttagaagttacacacaccgatcaacag cgggcgtggcataccagccgcgtcttgatcaagcactcctgtttccccggaccgagtatcaataga ctgctcacgcggttgaaggagaaaacgttcgttacccggctaactacttcgagaaacctagtagca tcatgaaagttgcgaagcgtttcgctcagcacatccccagtgtagatcaggtcgatgagtcaccgc attccccacgggcgaccgtggcggtggctgcgttggcggcctgcctacggggcaacccgtagg acgcttcaatacagacatggtgcgaagagtcgattgagctagttagtagtcctccggcccctgaatc cggctaatcctaactgcggagcacataccctcaacccaggggcattgtgtcgtaacgggtaact ctgcagcggaaccgactactttgggtgtccgtgtttccttttattcttataatggctgcttatggtgaca attgaaagattgttaccatatagctattggattggccatccggtgtctaacagagctattatatacctct ttgttggatttgtaccacttgatctaaaggaagtcaagacactacaattcatcatacaattgaacacag caaa |
| 692 | Coxsackie-virus A10 | tttgtgcgcctgttttacaacccttccccaacttgtaacgtagaagtaatacacactactgatcaatag caggcatggcgcgccagtcatgtctcgatcaagcacttctgttcccccggactgagtatcaataga ctgctcacgcggagaaggagaaaacgttcgttacccggctaactacttcgagaaacctagtagca ccatagaagctgcagagtgtttcgctcagcacttccccgtgtagatcaggctgatgagtcactgca atccccacgggtgaccgtggcagtggctgcgttggcggcctgcctatggggcaacccataggac gctctaatgtggacatggtgcgaagagtctattgagctagttagtagtcctccggcccctgaatgcg gctaatcctaactgcggagcacatgccttcaacccagaaggtagtgtgtcgtaacgggcaactctg cagcggaaccgactactttgggtgtccgtgtttctttttattcctatattggctgcttatggtgacaatca cggaattgttgccatatagctattggattggccatccggtgtctaatagagctattgtgtacctatttgtt ggatttactccgctatcacataaatctctgaacactttgtgctttatattgaacttaaacacccgaaa |

In some embodiments, an IRES of the invention is an IRES having a sequence as listed in Table 17 (SEQ ID NOs: 1-72 and 348-389). In some embodiments, an IRES is a Salivirus IRES. In some embodiments, an IRES is a Salivirus SZ1 IRES. In some embodiments, an IRES is a AP1.0 (SEQ ID NO:348). In some embodiments, an IRES is a CK1.0 (SEQ ID NO:349). In some embodiments, an IRES is a PV1.0 (SEQ ID NO:350). In some embodiments, an IRES is a SV1.0 (SEQ ID NO:351).

TABLE 18

Anabaena permutation site 5' intron fragment sequences.

| SEQ ID NO | Permutation site | Sequence |
|---|---|---|
| 73 | L2-1 | GAAGAAATTCTTTAAGTGGATGCTCTCAAACTCAGGGAAACC TAAATCTAGTTATAGACAAGGCAATCCTGAGCCAAGCCGAAG TAGTAATTAGTAAGTTAACAATAGATGACTTACAACTAATCG GAAGGTGCAGAGACTCGACGGGAGCTACCCTAACGTCAAGAC GAGGGTAAAGAGAGAGTCCAATTCTCAAAGCCAATAGGCAGT AGCGAAAGCTGCAAGAGAATGAAAATCCGT |
| 74 | L2-2 | AAGAAATTCTTTAAGTGGATGCTCTCAAACTCAGGGAAACCT AAATCTAGTTATAGACAAGGCAATCCTGAGCCAAGCCGAAGT AGTAATTAGTAAGTTAACAATAGATGACTTACAACTAATCGG AAGGTGCAGAGACTCGACGGGAGCTACCCTAACGTCAAGACG AGGGTAAAGAGAGAGTCCAATTCTCAAAGCCAATAGGCAGTA GCGAAAGCTGCAAGAGAATGAAAATCCGT |

TABLE 18-continued

| Anabaena permutation site 5' intron fragment sequences. | | |
|---|---|---|
| SEQ ID NO | Permutation site | Sequence |
| 75 | L2-3 | AGAAATTCTTTAAGTGGATGCTCTCAAACTCAGGGAAACCTA AATCTAGTTATAGACAAGGCAATCCTGAGCCAAGCCGAAGTA GTAATTAGTAAGTTAACAATAGATGACTTACAACTAATCGGA AGGTGCAGAGACTCGACGGGAGCTACCCTAACGTCAAGACGA GGGTAAAGAGAGAGTCCAATTCTCAAAGCCAATAGGCAGTAG CGAAAGCTGCAAGAGAATGAAAATCCGT |
| 76 | L5-1 | GTTATAGACAAGGCAATCCTGAGCCAAGCCGAAGTAGTAATT AGTAAGTTAACAATAGATGACTTACAACTAATCGGAAGGTGC AGAGACTCGACGGGAGCTACCCTAACGTCAAGACGAGGGTAA AGAGAGAGTCCAATTCTCAAAGCCAATAGGCAGTAGCGAAAG CTGCAAGAGAATGAAAATCCGT |
| 77 | L5-2 | TTATAGACAAGGCAATCCTGAGCCAAGCCGAAGTAGTAATTA GTAAGTTAACAATAGATGACTTACAACTAATCGGAAGGTGCA GAGACTCGACGGGAGCTACCCTAACGTCAAGACGAGGGTAAA GAGAGAGTCCAATTCTCAAAGCCAATAGGCAGTAGCGAAAGC TGCAAGAGAATGAAAATCCGT |
| 78 | L5-3 | TATAGACAAGGCAATCCTGAGCCAAGCCGAAGTAGTAATTAG TAAGTTAACAATAGATGACTTACAACTAATCGGAAGGTGCAG AGACTCGACGGGAGCTACCCTAACGTCAAGACGAGGGTAAAG AGAGAGTCCAATTCTCAAAGCCAATAGGCAGTAGCGAAAGCT GCAAGAGAATGAAAATCCGT |
| 79 | L5-4 | ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAGGCAGTAGCGAAAGCTG CAAGAGAATGAAAATCCGT |
| 80 | L5-5 | TAGACAAGGCAATCCTGAGCCAAGCCGAAGTAGTAATTAGTA AGTTAACAATAGATGACTTACAACTAATCGGAAGGTGCAGAG ACTCGACGGGAGCTACCCTAACGTCAAGACGAGGGTAAAGAG AGAGTCCAATTCTCAAAGCCAATAGGCAGTAGCGAAAGCTGC AAGAGAATGAAAATCCGT |
| 81 | L6-1 | ACAATAGATGACTTACAACTAATCGGAAGGTGCAGAGACTCG ACGGGAGCTACCCTAACGTCAAGACGAGGGTAAAGAGAGAG TCCAATTCTCAAAGCCAATAGGCAGTAGCGAAAGCTGCAAGA GAATGAAAATCCGT |
| 82 | L6-2 | CAATAGATGACTTACAACTAATCGGAAGGTGCAGAGACTCGA CGGGAGCTACCCTAACGTCAAGACGAGGGTAAAGAGAGAGTC CAATTCTCAAAGCCAATAGGCAGTAGCGAAAGCTGCAAGAGA ATGAAAATCCGT |
| 83 | L6-3 | AATAGATGACTTACAACTAATCGGAAGGTGCAGAGACTCGAC GGGAGCTACCCTAACGTCAAGACGAGGGTAAAGAGAGAGTCC AATTCTCAAAGCCAATAGGCAGTAGCGAAAGCTGCAAGAGAA TGAAAATCCGT |
| 84 | L6-4 | ATAGATGACTTACAACTAATCGGAAGGTGCAGAGACTCGACG GGAGCTACCCTAACGTCAAGACGAGGGTAAAGAGAGAGTCCA ATTCTCAAAGCCAATAGGCAGTAGCGAAAGCTGCAAGAGAAT GAAAATCCGT |
| 85 | L6-5 | TAGATGACTTACAACTAATCGGAAGGTGCAGAGACTCGACGG GAGCTACCCTAACGTCAAGACGAGGGTAAAGAGAGAGTCCAA TTCTCAAAGCCAATAGGCAGTAGCGAAAGCTGCAAGAGAATG AAAATCCGT |
| 86 | L6-6 | AGATGACTTACAACTAATCGGAAGGTGCAGAGACTCGACGGG AGCTACCCTAACGTCAAGACGAGGGTAAAGAGAGAGTCCAAT TCTCAAAGCCAATAGGCAGTAGCGAAAGCTGCAAGAGAATGA AAATCCGT |
| 87 | L6-7 | GATGACTTACAACTAATCGGAAGGTGCAGAGACTCGACGGGA GCTACCCTAACGTCAAGACGAGGGTAAAGAGAGAGTCCAATT CTCAAAGCCAATAGGCAGTAGCGAAAGCTGCAAGAGAATGA AAATCCGT |
| 88 | L6-8 | ATGACTTACAACTAATCGGAAGGTGCAGAGACTCGACGGGAG CTACCCTAACGTCAAGACGAGGGTAAAGAGAGAGTCCAATTC |

TABLE 18-continued

Anabaena permutation site 5' intron fragment sequences.

| SEQ ID NO | Permutation site | Sequence |
|---|---|---|
| | | TCAAAGCCAATAGGCAGTAGCGAAAGCTGCAAGAGAATGAA AATCCGT |
| 89 | L6-9 | TGACTTACAACTAATCGGAAGGTGCAGAGACTCGACGGGAGC TACCCTAACGTCAAGACGAGGGTAAAGAGAGAGTCCAATTCT CAAAGCCAATAGGCAGTAGCGAAAGCTGCAAGAGAATGAAA ATCCGT |
| 90 | L8-1 | CAAGACGAGGGTAAAGAGAGAGTCCAATTCTCAAAGCCAATA GGCAGTAGCGAAAGCTGCAAGAGAATGAAAATCCGT |
| 91 | L8-2 | AAGACGAGGGTAAAGAGAGAGTCCAATTCTCAAAGCCAATAG GCAGTAGCGAAAGCTGCAAGAGAATGAAAATCCGT |
| 92 | L8-3 | AGACGAGGGTAAAGAGAGAGTCCAATTCTCAAAGCCAATAGG CAGTAGCGAAAGCTGCAAGAGAATGAAAATCCGT |
| 93 | L8-4 | GACGAGGGTAAAGAGAGAGTCCAATTCTCAAAGCCAATAGGC AGTAGCGAAAGCTGCAAGAGAATGAAAATCCGT |
| 94 | L8-5 | ACGAGGGTAAAGAGAGAGTCCAATTCTCAAAGCCAATAGGCA GTAGCGAAAGCTGCAAGAGAATGAAAATCCGT |
| 95 | L9a-1 | AATAGGCAGTAGCGAAAGCTGCAAGAGAATGAAAATCCGT |
| 96 | L9a-2 | ATAGGCAGTAGCGAAAGCTGCAAGAGAATGAAAATCCGT |
| 97 | L9a-3 | TAGGCAGTAGCGAAAGCTGCAAGAGAATGAAAATCCGT |
| 98 | L9a-4 | AGGCAGTAGCGAAAGCTGCAAGAGAATGAAAATCCGT |
| 99 | L9a-5 | GGCAGTAGCGAAAGCTGCAAGAGAATGAAAATCCGT |
| 100 | L9-1 | GAAAGCTGCAAGAGAATGAAAATCCGT |
| 101 | L9-2 | AAAGCTGCAAGAGAATGAAAATCCGT |
| 102 | L9-3 | AAGCTGCAAGAGAATGAAAATCCGT |
| 103 | L9-4 | AGCTGCAAGAGAATGAAAATCCGT |
| 104 | L9-5 | GCTGCAAGAGAATGAAAATCCGT |
| 105 | L9-6 | CTGCAAGAGAATGAAAATCCGT |
| 106 | L9-7 | AAGAGAATGAAAATCCGT |
| 107 | L9-8 | AGAGAATGAAAATCCGT |
| 108 | L9-9 | GAGAATGAAAATCCGT |
| 109 | L9a-6 | GCAGTAGCGAAAGCTGCAAGAGAATGAAAATCCGT |
| 110 | L9a-7 | AGTAGCGAAAGCTGCAAGAGAATGAAAATCCGT |
| 111 | L9a-8 | GTAGCGAAAGCTGCAAGAGAATGAAAATCCGT |

In some embodiments, a 5' intron fragment is a fragment having a sequence listed in Table 18. Typically, a construct containing a 5' intron fragment listed in Table 18 will contain a corresponding 3' intron fragment as listed in Table 19 (e.g., both representing fragments with the L9a-8 permutation site).

TABLE 19

Anabaena permutation site 3′ intron fragment sequences.

| SEQ ID NO | Permutation site | Sequence |
|---|---|---|
| 112 | L2-1 | ACGGACTTAAATAATTGAGCCTTAAA |
| 113 | L2-2 | ACGGACTTAAATAATTGAGCCTTAAAG |

TABLE 19-continued

Anabaena permutation site 3′ intron fragment sequences.

| SEQ ID NO | Permutation site | Sequence |
|---|---|---|
| 114 | L2-3 | ACGGACTTAAATAATTGAGCCTTAAAGA |
| 115 | L5-1 | ACGGACTTAAATAATTGAGCCTTAAAGAAGAAATTCTTTAAG TGGATGCTCTCAAACTCAGGGAAACCTAAATCTA |
| 116 | L5-2 | ACGGACTTAAATAATTGAGCCTTAAAGAAGAAATTCTTTAAG TGGATGCTCTCAAACTCAGGGAAACCTAAATCTAG |
| 117 | L5-3 | ACGGACTTAAATAATTGAGCCTTAAAGAAGAAATTCTTTAAG TGGATGCTCTCAAACTCAGGGAAACCTAAATCTAGT |
| 118 | L5-4 | ACGGACTTAAATAATTGAGCCTTAAAGAAGAAATTCTTTAAG TGGATGCTCTCAAACTCAGGGAAACCTAAATCTAGTT |
| 119 | L5-5 | ACGGACTTAAATAATTGAGCCTTAAAGAAGAAATTCTTTAAG TGGATGCTCTCAAACTCAGGGAAACCTAAATCTAGTTA |
| 120 | L6-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT A |
| 121 | L6-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AA |
| 122 | L6-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AAC |
| 123 | L6-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACA |
| 124 | L6-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAA |
| 125 | L6-6 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAAT |
| 126 | L6-7 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATA |
| 127 | L6-8 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAG |
| 128 | L6-9 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGA |
| 129 | L8-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGT |
| 130 | L8-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTC |

TABLE 19-continued

| Anabaena permutation site 3′ intron fragment sequences. | | |
|---|---|---|
| SEQ ID NO | Permutation site | Sequence |
| 131 | L8-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCA |
| 132 | L8-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAA |
| 133 | L8-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAG |
| 134 | L9a-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCC |
| 135 | L9a-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCA |
| 136 | L9a-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAA |
| 137 | L9a-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAAT |
| 138 | L9a-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATA |
| 139 | L9-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGC |
| 140 | L9-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCG |
| 141 | L9-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGA |

TABLE 19-continued

Anabaena permutation site 3' intron fragment sequences.

| SEQ ID NO | Permutation site | Sequence |
|---|---|---|
| 142 | L9-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAA |
| 143 | L9-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAA |
| 144 | L9-6 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAG |
| 145 | L9-7 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAGCTGC |
| 146 | L9-8 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAGCTGCA |
| 147 | L9-9 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAGCTGCA A |
| 148 | L9a-6 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAG |
| 149 | L9a-7 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGC |
| 150 | L9a-8 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCA |

In some embodiments, a 3' intron fragment is a fragment having a sequence listed in Table 19. In some embodiments, a construct containing a 3' intron fragment listed in Table 19 will contain a corresponding 5' intron fragment as listed in Table 18 (e.g., both representing fragments with the L9a-8 permutation site).

TABLE 20

Non-anabaena permutation site 5' intron fragment sequences.

| SEQ ID NO | Intron | Sequence |
|---|---|---|
| 151 | Azop1 | tgcgccgatgaaggtgtagagactagacggcacccacctaaggcaaacgctatggtgaaggcatagtcca gggagtggcgaaagtcacacaaaccggaatccgt |
| 152 | Azop2 | ccgggcgtatggcaacgccgagccaagcttcggcgcctgcgccgatgaaggtgtagagactagacggc acccacctaaggcaaacgctatggtgaaggcatagtccagggagtggcgaaagtcacacaaaccggaat ccgt |
| 153 | Azop3 | acggcacccacctaaggcaaacgctatggtgaaggcatagtccagggagtggcgaaagtcacacaaacc ggaatccgt |
| 154 | Azop4 | acgctatggtgaaggcatagtccagggagtggcgaaagtcacacaaaccggaatccgt |
| 155 | S7951p1 | attaaagttatagaattatcagagaatgatatagtccaagccttatggtaacatgagggcacttgaccctggta g |
| 156 | Twortp1 | aagatgtaggcaatcctgagctaagctcttagtaataagagaaagtgcaacgactattccgataggaagtag ggtcaagtgactcgaaatggggattaccattctagggtagtgatatagtctgaacatatatggaaacatatag aaggataggagtaacgaacctattcgtaacataattgaacttttagttat |
| 157 | Twortp2 | taataagagaaagtgcaacgactattccgataggaagtagggtcaagtgactcgaaatggggattaccatc tagggtagtgatatagtctgaacatatatggaaacatatagaaggataggagtaacgaacctattcgtaacat aattgaacttttagttat |
| 158 | Twortp3 | taggaagtagggtcaagtgactcgaaatggggattacccttctagggtagtgatatagtctgaacatatatgg aaacatatagaaggataggagtaacgaacctattcgtaacataattgaacttttagttat |
| 159 | Twortp4 | ctagggtagtgatatagtctgaacatatatggaaacatatagaaggataggagtaacgaacctattcgtaaca taattgaacttttagttat |
| 160 | LSUp1 | agttaataaagatgatgaaatagtctgaaccattttgagaaaagtggaaataaaagaaaatcttttatgataac ataaattgaacaggctaa |
| 161 | Phip1 | caaagactgatgatatagtccgacactcctagtaataggagaatacagaaaggatgaaatcc |
| 162 | Nostoc | agtcgagggtaaagggagagtccaattctcaaagcctattggcagtagcgaaagctgcgggagaatgaaa atccgt |
| 163 | Nostoc | agccgagggtaaagggagagtccaattctcaaagccaataggcagtagcgaaagctgcgggagaatgaa aatccgt |
| 164 | Nodularia | agccgagggtaaagggagagtccaattctcaaagccgaaggttattaaaacctggcagcagtgaaagctg cgggagaatgaaaatccgt |
| 165 | Pleurocapsa | agctgagggtaaagagagagtccaattctcaaagccagcagatggcagtagcgaaagctgcgggagaat gaaaatccgt |
| 166 | Planktothrix | agccgagggtaaagagagagtccaattctcaaagccaattggtagtagcgaaagctacgggagaatgaaa atccgt |

In some embodiments, a 5' intron fragment is a fragment having a sequence listed in Table 20. A construct containing a 5' intron fragment listed in Table 20 will contain a corresponding 3' intron fragment in Table 21 (e.g., both representing fragments with the Azop1 intron).

TABLE 21

Non-anabaena permutation site 3' intron fragment sequences.

| SEQ ID NO | Intron | Sequence |
|---|---|---|
| 167 | Azop1 | gcggactcatatttcgatgtgccttgcgccgggaaaccacgcaagggatggtgtcaaattcggcgaaac ctaagcgcccgcccgggcgtatggcaacgccgagccaagcttcggcgcc |
| 168 | Azop2 | gcggactcatatttcgatgtgccttgcgccgggaaaccacgcaagggatggtgtcaaattcggcgaaac ctaagcgcccgc |

TABLE 21-continued

Non-anabaena permutation site 3' intron fragment sequences.

| SEQ ID NO | Intron | Sequence |
|---|---|---|
| 169 | Azop3 | gcggactcatatttcgatgtgccttgcgccgggaaaccacgcaagggatggtgtcaaattcggcgaaac ctaagcgcccgcccgggcgtatggcaacgccgagccaagcttcggcgcctgcgccgatgaaggtgta gagactag |
| 170 | Azop4 | gcggactcatatttcgatgtgccttgcgccgggaaaccacgcaagggatggtgtcaaattcggcgaaac ctaagcgcccgcccgggcgtatggcaacgccgagccaagcttcggcgcctgcgccgatgaaggtgta gagactagacggcacccacctaaggcaa |
| 171 | S795p1 | aggattagatactacactaagtgtcccccagactggtgacagtctggtgtgcatccagctatatcggtgaa accccattggggtaataccgagggaagctatattatatatatattaataaatagccccgtagagactatgta ggtaaggagatagaagatgataaaatcaaaatcatc |
| 172 | Twortp1 | actactgaaagcataaataattgtgcctttatacagtaatgtatatcgaaaaatcctctaattcagggaacac ctaaacaaact |
| 173 | Twortp2 | actactgaaagcataaataattgtgcctttatacagtaatgtatatcgaaaaatcctctaattcagggaacac ctaaacaaactaagatgtaggcaatcctgagctaagctcttag |
| 174 | Twortp3 | actactgaaagcataaataattgtgcctttatacagtaatgtatatcgaaaaatcctctaattcagggaacac ctaaacaaactaagatgtaggcaatcctgagctaagctcttagtaataagagaaagtgcaacgactattcc ga |
| 175 | Twortp4 | actactgaaagcataaataattgtgcctttatacagtaatgtatatcgaaaaatcctctaattcagggaacac ctaaacaaactaagatgtaggcaatcctgagctaagctcttagtaataagagaaagtgcaacgactattcc gataggaagtagggtcaagtgactcgaaatggggattaccctt |
| 176 | LSUp1 | cgctagggatttataactgtgagtcctccaatattataaaatgttggtaatatattgggtaaatttcaaagaca acttttctccacgtcaggatatagtgtatttgaagcgaaacttattttagcagtgaaaaagcaaataaggac gttcaacgactaaaaggtgagtattgctaacaataatcctttttttaatgcccaacatctttattaact |
| 177 | Phip1 | gtgggtgcataaactatttcattgtgcacattaaatctggtgaactcggtgaaaccctaatggggcaatacc gagccaagccatagggaggatatatgagaggcaagaagttaattcttgaggccactgagactggctgta tcatccctacgtcacacaaacttaatgccgatggttatttcagaaagaaaaccaatggcgtcttagagatgt atcacagaacggtgtggaaggagcataacggagacatacctgatggcttcgagatagaccataagtgtc gcaatagggcttgctgtaatatagagcatttacagatgcttgagggtacagcccacactgttaagaccaat cgtgaacgctacgcagacagaaaggaaacagctagggaatactggctggagactggatgtaccggcc tagcactcggtgagaagtttggtgtgtcgttctcttctgcttgtaagtggattagagaatggaaggcgtaga gactatccgaaaggagtagggccgagggtgagactccctcgtaacccgaagcgccagacagtcaact |
| 178 | Nostoc | acggacttaagtaattgagccttaaagaagaaattctttaagtggcagctctcaaactcagggaaacctaa atctgttcacagacaaggcaatcctgagccaagccgaaagagtcatgagtgctgagtagtgagtaaaat aaaagctcacaactcagaggttgtaactctaagctagtcggaaggtgcagagactcgacgggagctac cctaacgtaa |
| 179 | Nostoc | acggacttaaactgaattgagccttagagaagaaattctttaagtgtcagctctcaaactcagggaaacct aaatctgttgacagacaaggcaatcctgagccaagccgagaactctaagttattcggaaggtgcagaga ctcgacgggagctaccctaacgtca |
| 180 | Nodularia | acggacttagaaaactgagccttgatcgagaaatctttcaagtggaagctctcaaattcagggaaacctaa atctgtttacagatatggcaatcctgagccaagccgaaacaagtcctgagtgttaaagctcataactcatc ggaaggtgcagagactcgacgggagctaccctaacgtta |
| 181 | Pleurocapsa | acggacttaaaaaaattgagccttggcagagaaatctgtcatgcgaacgctctcaaattcagggaaacct aagtctggcaacagatatggcaatcctgagccaagccttaatcaaggaaaaaaacatttttaccttttacctt gaaaggaaggtgcagagactcaacgggagctaccctaacaggtca |
| 182 | Planktothrix | acggacttaaagataaattgagccttgaggcgagaaatctctcaagtgtaagctgtcaaattcagggaaa cctaaatctgtaaattcagacaaggcaatcctgagccaagcctaggggtattagaaatgagggagtttcc ccaatctaagatcaatacctaggaaggtgcagagactcgacgggagctaccctaacgtta |

In some embodiments, a 3' intron fragment is a fragment having a sequence listed in Table 21. A construct containing a 3' intron fragment listed in Table 21 will contain the corresponding 5' intron fragment as listed in Table 20 (e.g., both representing fragments with the Azop1 intron).

TABLE 22

Spacer and Anabaena 5' intron fragment sequences.

| SEQ ID NO | Spacer | Sequence |
|---|---|---|
| 183 | T25 L10 | agtatataagaaacaaaccacTAGATGACTTACAACTAATCGGAAGGTGC AGAGACTCGACGGGAGCTACCCTAACGTCAAGACGAGGGTAA AGAGAGAGTCCAATTCTCAAAGCCAATAGGCAGTAGCGAAAG CTGCAAGAGAATGAAAATCCGTggctcgcagc |
| 184 | T25L20 | ctgaaattatacttatactcaaacaaaccacTAGATGACTTACAACTAATCGGAA GGTGCAGAGACTCGACGGGAGCTACCCTAACGTCAAGACGAG GGTAAAGAGAGAGTCCAATTCTCAAAGCCAATAGGCAGTAGC GAAAGCTGCAAGAGAATGAAAATCCGTggctcgcagc |
| 185 | T25 L30 (I80-10) [Control] | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 186 | T25 L40 | catcaacaatatgaaattatacttatactcagtatatgacaaacaaaccacTAGATGACTTAC AACTAATCGGAAGGTGCAGAGACTCGACGGGAGCTACCCTAA CGTCAAGACGAGGGTAAAGAGAGAGTCCAATTCTCAAAGCCA ATAGGCAGTAGCGAAAGCTGCAAGAGAATGAAAATCCGTggct cgcagc |
| 187 | T25 L50 | catcaacaatatgaaactatacttatactcagtatatgaagcattatcgcaaacaaac- cacTAGATG ACTTACAACTAATCGGAAGGTGCAGAGACTCGACGGGAGCTA CCCTAACGTCAAGACGAGGGTAAAGAGAGAGTCCAATTCTCA AAGCCAATAGGCAGTAGCGAAAGCTGCAAGAGAATGAAAAT CCGTggctcgcagc |
| 188 | T50 L10 | tagcgtcagcaaacaaacaaaTAGATGACTTACAACTAATCGGAAGGTGC AGAGACTCGACGGGAGCTACCCTAACGTCAAGACGAGGGTAA AGAGAGAGTCCAATTCTCAAAGCCAATAGGCAGTAGCGAAAG CTGCAAGAGAATGAAAATCCGTggctcgcagc |
| 189 | T50 L20 | atactcatactagcgtcagcaaacaaacaaaTAGATGACTTACAACTAATCGGA AGGTGCAGAGACTCGACGGGAGCTACCCTAACGTCAAGACGA GGGTAAAGAGAGAGTCCAATTCTCAAAGCCAATAGGCAGTAG CGAAAGCTGCAAGAGAATGAAAATCCGTggctcgcagc |
| 190 | T50 L30 | gtgtgaagctatactcatactagcgtcagcaaacaaacaaaTAGATGACTTACAACTA ATCGGAAGGTGCAGAGACTCGACGGGAGCTACCCTAACGTCA AGACGAGGGTAAAGAGAGAGTCCAATTCTCAAAGCCAATAGG CAGTAGCGAAAGCTGCAAGAGAATGAAAATCCGTggctcgcagc |
| 191 | T50 L40 | cctcacctgagtgtgaagctatactcatactagcgtcagcaaacaaacaaaTAGATGACTTA CAACTAATCGGAAGGTGCAGAGACTCGACGGGAGCTACCCTA ACGTCAAGACGAGGGTAAAGAGAGAGTCCAATTCTCAAAGCC AATAGGCAGTAGCGAAAGCTGCAAGAGAATGAAAATCCGTgg ctcgcagc |
| 192 | T50 L50 | ccgaatgatgcctcacctgagtgtgaagctatactcatactagcgtcagcaaacaaacaaaTAGAT GACTTACAACTAATCGGAAGGTGCAGAGACTCGACGGGAGCT ACCCTAACGTCAAGACGAGGGTAAAGAGAGAGTCCAATTCTC AAAGCCAATAGGCAGTAGCGAAAGCTGCAAGAGAATGAAAA TCCGTggctcgcagc |
| 193 | T75 L10 | cggtgcgagcaaacaaacaaaTAGATGACTTACAACTAATCGGAAGGTG CAGAGACTCGACGGGAGCTACCCTAACGTCAAGACGAGGGTA AAGAGAGAGTCCAATTCTCAAAGCCAATAGGCAGTAGCGAAA GCTGCAAGAGAATGAAAATCCGTggctcgcagc |
| 194 | T75 L20 | cgctccgacccagtgcgagcaaacaaacaaaTAGATGACTTACAACTAATCGG AAGGTGCAGAGACTCGACGGGAGCTACCCTAACGTCAAGACG AGGGTAAAGAGAGAGTCCAATTCTCAAAGCCAATAGGCAGTA GCGAAAGCTGCAAGAGAATGAAAATCCGTggctcgcagc |

TABLE 22-continued

Spacer and Anabaena 5' intron fragment sequences.

| SEQ ID NO | Spacer | Sequence |
|---|---|---|
| 195 | T25 L30 1 MM | ctgaaattatactAatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 196 | T25 L30 3 MM | ctgaaaAtatactAatactcaCtatatgacaaacaaaccacTAGATGACTTACAACTA ATCGGAAGGTGCAGAGACTCGACGGGAGCTACCCTAACGTCA AGACGAGGGTAAAGAGAGAGTCCAATTCTCAAAGCCAATAGG CAGTAGCGAAAGCTGCAAGAGAATGAAAATCCGTggctcgcagc |
| 197 | T25 L30 5 MM | ctgaTaAtataGtAatactcaCtatatgacaaacaaaccacTAGATGACTTACAACT AATCGGAAGGTGCAGAGACTCGACGGGAGCTACCCTAACGTC AAGACGAGGGTAAAGAGAGAGTCCAATTCTCAAAGCCAATAG GCAGTAGCGAAAGCTGCAAGAGAATGAAAATCCGTggctcgcagc |
| 198 | T25 L30 8 MM | ctgaTaAtaAaGtAatacAcaCtataAgacaaacaaaccacTAGATGACTTACAA CTAATCGGAAGGTGCAGAGACTCGACGGGAGCTACCCTAACG TCAAGACGAGGGTAAAGAGAGAGTCCAATTCTCAAAGCCAAT AGGCAGTAGCGAAAGCTGCAAGAGAATGAAAATCCGTggctcgc agc |
| 199 | T25 L30 OffTarget 10 | ctgaaattatacttatactctctaagttacaaacaaaccacTAGATGACTTACAACTAAT CGGAAGGTGCAGAGACTCGACGGGAGCTACCCTAACGTCAAG ACGAGGGTAAAGAGAGAGTCCAATTCTCAAAGCCAATAGGCA GTAGCGAAAGCTGCAAGAGAATGAAAATCCGTggctcgcagc |
| 200 | T25 L30 OffTarget 20 | ctgaaattatgtgtgttacAtctaagttacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 201 | T25 L30 OffTarget 30 | gagatcggtgtgtgttacAtctaagttacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 202 | T25 L30 I25-10 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTgattaaacag |
| 203 | T25 L30 I25-20 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTgattcacaatataaa ttacg |
| 204 | T25 L30 I50-10 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggatcatagc |
| 205 | T25 L30 I50-20 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggatcgcagcataa tatccg |
| 206 | T25 L30 I80-20 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagcgcg cctaccg |
| 207 | T25 L30 I80-20x2 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagcgcg cctaccgaaagccggcgtcgacgttagcgc |

TABLE 22-continued

| Spacer and Anabaena 5' intron fragment sequences. | | |
|---|---|---|
| SEQ ID NO | Spacer | Sequence |
| 208 | T25 L30 I50-20x2 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggatcgcagcataa tatccgaaacgaggatacaagtgacatgc |
| 209 | T25 L30 I25-20x2 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTgattcacaatctaaa ttacgaaacgataaatgataactctaac |
| 210 | T0 L0 | aaacaaaccacTAGATGACTTACAACTAATCGGAAGGTGCAGAGAC TCGACGGGAGCTACCCTAACGTCAAGACGAGGGTAAAGAGAG AGTCCAATTCTCAAAGCCAATAGGCAGTAGCGAAAGCTGCAA GAGAATGAAAATCCGTggctcgcagc |
| 211 | T100 L5 | cgggcaaacaaacaaaTAGATGACTTACAACTAATCGGAAGGTGCAG AGACTCGACGGGAGCTACCCTAACGTCAAGACGAGGGTAAAG AGAGAGTCCAATTCTCAAAGCCAATAGGCAGTAGCGAAAGCT GCAAGAGAATGAAAATCCGTggctcgcagc |
| 212 | T75 L30 | cgctccgacgagatccggccagtgcgagcaaacaaacaaaTAGATGACTTACAACT AATCGGAAGGTGCAGAGACTCGACGGGAGCTACCCTAACGTC AAGACGAGGGTAAAGAGAGAGTCCAATTCTCAAAGCCAATAG GCAGTAGCGAAAGCTGCAAGAGAATGAAAATCCGTggctcgcagc |
| 213 | T0 L0a | aaacaaaccacGGCAGTAGCGAAAGCTGCAAGAGAATGAAAATCC GTggctcgcagc |
| 214 | T25 L10a | agtatataagaaacaaaccacGGCAGTAGCGAAAGCTGCAAGAGAATGA AAATCCGTggctcgcagc |
| 215 | T25 L20a | ctgaaattatacttatactcaaacaaaccacGGCAGTAGCGAAAGCTGCAAGAG AATGAAAATCCGTggctcgcagc |
| 216 | T25 L30a (I80-10) [Control] | ctgaaattatacttatactcagtatatgacaaacaaaccacGGCAGTAGCGAAAGCTGC AAGAGAATGAAAATCCGTggctcgcagc |
| 217 | T50 L10a | tagcgtcagcaaacaaacaaaGGCAGTAGCGAAAGCTGCAAGAGAATGA AAATCCGTggctcgcagc |
| 218 | T50 L20a | atactcatactagcgtcagcaaacaaacaaaGGCAGTAGCGAAAGCTGCAAGAG AATGAAAATCCGTggctcgcagc |
| 219 | T50 L30a | gtgtgaagctatactcatactagcgtcagcaaacaaacaaaGGCAGTAGCGAAAGCTG CAAGAGAATGAAAATCCGTggctcgcagc |
| 220 | T75 L10a | cggtgcgagcaaacaaacaaaGGCAGTAGCGAAAGCTGCAAGAGAATGA AAATCCGTggctcgcagc |
| 221 | T75 L20a | cgctccgacccagtgcgagcaaacaaacaaaGGCAGTAGCGAAAGCTGCAAGA GAATGAAAATCCGTggctcgcagc |
| 222 | T75 L30a | cgctccgacgagatccggccagtgcgagcaaacaaacaaaGGCAGTAGCGAAAGCT GCAAGAGAATGAAAATCCGTggctcgcagc |
| 223 | T0 L0b | aaacaaaccacAAGACGAGGGTAAAGAGAGAGTCCAATTCTCAAA GCCAATAGGCAGTAGCGAAAGCTGCAAGAGAATGAAAATCC GTggctcgcagc |
| 224 | T25 L10b | agtatataagaaacaaaccacAAGACGAGGGTAAAGAGAGAGTCCAATTC TCAAAGCCAATAGGCAGTAGCGAAAGCTGCAAGAGAATGAA AATCCGTggctcgcagc |
| 225 | T25 L20b | ctgaaattatacttatactcaaacaaaccacAAGACGAGGGTAAAGAGAGAGTC CAATTCTCAAAGCCAATAGGCAGTAGCGAAAGCTGCAAGAGA ATGAAAATCCGTggctcgcagc |
| 226 | T25 L30b (I80-10) [Control] | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggctcgcagc |

TABLE 22-continued

Spacer and Anabaena 5' intron fragment sequences.

| SEQ ID NO | Spacer | Sequence |
|---|---|---|
| 227 | T50 L10b | tagcgtcagcaaacaaacaaaAAGACGAGGGTAAAGAGAGAGTCCAATT CTCAAAGCCAATAGGCAGTAGCGAAAGCTGCAAGAGAATGA AAATCCGTggctcgcagc |
| 228 | T50 L20b | atactcatactagcgtcagcaaacaaacaaaAAGACGAGGGTAAAGAGAGAGT CCAATTCTCAAAGCCAATAGGCAGTAGCGAAAGCTGCAAGAG AATGAAAATCCGTggctcgcagc |
| 229 | T50 L30b | gtgtgaagctatactcatactagcgtcagcaaacaaacaaaAAGACGAGGGTAAAGA GAGAGTCCAATTCTCAAAGCCAATAGGCAGTAGCGAAAGCTG CAAGAGAATGAAAATCCGTggctcgcagc |
| 230 | T75 L10b | cggtgcgagcaaacaaacaaaAAGACGAGGGTAAAGAGAGAGTCCAATT CTCAAAGCCAATAGGCAGTAGCGAAAGCTGCAAGAGAATGA AAATCCGTggctcgcagc |
| 231 | T75 L20b | cgctccgacccagtgcgagcaaacaaacaaaAAGACGAGGGTAAAGAGAGAG TCCAATTCTCAAAGCCAATAGGCAGTAGCGAAAGCTGCAAGA GAATGAAAATCCGTggctcgcagc |
| 232 | T75 L30b | cgctccgacgagatccggccagtgcgagcaaacaaacaaaAAGACGAGGGTAAAG AGAGAGTCCAATTCTCAAAGCCAATAGGCAGTAGCGAAAGCT GCAAGAGAATGAAAATCCGTggctcgcagc |
| 233 | T25 L30 I0-0 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGT |
| 234 | T25 L30a I0-0 | ctgaaattatacttatactcagtatatgacaaacaaaccacGGCAGTAGCGAAAGCTGC AAGAGAATGAAAATCCGT |
| 235 | T25 L30a I25-10 | ctgaaattatacttatactcagtatatgacaaacaaaccacGGCAGTAGCGAAAGCTGC AAGAGAATGAAAATCCGTgattaaacag |
| 236 | T25 L30a I25-20 | ctgaaattatacttatactcagtatatgacaaacaaaccacGGCAGTAGCGAAAGCTGC AAGAGAATGAAAATCCGTgattcacaatataaattacg |
| 237 | T25 L30a I50-10 | ctgaaattatacttatactcagtatatgacaaacaaaccacGGCAGTAGCGAAAGCTGC AAGAGAATGAAAATCCGTggatcatagc |
| 238 | T25 L30a I50-20 | ctgaaattatacttatactcagtatatgacaaacaaaccacGGCAGTAGCGAAAGCTGC AAGAGAATGAAAATCCGTggatcgcagcataatatccg |
| 239 | T25 L30a I80-20 | ctgaaattatacttatactcagtatatgacaaacaaaccacGGCAGTAGCGAAAGCTGC AAGAGAATGAAAATCCGTggctcgcagcgcgcctaccg |
| 240 | T25 L30b I0-0 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGT |
| 241 | T25 L30b I25-10 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTgattaaacag |
| 242 | T25 L30b I25-20 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTgattcacaatataaattacg |
| 243 | T25 L30b I50-10 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggatcatagc |
| 244 | T25 L30b I50-20 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggatcgcagcataatatccg |
| 245 | T25 L30b I80-20 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggctcgcagcgcgcctaccg |

In some embodiments, a spacer and 5' intron fragment are spacers and fragments having sequences as listed in Table 22.

TABLE 23

Spacer and Anabaena 3' intron fragment sequences.

| SEQ ID NO | Spacer | Sequence |
|---|---|---|
| 246 | T25 L10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaacttatatact |
| 247 | T25 L20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagagtataagtataatttcag |
| 248 | T25 L30 (I80-10) [Control] | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 249 | T25 L40 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcatattgttgatg |
| 250 | T25 L50 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagcgataatgcttcatatactgagtataagtatagatcatattg ttgatg |
| 251 | T50 L10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgcta |
| 252 | T50 L20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtat |
| 253 | T50 L30 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtatagcttcacac |
| 254 | T50 L40 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtatagcttcacactcaggtgagg |
| 255 | T50 L50 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtatagcttcacactcaggtgaggc atcattcgg |
| 256 | T75 L10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctcgcaccg |
| 257 | T75 L20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctcgcactgggtcggagcg |
| 258 | T25 L30 1 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |

TABLE 23-continued

Spacer and Anabaena 3' intron fragment sequences.

| SEQ ID NO | Spacer | Sequence |
|---|---|---|
| 259 | T25 L30 3 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 260 | T25 L30 5 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 261 | T25 L30 8 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 262 | T25 L30 OffTarget 10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtaacttagagagtataagtataatttcag |
| 263 | T25 L30 OffTarget 20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtaacttagaTgtaacacacataatttcag |
| 264 | T25 L30 OffTarget 30 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtaacttagaTgtaacacacaccgatcaac |
| 265 | T25 L30 I25-10 | ctgtttaatcACGGACTTAAATAATTGAGCCTTAAAGAAGAAATTCT TTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 266 | T25 L30 I25-20 | cgtaatttatattgtgaatcACGGACTTAAATAATTGAGCCTTAAAGAAGA AATTCTTTAAGTGGATGCTCTCAAACTCAGGGAAACCTAAATC TAGTTATAGACAAGGCAATCCTGAGCCAAGCCGAAGTAGTAA TTAGTAAGTTAACAAcacaaacacaagtcatatactgagtataagtataatttcag |
| 267 | T25 L30 I50-00 | gctatgatccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 268 | T25 L30 I50-20 | cggatattatgctgcgatccACGGACTTAAATAATTGAGCCTTAAAGAAG AAATTCTTTAAGTGGATGCTCTCAAACTCAGGGAAACCTAAA TCTAGTTATAGACAAGGCAATCCTGAGCCAAGCCGAAGTAGT AATTAGTAAGTTAACAAcaeaaacacaagtcatatactgagtataagtataatttcag |
| 269 | T25 L30 I80-00 | cggtaggcgctgctgcgagccACGGACTTAAATAATTGAGCCTTAAAGAA GAAATTCTTTAAGTGGATGCTCTCAAACTCAGGGAAACCTAA ATCTAGTTATAGACAAGGCAATCCTGAGCCAAGCCGAAGTAG TAATTAGTAAGTTAACAAcaeaaacacaagtcatatactgagtataagtataatttcag |
| 270 | T25 L30 I80-20x2 | gcgctaacgtcgacgccggcaaacggtaggcgcgctgcgagccACGGACTTAAATAA TTGAGCCTTAAAGAAGAAATTCTTTAAGTGGATGCrCTCAAAC TCAGGGAAACCTAAATCTAGTTATAGACAAGGCAATCCTGAG CCAAGCCGAAGTAGTAATTAGTAAGTTAACAAcacaaacacaagtcat atactgagtataagtataatttcag |
| 271 | T25 L30 I50-20x2 | gcatgtcacttgtatcctcgaaacggatattatgctgcgatccACGGACTTAAATAATTG AGCCTTAAAGAAGAAATTCTTTAAGTGGATGCTCTCAAACTC AGGGAAACCTAAATCTAGTTATAGACAAGGCAATCCTGAGCC AAGCCGAAGTAGTAATTAGTAAGTTAACAAcacaaacacaagtcatatac tgagtataagtataatttcag |
| 272 | T25 L30 I25-20x2 | gttagagttatcatttatcgaaacgtaatttagattgtgaatcACGGACTTAAATAATTGA GCCTTAAAGAAGAAATTCTTTAAGTGGATGCTCTCAAACTCA GGGAAACCTAAATCTAGTTATAGACAAGGCAATCCTGAGCCA AGCCGAAGTAGTAATTAGTAAGTTAACAAcacaaacacaagtcatatactg agtataagtataatttcag |

TABLE 23-continued

Spacer and Anabaena 3' intron fragment sequences.

| SEQ ID NO | Spacer | Sequence |
|---|---|---|
| 273 | T0 L0 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaa |
| 274 | T100 L5 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagcccg |
| 275 | T75 L30 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctcgcactggccggaagctcgtcggagcg |
| 276 | T0 L0a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaa |
| 277 | T25 L10a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaacttatatact |
| 278 | T25 L20a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaagagtataagtataatttc ag |
| 279 | T25 L30a (I80-10) [Control] | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaagtcatatactgagtataa gtataatttcag |
| 280 | T50 L10a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctgacgcta |
| 281 | T50 L20a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctgacgctagtatga gtat |
| 282 | T50 L30a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctgacgctagtatga gtatagcttcacac |
| 283 | T75 L10a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctcgcaccg |

TABLE 23-continued

Spacer and Anabaena 3' intron fragment sequences.

| SEQ ID NO | Spacer | Sequence |
|---|---|---|
| 284 | T75 L20a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctcgcactgggtcgg agcg |
| 285 | T75 L30a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctcgcactggccgga agctcgtcggagcg |
| 286 | T0 L0b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaa |
| 287 | T25 L10b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaacttatatact |
| 288 | T25 L20b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaagagtataagtataatt tcag |
| 289 | T25 L30b (I80-10) [Control] | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaagtcatatactgagtat aagtataatttcag |
| 290 | T50 L10b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctgacgcta |
| 291 | T50 L20b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctgacgctagtatg agtat |
| 292 | T50 L30b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctgacgctagtatg agtatagcttcacac |
| 293 | T75 L10b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctcgcaccg |
| 294 | T75 L20b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctcgcactgggtcg gagcg |

TABLE 23-continued

| Spacer and Anabaena 3' intron fragment sequences. | | |
|---|---|---|
| SEQ ID NO | Spacer | Sequence |
| 295 | T75 L30b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctcgcactggccg gaagctcgtcggagcg |
| 296 | T25 L30 I0-0 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAAcacaaacacaagtcatatactgagtataagtataatttcag |
| 297 | T25 L30a I0-0 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACTC GACGGGAGCTACCCTAACGTCAAGACGAGGGTAAAGAGAGA GTCCAATTCTCAAAGCCAATAcacaaacacaagtcatatactgagtataagtataat ttcag |
| 298 | T25 L30 I25-10a | ctgataatcACGGACTTAAATAATTGAGCCTTAAAGAAGAAATTCT TTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaagtcatatactgagtataa gtataatttcag |
| 299 | T25 L30 I25-20a | cgtaatttatattgtgaatcACGGACTTAAATAATTGAGCCTTAAAGAAGA AATTCTTTAAGTGGATGCTCTCAAACTCAGGGAAACCTAAATC TAGTTATAGACAAGGCAATCCTGAGCCAAGCCGAAGTAGTAA TTAGTAAGTTAACAATAGATGACTTACAACTAATCGGAAGGT GCAGAGACTCGACGGGAGCTACCCTAACGTCAAGACGAGGGT AAAGAGAGAGTCCAATTCTCAAAGCCAATAcacaaacacaagtcatatac tgagtataagtataatttcag |
| 300 | T25 L30 I50-10a | gctatgatccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaagtcatatactgagtataa gtataatttcag |

In some embodiments, a spacer and 3' intron fragment is a spacer and intron fragment having sequences as listed in Table 23.

TABLE 24

| CAR sequences | | |
|---|---|---|
| SEQ ID NO | CAR | Sequence |
| 309 | FMC63-4-1BB | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT GATCTGGGGCAGCGAGACAACCTACTACAACAGCGCCCTGAA GTCCCGGCTGACCATCATCAAGGACAACTCCAAGAGCCAGGT |

TABLE 24-continued

| CAR sequences | | |
|---|---|---|
| SEQ ID NO | CAR | Sequence |
| | | GTTCCTGAAGATGAACAGCCTGCAGACCGACGACACCGCCAT CTACTATTGCGCCAAGCACTACTACTACGGCGGCAGCTACGC CATGGATTATTGGGGCCAGGGCACCAGCGTGACCGTTTCTTCT GCCGCCGCTATCGAAGTGATGTACCCTCCTCCTTACCTGGACA ACGAGAAGTCCAACGGCACCATCATCCACGTGAAGGGCAAG CACCTGTGTCCTTCTCCACTGTTCCCCGGACCTAGCAAGCCTT TCTGGGTGCTCGTTGTTGTTGGCGGCGTGCTGGCCTGTTACAG CCTGCTGGTTACCGTGGCCTTCATCATCTTTTGGGTCAAGAGA GGCCGGAAGAAACTTCTTTATATATTCAAGCAGCCCTTTATGC GACCCGTTCAGACTACCCAAGAGGAAGATGGATGCAGTTGCC GCTTTCCAGAAGAGGAGGAGGGCGGGTGCGAACTGtaa |
| 310 | FMC63-CD28 | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT GATCTGGGGCAGCGAGACAACCTACTACAACAGCGCCCTGAA GTCCCGGCTGACCATCATCAAGGACAACTCCAAGAGCCAGGT GTTCCTGAAGATGAACAGCCTGCAGACCGACGACACCGCCAT CTACTATTGCGCCAAGCACTACTACTACGGCGGCAGCTACGC CATGGATTATTGGGGCCAGGGCACCAGCGTGACCGTTTCTTCT GCCGCCGCTATCGAAGTGATGTACCCTCCTCCTTACCTGGACA ACGAGAAGTCCAACGGCACCATCATCCACGTGAAGGGCAAG CACCTGTGTCCTTCTCCACTGTTCCCCGGACCTAGCAAGCCTT TCTGGGTGCTCGTTGTTGTTGGCGGCGTGCTGGCCTGTTACAG CCTGCTGGTTACCGTGGCCTTCATCATCTTTTGGGTCCGAAGC AAGCGGAGCCGGCTGCTGCACTCCGACTACATGAACATGACC CCTAGACGGCCCGGACCAACCAGAAAGCACTACCAGCCTTAC GCTCCTCCTAGAGACTTCGCCGCCTACCGGTCCtaa |
| 311 | FMC63-CD28-zeta | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT GATCTGGGGCAGCGAGACAACCTACTACAACAGCGCCCTGAA GTCCCGGCTGACCATCATCAAGGACAACTCCAAGAGCCAGGT GTTCCTGAAGATGAACAGCCTGCAGACCGACGACACCGCCAT CTACTATTGCGCCAAGCACTACTACTACGGCGGCAGCTACGC CATGGATTATTGGGGCCAGGGCACCAGCGTGACCGTTTCTTCT GCCGCCGCTATCGAAGTGATGTACCCTCCTCCTTACCTGGACA ACGAGAAGTCCAACGGCACCATCATCCACGTGAAGGGCAAG CACCTGTGTCCTTCTCCACTGTTCCCCGGACCTAGCAAGCCTT TCTGGGTGCTCGTTGTTGTTGGCGGCGTGCTGGCCTGTTACAG CCTGCTGGTTACCGTGGCCTTCATCATCTTTTGGGTCCGAAGC AAGCGGAGCCGGCTGCTGCACTCCGACTACATGAACATGACC CCTAGACGGCCCGGACCAACCAGAAAGCACTACCAGCCTTAC GCTCCTCCTAGAGACTTCGCCGCCTACCGGTCCAGAGTGAAG TTCAGCAGATCCGCCGATGCTCCCGCCTATCAGCAGGGCCAA AACCAGCTGTACAACGAGCTGAACCTGGGGAGAAGAGAAGA GTACGACGTGCTGGACAAGCGGAGAGGCAGAGATCCTGAAA TGGGCGGCAAGCCCAGACGGAAGAATCCTCAAGAGGGCCTG TATAATGAGCTGCAGAAAGACAAGATGGCCGAGGCCTACAG CGAGATCGGAATGAAGGGCGAGCGCAGAAGAGGCAAGGGAC ACGATGGACTGTACCAGGGACTGAGCACCGCCACCAAGGATA CCTATGACGCCCTGCACATGCAGGCCCTGCCTCCAAGAtaa |

TABLE 24-continued

CAR sequences

| SEQ ID NO | CAR | Sequence |
|---|---|---|
| 312 | FMC63-zeta | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT GATCTGGGGCAGCGAGACAACCTACTACAACAGCGCCCTGAA GTCCCGGCTGACCATCATCAAGGACAACTCCAAGAGCCAGGT GTTCCTGAAGATGAACAGCCTGCAGACCGACGACACCGCCAT CTACTATTGCGCCAAGCACTACTACTACGGCGGCAGCTACGC CATGGATTATTGGGGCCAGGGCACCAGCGTGACCGTTTCTTCT GCCGCCGCTATCGAAGTGATGTACCCTCCTCCTTACCTGGACA ACGAGAAGTCCAACGGCACCATCATCCACGTGAAGGGCAAG CACCTGTGTCCTTCTCCACTGTTCCCCGGACCTAGCAAGCCTT TCTGGGTGCTCGTTGTTGTTGGCGGCGTGCTGGCCTGTTACAG CCTGCTGGTTACCGTGGCCTTCATCATCTTTTGGGTCAGAGTG AAGTTCAGCAGATCCGCCGATGCTCCCGCCTATCAGCAGGGC CAAAACCAGCTGTACAACGAGCTGAACCTGGGGAGAAGAGA AGAGTACGACGTGCTGGACAAGCGGAGAGGCAGAGATCCTG AAATGGGCGGCAAGCCCAGACGGAAGAATCCTCAAGAGGGC CTGTATAATGAGCTGCAGAAAGACAAGATGGCCGAGGCCTAC AGCGAGATCGGAATGAAGGGCGAGCGCAGAAGAGGCAAGGG ACACGATGGACTGTACCAGGGACTGAGCACCGCCACCAAGG ATACCTATGACGCCCTGCACATGCAGGCCCTGCCTCCAAGAtaa |
| 313 | CircKymriah-Q388 | ATGGCTCTCCCGGTCACAGCCCTTCTCCTGCCCCTGGCACTCT TGCTGCATGCGGCACGACCCGACATCCAGATGACCCAGACCA CAAGCAGCCTGTCTGCCAGCCTGGGCGATAGAGTGACCATCA GCTGTAGAGCCAGCCAGGACATCAGCAAGTACCTGAACTGGT ATCAGCAAAAGCCCGACGGCACCGTGAAGCTGCTGATCTACC ACACCAGCAGACTGCACAGCGGCGTGCCAAGCAGATTTTCTG GCAGCGGCTCTGGCACCGACTACAGCCTGACAATCAGCAACC TGGAACAAGAGGATATCGCTACCTACTTCTGCCAGCAAGGCA ACACCCTGCCTTACACCTTTGGCGGAGGCACCAAGCTGGAAA TCACCGGTGGAGGTGGTTCTGGCGGAGGGGGATCTGGTGGAG GCGGTTCAGAAGTGAAACTGCAAGAGTCTGGCCCTGGACTGG TGGCCCCATCTCAGTCTCTGAGCGTGACCTGTACAGTCAGCG GAGTGTCCCTGCCTGATTACGGCGTGTCCTGGATCAGACAGC CTCCTCGGAAAGGCCTGGAATGGCTGGGAGTGATCTGGGGCA GCGAGACAACCTACTACAACAGCGCCCTGAAGTCCCGGCTGA CCATCATCAAGGACAACTCCAAGAGCCAGGTGTTCCTGAAGA TGAACAGCCTGCAGACCGACGACACCGCCATCTACTATTGCG CCAAGCACTACTACTACGGCGGCAGCTACGCCATGGATTATT GGGGCCAGGGCACCAGCGTGACCGTTTCTTCTACCACAACGC CCGCCCCGCGACCGCCTACTCCCGCTCCCACAATTGCATCACA ACCCCTGTCTTTGAGACCCGAAGCTTGTCGACCAGCTGCCGGT GGCGCGGTTCACACGCGGGGGCTCGATTTCGCCTGTGATATA TATATATGGGCCCCATTGGCTGGAACATGCGGAGTATTGCTTC TGAGCCTGGTGATTACCCTCTACTGTAAGAGAGGCCGGAAGA AACTTCTTTATATATTCAAGCAGCCCTTTATGCGACCCGTTCA GACTACCCAAGAGGAAGATGGATGCAGTTGCCGCTTTCCAGA AGAGGAGGAGGGCGGGTGCGAACTGAGAGTGAAGTTCAGCA GATCCGCCGATGCTCCCGCCTATCAGCAGGGCCAAAACCAGC TGTACAACGAGCTGAACCTGGGGAGAAGAGAAGAGTACGAC GTGCTGGACAAGCGGAGAGGCAGAGATCCTGAAATGGGCGG CAAGCCCAGACGGAAGAATCCTCAAGAGGGCCTGTATAATGA GCTGCAGAAAGACAAGATGGCCGAGGCCTACAGCGAGATCG GAATGAAGGGCGAGCGCAGAAGAGGCAAGGGACACGATGGA CTGTACCAGGGACTGAGCACCGCCACCAAGGATACCTATGAC GCCCTGCACATGCAGGCCCTGCCTCCAAGAtaa |
| 314 | CircKymriah-K388 | ATGGCTCTCCCGGTCACAGCCCTTCTCCTGCCCCTGGCACTCT TGCTGCATGCGGCACGACCCGACATCCAGATGACCCAGACCA CAAGCAGCCTGTCTGCCAGCCTGGGCGATAGAGTGACCATCA GCTGTAGAGCCAGCCAGGACATCAGCAAGTACCTGAACTGGT ATCAGCAAAAGCCCGACGGCACCGTGAAGCTGCTGATCTACC |

TABLE 24-continued

CAR sequences

| SEQ ID NO | CAR | Sequence |
|---|---|---|
| | | ACACCAGCAGACTGCACAGCGGCGTGCCAAGCAGATTTTCTG GCAGCGGCTCTGGCACCGACTACAGCCTGACAATCAGCAACC TGGAACAAGAGGATATCGCTACCTACTTCTGCCAGCAAGGCA ACACCCTGCCTTACACCTTTGGCGGAGGCACCAAGCTGGAAA TCACCGGTGGAGGTGGTTCTGGCGGAGGGGGATCTGGTGGAG GCGGTTCAGAAGTGAAACTGCAAGAGTCTGGCCCTGGACTGG TGGCCCCATCTCAGTCTCTGAGCGTGACCTGTACAGTCAGCG GAGTGTCCCTGCCTGATTACGGCGTGTCCTGGATCAGACAGC CTCCTCGGAAAGGCCTGGAATGGCTGGGAGTGATCTGGGGCA GCGAGACAACCTACTACAACAGCGCCCTGAAGTCCCGGCTGA CCATCATCAAGGACAACTCCAAGAGCCAGGTGTTCCTGAAGA TGAACAGCCTGCAGACCGACGACACCGCCATCTACTATTGCG CCAAGCACTACTACTACGGCGGCAGCTACGCCATGGATTATT GGGGCCAGGGCACCAGCGTGACCGTTTCTTCTACCACAACGC CCGCCCCGCGACCGCCTACTCCCGCTCCCACAATTGCATCACA ACCCCTGTCTTTGAGACCCGAAGCTTGTCGACCAGCTGCCGGT GGCGCGGTTCACACGCGGGGGCTCGATTTCGCCTGTGATATA TATATATGGGCCCCATTGGCTGGAACATGCGGAGTATTGCTTC TGAGCCTGGTGATTACCCTCTACTGTAAGAGAGGCCGGAAGA AACTTCTTTATATATTCAAGCAGCCCTTTATGCGACCCGTTCA GACTACCCAAGAGGAAGATGGATGCAGTTGCCGCTTTCCAGA AGAGGAGGAGGGCGGGTGCGAACTGAGAGTGAAGTTCAGCA GATCCGCCGATGCTCCCGCCTATAAGCAGGGCCAAAACCAGC TGTACAACGAGCTGAACCTGGGGAGAAGAGAAGAGTACGAC GTGCTGGACAAGCGGAGAGGCAGAGATCCTGAAATGGGCGG CAAGCCCAGACGGAAGAATCCTCAAGAGGGCCTGTATAATGA GCTGCAGAAAGACAAGATGGCCGAGGCCTACAGCGAGATCG GAATGAAGGGCGAGCGCAGAAGAGGCAAGGGACACGATGGA CTGTACCAGGGACTGAGCACCGCCACCAAGGATACCTATGAC GCCCTGCACATGCAGGCCCTGCCTCCAAGAtaa |
| 315 | CircM971-CD22 | ATGCTGCTGCTGGTCACATCTCTGCTGCTGTGCGAGCTGCCCC ATCCTGCCTTTCTGCTGATCCCCCAGGTTCAACTCCAGCAGTC TGGTCCCGGCCTCGTTAAACCAAGCCAGACTTTGTCTCTTACC TGTGCTATCAGTGGCGATAGCGTGTCTAGTAATTCAGCCGCAT GGAACTGGATCCGACAATCACCGAGTAGGGGACTTGAATGGC TGGGTAGAACCTATTACCGGTCCAAATGGTACAATGACTATG CAGTGTCTGTAAAAAGCAGGATCACGATCAACCCTGATACGT CTAAAAACCAGTTTTCTCTGCAACTTAATAGTGTGACCCCTGA AGACACCGCTGTGTATTACTGTGCACGGGAGGTTACCGGTGA TCTTGAAGATGCTTTTGATATATGGGGCCAAGGTACGATGGT CACGGTGTCTAGTgggggaggcggcagcGACATACAGATGACGCAG AGCCCATCCAGTCTCTCCGCGTCTGTTGGTGACAGAGTGACTA TTACATGTAGGGCGTCTCAGACCATTTGGTCTTACCTCAATTG GTATCAACAGCGACCAGGCAAAGCACCGAACTTGCTCATTTA CGCTGCCAGCTCACTCCAAAGTGGTGTGCCGTCCAGATTTAGT GGTAGGGGCAGTGGCACTGATTTCACTCTGACTATTTCAAGTC TTCAAGCTGAGGATTTTGCCACATACTACTGCCAGCAAAGTT ACTCAATACCTCAGACTTTTGGACAGGGGACAAAATTGGAGA TTAAAtccggaACCACAACGCCCGCCCCGCGACCGCCTACTCCC GCTCCCACAATTGCATCACAACCCCTGTCTTTGAGACCCGAA GCTTGTCGACCAGCTGCCGGTGGCGCGGTTCACACGCGGGGG CTCGATTTCGCCTGTGATATATATATATGGGCCCCATTGGCTG GAACATGCGGAGTATTGCTTCTGAGCCTGGTGATTACCCTCTA CTGTAAGAGAGGCCGGAAGAAACTTCTTTATATATTCAAGCA GCCCTTTATGCGACCCGTTCAGACTACCCAAGAGGAAGATGG ATGCAGTTGCCGCTTTCCAGAAGAGGAGGAGGGCGGGTGCGA ACTGAGAGTGAAGTTCAGCAGATCCGCCGATGCTCCCGCCTA TAAGCAGGGCCAAAACCAGCTGTACAACGAGCTGAACCTGG GGAGAAGAGAAGAGTACGACGTGCTGGACAAGCGGAGAGGC AGAGATCCTGAAATGGGCGGCAAGCCCAGACGGAAGAATCC TCAAGAGGGCCTGTATAATGAGCTGCAGAAAGACAAGATGG CCGAGGCCTACAGCGAGATCGGAATGAAGGGCGAGCGCAGA AGAGGCAAGGGACACGATGGACTGTACCAGGGACTGAGCAC CGCCACCAAGGATACCTATGACGCCCTGCACATGCAGGCCCT GCCTCCAAGAtaa |

TABLE 24-continued

| CAR sequences | | |
|---|---|---|
| SEQ ID NO | CAR | Sequence |
| 316 | CircCD19_22 Bispecific 29 | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCggcggcggaggatcccCAGGTTCAACTCCAGCAGTCTGGTC CCGGCCTCGTTAAACCAAGCCAGACTTTGTCTCTTACCTGTGC TATCAGTGGCGATAGCGTGTCTAGTAATTCAGCCGCATGGAA CTGGATCCGACAATCACCGAGTAGGGGACTTGAATGGCTGGG TAGAACCTATTACCGGTCCAAATGGTACAATGACTATGCAGT GTCTGTAAAAAGCAGGATCACGATCAACCCTGATACGTCTAA AAACCAGTTTTCTCTGCAACTTAATAGTGTGACCCCTGAAGAC ACCGCTGTGTATTACTGTGCACGGGAGGTTACCGGTGATCTTG AAGATGCTTTTGATATATGGGGCCAAGGTACGATGGTCACGG TGTCTAGTGGCTCTACAAGCGGCAGCGGCAAACCTGGATCTG GCGAGGGATCTACCAAGGGCGACATACAGATGACGCAGAGC CCATCCAGTCTCTCCGCGTCTGTTGGTGACAGAGTGACTATTA CATGTAGGGCGTCTCAGACCATTTGGTCTTACCTCAATTGGTA TCAACAGCGACCAGGCAAAGCACCGAACTTGCTCATTTACGC TGCCAGCTCACTCCAAAGTGGTGTGCCGTCCAGATTTAGTGGT AGGGGCAGTGGCACTGATTTCACTCTGACTATTTCAAGTCTTC AAGCTGAGGATTTTGCCACATACTACTGCCAGCAAAGTTACT CAATACCTCAGACTTTTGGACAGGGGACAAAATTGGAGATTA AAgggggaggcggcagcGAAGTGAAACTGCAAGAGTCTGGCCCTGG ACTGGTGGCCCCATCTCAGTCTCTGAGCGTGACCTGTACAGTC AGCGGAGTGTCCCTGCCTGATTACGGCGTGTCCTGGATCAGA CAGCCTCCTCGGAAAGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTG AAGATGAACAGCCTGCAGACCGACGACACCGCCATCTACTAT TGCGCCAAGCACTACTACTACGGCGGCAGCTACGCCATGGAT TATTGGGGCCAGGGCACCAGCGTGACCGTTTCTTCTtccggaACC ACAACGCCCGCCCCGCGACCGCCTACTCCCGCTCCCACAATT GCATCACAACCCCTGTCTTTGAGACCCGAAGCTTGTCGACCA GCTGCCGGTGGCGCGGTTCACACGCGGGGGCTCGATTTCGCC TGTGATATATATATATGGGCCCCATTGGCTGGAACATGCGGA GTATTGCTTCTGAGCCTGGTGATTACCCTCTACTGTAAGAGAG GCCGGAAGAAACTTCTTTATATATTCAAGCAGCCCTTTATGCG ACCCGTTCAGACTACCCAAGAGGAAGATGGATGCAGTTGCCG CTTTCCAGAAGAGGAGGAGGGCGGGTGCGAACTGAGAGTGA AGTTCAGCAGATCCGCCGATGCTCCCGCCTATAAGCAGGGCC AAAACCAGCTGTACAACGAGCTGAACCTGGGGAGAAGAGAA GAGTACGACGTGCTGGACAAGCGGAGAGGCAGAGATCCTGA AATGGGCGGCAAGCCCAGACGGAAGAATCCTCAAGAGGGCC TGTATAATGAGCTGCAGAAAGACAAGATGGCCGAGGCCTACA GCGAGATCGGAATGAAGGGCGAGCGCAGAAGAGGCAAGGGA CACGATGGACTGTACCAGGGACTGAGCACCGCCACCAAGGAT ACCTATGACGCCCTGCACATGCAGGCCCTGCCTCCAAGAtaa |
| 317 | CircCD19_22 Bispecific 30 | ATGCTGCTGCTGGTCACATCTCTGCTGCTGTGCGAGCTGCCCC ATCCTGCCTTTCTGCTGATCCCCCAGGTTCAACTCCAGCAGTC TGGTCCCGGCCTCGTTAAACCAAGCCAGACTTTGTCTCTTACC TGTGCTATCAGTGGCGATAGCGTGTCTAGTAATTCAGCCGCAT GGAACTGGATCCGACAATCACCGAGTAGGGGACTTGAATGGC TGGGTAGAACCTATTACCGGTCCAAATGGTACAATGACTATG CAGTGTCTGTAAAAAGCAGGATCACGATCAACCCTGATACGT CTAAAAACCAGTTTTCTCTGCAACTTAATAGTGTGACCCCTGA AGACACCGCTGTGTATTACTGTGCACGGGAGGTTACCGGTGA TCTTGAAGATGCTTTTGATATATGGGGCCAAGGTACGATGGT CACGGTGTCTAGTgggggaggcggcagcGACATACAGATGACGCAG AGCCCATCCAGTCTCTCCGCGTCTGTTGGTGACAGAGTGACTA TTACATGTAGGGCGTCTCAGACCATTTGGTCTTACCTCAATTG GTATCAACAGCGACCAGGCAAAGCACCGAACTTGCTCATTTA CGCTGCCAGCTCACTCCAAAGTGGTGTGCCGTCCAGATTTAGT GGTAGGGGCAGTGGCACTGATTTCACTCTGACTATTTCAAGTC TTCAAGCTGAGGATTTTGCCACATACTACTGCCAGCAAAGTT ACTCAATACCTCAGACTTTTGGACAGGGGACAAAATTGGAGA TTAAAGGGGGAGGCGGATCCGGCGGTGGTGGCTCCGGCGGTG GTGGTTCTGGAGGCGGCGGAAGCGGTGGGGGTGGTAGCGAC ATCCAGATGACCCAGACCACAAGCAGCCTGTCTGCCAGCCTG |

TABLE 24-continued

CAR sequences

| SEQ ID NO | CAR | Sequence |
|---|---|---|
| | | GGCGATAGAGTGACCATCAGCTGTAGAGCCAGCCAGGACATC<br>AGCAAGTACCTGAACTGGTATCAGCAAAAGCCCGACGGCACC<br>GTGAAGCTGCTGATCTACCACACCAGCAGACTGCACAGCGGC<br>GTGCCAAGCAGATTTTCTGGCAGCGGCTCTGGCACCGACTAC<br>AGCCTGACAATCAGCAACCTGGAACAAGAGGATATCGCTACC<br>TACTTCTGCCAGCAAGGCAACACCCTGCCTTACACCTTTGGCG<br>GAGGCACCAAGCTGGAAATCACCGGCTCTACAAGCGGCAGC<br>GGCAAACCTGGATCTGGCGAGGGATCTACCAAGGGCGAAGT<br>GAAACTGCAAGAGTCTGGCCCTGGACTGGTGGCCCCATCTCA<br>GTCTCTGAGCGTGACCTGTACAGTCAGCGGAGTGTCCCTGCCT<br>GATTACGGCGTGTCCTGGATCAGACAGCCTCCTCGGAAAGGC<br>CTGGAATGGCTGGGAGTGATCTGGGGCAGCGAGACAACCTAC<br>TACAACAGCGCCCTGAAGTCCCGGCTGACCATCATCAAGGAC<br>AACTCCAAGAGCCAGGTGTTCCTGAAGATGAACAGCCTGCAG<br>ACCGACGACACCGCCATCTACTATTGCGCCAAGCACTACTAC<br>TACGGCGGCAGCTACGCCATGGATTATTGGGGCCAGGGCACC<br>AGCGTGACCGTTTCTTCTtccggaACCACAACGCCCGCCCCGCGA<br>CCGCCTACTCCCGCTCCCACAATTGCATCACAACCCCTGTCTT<br>TGAGACCCGAAGCTTGTCGACCAGCTGCCGGTGGCGCGGTTC<br>ACACGCGGGGGCTCGATTTCGCCTGTGATATATATATATGGG<br>CCCCATTGGCTGGAACATGCGGAGTATTGCTTCTGAGCCTGGT<br>GATTACCCTCTACTGTAAGAGAGGCCGGAAGAAACTTCTTTA<br>TATATTCAAGCAGCCCTTTATGCGACCCGTTCAGACTACCCAA<br>GAGGAAGATGGATGCAGTTGCCGCTTTCCAGAAGAGGAGGA<br>GGGCGGGTGCGAACTGAGAGTGAAGTTCAGCAGATCCGCCG<br>ATGCTCCCGCCTATAAGCAGGGCCAAAACCAGCTGTACAACG<br>AGCTGAACCTGGGGAGAAGAGAAGAGTACGACGTGCTGGAC<br>AAGCGGAGAGGCAGAGATCCTGAAATGGGCGGCAAGCCCAG<br>ACGGAAGAATCCTCAAGAGGGCCTGTATAATGAGCTGCAGAA<br>AGACAAGATGGCCGAGGCCTACAGCGAGATCGGAATGAAGG<br>GCGAGCGCAGAAGAGGCAAGGGACACGATGGACTGTACCAG<br>GGACTGAGCACCGCCACCAAGGATACCTATGACGCCCTGCAC<br>ATGCAGGCCCTGCCTCCAAGAtaa |

In some embodiments, a CAR is encoded by a nucleotide sequence as listed in Table 24.

TABLE 25

CAR domain sequences.

| SEQ ID NO | Protein | Sequence |
|---|---|---|
| 318 | 4-1BB | KRGRKKLLYIFKQPFMRPVQTTQEEDGCSCRFPEEEEGGCEL |
| 319 | CD3ζ intracellular domain | RVKFSRSADAPAYKQGQNQLYNELNLGRREEYDVLDKRRGRDPE<br>MGGKPRRKNPQEGLYNELQKDKMAEAYSEIGMKGERRRGKGHD<br>GLYQGLSTATKDTYDALHMQALPPR |
| 320 | CD28 intracellular signaling domain | QVQLVQSGAEVEKPGASVKVSCKASGYTFTDYYMHWVRQAPGQ<br>GLEWMGWINPNSGGTNYAQKFQGRVTMTRDTSISTAYMELSRLR<br>SDDTAVYYCASGWDFDYWGQGTLVTVSSGGGGSGGGGSGGGGS<br>GGGGSDIVMTQSPSSLSASVGDRVTITCRASQSIRYYLSWYQQKP<br>GKAPKLLIYTASILQNGVPSRFSGSGSGTDFTLTISSLQPEDFATYY<br>CLQTYTTPDFGPGTKVEIK |
| 321 | FMC63 VH | EVKLQESGPGLVAPSQSLSVTCTVSGVSLPDYGVSWIRQPPRKGLE<br>WLGVIWGSETTYYNSALKSRLTIIKDNSKSQVFLKMNSLQTDDTA<br>IYYCAKHYYYGGSYAMDYWGQGTSVTVSS |
| 322 | FMC63 VL | DIQMTQTTSSLSASLGDRVTISCRASQDISKYLNWYQQKPDGTVK<br>LLIYHTSRLHSGVPSRFSGSGSGTDYSLTISNLEQEDIATYFCQQGN<br>TLPYTFGGGTKLEIT |

In some embodiments, a CAR domain encoded by an inventive polynucleotide has a sequence as listed in Table 25.

TABLE 26

PD-1 or PD-L1 sequences.

| SEQ ID NO | Description | Sequence |
|---|---|---|
| 323 | Pembrolizumab heavy chain | QVQLVQSGVEVKKPGASVKVSCKASGYTFTNYYMYWV RQAPGQGLEWMGGINPSNGGTNFNEKFKNRVTLTTDSST TTAYMELKSLQFDDTAVYYCARRDYRFDMGFDYWGQG TTVTVSSASTKGPSVFPLAPCSRSTSESTAALGCLVKDYFP EPVTVSWNSGALTSGVHTFPAVLQSSGLYSLSSVVTVPSS SLGTKTYTCNVDHKPSNTKVDKRVESKYGPPCPPCPAPE FLGGPSVFLFPPKPKDTLMISRTPEVTCVVVDVSQEDPEV QFNWYVDGVEVHNAKTKPREEQFNSTYRVVSVLTVLHQ DWLNGKEYKCKVSNKGLPSSIEKTISKAKGQPREPQVYT LPPSQEEMTKNQVSLTCLVKGFYPSDIAVEWESNGQPEN NYKTTPPVLDSDGSFFLYSRLTVDKSRWQEGNVFSCSVM HEALHNHYTQKSLSLSLGK |
| 324 | Pembrolizumab light chain | EIVLTQSPATLSLSPGERATLSCRASKGVSTSGYSYLHWY QQKPGQAPRLLIYLASYLESGVPARFSGSGSGTDFTLTISS LEPEDFAVYYCQHSRDLPLTFGGGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| 325 | Nivolumab heavy chain | QVQLVESGGGVVQPGRSLRLDCKASGITFSNSGMHWVR QAPGKGLEWVAVIWYDGSKRYYADSVKGRFTISRDNSK NTLFLQMNSLRAEDTAVYYCATNDDYWGQGTLVTVSSA STKGPSVFPLAPCSRSTSESTAALGCLVKDYFPEPVTVSW NSGALTSGVHTFPAVLQSSGLYSLSSVVTVPSSSLGTKTY TCNVDHKPSNTKVDKRVESKYGPPCPPCPAPEFLGGPSVF LFPPKPKDTLMISRTPEVTCVVVDVSQEDPEVQFNWYVD GVEVHNAKTKPREEQFNSTYRVVSVLTVLHQDWLNGKE YKCKVSNKGLPSSIEKTISKAKGQPREPQVYTLPPSQEEM TKNQVSLTCLVKGFYPSDIAVEWESNGQPENNYKTTPPV LDSDGSFFLYSRLTVDKSRWQEGNVFSCSVMHEALHNH YTQKSLSLSLGK |
| 326 | Nivolumab light chain | EIVLTQSPATLSLSPGERATLSCRASQSVSSYLAWYQQKP GQAPRLLIYDASNRATGIPARFSGSGSGTDFTLTISSLEPE DFAVYYCQQSSNWPRTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |
| 327 | Atezolizumab heavy chain | EVQLVESGGGLVQPGGSLRLSCAASGFTFSDSWIHWVRQ APGKGLEWVAWISPYGGSTYYADSVKGRFTISADTSKNT AYLQMNSLRAEDTAVYYCARRHWPGGFDYWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPE LLGGPSVFLFPPKPKDTLMISRTPEVTCVVVDVSHEDPEV KFNWYVDGVEVHNAKTKPREEQYASTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| 328 | Atezolizumab light chain | DIQMTQSPSSLSASVGDRVTITCRASQDVSTAVAWYQQK PGKAPKLLIYSASFLYSGVPSRFSGSGSGTDFTLTISSLQPE DFATYYCQQYLYHPATFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |
| 329 | Avelumab heavy chain | EVQLLESGGGLVQPGGSLRLSCAASGFTFSSYIMMWVRQ APGKGLEWVSSIYPSGGITFYADTVKGRFTISRDNSKNTL YLQMNSLRAEDTAVYYCARIKLGTVTTVDYWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPE |

TABLE 26-continued

| PD-1 or PD-L1 sequences. | | |
|---|---|---|
| SEQ ID NO | Description | Sequence |
| | | LLGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYT LPPSRDELTKNQVSLTCLVKGFYPSDIAVEWESNGQPENN |

In some embodiments, a cleavage site separating expression sequences encoded by an inventive polynucleotide has a sequence listed in Table 26.

TABLE 27

| Cytokine sequences. | | |
|---|---|---|
| SEQ ID NO | Cytokine | Sequence |
| 333 | IL-2 | APTSSSTKKTQLQLEHLLLDLQMILNGINNYKNPKLTRMLTFKFY MPKKATELKHLQCLEEELKPLEEVLNLAQSKNFHLRPRDLISNINV IVLELKGSETTFMCEYADETATIVEFLNRWITFCQSIISTLT |
| 334 | IL-12A | RNLPVATPDPGMFPCLHHSQNLLRAVSNMLQKARQTLEFYPCTSE EIDHEDITKDKTSTVEACLPLELTKNESCLNSRETSFITNGSCLASR KTSFMMALCLSSIYEDLKMYQVEFKTMNAKLLMDPKRQIFLDQN MLAVIDELMQALNFNSETVPQKSSLEEPDFYKTKIKLCILLHAFRIR AVTIDRVMSYLNAS |
| 335 | IL-12B | IWELKKDVYVVELDWYPDAPGEMVVLTCDTPEEDGITWTLDQSS EVLGSGKTLTIQVKEFGDAGQYTCHKGGEVLSHSLLLLHKKEDGI WSTDILKDQKEPKNKTFLRCEAKNYSGRFTCWWLTTISTDLTFSV KSSRGSSDPQGVTCGAATLSAERVRGDNKEYEYSVECQEDSACPA AEESLPIEVMVDAVHKLKYENYTSSFFIRDIIKPDPPKNLQLKPLKN SRQVEVSWEYPDTWSTPHSYFSLTFCVQVQGKSKREKKDRVFTD KTSATVICRKNASISVRAQDRYYSSSWSEWASVPCS |
| 336 | IL-7 | DCDIEGKDGKQYESVLMVSIDQLLDSMKEIGSNCLNNEFNFFKRIa CDANKEGMFLFRAARKLRQFLKMNSTGDFDLHLLKVSEGTTIITN CTGQVKGRKPAALGEAQPTKSLEENKSLKEQKKLNDLCFLKRLL QEIKTCWNKILMGTKEH |
| 337 | IL-10 | SPGQGTQSENSCTHFPGNLPNMLRDLRDAFSRVKTFFQMKDQLD NLLLKESLLEDFKGYLGCQALSEMIQFYLFFVMPQAENQDPDIKA HVNSLGENLKTLRLRLRRCHRFLPCENKSKAVEQVKNAFNKLQE KGIYKAMSEFDIFINYIEAYMTMKIRN |
| 338 | IL-15 | NWVNVISDLKKIEDLIQSMHIDATLYTESDVHPSCKVTAMKCFLL ELQVISLESGDASIHDTVENLIILANNSLSSNGNVTESGCKECEELE EKNIKEFLQSFVHIVQMFINTS |
| 339 | IL-18 | YFGKLESKLSVIRNLNDQVLFIDQGNRPLFEDMTDSDCRDNAPRTI FIISMYKDSQPRGMAVTISVKCEKISTLSCENKIISFKEMNPPDNIKD TKSDIIFFQRSVPGHDNKMQFESSSYEGYFLACEKERDLFKLILKK EDELGDRSIMFTVQNED |
| 340 | IL-27beta | RKGPPAALTLPRVQCRASRYPIAVDCSWTLPPAPNSTSPVSFIATY RLGMAARGHSWPCLQQTPTSTSCTITDVQLFSMAPYVLNVTAVH PWGSSSSFVPFITEHIIKPDPPEGVRLSPLAERQLQVQWEPPGSWPF PEIFSLKYWIRYKRQGAARFHRVGPIEATSFILRAVRPRARYYVQV AAQDLTDYGELSDWSLPATATMSLGK |
| 341 | IFNgamma | QDPYVKEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFRG |

TABLE 27-continued

| Cytokine sequences. | | |
|---|---|---|
| SEQ ID NO | Cytokine | Sequence |
| 342 | TGFbeta1 | ALDTNYCFSSTEKNCCVRQLYIDFRKDLGWKWIHEPKGYHANFC LGPCPYIWSLDTQYSKVLALYNQHNPGASAAPCCVPQALEPLPIV YYVGRKPKVEQLSNMIVRSCKCS |

In some embodiments, a cytokine encoded by an inventive polynucleotide has a sequence as listed in Table 27.

TABLE 28

| Transcription factor sequences. | | |
|---|---|---|
| SEQ ID NO | Transcription factor | Sequence |
| 343 | FOXP3 | MPNPRPGKPSAPSLALGPSPGASPSWRAAPKASDLLGARGPGGT FQGRDLRGGAHASSSSLNPMPPSQLQLPTLPLVMVAPSGARLGP LPHLQALLQDRPHFMHQLSTVDAHARTPVLQVHPLESPAMISLT PPTTATGVFSLKARPGLPPGINVASLEWVSREPALLCTFPNPSAPR KDSTLSAVPQSSYPLLANGVCKWPGCEKVFEEPEDFLKHCQADH LLDEKGRAQCLLQREMVQSLEQQLVLEKEKLSAMQAHLAGKM ALTKASSVASSDKGSCCIVAAGSQGPVVPAWSGPREAPDSLFAV RRHLWGSHGNSTFPEFLHNMDYFKFHNMRPPFTYATLIRWAILE APEKQRTLNEIYHWFTRMFAFFRNHPATWKNAIRHNLSLHKCFV RVESEKGAVWTVDELEFRKKRSQRPSRCSNPTPGP |
| 344 | FOXP3 | MPNPRPGKPSAPSLALGPSPGASPSWRAAPKASDLLGARGPGGT FQGRDLRGGAHASSSSLNPMPPSQLQLPTLPLVMVAPSGARLGP LPHLQALLQDRPHFMHQLSTVDAHARTPVLQVHPLESPAMISLT PPTTATGVFSLKARPGLPPGINVASLEWVSREPALLCTFPNPSAPR KDSTLSAVPQSSYPLLANGVCKWPGCEKVFEEPEDFLKHCQADH LLDEKGRAQCLLQREMVQSLEQQLVLEKEKLSAMQAHLAGKM ALTKASSVASSDKGSCCIVAAGSQGPVVPAWSGPREAPDSLFAV RRHLWGSHGNSTFPEFLHNMDYFKFHNMRPPFTYATLIRWAILE APEKQRTLNEIYHWFTRMFAFFRNHPATWKNAIRHNLSLHKCFV RVESEKGAVWTVDELEFRKKR |
| 345 | FOXP3 | GGAHASSSSLNPMPPSQLQLPTLPLVMVAPSGARLGPLPHLQAL LQDRPHFMHQLSTVDAHARTPVLQVHPLESPAMISLTPPTTATG VFSLKARPGLPPGINVASLEWVSREPALLCTFPNPSAPRKDSTLS AVPQSSYPLLANGVCKWPGCEKVFEEPEDFLKHCQADHLLDEK GRAQCLLQREMVQSLEQQLVLEKEKLSAMQAHLAGKMALTKA SSVASSDKGSCCIVAAGSQGPVVPAWSGPREAPDSLFAVRRHLW GSHGNSTFPEFLHNMDYFKFHNMRPPFTYATLIRWAILEAPEKQ RTLNEIYHWFTRMFAFFRNHPATWKNAIRHNLSLHKCFVRVESE KGAVWTVDELEFRKKR |
| 346 | STAT5B | MAVWIQAQQLQGEALHQMQALYGQHFPIEVRHYLSQWIESQA WDSVDLDNPQENIKATQLLEGLVQELQKKAEHQVGEDGFLLKI KLGHYATQLQNTYDRCPMELVRCIRHILYNEQRLVREANNGSSP AGSLADAMSQKHLQINQTFEELRLVTQDTENELKKLQQTQEYFTI QYQESLRIQAQFGPLAQLSPQERLSRETALQQKQVSLEAWLQRE AQTLQQYRVELAEKHQKTLQLLRKQQTIILDDELIQWKRRQQLA GNGGPPEGSLDVLQSWCEKLAEIIWQNRQQIRRAEHLCQQLPIPG PVEEMLAEVNATITDIISALVTSTFIIEKQPPQVLKTQTKFAATVR LLVGGKLNVHMNPPQVKATIISEQQAKSLLKNENTRNDYSGEIL NNCCVMEYHQATGTLSAHFRNMSLKRIKRSDRRGAESVTEEKF TILFESQFSVGGNELVFQVKTLSLPVVVIVHGSQDNNATATVLW DNAFAEPGRVPFAVPDKVLWPQLCEALNMKFKAEVQSNRGLTK ENLVFLAQKLFNNSSSHLEDYSGLSVSWSQFNRENLPGRNYTFW QWFDGVMEVLKKHLKPHWNDGAILGFVNKQQAHDLLINKPDG TFLLRFSDSEIGGITIAWKFDSQERMFWNLMPFTTRDFSIRSLADR LGDLNYLIYVFPDRPKDEVYSKYYTPVPCESATAKAVDGYVKPQ IKQVVPEFVNASADAGGGSATYMDQAPSPAVCPQAHYNMYPQ NPDSVLDTDGDFDLEDTMDVARRVEELLGRPMDSQWIPHAQS |
| 347 | HELIOS | METEAIDGYITCDNELSPEREHSNMAIDLTSSTPNGQHASPSHMT STNSVKLEMQSDEECDRKPLSREDEIRGHDEGSSLEEPLIESSEVA DNRKVQELQGEGGIRLPNGKLKCDVCGMVCIGPNVLMVHKRSH TGERPFHCNQCGASFTQKGNLLRHIKLHSGEKPFKCPFCSYACRR RDALTGHLRTHSVGKPHKCNYCGRSYKQRSSLEEHKERCHNYL QNVSMEAAGQVMSHHVPPMEDCKEQEPIMDNNISLVPFERPAVI |

TABLE 28-continued

| Transcription factor sequences. | | |
|---|---|---|
| SEQ ID NO | Transcription factor | Sequence |
| | | EKLTGNMGKRKSSTPQKFVGEKLMRFSYPDIHFDMNLTYEKEA ELMQSHMMDQAINNAITYLGAEALHPLMQHPPSTIAEVAPVISS AYSQVYHPNRIERPISRETADSHENNMDGPISLIRPKSRPQEREAS PSNSCLDSTDSESSHDDHQSYQGHPALNPKRKQSPAYMKEDVK ALDTTKAPKGSLKDIYKVFNGEGEQIRAFKCEHCRVLFLDHVMY TIHMGCHGYRDPLECNICGYRSODRYEFSSHIVRGEHTFH |

In some embodiments, a transcription factor encoded by an inventive polynucleotide has a sequence as listed in Table 28.

TABLE 29

| Additional Accessory Sequences | | |
|---|---|---|
| SEQ ID NO | IRES | Sequence |
| 390 | CK 3' UTR Scr | ccctgcagccgtcaccgtaagtttgaagttaccgcatatcagcctctgcttcccagcgcgtccaatt cctgttcttattgtttcccctccaggcgttacgcgtgacgacgaactgtgtcgcagctaccacattatt ccggagccttcattctcgcggctctgatcgt |
| 391 | CK 3' UTR S2M | ggagaccgcggccacgccgagtaggatcgagggtacagtctcc |
| 392 | CK 3' UTR | gacaccaggatcactcttgctctgacccgccctgtgtagaatagactcatgcttccctaagacctgg atttcttcccaggcactttcacccgcctgccctgctccttcagtggactgcacccagggaggcggtc tctgactgtcctttactttctattctggattgc |
| 393 | CK 5' UTR 1 | AAACCCCCCTAAGCCGCCGCCGCCGCCACC |
| 394 | CK 5' UTR 2 | CCCCCCCAACCCGTCACG |
| 395 | CK 5' UTR 3 | GTCACG |
| 396 | SZ1 3' UTR Scr | tctgcgcactcgtaatcagtactaaccccccctttgtcggacactatgcgataatcgatccgcctttttc accgccttcggaattttatttacctcaactgatcctggagtctctcttggttttcacggaggcctccgcc ca |
| 397 | SZ1 S2M | ggagaccgcggccacgccgagtaggatcgagggtacagtctcc |
| 398 | SZ1 3' UTR | ccccttgaaaccccccgccccaggttcagtctctcttcatccctctgtcctgcatggtgatacaaagac cctttgtggaccctaagccatgtagttgctgctccctccttccagttgtgaatattggtttctgttaatca ca |
| 399 | SZ1 5' UTR 1 | AAACCCCCCTAAGCCGCCGCCGCCGCCACC |
| 400 | SZ1 5' UTR 2 | CCCCCCCAACCCGTCACG |
| 401 | SZ1 5' UTR 3 | GTCACG |
| 402 | UTR1 | gTcacG |
| 403 | UTR2 | AATAAGAGAGAAAAGAAGAGTAAGAAGAAATATAAGAGC CACC |
| 404 | UTR3 | cgaactagtattcttctggtccccacagactcagagagaacccgccacc |
| 405 | UTR4 | Agccacc |
| 406 | STOP1 | tgatAGctAaCtaG |
| 407 | STOP2 | tagtAGctAaCtaG |
| 408 | STOP3 | tGatGActGaGtGA |
| 409 | STOP4 | tagtagctagGtag |
| 410 | STOP5 | taa |

TABLE 29-continued

| Additional Accessory Sequences | | |
|---|---|---|
| SEQ ID NO | IRES | Sequence |
| 411 | STOP6 | taatagCtaaCtag |
| 412 | STOP7 | taaCtagCtaaCtag |

In some embodiments, a circular RNA or a precursor RNA (e.g., linear precursor RNA) disclosed herein comprises a sequence as listed in Table 29.

In some embodiments, a polynucleotide or a protein encoded by a polynucleotide contains a sequence with at least about 70%, 75%, 80%, 85%, 90%, 91%, 92%, 93%, 94%, 95%, 96%, 97%, 98%, 99%, or 99.5% similarity to one or more sequences disclosed herein. In some embodiments, a polynucleotide or a protein encoded by a polynucleotide contains a sequence that is identical to one or more sequences disclosed herein.

Preferred embodiments are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Wesselhoeft et al. (2019) RNA Circularization Diminishes Immunogenicity and Can Extend Translation Duration In Vivo. Molecular Cell. 74(3), 508-520 and Wesselhoeft et al. (2018) Engineering circular RNA for Potent and Stable Translation in Eukaryotic Cells. Nature Communications. 9, 2629 are incorporated by reference in their entirety.

The invention is further described in detail by reference to the following examples but are not intended to be limited to the following examples. These examples encompass any and all variations of the illustrations with the intention of providing those of ordinary skill in the art with complete disclosure and description of how to make and use the subject invention and are not intended to limit the scope of what is regarded as the invention.

Example 1

Example 1A: External Homology Regions Allow for Circularization of Long Precursor RNA Using the Permuted Intron Exon (PIE) Circularization Strategy A 1,100 nt sequence containing a full-length encephalomyocarditis virus (EMCV) IRES, a *Gaussia* luciferase (GLuc) expression sequence, and two short exon fragments of the permuted intron-exon (PIE) construct were inserted between the 3' and 5' introns of the permuted group I catalytic intron in the thymidylate synthase (Td) gene of the T4 phage. Precursor RNA was synthesized by run-off transcription. Circularization was attempted by heating the precursor RNA in the presence of magnesium ions and GTP, but splicing products were not obtained.

Perfectly complementary 9 nucleotide and 19 nucleotide long homology regions were designed and added at the 5' and 3' ends of the precursor RNA. Addition of these homology arms increased splicing efficiency from 0 to 16% for 9 nucleotide homology regions and to 48% for 19 nucleotide homology regions as assessed by disappearance of the precursor RNA band.

The splicing product was treated with RNase R. Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor. This shows that circular RNA is a major product of the splicing reactions of precursor RNA containing the 9 or 19 nucleotide long external homology regions.

Example 1B: Spacers that Conserve Secondary Structures of IRES and PIE Splice Sites Increase Circularization Efficiency A series of spacers was designed and inserted between the 3' PIE splice site and the IRES. These spacers were designed to either conserve or disrupt secondary structures within intron sequences in the IRES, 3' PIE splice site, and/or 5' splice site. The addition of spacer sequences designed to conserve secondary structures resulted in 87% splicing efficiency, while the addition of a disruptive spacer sequences resulted in no detectable splicing.

Example 2

Example 2A: Internal Homology Regions in Addition to External Homology Regions Creates a Splicing Bubble and Allows for Translation of Several Expression Sequences Spacers were designed to be unstructured, non-homologous to the intron and IRES sequences, and to contain spacer-spacer homology regions. These were inserted between the 5' exon and IRES and between the 3' exon and expression sequence in constructs containing external homology regions, EMCV IRES, and expression sequences for *Gaussia* luciferase (total length: 1289 nt), Firefly luciferase (2384 nt), eGFP (1451 nt), human erythropoietin (1313 nt), and Cas9 endonuclease (4934 nt). Circularization of all 5 constructs was achieved. Circularization of constructs utilizing T4 phage and *Anabaena* introns were roughly equal. Circularization efficiency was higher for shorter sequences. To measure translation, each construct was transfected into HEK293 cells. *Gaussia* and Firefly luciferase transfected cells produced a robust response as measured by luminescence, human erythropoietin was detectable in the media of cells transfected with erythropoietin circRNA, and EGFP fluorescence was observed from cells transfected with EGFP circRNA. Co-transfection of Cas9 circRNA with sgRNA directed against GFP into cells constitutively expressing GFP resulted in ablated fluorescence in up to 97% of cells in comparison to an sgRNA-only control.

Example 2B: Use of CVB3 IRES Increases Protein Production

Constructs with internal and external homology regions and differing IRES containing either *Gaussia* luciferase or Firefly luciferase expression sequences were made. Protein production was measured by luminescence in the supernatant of HEK293 cells 24 hours after transfection. The Coxsackievirus B3 (CVB3) IRES construct produced the most protein in both cases.

Example 2C: Use of polyA or polyAC Spacers Increases Protein Production

Thirty nucleotide long polyA or polyAC spacers were added between the IRES and splice junction in a construct with each IRES that produced protein in example 2B. *Gaussia* luciferase activity was measured by luminescence in the supernatant of HEK293 cells 24 hours after transfection. Both spacers improved expression in every construct over control constructs without spacers.

Example 3

HEK293 or HeLa Cells Transfected with Circular RNA Produce More Protein than Those Transfected with Comparable Unmodified or Modified Linear RNA HPLC-purified *Gaussia* luciferase-coding circRNA (CVB3-GLuc-pAC) was compared with a canonical unmodified 5' methylguanosine-capped and 3' polyA-tailed linear GLuc mRNA, and a commercially available nucleoside-modified (pseudouridine, 5-methylcytosine) linear GLuc mRNA (from Trilink). Luminescence was measured 24 h post-transfection, revealing that circRNA produced 811.2% more protein than the unmodified linear mRNA in HEK293 cells and 54.5% more protein than the modified mRNA Similar results were obtained in HeLa cells and a comparison of optimized circRNA coding for human erythropoietin with linear mRNA modified with 5-methoxyuridine.

Luminescence data was collected over 6 days. In HEK293 cells, circRNA transfection resulted in a protein production half-life of 80 hours, in comparison with the 43 hours of unmodified linear mRNA and 45 hours of modified linear mRNA. In HeLa cells, circRNA transfection resulted in a protein production half-life of 116 hours, in comparison with the 44 hours of unmodified linear mRNA and 49 hours of modified linear mRNA. CircRNA produced substantially more protein than both the unmodified and modified linear mRNAs over its lifetime in both cell types.

Example 4

Example 4A: Purification of circRNA by RNase Digestion, HPLC Purification, and Phosphatase Treatment Decreases Immunogenicity. Completely Purified Circular RNA is Significantly Less Immunogenic than Unpurified or Partially Purified Circular RNA. Protein Expression Stability and Cell Viability are Dependent on Cell Type and Circular RNA Purity Human embryonic kidney 293 (HEK293) and human lung carcinoma A549 cells were transfected with:

products of an unpurified GLuc circular RNA splicing reaction, products of RNase R digestion of the splicing reaction, products of RNase R digestion and HPLC purification of the splicing reaction, or products of RNase digestion, HPLC purification, and phosphatase treatment of the splicing reaction.

RNase R digestion of splicing reactions was insufficient to prevent cytokine release in A549 cells in comparison to untransfected controls.

The addition of HPLC purification was also insufficient to prevent cytokine release, although there was a significant reduction in interleukin-6 (IL-6) and a significant increase in interferon-al (IFN-$\alpha$1) compared to the unpurified splicing reaction.

The addition of a phosphatase treatment after HPLC purification and before RNase R digestion dramatically reduced the expression of all upregulated cytokines assessed in A549 cells. Secreted monocyte chemoattractant protein 1 (MCP1), IL-6, IFN-$\alpha$1, tumor necrosis factor $\alpha$ (TNF$\alpha$), and IFN$\gamma$ inducible protein-10 (IP-10) fell to undetectable or un-transfected baseline levels.

There was no substantial cytokine release in HEK293 cells. A549 cells had increased GLuc expression stability and cell viability when transfected with higher purity circular RNA. Completely purified circular RNA had a stability phenotype similar to that of transfected 293 cells.

Example 4B: Circular RNA does not Cause Significant Immunogenicity and is not a RIG-I Ligand A549 cells were transfected with the products of a splicing reaction:

A549 cells were transfected with:

unpurified circular RNA, high molecular weight (linear and circular concatenations) RNA, circular (nicked) RNA, an early fraction of purified circular RNA (more overlap with nicked RNA peak), a late fraction of purified circular RNA (less overlap with nicked RNA peak), introns excised during circularization, or vehicle (i.e. untransfected control).

Precursor RNA was separately synthesized and purified in the form of the splice site deletion mutant (DS) due to difficulties in obtaining suitably pure linear precursor RNA from the splicing reaction. Cytokine release and cell viability was measured in each case.

Robust IL-6, RANTES, and IP-10 release was observed in response to most of the species present within the splicing reaction, as well as precursor RNA. Early circRNA fractions elicited cytokine responses comparable to other non-circRNA fractions, indicating that even relatively small quantities of linear RNA contaminants are able to induce a substantial cellular immune response in A549 cells. Late circRNA fractions elicited no cytokine response in excess of that from untransfected controls. A549 cell viability 36 hours post-transfection was significantly greater for late circRNA fractions compared with all of the other fractions.

RIG-I and IFN-β1 transcript induction upon transfection of A549 cells with late circRNA HPLC fractions, precursor RNA or unpurified splicing reactions were analyzed. Induction of both RIG-I and IFN-β1 transcripts were weaker for late circRNA fractions than precursor RNA and unpurified splicing reactions. RNase R treatment of splicing reactions alone was not sufficient to ablate this effect. Addition of very small quantities of the RIG-I ligand 3p-hpRNA to circular RNA induced substantial RIG-I transcription. In HeLa cells, transfection of RNase R-digested splicing reactions induced RIG-I and IFN-β1, but purified circRNA did not. Overall, HeLa cells were less sensitive to contaminating RNA species than A549 cells.

A time course experiment monitoring RIG-I, IFN-β1, IL-6, and RANTES transcript induction within the first 8 hours after transfection of A549 cells with splicing reactions or fully purified circRNA did not reveal a transient response to circRNA. Purified circRNA similarly failed to induce pro-inflammatory transcripts in RAW264.7 murine macrophages.

A549 cells were transfected with purified circRNA containing an EMCV IRES and EGFP expression sequence. This failed to produce substantial induction of pro-inflammatory transcripts. These data demonstrate that non-circular components of the splicing reaction are responsible for the immunogenicity observed in previous studies and that circRNA is not a natural ligand for RIG-I.

Example 5

Circular RNA Avoids Detection by TLRs

TLR 3, 7, and 8 reporter cell lines were transfected with multiple linear or circular RNA constructs and secreted embryonic alkaline phosphatase (SEAP) was measured.

Linearized RNA was constructed by deleting the intron and homology arm sequences. The linear RNA constructs were then treated with phosphatase (in the case of capped RNAs, after capping) and purified by HPLC.

None of the attempted transfections produced a response in TLR7 reporter cells. TLR3 and TLR8 reporter cells were activated by capped linearized RNA, polyadenylated linearized RNA, the nicked circRNA HPLC fraction, and the early circRNA fraction. The late circRNA fraction and m1ψ-mRNA did not provoke TLR-mediated response in any cell line.

In a second experiment, circRNA was linearized using two methods: treatment of circRNA with heat in the presence of magnesium ions and DNA oligonucleotide-guided RNase H digestion. Both methods yielded a majority of full-length linear RNA with small amounts of intact circRNA. TLR3, 7, and 8 reporter cells were transfected with circular RNA, circular RNA degraded by heat, or circular RNA degraded by RNase H, and SEAP secretion was measured 36 hours after transfection. TLR8 reporter cells secreted SEAP in response to both forms of degraded circular RNA, but did not produce a greater response to circular RNA transfection than mock transfection. No activation was observed in TLR3 and TLR7 reporter cells for degraded or intact conditions, despite the activation of TLR3 by in vitro transcribed linearized RNA.

Example 6

Unmodified Circular RNA Produces Increased Sustained In Vivo Protein Expression than Linear RNA Mice were injected and HEK293 cells were transfected with unmodified and m1ψ-modified human erythropoietin (hEpo) linear mRNAs and circRNAs. Equimolar transfection of m1ψ-mRNA and unmodified circRNA resulted in robust protein expression in HEK293 cells. hEpo linear mRNA and circRNA displayed similar relative protein expression patterns and cell viabilities in comparison to GLuc linear mRNA and circRNA upon equal weight transfection of HEK293 and A549 cells.

In mice, hEpo was detected in serum after the injection of hEpo circRNA or linear mRNA into visceral adipose. hEpo detected after the injection of unmodified circRNA decayed more slowly than that from unmodified or m1ψ-mRNA and was still present 42 hours post-injection. Serum hEpo rapidly declined upon the injection of unpurified circRNA splicing reactions or unmodified linear mRNA. Injection of unpurified splicing reactions produced a cytokine response detectable in serum that was not observed for the other RNAs, including purified circRNA.

Example 7

Circular RNA can be Effectively Delivered In Vivo or In Vitro Via Lipid Nanoparticles Purified circular RNA was formulated into lipid nanoparticles (LNPs) with the ionizable lipidoid cKK-E12 (Dong et al., 2014; Kauffman et al., 2015). The particles formed uniform multilamellar structures with an average size, polydispersity index, and encapsulation efficiency similar to that of particles containing commercially available control linear mRNA modified with 5moU.

Purified hEpo circRNA displayed greater expression than 5moU-mRNA when encapsulated in LNPs and added to HEK293 cells. Expression stability from LNP-RNA in HEK293 cells was similar to that of RNA delivered by transfection reagent, with the exception of a slight delay in decay for both 5moU-mRNA and circRNA. Both unmodified circRNA and 5moU-mRNA failed to activate RIG-I/IFN-β1 in vitro.

In mice, LNP-RNA was delivered by local injection into visceral adipose tissue or intravenous delivery to the liver. Serum hEpo expression from circRNA was lower but comparable with that from 5moU-mRNA 6 hours after delivery in both cases. Serum hEpo detected after adipose injection of unmodified LNP-circRNA decayed more slowly than that from LNP-5moU-mRNA, with a delay in expression decay present in serum that was similar to that noted in vitro, but serum hEpo after intravenous injection of LNP-circRNA or LNP-5moU-mRNA decayed at approximately the same rate. There was no increase in serum cytokines or local RIG-I, TNFα, or IL-6 transcript induction in any of these cases.

Example 8

Figure 1B:
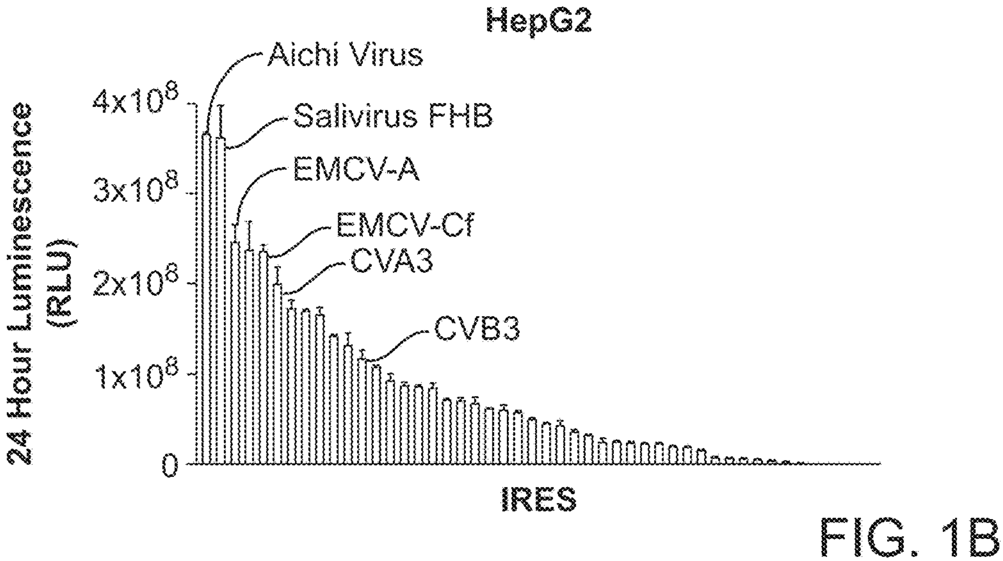
Figure 1C:
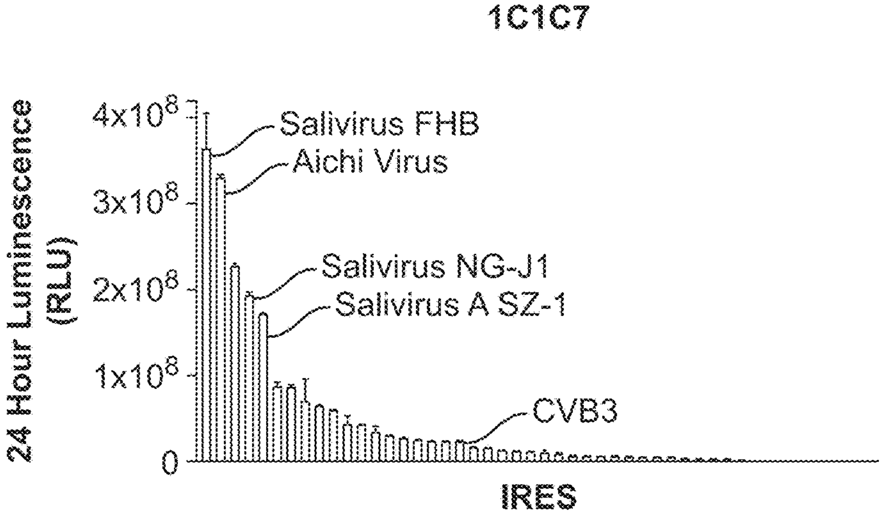

Example 8A: Expression and Functional Stability by IRES in HEK293, HepG2, and 1C1C7 Cells Constructs including *Anabaena* intron/exon regions, a *Gaussia* luciferase expression sequence, and varying IRES were circularized. 100 ng of each circularization reaction was separately transfected into 20,000 HEK293 cells, HepG2 cells, and 1C1C7 cells using Lipofectamine MessengerMax. Luminescence in each supernatant was assessed after 24 hours as a measure of protein expression. In HEK293 cells, constructs including Crohivirus B, Salivirus FHB, Aichi Virus, Salivirus HG-J1, and Enterovirus J IRES produced the most luminescence at 24 hours (FIG. 1A). In HepG2 cells, constructs including Aichi Virus, Salivirus FHB, EMCV-Cf, and CVA3 IRES produced high luminescence at 24 hours (FIG. 1B). In 1C1C7 cells, constructs including Salivirus FHB, Aichi Virus, Salivirus NG-J1, and Salivirus A SZ-1 IRES produced high luminescence at 24 hours (FIG. 1C).

Figure 2A:
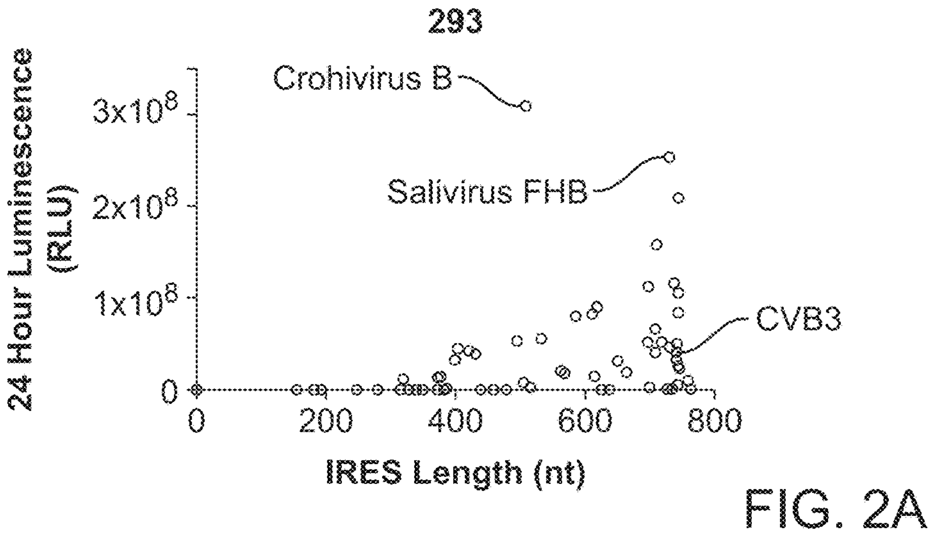
FIG. 2 depicts luminescence in supernatants of HEK293 (FIG. 2A), HepG2 (FIG. 2B), or 1C1C7 (FIG. 2C) cells 24 hours after transfection with circular RNA comprising a *Gaussia* luciferase expression sequence and various IRES sequences having different lengths.
Figure 2B:
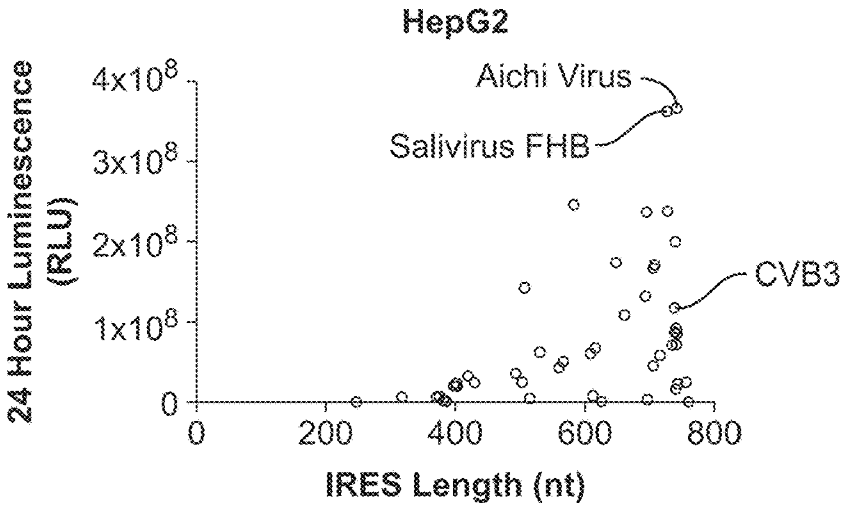
Figure 2C:
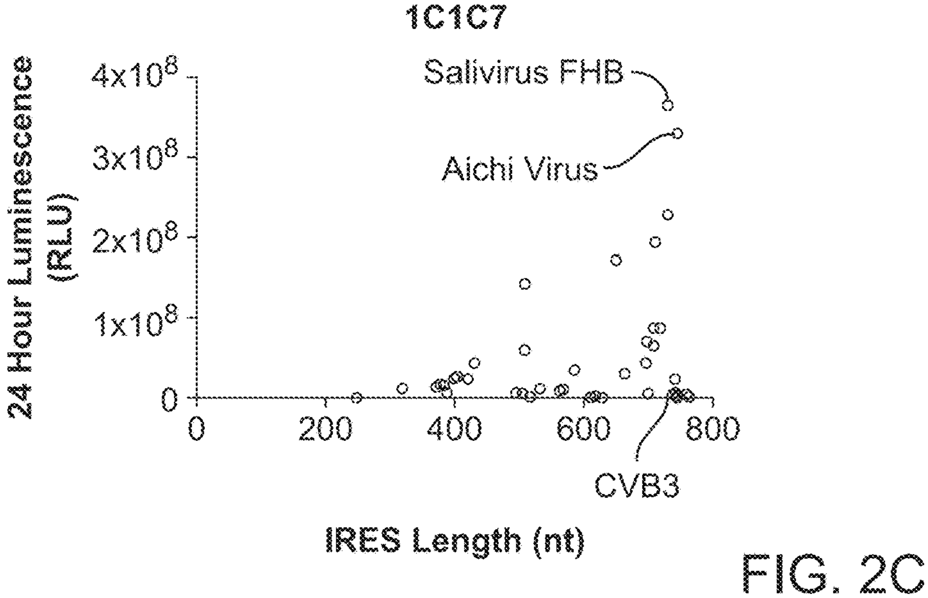

A trend of larger IRES producing greater luminescence at 24 hours was observed. Shorter total sequence length tends to increase circularization efficiency, so selecting a high expression and relatively short IRES may result in an improved construct. In HEK293 cells, a construct using the Crohivirus B IRES produced the highest luminescence, especially in comparison to other IRES of similar length (FIG. 2A). Expression from IRES constructs in HepG2 and 1C1C7 cells plotted against IRES size are in FIGS. 2B and 2C.

Figure 3A:
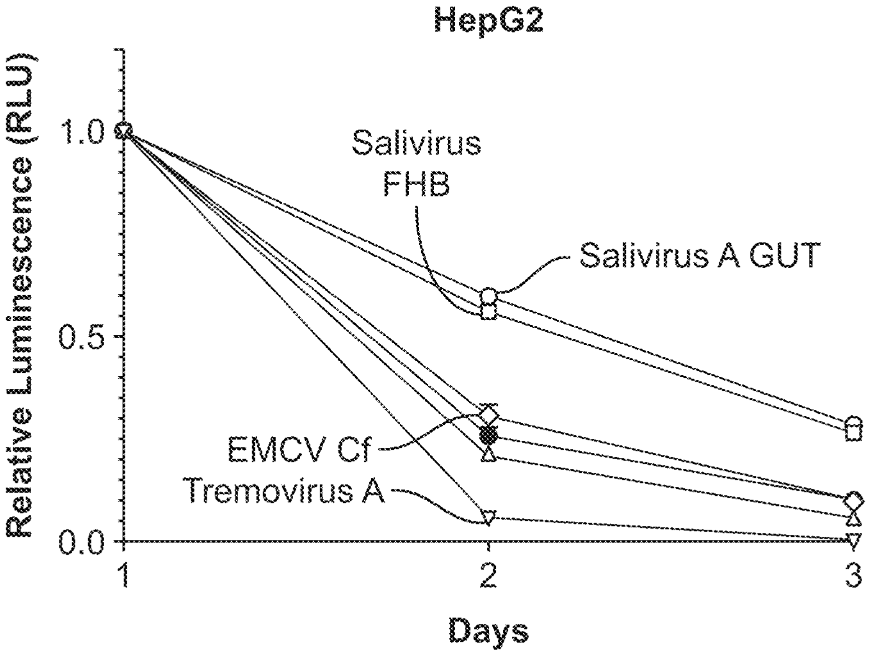
FIG. 3 depicts stability of select IRES constructs in HepG2 (FIG. 3A) or 1C1C7 (FIG. 3B) cells over 3 days as measured by luminescence.
Figure 3B:
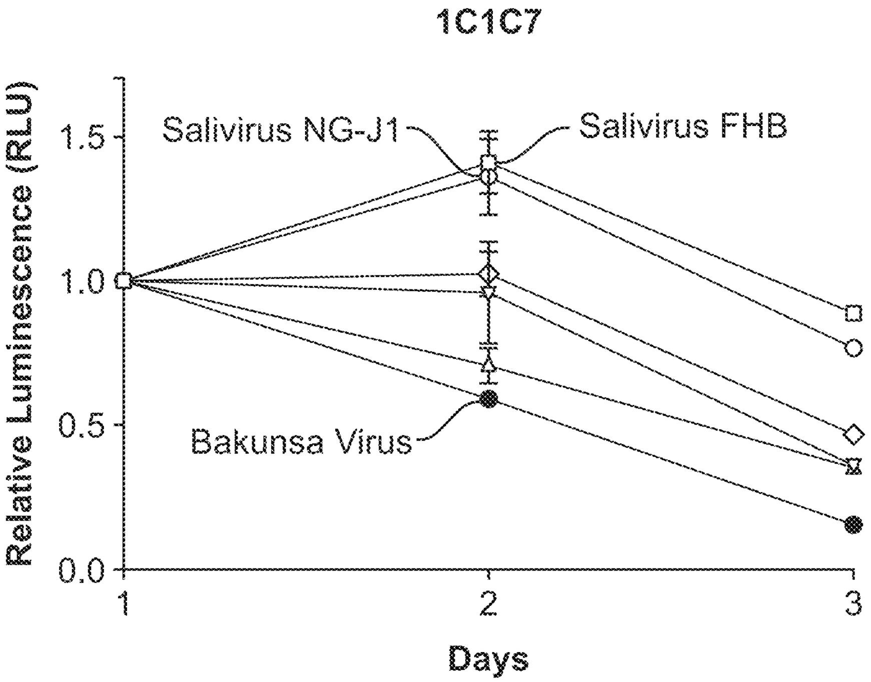

Functional stability of select IRES constructs in HepG2 and 1C1C7 cells were measured over 3 days. Luminescence from secreted *Gaussia* luciferase in supernatant was measured every 24 hours after transfection of 20,000 cells with 100 ng of each circularization reaction, followed by complete media replacement. Salivirus A GUT and Salivirus FHB exhibited the highest functional stability in HepG2 cells, and Salivirus N-J1 and Salivirus FHB produced the most stable expression in 1C1C7 cells (FIGS. 3A and 3B).

Example 8B: Screening of Additional IRES

Figure 1D:
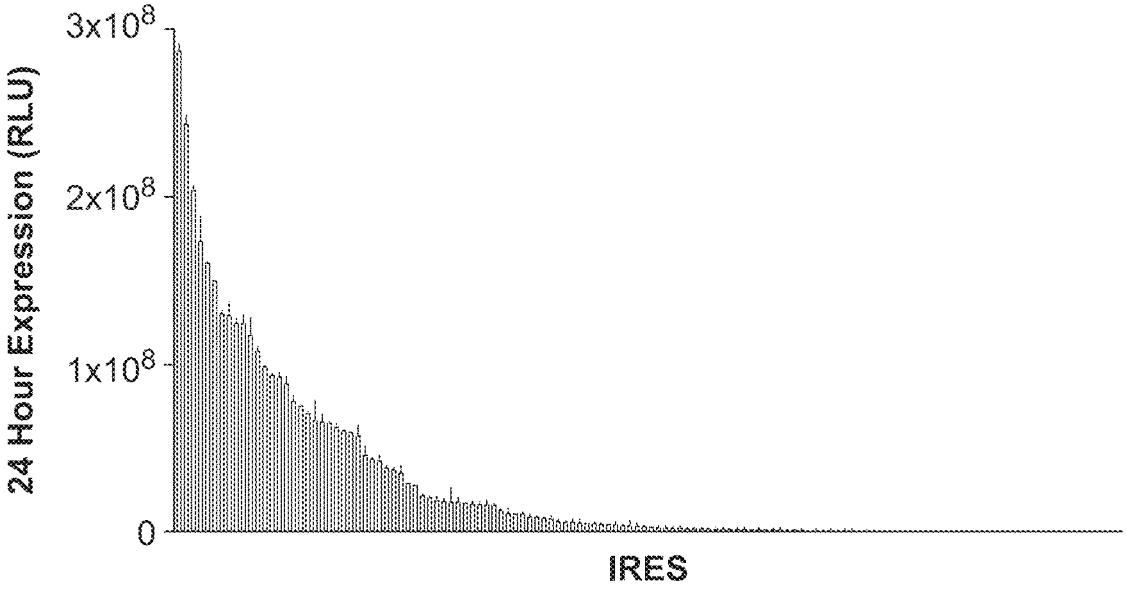
Figure 1E:
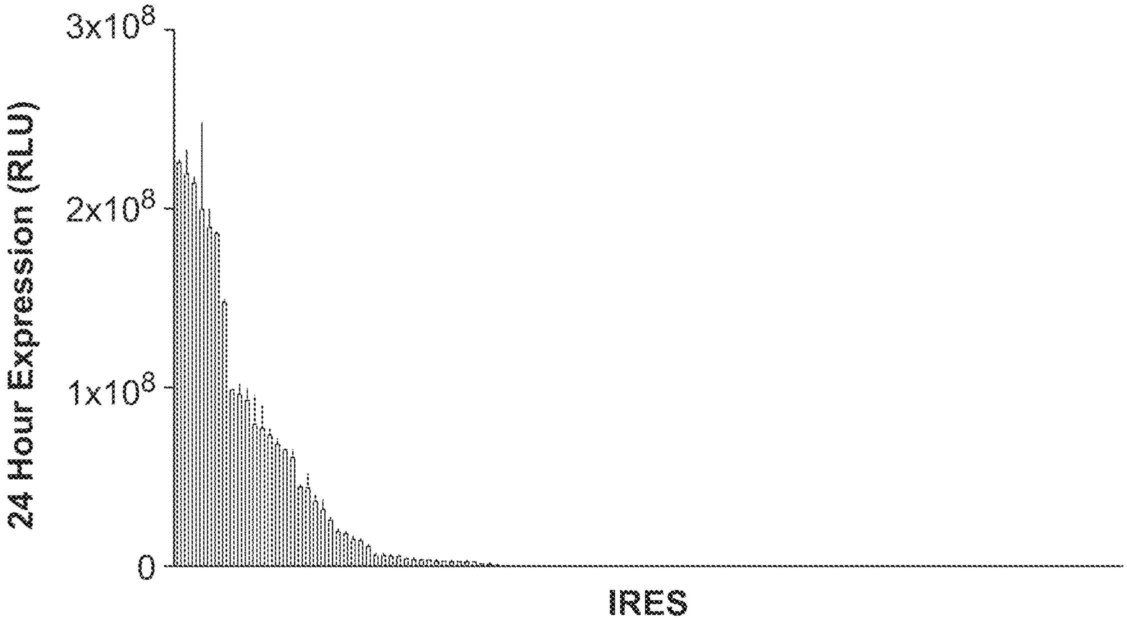

Functional stability of additional IRES constructs in HEK293 cells were measured. Briefly, 5' untranslated regions (UTRs) of interest were identified from GenBank. Selected UTRs UTRs were truncated to 675 nt from the 5' end and inserted into a circular RNA backbone construct encoding *Gaussia* Luciferase (Gluc) and in front of the Gluc coding region. The circular RNAs were transfected into HEK293 cells. After 24 hours, the supernatants were collected and the luminescence from secreted Gluc protein was measured using commercially available reagents. The results are depicted in FIGS. 1D and 1E and Table 30, suggesting that many natural IRES sequences enhance the protein expression in a circular RNA context.

TABLE 30

| SEQ ID NO | IRES | Expression |
|---|---|---|
| 413 | RhPV | 1.10E+05 |
| 414 | Halastavi arva (1x mut) | 9.46E+04 |
| 415 | Oscivirus | 4.55E+07 |
| 416 | Cadicivirus B | 2.10E+05 |
| 417 | PSIV (2x mut for Xba1) | 9.70E+04 |
| 418 | PSIV IGR | 1.01E+05 |
| 419 | PV Mahoney | 1.09E+05 |
| 420 | REV A | 9.44E+04 |
| 421 | Tropivirus A | 9.52E+04 |
| 422 | Symapivirus A | 1.27E+05 |
| 423 | Sakobuvirus A FFUP1 (1x mut) | 8.82E+06 |
| 424 | Rosavirus C NFSM6F | 6.84E+05 |
| 425 | Rosavirus 2 GA7403 | 5.05E+06 |

TABLE 30-continued

| SEQ ID NO | IRES | Expression |
|---|---|---|
| 426 | Rhimavirus A | 8.42E+05 |
| 427 | Rafivirus LPXYC222841 | 2.22E+05 |
| 428 | Rafivirus WHWGGF74766 | 4.53E+06 |
| 429 | Poecivirus BCCH-449 | 3.43E+05 |
| 430 | Megirivirus A LY | 1.80E+06 |
| 431 | Megirivirus E | 1.10E+07 |
| 432 | Megirivirus C | 1.24E+05 |
| 433 | Ludopivirus | 1.05E+05 |
| 434 | Livupivirus | 2.10E+05 |
| 435 | Aichivirus A FSS693 | 6.25E+07 |
| 436 | Aichivirus KVGH | 1.72E+07 |
| 437 | Aichivirus DV | 7.79E+07 |
| 438 | Murine Kobuvirus 1 | 1.60E+07 |
| 439 | Porcine Kobuvirus K-30 | N/A |
| 440 | Porcine Kobuvirus XX | 1.32E+07 |
| 441 | Caprine Kobuvirus 12Q108 | 2.87E+08 |
| 442 | Rabbit Kobuvirus | 3.73E+07 |
| 443 | Aalivirus | 2.65E+05 |
| 444 | Grusopivirus A | 1.09E+05 |
| 445 | Grusopivirus B | 2.12E+05 |
| 446 | Yanchengosbecks grenadier anchovy picornavirus | 1.57E+06 |
| 447 | Turkey Gallivirus M176 | 4.37E+05 |
| 448 | Falcovirus A1 | 1.48E+05 |
| 449 | Tremovirus B | 1.31E+05 |
| 450 | Didelphis aurita HAV | 1.38E+05 |
| 451 | Hepatovirus G1 | 1.41E+05 |
| 452 | Hepatovirus D | 1.47E+06 |
| 453 | Hepatovirus H2 | 1.08E+05 |
| 454 | Hepatovirus I | 8.79E+05 |
| 455 | Hepatovirus C | 5.08E+05 |
| 456 | Fipivirus A | 2.69E+05 |
| 457 | Fipivirus C | 1.09E+05 |
| 458 | Fipivirus E | 1.10E+05 |
| 459 | Aquamavirus | 4.51E+06 |
| 460 | Avisivirus A | 1.91E+05 |
| 461 | Avisivirus B | 8.68E+04 |
| 462 | Crohivirus A | 9.96E+04 |
| 463 | Kunsagivirus B | 8.01E+04 |
| 464 | Limnipivirus A | 8.30E+04 |
| 465 | Limnipivirus C | 1.35E+05 |
| 466 | Orivirus | 6.09E+05 |
| 467 | HAV FH1 | 1.24E+05 |
| 468 | HAV HM175 | 4.96E+05 |
| 469 | Parechovirus F | 6.56E+05 |
| 470 | Parechovirus D | 3.10E+05 |
| 471 | Parechovirus C | 1.24E+06 |
| 472 | Ljungan Virus 87-012 | 2.00E+06 |
| 473 | Parechovirus A2 | 1.80E+07 |
| 474 | Parechovirus A3 | 3.58E+06 |
| 475 | Parechovirus A8 | 1.61E+07 |
| 476 | Parechovirus A17 | 1.20E+06 |
| 477 | Potamipivirus A | 8.43E+05 |
| 478 | Potamipivirus B | 7.20E+05 |
| 479 | Beihai Conger Picornavirus | 1.15E+06 |
| 480 | Porcine Sapelovirus JD2011 | N/A |
| 481 | Porcine Sapelovirus A2 | 4.34E+06 |
| 482 | Simian Sapelovirus 1 | 6.55E+07 |
| 483 | Simian Sapelovirus 2 | 4.24E+07 |
| 484 | Rabovirus C | 2.49E+06 |
| 485 | Rabovirus A NYC-B10 | 1.24E+06 |
| 486 | Parabovirus C | 1.83E+07 |
| 487 | Parabovirus B | 7.85E+06 |
| 488 | Parabovirus A3 | 2.44E+08 |
| 489 | Felipivirus 127F | 8.92E+06 |
| 490 | Boosepivirus A | 7.07E+07 |
| 491 | Boosepivirus B | 1.17E+08 |
| 492 | Phacovirus Pf-CHK1 | 5.87E+06 |
| 493 | HRVC3 QPM | 1.64E+07 |

TABLE 30-continued

| SEQ ID NO | IRES | Expression |
|---|---|---|
| 494 | HRVB27 | 2.04E+08 |
| 495 | HRVA73 | 1.08E+08 |
| 496 | EV L | 6.49E+07 |
| 497 | EV K | 7.52E+07 |
| 498 | EV J 1631 | 9.88E+07 |
| 499 | EVJ N125 | 2.90E+07 |
| 500 | EV I | 1.31E+08 |
| 501 | EV F1 BEV 261 | 1.12E+07 |
| 502 | EV D94 | 9.25E+07 |
| 503 | PV3 | 1.25E+08 |
| 504 | EV C102 | 8.85E+07 |
| 505 | EV 30 | 5.48E+06 |
| 506 | SAS | 1.61E+08 |
| 507 | EV A114 | 1.50E+08 |
| 508 | Mobovirus A | 3.44E+06 |
| 509 | Burpengary Virus | 1.09E+07 |
| 510 | Hunnivirus A1 | 1.61E+06 |
| 511 | Hunnivirus A2 | 6.38E+06 |
| 512 | Ia Io | 1.35E+06 |
| 513 | Taura Syndrome Virus | 8.30E+05 |
| 514 | ABPV | 6.48E+05 |
| 515 | BRAV-2 | 3.98E+06 |
| 516 | BRBV-1 | 3.34E+06 |
| 517 | ERAV-1 U188 | N/A |
| 518 | GFTV | 1.23E+06 |
| 519 | SAFV V13C | 9.32E+07 |
| 520 | SAV P-113 | 4.37E+07 |
| 521 | VHEV | 1.74E+08 |
| 522 | TRV NGS910 | 3.84E+07 |
| 523 | EMCV2 RD1338 | 1.97E+06 |
| 524 | EMCV1 JZ1203 | N/A |
| 525 | EMCV1 AnrB-3741 | 2.55E+06 |
| 526 | Cosavirus D1 | 2.11E+06 |
| 527 | Cosavirus B1 | 1.91E+06 |
| 528 | Cosavirus A SH1 | 2.16E+06 |
| 529 | Malagasivirus B | 5.05E+06 |
| 530 | Mosavirus A2 SZAL6 | 8.27E+06 |
| 531 | SVV | 1.06E+06 |
| 532 | PTV A | 7.29E+05 |
| 533 | PTV B | 6.02E+06 |
| 534 | Tottorivirus | 2.76E+07 |
| 535 | Posavirus 1 | 1.55E+06 |
| 536 | A105-675 | 2.18E+07 |
| 537 | A110-675 | 1.24E+08 |
| 538 | 18-675 | 6.04E+07 |
| 539 | A115-675 | 5.93E+07 |
| 540 | A73-675 | 1.30E+08 |
| 541 | Kobuvirus 16317 | 2.03E+07 |
| 542 | Aichivirus Chshc7 | 1.87E+07 |
| 543 | Aichivirus Goiania | 1.66E+07 |
| 544 | Aichivirus ETHP4 | 1.78E+07 |
| 545 | Aichivirus DVI2169 | 2.98E+06 |
| 546 | Aichivirus DVI2321 | 6.63E+07 |
| 547 | Aichivirus rat08 | 3.51E+07 |
| 548 | Aichivirus Rt386 | 5.71E+07 |
| 549 | Norway Rat Pestivirus | N/A |
| 550 | Porcine Kobuvirus GS2 | 44200000 |
| 551 | Kobuvirus SZAL6 | 98850000 |
| 552 | Kobuvirus sheep TB3 | N/A |
| 553 | Pronghorn antelope pestivirus | 1.35E+06 |
| 554 | Porcine pestivirus isolate Bungowannah | 1.10E+07 |
| 555 | Porcine pestivirus 1 | 9.46E+04 |
| 556 | Pestivirus giraffe-1 | 4.72E+05 |
| 557 | Classical swine fever virus | 3.16E+05 |
| 558 | Human pegivirus isolate JD2B1I | 6.85E+05 |
| 559 | Human pegivirus isolate GBV-C-ZJ | N/A |
| 560 | Human pegivirus isolate JD2B8C | 5.36E+05 |
| 561 | Hepatitis GB virus A | N/A |
| 562 | Simian pegivirus | 8.56E+04 |
| 563 | Pegivirus I | 8.02E+04 |
| 564 | Pegivirus K | 8.07E+04 |
| 565 | Theiler's disease-associated virus | 7.84E+04 |
| 566 | Rodent pegivirus | 1.79E+05 |
| 567 | Human pegivirus 2 | 3.14E+05 |
| 568 | GB virus C/Hepatitis G virus | 1.36E+05 |
| 569 | Equine Pegivirus 1 | 8.80E+04 |
| 570 | Culex theileri flavivirus | 8.52E+04 |
| 571 | Bussuquara virus | 8.20E+04 |
| 572 | Zika Virus | 8.61E+04 |
| 573 | Yokose virus | 8.55E+04 |
| 574 | Wesselsbron virus | N/A |
| 575 | Equine hepacivirus | 8.40E+04 |
| 576 | Hepacivirus B | 8.84E+04 |
| 577 | Hepacivirus I | 7.50E+04 |
| 578 | Hepacivirus J | 7.65E+04 |
| 579 | Hepacivirus K | 8.91E+04 |
| 580 | Icavirus | 4.41E+06 |
| 581 | Antarctic penguin virus A | 8.42E+04 |
| 582 | Forest pouched giant rat arterivirus | N/A |
| 583 | Avisivirus Pf-CHK1 | 1.19E+05 |
| 584 | Avian paramyxovirus penguin | 9.91E+04 |
| 585 | Newcastle disease virus | 8.86E+04 |
| 586 | Bat Hp-betacoronavilus | 8.47E+04 |
| 587 | Basella alba endornavirus | 7.65E+04 |
| 588 | Ball python nidovirus | 8.25E+04 |
| 589 | Bat sapelovirus | 8.05E+04 |
| 590 | Bat Picornavirus 3 | N/A |
| 591 | Bat Picornavirus 2 | 7.99E+07 |
| 592 | Bat Picornavirus 1 | 1.85E+07 |
| 593 | Bat Iflavirus | 9.76E+04 |
| 594 | Bat dicibavirus | 7.43E+04 |
| 595 | Betacoronavirus HKU24 | 8.96E+04 |
| 596 | Betacoronavirus England 1 | 8.74E+04 |
| 597 | Boone cardiovirus 1 | 2.62E+06 |
| 598 | Breda virus | 1.16E+05 |
| 599 | Bovine viral diarrhea virus 3 | 2.70E+06 |
| 600 | Bovine rhinitis A virus | 3.62E+06 |
| 601 | Bovine picornavirus isolate TCH6 | 1.21E+05 |
| 602 | Bovine nidovirus TCH5 | 1.17E+05 |
| 603 | Bovine hepacivirus | 1.89E+05 |
| 604 | Botrytis cinerea mitovirus 4 RdRp | 9.68E+04 |
| 605 | Botrytis cinerea mitovirus 2 RdRp | 8.73E+04 |
| 606 | Canine picodicistrovirus strain 209 | 2.79E+06 |
| 607 | Canine distemper virus | 3.02E+05 |
| 608 | Canine kobuvirus | 1.48E+08 |
| 609 | Camel alphacoronavirus | 2.48E+05 |
| 610 | Cripavirus | 1.95E+05 |
| 611 | Human coxsackievirus A2 | 7.75E+07 |
| 612 | Coronavirus AcCoV-JC34 | 1.82E+05 |
| 613 | Chicken picornavirus 3 | 9.13E+04 |
| 614 | Chicken picornavirus 1 | 1.21E+05 |
| 615 | Chicken orivirus 1 | 3.16E+05 |
| 616 | Chicken gallivirus 1 | 1.51E+07 |
| 617 | Chicken calicivirus | 1.28E+05 |
| 618 | Carp picornavirus 1 | 1.13E+05 |
| 619 | Falcon picornavirus | 3.08E+06 |
| 620 | Equine rhinitis B virus 1 | 1.01E+05 |

TABLE 30-continued

| SEQ ID NO | IRES | Expression |
|---|---|---|
| 621 | Equine rhinitis A virus | 3.73E+05 |
| 622 | Equine arteritis virus | 1.89E+05 |
| 623 | Enterovirus sp. isolate CPML | 6.83E+07 |
| 624 | Enterovirus AN12 | 3.87E+06 |
| 625 | Dolphin morbillivirus | 1.22E+05 |
| 626 | Dianke virus | 1.35E+05 |
| 627 | Guereza hepacivirus | 1.38E+05 |
| 628 | Grapevine associated narnavirus-1 | 1.30E+05 |
| 629 | Goat torovirus | 1.19E+05 |
| 630 | Foot-and-mouth disease virus O isolate | 1.12E+05 |
| 631 | Feline infectious peritonitis virus | 1.35E+05 |
| 632 | Farmington virus | 1.22E+05 |
| 633 | Avian infectious bronchitis virus | 2.84E+05 |
| 634 | Human rhinovirus 1 | 7.40E+07 |
| 635 | EV22 | 1.95E+07 |
| 636 | Human TMEV-like cardiovirus | 4.48E+07 |
| 637 | Human coronavilus 229E | N/A |
| 638 | Hubei zhaovirus-like virus 1 | 1.03E+05 |
| 639 | Hubei tombus-like virus 9 | 9.28E+04 |
| 640 | Hubei tombus-like virus 32 | 9.23E+04 |
| 641 | Hubei sobemo-like virus 3 | 1.17E+05 |
| 642 | Hubei picorna-like virus 2 | 1.95E+05 |
| 643 | Hepacivirus P | 6.04E+05 |
| 644 | Harrier picornavirus 1 | 1.47E+05 |
| 645 | Kunsagivirus 1 | 4.15E+05 |
| 646 | Kagoshima-2-24-KoV | 9.30E+07 |
| 647 | Kashmir bee virus | 1.65E+05 |
| 648 | Jingmen picorna-like virus | 9.32E+04 |
| 649 | Mumps virus | 1.47E+05 |
| 650 | Mouse Mosavirus | 9.00E+04 |
| 651 | Miniopterus schreibersii picornavirus 1 | 6.05E+06 |
| 652 | Linda virus | 7.37E+05 |
| 653 | Lesavirus 2 | 3.67E+07 |
| 654 | Lesavirus 1 | 6.37E+06 |
| 655 | Phopivirus strain NewEngland | 1.06E+05 |
| 656 | Pestivirus strain Aydin | 3.11E+06 |
| 657 | Quail picornavirus QPV1 | 6.55E+07 |
| 658 | Porcine sapelovirus 1 | N/A |
| 659 | Porcine reproductive and respiratory syndrome virus 2 | 1.29E+05 |
| 660 | Porcine enterovirus 9 | 3.20E+07 |
| 661 | Pigeon picornavirus B | 1.24E+05 |
| 662 | Picornavirus HK21 | 4.09E+05 |
| 663 | Picornavirales Tottori-HG1 | 9.54E+04 |
| 664 | Rodent hepatovirus | 1.39E+05 |
| 665 | Rinderpest virus | 4.26E+05 |
| 666 | Rabovirus A | 2.88E+06 |
| 667 | Shingleback nidovirus 1 | 2.62E+05 |
| 668 | Seneca valley virus | 1.46E+07 |
| 669 | Sclerotinia sclerotiorum dsRNA mycovirus-L | 1.69E+05 |
| 670 | Yak enterovirus | 6.19E+06 |
| 671 | Wobbly possum disease virus | 2.60E+05 |
| 672 | Avian orthoreovirus segment S1 | 4.37E+05 |
| 673 | Caprine Kobuvirus d10 | 2.20E+08 |
| 674 | Caprine Kobuvirus d20 | 2.00E+08 |
| 675 | Caprine Kobuvirus d30 | 1.87E+08 |
| 676 | Caprine Kobuvirus d40 | 2.15E+08 |
| 677 | Caprine Kobuvirus d50 | 9.65E+07 |
| 678 | Picornavirales sp. isolate RtMruf-PicoV | 2'26E+08 |
| 679 | Apodemus agrarius picornavirus strain Longquan-Aa118 | 1.90E+08 |
| 680 | Niviventer confucianus picornavirus | 6.10E+07 |
| 681 | Bat picornavirus isolate BtRs-PicoV | 1.13E+06 |
| 682 | Rhinolophus picornavirus strain Guizhou -Rr100 | N/A |
| 683 | Rhinolophus picornavirus strain Henan-Rf265 | 3.85E+05 |
| 684 | Human enterovirus C105 | 5.49E+05 |
| 685 | Human poliovirus 1 strain NIE1116623 | 3.94E+05 |
| 686 | Human enterovirus 109 | 4.92E+05 |
| 687 | Human poliovirus 2 strain NIE0811460 | 2.59E+07 |
| 688 | Bovine picornavirus | 3.82E+06 |
| 689 | Human poliovirus 1 strain EQG1419328 | 2.44E+05 |
| 690 | Human poliovirus 2 isolate IS_061 | 5.84E+06 |
| 691 | Coxsackievirus B5 | N/A |
| 692 | Coxsackievirus A10 | N/A |

Example 9

Figure 4A:
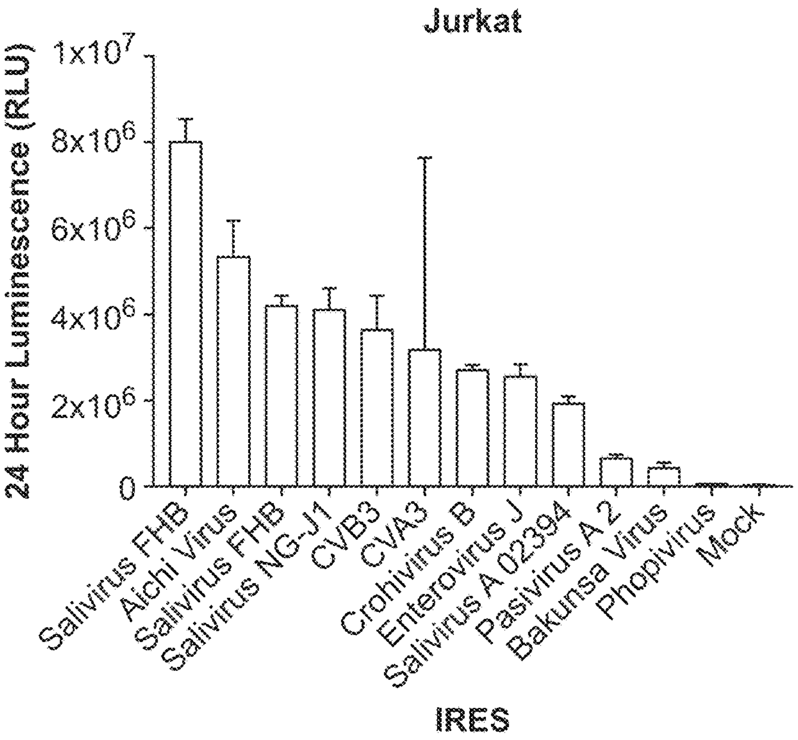
FIGS. 4A and 4B depict protein expression from select IRES constructs in Jurkat cells, as measured by luminescence from secreted *Gaussia* luciferase in cell supernatants.
Figure 4B:
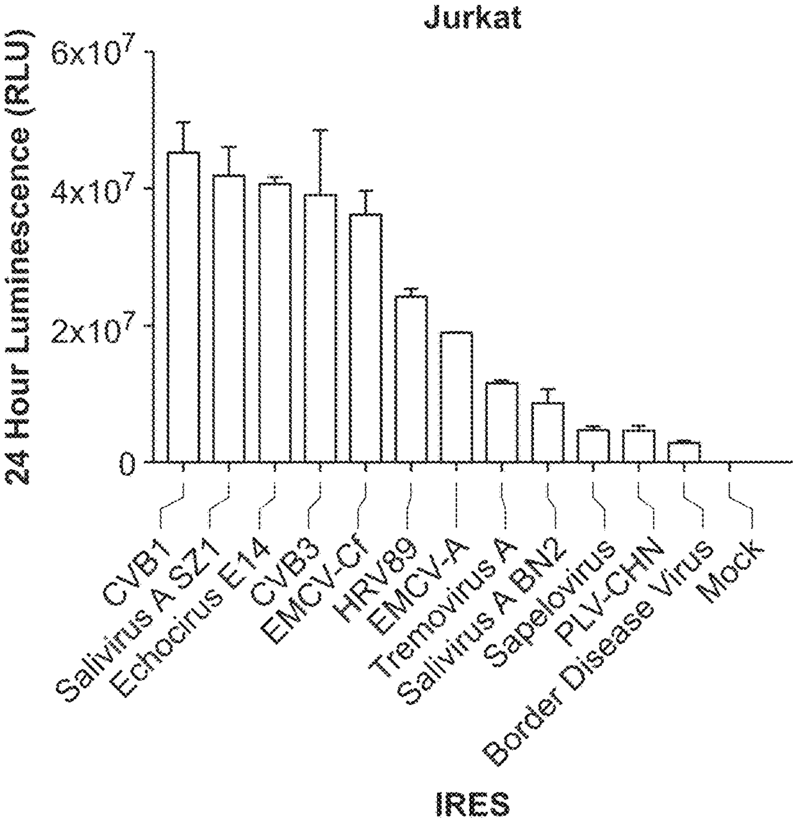

Expression and Functional Stability by IRES in Jurkat Cells 2 sets of constructs including *Anabaena* intron/exon regions, a *Gaussia* luciferase expression sequence, and a subset of previously tested IRES were circularized. 60,000 Jurkat cells were electroporated with 1 μg of each circularization reaction. Luminescence from secreted *Gaussia* luciferase in supernatant was measured 24 hours after electroporation. A CVB3 IRES construct was included in both sets for comparison between sets and to previously defined IRES efficacy. CVB1 and Salivirus A SZ1 IRES constructs produced the most expression at 24 h. Data can be found in FIGS. 4A and 4B.

Figure 5A:
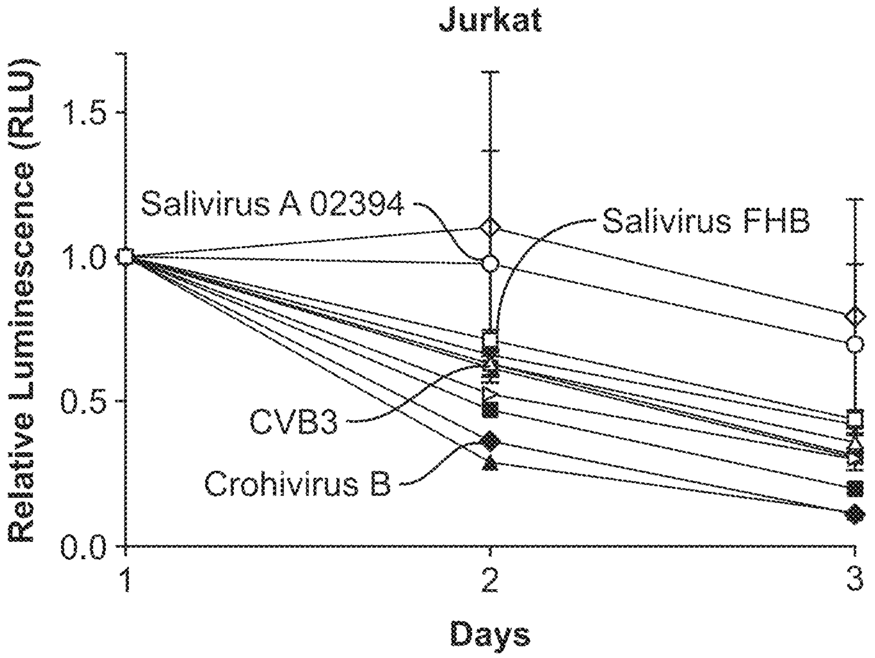
FIGS. 5A and 5B depict stability of select IRES constructs in Jurkat cells over 3 days as measured by luminescence.
Figure 5B:
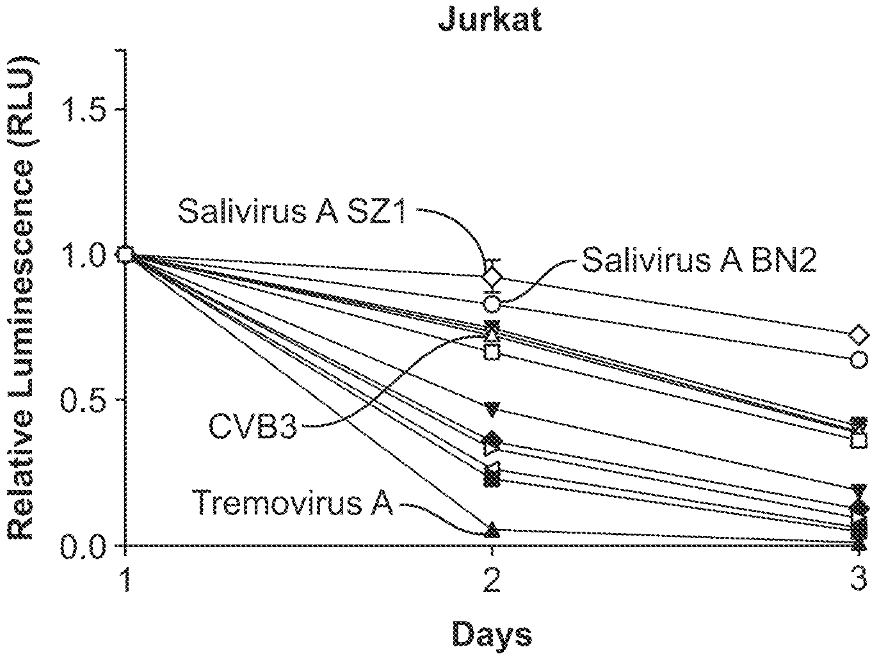

Functional stability of the IRES constructs in each round of electroporated Jurkat cells was measured over 3 days. Luminescence from secreted *Gaussia* luciferase in supernatant was measured every 24 hours after electroporation of 60,000 cells with 1 μg of each circularization reaction, followed by complete media replacement (FIGS. 5A and 5B).

Salivirus A SZ1 and Salivirus A BN2 IRES constructs had high functional stability compared to other constructs.

Example 10

Figure 6A:
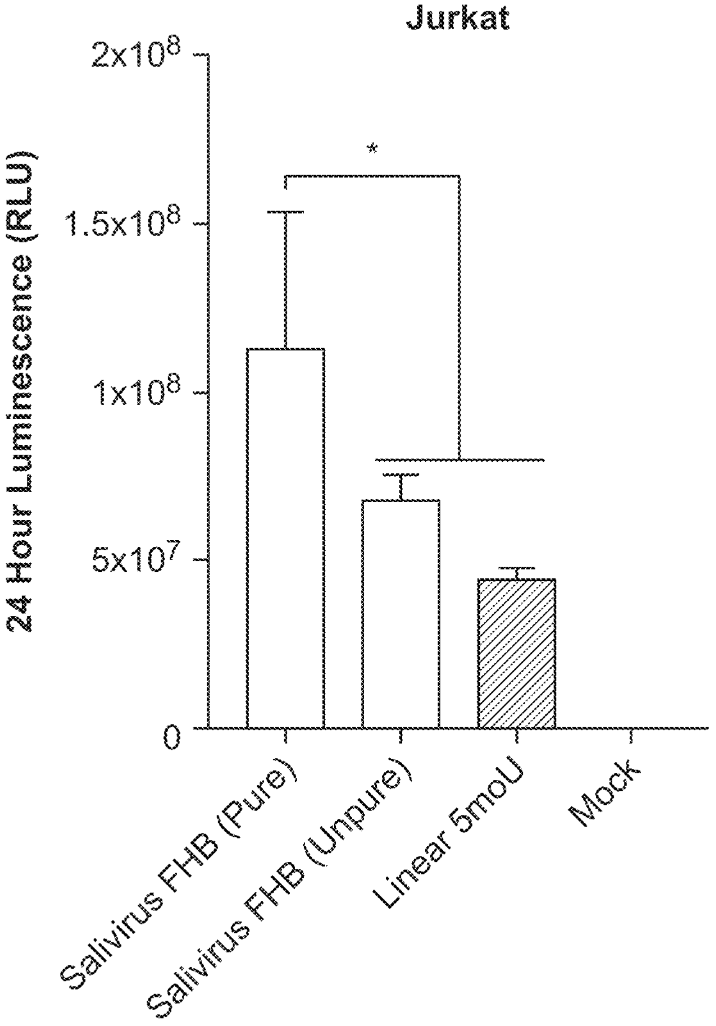
FIG. 6 depicts comparisons of 24 hour luminescence (FIG. 6A) or relative luminescence over 3 days (FIG. 6B) of modified linear, unpurified circular, or purified circular RNA encoding *Gaussia* luciferase.

Expression, Functional Stability, and Cytokine Release of Circular and Linear RNA in Jurkat Cells A construct including *Anabaena* intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) is commercially available and was purchased from Trilink. 5moU nucleotide modifications have been shown to improve mRNA stability and expression (Bioconjug Chem. 2016 Mar. 16; 27(3):849-53). Expression of modified mRNA, circularization reactions (unpure), and circRNA purified by size exclusion HPLC (pure) in Jurkat cells were measured and compared (FIG. 6A). Luminescence from secreted *Gaussia* luciferase in supernatant was measured 24 hours after electroporation of 60,000 cells with 1 μg of each RNA species.

Figure 6B:
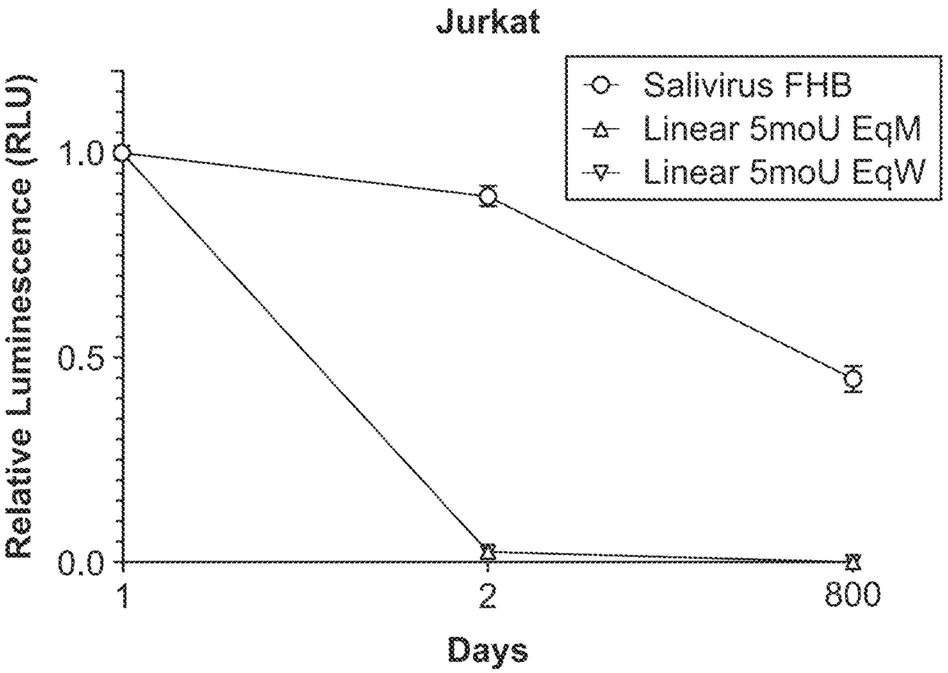

Luminescence from secreted *Gaussia* luciferase in supernatant was measured every 24 hours after electroporation of 60,000 cells with 1 ug of each RNA species, followed by complete media replacement. A comparison of functional stability data of modified mRNA and circRNA in Jurkat cells over 3 days is in FIG. 6B.

Figure 7A:
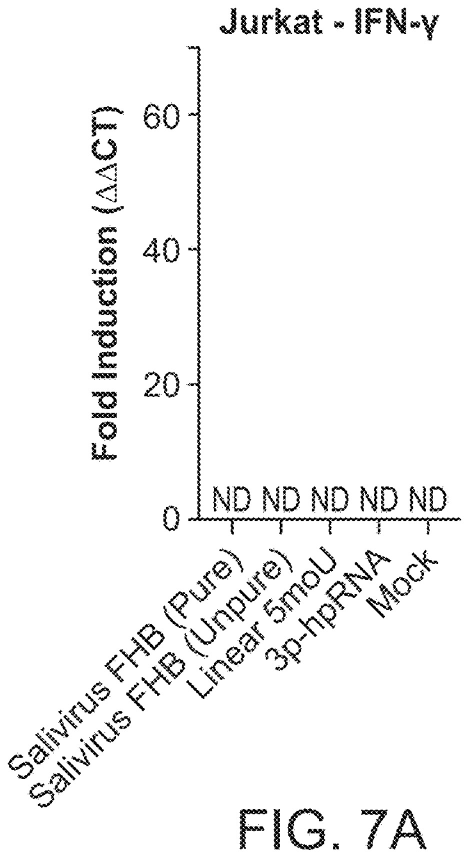
FIG. 7 depicts transcript induction of IFNγ (FIG. 7A), IL-6 (FIG. 7B), IL-2 (FIG. 7C), RIG-I (FIG. 7D), IFN-β1 (FIG. 7E), and TNFα (FIG. 7F) after electroporation of Jurkat cells with modified linear, unpurified circular, or purified circular RNA.
Figure 7B:
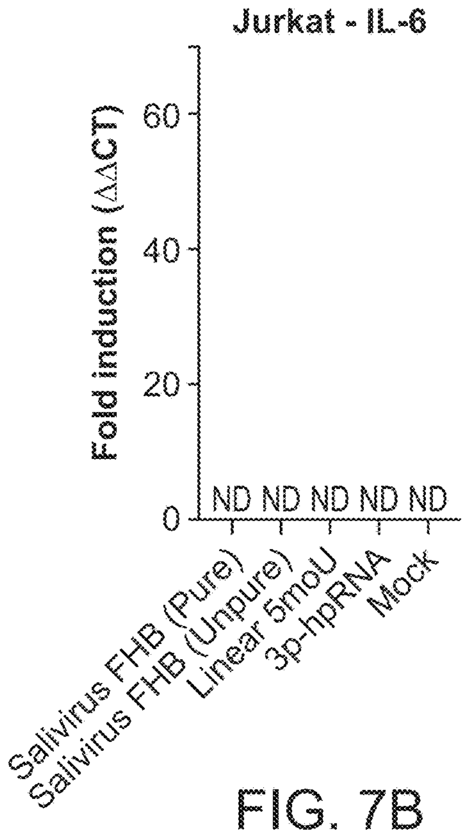
Figure 7C:
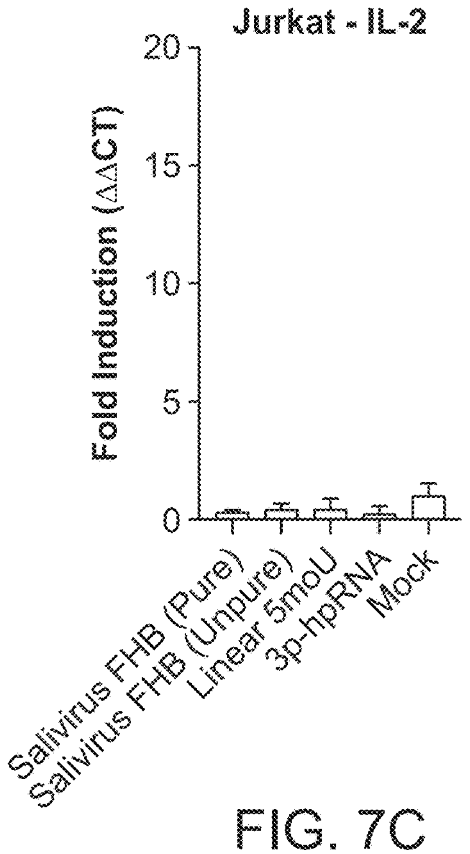
Figure 7D:
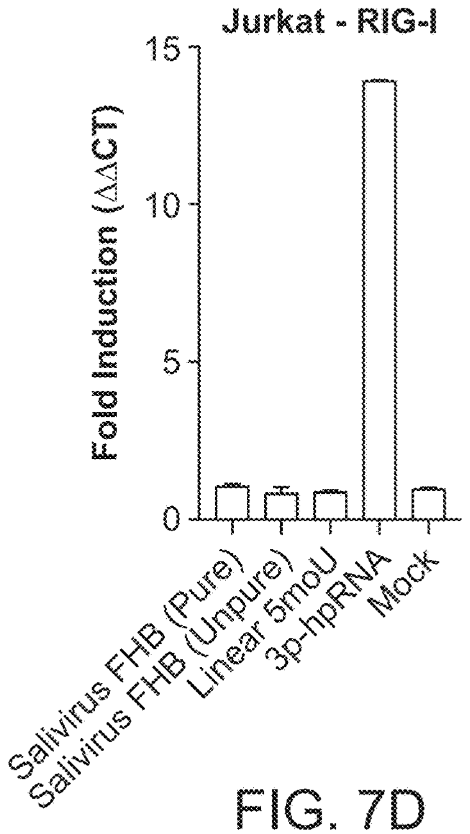
Figure 7E:
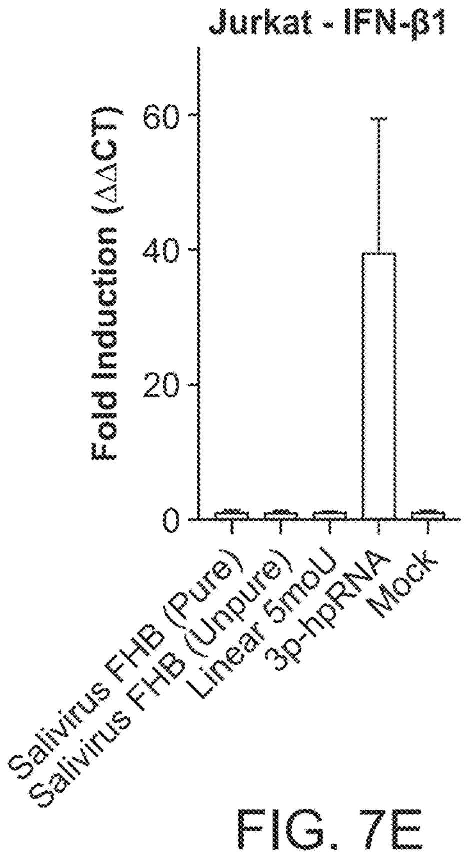
Figure 7F:
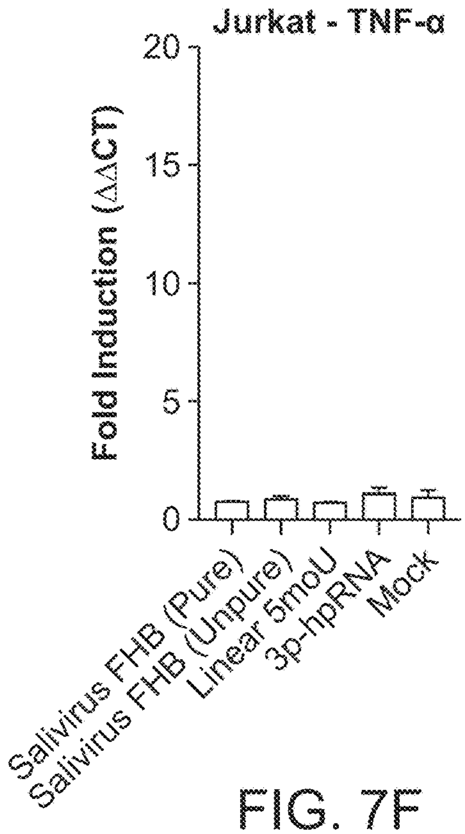

IFNγ (FIG. 7A), IL-6 (FIG. 7B), IL-2 (FIG. 7C), RIG-I (FIG. 7D), IFN-β1 (FIG. 7E), and TNFα (FIG. 7F) transcript induction was measured 18 hours after electroporation of 60,000 Jurkat cells with 1 μg of each RNA species described above and 3p-hpRNA (5' triphosphate hairpin RNA, which is a known RIG-I agonist).

Example 11

Expression of Circular and Linear RNA in Monocytes and Macrophages

Figure 8A:
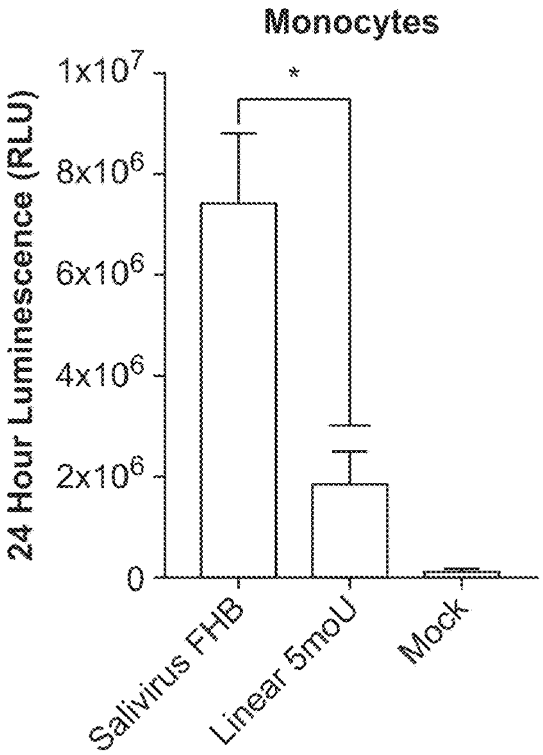
FIG. 8 depicts a comparison of luminescence of circular RNA and modified linear RNA encoding *Gaussia* luciferase in human primary monocytes (FIG. 8A) and macrophages (FIG. 8B and FIG. 8C).
Figure 8B:
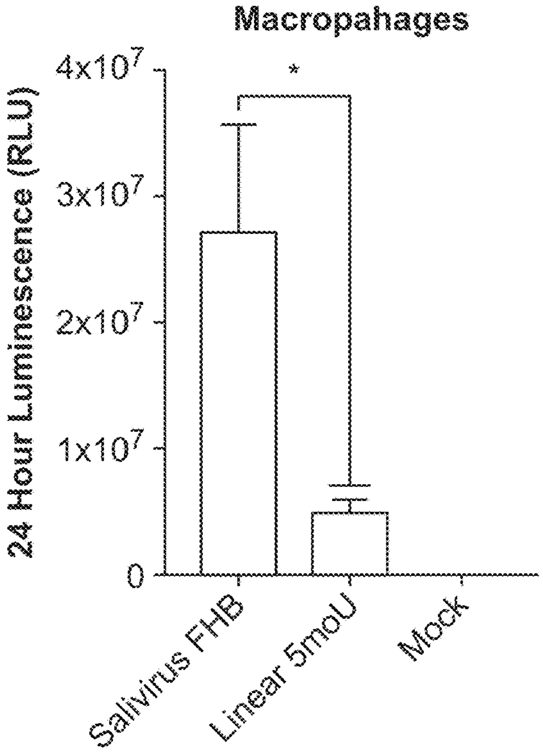
Figure 8C:
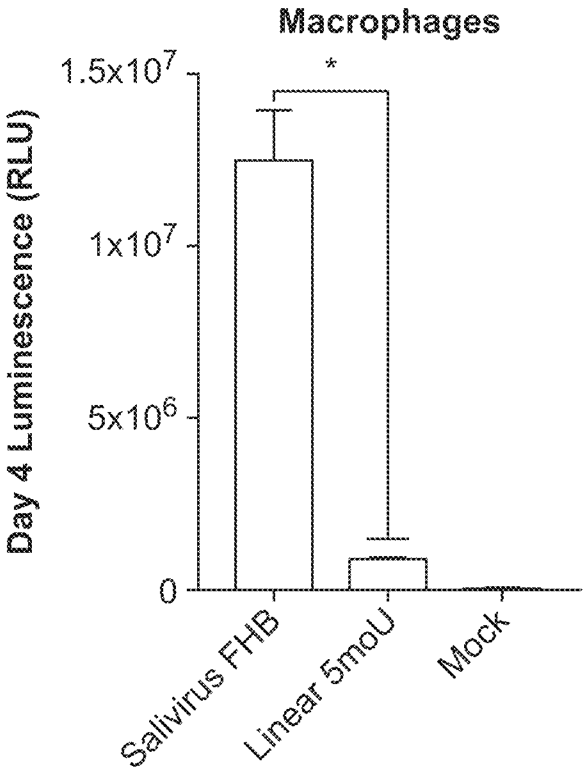

A construct including *Anabaena* intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) was purchased from Trilink. Expression of circular and modified mRNA was measured in human primary monocytes (FIG. 8A) and human primary macrophages (FIG. 8B). Luminescence from secreted *Gaussia* luciferase in supernatant was measured 24 hours after electroporation of 60,000 cells with 1 μg of each RNA species. Luminescence was also measured 4 days after electroporation of human primary macrophages with media changes every 24 hours (FIG. 8C). The results can be found in FIG. 8. The difference in luminescence was statistically significant in each case ($p<0.05$).

Example 12

Expression and Functional Stability by IRES in Primary T Cells

Figure 9A:
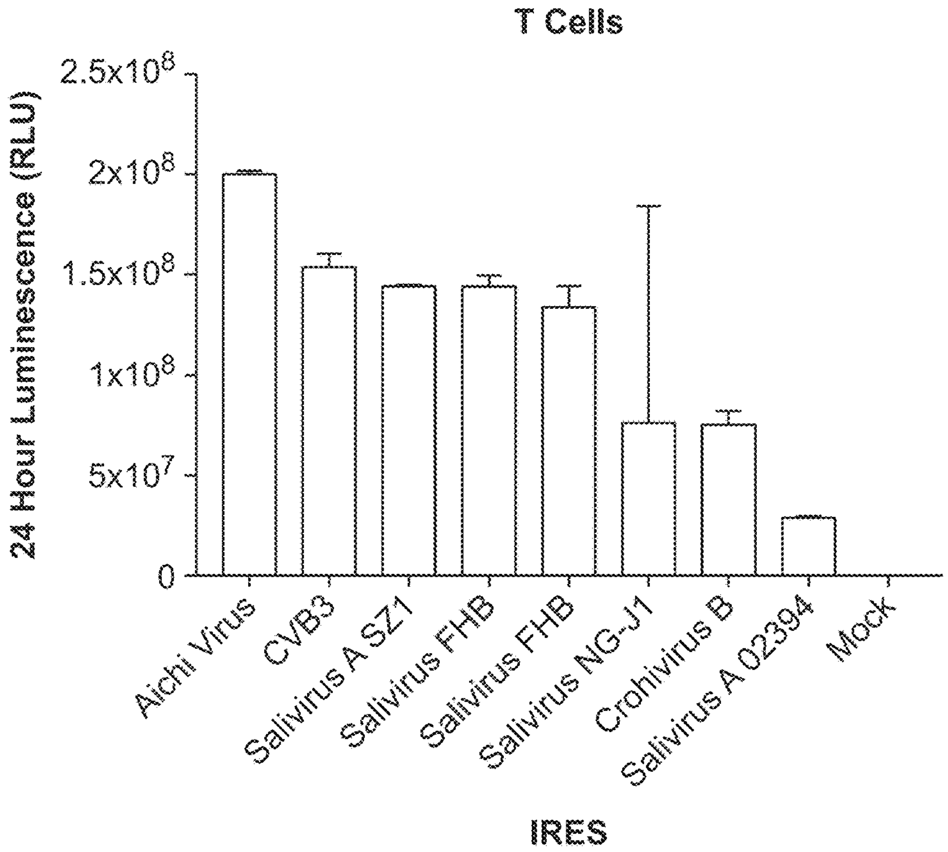
FIG. 9 depicts relative luminescence over 3 days (FIG. 9A) in supernatant of primary T cells after transduction with circular RNA comprising a *Gaussia* luciferase expression sequence and varying IRES sequences or 24 hour luminescence (FIG. 9B).

Constructs including *Anabaena* intron/exon regions, a *Gaussia* luciferase expression sequence, and a subset of previously tested IRES were circularized and reaction products were purified by size exclusion HPLC. 150,000 primary human CD3+ T cells were electroporated with 1 μg of each circRNA. Luminescence from secreted *Gaussia* luciferase in supernatant was measured 24 hours after electroporation (FIG. 9A). Aichi Virus and CVB3 IRES constructs had the most expression at 24 hours.

Figure 9B:
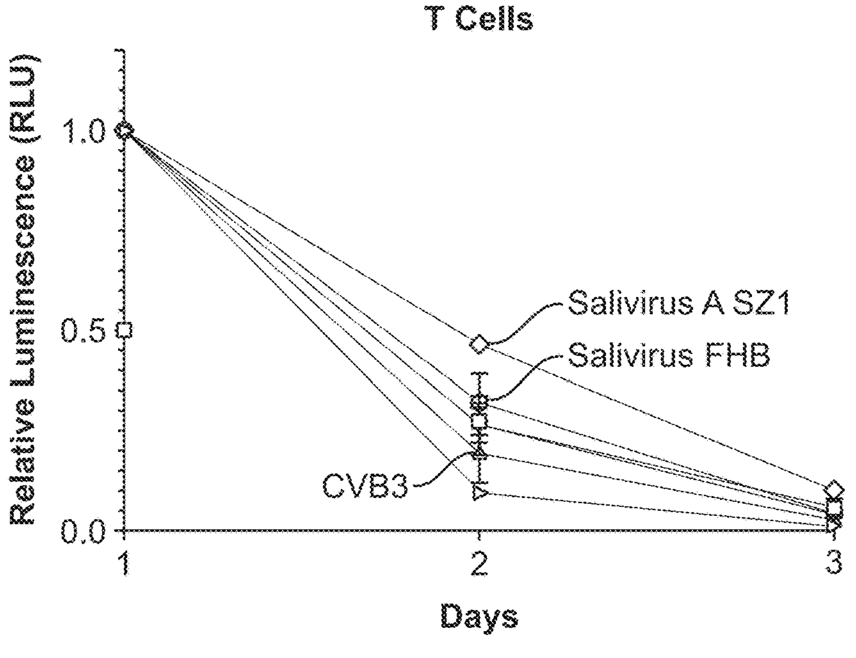

Luminescence was also measured every 24 hours after electroporation for 3 days in order to compare functional stability of each construct (FIG. 9B). The construct with a Salivirus A SZ1 IRES was the most stable.

Example 13

Figure 10A:
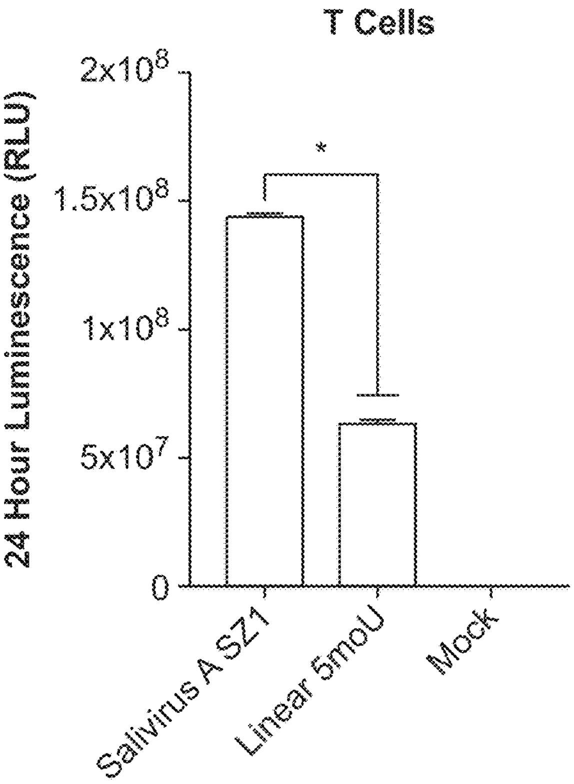
FIG. 10 depicts 24 hour luminescence in supernatant of primary T cells (FIG. 10A) after transduction with circular RNA or modified linear RNA comprising a *Gaussia* luciferase expression sequence, or relative luminescence over 3 days (FIG. 10B), and 24 hour luminescence in PBMCs (FIG. 10C).
Figure 10B:
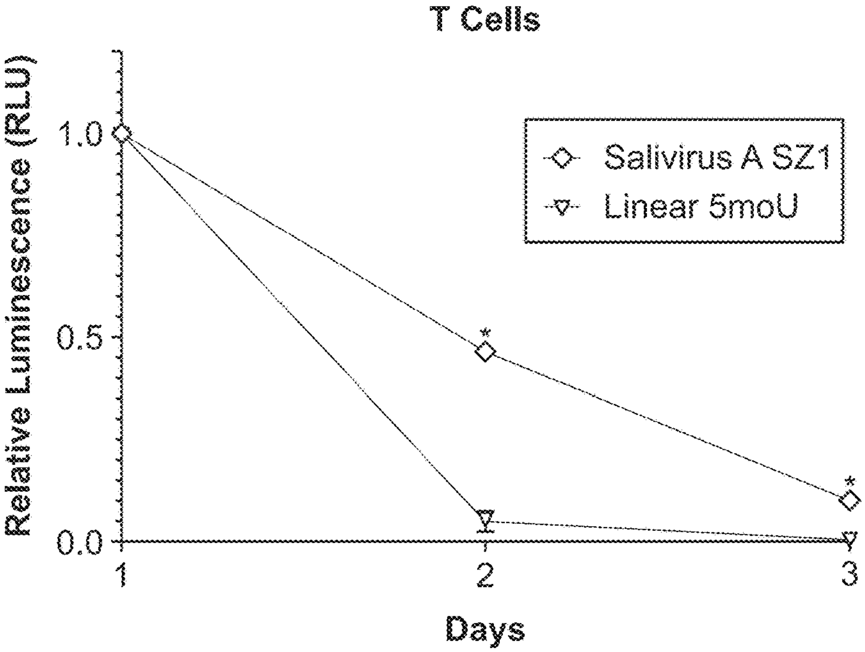
Figure 10C:
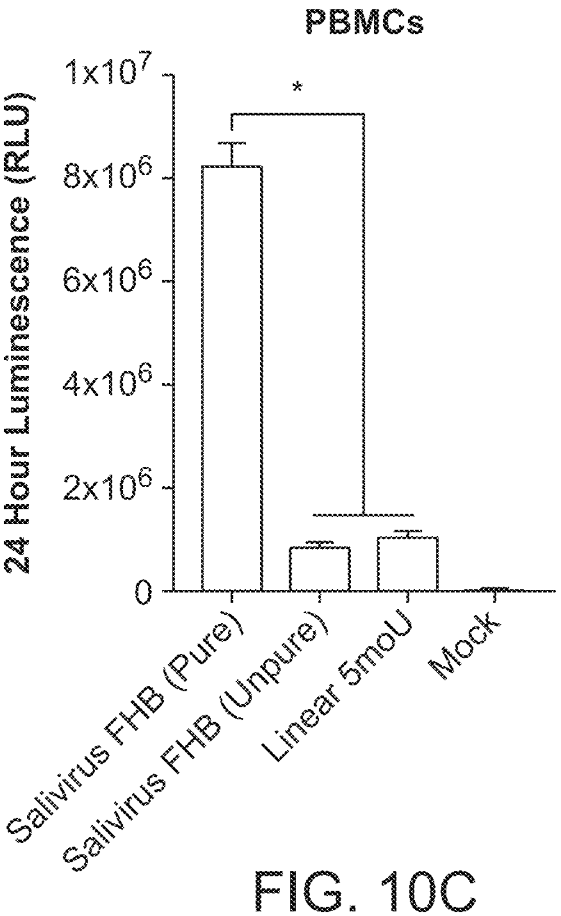

Expression and Functional Stability of Circular and Linear RNA in Primary T Cells and PBMCs Constructs including *Anabaena* intron/exon regions, a *Gaussia* luciferase expression sequence, and a Salivirus A SZ1 IRES or Salivirus FHB IRES were circularized. mRNA including a *Gaussia* luciferase expression sequence and a ~150 nt polyA tail, and modified to replace 100% of uridine with 5-methoxy uridine (5moU) and was purchased from Trilink. Expression of Salivirus A SZ1 IRES HPLC purified circular and modified mRNA was measured in human primary CD3+ T cells. Expression of Salivirus FHB HPLC purified circular, unpurified circular and modified mRNA was measured in human PBMCs. Luminescence from secreted *Gaussia* luciferase in supernatant was measured 24 hours after electroporation of 150,000 cells with 1 μg of each RNA species. Data for primary human T cells is shown in FIGS. 10A and 10B, and data for PBMCs is shown in FIG. 10C. The difference in expression between the purified circular RNA and unpurified circular RNA or linear RNA was significant in each case ($p<0.05$).

Luminescence from secreted *Gaussia* luciferase in primary T cell supernatant was measured every 24 hours after electroporation over 3 days in order to compare construct functional stability. Data is shown in FIG. 10B. The difference in relative luminescence from the day 1 measurement between purified circular RNA and linear RNA was significant at both day 2 and day 3 for primary T cells.

Example 14

Circularization Efficiency by Permutation Site in *Anabaena* Intron

Figure 11A:
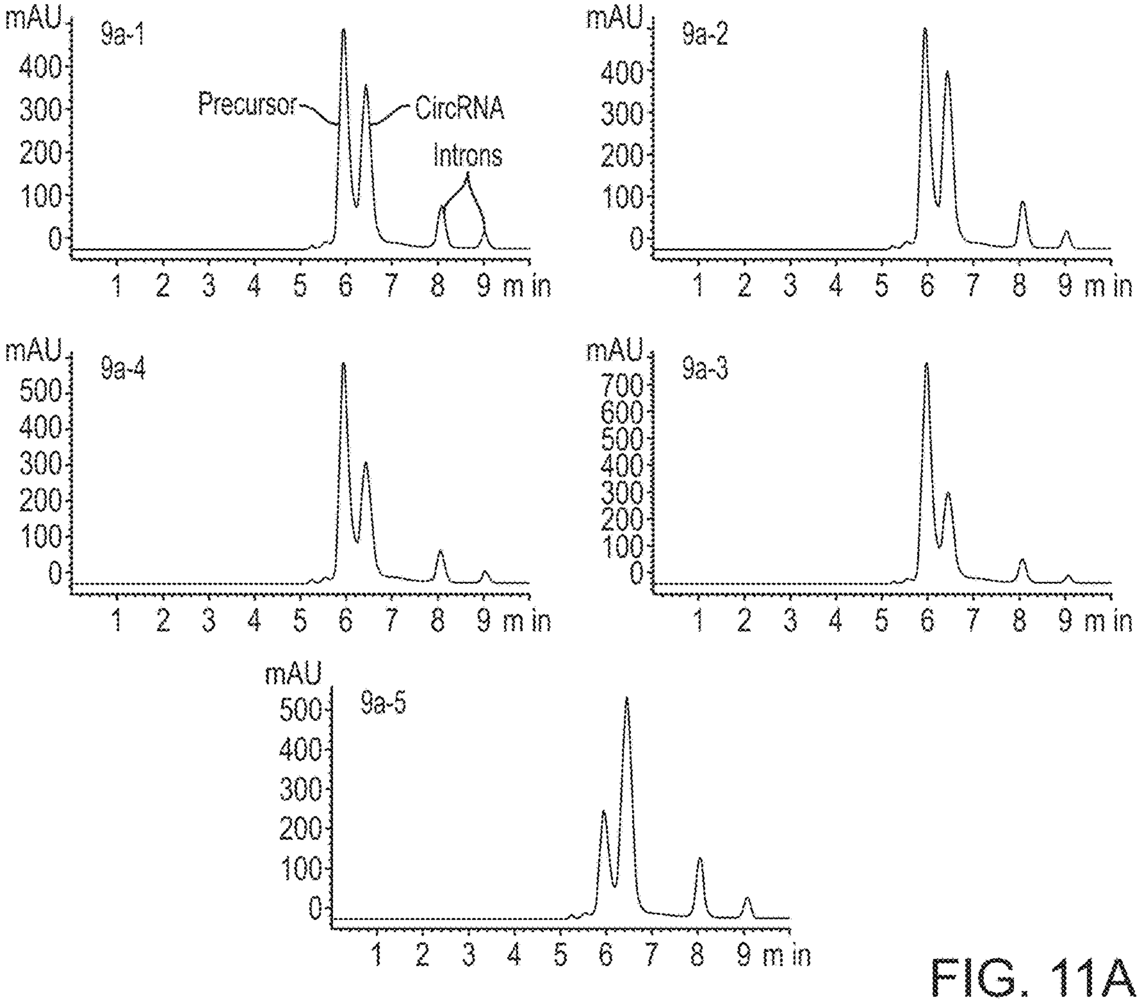
FIG. 11 depicts HPLC chromatograms (FIG. 11A) and circularization efficiencies (FIG. 11B) of RNA constructs having different permutation sites.

RNA constructs including a CVB3 IRES, a *Gaussia* luciferase expression sequence, *Anabaena* intron/exon regions, spacers, internal homology regions, and homology arms were produced. Circularization efficiency of constructs using the traditional *Anabaena* intron permutation site and 5 consecutive permutations sites in P9 was measured by HPLC. HPLC chromatograms for the 5 consecutive permutation sites in P9 are shown in FIG. 11A.

Figure 11B:
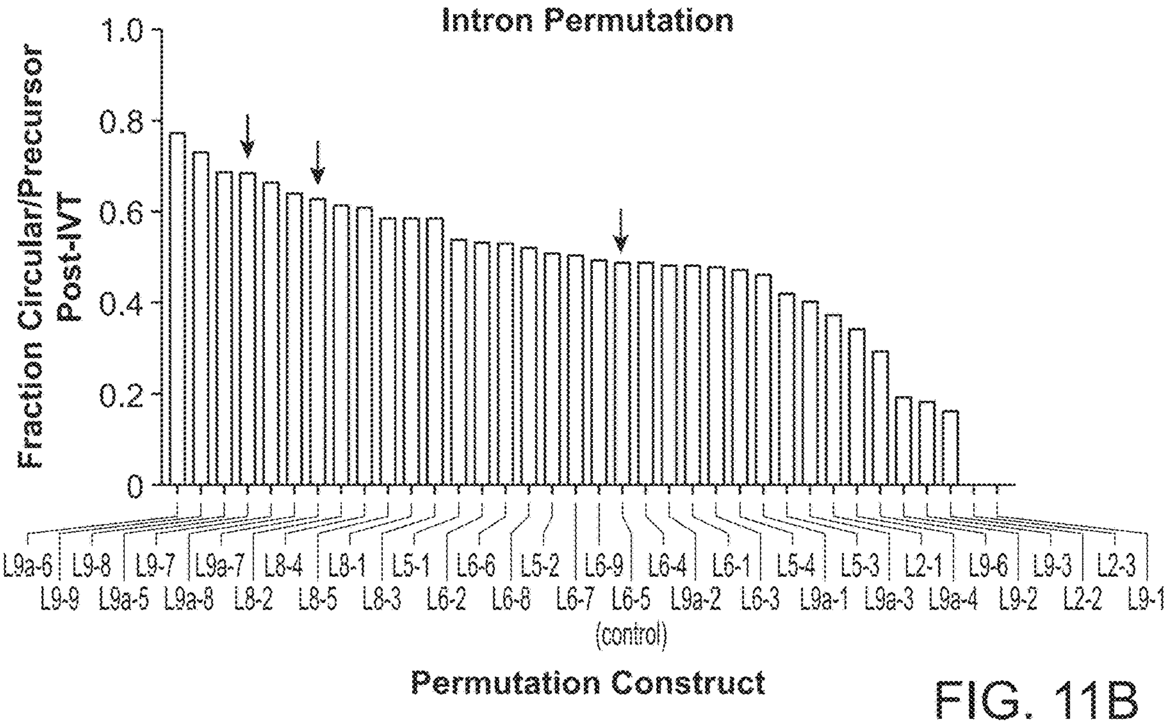

Circularization efficiency was measured at a variety of permutation sites. Circularization efficiency is defined as the area under the HPLC chromatogram curve for each of: circRNA/(circRNA+precursor RNA). Ranked quantification of circularization efficiency at each permutation site is in FIG. 11B. 3 permutation sites (indicated in FIG. 11B) were selected for further investigation.

Circular RNA in this example was circularized by in vitro transcription (IVT) then purified via spin column. Circularization efficiency for all constructs would likely be higher if the additional step of incubation with Mg2+ and guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 15

Circularization Efficiency of Alternative Introns

Figure 12A:
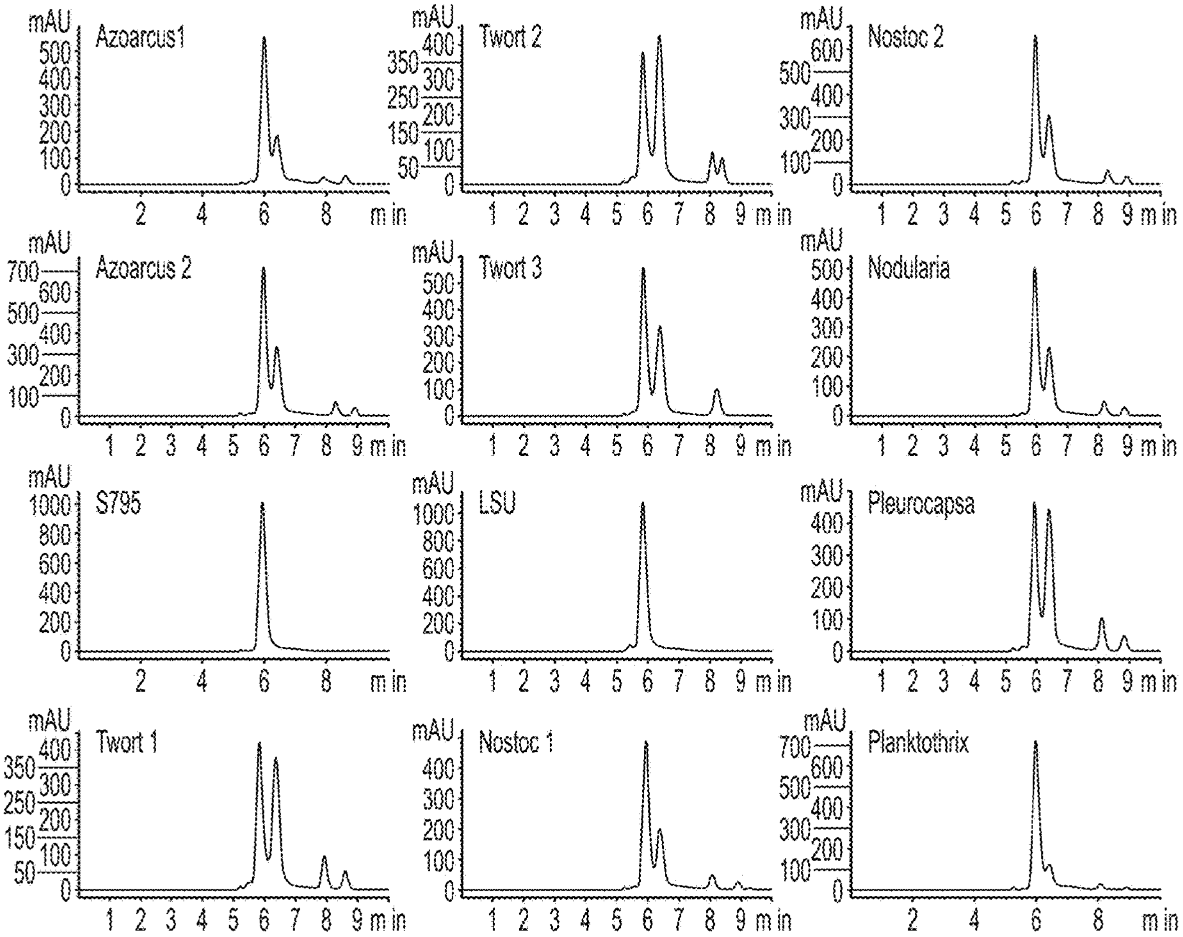
FIG. 12 depicts HPLC chromatograms (FIG. 12A) and circularization efficiencies (FIG. 12B) of RNA constructs having different introns and/or permutation sites.
Figure 12B:
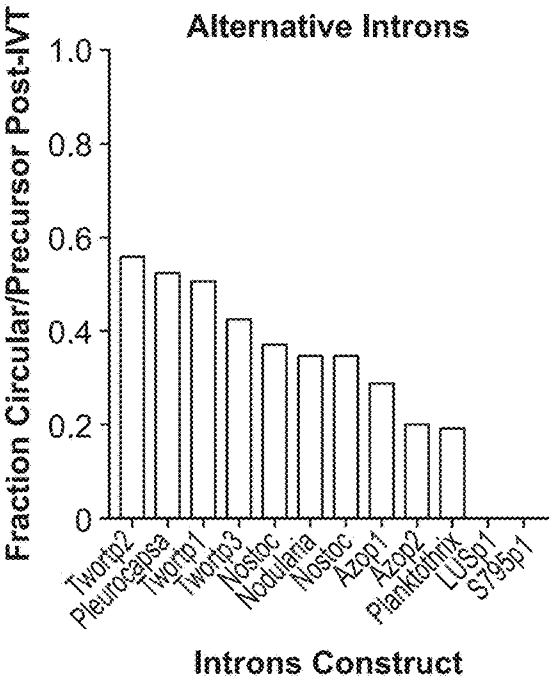

Precursor RNA containing a permuted group 1 intron of variable species origin or permutation site and several constant elements including: a CVB3 IRES, a *Gaussia* luciferase expression sequence, spacers, internal homology regions, and homology arms were created. Circularization data can be found in FIG. 12. FIG. 12A shows chromatograms resolving precursor, CircRNA and introns. FIG. 12B provides ranked quantification of circularization efficiency, based on the chromatograms shown in FIG. 12A, as a function of intron construct.

Circular RNA in this example was circularized by in vitro transcription (IVT) then spin column purification. Circularization efficiency for all constructs would likely be higher if the additional step of incubation with Mg2+ and guanosine nucleotide were included; however, removing this step allows for comparison between, and optimization of, circular RNA constructs. This level of optimization is especially useful for maintaining high circularization efficiency with large RNA constructs, such as those encoding chimeric antigen receptors.

Example 16

Circularization Efficiency by Homology Arm Presence or Length

Figure 13A:
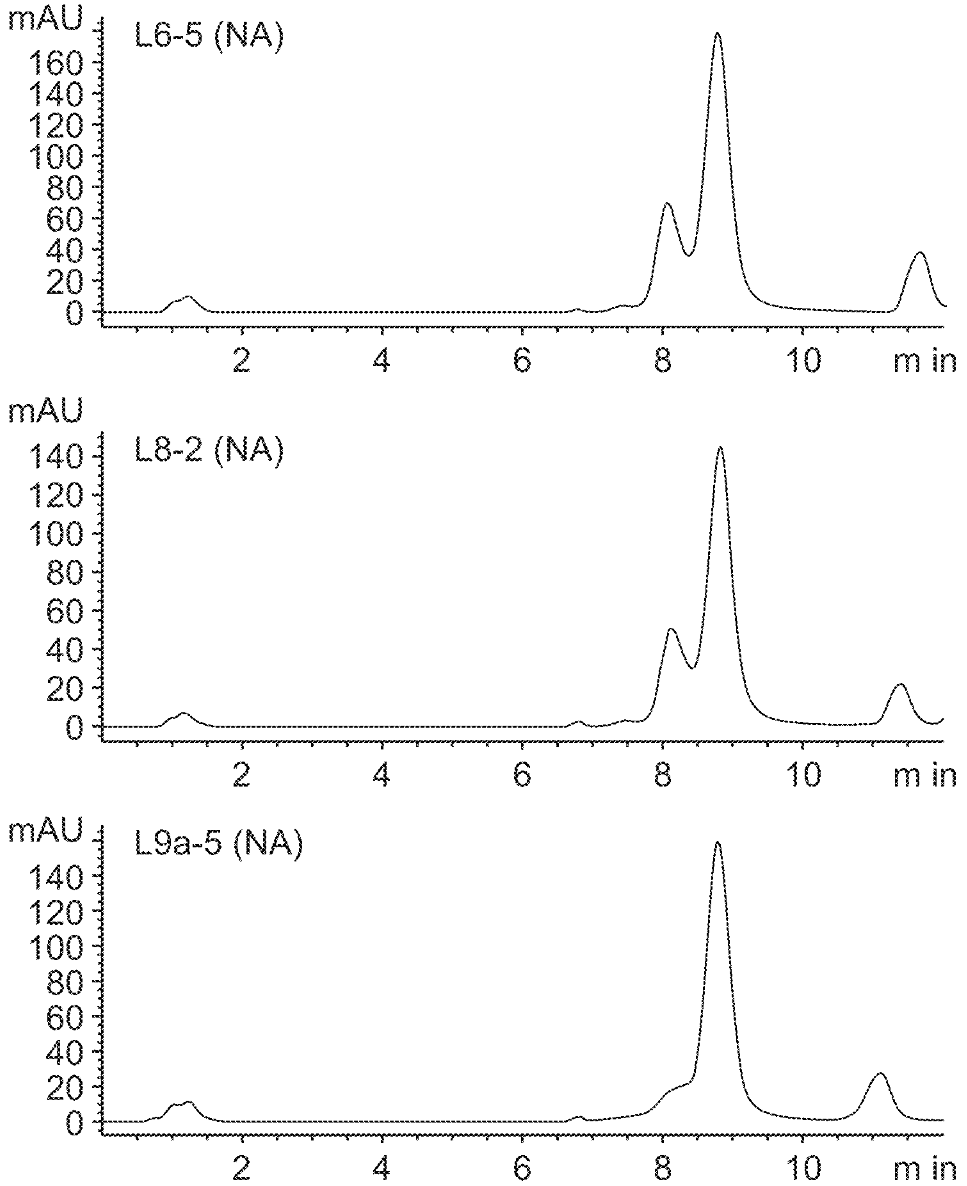
FIG. 13 depicts HPLC chromatograms (FIG. 13A) and circularization efficiencies (FIG. 13B) of 3 RNA constructs with or without homology arms.
Figure 13B:
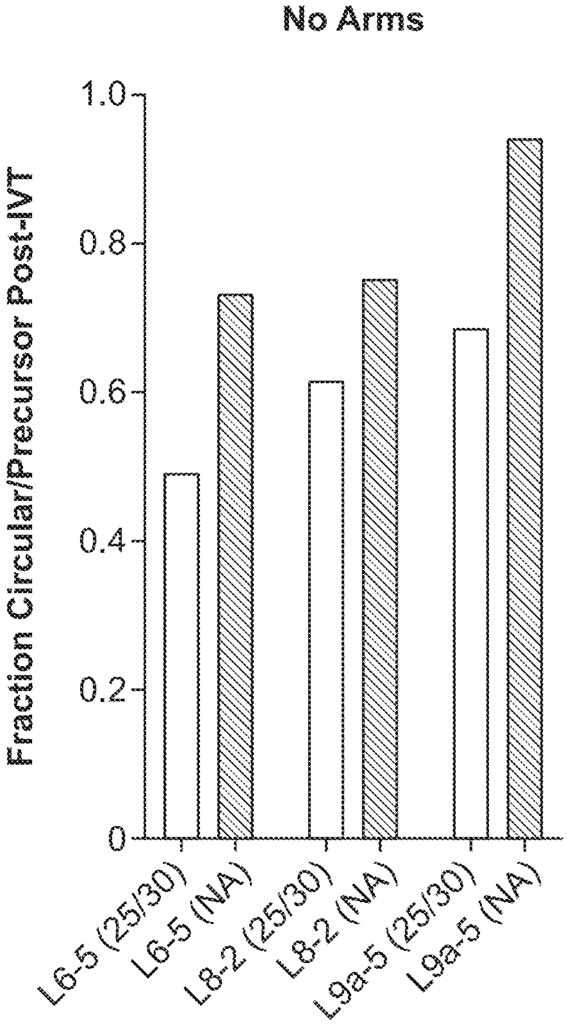

RNA constructs including a CVB3 IRES, a *Gaussia* luciferase expression sequence, *Anabaena* intron/exon regions, spacers, and internal homology regions were produced. Constructs representing 3 *Anabaena* intron permutation sites were tested with 30 nt, 25% GC homology arms or without homology arms ("NA"). These constructs were allowed to circularize without an $Mg^{2+}$ incubation step. Circularization efficiency was measured and compared. Data can be found in FIGS. 13A and 13B. Circularization efficiency was higher for each construct lacking homology arms. FIG. 13A provides ranked quantification of circularization efficiency; FIG. 13B provides chromatograms resolving precursor, circRNA and introns.

Figure 14:
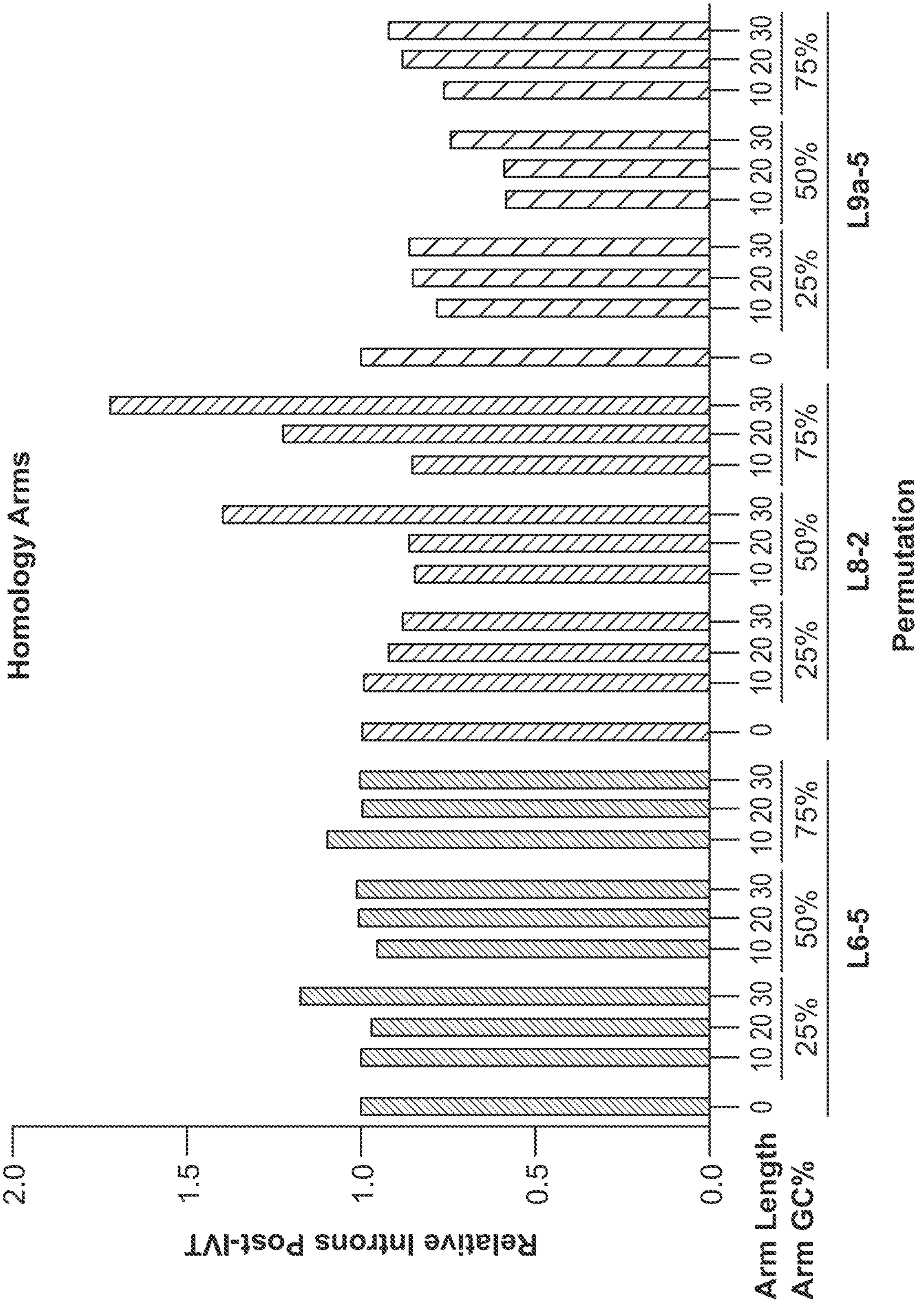
FIG. 14 depicts circularization efficiencies of 3 RNA constructs without homology arms or with homology arms having various lengths and GC content.

For each of the 3 permutation sites, constructs were created with 10 nt, 20 nt, and 30 nt arm lengths and 25%, 50%, and 75% GC content. Splicing efficiency of these constructs was measured and compared to constructs without homology arms (FIG. 14). Splicing efficiency is defined as the proportion of free introns relative to the total RNA in the splicing reaction.

Figure 15A:
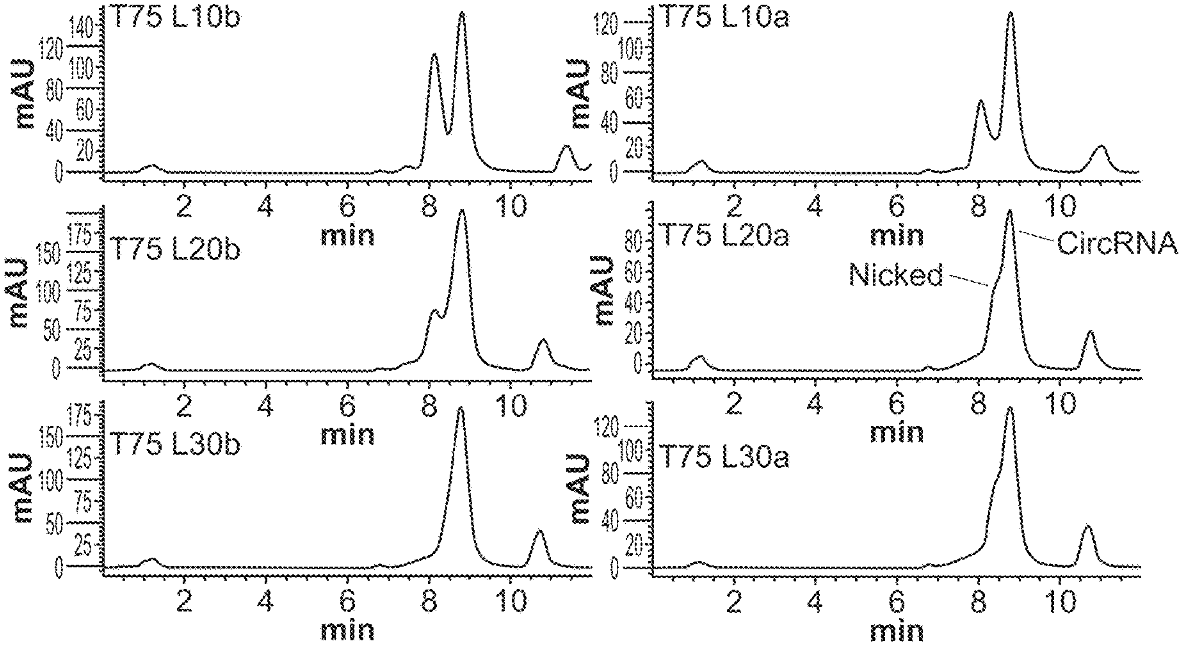
FIGS. 15A and 15B depict HPLC HPLC chromatograms showing the contribution of strong homology arms to improved splicing efficiency, the relationship between circularization efficiency and nicking in select constructs, and combinations of permutations sites and homology arms hypothesized to demonstrate improved circularization efficiency.
Figure 15B:
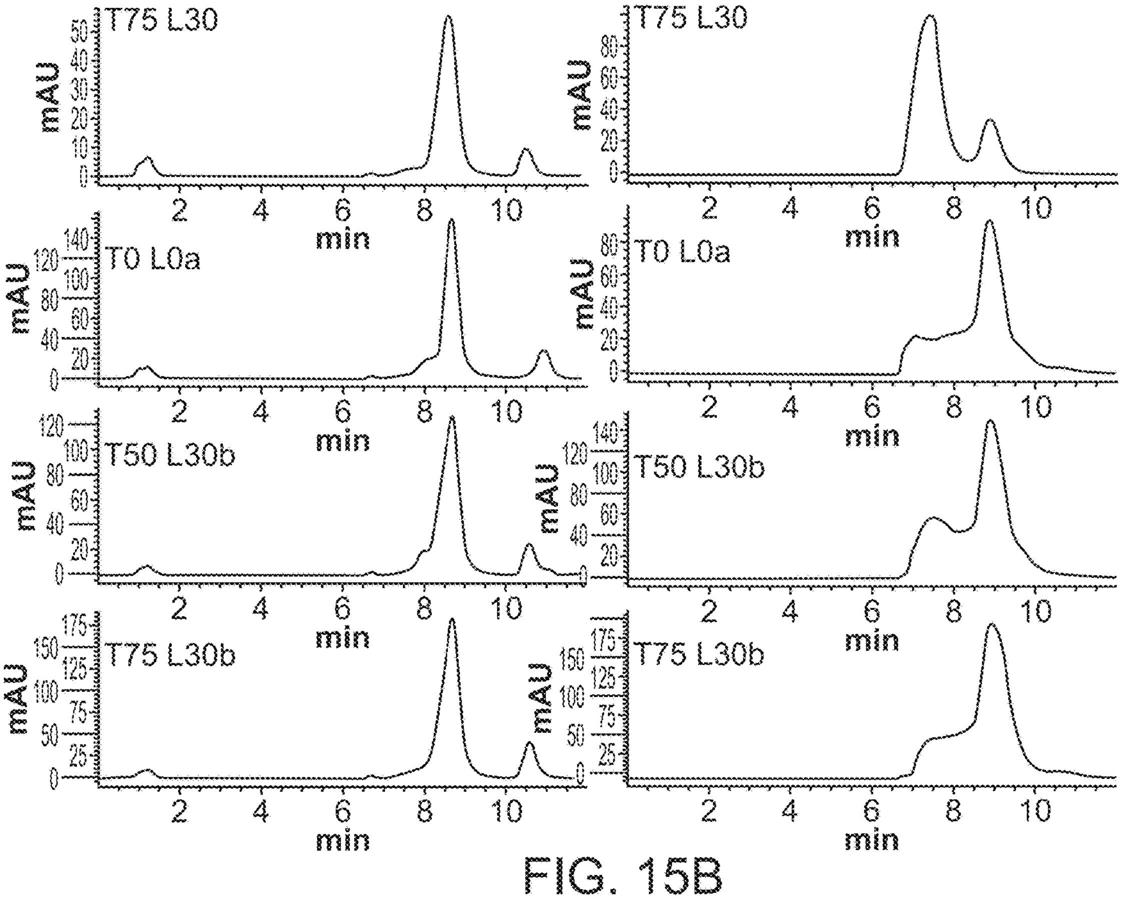

FIG. 15 A (left) shows HPLC chromatograms indicating the contribution of strong homology arms to improved splicing efficiency. Top left: 75% GC content, 10 nt homology arms. Center left: 75% GC content, 20 nt homology arms. Bottom left: 75% GC content, 30 nt homology arms.

FIG. 15 A (right) shows HPLC chromatograms showing increased splicing efficiency paired with increased nicking, appearing as a shoulder on the circRNA peak. Top right: 75% GC content, 10 nt homology arms. Center right: 75% GC content, 20 nt homology arms. Bottom right: 75% GC content, 30 nt homology arms.

FIG. 15 B (left) shows select combinations of permutation sites and homology arms hypothesized to demonstrate improved circularization efficiency.

FIG. 15 B (right) shows select combinations of permutation sites and homology arms hypothesized to demonstrate improved circularization efficiency, treated with *E. coli* polyA polymerase.

Circular RNA in this example was circularized by in vitro transcription (IVT) then spin-column purified. Circularization efficiency for all constructs would likely be higher if an additional Mg2+ incubation step with guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 17

Circular RNA Encoding Chimeric Antigen Receptors

Figure 16:
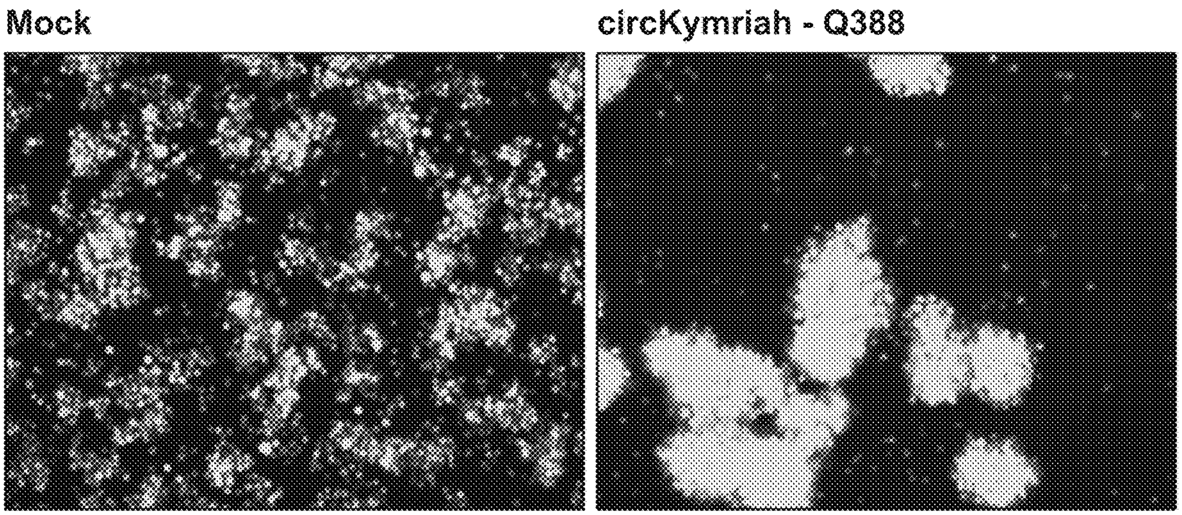
FIG. 16 shows fluorescent images of T cells mock electroporated (left) or electroporated with circular RNA encoding a CAR (right) and co-cultured with Raji cells expressing GFP and firefly luciferase.

Constructs including *Anabaena* intron/exon regions, a Kymriah chimeric antigen receptors (CAR) expression sequence, and a CVB3 IRES were circularized. 100,000 human primary CD3+ T cells were electroporated with 500 ng of circRNA and co-cultured for 24 hours with Raji cells stably expressing GFP and firefly luciferase. Effector to target ratio (E:T ratio) 0.75:1. 100,000 human primary CD3+ T cells were mock electroporated and co-cultured as a control (FIG. 16).

Figure 17:
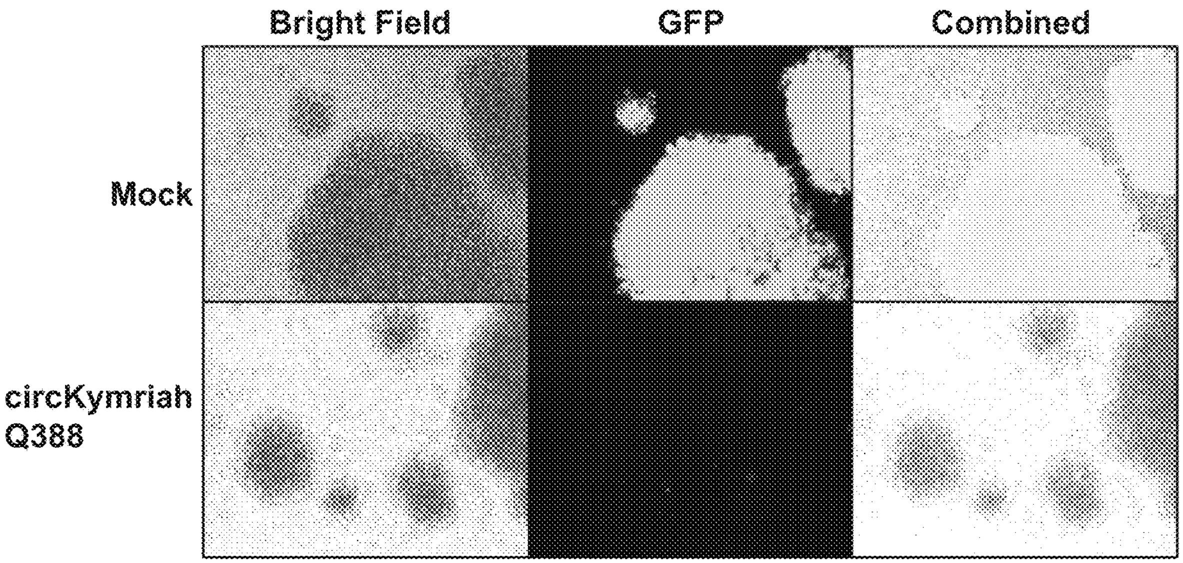
FIG. 17 shows bright field (left), fluorescent (center), and overlay (right) images of T cells mock electroporated (top) or electroporated with circular RNA encoding a CAR (bottom) and co-cultured with Raji cells expressing GFP and firefly luciferase.

Sets of 100,000 human primary CD3+ T cells were mock electroporated or electroporated with 1 μg of circRNA then co-cultured for 48 hours with Raji cells stably expressing GFP and firefly luciferase E:T ratio 10:1 (FIG. 17).

Figure 18:
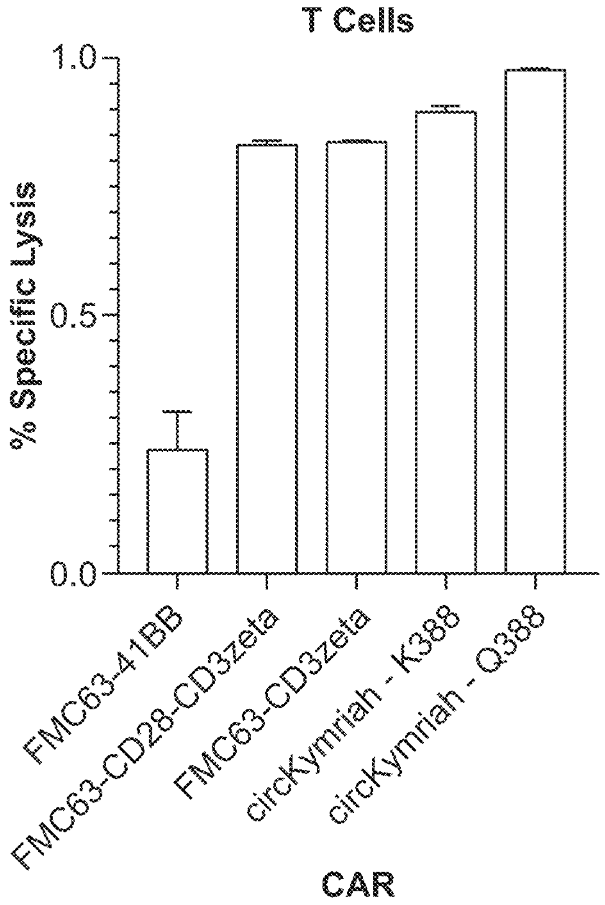
FIG. 18 depicts specific lysis of Raji target cells by T cells mock electroporated or electroporated with circular RNA encoding different CAR sequences.

Quantification of specific lysis of Raji target cells was determined by detection of firefly luminescence (FIG. 18). 100,000 human primary CD3+ T cells either mock electroporated or electroporated with circRNA encoding different CAR sequences were co-cultured for 48 hours with Raji cells stably expressing GFP and firefly luciferase. % Specific lysis defined as 1-[CAR condition luminescence]/[mock condition luminescence]. E:T ratio 10:1.

Example 18

Figure 19A:
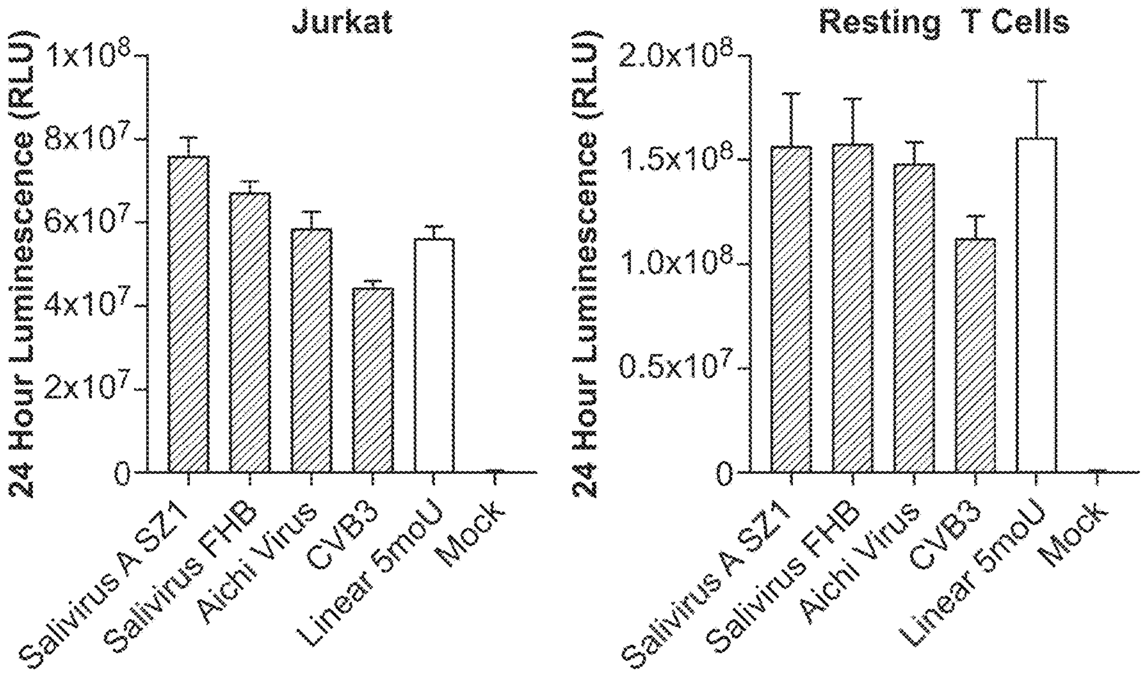
FIG. 19 depicts luminescence in supernatants of Jurkat cells (left) or resting primary human CD3+ T cells (right) 24 hours after transduction with linear or circular RNA comprising a *Gaussia* luciferase expression sequence and varying IRES sequences (FIG. 19A), and relative luminescence over 3 days (FIG. 19B).

Expression and Functional Stability of Circular and Linear RNA in Jurkat Cells and Resting Human T Cells Constructs including *Anabaena* intron/exon regions, a *Gaussia* luciferase expression sequence, and a subset of previously tested IRES were circularized and reaction products were purified by size exclusion HPLC. 150,000 Jurkat cells were electroporated with 1 μg of circular RNA or 5moU-mRNA. Luminescence from secreted *Gaussia* luciferase in supernatant was measured 24 hours after electroporation (FIG. 19A left). 150,000 resting primary human CD3+ T cells (10 days post-stimulation) were electroporated with 1 of circular RNA or 5moU-mRNA. Luminescence from secreted *Gaussia* luciferase in supernatant was measured 24 hours after electroporation (FIG. 19A right).

Figure 19B:
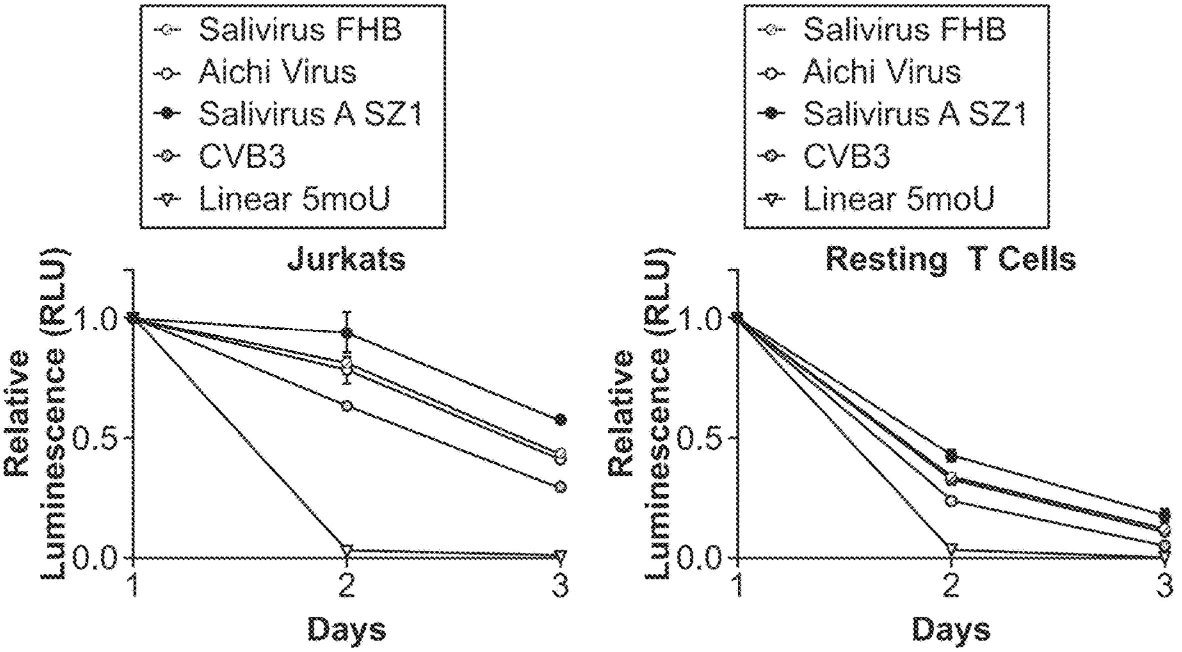

Luminescence from secreted *Gaussia* luciferase in supernatant was measured every 24 hours after electroporation, followed by complete media replacement. Functional stability data shown in FIG. 19B. Circular RNA had more functional stability than linear RNA in each case, with a more pronounced difference in Jurkat cells.

Example 19

Figure 20A:
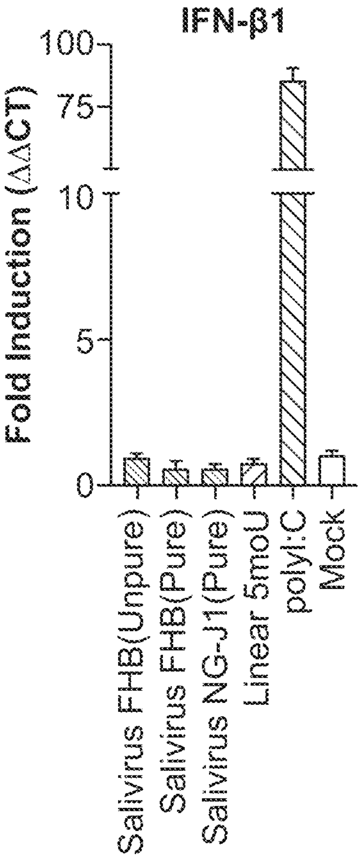
FIG. 20 depicts transcript induction of IFN-β1 (FIG. 20A), RIG-I (FIG. 20B), IL-2 (FIG. 20C), IL-6 (FIG. 20D), IFNγ (FIG. 20E), and TNFα (FIG. 20F) after electroporation of human CD3+ T cells with modified linear, unpurified circular, or purified circular RNA.
Figure 20B:
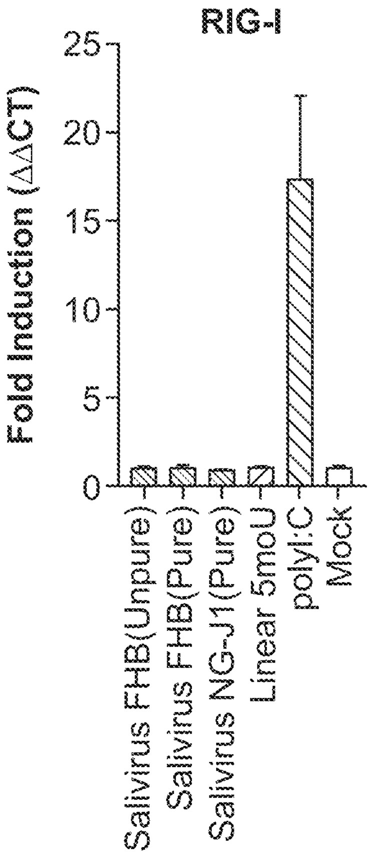
Figure 20C:
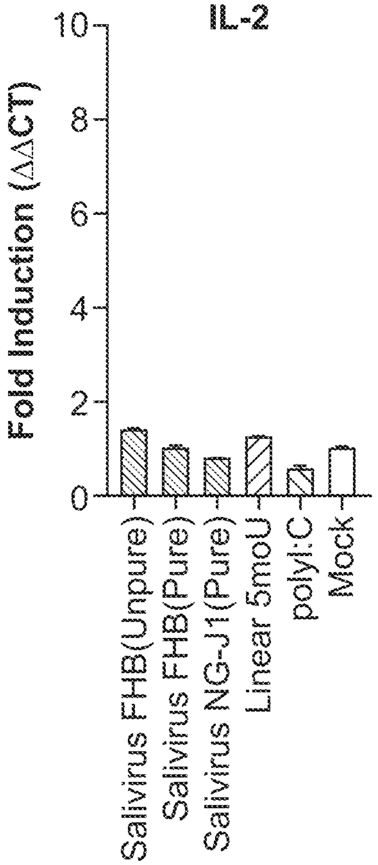
Figure 20D:
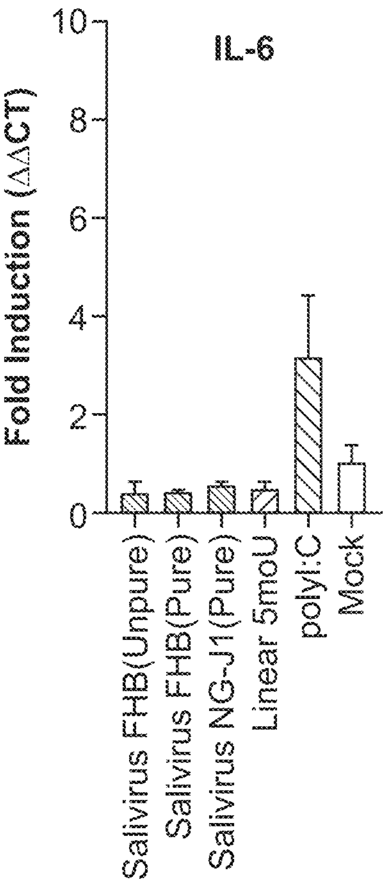
Figure 20E:
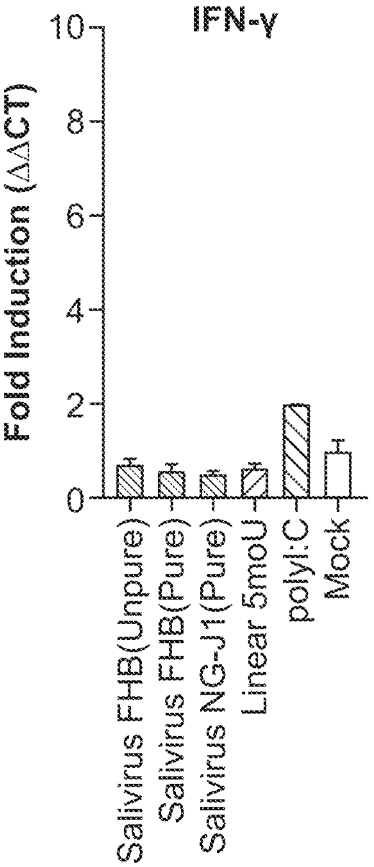
Figure 20F:
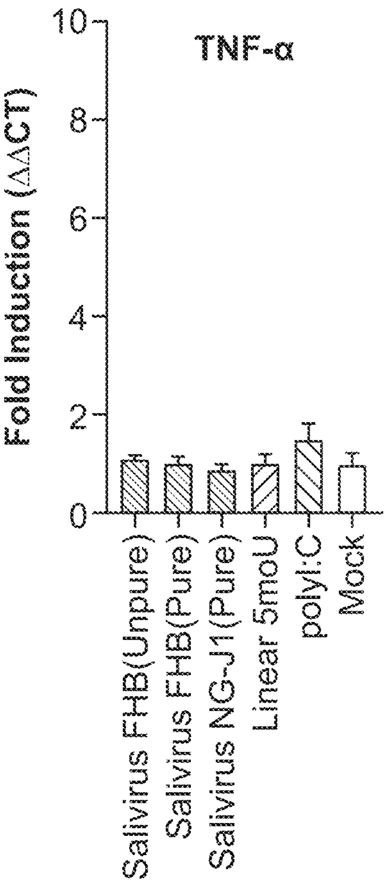

IFN-β1, RIG-I, IL-2, IL-6, IFNγ, and TNFα Transcript Induction of Cells Electroporated with Linear RNA or Varying Circular RNA Constructs Constructs including *Anabaena* intron/exon regions, a *Gaussia* luciferase expression sequence, and a subset of previously tested IRES were circularized and reaction products were purified by size exclusion HPLC. 150,000 CD3+ human T cells were electroporated with 1 μg of circular RNA, 5moU-mRNA, or immunostimulatory positive control poly inosine:cytosine. IFN-β1 (FIG. 20A), RIG-I (FIG. 20B), IL-2 (FIG. 20C), IL-6 (FIG. 20D), IFNγ (FIG. 20E), and TNFα (FIG. 20F) transcript induction was measured 18 hours after electroporation.

Example 20

Figure 21A:
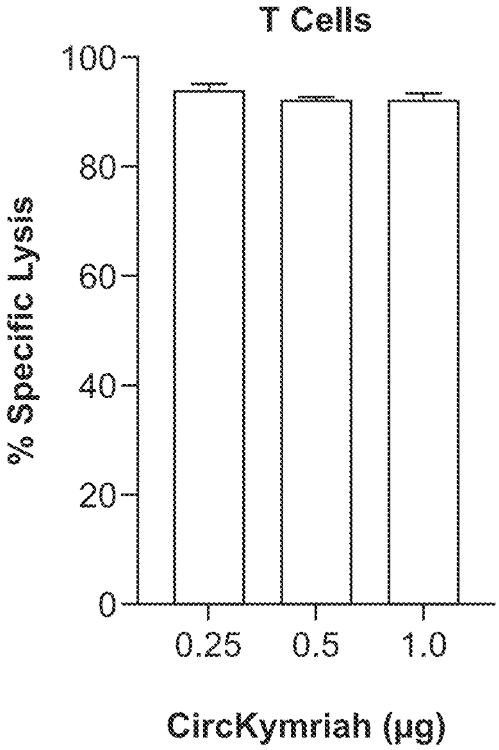
FIG. 21 depicts specific lysis of Raji target cells by human primary CD3+ T cells electroporated with circRNA encoding a CAR as determined by detection of firefly luminescence (FIG. 21A), and IFNγ transcript induction 24 hours after electroporation with different quantities of circular or linear RNA encoding a CAR sequence (FIG. 21B).
Figure 21B:
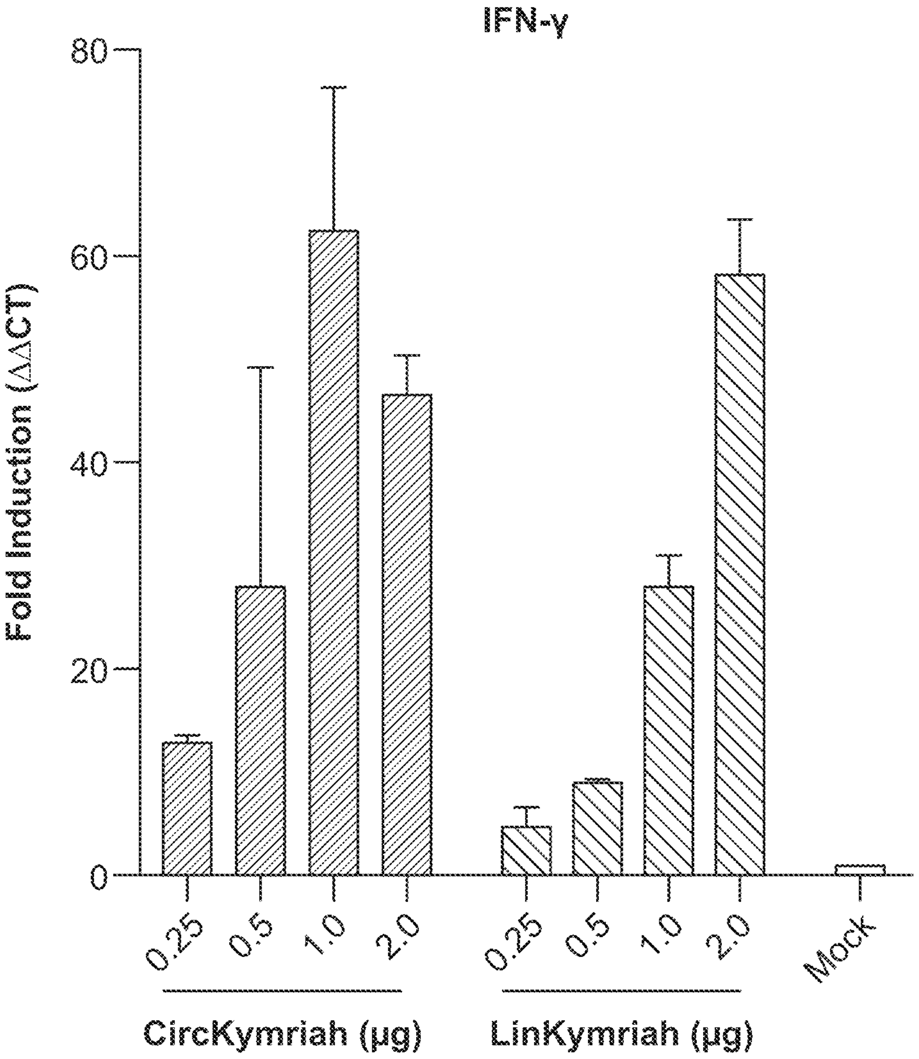

Specific Lysis of Target Cells and IFNγ Transcript Induction by CAR Expressing Cells Electroporated with Different Amounts of Circular or Linear RNA; Specific Lysis of Target and Non-Target Cells by CAR Expressing Cells at Different E:T Ratios Constructs including *Anabaena* intron/exon regions, an anti-CD19 CAR expression sequence, and a CVB3 IRES were circularized and reaction products were purified by size exclusion HPLC. 150,000 human primary CD3+ T cells either mock electroporated or electroporated with different quantities of circRNA encoding an anti-CD19 CAR sequence were co-cultured for 12 hours with Raji cells stably expressing GFP and firefly luciferase at an E:T ratio of 2:1. Specific lysis of Raji target cells was determined by detection of firefly luminescence (FIG. 21A). % Specific lysis was defined as 1-[CAR condition luminescence]/[mock condition luminescence]. IFNγ transcript induction was measured 24 hours after electroporation (FIG. 21B).

Figure 22A:
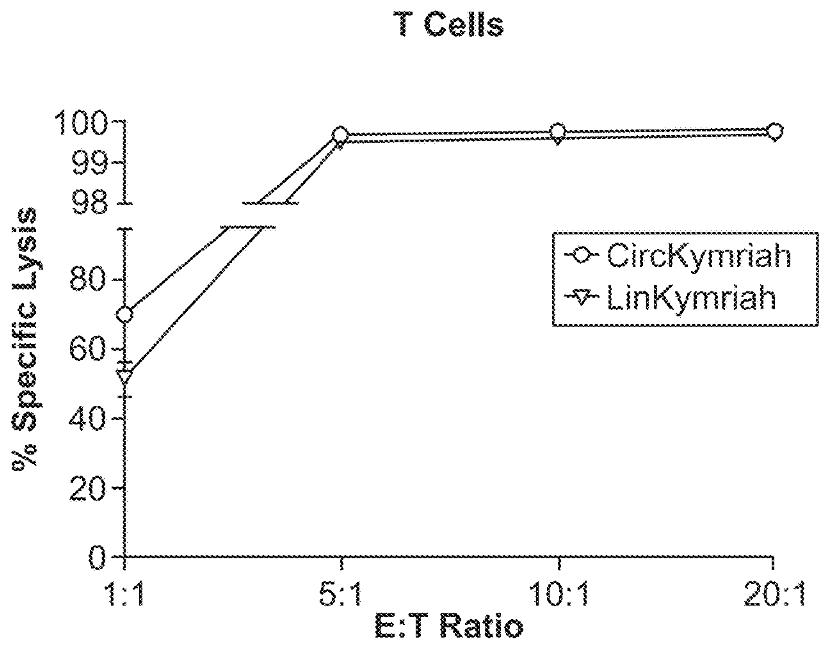
FIG. 22 depicts specific lysis of target or non-target cells by human primary CD3+ T cells electroporated with circular or linear RNA encoding a CAR at different E:T ratios (FIG. 22A and FIG. 22B) as determined by detection of firefly luminescence.

150,000 human primary CD3+ T cells were either mock electroporated or electroporated with 500 ng circRNA or m1ψ-mRNA encoding an anti-CD19 CAR sequence, then co-cultured for 24 hours with Raji cells stably expressing firefly luciferase at different E:T ratios. % Specific lysis of Raji target cells was determined by detection of firefly luminescence (FIG. 22A). % Specific lysis was defined as 1-[CAR condition luminescence]/[mock condition luminescence].

Figure 22B:
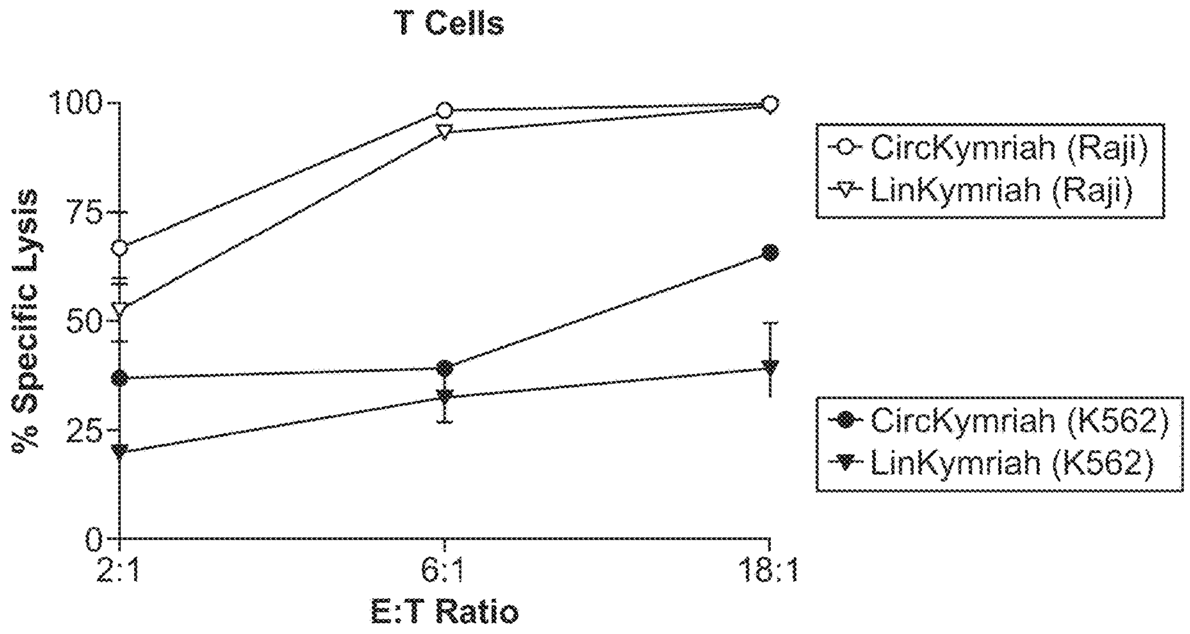

CAR expressing T cells were also co-cultured for 24 hours with Raji or K562 cells stably expressing firefly luciferase at different E:T ratios. Specific lysis of Raji target cells or K562 non-target cells was determined by detection of firefly luminescence (FIG. 22B). % Specific lysis is defined as 1-[CAR condition luminescence]/[mock condition luminescence].

Example 21

Figure 23:
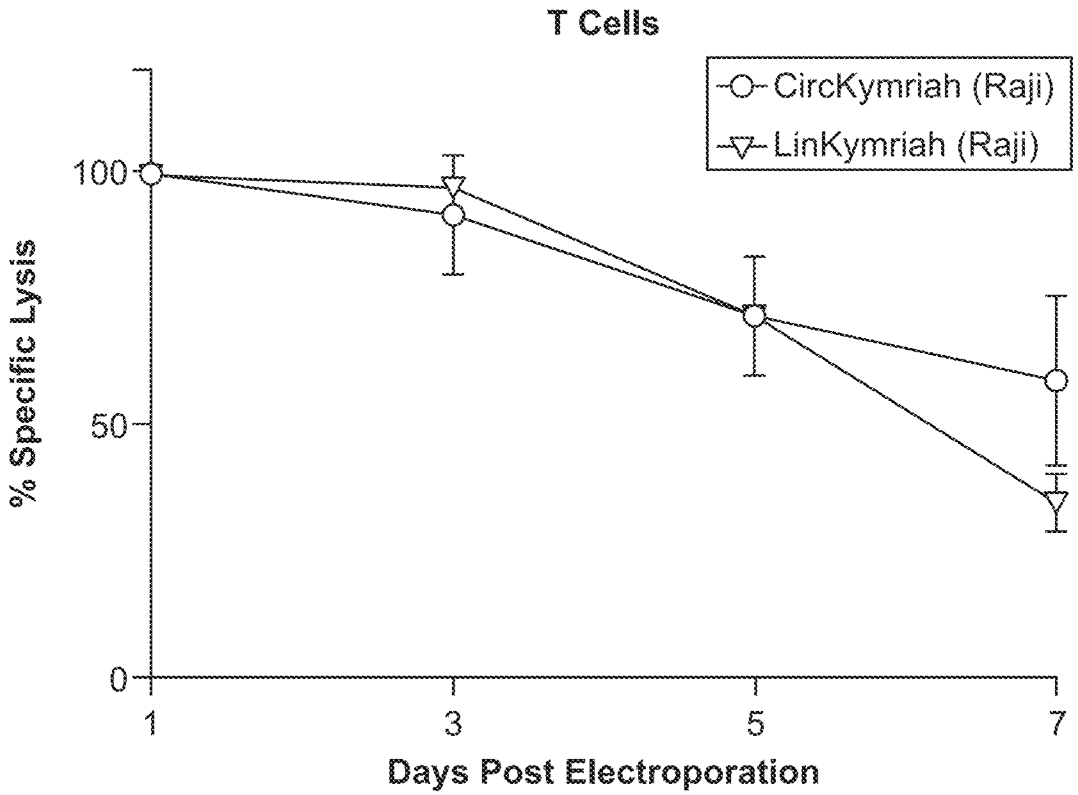
FIG. 23 depicts specific lysis of target cells by human CD3+ T cells electroporated with RNA encoding a CAR at 1, 3, 5, and 7 days post electroporation.

Specific Lysis of Target Cells by T Cells Electroporated with Circular RNA or Linear RNA Encoding a CAR Constructs including *Anabaena* intron/exon regions, an anti-CD19 CAR expression sequence, and a CVB3 IRES were circularized and reaction products were purified by size exclusion HPLC. Human primary CD3+ T cells were electroporated with 500 ng of circular RNA or an equimolar quantity of m1ψ-mRNA, each encoding a CD19-targeted CAR. Raji cells were added to CAR-T cell cultures over 7 days at an E:T ratio of 10:1. % Specific lysis was measured for both constructs at 1, 3, 5, and 7 days (FIG. 23).

Example 22

Figure 24:
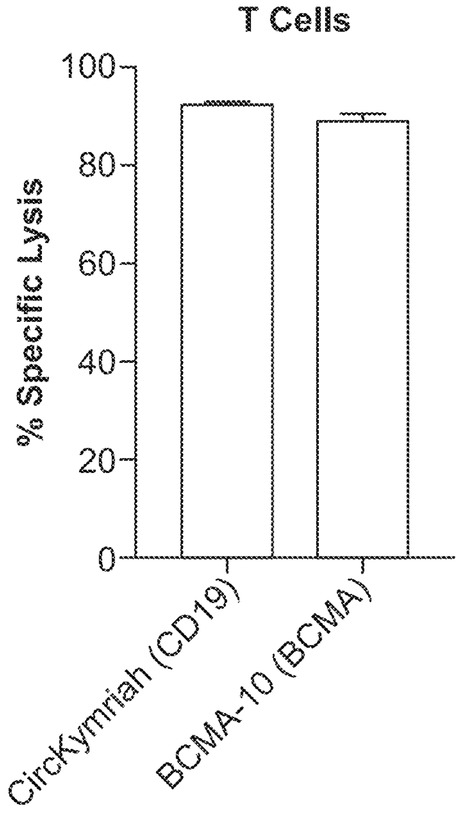
FIG. 24 depicts specific lysis of target cells by human CD3+ T cells electroporated with circular RNA encoding a CD19 or BCMA targeted CAR.

Specific Lysis of Raji Cells by T Cells Expressing an Anti-CD19 CAR or an Anti-BCMA CAR Constructs including *Anabaena* intron/exon regions, anti-CD19 or anti-BCMA CAR expression sequence, and a CVB3 IRES were circularized and reaction products were purified by size exclusion HPLC. 150,000 primary human CD3+ T cells were electroporated with 500 ng of circRNA, then were co-cultured with Raji cells at an E:T ratio of 2:1. % Specific lysis was measured 12 hours after electroporation (FIG. 24).

Example 23

Example 23A: Synthesis of Compounds

Synthesis of representative ionizable lipids of the invention are described in PCT applications PCT/US2016/052352, PCT/US2016/068300, PCT/US2010/061058, PCT/US2018/058555, PCT/US2018/053569, PCT/US2017/028981, PCT/US2019/025246, PCT/US2018/035419, PCT/US2019/015913, and US applications with publication numbers 20190314524, 20190321489, and 20190314284, the contents of each of which are incorporated herein by reference in their entireties.

Example 23B: Synthesis of Compounds

Synthesis of representative ionizable lipids of the invention are described in US patent publication number US20170210697A1, the contents of of which is incorporated herein by reference in its entirety.

Example 24

Protein Expression by Organ

Figure 25:
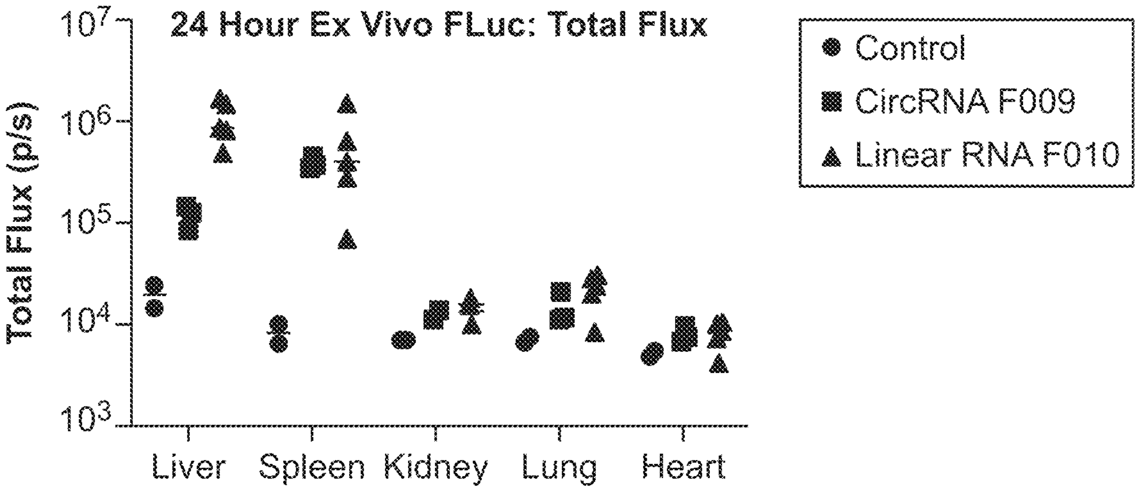
FIG. 25 depicts total Flux of organs harvested from CD-1 mice dosed with circular RNA encoding FLuc and formulated with 50% Lipid 15 (Table 10b), 10% DSPC, 1.5% PEG-DMG, and 38.5% cholesterol.
Figure 26:
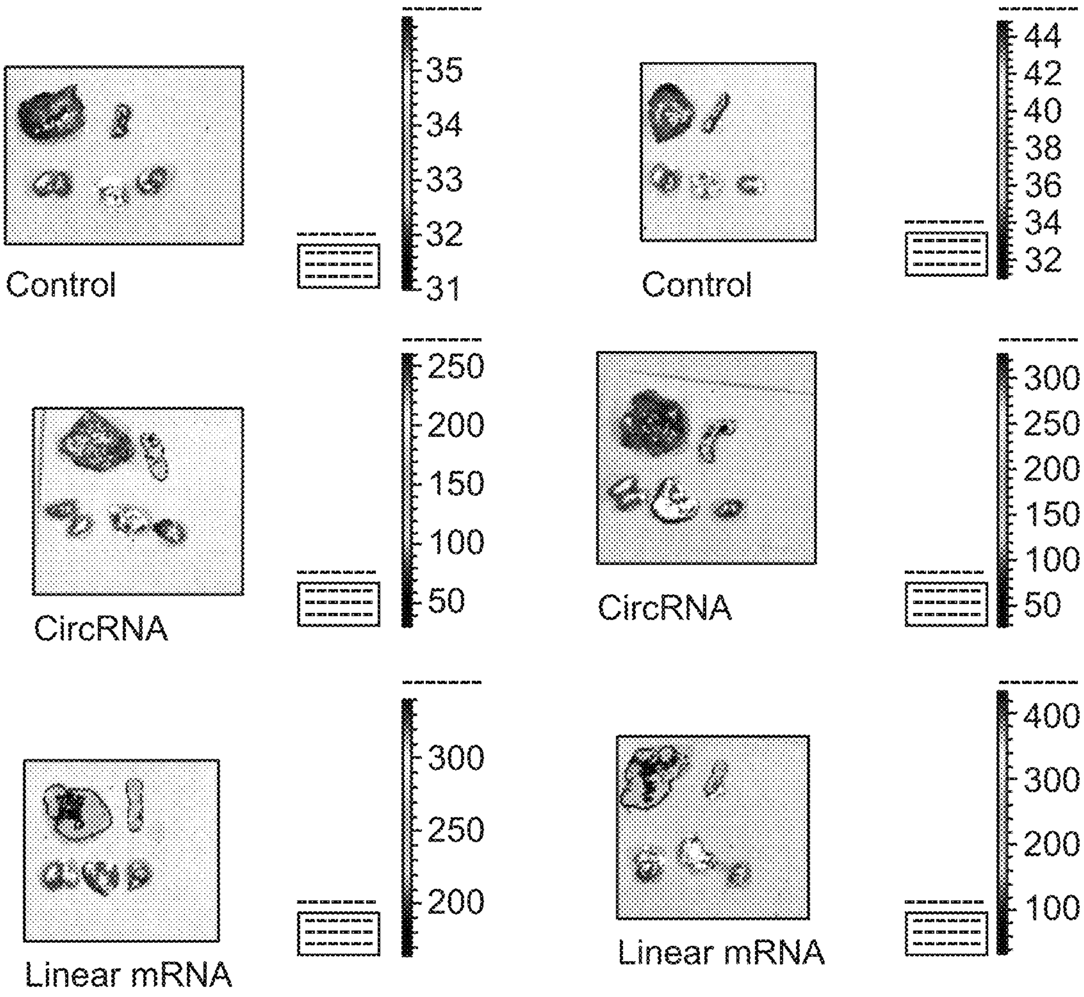
FIG. 26 shows images highlighting the luminescence of organs harvested from CD-1 mice dosed with circular RNA encoding FLuc and formulated with 50% Lipid 15 (Table 10b), 10% DSPC, 1.5% PEG-DMG, and 38.5% cholesterol.

Circular or linear RNA encoding FLuc was generated and loaded into transfer vehicles with the following formulation: 50% ionizable lipid 15 in Table 10b, 10% DSPC, 1.5% PEG-DMG, 38.5% cholesterol. CD-1 mice were dosed at 0.2 mg/kg and luminescence was measured at 6 hours (live IVIS) and 24 hours (live IVIS and ex vivo IVIS). Total Flux (photons/second over a region of interest) of the liver, spleen, kidney, lung, and heart was measured (FIGS. 25 and 26).

Example 25

Distribution of Expression in the Spleen

Circular or linear RNA encoding GFP is generated and loaded into transfer vehicles with the following formulation: 50% ionizable lipid 15 in Table 10b, 10% DSPC, 1.5% PEG-DMG, 38.5% cholesterol. The formulation is administered to CD-1 mice. Flow cytometry is run on spleen cells to determine the distribution of expression across cell types.

Example 26

Production of Nanoparticle Compositions

In order to investigate safe and efficacious nanoparticle compositions for use in the delivery of circular RNA to cells, a range of formulations are prepared and tested. Specifically, the particular elements and ratios thereof in the lipid component of nanoparticle compositions are optimized.

Nanoparticles can be made in a 1 fluid stream or with mixing processes such as microfluidics and T-junction mixing of two fluid streams, one of which contains the circular RNA and the other has the lipid components.

Lipid compositions are prepared by combining an ionizable lipid, optionally a helper lipid (such as DOPE, DSPC, or oleic acid obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala.), and a structural lipid such as cholesterol at concentrations of about, e.g., 40 or 50 mM in a solvent, e.g., ethanol. Solutions should be refrigerated for storage at, for example, −20° C. Lipids are combined to yield desired molar ratios (see, for example, Tables 31a and 31b below) and diluted with water and ethanol to a final lipid concentration of e.g., between about 5.5 mM and about 25 mM.

TABLE 31a

| Formulation number | Description |
|---|---|
| 1 | Aliquots of 50 mg/mL ethanolic solutions of C12-200, DOPE, Chol and DMG-PEG2K (40:30:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 2 | Aliquots of 50 mg/mL ethanolic solutions of DODAP, DOPE, cholesterol and DMG-PEG2K (18:56:20:6) are mixed and diluted with ethanol to 3 mL final volume. Separately, an aqueous buffered solution (10mM citrate/150mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.35 mg/mL EPO circRNA (encapsulated). Zave = 75.9 nm (Dv(50) = 57.3 nm; Dv(90) = 92.1 nm). |
| 3 | Aliquots of 50 mg/mL ethanolic solutions of HGT4003, DOPE, cholesterol and DMG-PEG2K (50:25:20:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 4 | Aliquots of 50 mg/mL ethanolic solutions of ICE, DOPE and DMG-PEG2K (70:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 5 | Aliquots of 50 mg/mL ethanolic solutions of HGT5000, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.82 mg/mL EPO mRNA (encapsulated). Zave = 105.6 nm (Dv(50) = 53.7 nm; Dv(90) = 157 nm). |
| 6 | Aliquots of 50 mg/mL ethanolic solutions of HGT5001, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |

In some embodiments, transfer vehicle has a formulation as described in Table 31a.

TABLE 31b

| Composition (mol %) | Components |
|---|---|
| 40:20:38.5:1.5 | Compound:Phospholipid:Phytosterol*:PEG-DMG |
| 45:15:38.5:1.5 | Compound:Phospholipid:Phytosterol*:PEG-DMG |
| 50:10:38.5:1.5 | Compound:Phospholipid:Phytosterol*:PEG-DMG |

TABLE 31b-continued

| Composition (mol %) | Components |
|---|---|
| 55:5:38.5:1.5 | Compound:Phospholipid:Phytosterol*:PEG-DMG |
| 60:5:33.5:1.5 | Compound:Phospholipid:Phytosterol*:PEG-DMG |
| 45:20:33.5:1.5 | Compound:Phospholipid:Phytosterol*:PEG-DMG |
| 50:20:28.5:1.5 | Compound:Phospholipid:Phytosterol*:PEG-DMG |
| 55:20:23.5:1.5 | Compound:Phospholipid:Phytosterol*:PEG-DMG |
| 60:20:18.5:1.5 | Compound:Phospholipid:Phytosterol*:PEG-DMG |
| 40:15:43.5:1.5 | Compound:Phospholipid:Phytosterol*:PEG-DMG |
| 50:15:33.5:1.5 | Compound:Phospholipid:Phytosterol*:PEG-DMG |
| 55:15:28.5:1.5 | Compound:Phospholipid:Phytosterol*:PEG-DMG |
| 60:15:23.5:1.5 | Compound:Phospholipid:Phytosterol*:PEG-DMG |

TABLE 31b-continued

| Composition (mol %) | Components |
|---|---|
| 40:10:48.5:1.5 | Compound:Phospholipid:Phytosterol*:PEG-DMG |
| 45:10:43.5:1.5 | Compound:Phospholipid:Phytosterol*:PEG-DMG |
| 55:10:33.5:1.5 | Compound:Phospholipid:Phytosterol*:PEG-DMG |
| 60:10:28.5:1.5 | Compound:Phospholipid:Phytosterol*:PEG-DMG |
| 40:5:53.5:1.5 | Compound:Phospholipid:Phytosterol*:PEG-DMG |
| 45:5:48.5:1.5 | Compound:Phospholipid:Phytosterol*:PEG-DMG |
| 50:5:43.5:1.5 | Compound:Phospholipid:Phytosterol*:PEG-DMG |

TABLE 31b-continued

| Composition (mol %) | Components |
|---|---|
| 40:20:40:0 | Compound:Phospholipid:Phytosterol*:PEG-DMG |
| 45:20:35:0 | Compound:Phospholipid:Phytosterol*:PEG-DMG |
| 50:20:30:0 | Compound:Phospholipid:Phytosterol*:PEG-DMG |
| 55:20:25:0 | Compound:Phospholipid:Phytosterol*:PEG-DMG |
| 60:20:20:0 | Compound:Phospholipid:Phytosterol*:PEG-DMG |
| 40:15:45:0 | Compound:Phospholipid:Phytosterol*:PEG-DMG |

In some embodiments, transfer vehicle has a formulation as described in Table 31b.

For nanoparticle compositions including circRNA, solutions of the circRNA at concentrations of 0.1 mg/ml in deionized water are diluted in a buffer, e.g., 50 mM sodium citrate buffer at a pH between 3 and 4 to form a stock solution. Alternatively, solutions of the circRNA at concentrations of 0.15 mg/ml in deionized water are diluted in a buffer, e.g., 6.25 mM sodium acetate buffer at a pH between 3 and 4.5 to form a stock solution.

Nanoparticle compositions including a circular RNA and a lipid component are prepared by combining the lipid solution with a solution including the circular RNA at lipid component to circRNA wt:wt ratios between about 5:1 and about 50:1. The lipid solution is rapidly injected using, e.g., a NanoAssemblr microfluidic based system at flow rates between about 10 ml/min and about 18 ml/min or between about 5 ml/min and about 18 ml/min into the circRNA solution, to produce a suspension with a water to ethanol ratio between about 1:1 and about 4:1.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kDa or 20 kDa. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.15 mg/ml are generally obtained.

The method described above induces nano-precipitation and particle formation.

Alternative processes including, but not limited to, T-junction and direct injection, may be used to achieve the same nano-precipitation. B. Characterization of nanoparticle compositions A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of circRNA in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

A QUANT-IT™ RIBOGREEN® RNA assay (Invitrogen Corporation Carlsbad, Calif.) can be used to evaluate the encapsulation of circRNA by the nanoparticle composition. The samples are diluted to a concentration of approximately 5 μg/mL or 1 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2-4% Triton X-100 solution is added to the wells. The plate is incubated at a temperature of 37° C. for 15 minutes. The RIBOGREEN® reagent is diluted 1:100 or 1:200 in TE buffer, and 100 μL of this solution is added to each well. The fluorescence intensity can be measured using a fluorescence plate reader (Wallac Victor 1420 Multilabel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free circRNA is determined by dividing the fluorescence intensity of the intact sample (without addition of Triton X-100) by the fluorescence value of the disrupted sample (caused by the addition of Triton X-100). C.

In Vivo Formulation Studies:

In order to monitor how effectively various nanoparticle compositions deliver circRNA to targeted cells, different nanoparticle compositions including circRNA are prepared and administered to rodent populations. Mice are intravenously, intramuscularly, intraarterially, or intratumorally administered a single dose including a nanoparticle composition with a lipid nanoparticle formulation. In some instances, mice may be made to inhale doses. Dose sizes may range from 0.001 mg/kg to 10 mg/kg, where 10 mg/kg describes a dose including 10 mg of a circRNA in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. Time courses of protein expression can also be evaluated. Samples collected from the rodents for evaluation may include blood and tissue (for example, muscle tissue from the site of an intramuscular injection and internal tissue); sample collection may involve sacrifice of the animals.

Higher levels of protein expression induced by administration of a composition including a circRNA will be indicative of higher circRNA translation and/or nanoparticle composition circRNA delivery efficiencies. As the non-RNA components are not thought to affect translational machineries themselves, a higher level of protein expression is likely indicative of a higher efficiency of delivery of the circRNA by a given nanoparticle composition relative to other nanoparticle compositions or the absence thereof.

Example 27

Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the transfer vehicle compositions in 1×PBS in determining particle size and 15 mM PBS in determining zeta potential.

Ultraviolet-visible spectroscopy can be used to determine the concentration of a therapeutic and/or prophylactic (e.g., RNA) in transfer vehicle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of therapeutic and/or prophylactic in the transfer vehicle composition can be calculated based on the extinction coefficient of the therapeutic and/or prophylactic used in the composition and on the difference between the absorbance at a wavelength of, for example, 260 nm and the baseline value at a wavelength of, for example, 330 nm.

For transfer vehicle compositions including RNA, a QUANT-IT™ RIBOGREEN® RNA assay (Invitrogen Corporation Carlsbad, Calif.) can be used to evaluate the encapsulation of RNA by the transfer vehicle composition. The samples are diluted to a concentration of approximately 5 μg/mL or 1 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2-4% Triton X-100 solution is added to the wells. The plate is incubated at a temperature of 37° C. for 15 minutes. The RIBOGREEN® reagent is diluted 1:100 or 1:200 in TE buffer, and 100 μL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Example 28

T Cell Targeting

To target transfer vehicles to T-cells, T cell antigen binders, e.g., anti-CD8 antibodies, are coupled to the surface of the transfer vehicle. Anti-T cell antigen antibodies are mildly reduced with an excess of DTT in the presence of EDTA in PBS to expose free hinge region thiols. To remove DTT, antibodies are passed through a desalting column. The heterobifunctional cross-linker SM(PEG)24 is used to anchor antibodies to the surface of circRNA-loaded transfer vehicles (Amine groups are present in the head groups of PEG lipids, free thiol groups on antibodies were created by DTT, SM(PEG)24 cross-links between amines and thiol groups). Transfer vehicles are first incubated with an excess of SM(PEG)24 and centrifuged to remove unreacted cross-linker. Activated transfer vehicles are then incubated with an excess of reduced anti-T cell antigen antibody. Unbound antibody is removed using a centrifugal filtration device.

Example 29

RNA Containing Transfer Vehicle Using RV88

In this example RNA containing transfer vehicles are synthesized using the 2-D vortex microfluidic chip with the cationic lipid RV88 for delivery of circRNA.

RV88

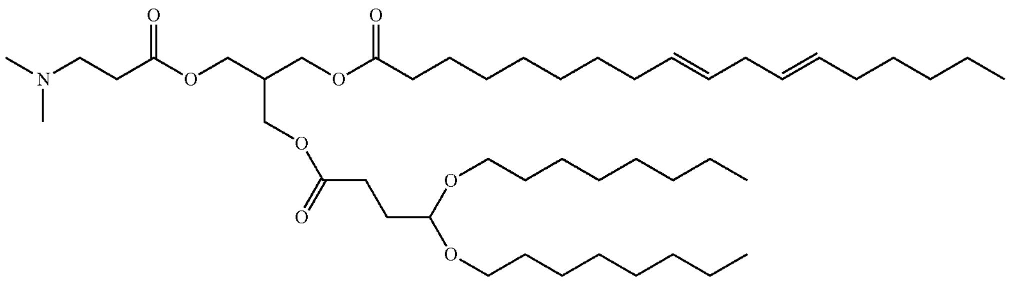

TABLE 32a

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV88 | GVK bio | |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-IT RiboGreen RNA Assay kit | Molecular Probes/ Life Technologies | R11490 |
| Black 96-well microplates | Greiner | 655900 |

RV88, DSPC, and cholesterol all being prepared in ethanol at a concentration of 10 mg/ml in borosilica vials. The lipid 14:0-PEG2K PE is prepared at a concentration of 4 mg/ml also in a borosilica glass vial. Dissolution of lipids at stock concentrations is attained by sonication of the lipids in ethanol for 2 min. The solutions are then heated on an orbital tilting shaker set at 170 rpm at 37° C. for 10 min. Vials are then equilibrated at 26° C. for a minimum of 45 min. The lipids are then mixed by adding volumes of stock lipid as shown in Table 32b. The solution is then adjusted with ethanol such that the final lipid concentration was 7.92 mg/ml.

TABLE 32b

| Composition | MW | % | nmoles | mg | Stock (mg/ml) | ul | Ethanol (ul) |
|---|---|---|---|---|---|---|---|
| RV88 | 794.2 | 40% | 7200 | 5.72 | 10 | 571.8 | 155.3 |
| DSPC | 790.15 | 10% | 1800 | 1.42 | 10 | 142.2 | |
| Cholesterol | 386.67 | 48% | 8640 | 3.34 | 10 | 334.1 | |
| PEG2K | 2693.3 | 2% | 380 | 0.97 | 4 | 242.4 | |

RNA is prepared as a stock solution with 75 mM Citrate buffer at pH 6.0 and a concentration of RNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the RNA-liposomes is exchanged by using G-25 mini desalting columns to 10 mM Tris-HCl, 1 mM EDTA, at pH 7.5. Following buffer exchange, the materials are characterized for size, and RNA entrapment through DLS analysis and Ribogreen assays, respectively.

Example 30

RNA Containing Transfer Vehicle Using RV94

In this example, RNA containing liposome are synthesized using the 2-D vortex microfluidic chip with the cationic lipid RV94 for delivery of circRNA.

TABLE 33-continued

| Materials and Instrument | Vendor | Cat # |
|---|---|---|
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-IT RiboGreen RNA Assay kit | Molecular Probes/ Life Technologies | R11490 |
| Black 96-well microplates | Greiner | 655900 |

The lipids were prepared as in Example 29 using the material amounts named in Table 34 to a final lipid concentration of 7.92 mg/ml.

TABLE 34

| Composition | MW | % | nmoles | mg | Stock (mg/ml) | ul | Ethanol (ul) |
|---|---|---|---|---|---|---|---|
| RV94 | 808.22 | 40% | 2880 | 2.33 | 10 | 232.8 | 155.3 |
| DSPC | 790.15 | 10% | 720 | 0.57 | 10 | 56.9 | |
| Cholesterol | 386.67 | 48% | 3456 | 1.34 | 10 | 133.6 | |
| PEG2K | 2693.3 | 2% | 144 | 0.39 | 4 | 97.0 | |

The aqueous solution of circRNA is prepared as a stock solution with 75 mM Citrate buffer at pH 6.0 the circRNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the circRNA-transfer vehicles is exchanged by using G-25 mini desalting columns to 10 mM Tris-HCl, 1 mM EDTA, at pH 7.5, as described above. Following buffer exchange, the materials are characterized for size, and RNA entrapment through DLS analysis and Ribogreen assays, respectively. The biophysical analysis of the liposomes is shown in Table 35.

RV94

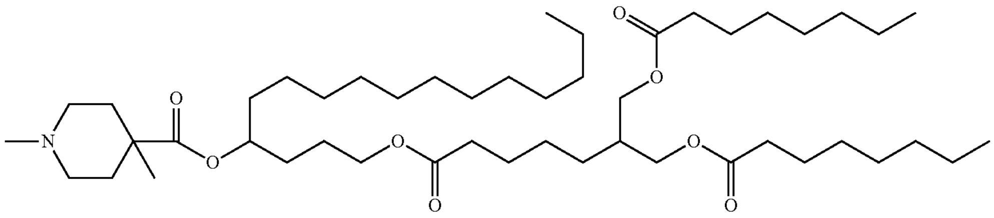

TABLE 33

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV94 | GVK bio | |
| DSPC | Lipoid | 556500 |

TABLE 35

| Sample Name | NP Ratio | TFR ml/min | Ratio (aqueous/org phase) | RNA encapsulatiom amount (μg/ml) | RNA encapsulatiom yield % | size d · nm | size PDI |
|---|---|---|---|---|---|---|---|
| SAM-RV94 | 8 | 22 | 2 | 31.46 | 86.9 | 113.1 | 0.12 |

Example 31

General Protocol for in Line Mixing

Individual and separate stock solutions are prepared—one containing lipid and the other circRNA. Lipid stock containing a desired lipid or lipid mixture, DSPC, cholesterol and PEG lipid is prepared by solubilized in 90% ethanol. The remaining 10% is low pH citrate buffer. The concentration of the lipid stock is 4 mg/mL. The pH of this citrate buffer can range between pH 3 and pH 5, depending on the type of lipid employed. The circRNA is also solubilized in citrate buffer at a concentration of 4 mg/mL. 5 mL of each stock solution is prepared.

Stock solutions are completely clear and lipids are ensured to be completely solubilized before combining with circRNA. Stock solutions may be heated to completely solubilize the lipids. The circRNAs used in the process may be unmodified or modified oligonucleotides and may be conjugated with lipophilic moieties such as cholesterol.

The individual stocks are combined by pumping each solution to a T-junction. A dual-head Watson-Marlow pump was used to simultaneously control the start and stop of the two streams. A 1.6 mm polypropylene tubing is further downsized to 0.8 mm tubing in order to increase the linear flow rate. The polypropylene line (ID=0.8 mm) are attached to either side of a T-junction. The polypropylene T has a linear edge of 1.6 mm for a resultant volume of 4.1 $mm^3$. Each of the large ends (1.6 mm) of polypropylene line is placed into test tubes containing either solubilized lipid stock or solubilized circRNA. After the T-junction, a single tubing is placed where the combined stream exited. The tubing is then extended into a container with 2× volume of PBS, which is rapidly stirred. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

C57BL/6 mice (Charles River Labs, MA) receive either saline or formulated circRNA via tail vein injection. At various time points after administration, serum samples are collected by retroorbital bleed. Serum levels of Factor VII protein are determined in samples using a chromogenic assay (Biophen FVTI, Aniara Corporation, OH). To determine liver RNA levels of Factor VII, animals are sacrificed and livers are harvested and snap frozen in liquid nitrogen. Tissue lysates are prepared from the frozen tissues and liver RNA levels of Factor VII are quantified using a branched DNA assay (QuantiGene Assay, Panomics, CA).

FVII activity is evaluated in FVTI siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 32 circRNA Formulation Using Preformed Vesicles

Cationic lipid containing transfer vehicles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. For cationic lipid mixtures which do not form small vesicles, hydrating the lipid mixture with a lower pH buffer (50 mM citrate, pH 3) to protonate the phosphate group on the DSPC headgroup helps form stable 70-90 nm vesicles.

The FVII circRNA (solubilised in a 50 mM citrate, pH 4 aqueous solution containing 30% ethanol) is added to the vesicles, pre-equilibrated to 35° C., at a rate of ~5 mL/min with mixing. After a final target circRNA/lipid ratio of 0.06 (wt wt) is achieved, the mixture is incubated for a further 30 min at 35° C. to allow vesicle re-organization and encapsulation of the FVII RNA. The ethanol is then removed and the external buffer replaced with PBS (155 mM NaCl, 3 mM Na2HP04, ImM KH2P04, pH 7.5) by either dialysis or tangential flow diafiltration. The final encapsulated circRNA-to-lipid ratio is determined after removal of unencapsulated RNA using size-exclusion spin columns or ion exchange spin columns.

Example 33

Expression of Trispecific Antigen Binding Proteins from Engineered Circular RNA

Circular RNAs are designed to include: (1) a 3' post splicing group I intron fragment; (2) an Internal Ribosome Entry Site (IRES); (3) a trispecific antigen-binding protein coding region; and (4) a 3' homology region. The trispecific antigen-binding protein regions are constructed to produce an exemplary trispecific antigen-binding protein that will bind to a target antigen, e.g., GPC3.

Generation of a scFv CD3 Binding Domain

The human CD3epsilon chain canonical sequence is Uniprot Accession No. P07766. The human CD3gamma chain canonical sequence is Uniprot Accession No. P09693. The human CD3delta chain canonical sequence is Uniprot Accession No. P043234. Antibodies against CD3epsilon, CD3gamma or CD3delta are generated via known technologies such as affinity maturation. Where murine anti-CD3 antibodies are used as a starting material, humanization of murine anti-CD3 antibodies is desired for the clinical setting, where the mouse-specific residues may induce a human-anti-mouse antigen (HAMA) response in subjects who receive treatment of a trispecific antigen-binding protein described herein. Humanization is accomplished by grafting CDR regions from murine anti-CD3 antibody onto appropriate human germline acceptor frameworks, optionally including other modifications to CDR and/or framework regions.

Human or humanized anti-CD3 antibodies are therefore used to generate scFv sequences for CD3 binding domains of a trispecific antigen-binding protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e. VL-VH, or VH-VL orientation), and three copies of the "G4S" or "$G_4S$" subunit $(G_4S)_3$ connect the variable domains to create the scFv domain. Anti-CD3 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD3-expressing cells.

Generation of a scFv Glypican-3 (GPC3) Binding Domain

Glypican-3 (GPC3) is one of the cell surface proteins present on Hepatocellular Carcinoma but not on healthy normal liver tissue. It is frequently observed to be elevated in hepatocellular carcinoma and is associated with poor prognosis for HCC patients. It is known to activate Wnt signalling. GPC3 antibodies have been generated including MDX-1414, HN3, GC33, and YP7.

A scFv binding to GPC-3 or another target antigen is generated similarly to the above method for generation of a scFv binding domain to CD3.

Expression of Trispecific Antigen-Binding Proteins In Vitro

A CHO cell expression system (FIp-In®, Life Technologies), a derivative of CHO-Kl Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted trispecific antigen-binding proteins are generated by transfection of suspension-adapted cells. During selection with the antibiotic Hygromycin B viable cell densities are measured twice a week, and cells are centrifuged and resuspended in fresh selection medium at a maximal density of $0.1\times10^6$ viable cells/mL. Cell pools stably expressing trispecific antigen-binding proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Trispecific antigen-binding proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Trispecific Antigen-Binding Proteins

Trispecific antigen-binding proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL Purity and homogeneity (typically >90%) of final samples are assessed by SDS PAGE under reducing and non-reducing conditions, followed by immunoblotting using an anti-(half-life extension domain) or anti idiotype antibody as well as by analytical SEC, respectively. Purified proteins are stored at aliquots at −80° C. until use.

Example 34

Expression of Engineered Circular RNA with a Half-Life Extension Domain has Improved Pharmacokinetic Parameters than without a Half-Life Extension Domain The trispecific antigen-binding protein encoded on a circRNA molecule of example 23 is administered to cynomolgus monkeys as a 0.5 mg/kg bolus injection intramuscularly. Another cynomolgus monkey group receives a comparable protein encoded on a circRNA molecule in size with binding domains to CD3 and GPC-3, but lacking a half-life extension domain. A third and fourth group receive a protein encoded on a circRNA molecule with CD3 and half-life extension domain binding domains and a protein with GPC-3 and half-life extension domains, respectively. Both proteins encoded by circRNA are comparable in size to the trispecific antigen-binding protein. Each test group consists of 5 monkeys. Serum samples are taken at indicated time points, serially diluted, and the concentration of the proteins is determined using a binding ELISA to CD3 and/or GPC-3.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-at}+Be^{-pt}$, where c(t) is the plasma concentration at time t, A and B are intercepts on the Y-axis, and a and β are the apparent first-order rate constants for the distribution and elimination phases, respectively. The a-phase is the initial phase of the clearance and reflects distribution of the protein into all extracellular fluid of the animal, whereas the second or β-phase portion of the decay curve represents true plasma clearance. Methods for fitting such equations are well known in the art. For example, A=D/V(a−k21)/(a−p), B=D/V(p−k21)/(a−p), and a and β (for α>β) are roots of the quadratic equation: $r^2$+(k12+k21+k10)r+k21k10=0 using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09

Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, EST: Handbook Of Basic Pharmacokinetics Including Clinical Applications, 5th edition, American Pharmaceutical Assoc., Washington, D C.

It is expected that the trispecific antigen-binding protein encoded on a circRNA molecule of Example 23 has improved pharmacokinetic parameters such as an increase in elimination half-time as compared to proteins lacking a half-life extension domain.

Example 35

Cytotoxicity of the Trispecific Antigen-Binding Protein

The trispecific antigen-binding protein encoded on a circRNA molecule of Example 23 is evaluated in vitro on its mediation of T cell dependent cytotoxicity to GPC-3+ target cells.

Fluorescence labeled GPC3 target cells are incubated with isolated PBMC of random donors or T-cells as effector cells in the presence of the trispecific antigen-binding protein of Example 23. After incubation for 4 h at 37° C. in a humidified incubator, the release of the fluorescent dye from the target cells into the supernatant is determined in a spectrofluorimeter. Target cells incubated without the trispecific antigen-binding protein of Example 23 and target cells totally lysed by the addition of saponin at the end of the incubation serve as negative and positive controls, respectively.

Based on the measured remaining living target cells, the percentage of specific cell lysis is calculated according to the following formula: [1-(number of living targets(sample)/number of living targets(spontaneous))]×100%. Sigmoidal dose response curves and EC50 values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 36

Synthesis of Ionizable Lipids

38.1 Synthesis of ((3-(2-methyl-1H-imidazol-1-yl)propyl)azanediyl)bis(hexane-6,1-diyl) bis(2-hexyldecanoate) (Lipid 27, Table 10a) and ((3-(1H-imidazol-1-yl)propyl)azanediyl)bis(hexane-6,1-diyl) bis(2-hexyldecanoate)) (Lipid 26, Table 10a)

In a 100 mL round bottom flask connected with condenser, 3-(1H-imidazol-1-yl)propan-1-amine (100 mg, 0.799 mmol) or 3-(2-methyl-1H-imidazol-1-yl)propan-1-amine (0.799 mmol), 6-bromohexyl 2-hexyldecanoate (737.2 mg, 1.757 mmol), potassium carbonate (485 mg, 3.515 mmol) and potassium iodide (13 mg, 0.08 mmol) were mixed in acetonitrile (30 mL), and the reaction mixture was heated to 80° C. for 48 h. The mixture was cooled to room temperature and was filtered through a pad of Celite. The filtrate was diluted with ethyl acetate. After washing with water, brine and dried over anhydrous sodium sulfate. The solvent was evaporated and the crude residue was purified by flash chromatography ($SiO_2$:$CH_2Cl_2$=100% to 10% of methanol in $CH_2Cl_2$) and colorless oil product was obtained (92 mg, 15%). Molecular formula of ((3-(1H-imidazol-1-yl)propyl)azanediyl)bis(hexane-6,1-diyl) bis(2-hexyldecanoate)) is $C_{50}H_{95}N_3O_4$ and molecular weight (Mw) is 801.7.

Reaction Scheme for Synthesis of ((3-(1H-imidazol-1-yl)propyl)azanediyl)bis(hexane-6,1-diyl) bis(2-hexyldecanoate)) (Lipid 26, Table 10a)

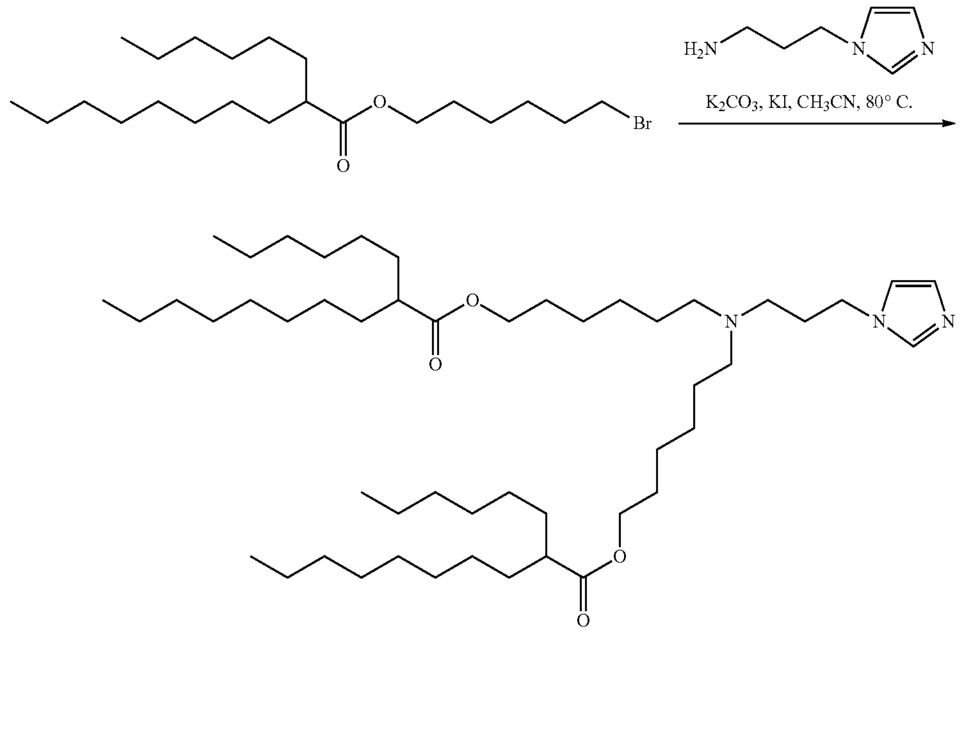 [SMILES: CCCCCCCCC(CCCCCC)C(=O)OCCCCCCBr ; NCCCn1ccnc1 ; CCCCCCCCC(CCCCCC)C(=O)OCCCCCCN(CCCCCCOC(=O)C(CCCCCC)CCCCCCCC)CCCn1ccnc1]

Figure 27A:
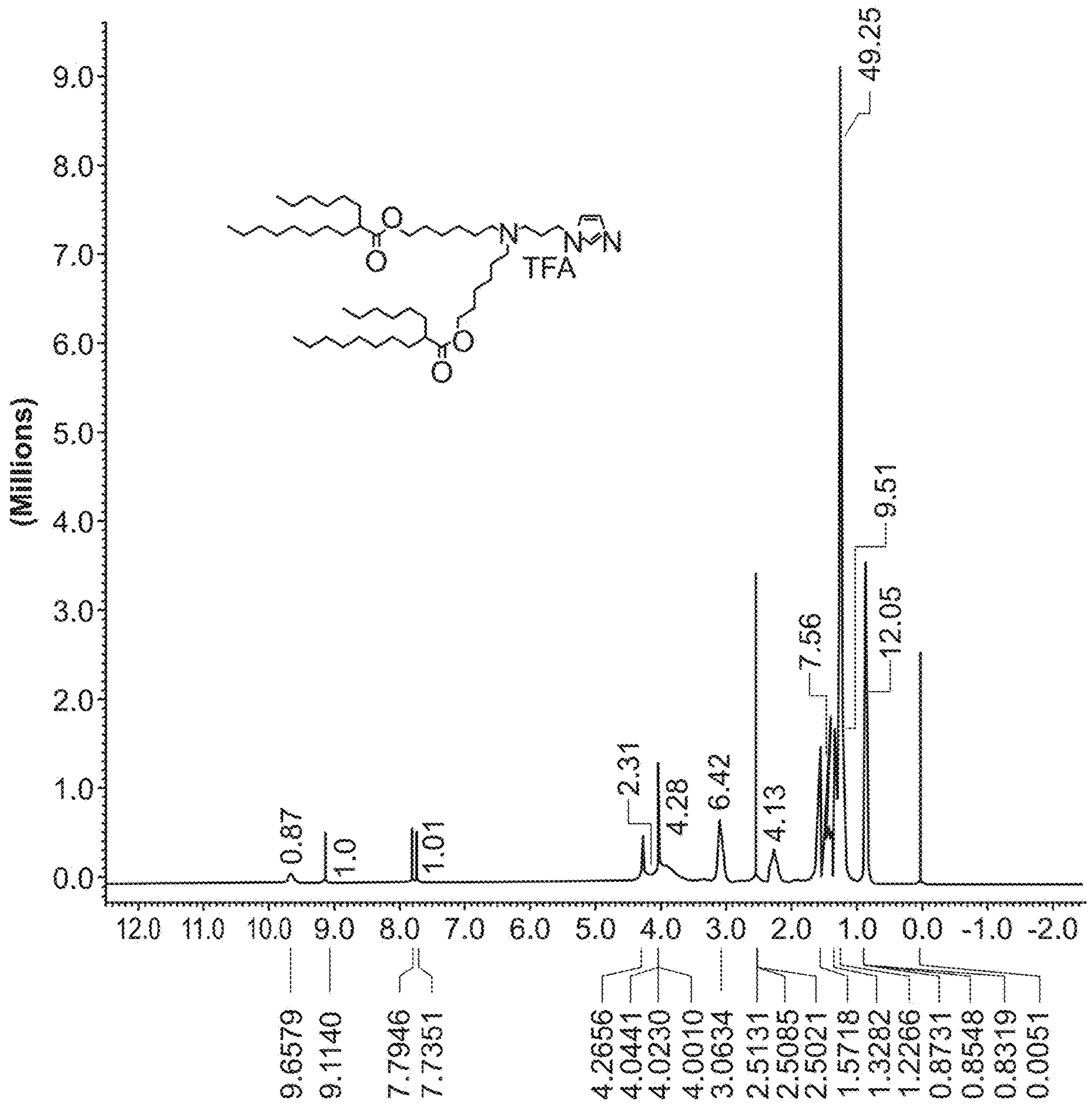
FIG. 27A shows the proton nuclear magnetic resonance (NMR) spectrum of Lipid 26.
Figure 27B:
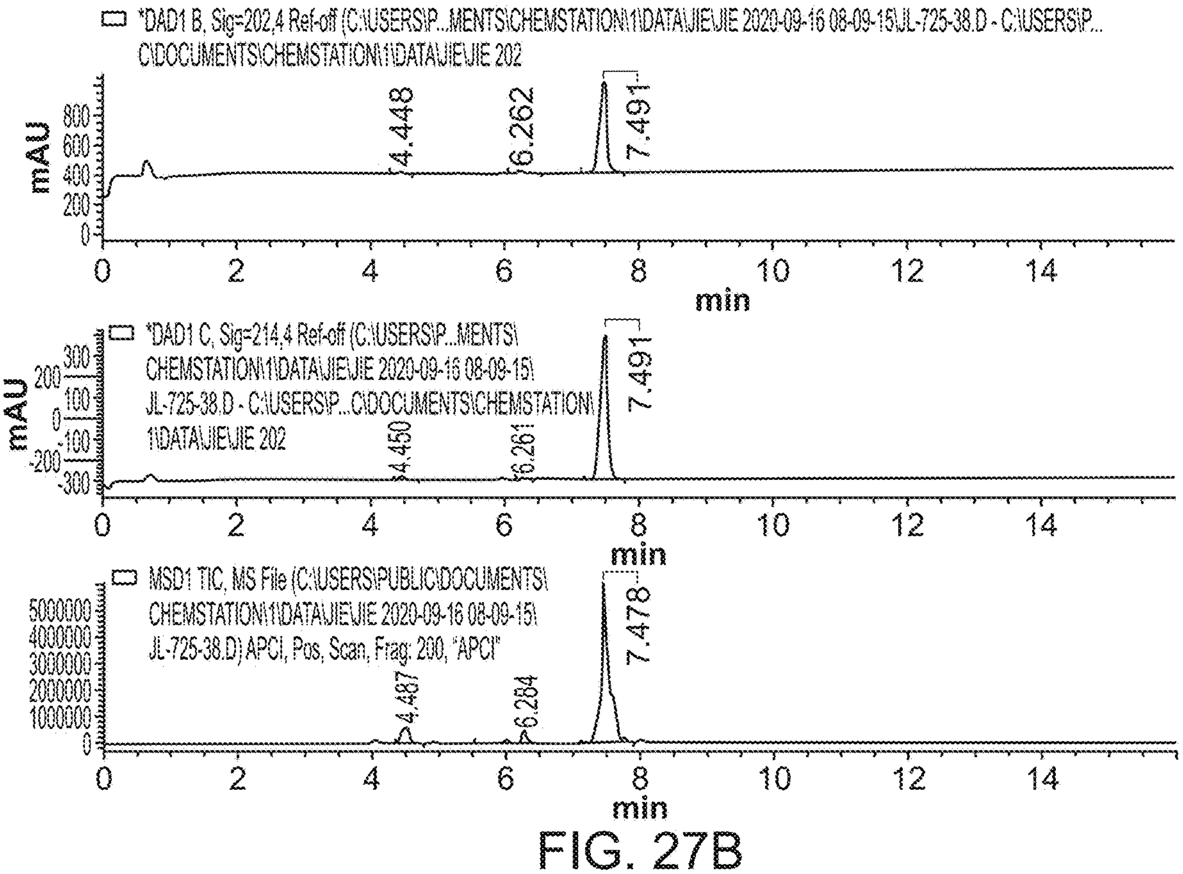
FIG. 27B shows the retention time of Lipid 26 measured by liquid chromatography-mass spectrometry (LC-MS).
Figure 27C:
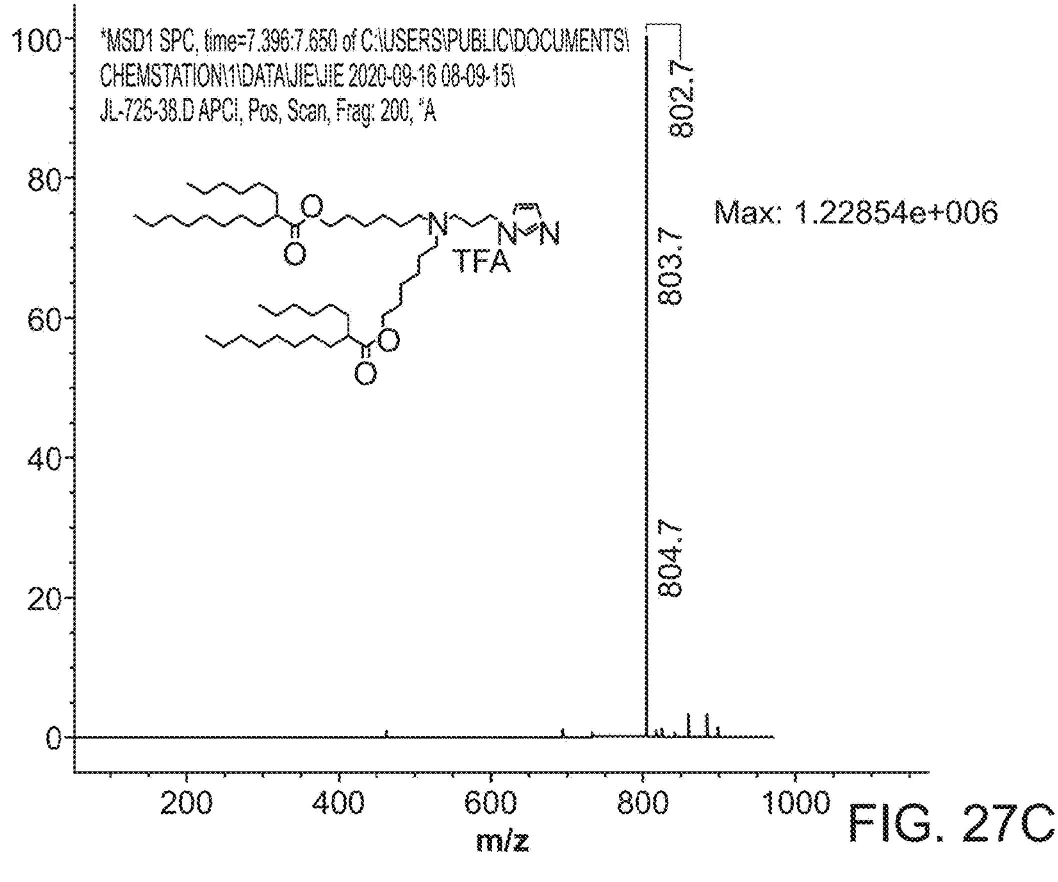
FIG. 27C shows the mass spectrum of Lipid 26.
Figure 27D:
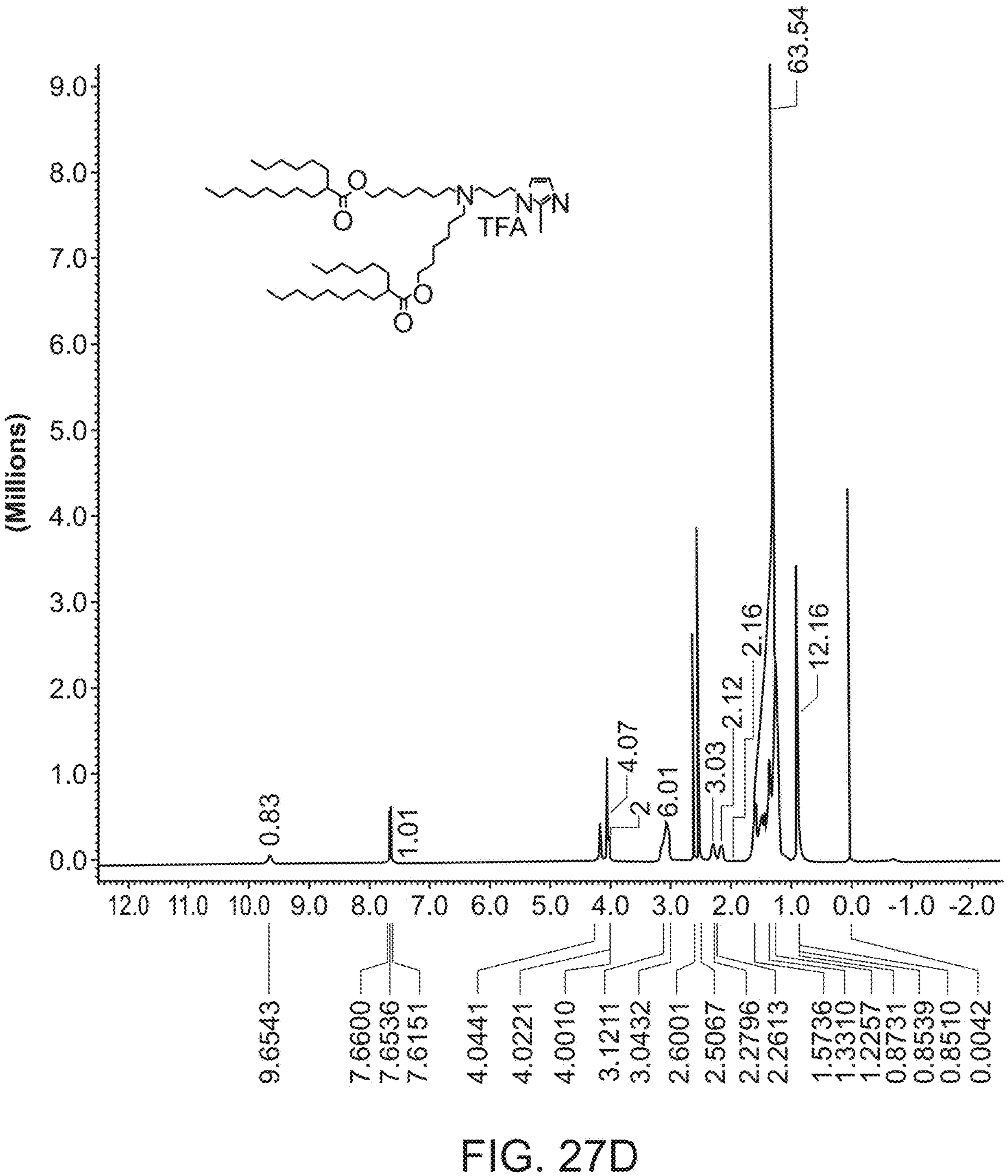
FIG. 27D shows the proton NMR spectrum of Lipid 27.
Figure 27E:
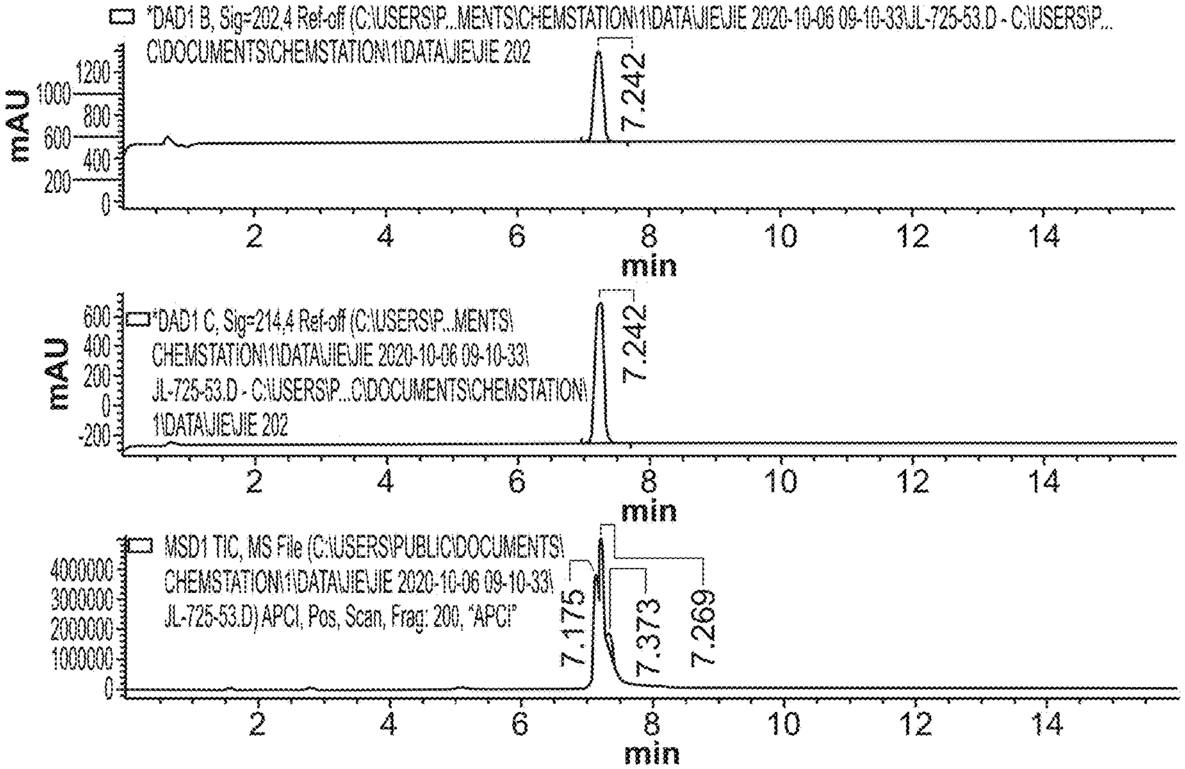
FIG. 27E shows the retention time of Lipid 27 measured by LC-MS.
Figure 27F:
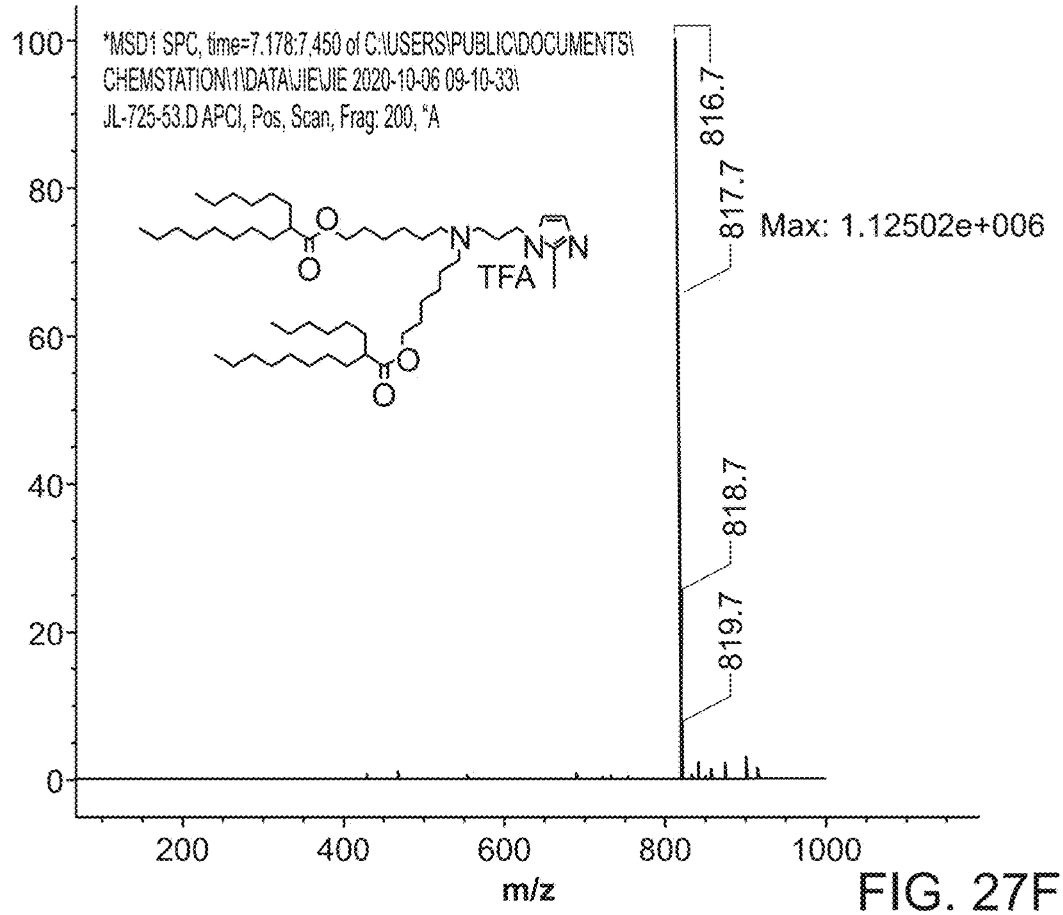
FIG. 27F shows the mass spectrum of Lipid 27.

Characterization of Lipid 26 was performed by LC-MS. FIG. 27A-C shows characterization of Lipid 26. FIG. 27A shows the proton NMR observed for Lipid 26. FIG. 27B is a representative LC/MS trace for Lipid 26 with total ion and UV chromatograms shown.

38.2 Synthesis of Lipid 22-514

38.2.1 Synthesis of 2-(tetradecylthio)ethan-1-ol

To a mixture of 2-sulfanylethanol (5.40 g, 69.11 mmol, 4.82 mL, 0.871 eq) in acetonitrile (200 mL) was added 1-Bromotetradecane (22 g, 79.34 mmol, 23.66 mL, 1 eq) and potassium carbonate (17.55 g, 126.95 mmol, 1.6 eq) at 25° C. The reaction mixture was warmed to 40° C. and stirred for 12 hr. TLC (ethyl acetate/petroleum ether=25/1, $R_f$=0.3, stained by $I_2$) showed the starting material was consumed completely and a new main spot was generated. The reaction mixture was filtered and the filter cake was washed with acetonitrile (50 mL) and then the filtrate was concentrated under vacuum to get a residue which was purified by column on silica gel (ethyl acetate/petroleum ether=1/100 to 1/25) to afford 2-(tetradecylthio)ethan-1-ol (14 g, yield 64.28%) as a white solid.

Figure 28A:
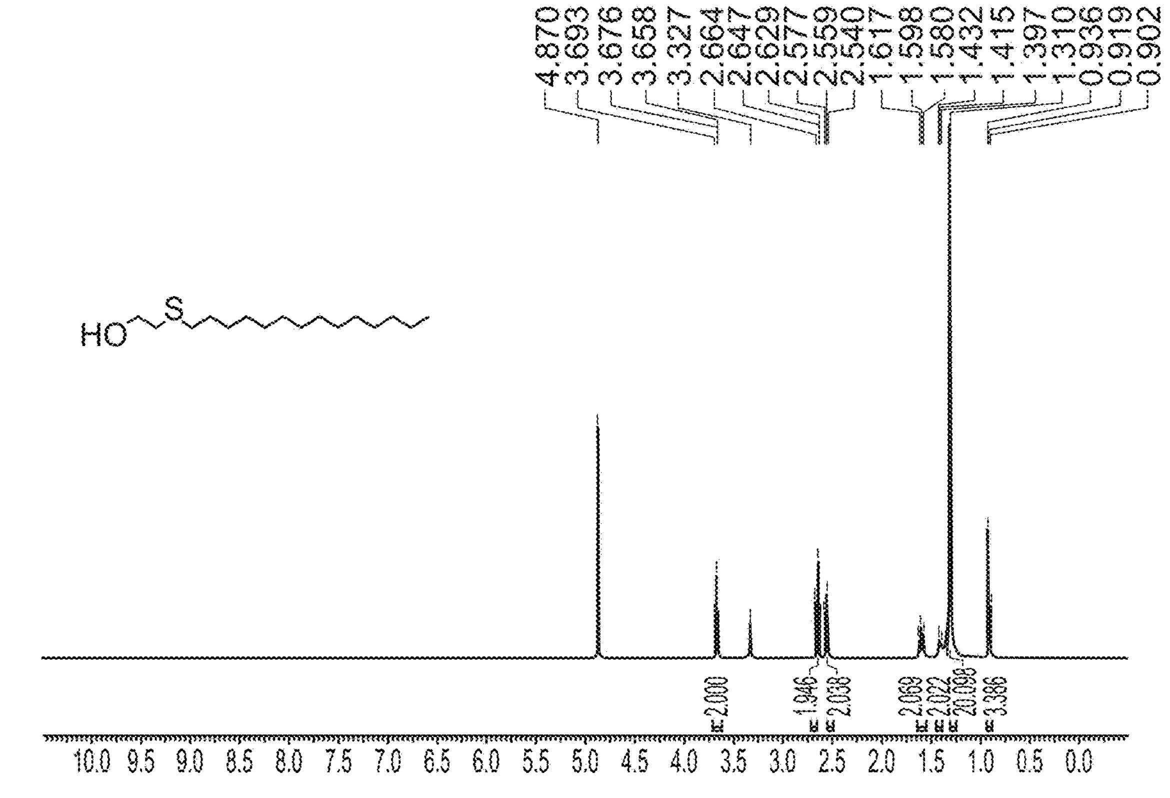
FIG. 28A depicts the NMR spectrum of 2-(tetradecylthio)ethan-1-ol.
Figure 28B:
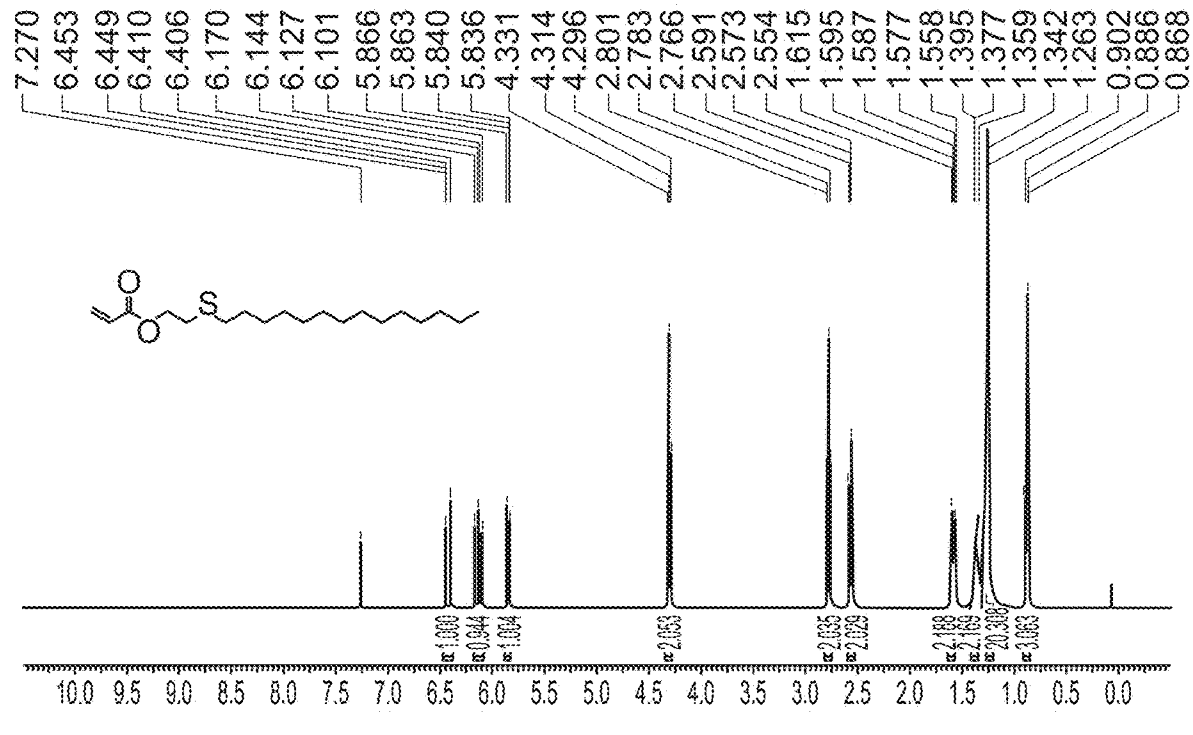
FIG. 28B depicts the NMR spectrum of 2-(tetradecylthio)ethyl acrylate.
Figure 28C:
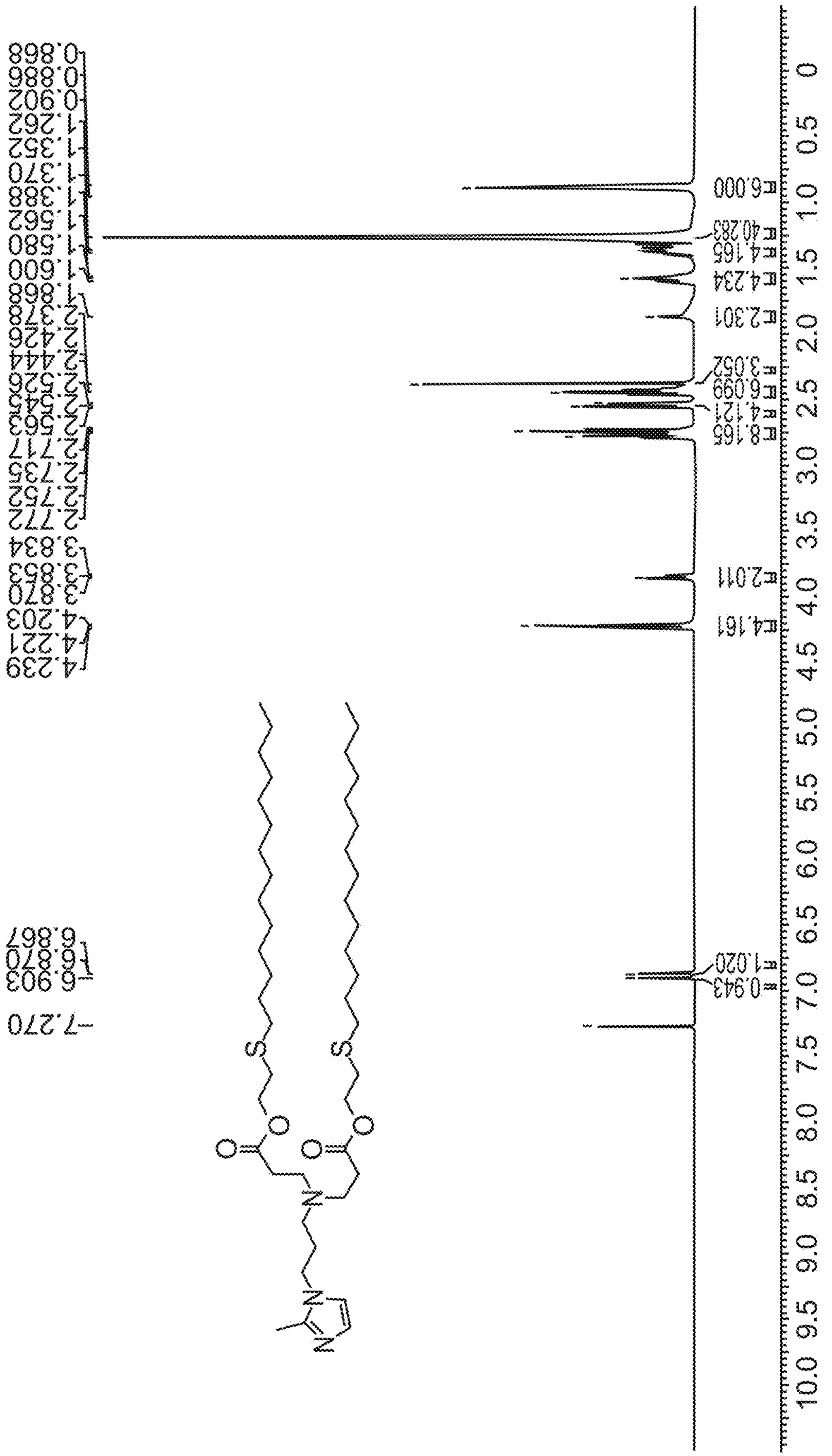
FIG. 28C depicts the NMR spectrum of bis(2-(tetradecylthio)ethyl) 3,3'-((3-(2-methyl-1H-imidazol-1-yl)propyl)azanediyl)dipropionate (Lipid 22-S14).

$^1$H NMR (ET36387-45-P1A, 400 MHz, CHLOROFORM-d) δ 0.87-0.91 (m, 3H) 1.27 (s, 20H) 1.35-1.43 (m, 2H) 1.53-1.64 (m, 2H) 2.16 (br s, 1H) 2.49-2.56 (m, 2H) 2.74 (t, J=5.93 Hz, 2H) 3.72 (br d, J=4.89 Hz, 2H). FIG. 28 shows corresponding Nuclear Magnetic Resonance (NMR) spectrum.

38.2.2 Synthesis of 2-(tetradecylthio)ethyl acrylate

To a solution of 2-(tetradecylthio)ethan-1-ol (14 g, 51.00 mmol, 1 eq) in dichloromethane (240 mL) was added triethylamine (7.74 g, 76.50 mmol, 10.65 mL, 1.5 eq) and prop-2-enoyl chloride (5.54 g, 61.20 mmol, 4.99 mL, 1.2 eq) dropwise at 0° C. under nitrogen. The reaction mixture was warmed to 25° C. and stirred for 12 hr. TLC (ethyl acetate/petroleum ether=25/1, Rf=0.5, stained by $I_2$) showed the starting material was consumed completely and a new main spot was generated. The reaction solution was concentrated under vacuum to get crude which was purified by column on silica gel (ethyl acetate/petroleum ether=1/100 to 1/25) to afford 2-(tetradecylthio)ethyl acrylate (12 g, yield 71.61%) as a colorless oil.

Figure 29:
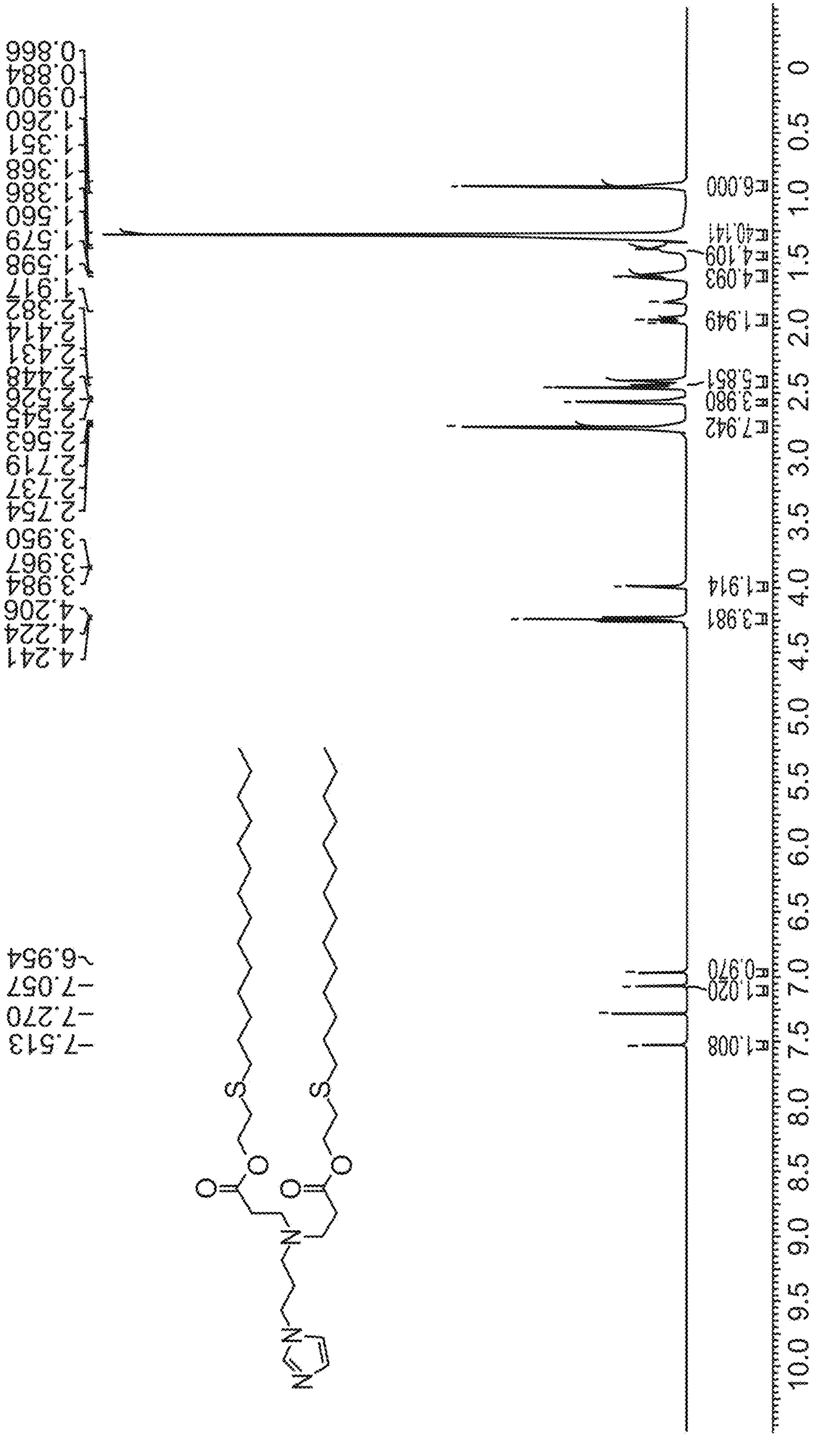
FIG. 29 depicts the NMR spectrum of bis(2-(tetradecylthio)ethyl) 3,3'-((3-(1H-imidazol-1-yl)propyl) azanediyl)dipropionate (Lipid 93-S 14).

$^1$H NMR (ET36387-49-P1A, 400 MHz, CHLOROFORM-d) δ 0.85-0.93 (m, 3H) 1.26 (s, 19H) 1.35-1.43 (m, 2H) 1.53-1.65 (m, 2H) 2.53-2.62 (m, 2H) 2.79 (t, J=7.03 Hz, 2H) 4.32 (t, J=7.03 Hz, 2H) 5.86 (dd, J=10.39, 1.47 Hz, 1H) 6.09-6.19 (m, 1H) 6.43 (dd, J=17.30, 1.41 Hz, 1H). FIG. 29 shows corresponding Nuclear Magnetic Resonance (NMR) spectrum.

38.2.3 Synthesis of bis(2-(tetradecylthio)ethyl) 3,3'-((3-(2-methyl-1H-imidazol-1-yl)propyl)azanediyl) dipropionate (Lipid 22-S14)

A flask was charged with 3-(2-methyl-1H-imidazol-1-yl)propan-1-amine (300 mg, 2.16 mmol) and 2-(tetradecylthio)ethyl acrylate (1.70 g, 5.17 mmol). The neat reaction mixture was heated to 80° C. and stirred for 48 hr. TLC (ethyl acetate, $R_f$=0.3, stained by $I_2$, one drop ammonium hydroxide added) showed the starting material was consumed completely and a new main spot was formed. The reaction mixture was diluted with dichloromethane (4 mL) and purified by column on silica gel (petroleum ether/ethyl acetate=3/1 to 0/1, 0.1% ammonium hydroxide added) to get bis(2-(tetradecylthio)ethyl) 3,3'-((3-(2-methyl-1H-imidazol-1-yl)propyl)azanediyl)dipropionate (501 mg, yield 29.1%) as colorless oil.

Figure 30A:
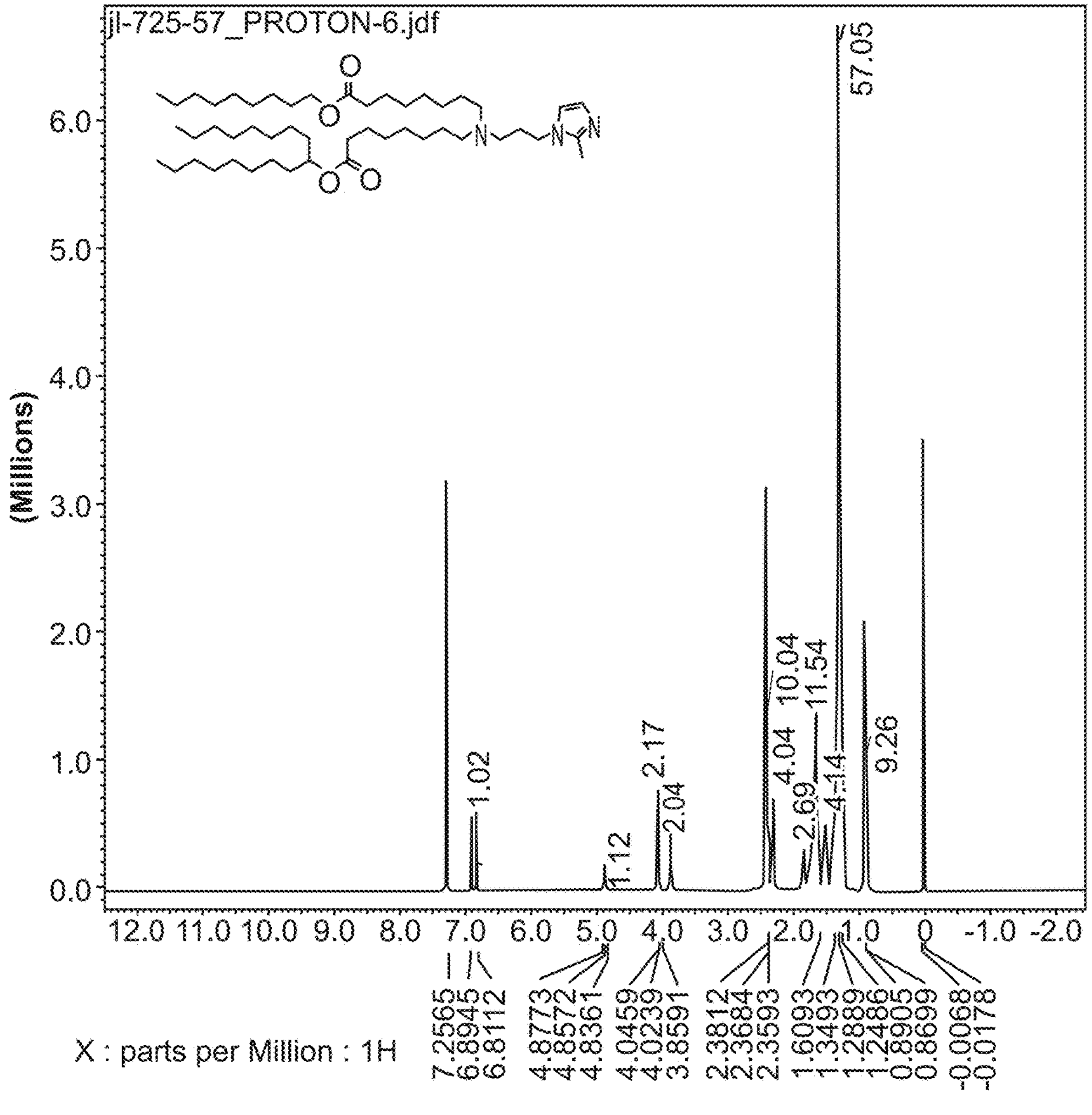
FIG. 30A shows the proton NMR spectrum of Lipid 54.
Figure 30B:
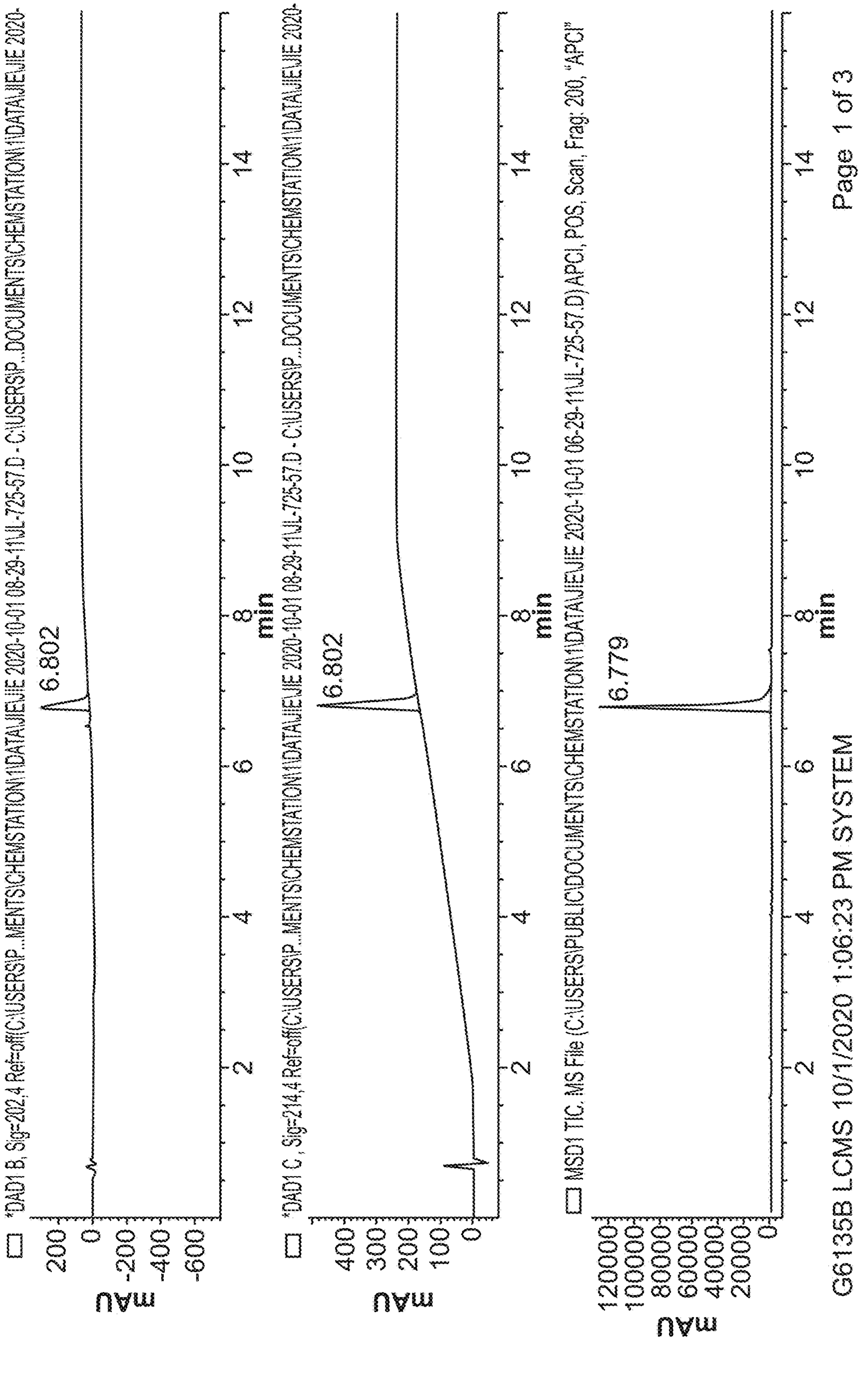
FIG. 30B shows the retention time of Lipid 54 measured by LC-MS.
Figure 30C:
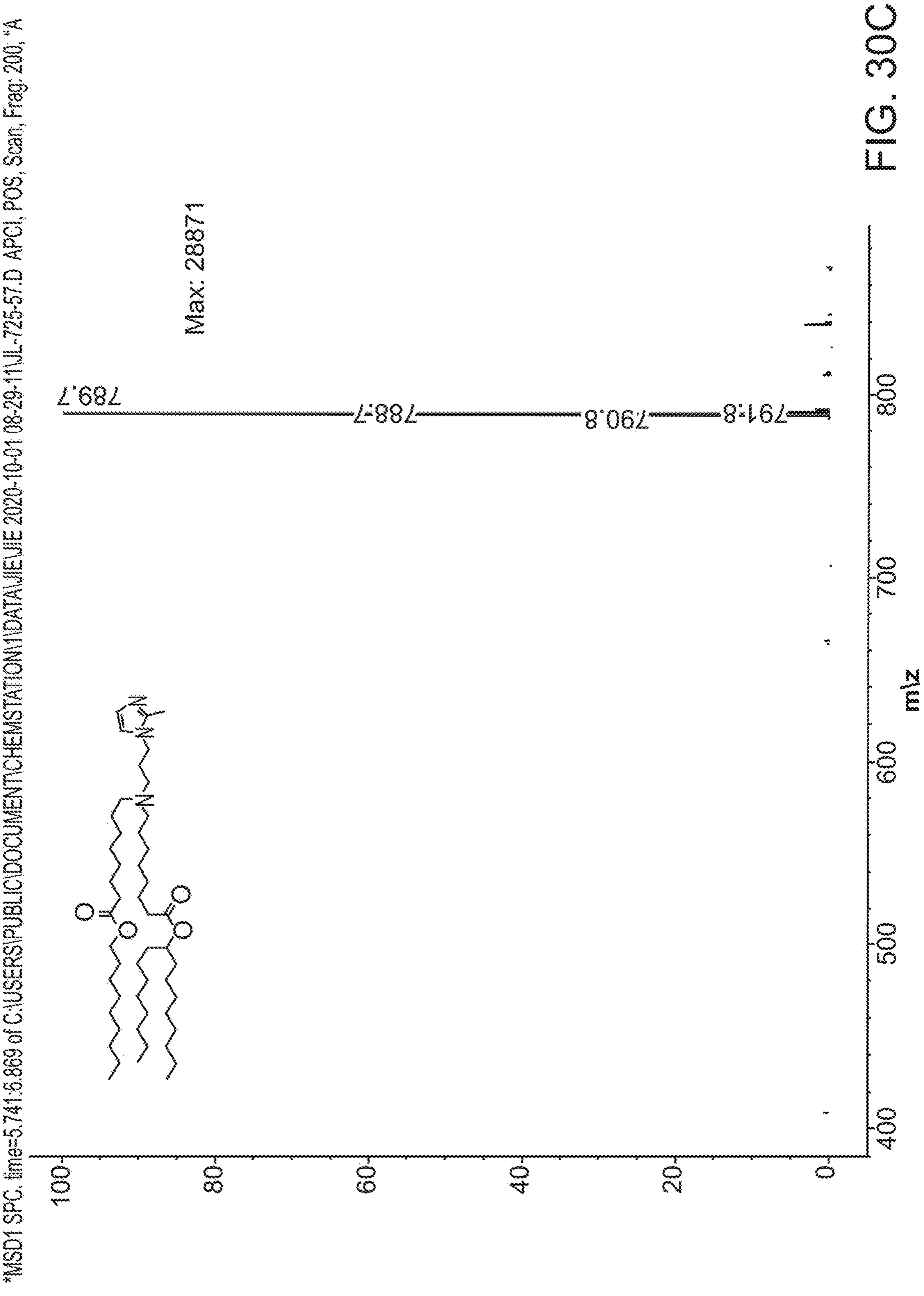
FIG. 30C shows the mass spectrum of Lipid 54.

$^1$H NMR (ET36387-51-P1A, 400 MHz, CHLOROFORM-d) δ 0.87 (t, J=6.73 Hz, 6H) 1.25 (s, 40H) 1.33-1.40 (m, 4H) 1.52-1.61 (m, 4H) 1.81-1.90 (m, 2H) 2.36 (s, 3H) 2.39-2.46 (m, 6H) 2.53 (t, J=7.39 Hz, 4H) 2.70-2.78 (m, 8H) 3.84 (t, J=7.17 Hz, 2H) 4.21 (t, J=6.95 Hz, 4H) 6.85 (s, 1H) 6.89 (s, 1H). FIG. 30 shows corresponding Nuclear Magnetic Resonance (NMR) spectrum.

38.3 Synthesis of bis(2-(tetradecylthio)ethyl) 3,3'-((3-(1H-imidazol-1-yl)propyl)azanediyl)dipropionate (Lipid 93-S14)

A flask was charged with 3-(1H-imidazol-1-yl)propan-1-amine (300 mg, 2.40 mmol, 1 eq) and 2-(tetradecylthio)ethyl acrylate (1.89 g, 5.75 mmol, 2.4 eq). The neat reaction mixture was heated to 80° C. and stirred for 48 hr. TLC (ethyl acetate, $R_f$=0.3, stained by $I_2$, one drop ammonium hydroxide added) showed the starting material was consumed completely and a new main spot was formed. The reaction mixture was diluted with dichloromethane (4 mL) and purified by column on silica gel (petroleum ether/ethyl acetate=1/20-0/100, 0.1% ammonium hydroxide added) to get bis(2-(tetradecylthio)ethyl) 3,3'-((3-(1H-imidazol-1-yl)propyl)azanediyl)dipropionate (512 mg, yield 27.22%) as colorless oil.

Figure 31A:
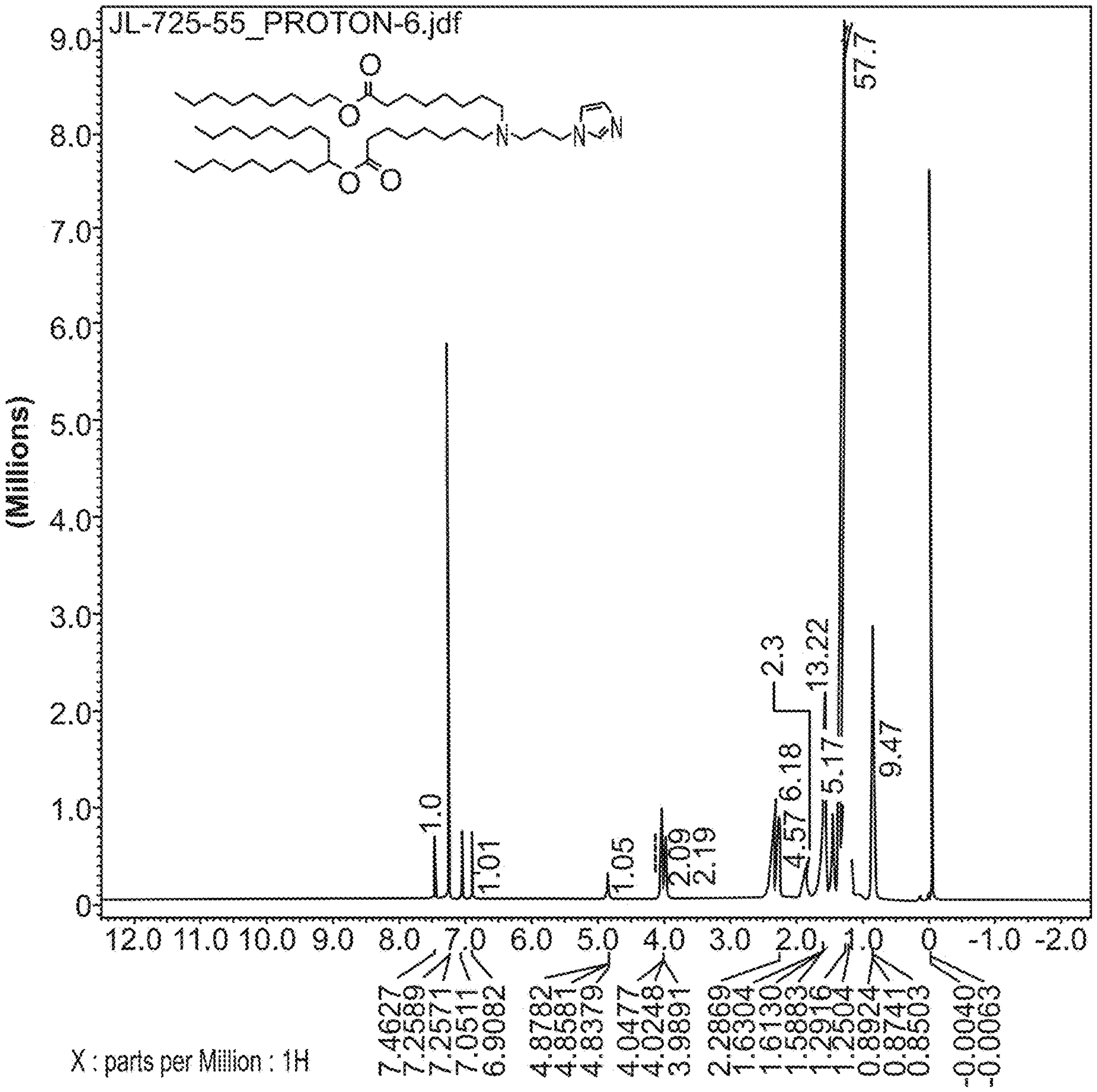
FIG. 31A shows the proton NMR spectrum of Lipid 53.
Figure 31B:
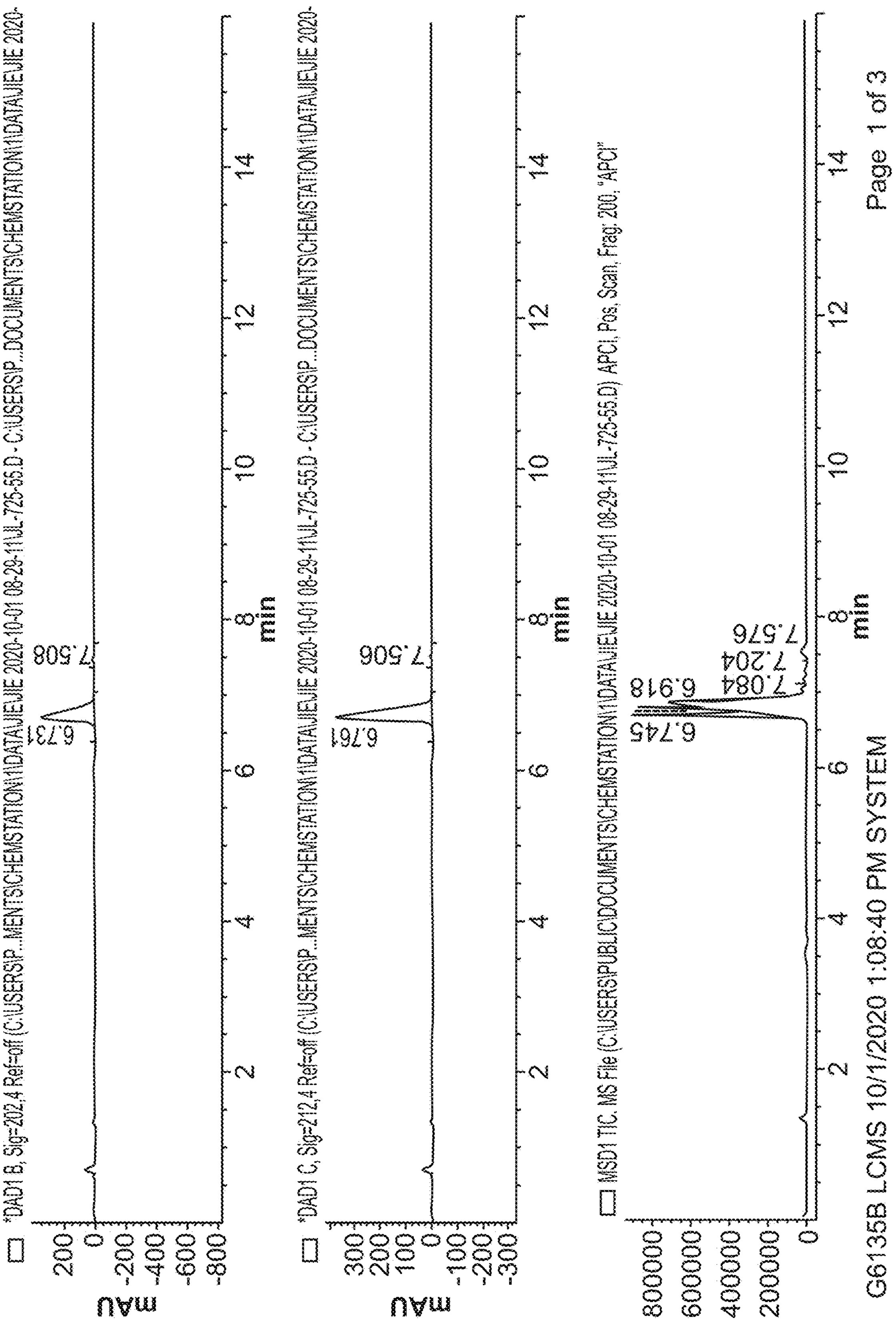
FIG. 31B shows the retention time of Lipid 53 measured by LC-MS.
Figure 31C:
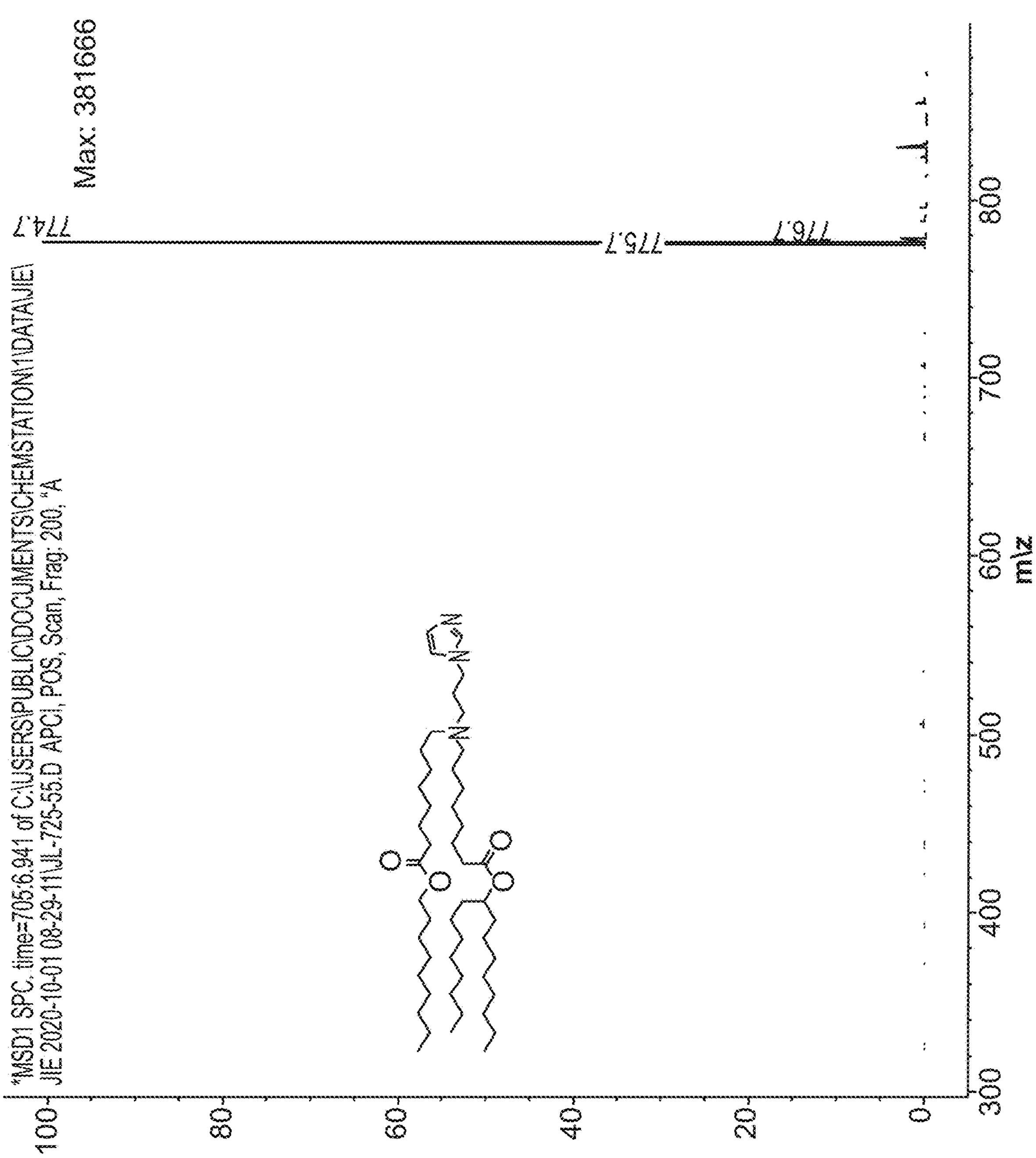
FIG. 31C shows the mass spectrum of Lipid 53.

$^1$H NMR (ET36387-54-P1A, 400 MHz, CHLOROFORM-d) δ 0.89 (t, J=6.84 Hz, 6H) 1.26 (s, 40H) 1.34-1.41 (m, 4H) 1.58 (br t, J=7.50 Hz, 4H) 1.92 (t, J=6.62 Hz, 2H) 2.36-2.46 (m, 6H) 2.55 (t, J=7.50 Hz, 4H) 2.75 (q, J=6.84 Hz, 8H) 3.97 (t, J=6.95 Hz, 2H) 4.23 (t, J=6.95 Hz, 4H) 6.95 (s, 1H) 7.06 (s, 1H) 7.51 (s, 1H). FIG. 31 shows corresponding Nuclear Magnetic Resonance (NMR) spectrum.

38.4 Synthesis of heptadecan-9-yl 8-((3-(2-methyl-1H-imidazol-1-yl)propyl)(8-(nonyloxy)-8-oxooctyl)amino)octanoate (Lipid 54, Table 10a)

38.4.1 Synthesis of nonyl 8-bromooctanoate (3)

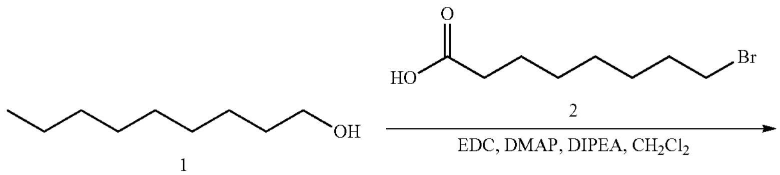

1

-continued

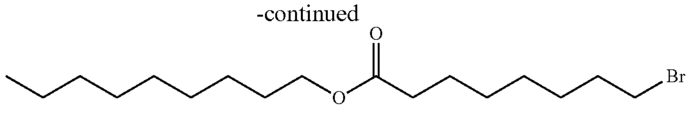

3

To a mixture of 8-bromooctanoic acid (2) (18.6 g, 83.18 mmol) and nonan-1-ol (1) (10 g, 69.32 mmol) in $CH_2Cl_2$ (500 mL) was added DMAP (1.7 g, 13.86 mmol), DIPEA (48 mL, 277.3 mmol) and EDC (16 g, 83.18 mmol). The reaction was stirred at room temperature overnight. After concentration of the reaction mixture, the crude residue was dissolved in ethyl acetate (500 mL), washed with IN HCl, sat. $NaHCO_3$, water and Brine. The organic layer was dried over anhydrous $Na_2SO_4$. The solvent was evaporated and the crude residue was purified by flash chromatography ($SiO_2$: Hexane=100% to 30% of EtOAc in Hexane) and colorless oil product 3 was obtained (9 g, 37%).

38.4.2 Synthesis of heptadecan-9-yl 8-bromooctanoate (5)

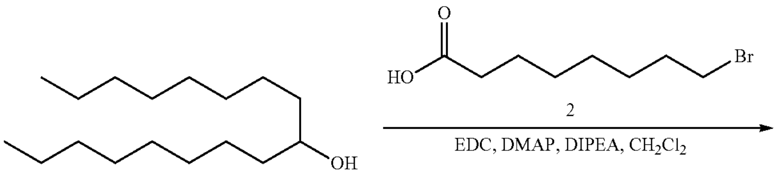

4

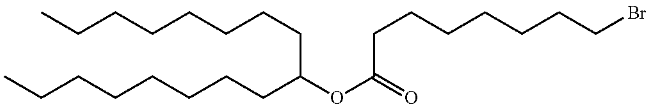

5

To a mixture of 8-bromooctanoic acid (2) (10 g, 44.82 mmol) and heptadecan-9-ol (4) (9.6 g, 37.35 mmol) in $CH_2Cl_2$ (300 mL) was added DMAP (900 mg, 7.48 mmol), DIPEA (26 mL, 149.7 mmol) and EDC (10.7 g, 56.03 mmol). The reaction was stirred at room temperature overnight. After concentration of the reaction mixture, the crude residue was dissolved in ethyl acetate (300 mL), washed with 1N HCl, sat. $NaHCO_3$, water and Brine. The organic layer was dried over anhydrous $Na_2SO_4$. The solvent was evaporated and the crude residue was purified by flash chromatography ($SiO_2$: Hexane=100% to 30% of EtOAc in Hexane) and colorless oil product 5 was obtained (5 g, 29%).

38.4.3 Synthesis of heptadecan-9-yl 8-((3-(2-methyl-1H-imidazol-1-yl)propyl)amino)octanoate (7)

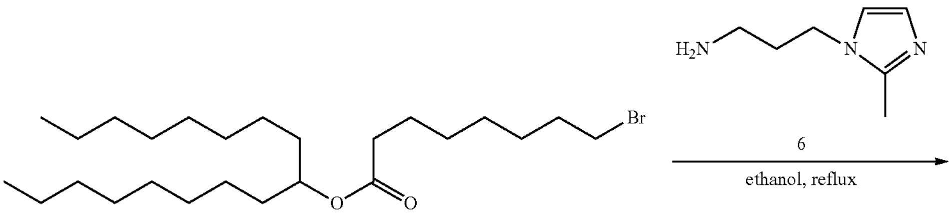

5

-continued

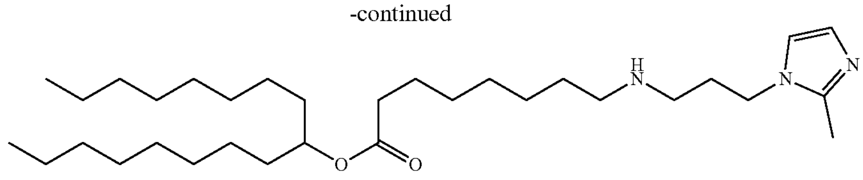

7

In a 100 mL round bottom flask connected with condenser, heptadecan-9-yl 8-bromooctanoate (5) (860 mg, 1.868 mmol) and 3-(2-methyl-1H-imidazol-1-yl)propan-1-amine (6) (1.3 g, 9.339 mmol) were mixed in ethanol (10 mL). The reaction mixture was heated to reflux overnight. MS (APCI) showed the expected product. The mixture was cooled to room temperature and concentrated. The crude residue was purified by flash chromatography ($SiO_2$: $CH_2Cl_{2=100}$% to 10% of methanol+1% $NH_4OH$ in $CH_2Cl_2$) and colorless oil product 7 was obtained (665 mg, 69%).

38.4.4 Synthesis of heptadecan-9-yl 8-((3-(2-methyl-1H-imidazol-1-yl)propyl)(8-(nonyloxy)-8-oxooctyl)amino)octanoate (Lipid 54, Table 10a)

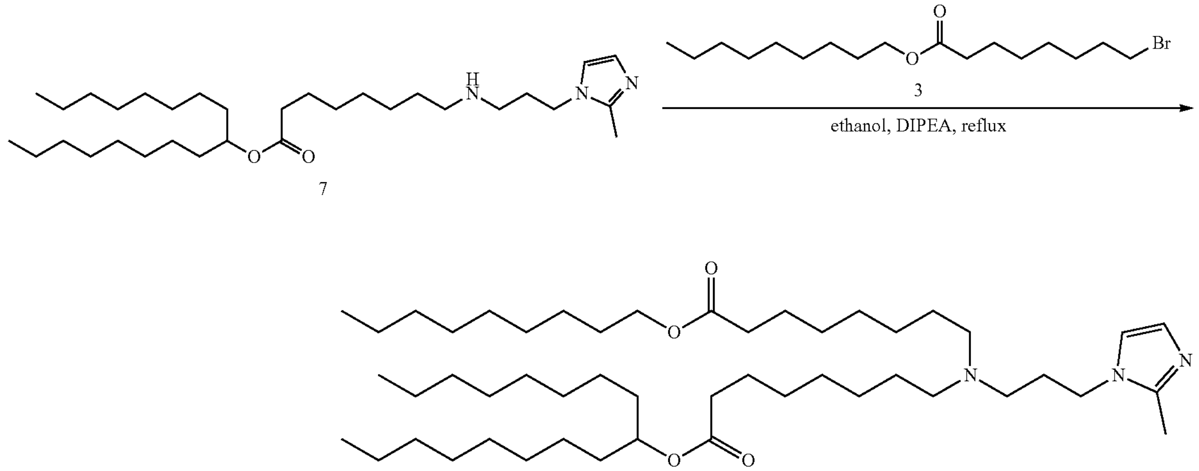 [SMILES: CCCCCCCCC(CCCCCCCC)OC(=O)CCCCCCCNCCCn1ccnc1C ; CCCCCCCCCOC(=O)CCCCCCCBr ; CCCCCCCCCOC(=O)CCCCCCCN(CCCCCCCC(=O)OC(CCCCCCCC)CCCCCCCC)CCCn1ccnc1C]

In a 100 mL round bottom flask connected with condenser, heptadecan-9-yl 8-((3-(2-methyl-1H-imidazol-1-yl)propyl)amino)octanoate (7) (665 mg, 1.279 mmol) and nonyl 8-bromooctanoate (3) (536 mg, 1.535 mmol) were mixed in ethanol (10 mL), then DIPEA (0.55 mL, 3.198 mmol) was added. The reaction mixture was heated to reflux overnight. Both MS (APCI) and TLC (10% MeOH+1% $NH_4OH$ in $CH_2Cl_2$) showed the product and some unreacted starting material. The mixture was cooled to room temperature and concentrated. The crude residue was purified by flash chromatography ($SiO_2$: $CH_2Cl_{2=100}$% to 10% of methanol+1% $NH_4OH$ in $CH_2Cl_2$) and colorless oil was obtained (170 mg, 17%).

38.5 Synthesis of heptadecan-9-yl 8-((3-(1H-imidazol-1-yl)propyl)(8-(nonyloxy)-8-oxooctyl)amino)octanoate (Lipid 53, Table 10a)

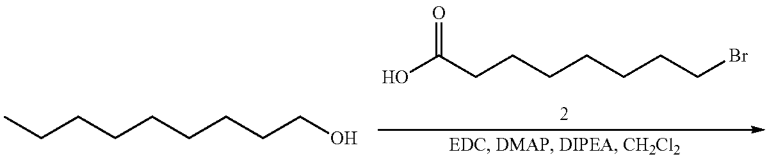

1

-continued

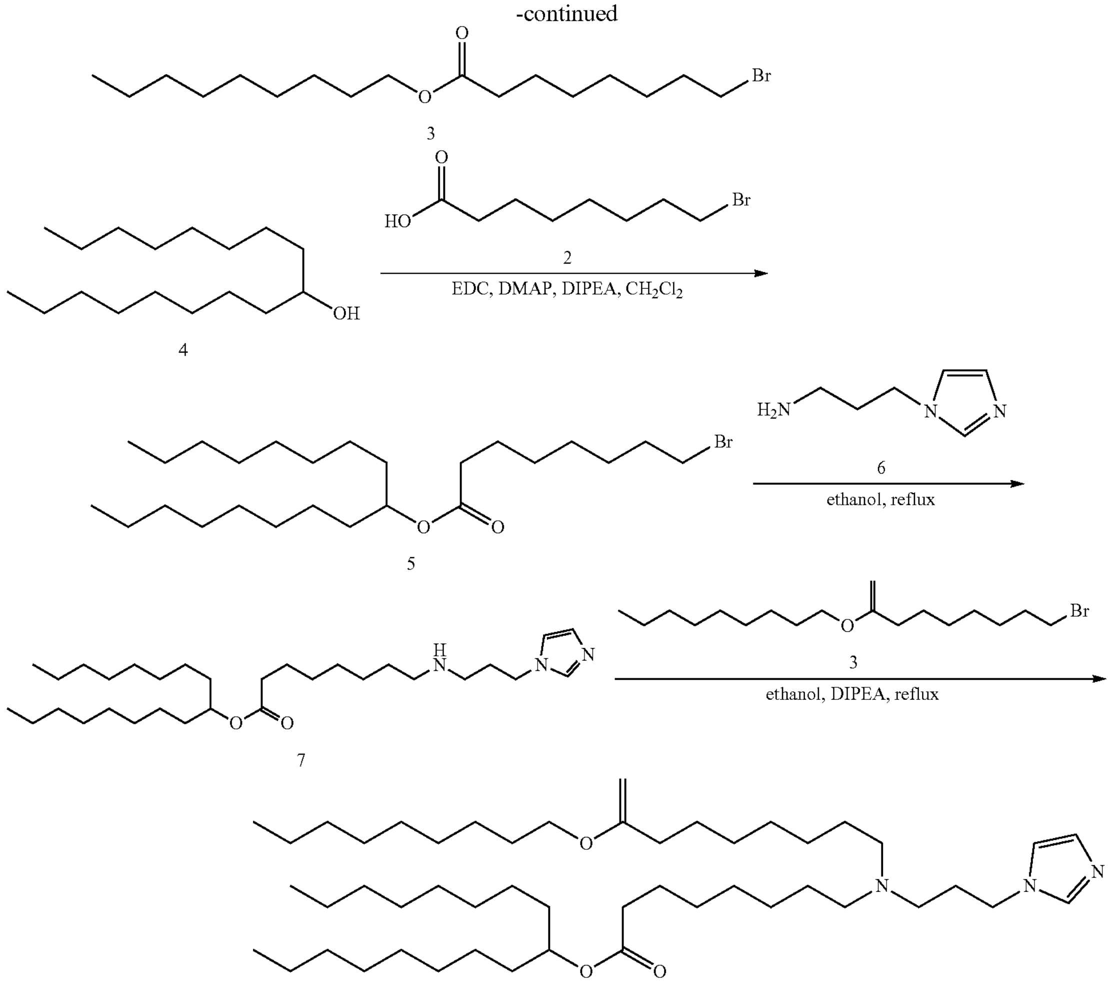

Lipid 53 from Table 10a is synthesized according to the scheme above. Reaction conditions are identical to Lipid 54 with the exception of 3-(1H-imidazol-1-yl)propan-1-amine as the imidazole amine.

Example 37

Lipid Nanoparticle Formulation with Circular RNA

Lipid Nanoparticles (LNPs) were formed using a Precision Nanosystems Ignite instrument with a ‘NextGen’ mixing chamber. Ethanol phase contained ionizable Lipid 26 from Table 10a, DSPC, Cholesterol, and DSPE-PEG 2000 (Avanti Polar Lipids Inc.) at a weight ratio of 16:1:4:1 or 62:4:33:1 molar ratio was combined with an aqueous phase containing circular RNA and 25 mM sodium acetate buffer at pH 5.2. A 3:1 aqueous to ethanol mixing ratio was used. The formulated LNP then were dialyzed in 1 L of water and exchanged 2 times over 18 hours. Dialyzed LNPs were filtered using 0.2 μm filter. Prior to in vivo dosing, LNPs were diluted in PBS. LNP sizes were determined by dynamic light scattering. A cuvette with 1 mL of 20 μg/mL LNPs in PBS (pH 7.4) was measured for Z-average using the Malvern Panalytical Zetasizer Pro. The Z-average and polydispersity index were recorded.

39.1 Formulation of Lipids 26 and 27 from Table 10a

Lipid Nanoparticles (LNPs) were formed using a Precision Nanosystems Ignite instrument with a ‘NextGen’ mixing chamber. Ethanol phase contained ionizable Lipid 26 or Lipid 27 from Table 10a, DOPE, Cholesterol, and DSPE-PEG 2000 (Avanti Polar Lipids Inc.) at a weight ratio of 16:1:4:1 or 62:4:33:1 molar ratio was combined with an aqueous phase containing circular RNA and 25 mM sodium acetate buffer at pH 5.2. A 3:1 aqueous to ethanol mixing ratio was used. The formulated LNPs were then dialyzed in 1 L of water and exchanged 2 times over 18 hours. Dialyzed LNPs were filtered using 0.2 μm filter. Prior to in vivo dosing, LNPs were diluted in PBS. LNP sizes were determined by dynamic light scattering. A cuvette with 1 mL of 20 μg/mL LNPs in PBS (pH 7.4) was measured for Z-average using the Malvern Panalytical Zetasizer Pro. The Z-average and polydispersity index were recorded.

39.2 Formulation of Lipids 53 and 54 from Table 10a

Lipid Nanoparticles (LNPs) were formed using a Precision Nanosystems Ignite instrument with a ‘NextGen’ mixing chamber. Ethanol phase contained ionizable Lipid 53 or 54 of Table 10a, DOPE, Cholesterol, and DSPE-PEG 2000

(Avanti Polar Lipids Inc.) at a molar ratio of 50:10:38.5:1.5 was combined with an aqueous phase containing circular RNA and 25 mM sodium acetate buffer at pH 5.2. A 3:1 aqueous to ethanol mixing ratio was used. The formulated LNPs were then dialyzed in 1 L of 1×PBS and exchanged 2 times over 18 hours. Dialyzed LNPs were filtered using 0.2 μm filter. Prior to in vivo dosing, LNPs were diluted in PBS. LNP sizes were determined by dynamic light scattering. A cuvette with 1 mL of 20 μg/mL LNPs in PBS (pH 7.4) was measured for Z-average using the Malvern Panalytical Zetasizer Pro. The Z-average and polydispersity index were recorded.

LNP zeta potential was measured using the Malvern Panalytical Zetasizer Pro. A mixture containing 200 μL of the particle solution in water and 800 μL of distilled RNAse-free water with a final particle concentration of 400 μg/mL was loaded into a zetasizer capillary cell for analysis.

RNA encapsulation was determined using a Ribogreen assay. Nanoparticle solutions were diluted in tris-ethylene-diaminetetraacetic acid (TE) buffer at a theoretical oRNA concentration of 2 μg/mL. Standard oRNA solutions diluted in TE buffer were made ranging from 2 μg/mL to 0.125 μg/mL. The particles and standards were added to all wells and a second incubation was performed (37° C. at 350 rpm for 3 minutes). Fluorescence was measured using a SPECTRAmax® GEMINI XS microplate spectrofluorometer. The concentration of circular RNA in each particle solution was calculated using the standard curve. The encapsulation efficiency was calculated from the ratio of oRNA detected between lysed and unlysed particles.

TABLE 36a

| Characterization of LNPs | | | | |
|---|---|---|---|---|
| Ionizable Lipid | Size (nm) | PDI | Encapsulation Efficiency (%) | Zeta Data Potential (mV) |
| 22-S14 | 88 | 0.09 | 96 | 3.968 |
| 93-S14 | 119 | 0.02 | 96 | −6.071 |
| Lipid 26, Table 10a | 86 | 0.08 | 92 | −15.24 |

TABLE 36b

| Characterization of LNPs | | | |
|---|---|---|---|
| Ionizable Lipid | Z-Average(nm) | PDI | RNA Entrapment(%) |
| 22-S14 | 64 | 0.05 | 97 |
| 93-S14 | 74 | 0.04 | 95 |
| Lipid 26, Table 10a | 84 | 0.04 | 96 |

Example 38

In Vivo Analysis

Female CD-1 or female c57BL/6J mice ranging from 22-25 g were dosed at 0.5 mg/kg RNA intravenously. Six hours after injection, mice were injected intraperitoneally with 200 μL of D-luciferin at 15 mg/mL concentration. 5 minutes after injection, mice were anesthetized using isoflurane, and placed inside the IVIS Spectrum In Vivo Imaging System (Perkin Elmer) with dorsal side up. Whole body total IVIS flux of Lipids 22-S14, 93-S14, Lipid 26 (Table 10a) is presented in FIG. 32A. Post 10 minutes injection, mice were scanned for luminescence. Mice were euthanized and organs were extracted within 25 minutes of luciferin injection to scan for luminescence in liver, spleen, kidneys, lungs, and heart. Images (FIGS. 33A-B, 34A-B, 35A-B) were analyzed using Living Images (Perkin Elmer) software. Regions of interest were drawn to obtain flux and average radiance and analyzed for biodistribution of protein expression (FIG. 32A-B).

Figure 32A:
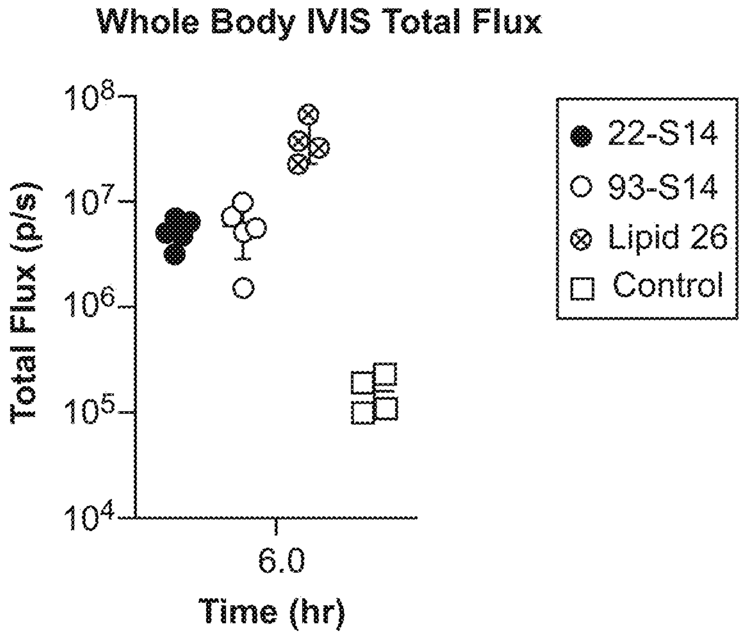
FIG. 32A depicts total flux of spleen and liver harvested from CD-1 mice dosed with circular RNA encoding firefly luciferase (FLuc) and formulated with ionizable lipid of interest, DSPC, cholesterol, and DSPE-PEG 2000 (Avanti Polar Lipids Inc.) at a weight ratio of 16:1:4:1 or 62:4:33:1 molar ratio.
Figure 32B:
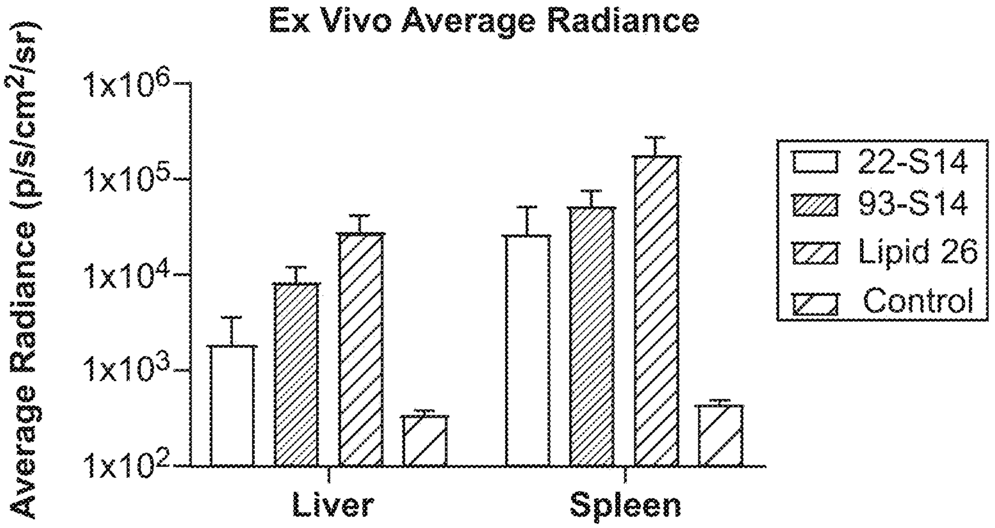
FIG. 32B depicts average radiance for biodistribution of protein expression.
Figure 33A:
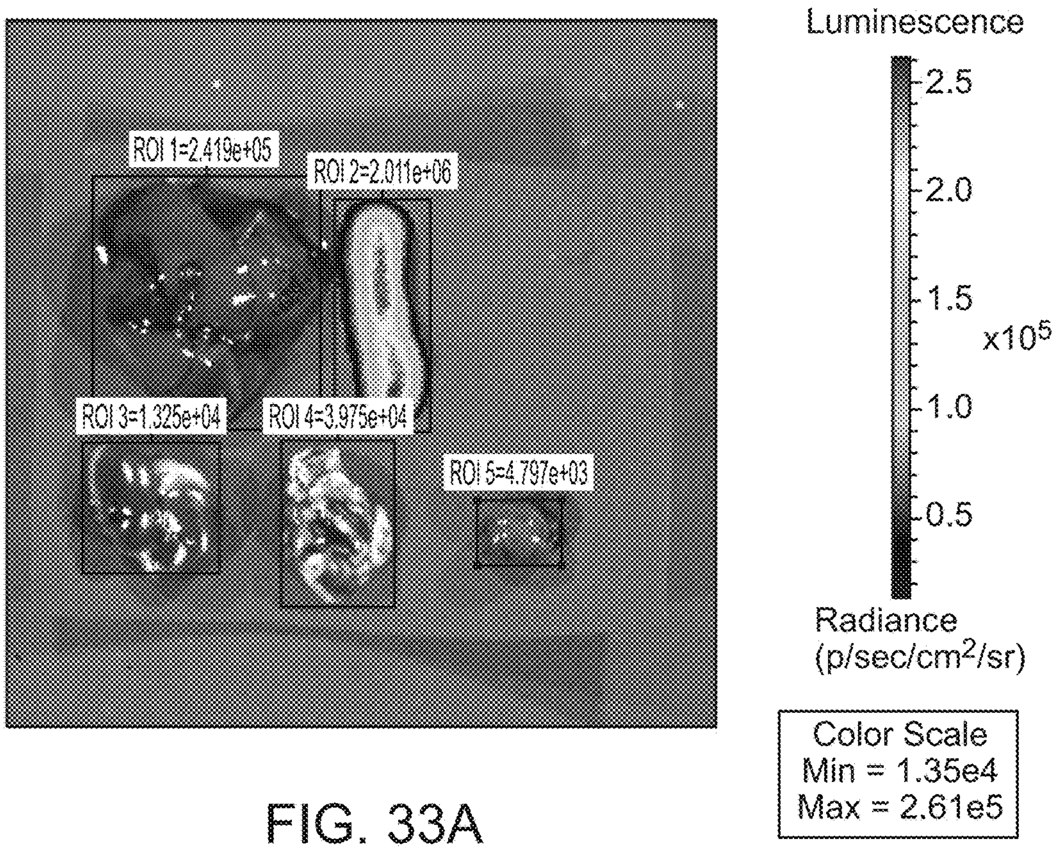
FIG. 33A depicts images highlighting the luminescence of organs harvested from CD-1 mice dosed with circular RNA encoding FLuc and formulated with ionizable Lipid 22-S14, DSPC, cholesterol, and DSPE-PEG 2000 (Avanti Polar Lipids Inc.) at a weight ratio of 16:1:4:1 or 62:4:33:1 molar ratio.
Figure 33B:
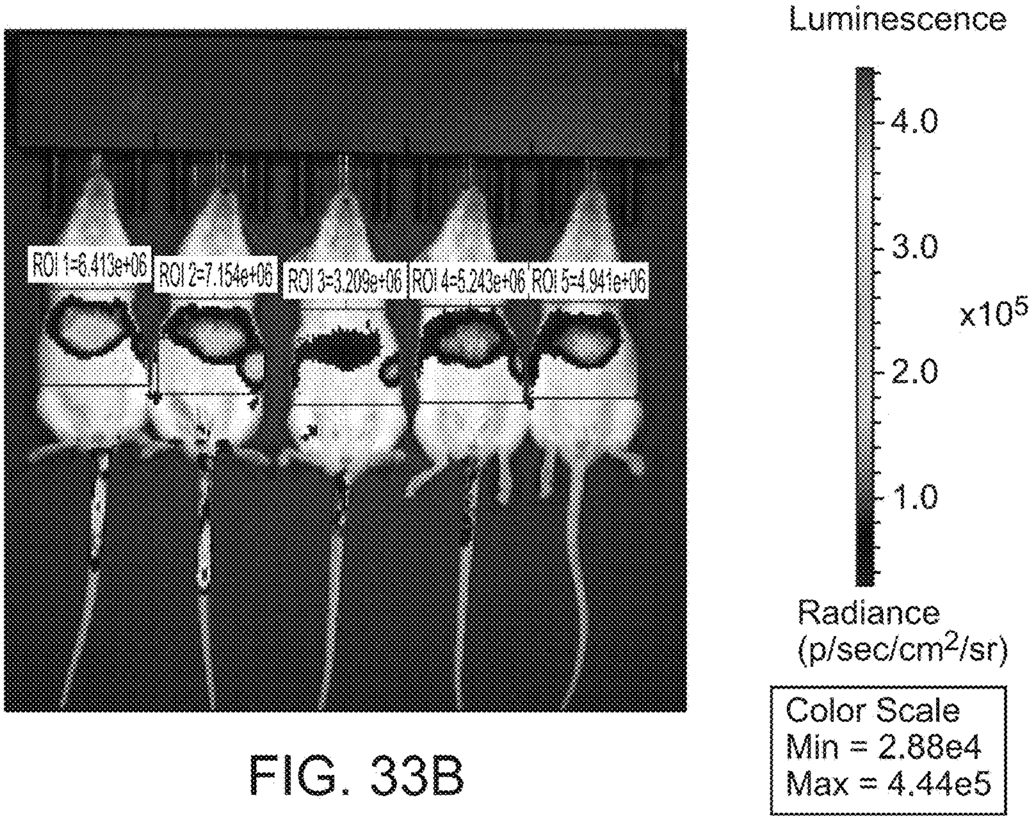
FIG. 33B depicts whole body IVIS images of CD-1 mice dosed with circular RNA encoding FLuc and formulated with ionizable Lipid 22-S14, DSPC, cholesterol, and DSPE-PEG 2000 (Avanti Polar Lipids Inc.) at a weight ratio of 16:1:4:1 or 62:4:33:1 molar ratio.
Figure 34A:
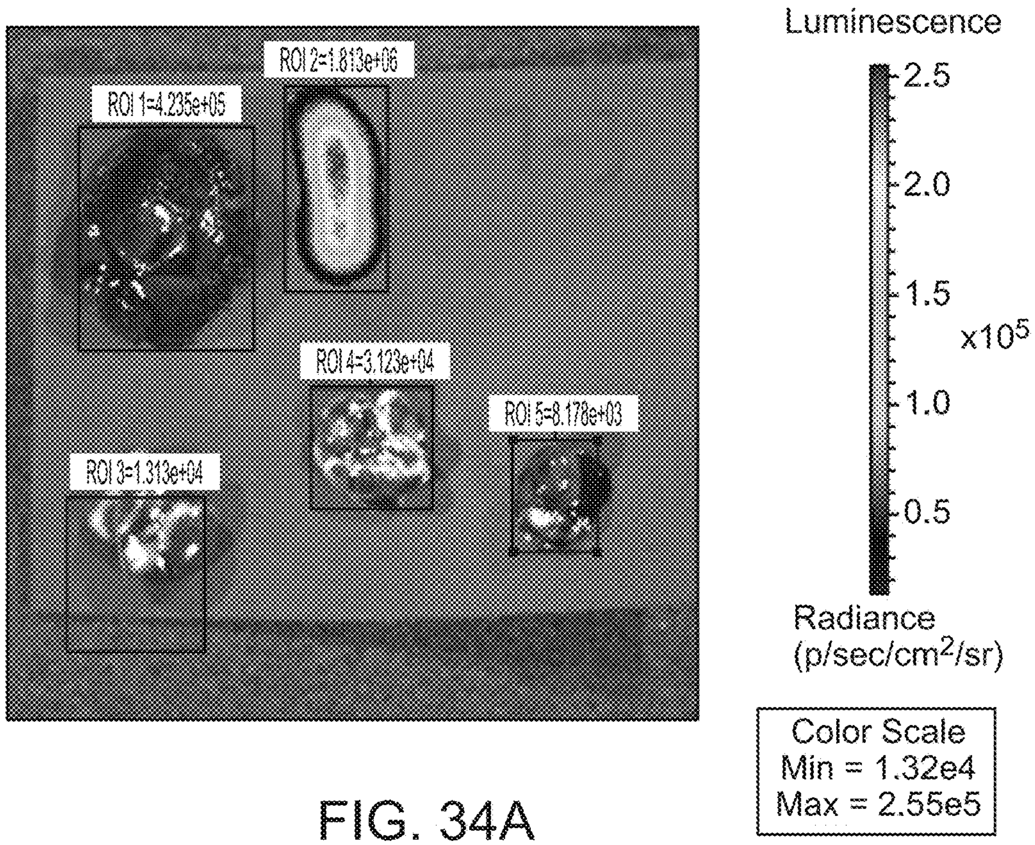
FIG. 34A depicts images highlighting the luminescence of organs harvested from CD-1 mice dosed with circular RNA encoding FLuc and formulated with ionizable Lipid 93-S14, DSPC, cholesterol, and DSPE-PEG 2000 (Avanti Polar Lipids Inc.) at a weight ratio of 16:1:4:1 or 62:4:33:1 molar ratio.
Figure 34B:
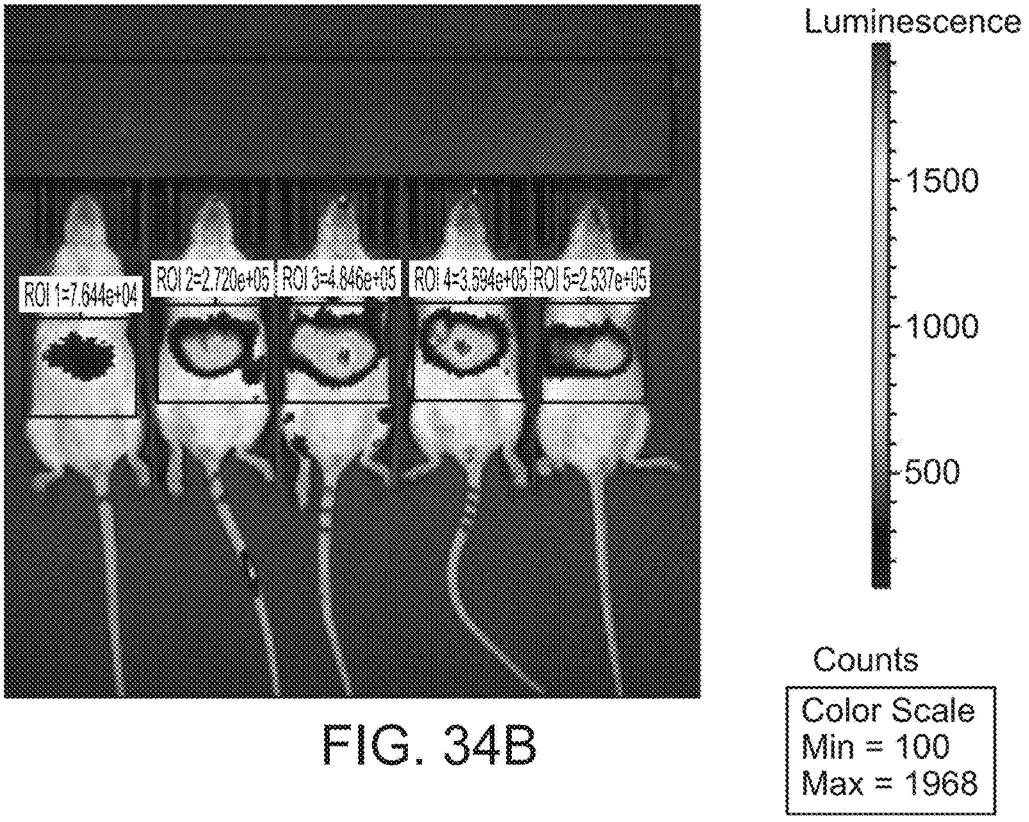
FIG. 34B depicts whole body IVIS images of CD-1 mice dosed with circular RNA encoding FLuc and formulated with ionizable Lipid 93-S14, DSPC, cholesterol, and DSPE-PEG 2000 (Avanti Polar Lipids Inc.) at a weight ratio of 16:1:4:1 or 62:4:33:1 molar ratio.
Figure 35A:
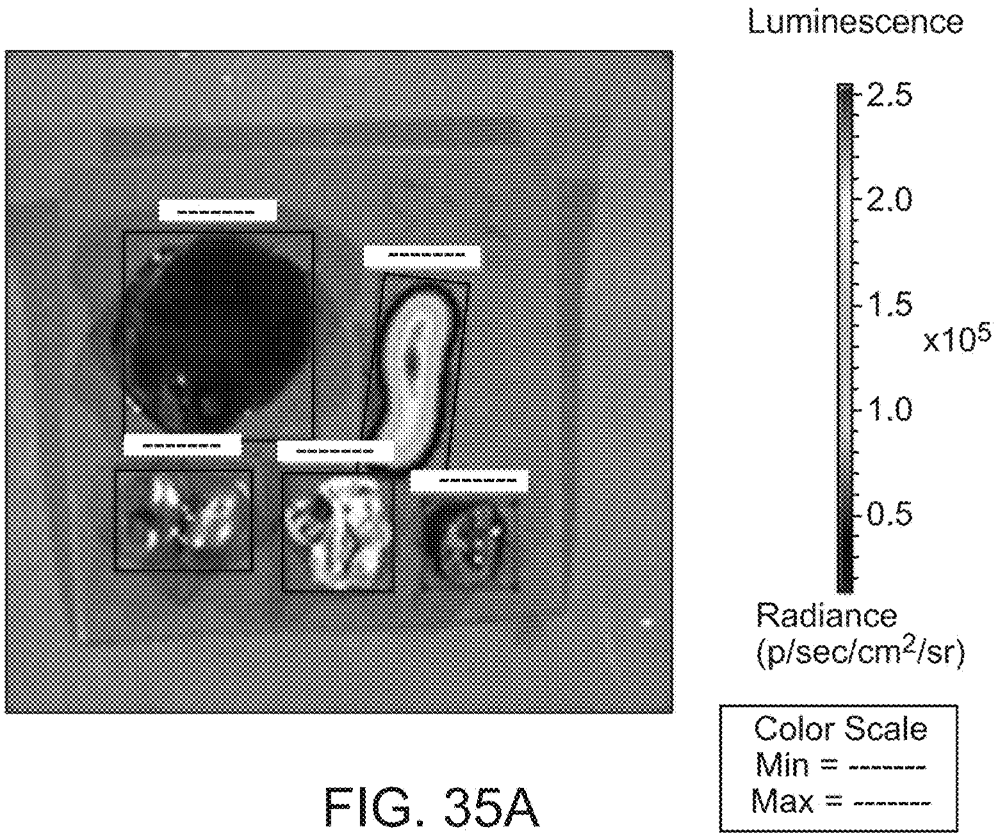
FIG. 35A depicts images highlighting the luminescence of organs harvested from CD-1 mice dosed with circular RNA encoding FLuc and formulated with ionizable Lipid 26 from Table 10a, DSPC, cholesterol, and DSPE-PEG 2000 (Avanti Polar Lipids Inc.) at a weight ratio of 16:1:4:1 or 62:4:33:1 molar ratio.
Figure 35B:
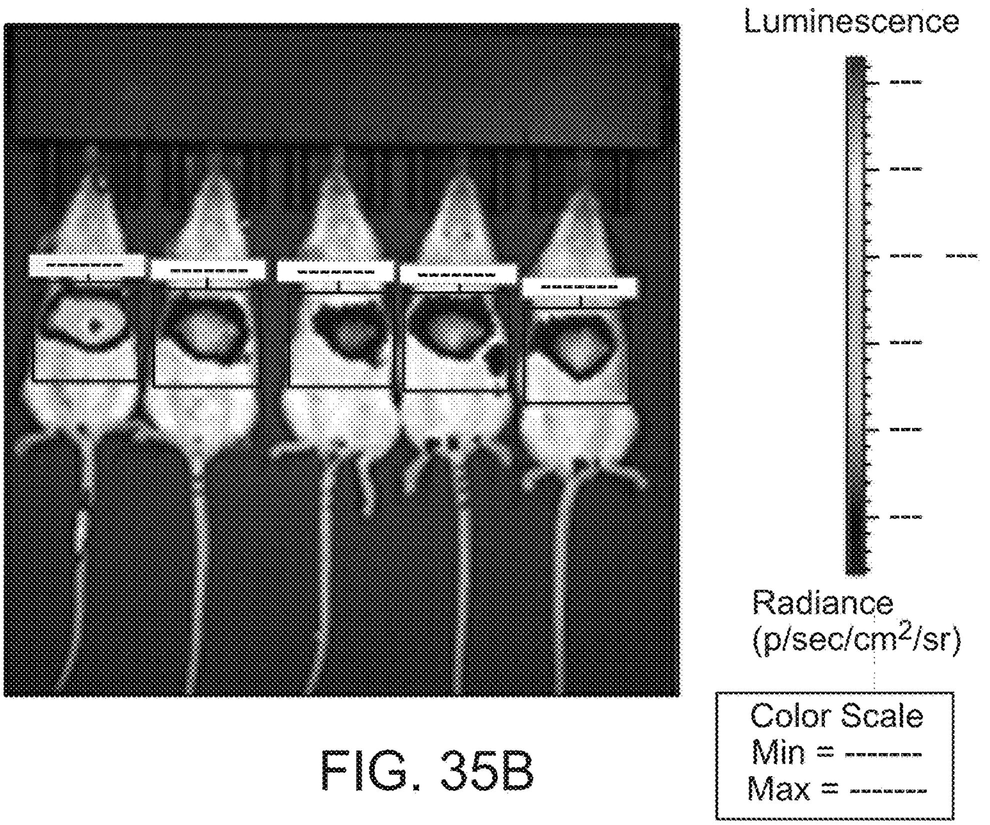
FIG. 35B depicts whole body IVIS images of CD-1 mice dosed with circular RNA encoding FLuc and formulated with ionizable Lipid 26, DSPC, cholesterol, and DSPE-PEG 2000 (Avanti Polar Lipids Inc.) at a weight ratio of 16:1:4:1 or 62:4:33:1 molar ratio.

FIG. 32A illustrates the increased whole-body total flux observed from luciferase oRNA with Lipid 26 (Table 10a) LNPs compared to LNPs made with lipids 22-S14 and 93-S14. FIG. 32B shows the ex vivo IVIS analysis of tissues further highlighting the increased overall expression with Lipid 26 (Table 10a) while maintaining the desired spleen to liver ratios observed with lipids 22-S14 and 93-S14 despite the significant structural changes designed to improve expression. These data highlight the improvements afforded by Lipid 26 (Table 10a) compared to previously reported lipids.

Figure 36A:
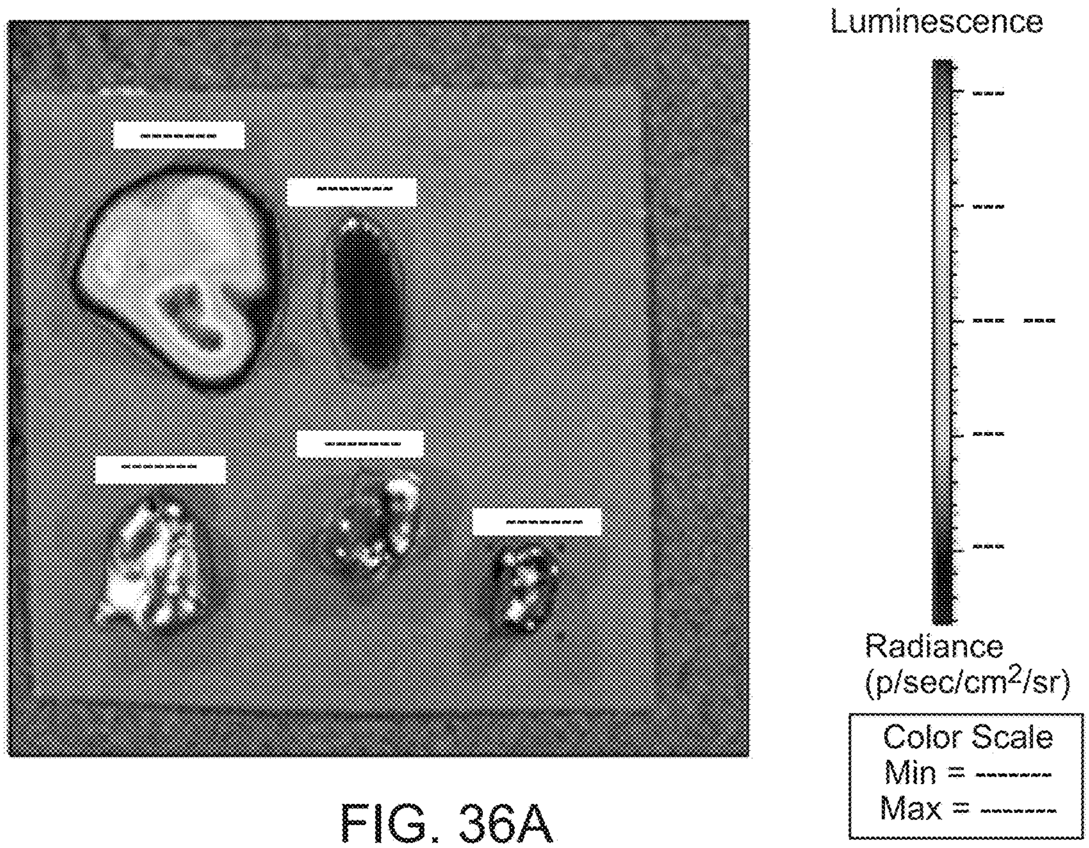
FIG. 36 depicts images highlighting the luminescence of organs harvested from c57BL/6J mice dosed with circular RNA encoding FLuc and encapsulated in lipid nanoparticles formed with Lipid 15 from Table 10b (FIG. 36A), Lipid 53 from Table 10a (FIG. 36B), or Lipid 54 from Table 10a (FIG. 36C). PBS was used as control (FIG. 36D).
Figure 36B:
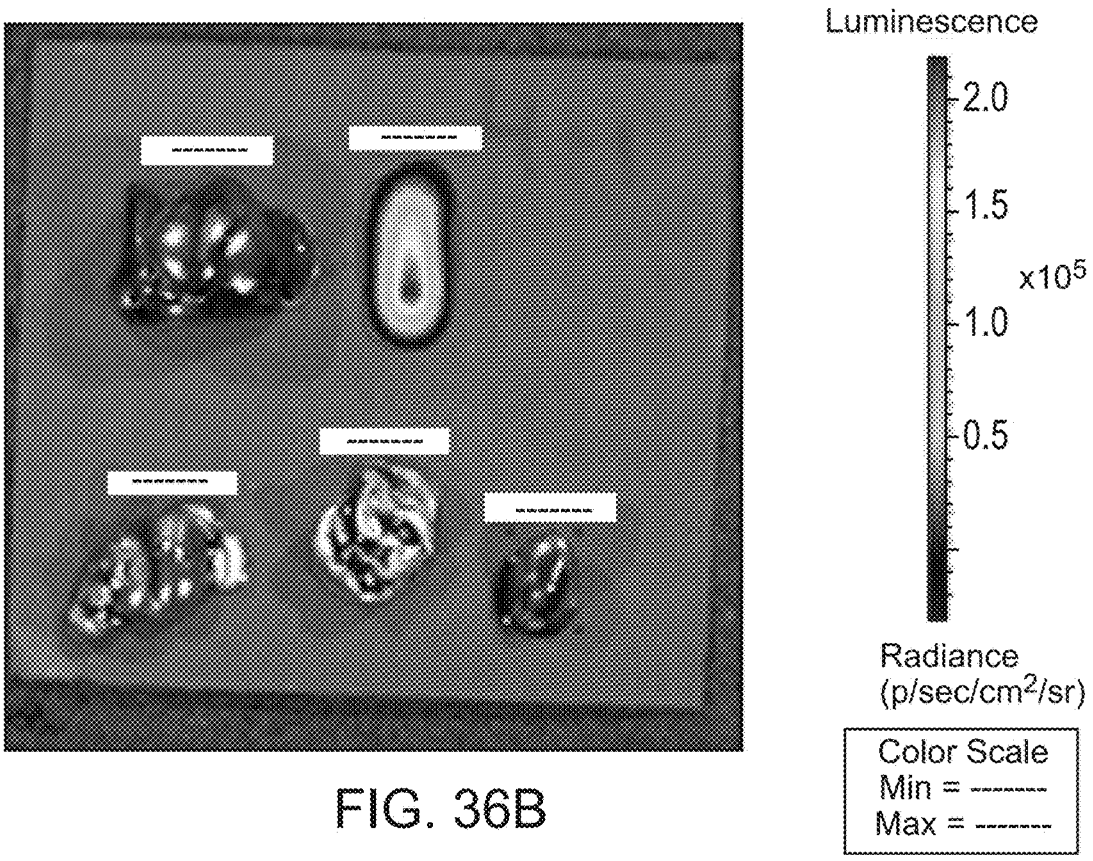
Figure 36C:
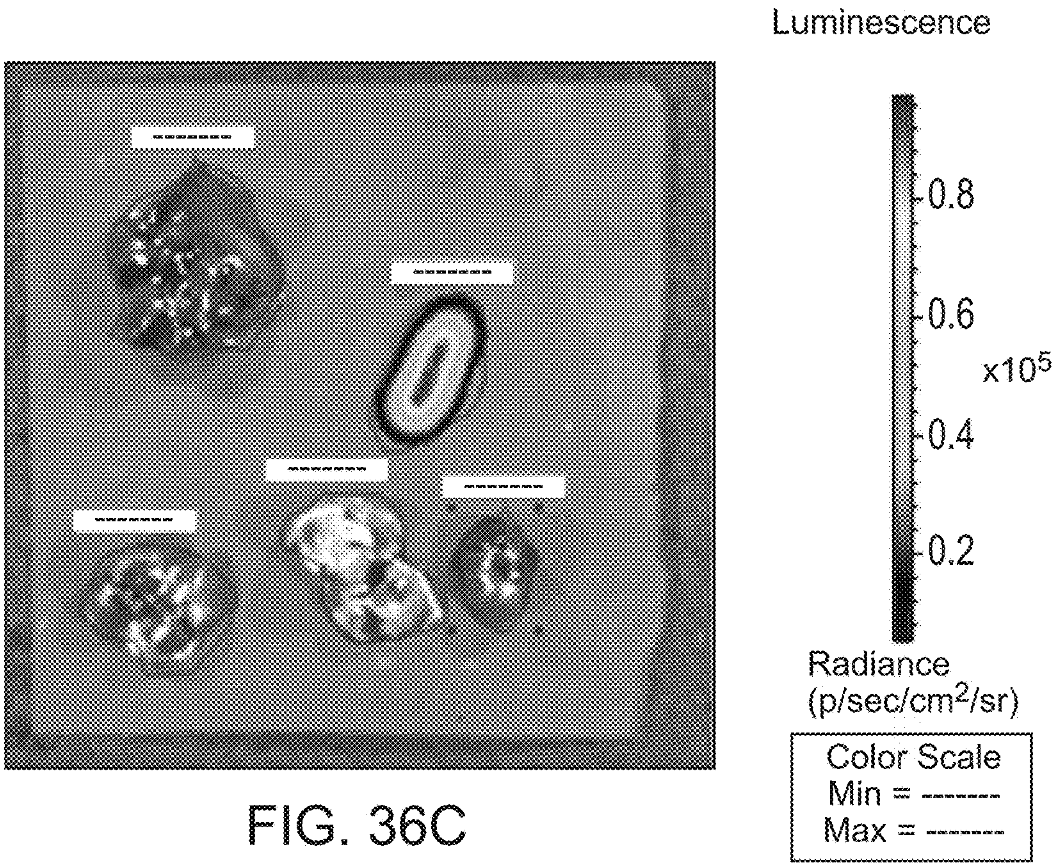
Figure 36D:
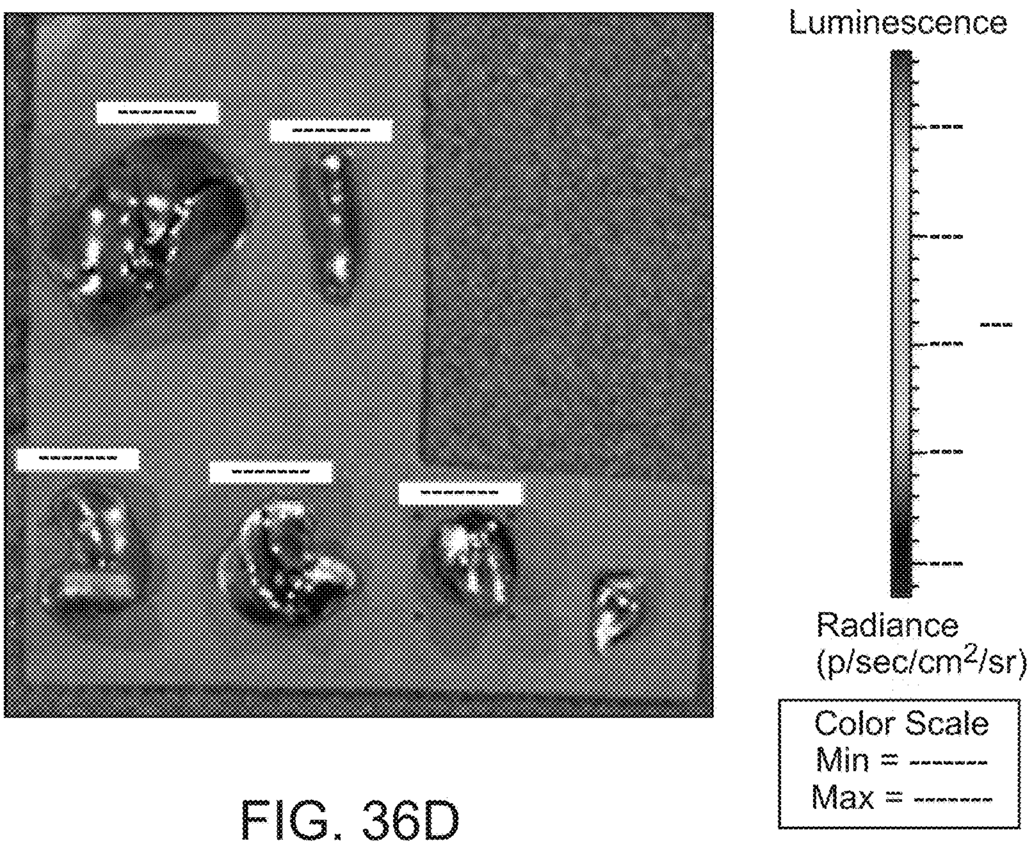

Similar analysis as described above was also performed with oRNA encapsulated in LNPs formed with Lipid 15 from Table 10b or Lipid 53 or 54 from Table 10a. FIGS. 36A-C show the ex vivo IVIS analysis of tissues, respectively highlighting the overall expression with Lipid 15, 53, and 54 while maintaining the desired spleen to liver ratios despite the significant structural changes designed to improve expression. FIG. 36D shows the results for PBS control. These data demonstrates the improvements afforded by Lipids 15, 53, and 54 from Table 10a compared to previously reported lipids such as 93-S14 and 22-S14.

Example 39

Delivery of Luciferase

Human peripheral blood mononuclear cells (PBMCs) (Stemcell Technologies) were transfected with lipid nanoparticles (LNP) encapsulating firefly luciferase (fluc) circular RNA and examined for luciferase expression. PBMCs from two different donors were incubated in vitro with five different LNP compositions, containing circular RNA encoding for firefly luciferase (200 ng), at 37° C. in RPMI, 2% human serum, IL-2 (10 ng/mL), and 50 uM BME. PBMCs incubated without LNP were used as a negative control. After 24 hours, the cells were lysed and analyzed for firefly luciferase expression based on bioluminescence (Promega BrightGlo).

Figure 37A:
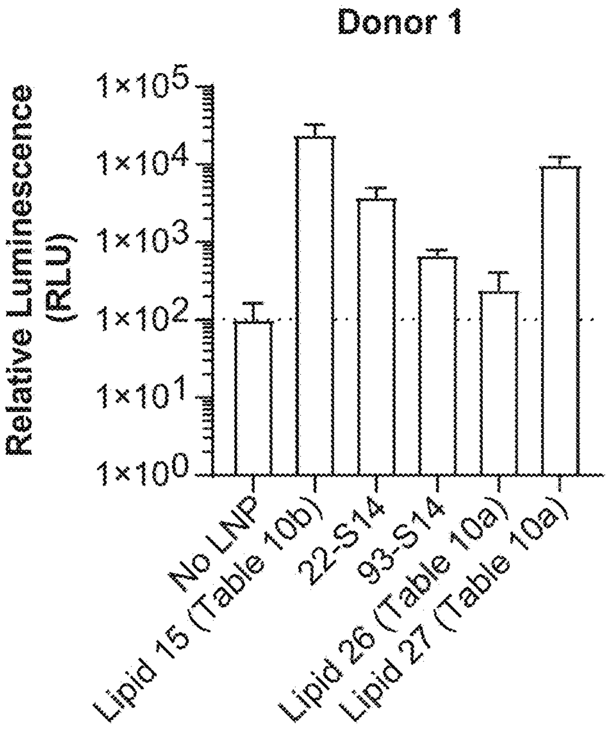
FIGS. 37A and 37B depict relative luminescence in the lysates of human PBMCs after 24-hour incubation with testing lipid nanoparticles containing circular RNA encoding firefly luciferase.
Figure 37B:
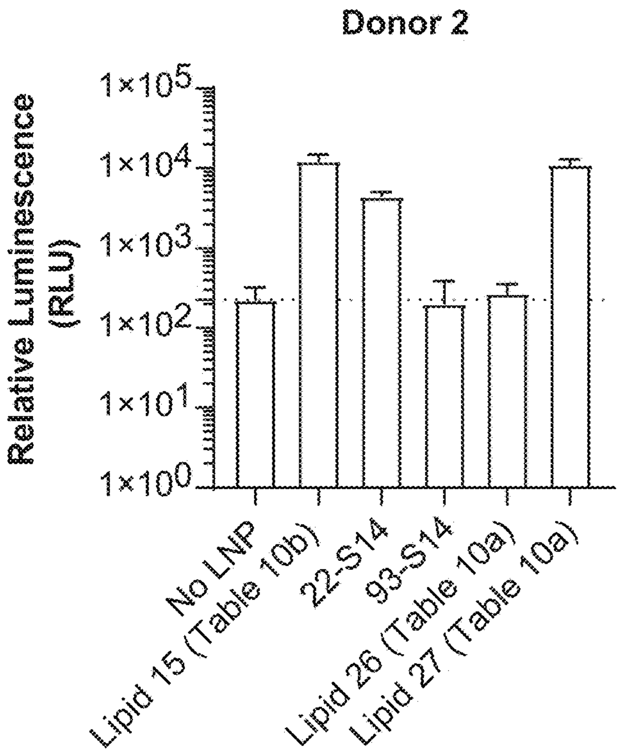

Representative data are presented in FIGS. 37A and 37B, showing that that the tested LNPs are capable of delivering circular RNA into primary human immune cells resulting in protein expression.

Example 40

In Vitro Delivery of Green Fluorescent Protein (GFP) or Chimeric Antigen Receptor (CAR)

Human PBMCs (Stemcell Technologies) were transfected with LNP encapsulating GFP and examined by flow cytometry. PBMCs from five different donors (PBMC A-E) were incubated in vitro with one LNP composition, containing circular RNA encoding either GFP or CD19-CAR (200 ng), at 37° C. in RPMI, 2% human serum, IL-2 (10 ng/mL), and 50 uM BME. PBMCs incubated without LNP were used as a negative control. After 24, 48, or 72 hours post-LNP incubation, cells were analyzed for CD3, CD19, CD56, CD14, CD11b, CD45, fixable live dead, and payload (GFP or CD19-CAR).

Figure 38A:
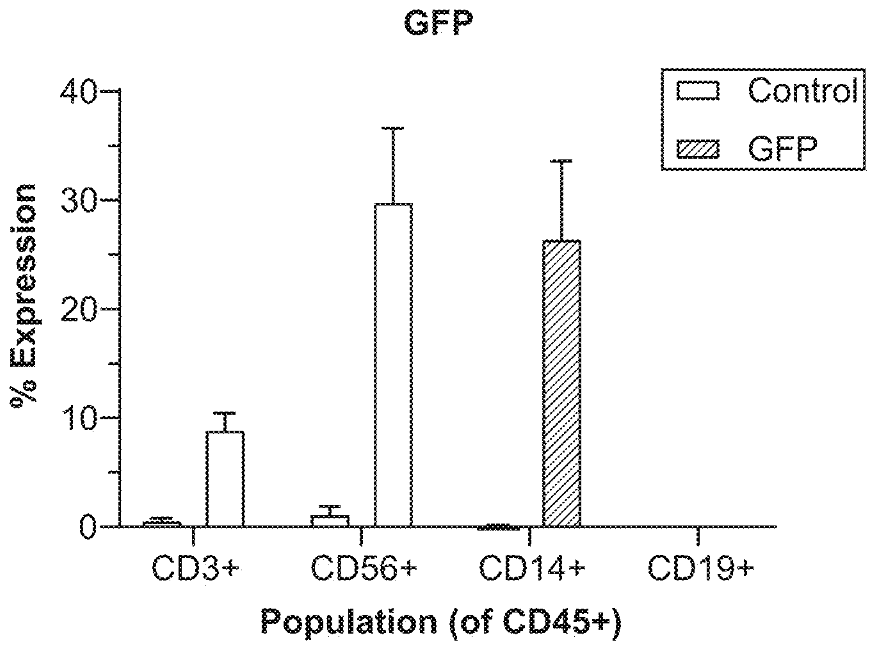
FIGS. 38A and 38B show the expression of GFP (FIG. 38A) and CD19 CAR (FIG. 38B) in human PBMCs after incubating with testing lipid nanoparticle containing circular RNA encoding either GFP or CD19 CAR.
Figure 38B:
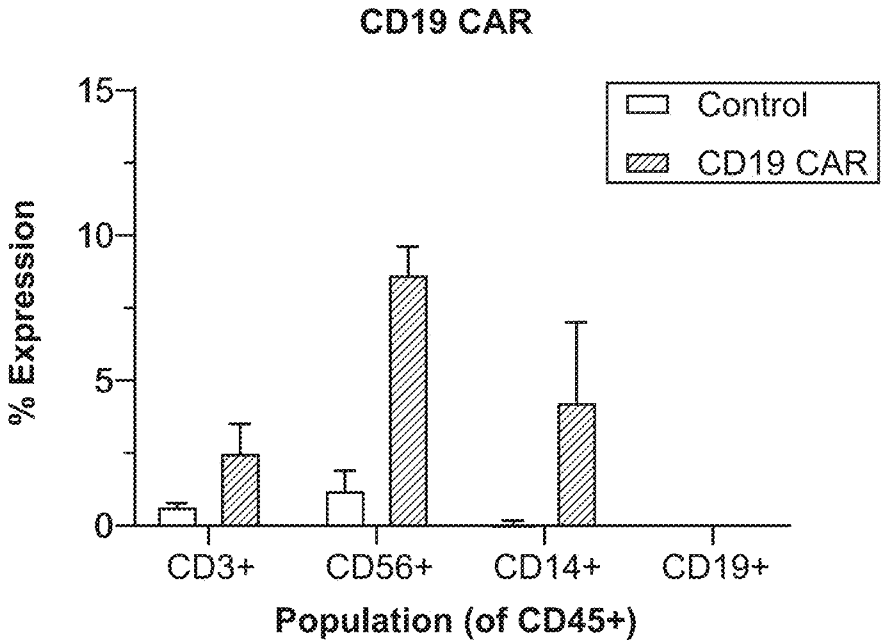

Representative data are presented in FIGS. 38A and 38B, showing that the tested LNP is capable of delivering circular RNA into primary human immune cells resulting in protein expression.

Example 41

Multiple IRES Variants can Mediate Expression of Murine CD19 CAR In Vitro

Multiple circular RNA constructs, encoding anti-murine CD19 CAR, contains unique IRES sequences and were lipotransfected into 1C1C7 cell lines. Prior to lipotransfection, 1C1C7 cells are expanded for several days in complete RPMI Once the cells expanded to appropriate numbers, 1C1C7 cells were lipotransfected (Invitrogen RNAiMAX) with four different circular RNA constructs. After 24 hours, 1C1C7 cells were incubated with His-tagged recombinant murine CD19 (Sino Biological) protein, then stained with a secondary anti-His antibody. Afterwards, the cells were analyzed via flow cytometry.

Figure 39:
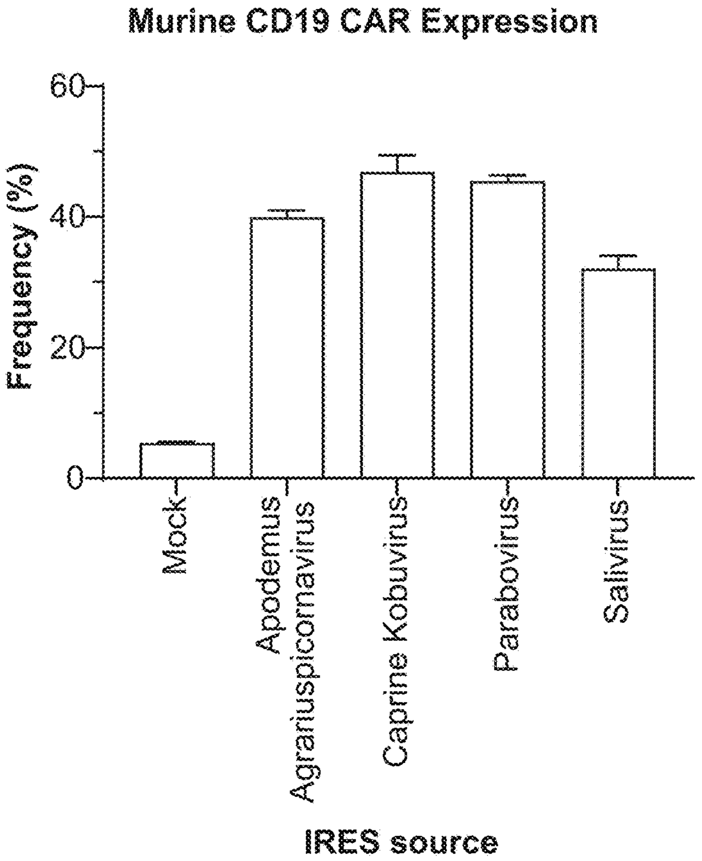
FIG. 39 depicts the expression of an anti-murine CD19 CAR in 1C1C7 cells lipotransfected with circular RNA comprising an anti-murine CD19 CAR expression sequence and varying IRES sequences.

Representative data are presented in FIG. 39, showing that IRES sourced from the indicated virus (*Apodemus agrarius* picornavirus, caprine kobuvirus, parabovirus, and salivirus) are capable of driving expression of an anti-mouse CD19 CAR in murine T cells.

Example 42

Murine CD19 CAR Mediates Tumor Cell Killing In Vitro

Circular RNA encoding anti-mouse CD19 CAR were electroporated into murine T cells to evaluate CAR-mediated cytotoxicity. For electroporation, T cells were electroporated with circular RNA encoding anti-mouse CD19 CAR using ThermoFisher's Neon Transfection System then rested overnight. For the cytotoxicity assay, electroporated T cells were co-cultured with Fluc+ target and non-target cells at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega Brightglo Luciferase System) to detect lysis of Fluc+ target and non-target cells. Values shown are calculated relative to the untransfected mock signal.

Figure 40:
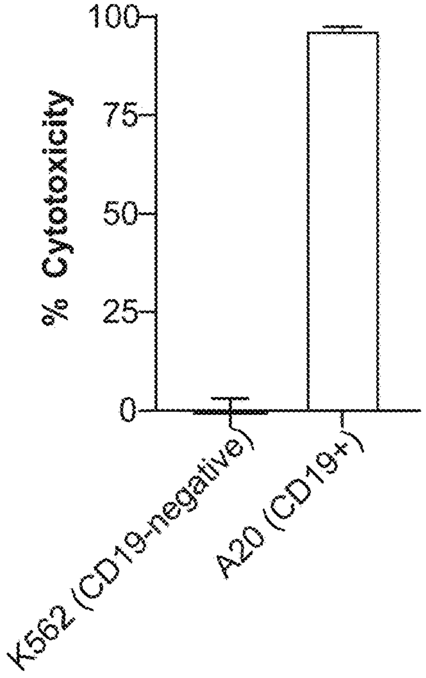
FIG. 40 shows the cytotoxicity of an anti-murine CD19 CAR to murine T cells. The CD19 CAR is encoded by and expressed from a circular RNA, which is electroporated into the murine T cells.

Representative data are presented in FIG. 40, showing that an anti-mouse CD19 CAR expressed from circular RNA is functional in murine T cells in vitro.

Example 43

Functional Depletion of B Cells with a Lipid Encapsulated Circular RNA Encoding Murine CD19 CAR C57BL/6J mice were injected with LNP formed with Lipid 15 in Table 10b, encapsulating circular RNA encoding anti-murine CD19 CAR. As a control, Lipid 15 in Table 10b encapsulating circular RNA encoding firefly luciferase (f.Luc) were injected in different group of mice. Female C57BL.6J, ranging from 20-25 g, were injected intravenously with 5 doses of 0.5 mg/kg of LNP, every other day. Between injections, blood draws were analyzed via flow cytometry for fixable live/dead, CD45, TCRvb, B220, CD11b, and anti-murine CAR. Two days after the last injection, spleens were harvested and processed for flow cytometry analysis. Splenocytes were stained with fixable live/dead, CD45, TCRvb, B220, CD11b, NK1.1, F4/80, CD11c, and anti-murine CAR. Data from mice injected with anti-murine CD19 CAR LNP were normalized to mice that received f.Luc LNP.

Figure 41A:
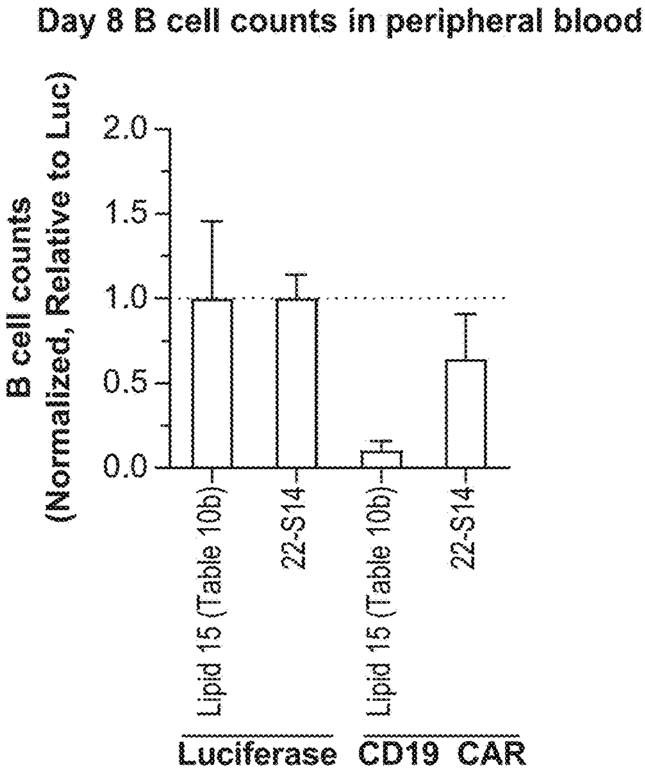
FIGS. 41A, 41B and 41C depict the B cell counts in peripheral blood (FIGS. 41A and 41B) or spleen (FIG. 41C) in C57BL/6J mice injected every other day with testing lipid nanoparticles encapsulating a circular RNA encoding an anti-murine CD19 CAR.
Figure 41B:
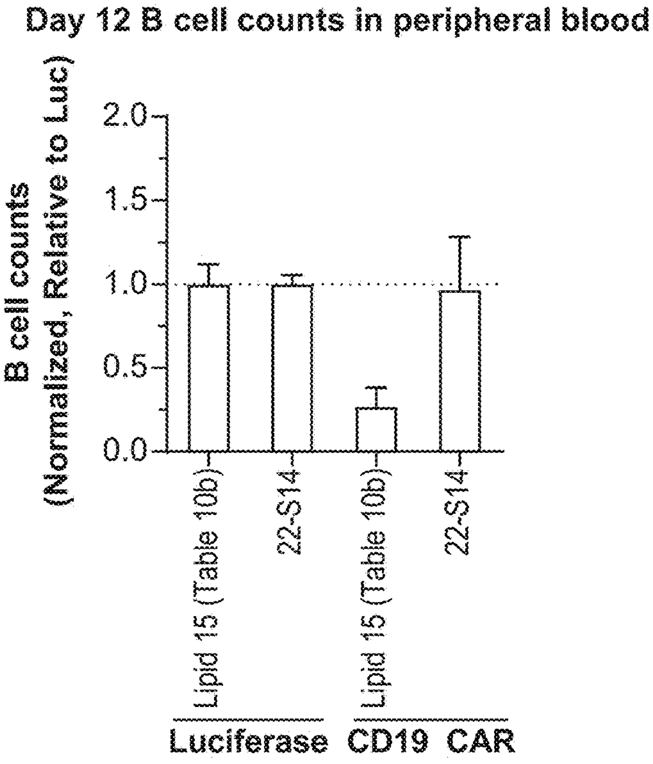
Figure 41C:
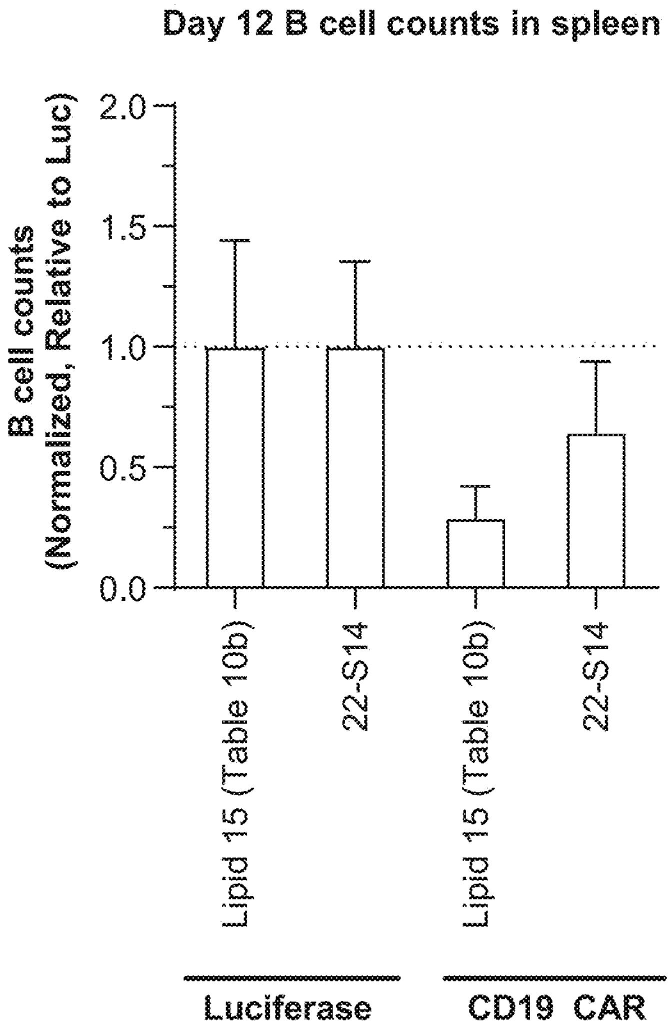

Representative data are presented in FIGS. 41A, 41B, and 41C, showing that an anti-mouse CD19 CAR expressed from circular oRNA delivered in vivo with LNPs is functional in murine T cells in vivo.

Example 44

CD19 CAR Expressed from Circular RNA has Higher Yield and Greater Cytotoxic Effect Compared to that Expressed from mRNA Circular RNA encoding encoding anti-CD19 chimeric antigen antigen receptor, which includes, from N-terminus to C-terminus, a FMC63-derived scFv, a CD8 transmembrane domain, a 4-1BB costimulatory domain, and a CD3ζ intracellular domain, were electroporated into human peripheral T cells to evaluate surface expression and CAR-mediated cytotoxicity. For comparison, circular RNA-electroporated T cells were compared to mRNA-electroporated T cells in this experiment. For electroporation, CD3+ T cells were isolated from human PBMCs using commercially available T cell isolation kits (Miltenyi Biotec) from donor human PBMCs. After isolation, T cells were stimulated with anti-CD3/anti-CD28 (Stemcell Technologies) and expanded over 5 days at 37° C. in complete RPMI containing 10% FBS, IL-2 (10 ng/mL), and 50 uM BME. Five days post stimulation, T cells were electroporated with circular RNA encoding anti-human CD19 CAR using ThermoFisher's Neon Transfection System and then rested overnight. For the cytotoxicity assay, electroporated T cells were co-cultured with Fluc+ target and non-target cells at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega Brightglo Luciferase System) to detect lysis of Fluc+ target and non-target cells. Furthermore, an aliquot of electroporated T cells were taken and stained for live dead fixable staining, CD3, CD45, and chimeric antigen receptors (FMC63) at the day of analysis.

Figure 42A:
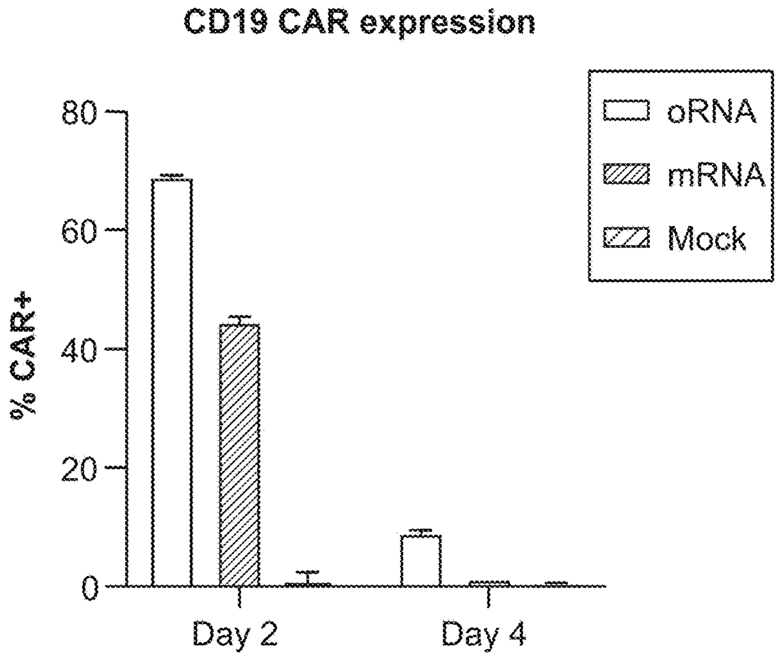
FIGS. 42A and 42B compares the expression level of an anti-human CD19 CAR expressed from a circular RNA with that expressed from a linear mRNA.
Figure 42B:
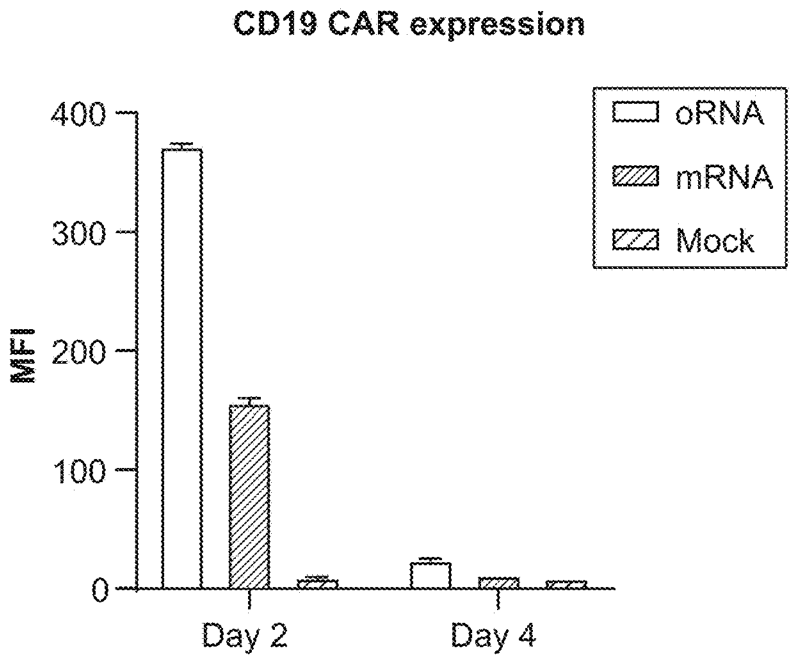
Figure 43A:
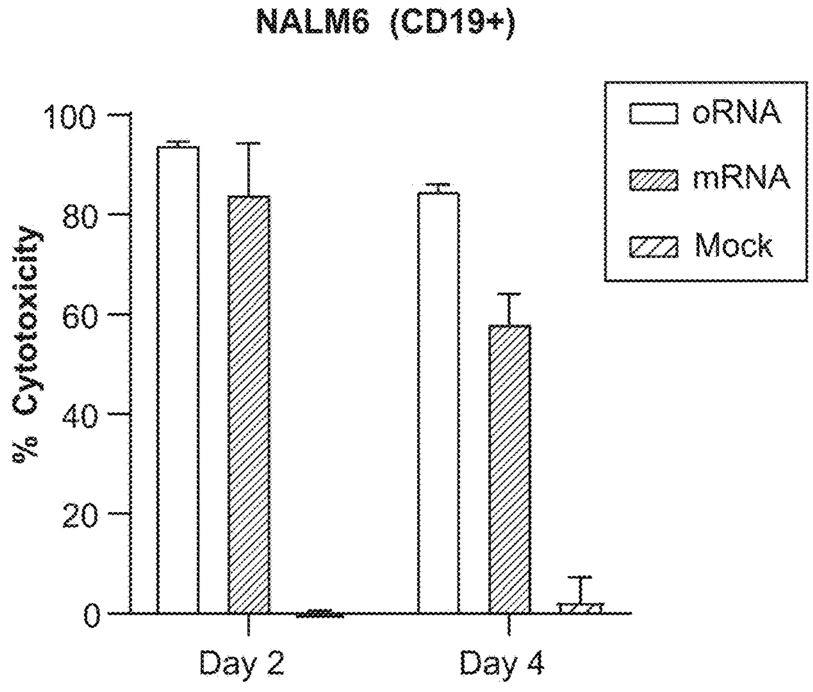
FIGS. 43A and 43B compares the cytotoxic effect of an anti-human CD19 CAR expressed from a circular RNA with that expressed from a linear mRNA
Figure 43B:
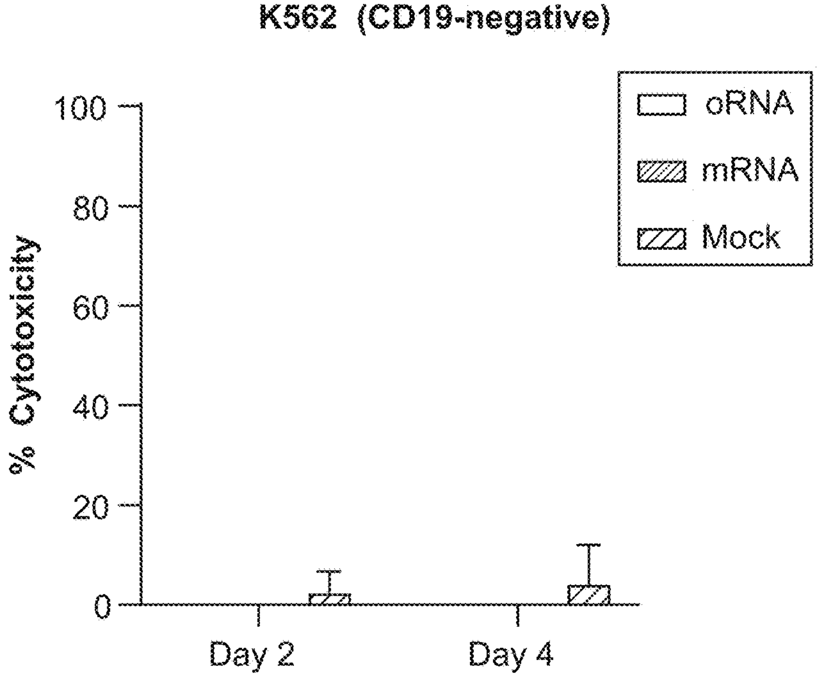

Representative data are presented in FIGS. 42 and 43. FIGS. 42A and 42B show that an anti-human CD19 CAR expressed from circular RNA is expressed at higher levels and longer than an anti-human CD19 CAR expressed from linear mRNA. FIGS. 43A and 43B show that an anti-human CD19 CAR expressed from circular RNA is exerts a greater cytotoxic effect relative to anti-human CD19 CAR expressed from linear mRNA.

Example 45

Functional Expression of Two CARs from a Single Circular RNA

Circular RNA encoding chimeric antigen receptors were electroporated into human peripheral T cells to evaluate surface expression and CAR-mediated cytotoxicity. The purpose of this study is to evaluate if circular RNA encoding for two CARs can be stochastically expressed with a 2A (P2A) or an IRES sequence. For electroporation, CD3+ T cells were commercially purchased (Cellero) and stimulated with anti-CD3/anti-CD28 (Stemcell Technologies) and expanded over 5 days at 37° C. in complete RPMI containing 10% FBS, IL-2 (10 ng/mL), and 50 uM BME. Four days post stimulation, T cells were electroporated with circular RNA encoding anti-human CD19 CAR, anti-human CD19 CAR-2A-anti-human BCMA CAR, and anti-human CD19 CAR-IRES-anti-human BCMA CAR using ThermoFisher's Neon Transfection System then rested overnight. For the cytotoxicity assay, electroporated T cells were co-cultured with Fluc+K562 cells expressing human CD19 or BCMA antigens at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega BrightGlo Luciferase System) to detect lysis of Fluc+ target cells.

Figure 44:
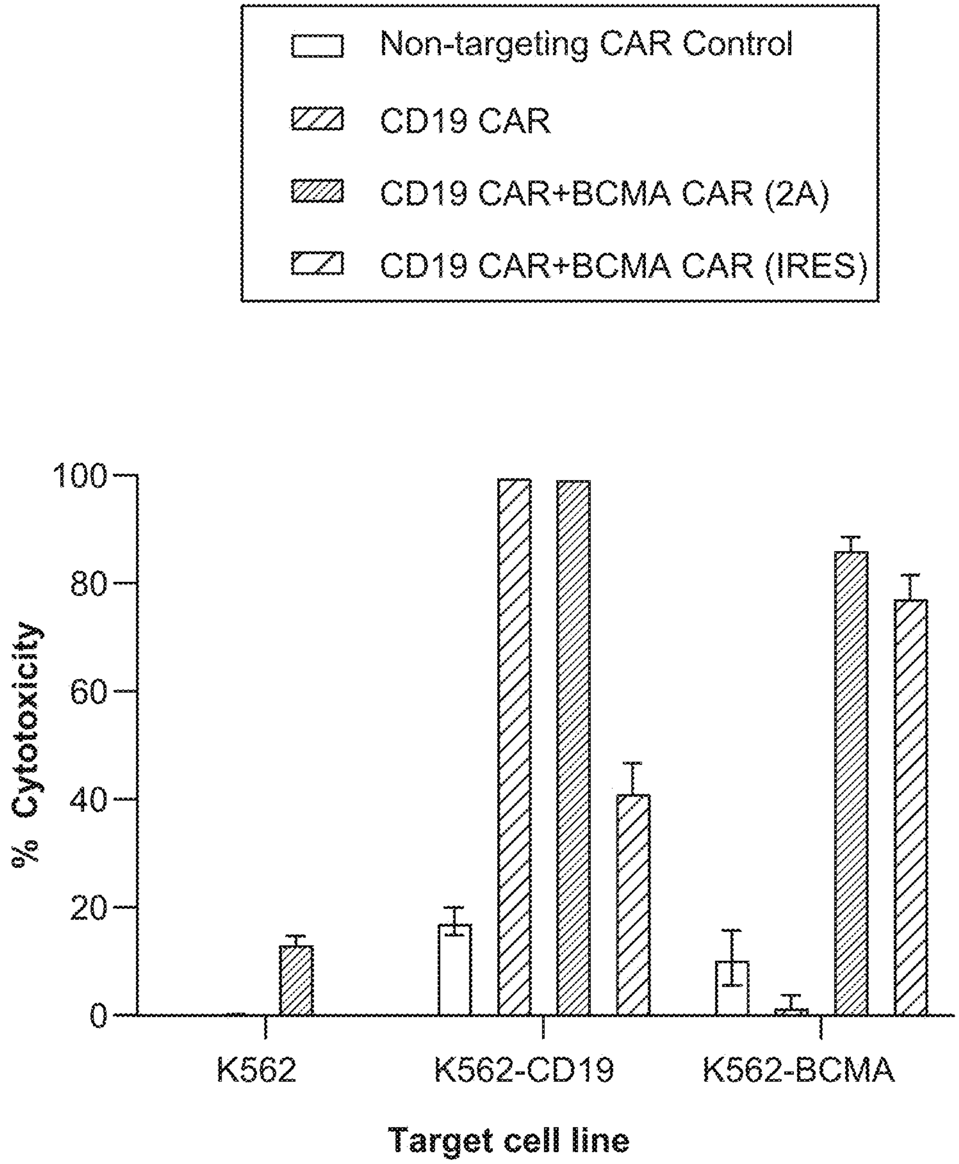
FIG. 44 depicts the cytotoxicity of two CARs (anti-human CD19 CAR and anti-human BCMA CAR) expressed from a single circular RNA in T cells.

Representative data are presented in FIG. 44, showing that two CARs can be functionally expressed from the same circular RNA construct and exert cytotoxic effector function.

Example 46

In Vivo Circular RNA Transfection Using Cre Reporter Mice

Circular RNAs encoding Cre recombinase (Cre) are encapsulated into lipid nanoparticles as previously described. Female, 6-8 week old B6.Cg-Gt(ROSA) 26Sortm9(CAG-tdTomato)Hze/J (Ai9) mice were dosed with lipid nanoparticles at 0.5 mg/kg RNA intravenously. Fluorescent tdTomato protein was transcribed and translated in Ai9 mice upon Cre recombination, meaning circular RNAs have been delivered to and translated in tdTomato+ cells. After 48 hr, mice were euthanized and the spleens were harvested, processed into a single cell suspension, and stained with various fluorophore-conjugated antibodies for immunophenotyping via flow cytometry.

Figure 45A:
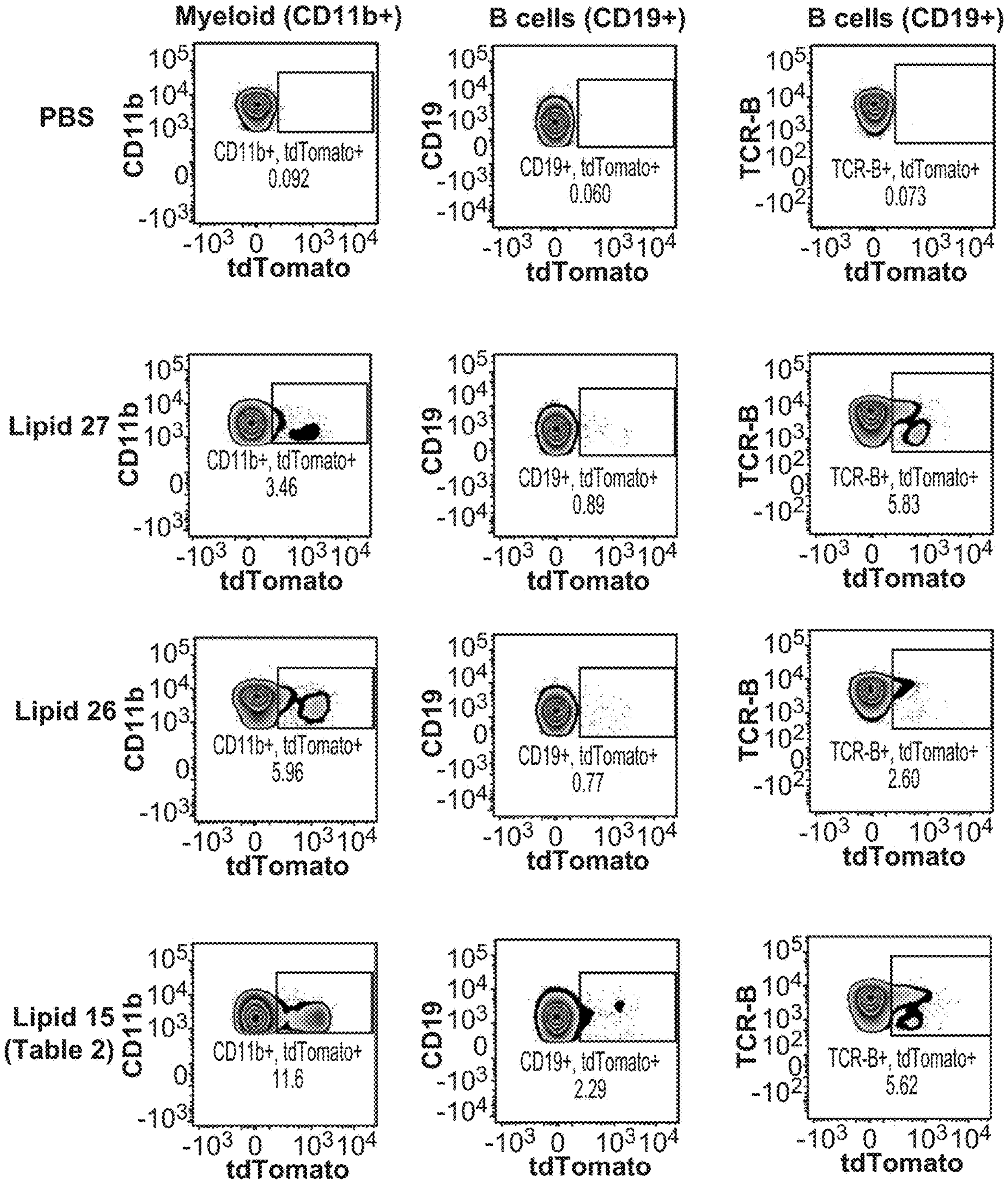
FIG. 45A shows representative FACS plots with frequencies of tdTomato expression in various spleen immune cell subsets following treatment with LNPs formed with Lipid 27 or 26 from Table 10a or Lipid 15 from Table 10b.
Figure 45B:
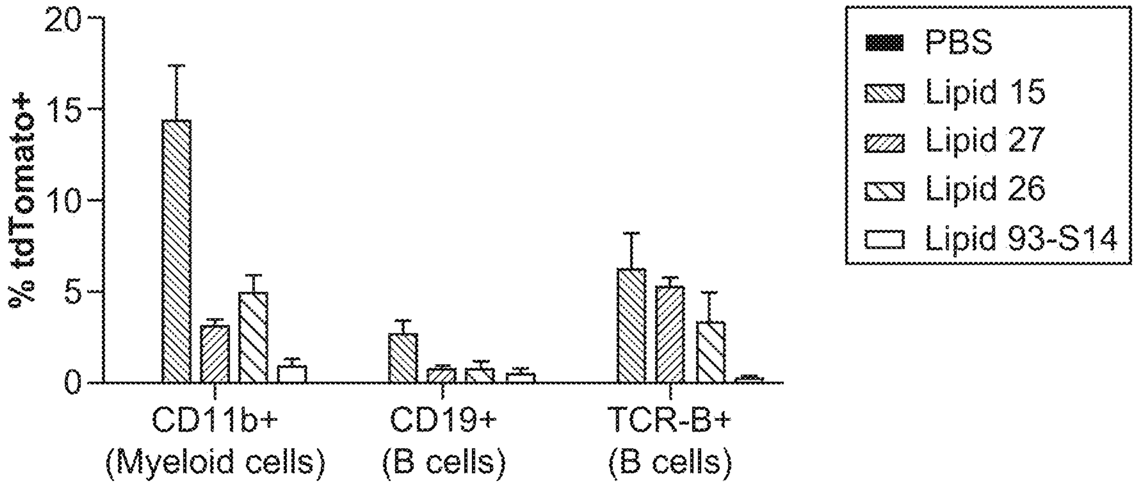
FIG. 45B shows the quantification of the proportion of myeloid cells, B cells, and T cells expressing tdTomato (mean+std. dev., n=3), equivalent to the proportion of each cell population successfully transfected with Cre circular RNA.

FIG. 45A shows representative FACS plots with frequencies of tdTomato expression in various spleen immune cell (CD45+, live) subsets, including total myeloid (CD11b+), B cells (CD19+), and T cells (TCR-B+) following treatment with LNPs formed with Lipid 27 or 26 from Table 10a or Lipid 15 from Table 10b. Ai9 mice injected with PBS represented background tdTomato fluorescence. FIG. 45B quantifies the proportion of myeloid cells, B cells, and T cells expressing tdTomato (mean+std. dev., n=3), which is equivalent to the proportion of each cell population which has been successfully transfected with Cre circular RNA. LNPs made with Lipids 27 and 26 from Table 10a exhibit significantly higher myeloid and T cell transfection compared with Lipid 93-S14, highlighting the improvements conferred by lipid structural modifications.

Figure 45C:
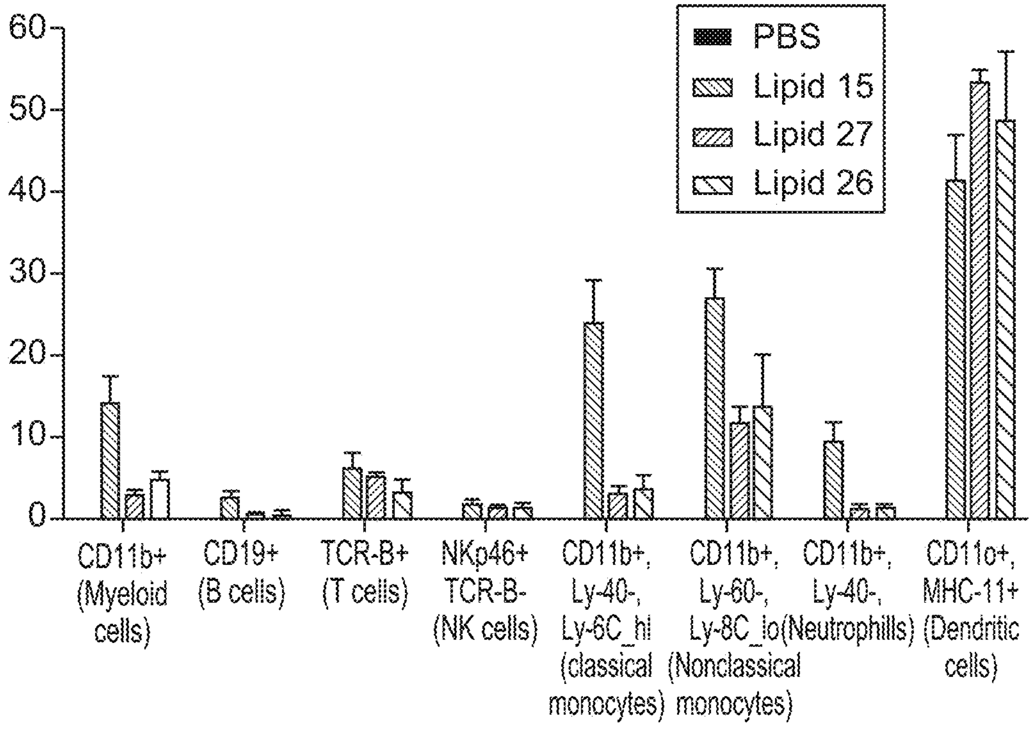
FIG. 45C illustrates the proportion of additional splenic immune cell populations, including NK cells, classical monocytes, nonclassical monocytes, neutrophils, and dendritic cells, expressing tdTomato after treatment with Lipids 27 and 26 (mean+std. dev., n=3).

FIG. 45C illustrates the proportion of additional splenic immune cell populations expressing tdTomato with Lipids 27 and 26 from Table 10a (mean+std. dev., n=3), which also include NK cells (NKp46+, TCR-B−), classical monocytes (CD11b+, Ly-6G-, Ly-6C_hi), nonclassical monocytes (CD11b+, Ly-6G-, Ly-6C_lo), neutrophils (CD11b+, Ly-6G+), and dendritic cells (CD11c+, MHC-II+). These experiments demonstrate that LNPs made with Lipids 27 and 26 from Table 10a and Lipid 15 from Table 10b are effective at delivering circular RNAs to many splenic immune cell subsets in mice and lead to successful protein expression from the circular RNA in those cells.

Example 47

Example 47A: Built-in polyA Sequences and Affinity-Purification to Produce Immune-Silent Circular RNA PolyA sequences (20-30 nt) were inserted into the 5' and 3' ends of the RNA construct (precursor RNA with built-in polyA sequences in the introns). Precursor RNA and introns can alternatively be polyadenylated post-transcriptionally using, e.g., *E coli.* polyA polymerase or yeast polyA polymerase, which requires the use of an additional enzyme.

Circular RNA in this example was circularized by in vitro transcription (IVT) and affinity-purified by washing over a commercially available oligo-dT resin to selectively remove polyA-tagged sequences (including free introns and precursor RNA) from the splicing reaction. The IVT was performed with a commercial IVT kit (New England Biolabs) or a customerized IVT mix (Orna Therapeutics), containing guanosine monophosphate (GMP) and guanosine triphosphate (GTP) at different ratios (GMP:GTP=8, 12.5, or 13.75). In some embodiments, GMP at a high GMP:GTP ratio may be preferentially included as the first nucleotide, yielding a majority of monophosphate-capped precursor RNAs. As a comparison, the circular RNA product was alternatively purified by the treatment with Xrn1, Rnase R, and Dnase I (enzyme purification).

Immunogenicity of the circular RNAs prepared using the affinity purification or enzyme purification process were then assessed. Briefly, the prepared circular RNAs were transfected into A549 cells. After 24 hours, the cells were lysed and interferon beta-1 induction relative to mock samples was measured by qPCR. 3p-hpRNA, a triphosphorylated RNA, was used as a positive control.

Figure 46A:
FIG. 46A depicts an exemplary RNA construct design with built-in polyA sequences in the introns.
Figure 46B:
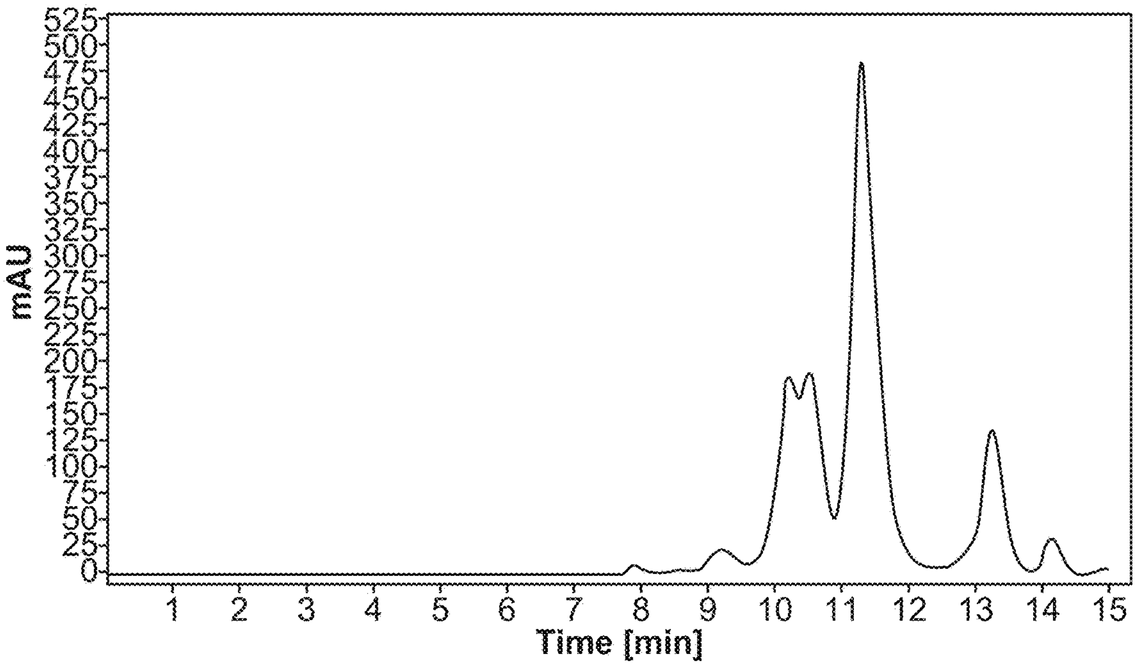
FIG. 46B shows the chromatography trace of unpurified circular RNA.
Figure 46C:
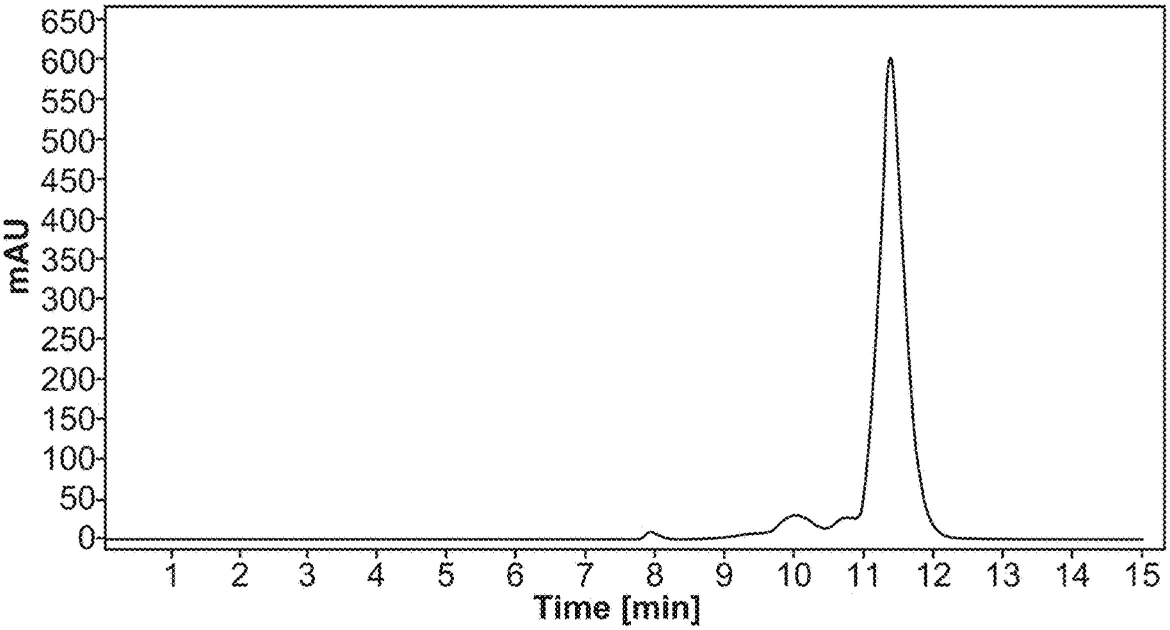
FIG. 46C shows the chromatography trace of affinity-purified circular RNA.
Figure 46D:
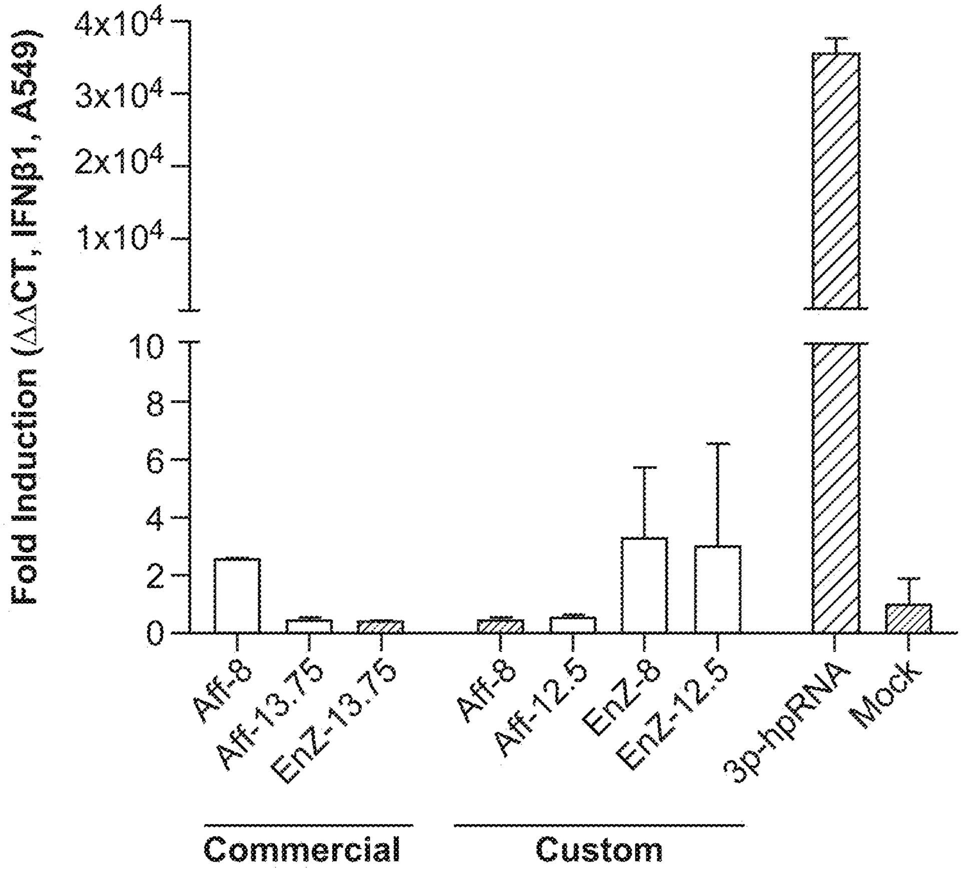
FIG. 46D shows the immunogenicity of the circular RNAs prepared with varying IVT conditions and purification methods. (Commercial=commercial IVT mix; Custom=customerized IVT mix; Aff=affinity purification; Enz=enzyme purification; GMP:GTP ratio=8, 12.5, or 13.75).

FIGS. 46B and 46C show that the negative selection affinity purification removes non-circular products from splicing reactions when polyA sequences are included on elements that are removed during splicing and present in unspliced precursor molecules. FIG. 46D shows circular RNAs prepared with tested IVT conditions and purification methods are all immunoquiescent. These results suggest the negative selection affinity purification is equivalent or superior to enzyme purification for circular RNA purification and that customized circular RNA synthesis conditions (IVT conditions) may reduce the reliance on GMP excess to achieve maximal immunoquiescence.

Example 47B: Dedicated Binding Site and Affinity Purification for Circular RNA Production Instead of polyA tags, one can include specifically design sequences (DBS, dedicated binding site).

Instead of a polyA tag, a dedicated binding site (DBS), such as a specifically designed complementary oligonucleotide that can bind to a resin, may be used to selectively deplete precursor RNA and free introns. In this example, DBS sequences (30 nt) were inserted into the 5' and 3' ends of the precursor RNA. RNA was transcribed and the transcribed product was washed over a custom complementary oligonucleotide linked to a resin.

Figure 47A:
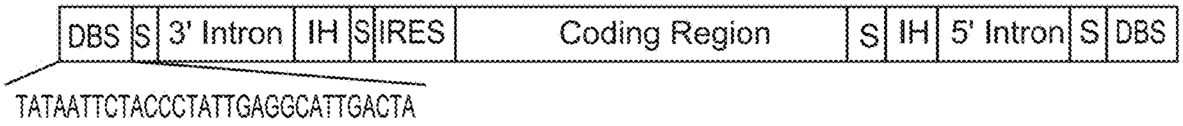
FIG. 47A depicts an exemplary RNA construct design with a dedicated binding sequence as an alternative to polyA for hybridization purification.
Figure 47B:
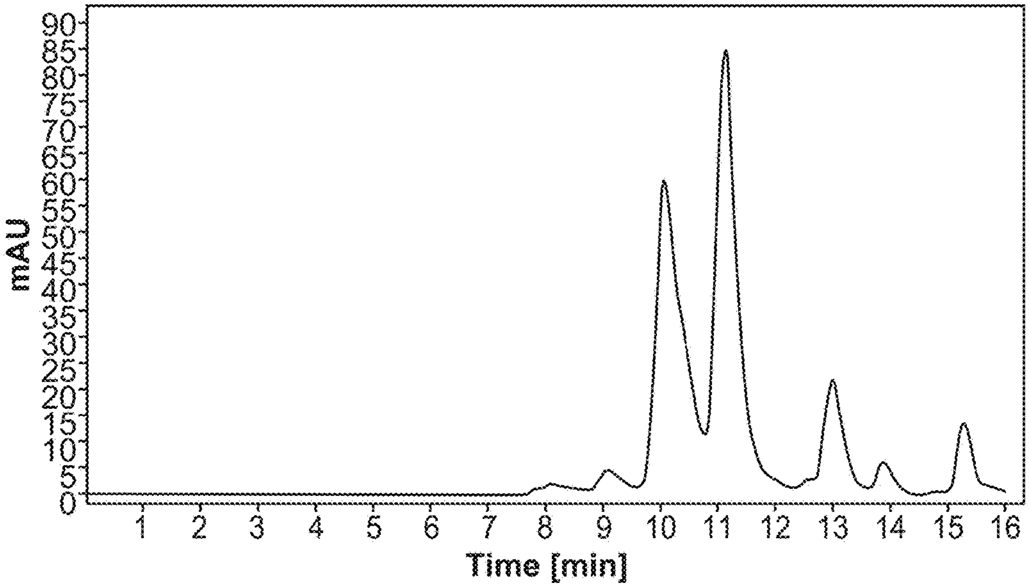
FIG. 47B shows the chromatography trace of unpurified circular RNA.
Figure 47C:
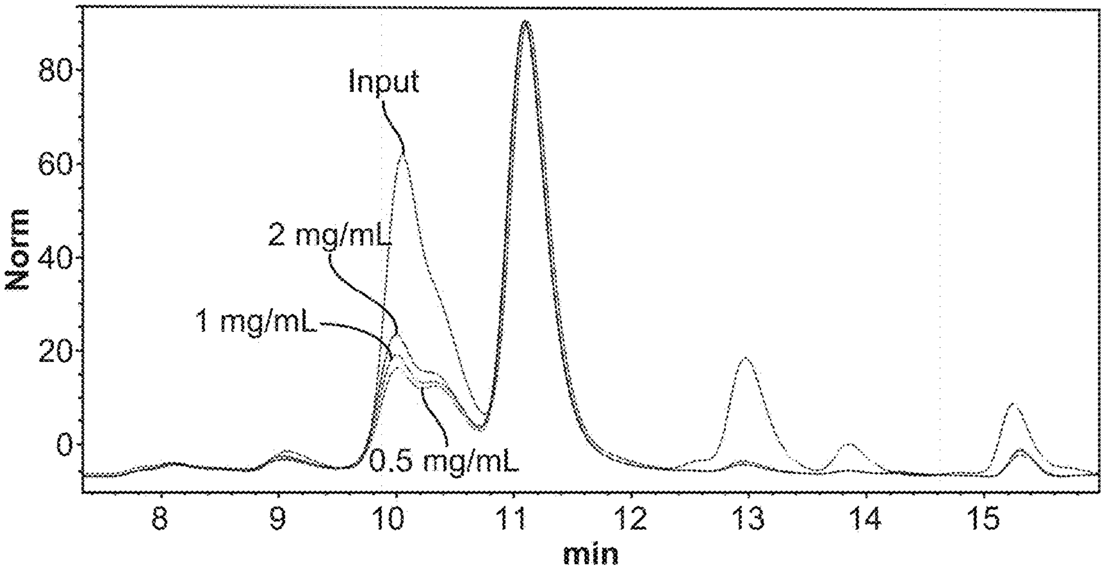
FIG. 47C shows the chromatography trace of affinity-purified circular RNA.

FIGS. 47B and 47C demonstrates that including the designed DBS sequence in elements that are removed during splicing enables the removal of unspliced precursor RNA and free intron components in a splicing reaction, via negative affinity purification.

Example 47C: Production of a Circular RNA Encoding Dystrophin

Figure 48A:
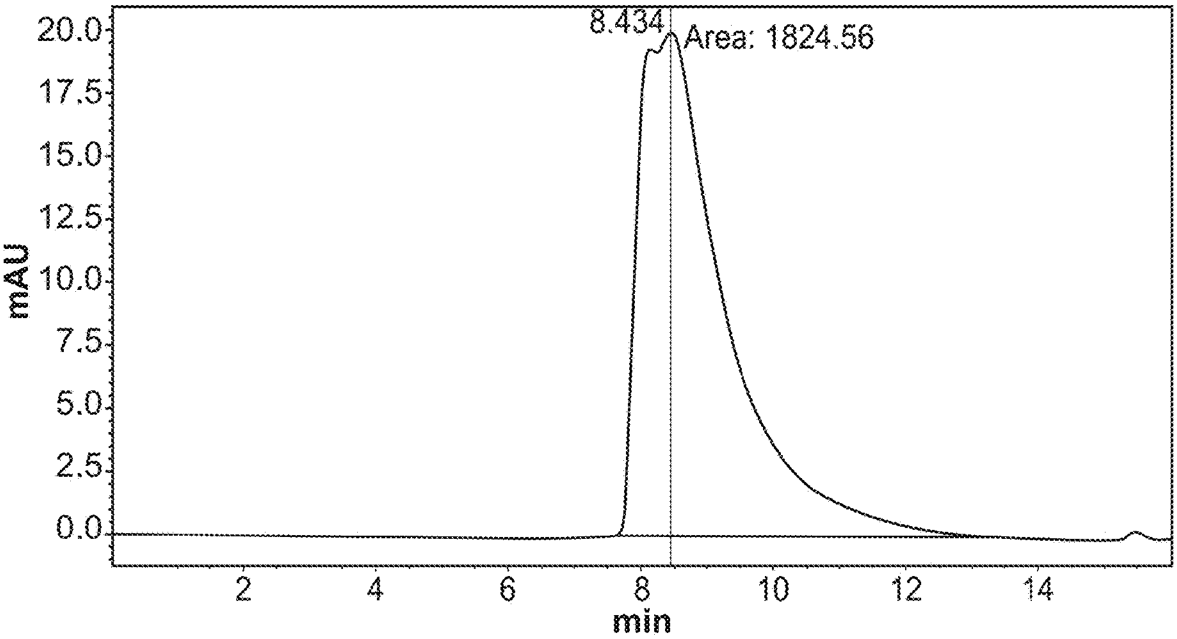
FIG. 48A shows the chromatography trace of unpurified circular RNA encoding dystrophin.
Figure 48B:
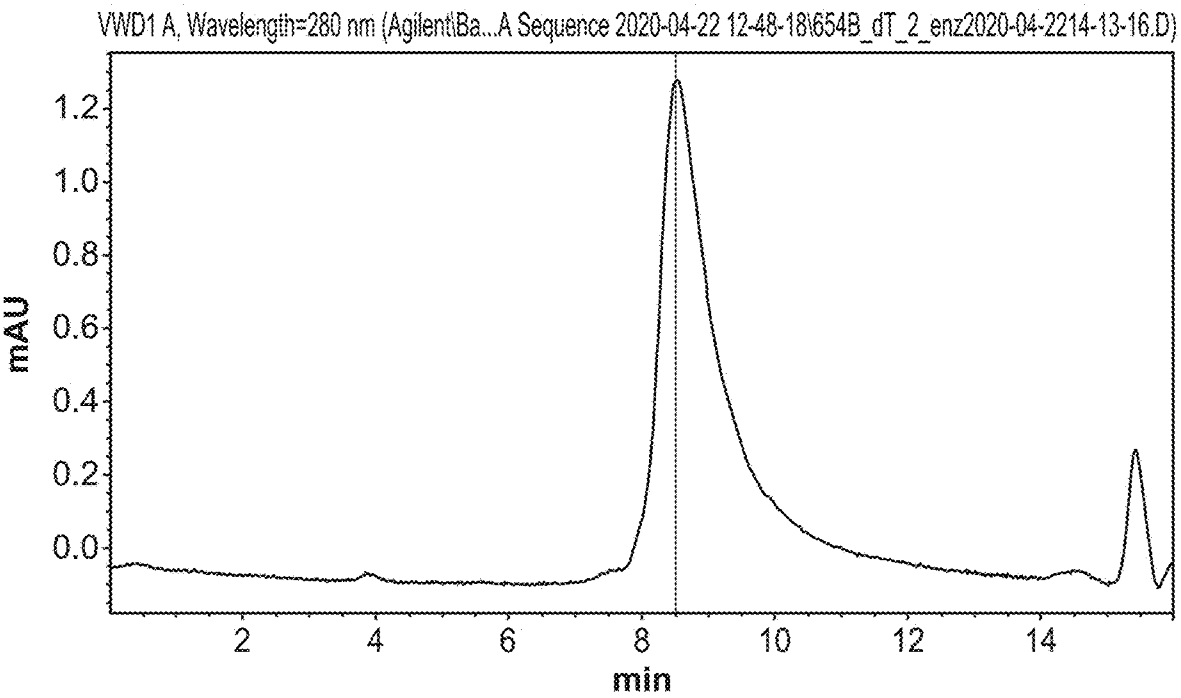
FIG. 48B shows the chromatography trace of enzyme-purified circular RNA encoding dystrophin.

A 12 kb12,000 nt circular RNA encoding dystrophin was produced by in vitro transcription of RNA precursors followed by enzyme purification using a mixture of Xrn1, DNase 1, and RNase R to degrade remaining linear components. FIG. 48 shows that the circular RNA encoding dystrophin was successfully produced.

Example 48

5' Spacer Between 3' Intron Fragment and the IRES Improves Circular RNA Expression Expression level of purified circRNAs with different 5' spacers between the 3' intron fragment and the IRES in Jurkat cells were compared. Briefly, luminescence from secreted *Gaussia* luciferase in supernatant was measured 24 hours after electroporation of 60,000 cells with 250 ng of each RNA.

Additionally, stability of purified circRNAs with different 5' spacers between the 3' intron fragment and the IRES in Jurkat cells were compared. Briefly, luminescence from secreted *Gaussia* luciferase in supernatant was measured over 2 days after electroporation of 60,000 cells with 250 ng of each RNA and normalized to day 1 expression.

Figure 49A:
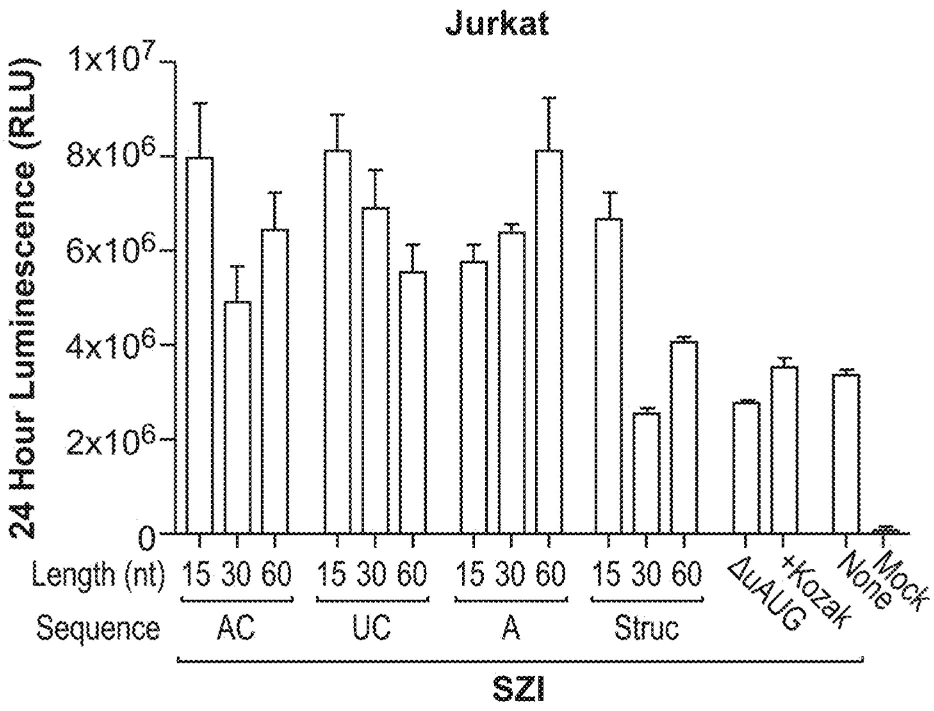
FIG. 49 compares the expression (FIG. 49A) and stability (FIG. 49B) of purified circRNAs with different 5' spacers between the 3' intron fragment/5' internal duplex region and the IRES in Jurkat cells. (AC=only A and C were used in the spacer sequence; UC=only U and C were used in the spacer sequence.)
Figure 49B:
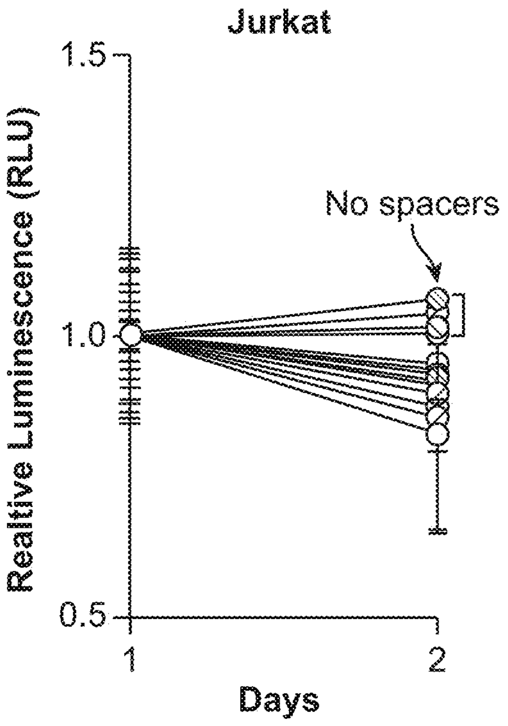

The results are shown in FIGS. 49A and 49B, indicating that adding a spacer can enhance IRES function and the importance of sequence identity and length of the added spacer. A potential explanation is that the spacer is added right before the IRES and likely functions by allowing the IRES to fold in isolation from other structured elements such as the intron fragments.

Example 49

This example describes deletion scanning from 5' or 3' end of the caprine kobuvirus IRES. IRES borders are generally poorly characterized and require empirical analysis, and this example can be used for locating the core functional sequences required for driving translation. Briefly, circular RNA constructs were generated with truncated IRES elements operably linked to a *Gaussia* luciferase coding sequence. The truncated IRES elements had nucleotide sequences of the indicated lengths removed from the 5' or 3' end. Luminescence from secreted *Gaussia* luciferase in supernatant was measured 24 and 48 hours after electroporation of primary human T cells with RNA. Stability of expression was calculated as the ratio of the expression level at the 48-hour time point relative to that at the 24-hour time point.

Figure 50:
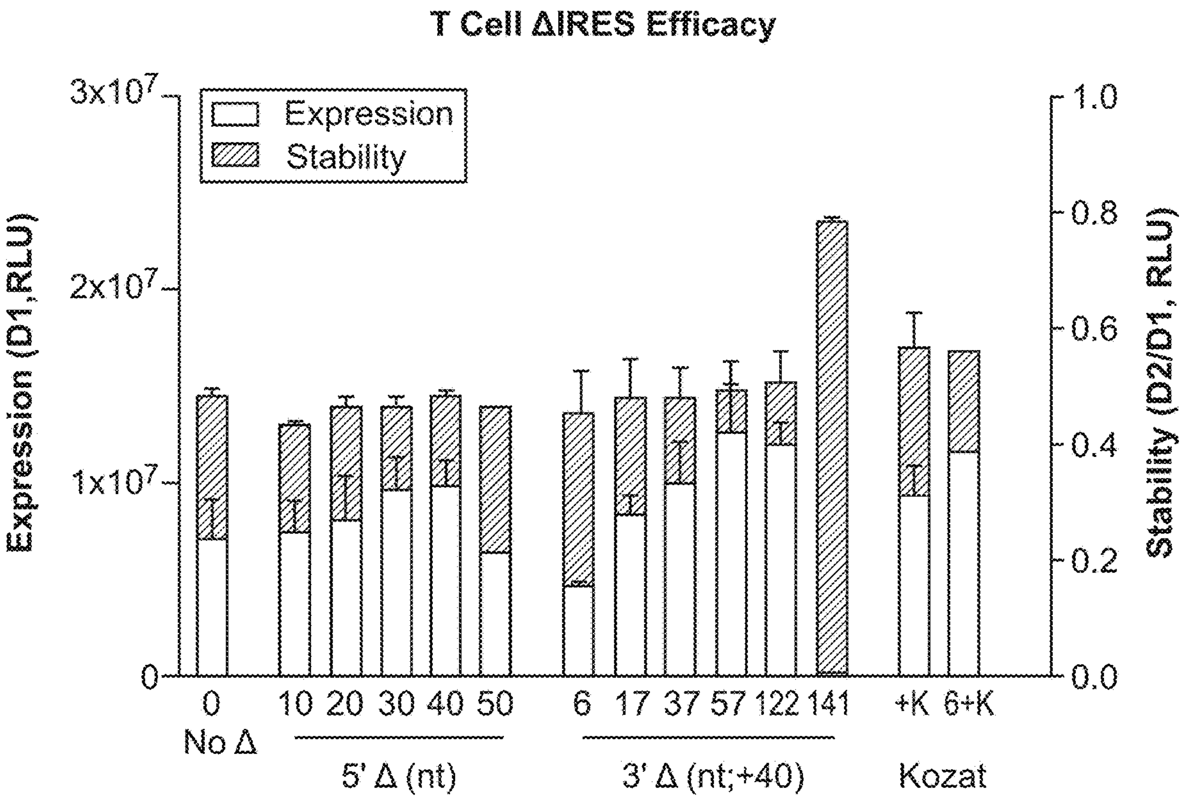
FIG. 50 shows luminescence expression levels and stability of expression in primary T cells from circular RNAs containing the original or modified IRES elements indicated.

As shown in FIG. 50, deletion of more than 40 nucleotides from the 5' end of the IRES reduced expression and disrupted IRES function. Stability of expression was relatively unaffected by the truncation of the IRES element but expression level was substantially reduced by deletion of 141 nucleotides from the 3' end of the IRES, whereas deletion of 57 or 122 nucleotides from the 3' end had a positive impact on the expression level.

It was also observed that deletion of the 6-nucleotide pre-start sequence reduced the expression level of the luciferase reporter. Replacement of the 6-nucleotide sequence with a classical kozak sequence (GCCACC) did not have a significant impact but at least maintained expression.

Example 50

This example describes modifications (e.g., truncations) of selected selected IRES sequences, including Caprine Kobuvirus (CKV) IRES, Parabovirus IRES, *Apodemus* Picornavirus (AP) IRES, Kobuvirus SZAL6 IRES, Crohivirus B (CrVB) IRES, CVB3 IRES, and SAFV IRES. The sequences of the IRES elements are provided in SEQ ID NOs: 348-389. Briefly, circular RNA constructs were generated with truncated IRES elements operably linked to a *Gaussia* luciferase coding sequence. HepG2 cells were transfected with the circular RNAs. Luminescence in the supernatant was assessed 24 and 48 hours after transfection. Stability of expression was calculated as the ratio of the expression level at the 48-hour time point relative to that at the 24-hour time point.

Figure 51:
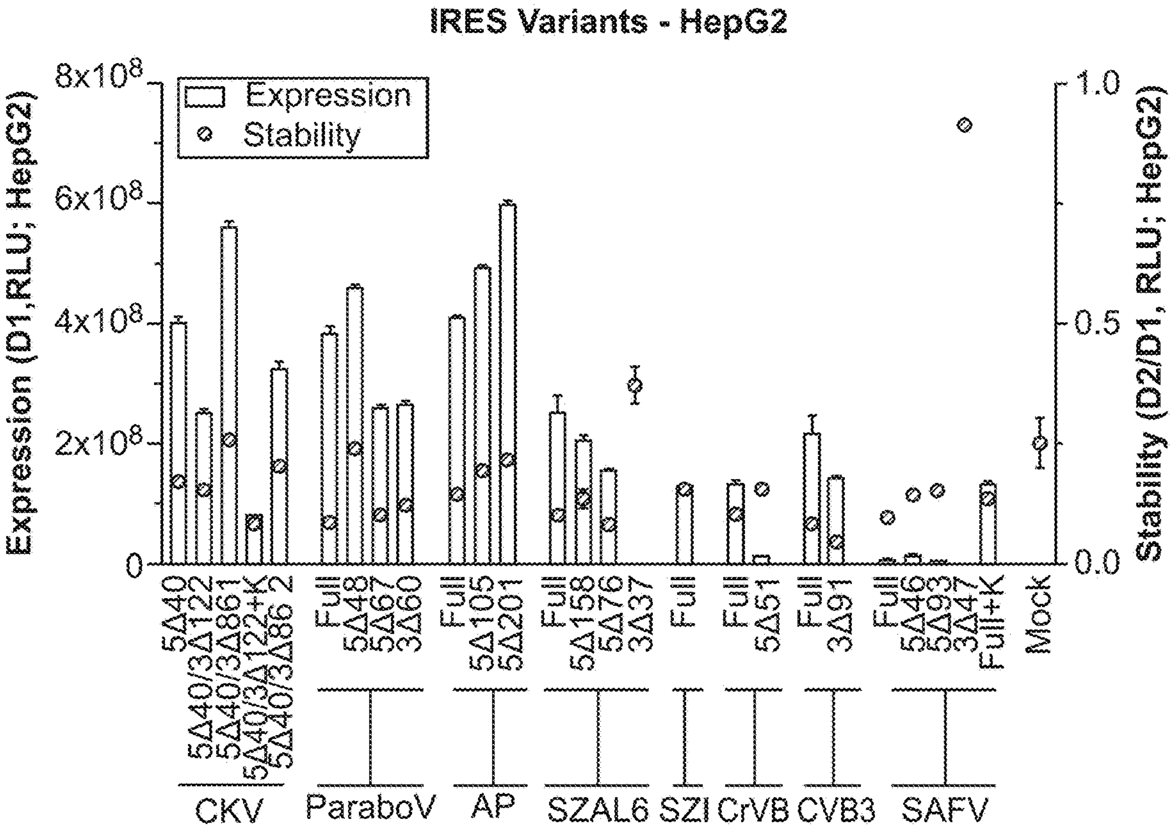
FIG. 51 shows luminescence expression levels and stability of expression in HepG2 cells from circular RNAs containing the original or modified IRES elements indicated.

As shown in FIG. 51, truncations had variable effects depending on the identity of the IRES, which may depend on the initiation mechanism and protein factors used for translation, which often differs between IRES s. 5' and 3' deletions can be effectively combined, for example, in the context of CKV IRES. Addition of a canonical Kozak sequence in some cases significantly improved expression (as in SAFV, Full vs Full+K) or diminished expression (as in CKV, 5d40/3d122 vs 5d40/3d122+K).

Example 51

This example describes modifications of CK-739, AP-748, and PV-743 IRES sequences, including mutations altative translation initiation sites. Briefly, circular RNA constructs were generated with modified IRES elements operably linked to a *Gaussia* luciferase coding sequence. Luminescence from secreted *Gaussia* luciferase in supernatant was measured 24 and 48 hours after transfection of 1C1C7 cells with RNA.

Figure 52:
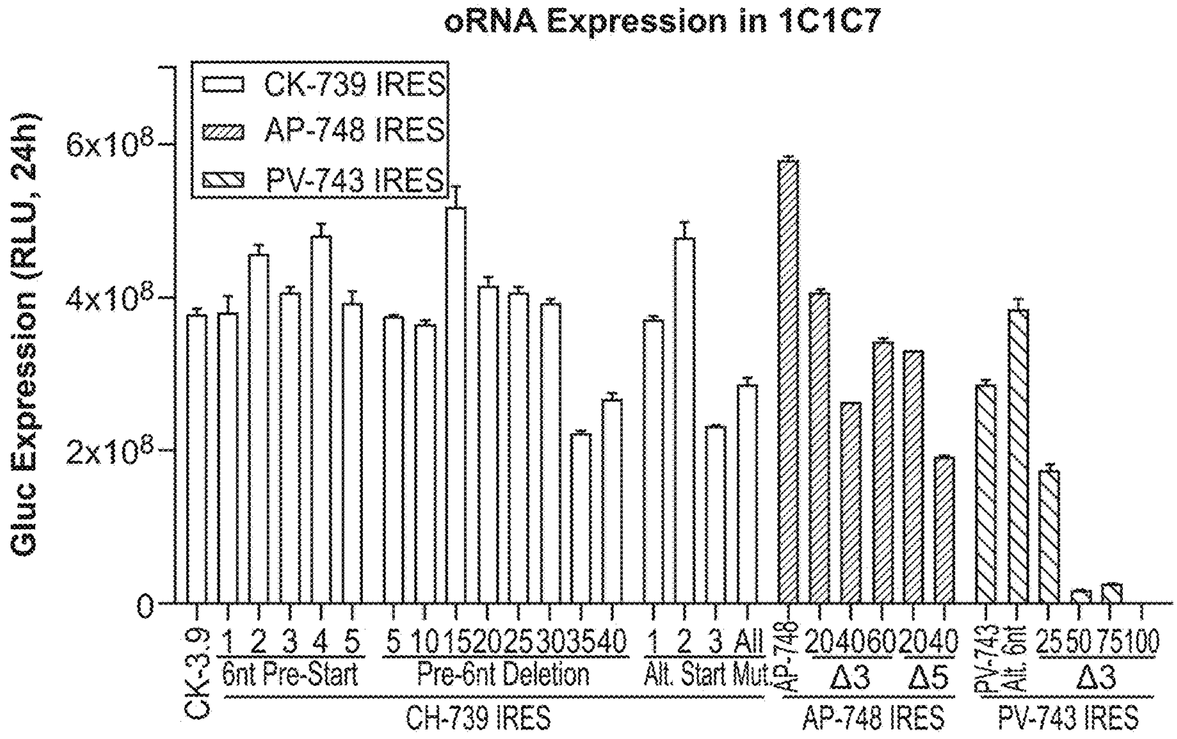
FIG. 52 shows luminescence expression levels and stability of expression in 1C1C7 cells from circular RNAs containing the original or modified IRES elements indicated.

CUG was the most commonly found alternative start site but many others were also characterized. These triplets can be present in the IRES scanning tract prior to the start codon and can affect translation of correct polypeptides. Four alternative start site mutations were created, with the IRES sequences provided in SEQ ID NOs: 378-380. As shown in FIG. 52, mutations of alternative translation initiation sites in the CK-739 IRES affected translation of correct polypeptides, positively in some instances and negatively in other instances. Mutation of all the alternative translation initiation sites reduced the level of translation.

Alternative Kozak sequences, 6 nucleotides before start codon, can also affect expression levels. The 6-nucleotide sequence upstream of the start codon were gTcacG, aaagtc, gTcacG, gtcatg, gcaaac, and acaacc, respectively, in CK-739 IRES and Sample Nos. 1-5 in the “6 nt Pre-Start” group. As shown in FIG. 52, substitution of certain 6-nucleotide sequences prior to the start codon affected translation.

It was also observed that 5' and 3' terminal deletions in AP-748 and PV-743 IRES sequences reduced expression. However, in the CK-739 IRES, which had a long scanning tract, translation was relatively unaffected by deletions in the scanning tract.

Example 52

This example describes modifications of selected IRES sequences by inserting 5' and/or 3' untranslated regions (UTRs) and creating IRES hybrids. Briefly, circular RNA constructs were generated with modified IRES elements operably linked to a *Gaussia* luciferase coding sequence. Luminescence from secreted *Gaussia* luciferase in supernatant was measured 24 and 48 hours after transfection of HepG2 cells with RNA.

Figure 53:
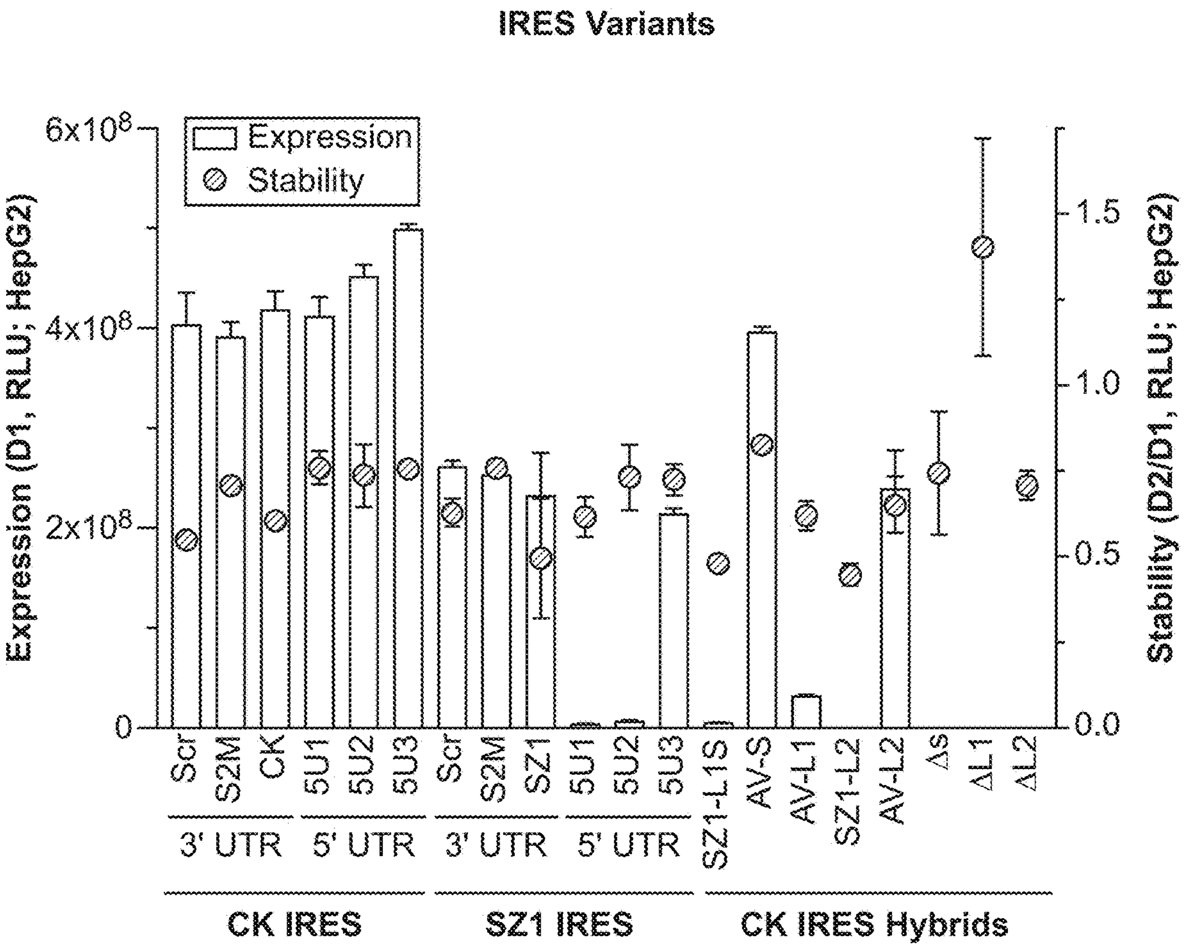
FIG. 53 shows luminescence expression levels and stability of expression in HepG2 cells from circular RNAs containing IRES elements with untranslated regions (UTRs) inserted or hybrid IRES elements. "Scr" means Scrambled, which was used as a control.

IRES sequences with UTRs inserted are provided in SEQ ID NOs: 390-401. As shown in FIG. 53, insertion of 5' UTR right after the 3' end of the IRES and before the start codon slightly increased the translation from Caprine Kobuvirus (CK) IRES but in some instances abrogated translation from Salivirus SZ1 IRES. Insertion of 3' UTR right after the stop cassette had no impact on both IRES sequences.

Hybrid CK IRES sequences are provided in SEQ ID NOs: 390-401. CK IRES was used as a base, and specific regions of the CK IRES were replaced with similar-looking structures from other IRES sequences, for example, SZ1 and AV (Aichivirus). As shown in FIG. 53, certain hybrid synthetic IRES sequences were functional, indicating that hybrid IRES can be constructed using parts from distinct IRES sequences that show similar predicted structures while deleting these structures completely abrogates IRES function.

Example 53

This example describes modifications of circular RNAs by introducing stop codon or cassette variants. Briefly, circular RNA constructs were generated with IRES elements operably linked to a *Gaussia* luciferase coding sequence followed by variable stop codon cassettes, which included a stop codon in each frame and two stop codons in the reading frame of the *Gaussia* luciferase coding sequence. 1C1C7 cells were transfected with the circular RNAs. Luminescence in supernatant was assessed 24 and 48 hours after transfection.

Figure 54:
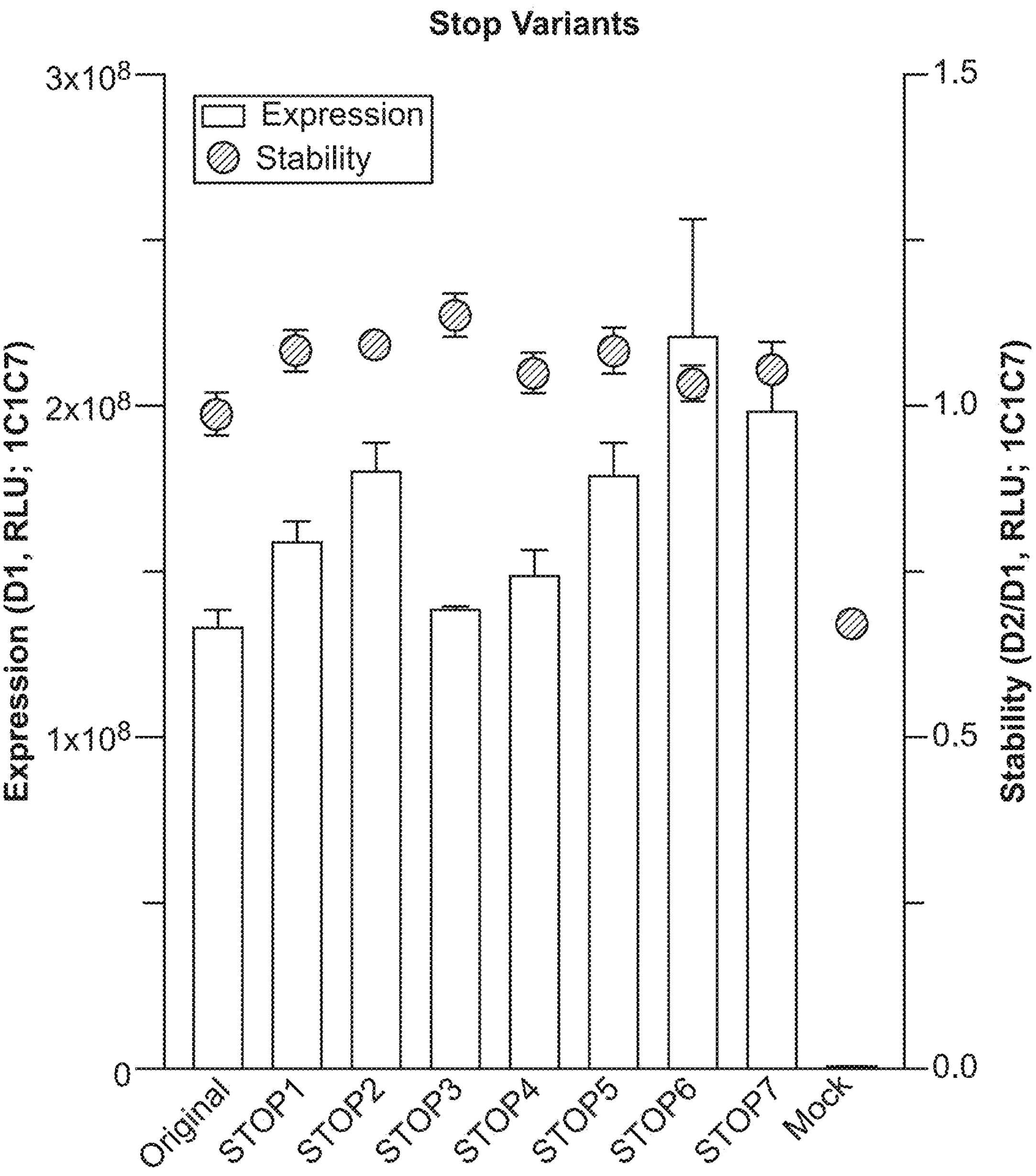
FIG. 54 shows luminescence expression levels and stability of expression in 1C1C7 cells from circular RNAs containing an IRES and variable stop codon cassettes operably linked to a *Gaussia* luciferase coding sequence.

The sequences of the stop codon cassettes are set forth in SEQ ID NOs: 406-412. As shown in FIG. 54, certain stop codon cassettes improved expression levels, although they had little impact on expression stability. In particular, a stop cassette with two frame 1 (the reading frame of the *Gaussia* luciferase coding sequence) stop codons, the first being TAA, followed by a frame 2 stop codon and a frame 3 stop codon, is effective for promoting functional translation.

Example 54

This example describes modifications of circular RNAs by inserting 5' UTR variants. Briefly, circular RNA constructs were generated with IRES elements with 5' UTR variants inserted between the 3' end of the IRES and the start codon, the IRES being operably linked to a *Gaussia* luciferase coding sequence. 1C1C7 cells were transfected with the circular RNAs. Luminescence in supernatant was assessed 24 and 48 hours after transfection.

Figure 55:
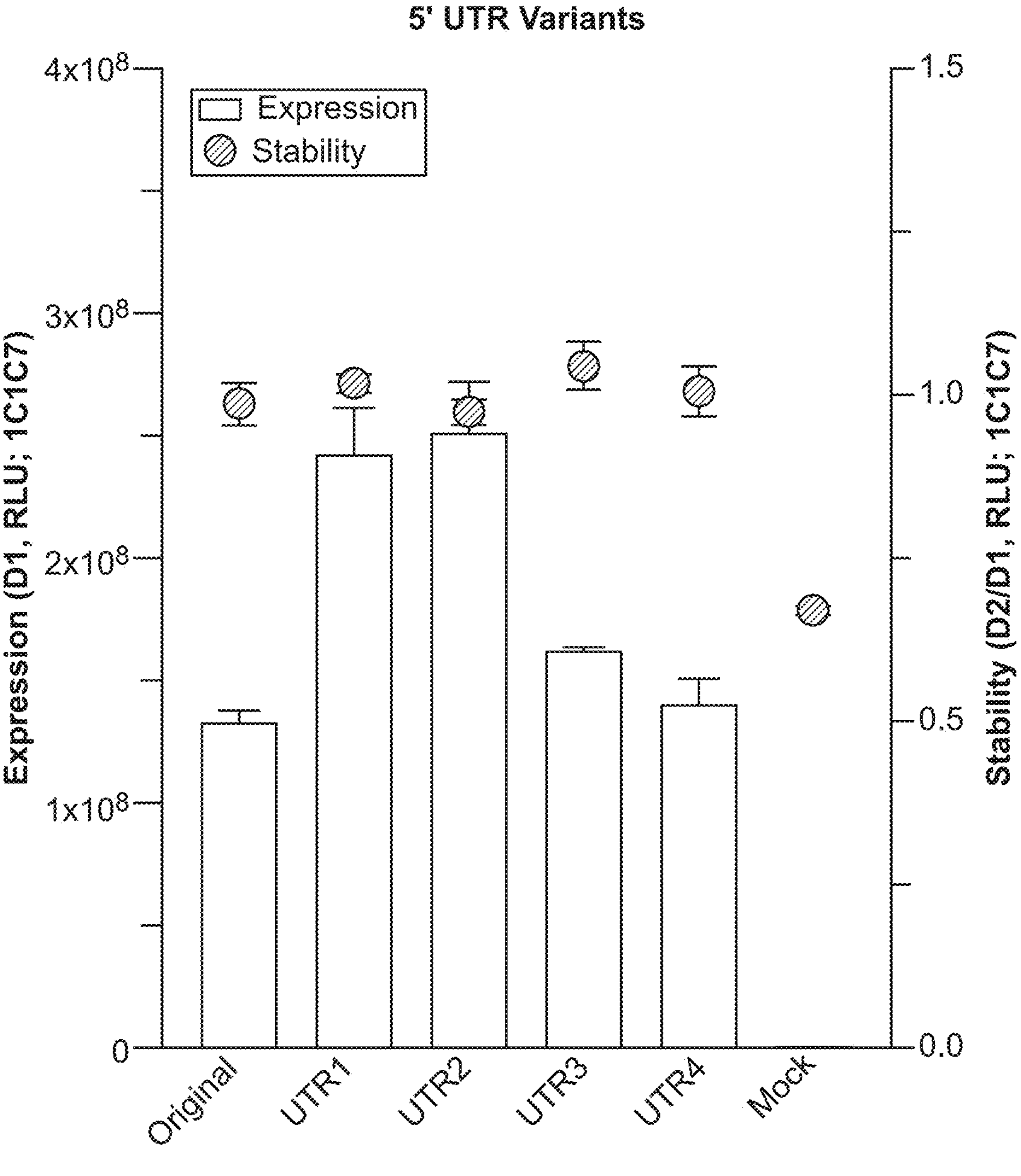
FIG. 55 shows luminescence expression levels and stability of expression in 1C1C7 cells from circular RNAs containing an IRES and variable untranslated regions (UTRs) inserted before the start codon of a Gaussian luciferase coding sequence.

The sequences of the 5' UTR variants are set forth in SEQ ID NOs: 402-405. As shown in FIG. 55, a CK IRES with a canonical Kozak sequence (UTR4) was more effective when a 36-nucleotide unstructured/low GC spacer sequence was added (UTR2), suggesting that the GC-rich Kozak sequences may interfere with core IRES folding. Using a higher-GC/structured spacer with a kozak sequence did not show the same benefit (UTR3), possibly due to interference with IRES folding by the spacer itself. Mutating the kozak sequence to gTcacG (UTR1) enhanced translation to the same level as the Kozak+spacer alternative without the need for a spacer.

Example 55

This example describes the impact of miRNA target sites in circular RNAs on expression levels. Briefly, circular RNA constructs were generated with IRES elements operably linked to a human erythropoietin (hEPO) coding sequence, where 2 tandem miR-122 target sites were inserted into the construct. miR-122-expressing Huh7 cells were transfected with the circular RNAs. hEPO expression in supernatant was assessed 24 and 48 hours after transfection by sandwich ELISA.

Figure 56:
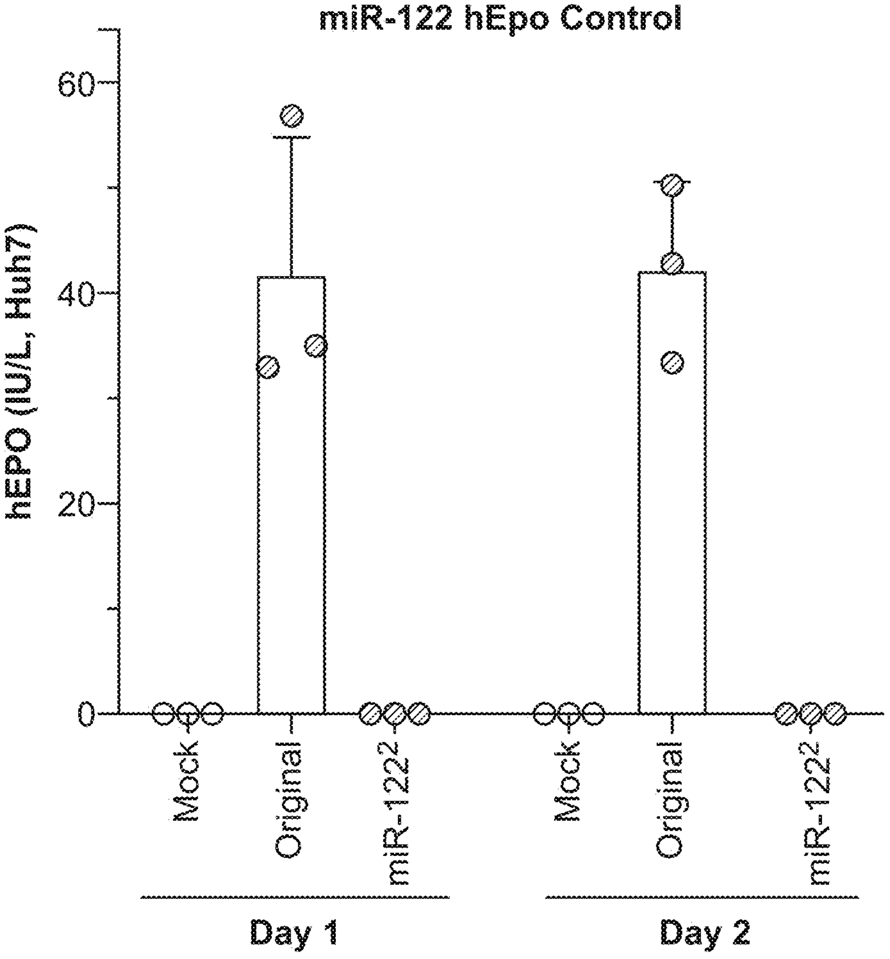
FIG. 56 shows expression levels of human erythropoietin (hEPO) in Huh7 cells from circular RNAs containing two miR-122 target sites downstream from the hEPO coding sequence.

As shown in FIG. 56, the hEPO expression level was obrogated where the miR-122 target sites were inserted into the circular RNA. This result demonstrates that expression from circular RNA can be regulated by miRNA. As such, cell type- or tissue-specific expression can be achieved by incorporating target sites of the miRNAs expressed in the cell types in which expression of the recombinant protein is undesirable.

INCORPORATION BY REFERENCE

All publications, patents, and patent applications mentioned in this specification are herein incorporated by reference to the same extent as if each individual publication, patent, or patent application was specifically and individually indicated as being incorporated by reference herein.

What is claimed is:
1. A pharmaceutical composition comprising:
a. a RNA polynucleotide, and
b. an in vivo transfer vehicle comprising an ionizable lipid selected from the group consisting of:
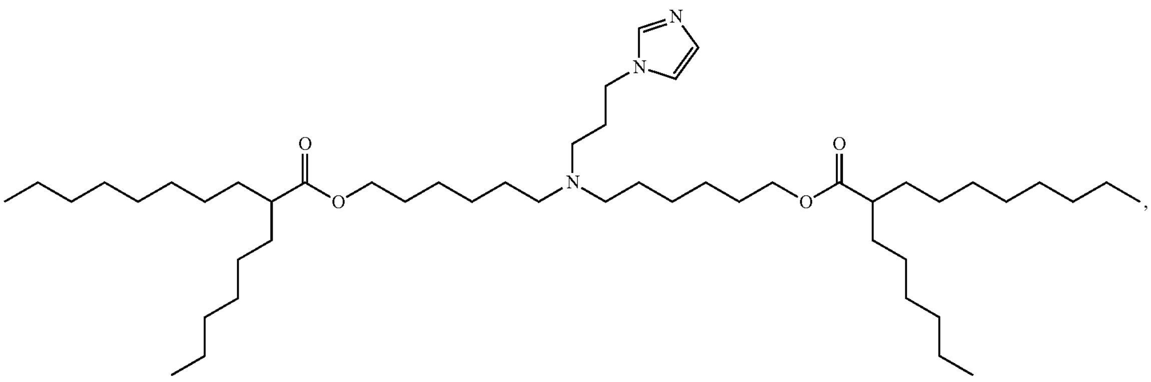
,
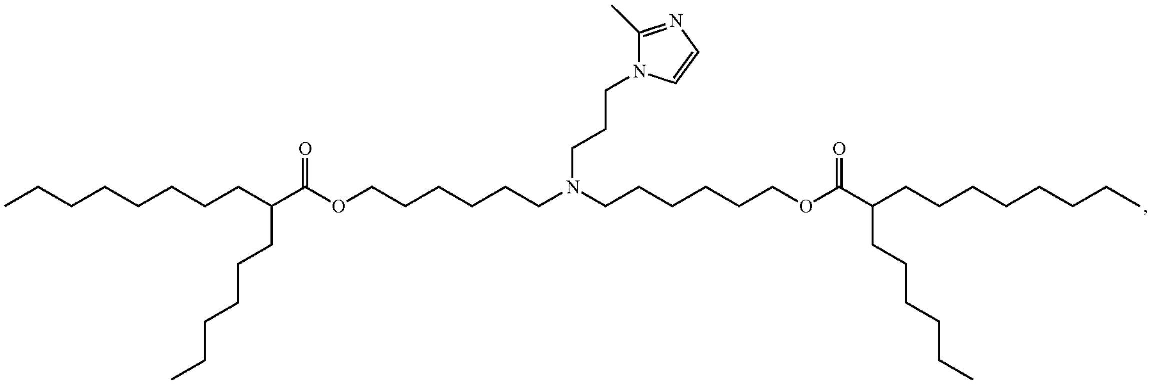
,
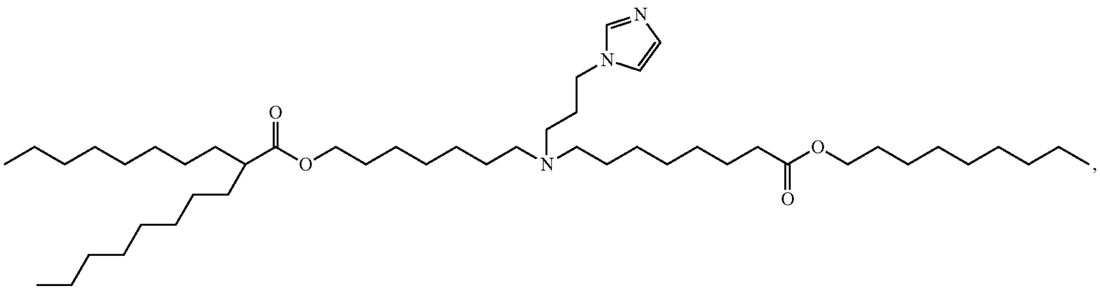
, and
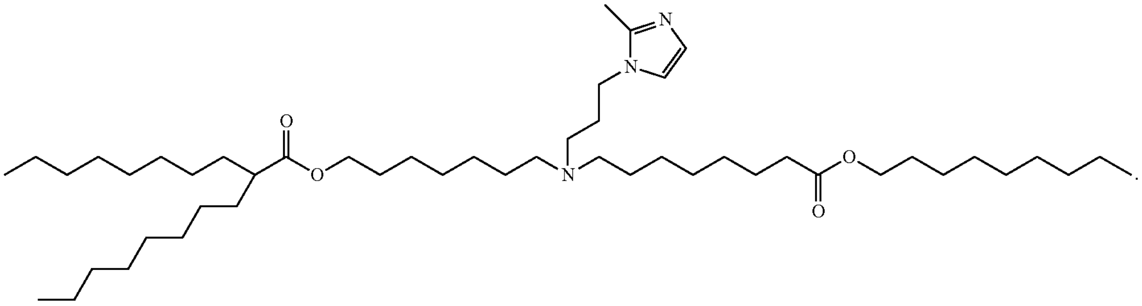
.

2. The pharmaceutical composition of claim 1, wherein said RNA polynucleotide is a circular RNA polynucleotide.

3. The pharmaceutical composition of claim 1, wherein the RNA polynucleotide comprises:
a. a post-splicing intron fragment of a 3' group I intron fragment,
b. an IRES,
c. an expression sequence, and
d. a post-splicing intron fragment of a 5' group I intron fragment.

4. The pharmaceutical composition of claim 3, wherein the RNA polynucleotide comprises a first spacer before the post-splicing intron fragment of the 3' group I intron fragment, and a second spacer after the post-splicing intron fragment of the 5' group I intron fragment.

5. The pharmaceutical composition of claim 4, wherein the first and second spacers each have a length of about 10 to about 60 nucleotides.

6. The pharmaceutical composition of claim 1, wherein the RNA polynucleotide is made via circularization of a precursor RNA polynucleotide comprising:
a. a 3' group I intron fragment,
b. an IRES,
c. an expression sequence, and
d. a 5' group I intron fragment.

7. The pharmaceutical composition of claim 6, wherein the RNA polynucleotide is made via circularization of a precursor RNA polynucleotide comprising:
a. a 5' external duplex forming region,
b. a 3' group I intron fragment,
c. a 5' internal spacer optionally comprising a 5' internal duplex forming region,
d. an IRES,
e. an expression sequence,
f. a 3' internal spacer optionally comprising a 3' internal duplex forming region,
g. a 5' group I intron fragment, and
h. a 3' external duplex forming region.

8. The pharmaceutical composition of claim 6, wherein the RNA polynucleotide is made via circularization of a precursor RNA polynucleotide comprising:
a. a 5' external duplex forming region,
b. a 5' external spacer,
c. a 3' group I intron fragment,
d. a 5' internal spacer optionally comprising a 5' internal duplex forming region,
e. an IRES,
f. an expression sequence,
g. a 3' internal spacer optionally comprising a 3' internal duplex forming region,
h. a 5' group I intron fragment,
i. a 3' external spacer, and
j. a 3' external duplex forming region.

9. The pharmaceutical composition of claim 6, wherein the RNA polynucleotide is made via circularization of a precursor RNA polynucleotide comprising:
a. a 3' group I intron fragment,
b. a 5' internal spacer comprising a 5' internal duplex forming region,
c. an IRES,
d. an expression sequence,
e. a 3' internal spacer comprising a 3' internal duplex forming region, and
f. a 5' group I intron fragment.

10. The pharmaceutical composition of claim 6, wherein the RNA polynucleotide is made via circularization of a precursor RNA polynucleotide comprising:
a. a 5' external duplex forming region,
b. a 5' external spacer,
c. a 3' group I intron fragment,
d. a 5' internal spacer comprising a 5' internal duplex forming region,
e. an IRES,
f. an expression sequence,
g. a 3' internal spacer comprising a 3' internal duplex forming region,
h. a 5' group I intron fragment,
i. a 3' external spacer, and
j. a 3' external duplex forming region.

11. The pharmaceutical composition of claim 6, wherein the RNA polynucleotide is made via circularization of a precursor RNA polynucleotide comprising:
a. a first polyA sequence,
b. a 5' external duplex forming region,
c. a 5' external spacer,
d. a 3' group I intron fragment,
e. a 5' internal spacer comprising a 5' internal duplex forming region,
f. an IRES,
g. an expression sequence,
h. a 3' internal spacer comprising a 3' internal duplex forming region,
i. a 5' group I intron fragment,
j. a 3' external spacer,
k. a 3' external duplex forming region, and
l. a second polyA sequence.

12. The pharmaceutical composition of claim 6, wherein the RNA polynucleotide is made via circularization of a precursor RNA polynucleotide comprising:
a. a first polyA sequence,
b. a 5' external spacer,
c. a 3' group I intron fragment,
d. a 5' internal spacer comprising a 5' internal duplex forming region,
e. an IRES,
f. an expression sequence,
g. a 3' internal spacer comprising a 3' internal duplex forming region,
h. a 5' group I intron fragment,
i. a 3' external spacer, and
j. a second polyA sequence.

13. The pharmaceutical composition of claim 6, wherein the RNA polynucleotide is made via circularization of a precursor RNA polynucleotide comprising:
a. a first polyA sequence,
b. a 5' external spacer,
c. a 3' group I intron fragment,
d. a 5' internal spacer comprising a 5' internal duplex forming region,
e. an IRES,
f. an expression sequence,
g. a stop condon cassette,
h. a 3' internal spacer comprising a 3' internal duplex forming region,
i. a 5' group I intron fragment,
j. a 3' external spacer, and
k. a second polyA sequence.

14. The pharmaceutical composition of claim 6, wherein the RNA polynucleotide is made via circularization of a precursor RNA polynucleotide comprising:

a. a binding site,
b. a 5' external spacer,
c. a 3' group I intron fragment,
d. a 5' internal spacer comprising a 5' internal duplex forming region,
e. an IRES,
f. an expression sequence,
g. a 3' internal spacer comprising a 3' internal duplex forming region,
h. a 5' group I intron fragment,
i. a 3' external spacer, and
j. a second binding site.

15. The pharmaceutical composition of claim 6, wherein the IRES has a sequence of an IRES from Taura syndrome virus, Triatoma virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, *Homalodisca coagulata* virus-1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, Drosophila reaper, Canine Scamper, Drosophila Ubx, Human UNR, Mouse UtrA, Human VEGF-A, Human XIAP, Drosophila hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, *Apodemus Agrarius* Picornavirus, Caprine Kobuvirus, Parabovirus, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24, or an aptamer to eIF4G.

16. The pharmaceutical composition of claim 1, wherein the composition has a duration of therapeutic effect in vivo in humans greater than that of a composition comprising a reference linear RNA polynucleotide having the same expression sequence as the circular RNA polynucleotide.

17. The pharmaceutical composition of claim 16, wherein the duration of therapeutic effect in vivo in humans is determined by a functional protein assay comprising measuring levels of protein encoded by the expression sequence of the circular RNA polynucleotide in a serum or tissue sample.

18. The pharmaceutic composition of claim 1, further comprising a structural lipid and a PEG-modified lipid.

19. The pharmaceutical composition of claim 18, wherein the structural lipid binds to C1q and/or promotes the binding of the transfer vehicle comprising said lipid to C1q compared to a control transfer vehicle lacking the structural lipid and/or increases uptake of C1q-bound transfer vehicle into an immune cell compared to a control transfer vehicle lacking the structural lipid.

* * * * *

SEQUENCE LISTING

```
<160> NUMBER OF SEQ ID NOS: 717

<210> SEQ ID NO 1
<211> LENGTH: 585
<212> TYPE: DNA
<213> ORGANISM: Unknown
<220> FEATURE:
<223> OTHER INFORMATION: Description of Unknown:
      Encephalomyocarditis virus sequence

<400> SEQUENCE: 1

ccccccctctc cctcccccc taacgttact ggccgaagcc gcttggaata aggccggtgt     60

gcgtttgtct atatgttatt ttccaccata ttgccgtctt ttggcaatgt gagggcccgg    120

aaacctggcc ctgtcttctt gacgagcatt cctaggggtc tttcccctct cgccaaagga    180

atgcaaggtc tgttgaatgt cgtgaaggaa gcagttcctc tggaagcttc ttgaagacaa    240

acaacgtctg tagcgaccct ttgcaggcag cggaaccccc cacctggcga caggtgcctc    300

tgcggccaaa agccacgtgt ataagataca cctgcaaagg cggcacaacc ccagtgccac    360

gttgtgagtt ggatagttgt ggaaagagtc aaatggctct cctcaagcgt attcaacaag    420
```

gggctgaagg atgcccagaa ggtaccccat tgtatgggat ctgatctggg gcctcggtgc 480
acatgcttta catgtgttta gtcgaggtta aaaaacgtct aggccccccg aaccacgggg 540
acgtggtttt cctttgaaaa acacgatgat aatatggcca caacc 585

<210> SEQ ID NO 2
<211> LENGTH: 568
<212> TYPE: DNA
<213> ORGANISM: Unknown
<220> FEATURE:
<223> OTHER INFORMATION: Description of Unknown:
Encephalomyocarditis virus sequence

<400> SEQUENCE: 2
ctccccctcc ccccccttac tatactggcc gaagccactt ggaataaggc cggtgtgcgt 60
ttgtctacat gctattttct accgcattac cgtcttatgg taatgtgagg gtccagaacc 120
tgaccctgtc ttcttgacga acactcctag ggtctttcc cctctcgaca aaggagtgta 180
aggtctgttg aatgtcgtga aggaagcagt tcctctggaa gcttcttaaa gacaaacaac 240
gtctgtagcg accctttgca ggcagcggaa ccccccacct ggtgacaggt gcctctgcgg 300
ccaaaagcca cgtgtataag atacacctgc aaaggcggca caaccccagt gccacgttgt 360
gagttggata gttgtggaaa gagtcaaatg gctctcctca agcgtattca acaaggggct 420
gaaggatgcc cagaaggtac cccattgtat gggatctgat ctggggcctc ggtgcacgtg 480
ctttacacgt gttgagtcga ggtgaaaaaa cgtctaggcc ccccgaacca cggggacgtg 540
gttttccttt gaaaaccacg attacaat 568

<210> SEQ ID NO 3
<211> LENGTH: 696
<212> TYPE: DNA
<213> ORGANISM: Unknown
<220> FEATURE:
<223> OTHER INFORMATION: Description of Unknown:
Encephalomyocarditis virus sequence

<400> SEQUENCE: 3
ttgccagtct gctcgatatc gcaggctggg tccgtgacta cccactcccc ctttcaacgt 60
gaaggctacg atagtgccag ggcgggtact gccgtaagtg ccaccccaaa caacaacaac 120
aaaacaaact ccccctcccc ccccttacta tactggccga agccacttgg aataaggccg 180
gtgtgcgttt gtctacatgc tattttctac cgcattaccg tcttatggta atgtgagggt 240
ccagaacctg accctgtctt cttgacgaac actcctaggg gtctttcccc tctcgacaaa 300
ggagtgtaag gtctgttgaa tgtcgtgaag gaagcagttc ctctggaagc ttcttaaaga 360
caaacaacgt ctgtagcgac cctttgcagg cagcggaacc ccccacctgg tgacaggtgc 420
ctctgcggcc aaaagccacg tgtataagat acacctgcaa aggcggcaca accccagtgc 480
cacgttgtga gttggatagt tgtggaaaga gtcaaatggc tctcctcaag cgtattcaac 540
aaggggctga aggatgccca gaaggtaccc cattgtatgg gatctgatct ggggcctcgg 600
tgcacgtgct ttacacgtgt tgagtcgagg tgaaaaaacg tctaggcccc ccgaaccacg 660
gggacgtggt tttcctttga aaaccacgat tacaat 696

<210> SEQ ID NO 4
<211> LENGTH: 697
<212> TYPE: DNA
<213> ORGANISM: Unknown
<220> FEATURE:

<223> OTHER INFORMATION: Description of Unknown:
      Encephalomyocarditis virus sequence

<400> SEQUENCE: 4
ttgccagtct gctcgatatc gcaggctggg tccgtgacta cccactcccc ctttcaacgt 60
gaaggctacg atagtgccag ggcgggtact gccgtaagtg ccaccccaaa acaacaacaa 120
ccccccctct ccctcctccc cccctaacgt tactggccga agccgcttgg aataaggccg 180
gtgtgcgttt gtctatatgt tattttccac catattgccg tcttttggca atgtgagggc 240
ccggaaacct ggccctgtct tcttgacgag cattcctagg ggtctttccc ctctcgccaa 300
aggaatgcaa ggtctgttga atgtcgtgaa ggaagcagtt cctctggaag cttcttgaag 360
acaaacaacg tctgtagcga ccctttgcag gcagcggaac cccccacctg gcgacaggtg 420
cctctgcggc caaaagccac gtgtataaga tacacctgca aaggcggcac aaccccagtg 480
ccacgttgtg agttggatag ttgtggaaag agtcaaatgg ctctcctcaa gcgtattcaa 540
caaggggctg aaggatgccc agaaggtacc ccattgtatg ggatctgatc tggggcctcg 600
gtgcacatgc tttacatgtg tttagtcgag gttaaaaaac gtctaggccc cccgaaccac 660
ggggacgtgg ttttcctttg aaaaacacga tgataat 697

<210> SEQ ID NO 5
<211> LENGTH: 562
<212> TYPE: DNA
<213> ORGANISM: Unknown
<220> FEATURE:
<223> OTHER INFORMATION: Description of Unknown:
      Encephalomyocarditis virus sequence

<400> SEQUENCE: 5
ccccccccct aacgttactg gccgaagccg cttggaataa ggccggtgtg cgtttgtcta 60
tatgttattt tccaccatat tgccgtcttt tggcaatgtg agggcccgga aacctggccc 120
tgtcttcttg acgagcattc ctaggggtct ttcccctctc gccaaaggaa tgcaaggtct 180
gttgaatgtc gtgaaggaag cagttcctct ggaagcttct tgaagacaaa caacgtctgt 240
agcgaccctt tgcaggcagc ggaacccccc acctggcgac aggtgcctct gcggccaaaa 300
gccacgtgta taagatacac ctgcaaaggc ggcacaaccc cagtgccacg ttgtgagttg 360
gatagttgtg gaaagagtca aatggctctc ctcaagcgta ttcaacaagg ggctgaagga 420
tgcccagaag gtaccccatt gtatgggatc tgatctgggg cctcggtgca catgctttac 480
atgtgtttag tcgaggttaa aaaacgtcta ggccccccga accacgggga cgtggttttc 540
ctttgaaaaa cacgatgata at 562

<210> SEQ ID NO 6
<211> LENGTH: 156
<212> TYPE: DNA
<213> ORGANISM: Unknown
<220> FEATURE:
<223> OTHER INFORMATION: Description of Unknown:
      Picobirnavirus sp. sequence

<400> SEQUENCE: 6
gtaaattaaa tgctatttac aaaatttaaa cagaaaggag agatgttatg aaccggtttt 60
acaaggtttc atacatcgaa aatagcacta cctggggcag ccgacacact aacatcgtct 120
gtttaaccag aagtgttact gaaaggaggt tattta 156

<210> SEQ ID NO 7

<211> LENGTH: 340
<212> TYPE: DNA
<213> ORGANISM: Unknown
<220> FEATURE:
<223> OTHER INFORMATION: Description of Unknown:
Hepatitis C virus sequence

<400> SEQUENCE: 7
acctgcccct aataggggcg acactccgcc atgaatcact cccctgtgag gaactactgt 60
cttcacgcag aaagcgtcta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gacatttggg cgtgcccccg 240
caagactgct agccgagtag cgttgggttg cgaaaggcct tgtggtactg cctgataggg 300
tgcttgcgag tgccccggga ggtctcgtag accgtgcatc 340

<210> SEQ ID NO 8
<211> LENGTH: 315
<212> TYPE: DNA
<213> ORGANISM: Unknown
<220> FEATURE:
<223> OTHER INFORMATION: Description of Unknown:
Human Cosavirus sequence

<400> SEQUENCE: 8
ctacaagctt tgtgtaaaca aacttttgtt tggcttttct caagcttctc tcacatcagg 60
ccccaaagat gtcctgaagg taccccgtgt atctgaggat gagcaccatc gactacccgg 120
acctgcaaaa ttttgcaaac gcatgtggta tcccagcccc ctcctctcgg ggagggggct 180
ttgctcactc agcacaggat ctgatcagga gatccacctc cggtgcttta caccggggcg 240
tggatttaaa aattgcccaa ggcctggcgc acaacctagg ggactaggtt ttccttatat 300
tttaaagctg tcaat 315

<210> SEQ ID NO 9
<211> LENGTH: 182
<212> TYPE: DNA
<213> ORGANISM: Unknown
<220> FEATURE:
<223> OTHER INFORMATION: Description of Unknown:
Human Cosavirus sequence

<400> SEQUENCE: 9
gtcttaggac gacgcatgtg gtatcccagc ccccgcctac attggcgggg gcttttgaag 60
caccagacac tggatctgat caggaggagg gtagctgctt tacagcccct cttaaaaatt 120
gcccaaggtc cggccaccca acctagggga ctaggttttc cttttatttt taaattgtca 180
tt 182

<210> SEQ ID NO 10
<211> LENGTH: 759
<212> TYPE: DNA
<213> ORGANISM: Unknown
<220> FEATURE:
<223> OTHER INFORMATION: Description of Unknown:
Human Cosavirus sequence

<400> SEQUENCE: 10
acatggggga gactgcatgt ggcagtcttg aaacgtgtgg tttgacgtct accttatatg 60
gcagtgggtg gagtactgca aagatgtcac cgtgctttac acggtttttg aaccccacac 120
cggctgtttg acgctcgtag ggcagcaggt ttattttcat taaaattctt actttctagc 180

```
tgcatgagtt ctattcatgc agacggagtg atactcccgt tccttcttgg acaggttgcc    240

tccacgccct ttgtggatct taaggtgacc aagtcactgg tgttggaggt gaagatagag    300

agtcctcttg ggaatgtcat gtggctgtgc caggggttgt agcgatgcca ttcgtgtgtg    360

cggatttcct ctcgtggtga cacgagcctc acaggccaaa agccccgtcc gaaaggaccc    420

gaatggtgga gtgaccctga ctccccccctg catagttttg tgattaggaa cttgaggaat    480

ttctgtcata aatctctatc acatcaggcc ccaaagatgt cctgaaggta ccctgtgtat    540

ctgaggatga gcaccaccga ctacccggac ttgcattagc agacacatgt ggttgcccag    600

ccccacctct tcagaggtgg ggctttgctc actcagcaca ggatctgatc aggagccccg    660

ctcgtgtgct ttacactcga cgcggggtta aaaattgccc aaggcctggc acaacaacct    720

aggggactag gttttcctat ttttgtaaat tatgtcaat                           759
```

<210> SEQ ID NO 11
<211> LENGTH: 478
<212> TYPE: DNA
<213> ORGANISM: Unknown
<220> FEATURE:
<223> OTHER INFORMATION: Description of Unknown:
      Human rhinovirus sequence

<400> SEQUENCE: 11

```
gtgacaatca gccagattgt taacggtcaa gcacttctgt ttccccggta cccttgtata     60

cgcttcaccc gaggcgaaaa gtgaggttat cgttatccgc aaagtgccta cgagaagcct    120

agtagcactt ttgaagccta tggctggtcg ctcaactgtt tacccagcag tagacctggc    180

agatgaggct agatgttccc caccagcgat ggtgatctag cctgcgtggc tgcctgcaca    240

ctctattgag tgtgaagcca gaaagtggac aaggtgtgaa gagcctattg tgctcacttt    300

gagtcctccg gcccctgaat gtggctaatc ctaaccccgt agctgttgca tgtaatccaa    360

catgtctgca gtcgtaatgg gcaactatgg gatggaacca actactttgg gtgtccgtgt    420

ttcttgtttt tctttatgct tgcttatggt gacaactgta gttattacat ttgttacc      478
```

<210> SEQ ID NO 12
<211> LENGTH: 628
<212> TYPE: DNA
<213> ORGANISM: Unknown
<220> FEATURE:
<223> OTHER INFORMATION: Description of Unknown:
      Human rhinovirus sequence

<400> SEQUENCE: 12

```
ttaaaacagc ggatgggtat cccaccattc gacccattgg gtgtagtact ctggtactat     60

gtacctttgt acgcctgttt ctccccaacc acccttcctt aaaattccca cccatgaaac    120

gttagaagct tgacattaaa gtacaatagg tggcgccata tccaatggtg tctatgtaca    180

agcacttctg tttcccagga gcgaggtata ggctgtaccc actgccaaaa gcctttaacc    240

gttatccgcc aaccaactac gtaacagtta gtaccatctt gttcttgact ggacgttcga    300

tcaggtggat tttccctcca ctagtttggt cgatgaggct aggaattccc cacgggtgac    360

cgtgtcctag cctgcgtggc ggccaaccca gcttatgctg ggacgccctt ttaaggacat    420

ggtgtgaaga ctcgcatgtg cttggttgtg agtcctccgg cccctgaatg cggctaacct    480
```

taaccctaga gccttatgcc acgatccagt ggttgtaagg tcgtaatgag caattccggg 540
acgggaccga ctactttggg tgtccgtgtt tctcattttt cttcatattg tcttatggtc 600
acagcatata tatacatata ctgtgatc 628

<210> SEQ ID NO 13
<211> LENGTH: 618
<212> TYPE: DNA
<213> ORGANISM: Unknown
<220> FEATURE:
<223> OTHER INFORMATION: Description of Unknown:
Human rhinovirus sequence

<400> SEQUENCE: 13
ttaaaactgg gagtgggttg ttcccactca ctccacccat gcggtgttgt actctgttat 60
tacggtaact ttgtacgcca gtttttccca cccttcccca taatgtaact tagaagtttg 120
tacaatatga ccaataggtg acaatcatcc agactgtcaa aggtcaagca cttctgtttc 180
cccggtcaat gaggatatgc tttacccaag gcaaaaacct tagagatcgt tatccccaca 240
ctgcctacac agagcccagt accatttttg atataattgg gttggtcgct ccctgcaaac 300
ccagcagtag acctggcaga tgaggctgga cattccccac tggcgacagt ggtccagcct 360
gcgtggctgc ctgctcaccc ttcttgggtg agaagcctaa ttattgacaa ggtgtgaaga 420
gccgcgtgtg ctcagtgtgc ttcctccggc ccctgaatgt ggctaacctt aaccctgcag 480
ccgttgccca taatccaatg ggtttgcggt cgtaatgcgt aagtgcggga tgggaccaac 540
tactttgggt gtccgtgttt cctgtttttc ttttgattgc attttatggt gacaatttat 600
agtgtataga ttgtcatc 618

<210> SEQ ID NO 14
<211> LENGTH: 610
<212> TYPE: DNA
<213> ORGANISM: Unknown
<220> FEATURE:
<223> OTHER INFORMATION: Description of Unknown:
Human rhinovirus sequence

<400> SEQUENCE: 14
ttaaaactgg gtacaggttg ttcccacctg tatcacccac gtggtgtggt gctcttgtat 60
tccggtacac ttgcacgcca gtttgccacc cctcacccgt cgtaacttag aagctaacaa 120
ctcgaccaac aggcggtggt aaaccatacc acttacggtc aagcactcct gtttccccgg 180
tatgcgagga atagactcct acagggttga agcctcaagt atcgttatcc gcattggtac 240
tacgcaaagc ttagtagtgc cttgaaagtc ccttggttgg tcgctccgct agtttcccct 300
agtagacctg gcagatgagg caggacactc cccactggcg acagtggtcc tgcctgcgtg 360
gctgcctgcg cacccttagg ggtgcgaagc caagtgacag acaaggtgtg aagagccccg 420
tgtgctacca atgagtcctc cggcccctga atgcggctaa tccaacccca cagctattgc 480
acacaagcca gtgtgtatgt agtcgtaatg agcaattgtg ggacggaacc gactactttg 540
ggtgtccgtg tttcctttta ttcttatcat tctgcttatg gtgacaatac tgtgaaatag 600
tgttgttacc 610

<210> SEQ ID NO 15
<211> LENGTH: 614
<212> TYPE: DNA
<213> ORGANISM: Unknown
<220> FEATURE:

<223> OTHER INFORMATION: Description of Unknown:
      Human rhinovirus sequence

<400> SEQUENCE: 15

```
taaaactgga tccaggttgt tcccacctgg atctcctatt gggagttgta ctctattatt     60

ccggtaattt tgtacgccag ttttatcttc cccctcccca attgtaactt agaaggttat    120

caatacgacc aataggtggt agttagccaa actaccaaag gtcaagcact tctgtttccc    180

cggtcaaagt tgatatgctc caacagggca aaaacaactg agatcgttat ccgcaaagtg    240

cctacgcaaa gcctagtaac acctttgaag atttatggtt ggtcgttccg ctatttccca    300

tagtagacct ggcagatgag gctagaaatc ccccactggc gacagtgctc tagcctgcgt    360

ggctgcctgc gcaccccttg ggtgcgaagc catacattgg acaaggtgtg aagagccccg    420

tgtgctcact ttgagtcctc cggcccctga atgtggctaa ccttaaccct gcagctagtg    480

catgtaatcc aacatgttgc tagtcgtaat gagtaattgc gggacgggac caactacttt    540

gggtgtccgt gtttcacttt ttccttttaa tattgcttat ggtgacaata tatatagcta    600

tatatattga cacc                                                      614
```

<210> SEQ ID NO 16
<211> LENGTH: 624
<212> TYPE: DNA
<213> ORGANISM: Unknown
<220> FEATURE:
<223> OTHER INFORMATION: Description of Unknown:
      Salivirus A sequence

<400> SEQUENCE: 16

```
ttcccctgca accattacgc ttactcgcat gtgcattgag tggtgcatgt gttgaacaaa     60

cagctacact cacatggggg cgggttttcc cgccctacgg cttctcgcga ggcccacccc    120

tcccctttct cccataacta cagtgctttg gtaggtaagc atcctgatcc cccgcggaag    180

ctgctcacgt ggcaactgtg gggacccaga caggttatca aaggcacccg gtctttccgc    240

cttcaggagt atccctgcta gcgaattcta gtagggctct gcttggtgcc aacctccccc    300

aaatgcgcgc tgcgggagtg ctcttcccca actcacccta gtatcctctc atgtgtgtgc    360

ttggtcagca tatctgagac gatgttccgc tgtcccagac cagtccagta atggacgggc    420

cagtgtgcgt agtcgtcttc cggcttgtcc ggcgcatgtt tggtgaaccg gtggggtaag    480

gttggtgtgc ccaacgcccg tactcagggg atacctcaag gcacccagga atgccaggga    540

ggtaccccgc ttcacagcgg gatctgaccc tggggtaaat gtctgcgggg ggtcttcttg    600

gcccacttct cagtactttt cagg                                           624
```

<210> SEQ ID NO 17
<211> LENGTH: 730
<212> TYPE: DNA
<213> ORGANISM: Unknown
<220> FEATURE:
<223> OTHER INFORMATION: Description of Unknown:
      Salivirus FHB sequence

<400> SEQUENCE: 17

```
acatgggggg tctgcggacg gcttcggccc acccgcgaca agaatgccgt catctgtcct     60

cattacccgt attccttccc ttcccccgca accaccacgc ttactcgcgc acgtgttgag    120

tggcacgtgc gttgtccaaa cagctacacc cacacccttc ggggcgggtt tgtcccgccc    180

tcgggttcct cgcggaaccc ccccctccct ctctctcttt ctatccgccc tcacttccca    240
```

-continued

```
taactacagt gctttggtag gtgagcaccc tgaccccccg cggaagctgc taacgtggca    300

actgtgggga tccaggcagg ttatcaaagg cacccggtct ttccgccttc aggagtatct    360

ctgccggtga attccggtag ggctctgctt ggtgccaacc tcccccaaat gcgcgctgcg    420

ggagtgctct tccccaactc atcttagtaa cctctcatgt gtgtgcttgg tcagcatatc    480

tgaggcgacg ttccgctgtc ccagaccagt ccagcaatgg acgggccagt gtgcgtagtc    540

gctttccggt tttccggcgc atgtttggcg aaacgctgag gtaaggttgg tgtgcccaac    600

gcccgtaatt tggtgatacc tcaagaccac ccaggaatgc cagggaggta ccccacttcg    660

gtgggatctg accctgggct aattgtctac ggtggttctt cttgcttcca cttctctttt    720

ttctggcatg                                                           730
```

```
<210> SEQ ID NO 18
<211> LENGTH: 709
<212> TYPE: DNA
<213> ORGANISM: Unknown
<220> FEATURE:
<223> OTHER INFORMATION: Description of Unknown:
      Salivirus NG-J1 sequence

<400> SEQUENCE: 18

tatggcaggc gggcttgtgg acggcttcgg cccacccaca gcaagaatgc catcatctgt     60

cctcaccccc aattttccct tttcttcccc tgcaaccatt acgcttactc gcatgtgcat    120

tgagtggtgc atgtgttgaa caaacagcta cactcacatg gggcgggttt ttcccgccct    180

acggcctctc gcgaggccca ccccttccct cccccttataa ctacagtgct ttggtaggta    240

agcatcctga tcccccgcgg aagctgctca cgtggcaact gtggggaccc agacaggtta    300

tcaaaggcac ccggtctttc cgccttcagg agtatcccta ctagtgaatt ctagcggggc    360

tctgcttggt gccaacctcc cccaaatgcg cgctgcggga gtgctcttcc ccaactcacc    420

ctagtatcct ctcatgtgtg tgcttggtca gcatatctga gacgatgttc cgctgtccca    480

gaccagtcca gtaatggacg ggccagtgcg tgtagtcgtc ttccggcttg tccggggcat    540

gtttggtgaa ccggtggggt aaggttggtg tgcccaacgc ccgtactttg gtgacacctc    600

aagaccaccc aggaatgcca gggaggtacc ccacctcacg gtgggatctg accctgggct    660

aattgtctac ggtggttctt cttgcttcca cttctttctt ctgttcacg                709
```

```
<210> SEQ ID NO 19
<211> LENGTH: 708
<212> TYPE: DNA
<213> ORGANISM: Unknown
<220> FEATURE:
<223> OTHER INFORMATION: Description of Unknown:
      Human Parechovirus sequence

<400> SEQUENCE: 19

tttgaaaggg gtctcctaga gagcttggcc gtcgggcctt ataccccgac ttgctgagtt     60

tctctaggag agcccttttc ccagccctga ggcggctggt caataaaagc ctcaaacgta    120

actaacacct aagaagatca tgtaaaccct atgcctggtc tccactattc gaaggcaact    180

tgcaataaga agagtgggat caagacgctt aaagcataga gacagttttc ttttctaacc    240

cacatttgtg tggggtggca gatggcgtgc cataactcta atagtgagat accacgcttg    300

tggaccttat gctcacacag ccatcctcta gtaagtttgt gagacgtctg gtgacgtgtg    360

ggaacttatt ggaaacaaca ttttgctgca aagcatccta ctgccagcgg aaaaacacct    420

ggtaacaggt gcctctgggg ccaaaagcca aggtttaaca gaccctttag gattggttct    480
```

aaacctgaga tgttgtggaa gatatttagt acctgctgat ctggtagtta tgcaaacact 540
agttgtaagg cccatgaagg atgcccagaa ggtacccgta ggtaacaagt gacactatgg 600
atctgatttg gggccagata cctctatctt ggtgatctgg ttaaaaaaca tctaatgggc 660
caaacccggg ggggatcccc ggtttcctct tattctatca atgccact 708

<210> SEQ ID NO 20
<211> LENGTH: 508
<212> TYPE: DNA
<213> ORGANISM: Unknown
<220> FEATURE:
<223> OTHER INFORMATION: Description of Unknown:
Crohivirus B sequence

<400> SEQUENCE: 20
gtataagaga caggtgtttg ccttgtcttc ggactggcat cttgggacca accccccttt 60
tccccagcca tgggttaaat ggcaataaag gacgtaacaa ctttgtaacc attaagcttt 120
gtaattttgt aaccactaag ctttgtgcac ataatgtaac catcaagctt gttagtccca 180
gcaggaggtt tgcatgcttg tagccgaaat ggggctcgac cccccatagt aggatacttg 240
attttgcatt ccattgtgga cctgcaaact ctacacatag aggctttgtc ttgcatctaa 300
acacctgagt acagtgtgta cctagaccct atagtacggg aggaccgttt gtttcctcaa 360
taaccctaca taataggcta ggtgggcatg cccaatttgc aagatcccag actgggggtc 420
ggtctgggca gggttagatc cctgttagct actgcctgat agggtggtgc tcaaccatgt 480
gtagtttaaa ttgagctgtt catatacc 508

<210> SEQ ID NO 21
<211> LENGTH: 248
<212> TYPE: DNA
<213> ORGANISM: Unknown
<220> FEATURE:
<223> OTHER INFORMATION: Description of Unknown:
Picornaviridae sp. sequence

<400> SEQUENCE: 21
actgaagatc ctacagtaac tactgcccca atgaacgcca cagatgggtc tgctgatgac 60
tacctatctt agtgctagtt gaggtttgaa gtgagccggt ttttagaaga accagtttct 120
gaacattatc atccccagca tctattctat acgcacaaga tagatagtca tcagcagaca 180
catctgtgct actgcttgat agagttgcgg ctggtcaact tagattggta taaccagttg 240
agtggcaa 248

<210> SEQ ID NO 22
<211> LENGTH: 516
<212> TYPE: DNA
<213> ORGANISM: Unknown
<220> FEATURE:
<223> OTHER INFORMATION: Description of Unknown:
Rosavirus M-7 sequence

<400> SEQUENCE: 22
tatgcatcac tggacggcct aacctcggtc gtggcttctt gccgatttca gcgctaccag 60
gctttctggt ctcgccaggc gttgattagt aggtgcactg tctaagtgaa gacagcagtg 120
ctctctgtga aaagttgatg acactcttca ggtttgtagc gatcactcaa ggctagcgga 180
tttccccgtg tggtaacaca cgcctctagg cccagaaggc acggtgttga cagcacccct 240
tgagtggctg gtcttcccca ccagcacctg atttgtggat tcttcctagt aacggacaag 300

```
catggctgct cttaagcatt cagtgcgtcc ggggctgaag gatgcccaga aggtacccgc    360

aggtaacgat aagctcactg tggatctgat ctggggctgc gggctgggtg tctttccacc    420

cagccaaaac ccgtaaaacg gtagtcgcag ttaaaaaacg tctaggcccc acccccccag    480

ggatgggggg ttcccttaaa ccctcacaag ttcaac                              516
```

<210> SEQ ID NO 23
<211> LENGTH: 478
<212> TYPE: DNA
<213> ORGANISM: Unknown
<220> FEATURE:
<223> OTHER INFORMATION: Description of Unknown:
Shanbavirus A sequence

<400> SEQUENCE: 23

```
tgaaaagggg gcgcagggtg gtggtggtta ctaaataccc accatcgccc tgcacttccc     60

ttttcccctg tggctcaggg tcacttagcc ccctctttgg gttaccagta gttttctacc    120

cctgggcaca gggttaacta tgcaagacgg aacaacaatc tcttagtccc cctcgccgat    180

agtgggctcg acccccatgt gtaggagtgg ataagggacg gagtgagccg atacggggaa    240

gagtgtgcgg tcacacctta attccatgag cgctgcgaag aaggaagctg tgaacaatgg    300

cgacctgaac cgtacacatg gagctccaca ggcatggtac tcgttagact acgcagcctg    360

gttgggagtg ggtataccct gggtgagccg ccagtgaatg ggagttcact ggttaacaca    420

cactgcctga tagggtcagg gcctcctgtc cccgccgtaa tgaggtagac catatgcc      478
```

<210> SEQ ID NO 24
<211> LENGTH: 403
<212> TYPE: DNA
<213> ORGANISM: Unknown
<220> FEATURE:
<223> OTHER INFORMATION: Description of Unknown:
Pasivirus A sequence

<400> SEQUENCE: 24

```
gcggctggat attctggccg tgcaactgct tttgaccagt ggctctgggt aacttagcca     60

aagtgtcctt ctccctttcc ctattatatg ttttatggct ttgtctggtc ttgtttagtt    120

tatatataag atcctttccg ccgatataga cctcgacagt ctagtgtagg aggattggtg    180

atattaattt gccccagaag agtgaccgtg acacatagaa accatgagta catgtgtatc    240

cgtggaggat cgcccgggac tggattccat atcccattgc catcccaaca agcggagggt    300

atacccacta tgtgcacgtc tgcagtggga gtctgcagat ttagtcatac tgcctgatag    360

ggtgtgggcc tgcactctgg ggtactcagg ctgtttatat aat                      403
```

<210> SEQ ID NO 25
<211> LENGTH: 404
<212> TYPE: DNA
<213> ORGANISM: Unknown
<220> FEATURE:
<223> OTHER INFORMATION: Description of Unknown:
Pasivirus A sequence

<400> SEQUENCE: 25

```
gctggacttt ctggctgcgc aactgctttt aaccagtggc tctgggttac ttagccaaaa     60

ccccctttcc ccgtacccta gtttgtgtgt gtattattat tttgttgttg ttttgtaaat    120

ttttatataa gatcctttcc gccgatatag acctcgacag tctagtgtag gaggattggt    180

gatattaata tgccccagaa gagtgaccgt gacacataga aaccatgagt acatgtgtat    240
```

| | |
|---|---|
| ccgtggagga tcgcccggga ctggattcca tatcccattg ccatcccaac aaacggaggg | 300 |
| tatacccgct atgtgcgcgt ctacagtggg aatctgtaga tttagtcata ctgcctgata | 360 |
| gggtgtgggc ctgcactctg gggtactcag gctgtttata taat | 404 |

<210> SEQ ID NO 26
<211> LENGTH: 744
<212> TYPE: DNA
<213> ORGANISM: Unknown
<220> FEATURE:
<223> OTHER INFORMATION: Description of Unknown:
      Echovirus E14 sequence

<400> SEQUENCE: 26

| | |
|---|---|
| ttaaaacagc ctgtgggttg ttcccatcca cagggcccac tgggcgccag cactctggta | 60 |
| ttgcggtacc ttagtgcgcc tgttttatat acccgtcccc caaacgtaac ttagacgcat | 120 |
| gtcaacgaag accaatagta agcgcagcac accagctgtg ttccggtcaa gcacttctgt | 180 |
| taccccggac cgagtatcaa taagctactc acgtggctga aggagaaaac gttcgttacc | 240 |
| cgaccaatta cttcaagaaa cctagtaaca ccatgaaggt tgcgcagtgt ttcgctccgc | 300 |
| acaacccccag tgtagatcag gtcgatgagt caccgcattc cccacgggtg accgtggcgg | 360 |
| tggctgcgct ggcggcctgc ccatggggaa acccatggga cgcttcaata ctgacatggt | 420 |
| gcgaagagtc tattgagcta attggtagtc ctccggcccc tgaatgcggc taatcctaac | 480 |
| tgcggagcag atacccacac accagtgggc agtctgtcgt aacgggcaac tctgcagcgg | 540 |
| aaccgactac tttgggtgtc cgtgtttctc tttatcctta tactggctgc ttatggtgac | 600 |
| aattgagaga ttgttaccat atagctattg gattggccat ccggtgacaa atagagcaat | 660 |
| tgtgtatttg tttgttggtt tcgtgccatt aaattacaag gttctaaaca cccttaatct | 720 |
| tattatagca ttcaacacaa caaa | 744 |

<210> SEQ ID NO 27
<211> LENGTH: 663
<212> TYPE: DNA
<213> ORGANISM: Unknown
<220> FEATURE:
<223> OTHER INFORMATION: Description of Unknown:
      Human Parechovirus sequence

<400> SEQUENCE: 27

| | |
|---|---|
| gtacattaga tgcgtcatct gcaactttag tcaataaatt acctccaatg tcattaccaa | 60 |
| cattccctac cttttcacta acacctaaga caacaagtac ctatgcctgg tctccactat | 120 |
| tcgaaggcaa cttgcaataa gaagagtgga attaagacgc ttaaagcata gagctagtta | 180 |
| tcttttctaa cccacaaagt tttgtggggt ggcagatggc gtgccataac tctattagtg | 240 |
| agataccatg cttgtggatc ttatgctcac acagccatcc tctagtaagt tgataaggtg | 300 |
| tctggtgata tgtgggaact cacatgaacc attaatttac cgtaaggtat cctatagcca | 360 |
| gcggaatcac atctggtgac agatgcctct ggggccgaaa gccaaggttt aacagaccct | 420 |
| ataggattgg tttcaaaacc tgaattgatg tggattgtgt atagtacctg ttgatctggt | 480 |
| aacagtgtca acactagttg taaggcccac gaaggatgcc cagaaggtac ccgtaggtaa | 540 |
| caagtgacac tatggatctg atctggggcc agctacctct atcatggtga gttggttaaa | 600 |
| aaacgtctag tgggccaaac ccagggggga tccctggttt ccttttacct aatcaaagcc | 660 |
| act | 663 |

<210> SEQ ID NO 28
<211> LENGTH: 744
<212> TYPE: DNA
<213> ORGANISM: Unknown
<220> FEATURE:
<223> OTHER INFORMATION: Description of Unknown:
Aichi virus sequence

<400> SEQUENCE: 28
tttgaaaagg gggtgggggg gcctcggccc cctcaccctc ttttccggtg gtctggtccc 60
ggaccaccgt tactccattc agcttcttcg gaacctgttc ggaggaatta aacgggcacc 120
catactcccc ccaccccct tttgtaacta agtatgtgtg ctcgtgatct tgactcccac 180
ggaacggacc gatccgttgg tgaacaaaca gctaggtcca catcctccct tcccctggga 240
gggcccccgc cctcccacat cctcccccca gcctgacgta tcacaggctg tgtgaagccc 300
ccgcgaaagc tgctcacgtg gcaattgtgg gtcccccctt catcaagaca ccaggtcttt 360
cctccttaag gctagccccg gcgtgtgaat tcacgttggg caactagtgg tgtcactgtg 420
cgctcccaat ctcggccgcg gagtgctgtt ccccaagcca aacccctggc ccttcactat 480
gtgcctggca agcatatctg agaaggtgtt ccgctgtggc tgccaacctg gtgacaggtg 540
ccccagtgtg cgtaaccttc ttccgtctcc ggacggtagt gattggttaa gatttggtgt 600
aaggttcatg tgccaacgcc ctgtgcggga tgaaacctct actgccctag gaatgccagg 660
caggtacccc acctccgggt gggatctgag cctgggctaa ttgtctacgg gtagtttcat 720
ttccaatcct tttatgtcgg agtc 744

<210> SEQ ID NO 29
<211> LENGTH: 734
<212> TYPE: DNA
<213> ORGANISM: Unknown
<220> FEATURE:
<223> OTHER INFORMATION: Description of Unknown:
Hepatitis A virus sequence

<400> SEQUENCE: 29
ttcaagaggg gtctccggag ttttccggaa cccctcttgg aagtccatgg tgaggggact 60
tgatacctca ccgccgtttg cctaggctat aggctaaatt tccctttccc tgtccttccc 120
ctatttcctt ttgttttgtt tgtaaatatt aattcctgca ggttcagggt tctttaatct 180
gtttctctat aagaacactc aatttttcac gctttctgtc tcctttcttc cagggctctc 240
cccttgccct aggctctggc cgttgcgccc ggcggggtca actccatgat tagcatggag 300
ctgtaggagt ctaaattggg gacgcagatg tttgggacgt cgccttgcag tgttaacttg 360
gctttcatga acctctttga tcttccacaa ggggtaggct acgggtgaaa cctcttaggc 420
taatacttca atgaagagat gccttggata gggtaacagc ggcggatatt ggtgagttgt 480
taagacaaaa accattcaac gccggaggac tggctctcat ccagtggatg cattgaggga 540
attgattgtc agggctgtct ctaggtttaa tctcagacct ctctgtgctt agggcaaaca 600
ctatttggcc ttaaatggga tcctgtgaga gggggtccct ccattgacag ctggactgtt 660
ctttggggcc ttatgtggtg tttgcctctg aggtactcag gggcatttag gtttttcctc 720
attcttaaat aata 734

<210> SEQ ID NO 30
<211> LENGTH: 638
<212> TYPE: DNA
<213> ORGANISM: Unknown

<220> FEATURE:
<223> OTHER INFORMATION: Description of Unknown:
Phopivirus sequence

<400> SEQUENCE: 30
gggagtaaac ctcaccaccg tttgccgtgg tttacggcta cctatttttg gatgtaaata 60
ttaattcctg caggttcagg tctcttgaat tatgtccacg ctagtggcac tctcttaccc 120
ataagtgacg ccttagcgga acctttctac acttgatgtg gttaggggtt acattatttc 180
cctgggcctt ctttggccct ttttcccctg cactatcatt ctttcttccg ggctctcagc 240
atgccaatgt tccgaccggt gcgcccgccg gggttaactc catggttagc atggagctgt 300
aggccctaaa agtgctgaca ctggaactgg actattgaag catacactgt taactgaaac 360
atgtaactcc aatcgatctt ctacaagggg taggctacgg gtgaaacccc ttaggttaat 420
actcatattg agagatactt ctgataggtt aaggttgctg gataatggtg agtttaacga 480
caaaaaccat tcaacagctg tgggccaacc tcatcaggta gatgcttttg gagccaagtg 540
cgtaggggtg tgtgtggaaa tgcttcagtg gaaggtgccc tcccgaaagg tcgtaggggt 600
aatcaggggc agttaggttt ccacaattac aatttgaa 638

<210> SEQ ID NO 31
<211> LENGTH: 743
<212> TYPE: DNA
<213> ORGANISM: Unknown
<220> FEATURE:
<223> OTHER INFORMATION: Description of Unknown:
CVA10 sequence

<400> SEQUENCE: 31
gctcttccga tctgggttgt tcccacccac agggcccact gggcgccagc actctgattc 60
cacggaatct ttgtgcgcct gttttacaac ccttcccaat ttgtaacgta gaagcaatac 120
acactactga tcaatagtag gcatggcgcg ccagtcatgt catgatcaag cacttctgtt 180
cccccggact gagtatcaat agactgctca cgcggttgaa ggagaaaacg ttcgttaccc 240
ggctaactac ttcgagaaac ctagtagcac catggaagct gcggagtgtt tcgctcagca 300
ctttccccgt gtagatcagg tcgatgagtc actgcaatcc ccacgggcga ccgtggcagt 360
ggctgcgttg gcggcctgcc tatggggcaa cccataggac gctctaatgt ggacatggtg 420
cgaagagtct attgagctag ttagtagtcc tccggcccct gaatgcggct aatcctaact 480
gcggagcaca tgccttcaac ccaggaggtg gtgtgtcgta acgggtaact ctgcagcgga 540
accgactact ttgggtgtcc gtgtttcctt ttatccttat attggctgct tatggtgaca 600
atcacggaat tgttgccata tagctattgg attggccatc cggtgtctaa cagagctatt 660
gtatacctat ttgttggatt tactccccta tcatacaaat ctctgaacac tttgtgcttt 720
atactgaact taaacacacg aaa 743

<210> SEQ ID NO 32
<211> LENGTH: 746
<212> TYPE: DNA
<213> ORGANISM: Unknown
<220> FEATURE:
<223> OTHER INFORMATION: Description of Unknown:
Enterovirus C sequence

<400> SEQUENCE: 32
ttaaaacagc tctggggttg ttcccacccc agaggcccac gtggcggcca gtacaccggt 60
accacggtac ccttgtacgc ctgttttata ctcccctccc cgtaaactag aagcacgaaa 120

```
cacaagttca atagaagggg gtacagacca gtaccaccac gaacaagcac ttctgttccc    180

ccggtgaggt cacatagact gtccccacgg tcaaaagtga ctgatccgtt atccgctcac    240

gtacttcgga aagcctagta ccaccttgga atctacgatg cgttgcgctc agcactcgac    300

cccggagtgt agcttaggct gatgagtctg gacgttcccc actggtgaca gtggtccagg    360

ctgcgttggc ggcctacctg tggtccaaaa ccacaggacg ctagtagtga acaaggtgtg    420

aagagcccac tgagctacct gagaatcctc cggcccctga atgcggctaa tcccaaccac    480

ggagcaggta atcgcaaacc agcggtcagc ctgtcgtaac gcgtaagtct gtggcggaac    540

cgactacttt gggtgtccgt gtttcctttt atttttatgg tggctgctta tggtgacaat    600

catagattgt tatcataaag caaattggat tggccatccg gagtgagcta aactatctat    660

ttctctgagt gttggattcg tttcacccac attctgaaca atcagcctca ttagtgttac    720

cctgttaata agacgatatc atcacg                                         746
```

<210> SEQ ID NO 33
<211> LENGTH: 726
<212> TYPE: DNA
<213> ORGANISM: Unknown
<220> FEATURE:
<223> OTHER INFORMATION: Description of Unknown:
Enterovirus D sequence

<400> SEQUENCE: 33

```
ttaaaacagc tctggggttg ttcccacccc agaggcccac gtggcggcta gtactccggt     60

accccggtac ccttgtacgc ctgttttata ctccctttcc caagtaactt tagaagaaat    120

aaactaatgt tcaacaggag gggtacaaa ccagtaccac cacgaacaca cacttctgtt     180

tccccggtga agttgcatag actgtaccca cggttgaaag cgatgaatcc gttacccgct    240

taggtacttc gagaagccta gtatcatctt ggaatcttcg atgcgttgcg atcagcactc    300

taccccgagt gtagcttggg tcgatgagtc tggacacccc acaccggcga cgtggtccag    360

gctgcgttgg cggcctaccc atggctagca ccatgggacg ctagttgtga acaaggtgcg    420

aagagcctat tgagctacct gagagtcctc cggcccctga atgcggctaa tcccaaccac    480

ggagcaaatg ctcacaatcc agtgagtggt ttgtcgtaat gcgcaagtct gtggcggaac    540

cgactacttt gggtgtccgt gtttcctttt atttttatta tggctgctta tggtgacaat    600

ctgagattgt tatcatatag ctattggatt agccatccgg tgatatcttg aaattttgcc    660

ataacttttt cacaaatcct acaacattac actacacttt ctcttgaata attgagacaa    720

ctcata                                                               726
```

<210> SEQ ID NO 34
<211> LENGTH: 737
<212> TYPE: DNA
<213> ORGANISM: Unknown
<220> FEATURE:
<223> OTHER INFORMATION: Description of Unknown:
Enterovirus J sequence

<400> SEQUENCE: 34

```
ttaaaatagc ctcagggttg ttcccaccct gagggcccac gtggtgtagt actctggtat     60

tacggtacct ttgtacgcct attttatacc cccttcccca agtaatttag aagcaagcac    120

aaaccagttc agtagtaagc agtacaatcc agtactgtaa tgaacaagta cttctgttac    180

cccggaaggg tctatcggta agctgtaccc acggctgaag aatgacctac cgttaaccgg    240
```

-continued

```
ctacctactt cgagaagcct agtaatgccg ttgaagtttt attgacgtta cgctcagcac    300

actaccccgt gtgtagtttt ggctgatgag tcacggcact ccccacgggc gaccgtggcc    360

gtggctgcgt tggcggccaa ccaaggagtg caagctcctt ggacgtcata ttacagacat    420

ggtgtgaaga gcctattgag ctaggtggta gtcctccggc ccctgaatgc ggctaatcct    480

aactccggag catatcggtg cgaaccagca cttggtgtgt tgtaatacgt aagtctggag    540

cggaaccgac tactttgggt gtccgtgttt cctgttttaa cttttatggc tgcttatggt    600

gacaatttaa cattgttacc atatagctgt tgggttggcc atccggattt tgttataaaa    660

ccatttcctc gtgccttgac ctttaacaca tttgtgaact tctttaaatc ccttttatta    720

gtccttaaat actaaga                                                   737
```

<210> SEQ ID NO 35
<211> LENGTH: 327
<212> TYPE: DNA
<213> ORGANISM: Pegivirus sp.

<400> SEQUENCE: 35

```
aactgttgtt gtagcaatgc gcatattgct acttcggtac gcctaattgg taggcgcccg     60

gccgaccggc cccgcaaggg cctagtagga cgtgtgacaa tgccatgagg gatcatgaca    120

ctggggtgag cggaggcagc accgaagtcg ggtgaactcg actcccagtg cgaccacctg    180

gcttggtcgt tcatggaggg catgcccacg ggaacgctga tcgtgcaaag ggatgggtcc    240

ctgcactggt gccatgcgcg gcaccactcc gtacagcctg atagggtggc ggcgggcccc    300

cccagtgtga cgtccgtgga gcgcaac                                        327
```

<210> SEQ ID NO 36
<211> LENGTH: 281
<212> TYPE: DNA
<213> ORGANISM: Unknown
<220> FEATURE:
<223> OTHER INFORMATION: Description of Unknown:
      GB virus C sequence

<400> SEQUENCE: 36

```
tgacgtgggg gggttgattt tcccccccg gcactgggtg caagccccag aaaccgacgc     60

ctatctaagt agacgcaatg actcggcgcc gactcggcga ccggccaaaa ggtggtggat    120

gggtgatgac agggttggta ggtcgtaaat cccggtcatc ctggtagcca ctataggtgg    180

gtcttaagag aaggtcaaga ttcctcttac gcctgcggcg agaccgcgca cggtccacag    240

gtgttggccc taccggtgtg aataagggcc cgacatcagg c                        281
```

<210> SEQ ID NO 37
<211> LENGTH: 459
<212> TYPE: DNA
<213> ORGANISM: Unknown
<220> FEATURE:
<223> OTHER INFORMATION: Description of Unknown:
      GB virus C sequence

<400> SEQUENCE: 37

```
gacgtggggg ggttgatccc ccccctttgg cactgggtgc aagccccaga aaccgacgcc     60

tatttaaaca gacgttaaga accggcgccg acccggcgac cggccaaaag gtggtggatg    120

ggtgatgcca gggttggtag gtcgtaaatc ccggtcatct tggtagccac tataggtggg    180

tcttaagggt tggttaaggt ccctctggcg cttgtggcga gaaagcgcac ggtccacagg    240

tgttggccct accggtgtga ataagggccc gacgtcaggc tcgtcgttaa accgagccca    300
```

ctacccacct gggcaaacaa cgcccacgta cggtccacgt cgcccttcaa tgtctctctt 360
gaccaatagg cttagccggc gagttgacaa ggaccagtgg gggctgggcg gtaggggaag 420
gacccctgcc gctgcccttc ccggtggagt gggaaatgc 459

<210> SEQ ID NO 38
<211> LENGTH: 350
<212> TYPE: DNA
<213> ORGANISM: Unknown
<220> FEATURE:
<223> OTHER INFORMATION: Description of Unknown:
GB virus C sequence

<400> SEQUENCE: 38
tgacgtgggg gggttgatcc gcccccccg gcactcggtg caagccccat aaaccgacgc 60
ctatctaagt agacgcaatg actcggcgcc gactcggcga ccggccaaaa ggtggtggat 120
gggtggtgac agggttggta ggtcgtaaat cccggtcatc ctggtagcca ctataggtgg 180
gtcttaagag aaggtcaaga ctcctcttgt gcctgcggcg agaccgcgca cggtccacag 240
gtgctggccc taccggtgtg aataagggcc cgacgtcagg ctcgtcgtta aaccgagccc 300
gtcacccacc tgggcaaacg acgcccacgt acggtccacg tcgcccttca 350

<210> SEQ ID NO 39
<211> LENGTH: 318
<212> TYPE: DNA
<213> ORGANISM: Pegivirus A

<400> SEQUENCE: 39
tgtagcaatg cgcatattgc tacttcggta cgcctaattg gtaggcgccc ggccgaccgg 60
ccccgcaagg gcctagtagg acgtgtgaca atgccatgcg ggatcatgac actggggtga 120
gcggaggcag caccgaagtc gggtgaactc gactcccagt gcgaccacct ggcttggtcg 180
ttcatggagg gcatgcccac gggaacgctg atcgtgcaaa gggatgggtc cctgcactgg 240
tgccatgcgc ggcaccactc cgtacagcct gatagggtgg cggcgggccc ccccagtgtg 300
acgtccgtgg agcgcaac 318

<210> SEQ ID NO 40
<211> LENGTH: 399
<212> TYPE: DNA
<213> ORGANISM: Unknown
<220> FEATURE:
<223> OTHER INFORMATION: Description of Unknown:
Pasivirus A sequence

<400> SEQUENCE: 40 atttctggc cgtgtagctg cttttgacca gtggctctgg gttacttagc caaatccccc 60
ttccttcacc cttttaaatt tgatggtctg tgttgtttgt tttgtcttgt ctaaataata 120
tataagatcc ttcccgccga tacagacctc gacagtctgg tgtaggaggg ttggtgttat 180
taatttgccc cagaagagtg accgtgacac atagaaacca tgagtacatg tgtatccgtg 240
gaggatcgcc cgggactgga ttccatatcc cattgccatc ccaacaagcg gagggtatac 300
ccactatgtg cgcgtttgca gtgggaatct gcaaatttag tcatactgcc tgatagggtg 360
tgggcctgca ctctggggta ctcaggctgt tcatataat 399

<210> SEQ ID NO 41
<211> LENGTH: 430
<212> TYPE: DNA

<213> ORGANISM: Sapelovirus sp.

<400> SEQUENCE: 41
cccctccacc cttaaggtgg ttgtatccca catacccac cctcccttcc aaagtggacg 60
gacaactgga ttttgactaa cggcaagtct gaatggtatg atttggatac gtttaaacgg 120
cagtagcgtg gcgagctatg gaaaaatcgc aattgtcgat agccatgtta gtgacgcgct 180
tcggcgtgct cctttggtga ttcggcgact ggttacagga gagtaggcag tgagctatgg 240
gcaaacctct acagtattac ttagagggaa tgtgcaattg agacttgacg agcgtctctt 300
tgagatgtgg cgcatgctct tggcattacc atagtgagct tccaggttgg gaaacctgga 360
ctgggcctat actacctgat agggtcgcgg ctggccgcct gtaactagta tagtcagttg 420
aaaccccccc 430

<210> SEQ ID NO 42
<211> LENGTH: 504
<212> TYPE: DNA
<213> ORGANISM: Rosavirus B

<400> SEQUENCE: 42
gtctctttag tgtctatgct tcagagagcg gtgaactgac accgttgctt cttgcacagc 60
ccttcgtgcc ggtctttccg gttctcgaca gcgttgggca tcatggctag ttaggctaag 120
atagtggatg atctagtgaa cagttttgga ttgtttggag ttttgtagcg atgctagtag 180
tgtgtgtgga cctccccacg tggtaacacg tgccccacag gccaaaagcc aaggtgttga 240
aagcacccct actagtccca gactcaccca tctgggaact cctctcatga aaaatcttag 300
taacttttga ttcggctatt catcaacctc tctagtcaag ggctgaagga tgcccggaag 360
gtacccgcag gtaacgataa gctcactgtg gatctgatcc ggggctttgg tgcgaccgtc 420
tgtccggcgt agccagagtt aaaaaacgtc taggcccttc caccccaagg gattggggtt 480
tccccaatca tttgaaagtt cact 504

<210> SEQ ID NO 43
<211> LENGTH: 532
<212> TYPE: DNA
<213> ORGANISM: Unknown
<220> FEATURE:
<223> OTHER INFORMATION: Description of Unknown:
Bakunsa virus sequence

<400> SEQUENCE: 43
ttttgaacgc cacctcggag cgatatccgg ggaccccctc cccttttcc ttcctacctt 60 cttcccaaat ttccctcttc ccttgttatt ttggtttgga tttcctggac atgactcgga 120
cggatctatc tcatttgctt tgtgtctgct ccaccagtgg catggtcgaa agatcatcaa 180
cactggacgt gtactgtaat ggccaaacgt gcccacaggg gaaaccatgc cggtcgctgt 240
agcggcgggt ggacgtggtg gacccctctc cctgctcata aactttgggt aggtgaaggg 300
ttcaagcgac gcttgccgtg agggcgcatc cggatggtgg gaaccaacaa actaggctgt 360
aatggccgac ctcaggtgga tgagctaggg ctgctgcacc aaaagggact cgattcgata 420
tcccggcctg gtagcctagt gcagtggact cgtagttggg aatctacgac tggcctagta 480
cagggtgata gccccgtttc ccacgcccac ctgttgtagg gacaccccc cc 532

<210> SEQ ID NO 44
<211> LENGTH: 494
<212> TYPE: DNA

<213> ORGANISM: Tremovirus A

<400> SEQUENCE: 44
tttgaaagag gcctccggag tgtccggagg ctctctttcg acccaaccca tactgggggg 60
tgtgtgggac cgtacctgga gtgcacggta tatatgcatt cccgcatggc aagggcgtgc 120
taccttgccc cttgacgcat ggtatgcgtc atcatttgcc ttggttaagc cccatagaaa 180
cgaggcgtca cgtgccgaaa atccctttgc gtttcacaga accatcctaa ccatgggtgt 240
agtatgggaa tcgtgtatgg ggatgattag gatctctcgt agagggatag gtgtgccatt 300
caaatccagg gagtactctg gctctgacat tgggacattt gatgtaaccg gacctggttc 360
agtatccggg ttgtcctgta ttgttacggt gtatccgtct tggcacactg aaagggtatt 420
tttgggtaat cctttcctac tgcctgatag ggtggcgtgc ccggccacga gagattaagg 480
gtagcaattt aaac 494

<210> SEQ ID NO 45
<211> LENGTH: 378
<212> TYPE: DNA
<213> ORGANISM: Unknown
<220> FEATURE:
<223> OTHER INFORMATION: Description of Unknown:
Swine Pasivirus 1 sequence

<400> SEQUENCE: 45
gcttttgacc agtggctctg ggttacttag ccaagtccct ttctcttatt ttcactagtt 60
tatgttgtgt gttgtctgtt ttgttttgtt taaattgtat acaagatcct tcccgccgac 120
acagacctcg acagtctggt gtaggagggt tggtgatatt aatttgcccc aaaagagtga 180
ccgtgatacg tggaaaccat gagtacatgt gtatccgtgg aggatcgccc gggactggat 240
tccatatccc attgccatcc caacaaacgg agggtatacc caccacgtgc gcgtttgcag 300
tgggaatctg caaatttagt catactgcct gatagggtgt gggcctgcac tttggggtac 360
tcaggctgtt catataat 378

<210> SEQ ID NO 46
<211> LENGTH: 319
<212> TYPE: DNA
<213> ORGANISM: Unknown
<220> FEATURE:
<223> OTHER INFORMATION: Description of Unknown:
Parechovirus-like virus PLV-CHN sequence

<400> SEQUENCE: 46
acatggggta tgttgtctgt cctgttttgt tgaaacaata tataagatcc tttccgccga 60
tatagacctc gacagtctag tgtaggagga ttggtgatag taacttgccc cagaagagtg 120
accgtgacac atagaaacca tgagtacatg tgtatccgtg gaggatcgcc cgggactgga 180
ttccatatcc cattgccatc ccaacaaacg gagggtatac ccactatgtg cgcgtttgca 240
gtgggagcct gcaaatttag tcatactgcc tgatagggtg tgggcctgca ctctggggta 300
ctcaggctgt ttatataat 319

<210> SEQ ID NO 47
<211> LENGTH: 420
<212> TYPE: DNA
<213> ORGANISM: Unknown
<220> FEATURE:
<223> OTHER INFORMATION: Description of Unknown:
Pasivirus A sequence -continued

<400> SEQUENCE: 47
tgaaaaagtg gttgtgcagc tggattttcc ggctgtgcaa ctgcttttga ccagtggctc 60
tgggttactt agccaaattc ctttccctta tccctattgg tttgtgttgt gtgttgtttg 120
ttttgttttg tcttaactat atacaagatc cttcccgccg atacagacct cgacagtctg 180
gtgtaggagg gttggtgtta ttaatttgcc ccaaaagagt gaccgtgaca cgtggaaacc 240
atgagtacat gtgtatccgt ggaggatcgc ccgggactgg attccatatc ccattgccat 300
cccaacaaac ggagggtata cccaccacgt gcgcgtttgc agtgggaatc tgcaaattta 360
gtcatactgc ctgatagggt gtgggcctgc actttggggt actcaggctg tttatataat 420

<210> SEQ ID NO 48
<211> LENGTH: 373
<212> TYPE: DNA
<213> ORGANISM: Sicinivirus sp.

<400> SEQUENCE: 48
gtgtcattaa ggtgtgtttg gaagttcgaa ttagctggtt tgtggtgatt agtagacccc 60
ctggaggtac ccaattcgga tctgaccagg gacccgtgac tataccgctc cggtaattcg 120
ggtttaaaac aatgaacgtc accacacaat tacttttctc attttatttt catcattgtc 180
ttcctattta ccgattacac tcgatttcct tggatgttcc tggagatttc cctggttacc 240
tggaccctca ttattgttgt tgtttcaccc agcgagctgt cccaattgct tattatttgc 300
gcttacaact tcgtcctaat atttttctgg ttgatcgggt tgattgagct cccgggctat 360
cctgccattc aac 373

<210> SEQ ID NO 49
<211> LENGTH: 280
<212> TYPE: DNA
<213> ORGANISM: Hepacivirus K

<400> SEQUENCE: 49
gggaacaatg gtccgtccgc ggaacgactc tagccatgag tctagtacga gtgcgtgcca 60
cccattagca caaaaaccac tgactgagcc acacccctcc cggaatcctg agtacaggac 120
attcgctcgg acgacgcatg agcctccatg ccgagaaaat tgggtatacc cacgggtaag 180
gggtggccac ccagcgggaa tctgggggct ggtcactgac tatggtacag cctgataggg 240
tgctgccgca gcgtcagtgg tatgcggctg ttcatggaac 280

<210> SEQ ID NO 50
<211> LENGTH: 384
<212> TYPE: DNA
<213> ORGANISM: Hepacivirus A

<400> SEQUENCE: 50
acctccgtgc taggcacggt gcgttgtcag cgttttgcgc ttgcatgcgc tacacgcgtc 60
gtccaacgcg gagggaactt cacatcacca tgtgtcactc cccctatgga gggttccacc 120
ccgcttacac ggaaatgggt taaccatacc caaagtacgg gtatgcgggt cctcctaggg 180
cccccccggc aggtcgaggg agctggaatt cgtgaattcg tgagtacacg aaaatcgcgg 240
cttgaacgtc tttgaccttc ggagccgaaa tttgggcgtg ccccacgaag gaaggcgggg 300
gcggtgttgg gccgccgccc cctttatccc acggtctgat aggatgcttg cgagggcacc 360
tgccggtctc gtagaccata ggac 384

-continued

<210> SEQ ID NO 51
<211> LENGTH: 384
<212> TYPE: DNA
<213> ORGANISM: Unknown
<220> FEATURE:
<223> OTHER INFORMATION: Description of Unknown:
Bovine viral diarrhea virus 1 sequence

<400> SEQUENCE: 51
gtatacgaga atttgcctag gacctcgttt acaatatggg caatctaaaa ttataattag 60
gcctaaggga caaatcctcc tcagcgaagg ccgaaaagag gctagccatg cccttagtag 120
gactagcaaa ataagggggg tagcaacagt ggtgagttcg ttggatggct gaagccctga 180
gtacagggta gtcgtcagtg gttcgacgct tcggaggaca agcctcgaga taccacgtgg 240
acgagggcat gcccacagca catcttaacc tggacggggg tcgttcaggt gaaaacggtt 300
taaccaaccg ctacgaatac agcctgatag ggtgctgcag aggcccactg tattgctact 360
gaaaatctct gctgtacatg gcac 384

<210> SEQ ID NO 52
<211> LENGTH: 372
<212> TYPE: DNA
<213> ORGANISM: Unknown
<220> FEATURE:
<223> OTHER INFORMATION: Description of Unknown:
Border Disease virus sequence

<400> SEQUENCE: 52
gtatacggga gtagctcatg cccgtataca aaattggata ttccaaaact cgattgggtt 60
agggagccct cctagcgacg gccgaaccgt gttaaccata cacgtagtag gactagcaga 120
cgggaggact agccatcgtg gtgagatccc tgagcagtct aaatcctgag tacaggatag 180
tcgtcagtag ttcaacgcag gcacggttct gccttgagat gctacgtgga cgagggcatg 240
cccaagactt gctttaatct cggcgggggt cgccgaggtg aaaacaccta acggtgttgg 300
ggttacagcc tgatagggtg ctgcagaggc ccacgaatag gctagtataa aaatctctgc 360
tgtacatggc ac 372

<210> SEQ ID NO 53
<211> LENGTH: 388
<212> TYPE: DNA
<213> ORGANISM: Unknown
<220> FEATURE:
<223> OTHER INFORMATION: Description of Unknown:
Bovine viral diarrhea virus 2 sequence

<400> SEQUENCE: 53
gtatacgaga ttagctaaag tactcgtata tggattggac gtcaacaaat ttttaattgg 60
caacgtaggg aaccttcccc tcagcgaagg ccgaaaagag gctagccatg ccctttagta 120
ggactagcaa aagtaggggg actagcggta gcagtgagtt cgttggatgg ccgaacccct 180
gagtacaggg gagtcgtcaa tggttcgaca ctccattagt cgaggagtct cgagatgcca 240
tgtggacgag ggcatgccca cggcacatct taacccatgc gggggttgca tgggtgaaag 300
cgctaatcgt ggcgttatgg acacagcctg atagggtgta gcagagacct gctattccgc 360
tagtaaaaaa ctctgctgta catggcac 388

<210> SEQ ID NO 54
<211> LENGTH: 373
<212> TYPE: DNA
<213> ORGANISM: Unknown

<220> FEATURE:
<223> OTHER INFORMATION: Description of Unknown:
Classical swine fever virus sequence

<400> SEQUENCE: 54
gtatacgagg ttagttcatt ctcgtatgca ttattggaca aatcaaaatt tcaatttggt 60
tcagggcctc cctccagcga cggccgaact gggctagcca tgcccatagt aggactagca 120
aacggaggga ctagccgtag tggcgagctc cctgggtgtt ctaagtcctg agtacaggac 180
agtcgtcagt agttcgacgt gagcagaagc ccacctcgag atgctatgtg gacgagggca 240
tgcccaagac gcaccttaac cctagcgggg gtcgctaggg tgaaatcaca ccacgtgatg 300
ggagtccgac ctgatagggt gctgcagagg ctcactatta ggctagtata aaaatctctg 360
ctgtacatgg cac 373

<210> SEQ ID NO 55
<211> LENGTH: 191
<212> TYPE: DNA
<213> ORGANISM: Unknown
<220> FEATURE:
<223> OTHER INFORMATION: Description of Unknown:
Human blood-associated dicistrovirus sequence

<400> SEQUENCE: 55
aaaaccgacc ccagagatca gaaagtcgtt gacgcgatct tttattagag gacgttgcgc 60
tggcgcgagc tttaattagc agacgccaaa aataaacaac aaaatgctga tcgcgagact 120
taattgtcag acgattggcc aaatccgatg tgatctttgc tgctcccaga ttgccgaaat 180
aggagtagta g 191

<210> SEQ ID NO 56
<211> LENGTH: 438
<212> TYPE: DNA
<213> ORGANISM: Unknown
<220> FEATURE:
<223> OTHER INFORMATION: Description of Unknown:
Hubei Picorna-like virus sequence

<400> SEQUENCE: 56
ccccaaaacc ccccccttaa actcaacact gtagtggatt cattttccgt tgcaaaacaa 60
aacattacta cccgcattta tgtaggctct gtgttttcta tgcgaccgtt acattaatct 120
ctactctgac ccactagttt ataaaaccga agacctgaat gaaacgattt tccttctttt 180
caacctctaa cgaacctctg acggcttgag aaacctgaag ttagtaatta tgtttaaaag 240
aaaggaaagt caaacgcgat gactcttaca tccctattcc ataccgttgc tccacaatgt 300
gagcgatgcg aggtcgggac tgcagtatta ggggaacgag ctacatggag agttaattat 360
ctctcccctc ctacgggagt ctcatgtgag ctgtagaaag cggttggcac ctctcgttac 420
ctcgcctgta catgatcc 438

<210> SEQ ID NO 57
<211> LENGTH: 193
<212> TYPE: DNA
<213> ORGANISM: Cricket paralysis virus

<400> SEQUENCE: 57
aaaagcaaaa atgtgatctt gcttgtaaat acaattttga gaggttaata aattacaagt 60
agtgctattt ttgtatttag gttagctatt tagctttacg ttccaggatg cctagtggca 120
gccccacaat atccaggaag ccctctctgc ggtttttcag attaggtagt cgaaaaacct 180
aagaaattta cct 193

<210> SEQ ID NO 58
<211> LENGTH: 752
<212> TYPE: DNA
<213> ORGANISM: Unknown
<220> FEATURE:
<223> OTHER INFORMATION: Description of Unknown:
Salivirus A sequence

<400> SEQUENCE: 58
tttcctcctt tcgaccgcct tacggcaggc gggtccgcgg acggcttcgg cctacccgcg 60
acaagaatgc cgtcatctgt ccttatcacc catattcttt cccttccccc gcaaccatca 120
cgcttactcg cgcacgtgtt gagtggcacg tgcgttgtcc aaacagttac actcacaccc 180
ttggggcggg tttgtcccgc cctcgggttc ctcgcggaac cctccctctt ctctctccct 240
ttctatccgc cttcactttc cataactaca gtgctttggt aggtaagcat cctgaccccc 300
cgcggaagct gccaacgtgg caactgtggg gatccaggca ggttatcaaa ggcacccggt 360
ctttccgcct tcaggagtat ccctgccggt gaattccgac agggctctgc ttggtgccaa 420
cctcccccaa atgcgcgctg cgggagtgct cttccccaac tcatcttagt aacctctcat 480
gtgtgtgctt ggtcagcata tctgaggcga cgttccgctg tcccagacca gtccagcaat 540
ggacgggcca gtgtgcgtag tcgctttccg gtttcccggc gcatgtttgg cgaaacgctg 600
aggtaaggtt ggtgtgccca atgcccgtaa tttggtgaca cctcaagacc acccaggaat 660
gccagggagg taccccactt cggtgggatc tgaccctggg ctaattgtct acggtggttc 720
ttcttgcttc cacttctctt ttttctggca tg 752

<210> SEQ ID NO 59
<211> LENGTH: 708
<212> TYPE: DNA
<213> ORGANISM: Unknown
<220> FEATURE:
<223> OTHER INFORMATION: Description of Unknown:
Salivirus A sequence

<400> SEQUENCE: 59
tatggcaggc gggcttgtgg acggcttcgg cccacccaca gcaagaatgc catcatctgt 60
cctcaccccc atgtttcccc tttctttccc tgcaaccgtt acgcttactc gcaggtgcat 120
ttgagtggtg cacgtgttga ataaacagct acactcacat gggggcgggt tttcccgccc 180
tgcggcctct cgcgaggccc acccctcccc ttcctcccat aactacagtg ctttggtagg 240
taagcatcct gatcccccgc ggaagctgct cacgtggcaa ctgtggggac ccagacaggt 300
tatcaaaggc acccggtctt tccgccttca ggagtatccc tgctagtgaa ttctagtagg 360
gctctgcttg gtgccaacct cccccaaatg cgcgctgcgg gagtgctctt ccccaactca 420
ccctagtatc ctctcatgtg tgtgcttggt cagcatatct gagacgatgt tccgctgtcc 480
cagaccagtc cagtaatgga cgggccagtg tgcgtagtcg tcttccggct tttccggcgc 540
atgtttggtg aaccggtggg gtaaggttgg tgtgcccaac gcccgtactt tggtgatacc 600
tcaagaccac ccaggaatgc cagggaggta ccccgcttca cagcgggatc tgaccctggg 660
ctaattgtct acggtggttc ttcttgcttc cacttctttc tactgttc 708

<210> SEQ ID NO 60
<211> LENGTH: 718
<212> TYPE: DNA
<213> ORGANISM: Unknown
<220> FEATURE:
<223> OTHER INFORMATION: Description of Unknown:
Salivirus A sequence

<400> SEQUENCE: 60
tttcgaccgc cttatggcag gcgggcttgt ggacggcttc ggcccaccca cagcaagaat 60
gccatcatct gtcctcaccc ccatttctcc cctccttccc ctgcaaccat tacgcttact 120
cgcatgtgca ttgagtggtg cacgtgttga acaaacagct acactcacgt gggggcgggt 180
tttcccgccc ttcggcctct cgcgaggccc acccttcccc ttcctcccat aactacagtg 240
ctttggtagg taagcatcct gatcccccgc ggaagctgct cgcgtggcaa ctgtggggac 300
ccagacaggt tatcaaaggc acccggtctt tccgcctcca ggagtatccc tgctagtgaa 360
ttctagtggg gctctgcttg gtgccaacct cccccaaatg cgcgctgcgg gagtgctctt 420
ccccaactca ccctagtatc ctctcatgtg tgtgcttggt cagcatatct gagacgatgt 480
tccgctgtcc cagaccagtc cagcaatgga cgggccagtg tgcgtagtcg tcttccggct 540
tgtccggcgc atgtttggtg aaccggtggg gtaaggttgg tgtgcccaac gcccgtactt 600
tggtgacaac tcaagaccac ccaggaatgc cagggaggta ccccgcctca cggcgggatc 660
tgaccctggg ctaattgtct acggtggttc ttcttgcttc catttctttc ttctgttc 718

<210> SEQ ID NO 61
<211> LENGTH: 699
<212> TYPE: DNA
<213> ORGANISM: Unknown
<220> FEATURE:
<223> OTHER INFORMATION: Description of Unknown:
Salivirus A sequence

<400> SEQUENCE: 61
tatggcaggc gggcttgtgg acggtttcgg cccacccaca gcaagaatgc catcatctgt 60
cctcaccccc aatttttccct ttcttcccct gcaatcatca cgcttactcg catgtgcatt 120
gagtggtgca tgtgttgaac aaacagctac actcacatgg gggcgggttt tcccgcccta 180
cggcctctcg cgaggcccac ccttcccctc cccttataac tacagtgctt tggcaggtaa 240
gcatcctgat cccccgcgga agctgctcac gtggcaactg tggggaccca gacaggttat 300
caaaggcacc cggtctttcc gccttcagga gcatccccac tagtgaattc tagtggggct 360
ctgcttggtg ccaacctccc ccaaatgcgc gctgcgggag tgctcttccc caacccatcc 420
tagtatcctc tcatgtgtgt gcttggtcag catatctgag acgacgttcc gctgtcccag 480
accagtccag taatggacgg gccagtgtgc gtagtcgtct tccggcttgt ccggcgcatg 540
tttggtgaac cggtggggta aggttggtgt gcccaacgcc cgtactttgg tgacacctca 600
agaccaccca ggaatgccag ggaggtaccc cgcctcacgg cgggatctga ccctgggcta 660
attgtctacg gtggttcttc ttgcttccac ttctttctt 699

<210> SEQ ID NO 62
<211> LENGTH: 624
<212> TYPE: DNA
<213> ORGANISM: Unknown

<220> FEATURE:
<223> OTHER INFORMATION: Description of Unknown:
Salivirus A sequence

<400> SEQUENCE: 62

```
ttctcctgca accattacgc ttaatcgcat gtgcattgag tggtgcatgt gttgaacaaa     60

cagctacaat cacatggggg cgggttttcc cgccccacgg cttctcgcga ggcccatccc    120

tccctttctc cccataacta cagtgctttg gtaggtaagc atcccgatct cccgcggaag    180

ctgctcacgt ggcaactgtg gggacccaga caggttatca aaggcacccg gtctttccgc    240

cttcaggagt atccctgcta gcgaattcta gtagggctct gcttggtgcc aacctctccc    300

aaatgcgcgc tgcgggagtg ctcttcccca aatcacccca gtatcctctc atgtgtgtgc    360

ctggtcagca tatctgagac gatgttccgc tgtcccagac cagtccagta atggacgggc    420

cagtgtgcgt agtcgtcctc cggcttgtcc ggcgcatgtt tggtgaaccg gtggggtaag    480

gttggtgtgc ccaacgcccg taatcagggg atacctcaag gcacccagga atgccaggga    540

ggtatcccgc ctcacagcgg gatctgaccc tggggtaaat gtctgcgggg ggtcctcttg    600

gcccaattct cagtaatttt cagg                                           624
```

<210> SEQ ID NO 63
<211> LENGTH: 650
<212> TYPE: DNA
<213> ORGANISM: Unknown
<220> FEATURE:
<223> OTHER INFORMATION: Description of Unknown:
Salivirus A sequence

<400> SEQUENCE: 63

```
tctgtcctca ccccatcttc ccttctttcc tgcaccgtta cgcttactcg catgtgcatt     60

gagtggtgca cgtgcttgaa caaacagcta cactcacatg gggcgggtt ttcccgccct    120

gcggcctctc gcgaggccca cccctcccct tcctcccata actacagtgc tttggtaggt    180

aagcatcctg atcccccgcg gaagctgctc acgtggcaac tgtggggacc cagacaggtt    240

atcaaaggca cccggtcttt ccgccttcag gagtatccct gctagtgaat tctagtaggg    300

ctctgcttgg tgccaacctc ccccaaatgc gcgctgcggg agtgctcttc cccaactcac    360

cctagtatcc tctcatgtgt gtgcttggtc agcatatctg agacgatgtt ccgctgtccc    420

agaccagtcc agtaatggac gggccagtgt gcgtagtcgt cttccggctt gtccggcgca    480

tgtttggtga accggtgggg taaggttggt gtgcccaacg cccgtacttt ggtgatacct    540

caagaccacc caggaatgcc agggaggtac cccgcttcac agcgggatct gaccctgggc    600

taattgtcta cggtggttct tcttgcttcc acttctttct actgttcatg               650
```

<210> SEQ ID NO 64
<211> LENGTH: 730
<212> TYPE: DNA
<213> ORGANISM: Unknown
<220> FEATURE:
<223> OTHER INFORMATION: Description of Unknown:
Salivirus FHB sequence

<400> SEQUENCE: 64

```
acatgggggg tctgcggacg gcttcggccc acccgcgaca agaatgccgt catctgtcct     60

cattacccgt attccttccc ttccccgca accaccacgc ttactcgcgc acgtgttgag    120

tggcacgtgc gttgtccaaa cagctacacc cacacccttc ggggcgggtt tgtcccgccc    180

tcgggttcct cgcggaaccc ccccctccct ctctctcttt ctatccgccc tcacttccca    240
```

taactacagt gctttggtag gtgagcaccc tgaccccccg cggaagctgc taacgtggca 300
actgtgggga tccaggcagg ttatcaaagg cacccggtct ttccgccttc aggagtatct 360
ctgccggtga attccggtag ggctctgctt ggtgccaacc tcccccaaat gcgcgctgcg 420
ggagtgctct tccccaactc atcttagtaa cctctcatgt gtgtgcttgg tcagcatatc 480
tgaggcgacg ttccgctgtc ccagaccagt ccagcaatgg acgggccagt gtgcgtagtc 540
gctttccggt tttccggcgc atgtttggcg aaacgctgag gtaaggttgg tgtgcccaac 600
gcccgtaatt tggtgatacc tcaagaccac ccaggaatgc cagggaggta ccccacttcg 660
gtgggatctg accctgggct aattgtctac ggtggttctt cttgcttcca cttctctttt 720
ttctggcatg 730

<210> SEQ ID NO 65
<211> LENGTH: 741
<212> TYPE: DNA
<213> ORGANISM: Unknown
<220> FEATURE:
<223> OTHER INFORMATION: Description of Unknown:
CVB3 sequence

<400> SEQUENCE: 65
ttaaaacagc ctgtgggttg atcccaccca caggcccatt gggcgctagc actctggtat 60
cacggtacct ttgtgcgcct gttttatacc ccctccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tggggaaacc catgggacgc tctaatacag acatggtgcg 420
aagagtctat tgagctagtt ggtagtcctc cggcccctga atgcggctaa tcctaactgc 480
ggagcacaca ccctcaagcc agagggcagt gtgtcgtaac gggcaactct gcagcggaac 540
cgactacttt gggtgtccgt gtttcatttt attcctatac tggctgctta tggtgacaat 600
tgagagatcg ttaccatata gctattggat tggccatccg gtgactaata gagctattat 660
atatcccttt gttgggttta taccacttag cttgaaagag gttaaaacat tacaattcat 720
tgttaagttg aatacagcaa a 741

<210> SEQ ID NO 66
<211> LENGTH: 741
<212> TYPE: DNA
<213> ORGANISM: Unknown
<220> FEATURE:
<223> OTHER INFORMATION: Description of Unknown:
CVB1 sequence

<400> SEQUENCE: 66
ttaaaacagc ctgtgggttg ttcccaccca caggcccatt gggcgctagc actctggtat 60
cacggtacct ttgtgcgcct gttttacatc ccctccccaa attgtaattt agaagtttca 120
cacaccgatc attagcaagc gtggcacacc agccatgttt tgatcaagca cttctgttac 180
cccggactga gtatcaatag accgctaacg cggttgaagg agaaaacgtt cgttacccgg 240
ccaactactt cgaaaaacct agtaacacca tggaagttgc ggagtgtttc gctcagcact 300
accccagtgt agatcaggtc gatgagtcac cgcgttcccc acgggcgacc gtggcggtgg 360

```
ctgcgttggc ggcctgccta cggggaaacc cgtaggacgc tctaatacag acatggtgcg    420

aagagtctat tgagctagtt ggtaatcctc cggcccctga atgcggctaa tcctaactgc    480

ggagcacata ccctcaaacc agggggcagt gtgtcgtaac gggcaactct gcagcggaac    540

cgactacttt gggtgtccgt gtttcatttt attcctatac tggctgctta tggtgacaat    600

tgacaggttg ttaccatata gttattggat tggccatccg gtgactaaca gagcaattat    660

atatctcttt gttgggttta taccacttag cttgaaagag gttaaaacac tacatctcat    720

cattaaacta aatacaacaa a                                              741
```

```
<210> SEQ ID NO 67
<211> LENGTH: 742
<212> TYPE: DNA
<213> ORGANISM: Unknown
<220> FEATURE:
<223> OTHER INFORMATION: Description of Unknown:
      Echovirus 7 sequence

<400> SEQUENCE: 67

ttaaaacagc ctgtgggttg ttcccaccca cagggcccat tgggcgtcag caccctggta     60

tcacggtacc tttgtgcgcc tgttttatat cccttccccc aattgtaact tagaagaaac    120

acacaccgat caacagcaag cgtggcacac cagccatgtt ttggtcaagc acttctgtta    180

ccccggactg agtatcaata gactgctcac gcggttgaag gagaaagcgt ccgttatccg    240

gccagctact tcgagaaacc tagtaacacc atggaagttg cggagtgttt cgctcagcac    300

taccccagtg tagatcaggt cgatgagtca ccgctttccc cacgggcgac cgtggcggtg    360

gctgcgttgg cggcctgcct atgggggaac ccataggacg ctctaataca gacatggtgc    420

gaagagtcta ttgagctagc tggtattcct ccggcccctg aatgcggcta atcctaactg    480

tggagcacat gcccctaatc caaggggtag tgtgtcgtaa tgagcaattc cgcagcggaa    540

ccgactactt tgggtgtccg tgtttcctct tattcttgta ctggctgctt atggtgacaa    600

ttgagagatt gttaccatat agctattgga ttggccatcc ggtgactaat agagctattg    660

tgtatctctt tgttggattt gtaccactta atttgaaaga aatcaggaca ctacgctaca    720

ttttactatt gaacaccgca aa                                             742
```

```
<210> SEQ ID NO 68
<211> LENGTH: 743
<212> TYPE: DNA
<213> ORGANISM: Unknown
<220> FEATURE:
<223> OTHER INFORMATION: Description of Unknown:
      CVB5 sequence

<400> SEQUENCE: 68

ttaaaacagc ctgtgggttg tacccaccca cagggcccac tgggcgctag cactctggta     60

tcacggtacc tttgtgcgcc tgttttatgc ccccttcccc caattgaaac ttagaagtta    120

cacacaccga tcaacagcgg gcgtggcata ccagccgcgt cttgatcaag cactcctgtt    180

tccccggacc gagtatcaat agactgctca cgcggttgaa ggagaaaacg ttcgttaccc    240

ggctaactac ttcgagaaac ctagtagcat catgaaagtt gcgaagcgtt tcgctcagca    300

catccccagt gtagatcagg tcgatgagtc accgcattcc ccacgggcga ccgtggcggt    360

ggctgcgttg gcggcctgcc tacggggcaa cccgtaggac gcttcaatac agacatggtg    420

cgaagagtcg attgagctag ttagtagtcc tccggcccct gaatccggct aatcctaact    480

gcggagcaca taccctcaac ccagggggca ttgtgtcgta acgggtaact ctgcagcgga    540
```

accgactact ttgggtgtcc gtgtttcctt ttattcttat aatggctgct tatggtgaca 600
attgaaagat tgttaccata tagctattgg attggccatc cggtgtctaa cagagctatt 660
atatacctct ttgttggatt tgtaccactt gatctaaagg aagtcaagac actacaattc 720
atcatacaat tgaacacagc aaa 743

<210> SEQ ID NO 69
<211> LENGTH: 743
<212> TYPE: DNA
<213> ORGANISM: Unknown
<220> FEATURE:
<223> OTHER INFORMATION: Description of Unknown:
Enterovirus A71 sequence

<400> SEQUENCE: 69
ttaaaacagc ctgtgggttg cacccactca cagggcccac tgggcgcaag cactctggca 60
cttcggtacc tttgtgcgcc tgttttatat cccctccccc aatgaaattt agaagcagca 120
aaccccgatc aatagcaggc ataacgctcc agttatgtct tgatcaagca cttctgtttc 180
cccggactga gtatcaatag actgctcacg cggttgaagg agaaaacgtt cgttatccgg 240
ctaactactt cggaaagcct agtaacacca tggaagttgc ggagagtttc gttcagcact 300
tccccagtgt agatcaggtc gatgagtcac cgcattcccc acgggcgacc gtggcggtgg 360
ctgcgttggc ggcctgccca tggggtaacc catgggacgc tctaatacgg acatggtgtg 420
aagagtctac tgagctagtt agtagtcctc cggcccctga atgcggctaa tcccaactgc 480
ggagcacacg cccacaagcc agtgggtagt gtgtcgtaac gggcaactct gcagcggaac 540
cgactacttt gggtgtccgt gtttcctttt attcttatgt tggctgctta tggtgacaat 600
taaagagttg ttaccatata gctattggat tggccatccg gtgtgcaaca gagcgatcgt 660
ttacctattt attggttttg taccattgac actgaagtct gtgatcaccc ttaattttat 720
cttaaccctc aacacagcca aac 743

<210> SEQ ID NO 70
<211> LENGTH: 742
<212> TYPE: DNA
<213> ORGANISM: Unknown
<220> FEATURE:
<223> OTHER INFORMATION: Description of Unknown:
CVA3 sequence

<400> SEQUENCE: 70
ttaaaacagc ctgtgggttg tacccaccca cagggcccac tgggcgctag cacactggta 60
ttacggtacc tttgtgcgcc tgttttatac ccccccccaac ctcgaaactt agaagtaaag 120
caaacccgat caatagcagg tgcggcgcac cagtcgcatc ttgatcaagc acttctgtaa 180
ccccggaccg agtatcaata gactgctcac gcggttgaag gagaaaacgt tcgttacccg 240
gctaactact tcgagaaacc cagtagcatc atgaaagttg cagagtgttt cgctcagcac 300
tacccccgtg tagatcaggc cgatgagtca ccgcacttcc ccacgggcga ccgtggcggt 360
ggctgcgttg gcggcctgcc tatggggcaa cccataggac gctctaatac ggacatggtg 420
cgaagagtct attgagctag ttagtagtcc tccggcccct gaatgcggct aatcctaact 480
gcggagcaca taccccttaat ccaaagggca gtgtgtcgta acgggtaact ctgcagcgga 540
accgactact ttgggtgtcc gtgtttcctt ttaattttta ctggctgctt atggtgacaa 600
ttgaggaatt gttgccatat agctattgga ttggccatcc ggtgactaac agagctattg 660
tgttccaatt tgttggattt accccgctca cactcacagt cgtaagaacc cttcattacg 720
tgttatttct caactcaaga aa 742

<210> SEQ ID NO 71
<211> LENGTH: 745
<212> TYPE: DNA
<213> ORGANISM: Unknown
<220> FEATURE:
<223> OTHER INFORMATION: Description of Unknown:
CVA12 sequence

<400> SEQUENCE: 71
ttaaaacagc ctgtgggttg tacccaccca cagggcccac tgggcgctag cactctggta 60
ctacggtacc tttgtgtgcc tgttttaagc ccctaccccc cactcgtaac ttagaaggct 120
tctcacactc gatcaatagt aggtgtggca cgccagtcac accgtgatca agcacttctg 180
ttaccccggt ctgagtacca ataagctgct aacgcggctg aaggggaaaa cgatcgttat 240
ccggctaact acttcgagaa acccagtacc accatgaacg ttgcagggtg tttcgctcgg 300
cacaacccca gtgtagatca ggtcgatgag tcaccgtatt ccccacgggc gaccgtggcg 360
gtggctgcgt tggcggcctg cccatggggt gacccatggg acgctctaat actgacatgg 420
tgcgaagagt ctattgagct agttagtagt cctccggccc ctgaatgcgg ctaatcctaa 480
ctgcggagca cataccctta atccaaaggg cagtgtgtcg taacgggcaa ctctgcagcg 540
gaaccgacta ctttgggtgt ccgtgtttcc ttttattctt acattggctg cttatggtga 600
caattgaaaa gttgttacca tatagctatt ggattggcca tccggtgaca aatagagcta 660
ttgtatatct ttttgttggt tacgtacccc ttaattacaa agtggtttca actttgaaat 720
acatcctaac actaaattgt agaaa 745

<210> SEQ ID NO 72
<211> LENGTH: 742
<212> TYPE: DNA
<213> ORGANISM: Unknown
<220> FEATURE:
<223> OTHER INFORMATION: Description of Unknown:
Echovirus E24 sequence

<400> SEQUENCE: 72
ttaaaacagc ctgtgggttg cacccaccca cagggcccac agggcgctag cactctggta 60
tcacggtacc tttgtgcgcc tgttttatta ccccttcccc aattgaaaat tagaagcaat 120
gcacaccgat caacagcagg cgtggcgcac cagtcacgtc tcgatcaagc acttctgttt 180
ccccggaccg agtatcaata gactgctcac gcggttgaag gagaaagtgt tcgttatccg 240
gctaaccact tcgagaaacc cagtaacacc atgaaagttg cagggtgttt cgctcagcac 300
ttccccagtg tagatcaggt cgatgagtca ccgcgttccc cacgggcgac cgtggcggtg 360
gctgcgttgg cggcctgcct atgggttaac ccataggacg ctctaataca gacatggtgc 420
gaagagttta ttgagctggt tagtatccct ccggcccctg aatgcggcta atcctaactg 480
cggagcacgt gcctccaatc caggggggttg catgtcgtaa cgggtaactc tgcagcggaa 540
ccgactactt tgggtgtccg tgtttccttt tattcttata ctggctgctt atggtgacaa 600
tcgaggaatt gttaccatat agctattgga ttggccatcc ggtgtctaac agagcgatta 660
tatacctctt tgttggattt atgcagctca ataccaccaa ctttaacaca ttgaaatata 720
tcttaaagtt aaacacagca aa 742

<210> SEQ ID NO 73
<211> LENGTH: 240
<212> TYPE: DNA
<213> ORGANISM: Anabaena sp.

<400> SEQUENCE: 73
gaagaaattc tttaagtgga tgctctcaaa ctcagggaaa cctaaatcta gttatagaca 60
aggcaatcct gagccaagcc gaagtagtaa ttagtaagtt aacaatagat gacttacaac 120
taatcggaag gtgcagagac tcgacgggag ctaccctaac gtcaagacga gggtaaagag 180
agagtccaat tctcaaagcc aataggcagt agcgaaagct gcaagagaat gaaaatccgt 240

<210> SEQ ID NO 74
<211> LENGTH: 239
<212> TYPE: DNA
<213> ORGANISM: Anabaena sp.

<400> SEQUENCE: 74
aagaaattct ttaagtggat gctctcaaac tcagggaaac ctaaatctag ttatagacaa 60
ggcaatcctg agccaagccg aagtagtaat tagtaagtta acaatagatg acttacaact 120
aatcggaagg tgcagagact cgacgggagc taccctaacg tcaagacgag ggtaaagaga 180
gagtccaatt ctcaaagcca ataggcagta gcgaaagctg caagagaatg aaaatccgt 239

<210> SEQ ID NO 75
<211> LENGTH: 238
<212> TYPE: DNA
<213> ORGANISM: Anabaena sp.

<400> SEQUENCE: 75
agaaattctt taagtggatg ctctcaaact cagggaaacc taaatctagt tatagacaag 60
gcaatcctga gccaagccga agtagtaatt agtaagttaa caatagatga cttacaacta 120
atcggaaggt gcagagactc gacgggagct accctaacgt caagacgagg gtaaagagag 180
agtccaattc tcaaagccaa taggcagtag cgaaagctgc aagagaatga aaatccgt 238

<210> SEQ ID NO 76
<211> LENGTH: 190
<212> TYPE: DNA
<213> ORGANISM: Anabaena sp.

<400> SEQUENCE: 76
gttatagaca aggcaatcct gagccaagcc gaagtagtaa ttagtaagtt aacaatagat 60
gacttacaac taatcggaag gtgcagagac tcgacgggag ctaccctaac gtcaagacga 120
gggtaaagag agagtccaat tctcaaagcc aataggcagt agcgaaagct gcaagagaat 180
gaaaatccgt 190

<210> SEQ ID NO 77
<211> LENGTH: 189
<212> TYPE: DNA
<213> ORGANISM: Anabaena sp.

<400> SEQUENCE: 77
ttatagacaa ggcaatcctg agccaagccg aagtagtaat tagtaagtta acaatagatg 60
acttacaact aatcggaagg tgcagagact cgacgggagc taccctaacg tcaagacgag 120
ggtaaagaga gagtccaatt ctcaaagcca ataggcagta gcgaaagctg caagagaatg 180
aaaatccgt 189

<210> SEQ ID NO 78
<211> LENGTH: 188
<212> TYPE: DNA
<213> ORGANISM: Anabaena sp.

<400> SEQUENCE: 78
tatagacaag gcaatcctga gccaagccga agtagtaatt agtaagttaa caatagatga 60
cttacaacta atcggaaggt gcagagactc gacgggagct accctaacgt caagacgagg 120
gtaaagagag agtccaattc tcaaagccaa taggcagtag cgaaagctgc aagagaatga 180
aaatccgt 188

<210> SEQ ID NO 79
<211> LENGTH: 187
<212> TYPE: DNA
<213> ORGANISM: Anabaena sp.

<400> SEQUENCE: 79
atagacaagg caatcctgag ccaagccgaa gtagtaatta gtaagttaac aatagatgac 60
ttacaactaa tcggaaggtg cagagactcg acgggagcta ccctaacgtc aagacgaggg 120
taaagagaga gtccaattct caaagccaat aggcagtagc gaaagctgca agagaatgaa 180
aatccgt 187

<210> SEQ ID NO 80
<211> LENGTH: 186
<212> TYPE: DNA
<213> ORGANISM: Anabaena sp.

<400> SEQUENCE: 80
tagacaaggc aatcctgagc caagccgaag tagtaattag taagttaaca atagatgact 60
tacaactaat cggaaggtgc agagactcga cgggagctac cctaacgtca agacgagggt 120
aaagagagag tccaattctc aaagccaata ggcagtagcg aaagctgcaa gagaatgaaa 180
atccgt 186

<210> SEQ ID NO 81
<211> LENGTH: 139
<212> TYPE: DNA
<213> ORGANISM: Anabaena sp.

<400> SEQUENCE: 81
acaatagatg acttacaact aatcggaagg tgcagagact cgacgggagc taccctaacg 60
tcaagacgag ggtaaagaga gagtccaatt ctcaaagcca ataggcagta gcgaaagctg 120
caagagaatg aaaatccgt 139

<210> SEQ ID NO 82
<211> LENGTH: 138
<212> TYPE: DNA
<213> ORGANISM: Anabaena sp.

<400> SEQUENCE: 82
caatagatga cttacaacta atcggaaggt gcagagactc gacgggagct accctaacgt 60
caagacgagg gtaaagagag agtccaattc tcaaagccaa taggcagtag cgaaagctgc 120
aagagaatga aaatccgt 138

<210> SEQ ID NO 83
<211> LENGTH: 137

<212> TYPE: DNA
<213> ORGANISM: Anabaena sp.

<400> SEQUENCE: 83
aatagatgac ttacaactaa tcggaaggtg cagagactcg acgggagcta ccctaacgtc 60
aagacgaggg taaagagaga gtccaattct caaagccaat aggcagtagc gaaagctgca 120
agagaatgaa aatccgt 137

<210> SEQ ID NO 84
<211> LENGTH: 136
<212> TYPE: DNA
<213> ORGANISM: Anabaena sp.

<400> SEQUENCE: 84
atagatgact tacaactaat cggaaggtgc agagactcga cgggagctac cctaacgtca 60
agacgagggt aaagagagag tccaattctc aaagccaata ggcagtagcg aaagctgcaa 120
gagaatgaaa atccgt 136

<210> SEQ ID NO 85
<211> LENGTH: 135
<212> TYPE: DNA
<213> ORGANISM: Anabaena sp.

<400> SEQUENCE: 85
tagatgactt acaactaatc ggaaggtgca gagactcgac gggagctacc ctaacgtcaa 60
gacgagggta aagagagagt ccaattctca aagccaatag gcagtagcga aagctgcaag 120
agaatgaaaa tccgt 135

<210> SEQ ID NO 86
<211> LENGTH: 134
<212> TYPE: DNA
<213> ORGANISM: Anabaena sp.

<400> SEQUENCE: 86
agatgactta caactaatcg gaaggtgcag agactcgacg ggagctaccc taacgtcaag 60
acgagggtaa agagagagtc caattctcaa agccaatagg cagtagcgaa agctgcaaga 120
gaatgaaaat ccgt 134

<210> SEQ ID NO 87
<211> LENGTH: 133
<212> TYPE: DNA
<213> ORGANISM: Anabaena sp.

<400> SEQUENCE: 87
gatgacttac aactaatcgg aaggtgcaga gactcgacgg gagctaccct aacgtcaaga 60
cgagggtaaa gagagagtcc aattctcaaa gccaataggc agtagcgaaa gctgcaagag 120
aatgaaaatc cgt 133

<210> SEQ ID NO 88
<211> LENGTH: 132
<212> TYPE: DNA
<213> ORGANISM: Anabaena sp.

<400> SEQUENCE: 88
atgacttaca actaatcgga aggtgcagag actcgacggg agctacccta acgtcaagac 60
gagggtaaag agagagtcca attctcaaag ccaataggca gtagcgaaag ctgcaagaga 120
atgaaaatcc gt 132

<210> SEQ ID NO 89
<211> LENGTH: 131
<212> TYPE: DNA
<213> ORGANISM: Anabaena sp.

<400> SEQUENCE: 89
tgacttacaa ctaatcggaa ggtgcagaga ctcgacggga gctaccctaa cgtcaagacg 60
agggtaaaga gagagtccaa ttctcaaagc caataggcag tagcgaaagc tgcaagagaa 120
tgaaaatccg t 131

<210> SEQ ID NO 90
<211> LENGTH: 78
<212> TYPE: DNA
<213> ORGANISM: Anabaena sp.

<400> SEQUENCE: 90
caagacgagg gtaaagagag agtccaattc tcaaagccaa taggcagtag cgaaagctgc 60
aagagaatga aaatccgt 78

<210> SEQ ID NO 91
<211> LENGTH: 77
<212> TYPE: DNA
<213> ORGANISM: Anabaena sp.

<400> SEQUENCE: 91
aagacgaggg taaagagaga gtccaattct caaagccaat aggcagtagc gaaagctgca 60
agagaatgaa aatccgt 77

<210> SEQ ID NO 92
<211> LENGTH: 76
<212> TYPE: DNA
<213> ORGANISM: Anabaena sp.

<400> SEQUENCE: 92
agacgagggt aaagagagag tccaattctc aaagccaata ggcagtagcg aaagctgcaa 60
gagaatgaaa atccgt 76

<210> SEQ ID NO 93
<211> LENGTH: 75
<212> TYPE: DNA
<213> ORGANISM: Anabaena sp.

<400> SEQUENCE: 93
gacgagggta aagagagagt ccaattctca aagccaatag gcagtagcga aagctgcaag 60
agaatgaaaa tccgt 75

<210> SEQ ID NO 94
<211> LENGTH: 74
<212> TYPE: DNA
<213> ORGANISM: Anabaena sp.

<400> SEQUENCE: 94
acgagggtaa agagagagtc caattctcaa agccaatagg cagtagcgaa agctgcaaga 60
gaatgaaaat ccgt 74

<210> SEQ ID NO 95
<211> LENGTH: 40
<212> TYPE: DNA
<213> ORGANISM: Anabaena sp.

<400> SEQUENCE: 95
aataggcagt agcgaaagct gcaagagaat gaaaatccgt 40

<210> SEQ ID NO 96
<211> LENGTH: 39
<212> TYPE: DNA
<213> ORGANISM: Anabaena sp.

<400> SEQUENCE: 96
ataggcagta gcgaaagctg caagagaatg aaaatccgt 39

<210> SEQ ID NO 97
<211> LENGTH: 38
<212> TYPE: DNA
<213> ORGANISM: Anabaena sp.

<400> SEQUENCE: 97
taggcagtag cgaaagctgc aagagaatga aaatccgt 38

<210> SEQ ID NO 98
<211> LENGTH: 37
<212> TYPE: DNA
<213> ORGANISM: Anabaena sp.

<400> SEQUENCE: 98
aggcagtagc gaaagctgca agagaatgaa aatccgt 37

<210> SEQ ID NO 99
<211> LENGTH: 36
<212> TYPE: DNA
<213> ORGANISM: Anabaena sp.

<400> SEQUENCE: 99
ggcagtagcg aaagctgcaa gagaatgaaa atccgt 36

<210> SEQ ID NO 100
<211> LENGTH: 27
<212> TYPE: DNA
<213> ORGANISM: Anabaena sp.

<400> SEQUENCE: 100
gaaagctgca agagaatgaa aatccgt 27

<210> SEQ ID NO 101
<211> LENGTH: 26
<212> TYPE: DNA
<213> ORGANISM: Anabaena sp.

<400> SEQUENCE: 101
aaagctgcaa gagaatgaaa atccgt 26

<210> SEQ ID NO 102

<211> LENGTH: 25
<212> TYPE: DNA
<213> ORGANISM: Anabaena sp.

<400> SEQUENCE: 102
aagctgcaag agaatgaaaa tccgt 25

<210> SEQ ID NO 103
<211> LENGTH: 24
<212> TYPE: DNA
<213> ORGANISM: Anabaena sp.

<400> SEQUENCE: 103
agctgcaaga gaatgaaaat ccgt 24

<210> SEQ ID NO 104
<211> LENGTH: 23
<212> TYPE: DNA
<213> ORGANISM: Anabaena sp.

<400> SEQUENCE: 104
gctgcaagag aatgaaaatc cgt 23

<210> SEQ ID NO 105
<211> LENGTH: 22
<212> TYPE: DNA
<213> ORGANISM: Anabaena sp.

<400> SEQUENCE: 105
ctgcaagaga atgaaaatcc gt 22

<210> SEQ ID NO 106
<211> LENGTH: 18
<212> TYPE: DNA
<213> ORGANISM: Anabaena sp.

<400> SEQUENCE: 106
aagagaatga aaatccgt 18

<210> SEQ ID NO 107
<211> LENGTH: 17
<212> TYPE: DNA
<213> ORGANISM: Anabaena sp.

<400> SEQUENCE: 107
agagaatgaa aatccgt 17

<210> SEQ ID NO 108
<211> LENGTH: 16
<212> TYPE: DNA
<213> ORGANISM: Anabaena sp.

<400> SEQUENCE: 108
gagaatgaaa atccgt 16

<210> SEQ ID NO 109
<211> LENGTH: 35
<212> TYPE: DNA
<213> ORGANISM: Anabaena sp.

<400> SEQUENCE: 109
gcagtagcga aagctgcaag agaatgaaaa tccgt 35

<210> SEQ ID NO 110
<211> LENGTH: 33
<212> TYPE: DNA
<213> ORGANISM: Anabaena sp.

<400> SEQUENCE: 110
agtagcgaaa gctgcaagag aatgaaaatc cgt 33

<210> SEQ ID NO 111
<211> LENGTH: 32
<212> TYPE: DNA
<213> ORGANISM: Anabaena sp.

<400> SEQUENCE: 111
gtagcgaaag ctgcaagaga atgaaaatcc gt 32

<210> SEQ ID NO 112
<211> LENGTH: 26
<212> TYPE: DNA
<213> ORGANISM: Anabaena sp.

<400> SEQUENCE: 112
acggacttaa ataattgagc cttaaa 26

<210> SEQ ID NO 113
<211> LENGTH: 27
<212> TYPE: DNA
<213> ORGANISM: Anabaena sp.

<400> SEQUENCE: 113
acggacttaa ataattgagc cttaaag 27

<210> SEQ ID NO 114
<211> LENGTH: 28
<212> TYPE: DNA
<213> ORGANISM: Anabaena sp.

<400> SEQUENCE: 114
acggacttaa ataattgagc cttaaaga 28

<210> SEQ ID NO 115
<211> LENGTH: 76
<212> TYPE: DNA
<213> ORGANISM: Anabaena sp.

<400> SEQUENCE: 115
acggacttaa ataattgagc cttaaagaag aaattcttta agtggatgct ctcaaactca 60
gggaaaccta aatcta 76

<210> SEQ ID NO 116
<211> LENGTH: 77
<212> TYPE: DNA
<213> ORGANISM: Anabaena sp.

<400> SEQUENCE: 116
acggacttaa ataattgagc cttaaagaag aaattcttta agtggatgct ctcaaactca 60
gggaaaccta aatctag 77

<210> SEQ ID NO 117
<211> LENGTH: 78
<212> TYPE: DNA
<213> ORGANISM: Anabaena sp.

<400> SEQUENCE: 117
acggacttaa ataattgagc cttaaagaag aaattcttta agtggatgct ctcaaactca 60
gggaaaccta aatctagt 78

<210> SEQ ID NO 118
<211> LENGTH: 79
<212> TYPE: DNA
<213> ORGANISM: Anabaena sp.

<400> SEQUENCE: 118
acggacttaa ataattgagc cttaaagaag aaattcttta agtggatgct ctcaaactca 60
gggaaaccta aatctagtt 79

<210> SEQ ID NO 119
<211> LENGTH: 80
<212> TYPE: DNA
<213> ORGANISM: Anabaena sp.

<400> SEQUENCE: 119
acggacttaa ataattgagc cttaaagaag aaattcttta agtggatgct ctcaaactca 60
gggaaaccta aatctagtta 80

<210> SEQ ID NO 120
<211> LENGTH: 127
<212> TYPE: DNA
<213> ORGANISM: Anabaena sp.

<400> SEQUENCE: 120
acggacttaa ataattgagc cttaaagaag aaattcttta agtggatgct ctcaaactca 60
gggaaaccta aatctagtta tagacaaggc aatcctgagc caagccgaag tagtaattag 120
taagtta 127

<210> SEQ ID NO 121
<211> LENGTH: 128
<212> TYPE: DNA
<213> ORGANISM: Anabaena sp.

<400> SEQUENCE: 121
acggacttaa ataattgagc cttaaagaag aaattcttta agtggatgct ctcaaactca 60
gggaaaccta aatctagtta tagacaaggc aatcctgagc caagccgaag tagtaattag 120
taagttaa 128

<210> SEQ ID NO 122
<211> LENGTH: 129
<212> TYPE: DNA
<213> ORGANISM: Anabaena sp.

<400> SEQUENCE: 122
acggacttaa ataattgagc cttaaagaag aaattcttta agtggatgct ctcaaactca 60
gggaaaccta aatctagtta tagacaaggc aatcctgagc caagccgaag tagtaattag 120
taagttaac 129

<210> SEQ ID NO 123
<211> LENGTH: 130
<212> TYPE: DNA
<213> ORGANISM: Anabaena sp.

<400> SEQUENCE: 123
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca 130

<210> SEQ ID NO 124
<211> LENGTH: 131
<212> TYPE: DNA
<213> ORGANISM: Anabaena sp.

<400> SEQUENCE: 124
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca a 131

<210> SEQ ID NO 125
<211> LENGTH: 132
<212> TYPE: DNA
<213> ORGANISM: Anabaena sp.

<400> SEQUENCE: 125
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca at 132

<210> SEQ ID NO 126
<211> LENGTH: 133
<212> TYPE: DNA
<213> ORGANISM: Anabaena sp.

<400> SEQUENCE: 126
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca ata 133

<210> SEQ ID NO 127
<211> LENGTH: 134
<212> TYPE: DNA
<213> ORGANISM: Anabaena sp.

<400> SEQUENCE: 127
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atag 134

<210> SEQ ID NO 128
<211> LENGTH: 135
<212> TYPE: DNA
<213> ORGANISM: Anabaena sp.

<400> SEQUENCE: 128
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca ataga 135

<210> SEQ ID NO 129
<211> LENGTH: 188
<212> TYPE: DNA
<213> ORGANISM: Anabaena sp.

<400> SEQUENCE: 129
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgt 188

<210> SEQ ID NO 130
<211> LENGTH: 189
<212> TYPE: DNA
<213> ORGANISM: Anabaena sp.

<400> SEQUENCE: 130
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtc 189

<210> SEQ ID NO 131
<211> LENGTH: 190
<212> TYPE: DNA
<213> ORGANISM: Anabaena sp.

<400> SEQUENCE: 131
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca 190

<210> SEQ ID NO 132
<211> LENGTH: 191
<212> TYPE: DNA
<213> ORGANISM: Anabaena sp.

<400> SEQUENCE: 132
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca a 191

<210> SEQ ID NO 133
<211> LENGTH: 192
<212> TYPE: DNA
<213> ORGANISM: Anabaena sp.

<400> SEQUENCE: 133
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca ag 192

<210> SEQ ID NO 134
<211> LENGTH: 226
<212> TYPE: DNA
<213> ORGANISM: Anabaena sp.

<400> SEQUENCE: 134
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagcc 226

<210> SEQ ID NO 135
<211> LENGTH: 227
<212> TYPE: DNA
<213> ORGANISM: Anabaena sp.

<400> SEQUENCE: 135
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagcca 227

<210> SEQ ID NO 136
<211> LENGTH: 228
<212> TYPE: DNA
<213> ORGANISM: Anabaena sp.

<400> SEQUENCE: 136
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaa 228

<210> SEQ ID NO 137
<211> LENGTH: 229
<212> TYPE: DNA
<213> ORGANISM: Anabaena sp.

<400> SEQUENCE: 137
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaat 229

<210> SEQ ID NO 138
<211> LENGTH: 230
<212> TYPE: DNA
<213> ORGANISM: Anabaena sp.

<400> SEQUENCE: 138
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata 230

<210> SEQ ID NO 139
<211> LENGTH: 239
<212> TYPE: DNA
<213> ORGANISM: Anabaena sp.

<400> SEQUENCE: 139
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagc 239

<210> SEQ ID NO 140
<211> LENGTH: 240
<212> TYPE: DNA
<213> ORGANISM: Anabaena sp.

<400> SEQUENCE: 140
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240

<210> SEQ ID NO 141
<211> LENGTH: 241
<212> TYPE: DNA
<213> ORGANISM: Anabaena sp.

<400> SEQUENCE: 141
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
a 241

<210> SEQ ID NO 142
<211> LENGTH: 242
<212> TYPE: DNA
<213> ORGANISM: Anabaena sp.

<400> SEQUENCE: 142
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aa 242

<210> SEQ ID NO 143
<211> LENGTH: 243
<212> TYPE: DNA
<213> ORGANISM: Anabaena sp.

<400> SEQUENCE: 143
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaa 243

<210> SEQ ID NO 144
<211> LENGTH: 244
<212> TYPE: DNA
<213> ORGANISM: Anabaena sp.

<400> SEQUENCE: 144
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaag 244

<210> SEQ ID NO 145
<211> LENGTH: 248
<212> TYPE: DNA
<213> ORGANISM: Anabaena sp.

<400> SEQUENCE: 145
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaagctgc 248

<210> SEQ ID NO 146
<211> LENGTH: 249
<212> TYPE: DNA
<213> ORGANISM: Anabaena sp.

<400> SEQUENCE: 146
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaagctgca 249

<210> SEQ ID NO 147
<211> LENGTH: 250
<212> TYPE: DNA
<213> ORGANISM: Anabaena sp.

<400> SEQUENCE: 147
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaagctgcaa 250

<210> SEQ ID NO 148
<211> LENGTH: 231
<212> TYPE: DNA
<213> ORGANISM: Anabaena sp.

<400> SEQUENCE: 148
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata g 231

<210> SEQ ID NO 149
<211> LENGTH: 233
<212> TYPE: DNA
<213> ORGANISM: Anabaena sp.

<400> SEQUENCE: 149
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggc 233

<210> SEQ ID NO 150
<211> LENGTH: 234
<212> TYPE: DNA
<213> ORGANISM: Anabaena sp.

<400> SEQUENCE: 150
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggca 234

<210> SEQ ID NO 151
<211> LENGTH: 104
<212> TYPE: DNA
<213> ORGANISM: Azoarcus sp.

<400> SEQUENCE: 151
tgcgccgatg aaggtgtaga gactagacgg cacccaccta aggcaaacgc tatggtgaag 60
gcatagtcca gggagtggcg aaagtcacac aaaccggaat ccgt 104

<210> SEQ ID NO 152
<211> LENGTH: 141
<212> TYPE: DNA
<213> ORGANISM: Azoarcus sp.

<400> SEQUENCE: 152
ccgggcgtat ggcaacgccg agccaagctt cggcgcctgc gccgatgaag gtgtagagac 60
tagacggcac ccacctaagg caaacgctat ggtgaaggca tagtccaggg agtggcgaaa 120
gtcacacaaa ccggaatccg t 141

<210> SEQ ID NO 153
<211> LENGTH: 78
<212> TYPE: DNA
<213> ORGANISM: Azoarcus sp.

<400> SEQUENCE: 153
acggcaccca cctaaggcaa acgctatggt gaaggcatag tccagggagt ggcgaaagtc 60
acacaaaccg gaatccgt 78

<210> SEQ ID NO 154
<211> LENGTH: 58
<212> TYPE: DNA
<213> ORGANISM: Azoarcus sp.

<400> SEQUENCE: 154
acgctatggt gaaggcatag tccagggagt ggcgaaagtc acacaaaccg gaatccgt 58

<210> SEQ ID NO 155
<211> LENGTH: 75
<212> TYPE: DNA
<213> ORGANISM: Thiomargarita sp.

<400> SEQUENCE: 155
attaaagtta tagaattatc agagaatgat atagtccaag ccttatggta acatgagggc 60
acttgaccct ggtag 75

<210> SEQ ID NO 156
<211> LENGTH: 195
<212> TYPE: DNA
<213> ORGANISM: Staphylococcus virus Twort

<400> SEQUENCE: 156
aagatgtagg caatcctgag ctaagctctt agtaataaga gaaagtgcaa cgactattcc 60
gataggaagt agggtcaagt gactcgaaat ggggattacc cttctagggt agtgatatag 120
tctgaacata tatggaaaca tatagaagga taggagtaac gaacctattc gtaacataat 180
tgaactttta gttat 195

<210> SEQ ID NO 157
<211> LENGTH: 163
<212> TYPE: DNA
<213> ORGANISM: Staphylococcus virus Twort

<400> SEQUENCE: 157
taataagaga aagtgcaacg actattccga taggaagtag ggtcaagtga ctcgaaatgg 60
ggattaccct tctagggtag tgatatagtc tgaacatata tggaaacata tagaaggata 120
ggagtaacga acctattcgt aacataattg aacttttagt tat 163

<210> SEQ ID NO 158
<211> LENGTH: 133
<212> TYPE: DNA
<213> ORGANISM: Staphylococcus virus Twort

<400> SEQUENCE: 158
taggaagtag ggtcaagtga ctcgaaatgg ggattaccct tctagggtag tgatatagtc 60
tgaacatata tggaaacata tagaaggata ggagtaacga acctattcgt aacataattg 120
aacttttagt tat 133

<210> SEQ ID NO 159
<211> LENGTH: 92
<212> TYPE: DNA
<213> ORGANISM: Staphylococcus virus Twort

<400> SEQUENCE: 159
ctagggtagt gatatagtct gaacatatat ggaaacatat agaaggatag gagtaacgaa 60
cctattcgta acataattga acttttagtt at 92

<210> SEQ ID NO 160
<211> LENGTH: 92
<212> TYPE: DNA
<213> ORGANISM: Unknown
<220> FEATURE:
<223> OTHER INFORMATION: Description of Unknown:
LSUp1 sequence

<400> SEQUENCE: 160
agttaataaa gatgatgaaa tagtctgaac cattttgaga aaagtggaaa taaaagaaaa 60
tcttttatga taacataaat tgaacaggct aa 92

<210> SEQ ID NO 161
<211> LENGTH: 62
<212> TYPE: DNA
<213> ORGANISM: Unknown
<220> FEATURE:
<223> OTHER INFORMATION: Description of Unknown:
Bacteriophage Phi I sequence

<400> SEQUENCE: 161
caaagactga tgatatagtc cgacactcct agtaatagga gaatacagaa aggatgaaat 60
cc 62

<210> SEQ ID NO 162
<211> LENGTH: 76
<212> TYPE: DNA
<213> ORGANISM: Nostoc sp.

<400> SEQUENCE: 162
agtcgagggt aaagggagag tccaattctc aaagcctatt ggcagtagcg aaagctgcgg 60
gagaatgaaa atccgt 76

<210> SEQ ID NO 163
<211> LENGTH: 76
<212> TYPE: DNA
<213> ORGANISM: Nostoc sp.

<400> SEQUENCE: 163
agccgagggt aaagggagag tccaattctc aaagccaata ggcagtagcg aaagctgcgg 60
gagaatgaaa atccgt 76

<210> SEQ ID NO 164
<211> LENGTH: 89
<212> TYPE: DNA
<213> ORGANISM: Nodularia sp.

<400> SEQUENCE: 164
agccgagggt aaagggagag tccaattctc aaagccgaag gttattaaaa cctggcagca 60
gtgaaagctg cgggagaatg aaaatccgt 89

<210> SEQ ID NO 165

<211> LENGTH: 79
<212> TYPE: DNA
<213> ORGANISM: Pleurocapsa sp.

<400> SEQUENCE: 165
agctgagggt aaagagagag tccaattctc aaagccagca gatggcagta gcgaaagctg 60
cgggagaatg aaaatccgt 79

<210> SEQ ID NO 166
<211> LENGTH: 76
<212> TYPE: DNA
<213> ORGANISM: Planktothrix sp.

<400> SEQUENCE: 166
agccgagggt aaagagagag tccaattctc aaagccaatt ggtagtagcg aaagctacgg 60
gagaatgaaa atccgt 76

<210> SEQ ID NO 167
<211> LENGTH: 118
<212> TYPE: DNA
<213> ORGANISM: Azoarcus sp.

<400> SEQUENCE: 167
gcggactcat atttcgatgt gccttgcgcc gggaaaccac gcaagggatg gtgtcaaatt 60
cggcgaaacc taagcgcccg cccgggcgta tggcaacgcc gagccaagct tcggcgcc 118

<210> SEQ ID NO 168
<211> LENGTH: 81
<212> TYPE: DNA
<213> ORGANISM: Azoarcus sp.

<400> SEQUENCE: 168
gcggactcat atttcgatgt gccttgcgcc gggaaaccac gcaagggatg gtgtcaaatt 60
cggcgaaacc taagcgcccg c 81

<210> SEQ ID NO 169
<211> LENGTH: 144
<212> TYPE: DNA
<213> ORGANISM: Azoarcus sp.

<400> SEQUENCE: 169
gcggactcat atttcgatgt gccttgcgcc gggaaaccac gcaagggatg gtgtcaaatt 60
cggcgaaacc taagcgcccg cccgggcgta tggcaacgcc gagccaagct tcggcgcctg 120
cgccgatgaa ggtgtagaga ctag 144

<210> SEQ ID NO 170
<211> LENGTH: 164
<212> TYPE: DNA
<213> ORGANISM: Azoarcus sp.

<400> SEQUENCE: 170
gcggactcat atttcgatgt gccttgcgcc gggaaaccac gcaagggatg gtgtcaaatt 60
cggcgaaacc taagcgcccg cccgggcgta tggcaacgcc gagccaagct tcggcgcctg 120
cgccgatgaa ggtgtagaga ctagacggca cccacctaag gcaa 164

<210> SEQ ID NO 171
<211> LENGTH: 179
<212> TYPE: DNA
<213> ORGANISM: Thiomargarita sp.

<400> SEQUENCE: 171
aggattagat actacactaa gtgtccccca gactggtgac agtctggtgt gcatccagct 60
atatcggtga aaccccattg gggtaatacc gagggaagct atattatata tatattaata 120
aatagccccg tagagactat gtaggtaagg agatagaaga tgataaaatc aaaatcatc 179

<210> SEQ ID NO 172
<211> LENGTH: 84
<212> TYPE: DNA
<213> ORGANISM: Staphylococcus virus Twort

<400> SEQUENCE: 172
actactgaaa gcataaataa ttgtgccttt atacagtaat gtatatcgaa aaatcctcta 60
attcagggaa cacctaaaca aact 84

<210> SEQ ID NO 173
<211> LENGTH: 116
<212> TYPE: DNA
<213> ORGANISM: Staphylococcus virus Twort

<400> SEQUENCE: 173
actactgaaa gcataaataa ttgtgccttt atacagtaat gtatatcgaa aaatcctcta 60
attcagggaa cacctaaaca aactaagatg taggcaatcc tgagctaagc tcttag 116

<210> SEQ ID NO 174
<211> LENGTH: 146
<212> TYPE: DNA
<213> ORGANISM: Staphylococcus virus Twort

<400> SEQUENCE: 174
actactgaaa gcataaataa ttgtgccttt atacagtaat gtatatcgaa aaatcctcta 60
attcagggaa cacctaaaca aactaagatg taggcaatcc tgagctaagc tcttagtaat 120
aagagaaagt gcaacgacta ttccga 146

<210> SEQ ID NO 175
<211> LENGTH: 187
<212> TYPE: DNA
<213> ORGANISM: Staphylococcus virus Twort

<400> SEQUENCE: 175
actactgaaa gcataaataa ttgtgccttt atacagtaat gtatatcgaa aaatcctcta 60
attcagggaa cacctaaaca aactaagatg taggcaatcc tgagctaagc tcttagtaat 120
aagagaaagt gcaacgacta ttccgatagg aagtagggtc aagtgactcg aaatggggat 180
taccctt 187

<210> SEQ ID NO 176
<211> LENGTH: 216
<212> TYPE: DNA
<213> ORGANISM: Unknown
<220> FEATURE:
<223> OTHER INFORMATION: Description of Unknown:
LSUp1 sequence

<400> SEQUENCE: 176
cgctagggat ttataactgt gagtcctcca atattataaa atgttggtaa tatattgggt 60
aaatttcaaa gacaactttt ctccacgtca ggatatagtg tatttgaagc gaaacttatt 120
ttagcagtga aaaagcaaat aaggacgttc aacgactaaa aggtgagtat tgctaacaat 180
aatccttttt tttaatgccc aacatcttta ttaact 216

<210> SEQ ID NO 177
<211> LENGTH: 559
<212> TYPE: DNA
<213> ORGANISM: Unknown
<220> FEATURE:
<223> OTHER INFORMATION: Description of Unknown:
Bacteriophage Phi I sequence

<400> SEQUENCE: 177
gtgggtgcat aaactatttc attgtgcaca ttaaatctgg tgaactcggt gaaaccctaa 60
tggggcaata ccgagccaag ccatagggag gatatatgag aggcaagaag ttaattcttg 120
aggccactga gactggctgt atcatcccta cgtcacacaa acttaatgcc gatggttatt 180
tcagaaagaa aaccaatggc gtcttagaga tgtatcacag aacggtgtgg aaggagcata 240
acggagacat acctgatggc ttcgagatag accataagtg tcgcaatagg gcttgctgta 300
atatagagca tttacagatg cttgagggta cagcccacac tgttaagacc aatcgtgaac 360
gctacgcaga cagaaaggaa acagctaggg aatactggct ggagactgga tgtaccggcc 420
tagcactcgg tgagaagttt ggtgtgtcgt tctcttctgc ttgtaagtgg attagagaat 480
ggaaggcgta gagactatcc gaaaggagta gggccgaggg tgagactccc tcgtaacccg 540
aagcgccaga cagtcaact 559

<210> SEQ ID NO 178
<211> LENGTH: 218
<212> TYPE: DNA
<213> ORGANISM: Nostoc sp.

<400> SEQUENCE: 178
acggacttaa gtaattgagc cttaaagaag aaattcttta agtggcagct ctcaaactca 60
gggaaaccta aatctgttca cagacaaggc aatcctgagc caagccgaaa gagtcatgag 120
tgctgagtag tgagtaaaat aaaagctcac aactcagagg ttgtaactct aagctagtcg 180
gaaggtgcag agactcgacg ggagctaccc taacgtaa 218

<210> SEQ ID NO 179
<211> LENGTH: 165
<212> TYPE: DNA
<213> ORGANISM: Nostoc sp.

<400> SEQUENCE: 179
acggacttaa actgaattga gccttagaga agaaattctt taagtgtcag ctctcaaact 60
cagggaaacc taaatctgtt gacagacaag gcaatcctga gccaagccga gaactctaag 120
ttattcggaa ggtgcagaga ctcgacggga gctaccctaa cgtca 165

<210> SEQ ID NO 180
<211> LENGTH: 181
<212> TYPE: DNA
<213> ORGANISM: Nodularia sp.

<400> SEQUENCE: 180
acggacttag aaaactgagc cttgatcgag aaatctttca agtggaagct ctcaaattca 60
gggaaaccta aatctgttta cagatatggc aatcctgagc caagccgaaa caagtcctga 120
gtgttaaagc tcataactca tcggaaggtg cagagactcg acgggagcta ccctaacgtt 180
a 181

<210> SEQ ID NO 181
<211> LENGTH: 188
<212> TYPE: DNA
<213> ORGANISM: Pleurocapsa sp.

<400> SEQUENCE: 181
acggacttaa aaaaattgag ccttggcaga gaaatctgtc atgcgaacgc tctcaaattc 60
agggaaacct aagtctggca acagatatgg caatcctgag ccaagcctta atcaaggaaa 120
aaaacatttt taccttttac cttgaaagga aggtgcagag actcaacggg agctacccta 180
acaggtca 188

<210> SEQ ID NO 182
<211> LENGTH: 200
<212> TYPE: DNA
<213> ORGANISM: Planktothrix sp.

<400> SEQUENCE: 182
acggacttaa agataaattg agccttgagg cgagaaatct ctcaagtgta agctgtcaaa 60
ttcagggaaa cctaaatctg taaattcaga caaggcaatc ctgagccaag cctaggggta 120
ttagaaatga gggagtttcc ccaatctaag atcaatacct aggaaggtgc agagactcga 180
cgggagctac cctaacgtta 200

<210> SEQ ID NO 183
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 183
agtatataag aaacaaacca ctagatgact tacaactaat cggaaggtgc agagactcga 60
cgggagctac cctaacgtca agacgagggt aaagagagag tccaattctc aaagccaata 120
ggcagtagcg aaagctgcaa gagaatgaaa atccgtggct cgcagc 166

<210> SEQ ID NO 184
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 184
ctgaaattat acttatactc aaacaaacca ctagatgact tacaactaat cggaaggtgc 60
agagactcga cgggagctac cctaacgtca agacgagggt aaagagagag tccaattctc 120
aaagccaata ggcagtagcg aaagctgcaa gagaatgaaa atccgtggct cgcagc 176

<210> SEQ ID NO 185

<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 185
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 186
<211> LENGTH: 196
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 186
catcaacaat atgaaattat acttatactc agtatatgac aaacaaacca ctagatgact 60
tacaactaat cggaaggtgc agagactcga cgggagctac cctaacgtca agacgagggt 120
aaagagagag tccaattctc aaagccaata ggcagtagcg aaagctgcaa gagaatgaaa 180
atccgtggct cgcagc 196

<210> SEQ ID NO 187
<211> LENGTH: 206
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 187
catcaacaat atgaaactat acttatactc agtatatgaa gcattatcgc aaacaaacca 60
ctagatgact tacaactaat cggaaggtgc agagactcga cgggagctac cctaacgtca 120
agacgagggt aaagagagag tccaattctc aaagccaata ggcagtagcg aaagctgcaa 180
gagaatgaaa atccgtggct cgcagc 206

<210> SEQ ID NO 188
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 188
tagcgtcagc aaacaaacaa atagatgact tacaactaat cggaaggtgc agagactcga 60
cgggagctac cctaacgtca agacgagggt aaagagagag tccaattctc aaagccaata 120
ggcagtagcg aaagctgcaa gagaatgaaa atccgtggct cgcagc 166

<210> SEQ ID NO 189
<211> LENGTH: 176
<212> TYPE: DNA
<213> ORGANISM: Artificial Sequence -continued
<220> FEATURE:
<223> OTHER INFORMATION: Description of Artificial Sequence: Synthetic
polynucleotide

<400> SEQUENCE: 189
atactcatac tagcgtcagc aaacaaacaa atagatgact tacaactaat cggaaggtgc 60
agagactcga cgggagctac cctaacgtca agacgagggt aaagagagag tccaattctc 120
aaagccaata ggcagtagcg aaagctgcaa gagaatgaaa atccgtggct cgcagc 176

<210> SEQ ID NO 190
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 190
gtgtgaagct atactcatac tagcgtcagc aaacaaacaa atagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 191
<211> LENGTH: 196
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 191
cctcacctga gtgtgaagct atactcatac tagcgtcagc aaacaaacaa atagatgact 60
tacaactaat cggaaggtgc agagactcga cgggagctac cctaacgtca agacgagggt 120
aaagagagag tccaattctc aaagccaata ggcagtagcg aaagctgcaa gagaatgaaa 180
atccgtggct cgcagc 196

<210> SEQ ID NO 192
<211> LENGTH: 206
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 192
ccgaatgatg cctcacctga gtgtgaagct atactcatac tagcgtcagc aaacaaacaa 60
atagatgact tacaactaat cggaaggtgc agagactcga cgggagctac cctaacgtca 120
agacgagggt aaagagagag tccaattctc aaagccaata ggcagtagcg aaagctgcaa 180
gagaatgaaa atccgtggct cgcagc 206

<210> SEQ ID NO 193
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 193
cggtgcgagc aaacaaacaa atagatgact tacaactaat cggaaggtgc agagactcga 60
cgggagctac cctaacgtca agacgagggt aaagagagag tccaattctc aaagccaata 120
ggcagtagcg aaagctgcaa gagaatgaaa atccgtggct cgcagc 166

<210> SEQ ID NO 194
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 194
cgctccgacc cagtgcgagc aaacaaacaa atagatgact tacaactaat cggaaggtgc 60
agagactcga cgggagctac cctaacgtca agacgagggt aaagagagag tccaattctc 120
aaagccaata ggcagtagcg aaagctgcaa gagaatgaaa atccgtggct cgcagc 176

<210> SEQ ID NO 195
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 195
ctgaaattat actaatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 196
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 196
ctgaaaatat actaatactc actatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 197
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197
ctgataatat agtaatactc actatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 198
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198
ctgataataa agtaatacac actataagac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 199
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199
ctgaaattat acttatactc tctaagttac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 200
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200
ctgaaattat gtgtgttaca tctaagttac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 201
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide -continued

<400> SEQUENCE: 201
gttgatcggt gtgtgttaca tctaagttac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 202
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
aaacag 186

<210> SEQ ID NO 203
<211> LENGTH: 196
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 203
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
cacaatataa attacg 196

<210> SEQ ID NO 204
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 204
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
catagc 186

<210> SEQ ID NO 205
<211> LENGTH: 196
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 205
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
cgcagcataa tatccg 196

<210> SEQ ID NO 206
<211> LENGTH: 196
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagcgcgc ctaccg 196

<210> SEQ ID NO 207
<211> LENGTH: 219
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagcgcgc ctaccgaaag ccggcgtcga cgttagcgc 219

<210> SEQ ID NO 208
<211> LENGTH: 219
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 208
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
cgcagcataa tatccgaaac gaggatacaa gtgacatgc 219

<210> SEQ ID NO 209
<211> LENGTH: 219
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 209
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
cacaatctaa attacgaaac gataaatgat aactctaac 219

<210> SEQ ID NO 210
<211> LENGTH: 156
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210
aaacaaacca ctagatgact tacaactaat cggaaggtgc agagactcga cgggagctac 60
cctaacgtca agacgagggt aaagagagag tccaattctc aaagccaata ggcagtagcg 120
aaagctgcaa gagaatgaaa atccgtggct cgcagc 156

<210> SEQ ID NO 211
<211> LENGTH: 161
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 211
cgggcaaaca aacaaataga tgacttacaa ctaatcggaa ggtgcagaga ctcgacggga 60
gctaccctaa cgtcaagacg agggtaaaga gagagtccaa ttctcaaagc caataggcag 120
tagcgaaagc tgcaagagaa tgaaaatccg tggctcgcag c 161

<210> SEQ ID NO 212
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212
cgctccgacg agcttccggc cagtgcgagc aaacaaacaa atagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 213
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 213
aaacaaacca cggcagtagc gaaagctgca agagaatgaa aatccgtggc tcgcagc 57

<210> SEQ ID NO 214

<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
agtatataag aaacaaacca cggcagtagc gaaagctgca agagaatgaa aatccgtggc 60
tcgcagc 67

<210> SEQ ID NO 215
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
ctgaaattat acttatactc aaacaaacca cggcagtagc gaaagctgca agagaatgaa 60
aatccgtggc tcgcagc 77

<210> SEQ ID NO 216
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
ctgaaattat acttatactc agtatatgac aaacaaacca cggcagtagc gaaagctgca 60
agagaatgaa aatccgtggc tcgcagc 87

<210> SEQ ID NO 217
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
tagcgtcagc aaacaaacaa aggcagtagc gaaagctgca agagaatgaa aatccgtggc 60
tcgcagc 67

<210> SEQ ID NO 218
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
atactcatac tagcgtcagc aaacaaacaa aggcagtagc gaaagctgca agagaatgaa 60
aatccgtggc tcgcagc 77

<210> SEQ ID NO 219
<211> LENGTH: 87
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 219
gtgtgaagct atactcatac tagcgtcagc aaacaaacaa aggcagtagc gaaagctgca     60
agagaatgaa aatccgtggc tcgcagc                                         87

<210> SEQ ID NO 220
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
cggtgcgagc aaacaaacaa aggcagtagc gaaagctgca agagaatgaa aatccgtggc     60
tcgcagc                                                               67

<210> SEQ ID NO 221
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cgctccgacc cagtgcgagc aaacaaacaa aggcagtagc gaaagctgca agagaatgaa     60
aatccgtggc tcgcagc                                                    77

<210> SEQ ID NO 222
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cgctccgacg agcttccggc cagtgcgagc aaacaaacaa aggcagtagc gaaagctgca     60
agagaatgaa aatccgtggc tcgcagc                                         87

<210> SEQ ID NO 223
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aaacaaacca caagacgagg gtaaagagag agtccaattc tcaaagccaa taggcagtag     60
cgaaagctgc aagagaatga aaatccgtgg ctcgcagc                             98

<210> SEQ ID NO 224
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224
agtatataag aaacaaacca caagacgagg gtaaagagag agtccaattc tcaaagccaa 60
taggcagtag cgaaagctgc aagagaatga aaatccgtgg ctcgcagc 108

<210> SEQ ID NO 225
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 225
ctgaaattat acttatactc aaacaaacca caagacgagg gtaaagagag agtccaattc 60
tcaaagccaa taggcagtag cgaaagctgc aagagaatga aaatccgtgg ctcgcagc 118

<210> SEQ ID NO 226
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 226
ctgaaattat acttatactc agtatatgac aaacaaacca caagacgagg gtaaagagag 60
agtccaattc tcaaagccaa taggcagtag cgaaagctgc aagagaatga aaatccgtgg 120
ctcgcagc 128

<210> SEQ ID NO 227
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 227
tagcgtcagc aaacaaacaa aaagacgagg gtaaagagag agtccaattc tcaaagccaa 60
taggcagtag cgaaagctgc aagagaatga aaatccgtgg ctcgcagc 108

<210> SEQ ID NO 228
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 228
atactcatac tagcgtcagc aaacaaacaa aaagacgagg gtaaagagag agtccaattc 60
tcaaagccaa taggcagtag cgaaagctgc aagagaatga aaatccgtgg ctcgcagc 118

<210> SEQ ID NO 229
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 229
gtgtgaagct atactcatac tagcgtcagc aaacaaacaa aaagacgagg gtaaagagag 60
agtccaattc tcaaagccaa taggcagtag cgaaagctgc aagagaatga aaatccgtgg 120
ctcgcagc 128

<210> SEQ ID NO 230
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 230
cggtgcgagc aaacaaacaa aaagacgagg gtaaagagag agtccaattc tcaaagccaa 60
taggcagtag cgaaagctgc aagagaatga aaatccgtgg ctcgcagc 108

<210> SEQ ID NO 231
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 231
cgctccgacc cagtgcgagc aaacaaacaa aaagacgagg gtaaagagag agtccaattc 60
tcaaagccaa taggcagtag cgaaagctgc aagagaatga aaatccgtgg ctcgcagc 118

<210> SEQ ID NO 232
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 232
cgctccgacg agcttccggc cagtgcgagc aaacaaacaa aaagacgagg gtaaagagag 60
agtccaattc tcaaagccaa taggcagtag cgaaagctgc aagagaatga aaatccgtgg 120
ctcgcagc 128

<210> SEQ ID NO 233
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgt 176

<210> SEQ ID NO 234
<211> LENGTH: 77
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 234
ctgaaattat acttatactc agtatatgac aaacaaacca cggcagtagc gaaagctgca     60
agagaatgaa aatccgt                                                    77

<210> SEQ ID NO 235
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ctgaaattat acttatactc agtatatgac aaacaaacca cggcagtagc gaaagctgca     60
agagaatgaa aatccgtgat taaacag                                         87

<210> SEQ ID NO 236
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ctgaaattat acttatactc agtatatgac aaacaaacca cggcagtagc gaaagctgca     60
agagaatgaa aatccgtgat tcacaatata aattacg                              97

<210> SEQ ID NO 237
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ctgaaattat acttatactc agtatatgac aaacaaacca cggcagtagc gaaagctgca     60
agagaatgaa aatccgtgga tcatagc                                         87

<210> SEQ ID NO 238
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ctgaaattat acttatactc agtatatgac aaacaaacca cggcagtagc gaaagctgca     60
agagaatgaa aatccgtgga tcgcagcata atatccg                              97

<210> SEQ ID NO 239
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctgaaattat acttatactc agtatatgac aaacaaacca cggcagtagc gaaagctgca 60
agagaatgaa aatccgtggc tcgcagcgcg cctaccg 97

<210> SEQ ID NO 240
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 240
ctgaaattat acttatactc agtatatgac aaacaaacca caagacgagg gtaaagagag 60
agtccaattc tcaaagccaa taggcagtag cgaaagctgc aagagaatga aaatccgt 118

<210> SEQ ID NO 241
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 241
ctgaaattat acttatactc agtatatgac aaacaaacca caagacgagg gtaaagagag 60
agtccaattc tcaaagccaa taggcagtag cgaaagctgc aagagaatga aaatccgtga 120
ttaaacag 128

<210> SEQ ID NO 242
<211> LENGTH: 138
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 242
ctgaaattat acttatactc agtatatgac aaacaaacca caagacgagg gtaaagagag 60
agtccaattc tcaaagccaa taggcagtag cgaaagctgc aagagaatga aaatccgtga 120
ttcacaatat aaattacg 138

<210> SEQ ID NO 243
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 243
ctgaaattat acttatactc agtatatgac aaacaaacca caagacgagg gtaaagagag 60
agtccaattc tcaaagccaa taggcagtag cgaaagctgc aagagaatga aaatccgtgg 120
atcatagc 128

<210> SEQ ID NO 244
<211> LENGTH: 138
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 244
ctgaaattat acttatactc agtatatgac aaacaaacca caagacgagg gtaaagagag 60
agtccaattc tcaaagccaa taggcagtag cgaaagctgc aagagaatga aaatccgtgg 120
atcgcagcat aatatccg 138

<210> SEQ ID NO 245
<211> LENGTH: 138
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 245
ctgaaattat acttatactc agtatatgac aaacaaacca caagacgagg gtaaagagag 60
agtccaattc tcaaagccaa taggcagtag cgaaagctgc aagagaatga aaatccgtgg 120
ctcgcagcgc gcctaccg 138

<210> SEQ ID NO 246
<211> LENGTH: 162
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 246
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aacttatata ct 162

<210> SEQ ID NO 247
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 247
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagagtataa gtataatttc ag 172

<210> SEQ ID NO 248
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 248
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 249
<211> LENGTH: 192
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 249
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
atattgttga tg 192

<210> SEQ ID NO 250
<211> LENGTH: 202
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 250
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagcgataat gcttcatata ctgagtataa 180
gtatagtttc atattgttga tg 202

<210> SEQ ID NO 251
<211> LENGTH: 162
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 251
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctgacgc ta 162

<210> SEQ ID NO 252
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 252
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctgacgc tagtatgagt at 172

<210> SEQ ID NO 253
<211> LENGTH: 182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 253
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctgacgc tagtatgagt atagcttcac 180
ac 182

<210> SEQ ID NO 254
<211> LENGTH: 192
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 254
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctgacgc tagtatgagt atagcttcac 180
actcaggtga gg 192

<210> SEQ ID NO 255
<211> LENGTH: 202
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctgacgc tagtatgagt atagcttcac 180
actcaggtga ggcatcattc gg 202

<210> SEQ ID NO 256
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 256
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctcgcac cg 162

<210> SEQ ID NO 257
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 257
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctcgcac tgggtcggag cg 172

<210> SEQ ID NO 258
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 258
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 259
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 259
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 260
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide -continued

<400> SEQUENCE: 260
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 261
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 261
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 262
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 262
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtaactta gagagtataa gtataatttc 180
ag 182

<210> SEQ ID NO 263
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 263
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtaactta gatgtaacac acataatttc 180
ag 182

<210> SEQ ID NO 264
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 264
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtaactta gatgtaacac acaccgatca 180
ac 182

<210> SEQ ID NO 265
<211> LENGTH: 182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 265
ctgtttaatc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 266
<211> LENGTH: 192
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 266
cgtaatttat attgtgaatc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca acacaaacac aagtcatata ctgagtataa 180
gtataatttc ag 192

<210> SEQ ID NO 267
<211> LENGTH: 182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 267
gctatgatcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 268
<211> LENGTH: 192
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 268
cggatattat gctgcgatcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca acacaaacac aagtcatata ctgagtataa 180
gtataatttc ag 192

<210> SEQ ID NO 269
<211> LENGTH: 192
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 269
cggtaggcgc gctgcgagcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca acacaaacac aagtcatata ctgagtataa 180
gtataatttc ag 192

<210> SEQ ID NO 270
<211> LENGTH: 215
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 270
gcgctaacgt cgacgccggc aaacggtagg cgcgctgcga gccacggact taaataattg 60
agccttaaag aagaaattct ttaagtggat gctctcaaac tcagggaaac ctaaatctag 120
ttatagacaa ggcaatcctg agccaagccg aagtagtaat tagtaagtta acaacacaaa 180
cacaagtcat atactgagta taagtataat ttcag 215

<210> SEQ ID NO 271
<211> LENGTH: 215
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 271
gcatgtcact tgtatcctcg aaacggatat tatgctgcga tccacggact taaataattg 60
agccttaaag aagaaattct ttaagtggat gctctcaaac tcagggaaac ctaaatctag 120
ttatagacaa ggcaatcctg agccaagccg aagtagtaat tagtaagtta acaacacaaa 180
cacaagtcat atactgagta taagtataat ttcag 215

<210> SEQ ID NO 272
<211> LENGTH: 215
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 272
gttagagtta tcatttatcg aaacgtaatt tagattgtga atcacggact taaataattg 60
agccttaaag aagaaattct ttaagtggat gctctcaaac tcagggaaac ctaaatctag 120
ttatagacaa ggcaatcctg agccaagccg aagtagtaat tagtaagtta acaacacaaa 180
cacaagtcat atactgagta taagtataat ttcag 215

<210> SEQ ID NO 273
<211> LENGTH: 152
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 273
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aa 152

<210> SEQ ID NO 274
<211> LENGTH: 157
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 274
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagcccg 157

<210> SEQ ID NO 275
<211> LENGTH: 182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 275
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctcgcac tggccggaag ctcgtcggag 180
cg 182

<210> SEQ ID NO 276
<211> LENGTH: 251
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 276
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca a 251

<210> SEQ ID NO 277
<211> LENGTH: 261
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 277
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca acttatatac t 261

<210> SEQ ID NO 278
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 278
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca agagtataag tataatttca g 271

<210> SEQ ID NO 279
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 279
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca agtcatatac tgagtataag tataatttca g 281

<210> SEQ ID NO 280
<211> LENGTH: 261

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 280
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctgacgct a 261

<210> SEQ ID NO 281
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 281
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctgacgct agtatgagta t 271

<210> SEQ ID NO 282
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 282
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctgacgct agtatgagta tagcttcaca c 281

<210> SEQ ID NO 283
<211> LENGTH: 261
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 283
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctcgcacc g 261

<210> SEQ ID NO 284
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 284
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctcgcact gggtcggagc g 271

<210> SEQ ID NO 285
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 285
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctcgcact ggccggaagc tcgtcggagc g 281

<210> SEQ ID NO 286
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 286
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa 210

<210> SEQ ID NO 287
<211> LENGTH: 220
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 287
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa cttatatact 220

<210> SEQ ID NO 288
<211> LENGTH: 230
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 288
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa gagtataagt ataatttcag 230

<210> SEQ ID NO 289
<211> LENGTH: 240
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 289
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa gtcatatact gagtataagt ataatttcag 240

<210> SEQ ID NO 290
<211> LENGTH: 220
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 290
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca acaaaaacaa gctgacgcta 220

<210> SEQ ID NO 291
<211> LENGTH: 230
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 291
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca acaaaaacaa gctgacgcta gtatgagtat 230

<210> SEQ ID NO 292
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca acaaaaacaa gctgacgcta gtatgagtat agcttcacac 240

<210> SEQ ID NO 293
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca acaaaaacaa gctcgcaccg 220

<210> SEQ ID NO 294
<211> LENGTH: 230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 294
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca acaaaaacaa gctcgcactg ggtcggagcg 230

<210> SEQ ID NO 295
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca acaaaaacaa gctcgcactg gccggaagct cgtcggagcg 240

<210> SEQ ID NO 296
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 296
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca acacaaacac aagtcatata ctgagtataa gtataatttc ag 172

<210> SEQ ID NO 297
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 297
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata cacaaacaca 240
agtcatatac tgagtataag tataatttca g 271

<210> SEQ ID NO 298
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 298
ctgtttaatc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca agtcatatac tgagtataag tataatttca g 281

<210> SEQ ID NO 299
<211> LENGTH: 291
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 299
cgtaatttat attgtgaatc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtca agacgagggt aaagagagag tccaattctc 240
aaagccaata cacaaacaca agtcatatac tgagtataag tataatttca g 291

<210> SEQ ID NO 300
<211> LENGTH: 281
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 300
gctatgatcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca agtcatatac tgagtataag tataatttca g 281

<210> SEQ ID NO 301
<211> LENGTH: 291
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 301
cggatattat gctgcgatcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtca agacgagggt aaagagagag tccaattctc 240
aaagccaata cacaaacaca agtcatatac tgagtataag tataatttca g 291

<210> SEQ ID NO 302
<211> LENGTH: 291
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302
cggtaggcgc gctgcgagcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtca agacgagggt aaagagagag tccaattctc 240
aaagccaata cacaaacaca agtcatatac tgagtataag tataatttca g 291

<210> SEQ ID NO 303
<211> LENGTH: 230

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 303
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtcc acaaacacaa gtcatatact gagtataagt ataatttcag 230

<210> SEQ ID NO 304
<211> LENGTH: 240
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 304
ctgtttaatc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa gtcatatact gagtataagt ataatttcag 240

<210> SEQ ID NO 305
<211> LENGTH: 250
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 305
cgtaatttat attgtgaatc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtcc acaaacacaa gtcatatact gagtataagt 240
ataatttcag 250

<210> SEQ ID NO 306
<211> LENGTH: 240
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 306
gctatgatcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa gtcatatact gagtataagt ataatttcag 240

<210> SEQ ID NO 307
<211> LENGTH: 250
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 307
cggatattat gctgcgatcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtcc acaaacacaa gtcatatact gagtataagt 240
ataatttcag 250

<210> SEQ ID NO 308
<211> LENGTH: 250
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 308
cggtaggcgc gctgcgagcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtcc acaaacacaa gtcatatact gagtataagt 240
ataatttcag 250

<210> SEQ ID NO 309
<211> LENGTH: 1137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 309
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300
gaacaagagg atatcgctac ctacttctgc cagcaaggca acaccctgcc ttacaccttt 360
ggcggaggca ccaagctgga aatcaccggc tctacaagcg gcagcggcaa acctggatct 420
ggcgagggat ctaccaaggg cgaagtgaaa ctgcaagagt ctggccctgg actggtggcc 480
ccatctcagt ctctgagcgt gacctgtaca gtcagcggag tgtccctgcc tgattacggc 540
gtgtcctgga tcagacagcc tcctcggaaa ggcctggaat ggctgggagt gatctggggc 600
agcgagacaa cctactacaa cagcgccctg aagtcccggc tgaccatcat caaggacaac 660
tccaagagcc aggtgttcct gaagatgaac agcctgcaga ccgacgacac cgccatctac 720
tattgcgcca agcactacta ctacggcggc agctacgcca tggattattg gggccagggc 780
accagcgtga ccgtttcttc tgccgccgct atcgaagtga tgtaccctcc tccttacctg 840
gacaacgaga agtccaacgg caccatcatc cacgtgaagg gcaagcacct gtgtccttct 900
ccactgttcc ccggacctag caagcctttc tgggtgctcg ttgttgttgg cggcgtgctg 960
gcctgttaca gcctgctggt taccgtggcc ttcatcatct tttgggtcaa gagaggccgg 1020
aagaaacttc tttatatatt caagcagccc tttatgcgac ccgttcagac tacccaagag 1080
gaagatggat gcagttgccg ctttccagaa gaggaggagg gcgggtgcga actgtaa 1137

<210> SEQ ID NO 310
<211> LENGTH: 1134
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 310
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300
gaacaagagg atatcgctac ctacttctgc cagcaaggca acaccctgcc ttacaccttt 360
ggcggaggca ccaagctgga aatcaccggc tctacaagcg gcagcggcaa acctggatct 420
ggcgagggat ctaccaaggg cgaagtgaaa ctgcaagagt ctggccctgg actggtggcc 480
ccatctcagt ctctgagcgt gacctgtaca gtcagcggag tgtccctgcc tgattacggc 540
gtgtcctgga tcagacagcc tcctcggaaa ggcctggaat ggctgggagt gatctggggc 600
agcgagacaa cctactacaa cagcgccctg aagtcccggc tgaccatcat caaggacaac 660
tccaagagcc aggtgttcct gaagatgaac agcctgcaga ccgacgacac cgccatctac 720
tattgcgcca agcactacta ctacggcggc agctacgcca tggattattg gggccagggc 780
accagcgtga ccgtttcttc tgccgccgct atcgaagtga tgtaccctcc tccttacctg 840
gacaacgaga agtccaacgg caccatcatc cacgtgaagg gcaagcacct gtgtccttct 900
ccactgttcc ccggacctag caagcctttc tgggtgctcg ttgttgttgg cggcgtgctg 960
gcctgttaca gcctgctggt taccgtggcc ttcatcatct tttgggtccg aagcaagcgg 1020
agccggctgc tgcactccga ctacatgaac atgaccccta gacggcccgg accaaccaga 1080
aagcactacc agccttacgc tcctcctaga gacttcgccg cctaccggtc ctaa 1134

<210> SEQ ID NO 311
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 311
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300
gaacaagagg atatcgctac ctacttctgc cagcaaggca acaccctgcc ttacaccttt 360

```
ggcggaggca ccaagctgga aatcaccggc tctacaagcg gcagcggcaa acctggatct    420
ggcgagggat ctaccaaggg cgaagtgaaa ctgcaagagt ctggccctgg actggtggcc    480
ccatctcagt ctctgagcgt gacctgtaca gtcagcggag tgtccctgcc tgattacggc    540
gtgtcctgga tcagacagcc tcctcggaaa ggcctggaat ggctgggagt gatctggggc    600
agcgagacaa cctactacaa cagcgccctg aagtcccggc tgaccatcat caaggacaac    660
tccaagagcc aggtgttcct gaagatgaac agcctgcaga ccgacgacac cgccatctac    720
tattgcgcca agcactacta ctacggcggc agctacgcca tggattattg gggccagggc    780
accagcgtga ccgtttcttc tgccgccgct atcgaagtga tgtaccctcc tccttacctg    840
gacaacgaga agtccaacgg caccatcatc cacgtgaagg gcaagcacct gtgtccttct    900
ccactgttcc ccggacctag caagcctttc tgggtgctcg ttgttgttgg cggcgtgctg    960
gcctgttaca gcctgctggt taccgtggcc ttcatcatct tttgggtccg aagcaagcgg   1020
agccggctgc tgcactccga ctacatgaac atgacccccta gacggcccgg accaaccaga   1080
aagcactacc agccttacgc tcctcctaga gacttcgccg cctaccggtc cagagtgaag   1140
ttcagcagat ccgccgatgc tcccgcctat cagcagggcc aaaaccagct gtacaacgag   1200
ctgaacctgg ggagaagaga agagtacgac gtgctggaca agcggagagg cagagatcct   1260
gaaatgggcg gcaagcccag acggaagaat cctcaagagg gcctgtataa tgagctgcag   1320
aaagacaaga tggccgaggc ctacagcgag atcggaatga agggcgagcg cagaagaggc   1380
aagggacacg atggactgta ccagggactg agcaccgcca ccaaggatac ctatgacgcc   1440
ctgcacatgc aggccctgcc tccaagataa                                   1470
```

<210> SEQ ID NO 312
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 312

```
atgctgctgc tggtcacatc tctgctgctg tgcgagctgc cccatcctgc ctttctgctg     60
atccccgaca tccagatgac ccagaccaca agcagcctgt ctgccagcct gggcgataga    120
gtgaccatca gctgtagagc cagccaggac atcagcaagt acctgaactg gtatcagcaa    180
aagcccgacg gcaccgtgaa gctgctgatc taccacacca gcagactgca cagcggcgtg    240
ccaagcagat tttctggcag cggctctggc accgactaca gcctgacaat cagcaacctg    300
gaacaagagg atatcgctac ctacttctgc cagcaaggca acaccctgcc ttacaccttt    360
ggcggaggca ccaagctgga aatcaccggc tctacaagcg gcagcggcaa acctggatct    420
ggcgagggat ctaccaaggg cgaagtgaaa ctgcaagagt ctggccctgg actggtggcc    480
ccatctcagt ctctgagcgt gacctgtaca gtcagcggag tgtccctgcc tgattacggc    540
gtgtcctgga tcagacagcc tcctcggaaa ggcctggaat ggctgggagt gatctggggc    600
agcgagacaa cctactacaa cagcgccctg aagtcccggc tgaccatcat caaggacaac    660
tccaagagcc aggtgttcct gaagatgaac agcctgcaga ccgacgacac cgccatctac    720
tattgcgcca agcactacta ctacggcggc agctacgcca tggattattg gggccagggc    780
accagcgtga ccgtttcttc tgccgccgct atcgaagtga tgtaccctcc tccttacctg    840
gacaacgaga agtccaacgg caccatcatc cacgtgaagg gcaagcacct gtgtccttct    900
```

-continued

```
ccactgttcc ccggacctag caagcctttc tgggtgctcg ttgttgttgg cggcgtgctg    960

gcctgttaca gcctgctggt taccgtggcc ttcatcatct tttgggtcag agtgaagttc   1020

agcagatccg ccgatgctcc cgcctatcag cagggccaaa accagctgta caacgagctg   1080

aacctgggga gaagagaaga gtacgacgtg ctggacaagc ggagaggcag agatcctgaa   1140

atgggcggca agcccagacg gaagaatcct caagagggcc tgtataatga gctgcagaaa   1200

gacaagatgg ccgaggccta cagcgagatc ggaatgaagg gcgagcgcag aagaggcaag   1260

ggacacgatg gactgtacca gggactgagc accgccacca aggataccta tgacgccctg   1320

cacatgcagg ccctgcctcc aagataa                                       1347
```

<210> SEQ ID NO 313
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 313

```
atggctctcc cggtcacagc ccttctcctg cccctggcac tcttgctgca tgcggcacga     60

cccgacatcc agatgaccca gaccacaagc agcctgtctg ccagcctggg cgatagagtg    120

accatcagct gtagagccag ccaggacatc agcaagtacc tgaactggta tcagcaaaag    180

cccgacggca ccgtgaagct gctgatctac cacaccagca gactgcacag cggcgtgcca    240

agcagatttt ctggcagcgg ctctggcacc gactacagcc tgacaatcag caacctggaa    300

caagaggata tcgctaccta cttctgccag caaggcaaca ccctgcctta cacctttggc    360

ggaggcacca agctggaaat caccggtgga ggtggttctg gcggaggggg atctggtgga    420

ggcggttcag aagtgaaact gcaagagtct ggccctggac tggtggcccc atctcagtct    480

ctgagcgtga cctgtacagt cagcggagtg tccctgcctg attacggcgt gtcctggatc    540

agacagcctc ctcggaaagg cctggaatgg ctgggagtga tctggggcag cgagacaacc    600

tactacaaca gcgccctgaa gtcccggctg accatcatca aggacaactc caagagccag    660

gtgttcctga agatgaacag cctgcagacc gacgacaccg ccatctacta ttgcgccaag    720

cactactact acggcggcag ctacgccatg gattattggg gccagggcac cagcgtgacc    780

gtttcttcta ccacaacgcc cgccccgcga ccgcctactc ccgctcccac aattgcatca    840

caacccctgt ctttgagacc cgaagcttgt cgaccagctg ccggtggcgc ggttcacacg    900

cgggggctcg atttcgcctg tgatatatat atatgggccc cattggctgg aacatgcgga    960

gtattgcttc tgagcctggt gattaccctc tactgtaaga gaggccggaa gaaacttctt   1020

tatatattca agcagccctt tatgcgaccc gttcagacta cccaagagga agatggatgc   1080

agttgccgct ttccagaaga ggaggagggc gggtgcgaac tgagagtgaa gttcagcaga   1140

tccgccgatg ctcccgccta tcagcagggc caaaaccagc tgtacaacga gctgaacctg   1200

ggagaagag aagagtacga cgtgctggac aagcggagag gcagagatcc tgaaatgggc    1260

ggcaagccca gacggaagaa tcctcaagag ggcctgtata atgagctgca gaaagacaag   1320

atggccgagg cctacagcga gatcggaatg aagggcgagc gcagaagagg caagggacac   1380

gatggactgt accagggact gagcaccgcc accaaggata cctatgacgc cctgcacatg   1440

caggccctgc ctccaagata a                                             1461
```

<210> SEQ ID NO 314
<211> LENGTH: 1461
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 314
atggctctcc cggtcacagc ccttctcctg cccctggcac tcttgctgca tgcggcacga 60
cccgacatcc agatgaccca gaccacaagc agcctgtctg ccagcctggg cgatagagtg 120
accatcagct gtagagccag ccaggacatc agcaagtacc tgaactggta tcagcaaaag 180
cccgacggca ccgtgaagct gctgatctac cacaccagca gactgcacag cggcgtgcca 240
agcagatttt ctggcagcgg ctctggcacc gactacagcc tgacaatcag caacctggaa 300
caagaggata tcgctaccta cttctgccag caaggcaaca ccctgcctta cacctttggc 360
ggaggcacca agctggaaat caccggtgga ggtggttctg gcggaggggg atctggtgga 420
ggcggttcag aagtgaaact gcaagagtct ggccctggac tggtggcccc atctcagtct 480
ctgagcgtga cctgtacagt cagcggagtg tccctgcctg attacggcgt gtcctggatc 540
agacagcctc ctcggaaagg cctggaatgg ctgggagtga tctggggcag cgagacaacc 600
tactacaaca gcgccctgaa gtcccggctg accatcatca aggacaactc caagagccag 660
gtgttcctga agatgaacag cctgcagacc gacgacaccg ccatctacta ttgcgccaag 720
cactactact acggcggcag ctacgccatg gattattggg gccagggcac cagcgtgacc 780
gtttcttcta ccacaacgcc cgccccgcga ccgcctactc ccgctcccac aattgcatca 840
caacccctgt ctttgagacc cgaagcttgt cgaccagctg ccggtggcgc ggttcacacg 900
cgggggctcg atttcgcctg tgatatatat atatgggccc cattggctgg aacatgcgga 960
gtattgcttc tgagcctggt gattaccctc tactgtaaga gaggccggaa gaaacttctt 1020
tatatattca agcagccctt tatgcgaccc gttcagacta cccaagagga agatggatgc 1080
agttgccgct ttccagaaga ggaggagggc gggtgcgaac tgagagtgaa gttcagcaga 1140
tccgccgatg ctcccgccta taagcagggc caaaaccagc tgtacaacga gctgaacctg 1200
gggagaagag aagagtacga cgtgctggac aagcggagag gcagagatcc tgaaatgggc 1260
ggcaagccca gacggaagaa tcctcaagag ggcctgtata atgagctgca gaaagacaag 1320
atggccgagg cctacagcga gatcggaatg aagggcgagc gcagaagagg caagggacac 1380
gatggactgt accagggact gagcaccgcc accaaggata cctatgacgc cctgcacatg 1440
caggccctgc ctccaagata a 1461

<210> SEQ ID NO 315
<211> LENGTH: 1452
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 315
atgctgctgc tggtcacatc tctgctgctg tgcgagctgc cccatcctgc ctttctgctg 60
atcccccagg ttcaactcca gcagtctggt cccggcctcg ttaaaccaag ccagactttg 120
tctcttacct gtgctatcag tggcgatagc gtgtctagta attcagccgc atggaactgg 180
atccgacaat caccgagtag gggacttgaa tggctgggta gaacctatta ccggtccaaa 240

```
tggtacaatg actatgcagt gtctgtaaaa agcaggatca cgatcaaccc tgatacgtct    300

aaaaaccagt tttctctgca acttaatagt gtgacccctg aagacaccgc tgtgtattac    360

tgtgcacggg aggttaccgg tgatcttgaa gatgcttttg atatatgggg ccaaggtacg    420

atggtcacgg tgtctagtgg gggaggcggc agcgacatac agatgacgca gagcccatcc    480

agtctctccg cgtctgttgg tgacagagtg actattacat gtagggcgtc tcagaccatt    540

tggtcttacc tcaattggta tcaacagcga ccaggcaaag caccgaactt gctcatttac    600

gctgccagct cactccaaag tggtgtgccg tccagattta gtggtagggg cagtggcact    660

gatttcactc tgactatttc aagtcttcaa gctgaggatt ttgccacata ctactgccag    720

caaagttact caatacctca gacttttgga caggggacaa aattggagat taaatccgga    780

accacaacgc ccgccccgcg accgcctact cccgctccca caattgcatc acaacccctg    840

tctttgagac ccgaagcttg tcgaccagct gccggtggcg cggttcacac gcgggggctc    900

gatttcgcct gtgatatata tatatgggcc ccattggctg gaacatgcgg agtattgctt    960

ctgagcctgg tgattaccct ctactgtaag agaggccgga agaaacttct ttatatattc   1020

aagcagccct ttatgcgacc cgttcagact acccaagagg aagatggatg cagttgccgc   1080

tttccagaag aggaggaggg cgggtgcgaa ctgagagtga agttcagcag atccgccgat   1140

gctcccgcct ataagcaggg ccaaaaccag ctgtacaacg agctgaacct ggggagaaga   1200

gaagagtacg acgtgctgga caagcggaga ggcagagatc ctgaaatggg cggcaagccc   1260

agacggaaga atcctcaaga gggcctgtat aatgagctgc agaaagacaa gatggccgag   1320

gcctacagcg agatcggaat gaagggcgag cgcagaagag gcaagggaca cgatggactg   1380

taccagggac tgagcaccgc caccaaggat acctatgacg ccctgcacat gcaggccctg   1440

cctccaagat aa                                                       1452
```

```
<210> SEQ ID NO 316
<211> LENGTH: 2202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316

atgctgctgc tggtcacatc tctgctgctg tgcgagctgc cccatcctgc ctttctgctg     60

atccccgaca tccagatgac ccagaccaca agcagcctgt ctgccagcct gggcgataga    120

gtgaccatca gctgtagagc cagccaggac atcagcaagt acctgaactg gtatcagcaa    180

aagcccgacg gcaccgtgaa gctgctgatc taccacacca gcagactgca cagcggcgtg    240

ccaagcagat ttctggcag cggctctggc accgactaca gcctgacaat cagcaacctg     300

gaacaagagg atatcgctac ctacttctgc cagcaaggca acaccctgcc ttacaccttt    360

ggcggaggca ccaagctgga aatcaccggc ggcggaggat cccaggttca actccagcag    420

tctggtcccg gcctcgttaa accaagccag actttgtctc ttacctgtgc tatcagtggc    480

gatagcgtgt ctagtaattc agccgcatgg aactggatcc gacaatcacc gagtagggga    540

cttgaatggc tgggtagaac ctattaccgg tccaaatggt acaatgacta tgcagtgtct    600

gtaaaaagca ggatcacgat caaccctgat acgtctaaaa accagttttc tctgcaactt    660

aatagtgtga cccctgaaga caccgctgtg tattactgtg cacgggaggt taccggtgat    720

cttgaagatg cttttgatat atggggccaa ggtacgatgg tcacggtgtc tagtggctct    780
```

```
acaagcggca gcggcaaacc tggatctggc gagggatcta ccaagggcga catacagatg    840

acgcagagcc catccagtct ctccgcgtct gttggtgaca gagtgactat tacatgtagg    900

gcgtctcaga ccatttggtc ttacctcaat tggtatcaac agcgaccagg caaagcaccg    960

aacttgctca tttacgctgc cagctcactc caaagtggtg tgccgtccag atttagtggt   1020

aggggcagtg gcactgattt cactctgact atttcaagtc ttcaagctga ggattttgcc   1080

acatactact gccagcaaag ttactcaata cctcagactt ttggacaggg gacaaaattg   1140

gagattaaag gggaggcgg cagcgaagtg aaactgcaag agtctggccc tggactggtg    1200

gccccatctc agtctctgag cgtgacctgt acagtcagcg gagtgtccct gcctgattac   1260

ggcgtgtcct ggatcagaca gcctcctcgg aaaggcctgg aatggctggg agtgatctgg   1320

ggcagcgaga caacctacta caacagcgcc ctgaagtccc ggctgaccat catcaaggac   1380

aactccaaga gccaggtgtt cctgaagatg aacagcctgc agaccgacga caccgccatc   1440

tactattgcg ccaagcacta ctactacggc ggcagctacg ccatggatta ttggggccag   1500

ggcaccagcg tgaccgtttc ttcttccgga accacaacgc ccgcccccgcg accgcctact  1560

cccgctccca caattgcatc acaacccctg tctttgagac ccgaagcttg tcgaccagct   1620

gccggtggcg cggttcacac gcgggggctc gatttcgcct gtgatatata tatatgggcc   1680

ccattggctg gaacatgcgg agtattgctt ctgagcctgg tgattaccct ctactgtaag   1740

agaggccgga agaaacttct ttatatattc aagcagccct ttatgcgacc cgttcagact   1800

acccaagagg aagatggatg cagttgccgc tttccagaag aggaggaggg cgggtgcgaa   1860

ctgagagtga agttcagcag atccgccgat gctcccgcct ataagcaggg ccaaaaccag   1920

ctgtacaacg agctgaacct ggggagaaga gaagagtacg acgtgctgga caagcggaga   1980

ggcagagatc ctgaaatggg cggcaagccc agacggaaga atcctcaaga gggcctgtat   2040

aatgagctgc agaaagacaa gatggccgag gcctacagcg agatcggaat gaagggcgag   2100

cgcagaagag gcaagggaca cgatggactg taccagggac tgagcaccgc caccaaggat   2160

acctatgacg ccctgcacat gcaggccctg cctccaagat aa                      2202
```

<210> SEQ ID NO 317
<211> LENGTH: 2262
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 317

```
atgctgctgc tggtcacatc tctgctgctg tgcgagctgc cccatcctgc ctttctgctg     60

atcccccagg ttcaactcca gcagtctggt cccggcctcg ttaaaccaag ccagactttg    120

tctcttacct gtgctatcag tggcgatagc gtgtctagta attcagccgc atggaactgg    180

atccgacaat caccgagtag gggacttgaa tggctgggta gaacctatta ccggtccaaa    240

tggtacaatg actatgcagt gtctgtaaaa agcaggatca cgatcaaccc tgatacgtct    300

aaaaaccagt tttctctgca acttaatagt gtgaccccctg aagacaccgc tgtgtattac   360

tgtgcacggg aggttaccgg tgatcttgaa gatgcttttg atatatgggg ccaaggtacg    420

atggtcacgg tgtctagtgg gggaggcggc agcgacatac agatgacgca gagcccatcc    480

agtctctccg cgtctgttgg tgacagagtg actattacat gtagggcgtc tcagaccatt    540

tggtcttacc tcaattggta tcaacagcga ccaggcaaag caccgaactt gctcatttac    600
```

```
gctgccagct cactccaaag tggtgtgccg tccagattta gtggtagggg cagtggcact    660

gatttcactc tgactatttc aagtcttcaa gctgaggatt ttgccacata ctactgccag    720

caaagttact caatacctca gacttttgga caggggacaa aattggagat taaaggggga    780

ggcggatccg gcggtggtgg ctccggcggt ggtggttctg gaggcggcgg aagcggtggg    840

ggtggtagcg acatccagat gacccagacc acaagcagcc tgtctgccag cctgggcgat    900

agagtgacca tcagctgtag agccagccag gacatcagca agtacctgaa ctggtatcag    960

caaaagcccg acggcaccgt gaagctgctg atctaccaca ccagcagact gcacagcggc   1020

gtgccaagca gattttctgg cagcggctct ggcaccgact acagcctgac aatcagcaac   1080

ctggaacaag aggatatcgc tacctacttc tgccagcaag gcaacaccct gccttacacc   1140

tttggcggag gcaccaagct ggaaatcacc ggctctacaa gcggcagcgg caaacctgga   1200

tctggcgagg gatctaccaa gggcgaagtg aaactgcaag agtctggccc tggactggtg   1260

gccccatctc agtctctgag cgtgacctgt acagtcagcg gagtgtccct gcctgattac   1320

ggcgtgtcct ggatcagaca gcctcctcgg aaaggcctgg aatggctggg agtgatctgg   1380

ggcagcgaga caacctacta caacagcgcc ctgaagtccc ggctgaccat catcaaggac   1440

aactccaaga gccaggtgtt cctgaagatg aacagcctgc agaccgacga caccgccatc   1500

tactattgcg ccaagcacta ctactacggc ggcagctacg ccatggatta ttggggccag   1560

ggcaccagcg tgaccgtttc ttcttccgga accacaacgc ccgcccccgcg accgcctact   1620

cccgctccca caattgcatc acaacccctg tctttgagac ccgaagcttg tcgaccagct   1680

gccggtggcg cggttcacac gcgggggctc gatttcgcct gtgatatata tatatgggcc   1740

ccattggctg gaacatgcgg agtattgctt ctgagcctgg tgattaccct ctactgtaag   1800

agaggccgga agaaacttct ttatatattc aagcagccct ttatgcgacc cgttcagact   1860

acccaagagg aagatggatg cagttgccgc tttccagaag aggaggaggg cgggtgcgaa   1920

ctgagagtga agttcagcag atccgccgat gctcccgcct ataagcaggg ccaaaaccag   1980

ctgtacaacg agctgaacct ggggagaaga gaagagtacg acgtgctgga caagcggaga   2040

ggcagagatc ctgaaatggg cggcaagccc agacggaaga atcctcaaga gggcctgtat   2100

aatgagctgc agaaagacaa gatggccgag gcctacagcg agatcggaat gaagggcgag   2160

cgcagaagag gcaagggaca cgatggactg taccagggac tgagcaccgc caccaaggat   2220

acctatgacg ccctgcacat gcaggccctg cctccaagat aa                      2262
```

```
<210> SEQ ID NO 318
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 319
<211> LENGTH: 112
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 319

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 320
<211> LENGTH: 241
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 320

```
Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205
```

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys

<210> SEQ ID NO 321
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 322
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 323
<211> LENGTH: 447
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 323

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

-continued

```
Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 324
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 325
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Val Glu Ser Gly Gly Gly Val Val Gln Pro Gly Arg
1               5                   10                  15
```

-continued

```
Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415
```

```
Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 326
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 327
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

```
Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 328
<211> LENGTH: 214

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 329
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 330
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Arg Val Phe Gly Thr Gly Thr Lys Val Thr Val Leu Gly Gln
100 105 110

Pro Lys Ala Asn Pro Thr Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Gly Ser Pro Val Lys
145 150 155 160

Ala Gly Val Glu Thr Thr Lys Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 331
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 331

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Gly Trp Phe Gly Glu Leu Ala Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 332
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Glu Ile Val Leu Thr Gln Ser Pro Gly Thr Leu Ser Leu Ser Pro Gly
1               5                   10                  15

-continued

```
Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 333
<211> LENGTH: 133
<212> TYPE: PRT
<213> ORGANISM: Homo sapiens

<400> SEQUENCE: 333

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 334
<211> LENGTH: 197
<212> TYPE: PRT
```

<213> ORGANISM: Homo sapiens

<400> SEQUENCE: 334

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 335
<211> LENGTH: 306
<212> TYPE: PRT
<213> ORGANISM: Homo sapiens

<400> SEQUENCE: 335

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

```
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 336
<211> LENGTH: 152
<212> TYPE: PRT
<213> ORGANISM: Homo sapiens

<400> SEQUENCE: 336

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 337
<211> LENGTH: 160
<212> TYPE: PRT
<213> ORGANISM: Homo sapiens

<400> SEQUENCE: 337

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Ser Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
50 55 60

Leu Ser Glu Met Ile Gln Phe Tyr Leu Glu Glu Val Met Pro Gln Ala
65 70 75 80

Glu Asn Gln Asp Pro Asp Ile Lys Ala His Val Asn Ser Leu Gly Glu
85 90 95

Asn Leu Lys Thr Leu Arg Leu Arg Leu Arg Arg Cys His Arg Phe Leu
100 105 110

Pro Cys Glu Asn Lys Ser Lys Ala Val Glu Gln Val Lys Asn Ala Phe
115 120 125

Asn Lys Leu Gln Glu Lys Gly Ile Tyr Lys Ala Met Ser Glu Phe Asp
130 135 140

Ile Phe Ile Asn Tyr Ile Glu Ala Tyr Met Thr Met Lys Ile Arg Asn
145 150 155 160

<210> SEQ ID NO 338
<211> LENGTH: 114
<212> TYPE: PRT
<213> ORGANISM: Homo sapiens

<400> SEQUENCE: 338

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser

<210> SEQ ID NO 339
<211> LENGTH: 157
<212> TYPE: PRT
<213> ORGANISM: Homo sapiens

<400> SEQUENCE: 339

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

```
Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 340
<211> LENGTH: 209
<212> TYPE: PRT
<213> ORGANISM: Homo sapiens

<400> SEQUENCE: 340

```
Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
65                  70                  75                  80

Pro Tyr Val Leu Asn Val Thr Ala Val His Pro Trp Gly Ser Ser Ser
                85                  90                  95

Ser Phe Val Pro Phe Ile Thr Glu His Ile Ile Lys Pro Asp Pro Pro
            100                 105                 110

Glu Gly Val Arg Leu Ser Pro Leu Ala Glu Arg Gln Leu Gln Val Gln
        115                 120                 125

Trp Glu Pro Pro Gly Ser Trp Pro Phe Pro Glu Ile Phe Ser Leu Lys
    130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
            180                 185                 190

Glu Leu Ser Asp Trp Ser Leu Pro Ala Thr Ala Thr Met Ser Leu Gly
        195                 200                 205

Lys
```

<210> SEQ ID NO 341
<211> LENGTH: 138
<212> TYPE: PRT
<213> ORGANISM: Homo sapiens

<400> SEQUENCE: 341

Gln Asp Pro Tyr Val Lys Glu Ala Glu Asn Leu Lys Lys Tyr Phe Asn
1 5 10 15

Ala Gly His Ser Asp Val Ala Asp Asn Gly Thr Leu Phe Leu Gly Ile
20 25 30

Leu Lys Asn Trp Lys Glu Glu Ser Asp Arg Lys Ile Met Gln Ser Gln
35 40 45

Ile Val Ser Phe Tyr Phe Lys Leu Phe Lys Asn Phe Lys Asp Asp Gln
50 55 60

Ser Ile Gln Lys Ser Val Glu Thr Ile Lys Glu Asp Met Asn Val Lys
65 70 75 80

Phe Phe Asn Ser Asn Lys Lys Lys Arg Asp Asp Phe Glu Lys Leu Thr
85 90 95

Asn Tyr Ser Val Thr Asp Leu Asn Val Gln Arg Lys Ala Ile His Glu
100 105 110

Leu Ile Gln Val Met Ala Glu Leu Ser Pro Ala Ala Lys Thr Gly Lys
115 120 125

Arg Lys Arg Ser Gln Met Leu Phe Arg Gly
130 135

<210> SEQ ID NO 342
<211> LENGTH: 112
<212> TYPE: PRT
<213> ORGANISM: Homo sapiens

<400> SEQUENCE: 342

Ala Leu Asp Thr Asn Tyr Cys Phe Ser Ser Thr Glu Lys Asn Cys Cys
1 5 10 15

Val Arg Gln Leu Tyr Ile Asp Phe Arg Lys Asp Leu Gly Trp Lys Trp
20 25 30

Ile His Glu Pro Lys Gly Tyr His Ala Asn Phe Cys Leu Gly Pro Cys
35 40 45

Pro Tyr Ile Trp Ser Leu Asp Thr Gln Tyr Ser Lys Val Leu Ala Leu
50 55 60

Tyr Asn Gln His Asn Pro Gly Ala Ser Ala Ala Pro Cys Cys Val Pro
65 70 75 80

Gln Ala Leu Glu Pro Leu Pro Ile Val Tyr Tyr Val Gly Arg Lys Pro
85 90 95

Lys Val Glu Gln Leu Ser Asn Met Ile Val Arg Ser Cys Lys Cys Ser
100 105 110

<210> SEQ ID NO 343
<211> LENGTH: 431
<212> TYPE: PRT
<213> ORGANISM: Homo sapiens

<400> SEQUENCE: 343

Met Pro Asn Pro Arg Pro Gly Lys Pro Ser Ala Pro Ser Leu Ala Leu
1 5 10 15

Gly Pro Ser Pro Gly Ala Ser Pro Ser Trp Arg Ala Ala Pro Lys Ala
20 25 30

Ser Asp Leu Leu Gly Ala Arg Gly Pro Gly Gly Thr Phe Gln Gly Arg
35 40 45

Asp Leu Arg Gly Gly Ala His Ala Ser Ser Ser Ser Leu Asn Pro Met
50 55 60

```
Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430


<210> SEQ ID NO 344
<211> LENGTH: 417
<212> TYPE: PRT
<213> ORGANISM: Homo sapiens

<400> SEQUENCE: 344

Met Pro Asn Pro Arg Pro Gly Lys Pro Ser Ala Pro Ser Leu Ala Leu
1               5                   10                  15
```

-continued

```
Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg
```

<210> SEQ ID NO 345
<211> LENGTH: 366
<212> TYPE: PRT
<213> ORGANISM: Homo sapiens

<400> SEQUENCE: 345

```
Gly Gly Ala His Ala Ser Ser Ser Ser Leu Asn Pro Met Pro Pro Ser
1               5                   10                  15

Gln Leu Gln Leu Pro Thr Leu Pro Leu Val Met Val Ala Pro Ser Gly
            20                  25                  30

Ala Arg Leu Gly Pro Leu Pro His Leu Gln Ala Leu Leu Gln Asp Arg
        35                  40                  45

Pro His Phe Met His Gln Leu Ser Thr Val Asp Ala His Ala Arg Thr
    50                  55                  60

Pro Val Leu Gln Val His Pro Leu Glu Ser Pro Ala Met Ile Ser Leu
65                  70                  75                  80

Thr Pro Pro Thr Thr Ala Thr Gly Val Phe Ser Leu Lys Ala Arg Pro
                85                  90                  95

Gly Leu Pro Pro Gly Ile Asn Val Ala Ser Leu Glu Trp Val Ser Arg
            100                 105                 110

Glu Pro Ala Leu Leu Cys Thr Phe Pro Asn Pro Ser Ala Pro Arg Lys
        115                 120                 125

Asp Ser Thr Leu Ser Ala Val Pro Gln Ser Ser Tyr Pro Leu Leu Ala
    130                 135                 140

Asn Gly Val Cys Lys Trp Pro Gly Cys Glu Lys Val Phe Glu Glu Pro
145                 150                 155                 160

Glu Asp Phe Leu Lys His Cys Gln Ala Asp His Leu Leu Asp Glu Lys
                165                 170                 175

Gly Arg Ala Gln Cys Leu Leu Gln Arg Glu Met Val Gln Ser Leu Glu
            180                 185                 190

Gln Gln Leu Val Leu Glu Lys Glu Lys Leu Ser Ala Met Gln Ala His
        195                 200                 205

Leu Ala Gly Lys Met Ala Leu Thr Lys Ala Ser Ser Val Ala Ser Ser
    210                 215                 220

Asp Lys Gly Ser Cys Cys Ile Val Ala Ala Gly Ser Gln Gly Pro Val
225                 230                 235                 240

Val Pro Ala Trp Ser Gly Pro Arg Glu Ala Pro Asp Ser Leu Phe Ala
                245                 250                 255

Val Arg Arg His Leu Trp Gly Ser His Gly Asn Ser Thr Phe Pro Glu
            260                 265                 270

Phe Leu His Asn Met Asp Tyr Phe Lys Phe His Asn Met Arg Pro Pro
        275                 280                 285

Phe Thr Tyr Ala Thr Leu Ile Arg Trp Ala Ile Leu Glu Ala Pro Glu
    290                 295                 300

Lys Gln Arg Thr Leu Asn Glu Ile Tyr His Trp Phe Thr Arg Met Phe
305                 310                 315                 320

Ala Phe Phe Arg Asn His Pro Ala Thr Trp Lys Asn Ala Ile Arg His
                325                 330                 335

Asn Leu Ser Leu His Lys Cys Phe Val Arg Val Glu Ser Glu Lys Gly
            340                 345                 350

Ala Val Trp Thr Val Asp Glu Leu Glu Phe Arg Lys Lys Arg
        355                 360                 365
```

<210> SEQ ID NO 346
<211> LENGTH: 787

<212> TYPE: PRT
<213> ORGANISM: Homo sapiens

<400> SEQUENCE: 346

```
Met Ala Val Trp Ile Gln Ala Gln Gln Leu Gln Gly Glu Ala Leu His
1               5                   10                  15

Gln Met Gln Ala Leu Tyr Gly Gln His Phe Pro Ile Glu Val Arg His
            20                  25                  30

Tyr Leu Ser Gln Trp Ile Glu Ser Gln Ala Trp Asp Ser Val Asp Leu
        35                  40                  45

Asp Asn Pro Gln Glu Asn Ile Lys Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Asn
                85                  90                  95

Thr Tyr Asp Arg Cys Pro Met Glu Leu Val Arg Cys Ile Arg His Ile
            100                 105                 110

Leu Tyr Asn Glu Gln Arg Leu Val Arg Glu Ala Asn Asn Gly Ser Ser
        115                 120                 125

Pro Ala Gly Ser Leu Ala Asp Ala Met Ser Gln Lys His Leu Gln Ile
    130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Gly Pro Leu Ala Gln Leu
            180                 185                 190

Ser Pro Gln Glu Arg Leu Ser Arg Glu Thr Ala Leu Gln Gln Lys Gln
        195                 200                 205

Val Ser Leu Glu Ala Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
        275                 280                 285

Asn Arg Gln Gln Ile Arg Arg Ala Glu His Leu Cys Gln Gln Leu Pro
    290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
    370                 375                 380

Asn Glu Asn Thr Arg Asn Asp Tyr Ser Gly Glu Ile Leu Asn Asn Cys
385                 390                 395                 400
```

-continued

```
Cys Val Met Glu Tyr His Gln Ala Thr Gly Thr Leu Ser Ala His Phe
                405                 410                 415

Arg Asn Met Ser Leu Lys Arg Ile Lys Arg Ser Asp Arg Arg Gly Ala
            420                 425                 430

Glu Ser Val Thr Glu Glu Lys Phe Thr Ile Leu Phe Glu Ser Gln Phe
        435                 440                 445

Ser Val Gly Gly Asn Glu Leu Val Phe Gln Val Lys Thr Leu Ser Leu
    450                 455                 460

Pro Val Val Val Ile Val His Gly Ser Gln Asp Asn Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
        515                 520                 525

Asn Leu Val Phe Leu Ala Gln Lys Leu Phe Asn Asn Ser Ser Ser His
    530                 535                 540

Leu Glu Asp Tyr Ser Gly Leu Ser Val Ser Trp Ser Gln Phe Asn Arg
545                 550                 555                 560

Glu Asn Leu Pro Gly Arg Asn Tyr Thr Phe Trp Gln Trp Phe Asp Gly
                565                 570                 575

Val Met Glu Val Leu Lys Lys His Leu Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Gln Glu Arg Met Phe
625                 630                 635                 640

Trp Asn Leu Met Pro Phe Thr Thr Arg Asp Phe Ser Ile Arg Ser Leu
                645                 650                 655

Ala Asp Arg Leu Gly Asp Leu Asn Tyr Leu Ile Tyr Val Phe Pro Asp
            660                 665                 670

Arg Pro Lys Asp Glu Val Tyr Ser Lys Tyr Tyr Thr Pro Val Pro Cys
        675                 680                 685

Glu Ser Ala Thr Ala Lys Ala Val Asp Gly Tyr Val Lys Pro Gln Ile
    690                 695                 700

Lys Gln Val Val Pro Glu Phe Val Asn Ala Ser Ala Asp Ala Gly Gly
705                 710                 715                 720

Gly Ser Ala Thr Tyr Met Asp Gln Ala Pro Ser Pro Ala Val Cys Pro
                725                 730                 735

Gln Ala His Tyr Asn Met Tyr Pro Gln Asn Pro Asp Ser Val Leu Asp
            740                 745                 750

Thr Asp Gly Asp Phe Asp Leu Glu Asp Thr Met Asp Val Ala Arg Arg
        755                 760                 765

Val Glu Glu Leu Leu Gly Arg Pro Met Asp Ser Gln Trp Ile Pro His
    770                 775                 780

Ala Gln Ser
785
```

<210> SEQ ID NO 347
<211> LENGTH: 526

<212> TYPE: PRT
<213> ORGANISM: Homo sapiens

<400> SEQUENCE: 347

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Lys Leu
            100                 105                 110

Lys Cys Asp Val Cys Gly Met Val Cys Ile Gly Pro Asn Val Leu Met
        115                 120                 125

Val His Lys Arg Ser His Thr Gly Glu Arg Pro Phe His Cys Asn Gln
    130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
                165                 170                 175

Cys Arg Arg Arg Asp Ala Leu Thr Gly His Leu Arg Thr His Ser Val
            180                 185                 190

Gly Lys Pro His Lys Cys Asn Tyr Cys Gly Arg Ser Tyr Lys Gln Arg
        195                 200                 205

Ser Ser Leu Glu Glu His Lys Glu Arg Cys His Asn Tyr Leu Gln Asn
    210                 215                 220

Val Ser Met Glu Ala Ala Gly Gln Val Met Ser His His Val Pro Pro
225                 230                 235                 240

Met Glu Asp Cys Lys Glu Gln Glu Pro Ile Met Asp Asn Asn Ile Ser
                245                 250                 255

Leu Val Pro Phe Glu Arg Pro Ala Val Ile Glu Lys Leu Thr Gly Asn
            260                 265                 270

Met Gly Lys Arg Lys Ser Ser Thr Pro Gln Lys Phe Val Gly Glu Lys
        275                 280                 285

Leu Met Arg Phe Ser Tyr Pro Asp Ile His Phe Asp Met Asn Leu Thr
    290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
                325                 330                 335

Met Gln His Pro Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
        355                 360                 365

Ser Arg Glu Thr Ala Asp Ser His Glu Asn Asn Met Asp Gly Pro Ile
    370                 375                 380

Ser Leu Ile Arg Pro Lys Ser Arg Pro Gln Glu Arg Glu Ala Ser Pro
385                 390                 395                 400

Ser Asn Ser Cys Leu Asp Ser Thr Asp Ser Glu Ser Ser His Asp Asp
405 410 415

His Gln Ser Tyr Gln Gly His Pro Ala Leu Asn Pro Lys Arg Lys Gln
420 425 430

Ser Pro Ala Tyr Met Lys Glu Asp Val Lys Ala Leu Asp Thr Thr Lys
435 440 445

Ala Pro Lys Gly Ser Leu Lys Asp Ile Tyr Lys Val Phe Asn Gly Glu
450 455 460

Gly Glu Gln Ile Arg Ala Phe Lys Cys Glu His Cys Arg Val Leu Phe
465 470 475 480

Leu Asp His Val Met Tyr Thr Ile His Met Gly Cys His Gly Tyr Arg
485 490 495

Asp Pro Leu Glu Cys Asn Ile Cys Gly Tyr Arg Ser Gln Asp Arg Tyr
500 505 510

Glu Phe Ser Ser His Ile Val Arg Gly Glu His Thr Phe His
515 520 525

<210> SEQ ID NO 348
<211> LENGTH: 625
<212> TYPE: DNA
<213> ORGANISM: Unknown
<220> FEATURE:
<223> OTHER INFORMATION: Description of Unknown:
AP1.0 sequence

<400> SEQUENCE: 348
attctcgggc tacggccctg gagccactcc ggctcctaaa gatttagaag tttgagcaca 60
cccgcccact agggcccccc atccaggggg gcaacgggca agcacttctg tttccccggt 120
atgatctgat aggctgtaac cacggctgaa acagagatta tcgttatccg cttcactact 180
tcgagaagcc tagtaatgat gggtgaaatt gaatccgttg atccggtgtc tcccccacac 240
cagaaactca tgatgagggt tgccatcccg gctacggcga cgtagcgggc atccctgcgc 300
tggcatgagg cctcttagga ggacggatga tatggatctt gtcgtgaaga gcctattgag 360
ctagtgtcga ctcctccgcc cccgtgaatg cggctaatcc taaccccgga gcaggtgggt 420
ccaatccagg gcctggcctg tcgtaatgcg taagtctggg acggaaccga ctactttcgg 480
gaaggcgtgt ttccatttgt tcattatttg tgtgtttatg gtgacaactc tgggtaaacg 540
ttctattgcg tttattgaga gattcccaac aattgaacaa acgagaacta cctgttttat 600
taaatttaca cagagaagaa ttaca 625

<210> SEQ ID NO 349
<211> LENGTH: 549
<212> TYPE: DNA
<213> ORGANISM: Unknown
<220> FEATURE:
<223> OTHER INFORMATION: Description of Unknown:
CK1.0 sequence

<400> SEQUENCE: 349
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300

```
tccccagtgt gtgtagtgcg atcttccagg tcctcctggt tggcgttgtc cagaaactgc    360

ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactcta ctgctgacaa ctcactgact atccacttgc    540

tctgtcacg                                                            549


<210> SEQ ID NO 350
<211> LENGTH: 630
<212> TYPE: DNA
<213> ORGANISM: Unknown
<220> FEATURE:
<223> OTHER INFORMATION: Description of Unknown:
      PV1.0 sequence

<400> SEQUENCE: 350

aacaaaaggc tacaccactt gggctacggc ccgcgccacc ttgtggcgca aagacattag     60

aagaatagca taccgcccac tagggccctg cagccagcag ggtaacgggc aagcacttct    120

gtctccccgg tagaacggta taggctgtac ccacggccga aaactgaact atcgttaccc    180

gactccgtac ttcgcaaagc ttagtaggaa actggaaagt tcgagttatt gacccggagt    240

gttcccccca ctccagaaac gcgtgatgag ggttgccacc ccgaccatgg cgacatggtg    300

ggcatccctg cgctggcacg cggcctctaa gaggataact cgctcctact ggtaaccgaa    360

gagccccgtg agctacggtt tattcctccg cctccctgaa tgcggctaat cctaacccat    420

gagcagttgc catagatcca tatggtggac tgtcgtaacg cgtaagttgt gggcggaacc    480

gactactttg ggatggcgtg tttccttgtt ttctccattt gttgttgtat ggtgacaagt    540

tatagatctc gatctatagc gtttcttgag agatttccaa acatttattc aagtcgtaca    600

attcttgtgt ttaagcagta cagtgtaacc                                     630


<210> SEQ ID NO 351
<211> LENGTH: 653
<212> TYPE: DNA
<213> ORGANISM: Unknown
<220> FEATURE:
<223> OTHER INFORMATION: Description of Unknown:
      SV1.0 sequence

<400> SEQUENCE: 351

tctgtcctca ccccatcttc ccttctttcc tgcaccgtta cgcttactcg catgtgcatt     60

gagtggtgca cgtgcttgaa caaacagcta cactcacatg gggcgggtt ttcccgccct    120

gcggcctctc gcgaggccca cccctcccct tcctcccata actacagtgc tttggtaggt    180

aagcatcctg atcccccgcg gaagctgctc acgtggcaac tgtggggacc cagacaggtt    240

atcaaaggca cccggtcttt ccgccttcag gagtatccct gctagtgaat tctagtaggg    300

ctctgcttgg tgccaacctc ccccaaatgc gcgctgcggg agtgctcttc cccaactcac    360

cctagtatcc tctcatgtgt gtgcttggtc agcatatctg agacgatgtt ccgctgtccc    420

agaccagtcc agtaatggac gggccagtgt gcgtagtcgt cttccggctt gtccggcgca    480

tgtttggtga accggtgggg taaggttggt gtgcccaacg cccgtacttt ggtgatacct    540

caagaccacc caggaatgcc agggaggtac cccgcttcac agcgggatct gaccctgggc    600

taattgtcta cggtggttct tcttgcttcc acttctttct actgttcgcc acc           653


<210> SEQ ID NO 352
<211> LENGTH: 635
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 352
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta ctgctgacaa ctcactgact atccacttgc 540
tctcttgtgc ctttctgctc tggttcaagt tccttgattg tttttgactg cttttcactg 600
cttttcttct cacaatcctt gctcagttca aagtc 635

<210> SEQ ID NO 353
<211> LENGTH: 513
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 353
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactaaa gtc 513

<210> SEQ ID NO 354
<211> LENGTH: 549
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 354
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta ctgctgacaa ctcactgact atccacttgc 540
tctaaagtc 549

<210> SEQ ID NO 355
<211> LENGTH: 513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 355
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactgcc acc 513

<210> SEQ ID NO 356
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 356
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactttc actgcttttc ttctcacaat ccttgctcag 540
ttcaaagtc 549

<210> SEQ ID NO 357
<211> LENGTH: 678
<212> TYPE: DNA
<213> ORGANISM: Parabovirus sp.

<400> SEQUENCE: 357
tgaaccgtta cgcaccactc agttggtgtt tggtggcacc aatgatggaa caaaaggcta 60
caccacttgg gctacggccc gcgccacctt gtggcgcaaa gacattagaa gaatagcata 120
ccgcccacta gggccctgca gccagcaggg taacgggcaa gcacttctgt ctccccggta 180
gaacggtata ggctgtaccc acggccgaaa actgaactat cgttacccga ctccgtactt 240
cgcaaagctt agtaggaaac tggaaagttc gagttattga cccggagtgt tccccccact 300
ccagaaacgc gtgatgaggg ttgccacccc gaccatggcg acatggtggg catccctgcg 360
ctggcacgcg gcctctaaga ggataactcg ctcctactgg taaccgaaga gccccgtgag 420
ctacggttta ttcctccgcc tccctgaatg cggctaatcc taacccatga gcagttgcca 480
tagatccata tggtggactg tcgtaacgcg taagttgtgg gcggaaccga ctactttggg 540
atggcgtgtt tccttgtttt ctccatttgt tgttgtatgg tgacaagtta tagatctcga 600
tctatagcgt ttcttgagag atttccaaac atttattcaa gtcgtacaat tcttgtgttt 660
aagcagtaca gtgtaagg 678

<210> SEQ ID NO 358
<211> LENGTH: 630
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 358
aacaaaaggc tacaccactt gggctacggc ccgcgccacc ttgtggcgca aagacattag 60
aagaatagca taccgcccac tagggccctg cagccagcag ggtaacgggc aagcacttct 120
gtctccccgg tagaacggta taggctgtac ccacggccga aaactgaact atcgttaccc 180
gactccgtac ttcgcaaagc ttagtaggaa actggaaagt tcgagttatt gacccggagt 240
gttcccccca ctccagaaac gcgtgatgag ggttgccacc ccgaccatgg cgacatggtg 300
ggcatccctg cgctggcacg cggcctctaa gaggataact cgctcctact ggtaaccgaa 360
gagccccgtg agctacggtt tattcctccg cctccctgaa tgcggctaat cctaacccat 420
gagcagttgc catagatcca tatggtggac tgtcgtaacg cgtaagttgt gggcggaacc 480
gactactttg ggatggcgtg tttccttgtt ttctccattt gttgttgtat ggtgacaagt 540
tatagatctc gatctatagc gtttcttgag agatttccaa acatttattc aagtcgtaca 600
attcttgtgt ttaagcagta cagtgtaagg 630

<210> SEQ ID NO 359
<211> LENGTH: 611
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 359
tgggctacgg cccgcgccac cttgtggcgc aaagacatta gaagaatagc ataccgccca 60
ctagggccct gcagccagca gggtaacggg caagcacttc tgtctccccg gtagaacggt 120
ataggctgta cccacggccg aaaactgaac tatcgttacc cgactccgta cttcgcaaag 180
cttagtagga aactggaaag ttcgagttat tgacccggag tgttcccccc actccagaaa 240

-continued

```
cgcgtgatga gggttgccac cccgaccatg gcgacatggt gggcatccct gcgctggcac    300

gcggcctcta agaggataac tcgctcctac tggtaaccga agagccccgt gagctacggt    360

ttattcctcc gcctccctga atgcggctaa tcctaaccca tgagcagttg ccatagatcc    420

atatggtgga ctgtcgtaac gcgtaagttg tgggcggaac cgactacttt gggatggcgt    480

gtttccttgt tttctccatt tgttgttgta tggtgacaag ttatagatct cgatctatag    540

cgtttcttga gagatttcca aacatttatt caagtcgtac aattcttgtg tttaagcagt    600

acagtgtaag g                                                          611
```

<210> SEQ ID NO 360
<211> LENGTH: 618
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360

```
tgaaccgtta cgcaccactc agttggtgtt tggtggcacc aatgatggaa caaaaggcta     60

caccacttgg gctacggccc gcgccacctt gtggcgcaaa gacattagaa gaatagcata    120

ccgcccacta gggccctgca gccagcaggg taacgggcaa gcacttctgt ctccccggta    180

gaacggtata ggctgtaccc acggccgaaa actgaactat cgttacccga ctccgtactt    240

cgcaaagctt agtaggaaac tggaaagttc gagttattga cccggagtgt tccccccact    300

ccagaaacgc gtgatgaggg ttgccacccc gaccatggcg acatggtggg catccctgcg    360

ctggcacgcg gcctctaaga ggataactcg ctcctactgg taaccgaaga gccccgtgag    420

ctacggttta ttcctccgcc tccctgaatg cggctaatcc taacccatga gcagttgcca    480

tagatccata tggtggactg tcgtaacgcg taagttgtgg gcggaaccga ctactttggg    540

atggcgtgtt tccttgtttt ctccatttgt tgttgtatgg tgacaagtta tagatctcga    600

tctatagcgt ttgtaagg                                                   618
```

<210> SEQ ID NO 361
<211> LENGTH: 826
<212> TYPE: DNA
<213> ORGANISM: Unknown
<220> FEATURE:
<223> OTHER INFORMATION: Description of Unknown:
      Apodemus Picornavirus sequence

<400> SEQUENCE: 361

```
tttgaaaggg gtgcggatat catggcgttt ctcgccatga tatccgcaca ttgcaaaccc     60

atattgcata cccactgggt atgcattatg gggaggcccc tttcacccct cccccccaa    120

ttacctttc cccctctagt aaccatacgc tttactcagc gtaactactc cgggttacgt    180

gatgaagaag aggctacgga gattctcggg ctacggccct ggagccactc cggctcctaa    240

agatttagaa gtttgagcac acccgcccac tagggccccc catccagggg ggcaacgggc    300

aagcacttct gtttccccgg tatgatctga taggctgtaa ccacggctga aacagagatt    360

atcgttatcc gcttcactac ttcgagaagc ctagtaatga tgggtgaaat tgaatccgtt    420

gatccggtgt ctcccccaca ccagaaactc atgatgaggg ttgccatccc ggctacggcg    480

acgtagcggg catccctgcg ctggcatgag gcctcttagg aggacggatg atatggatct    540

tgtcgtgaag agcctattga gctagtgtcg actcctccgc ccccgtgaat gcggctaatc    600

ctaaccccgg agcaggtggg tccaatccag ggcctggcct gtcgtaatgc gtaagtctgg    660
```

gacggaaccg actactttcg ggaaggcgtg tttccatttg ttcattattt gtgtgtttat 720
ggtgacaact ctgggtaaac gttctattgc gtttattgag agattcccaa caattgaaca 780
aacgagaact acctgtttta ttaaatttac acagagaaga attaca 826

<210> SEQ ID NO 362
<211> LENGTH: 721
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 362
cccctccccc cccaattacc ttttccccct ctagtaacca tacgctttac tcagcgtaac 60
tactccgggt tacgtgatga agaagaggct acggagattc tcgggctacg gccctggagc 120
cactccggct cctaaagatt tagaagtttg agcacacccg cccactaggg ccccccatcc 180
aggggggcaa cgggcaagca cttctgtttc cccggtatga tctgataggc tgtaaccacg 240
gctgaaacag agattatcgt tatccgcttc actacttcga gaagcctagt aatgatgggt 300
gaaattgaat ccgttgatcc ggtgtctccc ccacaccaga aactcatgat gagggttgcc 360
atcccggcta cggcgacgta gcgggcatcc ctgcgctggc atgaggcctc ttaggaggac 420
ggatgatatg gatcttgtcg tgaagagcct attgagctag tgtcgactcc tccgcccccg 480
tgaatgcggc taatcctaac ccccggagcag gtgggtccaa tccagggcct ggcctgtcgt 540
aatgcgtaag tctgggacgg aaccgactac tttcgggaag gcgtgtttcc atttgttcat 600
tatttgtgtg tttatggtga caactctggg taaacgttct attgcgttta ttgagagatt 660
cccaacaatt gaacaaacga gaactacctg ttttattaaa tttacacaga gaagaattac 720
a 721

<210> SEQ ID NO 363
<211> LENGTH: 625
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 363
attctcgggc tacggccctg gagccactcc ggctcctaaa gatttagaag tttgagcaca 60
cccgcccact agggcccccc atccaggggg gcaacgggca agcacttctg tttccccggt 120
atgatctgat aggctgtaac cacggctgaa acagagatta tcgttatccg cttcactact 180
tcgagaagcc tagtaatgat gggtgaaatt gaatccgttg atccggtgtc tcccccacac 240
cagaaactca tgatgagggt tgccatcccg gctacggcga cgtagcgggc atccctgcgc 300
tggcatgagg cctcttagga ggacggatga tatggatctt gtcgtgaaga gcctattgag 360
ctagtgtcga ctcctccgcc cccgtgaatg cggctaatcc taacccccgga gcaggtgggt 420 ccaatccagg gcctggcctg tcgtaatgcg taagtctggg acggaaccga ctactttcgg 480
gaaggcgtgt ttccatttgt tcattatttg tgtgtttatg gtgacaactc tgggtaaacg 540
ttctattgcg tttattgaga gattcccaac aattgaacaa acgagaacta cctgttttat 600
taaatttaca cagagaagaa ttaca 625

<210> SEQ ID NO 364

<211> LENGTH: 766
<212> TYPE: DNA
<213> ORGANISM: Kobuvirus sp.

<400> SEQUENCE: 364
tttcacaccc tcttttccgg tggtccggac ccagaccacc gttactccat tcagctactt 60
cggtacctgt tcggaggaat taaacgggca ccctacccaa gggttacatg ggaccatatt 120
cctcctcccc tgtaacttta agttttgtgc ccgtattctt gactccaggc ggatgttgtg 180
tcgcccgtcc tgtgaacaaa cagctagaca ctttcctccc ctccctctgg gctgctccgg 240
cagtccactc cctcccccca gcgtaacatg ccccgctgga gtgatgcacc tggaagtcgt 300
ggacgtgggt tagtaacttc ggtgaaaacc cactataatg acaactggtt gaccccccaca 360 ctcaaaggac tcgagtcttt ctcccttaag gctagcccgg ccacatgaat ttgcagctgg 420
caactagtga gtccaccatg tcccgcaacc tcggctgcgg agtgctgttc cccaagcgta 480
tgccttcctt ctgtaagagt gcgcctggca agcacatctg agaagtcgtt ccgctgcgtc 540
gtgccaacct ggcgacaggt gacccagtgt gcgtagactt cttccggatt cgtccggctc 600
ttctctagga aacatgcgtg taaggttcat gtgccaaagc cctgcgcgcg gtgttcttct 660
actgccctag gaatgtgccg caggtacccc tacttcggta gggatctgag cggtagctaa 720
ttgtctacgg gtagtttcat ttccatcttc tcttcaggtc gacatc 766

<210> SEQ ID NO 365
<211> LENGTH: 608
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 365
ttgactccag gcggatgttg tgtcgcccgt cctgtgaaca aacagctaga cactttcctc 60
ccctccctct gggctgctcc ggcagtccac tccctccccc cagcgtaaca tgccccgctg 120
gagtgatgca cctggaagtc gtggacgtgg gttagtaact tcggtgaaaa cccactataa 180
tgacaactgg ttgaccccca cactcaaagg actcgagtct ttctccctta aggctagccc 240
ggccacatga atttgcagct ggcaactagt gagtccacca tgtcccgcaa cctcggctgc 300
ggagtgctgt tccccaagcg tatgccttcc ttctgtaaga gtgcgcctgg caagcacatc 360
tgagaagtcg ttccgctgcg tcgtgccaac ctggcgacag gtgacccagt gtgcgtagac 420
ttcttccgga ttcgtccggc tcttctctag gaaacatgcg tgtaaggttc atgtgccaaa 480
gccctgcgcg cggtgttctt ctactgccct aggaatgtgc cgcaggtacc cctacttcgg 540
tagggatctg agcggtagct aattgtctac gggtagtttc atttccatct tctcttcagg 600
tcgacatc 608

<210> SEQ ID NO 366
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 366
gaattaaacg ggcaccctac ccaagggtta catgggacca tattcctcct cccctgtaac 60
tttaagtttt gtgcccgtat tcttgactcc aggcggatgt tgtgtcgccc gtcctgtgaa 120
caaacagcta gacactttcc tcccctccct ctgggctgct ccggcagtcc actccctccc 180
cccagcgtaa catgccccgc tggagtgatg cacctggaag tcgtggacgt gggttagtaa 240
cttcggtgaa aacccactat aatgacaact ggttgacccc cacactcaaa ggactcgagt 300
ctttctccct taaggctagc ccggccacat gaatttgcag ctggcaacta gtgagtccac 360
catgtcccgc aacctcggct gcggagtgct gttccccaag cgtatgcctt ccttctgtaa 420
gagtgcgcct ggcaagcaca tctgagaagt cgttccgctg cgtcgtgcca acctggcgac 480
aggtgaccca gtgtgcgtag acttcttccg gattcgtccg gctcttctct aggaaacatg 540
cgtgtaaggt tcatgtgcca aagccctgcg cgcggtgttc ttctactgcc ctaggaatgt 600
gccgcaggta cccctacttc ggtagggatc tgagcggtag ctaattgtct acgggtagtt 660
tcatttccat cttctcttca ggtcgacatc 690

<210> SEQ ID NO 367
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 367
tttcacaccc tcttttccgg tggtccggac ccagaccacc gttactccat tcagctactt 60
cggtacctgt tcggaggaat taaacgggca ccctacccaa gggttacatg ggaccatatt 120
cctcctcccc tgtaacttta agttttgtgc ccgtattctt gactccaggc ggatgttgtg 180
tcgcccgtcc tgtgaacaaa cagctagaca ctttcctccc ctccctctgg gctgctccgg 240
cagtccactc cctccccca gcgtaacatg ccccgctgga gtgatgcacc tggaagtcgt 300
ggacgtgggt tagtaacttc ggtgaaaacc cactataatg acaactggtt gacccccaca 360
ctcaaaggac tcgagtcttt ctcccttaag gctagcccgg ccacatgaat ttgcagctgg 420
caactagtga gtccaccatg tcccgcaacc tcggctgcgg agtgctgttc cccaagcgta 480
tgccttcctt ctgtaagagt gcgcctggca agcacatctg agaagtcgtt ccgctgcgtc 540
gtgccaacct ggcgacaggt gacccagtgt gcgtagactt cttccggatt cgtccggctc 600
ttctctagga aacatgcgtg taaggttcat gtgccaaagc cctgcgcgcg gtgttcttct 660
actgccctag gaatgtgccg caggtacccc tacttcggta gggatctgag cggtagctaa 720
ttggacatc 729

<210> SEQ ID NO 368
<211> LENGTH: 650
<212> TYPE: DNA
<213> ORGANISM: Salivirus sp.

<400> SEQUENCE: 368
tctgtcctca ccccatcttc ccttctttcc tgcaccgtta cgcttactcg catgtgcatt 60
gagtggtgca cgtgcttgaa caaacagcta cactcacatg ggggcgggtt ttcccgccct 120
gcggcctctc gcgaggccca cccctcccct tcctcccata actacagtgc tttggtaggt 180
aagcatcctg atcccccgcg gaagctgctc acgtggcaac tgtggggacc cagacaggtt 240
atcaaaggca cccggtcttt ccgccttcag gagtatccct gctagtgaat tctagtaggg 300
ctctgcttgg tgccaacctc ccccaaatgc gcgctgcggg agtgctcttc cccaactcac 360
cctagtatcc tctcatgtgt gtgcttggtc agcatatctg agacgatgtt ccgctgtccc 420
agaccagtcc agtaatggac gggccagtgt gcgtagtcgt cttccggctt gtccggcgca 480
tgtttggtga accggtgggg taaggttggt gtgcccaacg cccgtacttt ggtgatacct 540
caagaccacc caggaatgcc agggaggtac cccgcttcac agcgggatct gaccctgggc 600
taattgtcta cggtggttct tcttgcttcc acttctttct actgttcatg 650

<210> SEQ ID NO 369
<211> LENGTH: 508
<212> TYPE: DNA
<213> ORGANISM: Crohivirus B

<400> SEQUENCE: 369
gtataagaga caggtgtttg ccttgtcttc ggactggcat cttgggacca acccccttt 60 tccccagcca tgggttaaat ggcaataaag gacgtaacaa ctttgtaacc attaagcttt 120
gtaattttgt aaccactaag ctttgtgcac ataatgtaac catcaagctt gttagtccca 180
gcaggaggtt tgcatgcttg tagccgaaat ggggctcgac cccccatagt aggatacttg 240
attttgcatt ccattgtgga cctgcaaact ctacacatag aggctttgtc ttgcatctaa 300
acacctgagt acagtgtgta cctagaccct atagtacggg aggaccgttt gtttcctcaa 360
taaccctaca taataggcta ggtgggcatg cccaatttgc aagatcccag actgggggtc 420
ggtctgggca gggttagatc cctgttagct actgcctgat agggtggtgc tcaaccatgt 480
gtagtttaaa ttgagctgtt catatacc 508

<210> SEQ ID NO 370
<211> LENGTH: 457
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 370
cccccctttt ccccagccat gggttaaatg gcaataaagg acgtaacaac tttgtaacca 60
ttaagctttg taattttgta accactaagc tttgtgcaca taatgtaacc atcaagcttg 120
ttagtcccag caggaggttt gcatgcttgt agccgaaatg gggctcgacc ccccatagta 180
ggatacttga ttttgcattc cattgtggac ctgcaaactc tacacataga ggctttgtct 240
tgcatctaaa cacctgagta cagtgtgtac ctagacccta tagtacggga ggaccgtttg 300
tttcctcaat aaccctacat aataggctag gtgggcatgc ccaatttgca agatcccaga 360
ctgggggtcg gtctgggcag ggttagatcc ctgttagcta ctgcctgata gggtggtgct 420
caaccatgtg tagtttaaat tgagctgttc atatacc 457

<210> SEQ ID NO 371
<211> LENGTH: 742
<212> TYPE: DNA
<213> ORGANISM: Unknown
<220> FEATURE:
<223> OTHER INFORMATION: Description of Unknown:
CVB3 sequence

<400> SEQUENCE: 371
ttaaaacagc ctgtgggttg atcccaccca cagggcccat tgggcgctag cactctggta 60
tcacggtacc tttgtgcgcc tgttttatac cccctccccc aactgtaact tagaagtaac 120
acacaccgat caacagtcag cgtggcacac cagccacgtt ttgatcaagc acttctgtta 180

```
ccccggactg agtatcaata gactgctcac gcggttgaag gagaaagcgt tcgttatccg    240

gccaactact tcgaaaaacc tagtaacacc gtggaagttg cagagtgttt cgctcagcac    300

taccccagtg tagatcaggt cgatgagtca ccgcattccc cacgggcgac cgtggcggtg    360

gctgcgttgg cggcctgccc atggggaaac ccatgggacg ctctaataca gacatggtgc    420

gaagagtcta ttgagctagt tggtagtcct ccggcccctg aatgcggcta atcctaactg    480

cggagcacac accctcaagc cagagggcag tgtgtcgtaa cgggcaactc tgcagcggaa    540

ccgactactt tgggtgtccg tgtttcattt tattcctata ctggctgctt atggtgacaa    600

ttgagagatt gttaccatat agctattgga ttggccatcc ggtgaccaat agagctatta    660

tatatctctt tgttgggttt ataccactta gcttgaaaga ggttaaaaca ttacaattca    720

ttgttaagtt gaatacagca aa                                             742


<210> SEQ ID NO 372
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372

ttaaaacagc ctgtgggttg atcccaccca cagggcccat tgggcgctag cactctggta     60

tcacggtacc tttgtgcgcc tgttttatac cccctccccc aactgtaact tagaagtaac    120

acacaccgat caacagtcag cgtggcacac cagccacgtt ttgatcaagc acttctgtta    180

ccccggactg agtatcaata gactgctcac gcggttgaag gagaaagcgt tcgttatccg    240

gccaactact tcgaaaaacc tagtaacacc gtggaagttg cagagtgttt cgctcagcac    300

taccccagtg tagatcaggt cgatgagtca ccgcattccc cacgggcgac cgtggcggtg    360

gctgcgttgg cggcctgccc atggggaaac ccatgggacg ctctaataca gacatggtgc    420

gaagagtcta ttgagctagt tggtagtcct ccggcccctg aatgcggcta atcctaactg    480

cggagcacac accctcaagc cagagggcag tgtgtcgtaa cgggcaactc tgcagcggaa    540

ccgactactt tgggtgtccg tgtttcattt tattcctata ctggctgctt atggtgacaa    600

ttgagagatt gttaccatat agctattgga ttggccatcc ggtgaagcaa a             651


<210> SEQ ID NO 373
<211> LENGTH: 721
<212> TYPE: DNA
<213> ORGANISM: Unknown
<220> FEATURE:
<223> OTHER INFORMATION: Description of Unknown:
      SAFV sequence

<400> SEQUENCE: 373

cacttattta attcggcctt ttgtgacaag cccctcggtg aaagaacctc tctcttttcg     60

acgtggttgg aattgccatc atttccgacg aaagtgctat catgcctccc cgattatgtg    120

atgttttctg ccctgctggg cggagcattc tcgggttgag aaaccttgaa tctttttctt    180

tggaaccttg gttcccccgg tctaagccgc ttggaatatg acagggttat tttcttgatc    240

ttatttctac ttttgcgggt tctatccgta aaaagggtac gtgctgcccc ttccttctct    300

ggagaattca cacggcggtc tttccgtctc tcaacaagtg tgaatgcagc atgccggaaa    360

cggtgaagaa aacagttttc tgtggaaatt tagagtgcac atcgaaacag ctgtagcgac    420

ctcacagtag cagcggactc ccctcttggc gacaagagcc tctgcggcca aaagccccgt    480
```

```
ggataagatc cactgctgtg agcggtgcaa ccccagcacc ctggttcgat gatcattctc    540

tatggaacca gaaaatggtt ttctcaagcc ctccggtaga gaagccaaga atgtcctgaa    600

ggtaccccgc gtgcgggatc tgatcaggag accaattggc ggtgctttac actgtcactt    660

tggtttaaaa attgtcacag cttctccaaa ccaagtggtc ttggttttcc aattttgttg    720

a                                                                    721
```

<210> SEQ ID NO 374
<211> LENGTH: 675
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 374

```
cctctctctt ttcgacgtgg ttggaattgc catcatttcc gacgaaagtg ctatcatgcc     60

tccccgatta tgtgatgttt tctgccctgc tgggcggagc attctcgggt tgagaaacct    120

tgaatctttt tctttggaac cttggttccc ccggtctaag ccgcttggaa tatgacaggg    180

ttattttctt gatcttattt ctacttttgc gggttctatc cgtaaaaagg gtacgtgctg    240

ccccttcctt ctctggagaa ttcacacggc ggtctttccg tctctcaaca agtgtgaatg    300

cagcatgccg gaaacggtga agaaaacagt tttctgtgga aatttagagt gcacatcgaa    360

acagctgtag cgacctcaca gtagcagcgg actcccctct tggcgacaag agcctctgcg    420

gccaaaagcc ccgtggataa gatccactgc tgtgagcggt gcaaccccag caccctggtt    480

cgatgatcat tctctatgga accagaaaat ggttttctca agccctccgg tagagaagcc    540

aagaatgtcc tgaaggtacc ccgcgtgcgg gatctgatca ggagaccaat tggcggtgct    600

ttacactgtc actttggttt aaaaattgtc acagcttctc caaaccaagt ggtcttggtt    660

ttccaatttt gttga                                                     675
```

<210> SEQ ID NO 375
<211> LENGTH: 628
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 375

```
gtgctatcat gcctccccga ttatgtgatg ttttctgccc tgctgggcgg agcattctcg     60

ggttgagaaa ccttgaatct ttttctttgg aaccttggtt cccccggtct aagccgcttg    120

gaatatgaca gggttatttt cttgatctta tttctacttt tgcgggttct atccgtaaaa    180

agggtacgtg ctgccccttc cttctctgga gaattcacac ggcggtcttt ccgtctctca    240

acaagtgtga atgcagcatg ccggaaacgg tgaagaaaac agttttctgt ggaaatttag    300

agtgcacatc gaaacagctg tagcgacctc acagtagcag cggactcccc tcttggcgac    360

aagagcctct gcggccaaaa gccccgtgga taagatccac tgctgtgagc ggtgcaaccc    420

cagcaccctg gttcgatgat cattctctat ggaaccagaa aatggttttc tcaagccctc    480

cggtagagaa gccaagaatg tcctgaaggt accccgcgtg cgggatctga tcaggagacc    540

aattggcggt gctttacact gtcactttgg tttaaaaatt gtcacagctt ctccaaacca    600

agtggtcttg gttttccaat tttgttga                                       628
```

<210> SEQ ID NO 376
<211> LENGTH: 674
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 376
cacttattta attcggcctt ttgtgacaag cccctcggtg aaagaacctc tctcttttcg 60
acgtggttgg aattgccatc atttccgacg aaagtgctat catgcctccc cgattatgtg 120
atgttttctg ccctgctggg cggagcattc tcgggttgag aaaccttgaa tctttttctt 180
tggaaccttg gttcccccgg tctaagccgc ttggaatatg acagggttat tttcttgatc 240
ttatttctac ttttgcgggt tctatccgta aaaagggtac gtgctgcccc ttccttctct 300
ggagaattca cacggcggtc tttccgtctc tcaacaagtg tgaatgcagc atgccggaaa 360
cggtgaagaa aacagttttc tgtggaaatt tagagtgcac atcgaaacag ctgtagcgac 420
ctcacagtag cagcggactc ccctcttggc gacaagagcc tctgcggcca aaagccccgt 480
ggataagatc cactgctgtg agcggtgcaa ccccagcacc ctggttcgat gatcattctc 540
tatggaacca gaaaatggtt ttctcaagcc ctccggtaga gaagccaaga atgtcctgaa 600
ggtaccccgc gtgcgggatc tgatcaggag accaattggc ggtgctttac actgtcactt 660
tggtttaatg ttga 674

<210> SEQ ID NO 377
<211> LENGTH: 726
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 377
cacttattta attcggcctt ttgtgacaag cccctcggtg aaagaacctc tctcttttcg 60
acgtggttgg aattgccatc atttccgacg aaagtgctat catgcctccc cgattatgtg 120
atgttttctg ccctgctggg cggagcattc tcgggttgag aaaccttgaa tctttttctt 180
tggaaccttg gttcccccgg tctaagccgc ttggaatatg acagggttat tttcttgatc 240
ttatttctac ttttgcgggt tctatccgta aaaagggtac gtgctgcccc ttccttctct 300
ggagaattca cacggcggtc tttccgtctc tcaacaagtg tgaatgcagc atgccggaaa 360
cggtgaagaa aacagttttc tgtggaaatt tagagtgcac atcgaaacag ctgtagcgac 420
ctcacagtag cagcggactc ccctcttggc gacaagagcc tctgcggcca aaagccccgt 480
ggataagatc cactgctgtg agcggtgcaa ccccagcacc ctggttcgat gatcattctc 540
tatggaacca gaaaatggtt ttctcaagcc ctccggtaga gaagccaaga atgtcctgaa 600
ggtaccccgc gtgcgggatc tgatcaggag accaattggc ggtgctttac actgtcactt 660
tggtttaaaa attgtcacag cttctccaaa ccaagtggtc ttggttttcc aattttgttg 720
accgcc 726

<210> SEQ ID NO 378
<211> LENGTH: 549
<212> TYPE: DNA
<213> ORGANISM: Unknown
<220> FEATURE:

<223> OTHER INFORMATION: Description of Unknown:
      GLuc CK dCTG1 sequence

<400> SEQUENCE: 378
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta cgtctgacaa ctcactgact atccacttgc 540
tctaaagtc 549

<210> SEQ ID NO 379
<211> LENGTH: 549
<212> TYPE: DNA
<213> ORGANISM: Unknown
<220> FEATURE:
<223> OTHER INFORMATION: Description of Unknown:
      GLuc CK dCTG1_2 sequence

<400> SEQUENCE: 379
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta cgtcgtacaa ctcactgact atccacttgc 540
tctaaagtc 549

<210> SEQ ID NO 380
<211> LENGTH: 549
<212> TYPE: DNA
<213> ORGANISM: Unknown
<220> FEATURE:
<223> OTHER INFORMATION: Description of Unknown:
      GLuc CK dCTG1_2_3 sequence

<400> SEQUENCE: 380
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta cgtcgtacaa ctcacgtact atccacttgc 540
tctaaagtc 549

<210> SEQ ID NO 381
<211> LENGTH: 549
<212> TYPE: DNA
<213> ORGANISM: Unknown
<220> FEATURE:
<223> OTHER INFORMATION: Description of Unknown:
GLuc CK dAll sequence

<400> SEQUENCE: 381
gtggccacgc ccgggccacc gatacttccc ttcactcctt cgggactgtt ggggaggaac 60
acaacagggc tcccctgttt tcccattcct tcccccttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta cgtcgtacaa ctcacgtact actcactgtc 540
tctaaagtc 549

<210> SEQ ID NO 382
<211> LENGTH: 549
<212> TYPE: DNA
<213> ORGANISM: Unknown
<220> FEATURE:
<223> OTHER INFORMATION: Description of Unknown:
CK SZ1-L1S sequence

<400> SEQUENCE: 382
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tcccccttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga accacccagg aatgccaggg aggtaccccg cttcacagcg 480
ggatctgacc ctgggctaat tgtctacggt ggttcttctt gcttccactt ctttctactg 540
ttcgccacc 549

<210> SEQ ID NO 383
<211> LENGTH: 553
<212> TYPE: DNA
<213> ORGANISM: Unknown
<220> FEATURE:
<223> OTHER INFORMATION: Description of Unknown:
CK Aichi Scan (AV-S) sequence

<400> SEQUENCE: 383
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga ttctttcacc accttaggaa tgctccggag gtaccccagc 480
aacagctggg atctgaccgg aggctaattg tctacgggtg gtgtttcatt tccaatcctt 540
ttatgtcgga gtc 553

<210> SEQ ID NO 384
<211> LENGTH: 667
<212> TYPE: DNA
<213> ORGANISM: Unknown
<220> FEATURE:
<223> OTHER INFORMATION: Description of Unknown:
CK Aichi Loop (AV-L1) sequence

<400> SEQUENCE: 384
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga actgccctag gaatgccagg caggtacccc acctccgggt 480
gggatctgag cctgggctaa ttgtctacgg gtagttttcc tttttctttt cacacaactc 540
tactgctgac aactcactga ctatccactt gctctcttgt gcctttctgc tctggttcaa 600
gttccttgat tgtttttgac tgcttttcac tgcttttctt ctcacaatcc ttgctcagtt 660
caaagtc 667

<210> SEQ ID NO 385
<211> LENGTH: 693
<212> TYPE: DNA
<213> ORGANISM: Unknown
<220> FEATURE:
<223> OTHER INFORMATION: Description of Unknown:
CK SZ1-L2 sequence

<400> SEQUENCE: 385
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcc tgatccccccg cggaagctgc 300 tcacgtggca actgtgggga cccagacagg ttatcaaagg cacccggtct ttccgccttc 360

```
aggagtatcc ctgctagtga attctagtag ggctctgctt gcgttgtcca gaaactgctt    420

caggtaagtg gggtgtgccc aatccctaca aaggttgatt ctttcaccac cttaggaatg    480

ctccggaggt accccagcaa cagctgggat ctgaccggag gctaattgtc tacgggtggt    540

gtttcctttt tcttttcaca caactctact gctgacaact cactgactat ccacttgctc    600

tcttgtgcct ttctgctctg gttcaagttc cttgattgtt tttgactgct tttcactgct    660

tttcttctca caatccttgc tcagttcaaa gtc                                 693


<210> SEQ ID NO 386
<211> LENGTH: 671
<212> TYPE: DNA
<213> ORGANISM: Unknown
<220> FEATURE:
<223> OTHER INFORMATION: Description of Unknown:
      CK Aichi TriLoop (AV-L2) sequence

<400> SEQUENCE: 386

gggggtgggg ggggcctcgg ccccctcacc ctcttttccg gtggccacgc ccgggccacc     60

gatacttccc ttcactcctt cgggactgtt ggggaggaac acaacagggc tcccctgttt    120

tcccattcct tccccctttt cccaacccca accgccgtat ctggtggcgg caagacacac    180

gggtctttcc ctctaaagca caattgtgtg tgtgtcccag gtcctcctgc gtacggtgcg    240

ggagtgctcc cacccaactg ttgtaagcct gtccaacgca tgtgcctggc aagcatatct    300

gagaaggtgt tccgctgtgg ctgccaacct ggtgacaggt gccccagtgt gcgtaacctt    360

cttccgtctc cggacggtgc gttgtccaga aactgcttca ggtaagtggg gtgtgcccaa    420

tccctacaaa ggttgattct ttcaccacct taggaatgct ccggaggtac cccagcaaca    480

gctgggatct gaccggaggc taattgtcta cgggtggtgt ttcctttttc ttttcacaca    540

actctactgc tgacaactca ctgactatcc acttgctctc ttgtgccttt ctgctctggt    600

tcaagttcct tgattgtttt tgactgcttt tcactgcttt tcttctcaca atccttgctc    660

agttcaaagt c                                                         671


<210> SEQ ID NO 387
<211> LENGTH: 523
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387

gggggtgggg ggggcctcgg ccccctcacc ctcttttccg gtggccacgc ccgggccacc     60

gatacttccc ttcactcctt cgggactgtt ggggaggaac acaacagggc tcccctgttt    120

tcccattcct tccccctttt cccaacccca accgccgtat ctggtggcgg caagacacac    180

gggtctttcc ctctaaagca caattgtgtg tgtgtcccag gtcctcctgc gtacggtgcg    240

ggagtgctcc cacccaactg ttgtaagcct gtccaacgcg tcgtcctggc aagactatga    300

cgtcgcatgt tccgctgcgg atgccgaccg ggtaaccggt tccccagtgt gtgtagtgcg    360

atcttccagg tcctcctggt tggcgttgtc cagaaactgc ttcaggtaag tggggtgtgc    420

ccaatcccta caaaggttga ttctttcacc accttaggaa tgctccggag gtaccccagc    480

aacagctggg atctgaccgg aggctaattg tctacgggtg gtg                      523


<210> SEQ ID NO 388
```

<211> LENGTH: 592
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 388
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga tttccttttt cttttcacac aactctactg ctgacaactc 480
actgactatc cacttgctct cttgtgcctt tctgctctgg ttcaagttcc ttgattgttt 540
ttgactgctt ttcactgctt ttcttctcac aatccttgct cagttcaaag tc 592

<210> SEQ ID NO 389
<211> LENGTH: 572
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 389
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg cgttgtccag aaactgcttc 300
aggtaagtgg ggtgtgccca atccctacaa aggttgattc tttcaccacc ttaggaatgc 360
tccggaggta ccccagcaac agctgggatc tgaccggagg ctaattgtct acgggtggtg 420
tttccttttt cttttcacac aactctactg ctgacaactc actgactatc cacttgctct 480
cttgtgcctt tctgctctgg ttcaagttcc ttgattgttt ttgactgctt ttcactgctt 540
ttcttctcac aatccttgct cagttcaaag tc 572

<210> SEQ ID NO 390
<211> LENGTH: 167
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 390
ccctgcagcc gtcaccgtaa gtttgaagtt accgcatatc agcctctgct tcccagcgcg 60
tccaattcct gttcttattg tttcccctcc aggcgttacg cgtgacgacg aactgtgtcg 120
cagctaccac attattccgg agccttcatt ctcgcggctc tgatcgt 167

<210> SEQ ID NO 391

<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 391
ggagaccgcg gccacgccga gtaggatcga gggtacagtc tcc 43

<210> SEQ ID NO 392
<211> LENGTH: 167
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 392
gacaccagga tcactcttgc tctgacccgc cctgtgtaga atagactcat gcttccctaa 60
gacctggatt tcttcccagg cactttcacc cgcctgccct gctccttcag tggactgcac 120
ccagggaggc ggtctctgac tgtcctttac tttctattct ggattgc 167

<210> SEQ ID NO 393
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 393 aaaccccccct aagccgccgc cgccgccacc 30

<210> SEQ ID NO 394
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 394
cccccccaac ccgtcacg 18

<210> SEQ ID NO 395
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 395 gtcacg 6

<210> SEQ ID NO 396
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 396
tctgcgcact cgtaatcagt actaaccccc ctttgtcgga cactatgcga taatcgatcc 60
gcctttttca ccgccttcgg aattttattt acctcaactg atcctggagt ctctcttggt 120
tttcacggag gcctccgccc a 141

<210> SEQ ID NO 397
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 397
ggagaccgcg gccacgccga gtaggatcga gggtacagtc tcc 43

<210> SEQ ID NO 398
<211> LENGTH: 141
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 398
ccccttgaaa cccccgcccc aggttcagtc tctcttcatc cctctgtcct gcatggtgat 60
acaaagaccc tttgtggacc ctaagccatg tagttgctgc tccctccttc cagttgtgaa 120
tattggtttc tgttaatcac a 141

<210> SEQ ID NO 399
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 399 aaaccccccct aagccgccgc cgccgccacc 30

<210> SEQ ID NO 400
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 400
cccccccaac ccgtcacg 18

<210> SEQ ID NO 401
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 401 gtcacg 6

-continued

<210> SEQ ID NO 402
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 402 gtcacg 6

<210> SEQ ID NO 403
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 403
aataagagag aaaagaagag taagaagaaa tataagagcc acc 43

<210> SEQ ID NO 404
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 404
cgaactagta ttcttctggt ccccacagac tcagagagaa cccgccacc 49

<210> SEQ ID NO 405
<211> LENGTH: 7
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 405 agccacc 7

<210> SEQ ID NO 406
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 406
tgatagctaa ctag 14

<210> SEQ ID NO 407
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 407
tagtagctaa ctag 14

<210> SEQ ID NO 408

<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 408
tgatgactga gtga 14

<210> SEQ ID NO 409
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 409
tagtagctag gtag 14

<210> SEQ ID NO 410
<211> LENGTH: 3
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410 taa 3

<210> SEQ ID NO 411
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 411
taatagctaa ctag 14

<210> SEQ ID NO 412
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 412
taactagcta actag 15

<210> SEQ ID NO 413
<211> LENGTH: 579
<212> TYPE: DNA
<213> ORGANISM: Rhopalosiphum padi virus

<400> SEQUENCE: 413
gataaaagaa cctataatcc cttcgcacac cgcgtcacac cgcgctatat gctgctcatt 60
aggaattacg gctccttttt tgtggataca atctcttgta tacgatatac ttattgttaa 120
tttcattgac ctttacgcaa tcctgcgtaa atgctggtat agggtgtact tcggatttcc 180
gagcctatat tggttttgaa aggaccttta agtccctact atactacatt gtactagcgt 240

```
aggccacgta ggcccgtaag atattataac tattttatta tattttattc accccccaca    300
ttaatcccag ttaaagcttt ataactataa gtaagccgtg ccgaaacgtt aatcggtcgc    360
tagttgcgta acaactgtta gtttaatttt ccaaaattta tttttcacaa tttttagtta    420
agattttagc ttgccttaag cagtctttat atcttctgta tattatttta aagtttatag    480
gagcaaagtt cgctttactc gcaatagcta ttttatttat tttaggaata ttatcacctc    540
gtaattattt aattataaca ttagctttat ctatttata                           579
```

<210> SEQ ID NO 414
<211> LENGTH: 675
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 414

```
cttgattcta accttgccgt atggtgccct aacgggttca tttaatcatg cgatgagggt     60
tgctataccg catccattct aaggcgattc aatgcttcat ttaggaattt tgttgacgat    120
taaaaggtac ccccacaaaa acaaaaccaa tcttacttga ttttcgtttt aactgaccac    180
tgcgatccca aattttcgcc ttcttatcaa agtatgttgt gttctttggg tgtacaacct    240
gagaacttgt ctacaactac atattactcg aggaagaaat tcggtttaag ccgtgccttc    300
tcacgtttag tatatctatc tggacacacc ttcttcatct tctaatcccc atctagtctc    360
ctgatcagag acgtcgttat taacaaataa cccccccttgt taataagaga caaagtacaa   420
tcaagctaag ttctcttgga gttcctgtag gaacttagcc attgtgatag agtcataagt    480
ctatgtgcat agacagctct agctcaccat ttccttccca acccatcttt tcatcagctt    540
aactctatga atccgatgca aaaaccattc taacatctta tggtgctttc caagccaaat    600
gagagctcac tcttttgagc cgctatttaa tggacaataa acgttttata gtgtacatca    660
tattgtaaaa acaaa                                                     675
```

<210> SEQ ID NO 415
<211> LENGTH: 636
<212> TYPE: DNA
<213> ORGANISM: Oscivirus sp.

<400> SEQUENCE: 415

```
cctcggtccc tctttccgtc gccgcccacg acgttaaatg cggtgttgtg gtgcttaggt     60
gccacaccac tgctatttgg gtcccccttt cccctatata tgtttgtttg tttatttcaa    120
tttcttgagg attggcacct ccttatgcca aatctaaatc gtggaggatc ccaggctttc    180
tggtctttaa cagaactcca cgtccaggtc atagaaactg gttggtaggc tgcctgagta    240
gtccatttgc tagtagtccc ttgtgaacag ggtggctccc gtttactgct ggtattcccg    300
gtgtaggtcg ccatggtggt aacaccatcc tgcattgtgt gtgaaccagt accgcaagga    360
tagcaaggta tgaacacttg tggacgaaat ggtaagtgat caattcactt tcatggccgg    420
aaggtcacgt ggcaatcatg ccacccaggt accctcctct gggaggatct gagggtgggc    480
taagcagacc ctgccatgtg gctgaacttt tcccttattg ttttactttg taacatttat    540
agttgtgtta gtgatttgtg tgttgtgccc ttgtgagcta tatccagtat aagttcgcag    600
ctagaagtta atccttcgac atcggctgta ttggaa                              636
```

<210> SEQ ID NO 416

<211> LENGTH: 675
<212> TYPE: DNA
<213> ORGANISM: Cadicivirus B

<400> SEQUENCE: 416
caccaaccct tgacctgtaa tgtcagtgga cagagtgctc ctctgttccc ggttaccgtg 60
ttccaggaca cgattgtaat cctgcgcctc accagcgctg cgtgcacgtc tgcataagga 120
aacgtgcctt ccccatgtct ctatcaattc tttggtgagt gaccgcccta gttgctcatc 180
ctatgggatt cttctctcat gggttctttg tggcatgcga atgtcacctt aattggaggt 240
ctttaattag atatcctttc ttcatctttg atatgagtgt cggaatttga ttcctagtct 300
ctgcaaaaca accccacttg atgaattcaa cttttcaacc gcacaaacat aatcaggttt 360
ttaaattgaa tgtttctaaa ttctaaattt agtttattta agtagtttgc catcttgact 420
cgatgtaaaa ttgtcataca agtcttcttt tcttttcttt acactttgaa gtttgcactt 480
agcagtcgtt ctgcacagct ttcgagtttt gtttgatcga catcgcaact tccacccacc 540
tctctttttc tagtgttgaa tgcggctaat cctaacccga gagcaataaa cccaggttta 600
ttgtcgtaac gcgcaagtct tggacggaac cgactataca cacacctctt taccctttag 660
tacacccttg gtacg 675

<210> SEQ ID NO 417
<211> LENGTH: 570
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 417
gcaaaatggg tacgtagtta accactgcgt atcaggattg caggccacga agggtatttg 60
catatctttc tatgcggtat tacggcttaa aacccgttgt atcttgttgt ttgactgcct 120
gtatcactag tggccatttt atttaggtta gagacccctg atagtaggag agttacaaac 180
tctttaaaaa ttgttgaccc cggaaaagat ggtgacccct gtaagtagtt gatcaagaag 240
atctatgcgc tggcatagta atccagtgtt tcctgtttta ggatgacctc tgaaagtaga 300
tgaccgtgga aagtcacgta gtgccccaat aagcacgttt gggcagcgtg cgctatcaca 360
aggcttgatc tccgaggagc cccttgtttt agctggctgg aagccaatga tcttaagtag 420
ataagtgctg ttgcttgtag ttcaacagaa agctttgagt acgtctttct tgcgagaaag 480
aacacatgca ttcttatgct ctcaattcta ttatttttat tttgggcgaa aggaaagctc 540
tcacgcgagt acgaatagcc aaccctttat 570

<210> SEQ ID NO 418
<211> LENGTH: 145
<212> TYPE: DNA
<213> ORGANISM: Plautia stali intestine virus

<400> SEQUENCE: 418
gctgactatg tgatcttatt aaaattaggt taaatttcga ggttaaaaat agttttaata 60
ttgctatagt cttagaggtc ttgtatattt atacttacca cacaagatgg accggagcag 120
ccctccaata tctagtgtac cctcg 145

<210> SEQ ID NO 419
<211> LENGTH: 312
<212> TYPE: DNA

<213> ORGANISM: Unknown
<220> FEATURE:
<223> OTHER INFORMATION: Description of Unknown:
PV Mahoney sequence

<400> SEQUENCE: 419

```
atgagtctgg acatccctca ccggtgacgg tggtccaggc tgcgttggcg gcctacctat     60

ggctaacgcc atgggacgct agttgtgaac aaggtgtgaa gagcctattg agctacataa    120

gaatcctccg gcccctgaat gcggctaatc ccaacctcgg agcaggtggt cacaaaccag    180

tgattggcct gtcgtaacgc gcaagtccgt ggcggaaccg actactttgg gtgtccgtgt    240

ttccttttat tttattgtgg ctgcttatgg tgacaatcac agattgttat cataaagcga    300

attggattgg cc                                                        312
```

<210> SEQ ID NO 420
<211> LENGTH: 577
<212> TYPE: DNA
<213> ORGANISM: Reticuloendotheliosis virus

<400> SEQUENCE: 420

```
ggggtcgccg tcctacacat tgttgtgacg tgcggcccag attcgaatct gtaataaaag     60

ctttttcttc tatatcctca gattggcagt gagaggagat tttgttcgtg gtgttggctg    120

gcctactggg tggggtaggg atccggactg aatccgtagt atttcggtac aacatttggg    180

ggctcgtccg ggattcctcc ccatcggcag aggtgcctac tgtttcttcg aactccggcg    240

ccggtaagta agtacttgat tttggtacct cgcgagggtt tgggaggatc ggagtggcgg    300

gacgctgccg ggaagctcca cctccgctca gcaggggacg ccctggtctg agctctgtgg    360

tatctgattg ttgttgaacc gtctctaaga cggtgatact ataagtcgtg gtttgtgtgt    420

ttgtttgtta ccttgtgttt gttcgtcact tgtcgacagc gccctgcgaa ttggtgtacc    480

cacaccgcgc ggcttgcgaa taatactttg gagagtcttt tgcctccagt gtcttccgtt    540

tgtactcgtc ctcctctccc tctccggccg ggatggg                             577
```

<210> SEQ ID NO 421
<211> LENGTH: 675
<212> TYPE: DNA
<213> ORGANISM: Tropivirus A

<400> SEQUENCE: 421

```
tgtcgcatgt tgccaacatc aaaattctgg gagagtcgcg aactccttaa cactgccttg     60

cctcgacgga gccgttgtta tagtgtcgac gggatacaaa cattaaacta aacccacttg    120

cctcgacgga acccccttacc ttttatttta ttttatagta tgaaagtgaa tcttgtatga    180

atgttcatag aaaactgcaa atgagtacca cgtctaacat gagagaatga tactggagaa    240

atccaagttt agaagtcact acgaatccca gcggaaacaa gggaattctg agcttctaat    300

aggcgtttaa gactatttgc aaaattctgg tgcgtaagtg atattttcat tgcgtagaac    360

gctggtaacc actccggcta gtataagcat tgttagtcac ttattatgaa actccacact    420

atcctttctg gagaagcaca caaacttaca tggtaaagct agaccattat cttaagcggt    480

gagtacactg caaccttgta acaatgcttg tatgactact ttttgtatat cttgagcaat    540

attgttgagg tggacatgtc caaaggtaat gttgttggga atggaggggt ccattttccc    600

gtgcacgtag tgtactagta ttgggtgata gccttgcggc ggatcaacca tgtattttaa    660

tccgttgact ttcac                                                     675
```

<210> SEQ ID NO 422
<211> LENGTH: 592
<212> TYPE: DNA
<213> ORGANISM: Symapivirus A

<400> SEQUENCE: 422
ttgggaaatc cccaatgctt ctttcaacac cgcctgacta tgcggtggcg cttcggctca 60
aacaactagt cacttccccc tcttaactac tacccaagac ttctaactac ccttacctac 120
ttatttgtct aaatttcaaa cttttattct cacgcgtctt ataaacatct tttctatttg 180
ttatggtatg ttttgtgatt tgtgtggtgt atttcattta atgggatcta gtggaccgtg 240
ccccggttgg gtatccgctc cctttaaatg tttgcaagca ctcttgacat tataacctat 300
catttagttt acttgtttgt atgatcgtat ttctgaatcg taacatttat gcaattcttt 360
ctcgccgaga cttgtctagg agataaagtt cctgcatatt tagtgttacg gttgtataat 420
ggagacttag atagcttcac actgaggacg ctttttcgct atccttttga cctgattcag 480
gccagtgtgg agttaatgat tgtatggatg ggccctacaa tttgtctaag acttggtgat 540
agcctcgcgg ccgctcgcca tttatacaac tgaatagcgg ttgaaactct ct 592

<210> SEQ ID NO 423
<211> LENGTH: 591
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 423
tcacgcgctt ttccggtggt cacccaccgt tagggagcgc cagcgttcgc gcttccgcta 60
ccaggtgaca cactcctttc ccctccccca ttcccgttcc catcctctgg actggtttct 120
cctcacgatt gaccagcagc tgggagctgt taccagacgt tggacagtaa gtcccggatg 180
cactataggg ctggtggcta gtgcttggta agcactcaac gccataccta atgtgtacct 240
cggcttgccc tcctggtcgt ggtgaccggc tgtttctctt cccttggctc cagacgggct 300
ggtgtcctac caccaccgtt gcatgcagac ctccccctgc gcactcgaac gccctgtccc 360
agcagggtta gtatgtgctg tgcagatctg catgtgacac cccatccact ggtagagcag 420
gaagttgccc tagctaacgc ggcaagtatt actttccgct acacgtcctt gagattcctc 480
ggacctctgg aactagggtg actgtgggct tgggaaaacc caccttggtc ctgtactgcc 540
tgatagggtc gcggctggcc gaccagtgga tgtagccagt tgttttggga t 591

<210> SEQ ID NO 424
<211> LENGTH: 538
<212> TYPE: DNA
<213> ORGANISM: Rosavirus C

<400> SEQUENCE: 424
cagggagatc tccatgaata atcttttcca ccctctttag cgtctatgct attgaggacg 60
ggttggagcc ccgttgaccc agcgtcagag tgtgtcggta gcaggctttc tgctctcgcc 120
ccatgccggc cacacctccc attagtgatg tgaaggttgt aagttacatg tgaaaaggtt 180
tctaataatt gagctgaatg tagcgattac ctaaggtgag cggattcccc cacgtggtaa 240
cacgtgcctc tcaggccaaa agccaaggtg ttaaaagcac cccttaggta ggccactacc 300
ccgtggcctc agttctctta gaagattcac ttagtagtgt gtgcactggc aactcttaag 360

```
cagagctagt gagtgggcta aggatgccct gaaggtaccc gcaggtaacg ttaagacact    420

gtggatctga tcaggggctc gagtgctgaa gctttacaga ggtagctcga gttaaaaaac    480

gtctatgccc ctcccccacg ggagtggggg ttcccccaca ccaattttag attgcact      538


<210> SEQ ID NO 425
<211> LENGTH: 675
<212> TYPE: DNA
<213> ORGANISM: Rosavirus sp.

<400> SEQUENCE: 425

ccaggcatgg cgttaaacat gcattccctt cccctagtaa cctcccttcg ccccttcccc     60

acgttgtacc ccctccgaga tggctgctaa ggcgcttgct gctacagcag tctcgtgttt    120

cgggtgttat aagtgctttc ttttccactc cactccctgc ctatggggag cggaacggcc    180

ttgtctcggt cgttgcttct tgcagatctt cacccctcca ggctttctgg actcgccagg    240

ggtggagtag taggcgcact gtctaagtga aggtagcagt gttgttggcg aagagttgtg    300

gacctacttt gagtttgtag cgatcatcca gagctagcgg atctccccac gcggtaacgc    360

gtgcctctag gcccaaaagg cacggtgttc acagcaccct ttggatggcg ggggtgcccc    420

cctccgcact taaagtagaa aaacagctta gtagtcaaat aacatggctt tcctcaagca    480

ttcagtgcta catgggactg aaggatgccc agaaggtacc cgcaggcaac gataagctca    540

ctgtggatct gatctggggc cctgggccag gtgctataca cctggttaaa accaaatctg    600

gtagtcaggg ttaaaaaacg tctaagtccc acccccccgg ggacgggggg ttcccttaaa    660

ccctcaactg acacc                                                     675


<210> SEQ ID NO 426
<211> LENGTH: 656
<212> TYPE: DNA
<213> ORGANISM: Unknown
<220> FEATURE:
<223> OTHER INFORMATION: Description of Unknown:
      Rhimavirus A sequence

<400> SEQUENCE: 426

cgaattccgg acatctcctt tcgggggcga gcgtcaccgt gcccctcatg gaggcaactg     60

tgcctctaat cggtgaccca ctgagaaaat tttctttcta cgtggctaaa caatgcaact    120

ttataataac acaaatttaa tgcttaatct taacaccaaa gatttgaaca tatgtttgga    180

aagtggcaca cttcaaacat tgcatagttg ctaggggtga agtcccttta aggggttgca    240

gaggatcttt cctctttatg agcggctagg agtatcttct tgatattatg tggtcgtgca    300

actcacttcc cagatgtatg acggtgtact aagcgattgg aactagtcat aacctctttg    360

aattttggta ttgcgagtct agcaggggga tatttaccgc taaagggtga cacactcgtg    420

agggtggcct ttggtgtgtg tatatttatt ccgcccatct tgcatggggt gctaaaattc    480

taatgctgtg aaataaccat tttctgaata cattctctac atttggagtc aaatatgagg    540

aatgccactc aggtaccctt gacatgatct tggatctgag agtgggctaa ttatctaatt    600

atttggcgac tttctaaaat cttctgtttt tagtggtgac aatttatggt tataaa        656


<210> SEQ ID NO 427
<211> LENGTH: 487
<212> TYPE: DNA
<213> ORGANISM: Rafivirus sp.
```

<400> SEQUENCE: 427
gtgtccggga agcgactcaa gcttttgact gagtctctac accttcatcc gtaacatctt 60
taagtttatg tgcctatgga cctctagtgc actgccatca ccgggggtgt attggactgg 120
tttttccaca atccattcat cctgaggaat tttggctttg ttactaggat ggtcccacca 180
cacgcttatc tgtgcctatt gtgtcaacca tgttcttaag tagttgtgcc cgtgggtgag 240
tagataacca caacaatccg ataaagcatc tcgcaaggat gtgagtaatg gagtgtatgt 300
gctacagaga cccacaacct gaaccaagag agacacagtg aggattgtaa agggggaact 360
ctttgaaagg gcatgtcccg caattcctac tgactgacac cgggggttgg tgtcggtgga 420
ttttagcaaa tcctgttact gggtgatagc cttgtgcact tcacttggtt cttgtataag 480
tgctgta 487

<210> SEQ ID NO 428
<211> LENGTH: 560
<212> TYPE: DNA
<213> ORGANISM: Rafivirus sp.

<400> SEQUENCE: 428
tgcgaattta ttcgcacagt ctcttttccc ccatcttgtg tgtgtgatgg ggtaagccgc 60
agagtaatac ctactctgct gcaaacacac tcactctttt ctatctactt tatatcatgt 120
aataataagt agggaacata ttcaattcat attgttcatc tcactgaacc cgcatgaagg 180
actgcattgc atatcctgga cgaagtgacg tggaatattt ggacatttat ggattggaca 240
ccattacgct ttgtgcctct acggagatgt aaccataatc ttaagtagta gtaccccagc 300
acaagaggat aaagtggcat acacgacaac gggtgttgct cgcaccttag taatgtggat 360
gttcaccctt ggagcgtgct gaaactctgt gggtaaagac acacattagt acaaatgtgg 420
gggaactcac tgaaagggca tgtcccgtgt actggtgtgc cggaaagtgg gggtcgcttt 480
ctggagaact tagtagttct tgttattggg tgatagcctt gcggcggatc aactcacagt 540
tttaatccgt tgttttgcat 560

<210> SEQ ID NO 429
<211> LENGTH: 675
<212> TYPE: DNA
<213> ORGANISM: Poecivirus sp.

<400> SEQUENCE: 429
actacacaat cgcaacacgc gcaagtttgt agtttgattg gcgtgcaaat gtcaaatcaa 60
gcatataaca caatttggtg gctgttggtg tttgttatag gaattttggt tgtgttgaaa 120
ttgtggatgt gtaggaaata tgcacaatta cgtcagcgtc aggagtttta taacctggcg 180
caacaccaaa atggtcttcg cgctttaaca tcaccagcga ggtgtaaaca aattgaagtt 240
gaattagatc gtgtataggc cagggaacca tccctcccaa cgccacatct tgtggggaag 300
ttgggataat ggtgggtcta tatgaattgg tctgtagacc cacagtgaag agtgaatagt 360
atgcttgcgg ttccatttgt taatggtcta gcatgggtgg gggcggcaac cccgtgaggg 420
gttccccact ggccaaaagc ccaggggtta gtcatttcaa ccaaggaagc tggtaacctg 480
gtgacctgaa cttgagtggt gagaccccct tgctagagtg tgtaaaccga ttgtaagcat 540

```
tttgtttgct tagtatctgt ggtataagca gtcaattttg tataggctca aggctgtggt    600

agttagtaga tgcccggaag gttattactg atccggggac cgtgactata cattaggtaa    660

accggtttaa aaacc                                                     675
```

```
<210> SEQ ID NO 430
<211> LENGTH: 519
<212> TYPE: DNA
<213> ORGANISM: Unknown
<220> FEATURE:
<223> OTHER INFORMATION: Description of Unknown:
      Megirivirus A LY sequence

<400> SEQUENCE: 430

ttcgggacac tggatgggcg acttggtggg gctgccactc tatcttgacc tttcgttact     60

gactttcgga tctctgactc ctccttgtct cttgcgtttg gtccacggac ggactaattg    120

gaatgtttac tggctaagcc tcgttctgaa ataccctagc caatgggttg tagtaggatc    180

ctggtgtttc cattaaacct cttccgacca tagtagctag agttatggct gtgtaggatg    240

tgggtaagac cgctttttgc gtatctccca caagacaccg gattatggat gtgtccgctg    300

gataaggctc gaaacctccc aactgaaggt ggtgctgaaa tattgcaagc ctaggttgtg    360

tagaggcaag tagatgcctg ccgcgacatt cgtcttccgc ccttttgggt tagtagtgta    420

cctacatgga cgtggggctg ggaatcccca ccttgcataa cactggttga tagacctgcg    480

gctggtcaag ttactatggt ataaccagtt gaaatggct                           519
```

```
<210> SEQ ID NO 431
<211> LENGTH: 675
<212> TYPE: DNA
<213> ORGANISM: Unknown
<220> FEATURE:
<223> OTHER INFORMATION: Description of Unknown:
      Megirivirus E sequence

<400> SEQUENCE: 431

gcttggcaac ctcatatcgt tactctgccg accagtctgg gtcgtgtggc cacacaatgg     60

gattcgttct gttgtgtaga gtcacatggc attactgggc tgatcggtgg ggatccgttg    120

ccacccctaa acccttacat ttactggact gcttttcttg gccccggaat gattcgctca    180

cccgcgatga ggactgttgt tcttattatg gcaggattac gcgtctggtc cgcgtaagga    240

ctaattccta tgtttatacg ttactacctt gttctgaacg gtgggcgcca ccccgcctag    300

taggatcctg gcttatcgtg tagacctcta gggaccacat tagctagagt gtaggctgct    360

atggatggag tagtgacccc tttttgggta tcactctcta agactccgga atgtgtcata    420

gtacgctgga aatccttact tgtttttcca tgagggggag gtggtgctga aatattgcaa    480

gccacccctc ggttaaaaca gtttggtgcc gcttatgcca tattaccgcc ccttgtagtt    540

gggctgtttt tgcagctccg ggttagtaga gtaccatagt ggacgcggtg ttgggaatca    600

ccgccttggc tgcacactgc ttgatagagc tgcggctggt caagctaatt gtggtataac    660

cagttgattt ggcat                                                     675
```

```
<210> SEQ ID NO 432
<211> LENGTH: 639
<212> TYPE: DNA
<213> ORGANISM: Unknown
<220> FEATURE:
<223> OTHER INFORMATION: Description of Unknown:
      Megirivirus C sequence
```

<400> SEQUENCE: 432
ttcccgaccg gtctggcaaa ccggacggtt atcctggtta gatgtctgat ggttgctgga 60
acgtggtggc tactgctgcc accttctggc ttcctttaat gggcatctag ctgggttctt 120
tgccacaatc catcttactc tcttacccat tttctattac ccagacttgt tgttaactgg 180
taaagttgac ctactggctt cgttttgaga ctattctggt gttggtggac actctttcca 240
caagtagatt gtatggagtt catgctcgtt ttgaaccggg aatggcacaa cccgtagtag 300
gatcttgcct ctgccatact aatctgcgcc tgttgctttt agactatggg ctgctaagga 360
tgacattgga accccttttt ggatattcca tgtcaagtca actgtttcat ctggtgtacg 420
ctggaaatcc ttgttccgag gtcttgtctg gaggtggtgc tgaaatattg caagccacag 480
gcagttcctt ggacttggtg ccgctatcag atgctacacc ctctatgggc aaatgttgaa 540
ccttagtgga cgcgtgagat gggaatccac gccggccata gactggctga taagctcgcg 600
gctgatcgag ttgcaacagt aatcagttga tttgccact 639

<210> SEQ ID NO 433
<211> LENGTH: 497
<212> TYPE: DNA
<213> ORGANISM: Ludopivirus sp.

<400> SEQUENCE: 433 tagacccccca cctagccctt ttccccgtca gtggggggct tactcactgg gcatctgtta 60
atctggccta actagattga caccactccc ttggaacgta actccacgct aactcactgg 120
ctctacgcac agacacacgg tctttctgct atccccgggg aagataccag atggcgaccg 180
gctgtcccag cggcctagta gctactcggg ttgagtaccc accacggttt tgacgcctgc 240
taaaattcaa gagacagagg taggggtgct tagtgtgtgg gggaagttcc cacaagcgag 300
gcaaagcatt gctccctcgc gtcaccgggt gcaaggtaaa ttggctggac ttccgctcta 360
cccttgctac tcgccctctt cggagggttc gaagtgacac taggtatacg catggttggg 420
aaaccatgcc tggcctacta ctgggtgata gcctggcggc gggtccgtct cttggcttat 480
acccgttgat ttgggat 497

<210> SEQ ID NO 434
<211> LENGTH: 610
<212> TYPE: DNA
<213> ORGANISM: Livupivirus sp.

<400> SEQUENCE: 434
tatctacatg gggatccagg ctgtatggaa tgtctgtctt aacaagcact ataccagaaa 60
gatccaccca aagtggtggg actgggactg tgaggtgaga aatcccgaaa ccagccttct 120
caagcgtcgg acgatctttc tgttttagtg aacaccttgc cttttaaatg gatgacaaca 180
ccccttcagc aaatcgcaat ctgaaatccc aaaagactgt ttagccgaac tctggtaatc 240
actccggaga agtaggatac gcagcccctg tggactcttg atttcaggac tcaaggtagc 300
tagagctgga acttcatgga atgacaaagg aatatatgca cattgtgcgc tttcctggcc 360
ttgtagcccg tcgtgaggat atgtcgttgg gaatcgacat cttagtccag tactgcttga 420
tagagtgtcg gctggcacag ttacctgaga ataagtcagt tgtacttaac atgaacaaaa 480

```
aaaataacta ccacaactac cacaatctac caatacttga attatgctga atctcgtaca    540

gtaaaaacgt tccgtggaag gacaagtatt gaagtgcggt tacatcatcc gatacgcgct    600

ggatccctca                                                            610
```

<210> SEQ ID NO 435
<211> LENGTH: 629
<212> TYPE: DNA
<213> ORGANISM: Aichivirus A

<400> SEQUENCE: 435

```
cacccataca cccccacccc cttttctgta actcaagtat gtgtgctcgt aatcttgact     60

cccacggaat ggatcgatcc gctggagaac aaactgctag atccacatcc tccctcccct    120

tgggaggacc tcggtcctcc cacatcctcc ctccagcctg acgtatcaca ggctgtgtga    180

agcccccgcg aaagctgctc acgtggcaat tgtgggtccc cccttcatca agacaccagg    240

tctttcctcc ttaaggctag ccccgatgtg tgaattcaca ttgggcaact agtggtgtca    300

ctgtgcgctc ccaatctcgg ccgcggagtg ctgttcccca agccaaaccc ctggcccttc    360

actatgtgcc tggcaagcat atctgagaag gtgttccgct gtggctgcca gcctggtaac    420

aggtgcccca gtgtgcgtaa ccttcttccg tctccggacg gtagtgattg gttaagattt    480

ggtgtaaggt tcatgtgcca acgccctgtg cgggatgaaa cctctactgc cctaggaatg    540

ccaggcaggt accccacctt cgggtgggat ctgagcctgg gctaattgtc tacgggtagt    600

ttcatttcca attcttttat gctggagtc                                       629
```

<210> SEQ ID NO 436
<211> LENGTH: 675
<212> TYPE: DNA
<213> ORGANISM: Aichivirus sp.

<400> SEQUENCE: 436

```
tactccattc agcttcttcg gaacctgttc ggaggaatta aacgggcacc catactcccc     60

cccacccccc ttttgtaact aagtatgtgt gctcgtgacc ttgactccca cggaacggac    120

cgatccgttg gtgaacaaac agctaggtcc acatcctcct ttcccctggg agggtccccg    180

ccctcccaca tccccccccc agcctgacgt gtcacaggct gtgtgaagcc cccgcgaaag    240

ctgctcacgt ggcaattgtg ggtcccccct tcatcaagac accaggtctt tcctccttaa    300

ggctagcccc ggcgtgtgaa ctcacgttgg gcaactagtg gtgtcactgt gcgctcccaa    360

tctcggccgc ggagtgctgt tccccaagcc aaacccctgg cccttcacta tgtgcctggc    420

aagcacacct gagaaggtgt tccgctgtgg ctgccagcct ggtaacaggt gccccagtgt    480

gcgtaacctt cttccgtctt cggacggtgg tgattggtta agatttggtg taaggttcat    540

gtgccaacgc cctgtgcggg atgaaacctc tactgcccta ggaatgccag gcaggtaccc    600

caccttcggg tgggatctga gcctgggcta attgtctacg ggtggtttca tttccaattc    660

tttcatgtcg gagtc                                                      675
```

<210> SEQ ID NO 437
<211> LENGTH: 675
<212> TYPE: DNA
<213> ORGANISM: Aichivirus sp.

<400> SEQUENCE: 437
tactccattc agcttcttcg gaacctgttc ggaggaatta aacgggcacc catacacccc 60
cacccccttt tctgcaactt aagtatgtgt gctcgtaatc ttgactccca cggaacggat 120
cgatccgctg gagaacaaac tgctagatcc acatcctccc ttcccctggg aggaccccgg 180
tcctcccaca tcctcccccc agcctgacgt aacacaggct gtgtgaagtc cccgcgaaag 240
ctgctcacgt ggcaattgtg ggtccccccct tcaccaagac accaggtctt tcctccttaa 300
ggctagcccc gatgtgtgaa ttcacattgg gcaactagtg gtgtcactgt gcgctcccaa 360
tctcggccgc ggagtgctgt tccccaagcc aaacccctgg cccttcacta tgtgcctggc 420
aagcatatct gagaaggtgt tccgctgtgg ctgccagcct ggtaacaggt gccccagtgt 480
gcgtaacctt cttccgtctc cggacggtag tgattggtta agatttggtg taaggttcat 540
gtgccaacgc cctgtgcggg atgaaacctc tactgcccta ggaatgccag gcaggtaccc 600
caccttcggg tgggatctga gcctgggcta attgtctacg ggtagtttca tttccaattc 660
ttttatgtcg gagtc 675

<210> SEQ ID NO 438
<211> LENGTH: 610
<212> TYPE: DNA
<213> ORGANISM: Kobuvirus sp.

<400> SEQUENCE: 438
gtaacttcaa gtgtgtgtgc tcgtaatctt gactcctgcc ggaatgccgc ccggttcagt 60
gaacaaacag ctaggcaagt ccctcccttc ccctgtggtc ggttctcacc ggccaccatc 120
cctcccccag cctgacgtgt tacaggctgt gcaaagcccc cgcgaaagct gctcacgtgg 180
caattgtggg tccccccttt gtcaagacac cgagtctttc tcccttaagg ctagcccggt 240
cccacgaacg tggaactggc aactagtggt gtcactacac gcctccgacc tcggacgcgg 300
agtgctgttc cccaagctgt aaccctgacc caagactgtg ctgcctggca agcaccgtct 360
gggaagatgt tccgctgtgg ctgccaaacc tggtaacagg tgccccagtg tgtgtagtct 420
tcctccagtc tccggactgg cagtcttgtg taaagatgca gtgtaaggtt caagtgccaa 480
atccctggaa ggagtgaccc tctactgccc taggaatgct gtgcaggtac cccccaacttc 540 ggttggggat ctgagcacag gctaattgtc tacgggtagt ttcatttccc atcctctctt 600
ttttggcatc 610

<210> SEQ ID NO 439
<211> LENGTH: 576
<212> TYPE: DNA
<213> ORGANISM: Kobuvirus sp.

<400> SEQUENCE: 439
tttgaaaagg gggtgggggg gcctcggccc cctcaccctc ttttccggtg gccacccgcc 60
cgggccaccg ttactccact ccactccttc gggactggtt tggaggaaca taacagggct 120
tcccatccct gtttaccctt actccactca cccctcccct tgaccaaccc tatccacacc 180
ccactgactg actcctttgg atcttgacct cggaatgcct acttgacctc ccacttgcct 240
ctcccttttc ggattgccgg tggtgcctgg cggaaaaagc acaagtgtgt tgttggctac 300
caaactccta cccgacaaag gtgcgtgtcc gcgtgctgag taatgggata ggagatgcca 360
ataacaggct cgcccatgag tagagcatgg actgcggtgc atgtgacttc ggtcaccagg 420

-continued ggcatagcat tgctcacccc tgaatcaagt catcgagatt tctctgacct ctgaagtgca 480
ctgtggttgc gtggctggga atccacgctt gaccatgtac tgcttgatag agtcgcggct 540
ggccgactca tgggttaaag tcagttgaca agacac 576

<210> SEQ ID NO 440
<211> LENGTH: 513
<212> TYPE: DNA
<213> ORGANISM: Kobuvirus sp.

<400> SEQUENCE: 440
ccaccgttac ttcactccac tccctcggga ctggtttgga ggagcataac agggcttccc 60
atccctgttc accctcaata ccacccaccc tttccctcaa ccatccctat ccacacccca 120
ctgactgatt cccttggatt ttgacctcag aacgcctact tgacctccca cttgcctttc 180
ccttctcgga ttgccggtgg tgcctggcgg aaaaagcaca agtgtgttgc aggctaccaa 240
actcctaccc gacaaaggta cgtgtccgcg tgctgagtaa tgggatagga gatgcctaca 300
acaggctcgc ccatgagtag agcatggact gcggtgcatg tgacttcggt caccacgggc 360
atagcattgc tcacccgtga atcaagtcat tgagattcct ctgacctctg aagtgcactg 420
tggttgcgtg gctgggaatc cacgcttgac catgtactgc ttgatagagt cgcggctggc 480
cgactcatgg gttaaagtca gttgataaga cac 513

<210> SEQ ID NO 441
<211> LENGTH: 675
<212> TYPE: DNA
<213> ORGANISM: Kobuvirus sp.

<400> SEQUENCE: 441
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga ttctttcacc accttaggaa tgctccggag gtaccccagc 480
aacagctggg atctgaccgg aggctaattg tctacgggtg gtgtttcctt tttcttttca 540
cacaactcta ctgctgacaa ctcactgact atccacttgc tctcttgtgc ctttctgctc 600
tggttcaagt tccttgattg tttttgactg cttttcactg cttttcttct cacaatcctt 660
gctcagttca aagtc 675

<210> SEQ ID NO 442
<211> LENGTH: 675
<212> TYPE: DNA
<213> ORGANISM: Kobuvirus sp.

<400> SEQUENCE: 442
gggctataaa tatgggcatt cctcttcccc cttccccttt tgaagatgag tgcgcatatt 60
cttgactccg cctggattgg ccgcccaagg cgtgaacaag cagctaggcc accatgacac 120
tgcggtggtg tccgaacccg cgggtgcctt cacgggcacc tgtggtatgt aggactccca 180
ccgtggtctt ccctttcccc ctcaatcttt ccccctggtt cgactaacgg gaccagtgct 240

```
ggaacctgtc cggtgaacgg tatagcaggc ccccccggca gaaacacccg gtgcttaccc    300

cttaaggcta gccccccttcc atgaatttgg ttggggcaac tagtgggtgt acagttggcg    360

tgaaccctcc ggtctaggag tgctcttgcc caatcctctg tgtgtgcctt gcagtaggga    420

ctggcaatcc ttcgcgtagg tgatccgctg tgccatgcca tcctggcgac aggaggccca    480

gtgtgcgcaa cctacgtccc ttctgggtgc tgcattgcat tacctttgga gtaagcttgg    540

tgtgccgaaa ccccagggtt tacgtaccac tcgtggtgtg aggaatgtgc cgcaggtacc    600

ccatccttga ggtgggatct gagcggtagc taattgtcta gcaccacttt cttccttttt    660

tctttgctgg tcacg                                                      675
```

<210> SEQ ID NO 443
<211> LENGTH: 604
<212> TYPE: DNA
<213> ORGANISM: Aalivirus sp.

<400> SEQUENCE: 443

```
ttgaaagggg gtgctcaggg tagctccctg agctcttccc tccaccctct ttcaacgtct     60

ggcccacgat acgggccacc tttcaatctt aactaactat ccctttaatc tatttggatt    120

ttctggttta gaataatttg gaacacataa ttggattatc ttttaggatt gtggatagga    180

tttgttcggg atatcactcc cttcctgtgc taacacatat tctaattccc tcctttgtct    240

attatctctt ggaggtggtg ctgaaatatt gcaagccact tgagtgtata gatgaagtag    300

gctcaagatg aatgttgtgt tactcaaggc aagtgtagct atcactaaga tattggtaac    360

gtgaaacgga ttaccggtag tagcgtgatc ttccgtctta gtgctctagt gactagagga    420

caacgacatg gcatcacata tcttaaccct ccagttttgg catccgggac agaatgggct    480

ggatatccgc tttctttctg ggtatgtga tgggtggtat tggggtaacc accttgacca    540

tgacgctcga taagagtgac cgcctgatca ttgaaacctc tagtataaaa ttcaggctga    600

aatc                                                                  604
```

<210> SEQ ID NO 444
<211> LENGTH: 445
<212> TYPE: DNA
<213> ORGANISM: Grusopivirus A

<400> SEQUENCE: 444

```
tgcctgagta ggattgtgaa tttaggtatg agagggttag ccaacccatt ctgaaccata     60

atagatacgt caatctgaat ccatctaaat ctatctctta ggcagtggtg ctgaaatatt    120

gcaagctact agggatagac gtgatctgat tcaagaacct atctaatgtg gtgatgagaa    180

ggctaggttt atccatagta atcccttgtt ctgaacaggc aatgcacatg ctctagtagg    240

atctcgggct ctgcgattgg ctctaaaccg accaatccag gtagaggcac taagtgtagg    300

acttgccaaa atgtattaca tgctggtacc gactcactag tctggaaact ccacactgaa    360

agtgactggg gggggcccca tcacatttgt gctactgctt gatagagttg cggctggtca    420

acttggattg gtataaccag ttgaa                                           445
```

<210> SEQ ID NO 445
<211> LENGTH: 537
<212> TYPE: DNA
<213> ORGANISM: Grusopivirus B

<400> SEQUENCE: 445
gccatccgta ggttctggta aggttccatc aactgttggg gcgctagttg ctatgaccgc 60
attcacggac ggatgattta tagtatcacc caatccgggc acaacttctt tagccacttc 120
ttccacatta ctaagggctc tcttgccgag tttcaacgtc tagtccacga cacggacctt 180
cctacttttc tatcttctta ttttctctac taaattggta tctggtactg aagatatgcg 240
gattgtgatt ttgtgcctgt ctaaactaac cctattctag ggttaggtgg gtaccatata 300
ctaatggtga acaggattac ctatgtatcc attagtccct atggatctgg cgacccacaa 360
actcatgttc atagagaggc taagctgagt gctcgccgaa taagcattgc ttcaggtgcc 420
gactattgtc tggaaaccac tcagtgatag ctataggggg gggccccgta gcatctgcct 480
tactgcctga tagggtggcg gctggtccat gaacatgcag taaccagttg acttgac 537

<210> SEQ ID NO 446
<211> LENGTH: 562
<212> TYPE: DNA
<213> ORGANISM: Unknown
<220> FEATURE:
<223> OTHER INFORMATION: Description of Unknown:
Yancheng osbecks grenadier anchovy picornavirus sequence

<400> SEQUENCE: 446
ccttagggtc tggaatgcgt cctttctggg cacttccaca atcctaaggt aattttcaac 60
gccagcgatg gagcgatatc caaagaacct ttatgtttta gttcgtcttg tatgtttata 120
aaatataaaa ttgggattag caacccacaa aaacattttt gttattctca ccacatgaga 180
gggtggttaa acctcttcgt aacctatctt gcttgattgg ctacttgggc tagatttagg 240
acaacctctt tagcaagcct aaattactcc tcgtacttgc acctggtaac aggcgtacct 300
ggaggttacg gtggcgctaa cttggacttc tcgttaattc gtgcaagttt aaatgatgcc 360
tattttgaat acaagaaagt atgatagtaa cttagggcgt gaagttccgc ttaacataag 420
gcagtataag tactaagata aggtgtaaga cctaccttaa taactgttgt cttttctcat 480
ggtctttccg tgggagccct tgctaggggt aaagttaagt attctcaaat aatttttcat 540
tcaaactctt tctctctgtt tt 562

<210> SEQ ID NO 447
<211> LENGTH: 675
<212> TYPE: DNA
<213> ORGANISM: Gallivirus sp.

<400> SEQUENCE: 447
ccactcgcac ttcctggata gtgcgttaga tatgcccgac atatcgcttc caggaccaaa 60 gcccccccttt tctctttccc aaccagcttc gccactcaag ctgtaattcc atgtccggtc 120
tttccggcct tagtatcatg gaaatgtggt cgtgctcaaa tgaaattgag ttgacattga 180
tcaatgaaag ttgcactgaa ctttgctaaa ctggctagcg ccacctggtg tgtgccgttg 240
gtctcctcac atggtaacat gtgccaacgg gcccgaaagg ctagtgggca attaccgctc 300
caagggaggg gtacccaccc cgacctgaac agcggtaatg aagctcacct cccaggctct 360
gaccccgaga agtttagtta tttagtaggt gtaattagta cttgtgattg gtcaatttga 420
tagtagtttg aaacgttatg gatgaatgag tagaccccct gaaggtaccc cattacatgg 480
gatctgatca gggccacatt ctgcgtgtct ccccgcactt gtggttaaaa ccatgaaagt 540
tcatcccaaa caatcttttc ctcttctttt tcttttagtg gtgacaacct actggattgg 600
tgattaccaa tctgtactag tgttgtatta agacttgttg tgtggagaaa atggactctt 660
tcaagaagat ttttg 675

<210> SEQ ID NO 448
<211> LENGTH: 673
<212> TYPE: DNA
<213> ORGANISM: Unknown
<220> FEATURE:
<223> OTHER INFORMATION: Description of Unknown:
Falcovirus A1 sequence

<400> SEQUENCE: 448
taaaagggga cgcggtgtgg cagctttggc tgtcatgccg tgttctcctt ttaccccaag 60
gactagcctt gggggtttc caaattcctt tccctgtagg ctttacttct ctttatctat 120
cttttctgta actaagtttt gcctattcta aaaatatttt agaatgtgtt tggatgtaac 180
taagtttgtg cctgccctaa aaatatttta gggcttgttt ggataacctc gtcccttgtg 240
ttcagtgccg cacaatttgc taggcactgt tcacttcctt tgtttgtcca ttatgtatgc 300
taaggtatga attccatcat atgcttagcc tctacatgca taatcttatt ccctccctgg 360
tgcaaactac gcccccaaca tatgtgaatc ttttaagcat attcctgacc ccacacatat 420
atatgtgttc tcgtgaattc ccccaccgtg aggtggtcac ttggacgtgg tgtgtgtcac 480
acagcatata tatgatgcag gatgttgttt ttaagataag catatgtcct tagtgctttg 540
catcatttcc tccacacccc gtgaatgcgg ctaatcttaa ccctgttggg tccgtgggta 600
aaccaaccca ttaaccacag gacggaaccg actactttcg ggagtgtgtg tttctttttc 660
ttcttttgtc act 673

<210> SEQ ID NO 449
<211> LENGTH: 665
<212> TYPE: DNA
<213> ORGANISM: Tremovirus B

<400> SEQUENCE: 449
ttcaaatggc ccctgggttg atacccagtg gtcatttgga cactttggta aggaggtgta 60
attatccttc ccatgtggaa cctagtgctt aggtttactt tatatgttct ttgtttgtcc 120
tttgtacttt ctatcgggca atcttgttgt tcaatacaat atgtatttga actgcctaag 180
ataaattcag ttttcaacca acccctctct tggggttgtg tctttctttc tttcttatat 240
cctcttaagc tgacttactt gctaatccga ctcctcgtca acgggagggt aaagcagtat 300
cactagggta ttgtgatgta ggagaaaaag taagtagaga tagtgcatgt aacgaaagtg 360
acttggtact ttaaactctc ttaatcccaa agtgtggtat tggtcatgtt ggagtaggct 420
acgggtgaaa ctccttcaca tttagtaatg tgttcacacg ctaacgctac ggtagatgac 480
agactaggtc ttattctcaa cgtagggga cgggtgtatg ttcatgatta gccacatatt 540
aaggttttga ggggctgagt catataagta tgtgcattaa tttctggtac tggtccctgg 600
ggactggccc ttttctaggt tgattttagt ttccccaatt tttaaaaact aatgagattt 660
acgac 665

<210> SEQ ID NO 450
<211> LENGTH: 675
<212> TYPE: DNA
<213> ORGANISM: Hepatovirus A

<400> SEQUENCE: 450
tctttggtct ggggaactaa aataccagac ccgcgtttgc ctagcgatat aggctttaat 60
tgttgtttgt cattgtgcgt ttgatatgtg ttttaatgta aataataatt ctagcaggtt 120
ctagttcttg atcatgtcct ctttaaggca ctcatttcaa cttgctatct ttcttttctt 180
ccttggttct ccctacacca aatgcactgg ccgctgcgcc cggcggggtc aaccacatga 240
ttagcatgtg gctgtaggtg ttgaaggctg ggacatgaac atcaatggaa tagtgcgcat 300
gcttactggg gtccattgaa gtagtgggat ctttctattg ggtaggcta cgggtgaaac 360 cccttaggtt aatactcata ttgagagata ccttggatag gttaactgtg ctggatatgg 420
ttgagtttaa cgacaaaaag ccatcaacag ctgtggacag aacctcatcc ttagattgct 480
cactatggat atgtgctctg ggcgtgtttc ttgcatgatg gccattggtc aattcatgcc 540
tgggccaatg taggattagc cttaaattac tttttaaaag tagcctcatt tagctggact 600
aatggtgggg cgtatgatcc tgcatttggc ctctggggta atcaggggca tttaggtttc 660
cacataatag caaat 675

<210> SEQ ID NO 451
<211> LENGTH: 675
<212> TYPE: DNA
<213> ORGANISM: Hepatovirus sp.

<400> SEQUENCE: 451
gcaaggggtg gttttaacct tgcacgcgtt taccgtgcgt taacggtttt ccatgtttgt 60
atgtcttgtt tgtattatgt gttttgtaaa tattaattcc tgcaggttca gggttcttta 120
atcatgttgg gctgtaccca cactcaactt ttggccataa gtgagtttct taacgaacct 180
tttaacacag gatgttatta gggcccaata ttttccctga ggccttcttt ggcctctatt 240
ttttcccctt ttctatctcc ttgtattccg ggctcacgtg atgccaatgg actgacccat 300
gcgcccgtgg gggttaacta ctggagtagc cagtagctgt aggtgctaaa agtcacgtac 360
gtgtaagact ggacgagacc tctcagctat aactgaaagt agtaagtatg tctgaacttc 420
ttgaaggggt aggctacggg tgaaacccct taggttaata ctcatattga gagatacctc 480
tgataggtga aggtttccgg tagaggtgag tttaacgaca aagcctctca acggatgtgg 540
gcccacctca tcagcaagat gctttcatac ccaataccgt aggggctggg ttgttgagtt 600
cagtcccaag cgtccctccc gcaaggttgt aggggtactc aggggcattt aggtttccac 660
aattaaacaa ataca 675

<210> SEQ ID NO 452
<211> LENGTH: 675
<212> TYPE: DNA
<213> ORGANISM: Hepatovirus D

<400> SEQUENCE: 452
ctttggatgc ccatagtgcg ggggtataaa taccgcactc cctttagctg ttccgagggt 60
atcggaacct atatgtttgt tttctgtctg tctgtcagct ttatgtgtgc tcgtcccctt 120
tagggcactc atttcagctt gctttcattc ttttcttccc cggttctcac cttaccggag 180
gcactggccg ttgcgcccgg cggggtcaac ctagtgatta gcactaggct gtaggtgtct 240
aaagtggtga cattaagact tggtaactga tttcagcact gttaactgat gttggggatg 300
acttgattga tcttctggaa ggggtaggct acgggtgaaa ccccttatct taataccact 360

-continued atgtagagat agattcagta ggttaagggc agtggataag gttgagttca ttttggacaa 420
taaaccttca acactggtgg acccaatctc actgaccaga tgctttcttg actgatcctt 480
cagaggggtg attcttctga ataggttgcc ttgacactga tgcctgagac ccattgggtc 540
gggccttaaa tcatggaact ccactggact ttcatggcct agcttctgcc ttagacagac 600
tctggggccc cacgaccctc tgggcccttc ggggtactca ggggcattta ggtttttcca 660
caattaaaag agtta 675

<210> SEQ ID NO 453
<211> LENGTH: 560
<212> TYPE: DNA
<213> ORGANISM: Hepatovirus sp.

<400> SEQUENCE: 453
gtcatgtttc tctttaagaa cactcaattt tggccataag tgagactctt gtcgaacctt 60
tcatgtcagg accatgttag ggccattatc cttttccctg gggcattctt cttgcccctg 120
tttcatcttt ctatcatctt tcttccgggc tctcacaatg ccaatggagc gaccgatgcg 180
cacgtcgggg ttaacccatg gattagccat gggctgtagc tgctaaaagt tgtgactcct 240
gaagcatact atcaatggta gtagatgtaa ctgaaacact gaagcttctc tgatcttgaa 300
agaagggtag gctacgggtg aaacccttca ggttaatact catattgaga gatacctttg 360
gtaggttaac gttggcggat aatgttgagt ttaacgacaa taaacattca acgcctgtgg 420
gcgaacctca ccaatttcat gctttgaagt gaatgtgcgt agggtctcta tcggagatgc 480
tatgtggatg gtgccctccc tggaaacagg ttgtaggggt actcaggtgc acttaggttt 540
ccacatttta aagatttttc 560

<210> SEQ ID NO 454
<211> LENGTH: 675
<212> TYPE: DNA
<213> ORGANISM: Hepatovirus I

<400> SEQUENCE: 454
ggctgcctgt gtctcagggg taagtactgg ggccgcgttg accgtgcggt acggttatgc 60
ttttagatta ggatgtccgt ctgtccggca ctctcttttg cttaaaatgg ccttaaatcc 120
atgggaggcg taaccatggg ccctttgtta cctagacatg attgcattgg gggccgtcct 180
tggggcttag gccccagcca tttctcttga ctcgtctaag agtttacttc atccttttct 240
ttactttatt ttccaggctc tcagcatgcc gacggctctg accactgcgc ccggtggggt 300
taactgcatg attagcatgc agctgtagga gttaaaagtg ctgacaggcc aattctgacg 360
taagtccact ctatattaac ttgatcaagt aaggttgatt gatctttgtg agagggtagg 420
ctacgggtga aaccctctag gttaatactc atattgagag atacctccag aaggtgaagg 480
ttggcggata ttggtgagtt cttttaggac aaaaaccttt caacgcctgt gggcccacct 540
cactggcaca atgctttcat ccccaattgt gatgggtagt ttggactgaa atcaggagta 600
acctgcccta cgagtttagg ggtagttcag gggtatttag gcttccacat ttgatagagt 660
ttatgagagt gagcc 675

<210> SEQ ID NO 455
<211> LENGTH: 527
<212> TYPE: DNA
<213> ORGANISM: Hepatovirus C

<400> SEQUENCE: 455
ttcaaaagcc ccagcggggt ttcattaccc cgctgtggct tttggacttc cctaggatgg 60
ggaagtaaat taccatcctc gcgtttgccg tgcgttaacg gctacttttc ttctagctgt 120
agaagtaaaa ttcagcatgt tttatgtttg tttgtcttgt ttgttatata catttttaca 180
ctcctacaaa tgcacatgaa gaacagtttg tagagattaa caaacgctta gctgaaccta 240
ggtggtgaat ctagtagtaa gataagtaga ggaagctata ccttaagttg gttgggccct 300
cgtgtttgct ctataaacaa aaccaagtga gtagagtgga tgaacagtac taaatccctg 360
agtacaggga acctcacagg tgtgatacac ttatgtctat gtgacctggt tggaggttgg 420
gcgtgcccta tgatactgga gtgggagatc ttttggggaa cccacgtttt cacactgcct 480
gatagggtct tgccgagaga ctcacttgtt tcggctgtac ttgtaac 527

<210> SEQ ID NO 456
<211> LENGTH: 665
<212> TYPE: DNA
<213> ORGANISM: Fipivirus A

<400> SEQUENCE: 456
tgcgggtaaa ctcccgcatg tgtgaatgag gcgatgtccc aggaactaac tgccgatcct 60
ggttttaact acgatccgta tttgttacta atgcgatatc cccccattgt ttgcctccat 120
gttgttttca acgcttttgg ccttgagtgt tatcaagtgt tttagcgaca tagtgggaag 180
ctacggctgc gtccccattt ttgagtggcg acccagtttt agtggccact ctgtccctga 240
actgcgctat aatgtgaatt tatgttcaca aaaacggact gatgtaactg ttaatgacta 300
aggaatagta cctcactgaa gtatcaagac cccgttcgag cggtgtacat atatggatgg 360
aaaccttgtc tgagtcatct cgaatactaa tcaatgaggg atgtcgagta agcatatcat 420
gaaccacata gaatagtggg gtttcggggt tagaggctct ctgcagcaat gtatctctaa 480
caccatggcc gaaatgagag atagagacca cgatgtttgt gtgtaagtaa tgatgtgtgg 540
aaagaaaatt ctgaatgttg gtatgatatc agtctaaggg gagtggctca cctaagagct 600
acccaaacat ttcacagcag acaacataac gtactgagag tagttggaag gttccagaaa 660
tcagt 665

<210> SEQ ID NO 457
<211> LENGTH: 467
<212> TYPE: DNA
<213> ORGANISM: Fipivirus C

<400> SEQUENCE: 457
cgcggttaaa cccgcgcaac cttctttcag ccgcgtctga gtagcgcggt tagtcctgat 60
acacagtttc ctgttgggta ctgtgtcttc gggtgaatgc tcttgtgtga atgttttagg 120
ctgtttaagg gaagcgtttc cccgtgcgct gtgagggttt ctcacgctct ttcggggtgc 180
agtctcttct gttgttcatt aagatgtatg gatgcactgt tgtgaaggat ttgtgaactg 240
gggatcgaca ccccgtgagg ggtgccccag tgtccatagg agtttgctgg agaggtgtgt 300
tgctgtagtg actatccgtg acctggcatt ctaaggtgtt gaccccaacc tgtgagggtc 360
tggatcgcag tgttgaagtg ctttggaggg ttcaatgggg tttctgtagt ggatattatg 420
tgcttgacga ctactggtac gagtgtattg gggtctaca tgtgtga 467

<210> SEQ ID NO 458

<211> LENGTH: 657
<212> TYPE: DNA
<213> ORGANISM: Fipivirus E

<400> SEQUENCE: 458
ctcttccgat cttgggggtt cgcccccatg tctcatttca actagccgtg tgtctagtta 60
acgcaccgcc tcaccctggt cgttatcggg tcggttcttg cgaccgttag atcgtgagcg 120
tttctgagga tcagttcgta taagttctcc ggtgtggcga ccgtaaaatc gtcacgtccc 180
atgcaataga tgacgttaaa ctcgtttgcc agttacataa aggaatgttg ttacttttaa 240
attgtctgtt acatttaaca tcttgccagt atgatgctac tgtacactac gggtgtagga 300
accttgtagt gtgacgtatc actcatatgt ggatgggtgc tccagacctt tatggaagct 360
ctcagttagt agtgatcctt gacttcattg agccctggta acagtggaag tcaagatgta 420
tatgttgctc aacacacttc ggtgctacga agctgtttgt ggaagtactg gcgaggttca 480
ttctgaatca tatgtttgtc acatagtcag ggagtgccgt cgcttacgac ggaccctttt 540
tctttataat tacaaatctg tgtctcaagt gttgttggct ggttttcttc ttctgttttc 600
attgttcata tatatacgtc agagtgaaag actcggtata tacaaaactg atccaga 657

<210> SEQ ID NO 459
<211> LENGTH: 506
<212> TYPE: DNA
<213> ORGANISM: Aquamavirus sp.

<400> SEQUENCE: 459
ttcaaaggtg gcgggagagt tggcctcacg ctgtttagcg tgagagctgg ctctcctgcc 60
ccttcccctg agccggggat cttggctcat tcccctcttt tctatcctcc ctcattggac 120
tttacggatg acccggcata aacttgacaa ccgatgttgg atttcccttg tggctgtgat 180
ggaggacata ccctcgggtg tagttgtgtg cgtgtcgctc tgcgactcga gcttcaaagt 240
ggtgctgaaa tattgcaagc gtcgttgctc gattaacgga gtggtacaat cctatgaacc 300
caagtgcatt catgcgaaag ccccggaggg gtgagtagca tggactcgaa tcagaagagc 360
tggagctcgc ttggtacggc acgtagcatt gctttgccta aagaccaagg gggtatggct 420
ataggtgggg gcctatagct tgtccagtgc tggttgacag actcgtgcta cgcgtctggt 480
tcgagtataa gtagctgcaa ctcact 506

<210> SEQ ID NO 460
<211> LENGTH: 548
<212> TYPE: DNA
<213> ORGANISM: Avisivirus A

<400> SEQUENCE: 460
ttcactcgct ttccccccct ctctataggg gcggtctttt aattcttatt aatttcctac 60
tttactatca aatttcttct aagtagggac tgaggtcact tagccctccc tctcctgggc 120
tttccagggt tatagaggtt ctaaagctaa gccatgtgtc ttgagctaca cttagtacaa 180
aggtttagta atgattgtac atgccagtaa ccttctagtg cccatggatt aaagagtggt 240
aacactctcc atggggcccg aaaggctagt gggcatagtt ggcatcaagg aaggggtccc 300
caccccaacc tgaattgctg gctagaagct caccttagaa gaagtgctgg gtgacaacgt 360
gtccaatcgt gaacgactga tggaaacgtg tggagatgga tatgtggggg ttcactgagt 420
agatgccctg aaggagaaat ctgatcaggg gcccgtgact atacgctagg taaaccgggt 480
ataaaaacca tgaaaggtgg cccaaaatct cttcctttta ttttatttct atgttggtga 540
cagtcaag 548

<210> SEQ ID NO 461
<211> LENGTH: 492
<212> TYPE: DNA
<213> ORGANISM: Avisivirus B

<400> SEQUENCE: 461 cacccctac tgccctaacc cccaaagtta gttatagggt ggctccctac ccttactcca 60
cggggtaagc cctaacccgg ttgaatctca agatcagcct tagcgaggac tattagtacc 120
gctcaaaccc tttgcctgta gtgcccaggg gtcacagagg ggtgaccctc tccctggggc 180
ccaaaaggct aggtggcaag acagggtcca agtgaggggc tactctaagt agccccaagc 240
tgaacatcct gtctgaagcc acccttgcag ggccaggttt gattggggaa actagacacc 300
agctttgtcc tgggattggg gggatatcga gttagtccag gaggtgcgag tagatgcccc 360
cgaaggtacc ccaggcacat ctgggatctg atcgggggcc cgtgactata caataggtaa 420
accgggttaa aaaacatgaa agcgcctctc tctttcctac ttcttttatt gactggtgac 480
aaaaatagca gt 492

<210> SEQ ID NO 462
<211> LENGTH: 517
<212> TYPE: DNA
<213> ORGANISM: Crohivirus A

<400> SEQUENCE: 462
gttgaagtcc atttcttgct tgcccccgat gaatcctgtt aaggcctcac ggccctaagg 60
gtgaaactcg gttatcccct cctgtacttc gagaagatta gtacaacact atgaaatcta 120
catcttgtga tccgggataa ccccaatccc agaaacctgt gatgggcgtc accacccctc 180
ttatggtaac ataagggtgt cgccgcgttg gcacaggacc ctttgggctg gatgttttta 240
gtaatggtgt cgaaggtcct attgagctac aggagtttcc tccgccctgg tgaatgcggc 300
taatcttatc cctgagccta aggttgcgat ccagcaactt gatggtcgta atgcgtaagt 360
tgggggcgga accgactact ttccagaagg cgtgtttctt tgttttgtct gttactatgg 420
tgcatgatat agatattgaa tatttgatct ttttgagctg tttcttatct tattgctaca 480
tcctttcagg tgttggattt acattttggt taataag 517

<210> SEQ ID NO 463
<211> LENGTH: 393
<212> TYPE: DNA
<213> ORGANISM: Kunsagivirus B

<400> SEQUENCE: 463
gattttctgg ttatcccttt tggacttggt aggggcccac gtgcccaccc acctctgtgt 60
gtgttgattt ctaatcgatg cctggcagtg gcggccacct ctccttactg gtaaacctcc 120
ggtgagtgaa gttgtcaagc tacaggtacc gtgcaggatg aaatgcgcac atgtgaacaa 180
actaggagtc atacaccggg tcaaactctg gaaacggagt ccgggactct gaccttggtt 240
gggtgagctc gaggcatcac attgatggac gcgattcgct atccttccct agtaggacct 300

```
tgtggtgtac ccctggttgg gaatccaggg ctggtcgggt gcagggtgac agcctgttct    360

ccacctcaac cattgtagga gaaatcaacc cct                                 393


<210> SEQ ID NO 464
<211> LENGTH: 675
<212> TYPE: DNA
<213> ORGANISM: Limnipivirus A

<400> SEQUENCE: 464

ttctttggat atccatttaa cgtgtaccct atacgataat tggggtggat tctggatgcc     60

tagttccagt gattggttaa gaactcgttt actacgtata gtatgattag caaagtgctc    120

gattgatcac gtaatgatct atgtggttaa aaacccagta gtatggtata tactcagtag    180

tgtacactgt gagtacaact cttggcgtag agagaacaat tcacccgaat ccgtggcgta    240

tccatggaaa taagtttacc taattgtatg ttacaaggca tatgagacat ttatgagata    300

tggtttattt tgactaaacg agtgtagagg tggtggagtc tatccaactt caagccatgc    360

aattgttgtg ttgattgata tcattgacca tttttgtgga ttgtgtacac atacaatttg    420

aaaattaacc ccctcaagaa taagacatgg gaccattcgt ggtagatacc gtgctcggat    480

gcttgagatt agatgggtta gactagtttt ggaatgagat tgccgagaaa gtcccgctag    540

acatgtttta caagtcgtgg tattccgcta gactttttcg cagacacatg gaagggtcca    600

tgtgttgtgc aattgcaggg tgacagccca actgcagagt tttccttact agaataaaaa    660

tctgttgtca atttt                                                     675


<210> SEQ ID NO 465
<211> LENGTH: 501
<212> TYPE: DNA
<213> ORGANISM: Limnipivirus C

<400> SEQUENCE: 465

gtttctgagc actggtaaga gcttagacaa acgtttttaa aatttatttt ctctgcaact     60

tttgtttgtg tttattttta tttgttaatt ttgcgcctaa gcatttgttg cgaagtattt    120

gattcattag taatattact tattgtttat ttagatggta ttcaaagtgg tgggagtatc    180

gaacccaagc gtcgtatgct atctccttga acaattttta atcattgcga agtgatcatt    240

gaaaaggata ggtgtttaag aactcaaaga gtgttaataa tgttgggtga caggtgtccc    300

catagaattt attaacatga tttggactgg ttatctagta agaagaacca tcgaacgcac    360

gagcgagcat tgcttgcggg gcagttaccc tgcgtcgatg taagtgtgta ccggggggtg    420

cacatgttga ttctttatgg cctgataggg tgcgtcattc gcgcctagat aattagtata    480

atgcgaatgg aataaattta c                                              501


<210> SEQ ID NO 466
<211> LENGTH: 675
<212> TYPE: DNA
<213> ORGANISM: Orivirus sp.

<400> SEQUENCE: 466

ggtcccaggc caatattctt cgtaaggctt ggttccaatt ttccaccact cgtgtttggg     60

ttctggccta tggtacccag aggggcggtt tgggggaatt aactccccct cccctgtggt    120

cctataccac cccacacctc tgtgggcttt ctttactatc ttcttgtttt ccgactttta    180

aacactaggc aggcgcgcct agtcatacac cgcccggctg gtctttccag ctcttgtggg    240
```

```
cggtgcgcgc tggtccatcg tgcccagcga catagcacct tgtggacacc tccgaacgcc    300

ctcccctgta tggggtggtg cccaggggtt tcagtgtggt gacacactcc ctggggcccg    360

aaaggctagt gtgcaacagg tgaggtacag ccagctgccc ccgtggctgg agggaccaag    420

cttgtgaagc acacctcacc ttcttggggg tgggctagta agtggtgaaa gcatagtgtc    480

cgtgtcgctg gccaacactt tgggtcaagt ccagccactc agtgagtaga tgcccaggag    540

gtacccctag tggatctgac ttggggcctg ttacttaatg caggttaaaa actatgaaag    600

ctgagtagtg tagcccggct ggtggcttct cttccttatt cattctattt tatggtgaca    660

aacgcaactg aagcc                                                      675
```

<210> SEQ ID NO 467
<211> LENGTH: 675
<212> TYPE: DNA
<213> ORGANISM: Hepatovirus A

<400> SEQUENCE: 467

```
cttgatacct caccgccgtt tgcctaggct ataggctaaa tttccctttc cctgtccttt     60

ccctatttcc ttttgttttg tttgtaaata ttaattcctg caggttcagg gttctttaat    120

ctgtttctct ataagaacac tcaattttca cgctttctgt ctcctttctt ccagggctct    180

ccccttgccc taggctctgg ccgttgcgcc cggcggggtc aactccatga ttagcatgga    240

gctgtaggag tctaaattgg ggacgcagat gtttgggacg tcgccttgca gtgttaactt    300

ggctttcatg aacctctttg atcttccaca aggggtaggc tacgggtgaa acctcttagg    360

ctaatacttc tatgaagaga tgccttggat agggtaacag cggcggatat tggtgagttg    420

ttaagacaaa aaccattcaa cgccgaagga ctggctctca tccagtggat gcattgaggg    480

aattgattgt cagggctgtc tctaggttta atctcagacc tctctgtgct tagggcaaac    540

actatttggc cttaaatggg atcctgtgag agggggtccc tccattgaca gctggactgt    600

tctttggggc cttatgtggt gtttgcctct gaggtactca ggggcattta ggtttttcct    660

cattcttaaa caata                                                      675
```

<210> SEQ ID NO 468
<211> LENGTH: 675
<212> TYPE: DNA
<213> ORGANISM: Hepatovirus A

<400> SEQUENCE: 468

```
cgccgtttgc ctaggctata ggctaaattt tccctttccc ttttcccttt cctattccct     60

ttgttttgct tgtaaatatt gatttgtaaa tattgattcc tgcaggttca gggttcttaa    120

atctgtttct ctataagaac actcatttca cgctttctgt cttctttctt ccagggctct    180

ccccttgccc taggctctgg ccgttgcgcc cggcggggtc aactccatga ttagcatgga    240

gctgtaggag tctaaattgg ggacacagat gtttggaacg tcaccttgca gtgttaactt    300

ggctttcatg aatctctttg atcttccaca aggggtaggc tacgggtgaa acctcttagg    360

ctaatacttc tatgaagaga tgccttggat agggtaacag cggcggatat tggtgagttg    420

ttaagacaaa aaccattcaa cgccggagga ctgactctca tccagtggat gcattgagtg    480

gattgactgt cggggctgtc tttaggctta attccagacc tctctgtgct tggggcaaac    540

atcatttggc cttaaatggg attctgtgag aggggatccc tccattgcca gctggactgt    600

tctttggggc cttatgtggt gtttgccgct gaggtactca ggggcattta ggtttttcct    660

cattcttaaa taata                                                      675
```

<210> SEQ ID NO 469
<211> LENGTH: 519
<212> TYPE: DNA
<213> ORGANISM: Parechovirus F

<400> SEQUENCE: 469
ggtcggggag atgtgttcat gatcggttaa caccatcatg gatcatctct ccccgacctc 60
tttttgaccc agctatgggt taaatagtac ttttcttttc tcttttgctt tcttttgtgt 120
tttgtttgtt ttgcaacata taacaagcat tttatcagta ttagtgtctg caactgtata 180
acaagcaagg tggagcaatc atgcgagtat atctcaattg aattgtgaca cacaagtgtg 240
cactatgtgg aataaatgcc attttggcca aacctggtta gccagaccag tagtaggaca 300
atttggcacc cttagtgggc gcgacctaga tgctagggat gagcaaacct atttcccctg 360
agtacagggg ctctccttca cctctacatt ttggacctct ttttgagtat cctcgataga 420
aggtgaagtg acggtgtacc ggatggttaa ttgatctcat tgctgggtga cagcccgcta 480
ggaccaggca gcatctttgt atggacctgt acatgtaac 519

<210> SEQ ID NO 470
<211> LENGTH: 343
<212> TYPE: DNA
<213> ORGANISM: Parechovirus D

<400> SEQUENCE: 470
acatggggca ggtgtgctgt gccaagagca acactacggt ggccgagccg atggttcgtc 60
accacgtagt aggactccgt agtgcttggt tacggcggac gtaagtcagt tgagtgatgt 120
ctaagtggca aaccatgagt acatggtaac cttgtgtgga ctcgcgggac ggaatttcct 180
atcccattga ctccttgtag caaggtgggt atacccaacc acaatggcag caccctgggt 240
gggaacccag gggcctggat tagtatccag tcacacagcc tgatagggtg gcggctcagc 300
cactgaccag cgtctctaaa taattgtgag ctgttcatgc acc 343

<210> SEQ ID NO 471
<211> LENGTH: 675
<212> TYPE: DNA
<213> ORGANISM: Parechovirus C

<400> SEQUENCE: 471
cggtcatccc cctttcccca cagccggtgt gggttctaat cggctcctac taaacaccta 60
agcatcactg cgcctctatc tctcctatcc acaggtctaa gacgcttgga ataagacatg 120
tgggtgcaat aggaagatta gctagtccaa tctctccttc cagctacgct tctcccttcg 180
atgagcgtag ggggggcccc cacctccctc atctctggat agggctcttg ctacggggct 240
ttcccgtctg gaccagcagg cccactggtg cgcttccatt caagtttagt gtgcattact 300
gtctgaaata ttgctttgct aggatctagt gtagcgacct gcatattgcc agcggacttc 360
cccacatggt aacatgtgcc tctgggccca aaaggcatgt ctttgaccgt atgcagtaca 420
accccagtat aggtcctttc tatggcagta tggatctcag tgatgagtct atacagaata 480
tggaagtggt tcggatatgt cagcccgaag gatgcccaga aggtacccgc agataacctt 540
aagagactgt ggatctgatc tggggcccac caccttcggg tgggtagaag ctaaccatgc 600
cttgggttaa aaaacgtcta agggctgacc agacccgggg gatccgggtt ttccctatct 660
tgacctactc taatc 675

<210> SEQ ID NO 472
<211> LENGTH: 675
<212> TYPE: DNA
<213> ORGANISM: Unknown
<220> FEATURE:
<223> OTHER INFORMATION: Description of Unknown:
Ljungan Virus 87-012 sequence

<400> SEQUENCE: 472
ctcattgccc acacctggtt ggttcccagg ttcatacaat aaccatcaat aaacttttaa 60
catctaagat agtattatcc catactagac tggacgaagc cgcttggaat aagtctagtc 120
ttatcttgta tgtgtcctgc actgaacttg tttctgtctc tggagtgctc tacacttcag 180
taggggctgt acccgggcgg tcccactctt cacaggaatc tgcacaggtg gctttcacct 240
ctggacagtg cattccacac ccgctccacg gtagaagatg atgtgtgtct ttgcttgtga 300
aaagcttgtg aaaatcgtgt gtaggcgtag cggctacttg agtgccagcg gattacccct 360
agtggtaaca ctagcctctg ggcccaaaag gcatgtcatt tgaccactca ggtacacaac 420
cccagtgatg cacacgctta gtaatggctt agtaacaaac attgattgat catttgaaag 480
ctgttaggag gtttaggtat gacgggctga aggatgccct gaaggtaccc ataggtaacc 540
ttaagcgact atggatctga tcaggggccc accatgtaac acatgggtag aagtcttcgg 600
accttgggtt aaaaaacgtc taggcccgcc ccccacaggg atgtggggtt tcccttataa 660
ccccaatatt gtata 675

<210> SEQ ID NO 473
<211> LENGTH: 675
<212> TYPE: DNA
<213> ORGANISM: Parechovirus sp.

<400> SEQUENCE: 473
gccgtcgggc cttacacccc gacttgctga gtttctctag gagagtccct ttcccagcca 60
gaggtggctg gtcaaacaat accaaacgta actaaacatc taagataaca tagccctatg 120
cctggtctcc accagttgaa ggcatcttgc aataaaatgg gtggattaag acgcttaaag 180
catggagtca attatctttt ctaactagtg atcttcactg ggtggcagat ggcgtgccat 240
aactctatta gtgggatacc acgctcgtgg atcttatgcc cacacagcca tcctctagta 300
agtttgcaag gtgtctgatg aggcgtggga acttattgga aataattact tgctgcgaag 360
catcctactg ccagcggatc aacacctggt aacaggtgcc cctggggcca aaagccacgg 420
tttaacagac cctttaggat tggttaaaac ctgagtaatt atggaagata cttagtacct 480
accaacttgg taacagtgca aacactagtt gtaaggccca cgaaggatgc ccagaaggta 540
cccgcaggta acaagagaca ctgtggatct gatctggggc cacctacctc tatcctggtg 600
aggtggttaa aaaacgtcta gtgggccaaa cccagggggg atccctggtt tccttatttt 660
agtgtaaatg tcatt 675

<210> SEQ ID NO 474
<211> LENGTH: 631
<212> TYPE: DNA
<213> ORGANISM: Parechovirus sp.

<400> SEQUENCE: 474
agagtccttt tcccagccag aggtggctgg ttaaataata cctactgtaa caaaacatct 60
aagatgtaac aaccacacac ctggtctcca ctggccgaag gcaactagca ataaggcagg 120

-continued

```
tgggttcaga cgcttaaagt gtgttgtaca tattcttttc taacctgtgt tttacacagg    180

gtggcagatg gcgtgccata actctaacag tgagatacca cgcttgtgga ccttatgctc    240

acacagccat cctctagtaa gtttgtaaga tgtctgatga cgtgtgggaa cctgttggag    300

ataacagttt gctgcaaagc atcccactgc cagcggatct acatctggta acagatgcct    360

ctggggccaa aagccaaggt ttaacagacc ctttgggatt ggttcaaacc tgaactgtta    420

tggaagacat ttagtacctg ctgatttggt agtaatgcaa acactagttg taaggcccac    480

gaaggatgcc cagaaggtac ccgtaggtaa caagtggcac tatggatctg atctggggcc    540

agctacctct atcttggtga gttggttaaa aaacgtctag tgggccaaac ccagggggga    600

tcctggtttc tttttaattt aagtaatcac t                                   631
```

<210> SEQ ID NO 475
<211> LENGTH: 675
<212> TYPE: DNA
<213> ORGANISM: Parechovirus sp.

<400> SEQUENCE: 475

```
gggccttata ccccgacttg ctgagtttct ctaggagagt ccctttccca gccctgaggc     60

ggctggataa taaaggcctc acatgtaaca aacatctaag acaaaataat ttgccttgca    120

cctggtcccc actagttgaa ggcatctagc aataagatga gtggaacaag gacgcttaaa    180

gtgcaatgat agttatcttt tctaacccac tatttatagt ggggtggtgg atggcgcacc    240

ataattctaa tagtgagata ccacgcttgt ggaccttatg ctcacacagc catcctctag    300

taagtttgtg agacgtctgg tgacgtgtgg gaacttactg gaaacaatgc tttgccgtaa    360

ggctttcatt agccagcgga ccaccacctg gtaacaggtg cctctggggc caaaagccaa    420

ggtttaatag accctaatgg aatggttcaa acctggagca ttgtggaaag tacttagtac    480

ctgctgatct ggtagtaatg caaacactag ttgtacggcc cacgaaggat gcccagaagg    540

tacccgtagg taacaagtga cactatggat ctgatctggg gccaactacc tctatcttgg    600

tgagttggtt aaaaaacgtc tagtgggcca aacccagggg ggatccctgg tttcctttta    660

ttttactttg tcaat                                                     675
```

<210> SEQ ID NO 476
<211> LENGTH: 433
<212> TYPE: DNA
<213> ORGANISM: Parechovirus sp.

<400> SEQUENCE: 476

```
ctctattagt gagataccac gcttgtggac cttatgctca cacagccatc ctctagtaag     60

tttgtaagac gtctggtgac gtgtgggaac ttgtgggaat caatattttg ctttaaagca    120

tccattagcc agcggataaa acacctggta acaggtgcct ctggggccaa aagccaaggt    180

ttaacagacc ctagtggatt ggtttcaaaa cctgaaatat tgtggaacac actcagtacc    240

tactgatctg gtagtaatgc aagcactagt tgtaaggccc acgaaggatg cccagaaggt    300

acctgtaggg aacaagagac actatagatc tgatctgggg ctggctacct ctattttggt    360

gagtcagtta aaaaacgtct agtgggccaa acccaggggg gaccctggtt tccatttatt    420

ttacaaaggc act                                                       433
```

<210> SEQ ID NO 477
<211> LENGTH: 488
<212> TYPE: DNA
<213> ORGANISM: Potamipivirus A

<400> SEQUENCE: 477
cacatggaaa gcttttcgct tccatgttta cgcacacact ctctttgaca ccctgttgta 60
tggtgttaaa ctacaacatt tgtctgtcta taatcgttta ttttgtttac cctatatgta 120
cccaagtatt tgattgcttg actcacataa gcatcggtaa cccatactgt tttatgagct 180
actacctctg ctgtctacat acattttata tgaatggttt gagctctgcc tcaggatcaa 240
acatggtaac atgttccttt ggtcagttag aatcttattg tataatctaa ggtgtctatt 300
agtacgtaga aagttgtaac acatatgggg cctgatagcc gctatctctg atggatgtaa 360
ggtaaccttc tttaggtctg atacattctg cacaggatcc aattttcggt gccctgtacg 420
agtgcactct tatgcacgag gacgagatat gctacaaccc actgcaaatt taaacccaaa 480
ctttaaca 488

<210> SEQ ID NO 478
<211> LENGTH: 675
<212> TYPE: DNA
<213> ORGANISM: Potamipivirus B

<400> SEQUENCE: 478
tttcaacgtc gtggctgacg ttaaaaagcc acaattccac ttacctttta ccttttatgt 60
ttaatgtttg ttagttttgt gatctttaac aaatagatct aaataatttg ttggtaacca 120
atctcggatg tttcggctgc attgtagttt atttatttca ttttagttgt aggtggccac 180
tacgtcctgg aatcatacat ggtaacatgt acctcggcgg ttatccacta ttacgctaat 240
ctaagaatat ttaaatgaaa atgtaagtgt tacggctgac tttgggcctg atagttaaat 300
gctcgcactg acagatagta ccctccttta ggatcgattc tgttacatgg gatccatttt 360
ggtgccccac tgattcaacc tctttgttga aaaagagtta gcatactaca aattttccaa 420
acaaaaaccc tttttaatga ctacaactta tgattttatg aattttactg ctcttgaaaa 480
agatattttg acattgatcg ctgtactgtt tcagacattc attgcatcca tttttgttgg 540
ctactcctca caaactcaaa acttttccac acgagaaacc ttgtttattg aattttgcct 600
ttatattttg gaacttgttg ttggatttat tgtttgctta attattgacc tcacacctgt 660
tttaaacact acaat 675

<210> SEQ ID NO 479
<211> LENGTH: 546
<212> TYPE: DNA
<213> ORGANISM: Unknown
<220> FEATURE:
<223> OTHER INFORMATION: Description of Unknown:
Beihai Conger Picornavirus sequence

<400> SEQUENCE: 479
gggacaaccc cacagctggt acaaccattg tgggttggtc tccacccttt ttcaaccgtg 60
gcaacttcgg ttaaagttgc aaatcccccc tctccctatt ccacctccct tactttcact 120
ccccatatat ggtcccagat tttattctac ctctttatat ttttatttag tacagtggtg 180
gtgaattact cccagcataa actttgctgg atcagtgttc atcaagcata ctaattacta 240
atgtactgag ctatactatt atctggcatc tcacctggat aaccggtgtg accatatttc 300
ctaggttgcc tccctatgta ttttgtagca cctgtgcatc tgcacgttgg ggcgacaaat 360
tgtaggtttc ctggcacggg taagaattgt ggaaagctag tatgcagtta atgcaagggc 420
gcgtttttcg ctaccccgac actgctaaag tttttgggag gggtccctta aacatttcta 480
gtattgagtg atagctttgc ggcaggtcac cacaacctta ctataaataa acctgttgaa 540
tctcac 546

<210> SEQ ID NO 480
<211> LENGTH: 457
<212> TYPE: DNA
<213> ORGANISM: Sapelovirus sp.

<400> SEQUENCE: 480
tacgcatgta ttccacactc atttcccccc tccaccctta aggtggttgt atccccatac 60
cttaccctcc cttccacaat ggacggacaa atggatttga cctcacggca aacacatatg 120
gtatgatttc ggatacacct taacggcagt agcgtggcga gctatggaaa aatcgcaatt 180
gtcgatagcc atgttagtga cgcgcttcgg cgtgctcctt tggtgattcg gcgactggtt 240
acaggagagt aggcagtgag ctatgggcaa acctctacag tattacttag agggaatgtg 300
caattgagac ttgacgagcg tctcctcgga gatgtggcgc atgctcttgg cattaccata 360
gtgagcttcc aggttgggaa acctggactg ggcctatact acctgatagg gtcgcggctg 420
gccgcctgta actagtatag tcagttgaaa ccccccc 457

<210> SEQ ID NO 481
<211> LENGTH: 489
<212> TYPE: DNA
<213> ORGANISM: Sapelovirus sp.

<400> SEQUENCE: 481
ttgaaatggg tgtggggtac atgcgtatta cggtacgcat atattccaca ctcatttccc 60
cccctccacc cttaaggtgg ttgtatcccc ataccttacc ctcccttcta aaacagatgg 120
acaaatggat ttgaacttat ggcaagtgaa tatggtatga ctttggatac actttaacgg 180
cagtagcgtg gcgagctatg gaaaaatcgc aattgtcgat agccatgtta gtgacgcgct 240
tcggcgtgct cctttggtga ttcggcgact ggttacagga gagtaggcag tgagctatgg 300
gcaaacctct acagtattac ttagagggaa tgtgcaattg agacttgacg agcgtctctt 360
agagatgtgg cgcatgctct tggcattacc atagtgagct tccaggttgg gaaacctgga 420
ctgggcctat actacctgat agggtcgcgg ctggccgcct gtaactagta tagtcagttg 480
aaaccccc 489

<210> SEQ ID NO 482
<211> LENGTH: 675
<212> TYPE: DNA
<213> ORGANISM: Sapelovirus sp.

<400> SEQUENCE: 482
ccaaggatct gttgcatagg cgttgtatcc cctaaccttt tacctaccca tcccaatagg 60
actggtattt cggttttgat tgagtaatgg atactgattc tatacctgtt acccattcag 120
gggaaaaatg gagtttcttt catggatctg acttgatatg accaagagtc aacactttgc 180
gtgttggccg tatggaatgc tttaaggttt attctttgga ttatgacttc agggttggcc 240
gcccaggata aaaggcaatt gtggtaagtg atgttagtca ttggtggttg aaacctgcct 300
aagacgtcct aggtctacgc tgtgcgggcc gaagtaagct taggaataac agggagtatg 360
ccattttctg ctttcaccca acacgaccgt acacgaaaga gctagaggca ctttggggca 420

```
aagggaaaag ctttgcttag cccgaatgtt catttgagtc cttgacgaat gcgtcccgtc    480

tgtcccgacg gtgaggcgta tggcgcatgc tcatggcatt acccaatggt gtatctgtga    540

gggggggct cctcacactt agtctagtgc tacctgacag ggccgcggct ggtcgtttgt    600

gtatggtata accagtagta atcccccatg gattgcttta acttcccctc ctcccttacc    660

aagacattct ctaag                                                     675
```

<210> SEQ ID NO 483
<211> LENGTH: 579
<212> TYPE: DNA
<213> ORGANISM: Sapelovirus sp.

<400> SEQUENCE: 483

```
ttttaacttg ttatgacatt caaggaaaaa atgtcttttt cattatggga ctgacctgtt     60

tatgaacatg agcagcggca ctgctccacg ggctatccgt gtaagaaata ttgattattc    120

ttatggatca tgatttcagg gttggccgcc cagtctaaaa ggcaattgtg gtaagctatg    180

taagtagttg gctgttgaaa ggagccaagt acatcctagg tctacgctgt gcgggccgaa    240

gtaagacttg gaacaactct gagtaggcag tttttctctt tagcccaaca cgaccgcata    300

ctgaagagct agaggcactt tggggcaaag gtaaaagcat tgcttagacc gaatgttcaa    360

tgagaccttg acgagtgctg tcacagtgtc ccctgatggc agtatggcgc atgctcttgg    420

cattacccat atgtgtatct atagggggg ggcccctat acttagtcta gtgctacctg    480

acagggccgc ggctggtcgt cggtgtgtgg tataaccagt agtaatcccc catggattgc    540

tttaactccc cctcctccct caacaaaact ttctctaag                            579
```

<210> SEQ ID NO 484
<211> LENGTH: 522
<212> TYPE: DNA
<213> ORGANISM: Rabovirus C

<400> SEQUENCE: 484

```
ccgggtataa cccggagttt tggggcaggt ccaagcccca cataggaaca tacgatccac     60

ggatcgtgtg ttcttttatg ctttctaacc ttaccctttg taaccattac gctttacgcc    120

gcatggtgtt tggcggcacc atgacgtgga caagaggtta cgccattacg atatgtaccc    180

tccccttttg gggagagacc gaccaattat ggtacagtat ccaactgtat tgtggtcaag    240

tacttctgtt tccccggtga tgcgggatag gctgtaccca cggccaaaac ctgctgatcc    300

gttacccgac tcacatctac gaggaggcta gtaaaaggca tgaagttcaa gagtatgatc    360

caaccagatc cccactggta aactagtgat gagggttccc gttccgaaca tggcaacatg    420

tgggttccct gcgttggcac taggcccctt ccgaggggtg ctctgaagat ggattgttga    480

tgaagaccaa tttgtgcatg tgtttatcct ccggccctct ga                       522
```

<210> SEQ ID NO 485
<211> LENGTH: 551
<212> TYPE: DNA
<213> ORGANISM: Rabovirus A

<400> SEQUENCE: 485

```
ccgaccccac tggtcgaagg ccacttggca ataagactgg tggaacaagg tcgcctgtag     60

ttgattggaa ccttctttct aatgacttat gtcagcggtg ctactcacac cgtaactctc    120

ctaccctatc cccacgcttg tggaactagg aggggatgag tgattcaagt aagtactgtc    180

agaatggtga aaataatctg attctgaaac gctatggatc catcgaaaga tggggctaca    240
```

```
cgcctgcgga acaacacatg gtaacatgtg ccccaggggc cgaaagccac ggtgatagga    300

tcacccgtgt agtttgagat catatcaatg ttcatagtct agtaagatga tttgaaatct    360

aactggtctg atggctaact gcttgtctta ttgcggccta aggatgtcct gcaggtacct    420

ttagagaacc ttaagagact attgatctga gcaggagcca aggtggtctt tcccagcctt    480

ggttaaaaag cgtctaagcc gcggcagggg gcgggaggcc ccctttcctc ccaaactata    540

atatagattg t                                                         551
```

<210> SEQ ID NO 486
<211> LENGTH: 675
<212> TYPE: DNA
<213> ORGANISM: Parabovirus C

<400> SEQUENCE: 486

```
gatgtatccc catcccccag tgtgtatgcc atactgcata gctcgcctat gccctatgga     60

ttcacaaccc tttcatatac cctccctacc caaccccgta accacatgct ttactccgct    120

tggggttttg cggccccatg ttgtgacgaa atggctacgc aatcaatgcg gctaatgggg    180

cctgccgctt ttaagtggcc ccagttagaa gtttatgcac acccgcccat taggaggcca    240

ccagccaggt ggtcagaggg caagcacttc tgtttccccg gtgaagtttg ataagctgtg    300

cccacggctg aagcagacag atccgttacc cgcctcacta ctacgagacg gctagtagtg    360

tgtaatatcc gaatttcatt gatccgggtg ttccccccac ccagaaacgt gtgatgagga    420

gcggcacccc tcctatggca acatagggcc tctcctgcgc tggcacacgg gctctatgag    480

catgaaatca ggagaaagtc acacgaagac cttattgtgc tagtgttgat tcctccgccc    540

ccctgaatgc ggctaatccc aactccggag cgcccgctgg caaacccgcc agaagagcgt    600

cgtaatgcgt aagtctggag cggaaccgac tactttgggt gtggcgtgtt tcctttattt    660

cctttgtatt tgtat                                                     675
```

<210> SEQ ID NO 487
<211> LENGTH: 675
<212> TYPE: DNA
<213> ORGANISM: Parabovirus B

<400> SEQUENCE: 487

```
aacccataat ccattgtcca tcaatgtttt atggggggga ccctttctcc cctccccctc     60

caaatacctt ttacccctct gtaaccaaga gtgtgcaaaa tctatttact agcccagaat    120

tgcggcttct ggggaggttt attcctcatg cctaacaaga tgttacgcaa actccgggct    180

acggccctgg gcttttgccc taaagattta gaagtttaca ctatcgtcca acaggaggac    240

aacaaaccag ttgttctaag gacaagcact tctgtttccc cggtgagact ggatagactg    300

tacccacggt tgaaactggt tgatccgtta cccgactcac tacttcgaga agattagtag    360

gaaactgtga aactgattcc attgatccgg atactttccc cgtatccaga aactactgat    420

gagggttgac ttcccgacta cggcgacgta gtgtcatccc tgcgctggca gtaggcctct    480

ttgaggatgg aagatgtgga tcggtaaccg aaggtcctat tgagctagtg tttatacctc    540

cggcctcctg aatgcggcta atcctaaccc atgatctagt gctcacaaac cagtgagtag    600

ctagtcgtaa cgcgtaagtc gtgggcggaa ccgactactt tggagtgacc gtgtttccta    660

ttttactttt gtttg                                                     675
```

<210> SEQ ID NO 488

-continued

<211> LENGTH: 675
<212> TYPE: DNA
<213> ORGANISM: Parabovirus sp.

<400> SEQUENCE: 488
accgttacgc accactcagt tggtgtttgg tggcaccaat gatggaacaa aaggctacac 60
cacttgggct acggcccgcg ccaccttgtg gcgcaaagac attagaagaa tagcataccg 120
cccactaggg ccctgcagcc agcagggtaa cgggcaagca cttctgtctc cccggtagaa 180
cggtataggc tgtacccacg gccgaaaact gaactatcgt tacccgactc cgtacttcgc 240
aaagcttagt aggaaactgg aaagttcgag ttattgaccc ggagtgttcc ccccactcca 300
gaaacgcgtg atgagggttg ccaccccgac catggcgaca tggtgggcat ccctgcgctg 360
gcacgcggcc tctaagagga taactcgctc ctactggtaa ccgaagagcc ccgtgagcta 420
cggtttattc ctccgcctcc ctgaatgcgg ctaatcctaa cccatgagca gttgccatag 480
atccatatgg tggactgtcg taacgcgtaa gttgtgggcg gaaccgacta ctttgggatg 540
gcgtgtttcc ttgttttctc catttgttgt tgtatggtga caagttatag atctcgatct 600
atagcgtttc ttgagagatt tccaaacatt tattcaagtc gtacaattct tgtgtttaag 660
cagtacagtg taagg 675

<210> SEQ ID NO 489
<211> LENGTH: 316
<212> TYPE: DNA
<213> ORGANISM: Felipivirus sp.

<400> SEQUENCE: 489
gatgtcggat gacggctggc caccggggaa aaacggcaaa tgtgcaccac ctctgcaacc 60
cacgccgacc acgtttaacc atggcgttag taggagtgga ccactgcagt gggctctggt 120
gtgcgacagt cagtggtaga gtagacagtc ctgactgggc aatgggaccg cgttgcgtat 180
ccctaggtgg catcgagatt cctctgctac ccaccagcgt ggactcctat ggggggggcc 240
ccataggcta ggtctatact gcctgatagg gtcgcggctg gtcgaccact gactgtataa 300
ccagttgtaa ctcact 316

<210> SEQ ID NO 490
<211> LENGTH: 553
<212> TYPE: DNA
<213> ORGANISM: Boosepivirus A

<400> SEQUENCE: 490
ttgaaagacc tcggcatata tcgttgtcac aacggtatat gtcgagatct ttctccccac 60
cccctccaat tccctttcc ccctcttgca acttagaagt ttgtacacac agggcaatag 120
gatacgtgat ccagccagga cacgtgagct caagcacttc tgtttccccg tccccttcac 180
gtactacggg aatgttagta atttgtgtgc actttagtaa ggttgatccg ggattaaccc 240
caaatcccag aaactggtga tgagcgttac cacccccgcc gggcgaccgg aaggtttcgc 300
tgcgttggca ccagggcttc ggcaccagaa aaaggtaaag caaatgaagg cgctactgtg 360
ctacgagaag tttcctccag gcccctgaat gcggctaatc ctaaccagtg atccaccggt 420
gcaaaaccat gtactaggtg gtcgtaacgc gcaagtcgct ggcggaaccg actactttgg 480
gtgtcctgtg tttccatatt ttattttatt caattttatg gtgacaagag taaagagata 540
cagatttgca gcc 553

<210> SEQ ID NO 491
<211> LENGTH: 512
<212> TYPE: DNA
<213> ORGANISM: Boosepivirus B

<400> SEQUENCE: 491
ttttctcccc tccccctcca actacctttt ccccctcttg taacgctaga agtttgtgca 60
aaccgcctgt agggtactgc aatccagcag tgcataggct aagcttttct tgttacccca 120
ccccacatta tactgaggag gattgtgaaa ttgtgttagt atgggttagt agcggtgacc 180
cgggtaaccc caacccagaa actcacggat gagatgaaca ggaccccaca tggtaacgtg 240
tgtgttcgtc tgccccgcaa ggtgaggccg tgagagcttt gcacgcgaaa accttgaaaa 300
cccaaaagta ccttgagctc ttcgctattt tgtgtttcct ccaggaccct gaatgcggct 360
aaacctaacc cgcgatccgc acgtagcaac ccagctagag tgtggtcgta atgcgcaagt 420
tgcgggcggt accgactact ttggtgttcc tgtgtttcct ttattttatt ttgaattttt 480
atggtgacaa cagctagaaa ataagagtga ac 512

<210> SEQ ID NO 492
<211> LENGTH: 506
<212> TYPE: DNA
<213> ORGANISM: Unknown
<220> FEATURE:
<223> OTHER INFORMATION: Description of Unknown:
Phacovirus Pf-CHK1 sequence

<400> SEQUENCE: 492
gtgtgtcatt tctcccctcc ccctcccaaa ccttttcccc ctctaatcgg attgattaac 60
ccggttaaag atgattaatg gtttgtgagt tgatatgatg gcccggcatt gaatccggga 120
attcttaagt aatggaattg catccaatat gaaagtgagt gtggcaagct cacaagtagt 180
acttggctct gcccattatt tgaggaccaa ctcttcttga ctacaatgtg tttaaagtaa 240
actggaccac attgtgtatc cagacaactc catttgataa tgtacgctgg aaacgttttc 300
agtgcatagg gtcctaaagt ggtgctgaaa tattgcaagc tcaatgggat actgaacgct 360
gaaaaccgcc gctgttatca tatgggcccc tagtgggtaa atgttggctt taggcatata 420
ctgcttggga atgcagtact ggttgtagac agggtgatag cctaccggct ggcgtagttg 480
agttggtata gccagttgat tgccat 506

<210> SEQ ID NO 493
<211> LENGTH: 612
<212> TYPE: DNA
<213> ORGANISM: Rhinovirus sp.

<400> SEQUENCE: 493
ttaaagctgg atcatggttg ttcccaccat gattacccac gcggtgcagt ggtcttgtat 60
tacggtacat ttccatacca gttttataca ccccaccccg aaactcatag aagtttgtac 120
acaatgacca ataggtggtg gccatccagg tcgctaatgg tcaagcactt ctgtttcccc 180
ggcacccttg tatacgcttc acccgaggcg aaaaatgagg ttgtcgttat ccgcaaagtg 240
cctacgaaaa gcctagtaac actttgaaaa cccatggttg gtcgctcagc tgtttaccca 300
acagtagacc tggcagatga ggctagacat tccccaccag cgatggtggt ctagcctgcg 360
tggctgcctg cacaccctgc cgggtgtgaa gccagaaagt ggacaaggtg tgaagagcct 420
attgtgctca ctttgagtcc tccggcccct gaatgtggct aaccctaacc ccgtagctgt 480
tgcatgtaac ccaacatgta tgcagtcgta atgggcaact atgggatggg accaactact 540
ttgggtgtcc gtgtttcctg ttttactttt tcattgctta tggtgacaat tgtatctgat 600
acacttgtta cc 612

<210> SEQ ID NO 494
<211> LENGTH: 627
<212> TYPE: DNA
<213> ORGANISM: Rhinovirus sp.

<400> SEQUENCE: 494
ttaaaacagc ggatgggtat cccaccatcc gacccacagg gtgtagtgct ctggtatttt 60
gtacctttgc acgcctgttt ccccattgta cccctcctta aatttcctcc ccaagtaacg 120
ttagaagttt aaggaaacaa atgtacaata ggaagcatca catccagtgg tgttatgtac 180
aagcacttct gtttccccgg agcgaggtat aagtggtacc caccgccgaa agcctttaac 240
cgttatccgc caatcaacta cgtaatggct agtattacca tgtttgtgac ttggtgttcg 300
atcaggtggt tccccccact agtttggtcg atgaggctag gaactcccca cgggtgaccg 360
tgtcctagcc tgcgtggcgg ccaacccagc ttttgctggg acgccttttt acagacatgg 420
tgtgaagacc tgcatgtgct tgattgtgag tcctccggcc cctgaatgcg gctaacctta 480
accccggagc cttgcaacat aatccaatgt tgttgaggtc gtaatgagta attctgggat 540
gggaccgact actttgggtg tccgtgtttc cttttattct ttatattgtc ttatggtcac 600
agcatatata gcatatatac tgtgatc 627

<210> SEQ ID NO 495
<211> LENGTH: 615
<212> TYPE: DNA
<213> ORGANISM: Rhinovirus sp.

<400> SEQUENCE: 495
ttaaaactgg gtttgggttg ttcccaccca aaccacccac gcggtgttgt acactgttat 60
tccggtaacc ttgtacgcca gttttatatc ccttcccccc cttgtaactt agaagacatg 120
cgaatcgacc aatagcaggc aatcaaccag attgtcaccg gtcaagcact tctgtttccc 180
cggctctcgt tgatatgctc caacagggca aaaacaattg gagtcgttac ccgcaagatg 240
cctacgcaaa acctagtagc atcttcgaag atttttggtt ggtcgctcag ttgctacccc 300
agcaatagac ctggcagatg aggctagaaa taccccactg gtgacagtgt tctagcctgc 360
gtggctgcct gcacacccac acgggtgtga agccaaagat tggacaaggt gtgaagagtc 420
acgtgtgctc atcttgagtc ctccggcccc tgaatgcggc taaccttaac cccgtagcca 480
ttgctcgcaa tccagcgagt atatggtcgt aatgagtaat tacgggatgg gaccgactac 540
tttgggtgtc cgtgtttcac tttttactta tcaatttgct tatggtgaca atatatatag 600
atatatattg acacc 615

<210> SEQ ID NO 496
<211> LENGTH: 660
<212> TYPE: DNA
<213> ORGANISM: Enterovirus L

<400> SEQUENCE: 496
acatgggcca gcccaccaca cccactgggt gtagtagtct ggttctatgg aacctttcta 60
cgcctctttt gcttccctcc cccatttctc cttcgattgc tccacctgtg atctttgcaa 120
cttagaagaa ataatgaacc cgcacaatag cgggcgctga gccacagcgt caatgtgcaa 180
gcacttctgt ttccccggaa tgggcccata ggctgtaccc acggctgaaa gggaccggcc 240
cgttacccgc cttggtactg cgagaatgtt agtaactccc tcgatagctt taggcgttac 300
gctcagccct ttgagcccga agggtagttc gggtcgatga ggctcgtcat tccccactgg 360
cgacagtgtg acttgcctgc gttggcggcc cggggtgggg ggcaaccccc atccacgcct 420
actgaaggac agggtgtgaa ggcgctattg cgctactaag gagtcctccg gcccctgaat 480
gcggctaacc cgaaccccga gcccacggtg gtaaacccgc cacaagtggg tcgtaatgag 540
taatttgggg cagggaccga ctactttggg tgtccgtgtt tcctgttttt ccatacgatg 600
gctgcttatg gtgacaacca taagcaattg gattggccat ccggtgttca tattgcgaat 660

<210> SEQ ID NO 497
<211> LENGTH: 675
<212> TYPE: DNA
<213> ORGANISM: Enterovirus K

<400> SEQUENCE: 497
tcagcctgac gcaagtgcct ccattggagt ctctccaagc cctccggggc ttggagggcg 60 ccgacccccct gcctaggggg agcccacgac acggctggag tccattggca caccgcagcc 120
acgattcaag ccagaattga aagcgggaag cacttctgtc tccccggtgt ggatcatacg 180
ctgtacccac ggcgaaaagt gaagcatcgt tacccgactc ggtacttcga gaagcccagt 240
acagttgtgg atctctgcag ggtatacgct cagcgtgacc cctacgtagt tccttgagat 300
ggctgagaga acaccccacg ggcgaccgtg tctctcggcg cgtggctcaa ggccgggcct 360
tcagtggctc ggtgccttgc agagtgaagc ctccgaacag cctattgagc taccgtttag 420
cctccgccct cttgaatgcg gctaatccta accatggagc gcccgcccac agtccagtgg 480
gtagagcgtc gtaacgcgca agtccgtggc ggaaccgact actttagagt ggcgtgtttc 540
caatttatcc tttataaagt tgcttatggt gacaccacaa gagatccacg atttcttgtt 600
tcttatcact gagacacaag tcatattcat caatctttat tgcggaatta acttggtgcg 660
tccaaacaca tcagc 675

<210> SEQ ID NO 498
<211> LENGTH: 675
<212> TYPE: DNA
<213> ORGANISM: Enterovirus sp.

<400> SEQUENCE: 498
caccctgagg gcccacgtgg cgtagtactc tggtatcaag gtacctttgt acgcctattt 60
tatttccctt cccccacagt aacttagaag cttatctcat agttcaacag tagggtcact 120
aaccaagtgg ctcagcgaac aagcacttct gtttccccgg tcctagtacc tgtgaagctg 180
tacccacggc ggaaggggaa aaagatcgtt atccggcccc ctacttcgga aagcctagta 240
acaccattga agcaatcgag tgttgcgctc agcacagtaa cccctgtgta gctttggttg 300
atgagtctgg gcactcccca ctggcgacag cggcccaggc tgcgttggcg gccaaccgac 360
tcgggcaacc gggtcggacg ctcgtttgtg gacatggtgt gaagagccta ctgagctaga 420
gggtagtcct ccggcccctg aatgcggata atcctaaccc cggagcaccc acactcaatc 480
cagagtgcag gatgtcgtaa cgcgtaagtc tgggacggaa ccgactactt tgggtgtccg 540
tgtttcctgt tttacttact ttggctgctt atggtgacaa tctagtgttg ttaccatata 600
gctattggat tggccatccg gtgttttgaa ttgtgtgttt atactaattc ttttacatat 660
cacagacaac caaat 675

<210> SEQ ID NO 499
<211> LENGTH: 675
<212> TYPE: DNA
<213> ORGANISM: Enterovirus sp.

<400> SEQUENCE: 499
cggtaccttt gtacgcctat tttacccccct tcccccttgta acttagaagc aaagcaaacc 60
agttcaatag taagcaacac aacccagtgt tgtgacgaac aagtacttct gtttccccgg 120
gagggtctga cggtaagctg tacccacggc tgaagtatga cctaccgtta accggctacc 180
tacttcgaga agtctagtaa taccattgaa gttttgttgg cgttacgctc aacacactac 240
cccgtgtgta gttttggctg atgagtcacg gcattcccca cgggcgaccg tggccgtggc 300
tgcgttgcgg ccaaccaagg ggcgcaagct ccttggacgt cacttaacag acatggtgtg 360
aagaacctat tgagctaggt agtagtcctc cggcccctga atgcggctaa tcctaactcc 420
ggagcacatc agtgcaaccc agcatttggt gtgttgtaat acgcaagtct ggagcggaac 480
cgactacttt gggtgtccgt gtttcctgtt ttaccttatt tggctgctta tggtgacaat 540
ttgatattgt taccatatag ctgttggatt ggccatccgg atttttgaaa gagacccaaa 600
actttcttct ctacttcaga ttcaagtgcg aagttttcct tttcatatat tacttactaa 660
tttgaagtac caaag 675

<210> SEQ ID NO 500
<211> LENGTH: 675
<212> TYPE: DNA
<213> ORGANISM: Enterovirus I

<400> SEQUENCE: 500
ttagtacttt ctcacgggga tagtggtatc cctccctagt aatttagaag acttgaaaaa 60
ccgaccaata ggcacctcgc atccagcggg gtaaaggtca agcacttctg tttccccggg 120
tcgagtagcg atagactgtg cccacggtcg aaggtgaaac aacccgttat ccgactttgt 180
acttcgggaa gcctagtacc accaaagatt atgcttgggg tttcgctcag cacgaccctg 240
gtgtagatca ggccgatgga tcaccgcatt cctcacaggc gactgtggcg gtggtcgcgt 300
ggcagcctgc cgatggggca acccatcgga cgccaagcat atgacagggt gtgaagagcc 360
tactgagcta caaagtattc ctccggcccc tgaatgcggc taatcccaac cacggagcat 420
ttgctaccaa accaggtagt ggaatgtcgt aacgggtaac tctgtggcgg aaccgactac 480
tttgggtgtc cgtgtttcct tttaatttat cattctgtat atggtgacaa ctatagtgct 540
atctcgattt gcattactat tgttgagatt aaaactttat tacattgttg cattttaccc 600
tttgagtgag ttttcacctg aacagattaa tttactcatc ctgtttatat attacaagca 660
gaaatacttg caaag 675

<210> SEQ ID NO 501
<211> LENGTH: 675
<212> TYPE: DNA
<213> ORGANISM: Enterovirus sp.

<400> SEQUENCE: 501
gcaatgctgc accagtgcac tggtacgcta gtaccttttc acggagtaga tggtatccct 60
taccccggaa cctagaagat tgcacacaaa ccgaccaata ggcgcaccgc atccagccgt 120
gcagcggtca agcacttctg tctccccggt ctgtaaagat cgttatccgc ccgacccact 180
acgaaaagcc tagtaactgg ccaagtgaac gcgaagttgc gctccgccac aaccccagtg 240
gtagctctgg aagatggggc tcgcaccacc cccgtggtaa cacggttgcc tgcccgcgtg 300
tgcttccggg ttcggtctcg tgccgttcac ttcaacttca cgcaaccagc caagagccta 360
ttgtgctggg acggttttcc tccggggccg tgaatgctgc taatcccaac ctccgagcgt 420
gtgcgcacaa tccagtgttg ctacgtcgta acgcgtaagt tggaggcgga acagactact 480
ttcggtaccc cgtgtttcct ctcattttat ttaatatttt atggtgacaa ttgttgagat 540
ttgcgctctt gcaacgttgc cattgaatat tggcttatac tatttggttg ccttttacaa 600
aacctctgat atacccagtt cttacattga tctgcttgtt tttctcaatt tgaagtatag 660
actacaaata gcaaa 675

<210> SEQ ID NO 502
<211> LENGTH: 675
<212> TYPE: DNA
<213> ORGANISM: Enterovirus sp.

<400> SEQUENCE: 502
cgtggcggcc agtactctgg tatcacggta cctttgtacg cctgttttat atccccttcc 60
cccgcaactt agaagaaaac aaatcaagtt cactaggagg gggtacaaac cagtaccacc 120
acgaacaagc acttctgttt ccccggtgat gtcgtataga ctgtaaccac ggttgaaaac 180
gattgatccg ttatccgctc ttgtacttcg aaaagcccag tatcaccttg gaatcttcga 240
tgcgttgcgc tcagcactca accccagagt gtagcttagg tcgatgagtc tggacactcc 300
tcaccggcga cggtggtcca ggctgcgttg gcggcctacc tgtggtccaa agccacagga 360
cgctagttgt gaacaaggtg tgaagagcct attgagctac aagagaatcc tccggcccct 420
gaatgcggct aatcctaacc acggagcaag ggtacacaaa ccagtgtata tcttgtcgta 480
acgcgcaagt ctgtggcgga accgactact ttgggtgtcc gtgtttcctt ttgtttttat 540
catggctgct tatggtgaca atctaagatt gttatcatat agctgttgga ttggccatcc 600
ggtaatttat tgagatttga gcatttgctt gtttcttcaa caatttcacc tattcattgc 660
atttcagcag tcaaa 675

<210> SEQ ID NO 503
<211> LENGTH: 675
<212> TYPE: DNA
<213> ORGANISM: Unknown
<220> FEATURE:
<223> OTHER INFORMATION: Description of Unknown:
PV3 sequence

<400> SEQUENCE: 503
tacctttgta cgcctgtttt atactccctc ccccgcaact tagaagcata caattcaagc 60
tcaataggag ggggtgcaag ccagcgcctc cgtgggcaag cactactgtt tccccggtga 120
ggccgcatag actgttccca cggttgaaag tggccgatcc gttatccgct catgtacttc 180
gagaagccta gtatcgctct ggaatcttcg acgcgttgcg ctcagcactc aaccccggag 240
tgtagcttgg gccgatgagt ctggacagtc cccactggcg acagtggtcc aggctgcgct 300
ggcggcccac ctgtggccca aagccacggg acgctagttg tgaacagggt gtgaagagcc 360
tattgagcta catgagagtc ctccggcccc tgaatgcggc taatcctaac catggagcag 420
gcagctgcaa cccagcagcc agcctgtcgt aacgcgcaag tccgtggcgg aaccgactac 480
tttgggtgtc cgtgtttcct tttattcttg aatggctgct tatggtgaca atcatagatt 540
gttatcataa agcgagttgg attggccatc cagtgtgaat cagattaatt actcccttgt 600
ttgttggatc cactcccgaa acgttttact ccttaactta ttgaaattgt ttgaagacag 660
gatttcagtg tcaca 675

<210> SEQ ID NO 504
<211> LENGTH: 675
<212> TYPE: DNA
<213> ORGANISM: Enterovirus sp.

<400> SEQUENCE: 504
ctttgtacgc ctgttttaca tcccctcccc cacgtaactt tagaagcaat tcaacaagtt 60
caatagaggg ggtacaaacc agtatcacca cgaacaagca cttctgtttc cccggtgatt 120
ttacataagc tgtgcccacg gctgaaagtg aatgatccgt tacccgctcg agtacttcga 180
aaagcctagt atcgctttgg gatcttcgac gcgttgcgct cagcactcta ccccgagtgt 240
agcttaggct gatgagtctg ggcattcccc atcggcgacg atggcccagg ctgcgttggc 300
ggcctaccca tggctaacgc catgggacgc tagttgtgaa caaggtgtga agagcctatt 360
gagctactcg agagtcctcc ggcccctgaa tgcggctaat cccaaccacg gatcaggtgc 420
ctccaaccca ggaggtggcc tgtcgtaacg cgcaagtctg tggcggaacc gactactttg 480
ggtgtccgtg tttcctttta tcttttaaat ggctgcttat ggtgacaatc atagattgtt 540
atcataaagc gaattggatt ggccatccgg tgaaatacaa acacattatt tacttgtttg 600
ttggatttac tccgctcaca cagcttactc ctaagataat atttattgta ttgctggtaa 660
ggagacacta ttata 675

<210> SEQ ID NO 505
<211> LENGTH: 636
<212> TYPE: DNA
<213> ORGANISM: Enterovirus sp.

<400> SEQUENCE: 505
aagcaaggca aacctgacca atagtaggtg tggcacacca gccgcatttt ggtcaagcac 60
ttctgtttcc ccggaccgag tatcaataag ctgctcacgc ggctgaagga gaaaccgttc 120
gttacccgac cagctacttc gagaaaccta gtaacactat gaacgttgcg gagtgtttcg 180
ttcagcactt cccccgtgta gatcaggtcg atgagtcacc gcattcctca cgggtgaccg 240
tggcggtggc tgcgttggcg gcctgcctac gggttcgccc gtaggacgct ctaataccga 300
catggtgtga agagtccatt gagctagctg gtagtcctcc ggcccctgaa tgcggctaat 360
cctaactgcg gagcaggtgc tcacagacca gtgagtagcc tgtcgtaacg ggcaactctg 420
cagcggaacc gactactttg ggtgtttttc ctttttttctt ctcttatatt ggctgcttat 480
ggtgacaatt aaagaattgt taccatatag ctattggatt ggccatccgg tgacgagcag 540
agccattgtt tacctctttg ttggatttgt acctttgaac cacaaagtct tgaataccat 600
tcatctcatt ttaaagttca actcagctaa aagaaa 636

<210> SEQ ID NO 506
<211> LENGTH: 675
<212> TYPE: DNA
<213> ORGANISM: Unknown
<220> FEATURE:
<223> OTHER INFORMATION: Description of Unknown:
SA5 sequence

<400> SEQUENCE: 506

-continued

```
agtacttggt attccggtac ctttgtacac ctatttacaa accctacccc ttgtaacctt     60

agaagcaatt atttaaccgc tcactagggg gtgtgctatc caagcacatc aagagcaagc    120

acttctgtct ccccgggagg ggctaatggt acgctgtgcc cacggcggaa atgagcccta    180

ccgttaaccg gcagtctact tcgggaagcc cagtaactac attgaaactt tgaggcgtta    240

cactcagcac ataaccccaa tgtgtagttc tggtcgatga gccttggcat cccccacagg    300

cgactgtggc caaggctgcg ttggcggcca gcctgcggac caaaagtccg taggacgcct    360

aattgtggac atggtgtgaa gagcctactg agctagactg tagtcctccg gcccctgaat    420

gcggctaatc ctaaccctgg agcatccgcg tgcaacccag tacgtagggt gtcgtaatgc    480

gtaagtctgg gatggaaccg actactttgg gtgtccgtgt ttcttgtttt tcatactggg    540

tcgcttatgg ttacaactaa ttgttgtaat cattggcagt gcgcgctgac cacgcgatta    600

ttgatatttc catttgttgg atactccaat agtgtcaact catatacaca acttttacca    660

ctgatcaaga taaaa                                                     675
```

<210> SEQ ID NO 507
<211> LENGTH: 675
<212> TYPE: DNA
<213> ORGANISM: Enterovirus sp.

<400> SEQUENCE: 507

```
tgtgcgcctg ttttgaaacc ccctccccca actcgaaacg tagaagtaat gtacactact     60

gatcagtagc aggcgtggcg caccagccat gtctcgatca agcacttctg tttccccgga    120

ctgagtatca atagactgct cacgcggttg aaggtgaaaa cgtccgttac ccggctaact    180

acttcgagaa acctagtagc accatagaaa ctgcagagtg tttcgctcag cacttccccc    240

gtgtagatca ggtcgatgag tcactgcaat ccccacgggt gaccgtggca gtggctgcgt    300

tggcggcctg cctatggggc aacccatagg acgctctaag gtggacatgg tgtgaagagt    360

ctattgagct agttagtagt cctccggccc ctgaatgcgg ctaatcctaa ctgtggagcg    420

catactccca aaccagggag cagtgcgtcg taacgggcaa ctccgcagcg gaaccgacta    480

ctttgggtgt ccgtgtttcc ttttattcct atactggctg cttatggtga caattgagag    540

attgttacca tatagctatt ggattggcca tccagtgtgt aatagagcaa tcatttacca    600

atttgttgga tttactccat taacccacac gtctctcaac acactacatt tcatcttact    660

actgaacact agaaa                                                     675
```

<210> SEQ ID NO 508
<211> LENGTH: 675
<212> TYPE: DNA
<213> ORGANISM: Unknown
<220> FEATURE:
<223> OTHER INFORMATION: Description of Unknown:
Mobovirus A sequence

<400> SEQUENCE: 508

```
tattctccca caaaccttct tgtaactctg ttaagccttt tacatccatg taatttaatt     60

ttctccacct aaaaggattt cccccatggt cctttttggc tcgaacaaat gctacatagg    120

gtcttgtttt ctccccctgg ctctcttgcc agggttccat accccaattc ctctatttcc    180

atgatttttc atcatggttt atttttactg tcttcttatt ttctgaggtg accaactcct    240

aagccgactg ggtcgcggaa gcccggactc ctcgcatcac tagggtgcgt agcgatgtag    300

gcgaaaatat tggttgctag atgcatacat atagtgaatt gatactacac caaactctgt    360
```

-continued

```
tctttttgaa actagctatt ttctaagtaa ggtaggctac gggtgaaacc ttaccattgc    420

aggtacgtga accgcaacgg acatttggcc gaagactggt gtacccacgt cagttatagg    480

acctcttcaa cgttggtgga cggcatgtca ctgattagtt aggctagtga atttaagttc    540

agggggtatc ttttagctta agcgtgtatt ctagtaggac ttgcagagcc tccccaccta    600

ggaggatctc tgtttatagc cccttttcct tgttccgtta gttttccaca cttttacaat    660

atttgatgat ttgtt                                                     675
```

<210> SEQ ID NO 509
<211> LENGTH: 509
<212> TYPE: DNA
<213> ORGANISM: Unknown
<220> FEATURE:
<223> OTHER INFORMATION: Description of Unknown:
Burpengary Virus sequence

<400> SEQUENCE: 509

```
ctcccccccc ttccccttcc cgagtaggag attggcatgt atgctctaca tgcccgattc     60

tctcttgctc actctcttaa atcctggtgg cggtctcgga ttaaacattt atgtcgtatc    120

tgggatcgtc ttacttggtg gtaattcctc tgttgcctag ggacctccgg actgccggat    180

taaaggtctc aacagagggc aatgtacaag gaagtcatta tacgctaatt aagtatttga    240

tgaatgacta gtgtgacagg gctgaggaac tccccccggg taaccggtgc ctcagcgtcc    300

gaaagacacg tggataggat ccaccctgtt atacccagca cgatgtaata gtcaaatacc    360

tctgatttgt gtaggatgta taaattgtgc attgtaaatt ttgggcgtag agatgctccg    420

aaggtacccc gttttacggg atctgatcgg aggctaatta cccaatgcgc cctaaataac    480

ttcatataat ttctttttct ttattcaaa                                      509
```

<210> SEQ ID NO 510
<211> LENGTH: 675
<212> TYPE: DNA
<213> ORGANISM: Hunnivirus sp.

<400> SEQUENCE: 510

```
taacgtttgg caagaaccct cacctgtcaa ttgggaccac cactttcagt gaccccatgc     60

gaagtagtga gagagaataa gctttcttac ccttcatttg tgaacccttc agtcgaagcc    120

gcttggaata agataggagg aaaagttcat tctaaatgga gtgaaacatg tacttcagaa    180

tttctagcac gcgctgggct ttcttgcgtg tgacggcact gtcttgccgg agctctccac    240

actgacaccc cacgcttgtg gaccttggtg gcagatgaca acactgcagc tggaattgag    300

tgtctggtac actctgtgta acagtgaaaa caatgtgatc acttcggtga gctagtagcc    360

tgtggaccaa caactggtaa cagttgcctc aggggccaaa agccacggtg tttacagcac    420

cctactggtt tgattggagc aatccaagat gtcacagagt tagtaattgc caagcagtcc    480

gtactggtat cttgacatac cgtgcagttt tggatagtga aggatgccct gacggtaccc    540

ataggtaaca agtgacacta tggatctaag caggggctca ctctacgctg ctttacagct    600

ggctgtgagt taaaaaacgt ctagctatcc acaacctagg ggactaggtt ttccttttat    660

ttagattaca attat                                                     675
```

<210> SEQ ID NO 511
<211> LENGTH: 675
<212> TYPE: DNA
<213> ORGANISM: Hunnivirus sp.

<400> SEQUENCE: 511
acagtttttg acaaggaccc tcacctgtca atcgggacca ccactttcag tgaccccgtg 60
cgaagtgttg agagaaagtg agctttctta cccttcattt gtgaaccctt cagtcgaagc 120
cgcttggaat aagatggaag gaaatgttca ttctaaatgg agtgaaacat atacttaatt 180
tccagtgttt agtggtcttt ccactagaca acggcactgt cttgccggaa ctctacacac 240
caacattcca cgcttgtggg actcaaatgt tggatgacac agttgtagct ggaactgagt 300
gtttagtgca ctctgtgtaa cagtgaaaac aatgtgatca cttcggtggg ctagtagcct 360
gtggactaac aactggtaac agttgcctca ggggccaaaa gccacggtgt taacagcacc 420
ctactagttt gattggagca atccatgatg ttacagagtt agtaactgcc aaacagattg 480
tactggtatc ttggcatacc gtgcaactta ggatagtgaa ggatgccctg gcggtaccca 540
taggtaacaa gtgacactat ggatctaaac aggggctcac tctacgttgc tttacaacta 600
gctgtgagtt aaaaaacgtc taactatcca caacctaggg gactaggttt tcctttttat 660
ttttatacac aacta 675

<210> SEQ ID NO 512
<211> LENGTH: 240
<212> TYPE: DNA
<213> ORGANISM: Unknown
<220> FEATURE:
<223> OTHER INFORMATION: Description of Unknown:
Ia Io sequence

<400> SEQUENCE: 512
ggtgtccggg tgtgtgggat agacccagat gtgcagtgga tgcgagcatt tgagtcagag 60
taggagcaag cccaggggca aagggaccac attgtgtatc ccgaatgaag gatcgagatt 120
tctctcctca ttacccggtg tcttgtcact gttggggggg cccaacagtc ttagtcctat 180
actgcctgat agggtcgcgg ctggccggac tcaagtgcta tagtcagttg attttcactc 240

<210> SEQ ID NO 513
<211> LENGTH: 416
<212> TYPE: DNA
<213> ORGANISM: Taura Syndrome Virus

<400> SEQUENCE: 513
ctttaaaagt cgtgcgtggc ttcaccacgc acgatcagta ctatcagtta accactcttg 60
aatatgctca atgaccctat tcaacactgg tgtctcttag tacattattt tagcacttaa 120
cgtgcatgag ttttgcccat ttctttcaaa aaaatgagta ttcgaggaga cgtcccgctc 180
cccgtcttat ttcaaccgta gactcgacat ctattggtgg acatttaatt ccagtcgccg 240
taagttgctt ctgccccgcg ctatattttc ttatacttat ggttctatag gtctggttta 300
aaacgtaaat agacggccca caaactatag aacgcgtacc cggaacgcca atcccggata 360
agtccctgga tatatagatg caccgcaata taagcctgca gactgtctca tatact 416

<210> SEQ ID NO 514
<211> LENGTH: 604
<212> TYPE: DNA
<213> ORGANISM: Acute bee paralysis virus

<400> SEQUENCE: 514
cccgtcaaaa taacaactta taacacgatg ttacccgaag aaaccatttt agtgtaacat 60
ttaagattag aagtagttca tctaatagag ataggcacta ttagaaggag gccttttcta 120

-continued

```
aaggagccgt tagtcagccc agacaagcgc agtactttag aagagagaag ttccccgata    180

gcgaccgaaa agacgcgttt tccgtgctaa ctaatttaaa tgtgggaacg aatattatta    240

ttgaaattat gtgagccacg tagcaatcaa gtcatgtttt tgtcactacg tttactcatc    300

taatgtagat aattttgttt aagtacctat ttaggtgtca tcccaccaga gaagaaataa    360

tacgtaccgg aacccagagt acacccctta ttttaagcct tactgggctt ctctgttagt    420

tagtaatctg gcccacgttt tgcgttgagt ggggtcccaa cagtaggaat tcgacggaca    480

agtagcaagc gagtcggtac caattggttt agccttcgaa attactctgg gcaggaagtt    540

actaaacgag aactttctgc ttaaatccca acgcacaaac aaatagagta aataaataat    600

tata                                                                  604
```

<210> SEQ ID NO 515
<211> LENGTH: 539
<212> TYPE: DNA
<213> ORGANISM: Bovine rhinitis A virus

<400> SEQUENCE: 515

```
tttgttttgc ggctttgccg ttgttcgggt tttacctgtt ttcacacagc aaaacaggcc     60

ttctagtttc gtgcttaaac gagatcatgc tcgaactaga actacatagc tggtcactgg    120

actcatacca caccttgtgg agctttatgg gaaaggtggc tagtgggctg tggaagtgac    180

tctgaccaca tgcctctcaa gtgtgggaaa tcacggatcg gtgtagcgac gacaacaggc    240

cttgggacac cctctccagt aatggagacc caaggggcca aaagccacgc ctcgtgccct    300

gttgttcaca accccagtgc gacccgtgtt agtacctatt tgcgagaact gtgtctggac    360

agctaaacac aaccctagtg ggagactaag gatgcccagg aggtacccgg aggtaacaag    420

tgacactctg gatctgacct ggggagagag ggcttgcttt acaggcgcct ctctttaaaa    480

agcttctatg tctcatcagg caccggaggc cgggcctttt ccttttaaaa ttacactta     539
```

<210> SEQ ID NO 516
<211> LENGTH: 608
<212> TYPE: DNA
<213> ORGANISM: Bovine rhinitis B virus

<400> SEQUENCE: 516

```
cccccctac ttaaagatgt acggttttgc tgctttcaca gagtaaagca gatagaggtt     60

ctgaactggc aaactttacc tcgaaacacg cccgtttttc tgctgtgtct cacagactgt    120

cctgtcacac ttgtggcggc ttgtgacact gtgaacatag tgagaccgac caagacaaca    180

gtttcaagtg atgaacatcg aacgtctaaa ctggatccgt aactggacat gttagggcaa    240

ggacttcccc cctggtaaca ggagcctggc tggccaaaag ccccgctcat tgagcctagc    300

atgttgtcga ccctggactg ttcagtttag ttagtacatg gaattcactt gtcacggttc    360

ttctgaactc ggtctctagt atgacagcct aaggatgccc tccaggtacc ccggggtaac    420

aagtgacacc cgggatctga ggaggggact actttacgta gtttaaaaaa cgtctaagct    480

gttatggtga ccagaggctg gcacctttca cttttaaaat tacactactg actacaattg    540

aagtgataac ggttttacag gctttcaaac tagttacaca agcactgttt tcctgacaca    600

cacacttt                                                              608
```

<210> SEQ ID NO 517
<211> LENGTH: 576
<212> TYPE: DNA
<213> ORGANISM: Equine rhinitis A virus

<400> SEQUENCE: 517
aatattggcg cgcgcatttg cgcgcccccc cccatttcag ccccctgtca ttgactggtc 60
gaaggcgttc gcaataagac tggtcgtcac ttggctgttc tatcgtttca ggctttagcg 120
cgccctcgcg cggcgggccg tcaagcccgt gcgctgtata gcgccaggta accggacagc 180
ggcttgctgg attttcccgg tgccattgct ctggatggtg tcaccaagct gacaaatgcg 240
gactgaacct cacaaagcga cacacctgtg gtagcgctgc ccaaaaggga gcggaactcc 300
cccgccgcga ggcggtcctc tctggccaaa agcccagcgt taatagcgcc ttttgggatg 360
caggagcccc acctgccagg tgtgaagtgg agtgagtgga tctccaattt ggtctgttct 420
gaactacacc atctactgct gtgaagaatg ccctggaggc aagctggtta cagccctgac 480
caggggccct gcccgtgact ctcgatcggc gcagggtcaa aaattgtcta agcagcagca 540
ggaacgcggg agcgtttctt ttccctttgt atcgac 576

<210> SEQ ID NO 518
<211> LENGTH: 466
<212> TYPE: DNA
<213> ORGANISM: Unknown
<220> FEATURE:
<223> OTHER INFORMATION: Description of Unknown:
GFTV sequence

<400> SEQUENCE: 518
atggggaagg gtatgacgtg ccccttcctt cttcggagaa ctcgctctag tggtctttcc 60
acttctggaa aagagtgagt gcacgtgatc aggaccgtcg aagacgacaa atacctggtg 120
ctctatctca tagacgtttc acagctgtag cgacccctca gtagcagcgg aagccccctc 180
ctggtgacag gagcctctgc ggccaaaagc cacgtggata agatccactg ctgagggcgg 240
tgcgacccta gcaccctgtg atgcatacta gttgtagcgt gccggactat tggtctgtca 300
taagacacct gatagagaga ccaagaatgt cctggaggta ccccgcgtgc gggatctgac 360
caggagacca ttgcccaatg ctttacaacg ggtctatggt ttaaaaactg tcgcagtctc 420
tccaaaccaa gtggtcttgg ttttcaatta ctttgaatat ttcact 466

<210> SEQ ID NO 519
<211> LENGTH: 675
<212> TYPE: DNA
<213> ORGANISM: Unknown
<220> FEATURE:
<223> OTHER INFORMATION: Description of Unknown:
SAFV V13C sequence

<400> SEQUENCE: 519
ttttcgacgt ggttggaatt gccatcattt ccgacgaaag tgctatcatg cctccccgat 60
tatgtgatgt tttctgccct gctgggcgga gcattctcgg gttgagaaac cttgaatctt 120
tttctttgga accttggttc ccccggtcta agccgcttgg aatatgacag ggttattttc 180
ttgatcttat ttctactttt gcgggttcta tccgtaaaaa gggtacgtgc tgccccttcc 240
ttctctggag aattcacacg gcggtctttc cgtctctcaa caagtgtgaa tgcagcatgc 300
cggaaacggt gaagaaaaca gttttctgtg gaaatttaga gtgcacatcg aaacagctgt 360
agcgacctca cagtagcagc ggactcccct cttggcgaca agagcctctg cggccaaaag 420
ccccgtggat aagatccact gctgtgagcg gtgcaacccc agcaccctgg ttcgatgatc 480
attctctatg gaaccagaaa atggttttct caagccctcc ggtagagaag ccaagaatgt 540
cctgaaggta ccccgcgtgc gggatctgat caggagacca attggcggtg ctttacactg 600
tcactttggt ttaaaaattg tcacagcttc tccaaaccaa gtggtcttgg ttttccaatt 660
ttgttgaatg gcaat 675

<210> SEQ ID NO 520
<211> LENGTH: 675
<212> TYPE: DNA
<213> ORGANISM: Unknown
<220> FEATURE:
<223> OTHER INFORMATION: Description of Unknown:
SAV P-113 sequence

<400> SEQUENCE: 520
ggagatctaa gtcaaccgac tccgacgaaa ctaccatcat gcctccccga ttatgtgatg 60
ctttctgccc tgctgggtgg agcatcctcg ggttgagaaa accttcttcc tttttccttg 120
gaccccggtc ccccggtcta agccgcttgg aataagacag ggttatcttc acctcttcct 180
tcttctactt catagtgttc tatactatga aagggtatgt gtcgcccctt ccttctttgg 240
agaacacgcg cggcggtctt tccgtctctc gaaaagcgcg tgtgcgacat gcagagaacc 300
gtgaagaaag cagtttgcgg actagcttta gtgcccacaa gaaaacagct gtagcgacca 360
cacaaaggca gcggaccccc cctcctggca acaggagcct ctgcggccaa aagccacgtg 420
gataagatcc acctttgtgt gcggcacaac cccagtgccc tggtttcttg gtgacacttc 480
agtgaaaacg caaatggcga tctgaagcgc ctctgtagga aagccaagaa tgtccaggag 540
gtaccccttc cctcgggaag ggatctgacc tggagacaca tcacatgtgc tttacacctg 600
tgcttgtgtt taaaaattgt cacagctttc ccaaaccaag tggtcttggt tttcactctt 660
taaactgatt tcact 675

<210> SEQ ID NO 521
<211> LENGTH: 612
<212> TYPE: DNA
<213> ORGANISM: Unknown
<220> FEATURE:
<223> OTHER INFORMATION: Description of Unknown:
VHEV sequence

<400> SEQUENCE: 521
aattccttct tcctttctcc ttggacctcg gtcccccggt ctaagccgct cggaatatga 60
cagggttatt ttcacctctt ctctcttcta cttcatagtg ttctatacta tgaaagggta 120
tgtgtcgccc cttccttctt ggagaacgtg cgtggcggtc tttccgtctc tcgaaaaacg 180
tgcgtgcgac atgcagagta acgcaaagaa agcagttctt ggtctagctc tggtgcccac 240
aagaaaacag ctgtagcgac cacacaaagg cagcggaaac cccctcctgg taacaggagc 300
ctctgcggcc aaaagccacg tggataagat ccacctttgt gtgcggtgca accccagcac 360
cctggtttct tggtgacacc ttagtgaacc ctcgaatggc aatctcaagc gcctctgtag 420
gaaagccaag aatgtccagg aggtacccct tcctcatgga gggatctgac ctggagacac 480
atcacacgtg ctatacactt gtgcttgtgt ttaaaaattg tcacagcttt cccaaaccaa 540
gtggtcttgg ttttccctta acttcgaaaa gtcactatgg cctgcaaaca tggataccca 600
gacgtgtgcc ct 612

<210> SEQ ID NO 522
<211> LENGTH: 675
<212> TYPE: DNA
<213> ORGANISM: Unknown

<220> FEATURE:
<223> OTHER INFORMATION: Description of Unknown:
TRV NGS910 sequence

<400> SEQUENCE: 522

```
atgcgacgtg gttggagatt aaaccgactc cgacgaaagt gctatcatgc ctccccgatt     60

atgtgatgtt ttctgccctg ctgggcggag cattctcggg ttgatacacc ttgaatcctt    120

catccttgga cctcaggtcc cccggtctaa gccgcttgga atacgacagg gttattttcc    180

aatcttctcc tttctacttt catgagtcct attcatgaaa agggtctgtg ctgccccttc    240

cttcttggag aatctgcgcg gcggtctttc cgtctctcga aaagcgcaga tgcagcatgc    300

tggaaccggt gaagaaaaca gttctttgtg gaaacttaga gcagacatcg aaacagctgt    360

agtgacctca cagtagcagc ggaacccccct cctggtaaca ggagcctctg cggccaaaag   420

ccccgtggat aagatccact gctgtgagcg gtgcaacccc agcaccctgg ttcgatggtt    480

gttctctgtg gaaccagaga atggtctttc tcaagccctc cagtagagaa gccaagaatg    540

tcctgaaggt accccgcatg cgggatctga tcaggagacc aatcgtcagt gctttacact    600

ggcgctttgg tttaaaaact gtcacagctt ctccaaacca agtggtcttg gttttcactt    660

ttatcaaact gtttc                                                      675
```

<210> SEQ ID NO 523
<211> LENGTH: 551
<212> TYPE: DNA
<213> ORGANISM: Unknown
<220> FEATURE:
<223> OTHER INFORMATION: Description of Unknown:
EMCV2 RD1338 sequence

<400> SEQUENCE: 523

```
aaatactggt cgaaaccgct tgggataaga ccggggtttg ttaatgtctc aatgttattc     60

tccacccaat tgacgtcttt tgtcaattgg agggcagtga aaccttgccc ttgcttcttg    120

cagaggattc ccagtggtct ttccgctctc gacaagggaa ttcatgatcc accaaaagtt    180

gtgaagagag caggtcccat ggaagctttc tgacgactga tgatgactgt agcgaccctt    240

tgcaggcagc ggaccccccc acctggtgac aggtgcctct gcggccaaaa gccacgtgtt    300

taacagacac ctgcaaaggc ggcacaaccc cagtgcctca tcaaaagtct gatgactgtg    360

gaaatagtca accggctttt cttaagcaaa tttggtgtcg gggctgaagg atgcccggaa    420

ggtaccacac tggttgtgat ctgatccggg gccacagtac atgtgcttta cacatgtagc    480

tgcggttaaa aaacgtctag gccccccgaa ccacggggac gtggttttcc tttgaaaacc    540

acgattacaa t                                                          551
```

<210> SEQ ID NO 524
<211> LENGTH: 675
<212> TYPE: DNA
<213> ORGANISM: Unknown
<220> FEATURE:
<223> OTHER INFORMATION: Description of Unknown:
EMCV1 JZ1203 sequence

<400> SEQUENCE: 524

```
gtctgctcga tatcgcaggc tgggtccgtg actacccact ccccctttca acgtgaaggc     60

tacgatagtg ccagggcggg tactgccgta agtgccaccc caaaacaaca acaaaccccc    120

cctaacatta ctggccgacg ccgcttggaa taaggccggt gtgcgtttgt ctatatgtta    180

tttcccacca cattgccgtc ttttggcaat gtgtgggccc ggaaacctgg ccctgtcttc    240
```

```
ttgacgagca ttcctagggg tctttcccct ctcgccaaag gaatgcaagg tctgttgaat    300

gtcgtgaagg aagcagttcc tctggaagct tcttgaagac aaacaacgtc tgtagcggcc    360

ctttgcaggc agcggaaccc cccacctggc gacaggtgcc tctgcggcca aaagccacgt    420

gtataagata cacctgcaaa ggcggcacaa ccccagtgcc acgttgtgag ttggatagtt    480

gtggaaagag tcaaatggct ctcctcaagc gtattcaaca aggggctgaa ggatgcccag    540

aaggtacccc attgtatggg atctgatctg gggcctcggt gcacatgctt tacatgtgtt    600

tagtcgaggt taaaaaacgt ctaggccccc cgaaccacgg ggacgtggtt ttcctttgaa    660

aaacacgatg ataat                                                     675
```

<210> SEQ ID NO 525
<211> LENGTH: 544
<212> TYPE: DNA
<213> ORGANISM: Unknown
<220> FEATURE:
<223> OTHER INFORMATION: Description of Unknown:
EMCV1 AnrB-3741 sequence

<400> SEQUENCE: 525

```
atgtggtcga agccacttgg aataagaccg gcgtgcgctt gtctatatgt tacttccacc     60

acattgccgt cttttggcaa tgtgagggcc cggaacctgg ccctgtcttc ttgacgaaca    120

ttcctagggg actttcccct ctcgccaaag gaatgtaagg tctgttgaat gtcgtgaagg    180

aagcagttcc tctggaagct tcttgaagac aaacagcgtc tgtagcgacc ctttgcaggc    240

agcggaaccc cccacctggt aacaggtgcc tctgcggccg aaagccacgt gtataagata    300

cacctgcaaa ggcggcacaa ccccagtgcc acgttgtgcg ttggatagtt gtggaaagag    360

tcaaatggct ttccccaagc gtattcaaca aggggctgaa ggatgcccag aaggtacccc    420

actggttggg atctgatctg gggcctcggt gcaggtgctt tacacctgtt gagtcgaggt    480

taaaaaacgt ctaggccccc cgaaccacgg ggacgtggtt ttcctagaaa accactatga    540

caat                                                                 544
```

<210> SEQ ID NO 526
<211> LENGTH: 675
<212> TYPE: DNA
<213> ORGANISM: Cosavirus sp.

<400> SEQUENCE: 526

```
cgtgctttac acggtttttg aaccccacac cggctgtttg gcgcttgcag gacagtaggt     60

atattttctt tcatttctct tttctagccg cgtaggttct atctacgcgg gcggagtgat    120

actcccgctc cttcttggac aggcggcctc cacgctcttt gtggatctta aggctgccaa    180

gtcactggtg tttgaagtga agaatggaga gacactaggg cgtttcatgt ggctttgcca    240

gggattgtag cgatgctgtg tgtgtgtgcg gatttcccct cgtggcgaca cgagcctcac    300

aggccaaaag ccctgtccga aaggacccac acagtggggt tgccccgacc cctcccttca    360

aagctttgtg taaacaaact tttgtttaga ctttcttaag cttctctcac atcaggcccc    420

aaagatgtcc tgaaggtacc ctgtgtatct gaggatgagc accaccaact acccggactt    480

gtgggacgtg tcccacagac gcatgtggta ttccagcccc ctccttttga ggagggggct    540

tttgctcgct cagcacagga tctgatcagg agattcatct ctggtgcttt acaccagagc    600

atggatttaa aaattgccca aggcctggca aacaacctag gggactaggt tttctctatt    660

ttaaaagatg tcaat                                                     675
```

<210> SEQ ID NO 527
<211> LENGTH: 675
<212> TYPE: DNA
<213> ORGANISM: Cosavirus sp.

<400> SEQUENCE: 527
cgtgctttac acggtttttg aaccccacac cggctgtttg gcgcttgcag gacagcaggt 60
ttattttctt ttaactctct ctttctagcc acacacgatc tatgtgtgtg ggcggagtga 120
tactcccgtt ccttcttgga caggcggcct ccacgccctt tgtggatctt aaggctacca 180
agtcactggt gttggaaagt gaagagaaag gagttccttg ggaactacat gtggcattga 240
cagaggttgt agcgatgctg tgtgtgtgtg cggattaccc ccgtggcgac acggacccca 300
caggccaaaa gccctgtccg aaaggaccca cacagtggag caaccccagc tcccctcttc 360
aatgttttgt gttagcaacc ttggtattat tttctctcaa gcttccaata caccgggccc 420
caaagatgtc ctgaaggtac cccgtgtatc tgaggatgag caccatcaac tacccggact 480
tgttctttcg agaacagacg catgtggtaa cccagccccg atcctaaggg gtcggggctt 540
ttgctcactc agcacaggat ctgatcagga gacctccccc ccctgcttta caggggggcgg 600 gggtttaaaa attgcccaag gcctggcaaa taacctaggg gactaggttt tcctttttat 660
tttaaagttg tcaat 675

<210> SEQ ID NO 528
<211> LENGTH: 675
<212> TYPE: DNA
<213> ORGANISM: Cosavirus A

<400> SEQUENCE: 528
ccgtgcttta cacggttttt gaaccccaca ccggctgttt ggcgcttgca ggacagcagg 60
tttattttct tatgctcttt atttctagcc aacagggttc tatcctgttg ggcggagtga 120
tactcccgtt ccttcttgga cagattgcct ccacgatctt tgtggatctc aaggtgatca 180
agtcactggt aaatagagcg aaggttgagg aaacctgagg aatttccatg tggttttgcc 240
aggagttgta gcgatgctgt gtgtgtgtgc ggatttcccc tcatggcaac atgagcctca 300
caggccaaaa gccctgtccg aaaggaccca cacagtggag caatcccagc tccctcctac 360
aaagctttgt gagaatgaac tcacgtttat tcttctttat tctctgttta catcaggccc 420
caaagatgtc ctgaaggtac cttgtgtatc tgggcatgag caccatcaac tacccggact 480
tgcatttcgg tgcagacaca tgtggttacc cagcccctct gctttggcag aggggctttt 540
gctcgctcag cacgagatct gatcaggagc ccttcccagt gtgctttaca cctggcgggg 600
ggttaaaaat tgcccaaggc ctggcaaaat aacctagggg actaggtttt ccttttatta 660
acaatgtctg tcatt 675

<210> SEQ ID NO 529
<211> LENGTH: 660
<212> TYPE: DNA
<213> ORGANISM: Malagasivirus B

<400> SEQUENCE: 529
ctttattttc ttatgtaact cttcttttta agttttattt tgcctacttg tgagcttatg 60
cgggaccact gtcttagaca accccacatt tgtcatgagt aagtacacgc aaccattacg 120
attacttttt aaccgtctga ccttttgata acaactgaag ttaggcgtga aacatgcatt 180

```
tataccaaag tagccccgca tttccccact acggtggggg ggctacccta ctggctttgg    240

aactgtagcc attatgtgtt gcctggcttt caggatctca caacacaaca gttctctcac    300

aatggaatat gggtgagatt gcagtgacat gaacaagtat ctagtagtac atagactcaa    360

gcctagttgc ctgcggaaca acatgtggta acacatgccc cagggtccaa aagacaaggg    420

ttaacagccc cttctaggtg tctgtgtgtg aagaatactt tagtagtgtt gttatgatct    480

cacctgttag tacagaatga gtatggcttg gtgaaggatg tcctacaggt acccattata    540

tggatctgag taggagacca ctagtggtgg ctttaccgcc aggtgagtgg tttaaaaagc    600

gtctagccaa gccaacagca ctagggatag tgctttctat attttatatt ttcagtgtat    660
```

<210> SEQ ID NO 530
<211> LENGTH: 654
<212> TYPE: DNA
<213> ORGANISM: Mosavirus sp.

<400> SEQUENCE: 530

```
cccccccctc aaattgcaac gatatagcta atggcgagat tgagatgcta tatcacctct     60

tctaagttat agacctcatc tgattgataa ggacgtaatt tggtcgaaac cgcttggaat    120

aagaccgatg cgcgtagtca tgatgatgat gtaagatcta ggaacttatc caatctgctt    180

atgtctatgt aagtagaggg gcaggcctca ttgccctaat tctttctacc gagtatctgc    240

tagggtttct agcggcttga atacttggat tgagggatac aagatactac tgatcgattg    300

tcgattggga aacttgtaga tacttcaaag ctaccagtag cgtggactca cagccagcgg    360

actacccctc atggtaacat gagcctctgg gcccacaagg cacgtcgcaa gacctgtgag    420

acggcaaccc cagcctagct ttgttgagga aacaagcgat aacatgacat gagagaccgg    480

aaggattctt gtattgtgag ccgaaggatg gcctctaggt acctcatttt atgagatctg    540

aggaggtgct cttgagttgg tgctttacac tgacaacaca gagttaaaaa gcgtctaagc    600

tcacccggaa attgggaaat ttccgttatt tccattttgt ttgcaaagtc gttc          654
```

<210> SEQ ID NO 531
<211> LENGTH: 654
<212> TYPE: DNA
<213> ORGANISM: Unknown
<220> FEATURE:
<223> OTHER INFORMATION: Description of Unknown:
      SVV sequence

<400> SEQUENCE: 531

```
ctgggccctc atgcccagtc cttcctttcc ccttccgggg ggtaaaccgg ctgtgtttgc     60

tagaggcaca gaggagcaac atccaacctg cttttgtggg gaacggtgcg gctccaattc    120

ctgcgtcgcc aaaggtgtta gcgcacccaa acggcgcatc taccaatgct attggtgtgg    180

tctgcgagtt ctagcctact cgtttctccc ctatccactc actcacgcac aaaaagtgtg    240

ctgtaattac aagatttagc cctcgcacga gatgtgcgat aaccgcaaga ttgactcaag    300

cgcggaaagc gctgtaacca catgctgtta gtcccttcat ggctgcgaga tggctatcca    360

cctcggatca ctgaactgga gctcgaccct ccttagtaag ggaaccgaga ggccttcttg    420

caacaagctc cgacacagag tccacgtgat tgctaccacc atgagtacat ggttctcccc    480

tctcgaccca ggacttcttt ttgaatatcc acggctcgat ccagagggtg gggcatgatc    540

cccctagcat agcgagctac agcgggaact gtagctaggc cttagcgtgc cttggatact    600

gcctgatagg gcgacggcct agtcgtgtcg gttctatagg tagcacatac aaat          654
```

<210> SEQ ID NO 532
<211> LENGTH: 331
<212> TYPE: DNA
<213> ORGANISM: Teschovirus A

<400> SEQUENCE: 532

```
actagtcctt ggacttttgt tgtgtttaaa cacagaaatt taattacctg gccatgaatt     60
cattggatta acccttctga aagacttgct ctggcgcgag ctaaagcgca attgtcacca    120
ggtattgcac cagtggtggc gacagggtac agaagagcaa gtactcctga ccgggcaatg    180
ggactgcatt gcatatccct aggcacctat tgagatttct ctggggccca ccggcgtgga    240
gttcctgtat gggaatgcag gactggactt gtgctgcctg acagggtcgc ggctggccgt    300
ctgtactttg tatagtcagt tgaaactcac c                                   331
```

<210> SEQ ID NO 533
<211> LENGTH: 416
<212> TYPE: DNA
<213> ORGANISM: Teschovirus B

<400> SEQUENCE: 533

```
cttcctttta attcgtaact gataagtgat agtccttgga agctaggtat ttgttacgct     60
agttttggat tatcttgtgc ccaacatttg ttttcgaaca tatgttgtgt ttaaacacag    120
aaatctagtt tctttggtta tgagtttaat ggaatatcct tttgaaagac ttgccttggc    180
gcgggctaga gcgcaattgt caccaggtat tgcaccaatg gtggcgacag ggtacagaag    240
agcaagtact cctgactggg taatgggact gcattgcata tccctaggca tctattgaga    300
tttctctgga gcccaccagc atggagttcc tgtatgggaa tgcaggactg gacttgtgct    360
gcctgacagg gtcgcggctg gccgtctgta ctttgtatag tcagttgaaa ctcatt        416
```

<210> SEQ ID NO 534
<211> LENGTH: 664
<212> TYPE: DNA
<213> ORGANISM: Tottorivirus sp.

<400> SEQUENCE: 534

```
cccctttacg taactgcaac ttaaagagta ccctactgca ttggatgtgt ggtaaacttt     60
tacgcacaca tttgtagtag tgttagttat gttctaccta atgagtatgc atgcacccgt    120
cgaaacacgc ttgtgataag ataggtgagt ccatgtgact aatctcatta agataaataa    180
gcaccctaca acgcacggca cgctcgtgtc ttccgtgcgg ggccgggaca acagcggcct    240
aaatcttcta ggtgaccacc atgcttttgg gactatggca ccactgtgga cgtgagtacc    300
tggcagtaag tctgtgaaaa gatggaaggt gtcccaagct atggggcgta tgcatatagc    360
ctgcggaaca aacaacggcg acgttgtccc cagggcccaa aaggcacgtg gataagatcc    420
acctatatgt ttaccccata gtgtaagtca ctggaagtcc tagtaatgga tgtctggagt    480
aaggctcacg gggtagggcg aaggatgccc agaaggtacc cgtaggtaac cttaagagac    540
tatggatctg atctggggac cggatggcgc catcaccatg acgtggaggc cggtttaaaa    600
aacgtctaag cccgaccaac aacctagggg actaggtttt cctttttat tcatgtatga     660
cgtt                                                                 664
```

<210> SEQ ID NO 535
<211> LENGTH: 675
<212> TYPE: DNA
<213> ORGANISM: Unknown

<220> FEATURE:
<223> OTHER INFORMATION: Description of Unknown:
Posavirus 1 sequence

<400> SEQUENCE: 535

```
acatttcctt gcgtgcgcac ccgaaaattt attgaacttg gcttgaatca taagtaatgc     60
ttcttatagc ggacactttg agaatataat gcttgtatgg attaatgtat actgttttaa    120
ataacaaacc tagacacgca gttgcgttga tggttgtatc aatcacatat aagtgttgaa    180
ctcgtgttaa tcctcgatcg ctatatgttt gccgcctact tccaataaaa tagattacat    240
gcgcgtcatg cctttgtggg ttacctattg gcctctgaca aaaacaagtc gtaagatttg    300
tagcttcccg gtgtaaaaag ctgggcgcgg tctggctctc gtagggtgga aaggtccacc    360
aatggctggt tgagtgtaag ctccggtgtc ctggttgtcg caattccagg cgtcgtaata    420
acctatattg catctgactc taactcttgt ggctctactg tatctagttc ttgttctact    480
aactctaata atactactgg ctctaatact gaaaaactta catatgttaa tatagataat    540
atccttgatc ctgatatccc tcacgtcact gaagttcgcc gaaaacgaat ttcagatcat    600
atcattgaat ctcaaggatg tacttgctct gaacctacta taactcctca tgcgttttca    660
ttttctactc ttggc                                                     675
```

<210> SEQ ID NO 536
<211> LENGTH: 675
<212> TYPE: DNA
<213> ORGANISM: Unknown
<220> FEATURE:
<223> OTHER INFORMATION: Description of Unknown:
A105-675 sequence

<400> SEQUENCE: 536

```
ccacccacag caagaatgcc atcatctgtc ctcaccccca tttctcccct ccttcccctg     60
caaccattac gcttactcgc atgtgcattg agtggtgcac gtgttgaaca aacagctaca    120
ctcacgtggg ggcgggtttt cccgcccttc ggcctctcgc gaggcccacc cttccccttc    180
ctcccataac tacagtgctt tggtaggtaa gcatcctgat cccccgcgga agctgctcgc    240
gtggcaactg tggggaccca gacaggttat caaaggcacc cggtctttcc gcctccagga    300
gtatccctgc tagtgaattc tagtggggct ctgcttggtg ccaacctccc ccaaatgcgc    360
gctgcgggag tgctcttccc caactcaccc tagtatcctc tcatgtgtgt gcttggtcag    420
catatctgag acgatgttcc gctgtcccag accagtccag caatggacgg gccagtgtgc    480
gtagtcgtct tccggcttgt ccggcgcatg tttggtgaac cggtggggta aggttggtgt    540
gcccaacgcc cgtactttgg tgacaactca agaccaccca ggaatgccag ggaggtaccc    600
cgcctcacgg cgggatctga ccctgggcta attgtctacg gtggttcttc ttgcttccat    660
ttctttcttc tgttc                                                     675
```

<210> SEQ ID NO 537
<211> LENGTH: 675
<212> TYPE: DNA
<213> ORGANISM: Unknown
<220> FEATURE:
<223> OTHER INFORMATION: Description of Unknown:
A110-675 sequence

<400> SEQUENCE: 537

```
acctttgtgc gcctgtttta taccccctcc cccaactgta acttagaagt aacacacacc     60
gatcaacagt cagcgtggca caccagccac gttttgatca agcacttctg ttaccccgga    120
```

ctgagtatca atagactgct cacgcggttg aaggagaaag cgttcgttat ccggccaact 180
acttcgaaaa acctagtaac accgtggaag ttgcagagtg tttcgctcag cactacccca 240
gtgtagatca ggtcgatgag tcaccgcatt ccccacgggc gaccgtggcg gtggctgcgt 300
tggcggcctg cccatgggga aacccatggg acgctctaat acagacatgg tgcgaagagt 360
ctattgagct agttggtagt cctccggccc ctgaatgcgg ctaatcctaa ctgcggagca 420
cacaccctca agccagaggg cagtgtgtcg taacgggcaa ctctgcagcg gaaccgacta 480
ctttgggtgt ccgtgtttca ttttattcct atactggctg cttatggtga caattgagag 540
atcgttacca tatagctatt ggattggcca tccggtgact aatagagcta ttatatatcc 600
ctttgttggg tttataccac ttagcttgaa agaggttaaa acattacaat tcattgttaa 660
gttgaataca gcaaa 675

<210> SEQ ID NO 538
<211> LENGTH: 675
<212> TYPE: DNA
<213> ORGANISM: Unknown
<220> FEATURE:
<223> OTHER INFORMATION: Description of Unknown:
18-675 sequence

<400> SEQUENCE: 538
cccacagcaa gaatgccatc atctgtcctc acccccaatt ttcccttttc ttcccctgca 60
accattacgc ttactcgcat gtgcattgag tggtgcatgt gttgaacaaa cagctacact 120
cacatggggg cgggttttcc cgccctacgg cctctcgcga ggcccacccc ttccctcccc 180
ttataactac agtgctttgg taggtaagca tcctgatccc ccgcggaagc tgctcacgtg 240
gcaactgtgg ggacccagac aggttatcaa aggcacccgg tctttccgcc ttcaggagta 300
tccctactag tgaattctag cggggctctg cttggtgcca acctccccca aatgcgcgct 360
gcgggagtgc tcttccccaa ctcaccctag tatcctctca tgtgtgtgct tggtcagcat 420
atctgagacg atgttccgct gtcccagacc agtccagtaa tggacgggcc agtgcgtgta 480
gtcgtcttcc ggcttgtccg gggcatgttt ggtgaaccgg tggggtaagg ttggtgtgcc 540
caacgcccgt actttggtga cacctcaaga ccacccagga atgccaggga ggtaccccac 600
ctcacggtgg gatctgaccc tgggctaatt gtctacggtg gttcttcttg cttccacttc 660
tttcttctgt tcacg 675

<210> SEQ ID NO 539
<211> LENGTH: 675
<212> TYPE: DNA
<213> ORGANISM: Unknown
<220> FEATURE:
<223> OTHER INFORMATION: Description of Unknown:
A115-675 sequence

<400> SEQUENCE: 539
acctttgtgc gcctgtttta taccccccc aacctcgaaa cttagaagta aagcaaaccc 60
gatcaatagc aggtgcggcg caccagtcgc atcttgatca agcacttctg taaccccgga 120
ccgagtatca atagactgct cacgcggttg aaggagaaaa cgttcgttac ccggctaact 180
acttcgagaa acccagtagc atcatgaaag ttgcagagtg tttcgctcag cactaccccc 240
gtgtagatca ggccgatgag tcaccgcact tccccacggg cgaccgtggc ggtggctgcg 300
ttggcggcct gcctatgggg caacccatag gacgctctaa tacggacatg gtgcgaagag 360
tctattgagc tagttagtag tcctccggcc cctgaatgcg gctaatccta actgcggagc 420
acataccctt aatccaaagg gcagtgtgtc gtaacgggta actctgcagc ggaaccgact 480
actttgggtg tccgtgtttc cttttaattt ttactggctg cttatggtga caattgagga 540
attgttgcca tatagctatt ggattggcca tccggtgact aacagagcta ttgtgttcca 600
atttgttgga tttaccccgc tcacactcac agtcgtaaga acccttcatt acgtgttatt 660
tctcaactca agaaa 675

<210> SEQ ID NO 540
<211> LENGTH: 675
<212> TYPE: DNA
<213> ORGANISM: Unknown
<220> FEATURE:
<223> OTHER INFORMATION: Description of Unknown:
A73-675 sequence

<400> SEQUENCE: 540
ttactccatt cagcttcttc ggaacctgtt cggaggaatt aaacgggcac ccatactccc 60
cccacccccc ttttgtaact aagtatgtgt gctcgtgatc ttgactccca cggaacggac 120
cgatccgttg gtgaacaaac agctaggtcc acatcctccc ttcccctggg agggcccccg 180
ccctcccaca tcctcccccc agcctgacgt atcacaggct gtgtgaagcc cccgcgaaag 240
ctgctcacgt ggcaattgtg ggtccccccct tcatcaagac accaggtctt tcctccttaa 300
ggctagcccc ggcgtgtgaa ttcacgttgg gcaactagtg gtgtcactgt gcgctcccaa 360
tctcggccgc ggagtgctgt tccccaagcc aaacccctgg cccttcacta tgtgcctggc 420
aagcatatct gagaaggtgt tccgctgtgg ctgccaacct ggtgacaggt gccccagtgt 480
gcgtaacctt cttccgtctc cggacggtag tgattggtta agatttggtg taaggttcat 540
gtgccaacgc cctgtgcggg atgaaacctc tactgcccta ggaatgccag gcaggtaccc 600
cacctccggg tgggatctga gcctgggcta attgtctacg ggtagtttca tttccaatcc 660
ttttatgtcg gagtc 675

<210> SEQ ID NO 541
<211> LENGTH: 675
<212> TYPE: DNA
<213> ORGANISM: Kobuvirus sp.

<400> SEQUENCE: 541
ttactccatt cagcttcttc ggaacctgtt cggaggaatt aaacgggcac ccatacaccc 60
ccatcccctt tctgcaactt aagtatgtgt gctcgtgatc ttgactccca cggaatggat 120
cgatccgctg gagaacaaac tgctagatcc acatcctccc ttcccctggg aggaccttgg 180
tcctcccaca tcctcccccc agcctgacgt accacaggct gtgtgaagcc cccgcgaaag 240
ctgctcacgt ggcaattgtg ggtccccccct tcatcaagac accaggtctt tcctccttaa 300
ggctagcccc gatgtgtgaa ttcacattgg gcaactagtg gtgtcactgt gcgctcccaa 360
tctcggccgc ggagtgctgt tccccaagcc aaacccctgg cccttcacta tgtgcctggc 420
aagcatacct gagaaggtgt tccgctgtgg ctgccagcct ggtaacaggt gccccagtgt 480
gcgtaacctt cttccgtctt cggacggtag tgattggtta agatttggtg taaggtccat 540
gtgccaacgc cctgtgcggg atgaaacctc tactgcccta ggaatgccag gcaggtaccc 600
cacccccggg tgggatctga gcctgggcta attgtctacg ggtagtttca tttccaattc 660
ttttatgtcg gagtc 675

<210> SEQ ID NO 542
<211> LENGTH: 675
<212> TYPE: DNA
<213> ORGANISM: Aichivirus sp.

<400> SEQUENCE: 542
ttactccatt cagcttcttc ggaacctgtt cggaggaatt aaacgggcac ccatacatcc 60
ccatcccctt tctgtaactt aagtatgtgt gcttgtaatc ttgactccca cggaatggat 120
cgatccgctg gagaacaaac tgctagatcc acatcctccc ttcccctggg aggaccttgg 180
tcctcccaca tcctcccccc agcctgacgt accacaggct gtgtgaagcc cccgcgaaag 240
ctgctcacgt ggcaattgtg ggtcccccct tcatcaagac accaggtctt tcctccttaa 300
ggctagcccc gatgtgtgaa ttcacattgg gcaactagtg gtgtcactgt gcgctcccaa 360
tctcggccgc ggagtgctgt tccccaagcc aaacccctgg cccttcacta tgtgcctggc 420
aagcatatct gagaaggtgt tccgctgtgg ctgccagcct ggtaacaggt gccccagtgt 480
gcgtaacctt cttccgtctc cggacggtag tgattggtta agatttggtg taaggttcat 540
gtgccaacgc cctgtgcggg atgaaatctc tactgcccta ggaatgccag gcaggtaccc 600
caccctcggg tgggatctga gcctgggcta attgtctacg ggtagtttca tttccaatcc 660
ttttatgtcg gagtc 675

<210> SEQ ID NO 543
<211> LENGTH: 675
<212> TYPE: DNA
<213> ORGANISM: Aichivirus sp.

<400> SEQUENCE: 543
actccattca gcttcttcgg aacctgttcg gaggaattaa acgggcaccc atacaccccc 60 atccccttt ttgcaactta agtatgtgtg ctcgtaatct tgactcccac ggaatggatc 120
gatccgctgg agaacaaact gctagatcca catcctccct ccccccctggg aggacctcgg 180 tcctcccaca tcctcccccc agcctgacgt atcacaggct gtgtgaagcc cccgcgaaag 240
ctgctcacgt ggcaattgtg ggtcccccct tcatcaagac accaggtctt tcctccttaa 300
ggctagtccc gatgtgtgaa ttcacatcgg gcaactagtg gtgtcactgt gcgctcccaa 360
tctcggccgc ggagtgctgt tccccaagcc aaacccctgg cccttcacta tgtgcctggc 420
aagcatatct gagaaggcgt tccgctgtgg ctgccagcct ggtaacaggt gccccagtgt 480
gcgtaacctt cttccgtccc cggacggtag tgattggtta agacttggcg taaggttcat 540
gtgccaacgc cctgtgcggg atgaaacctc tactgcccta ggaatgccag gcaggtaccc 600
caccttcggg tgggatctga gcctgggcta attgtctacg ggtagtttca tttctaattc 660
tttcatgtcg gagtc 675

<210> SEQ ID NO 544
<211> LENGTH: 675
<212> TYPE: DNA
<213> ORGANISM: Aichivirus sp.

<400> SEQUENCE: 544
ttactccatt cagcttcttc ggaacctgtt cggaggaatt aaacgggcac ccatacaccc 60
ccaccccctt tttgcaactt aagtatgtgt gctcgtgatc ttgactccca cggaatggat 120
cgatccgctg gagaacaaac tgctagatcc acatcctccc ttcccttggg aggacctcgg 180
tcctcccaca tcctcccccc agcctgacgt accacaggct gtgtgaagcc cccgcgaaag 240

```
ccgctcacgt ggcaattgtg ggtcccccct tcattaagac accaggtctt tcctccttaa    300

ggctagtccc gatgtgtgaa ttcacattgg gcaactagtg gtgtcactgt gcgctcccaa    360

tctcggccgc ggagtgctgt tccccaagcc aaacccctgg cccttcacta tgtgcctggc    420

aagcatatct gagaaggtgt tccgctgtgg ctgccagcct ggtaacaggt gccccagtgt    480

gcgtaacctt cttccgtctt cggacggtag tgattggtta agatttggcg taaggttcat    540

gtgccaacgc cctgtgcggg atgaaacctc tactacccta ggaatgccag gcaggtaccc    600

caccctcggg tgggatctga gcctgggcta attgtctacg ggtagtttca tttccaattc    660

ttctatgtcg gagtc                                                     675
```

<210> SEQ ID NO 545
<211> LENGTH: 675
<212> TYPE: DNA
<213> ORGANISM: Aichivirus sp.

<400> SEQUENCE: 545

```
tactccattc agcttcttcg gaacctgttc ggaggaatta aacgggcacc catacacccc     60

caccccccttt tctgcaactt aagtatgtgt gctcgtaatc ttgactccca cggaatggat    120

cgatccgctg gagaacaaac tgctagatcc acatcctccc ttcccctggg aggaccccgg    180

tcctcccaca tcctcccccc agcctgacgt atcacaggct gtgtgaagtc cccgcgaaag    240

ctgctcacgt ggcaattgtg ggtcccccct tcatcaagac accaggtctt tcctccttaa    300

ggctagcccc gatgtgtgaa ttcacattgg gcaactagtg gtgtcactgt gcgctcccaa    360

tctcggccgc ggagtgctgt tccccaagcc aaacccctgg cccttcacta tgtgcctggc    420

aagcatatct gagaaggtgt tccgctgtgg ctgccagcct ggtaacaggt gccccagtgt    480

gcgtaacctt cttccgtctc cggacggtag tgattggtta agatttggtg taaggttcat    540

gtgccaacgc cctgtgcggg atgaaacctc tactgcccta ggaatgccag gcaggtaccc    600

caccttcggg tgggatctga gcctgggcta attgtctacg ggtagtttca tttccaattc    660

ttttatgtcg gagtc                                                     675
```

<210> SEQ ID NO 546
<211> LENGTH: 664
<212> TYPE: DNA
<213> ORGANISM: Aichivirus sp.

<400> SEQUENCE: 546

```
gcttcttcgg aacctgttcg gaggaattaa acgggcaccc atacaccccc acccccttt     60

ctgcaactta agtatgtgtg ctcgtaatct tgactcccac ggaatggatc gatccgctgg    120

agaacaaact gctagatcca catcctccct tcccctggga ggaccccggt cctcccacat    180

cctcccccca gcctgacgta tcacaggctg tgtgaagtcc ccgcgaaagc tgctcacgtg    240

gcaattgtgg gtcccccctt catcaagaca ccaggtcttt cctccttaag gctagccccg    300

atgtgtgaat tcacattggg caactagtgg tgtcactgtg cgctcccaat ctcggccgcg    360

gagtgctgtt ccccaagcca aacccctggc ccttcactat gtgcctggca agcatatctg    420

agaaggtgtt ccgctgtggc tgccagcctg gtaacaggtg ccccagtgtg cgtaaccttc    480

ttccgtctcc ggacggtagt gattggttaa gatttggtgt aaggttcatg tgccaacgcc    540
```

ctgtgcggga tgaaacctct actgccctag gaatgccagg caggtacccc accttcgggt 600
gggatctgag cctgggctaa ttgtctacgg gtagtttcat ttccaattct tttatgtcgg 660
agtc 664

<210> SEQ ID NO 547
<211> LENGTH: 675
<212> TYPE: DNA
<213> ORGANISM: Aichivirus sp.

<400> SEQUENCE: 547
tactccattc agcttcttcg gaacctgttc ggaggaatta aacgggcacc cactttcctg 60
tcctctcccc ttttctgtaa ctccaagtgt gtgctcgtaa tcttgactcc cgcggattga 120
ccgctccgct ggtgaacaaa ctgctaggtc atctcctccc cacccttggg cgtccttccg 180
ggcgtccaca ccctcccccc agcctgacgt gtcacaggct gtacaaagac cccgcgaaag 240
ctgctaacgt ggcaattgtg ggtccccccct ttgtaaagga accgagtctt tctcccttaa 300
ggctagaccc ctgtgtgaat tcacaggtgg caactagtgg ttccactgca tgctcccgac 360
ctcggccgcg gagtgctgtt ccccaagtcg taacactgac cttcacttat gtgcctggca 420
agcatatctg agaagatgtt ccgctgtggc tgccaaacct ggtaacaggt gccccagtgt 480
gcgtagtctt cttccgtctt cggacggtag gtgttaggta aagatgcggc gtaaggttca 540
agtgccaacg ccctggaagg gatgaccctt ctactgccct aggaatgccg cgcaggtacc 600
ccaggttcgc ctgggatctg agcgcgggct aattgtctac gggtagtttc atttccctct 660
tcttccactg gcatc 675

<210> SEQ ID NO 548
<211> LENGTH: 675
<212> TYPE: DNA
<213> ORGANISM: Aichivirus sp.

<400> SEQUENCE: 548
actccattca gcttcttcgg aacctgttcg gaggaattaa acgggcaccc actttcctgt 60
cctctccccc tttctgcaac tcaagtgtgt gctcgtaatc ctgactccca cgggttgacc 120
gccccgttgg tgaacaaaca gctaggtcat tccctcccta cccctgggcg ccatttcagt 180
ggcgttcata tcctcccccc agcctgacgt gtcacaggct gtgcaaagtc cccgcgaaag 240
ctgctcacgt ggcaattgtg ggtccccccct ttgtgaagga accgagtctt tctcccttaa 300
ggctagaccc ctgtgtgaac tcacaggtgg caactagtgg ttccactgca tgctcccgac 360
ctcggccgcg gagtgctgtt ccccaagtcg tgacactgac ctccacttat gtgcctggca 420
agcatatctg agaagatgtt ccgctgtggc tgccaaacct ggtaacaggt gccccagtgc 480
gtgtagtctt cttccgtctc cggacggtaa gtgtgtggta aagatgcggc gtaaggttca 540
agtgccaacg ccctggaagg gatgaccctt ctactgccct aggaatgccg cgcaggtacc 600
ccaggttcgc ctgggatctg agcgcgggct aattgtctac gggtagtttc atttccctct 660
cttttcactg gcatc 675

<210> SEQ ID NO 549
<211> LENGTH: 498
<212> TYPE: DNA
<213> ORGANISM: Pestivirus sp.

<400> SEQUENCE: 549
gtataagggt tgggaacctt gtaccaagct acctctgcca ttcagtattt gggagtagaa 60
gtagatgtgt ttacaaactc acacgtgtgg gggcggggat agactgtgcc agcggtcgtg 120
taccagcacc tacgcatacg tgtggactgc gaaccaggag agcacctagg tctgacaagc 180
tgtgagaaca cagtagtcgt cagtgagtca gctggtaagg atcacccacc tggatactca 240
cgtggacgag ggagtttccc agtcagaaac ctacaccaga ggaggggtcc tctggagaca 300
tggatggtct gagtaacaga ctatctactg gggtgtgctg cctgacaggg tctcggctga 360
tagcctggct agcagtataa aaatcagttg aattggcata tgagttgtga acatctagta 420
aacaatgaaa gacaaaaaca aaaaatgagc ataataaaaa aattgtacaa tccactactc 480
aggtgtggct gcagactt 498

<210> SEQ ID NO 550
<211> LENGTH: 576
<212> TYPE: DNA
<213> ORGANISM: Kobuvirus sp.

<400> SEQUENCE: 550
tttgaaaagg gggtgggggg gcctcggccc cctcaccctc ttttccggtg gccattcgcc 60
cgggccaccg ttactccact ccactccttc gggactggtt tggaggaaca caacagggct 120
tcccatccct gtttaccctt tattccatca tcctttcccc aagtttaccc tatccacacc 180
ccactgactg actcctttgg attttgacct cagaatgcct atttgacctc ccactcgcct 240
ctcccttttc ggattgccgg tggtgcctgg cggaaaaagc acaagtgtgt tgcaggctac 300
caaactccta cccgacaaag gtgcgtgtcc gcgtgctgag taatgggata ggagatgcct 360
acaacaggct cgcccatgag tagagcatgg actgcggtgc atgtgacttc ggtcaccacg 420
ggcatagcat tgctcacccg tgaatcaagt catcgagatt tctctgacct ctgaagtgca 480
ctgtggttgc gtggctggga atccacgctt gaccatgtac tgcttgatag agtcgcggct 540
ggccgactca tgggttaaag tcagttgaca agacac 576

<210> SEQ ID NO 551
<211> LENGTH: 675
<212> TYPE: DNA
<213> ORGANISM: Kobuvirus sp.

<400> SEQUENCE: 551
cctacccaag ggttacatgg gaccatattc ctcctcccct gtaactttaa gttttgtgcc 60
cgtattcttg actccaggcg gatgttgtgt cgcccgtcct gtgaacaaac agctagacac 120
tttcctcccc tccctctggg ctgctccggc agtccactcc ctccccccag cgtaacatgc 180
cccgctggag tgatgcacct ggaagtcgtg gacgtgggtt agtaacttcg gtgaaaaccc 240
actataatga caactggttg acccccacac tcaaaggact cgagtctttc tcccttaagg 300
ctagcccggc cacatgaatt tgcagctggc aactagtgag tccaccatgt cccgcaacct 360
cggctgcgga gtgctgttcc ccaagcgtat gccttccttc tgtaagagtg cgcctggcaa 420
gcacatctga gaagtcgttc cgctgcgtcg tgccaacctg gcgacaggtg acccagtgtg 480
cgtagacttc ttccggattc gtccggctct tctctaggaa acatgcgtgt aaggttcatg 540
tgccaaagcc ctgcgcgcgg tgttcttcta ctgccctagg aatgtgccgc aggtacccct 600
acttcggtag ggatctgagc ggtagctaat tgtctacggg tagtttcatt tccatcttct 660
cttcaggtcg acatc 675

<210> SEQ ID NO 552
<211> LENGTH: 675
<212> TYPE: DNA
<213> ORGANISM: Kobuvirus sp.

<400> SEQUENCE: 552
gaccttctgg tacttcttcg cctgggtcac aaaagcgaag aacctgcctc tctaacgcca 60
gacgagcggc attaaacttg aacttctggc actctccact ctcccttttc cctgtccctt 120
tccccactgc gctctcaagg tcgcgcaatc ctgggactag cccagtttta aaagttcctg 180
gcaccctttg cccctctagg cccttaaggt aggaactgac cttgtgctgt gatctcggtg 240
cgggagtgct accacgtagt catcgtaagc ctcgtttctg gttctgccct ggcaaggcta 300
cagagtaccg tgttccgctg tggatgccat ccgggtaacc ggacccccag tgtgtgtagc 360
ggtatgttca cggtccgccg tgttcaccag attcctgacc tggctttgct agaaatggtg 420
tgtgcccaat ccctgtgacc agtatcaatt acatcaccta ggaatgctag gaaggtaccc 480
cagtcctgag ctgggatctg atcctaggct aattgtctac ggtgatgctc cttttatttt 540
cttacaactg ctattgactg tctgattgct gattctgctc ttgtgctctt ctgctctggc 600
tcattctcaa gggttctctt tgtccaagat cctttggttc tctccttgtt ccacttgcca 660
ctgccaacgc ttgtc 675

<210> SEQ ID NO 553
<211> LENGTH: 369
<212> TYPE: DNA
<213> ORGANISM: Pestivirus sp.

<400> SEQUENCE: 553
gtatacgcag ttagttcatc ctgtgtatac agattggaga ctctaaaaac aacgattcgg 60
aataggggcc cgcggcgaag accgaagaca ggctaaccat gccgttagta gggctagcac 120
caaaacgcgg gaactagaca cttaggagag tggtctggct actctaagag gtgagtacac 180
cttaaccgtc aagggttcta ctcctcagtt gaggactaga gatgccctgt ggacgggggc 240
atgcccaaga gttagcttag ccggggcggg ggttgttccg gtgaaagtag caatattgac 300
cacactgcct gatagggcgg agcaggcccc ctaggtagtc tagtataaaa tgtctgctgt 360
acatggcac 369

<210> SEQ ID NO 554
<211> LENGTH: 399
<212> TYPE: DNA
<213> ORGANISM: Pestivirus sp.

<400> SEQUENCE: 554
tacgcggggt ataacgacag tagttcaagt gtcgttatgc atcattggcc ataacaaatt 60
atctaatttg gaatagggac ctgcgacctg tacgaaggcc gagcgtcggt agccattccg 120
actagtagga ctagtacaaa taggtcaact ggttgagcag gtgagtgtgc tgcagcggct 180
aagcggtgag tacaccgtat tcgtcaacag gtgctactgg aaaggatcac ccactagcga 240
tgcctgtgtg gacgaggaca tgtccaagcc aatgttatca gtagcggggg tcgttactga 300
gaaagctgcc cagaatgggt agttgcacat acagtctgat aggatgccgg cggatgccct 360
gtattttgac cagtataaat attatccgtt gtaaagcat 399

<210> SEQ ID NO 555
<211> LENGTH: 123
<212> TYPE: DNA
<213> ORGANISM: Pestivirus sp.

<400> SEQUENCE: 555
gcagatatcg gtggtggacc tgggggttgg gctcaccgtg ccccttcatg gggtagacct 60
cactgcttga tagagtgccg gcggatgcct caggtaagag tataaaatcc gttgttcact 120
aac 123

<210> SEQ ID NO 556
<211> LENGTH: 382
<212> TYPE: DNA
<213> ORGANISM: Pestivirus sp.

<400> SEQUENCE: 556
gtatacgagt ttagctcaat cctcgtatac aatattgggc gtcaccaaat atagatttgg 60
cataggcaac accccgatgc gaaggccgaa aagggctaac catgccctta gtaggactag 120
caaaaaatcg gggactagcc caggtggtga gcttcctgga tgaccgaagc cctgagtaca 180
gggcagtcgt caacagttca acacgcagaa taggtttgcg tcttgatatg ctgtgtggac 240
gagggcatgc ccacggtaca tcttaaccta tccgggggtc ggataggcga aagtccagta 300
ttggactggg agtacagcct gatagggtgt tgcagagacc catctgatag gctagtataa 360
aaaactctgc tgtacatggc ac 382

<210> SEQ ID NO 557
<211> LENGTH: 373
<212> TYPE: DNA
<213> ORGANISM: Unknown
<220> FEATURE:
<223> OTHER INFORMATION: Description of Unknown:
Classical swine fever virus sequence

<400> SEQUENCE: 557
gtatacgagg ttagttcatt ctcgtatgca tgattggaca aattaaaatt tcaatttgga 60
tcagggcctc cctccagcga cggccgaact gggctagcca tgcccacagt aggactagca 120
aacggaggga ctagccgtag tggcgagctc cctgggtggt ctaagtcctg agtacaggac 180
agtcgtcagt agttcgacgt gagcagaagc ccacctcgat atgctatgtg gacgagggca 240
tgcccaagac acaccttaac cctagcgggg gtcgctaggg tgaaatcaca ccacgtgatg 300
ggagtacgac ctgatagggt gctgcagagg cccactatta ggctagtata aaaatctctg 360
ctgtacatgg cac 373

<210> SEQ ID NO 558
<211> LENGTH: 222
<212> TYPE: DNA
<213> ORGANISM: Pegivirus sp.

<400> SEQUENCE: 558
tcagggttgg taggtcgtaa atcccggtca ccttggtagc cactataggt gggtcttaag 60
agaaggttaa gattcctctt gtgcctgcgg cgagaccgcg cacggtccac aggtgttggc 120
cctaccggtg ggaataaggg cccgacgtca ggctcgtcgt taaaccgagc ccgtcaccca 180
cctgggcaaa cgacgcccac gtacggtcca cgtcgccctt ca 222

<210> SEQ ID NO 559
<211> LENGTH: 527
<212> TYPE: DNA
<213> ORGANISM: Pegivirus sp.

<400> SEQUENCE: 559
cccggcactg ggtgcaagcc ccagaaaccg acgcctattt aaacagacgt tatgaaccgg 60
cgccgacccg gcgaccggcc aaaaggtggt ggatgggtga tgccagggtt ggtaggtcgt 120
aaatcccggt catcttggta gccactatag gtgggtctta agggttggtc aaggtccctc 180
tggcgcttgt ggcgagaaag cgcacggtcc acaggtgttg gccctaccgg tgtgaataag 240
ggcccgacgt caggctcgtc gttaaaccga gcccattacc cacctgggca aacaacgccc 300
acgtacggtc cacgtcgccc tacaatgtct ctcttgacca ataggctttg ccggcgagtt 360
gacaaggacc agtgggggct gggcgacggg ggtcgtatag gaagaaaaat gccacccgcc 420
ctcacccgaa ggttcttggg ctaccccggc tgcaggccgc cgcggagctg ggtagcccca 480
agaaccttcg ggtgagggcg ggtggcattt ttcttcctat accgatc 527

<210> SEQ ID NO 560
<211> LENGTH: 402
<212> TYPE: DNA
<213> ORGANISM: Pegivirus sp.

<400> SEQUENCE: 560
tggtcacctt ggtagccact ataggtgggt cttaagagaa ggttaagatt cctcttgtgc 60
ctgcggcgag accgcgcacg gtccacaggt gttggcccta ccggtgtgaa taagggcccg 120
acgtcaggct cgtcgttaaa ccgagcccat ttcccgcctg ggcaaacgac gcccacgtac 180
ggtccacgtc gccctttttaa tgtctctctt gaccaatagg ttcatccggc gagttgacaa 240
ggaccagtgg gggccggggg tcacagggat ggaccctggg ccctgccctt cccggcgggg 300
tggggaaagc atggggccac ccagctccgc ggcggcctgc agccggggta gcccaagaac 360
cttcgggtga gggcgggtgg catttttctt cctataccga tc 402

<210> SEQ ID NO 561
<211> LENGTH: 531
<212> TYPE: DNA
<213> ORGANISM: Unknown
<220> FEATURE:
<223> OTHER INFORMATION: Description of Unknown:
Hepatitis GB virus A sequence

<400> SEQUENCE: 561
gccgggtgga aggcccggaa ccgccccacc acctcaacta ggtggtaagg gtacgtctat 60
cggtccggct ggcccgaaag gcggtggatc ctgtgtgtta gggttcgtag gtggtaaatc 120
ccagcacagg tggtaatcgc tatagggcag gcttatcccg gtgaccgctt ccctggatcc 180
tggagcgggt cgtggcggca cggtccacag gagtggggcc tccggtgtga ataagccctc 240
gtctggagca tcagacgtta aactgagacg tcccgaagag atcggaacga cgccccacgt 300
atggcaacgc cgcttaaaac ccttcgggga cagctatgcg ggttgacaat gccagtgggg 360
ggccgggccc actattgttg tgggctccga gttcctctag ggatggccga aaggcagcca 420
tggggccacc caggcggcgc cgtgctacag gcggcaaggg gaaaaatcct tcgggtgacc 480
ccgggtggca ttccctccct tagcagcatg agtgtggtgg tagctgcaac c 531

<210> SEQ ID NO 562
<211> LENGTH: 520
<212> TYPE: DNA
<213> ORGANISM: Pegivirus sp.

<400> SEQUENCE: 562
ggggaatctc accccccgtc cggttccgga agaatcggaa accgacaccc tgaccaatca 60
ttcttgatca tagagtggat gttagtgaaa gccagacgaa agccggcgga tgggtggtga 120
cagggttggt aggtcgtaaa tcccggccac cctggtaccc ggtataagtt gggcggaagc 180
tgactgaagc tccgtgctct tttctgtgcg ttcttggtgc acggtccaca ggtgacgcct 240
ataccggtgt gaataatagg ccgactcgag cggagtcgtt aaactgagaa cctccatacg 300
gatggcaact tggcttgcgt acggggacgc cgctaaagtc acagtgggtt aagtccggcg 360
ggttgacaac cccagcaagg cgagggggtc ctattgttgg actctgccag ttcccggtgg 420
aggtaggcat ggggtggccc agctccgcgg cgcgctacag ccggggtagc ccaaaatccg 480
aaaggtgagg gcgggccaca tgtccgaaat ttagtcaagc 520

<210> SEQ ID NO 563
<211> LENGTH: 524
<212> TYPE: DNA
<213> ORGANISM: Pegivirus I

<400> SEQUENCE: 563
agaatggtct aagtggttgc caccgtggtc cgaaggggag gaggacctac gctgccaggg 60
ttggcaggtc gtaaatcccg ggtgtaggag atccctcctt gttaggactg ctggtagctg 120
gggggtcggt gaccccctgg gcaaccgcca aacccggacg accgggtggc ggctccatgt 180
tggcacggtc cacaggtgtg aaccctaccg gtgtgaataa gggttggtgg ttgcggtcca 240
ccttaaacgt agtatgcatt gggcttggta aaacaccgct cgtagtacgg aacgccgcct 300
ttaaagacac agtaggcgta gccggcgggt tgacaatcca tacggggggt ggggtgtggt 360
catggatctg tccacaccac cttcatgcgg ccctctaagc aagccatacc ggggggaggc 420
gcgcggcacc gcactgccgg gcaaggggaa gaaccttcgg gtgacccccc cccaaccacc 480
gtccgatcaa tgctaatgtt gcgtttaggc gtgacaccgg caca 524

<210> SEQ ID NO 564
<211> LENGTH: 537
<212> TYPE: DNA
<213> ORGANISM: Pegivirus K

<400> SEQUENCE: 564
agaatggtgt gatccgtcgc cgctccagcg gaaagcgggc gggatctagt ggttagggtt 60
gttcgcgtaa atcccacact agtggtacgc tcgtataacg tgggagcagc cggtggggtc 120
gaccccccac ctggcggctg ctgagcaccg gacgaagcgc ggggggtgaa cgctaacccg 180
cggcccgggc tgccaacgtt aggcacgtct tggctggaag acgttaaaca cagggccccc 240
cctcaaccct gatccgaggc cagagaccaa ggtacgccgc ccttttaaag gcgttactcg 300

```
tccaatagga tctctccggc gggttgtcaa accttgctgg ccctggtgat ggttacggga    360

gggggtgggg cggggagtag aagccccgcc cggcatgggg gtaccaagct cggcacgccc    420

agcacgcgtg gcgtagggga aaaatccttc gggtgacccc tggtaccata aagtaattaa    480

catgagcatg ccgctagggt gtgctttttc ttccttcctt gggaaggcgg tggcacc       537
```

<210> SEQ ID NO 565
<211> LENGTH: 617
<212> TYPE: DNA
<213> ORGANISM: Unknown
<220> FEATURE:
<223> OTHER INFORMATION: Description of Unknown:
Theiler's disease-associated virus sequence

<400> SEQUENCE: 565

```
tgataccgtg tcccggtacg acctcgcgcg tccccaagct cgccctgagg ggggagcgta     60

agggcgcgta gtggggtagc cccccaaacc gagccaccct agtgagtgac tttagaatgg    120

ttagggagac taccgccttc gctgtttggg gacctaatga tccgcgtgcc agggttcttc    180

gggtaaatcc cggcgcggtg ttttgggttc agggcagtag gggcagacgg gccagcagtc    240

gctggttcct ggtaccacca ccctatccgg acgacctccc tcacgaaagg tcgccacggt    300

ctgtggctcg acgacgccta taattcagtc cgaggggcgc agccctcgtt aaacttaggc    360

aaggttcctc gccattgatt tggccagggg tttaagtgaa cgccgccctt ttaatgttta    420

atagggttct ttcccggcgg gttgacaaac acttccctgg gctcttcgtt ggcctcggtt    480

ccttgatgct tcggcaccca tgagcgcaca gggggggggac cctgcgacag tccgccaaga   540

ggaaaatcct tcgggtgacc tcgtgcgcaa cccaatccct tcttcttcca catggcgtgt    600

ctgtggtgca tgctgtg                                                   617
```

<210> SEQ ID NO 566
<211> LENGTH: 349
<212> TYPE: DNA
<213> ORGANISM: Pegivirus sp.

<400> SEQUENCE: 566

```
ggacttcggt cccccctgtta ctctgcgagc caccgcagag ccagggttgg tacgcccgag    60

gtgttagacc ccggccgaaa gctcctaacc atggggttag taggacgtgg taaatgccac    120

tgaggggttg gagagctggt agagcgagta agtcggcgta aggcccgagt acgggcctcc    180

cagcccgggt cagcctaaac ctggctgtga tacccggtgc atggagggcg tgtcccaacg    240

ctcgatcgct gtagggtggg tccctgcagt tgggtgtggc taccctgctc gtactgcttg    300

atagagtccc ggcggacgga ccagctctcg tcagtccgtg gagttgcac                349
```

<210> SEQ ID NO 567
<211> LENGTH: 327
<212> TYPE: DNA
<213> ORGANISM: Pegivirus sp.

<400> SEQUENCE: 567

```
aactgttgtt gtagcaatgc gcatattgct acttcggtac gcctaattgg taggcgcccg     60

gccgaccggc cccgcaaggg cctagtagga cgtgtgacaa tgccatgagg gatcatgaca    120

ctggggtgag cggaggcagc accgaagtcg ggtgaactcg actcccagtg cgaccacctg    180
```

gcttggtcgt tcatggaggg catgcccacg ggaacgctga tcgtgcaaag ggatgggtcc 240
ctgcactggt gccatgcgcg gcaccactcc gtacagcctg atagggtggc ggcgggcccc 300
cccagtgtga cgtccgtgga gcgcaac 327

<210> SEQ ID NO 568
<211> LENGTH: 436
<212> TYPE: DNA
<213> ORGANISM: Unknown
<220> FEATURE:
<223> OTHER INFORMATION: Description of Unknown:
GB virus C/Hepatitis G virus sequence

<400> SEQUENCE: 568
cccccggcac tgggtgcaag ccccagaaac cgacgcctat ctaagtagac gcaatgactc 60
ggcgccgact cggcgaccgg ccaaaaggtg gtggatgggt gatgacaggg ttggtaggtc 120
gtaaatcccg gtcaccttgg tagccactat aggtgggtct taagagaagg ttaagattcc 180
tcttgtgcct gcggcgagac cgcgcacggt ccacaggtgt tggccctacc ggtgggaata 240
agggcccgac gtcaggctcg tcgttaaacc gagcccgtta cccacctggg caaacgacgc 300
ccacgtacgg tccacgtcgc ccttcaatgt ctctcttgac caataggcgt agccggcgag 360
ttgacaagga ccagtggggg ccgggggctt ggagagggac tccaagtccc gcccttcccg 420
gtgggccggg aaatgc 436

<210> SEQ ID NO 569
<211> LENGTH: 393
<212> TYPE: DNA
<213> ORGANISM: Pegivirus sp.

<400> SEQUENCE: 569
agaatgggga gttaactcct ggcactggcc cgaagcatga actgatcgcg gtggcagggt 60
tcttcgggta aatcccggcc gcgtgttgtg attgtgttag ggcaggtgac agtcggcagg 120
gtcgaccccc tgcttcagga ccactgtctt cctggacgac cgttgctgaa aaagggccgc 180
cacggtctgt agctcgccga cgcttctaat tcaggccgga ggaccacgct ccgtaatcga 240
gcccaagtac tcaaacccca gcacccctgg gtcacgccct acgccgccct tttaacgctt 300
cggctaatag ggtctatccg gcgggttgac aaagggcgca gggttacctg gtactacgag 360
cttgggtgtc cctgggagta atcccagggt gcc 393

<210> SEQ ID NO 570
<211> LENGTH: 343
<212> TYPE: DNA
<213> ORGANISM: Flavivirus sp.

<400> SEQUENCE: 570
atataaatcc cagtttggtt aaacctattt caaggcttaa gttgtttatt attttatcgc 60
cgctcgtgac tataaagttg cctagcggag agagataaag aagaaggagt tcaaggctca 120
gggcagggcg caagttccct ggtccctagg ccgctcgcag gaaggaggag tgaagaagaa 180
gaaagagaag gagaggacca ccgccgaaag aaggcaggtg cctcacaaga gggccaacca 240
gcgtgttgga ccagtggcca acgccggacg gcgtggtggc ctgctgggac gcctggggat 300
tggatggagt gccttcctac aggaagacat cgttcaagcc atc 343

<210> SEQ ID NO 571
<211> LENGTH: 104

<212> TYPE: DNA
<213> ORGANISM: Unknown
<220> FEATURE:
<223> OTHER INFORMATION: Description of Unknown:
      Bussuquara virus sequence

<400> SEQUENCE: 571
agtatttctt ctgcgtgaga ccattgcgac agttcgtacc ggtgagtttt gacttaacgc     60
agtgagaaaa gttttcgagg aaagacgaga agcgaattct ctga                     104

<210> SEQ ID NO 572
<211> LENGTH: 106
<212> TYPE: DNA
<213> ORGANISM: Zika virus

<400> SEQUENCE: 572
agttgttgat ctgtgtgagt cagactgcga cagttcgagt ctgaagcgag agctaacaac     60
agtatcaaca ggtttaattt ggatttggaa acgagagttt ctggtc                   106

<210> SEQ ID NO 573
<211> LENGTH: 150
<212> TYPE: DNA
<213> ORGANISM: Yokose virus

<400> SEQUENCE: 573
agtaaatttt gcgtgctagt cgctgagcgt cagaccgcaa agtgagtttt tagtgatcta     60
aagtgaggag ttattcttac tgtcatcaaa cactacaaat aaacacgttg aaattatttc    120
cggaagaaca actgtccgga atcaaagacg                                     150

<210> SEQ ID NO 574
<211> LENGTH: 118
<212> TYPE: DNA
<213> ORGANISM: Wesselsbron virus

<400> SEQUENCE: 574
agtatattct gcgtgctaat cgttcgacgt tagtccgtgg agtgagcttc tattagagtc     60
gttaacacgt ttgaataatt tctactgaaa ggagtagaag aaaggagatt cattccca      118

<210> SEQ ID NO 575
<211> LENGTH: 389
<212> TYPE: DNA
<213> ORGANISM: Hepacivirus sp.

<400> SEQUENCE: 575
acctccgtgc tatgcacggt gcgttgtcag cgttttgcgc ttgcatgcgc tacacgcgtc     60
gtccaacgcg gagggattct tccacattac catgtgtcac tccccctatg gagggttcca    120
ccccgcccac acggaaatag gttaaccata cctatagtac gggtgagcgg gtcctcctag    180
ggcccccccg gcaggtcgag ggagctgaaa ttcgtgaatc cgtgagtaca cggaaatcgc    240
ggcttgaacg tcatacgtga ccttcggagc cgaaatttgg gcgtgcccca cgaaggaagg    300
cgggggcggt gttgggccgc cgcccccttt atcccacggt ctgataggat gcttgcgagg    360
gcacctgccg gtctcgtaga ccataggac                                      389

<210> SEQ ID NO 576
<211> LENGTH: 445
<212> TYPE: DNA
<213> ORGANISM: Hepacivirus B

<400> SEQUENCE: 576
accacaaaca ctccagtttg ttacactccg ctaggaatgc tcctggagca ccccccctag 60
cagggcgtgg gggatttccc ctgcccgtct gcagaagggt ggagccaacc accttagtat 120
gtaggcggcg ggactcatga cgctcgcgtg atgacaagcg ccaagcttga cttggatggc 180
cctgatgggc gttcatgggt tcggtggtgg tggcgcttta ggcagcctcc acgcccacca 240
cctcccagat agagcggcgg cactgtaggg aagaccgggg accggtcact accaaggacg 300
cagacctctt tttgagtatc acgcctccgg aagtagttgg gcaagcccac ctatatgtgt 360
tgggatggtt ggggttagcc atccataccg tactgcctga tagggtcctt gcgaggggat 420
ctgggagtct cgtagaccgt agcac 445

<210> SEQ ID NO 577
<211> LENGTH: 379
<212> TYPE: DNA
<213> ORGANISM: Hepacivirus I

<400> SEQUENCE: 577
cagggtttcg accctggccc ggatacctat cgccttacgc cgaaaggtaa cgagtaggag 60
tcgggtcccc aggcccttac cgccaccaag ccaggtgggg aggtatggga gccgggggt 120 gcagctggta gctccatggg ggacgccccg tgagcggatg ctgcatcgat accgggttag 180
ctctctggga gagcggcact tgacaccacg aatccgggaa ccggacaatc gccggcgtgg 240
gacgcgttgc ctccgtggcc gagcaatttg gcatgcccgt ggtgaagagt gatggtgggg 300
gggggccccc cttccagtac cgtactgcct gatagggtct tgcctcaagc ccagagagtc 360
gaggctgaaa accgccatc 379

<210> SEQ ID NO 578
<211> LENGTH: 557
<212> TYPE: DNA
<213> ORGANISM: Hepacivirus J

<400> SEQUENCE: 578
gccgctcccg aaagggagtc cggcgcgtca tcccactccg aggagtgggg tggcgtcccc 60
gtgtgccggg gaaccatgaa gcctaagggc atccacattt tagaatgaac ttgaagcttc 120
gtttcgctgg ccggaaagtc ctgggttccc atggccaggg ttccgcaggt gggtaaatcc 180
cggtggggtt ccatccagga tatacggcag gcgggcgtag tccggcggtt cggacgacgt 240
gtgggtcgcc tacggtggat tgttcacagg atgggcactc cggtgtgaat aggccccgtc 300
agggtgcgct gacgttaaac tcaggccttg cctggtgttc ggggaggatt gcagggccac 360
gccgcctcta agggccgtat ggcacagtac ttcttcgggc gggttgtcaa ggccctccaa 420
cgcgacacca gtgcctcggc aggcatgggg ccacccagct cggcgtcccg cacacagacg 480
gcgtagggga aaatcagcaa tgtgaccccg ggtggcattt tccttctctc tacttccatg 540
catgatcaac cgcaatc 557

<210> SEQ ID NO 579
<211> LENGTH: 280
<212> TYPE: DNA
<213> ORGANISM: Hepacivirus K

<400> SEQUENCE: 579
gggaacaatg gtccgtccgc ggaacgactc tagccatgag tctagtacga gtgcgtgcca 60
cccattagca caaaaaccac tgactgagcc acacccctcc cggaatcctg agtacaggac 120
attcgctcgg acgacgcatg agcctccatg ccgagaaaat tgggtatacc cacgggtaag 180
gggtggccac ccagcgggaa tctgggggct ggtcactgac tatggtacag cctgataggg 240
tgctgccgca gcgtcagtgg tatgcggctg ttcatggaac 280

<210> SEQ ID NO 580
<211> LENGTH: 675
<212> TYPE: DNA
<213> ORGANISM: Unknown
<220> FEATURE:
<223> OTHER INFORMATION: Description of Unknown:
Icavirus sequence

<400> SEQUENCE: 580
cgaagtttaa gctaagcacc ctcgggcgtt cccggattat gtgatcacat caatttgatg 60
gctggtcacc acgcaacgcc tggagagata ctcttacttt tctcttaaga tccccggtca 120
tttgacgctt gtaggatgat agggttattt tccactataa atactttcat actcttggat 180
gttctatatc caagacggga ggacctaccc cgtacccctt agaggtgaga tgccaagaac 240
aggccctttc tgttctctcg acaatggcat cataggcaac aagcatcaca ccaagattgc 300
taagttttgt taagagttct tcaagctata gggtggctgt agcgaccttc tgatgcctgc 360
ggatttcccc acggagcgat ccgtgccaca ggggccaaaa gccacggcta acgcccatca 420
ggagcggcac ttaccccgtg ccccaccctt gaaacttgaa tgttcacact ggcttctctc 480
ggctttctga actgtctgct tgttggggcc ccgaaggatg ccctggaggt accccatttt 540
atgggatctg accaggggac acctcagctc tctaagttgc tggtgtttaa aaaacgtcta 600
agggccccca ccccttaggt ggagggatcc acctttcctt tattttttaa aactctttta 660
tggtcacaat tgttt 675

<210> SEQ ID NO 581
<211> LENGTH: 113
<212> TYPE: DNA
<213> ORGANISM: Unknown
<220> FEATURE:
<223> OTHER INFORMATION: Description of Unknown:
Antarctic penguin virus A sequence

<400> SEQUENCE: 581
ctaggagact acgcagtggg ataagatgac tatgatgtcg tacgggcaga agccagtaca 60
gtcgaagtcg agaccgacgt cgaggatttg actctgcctg acctagtgcc atc 113

<210> SEQ ID NO 582
<211> LENGTH: 214
<212> TYPE: DNA
<213> ORGANISM: Unknown
<220> FEATURE:
<223> OTHER INFORMATION: Description of Unknown:
Forest pouched giant rat arterivirus sequence

<400> SEQUENCE: 582
tattggatcc gcctccgggc aaaggttact ttcttgtacc tcggcttagc cacagggtga 60
ccccttgtac gtaggggccc cgacgtagca ctggtctgac aacaccttct cggcatttca 120
ccttctgccc gctcttccgg gcggtggtgt caagaagcag cagtgctctt ctcttttctt 180
cctgcagttc accgagccct acggggggta ggtg 214

<210> SEQ ID NO 583
<211> LENGTH: 561
<212> TYPE: DNA
<213> ORGANISM: Avisivirus sp.

<400> SEQUENCE: 583
cattcccctt tccccagcca tgggttaaat ggcccctcac caggttcggt gctgtctagg 60
cttccagtaa agaagtcaac cgagcattga acaaaacctc agtgggtatg gtagttaacc 120
ccgtccactg gacaactttg tcctcttaaa agtggatcaa tccaccccaa ctccccccct 180
agccacctga gccatggtgg atagcagtga cgaaactagg gaccccaata cctctagtgc 240
caagagaatt ccccccctcgc gagaggtgct cttgggcccg aaaggctagt tggcagggtg 300
aagtgaagga agctgctagc gtggcaacct taagcgtagc ccgaagctga ccttagaggt 360
taaccctagt ggaccactgg atgaagctgt ggaggtggtg gataggaaag ttggccactt 420
gtgagtagat gcccagaagg cataaggctg atctggggcc agtgactata ccgttccggt 480
aaacctggta taaaaaccat gaaagcaagt gggtttaaaa tttcttctaa ttccttcatt 540
tcagtagtga taactggcag a 561

<210> SEQ ID NO 584
<211> LENGTH: 134
<212> TYPE: DNA
<213> ORGANISM: Unknown
<220> FEATURE:
<223> OTHER INFORMATION: Description of Unknown:
      Avian paramyxovirus penguin sequence

<400> SEQUENCE: 584
accaaacaag gactagataa cccacgtgac cgttaactgg aaaataagat gttgtagggg 60
cgacctagtt ggaattcgac cccggctccg aaacctctaa ttgtggttat tggcagtcta 120
gtctacttct aacg 134

<210> SEQ ID NO 585
<211> LENGTH: 121
<212> TYPE: DNA
<213> ORGANISM: Unknown
<220> FEATURE:
<223> OTHER INFORMATION: Description of Unknown:
      Newcastle disease virus sequence

<400> SEQUENCE: 585
accaaacaga gaatctgtga ggtacgataa aaggcgaaga agcaatcgag atcgtacggg 60
tagaaggtgt gaaccccgag cgcgaggccg aagctcgaac ctgagggaac cttctaccga 120
t 121

<210> SEQ ID NO 586
<211> LENGTH: 302
<212> TYPE: DNA
<213> ORGANISM: Bat Hp-betacoronavirus -continued

<400> SEQUENCE: 586
ttaagcttcg gcttgttgca taggaccgga aaggtactat ctaccctaac tcttgtagtt 60
agactctcta aacgaacttt aaaactggtt gtgtccttca gtagtctgta tggccattgg 120
aggcacaccg gtaattatca aatactaaga agattcatag tacatccttg tctagctttt 180
ggttggcagt gagcctacgg tttcgtccgt gtcgctcaca attatccaca cagtaggttt 240
cgtccgctgt ggttgagttg ctagtccgtt gctgtttcgt cagccatcta caactcgaca 300
cc 302

<210> SEQ ID NO 587
<211> LENGTH: 458
<212> TYPE: DNA
<213> ORGANISM: Unknown
<220> FEATURE:
<223> OTHER INFORMATION: Description of Unknown:
Basella alba endornavirus sequence

<400> SEQUENCE: 587
ggaatatggc taatcggctt attctaatca aacgcaaaag acttatgaca cagaccggac 60
ctgaacgagg tgataaaaca cctcgttcag gttcaaaacg tagaagattc attcctccga 120
ttagaaatac aactacgtct aagcacgata gagatggtat caagatcggt tttagaccac 180
gagaaaatcg gcaaatgaaa gtacaagttg ggtggtttaa attaccaaga acagtaacat 240
tcaagaacaa cggcaacccg tttgttacct catttcgtaa attgtttaga agtaacaaag 300
ataaattatt taatggtggg aagaacctaa gtacagtacc agccagaagt agtgaaatga 360
cagaaatgtt tatgttcatg tccacgctag agggccaatt gtcaatccaa gatcgagatc 420
caaaaataat caataagtct atatacatga tagaggta 458

<210> SEQ ID NO 588
<211> LENGTH: 675
<212> TYPE: DNA
<213> ORGANISM: Ball python nidovirus

<400> SEQUENCE: 588
ccccttcacc cataggcact aggagaacag gataacccct aacggggcat cctgcctgtg 60
acctttcaga ttcgctagtt agatatcttc acagactctg ctaggcttct gacccagtcc 120
gttcccaaag tccgttaccg cccgagtagc gcttaggcgc gaaagggacg gaagtacctc 180
cagtaagcga aagctgaagt aagggaaata cggcaagact aacttgttag tcttacagtg 240
tggataacct ggtagttatc cccgacaaga gacctgactc gatgtgaaaa catccaacta 300
ggttggcttc aaactagcta caggcaggat atcccccaac ggggcctcca aggaatcgag 360
aaccaaccct cattccacgt ctgtagtaag caaaaacagg ggcgatcttc accgacacct 420
ctcaccacag agcacaccaa cctctgtgaa gccaatttcc tcgtccaagg acaggttatt 480
gagggtcaac tttcttccga ccagaagaag ggatttccta ccaaaagaaa aaccaaatcc 540
accaacacca caaggtaaaa caacaacttg tgaagccaat acttagtcaa agactaacta 600
ttgagggtca actttctctt caatagagaa gggatttcct ggtaaaacaa ataacaacaa 660
ctaacatcag caact 675

<210> SEQ ID NO 589
<211> LENGTH: 150
<212> TYPE: DNA
<213> ORGANISM: Sapelovirus sp.

<400> SEQUENCE: 589
gacaggtgtt ttggagggcg gatgacgata tctggctggc caccagggaa taacggcaaa 60
tgtctgatca tacggttcac aagtctaccg gcgatagtgg ttcaacacca tgtgtagcag 120
ggattcttgc gtatgtgaag gcgacagtgc 150

<210> SEQ ID NO 590
<211> LENGTH: 496
<212> TYPE: DNA
<213> ORGANISM: Unknown
<220> FEATURE:
<223> OTHER INFORMATION: Description of Unknown:
Bat Picornavirus 3 sequence

<400> SEQUENCE: 590
taagcggaaa gcattcttgt cccccggtca gtaacctata ggctgttccc acggctgaaa 60
gggtgaacat ccgttacccg cctcagtact tcgagaaacc tagtacgcct gatgattcca 120
aattggtatg atccggtcaa ccccagacca gaaactgtgg atgggggtca ccattcctag 180
tatggcaaca tacaggtgtc cccgcgtgtg tcacaggccc ttacgggtgc catttcggat 240
gagtctggcc gaagagtcta ttgagctact gttgatacct ccggccccct gaatgcggct 300
aatctcaacc ccggagccac tgggtggtga accaaccact tggtggtcgt aatgagcaat 360
tctgggacgg aaccgactac tttggggtgt ccgtgtttct tttgttcata ttaaactgtt 420
ttatggtcac aacacaactt ggtacgattt gtgattattc actgctcact tgtcacagta 480
aatatacaca atcatc 496

<210> SEQ ID NO 591
<211> LENGTH: 419
<212> TYPE: DNA
<213> ORGANISM: Unknown
<220> FEATURE:
<223> OTHER INFORMATION: Description of Unknown:
Bat Picornavirus 2 sequence

<400> SEQUENCE: 591
gggttttacg aaacccgtat acaccagacc ttttctcccc tccccctcca cctacctttt 60
ccccctcttt ggaccgaaac aaggacacgt aagtggaaac gcgattttat atgtggttgg 120
ccaccacgga ataacggcaa ttgtctacat gtgggaagtg caacctccct agccgataac 180
ccctgaccgg gtgtgtagga taggaaaggt gcccactgtg ggcgacaggt tatggtagag 240
tggataccta gccaggggca atgggactgc tttgcatatc cctaatgaag tattgagatt 300
tctctgctca ttacccggtg atggttgtgt ggggggggcc ccatacacta gatccatact 360
gcctgatagg gtcgcggctg gccgaccata acctgtatag tcagttgaat tcagccaag 419

<210> SEQ ID NO 592
<211> LENGTH: 410
<212> TYPE: DNA
<213> ORGANISM: Unknown
<220> FEATURE:
<223> OTHER INFORMATION: Description of Unknown:
Bat Picornavirus 1 sequence

<400> SEQUENCE: 592
gaaacccgta tacaccggac cttttctccc ctccctctcc acttaccttt ttcccctctt 60
cggcatgaaa caaggattat tcaagtggaa acgcgattta atatgcggct ggccaccgcg 120
gaataacggc aattgtgtat ctgctggaag ccaagcctgc ctagccgata gcccttgacc 180
gggtgtgtag gatagcccag gaaccagcaa tacgcgacag gttatggtag agtagatacc 240
tagccagggg caatgggact gcattgcata tccctaatga accattgaga tttctctggt 300
cattacccgg tgatggttac tagagggggg cctctagtac tagatctata ctgcctgata 360
gggtcgcggc tggccgacca tgacctgtat agtcagttga tttgagcaat 410

<210> SEQ ID NO 593
<211> LENGTH: 675
<212> TYPE: DNA
<213> ORGANISM: Iflavirus sp.

<400> SEQUENCE: 593
acgaatcggt atacgcttcg gtacctattg ttgcaagttc gttccctatt ttcgatttgc 60
ctgcccgaat ttgactcaaa caattgtgac atactatgtc tctgtttgaa agcactacac 120
gagtttgcgc ccagcatgta tgttttcaag tcttttgtat aagtctgcct ctatagtggt 180
tttctttgac cttaaagcct tgtcaaccat cctatatgct gcatcgagac ttgatgtcaa 240
tctgcctcta ctacgcaaat gtctagtaat tagttataag gtttactat tttccctcat 300 ttccaatttt agtttgtagt gtatgtgagt atcattctta ctccgactgt taagagaaac 360
caatttatag tcgttaaata tgataaatgg aatgaatgat ggtgtcattt taaaaacact 420
cttctctata ggcgtaagca ttctcgctct tagagtcgta aagaagaaat gccgtgtcta 480
tcagtatgtt atgcgattta ttttctgcca cgcgcttcta gtgcaatcta gttgacatac 540
agacattgcc taccactcgc gagggtcgac cggtagtgta aggagtaagt gatgatttcc 600
gcttattctg taccctttgc ctggtgagga cagatcctga ctaattttaa atataaatga 660
acactagctt ccaag 675

<210> SEQ ID NO 594
<211> LENGTH: 210
<212> TYPE: DNA
<213> ORGANISM: Unknown
<220> FEATURE:
<223> OTHER INFORMATION: Description of Unknown:
Bat dicibavirus sequence

<400> SEQUENCE: 594
gtatagcacc ggaatggtat tttactactc caagtatacg tactaggagt taaaccctgt 60
aatttacagg ggatttagtg acttttatcc gtaaaagtcg attggacgtt aatcggtaac 120
gaggccaagt accgtgaacc aatttaaaaa cgtattttct catgtggtag aaccaacttg 180
gaaatagcat ggcatatagg ttgtttaggg 210

<210> SEQ ID NO 595
<211> LENGTH: 212
<212> TYPE: DNA
<213> ORGANISM: Betacoronavirus sp.

<400> SEQUENCE: 595
gataaagtgt gaatcgcttc cgtagcatcg caccctcgat ctcttgttag atctaatcta 60
atctaaactt tataaaaaca ctaggtccct gctagcctat gcctgagggt ttaggcgttg 120
catactagtg tcttaggaat ttgactgata acacttccct gctaacggcg tgttgcactc 180
tcagtctaag cctcccaccc ataggaggta tc 212

<210> SEQ ID NO 596
<211> LENGTH: 277
<212> TYPE: DNA

<213> ORGANISM: Betacoronavirus sp.

<400> SEQUENCE: 596
atttaagtga atagcttggc tatctcactt cccctcgttc tcttgcagaa ctttgatttt 60
aacgaactta aataaaagcc ctgttgttta gcgtattgtt gcacttgtct ggtgggattg 120
tggcattaat ttgcctgctc atctaggcag tggacatatg ctcaacactg ggtataattc 180
taattgaata ctatttttca gttagagcgt cgtgtctctt gtacgtctcg gtcacaatac 240
acggtttcgt ccggtgcgtg gcaattcggg gcacatc 277

<210> SEQ ID NO 597
<211> LENGTH: 675
<212> TYPE: DNA
<213> ORGANISM: Cardiovirus sp.

<400> SEQUENCE: 597
tacgatcgct gtacattcca ctactgccaa ttagctcccc cttcccgttg ctcccctcta 60
taaggagagc cttctcttgc aaaggtgaag ccttcacccc cggtcgaagc cgcttggaat 120
aagacagggt tattttctcc tctcctcggc gcttgcctct tctaagctga ataggttcta 180
tctattcagg cggatggtct ggtccgttcc ttcttggaca gagtgtgtat ctgggttttc 240
cggatctcga ccacacactc accagagctc aggagtgatt aagtcaaggc ccgatctgcg 300
gcgaaaagga aatgaagtat tttgcagctg tagcgacctc tcaaggccag cggatttccc 360
cacctggtga caggtgcctc tggggccaaa agccacgtgt taatagcacc cttgagagcg 420
gtggtacccc accaccctgc aaattatgga tttgacttag taactaaaag attgacttgg 480
catacctcaa cctgagcggc ggctaaggat gccctgaagg tacccgtgtt gaaatcgctt 540
cggcgaccat ggatctgatc aggggccctg cctggagtgg ttctatccca cacagcgtag 600
ggttaaaaaa cgtctaaccg ccccacaaag accccggcag ggatgccggt ttccttttta 660
ccaattcttg acact 675

<210> SEQ ID NO 598
<211> LENGTH: 675
<212> TYPE: DNA
<213> ORGANISM: Unknown
<220> FEATURE:
<223> OTHER INFORMATION: Description of Unknown:
Breda virus sequence

<400> SEQUENCE: 598
atcacctagt acttacaagc gggtcaaacc gccctccgga acggtcataa ccccctcccg 60
aacgtgcgct tgacgtgact ggtctttcag tctagctttc tgagaaatac tccggggttg 120
taacccacca ttttgacctt tggtcagttt ggtaacactc caaccaaaca gcatctgacc 180
cacctccagc ttgctgcagg ccatttggac caaacgggtt cagatatctt gtggctaaac 240
ctctgaccca cctccagttt actgcaggcc ttttggacta aacgggtaca gactctttgt 300
ggttagtttt taactaccca ctgtttagcc gccaacctga tttttattgt tacaaaattt 360
tgtgtttaca cattattttc ttacggttgg cagtttgttt ggttgtttgc acagtttttg 420
ctgataccaa tttttactgt gcttttggtg ttttcggcta aggctgtttt tcacatactt 480
agtttgcttg aagtaacctt cacaacatct gttttgtttt tggtttctaa ggtaaagagt 540
ttcaggaaaa aacataggcg cccatcttgt ggtgtctagt tttaattaat ctggcaaaca 600
agtatcaagt catcgactcc ctttggagtg agacttacga gtaccaattc gcctattttg 660
gccatccata taaaa 675

<210> SEQ ID NO 599
<211> LENGTH: 383
<212> TYPE: DNA
<213> ORGANISM: Unknown
<220> FEATURE:
<223> OTHER INFORMATION: Description of Unknown:
Bovine viral diarrhea virus 3 sequence

<400> SEQUENCE: 599
gtatacgccc agttagttca ggtggacgtg tacgattggg tatcccaaat taataatttg 60
gtttagggac taaatcccct ggcgaaggcc gaaacaggtt aaccatacct ttagtaggac 120
gagcataatg ggggactagt ggtggcagtg agctccctgg atcaccgaag ccccgagtac 180
ggggtagtcg tcaatggttc gacgcatcaa ggaatgcctc gagatgccat gtggacgagg 240
gcgtgcccac ggtgtatctt aacccaggcg ggggccgctt gggtgaaata gggttgttat 300
acaagccttt gggagtacag cctgataggg tgttgcagag acctgctaca ccactagtat 360
aaaaactctg ctgtacatgg cac 383

<210> SEQ ID NO 600
<211> LENGTH: 537
<212> TYPE: DNA
<213> ORGANISM: Bovine rhinitis A virus

<400> SEQUENCE: 600
ttttgcggct ctgccgccgt tcgggtttta cctgttttca cagagcaaaa caggacctct 60
agtttcgtgc ttaaacgaga tcatgctcga actagaacta taacgctggt cactggaccc 120
gtgccgcgcc ttgcggatct ttgcgggaat ggtggctagt gggctgtgga agtgactcta 180
accacacgcc cctcaagtgt gggaaaacac gaactggtgt agcgacgacg ataggccttg 240
ggacaccctc tccagtgatg gagacccaag gggccaaaag ccacgccttg tgccctgtcg 300
ttcacaaccc cagtgcagtt cgtgccagta cctgcttttg ggaagtgtgc tttggacagc 360
tgaaaacagt cctagtggga gactaaggat gcccaggagg tacccggagg taacaagtga 420
cactctggat ctgacttggg gagagcgggt ctgctttaca gacgccactc tttaaaaaac 480
ttctatgtct cgtcaggcac cggaggccgg gccttttcct ttaaaacaat acacttt 537

<210> SEQ ID NO 601
<211> LENGTH: 248
<212> TYPE: DNA
<213> ORGANISM: Unknown
<220> FEATURE:
<223> OTHER INFORMATION: Description of Unknown:
Bovine picornavirus isolate TCH6 sequence

<400> SEQUENCE: 601
ttggatctga gcaggggccc cctttgggtt gctttacaac tcaactgggg gttaaaaaac 60
gtctaacccg acacgccaga gggatctggt ttccttttat ttcttttact caccactgga 120
tgcagattga cgataaacgt tgttgtttgt gactattgac ttgatctgct tctacgggtt 180
tactttcact gttatacttc ttgctttgtt tggtgttcac tgtactttgt ctccttctac 240
atttcaca 248

<210> SEQ ID NO 602
<211> LENGTH: 486
<212> TYPE: DNA
<213> ORGANISM: Bovine nidovirus

<400> SEQUENCE: 602
caccaataga ttagtcaagc tgtctatagg cataaactaa cccccaaccc cattaccccg 60
gggccaggtg ggccgccgcc ttcgggcaaa cccgtgcgct ggtataatca aggttcacag 120
ccagattcac tgccggttag ctagtggggc ggtagcctgg caaaacccga agaggttgga 180
aagggaactt cagggtagtt tatcctaggc tagcgtagct acagttcggt caagataacc 240
gtcctggtgc tagggctagt agagacagtg gtaacttgga caagggtcca gggccacttt 300
agggaatacc ctacggaagg ctaggtccgt aaggaagacc cccgcagttg tccgcggttg 360
agcagagctc ctgcgtagac aaaaggcaaa aagtggatta cattcgcctg caggaaaagg 420
caaacgtcgt tggagtcgga gctaaagtac tggacgattg ataccacgcc tgctgcggta 480
gataaa 486

<210> SEQ ID NO 603
<211> LENGTH: 293
<212> TYPE: DNA
<213> ORGANISM: Hepacivirus sp.

<400> SEQUENCE: 603
ccatcgacac tccaggctca cggattaagt taggttccgc cgaagcgggc taaccaggcc 60
cctagtagga ggcgcctatc ccgtgagccc tttccccacg gattgagtgg agctggagct 120
gggaaggacc gagtacggtc caatcgagaa gaaccctgat gaacattcca ggcctcttcg 180
gtagatttgg atatatccac cagtgaaggc ggggtcgtgg gtacaggccc cctagtccac 240
acagcctgat agggtcctgc cgcaggatcc gtgggtgcgg ctgtacatgt acc 293

<210> SEQ ID NO 604
<211> LENGTH: 472
<212> TYPE: DNA
<213> ORGANISM: Mitovirus sp.

<400> SEQUENCE: 604
gccccgccga ccttcctatt tatttctaaa taggaaggtc ccgactagtc ggataattcg 60
gtttaacgaa ttatggttag atctattaaa gttaaaatag attgaatttc tttctcatcc 120
tccttattcc tatactttgg gagtaaatga caaatgtcta tcctcaaacc gaaatggctt 180
aagtgatgaa tttgaaagaa aggtaggttt taagaatata aggcatcaat atattatacc 240
cttgaatgtt aagtgaccac ggcgtgacga ttagggctat cttaggatag acagccatct 300
aacgcgacag cagtggaaat cagcttagca tctcaagatc atgtataata tatacataac 360
cttacaatta taaaaccaaa ccaaaacaca ctataatttt atataaatta tagaagtatc 420
ggacctggac ggtacctact attaactgat agtagccaaa tgcaggaagc tc 472

<210> SEQ ID NO 605
<211> LENGTH: 315
<212> TYPE: DNA
<213> ORGANISM: Mitovirus sp.

<400> SEQUENCE: 605
ggaacttttc agttccagaa gtggctttat taagccttca aagtttacac tttgaacctg 60
cgattaattc cccatagtga ctcttgttac tgtgaattag gaatagttgt agttcaactt 120
ctaatgaggt gaacaatata ataactcatc ttattaaccc tatacgtaga caattgtcca 180
aagagacagt tggaattctg ccaatctgga atgtttggta cgcgtagaag ataataagag 240
accctctatt cccctgcctc atgactaagt catggcccgg ggtgtaatag agatactttt 300
atatattata caatc 315

<210> SEQ ID NO 606
<211> LENGTH: 675
<212> TYPE: DNA
<213> ORGANISM: Unknown
<220> FEATURE:
<223> OTHER INFORMATION: Description of Unknown:
Canine picodicistrovirus strain 209 sequence

<400> SEQUENCE: 606
cgctctttat acaaatctgt caaccctttg tataactcta agccgaacaa ttatagctag 60
gctttttatt atataacatt aattaggcat tagcgttgtc gccaatctct tggtaatcct 120
aaggatacct ttcctgttga ctaagatgaa gcgccttcgg ttaccgatgc ccggtgtcca 180
cgaagccatc gtggtcggcc gcgtccccca cctctcccaa cttggactcc atgttttcag 240
taggtgtaat gattagtatt attgattctg ctcgttcaat gtgtttatct tcacgatctg 300
ggacccaaca catgcttcac tcatgtttaa atgttggttc cctcattttg aagacaccca 360
aaccatagag tgcgagaatg aggatttcta cttccattct ggtaacagaa atgaattcct 420
gcgtgtgtct cgtaaatgga atctttaaga acttcagata aatcgaacaa tacactaata 480
caagttgttt tctaccaaca tgttcaatgc ggctaatctg accgtggagc tgtgaagcgc 540
tcaaacccga gtgttgtata cagtcgtaat gcgtaagtcc atgaggaacc gactactgtt 600
acctctgttg gtgtgtttct cctttcctct cttttattat tatttgttat tgcaaatact 660
acaactttga tcaac 675

<210> SEQ ID NO 607
<211> LENGTH: 107
<212> TYPE: DNA
<213> ORGANISM: Canine morbillivirus

<400> SEQUENCE: 607
accagacaaa gttggctaag gatagttaaa ttattgaata ttttattaaa aacttagggt 60
caatgatcct accttaaaga acaaggctag ggttcagacc taccaat 107

<210> SEQ ID NO 608
<211> LENGTH: 601
<212> TYPE: DNA
<213> ORGANISM: Kobuvirus sp.

<400> SEQUENCE: 608
tttaagtgtt gtgcccaatc tcttgactcc tgctggaacc accgaccagt agtgtccaaa 60
atgccaggtg gaaaatcctc ccttcccctc tgggcttcat gcccggcatc ctccccccag 120
cctgacgtgc cacaggctgt gcaaagaccc cgcgaaagct gccaaaagtg gcaattgtgg 180
gtcccccctt tgtcaaggcg tcgagtcttt ctcccttaag gctagtcctg tcagtgaact 240
ctgtcgggca actagtgacg ccactgcatg cctccgacct cggccgcgga gtgctgcccc 300
ccaagtcatg cccctgacca caagttgtgc tgtctggcaa acattgtctg tgagaatgtt 360
ccgctgtggc tgccaagcct ggtaacaggc tgccccagtg tgcgtaattc tcatccagac 420
ttcggtctgg caacttgctg ttaagacatg gcgtaagggg cgtgtgccaa cgccctggaa 480

```
cgagtgtcca ctctaatacc ccgaggaatg ctacgcaggt acccctggct cgccagggat    540

ctgagcgtag gctaattgtc taagggtatt ttcatttccc accctcttct tcttgttcat    600

a                                                                    601
```

<210> SEQ ID NO 609
<211> LENGTH: 291
<212> TYPE: DNA
<213> ORGANISM: Alphacoronavirus sp.

<400> SEQUENCE: 609

```
cttaagtgtc ttatctatct atagatagaa aagtcgcttt ttagactttg tgtctactct     60

tctcaactaa acgaaatttt tgctacggcc ggcatctctg atgctggagt cgtggcgtaa    120

ttgaaatttc atttgggttg caacagtttg gaaataagtg ctgtgcgtcc tagtctaagg    180

gttctgtgtt ctgtcacggg attccattct acaaacgcct tactcgaggt tctgtctcgt    240

gtttgtgtgg aagcaaagtt ctgtctttgt ggaaaccagt aactgttcct a             291
```

<210> SEQ ID NO 610
<211> LENGTH: 623
<212> TYPE: DNA
<213> ORGANISM: Cripavirus sp.

<400> SEQUENCE: 610

```
gcaaaatcgg tagtacgtta aacgtacgac caccgatgag actgaaatga cactagttga     60

gattatttca atatcctagt gttataaagt caatatttgt tggttgatcg tttcgtcaat    120

cgatggcgct gacagccgga aagacggcaa taataaaaac caagatttag tttttaagtt    180

ttgattgaat tgcaaaagct atcttgaata gacaatcaaa atattaagta aagcaaaagc    240

ttcttaaaga agacaatatt taattagtta gtaaccaaac ctcatcgtgc ccctaagggt    300

taaccggtta cgtaaaagcg tagaggtatt aaggtcactg cggagaccta aaatccgcaa    360

ttttatgttt tgtaatgttt tagttataga cttagatgta actataagag tttataaata    420

cttgtttcaa gatttataga caagatctga tcctatggat tttagataac cttcatgtta    480

gtggatagtg tgtgtaccta tctaaacgca taaggctctt atttcatatt taaagtagga    540

ctatgtatta cggcgcatct aacggtaacg ttagtcaaga ccggagaatc tcggaatgaa    600

ttttagtaat tcccaaattt ata                                            623
```

<210> SEQ ID NO 611
<211> LENGTH: 675
<212> TYPE: DNA
<213> ORGANISM: Unknown
<220> FEATURE:
<223> OTHER INFORMATION: Description of Unknown:
      Human coxsackievirus A2 sequence

<400> SEQUENCE: 611

```
acctttgtgc gcctgtttta tatccccacc ccgagtaaac gttagaagtt acgcaacccc     60

gatcaatagt aggtgtagca ctccagctgc atcgagatca agcacttctg tctccccgga    120

ccgagtatca atagactgct aacgcggttg aaggagaaaa cgttcgttac ccggccaatt    180

acttcgagaa gcccagtagt gccgtgaaag ttgcggagtg tttcgctcag cacttccccc    240

gtgtagatca ggctgatgag tcaccgcgat ccccacaggt gactgtggcg gtggctgcgt    300

tggcggcctg cctatggggc aacccatagg acgctctaat acagacatgg tgcgaagagc    360

ctattgagct aattggtagt cctccggccc ctgaatgcgg ctaatcctaa ctgcggagca    420
```

```
catgccctca aaccaggggg tggtgtgtcg taacgggtaa ctctgcagcg gaaccgacta    480

ctttgggtgt ccgtgtttct ttttattctt ataatggctg cttatggtga caattaaaga    540

attgttacca tatagctatt ggattggcca tccggtgact aacaaatcgc tcatatacca    600

gtttgttggt tttgttccct tatcacatac agctcataac accctcttat atttactaca    660

attgaatagc aagaa                                                     675
```

<210> SEQ ID NO 612
<211> LENGTH: 436
<212> TYPE: DNA
<213> ORGANISM: Unknown
<220> FEATURE:
<223> OTHER INFORMATION: Description of Unknown:
Coronavirus AcCoV-JC34 sequence

<400> SEQUENCE: 612

```
agaaacaagt agtgttttaa aaaccttcaa attagtgcct gtaacatctt tgcaatgaaa     60

gtagcgctca ctagcctcta tgcaaagaat gttaaaagaa atacgaagca tttaaagaat    120

acaatctatc taggataggt acaattctcc tccccctctt gacttcggtc aactcaactc    180

aactaaacga aatcccccctt gcatggttcc gacccgtgta aggttgtgta tttcgtgcag    240

tcgttgccct tactagtgta agcgtaacgg catctaggtt tgcacgtctt ggaggaaacg    300

gtgtgtacgt ttctagtgtt tacgccgtat cggttccggc ccgataggta ttgcattaga    360

cgtcctgggt ggttctgcct gcccttgtgt gattcggctg ttccgtcagt ttggtcacct    420

cacacgtcct taagac                                                    436
```

<210> SEQ ID NO 613
<211> LENGTH: 457
<212> TYPE: DNA
<213> ORGANISM: Unknown
<220> FEATURE:
<223> OTHER INFORMATION: Description of Unknown:
Chicken picornavirus 3 sequence

<400> SEQUENCE: 613

```
gggtatggtg gttaaccccg tccactgggc atctttgccc tctcagaagt ggatcaatcc     60

accccaactc cccccctggt tacctgagcc acagtggact ccggtgacga agctagggac    120

cccaatacct caagtgccaa gagagtcccc ccctcgcgag aggtgctctt gggcccaaaa    180

ggctagttgg cagagtgaag tgaaggaagc tgctaacgtg gtgaccttaa gcgtaattcg    240

aagctgacct ttgaggttaa ccctagtgga ccactggagg aatctgtgga ggtggtggtt    300

aggaaagttg gccacttgtg agtagatgcc cagaaggcat aaggctgatc tggggccagt    360

gactataccg ttccggtaaa cctggtataa aaaccatgaa agcaagtggg tgaaattttc    420

tctttttatc cttcattcag cagttgatat tggcaaa                             457
```

<210> SEQ ID NO 614
<211> LENGTH: 675
<212> TYPE: DNA
<213> ORGANISM: Unknown
<220> FEATURE:
<223> OTHER INFORMATION: Description of Unknown:
Chicken picornavirus 1 sequence

<400> SEQUENCE: 614

```
gtggccgact tgcagaactt cctaccgaac caccacctca cccccataac tccttccctc     60

tacaccttcc gctatggtgg ttaccactgc tttattgcct tgactgagaa tggccacccc    120
```

```
ctcgacacct gccccctact gccccaccgc gcaacctttt gcttgtccac tcggttggag    180

aggcatgggg gccccgttca tatccccagt ccagttggtg accttccccc tccccgtccg    240

gtagatggtc cagagggctt tgccgacgcc ctctatgatg cttgcttgtc tttcctccgt    300

cagcgcgagc atgcacttgt cgagcccacg gaaacacagc ctagcttttg cttctctcac    360

cctgcgtacc ctgggcgcct tccgctcgag attcgctttg ttcgacaccc tggcgtcccc    420

ccaccgctac gtgattttac tcgtggcata caccgccctg gcgttcagta cattccactg    480

cctaatttgg gtggcctccc tcaatctccc gcaccccccca ttgcgcacgt catcaccgcc    540

gccgctaacg cgatccggcg cggttctcac tggcactgtc ccctcgtccg ccgggtttcc    600

actcatggtt ggcttttcac ttattctggt tactggtgtt ccatcctact tcatgatggt    660

cgccatgacc atgac                                                     675
```

```
<210> SEQ ID NO 615
<211> LENGTH: 675
<212> TYPE: DNA
<213> ORGANISM: Orivirus sp.

<400> SEQUENCE: 615

aaaccctcac gagtgcttgt ggtaggtccc aggccaatat tcttcgtaag gcttggttcc     60

aattttccac cactcgtgtt tgggttctgg cctatggtac ccagaggggc ggtttggggg    120

aattaactcc ccctccccctg tggtcctata ccaccccaca cctctgtggg ctttctttac    180

tatcttcttg ttttccgact tttaaacact aggcaggcgc gcctagtcat acaccgcccg    240

gctggtcttt ccagctcttg tgggcggtgc gcgctggtcc atcgtgccca gcgacatagc    300

accttgtgga cacctccgaa cgccctcccc tgtatggggt ggtgcccagg ggtttcagtg    360

tggtgacaca ctccctgggg cccgaaaggc tagtgtgcaa caggtgaggt acagccagct    420

gcccccgtgg ctggagggac caagcttgtg aagcacacct caccttcttg ggggtgggct    480

agtaagtggt gaaagcatag tgtccgtgtc gctggccaac actttgggtc aagtccagcc    540

actcagtgag tagatgccca ggaggtaccc ctagtggatc tgacttgggg cctgttactt    600

aatgcaggtt aaaaactatg aaagctgagt agtgtagccc ggctggtggc ttctcttcct    660

tattcattct atttt                                                     675
```

```
<210> SEQ ID NO 616
<211> LENGTH: 651
<212> TYPE: DNA
<213> ORGANISM: Gallivirus sp.

<400> SEQUENCE: 616

ggttaacttg tttaaccaag gcttccgtgc agggcttgca cgttaggagt tcatgttgat     60

tcatgctcca atgcccaaaa ctttgtgtgt ttgtttatgt ctttcccaaa gtttccccca    120

aggtttcggt actcaaacct taattcctag tcccatcttt tgggccttag tatctaggaa    180

atgtacccgt gccttgacga acgtaagaaa gctgtctttt attgaacggt tctaatgaac    240

taagtataac tggctcgcgc cacctggtgt gtgccgttgg aattccccca tggtaacatg    300

gtccaacggg cccgaaaggc tagtgggcaa tcggtcctcc aaggaagggg ttcccacccc    360

gacctgaaca ggatttgatg aagctcacct cccaggctcc taaccccaag gaagtttact    420

tatagtaatt agaatttagt atgtaattgc tggcaatctt gctagtagtc aggaacgtta    480

tgaccaaatg agtagacccc cagaaggtac cccattatat gggatctgat ctgggcctca    540
```

```
tactgtgtgt ctccccacat atgaggttaa aaccatgaaa gtttggtcca aaatattctt    600

ttccttttat cttttcttta gtggtgacgc cattatatca gcagtttgct g             651


<210> SEQ ID NO 617
<211> LENGTH: 303
<212> TYPE: DNA
<213> ORGANISM: Unknown
<220> FEATURE:
<223> OTHER INFORMATION: Description of Unknown:
      Chicken calicivirus sequence

<400> SEQUENCE: 617

ggtgcatcat cactgaacac cctcgggcag agatgcaagg gtggaagtca ctcctgcccc     60

ctggcaacat gcaggtgccc gatcccaagc ttagttctga cttcctctcc tgggtggtgc    120

aacactccaa ggttgatgaa caaacctgga gggacctctg ggcaacctgg tctctcgagg    180

atctccggcg catctccaca gactacctca tgctcccgga acctgagaag aacactgatg    240

cctatgatgg ctggctgatg gtcggcgaga tgttgacctt tgccggtctc attggctggg    300

agg                                                                  303


<210> SEQ ID NO 618
<211> LENGTH: 524
<212> TYPE: DNA
<213> ORGANISM: Unknown
<220> FEATURE:
<223> OTHER INFORMATION: Description of Unknown:
      Carp picornavirus 1 sequence

<400> SEQUENCE: 618

agctacagga aagagagaga taatcacagc acataaatac aactacagaa gagagccttt     60

ccctgagcac tatttacagc aaaccacgct gggaaaagtg gtagcatgac ccacttacgg    120

gttacttagt ataggatttt aatatcttcg attctttatt ttcttttctt aactaagttc    180

gcccggactt tatccgtgtt ttattttagt ttaagcaaaa ttgagtaact aagtttttaa    240

cctgccaaat ggtgagaagt aactctgtga aaataccatt tgtgcatgaa attgtcttga    300

aaactcttag gcttttgggg ggtcccactg ctgtttggag gactattgac agactctatt    360

gtagttgagt agtgactaat gataacgatt tgcgtattac gcaatgggct gtacccgtta    420

gatttagtat gccgggggga ggggtcccac tggattgcac tatgtaacct gacagggcgt    480

ctgccgacgc actacaatga ggataagatc ggctgttttt attt                     524


<210> SEQ ID NO 619
<211> LENGTH: 675
<212> TYPE: DNA
<213> ORGANISM: Unknown
<220> FEATURE:
<223> OTHER INFORMATION: Description of Unknown:
      Falcon picornavirus sequence

<400> SEQUENCE: 619

cgcttggaat aagttgagag gaattatgca tgctagttgt gtttgtttac aactaattgt     60

tctaatccaa gtgaagctct tcgcttgggg cggcacgaca cttgccgtaa ttcttctacc    120

gtccctccac accttgtgga tgaagggccg gatgtgtggc ctctggctaa cccctctctc    180

tggggtgatg ctactggatg ttttactcct agaccaaatc acatgaactc ctcttgatcc    240

acttcggtgg ggctatgagc ctgcggatta atagctggcg acagctaccc caggggccaa    300

aagccacggt gttagcagca ccctcatagt ctgatgccca agggctgatg ttgggagcta    360
```

-continued gtagtgtgtg tctggcctat gtttaggact tctggccaag cgcagaggag tggggctgaa 420
ggatgcccag aaggtacccg taggtaacct taagagacta tggatctgat ctggggcccc 480
ctcacgtggc tttaccacgt gttgggggtt aaaaaacgtc taggccccac cagcccacgg 540
gagtgggctt tcccttaaaa agcccaacaa tatttatggt gacaattcac tgtttcttct 600
ttgcaatttt tgtattcttg gactccttat tttttgtttg cttgatttta gtggacattc 660
agattcaaat acaaa 675

<210> SEQ ID NO 620
<211> LENGTH: 675
<212> TYPE: DNA
<213> ORGANISM: Unknown
<220> FEATURE:
<223> OTHER INFORMATION: Description of Unknown:
Equine rhinitis B virus 1 sequence

<400> SEQUENCE: 620
cgacaggcac aggtcgctcc gagttctagt agtgtgggaa cttgttacta ctgatgaaac 60
gaggtagtga cactcagtac ctgcgaacga ggtcggggcc ctcccttctt ccttcaccca 120
actttcactt ttcgttccac tttagcaggg gtcttctttc tatccccctg gcggcattgg 180
aactagccgt cgcgtcttaa cgcgcagccc tgaaggcccc acaccttgtg gatcttgccg 240
tgggtatgtt tctggcatgt gtttctcaag cctgcaaccg aagccgaaca gccacatgaa 300
cagtttgagc gtggtagcgc tgtgtgagtt ggcggtggat ccccctcgtg gtaacacgag 360
cccccgtggc caaaagccca gtgtttacag cacctctcac atccaggacg accccatcct 420
ggcgctcact cttagtagta tggcttagta cgcattaggt ggtaagccga gctctccctc 480
ggccttgttc tgaatgcaca catgtctagg ggctaaggat gtcctacagg tacccgcacg 540
taaccttcag agagtgcgga tctgagtagg agaccgtggt gcactgcttt acagatgcag 600
cccggtttaa aaagcgtcta tgcccctaca gggtagcggt gggccgcgcc ctttcctttt 660
aaaactactt gttct 675

<210> SEQ ID NO 621
<211> LENGTH: 675
<212> TYPE: DNA
<213> ORGANISM: Equine rhinitis A virus

<400> SEQUENCE: 621
aagggttact gctcgtaatg agagcacatg acattttgcc aagatttcct ggcaattgtc 60
acgggagaga ggagcccgtt ctcgggcact tttctctcaa acaatgttgg cgcgcctcgg 120
cgcgcccccc ctttttcagc cccctgtcat tgactggtcg aaggcgctcg caataagact 180
ggtcgttgct tggcttttct attgtttcag gctttagcgc gcccttgcgc ggcgggccgt 240
caagcccgtg tgctgtacag caccaggtaa ccggacagcg gcttgctgga ttttcccggt 300
gccattgctc tggatggtgt caccaagctg gcagatgcgg agtgaacctt acgaagcgac 360
acacctgtgg tagcgctgcc cagaagggag cggagctccc ccgccgcgag gcggtcctct 420
ctggccaaaa gcccagcgtt aatagcgcct tctgggatgc aggaacccca cctgccaggt 480
gtgaagtgga ctaagtggat ctccaatttg gcctgttctg aactacacca tctactgctg 540
tgaagaatgt cctgaaggca agctggttac agccctgatc aggagccccg ctcgtgactc 600
tcgatcgacg cggggtcaaa aactgtctaa gcagcagcag aaacgcggga gcgtttcttt 660
ttcctcattt gtttc 675

<210> SEQ ID NO 622
<211> LENGTH: 224
<212> TYPE: DNA
<213> ORGANISM: Unknown
<220> FEATURE:
<223> OTHER INFORMATION: Description of Unknown:
Equine arteritis virus sequence

<400> SEQUENCE: 622
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcca tcgtcgtcga tctctatcaa ctacccttgc gact 224

<210> SEQ ID NO 623
<211> LENGTH: 675
<212> TYPE: DNA
<213> ORGANISM: Enterovirus sp.

<400> SEQUENCE: 623
actctggtat cacggtacct ttgcacgcct attttatacc ccttccccat cgtaacttag 60
aagcaacaaa caaactgccc aatagcagca caacacccag ttgtgttagg ggcaagcact 120
tctgtttccc cggaagggtc tgacggtatg ctgtacccac ggcagaagta tgacctaccg 180
ttaaccggcc atgtacttcg agaagcctag taccattatg aaggttgatt gatgttacgc 240
tccccagcaa ccccagctgg tagttctggt cgatgagtct cggcattccc cacgggcgac 300
cgtggccgag gctgcgttgg cggccagcct acaccatacg gtgtaggacg tcaagatact 360
gacatggtgt gaagagccta ttgagctacg tggtagtcct ccggcccctg aatgcggcta 420
atcctaactc cggagcatcc gccagtaagc ccactggaag ggtgtcgtaa tgcgaaagtc 480
tggagcggaa ccgactactt tgggtgtccg tgtttcctgt tttacttatt gtttggctgc 540
ttatggtgac aacttatagt tatcatcata agctacttgg tcttgccaac cggagaatta 600
tttggttatt tgttggtttc ataaacctac agtcgtattt tcctgtctta ttaattgttc 660
tcaaaattaa caaca 675

<210> SEQ ID NO 624
<211> LENGTH: 675
<212> TYPE: DNA
<213> ORGANISM: Enterovirus sp.

<400> SEQUENCE: 624
taccgctgca ccagtgagct ggtacgctag taccttcgca cggagtagat ggcatccccc 60
accccgtaac ttagaagcaa agtacacatc tggccaatag tggcgctgca tccagccgcg 120
caacggtcaa gcacttctgt ttccccggtc cgcaagggtc gttatccgcc cagtccacta 180
cggaaagcct actaaccatt gaagctatcg agaggttgcg ctcggccacg accccggtgg 240
tagctctgag tgatggggct cgcaaacacc cccgtggtaa cacggatgct tgcccgcgcg 300
tgcactcggg ttcagcctat tggttgttca cctcaacata gtgtaaatgg ccaagagcct 360
actgtgctgg attggttttc ctccggagcc gtgaatgctg ctaatcccaa cctccgagcg 420
tgtgcgcaca atccagtgtt gctacgtcgt aacgcgtaag ttggaggcgg aacagactac 480
tttcggtact ccgtgtttct tttgttttat tttgaatttt atggtgacaa ttgctgagat 540
ttgcgaatta gcgactctac cgctgaacat tgccctgtac tacctaatcg catttcacaa 600
aacctcagag ataccaagct cttacattga tctgcttgtt ttcctgaatc tcaaatataa 660
attggaacaa gcaaa 675

<210> SEQ ID NO 625
<211> LENGTH: 107
<212> TYPE: DNA
<213> ORGANISM: Morbillivirus sp.

<400> SEQUENCE: 625
accagacaaa gctggctagg ggtagaataa cagataatga taaattatca tacttaggat 60
taatgatcct atcaattggc acaggatttg gataaaggtt cacagtc 107

<210> SEQ ID NO 626
<211> LENGTH: 348
<212> TYPE: DNA
<213> ORGANISM: Unknown
<220> FEATURE:
<223> OTHER INFORMATION: Description of Unknown:
Dianke virus sequence

<400> SEQUENCE: 626
tgttttcaac cataatacta ctactacaag tataaaaccc cgtccgtctg tcggagacgc 60
taaactctga ccaccaatct agccacatca gttgcttaaa gaacctcttg agacactctc 120
ccacttaaca tcttttagga atcttcgatg ctacaacaac ttggctagtg aacaataaat 180
ccgtacaatt cacagttgta agaggccata ggtccagact ttgaaaggtt tgtttctatt 240
gttacaaata cttagattaa cagaggctat ttaatagtgc tcatcacgtt aacagagtaa 300
ccttgtgcaa tagtatgagc ttgttgtaaa acgtcttgat acgacacc 348

<210> SEQ ID NO 627
<211> LENGTH: 270
<212> TYPE: DNA
<213> ORGANISM: Hepacivirus sp.

<400> SEQUENCE: 627
cactcaatac tacactccgc atttggggag aagcgctggc gttcgcggaa ccgcgttaac 60
catacgcgta gtacgagtgc gacagacccc ggtgctactg gtggtagcga gacacgagcc 120
gaagtctgtg gggggaactc cacttagagg gcatgcccgg gcgtaggctt ctgagttggg 180
atgggcccca acttggcccc tgagtggggg ggtgttacga cctgataggg tgcgggctgg 240
cgcctaccac tttccagtcg tacatgagtc 270

<210> SEQ ID NO 628
<211> LENGTH: 415
<212> TYPE: DNA
<213> ORGANISM: Narnavirus sp.

<400> SEQUENCE: 628
gcccgggggg tgcagtcctg tgaaagggtc tgcaccatac tatatatgta tatgattaca 60
tcccaaaagg cgacttcgtt caggttttaa atctgacgta ggtccagtaa ataagcatgt 120
caaaacatgt aagtttatcc tgtaatctac tctcataaga tgagataaga tgatattgca 180
gttcccatgt aaataaatcc attatgaatt cattcatata aggtagaagt ggtaactatg 240
gttgaaacat taatataaaa cggtcatttt gcatgaacgt cattaaggaa ctggcatacc 300
aatgtctatt tagtgactat gatatttaga gtatccctta tattaattaa caattattcc 360
ttttagcata tcatccgaca acaaatttta aaagaagaaa tattactcat taaaa 415

<210> SEQ ID NO 629
<211> LENGTH: 675
<212> TYPE: DNA
<213> ORGANISM: Torovirus sp.

<400> SEQUENCE: 629
gtacttacaa gcgggttaaa ccgccctccg gaacggttac aaccccctcc cgaacgtgcg 60
cttgacgtga ctggttctca gtctggcttt ctgagaaata ctccagggtt gtatcccacc 120
atcttgacct ctggtcattt tggtaacacc ataaccaaac aaactctaca cacctaaccc 180
acctccagct tgctgcaggc cttttggact aaacgggttt aggtgttttg tgaccaactc 240
gtctacccac ctccagtttt actgcaggcc tttttggact aaacggcttt agacttttgt 300
ggttagtttt taactaccca ctgtttagcc gccaacctga ttttcattgt tgtaaaattt 360
tgtgtttata cactattttc atacggttgg cagtttgttt ggttgtttgc acagtttttg 420
ttgataccaa tttttactgt gcttttagtg tattctgcta aggctgtatt ttacatactt 480
agtttggttg aagcaatttt tacaacattt atattgtttt tgatttctaa ggtaaagagt 540
cttaggaaac accatagacg ccattcttgt ggtgtctagt tccaactaat ctggcaaaca 600
agtaccaagt cattgactca ctttggagtg agacttacga gtaccaattt gcctatttcg 660
gacatccata taaag 675

<210> SEQ ID NO 630
<211> LENGTH: 675
<212> TYPE: DNA
<213> ORGANISM: Foot-and-mouth disease virus

<400> SEQUENCE: 630
acaagcttga caccgcctgt cccggcgtta aagggaagta accacaagct tacaaccgcc 60
taccccggtg ttaatgggat gtaaccacaa gatacacctt cacccggaag taaaacggca 120
aattcacaca gttttgcccg tttttcatga gaaacgggac gtctgcgcac gaaacgcgcc 180
gtcgcttgag gaggacttgt acaaacacga tctaaacagg tttccccaac tgacatacac 240
cgtgcaattt gaaactccgc ctggtctttc caggtctaga ggggtaacac tttgtactgt 300
gcttgactcc acgctcggtc cactggcgag tgttagtaac agcactggtg cttcgtagcg 360
gagcatggtg gccgtgggaa ctcctccttg gtaacaagga cccacggggc cgaaagccac 420
gtcctgacgg acccaccatg tgtgcaaccc cagcacggca acttttctgt gaaactcact 480
ctaaggtgac actgatactg gtattcaagt actggtgaca ggctaaggat gcccttcagg 540
taccccgagg taacacgcga cactcgggat ctgagaaggg gactggggct tctgtaaaag 600
cgcccagttt aaaaagcttc tatgcctgga taggtgaccg gaggccggcg cctttccatt 660
ataactactg acttt 675

<210> SEQ ID NO 631
<211> LENGTH: 310
<212> TYPE: DNA
<213> ORGANISM: Unknown
<220> FEATURE:
<223> OTHER INFORMATION: Description of Unknown:
      Feline infectious peritonitis virus sequence

<400> SEQUENCE: 631
acttttaaag taaagtgagt gtagcgtggc tataactctt cttttacttt aactagcctt 60
gtgctagatt tgtcttcgga caccaactcg aactaaacga aatatttgtc tctctatgaa 120

```
accatagaag acaagcgttg attatttcac cagtttggca atcactccta ggaacggggt    180

tgagagaacg gcgcaccagg gttccgtccc tgtttggtaa gtcgtctagt attagctgcg    240

gcggttccgc ccgtcgtagt tgggtagacc gggttccgtc ctgtgatctc cctcgccggc    300

cgccaggaga                                                           310


<210> SEQ ID NO 632
<211> LENGTH: 143
<212> TYPE: DNA
<213> ORGANISM: Unknown
<220> FEATURE:
<223> OTHER INFORMATION: Description of Unknown:
      Farmington virus sequence

<400> SEQUENCE: 632

acgacgcata agcagagaaa cataagagac tatgttcata gtcaccctgt attcattatt     60

gacttttatg acctattatt agacccttca cgggtaaatc cttctccttg cagttctcgc    120

caagtacctc caaagtcaga acg                                            143


<210> SEQ ID NO 633
<211> LENGTH: 528
<212> TYPE: DNA
<213> ORGANISM: Unknown
<220> FEATURE:
<223> OTHER INFORMATION: Description of Unknown:
      Avian infectious bronchitis virus sequence

<400> SEQUENCE: 633

acttaagata gatattaata tatatctatt acactagcct tgcgctagat ttttaactta     60

acaaaacgga cttaaatacc tacagctggt cctcataggt gttccattgc agtgcacttt    120

agtgccctgg atggcacctg gccacctgtc aggtttttgt tattaaaatc ttattgttgc    180

tggtatcact gcttgttttg ccgtgtctca ctttatacat ctgttgcttg ggctacctag    240

tgtccagcgt cctacgggcg tcgtggctgg ttcgagtgcg aggaacctct ggttcatcta    300

gcggtaggcg ggtgtgtgga agtagcactt cagacgtacc ggttctgttg tgtgaaatac    360

ggggtcacct ccccccacat acctctaagg gcttttgagc ctagcgttgg gctacgttct    420

cgcataaggt cggctatacg acgtttgtag ggggtagtgc caaacaaccc ctgaggtgac    480

aggttctggt ggtgtttagt gagcagacat acaatagaca gtgacaac                 528


<210> SEQ ID NO 634
<211> LENGTH: 626
<212> TYPE: DNA
<213> ORGANISM: Rhinovirus sp.

<400> SEQUENCE: 634

ttaaaactgg gtgtgggttg ttcccaccca caccacccaa tgggtgttgt actctgttat     60

tccggtaact ttgtacgcca gtttttccct cccctcccca tccttttacg taacttagaa    120

gttttaaata caagaccaat agtaggcaac tctccaggtt gtctaaggtc aagcacttct    180

gtttccccgg ttgatgttga tatgctccaa cagggcaaaa acaacagata ccgttatccg    240

caaagtgcct acacagagct tagtaggatt ctgaaagatc tttggttggt cgttcagctg    300

catacccagc agtagacctt gcagatgagg ctggacattc cccactggta acagtggtcc    360

agcctgcgtg gctgcctgcg cacctctcat gaggtgtgaa gccaaagatc ggacagggtg    420

tgaagagccg cgtgtgctca ctttgagtcc tccggcccct gaatgcggct aaccttaaac    480

ctgcagccat ggctcataag ccaatgagtt tatggtcgta acgagtaatt gcgggatggg    540
```

accgactact ttgggtgtcc gtgtttcact ttttccttta ttaattgctt atggtgacaa 600
tatatatatt gatatatatt ggcatc 626

<210> SEQ ID NO 635
<211> LENGTH: 675
<212> TYPE: DNA
<213> ORGANISM: Unknown
<220> FEATURE:
<223> OTHER INFORMATION: Description of Unknown:
EV22 sequence

<400> SEQUENCE: 635
ccttataacc cgacttgctg agcttctata ggaaaaaacc ctttcccagc cttggggtgg 60
ctggtcaata aaaacccccca tagtaaccaa cacctaagac aatttgatca accctatgcc 120
tggtccccac tattcgaagg caacttgcaa taagaagagt ggaacaagga tgcttaaagc 180
atagtgtaaa tgatcttttc taacctgtat tatgtacagg gtggcagatg gcgtgccata 240
aatctattag tgggatacca cgcttgtgga ccttatgccc acacagccat cctctagtaa 300
gtttgtaaaa tgtctggtga gatgtgggaa cttattggaa acaacaattt gcttaatagc 360
atcctagtgc cagcggaaca acatctggta acagatgcct ctggggccaa aagccaaggt 420
ttgacagacc cattaggatt ggtttcaaaa cctgaattgt tgtggaagat attcagtacc 480
tatcaatctg gtagtggtgc aaacactagt tgtaaggccc acgaaggatg cccagaaggt 540
acccgcaggt aacaagagac actgtggatc tgatctgggg ccaactacct ctatcaggtg 600
agttagttaa aaaacgtcta gtgggccaaa cccagggggg atccctggtt tccttttatt 660
gttaatattg acatt 675

<210> SEQ ID NO 636
<211> LENGTH: 675
<212> TYPE: DNA
<213> ORGANISM: Cardiovirus sp.

<400> SEQUENCE: 636
tccgacgtgg ttggaattaa catcttttcc gacgaaagtg ctattatgcc tccccgattg 60
tgtgatgctt tctgccctgc tgggcggagc gtcctcgggt tgagaaacct tgaatctttt 120
cctttggagc cttggctccc ccggtctaag ccgcttggaa tatgacaggg ttattttcca 180
aactctttat ttctactttc atgggttcta tccatgaaaa gggtatgtgt tgccccttcc 240
ttctttggag aatctgcgcg gcggtctttc cgtctctcaa caggcgtgga tgcaacatgc 300
cggaaacggt gaagaaaaca gtttctgtg gaaatttaga gtggacatcg aaacagctgt 360
agcgacctca cagtagcagc ggattcccct cttggcgaca agagcctctg cggccaaaag 420
ccccgtggat aagatccact gctgtgagcg gtgcaacccc agcaccctgg ttcgatggcc 480
attctctatg gaaccagaaa atggttttct caagccctcc ggtagagaag ccaagaatgt 540
cctgaaggta ccccgcgcgc gggatctgat caggagacca attggcagtg ctttacgctg 600
ccactttggt ttaaaaactg tcacagcttc tccaaaccaa gtggtcttgg ttttccaatt 660
ttgttgactg acaat 675

<210> SEQ ID NO 637
<211> LENGTH: 292
<212> TYPE: DNA
<213> ORGANISM: Human coronavirus 229E

<400> SEQUENCE: 637
acttaagtac cttatctatc tacagataga aaagttgctt tttagacttt gtgtctactt 60
ttctcaacta aacgaaattt ttgctatggc cggcatcttt gatgctggag tcgtagtgta 120
attgaaattt catttgggtt gcaacagttt ggaagcaagt gctgtgtgtc ctagtctaag 180
ggtttcgtgt tccgtcacga gattccattc tacaaacgcc ttactcgagg ttccgtctcg 240
tgtttgtgtg gaagcaaagt tctgtctttg tggaaaccag taactgttcc ta 292

<210> SEQ ID NO 638
<211> LENGTH: 282
<212> TYPE: DNA
<213> ORGANISM: Unknown
<220> FEATURE:
<223> OTHER INFORMATION: Description of Unknown:
Hubei zhaovirus-like virus 1 sequence

<400> SEQUENCE: 638
gtgcaggatg gcctttccca tcttaagtgg tttgtaggat ttcgtgggtc catacccccc 60
gatttcttgg tacgtattcc atgcacggag aatacgacca aaactcttat ttcaaaaaat 120
attatttttt actcttgtgg gctgagtgcg acccaccagt tccagcttag caacctggaa 180
gttgttggag atttatggaa ccaaattaca catgcgtgga gtgccgccac tccgtatctg 240
ttcactcatt acgcgattaa gttctgcgac gagacgagcg aa 282

<210> SEQ ID NO 639
<211> LENGTH: 600
<212> TYPE: DNA
<213> ORGANISM: Unknown
<220> FEATURE:
<223> OTHER INFORMATION: Description of Unknown:
Hubei tombus-like virus 9 sequence

<400> SEQUENCE: 639
ggaccatcca ggcaggtgta ggctagtacc ctcacctgac ctgtcgcgat gtttggcttt 60
gtgaggcttg tgggaggatc ccttggccca tgcattgctg ctgtcatcgt gaaaaatgtt 120
gtatgctcgc acctggcgtg gaggaaacgg catttgacgg atgctaagga ggatttgaag 180
gtcctcaact cccatgcctt attacaagtc ccctttcctt caagcttcga gcccacgtct 240
gtgacgagca gaggtgaggt tggagtcaag aggagtccta ttcaagctgt tcgcagcaag 300
aaccataaaa ctttcattgc tcaatgggca agagcggcta aggctcggtt ctcgtttgca 360
cgacagtgtg agcggagccc tgtaaatgtc gcggcccttc atcggtggtt tgcatcggag 420
tttaagaaaa ttggcatgaa cttgctccag gtttcgtacg tgatcgatga ggttgttgaa 480
cttagtttgg aaccaacgta tgagcgtatg gtgtccgaaa ctaagaagca attccgtcat 540
cgggcacgta tggaatacta caacgagaaa aaatgccttg aaaagatcca ctaggaacgc 600

<210> SEQ ID NO 640
<211> LENGTH: 251
<212> TYPE: DNA
<213> ORGANISM: Unknown
<220> FEATURE:
<223> OTHER INFORMATION: Description of Unknown:
Hubei tombus-like virus 32 sequence

<400> SEQUENCE: 640
ttcgggttta cccgcgtaag cggccacact gactggttgt cggtgttgaa tttgtatacc 60
agatgaggag acgttaccac cgtctcggca gtgctacgtc tgggaaagga ctgtgatagt 120

```
ggacagtcct accgtcttta gatacattgc gttgtgtata gcccgggagg gattaactaa    180

tagcaacgca atgcacacgg cggttcggat ttgcttgact gatggaaaga catctaagtt    240

ctaattgaac c                                                         251


<210> SEQ ID NO 641
<211> LENGTH: 341
<212> TYPE: DNA
<213> ORGANISM: Unknown
<220> FEATURE:
<223> OTHER INFORMATION: Description of Unknown:
      Hubei sobemo-like virus 3 sequence

<400> SEQUENCE: 641

gagatgtttg cgtgggccgt tgcgctgcgg gcggcccacc tccctacggg gaccgtgaga     60

caccgctggg gaaggccccc acccccggcc aaggggatcc tgccgagagg caggagaaag    120

aggcccagcc ctctggggcg cctttagggg tgcctgggag ggaagtaccc gagccgggcg    180

gccggtcggg tgcggctgtg cagttcgagg ctaaccgtaa ggaaggcctg agctgcctcg    240

gcttgtcgga aaggaagacg aaggcactta tcaaggcttt caggaagcag gagcgcaatt    300

acagcgcgcg ccgtgcggcc tggattaacc gcatttggcc g                        341


<210> SEQ ID NO 642
<211> LENGTH: 675
<212> TYPE: DNA
<213> ORGANISM: Unknown
<220> FEATURE:
<223> OTHER INFORMATION: Description of Unknown:
      Hubei picorna-like virus 2 sequence

<400> SEQUENCE: 642

agcaacttct ttctgaaaac tagctagagt tcgacgatct ctctggctaa tgacaaataa     60

ccaatcaaaa agtcaaatgt tcatgtatat atatatttag tagtgacctt tatttagaaa    120

aactttagat gatttatcgt caagttgccc tttgtgaagc gatcagcttt ttatatcgtt    180

tcatttttgt atacgtctta attgacgttg taagtacgtt ttgcatacct cacattgagg    240

atagtatcgt ttcctgacta agaagttaaa ctagtctacc aatagcaacc atataggata    300

tagctttgtt tttaacaagg tttaatctga tcttatgctc ttgcttacgg tgttttatgt    360

atagaaaagt ttttataaaa actacataat tgtcaaaaga aaaagcgtta cgtactgacg    420

catttatgtt cacagtgtga cacaaacctt ctatattttg attgtaaaat aggctttgcc    480

tgaccattta tcaaatacaa actgtttcaa acgcctctcc gagccatatt ggccgacgcg    540

aatcgacata acagggtgag tttacagctg cagttgcagc cgaggatcca cttatttgag    600

agagaattac tcttaacgaa attttgaagt cacttctaca cagttaagtc tgagtaggcg    660

ttatccaaac gtaaa                                                     675


<210> SEQ ID NO 643
<211> LENGTH: 174
<212> TYPE: DNA
<213> ORGANISM: Hepacivirus sp.

<400> SEQUENCE: 643

acatgggggg gggctgacag tgagtacact gtgccaagca ggtgctacgc tatgcctagg     60

tgctgctgta ggccaaggac atgtcccagt catcccaggt gagggggggg gttcccctca    120

ccgctgccac tgcctgatag ggtcctgccg gagggtctcg gtgtccggct gtac          174
```

<210> SEQ ID NO 644
<211> LENGTH: 675
<212> TYPE: DNA
<213> ORGANISM: Unknown
<220> FEATURE:
<223> OTHER INFORMATION: Description of Unknown:
Harrier picornavirus 1 sequence

<400> SEQUENCE: 644
gatgtgtgac ggtgtaatta ctttccggat cccactttcc tattataact ctttcatccc 60
aaggttaggg aaagaacctg gctcggtacc accagaccct ccgccacgct agtggactct 120
ccggagataa cggtaccccc tttgtagtca cctgtgctgg tgaagaacca cctagtattg 180
cttgggtgcg tgccgcctag cttccatttc ttctggagca ctgtgcaatg aggtttcccc 240
acttggtaac aagtgcctca ggtcccgcaa ggatactgtg gggtggtgtg accgcaggga 300
gctgtctcca cggctcctct aatgttacgc cgctatccac aggccagtgc gtgtcatcga 360
tcccggatga cagagctagt attgcgaacc cccaagtaag aaaagtggct agtaacctga 420
tagctggtga agagggtggg tcagttgagt agatgcccta gaggtacccg aaaggatctg 480
actagggacc cgtgactata cattaggtaa accgggtata aaaaccatga aaaactgacc 540
acttttcttt taacctcttc tttcttttta tgtgtgttaa gtgttttgag tttggactgt 600
accttgcccg cctttcttgg attttctcta tcgctcttct tacacctact gttatcaagg 660
cactctttag agata 675

<210> SEQ ID NO 645
<211> LENGTH: 500
<212> TYPE: DNA
<213> ORGANISM: Kunsagivirus sp.

<400> SEQUENCE: 645
tttcaaatcg gactccggta gttataccgg agcccggttt ggacgcttgg gccgcgttaa 60
cagcccccca cccctttccc actgactgat ttctcggatt ggactcattt gcattgctaa 120
ctctgattct ggatttcccc gtttatgtcg tcgcggtcgg aagtgcacgt acttcgacgt 180
tgatctgatg gcgtttgttt ccaggggggga ggtggcggca gaaacgcccc cgccgtaaac 240
ttcggcgggc cacgcctgtc aagccactcc ctggggccga gcgcctgagg tgatacagag 300
agataagcac actgggcgct gacaacgccc gggacctcag tgagaagagc agtagggccg 360
tgtttatggg actccattgg atatccccccg cttgtcggaa ctcacggcta ctccgggttg 420
ggaagcccgc gactggtact gtactgggtg atagcctggt gccttccctc tcactgttgt 480
atgaaggctg aaaacccccct 500

<210> SEQ ID NO 646
<211> LENGTH: 675
<212> TYPE: DNA
<213> ORGANISM: Kobuvirus sp.

<400> SEQUENCE: 646
tatagtttgc ctgtttctcg caccgttacc gctcgttcgg gaatgtgaaa ctggcacccc 60
tcctctcccc taccaccctt tctccttcgc ccccattcat aatttacaac gccgcacaca 120
gcggcggccg ccaagggcta gcctggcggt tataaaagga acctgggtct ttccctcttc 180
aagccaaaag gtaggttccc tgtgtccctg aatgctcggt gaggaatgct gcaccgtaac 240
gctttgtgaa gtgtttgcaa gttctggccc ggcaagccta cagagtgctg tgatccgctg 300

-continued

```
cggacgccat cctggtaaca ggacccccag tgtgcgcaac agtatgttca gacttcggtt    360

tgttcacttg ctttcatgga ccattgcgcg aaagtgcgtg cgccatatcc ctgtacttca    420

ggtgtgcttc tctggaccct aggaatgctg cgaaggtacc ccgtttcggc gggatctgat    480

cgcaggctaa ttgtctatgg gttcagtttc ctttttcttt actccacaat tgactgctta    540

actgactctg gatcttgtgc ttccactgct ctttctgctc tcaaaacggc ttcacttacc    600

aactctcacc tttcgaccaa caccatttac acactaactt ttttcgactc ttctgactcc    660

tggcttggtg aagac                                                     675
```

<210> SEQ ID NO 647
<211> LENGTH: 608
<212> TYPE: DNA
<213> ORGANISM: Kashmir bee virus

<400> SEQUENCE: 647

```
tacgtacaat tttgacgctt cgttcatgca acaatgaact cacatgtggc gctcggtagt     60

aaccagaggg gcgtcattcc cccgtatgga gtggagaata taagctaccg actcgagctg    120

tagaataatt cagcaactta taacgaacac gaattttagt cgacgaaacc attttagcct    180

ttaattctat gatttgatta taatgataaa cagctcatgt aactgtctaa actacataaa    240

tacaactgga ttacgaacct ttaagtaact atcttagatg aagtctagta gtctcccaat    300

atttccgtga aaagaatgag ggacgagata gctctattta aagacgtgag gctttaaatt    360

ctgataaata cattacctga gaattcctcc tttaggagtt agaatttgaa aagattagta    420

cctatactta atagaattta aatatgttaa taatgctgaa gacaagtatt tcgattatta    480

acctctatat ttctatataa agtatctgtg agtctcagtg gacatcacag taaggtcgca    540

gttaacttgt aatcttttca ttcctgtgtc ggagcagtgg taatggagcc ggacgatttc    600

gccaaaac                                                             608
```

<210> SEQ ID NO 648
<211> LENGTH: 332
<212> TYPE: DNA
<213> ORGANISM: Unknown
<220> FEATURE:
<223> OTHER INFORMATION: Description of Unknown:
      Jingmen picorna-like virus sequence

<400> SEQUENCE: 648

```
tgtgtttttg tcaagataat tgttctgtga ttaacagtga ttgtggttcg tgtaatgcga     60

cgcagtcaaa tgctagtttt gatgaagtgt atgagagagt ggaaaactta tctcataaga    120

agattgaaga gtgtgtagat caggctattg atcgagcttc taagcttcgt gattacaagc    180

ttaatgttca caatggctcc cgacgggaat catctgatcc tctctttatt tcgccccatt    240

cgttgttatc gcttggggta tctaagtttg ttgcgtttga gcagcatcac agtttcgctt    300

cagttgagtc tctgaagttg cttgctctgt ct                                  332
```

<210> SEQ ID NO 649
<211> LENGTH: 145
<212> TYPE: DNA
<213> ORGANISM: Mumps orthorubulavirus

<400> SEQUENCE: 649
accaagggga aaatgaagat gggatgttgg tagaacaaat agtgtaagaa acagtaagcc 60
cggaagtggt gttttgcgat ttcgaggccg ggctcgatcc tcacctttca ttgtcgatag 120
gggacatttt gacactacct ggaaa 145

<210> SEQ ID NO 650
<211> LENGTH: 138
<212> TYPE: DNA
<213> ORGANISM: Mosavirus sp.

<400> SEQUENCE: 650
gaagttgatc atgaacttgg ttattggtgg aacgcacatg aactcccaac aatgatcttg 60
aagacacagc gtggtaacaa ttaccatgcc cttgtggctg cccaagacat tgatggctat 120
tgggtgattt atgatgac 138

<210> SEQ ID NO 651
<211> LENGTH: 675
<212> TYPE: DNA
<213> ORGANISM: Unknown
<220> FEATURE:
<223> OTHER INFORMATION: Description of Unknown:
Miniopterus schreibersii picornavirus 1 sequence

<400> SEQUENCE: 651
gttgtcgacc cgttgcttgg tttaagcatg aggtggattc ccccgattat gtctacccgt 60
tactatggcg ggcggtcgtt tcagggtgtt tctactgagg actgcaccaa gtctttatct 120
tttattctca gatctccggc tgtttgacgc ttgtaggaca gcaggactat tttctcttaa 180
tctttttcta cccactaggg tcctatccta gtggagggag ggtgccaccc cttctctctt 240
tagagagtgc gcctggcggt ctttccgtct ctggaaaaag gagcacatgg catgctacaa 300
ttggcacaag aaaacaagct ttgcggattc tttctttgta ctagaggaag ctgtagcgac 360
cctgtatggc gagcggactc ccctctcggc gacgagagcc tctcgggcca aaagccaagt 420
gttaatagca cccatacagg cggcagtacc ccactgccct ttctcaacat acaatgactg 480
atgaaccact gttggttttt ctgacacctt tgtagtagga ttccaaggaa tgtcctgaag 540
gtaccctgtt agcttacgcg caggatctga tcaggagtct ctttacagtg ctgtacactg 600
tgcaagggat taaaaattgt ttgaggaatc cccgagatag tggtctatct cttcctattt 660
tgttttacag acacg 675

<210> SEQ ID NO 652
<211> LENGTH: 381
<212> TYPE: DNA
<213> ORGANISM: Unknown
<220> FEATURE:
<223> OTHER INFORMATION: Description of Unknown:
Linda virus sequence

<400> SEQUENCE: 652
gtatagcagc agtagctcaa ggctgctata cgattggaca taccaaattc caattggtgt 60
tagggaccac ctaggtgaag gccgacgaca ggtagccatt cctgttagta ggacgaaccg 120
ttatggtgga ctggttgctc aggtgagcag gctgcaatgc gtaagtggtg agtacaccac 180
agccgtcaaa ggtgccactg gtaaggatca cccactggcg atgccttgtg gacgggggcg 240
tgcccaacgc aatgttagcg gtggcggggg ctgccatcgt gaaagctagg tcttgatgga 300
ccttgttgcc tgtacagtct gataggatgc cggcggatgc cctgtgacag ccagtataaa 360
gaatatccgt tgtgattgca c 381

<210> SEQ ID NO 653
<211> LENGTH: 675
<212> TYPE: DNA
<213> ORGANISM: Unknown
<220> FEATURE:
<223> OTHER INFORMATION: Description of Unknown:
Lesavirus 2 sequence

<400> SEQUENCE: 653
tctttcttta ttttcttatg taactcttct ttttaagttt tattttgcct acttgtgagc 60
ttatgcggga ccactgtctt agacaacccc acatttgtca tgagtaagta cacgcaacca 120
ttacgattac tttttaaccg tctgaccttt tgataacaac tgaagttagg cgtgaaacat 180
gcatttatac caaagtagcc ccgcatttcc ccactacggt ggggggggcta ccctactggc 240 tttggaactg tagccattat gtgttgcctg gctttcagga tctcacaaca caacagttct 300
ctcacaatgg aatatgggtg agattgcagt gacatgaaca agtatctagt agtacataga 360
ctcaagccta gttgcctgcg gaacaacatg tggtaacaca tgccccaggg tccaaaagac 420
aagggttaac agccccttct aggtgtctgt gtgtgaagaa tactttagta gtgttgttat 480
gatctcacct gttagtacag aatgagtatg gcttggtgaa ggatgtccta caggtaccca 540
ttatatggat ctgagtagga gaccactagt ggtggcttta ccgccaggtg agtggtttaa 600
aaagcgtcta gccaagccaa cagcactagg gatagtgctt tctatatttt atattttcag 660
tgtatatggt gacaa 675

<210> SEQ ID NO 654
<211> LENGTH: 675
<212> TYPE: DNA
<213> ORGANISM: Unknown
<220> FEATURE:
<223> OTHER INFORMATION: Description of Unknown:
Lesavirus 1 sequence

<400> SEQUENCE: 654
gtaactaata agcaagtttt actgcctgca aactgcttca atgggaccac cgcttcggcg 60 accccttttgt tgagtttgta tgtttttaag taatctttgc aaccatacga ttattttagc 120
cgcctctcta taatgatctt gttatagtgg gacgtgaaac attggttttt ctcacacacg 180
tccggtcacc cgggcgtgtg ttcttccgta agtcctatcc acataccatc gtgggtaggc 240
cagcatgttt gcacaggctg tgacagtgtg ggtgggcttt ccacctctca acaacacact 300
gaattgcaat gcactcacgg aggaaatgac aatttggtta tagttttgaa ctgtgctagt 360
aatttctttc acattaagcc atgttgcctg cggaatcaca tgtggtaaca catgcctcag 420
ggcccaaaag gcacgggtta gcagcccctt catggtgtgt tagaagtgaa aacacatagt 480
atgagctata atatctttgt tgtcttctct gtagtgtacc ccgccaaatg taaggatgcc 540
cagcaggtac ccattttatg gatctgagct ggggattgat agtgtatcta taaatgcact 600
gatcaattta aaaagcgtct aagtttggca caaacactgg ggacagtgtt tttcctttat 660
tcttttattt gatta 675

<210> SEQ ID NO 655

<211> LENGTH: 638
<212> TYPE: DNA
<213> ORGANISM: Unknown
<220> FEATURE:
<223> OTHER INFORMATION: Description of Unknown:
Phopivirus strain NewEngland sequence

<400> SEQUENCE: 655
gggagtaaac ctcaccaccg tttgccgtgg tttacggcta cctatttttg gatgtaaata 60
ttaattcctg caggttcagg tctcttgaat tatgtccacg ctagtggcac tctcttaccc 120
ataagtgacg ccttagcgga acctttctac acttgatgtg gttaggggtt acattatttc 180
cctgggcctt ctttggccct ttttcccctg cactatcatt ctttcttccg ggctctcagc 240
atgccaatgt tccgaccggt gcgcccgccg gggttaactc catggttagc atggagctgt 300
aggccctaaa agtgctgaca ctggaactgg actattgaag catacactgt taactgaaac 360
atgtaactcc aatcgatctt ctacaagggg taggctacgg gtgaaacccc ttaggttaat 420
actcatattg agagatactt ctgataggtt aaggttgctg gataatggtg agtttaacga 480
caaaaaccat tcaacagctg tgggccaacc tcatcaggta gatgcttttg gagccaagtg 540
cgtaggggtg tgtgtggaaa tgcttcagtg gaaggtgccc tcccgaaagg tcgtaggggt 600
aatcaggggc agttaggttt ccacaattac aatttgaa 638

<210> SEQ ID NO 656
<211> LENGTH: 377
<212> TYPE: DNA
<213> ORGANISM: Pestivirus sp.

<400> SEQUENCE: 656
gtatacgaga ttagctcata ctcgtgtaca aattggacgt agcaaattta aaaattcgga 60
tagggtcccc atccagcgac ggccgaacgg ggttaaccat acctctagta ggactagcag 120
acggatggac tagccacagt ggtgagctcc ctgggaggtc taagttctga gtacagaaca 180
gtcgtcagta gttcaacgct ggtaaacccc agccttgaga tgctacgtgg acgagggcat 240
gcccaagaca caccttaacc tggacggggg tcgtccaggt gaaagtaccc atctttgggt 300
gctgggagta cagcctgata gggcgctgca gaggcccact gacaggctag tataaaaatc 360
tctgctgtac atggaac 377

<210> SEQ ID NO 657
<211> LENGTH: 494
<212> TYPE: DNA
<213> ORGANISM: Unknown
<220> FEATURE:
<223> OTHER INFORMATION: Description of Unknown:
Quail picornavirus QPV1 sequence

<400> SEQUENCE: 657
tttgcatcag ttcgcccctc ccctcaccat acctttttcc cctctttagg actgatactt 60
ggttatgatg agcagaggat ttcgcaagtt atgcttcttg ataaaaagta attcacgaat 120
catgggatta tagcctggaa gtgaacactc atgtggcaag tgggttagta gctctccatg 180
ttcccatgtg cagtggactg acaacagtga gttcggggtt gtgtagtaaa gggaaagtat 240
tacttacccg cacctgctat acgtggtgta cgtaggatac gagttagtag tgcttagcaa 300
ctttaaactg gtgctgaaat attgcaaggt cactgaagtt gtgaacgcga acgctccgcc 360
actgccatgt atagcgtgca atgcataaat ggtgcactac atgatacgag ggaatgggaa 420
accctccatg gccgaatgca gggtgacagc ctgccggcgg atgcctgttg ttagtataat 480
ccgttgtttg ccac 494

<210> SEQ ID NO 658
<211> LENGTH: 443
<212> TYPE: DNA
<213> ORGANISM: Sapelovirus sp.

<400> SEQUENCE: 658
acactcattt ccccctcca cccttaaggt ggttgtatcc cctacaccct accctccctt 60
ccacatagga cgaataaacg gacttgagat taaggcaagt acataaggta tggtttttgg 120
atacacttaa atggcagtag cgtggcgagc tatggaaaaa tcgcaattgt cgatagccat 180
gttagcgacg cgcttcggcg tgctcctttg gtgattcggc gactggttac aggagagtag 240
acagtgagct atgggcaaac ccctacagta ttacttaggg gaatgtgcaa ttgagacttg 300
acgagcgtct ctttgagatg tggcgcatgc tcttggcatt accatagtga gcttccaggt 360
tgggaaacct ggactgggtc tatactgcct gatagggtcg cggctggccg cctgtaacta 420
gtatagtcag ttgaaaaccc ccc 443

<210> SEQ ID NO 659
<211> LENGTH: 189
<212> TYPE: DNA
<213> ORGANISM: Unknown
<220> FEATURE:
<223> OTHER INFORMATION: Description of Unknown:
Porcine reproductive and respiratory syndrome virus 2 sequence

<400> SEQUENCE: 659
atgacgtata ggtgttggct ctatgccttg gcatttgtat tgtcaggagc tgtgaccatt 60
ggcacagccc aaaacttgct gcacagaaac acccttctgt gatagcctcc ttcaggggag 120
cttagggttt gtccctagca ccttgcttcc ggagttgcac tgctttacgg tctctccacc 180
cctttaacc 189

<210> SEQ ID NO 660
<211> LENGTH: 675
<212> TYPE: DNA
<213> ORGANISM: Enterovirus sp.

<400> SEQUENCE: 660
gaaccttaga agtttacaca aacaaagacc aataggagtc caacacccag ttggattgcg 60
gtcaagcact tctgtttccc cggacctagt agtgataggc tgtacccacg gccgaagatg 120
aacccgtccg ttatccggct acctacttcg ggaagcctag taacattctg aagtctctga 180
ggcgtttcgc tcagcacgac cccggtgtag atcgggctga tgggtctccg cataccccac 240
gggcgaccgt ggcggaggcc gcgttggcgg cccgcctatg gcgaaagcca taggacgcct 300
cttagatgac agggtgtgaa gagcctactg agctgggtag tagtcctccg gcccctgaat 360
gcggctaatc ctaaccacgg agcgtccacc agcaatccag ctggcagggc gtcgtaacgg 420
gcaactctgt ggcggaaccg actactttgg gtgtccgtgt ttccttttga tcctattttg 480
gctgcttatg gtgacaacga taagttgtta tcataaagct cttgggttgg ccacctggaa 540
aaagttatca gtgtttgata ttgttcggct ctcacgccta ccaataagac aagccctata 600
tttacttgtt gcattttact cgtcagaaga aatcacagag tatcatttgg atttgttact 660
cacattaagg acaag 675

<210> SEQ ID NO 661
<211> LENGTH: 591
<212> TYPE: DNA
<213> ORGANISM: Unknown
<220> FEATURE:
<223> OTHER INFORMATION: Description of Unknown:
Pigeon picornavirus B sequence

<400> SEQUENCE: 661
tttatttagc tgttaagttt tatttgtgcc gagaccccat agtaggatct tggtgttcca 60
cattaagctc tcccgaccac acatccaaac gataggcggt gtaagggctc cctggctaag 120
tgtttactca ttgctaggga agtgttgcga cccgttacca gtaggaatac aggaggtctt 180
agttgcctaa ccagataaag tggtgctgaa atattgcaag ctcaatgtct ggcgaacgac 240
ggactaccgt tgaactattg ttaacgcccg cgtgtgtagg caacacacgg gttagtaggt 300
cacttacatt gacatccgtg ccgggaaagc ggatctgagc tatcgattgc ctgatagggt 360
gccggcgggc gcggtacgtg tggtatagtc cgctgtcttg gggtatggcg tctactcggt 420
tttgttgtcg ttttggaatg tcccatgtcg gagatgtcgt taccggtgtt tgctttactt 480
gtgcacgaat aagaaaacag agtttggagt tttggaagtt aatggataac atcaagtttc 540
cattgcgttc ctcgtgcatt ttaggccaga aaatcgacca caaaatcgag a 591

<210> SEQ ID NO 662
<211> LENGTH: 620
<212> TYPE: DNA
<213> ORGANISM: Unknown
<220> FEATURE:
<223> OTHER INFORMATION: Description of Unknown:
Picornavirus HK21 sequence

<400> SEQUENCE: 662
aaacgggagg atcggctttg gcttatcctc ttaatagtct acaaaactgg gctgactggt 60
gggggagcta ctagatccgg gagaggacta gttaccccgc gtaacttccc tttttgtcac 120
tccctccacc taccccttcc ctgtccctta gactcttaag taggtgtgca ggcctggccc 180
cccggaaatg ggcaaatcgg acgtttgcgt gtagggtcgt tctgaaaggt ggggcccact 240
ccaccgtagt aggatcttcc tgtttcacgt ttaaacctct ccgggcaggt atcgctagac 300
actaggctgt ataggatggc acgcacttag gtttcgcacc ttcctagtgc gccaagatcc 360
cgcttttgag ctcaagtaca tggttctttg taagatgtct aaccagagga ggtggtgctg 420
aaatattgca agccactctg gcgaacgtcc actgcattgc ctggaacagg ctctctagcg 480
ccctccactg gtagcgcggt ggtgggttag taggatacct atatggacag gggatgcggg 540
aatacccctc actagctagt gactggttga tcgactggcg gcggatccag tgatacttgc 600
ataatccgca gacttgggag 620

<210> SEQ ID NO 663
<211> LENGTH: 675
<212> TYPE: DNA
<213> ORGANISM: Unknown
<220> FEATURE:
<223> OTHER INFORMATION: Description of Unknown:
Picornavirales Tottori-HG1 sequence

<400> SEQUENCE: 663
agccatgaac tagtgtgcga ttcccacagt gttggtcgaa agccccgcac tgtctactcg 60
catatttgac tccagtcctt ccgcagccag cggttaggtt ctggttaaag tgcattatgt 120
gcacggcgcc acgcagaact gccagaaatg gtaagctgcg cccaacgcca acggtttgtg 180
tatcccgtta gtcacacgtt tacagctgtt cgttaacagt agggttttgt cgacccggac 240
cccttaatgc gcgcgaattc aaccgcgcct agtcggcaat ggtatcattt aatcccatgc 300
actacgggag aaatttgaga ccaaagaatt cctgagggcc actgcttgct ctaagtgcaa 360
tgcctcggga gacttctgtc aggagcctag cggctttcaa ccgcgacagc taactcctgc 420
gggatgtttg gtgtccatac ttactggcgt cctcacaacg ctaagtggat gttgtccaca 480
ggtaggcaaa caccgagccc cacattcagg agacctgtat gaacgatcct atcagcatta 540
gagttggaat tgggtgtgct aacgtccgca taagtgcacc ccgtggtaac gctgggaaac 600
tatccagcgc aacgtactgt cctcaatgtc tagggaagga ccgccctaag cgtacaaccg 660
ggccatgtgt cgagc 675

<210> SEQ ID NO 664
<211> LENGTH: 549
<212> TYPE: DNA
<213> ORGANISM: Hepatovirus sp.

<400> SEQUENCE: 664
ttcaaagagg ggtccgggat tttcctggtc cccctctttg ggcacccttg gctcgggggt 60
gtgaataccg tgctcgcgtt tgccgtgcgt taacggcttc atttatgttt gtttgtctgt 120
tttattatgt tggtttgtct gtttgttatg ttggtattgt tcgtgtttaa tgttatgacc 180
acattacact ccagccaatg aagaacagat ggtgcggtta ttgctggcgg aattcctaac 240
gtcctggatc cgttggtacg catcacaaaa caatttgcag agagagtggt gaaacggctt 300
gggaatccct gagtacaggg aaatcacact gatagctcat cttggctgtt ttcagtcatg 360
gaccttatgc agtgtaattt gggtgtaccc cccatagctt aggaggaatg ttctgtcttg 420
gcactagagt gggacgctga tgcctccgtg tctaggatgg tctaagggac agaatggggt 480
gcctctgatg ccatactacc tgatagggtg ctctcacggc ctctgcatct tagtgagaag 540
ttcaatttt 549

<210> SEQ ID NO 665
<211> LENGTH: 107
<212> TYPE: DNA
<213> ORGANISM: Unknown
<220> FEATURE:
<223> OTHER INFORMATION: Description of Unknown:
Rinderpest virus sequence

<400> SEQUENCE: 665
accaaacaaa gttgggtaag gatcggtcta tcaatgatta tgatttagca cacttaggat 60
tcaagatcct atcgactgga gcaggcttaa ggtaaaggtt ctttaaa 107

<210> SEQ ID NO 666
<211> LENGTH: 675
<212> TYPE: DNA
<213> ORGANISM: Rabovirus A

<400> SEQUENCE: 666
ctacggatat ttgcatgacc cgctttctat cgccccaaca atcccctttg taaccacaag 60
ctttactcag gctagcagcc cgactagctg tttggaagaa aaggctaggg cacacaccaa 120
caacaccgac cccactggtc gaaggccgct tggcaataag actggtggaa cagggtcgcc 180
tgtagttgtt tggaacattc tttctaatga ctttgtcagc ggtgctactc acaccgtaac 240
tcttctaccc tatccccacg cttgtggaac taggagggga tgagtgattc aagtaagtac 300
tgtcagaatg gtgaaaatga tctgattctg aaacgctatg gatccatcga aagatggggc 360
tacacgcctg cggaacaaca catggtaaca tgtgccccag gggccgaaag ccacggtgat 420
aggatcaccc gtgtagtttg agatcatatc aatgttcata gtctagtaag atgatttgaa 480
atctaactga gctgatggct aactgcttgt cttattgcgg cctaaggatg tcctgcaggt 540
acctttagat aaccttaaga gactattgat ctgagcagga gccaaagtgg tctttcccag 600
ctttggttaa aaaacgtcta agccgcggca gggggcggga ggcccccttt cctcccaaaa 660
cttaatattg attgt 675

<210> SEQ ID NO 667
<211> LENGTH: 410
<212> TYPE: DNA
<213> ORGANISM: Shingleback nidovirus 1

<400> SEQUENCE: 667
ctgtgagtac cgacaggctc gaagtctatt atgaggcgtc gaaacagaaa acctgtaaca 60
actccggttt catctatcac tgccgtcaag aggcagaaga ggacgaccac gtgtcaccag 120
atcacttgta tctgtttcag tcaggaagtc aacttttcga cgaagttcga ccattcatcg 180
acccgctgaa aagcgtagaa gtcgatgaag atgagctcca aagagccatc gccgatttcg 240
acaaccaaag tgactgtttc cactccttcg agctcgtgaa tttcgagctg aaacaacaaa 300
tcaacgagaa cgagtggtac ggttattata attacgacaa ccaaaactgc aaagttcagt 360
tgccagtcac atgtcgaatc gaggacgtaa cctgggatca ggtttacgtg 410

<210> SEQ ID NO 668
<211> LENGTH: 666
<212> TYPE: DNA
<213> ORGANISM: Unknown
<220> FEATURE:
<223> OTHER INFORMATION: Description of Unknown:
Seneca valley virus sequence

<400> SEQUENCE: 668
tttgaaatgg ggggctgggc cctgatgccc agtccttcct ttccccttcc ggggggttaa 60
ccggctgtgt ttgctagagg cacagagggg caacatccaa cctgcttttg cggggaacgg 120
tgcggctccg attcctgcgt cgccaaaggt gttagcgcac ccaaacggcg cacctaccaa 180
tgttattggt gtggtctgcg agttctagcc tactcgtttc tcccccgacc attcactcac 240
ccacgaaaag tgtgttgtaa ccataagatt taacccccgc acgggatgtg cgataaccgt 300
aagactggct caagcgcgga aagcgctgta accacatgct gttagtccct ttatggctgc 360
aagatggcta cccacctcgg atcactgaac tggagctcga ccctccttag taagggaacc 420
gagaggcctt cgtgcaacaa gctccgacac agagtccacg tgactgctac caccatgagt 480
acatggttct cccctctcga cccaggactt ctttttgaat atccacggct cgatccagag 540
ggtggggcat gacccctagc atagcgagct acagcgggaa ctgtagctag gccttagcgt 600
gccttggata ctgcctgata gggcgacggc ctagtcgtgt cggttctata ggtagcacat 660
acaaat 666

<210> SEQ ID NO 669
<211> LENGTH: 675
<212> TYPE: DNA
<213> ORGANISM: Unknown
<220> FEATURE:
<223> OTHER INFORMATION: Description of Unknown:
Sclerotinia sclerotiorum dsRNA mycovirus-L sequence

<400> SEQUENCE: 669
ttgaattaat cttttacgtt tacgcgcata aaatcaggac acatctcttg tatactttag 60
tatatcaatg atgtttttgt tttatgcgat taatcgtaag agaacttctt tccatccgcc 120
tgtatgggcg ggataataag ttcaccgcct tggtcgaggc gcaaacttgt atgtgcaaag 180
gtgagctata tgctcgaaat agtcgtaact aacacacagc cactacctgt agagctctat 240
tgatccggaa tcctttagtg ggaatgcaga gctcacaccg gacctgcggg tatcttcggc 300
gttagggact tctgtttcag ccttgaatca tttaccttta taccttctct gaggcgcctg 360
ggccgggcgc gatattaagt acaagtcaag gacatcgcgg gtagtggtct aatcagccgc 420
tagtcctgct ggagagttcc aacttagttg ggtgtggtgc atactagctg gatagagtag 480
gtatgtattg ctaacgtatg ccggaggcta tccgtcctcg gtagaacgtg ccgaggagta 540
gtctctgcag acccccgaac gcgtggggtc tttacttaaa tgtaggcgga gggagcgctc 600
gtaggtggaa cgactgcctc ccagtcgaat gcaagatttt gcacgcggac cagtctgccc 660
ggcaattccc gggtg 675

<210> SEQ ID NO 670
<211> LENGTH: 675
<212> TYPE: DNA
<213> ORGANISM: Enterovirus sp.

<400> SEQUENCE: 670
ctccggcaca gccgcaccag tgcactggta cgctagtacc ttttcacggg gtagtcggta 60
tccccccccg taacttagaa gcatgtaaca aaccgaccaa taggtgcgcg gcagccagct 120
gcgttgcggt caagcacttc tgtctccccg gtccgcaagg atcgttaccc gcccactcca 180
ctacgaggag cctagtaact ggccaagtga ttgcggagtt gcgttcagcc acaaccccag 240
tggtagctct ggaagatggg gctcgcacat cccccgtggt aacacggttg cttgcccgcg 300
tgtgcttccg ggttcagtct ccgactgttc acttcaacat cacgcaacca gccaagagcc 360
gattgtgctg gagtggtctt cctccggggc cgtgaatgct gctaatccta acctccgagc 420
gtgtgcgcac aatccagtgt tgctacgtcg taacgcgtaa gttggaggcg gaacagacta 480
ctttcggcac cccgtgtttc ctttatttta ttcttatttt atggtgacaa ttgcagagat 540
ttgtgatatt gcgactttac cgttaaacat agcactgcat tacctggttg cattccacaa 600
aacttcagag attcctagtt cctacattga cctacttgtt tatttgaatc ttaaatacaa 660
acttgagcaa gtgaa 675

<210> SEQ ID NO 671
<211> LENGTH: 245
<212> TYPE: DNA
<213> ORGANISM: Unknown

<220> FEATURE:
<223> OTHER INFORMATION: Description of Unknown:
Wobbly possum disease virus sequence

<400> SEQUENCE: 671
cggctgtgag tgcttagcat atgctagagt actacagccg ggtgttggag tcatatgcac 60
tggttgcctg tataatagtc gggatctgtc tgacctacat tatctttggg agttgcttat 120
cacgacaatt ctcgaagtgt ctgtcgacag cttacccccg attcgacaag gccccttgtc 180
caccgcagac ctatcgattt tcaacgagaa cactatcaga ggtttaaatt taaaactcac 240
caaca 245

<210> SEQ ID NO 672
<211> LENGTH: 631
<212> TYPE: DNA
<213> ORGANISM: Avian orthoreovirus

<400> SEQUENCE: 672
gctttttcaa tcccttgtgt cgatgttccc gtatgtcatc tggttcatgt aacggtgcaa 60
cttctatttt tggtaacgtt cactgtcagg cagcgcaaaa ctcggcgggt ggtgatcttc 120
aagcgacttc ctctcttgtt gcttattggc cctacttggc tgcgggcggt ggtctgctcg 180
ttgttattat tataattgtt ggcgctgttt gttgttgcaa ggctaaggtt aaagcggacg 240
cagcccgaaa cgttttctac cgagagctgt tcgcacttaa ttcgggtaaa agtgatgcag 300
gacctccgat ttaccaggtt tagtgtacga cgatttgagt tttcaccttt cgtcttagag 360
gagtgcacta ctccatcttt cacgactata actaataccg atccggctct ctactttaac 420
attgagtttc cgtcaagtca tcgtctctcc cccttcattc cagaactgtt gtctcagcct 480
tgtaccgttc acgtttcatt gattcggaga ttcgctctct gtgcaacctt atctagtatt 540
tgtgaatacg actgtgcgct actgccatcc atcaacgcta ttacgacgat ccctacacca 600
ggtgcgtcat catctctgat tgttcattgg g 631

<210> SEQ ID NO 673
<211> LENGTH: 665
<212> TYPE: DNA
<213> ORGANISM: Kobuvirus sp.

<400> SEQUENCE: 673
ggggcctcgg ccccctcacc ctcttttccg gtggccacgc ccgggccacc gatacttccc 60
ttcactcctt cgggactgtt ggggaggaac acaacagggc tcccctgttt tcccattcct 120
tccccctttt cccaacccca accgccgtat ctggtggcgg caagacacac gggtctttcc 180
ctctaaagca caattgtgtg tgtgtcccag gtcctcctgc gtacggtgcg ggagtgctcc 240
cacccaactg ttgtaagcct gtccaacgcg tcgtcctggc aagactatga cgtcgcatgt 300
tccgctgcgg atgccgaccg ggtaaccggt tccccagtgt gtgtagtgcg atcttccagg 360
tcctcctggt tggcgttgtc cagaaactgc ttcaggtaag tggggtgtgc ccaatcccta 420
caaaggttga ttctttcacc accttaggaa tgctccggag gtaccccagc aacagctggg 480
atctgaccgg aggctaattg tctacgggtg gtgtttcctt tttcttttca cacaactcta 540
ctgctgacaa ctcactgact atccacttgc tctcttgtgc ctttctgctc tggttcaagt 600
tccttgattg tttttgactg cttttcactg cttttcttct cacaatcctt gctcagttca 660
aagtc 665

<210> SEQ ID NO 674
<211> LENGTH: 655
<212> TYPE: DNA
<213> ORGANISM: Kobuvirus sp.

<400> SEQUENCE: 674 cccccctcacc ctcttttccg gtggccacgc ccgggccacc gatacttccc ttcactcctt 60
cgggactgtt ggggaggaac acaacagggc tcccctgttt tcccattcct tccccctttt 120
cccaacccca accgccgtat ctggtggcgg caagacacac gggtctttcc ctctaaagca 180
caattgtgtg tgtgtcccag gtcctcctgc gtacggtgcg ggagtgctcc cacccaactg 240
ttgtaagcct gtccaacgcg tcgtcctggc aagactatga cgtcgcatgt tccgctgcgg 300
atgccgaccg ggtaaccggt tccccagtgt gtgtagtgcg atcttccagg tcctcctggt 360
tggcgttgtc cagaaactgc ttcaggtaag tggggtgtgc ccaatcccta caaaggttga 420
ttctttcacc accttaggaa tgctccggag gtaccccagc aacagctggg atctgaccgg 480
aggctaattg tctacgggtg gtgtttcctt tttcttttca cacaactcta ctgctgacaa 540
ctcactgact atccacttgc tctcttgtgc ctttctgctc tggttcaagt tccttgattg 600
tttttgactg cttttcactg cttttcttct cacaatcctt gctcagttca aagtc 655

<210> SEQ ID NO 675
<211> LENGTH: 645
<212> TYPE: DNA
<213> ORGANISM: Kobuvirus sp.

<400> SEQUENCE: 675
ctcttttccg gtggccacgc ccgggccacc gatacttccc ttcactcctt cgggactgtt 60
ggggaggaac acaacagggc tcccctgttt tcccattcct tccccctttt cccaacccca 120
accgccgtat ctggtggcgg caagacacac gggtctttcc ctctaaagca caattgtgtg 180
tgtgtcccag gtcctcctgc gtacggtgcg ggagtgctcc cacccaactg ttgtaagcct 240
gtccaacgcg tcgtcctggc aagactatga cgtcgcatgt tccgctgcgg atgccgaccg 300
ggtaaccggt tccccagtgt gtgtagtgcg atcttccagg tcctcctggt tggcgttgtc 360
cagaaactgc ttcaggtaag tggggtgtgc ccaatcccta caaaggttga ttctttcacc 420
accttaggaa tgctccggag gtaccccagc aacagctggg atctgaccgg aggctaattg 480
tctacgggtg gtgtttcctt tttcttttca cacaactcta ctgctgacaa ctcactgact 540
atccacttgc tctcttgtgc ctttctgctc tggttcaagt tccttgattg tttttgactg 600
cttttcactg cttttcttct cacaatcctt gctcagttca aagtc 645

<210> SEQ ID NO 676
<211> LENGTH: 635
<212> TYPE: DNA
<213> ORGANISM: Kobuvirus sp.

<400> SEQUENCE: 676
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360

```
ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactcta ctgctgacaa ctcactgact atccacttgc    540

tctcttgtgc ctttctgctc tggttcaagt tccttgattg tttttgactg cttttcactg    600

cttttcttct cacaatcctt gctcagttca aagtc                               635
```

<210> SEQ ID NO 677
<211> LENGTH: 625
<212> TYPE: DNA
<213> ORGANISM: Kobuvirus sp.

<400> SEQUENCE: 677

```
ccgggccacc gatacttccc ttcactcctt cgggactgtt ggggaggaac acaacagggc     60

tcccctgttt tcccattcct tccccctttt cccaacccca accgccgtat ctggtggcgg    120

caagacacac gggtctttcc ctctaaagca caattgtgtg tgtgtcccag gtcctcctgc    180

gtacggtgcg ggagtgctcc cacccaactg ttgtaagcct gtccaacgcg tcgtcctggc    240

aagactatga cgtcgcatgt tccgctgcgg atgccgaccg ggtaaccggt tccccagtgt    300

gtgtagtgcg atcttccagg tcctcctggt tggcgttgtc cagaaactgc ttcaggtaag    360

tggggtgtgc ccaatcccta caaaggttga ttctttcacc accttaggaa tgctccggag    420

gtaccccagc aacagctggg atctgaccgg aggctaattg tctacgggtg gtgtttcctt    480

tttcttttca cacaactcta ctgctgacaa ctcactgact atccacttgc tctcttgtgc    540

ctttctgctc tggttcaagt tccttgattg tttttgactg cttttcactg cttttcttct    600

cacaatcctt gctcagttca aagtc                                          625
```

<210> SEQ ID NO 678
<211> LENGTH: 675
<212> TYPE: DNA
<213> ORGANISM: Unknown
<220> FEATURE:
<223> OTHER INFORMATION: Description of Unknown:
      Picornavirales sp. isolate RtMruf-PicoV sequence

<400> SEQUENCE: 678

```
tttgctcagc gtaacttctc cgggttacgt ggagaccaaa aggctacgga gactcgggct     60

acggccctgg agcacctagg tgctcctaaa gacgttagaa gttgtacaaa ctcgcccaat    120

agggcccccc aaccaggggg gtagcgggca agcacttctg tttccccggt atgatctcat    180

aggctgtacc cacggctgaa agagagatta tcgttacccg cctcactact tcgagaagcc    240

cagtaatggt tcatgaagtt gatctcgttg acccggtgtt tcccccacac cagaaacctg    300

tgatgggggt ggtcatcccg gtcatggcga catgacggac ctccccgcgc cggcacaggg    360

cctcttcgga ggacgagtga catggattca accgtgaaga gcctattgag ctagtgttga    420

ttcctccgcc cccgtgaatg cggctaatcc caactccgga gcaggcgggc ccaaaccagg    480

gtctggcctg tcgtaacgcg aaagtctgga gcggaaccga ctactttcgg gaaggcgtgt    540

ttccttttgt tccttttatc aagttttatg gtgacaactc ctggtagacg ttttattgcg    600

tttattgaga gatttccaac aattgaacag actagaacca cttgttttat caaaccctca    660

cagaataaga taaca                                                     675
```

<210> SEQ ID NO 679
<211> LENGTH: 675
<212> TYPE: DNA

<213> ORGANISM: Unknown
<220> FEATURE:
<223> OTHER INFORMATION: Description of Unknown:
Apodemus agrarius picornavirus strain Longquan-Aa118 sequence

<400> SEQUENCE: 679
ttactcagcg taactactcc gggttacgtg atgaagaaga ggctacggag attctcgggc 60
tacggccctg gagccactcc ggctcctaaa gatttagaag tttgagcaca cccgcccact 120
agggcccccc atccaggggg gcaacgggca agcacttctg tttccccggt atgatctgat 180
aggctgtaac cacggctgaa acagagatta tcgttatccg cttcactact tcgagaagcc 240
tagtaatgat gggtgaaatt gaatccgttg atccggtgtc tcccccacac cagaaactca 300
tgatgagggt tgccatcccg gctacggcga cgtagcgggc atccctgcgc tggcatgagg 360
cctcttagga ggacggatga tatggatctt gtcgtgaaga gcctattgag ctagtgtcga 420
ctcctccgcc cccgtgaatg cggctaatcc taaccccgga gcaggtgggt ccaatccagg 480
gcctggcctg tcgtaatgcg taagtctggg acggaaccga ctactttcgg gaaggcgtgt 540
ttccatttgt tcattatttg tgtgtttatg gtgacaactc tgggtaaacg ttctattgcg 600
tttattgaga gattcccaac aattgaacaa acgagaacta cctgttttat taaatttaca 660
cagagaagaa ttaca 675

<210> SEQ ID NO 680
<211> LENGTH: 675
<212> TYPE: DNA
<213> ORGANISM: Unknown
<220> FEATURE:
<223> OTHER INFORMATION: Description of Unknown:
Niviventer confucianus picornavirus sequence

<400> SEQUENCE: 680
ccctttcata acccccccct tttaacccaa cccttcgtaa ccgtacgctt cactcgcctt 60
tgggtatagc ggcccaatgt gctgaagaaa aggatacgct ataaggggcc aacgggtggt 120
ggcccttaag accacccaac ctagaagctt gtacactcgg gcaatagtga ggcccacatc 180
cagtgggtca agcccaaagc attcttgttc cccggtatga tctcataagc tgtacccacg 240
gctgaaagag tgattatcgt tatcccactc agtacttcgg agagcctagt acaccacttg 300
gaaatggaag tctgtgatcc ggggttgacc ctgaacccca gaaactcatg atgaggctaa 360
ccttcccgaa cacggcgacg tgtggttagc ctgcgctggc atgaggcctc tttgtaggca 420
gactgaaatg gaagggtgac gaagagccga ctgagctact gttttattcc tccggccccc 480
tgaatgcggc taatcctaac tcctggtcca gtacttgtaa cccaacaggt ggctggtcgt 540
aatgcgtaag ccgggagcgg aaccgactac tttggggcgt ccgtgtttct caatattatt 600
catttctagc ttatggtgac aatttatgat tgcagagatt gtgctgtatt tgtgtctgag 660
agaagaagta acaat 675

<210> SEQ ID NO 681
<211> LENGTH: 619
<212> TYPE: DNA
<213> ORGANISM: Unknown
<220> FEATURE:
<223> OTHER INFORMATION: Description of Unknown:
Bat picornavirus isolate BtRs-PicoV sequence

<400> SEQUENCE: 681
tttcaaaagg ccctgggcat acggcgttat tcgtaacgtc gtatgtccag ggcggtagca 60
tcaggccaag gcctgatgct accacgtgtg gactaaacca cacactcttc ttgtgacacg 120
ttgtgtcacc tatccctttc ttggtaactt agaagcttgt acacttacgc acgtaggtgc 180
cccacatcca gtggggtttg tgcaaagcaa tcttgttccc cggtaaaccc tgataggctg 240
taaccacggc cgaaacaagg tttgtcgtta cccgactcac tactacacaa agcctagtaa 300
agttcaatga aagtgcgcag cgtgatccgg tcaaaacccc cttgaccaga aacacatgat 360
gagggtcacc aacccccact ggcgacagtg tggtgtccct gcgttggcat gtggcctcgt 420
agaggcgttg caatctggat ttgctccgaa gagccccgtg tgctagtgtt tatacctccg 480
gccccttgaa tgcggctaat cctaaccccc gagcatgtac acacaagcca gtgtgtagca 540
tgtcgtaatg agcaatttgg ggatggaacc gactacttta gggtgtccgt gtttctcatt 600
attctttgtt tgatgtttt 619

<210> SEQ ID NO 682
<211> LENGTH: 593
<212> TYPE: DNA
<213> ORGANISM: Unknown
<220> FEATURE:
<223> OTHER INFORMATION: Description of Unknown:
Rhinolophus picornavirus strain Guizhou-Rr100 sequence

<400> SEQUENCE: 682 tttttttct caggcggtag catccagcca aggcctgatg ctaccaacgt gtgactaaac 60
cacactctct ttttgtgata cattgtgtca cctatccctt tcttggtaac ttagaagctt 120
gtacacccac gcacgtaggt accccacatc cagtggggtt tgtgcaaagc attcttgttc 180
cccggtaaac cctgataggc tgtaaccacg gctgaaacaa ggtttgtcgt tacccgactc 240
actactacgc aaagcctagt aaagttcaat gaaagtgcgc agcgtgatcc ggtcaaaacc 300
cccttgacca gaaacacatg atgagggtca ccaaccccca ctggcgacag tgtggtgtcc 360
ctgcgttggc atgtggcctc atagaggcgt tgcaatctgg atttgctccg aagagccccg 420
tgtgctagtg tttatacctc cggccccttg aatgcggcta atcctaaccc ccgagcatgt 480
acacacacgc cagtgtgcag catgtcgtaa tgagcaattt ggggatggaa ccgactactt 540
tagggtgtcc gtgtttctca ttattctttg tttgatgttt tatggtgaca aca 593

<210> SEQ ID NO 683
<211> LENGTH: 597
<212> TYPE: DNA
<213> ORGANISM: Unknown
<220> FEATURE:
<223> OTHER INFORMATION: Description of Unknown:
Rhinolophus picornavirus strain Henan-Rf265 sequence

<400> SEQUENCE: 683
cggaacgttg tatgctcagg gcgtaggcac cacccacggg tggtgcctac acgtgtggac 60
taaaccacac actcttttca gcacttagtg ctgctatctc tttttgtaac ttagaagttt 120
gtacacaatg cgttagggcc acacatccag tgtggtatcg caaagcactt ctgtttcccc 180
ggtgctagta ggagggtggc tgctccacgg ccacttgccg aacccatcgt tacccgactc 240
attacttcgc aaagcctagt aacccagttg aagcaagccc ggcgtgttcc ggtcaggaaa 300 aacccccccct ggccagaaac atgtgatgag ggtgggctat ccccactggt gacagtgagc 360

```
cctccctgcg ttggcacatg gcccgatctg ggcgtggttc ttgtggatgc tgccgaagag    420

ccccgtgagc tagtgtttat accgccggcc tcgtgaatgc ggctaaccct aaccccggag    480

cagaggctac tgaagccaca gtagtcgctg tcgtaacgag taattctggg atgggaccga    540

ctactttcga gtgtccgtgt ttcctttatt cttttattgt tgtttatggt gacaaac       597


<210> SEQ ID NO 684
<211> LENGTH: 636
<212> TYPE: DNA
<213> ORGANISM: Enterovirus sp.

<400> SEQUENCE: 684

cccctaggat ccactggatg tcagtacact ggtatcgtgg tacctttgta cgcctgtttt     60

ataccccctt ccccgcaact ttagaagcat caaaagcacc gctcaatagt caccacaccc    120

ccagtgtggt ttcgagcaag cacttctgtt ttcccggttg cgtcccatat gctgtgcaaa    180

cggcaaaaag ggacaatatc gttacccgct tgtatactac gggaaaccta gtaccaccat    240

tgattgtgtt gagagttgcg ctcatcacct ttccccggtg tagctcaggc cgatgaggct    300

cagaatcccc cacaggtgac tgtgtctgag cctgcgttgg cggcctgccc tcgccttatg    360

gcgtgggacg cttgatacat gacatggtgc gaagagtcta ctgtgctatg caagagtcct    420

ccggcccctg aatgtggcta atcctaacca ctgatcccac gcacgcaaac cagtgtgtag    480

tgggtcgtaa cgcgcaagtc ggtggcggaa ccaactactt tgggtgaccg tgtttccttt    540

attacttatt gaatgtttat ggtgacaatt gtttgattca gttgttgcca ttctctacat    600

tcatttaccc agcatcaaac caattgaact gttaca                              636


<210> SEQ ID NO 685
<211> LENGTH: 421
<212> TYPE: DNA
<213> ORGANISM: Unknown
<220> FEATURE:
<223> OTHER INFORMATION: Description of Unknown:
      Human poliovirus 1 strain NIE1116623 sequence

<400> SEQUENCE: 685

agtctggaca tccctcaccg gcgacggtgg tccaggctgc gctggcggcc tacctgtggt     60

ccaaagccac gggacgctac atgtgaacaa ggtgtgaaga gcctattgag ctacaaaaga    120

gtcctccggc ccctgaatgc ggctaatccc aaccacggat caagggtgca caaaccagtg    180

tacaccttgt cgtaacgcgc aagtctgtgg cggaaccgac tactttgggt gtccgtgttt    240

ccttttttaat tttgatggct gcttatggtg acaatcatag attgttatca taaagctaat    300

tggattggcc atccggtgag agtgaaatat attgtttacc tccctgttgg gtttactcta    360

actaacttct ccatttataa acttgtcatc acagttttaa taattagaag tgcagtttac    420

a                                                                    421


<210> SEQ ID NO 686
<211> LENGTH: 663
<212> TYPE: DNA
<213> ORGANISM: Enterovirus sp.

<400> SEQUENCE: 686

tttaaaacag cctgggggtt gttcccaccc ccagggccca ctgggcgtta gtactctggt     60

atcgcggtac cttagtatgc ctgttttatg tctcctttcc cccgcaactt tagaagtaat    120

caagttatgg ctcaacagtc gccacacccc cagtgtggtt ccgagcaagc acttctgttc    180
```

```
cccggttgcg tcttatatgc tgtgtgaacg gcagaaaggg acaatatcgt tatccgctca    240

actactacgg gaagcctagt accaccatgg attgacctga aagttgcgtt cagcgcaccc    300

ccagcgcagc tcaggccgat gaggctccga ataccccacg ggcgaccgtg tcggagcctg    360

cgttggcggc ctgcccacgt tgcaaaacgt gggacgctca tttcatgaca tggtgcgaag    420

agcctactgt gctagttgag agtcctccgg cccctgaatg tggataatcc taaccactga    480

acctacgggc gcaaaccagc gtctggtagg ccgtaacgcg caagtcggtg gcggaaccaa    540

ctactttggg tgtccgtgtt tccttttatc tttttgaatg tttatggtga caattgttgt    600

gtacagttgt taccatagtt tgcattcaga aataaaccta acactttcca attatttgtt    660

aca                                                                   663
```

<210> SEQ ID NO 687
<211> LENGTH: 675
<212> TYPE: DNA
<213> ORGANISM: Unknown
<220> FEATURE:
<223> OTHER INFORMATION: Description of Unknown:
Human poliovirus 2 strain NIE0811460 sequence

<400> SEQUENCE: 687

```
ttgtgcgcct gttttatatt cccccccgc aacttagaag cacgaaacca agttcaatag      60

aagggggtac aaaccagtac caccacgaac aagcacttct gtttccccgg tgacattgca    120

tagactgctc acgcggttga aagtgatcga tccgttaccc gcttgtgtac ttcgaaaagc    180

ctagtattgc cttggaatct tcgacgcgtt gcgctcagca cccgaccccg gggtgtagct    240

taggctgatg agtctggaca ttcctcaccg gtgacggtgg tccaggctgc gttggcggcc    300

tacctatggc taatgccata ggacgctaga tgtgaacaag gtgtgaagag cctattgagc    360

tacataagag tcctccggcc cctgaatgcg gctaatccta accacggagc aggcggtcgc    420

aaaccagtga ctagcttgtc gtaacgcgca agtctgtggc ggaaccgact actttgggtg    480

tccgtgtttc ctgttatttt tattatggct gcttatggtg acaatcagag attgttatca    540

taaagcgaat tggattggcc atccggtgag tgttgtgtca ggtatacaac tgtttgttgg    600

aaccactgtg ttagtttaac ctctctttca accaattagt caaaaacaat acgaagatag    660

aacaacaata ctaca                                                      675
```

<210> SEQ ID NO 688
<211> LENGTH: 512
<212> TYPE: DNA
<213> ORGANISM: Unknown
<220> FEATURE:
<223> OTHER INFORMATION: Description of Unknown:
Bovine picornavirus sequence

<400> SEQUENCE: 688

```
ttttctcccc tccccctcca actacctttt cccccctcttg taacgctaga agtttgtgca    60

aaccgcctgt agggtactgc aatccagcag tgcataggct aagcttttct tgttacccca    120

ccccacatta tactgaggag gattgtgaaa ttgtgttagt atgggttagt agcggtgacc    180

cgggtaaccc caacccagaa actcacggat gagatgaaca ggaccccaca tggtaacgtg    240

tgtgttcgtc tgccccgcaa ggtgaggccg tgagagcttt gcacgcgaaa accttgaaaa    300

cccaaaagta ccttgagctc ttcgctattt tgtgtttcct ccaggaccct gaatgcggct    360
```

aaacctaacc cgcgatccgc acgtagcaac ccagctagag tgtggtcgta atgcgcaagt 420
tgcgggcggt accgactact ttggtgttcc tgtgtttcct ttatttttatt ttgaattttt 480 atggtgacaa cagctagaaa ataagagtga ac 512

<210> SEQ ID NO 689
<211> LENGTH: 675
<212> TYPE: DNA
<213> ORGANISM: Unknown
<220> FEATURE:
<223> OTHER INFORMATION: Description of Unknown:
Human poliovirus 1 strain EQG1419328 sequence

<400> SEQUENCE: 689
acccttgtac gcctgtttta tactcccctc cccgtaactt agaagaaaca aaataagttc 60
aataggaggg ggtacaaacc agtaccacca cgaacaagca cttctgtctc cccggtgaca 120
ttgcatagac tgtccccacg gttgaaagca attgatccgt tacccgctct tgtacttcga 180
gaagcctagt accatcttgg aatcatcgat gcgttgcgct ccacactcag tcccagagtg 240
tagcttaggc tgatgagtct ggacattcct caccggcgac ggtggtccag gctgcgttgg 300
cggcctacct gtggcccaaa gccacaggac gctagatgtg aacaaggtgt gaagagccta 360
ttgagctata agagagtcct ccggcccctg aatgcggcta atcccaacca cggatcaagg 420
gtgcacgaac cagtgtatac cttgtcgtaa cgcgcaagtc cgtggcggaa ccgactactt 480
tgggtgaccg tgtttccttt tattatttca atggctgctt atggtgacaa tcattgattg 540
ttatcataaa gcgaattgga ctggccatcc ggtgaaagtg aaacatattg tttgcctcct 600
cgttgggtct acttcaacca atctttactt acaatcttac cactacagtt ttgctggtta 660
gaagtgtgtt tcacg 675

<210> SEQ ID NO 690
<211> LENGTH: 675
<212> TYPE: DNA
<213> ORGANISM: Unknown
<220> FEATURE:
<223> OTHER INFORMATION: Description of Unknown:
Human poliovirus 2 isolate IS_061 sequence

<400> SEQUENCE: 690
ttgtgcgcct gttttatact cccctcccgc aacttagaag cacgaaacca agttcaatag 60
aagggggtac aaaccagtac cactacgaac aagcacttct gtttccccgg tgacattgca 120
tagactgctc acgcggttga aagtgatcga tccgttaccc gcttgtgtac ttcgaaaagc 180
ctagtatcgc cttggaatct tcgacgcgtt gcgctcagca cccgaccccg gggtgtagct 240
taggccgatg agtctggaca ttcctcaccg gtgacggtgg tccaggctgc gttggcggcc 300
tacctatggc taacgccata ggacgttaga tgtgaacaag gtgtgaagag cctattgagc 360
tacataagag tcctccggcc cctgaatgcg gctaatccta accacggagc aggcggtcgc 420
gaaccagtga ctggcttgtc gtaacgcgca agtctgtggc ggaaccgact actttgggtg 480
tccgtgtttc ctgttatttt tatcatggct gcttatggtg acaatcagag attgttatca 540
taaagcgaat tggattggcc atccggtgag tgttgtgtca ggtatacaac tgtttgttgg 600
aaccactgtg ttagctttgc ttctcattta accaattaat caaaaacaat acgaggataa 660
aacaacaata ctaca 675

<210> SEQ ID NO 691

```
<211> LENGTH: 675
<212> TYPE: DNA
<213> ORGANISM: Unknown
<220> FEATURE:
<223> OTHER INFORMATION: Description of Unknown:
      Coxsackievirus B5 sequence

<400> SEQUENCE: 691

cctttgtgcg cctgttttat gcccccttcc cccaattgaa acttagaagt tacacacacc       60

gatcaacagc gggcgtggca taccagccgc gtcttgatca agcactcctg tttccccgga      120

ccgagtatca atagactgct cacgcggttg aaggagaaaa cgttcgttac ccggctaact      180

acttcgagaa acctagtagc atcatgaaag ttgcgaagcg tttcgctcag cacatcccca      240

gtgtagatca ggtcgatgag tcaccgcatt ccccacgggc gaccgtggcg gtggctgcgt      300

tggcggcctg cctacggggc aacccgtagg acgcttcaat acagacatgg tgcgaagagt      360

cgattgagct agttagtagt cctccggccc ctgaatccgg ctaatcctaa ctgcggagca      420

catacccctca acccaggggg cattgtgtcg taacgggtaa ctctgcagcg gaaccgacta      480

ctttgggtgt ccgtgtttcc ttttattctt ataatggctg cttatggtga caattgaaag      540

attgttacca tatagctatt ggattggcca tccggtgtct aacagagcta ttatatacct      600

ctttgttgga tttgtaccac ttgatctaaa ggaagtcaag acactacaat tcatcataca      660

attgaacaca gcaaa                                                        675

<210> SEQ ID NO 692
<211> LENGTH: 675
<212> TYPE: DNA
<213> ORGANISM: Unknown
<220> FEATURE:
<223> OTHER INFORMATION: Description of Unknown:
      Coxsackievirus A10 sequence

<400> SEQUENCE: 692

tttgtgcgcc tgttttacaa cccttcccca acttgtaacg tagaagtaat acacactact       60

gatcaatagc aggcatggcg cgccagtcat gtctcgatca agcacttctg ttcccccgga      120

ctgagtatca atagactgct cacgcggttg aaggagaaaa cgttcgttac ccggctaact      180

acttcgagaa acctagtagc accatagaag ctgcagagtg tttcgctcag cacttccccc      240

gtgtagatca ggctgatgag tcactgcaat ccccacgggt gaccgtggca gtggctgcgt      300

tggcggcctg cctatggggc aacccatagg acgctctaat gtggacatgg tgcgaagagt      360

ctattgagct agttagtagt cctccggccc ctgaatgcgg ctaatcctaa ctgcggagca      420

catgccttca acccagaagg tagtgtgtcg taacgggcaa ctctgcagcg gaaccgacta      480

ctttgggtgt ccgtgtttct ttttattcct atattggctg cttatggtga caatcacgga      540

attgttgcca tatagctatt ggattggcca tccggtgtct aatagagcta ttgtgtacct      600

atttgttgga tttactccgc tatcacataa atctctgaac actttgtgct ttatattgaa      660

cttaaacacc cgaaa                                                        675

<210> SEQ ID NO 693
<211> LENGTH: 18
<212> TYPE: PRT
<213> ORGANISM: Unknown
<220> FEATURE:
<223> OTHER INFORMATION: Description of Unknown:
      Liver targeting moiety sequence
```

<400> SEQUENCE: 693

Cys Lys Asn Glu Lys Lys Asn Ile Glu Arg Asn Asn Lys Leu Lys Gln
1 5 10 15

Pro Pro

<210> SEQ ID NO 694
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 694
tataattcta ccctattgag gcattgacta 30

<210> SEQ ID NO 695
<211> LENGTH: 493
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 695

Met Ala Leu Pro Val Thr Ala Leu Leu Leu Pro Leu Ala Leu Leu Leu
1 5 10 15

His Ala Ala Arg Pro Asp Ile Val Leu Thr Gln Ser Pro Ala Ser Leu
20 25 30

Ala Val Ser Leu Gly Glu Arg Ala Thr Ile Asn Cys Arg Ala Ser Glu
35 40 45

Ser Val Ser Val Ile Gly Ala His Leu Ile His Trp Tyr Gln Gln Lys
50 55 60

Pro Gly Gln Pro Pro Lys Leu Leu Ile Tyr Leu Ala Ser Asn Leu Glu
65 70 75 80

Thr Gly Val Pro Ala Arg Phe Ser Gly Ser Gly Ser Gly Thr Asp Phe
85 90 95

Thr Leu Thr Ile Ser Ser Leu Gln Ala Glu Asp Ala Ala Ile Tyr Tyr
100 105 110

Cys Leu Gln Ser Arg Ile Phe Pro Arg Thr Phe Gly Gln Gly Thr Lys
115 120 125

Leu Glu Ile Lys Gly Ser Thr Ser Gly Ser Gly Lys Pro Gly Ser Gly
130 135 140

Glu Gly Ser Thr Lys Gly Gln Val Gln Leu Val Gln Ser Gly Ser Glu
145 150 155 160

Leu Lys Lys Pro Gly Ala Ser Val Lys Val Ser Cys Lys Ala Ser Gly
165 170 175

Tyr Thr Phe Thr Asp Tyr Ser Ile Asn Trp Val Arg Gln Ala Pro Gly
180 185 190

Gln Gly Leu Glu Trp Met Gly Trp Ile Asn Thr Glu Thr Arg Glu Pro
195 200 205

Ala Tyr Ala Tyr Asp Phe Arg Gly Arg Phe Val Phe Ser Leu Asp Thr
210 215 220

Ser Val Ser Thr Ala Tyr Leu Gln Ile Ser Ser Leu Lys Ala Glu Asp
225 230 235 240

Thr Ala Val Tyr Tyr Cys Ala Arg Asp Tyr Ser Tyr Ala Met Asp Tyr
245 250 255

```
Trp Gly Gln Gly Thr Leu Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 696
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 696

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ser Gly
                85                  90                  95

Gly Ser Tyr Ile Pro Thr Phe Gly Arg Gly Thr Ser Leu Ile Val His
            100                 105                 110
```

```
Pro Tyr Ile Gln Lys Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
        195                 200                 205


<210> SEQ ID NO 697
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 697

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Leu
                85                  90                  95

Met Thr Ser Gly Asp Pro Tyr Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245
```

<210> SEQ ID NO 698
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 698

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115
```

<210> SEQ ID NO 699
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 699

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110
```

<210> SEQ ID NO 700
<211> LENGTH: 166
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 700

```
Ala Pro Pro Arg Leu Ile Cys Asp Ser Arg Val Leu Glu Arg Tyr Leu
1               5                   10                  15
```

```
Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165


<210> SEQ ID NO 701
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190
```

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 702
<211> LENGTH: 1462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Leu Ser Val Lys Ala Gln Thr Ala His Ile Val Leu Glu Asp Gly Thr
1               5                   10                  15

Lys Met Lys Gly Tyr Ser Phe Gly His Pro Ser Ser Val Ala Gly Glu
            20                  25                  30

Val Val Phe Asn Thr Gly Leu Gly Gly Tyr Pro Glu Ala Ile Thr Asp
        35                  40                  45

Pro Ala Tyr Lys Gly Gln Ile Leu Thr Met Ala Asn Pro Ile Ile Gly
    50                  55                  60

Asn Gly Gly Ala Pro Asp Thr Thr Ala Leu Asp Glu Leu Gly Leu Ser
65                  70                  75                  80

```
Lys Tyr Leu Glu Ser Asn Gly Ile Lys Val Ser Gly Leu Leu Val Leu
                85                  90                  95

Asp Tyr Ser Lys Asp Tyr Asn His Trp Leu Ala Thr Lys Ser Leu Gly
            100                 105                 110

Gln Trp Leu Gln Glu Glu Lys Val Pro Ala Ile Tyr Gly Val Asp Thr
        115                 120                 125

Arg Met Leu Thr Lys Ile Ile Arg Asp Lys Gly Thr Met Leu Gly Lys
    130                 135                 140

Ile Glu Phe Glu Gly Gln Pro Val Asp Phe Val Asp Pro Asn Lys Gln
145                 150                 155                 160

Asn Leu Ile Ala Glu Val Ser Thr Lys Asp Val Lys Val Tyr Gly Lys
                165                 170                 175

Gly Asn Pro Thr Lys Val Val Ala Val Asp Cys Gly Ile Lys Asn Asn
            180                 185                 190

Val Ile Arg Leu Leu Val Lys Arg Gly Ala Glu Val His Leu Val Pro
        195                 200                 205

Trp Asn His Asp Phe Thr Lys Met Glu Tyr Asp Gly Ile Leu Ile Ala
    210                 215                 220

Gly Gly Pro Gly Asn Pro Ala Leu Ala Glu Pro Leu Ile Gln Asn Val
225                 230                 235                 240

Arg Lys Ile Leu Glu Ser Asp Arg Lys Glu Pro Leu Phe Gly Ile Ser
                245                 250                 255

Thr Gly Asn Leu Ile Thr Gly Leu Ala Ala Gly Ala Lys Thr Tyr Lys
            260                 265                 270

Met Ser Met Ala Asn Arg Gly Gln Asn Gln Pro Val Leu Asn Ile Thr
        275                 280                 285

Asn Lys Gln Ala Phe Ile Thr Ala Gln Asn His Gly Tyr Ala Leu Asp
    290                 295                 300

Asn Thr Leu Pro Ala Gly Trp Lys Pro Leu Phe Val Asn Val Asn Asp
305                 310                 315                 320

Gln Thr Asn Glu Gly Ile Met His Glu Ser Lys Pro Phe Phe Ala Val
                325                 330                 335

Gln Phe His Pro Glu Val Thr Pro Gly Pro Ile Asp Thr Glu Tyr Leu
            340                 345                 350

Phe Asp Ser Phe Phe Ser Leu Ile Lys Lys Gly Lys Ala Thr Thr Ile
        355                 360                 365

Thr Ser Val Leu Pro Lys Pro Ala Leu Val Ala Ser Arg Val Glu Val
    370                 375                 380

Ser Lys Val Leu Ile Leu Gly Ser Gly Gly Leu Ser Ile Gly Gln Ala
385                 390                 395                 400

Gly Glu Phe Asp Tyr Ser Gly Ser Gln Ala Val Lys Ala Met Lys Glu
                405                 410                 415

Glu Asn Val Lys Thr Val Leu Met Asn Pro Asn Ile Ala Ser Val Gln
            420                 425                 430

Thr Asn Glu Val Gly Leu Lys Gln Ala Asp Thr Val Tyr Phe Leu Pro
        435                 440                 445

Ile Thr Pro Gln Phe Val Thr Glu Val Ile Lys Ala Glu Gln Pro Asp
    450                 455                 460

Gly Leu Ile Leu Gly Met Gly Gly Gln Thr Ala Leu Asn Cys Gly Val
465                 470                 475                 480

Glu Leu Phe Lys Arg Gly Val Leu Lys Glu Tyr Gly Val Lys Val Leu
                485                 490                 495
```

-continued

```
Gly Thr Ser Val Glu Ser Ile Met Ala Thr Glu Asp Arg Gln Leu Phe
            500                 505                 510

Ser Asp Lys Leu Asn Glu Ile Asn Glu Lys Ile Ala Pro Ser Phe Ala
        515                 520                 525

Val Glu Ser Ile Glu Asp Ala Leu Lys Ala Ala Asp Thr Ile Gly Tyr
    530                 535                 540

Pro Val Met Ile Arg Ser Ala Tyr Ala Leu Gly Gly Leu Gly Ser Gly
545                 550                 555                 560

Ile Cys Pro Asn Arg Glu Thr Leu Met Asp Leu Ser Thr Lys Ala Phe
                565                 570                 575

Ala Met Thr Asn Gln Ile Leu Val Glu Lys Ser Val Thr Gly Trp Lys
            580                 585                 590

Glu Ile Glu Tyr Glu Val Val Arg Asp Ala Asp Asp Asn Cys Val Thr
        595                 600                 605

Val Cys Asn Met Glu Asn Val Asp Ala Met Gly Val His Thr Gly Asp
    610                 615                 620

Ser Val Val Val Ala Pro Ala Gln Thr Leu Ser Asn Ala Glu Phe Gln
625                 630                 635                 640

Met Leu Arg Arg Thr Ser Ile Asn Val Val Arg His Leu Gly Ile Val
                645                 650                 655

Gly Glu Cys Asn Ile Gln Phe Ala Leu His Pro Thr Ser Met Glu Tyr
            660                 665                 670

Cys Ile Ile Glu Val Asn Ala Arg Leu Ser Arg Ser Ser Ala Leu Ala
        675                 680                 685

Ser Lys Ala Thr Gly Tyr Pro Leu Ala Phe Ile Ala Ala Lys Ile Ala
    690                 695                 700

Leu Gly Ile Pro Leu Pro Glu Ile Lys Asn Val Val Ser Gly Lys Thr
705                 710                 715                 720

Ser Ala Cys Phe Glu Pro Ser Leu Asp Tyr Met Val Thr Lys Ile Pro
                725                 730                 735

Arg Trp Asp Leu Asp Arg Phe His Gly Thr Ser Ser Arg Ile Gly Ser
            740                 745                 750

Ser Met Lys Ser Val Gly Glu Val Met Ala Ile Gly Arg Thr Phe Glu
        755                 760                 765

Glu Ser Phe Gln Lys Ala Leu Arg Met Cys His Pro Ser Ile Glu Gly
    770                 775                 780

Phe Thr Pro Arg Leu Pro Met Asn Lys Glu Trp Pro Ser Asn Leu Asp
785                 790                 795                 800

Leu Arg Lys Glu Leu Ser Glu Pro Ser Ser Thr Arg Ile Tyr Ala Ile
                805                 810                 815

Ala Lys Ala Ile Asp Asp Asn Met Ser Leu Asp Glu Ile Glu Lys Leu
            820                 825                 830

Thr Tyr Ile Asp Lys Trp Phe Leu Tyr Lys Met Arg Asp Ile Leu Asn
        835                 840                 845

Met Glu Lys Thr Leu Lys Gly Leu Asn Ser Glu Ser Met Thr Glu Glu
    850                 855                 860

Thr Leu Lys Arg Ala Lys Glu Ile Gly Phe Ser Asp Lys Gln Ile Ser
865                 870                 875                 880

Lys Cys Leu Gly Leu Thr Glu Ala Gln Thr Arg Glu Leu Arg Leu Lys
                885                 890                 895

Lys Asn Ile His Pro Trp Val Lys Gln Ile Asp Thr Leu Ala Ala Glu
            900                 905                 910
```

-continued

Tyr Pro Ser Val Thr Asn Tyr Leu Tyr Val Thr Tyr Asn Gly Gln Glu
915 920 925

His Asp Val Asn Phe Asp Asp His Gly Met Met Val Leu Gly Cys Gly
930 935 940

Pro Tyr His Ile Gly Ser Ser Val Glu Phe Asp Trp Cys Ala Val Ser
945 950 955 960

Ser Ile Arg Thr Leu Arg Gln Leu Gly Lys Lys Thr Val Val Val Asn
965 970 975

Cys Asn Pro Glu Thr Val Ser Thr Asp Phe Asp Glu Cys Asp Lys Leu
980 985 990

Tyr Phe Glu Glu Leu Ser Leu Glu Arg Ile Leu Asp Ile Tyr His Gln
995 1000 1005

Glu Ala Cys Gly Gly Cys Ile Ile Ser Val Gly Gly Gln Ile Pro
1010 1015 1020

Asn Asn Leu Ala Val Pro Leu Tyr Lys Asn Gly Val Lys Ile Met
1025 1030 1035

Gly Thr Ser Pro Leu Gln Ile Asp Arg Ala Glu Asp Arg Ser Ile
1040 1045 1050

Phe Ser Ala Val Leu Asp Glu Leu Lys Val Ala Gln Ala Pro Trp
1055 1060 1065

Lys Ala Val Asn Thr Leu Asn Glu Ala Leu Glu Phe Ala Lys Ser
1070 1075 1080

Val Asp Tyr Pro Cys Leu Leu Arg Pro Ser Tyr Val Leu Ser Gly
1085 1090 1095

Ser Ala Met Asn Val Val Phe Ser Glu Asp Glu Met Lys Lys Phe
1100 1105 1110

Leu Glu Glu Ala Thr Arg Val Ser Gln Glu His Pro Val Val Leu
1115 1120 1125

Thr Lys Phe Val Glu Gly Ala Arg Glu Val Glu Met Asp Ala Val
1130 1135 1140

Gly Lys Asp Gly Arg Val Ile Ser His Ala Ile Ser Glu His Val
1145 1150 1155

Glu Asp Ala Gly Val His Ser Gly Asp Ala Thr Leu Met Leu Pro
1160 1165 1170

Thr Gln Thr Ile Ser Gln Gly Ala Ile Glu Lys Val Lys Asp Ala
1175 1180 1185

Thr Arg Lys Ile Ala Lys Ala Phe Ala Ile Ser Gly Pro Phe Asn
1190 1195 1200

Val Gln Phe Leu Val Lys Gly Asn Asp Val Leu Val Ile Glu Cys
1205 1210 1215

Asn Leu Arg Ala Ser Arg Ser Phe Pro Phe Val Ser Lys Thr Leu
1220 1225 1230

Gly Val Asp Phe Ile Asp Val Ala Thr Lys Val Met Ile Gly Glu
1235 1240 1245

Asn Val Asp Glu Lys His Leu Pro Thr Leu Asp His Pro Ile Ile
1250 1255 1260

Pro Ala Asp Tyr Val Ala Ile Lys Ala Pro Met Phe Ser Trp Pro
1265 1270 1275

Arg Leu Arg Asp Ala Asp Pro Ile Leu Arg Cys Glu Met Ala Ser
1280 1285 1290

Thr Gly Glu Val Ala Cys Phe Gly Glu Gly Ile His Thr Ala Phe
1295 1300 1305

```
Leu Lys  Ala Met Leu Ser Thr  Gly Phe Lys Ile Pro  Gln Lys Gly
    1310                1315                1320

Ile Leu  Ile Gly Ile Gln Gln  Ser Phe Arg Pro Arg  Phe Leu Gly
    1325                1330                1335

Val Ala  Glu Gln Leu His Asn  Glu Gly Phe Lys Leu  Phe Ala Thr
    1340                1345                1350

Glu Ala  Thr Ser Asp Trp Leu  Asn Ala Asn Asn Val  Pro Ala Thr
    1355                1360                1365

Pro Val  Ala Trp Pro Ser Gln  Glu Gly Gln Asn Pro  Ser Leu Ser
    1370                1375                1380

Ser Ile  Arg Lys Leu Ile Arg  Asp Gly Ser Ile Asp  Leu Val Ile
    1385                1390                1395

Asn Leu  Pro Asn Asn Asn Thr  Lys Phe Val His Asp  Asn Tyr Val
    1400                1405                1410

Ile Arg  Arg Thr Ala Val Asp  Ser Gly Ile Pro Leu  Leu Thr Asn
    1415                1420                1425

Phe Gln  Val Thr Lys Leu Phe  Ala Glu Ala Val Gln  Lys Ser Arg
    1430                1435                1440

Lys Val  Asp Ser Lys Ser Leu  Phe His Tyr Arg Gln  Tyr Ser Ala
    1445                1450                1455

Gly Lys  Ala Ala
    1460


<210> SEQ ID NO 703
<211> LENGTH: 1053
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190
```

```
Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605
```

-continued

```
Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020
```

```
Thr Gln  Ser Ile Lys Lys Tyr  Ser Thr Asp Ile Leu  Gly Asn Leu
    1025                 1030                 1035

Tyr Glu  Val Lys Ser Lys Lys  His Pro Gln Ile Ile  Lys Lys Gly
    1040                 1045                 1050


<210> SEQ ID NO 704
<211> LENGTH: 1353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

Ala Ala Gly Gly Ile Leu His Leu Glu Leu Leu Val Ala Val Gly Pro
1               5                   10                  15

Asp Val Phe Gln Ala His Gln Glu Asp Thr Glu Arg Tyr Val Leu Thr
            20                  25                  30

Asn Leu Asn Ile Gly Ala Glu Leu Leu Arg Asp Pro Ser Leu Gly Ala
        35                  40                  45

Gln Phe Arg Val His Leu Val Lys Met Val Ile Leu Thr Glu Pro Glu
    50                  55                  60

Gly Ala Pro Asn Ile Thr Ala Asn Leu Thr Ser Ser Leu Leu Ser Val
65                  70                  75                  80

Cys Gly Trp Ser Gln Thr Ile Asn Pro Glu Asp Asp Thr Asp Pro Gly
                85                  90                  95

His Ala Asp Leu Val Leu Tyr Ile Thr Arg Phe Asp Leu Glu Leu Pro
            100                 105                 110

Asp Gly Asn Arg Gln Val Arg Gly Val Thr Gln Leu Gly Gly Ala Cys
        115                 120                 125

Ser Pro Thr Trp Ser Cys Leu Ile Thr Glu Asp Thr Gly Phe Asp Leu
    130                 135                 140

Gly Val Thr Ile Ala His Glu Ile Gly His Ser Phe Gly Leu Glu His
145                 150                 155                 160

Asp Gly Ala Pro Gly Ser Gly Cys Gly Pro Ser Gly His Val Met Ala
                165                 170                 175

Ser Asp Gly Ala Ala Pro Arg Ala Gly Leu Ala Trp Ser Pro Cys Ser
            180                 185                 190

Arg Arg Gln Leu Leu Ser Leu Leu Ser Ala Gly Arg Ala Arg Cys Val
        195                 200                 205

Trp Asp Pro Pro Arg Pro Gln Pro Gly Ser Ala Gly His Pro Pro Asp
    210                 215                 220

Ala Gln Pro Gly Leu Tyr Tyr Ser Ala Asn Glu Gln Cys Arg Val Ala
225                 230                 235                 240

Phe Gly Pro Lys Ala Val Ala Cys Thr Phe Ala Arg Glu His Leu Asp
                245                 250                 255

Met Cys Gln Ala Leu Ser Cys His Thr Asp Pro Leu Asp Gln Ser Ser
            260                 265                 270

Cys Ser Arg Leu Leu Val Pro Leu Leu Asp Gly Thr Glu Cys Gly Val
        275                 280                 285

Glu Lys Trp Cys Ser Lys Gly Arg Cys Arg Ser Leu Val Glu Leu Thr
    290                 295                 300

Pro Ile Ala Ala Val His Gly Arg Trp Ser Ser Trp Gly Pro Arg Ser
305                 310                 315                 320
```

-continued

```
Pro Cys Ser Arg Ser Cys Gly Gly Gly Val Val Thr Arg Arg Arg Gln
                325                 330                 335

Cys Asn Asn Pro Arg Pro Ala Phe Gly Gly Arg Ala Cys Val Gly Ala
            340                 345                 350

Asp Leu Gln Ala Glu Met Cys Asn Thr Gln Ala Cys Glu Lys Thr Gln
        355                 360                 365

Leu Glu Phe Met Ser Gln Gln Cys Ala Arg Thr Asp Gly Gln Pro Leu
    370                 375                 380

Arg Ser Ser Pro Gly Gly Ala Ser Phe Tyr His Trp Gly Ala Ala Val
385                 390                 395                 400

Pro His Ser Gln Gly Asp Ala Leu Cys Arg His Met Cys Arg Ala Ile
                405                 410                 415

Gly Glu Ser Phe Ile Met Lys Arg Gly Asp Ser Phe Leu Asp Gly Thr
            420                 425                 430

Arg Cys Met Pro Ser Gly Pro Arg Glu Asp Gly Thr Leu Ser Leu Cys
        435                 440                 445

Val Ser Gly Ser Cys Arg Thr Phe Gly Cys Asp Gly Arg Met Asp Ser
    450                 455                 460

Gln Gln Val Trp Asp Arg Cys Gln Val Cys Gly Gly Asp Asn Ser Thr
465                 470                 475                 480

Cys Ser Pro Arg Lys Gly Ser Phe Thr Ala Gly Arg Ala Arg Glu Tyr
                485                 490                 495

Val Thr Phe Leu Thr Val Thr Pro Asn Leu Thr Ser Val Tyr Ile Ala
            500                 505                 510

Asn His Arg Pro Leu Phe Thr His Leu Ala Val Arg Ile Gly Gly Arg
        515                 520                 525

Tyr Val Val Ala Gly Lys Met Ser Ile Ser Pro Asn Thr Thr Tyr Pro
    530                 535                 540

Ser Leu Leu Glu Asp Gly Arg Val Glu Tyr Arg Val Ala Leu Thr Glu
545                 550                 555                 560

Asp Arg Leu Pro Arg Leu Glu Glu Ile Arg Ile Trp Gly Pro Leu Gln
                565                 570                 575

Glu Asp Ala Asp Ile Gln Val Tyr Arg Arg Tyr Gly Glu Glu Tyr Gly
            580                 585                 590

Asn Leu Thr Arg Pro Asp Ile Thr Phe Thr Tyr Phe Gln Pro Lys Pro
        595                 600                 605

Arg Gln Ala Trp Val Trp Ala Ala Val Arg Gly Pro Cys Ser Val Ser
    610                 615                 620

Cys Gly Ala Gly Leu Arg Trp Val Asn Tyr Ser Cys Leu Asp Gln Ala
625                 630                 635                 640

Arg Lys Glu Leu Val Glu Thr Val Gln Cys Gln Gly Ser Gln Gln Pro
                645                 650                 655

Pro Ala Trp Pro Glu Ala Cys Val Leu Glu Pro Cys Pro Pro Tyr Trp
            660                 665                 670

Ala Val Gly Asp Phe Gly Pro Cys Ser Ala Ser Cys Gly Gly Gly Leu
        675                 680                 685

Arg Glu Arg Pro Val Arg Cys Val Glu Ala Gln Gly Ser Leu Leu Lys
    690                 695                 700

Thr Leu Pro Pro Ala Arg Cys Arg Ala Gly Ala Gln Gln Pro Ala Val
705                 710                 715                 720

Ala Leu Glu Thr Cys Asn Pro Gln Pro Cys Pro Ala Arg Trp Glu Val
                725                 730                 735
```

```
Ser Glu Pro Ser Ser Cys Thr Ser Ala Gly Gly Ala Gly Leu Ala Leu
            740                 745                 750

Glu Asn Glu Thr Cys Val Pro Gly Ala Asp Gly Leu Glu Ala Pro Val
        755                 760                 765

Thr Glu Gly Pro Gly Ser Val Asp Glu Lys Leu Pro Ala Pro Glu Pro
    770                 775                 780

Cys Val Gly Met Ser Cys Pro Pro Gly Trp Gly His Leu Asp Ala Thr
785                 790                 795                 800

Ser Ala Gly Glu Lys Ala Pro Ser Pro Trp Gly Ser Ile Arg Thr Gly
                805                 810                 815

Ala Gln Ala Ala His Val Trp Thr Pro Ala Ala Gly Ser Cys Ser Val
            820                 825                 830

Ser Cys Gly Arg Gly Leu Met Glu Leu Arg Phe Leu Cys Met Asp Ser
        835                 840                 845

Ala Leu Arg Val Pro Val Gln Glu Glu Leu Cys Gly Leu Ala Ser Lys
    850                 855                 860

Pro Gly Ser Arg Arg Glu Val Cys Gln Ala Val Pro Cys Pro Ala Arg
865                 870                 875                 880

Trp Gln Tyr Lys Leu Ala Ala Cys Ser Val Ser Cys Gly Arg Gly Val
                885                 890                 895

Val Arg Arg Ile Leu Tyr Cys Ala Arg Ala His Gly Glu Asp Asp Gly
            900                 905                 910

Glu Glu Ile Leu Leu Asp Thr Gln Cys Gln Gly Leu Pro Arg Pro Glu
        915                 920                 925

Pro Gln Glu Ala Cys Ser Leu Glu Pro Cys Pro Pro Arg Trp Lys Val
    930                 935                 940

Met Ser Leu Gly Pro Cys Ser Ala Ser Cys Gly Leu Gly Thr Ala Arg
945                 950                 955                 960

Arg Ser Val Ala Cys Val Gln Leu Asp Gln Gly Gln Asp Val Glu Val
                965                 970                 975

Asp Glu Ala Ala Cys Ala Ala Leu Val Arg Pro Glu Ala Ser Val Pro
            980                 985                 990

Cys Leu Ile Ala Asp Cys Thr Tyr  Arg Trp His Val Gly  Thr Trp Met
        995                 1000                1005

Glu Cys  Ser Val Ser Cys Gly  Asp Gly Ile Gln Arg  Arg Arg Asp
    1010                1015                1020

Thr Cys  Leu Gly Pro Gln Ala  Gln Ala Pro Val Pro  Ala Asp Phe
    1025                1030                1035

Cys Gln  His Leu Pro Lys Pro  Val Thr Val Arg Gly  Cys Trp Ala
    1040                1045                1050

Gly Pro  Cys Val Gly Gln Gly  Thr Pro Ser Leu Val  Pro His Glu
    1055                1060                1065

Glu Ala  Ala Ala Pro Gly Arg  Thr Thr Ala Thr Pro  Ala Gly Ala
    1070                1075                1080

Ser Leu  Glu Trp Ser Gln Ala  Arg Gly Leu Leu Phe  Ser Pro Ala
    1085                1090                1095

Pro Gln  Pro Arg Arg Leu Leu  Pro Gly Pro Gln Glu  Asn Ser Val
    1100                1105                1110

Gln Ser  Ser Ala Cys Gly Arg  Gln His Leu Glu Pro  Thr Gly Thr
    1115                1120                1125

Ile Asp  Met Arg Gly Pro Gly  Gln Ala Asp Cys Ala  Val Ala Ile
    1130                1135                1140
```

```
Gly Arg  Pro Leu Gly Glu Val  Val Thr Leu Arg Val  Leu Glu Ser
    1145                 1150                 1155

Ser Leu  Asn Cys Ser Ala Gly  Asp Met Leu Leu Leu  Trp Gly Arg
    1160                 1165                 1170

Leu Thr  Trp Arg Lys Met Cys  Arg Lys Leu Leu Asp  Met Thr Phe
    1175                 1180                 1185

Ser Ser  Lys Thr Asn Thr Leu  Val Val Arg Gln Arg  Cys Gly Arg
    1190                 1195                 1200

Pro Gly  Gly Gly Val Leu Leu  Arg Tyr Gly Ser Gln  Leu Ala Pro
    1205                 1210                 1215

Glu Thr  Phe Tyr Arg Glu Cys  Asp Met Gln Leu Phe  Gly Pro Trp
    1220                 1225                 1230

Gly Glu  Ile Val Ser Pro Ser  Leu Ser Pro Ala Thr  Ser Asn Ala
    1235                 1240                 1245

Gly Gly  Cys Arg Leu Phe Ile  Asn Val Ala Pro His  Ala Arg Ile
    1250                 1255                 1260

Ala Ile  His Ala Leu Ala Thr  Asn Met Gly Ala Gly  Thr Glu Gly
    1265                 1270                 1275

Ala Asn  Ala Ser Tyr Ile Leu  Ile Arg Asp Thr His  Ser Leu Arg
    1280                 1285                 1290

Thr Thr  Ala Phe His Gly Gln  Gln Val Leu Tyr Trp  Glu Ser Glu
    1295                 1300                 1305

Ser Ser  Gln Ala Glu Met Glu  Phe Ser Glu Gly Phe  Leu Lys Ala
    1310                 1315                 1320

Gln Ala  Ser Leu Arg Gly Gln  Tyr Trp Thr Leu Gln  Ser Trp Val
    1325                 1330                 1335

Pro Glu  Met Gln Asp Pro Gln  Ser Trp Lys Gly Lys  Glu Gly Thr
    1340                 1345                 1350
```

<210> SEQ ID NO 705
<211> LENGTH: 431
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 705

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125
```

```
Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430


<210> SEQ ID NO 706
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45
```

```
Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160
```

<210> SEQ ID NO 707
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 707

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 708
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(20)
<223> OTHER INFORMATION: This sequence may encompass 1-10 “Gly Ser” repeating units

<400> SEQUENCE: 708

Gly Ser Gly Ser Gly Ser Gly Ser Gly Ser Gly Ser Gly Ser Gly Ser
1 5 10 15

Gly Ser Gly Ser
20

<210> SEQ ID NO 709
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 1-10 “Gly Gly Ser” repeating units

<400> SEQUENCE: 709

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser
20 25 30

<210> SEQ ID NO 710
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(40)
<223> OTHER INFORMATION: This sequence may encompass 1-10 “Gly Gly Gly Ser” repeating units

<400> SEQUENCE: 710

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser
35 40

<210> SEQ ID NO 711
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(40)
<223> OTHER INFORMATION: This sequence may encompass 1-10 “Gly Gly Ser Gly” repeating units

<400> SEQUENCE: 711

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 712
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser Gly Gly" repeating units

<400> SEQUENCE: 712

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly
    50

<210> SEQ ID NO 713
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly Gly Ser" repeating units

<400> SEQUENCE: 713

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 714
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)

<223> OTHER INFORMATION: This sequence may encompass 1-10 "Gly Gly Gly Gly Gly" repeating units

<400> SEQUENCE: 714

```
Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly
    50
```

<210> SEQ ID NO 715
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 1-10 "Gly Gly Gly" repeating units

<400> SEQUENCE: 715

```
Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30
```

<210> SEQ ID NO 716
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 716

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 717
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 717

```
Gly Gly Gly Gly Ser Gly Gly Gly Gly Ser Gly Gly Gly Gly Ser
1               5                   10                  15
```